(12) United States Patent
Saxty et al.

(10) Patent No.: US 9,464,071 B2
(45) Date of Patent: Oct. 11, 2016

(54) PYRAZOLYL QUINOXALINE KINASE INHIBITORS

(71) Applicant: ASTEX THERAPEUTICS LTD, Cambridge (GB)

(72) Inventors: Gordon Saxty, Cambridge (GB); Christopher William Murray, Cambridge (GB); Valerio Berdini, Cambridge (GB); Gilbert Ebai Besong, Bad Duerkheim (DE); Christopher Charles Frederick Hamlett, Cambridge (GB); Christopher Norbert Johnson, Cambridge (GB); Steven John Woodhead, San Diego, CA (US); Michael Reader, Bishop's Stortford (GB); David Charles Rees, Cambridge (GB); Laurence Anne Mevellec, Louviers (FR); Patrick René Angibaud, Fontaine-Bellenger (FR); Eddy Jean Edgard Freyne, Rumst (BE); Tom Cornelis Hortense Govaerts, Betekom (BE); Johan Erwin Edmond Weerts, Beerse (BE); Timothy Pietro Suren Perera, Geel (BE); Ronaldus Arnodus Hendrika Joseph Gilissen, Kasterlee (BE); Berthold Wroblowski, Vosselaar (BE); Jean Fernand Armand Lacrampe, Le Mesnil-Esnard (FR); Alexandra Papanikos, Antwerp (BE); Olivier Alexis Georges Querolle, Evreux (FR); Elisabeth Thérèse Jeanne Pasquier, Le Neubourg (FR); Isabelle Noëlle Constance Pilatte, Louviers (FR); Pascal Ghislain André Bonnet, Berchem (BE); Werner Constant Johan Embrechts, Beerse (BE); Rhalid Akkari, Vacquieres (FR); Lieven Meerpoel, Beerse (BE)

(73) Assignee: ASTEX THERAPEUTICS LTD, Cambridge (GB)

( * ) Notice: Subject to any disclaimer, the term of this patent is extended or adjusted under 35 U.S.C. 154(b) by 0 days.

(21) Appl. No.: 14/505,020

(22) Filed: Oct. 2, 2014

(65) Prior Publication Data

US 2015/0105368 A1    Apr. 16, 2015

Related U.S. Application Data

(62) Division of application No. 13/643,741, filed as application No. PCT/GB2011/050851 on Apr. 28, 2011, now Pat. No. 8,895,601.

(60) Provisional application No. 61/329,884, filed on Apr. 30, 2010.

(30) Foreign Application Priority Data

Apr. 30, 2010 (GB) .................... 1007286.6

(51) Int. Cl.

| A61K 31/415 | (2006.01) |
|---|---|
| C07D 231/10 | (2006.01) |
| C07D 231/12 | (2006.01) |
| C07D 403/04 | (2006.01) |
| C07D 403/14 | (2006.01) |
| C07D 405/14 | (2006.01) |
| C07D 409/14 | (2006.01) |
| C07D 413/14 | (2006.01) |
| C07D 487/08 | (2006.01) |
| A61K 31/498 | (2006.01) |
| A61K 31/5377 | (2006.01) |

(Continued)

(52) U.S. Cl.
CPC ........... *C07D 403/04* (2013.01); *A61K 31/498* (2013.01); *A61K 31/5377* (2013.01); *A61K 45/06* (2013.01); *C07D 403/14* (2013.01); *C07D 405/14* (2013.01); *C07D 409/14* (2013.01); *C07D 413/14* (2013.01); *C07D 487/08* (2013.01); *C07D 491/113* (2013.01)

(58) Field of Classification Search
None
See application file for complete search history.

(56) References Cited

U.S. PATENT DOCUMENTS

| 2,940,972 A | 6/1960 | Roch |
| 4,666,828 A | 5/1987 | Gusella |
| 4,683,202 A | 7/1987 | Mullis |

(Continued)

FOREIGN PATENT DOCUMENTS

| CA | 2 524 525 A1 | 12/2004 |
| CA | 2 524 948 A1 | 12/2004 |

(Continued)

OTHER PUBLICATIONS

International Search Report for PCT/GB2011/050851 dated Jul. 12, 2011.

(Continued)

*Primary Examiner* — Jeffrey S Lundgren
*Assistant Examiner* — Michael Schmitt
(74) *Attorney, Agent, or Firm* — Heslin Rothenberg Farley & Mesiti P.C.

(57) ABSTRACT

The invention relates to new quinoxaline derivative compounds, to pharmaceutical compositions comprising said compounds, to processes for the preparation of said compounds and to the use of said compounds in the treatment of diseases, e.g. cancer.

45 Claims, No Drawings

(51) Int. Cl.
  *A61K 45/06* (2006.01)
  *C07D 491/113* (2006.01)

(56) References Cited

U.S. PATENT DOCUMENTS

| | | |
|---|---|---|
| 4,801,531 A | 1/1989 | Frossard |
| 5,192,659 A | 3/1993 | Simons |
| 5,272,057 A | 12/1993 | Smulson et al. |
| 5,700,823 A | 12/1997 | Hirth et al. |
| 5,882,864 A | 3/1999 | An et al. |
| 6,218,529 B1 | 4/2001 | An et al. |
| 6,271,231 B1 | 8/2001 | Bergstrand et al. |
| 6,331,555 B1 | 12/2001 | Hirth et al. |
| 9,145,367 B2 | 9/2015 | Tazi et al. |
| 9,221,804 B2 | 12/2015 | Leonard et al. |
| 9,290,478 B2 | 3/2016 | Saxty et al. |
| 9,303,029 B2 | 4/2016 | Woodhead et al. |
| 9,303,030 B2 | 4/2016 | Angibaud et al. |
| 9,309,241 B2 | 4/2016 | Angibaud et al. |
| 9,309,242 B2 | 4/2016 | Berdini et al. |
| 2003/0207886 A1 | 11/2003 | Plücker et al. |
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0221591 A1 | 9/2009 | Hartmann et al. |
| 2010/0234347 A1 | 9/2010 | Dollinger et al. |
| 2013/0072457 A1 | 3/2013 | Saxty et al. |
| 2013/0267525 A1 | 10/2013 | Saxty et al. |
| 2014/0288053 A1 | 9/2014 | Berdini et al. |
| 2014/0296236 A1 | 10/2014 | Berdini et al. |
| 2015/0031669 A1 | 1/2015 | Woodhead et al. |
| 2015/0057293 A1 | 2/2015 | Angibaud et al. |
| 2015/0239883 A1 | 8/2015 | Angibaud et al. |
| 2015/0291589 A1 | 10/2015 | Saxty et al. |
| 2016/0031856 A1 | 2/2016 | Saxty et al. |
| 2016/0075666 A1 | 3/2016 | Angibaud et al. |
| 2016/0108034 A1 | 4/2016 | Angibaud et al. |

FOREIGN PATENT DOCUMENTS

| | | |
|---|---|---|
| CN | 1128496 A | 8/1996 |
| CN | 102036963 A | 4/2011 |
| EP | 0544445 A2 | 6/1993 |
| EP | 1001946 B1 | 5/2000 |
| EP | 1 990 342 A1 | 11/2008 |
| EP | 2 332 939 A1 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 95/19169 A2 | 7/1995 |
| WO | 99/17759 A2 | 4/1999 |
| WO | 0042026 | 7/2000 |
| WO | 01/19825 A1 | 2/2001 |
| WO | 0168047 A2 | 9/2001 |
| WO | 02/076985 A1 | 10/2002 |
| WO | 03/051833 A2 | 6/2003 |
| WO | 03/055491 A1 | 7/2003 |
| WO | 2004/006355 A2 | 1/2004 |
| WO | 2004030635 A2 | 4/2004 |
| WO | 2004/043950 A1 | 5/2004 |
| WO | 2004065378 A1 | 8/2004 |
| WO | 2004098494 A2 | 11/2004 |
| WO | 2004/110350 A2 | 12/2004 |
| WO | 2005007099 A2 | 1/2005 |
| WO | 2005/009437 A1 | 2/2005 |
| WO | 2005/047244 A2 | 5/2005 |
| WO | 2005/054201 A1 | 6/2005 |
| WO | 2005054231 A1 | 6/2005 |
| WO | 2005061463 A1 | 7/2005 |
| WO | 2006/066361 A1 | 6/2006 |
| WO | 2006084338 A1 | 8/2006 |
| WO | 2006092430 A1 | 9/2006 |
| WO | 2006124354 A2 | 11/2006 |
| WO | 2007/075567 A1 | 7/2007 |
| WO | 2007/125405 A2 | 11/2007 |
| WO | 2007/132227 A1 | 11/2007 |
| WO | 2007003419 A1 | 11/2007 |
| WO | 2008003702 A2 | 1/2008 |
| WO | 2008/076278 A2 | 6/2008 |
| WO | 2008/082198 A1 | 7/2008 |
| WO | 2008078091 A1 | 7/2008 |
| WO | 2008079988 A2 | 7/2008 |
| WO | 2008080015 A2 | 7/2008 |
| WO | 2008/138878 A2 | 11/2008 |
| WO | 2008141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009021083 A1 | 2/2009 |
| WO | 2009/064835 A1 | 5/2009 |
| WO | 2009/137378 A2 | 11/2009 |
| WO | 2009/141386 A1 | 11/2009 |
| WO | 2009141386 A1 | 11/2009 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2011026579 A1 | 3/2011 |
| WO | 2011028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013/179033 A1 | 12/2013 |
| WO | 2013/179034 A1 | 12/2013 |
| WO | 2014/174307 A1 | 10/2014 |
| WO | 2015144803 A1 | 10/2015 |
| WO | 2015144804 A1 | 10/2015 |
| WO | 2015144808 A1 | 10/2015 |

OTHER PUBLICATIONS

GB Search Report for GB Application No. GB1007286.6 dated Aug. 27, 2010.
Yan, Lin et al. "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.
Thompson, Andrew M. et al. "Synthesis and Structure—Activity Relationships of 7-Substituted 3-(2,6-Dichlorophenyl)-1,6-napthyridin-2(1*H*)-ones as Selective Inhibitors of pp60$^{c\text{-}src}$", *Journal of Medicinal Chemistry*, vol. 43, No. 16, 2000, pp. 3134-3147.
Berge, Stephen M. et al. "Pharmaceutical Salts", *Journal of Pharmaceutical Sciences*, vol. 66, No. 1, 1977, pp. 1-19.
Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.

(56) References Cited

OTHER PUBLICATIONS

Knights, Victoria et al. "De-regulated FGF receptors as therapeutic targets in cancer", *Pharmacology & Therapeutics*, 2010; vol. 125(1), pp. 105-117.
Korc, M. et al. "The Role of Fibroblast Growth Factors in Tumor Growth", *Current Cancer Drug Targets*, vol. 9(5), 2009, pp. 639-651.
Angerer, Lynne M. et al. "Demonstration of Tissue-Specific Gene Expression by in Situ Hybridization", *Methods in Enzymology*, vol. 152, 1987, pp. 649-661.
Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.
Orre, Maxine and Rogers, Peter A.W. "VEGF, VEGFR1, VEGFR-2, Microvessel Density and Endothelial Cell Proliferation in Tumours of the Ovary", *Int. J. Cancer (Pred. Oncol.)*, vol. 84(2), 1999, pp. 101-108.
Zhou, Wenjun et al., "A Structure-Guided Approach to Creating Covalent FGFR Inhibitors", *Chemistry & Biology*, vol. 17, pp. 285-295 (2010).
"Drugs That Inhibit Signalling Pathways for Tumor Cell Growth and Proliferation", *Medicinal Chemistry of Anticancer Drugs*, pp. 251-305 (2008).
Garuti, L., et al., Irreversible Protein Kinase Inhibitors, *Current Medicinal Chemistry*, vol. 18, No. 20, Jul. 1, 2011, pp. 2981-2994.
Vippagunta, S.R. et al., Crystalline Solids, *Advanced Drug Delivery Reviews*, vol. 48, pp. 3-26 (2001).
Jordan, V.C., Tamoxifen: A Most Unlikely Pioneering Medicine, *Nature Reviews: Drug Discovery*, vol. 2, pp. 205-213 (2003).
Hackam, D.G., et al., Translation of Research Evidence From Animals to Humans, *JAMA*, vol. 14, pp. 1731-1732 (2006).
"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).
V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).
Dorwald, F.Z., Side Reactions in Organic Synthesis: A Guide to Successful Synthesis Design, Weinheim:Wiley-VCH Verlag GmbH & Co. KGaA, 2005, ISBN: 3-527-31021.5.
Lima, L.M., et al., "Bioisosterism: A Useful Strategy for Molecular Modification and Drug Design", *Current Medical Chemistry*, vol. 12(1), pp. 23-49 (2005).
Patani, G.A., et al., "Bioisosterism: A Rational Approach in Drug Design", *Chem. Rev.* vol. 96, pp. 3147-3176 (1996).
Fujita, M., et al., Generation of Formaldehyde by Pharmaceutical Excipients and Its Absorption by Meglumine, Chem. Pharm. Bull, vol. 57, No. 10, pp. 1096-1099 (2009).
Adcock, J., et al., Diversity oriented synthesis: substitution at C5 in unreactive pyrimidines by Claisen rearrangement and reactivity in nucleophilic substitution at C2 and C4 in pteridines and pyrido [2,3-*d*]pyrimidines, Tetrahedron, vol. 67, pp. 3226-3237 (2011).
Dieci, M.V., et al., Fibroblast Growth Factor Receptor Inhibitors as a Cancer Treatment: From a Biologic Rationale to Medical Perspectives, Cancer Discovery, vol. 3, No. 3, pp. 264-279 (Feb. 2013).
Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., Fibroblast Growth Factor Receptor-2 IIIc as a Novel Molecular Target in Colorectal Cancer, Current Colorectal Cancer Reports, vol. 10, No. 1, pp. 20-26 (2014).
Carneiro, B.A., et al., Emerging therapeutic targets in bladder cancer, Cancer Treatment Reviews, vol. 41, No. 2, pp. 170-178 (2015).
Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).

PYRAZOLYL QUINOXALINE KINASE INHIBITORS

CROSS REFERENCE TO RELATED APPLICATIONS

This application is a divisional application of U.S. application Ser. No. 13/643,741 (published as US 2013-0072457 A1 on Mar. 21, 2013), which is a national stage filing under section 371 of International Application No. PCT/GB2011/050851, filed on Apr. 28, 2011, and published in English on Nov. 3, 2011, as WO 2011/135376, and claims priority to British Application No. 1007286.6 filed on Apr. 30, 2010, and to U.S. Provisional Application No. 61/329,884, filed on Apr. 30, 2010. The entire disclosures of each of the prior applications are hereby incorporated herein by reference.

FIELD OF THE INVENTION

The invention relates to new quinoxaline derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I):

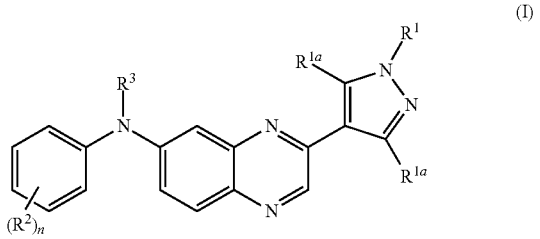

including any tautomeric or stereochemically isomeric form thereof, wherein
n represents an integer equal to 0, 1, 2, 3 or 4;
$R^1$ represents hydrogen, $C_{1-6}$alkyl, $C_{2-4}$alkenyl, hydroxy $C_{1-6}$alkyl, halo$C_{1-6}$alkyl, hydroxyhalo$C_{1-6}$alkyl, cyano $C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy $C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;
each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms;
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo $C_{1-4}$alkoxy, $C_{1-4}$alkoxy$C_{1-4}$alkyl, halo$C_{1-4}$alkoxy $C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ and —C(=O)—$NR^7R^8$; or when two $R^2$ groups are attached to adjacent carbon atoms they may be taken together to form a radical of formula:
—O—(C($R^{17}$)$_2$)$_p$—O—;
—X—CH=CH—; or
—X—CH=N—; wherein $R^{17}$ represents hydrogen or fluorine, p represents 1 or 2 and X represents O or S;
$R^3$ represents hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy $C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—, $C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo $C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;
$R^4$ and $R^5$ each independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NH—S(=O)$_2$—NR$^{14}$R$^{15}$, R$^{13}$ or C$_{1-6}$alkyl substituted with R$^{13}$;

R$^6$ represents C$_{3-8}$cycloalkyl, C$_{3-8}$cycloalkenyl, phenyl, 4 to 7-membered monocyclic heterocyclyl containing at least one heteroatom selected from N, O or S; said C$_{3-8}$cycloalkyl, C$_{3-8}$cycloalkenyl, phenyl, 4 to 7-membered monocyclic heterocyclyl, optionally and each independently being substituted by 1, 2, 3, 4 or 5 substituents, each substituent independently being selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^7$ and R$^8$ each independently represent hydrogen, C$_{1-6}$alkyl, hydroxyC$_{1-6}$alkyl, haloC$_{1-6}$alkyl, hydroxyhaloC$_{1-6}$alkyl or C$_{1-6}$alkoxyC$_{1-6}$alkyl;

R$^9$ represents C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O or S, said C$_{3-8}$cycloalkyl, C$_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, C$_{1-4}$alkyl, hydroxyl, carboxyl, hydroxyC$_{1-4}$alkyl, cyano, cyanoC$_{1-4}$alkyl, C$_{1-4}$alkyl-O—C(=O)—, C$_{1-4}$alkyl substituted with C$_{1-4}$alkyl-O—C(=O)—, C$_{1-4}$alkyl-C(=O)—, C$_{1-4}$alkoxyC$_{1-4}$alkyl wherein each C$_{1-4}$alkyl may optionally be substituted with one or two hydroxyl groups, halogen, haloC$_{1-4}$alkyl, hydroxyhaloC$_{1-4}$alkyl, —NR$^{14}$R$^{15}$, —C(=O)—NR$^{14}$R$^{15}$, C$_{1-4}$alkyl substituted with —NR$^{14}$R$^{15}$, C$_{1-4}$alkyl substituted with —C(=O)—NR$^{14}$R$^{15}$, C$_{1-4}$alkoxy, —S(=O)$_2$—C$_{1-4}$alkyl, —S(=O)$_2$-haloC$_{1-4}$alkyl, —S(=O)$_2$—NR$^{14}$R$^{15}$, C$_{1-4}$alkyl substituted with —S(=O)$_2$—NR$^{14}$R$^{15}$, C$_{1-4}$alkyl substituted with —NH—S(=O)$_2$—C$_{1-4}$alkyl, C$_{1-4}$alkyl substituted with —NH—S(=O)$_2$-haloC$_{1-4}$alkyl, C$_{1-4}$alkyl substituted with —NH—S(=O)$_2$—NR$^{14}$R$^{15}$, R$^{13}$, —C(=O)—R$^{13}$, C$_{1-4}$alkyl substituted with R$^{13}$, phenyl optionally substituted with R$^{16}$, phenylC$_{1-4}$alkyl wherein the phenyl is optionally substituted with R$^{16}$, a 5 or 6-membered aromatic monocyclic heterocyclyl containing at least one heteroatom selected from N, O or S wherein said heterocyclyl is optionally substituted with R$^{16}$; or when two of the substituents of R$^9$ are attached to the same atom, they may be taken together to form a 4 to 7-membered saturated monocyclic heterocyclyl containing at least one heteroatom selected from N, O or S;

R$^{10}$ and R$^{11}$ each independently represent hydrogen, carboxyl, C$_{1-6}$alkyl, cyanoC$_{1-6}$alkyl, C$_{1-6}$alkyl substituted with —NR$^{14}$R$^{15}$, C$_{1-6}$alkyl substituted with —C(=O)—NR$^{14}$R$^{15}$, haloC$_{1-6}$alkyl, hydroxyC$_{1-6}$alkyl, hydroxyhaloC$_{1-6}$alkyl, C$_{1-6}$alkoxy, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl, —C(=O)-hydroxyC$_{1-6}$alkyl, —C(=O)-haloC$_{1-6}$alkyl, —C(=O)-hydroxyhaloC$_{1-6}$alkyl, C$_{1-6}$alkyl substituted with —Si(CH$_3$)$_3$, —S(=O)$_2$—C$_{1-6}$alkyl, —S(=O)$_2$-halo C$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O or S, wherein said C$_{3-8}$cycloalkyl or monocyclic heterocyclyl is optionally substituted with 1, 2 or 3 substituents each independently selected from halogen, hydroxyl, C$_{1-6}$alkyl, —C(=O)—C$_{1-6}$alkyl, C$_{1-6}$alkoxy, or —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino or mono- or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or —C(=O)NR$^{14}$R$^{15}$;

the N-oxides thereof, the pharmaceutically acceptable salts thereof or the solvates thereof.

In one embodiment there is provided compounds of formula (I$^0$):

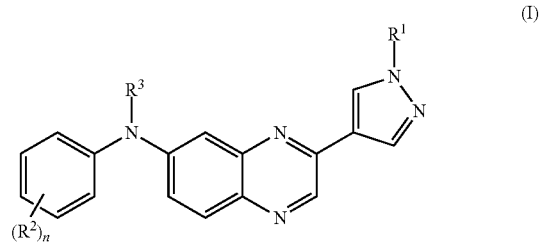

(I)

including any stereochemically isomeric form thereof, wherein n represents an integer equal to 0, 1, 2, 3 or 4;

R$^1$ represents hydrogen, C$_{1-6}$alkyl, C$_{2-4}$alkenyl, hydroxy C$_{1-6}$alkyl, haloC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-halo C$_{1-6}$alkyl, C$_{1-6}$alkyl substituted with —NR$^{12}$—S(=O)$_2$—NR$^{14}$R$^{15}$, R$^6$, C$_{1-6}$alkyl substituted with R$^6$, C$_{1-6}$alkyl substituted with —C(=O)—R$^6$, hydroxy C$_{1-6}$alkyl substituted with R$^6$, C$_{1-6}$alkyl substituted with —Si(CH$_3$)$_3$, C$_{1-6}$alkyl substituted with —P(=O)(OH)$_2$ or C$_{1-6}$alkyl substituted with —P(=O)(OC$_{1-6}$alkyl)$_2$;

each R$^2$ is independently selected from halogen, cyano, C$_{1-14}$alkyl, C$_{2-4}$alkenyl, C$_{2-4}$alkynyl, C$_{1-4}$alkoxy, hydroxyC$_{1-4}$alkyl, hydroxyC$_{1-4}$alkoxy, haloC$_{1-4}$alkyl, haloC$_{1-4}$alkoxy, hydroxyhaloC$_{1-4}$alkyl, hydroxyhalo C$_{1-4}$alkoxy, C$_{1-4}$alkoxyC$_{1-4}$alkyl, haloC$_{1-4}$alkoxy C$_{1-4}$alkyl, C$_{1-4}$alkoxyC$_{1-4}$alkyl wherein each C$_{1-4}$alkyl may optionally be substituted with one or two hydroxyl groups, hydroxyhaloC$_{1-4}$alkoxyC$_{1-4}$alkyl, R$^{13}$, C$_{1-4}$alkyl substituted with R$^{13}$, C$_{1-4}$alkyl substituted with —C(=O)—R$^{13}$, C$_{1-4}$alkoxy substituted with R$^{13}$, C$_{1-4}$alkoxy substituted with —C(=O)—R$^{13}$, —C(=O)—R$^{13}$, C$_{1-4}$alkyl substituted with —NR$^7$R$^8$, C$_{1-4}$alkyl substituted with —C(=O)—NR$^7$R$^8$, C$_{1-4}$alkoxy substituted with —NR$^7$R$^8$, C$_{1-4}$alkoxy substituted with —C(=O)—NR$^7$R$^8$, —NR$^7$R$^8$ or —C(=O)—NR$^7$R$^8$;

R$^3$ represents hydroxyl, C$_{1-6}$alkoxy, hydroxyC$_{1-6}$alkoxy, C$_{1-6}$alkoxy substituted with —NR$^{10}$R$^{11}$, C$_{1-6}$alkyl, C$_{2-6}$alkenyl, C$_{2-6}$alkynyl, haloC$_{1-6}$alkyl, hydroxy C$_{1-6}$alkyl, hydroxyC$_{2-6}$alkenyl, hydroxyC$_{2-6}$alkynyl, hydroxyhaloC$_{1-6}$alkyl, cyanoC$_{1-6}$alkyl, C$_{1-6}$alkyl substituted with carboxyl, C$_{1-6}$alkyl substituted with —C(=O)—C$_{1-6}$alkyl, C$_{1-6}$alkyl substituted with —C(=O)—O—C$_{1-6}$alkyl, C$_{1-6}$alkyl substituted with C$_{1-6}$alkoxyC$_{1-6}$alkyl-O—C(=O)—, C$_{1-6}$alkyl substituted with C$_{1-6}$alkoxyC$_{1-6}$alkyl-C(=O)—, C$_{1-6}$alkyl substituted with —O—C(=O)—C$_{1-6}$alkyl, C$_{1-6}$alkoxy C$_{1-6}$alkyl wherein each C$_{1-6}$alkyl may optionally be substituted with one or two hydroxyl groups, C$_{2-6}$alkenyl substituted with C$_{1-6}$alkoxy, C$_{2-6}$alkynyl substituted with C$_{1-6}$alkoxy, C$_{1-6}$alkyl substituted with R$^9$, C$_{1-6}$alkyl substituted with —C(=O)—R$^9$, C$_{1-6}$alkyl substituted with hydroxyl and R$^9$, C$_{2-6}$alkenyl substituted with R$^9$, C$_{2-6}$alkynyl substituted with R$^9$, C$_{1-6}$alkyl substituted with —NR$^{10}$R$^{11}$, C$_{2-6}$alkenyl substituted with —NR$^{10}$R$^{11}$, C$_{2-6}$alkynyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, —C$_{1-6}$alkyl-C(R$^{12}$)=N—O—R$^{12}$, C$_{1-6}$alkyl substituted with —C(=O)—NR$^{10}$R$^{11}$, C$_{1-6}$alkyl substituted with —O—C(=O)—NR$^{10}$R$^{11}$, —S(=O)$_2$—C$_{1-6}$alkyl, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NR$^{12}$—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^{13}$, C$_{1-6}$alkyl substituted with —P(=O)(OH)$_2$ or C$_{1-6}$alkyl substituted with —P(=O)(OC$_{1-6}$alkyl)$_2$;

R$^4$ and R$^5$ independently represent hydrogen, C$_{1-6}$alkyl, hydroxyC$_{1-6}$alkyl, haloC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NH—S(=O)$_2$—NR$^{14}$R$^{15}$, R$^{13}$ or C$_{1-6}$alkyl substituted with R$^{13}$;

R$^6$ represents C$_{3-8}$cycloalkyl, C$_{3-8}$cycloalkenyl, phenyl, 4 to 7-membered monocyclic heterocyclyl containing at least one heteroatom selected from N, O or S; said C$_{3-8}$cycloalkyl, C$_{3-8}$cycloalkenyl, phenyl, 4 to 7-membered monocyclic heterocyclyl, optionally and each independently being substituted by 1, 2, 3, 4 or 5 substituents, each substituent independently being selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^7$ and R$^8$ independently represent hydrogen, C$_{1-6}$alkyl, hydroxyC$_{1-6}$alkyl, haloC$_{1-6}$alkyl, hydroxyhaloC$_{1-6}$alkyl or C$_{1-6}$alkoxyC$_{1-6}$alkyl;

R$^9$ represents C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O or S, said C$_{3-8}$cycloalkyl, C$_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, C$_{1-4}$alkyl, hydroxyl, carboxyl, hydroxyC$_{1-4}$alkyl, cyano, cyanoC$_{1-4}$alkyl, C$_{1-4}$alkyl-O—C(=O)—, C$_{1-4}$alkyl substituted with C$_{1-4}$alkyl-O—C(=O)—, C$_{1-4}$alkyl-C(=O)—, C$_{1-4}$alkoxyC$_{1-4}$alkyl wherein each C$_{1-4}$alkyl may optionally be substituted with one or two hydroxyl groups, halogen, haloC$_{1-4}$alkyl, hydroxyhaloC$_{1-4}$alkyl, —NR$^{14}$R$^{15}$, —C(=O)—NR$^{14}$R$^{15}$, C$_{1-4}$alkyl substituted with —NR$^{14}$R$^{15}$, C$_{1-4}$alkyl substituted with —C(=O)—NR$^{14}$R$^{15}$, C$_{1-4}$alkoxy, —S(=O)$_2$—C$_{1-4}$alkyl, —S(=O)$_2$-haloC$_{1-4}$alkyl, —S(=O)$_2$—NR$^{14}$R$^{15}$, C$_{1-4}$alkyl substituted with —S(=O)$_2$—NR$^{14}$R$^{15}$, C$_{1-4}$alkyl substituted with —NH—S(=O)$_2$—C$_{1-4}$alkyl, C$_{1-4}$alkyl substituted with —NH—S(=O)$_2$-haloC$_{1-4}$alkyl, C$_{1-4}$alkyl substituted with —NH—S(=O)$_2$—NR$^{14}$R$^{15}$, R$^{13}$, —C(=O)—R$^{13}$, C$_{1-4}$alkyl substituted with R$^{13}$, phenyl optionally substituted with R$^{16}$, phenylC$_{1-6}$alkyl wherein the phenyl is optionally substituted with R$^{16}$, a 5 or 6-membered aromatic monocyclic heterocyclyl containing at least one heteroatom selected from N, O or S wherein said heterocyclyl is optionally substituted with R$^{16}$; or when two of the substituents of R$^9$ are attached to the same atom, they may be taken together to form a 4 to 7-membered saturated monocyclic heterocyclyl containing at least one heteroatom selected from N, O or S;

R$^{10}$ and R$^{11}$ each independently represent hydrogen, C$_{1-6}$alkyl, cyanoC$_{1-6}$alkyl, C$_{1-6}$alkyl substituted with —NR$^{14}$R$^{15}$, haloC$_{1-6}$alkyl, hydroxyC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl, —C(=O)-hydroxyC$_{1-6}$alkyl, —C(=O)-haloC$_{1-6}$alkyl, —C(=O)-hydroxyhaloC$_{1-6}$alkyl, C$_{1-6}$alkyl substituted with —Si(CH$_3$)$_3$, —S(=O)$_2$—C$_{1-6}$alkyl, —S(=O)$_2$-halo $C_{1-6}$alkyl, $-S(=O)_2-NR^{14}R^{15}$, $C_{1-6}$alkyl substituted with $-S(=O)_2-C_{1-6}$alkyl, $C_{1-6}$alkyl substituted with $-S(=O)_2$-halo$C_{1-6}$alkyl, $C_{1-6}$alkyl substituted with $-S(=O)_2-NR^{14}R^{15}$, $C_{1-6}$alkyl substituted with $-NH-S(=O)_2-C_{1-6}$alkyl, $C_{1-6}$alkyl substituted with $-NH-S(=O)_2$-halo$C_{1-6}$alkyl or $C_{1-6}$alkyl substituted with $-NH-S(=O)_2-NR^{14}R^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, $-C(=O)-C_{1-6}$alkyl, $C_{1-6}$alkoxy, or $-NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, $-NR^{14}R^{15}$ or $-C(=O)NR^{14}R^{15}$;

the N-oxides thereof, the pharmaceutically acceptable salts thereof or the solvates thereof.

WO2006/092430, WO2008/003702, WO01/68047, WO2005/007099, WO2004/098494, WO2009/141386, WO 2004/030635, WO 2008/141065, WO 2011/026579, WO 2011/028947 and WO 00/42026 which each disclose a series of heterocyclyl derivatives.

DETAILED DESCRIPTION OF THE INVENTION

Unless the context indicates otherwise, references to formula (I) in all sections of this document (including the uses, methods and other aspects of the invention) include references to all other sub-formula (e.g. I', I'', I''', $I^0$, $I^{0'}$, $I^{0''}$, $I^{0'''}$), sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an $-O-C_{1-4}$alkyl group or an $-O-C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-4}$alkoxy$C_{1-4}$alkyl' or '$C_{1-6}$alkoxy$C_{1-6}$alkyl' as used herein as a group or part of a group refers to a $C_{1-4}$alkyl-$O-C_{1-4}$alkyl group or a $C_{1-6}$alkyl-$O-C_{1-6}$alkyl group wherein $C_{1-4}$alkyl and $C_{1-6}$alkyl are as defined herein. Examples of such groups include methoxyethyl, ethoxyethyl, propoxymethyl, butoxypropyl, and the like.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy $C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo $C_{1-4}$alkyl' or 'halo$C_{1-6}$alkyl' therefore include monohalo $C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo $C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'hydroxyhalo$C_{1-4}$alkyl' or 'hydroxyhalo $C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group and one or more than one hydrogen atom is replaced with a halogen. The term 'hydroxyhalo$C_{1-4}$alkyl' or 'hydroxyhalo$C_{1-6}$alkyl' therefore refers to a $C_{1-4}$alkyl or $C_{1-6}$alkyl group wherein one, two, three or more hydrogen atoms are replaced with a hydroxyl group and one, two, three or more hydrogen atoms are replaced with a halogen.

The term 'hydroxy$C_{1-4}$alkoxy' or 'hydroxy$C_{1-6}$alkoxy' as used herein as a group or part of a group refers to an $-O-C_{1-4}$alkyl group or an $-O-C_{1-6}$alkyl group wherein the $C_{1-4}$alkyl and $C_{1-6}$alkyl group is as defined above and one or more than one hydrogen atom of the $C_{1-4}$alkyl or $C_{1-6}$alkyl group is replaced with a hydroxyl group. The term 'hydroxy$C_{1-4}$alkoxy' or 'hydroxy$C_{1-6}$alkoxy' therefore include monohydroxy$C_{1-4}$alkoxy, monohydroxy$C_{1-6}$alkoxy and also polyhydroxy$C_{1-4}$alkoxy and polyhydroxy $C_{1-6}$alkoxy. There may be one, two, three or more hydrogen atoms replaced with a hydroxyl group so the hydroxy $C_{1-4}$alkoxy or hydroxy$C_{1-6}$alkoxy may have one, two, three or more hydroxyl groups. Examples of such groups include hydroxymethoxy, hydroxyethoxy, hydroxypropoxy and the like.

The term 'halo$C_{1-4}$alkoxy' or 'halo$C_{1-6}$alkoxy' as used herein as a group or part of a group refers to a $-O-C_{1-4}$alkyl group or a $-O-C_{1-6}$ alkyl group as defined herein wherein one or more than one hydrogen atom is replaced with a halogen. The terms 'haloC$_{1-4}$alkoxy' or 'haloC$_{1-6}$alkoxy' therefore include monohaloC$_{1-4}$alkoxy, monohaloC$_{1-6}$alkoxy and also polyhaloC$_{1-4}$alkoxy and polyhaloC$_{1-6}$alkoxy. There may be one, two, three or more hydrogen atoms replaced with a halogen, so the haloC$_{1-4}$alkoxy or haloC$_{1-6}$alkoxy may have one, two, three or more halogens. Examples of such groups include fluoroethyloxy, difluoromethoxy or trifluoromethoxy and the like.

The term 'hydroxyhaloC$_{1-4}$alkoxy' as used herein as a group or part of a group refers to an —O—C$_{1-4}$alkyl group wherein the C$_{1-4}$alkyl group is as defined herein and wherein one or more than one hydrogen atom is replaced with a hydroxyl group and one or more than one hydrogen atom is replaced with a halogen. The term 'hydroxyhaloC$_{1-4}$alkoxy' therefore refers to a —O—C$_{1-4}$alkyl group wherein one, two, three or more hydrogen atoms are replaced with a hydroxyl group and one, two, three or more hydrogen atoms are replaced with a halogen.

The term 'haloC$_{1-4}$alkoxyC$_{1-4}$alkyl' as used herein as a group or part of a group refers to a C$_{1-4}$alkyl-O—C$_{1-4}$alkyl group wherein C$_{1-4}$alkyl is as defined herein and wherein in one or both of the C$_{1-4}$alkyl groups one or more than one hydrogen atom is replaced with a halogen. The term 'haloC$_{1-4}$alkoxyC$_{1-4}$alkyl' therefore refers to a C$_{1-4}$alkyl-O—C$_{1-4}$alkyl group wherein in one or both of the C$_{1-4}$alkyl groups one, two, three or more hydrogen atoms are replaced with a halogen and wherein C$_{1-4}$ alkyl is as defined herein. Preferably, in one of the C$_{1-4}$alkyl groups one or more than one hydrogen atom is replaced with a halogen. Preferably, haloC$_{1-4}$alkoxyC$_{1-4}$alkyl means C$_{1-4}$alkyl substituted with haloC$_{1-4}$alkoxy.

The term 'hydroxyhaloC$_{1-4}$alkoxyC$_{1-4}$alkyl' as used herein refers to a C$_{1-4}$alkyl-O—C$_{1-4}$alkyl group wherein C$_{1-4}$alkyl is as defined herein and wherein in one or both of the C$_{1-4}$alkyl groups one or more than one hydrogen atom is replaced with a hydroxyl group and one or more than one hydrogen atom is replaced with a halogen. The terms 'hydroxyhaloC$_{1-4}$alkoxyC$_{1-4}$alkyl' therefore refers to a C$_{1-4}$alkyl-O—C$_{1-4}$alkyl group wherein in one or both of the C$_{1-4}$alkyl groups one, two, three or more hydrogen atoms are replaced with a hydroxyl group and one, two, three or more hydrogen atoms are replaced with a halogen and wherein C$_{1-4}$alkyl is as defined herein.

The term 'hydroxyC$_{2-6}$alkenyl' as used herein refers to a C$_{2-6}$alkenyl group wherein one or more than one hydrogen atom is replaced with a hydroxyl group and wherein C$_{2-6}$alkenyl is as defined herein.

The term 'hydroxyC$_{2-6}$alkynyl' as used herein refers to a C$_{2-6}$alkynyl group wherein one or more than one hydrogen atom is replaced with a hydroxyl group and wherein C$_{2-6}$alkynyl is as defined herein.

The term phenylC$_{1-6}$alkyl as used herein refers to a C$_{1-6}$alkyl group as defined herein which is substituted with one phenyl group.

The term cyanoC$_{1-4}$alkyl or cyanoC$_{1-6}$alkyl as used herein refers to a C$_{1-4}$alkyl or C$_{1-6}$alkyl group as defined herein which is substituted with one cyano group.

The term "heterocyclyl" as used herein shall, unless the context indicates otherwise, include both aromatic and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to heterocyclyl groups, the heterocyclyl ring can, unless the context indicates otherwise, be optionally substituted (i.e. unsubstituted or substituted) by one or more substituents as discussed herein.

The heterocyclyl groups can be heteroaryl groups having from 5 to 12 ring members, more usually from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;

j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see

*Advanced Organic Chemistry*, by Jerry March, 4$^{th}$ Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

The term 'aryl' as used herein refers to carbocyclyl aromatic groups including phenyl, naphthyl, indenyl, and tetrahydronaphthyl groups.

In one embodiment $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(OC$_{1-6}$alkyl)$_2$.

In one embodiment $R^1$ represents hydrogen, $C_{1-6}$alkyl, $C_{2-4}$alkenyl, hydroxy$C_{1-6}$alkyl, halo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —NH—S(=O)$_2$—$C_{1-6}$alkyl, $R^6$, $C_{1-6}$alkyl substituted with $R^6$, $C_{1-6}$alkyl substituted with —C(=O)—$R^6$, hydroxy$C_{1-6}$alkyl substituted with $R^6$, or $C_{1-6}$alkyl substituted with —Si(CH$_3$)$_3$.

In one embodiment $R^1$ represents hydrogen.

In one embodiment $R^1$ represents $C_{1-6}$alkyl. $R^1$ may represent —CH$_3$, —CD$_3$, —CH$_2$CH$_3$, —CH$_2$CH$_2$CH$_3$, —CH$_2$CH(CH$_3$)$_2$, —CH(CH$_3$)$_2$, —CH$_2$CH(CH$_3$)$_2$. In one embodiment $R^1$ represents —CH$_3$. In another embodiment $R^1$ represents —CD$_3$.

In one embodiment $R^1$ represents $C_{2-4}$alkenyl. $R^1$ may represent —CH$_2$—CH=CH$_2$.

In one embodiment $R^1$ represents hydroxy$C_{1-6}$alkyl. $R^1$ may represent —CH$_2$CH$_2$OH, —CH$_2$C(CH$_3$)$_2$OH or CH$_2$CHOHCH$_2$OH.

In one embodiment $R^1$ represents halo$C_{1-6}$alkyl. $R^1$ may represent —CH$_2$CH$_2$F, CH$_2$CH$_2$CH$_2$Cl or CH$_2$CH$_2$Br.

In one embodiment $R^1$ represents $C_{1-6}$alkoxy$C_{1-6}$alkyl wherein each $C_{1-6}$alkyl may optionally be substituted with one or two hydroxyl groups. $R^1$ may represent —CH$_2$CH$_2$OCH$_3$.

In one embodiment $R^1$ represents $C_{1-6}$alkyl substituted with —$NR^4R^5$.

In one embodiment when $R^1$ represents $C_{1-6}$alkyl substituted with —$NR^4R^5$, $R^4$ and $R^5$ each represent hydrogen. $R^1$ may represent —CH$_2$CH$_2$NH$_2$ or —CH$_2$CH$_2$CH$_2$NH$_2$.

In another embodiment when $R^1$ represents $C_{1-6}$alkyl substituted with —$NR^4R^5$, one of $R^4$ and $R^5$ represents hydrogen and the other represents $C_{1-6}$alkyl, for example —CH$_3$. $R^1$ may represent —CH$_2$CH$_2$NHCH$_3$.

In another embodiment when $R^1$ represents $C_{1-6}$alkyl substituted with —$NR^4R^5$, one of $R^4$ and $R^5$ represents hydrogen and the other represents —S(=O)$_2$—$NR^{14}R^{15}$ where $R^{14}$ and $R^{15}$ each represent $C_{1-4}$alkyl optionally substituted with hydroxyl, for example —CH$_3$. $R^1$ may represent —CH$_2$CH$_2$NHS(=O)$_2$N(CH$_3$)$_2$.

In another embodiment when $R^1$ represents $C_{1-6}$alkyl substituted with —$NR^4R^5$, one of $R^4$ and $R^5$ represents hydrogen and the other represents —S(=O)$_2$—$C_{1-6}$alkyl. $R^1$ may represent —CH$_2$CH$_2$NHS(=O)$_2$CH$_3$.

In one embodiment $R^1$ represents $C_{1-6}$alkyl substituted with —C(=O)—$NR^4R^5$.

In one embodiment when $R^1$ represents $C_{1-6}$alkyl substituted with —C(=O)—$NR^4R^5$, $R^4$ and $R^5$ each represent $C_{1-6}$alkyl, for example —CH$_3$. $R^1$ may represent —CH$_2$C(=O)N(CH$_3$)$_2$.

In another embodiment when $R^1$ represents $C_{1-6}$alkyl substituted with —C(=O)—$NR^4R^5$, one of $R^4$ and $R^5$ represents hydrogen and the other represents $C_{1-6}$alkyl, for example —CH$_3$. $R^1$ may represent —CH$_2$C(=O)NHCH$_3$ or —C(CH$_3$)$_2$C(=O)NHCH$_3$.

In another embodiment when $R^1$ represents $C_{1-6}$alkyl substituted with —C(=O)—$NR^4R^5$, one of $R^4$ and $R^5$ represents hydrogen and the other represents hydroxy$C_{1-6}$alkyl, for example —CH$_2$CH$_2$OH. $R^1$ may represent —C(CH$_3$)$_2$C(=O)NHCH$_2$CH$_2$OH or —CH$_2$C(=O)NHCH$_2$CH$_2$OH.

In another embodiment when $R^1$ represents $C_{1-6}$alkyl substituted with —C(=O)—$NR^4R^5$, one of $R^4$ and $R^5$ represents hydrogen and the other represents $C_{1-6}$alkoxy$C_{1-6}$alkyl wherein each $C_{1-6}$alkyl may optionally be substituted with one or two hydroxyl groups, for example —CH$_2$CH$_2$OCH$_3$. $R^1$ may represent —CH$_2$C(=O)NHCH$_2$CH$_2$OCH$_3$ or —C(CH$_3$)$_2$C(=O)NHCH$_2$CH$_2$OCH$_3$.

In another embodiment when $R^1$ represents $C_{1-6}$alkyl substituted with —C(=O)—$NR^4R^5$, one of $R^4$ and $R^5$ represents hydrogen and the other represents $C_{1-6}$alkyl substituted with $R^{13}$. $R^{13}$ may represent a saturated 5 membered monocyclic heterocyclyl containing at least one nitrogen heteroatom, for example pyrrolidine. $R^1$ may represent —CH$_2$—C(=O)—NH—CH$_2$—CH$_2$— (pyrrolidin-1-yl).

In another embodiment when $R^1$ represents $C_{1-6}$alkyl substituted with —C(=O)—$NR^4R^5$, one of $R^4$ and $R^5$ represents hydrogen and the other represents $C_{1-6}$alkyl substituted with —S(=O)$_2$—$C_{1-6}$alkyl. $R^1$ may represent —CH$_2$CH$_2$CH$_2$NHCH$_2$CH$_2$—S(=O)$_2$—CH$_3$.

In one embodiment $R^1$ represents —S(=O)$_2$—$C_{1-6}$alkyl. $R^1$ may represent —S(=O)$_2$—CH$_3$.

In one embodiment $R^1$ represents —S(=O)$_2$—$NR^{14}R^{15}$. $R^{14}$ and $R^{15}$ may each represent $C_{1-4}$alkyl optionally substituted with hydroxyl, for example $R^{14}$ and $R^{15}$ may both represent —CH$_3$. $R^1$ may represent —S(=O)$_2$—N(CH$_3$)$_2$.

In one embodiment $R^1$ represents $C_{1-6}$alkyl substituted with —S(=O)$_2$—$C_{1-6}$alkyl. $R^1$ may represent —CH$_2$CH$_2$S(=O)$_2$—CH$_3$.

In one embodiment $R^1$ represents $C_{1-6}$alkyl substituted with —NH—S(=O)$_2$—$C_{1-6}$alkyl. $R^1$ may represent —CH$_2$CH$_2$NHS(=O)$_2$—CH$_3$.

In one embodiment $R^1$ represents $R^6$. $R^6$ may represent a saturated 4, 5 or 6 membered monocyclic heterocyclyl containing at least one heteroatom selected from N, O or S, which may optionally be substituted.

In one embodiment when $R^1$ represents $R^6$, $R^6$ represents piperidinyl, for example 4-piperidinyl.

In one embodiment when $R^1$ represents $R^6$, $R^6$ represents tetrahydropyranyl, for example 2-tetrahydropyranyl or 4-tetrahydropyranyl.

In one embodiment when $R^1$ represents $R^6$, $R^6$ represents tetrahydrofuranyl, for example 3-tetrahydrofuranyl.

In another embodiment when $R^1$ represents $R^6$, $R^6$ represents azetidinyl substituted by one hydroxy$C_{1-6}$alkyl group. The hydroxy$C_{1-6}$alkyl group may be —$CH_2CH_2OH$. $R^6$ may represent

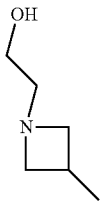

In another embodiment when $R^1$ represents $R^6$, $R^6$ represents piperidinyl substituted by one $C_{1-6}$alkyl-O—C(=O)— group. The $C_{1-6}$alkyl-O—C(=O)— group may be $(CH_3)_3C$—O—C(=O)—. $R^6$ may represent 4-piperidinyl substituted on the nitrogen atom with $(CH_3)_3C$—O—C(=O)—. In another embodiment when $R^1$ represents $R^6$, $R^6$ represents piperidinyl substituted by one —S(=O)$_2$—$C_{1-6}$alkyl group. The —S(=O)$_2$—$C_{1-6}$alkyl group may be —S(=O)$_2CH_3$. $R^6$ may represent 4-piperidinyl substituted on the nitrogen atom with —S(=O)$_2CH_3$. In another embodiment when $R^1$ represents $R^6$, $R^6$ represents piperidinyl substituted by one $C_{1-6}$alkyl group. The $C_{1-6}$alkyl group may be —$CH_3$. $R^6$ may represent 4-piperidinyl substituted on the nitrogen atom with —$CH_3$.

In one embodiment $R^1$ represents $C_{1-6}$alkyl substituted with $R^6$. $R^6$ may represent a saturated 4, 5 or 6 membered monocyclic heterocyclyl containing at least one heteroatom selected from N, O or S, which may optionally be substituted. $R^6$ may represent pyrrolidinyl, thiophenyl, piperidinyl, morpholinyl, piperazinyl, tetrahydropyranyl. $R^1$ may represent methyl or ethyl each substituted with 4-piperidinyl, 4-piperazinyl, 1-pyrrolidinyl or 4-tetrahydropyranyl. $R^1$ may represent propyl substituted with morpholinyl where the morpholinyl is linked to the propyl through the N heteroatom. In another embodiment the heterocyclyl may be substituted by one substituent selected from halogen, $C_{1-6}$alkyl, hydroxyl, hydroxy$C_{1-6}$alkyl, $C_{1-6}$alkoxy, $C_{1-6}$alkyl-O—C(=O)—. The substituent may be —Cl, —$CH_3$, —OH, —$CH_2CH_2OH$, —$CH_2CH_2CH_2OH$, —$OCH_3$, $(CH_3)_3C$—O—C(=O)—.

$R^1$ may represent methyl, ethyl or propyl each substituted with 4-piperidinyl substituted on the nitrogen atom with $(CH_3)_3C$—O—C(=O)—, 4-piperidinyl substituted on the nitrogen atom with —$CH_3$, 4-piperazinyl substituted on the nitrogen atom (N1) with $(CH_3)_3C$—O—C(=O)—, 4-piperazinyl substituted on the nitrogen atom (N1) with —$CH_2CH_2OH$, 4-piperazinyl substituted on the nitrogen atom (N1) with —$CH_2CH_2CH_2OH$, 4-piperidinyl substituted in the 4 position by —OH, or 4-piperidinyl substituted in the 4 position by —O—$CH_3$. $R^1$ may represent methyl substituted with 2-thiophenyl substituted in the 5 position with chlorine. In another embodiment the heterocyclyl may be substituted by two substituents selected from hydroxyl, $C_{1-6}$alkoxy, $C_{1-6}$alkyl-O—C(=O)—. The substituent may be —OH, —$OCH_3$, $(CH_3)_3C$—O—C(=O)—. $R^1$ may represent methyl substituted with 4-piperidinyl substituted on the nitrogen atom with $(CH_3)_3C$—O—C(=O)— and in the 4 position by —OH.

In one embodiment $R^1$ represents $C_{1-6}$alkyl substituted with —C(=O)—$R^6$. $R^6$ may represent a saturated 4, 5 or 6 membered monocyclic heterocyclyl containing at least one heteroatom selected from N, O or S, which may optionally be substituted. $R^6$ may represent piperazinyl or pyrrolidinyl.

In one embodiment when $R^1$ represents $C_{1-6}$alkyl substituted with —C(=O)—$R^6$, $R^6$ represents piperazinyl. $R^1$ may represent —C(CH$_3$)$_2$—C(=O)-(piperazin-4-yl).

In another embodiment when $R^1$ represents $C_{1-6}$alkyl substituted with —C(=O)—$R^6$, $R^6$ represents piperazinyl substituted by one $C_{1-6}$alkyl-O—C(=O)— group, for example C(CH$_3$)$_3$—O—C(=O)—. $R^1$ may represent —C(CH$_3$)$_2$—C(=O)-(piperazin-4-yl) substituted on the nitrogen atom in the 1 position by C(CH$_3$)$_3$—O—C(=O)—.

In another embodiment when $R^1$ represents $C_{1-6}$alkyl substituted with —C(=O)—$R^6$, $R^6$ represents pyrrolidinyl substituted by one hydroxyl group. $R^1$ may represent —$CH_2$—C(=O)-(pyrrolidin-1-yl) substituted in the 3 position by —OH.

In one embodiment $R^1$ represents hydroxy$C_{1-6}$alkyl substituted with $R^6$, $R^6$ may represent a saturated 4, 5 or 6 membered monocyclic heterocyclyl containing at least one heteroatom selected from N, O or S, which may optionally be substituted. $R^6$ may represent piperidinyl, for example 1-piperidinyl. $R^1$ may represent —$CH_2$CHOH$CH_2$-piperidin-1-yl.

In one embodiment $R^1$ represents $C_{1-6}$alkyl substituted with —Si(CH$_3$)$_3$. $R^1$ may represent —$CH_2Si(CH_3)_3$.

In one embodiment $R^1$ represents cyano$C_{1-4}$alkyl. $R^1$ may represent —$CH_2CH_2CN$.

In one embodiment each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms.

In one embodiment each $R^{1a}$ is independently selected from hydrogen, $C_{1-4}$alkyl, hydroxy$C_{1-4}$alkyl, $C_{1-4}$alkyl substituted with di($C_{1-4}$alkyl)amino, and $C_{1-4}$alkyl substituted with one or more fluoro atoms.

In one embodiment one or two $R^{1a}$ represents hydrogen. In one embodiment each $R^{1a}$ represents hydrogen.

In one embodiment one or two $R^{1a}$ represents $C_{1-4}$alkyl, for example —$CH_3$, —$CH_2CH_3$. In one embodiment each $R^{1a}$ represents $C_{1-4}$alkyl, for example —$CH_3$.

In one embodiment one or two $R^{1a}$ represents hydroxy$C_{1-4}$alkyl, for example —$CH_2OH$, —$CH_2CH_2OH$, —$CH_2CH_2CH_2OH$.

In one embodiment one or two $R^{1a}$ represents $C_{1-4}$alkyl substituted with di($C_{1-4}$alkyl)amino, for example —$CH_2$N(CH$_3$)$_2$. In one embodiment one or two $R^{1a}$ represents $C_{1-4}$alkyl substituted with one or more fluoro atoms, for example —$CF_3$.

In one embodiment:
(i) one $R^{1a}$ represents hydrogen and the other $R^{1a}$ represents $C_{1-4}$alkyl, for example —$CH_3$, —$CH_2CH_3$;
(ii) one $R^{1a}$ represents hydrogen and the other $R^{1a}$ represents hydroxy$C_{1-4}$alkyl, for example —$CH_2OH$, —$CH_2CH_2OH$, —$CH_2CH_2CH_2OH$;
(iii) one $R^{1a}$ represents hydrogen and the other $R^{1a}$ represents $C_{1-4}$alkyl substituted with one or more fluoro atoms, for example —$CF_3$; or
(iv) each $R^{1a}$ independently represents $C_{1-4}$alkyl, for example each $R^{1a}$ represents —$CH_3$.

In one embodiment, $R^1$ is methyl and $R^{1a}$ is hydrogen or methyl.

In one embodiment each $R^2$ is independently selected from hydroxyl, halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, haloC$_{1-4}$alkyl, haloC$_{1-4}$alkoxy, C$_{1-4}$alkoxyC$_{1-4}$alkyl, R$^{13}$, C$_{1-4}$alkoxy substituted with R$^{13}$, —C(=O)—R$^{13}$, C$_{1-4}$alkyl substituted with NR$^7$R$^8$, C$_{1-4}$alkoxy substituted with NR$^7$R$^8$, —NR$^7$R$^8$ and —C(=O)—NR$^7$R$^8$; or when two R$^2$ groups are attached to adjacent carbon atoms they may be taken together to form a radical of formula —O—(C(R$^{17}$)$_2$)$_p$—O— wherein R$^{17}$ represents hydrogen or fluorine and p represents 1 or 2.

In one embodiment each R$^2$ is independently selected from halogen, cyano, C$_{1-4}$alkyl, C$_{2-4}$alkenyl, C$_{1-4}$alkoxy, hydroxyC$_{1-4}$alkyl, hydroxyC$_{1-4}$alkoxy, haloC$_{1-4}$alkoxy, C$_{1-4}$alkoxyC$_{1-4}$alkyl, R$^{13}$, C$_{1-4}$alkoxy substituted with R$^{13}$, —C(=O)—R$^{13}$, C$_{1-4}$alkyl substituted with NR$^7$R$^8$, C$_{1-4}$alkoxy substituted with NR$^7$R$^8$, —NR$^7$R$^8$ or —C(=O)—NR$^7$R$^8$;

In one embodiment one or more R$^2$ represents hydroxyl.

In one embodiment one or more R$^2$ represents halogen, for example fluorine, chlorine or bromine.

In one embodiment one or more R$^2$ represents cyano.

In one embodiment one or more R$^2$ represents C$_{1-4}$alkyl, for example —CH$_3$.

In one embodiment one or more R$^2$ represents C$_{2-4}$alkenyl, for example —CH=CH$_2$.

In one embodiment one or more R$^2$ represents C$_{1-4}$alkoxy, for example CH$_3$O—, (CH$_3$)$_2$CHO—, CH$_3$CH$_2$O—, or CD$_3$O—.

In one embodiment one or more R$^2$ represents hydroxy C$_{1-4}$alkyl, for example —CH$_2$OH.

In one embodiment one or more R$^2$ represents hydroxy C$_{1-4}$alkoxy, for example —OCH$_2$CH$_2$OH.

In one embodiment one or more R$^2$ represents halo C$_{1-4}$alkyl, for example —CF$_3$.

In one embodiment one or more R$^2$ represents halo C$_{1-4}$alkoxy, for example —OCH$_2$CH$_2$F or —O—CHF$_2$—. In one embodiment one or more R$^2$ represents —OCH$_2$CH$_2$F or —O—CHF$_2$ or —OCF$_3$.

In one embodiment one or more R$^2$ represents C$_{1-4}$alkoxyC$_{1-4}$alkyl, for example —CH$_2$CH$_2$OCH$_3$.

In one embodiment one or more R$^2$ represents R$^{13}$. R$^{13}$ may represent a saturated 5 membered monocyclic heterocyclyl containing two oxygen heteroatoms, for example dioxolanyl, particularly 2-dioxolanyl.

In one embodiment one or more R$^2$ represents C$_{1-4}$alkoxy substituted with R$^{13}$. R$^{13}$ may represent C$_{3-8}$cycloalkyl, for example cyclopropyl. One or more R$^2$ may represent —OCH$_2$C$_3$H$_5$.

In one embodiment one or more R$^2$ represents —C(=O)—R$^{13}$. R$^{13}$ may represent a saturated 5 membered monocyclic heterocyclyl containing one nitrogen heteroatom, for example pyrrolidinyl. R$^2$ may represent —C(=O)-(1-pyrrolidinyl).

In one embodiment one or more R$^2$ represents C$_{1-4}$alkyl substituted with —NR$^7$R$^8$. In one embodiment R$^7$ and R$^8$ each represent hydrogen. One or more R$^2$ may represent —CH$_2$NH$_2$. In another embodiment R$^7$ and R$^8$ may each independently represent C$_{1-6}$alkyl, for example —CH$_2$CH$_3$ or —CH$_3$. One or more R$^2$ may represent —CH$_2$N(CH$_2$CH$_3$)$_2$, —CH$_2$N(CH$_3$)$_2$ or —CH$_2$N(CH$_2$CH$_3$)(CH$_3$).

In one embodiment one or more R$^2$ represents C$_{1-4}$alkoxy substituted with —NR$^7$R$^8$. In one embodiment one of R$^7$ and R$^8$ represents hydrogen and the other represents C$_{1-6}$alkyl, for example —CH$_3$. One or more R$^2$ may represent —OCH$_2$CH$_2$NHCH$_3$. In one embodiment R$^7$ and R$^8$ each represent hydrogen. One or more R$^2$ may represent —OCH$_2$CH$_2$NH$_2$.

In one embodiment one or more R$^2$ represents —NR$^7$R$^8$. In one embodiment one of R$^7$ and R$^8$ represents hydrogen and the other represents C$_{1-6}$alkyl, for example —CH$_3$. In one embodiment each of R$^7$ and R$^8$ represents C$_{1-6}$alkyl, for example —CH$_3$.

In one embodiment one or more R$^2$ represents —C(=O)—NR$^7$R$^8$. In one embodiment one of R$^7$ and R$^8$ represents hydrogen and the other represents C$_{1-6}$alkyl, for example —CH$_3$.

In one embodiment when two R$^2$ groups are attached to adjacent carbon atoms they may be taken together to form a radical of formula —O—(C(R$^{17}$)$_2$)$_p$—O— wherein R$^{17}$ represents hydrogen and p represents 1.

In one embodiment n is equal to 0. In one embodiment n is equal to 1. In one embodiment n is equal to 2. In one embodiment n is equal to 3. In one embodiment n is equal to 4.

In one embodiment n is equal to 1. R$^2$ may be at the 3-position. R$^2$ may represent
(i) haloC$_{1-4}$alkoxy, for example —O—CHF$_2$;
(ii) C$_{1-4}$alkoxy, for example CH$_3$O— or (CH$_3$)$_2$CHO—;
(iii) cyano; or
(iv) —NR$^7$R$^8$, for example —NHCH$_3$.

In one embodiment n is equal to 1. R$^2$ may be at the 3-position. R$^2$ may represent haloC$_{1-4}$alkoxy, for example —OCF$_3$.

In one embodiment n is equal to 1. R$^2$ may be at the 3-position. R$^2$ may represent C$_{1-4}$alkoxy, for example CH$_3$O—. In one embodiment n is equal to 1. R$^2$ may be at the 3-position. R$^2$ may represent —NR$^7$R$^8$ where R$^7$ and R$^8$ each independently represent C$_{1-6}$alkyl, for example —N(CH$_3$)$_2$.

In one embodiment n is equal to 2. One R$^2$ may be at the 3-position and the other may be at the 5-position:
(i) each R$^2$ may represent C$_{1-4}$alkoxy, for example each R$^2$ may be CH$_3$O—, or the R$^2$ at the 3-position may be (CH$_3$)$_2$CHO— and the R$^2$ at the 5-position may be CH$_3$O—, or the R$^2$ at the 3-position may be CH$_3$O— and the R$^2$ at the 5-position may be CD$_3$O—;
(ii) the R$^2$ at the 3-position may represent halogen, for example fluorine, chlorine or bromine, and the R$^2$ at the 5-position may represent C$_{1-4}$alkoxy, for example CH$_3$O—, CD$_3$O— or CH$_3$CH$_2$O—;
(iii) the R$^2$ at the 3-position may represent C$_{1-4}$alkyl, for example —CH$_3$, and the R$^2$ at the 5-position may represent C$_{1-4}$alkoxy, for example CH$_3$O—;
(iv) the R$^2$ at the 3-position may represent cyano, and the R$^2$ at the 5-position may represent C$_{1-4}$alkoxy, for example CH$_3$O—;
(v) the R$^2$ at the 3-position may represent C$_{1-4}$alkyl substituted with NR$^7$R$^8$, for example —CH$_2$NH$_2$ or —CH$_2$N(CH$_3$)$_2$ or —CH$_2$N(CH$_2$CH$_3$)$_2$ or —CH$_2$N(CH$_2$CH$_3$)(CH$_3$), and the R$^2$ at the 5-position may represent C$_{1-4}$alkoxy, for example CH$_3$O—;
(vi) the R$^2$ at the 3-position may represent C$_{1-4}$alkoxy, for example CH$_3$O—, and the R$^2$ at the 5-position may represent —C(=O)—NR$^7$R$^8$, for example —C(=O)NHCH$_3$ or —C(=O)NH$_2$;
(vii) the R$^2$ at the 3-position may represent hydroxy C$_{1-4}$alkoxy, for example —OCH$_2$CH$_2$OH, and the R$^2$ at the 5-position may represent C$_{1-4}$alkoxy, for example CH$_3$O-
(viii) the R$^2$ at the 3-position may represent —C(=O)—R$^{13}$, for example —C(=O)-(pyrrolidin-1-yl), and the R$^2$ at the 5-position may represent C$_{1-4}$alkoxy, for example CH$_3$O—;
(ix) the R$^2$ at the 3-position may represent C$_{1-4}$alkoxy substituted with R$^{13}$, for example —OCH$_2$C$_3$H$_5$, and the R$^2$ at the 5-position may represent C$_{1-4}$alkoxy, for example CH$_3$O—;

(x) the $R^2$ at the 3-position may represent $C_{1-4}$alkoxy, for example $CH_3O$—, and the $R^2$ at the 5-position may represent $C_{1-4}$alkoxy substituted with $NR^7R^8$, for example —$OCH_2CH_2NHCH_3$ or —$OCH_2CH_2NH_2$;

(xi) the $R^2$ at the 3-position may represent $C_{1-4}$alkoxy, for example $CH_3O$—, and the $R^2$ at the 5-position may represent $C_{2-4}$alkenyl, for example —$CH=CH_2$;

(xii) the $R^2$ at the 3-position may represent $C_{1-4}$alkoxy, for example $CH_3O$—, and the $R^2$ at the 5-position may represent $C_{1-4}$alkoxy$C_{1-4}$alkyl, for example —$CH_2CH_2OCH_3$; or the $R^2$ at the 3-position may be $CH_3O$— and the $R^2$ at the 5-position may be $CH_3OCH_2$—;

(xiii) the $R^2$ at the 3-position may represent $R^{13}$, for example 2-dioxolanyl, and the $R^2$ at the 5-position may represent $C_{1-4}$alkoxy, for example $CH_3O$—;

(xiv) the $R^2$ at the 3-position may represent hydroxy $C_{1-4}$alkoxy, for example —$OCH_2CH_2OH$, and the $R^2$ at the 5-position may represent halogen, for example fluorine;

(xv) the $R^2$ at the 3-position may represent halo$C_{1-4}$alkoxy, for example —$OCH_2CH_2F$, and the $R^2$ at the 5-position may represent $C_{1-4}$alkoxy, for example $CH_3O$—;

(xvi) the $R^2$ at the 3-position may represent halogen, for example fluorine, and the $R^2$ at the 5-position may represent —$C(=O)$—$NR^7R^8$, for example —$C(=O)NHCH_3$;

(xvii) the $R^2$ at the 3-position may represent $C_{1-4}$alkoxy, for example $CH_3O$—, and the $R^2$ at the 5-position may represent halogen, for example fluorine; or (xviii) the $R^2$ at the 3-position may represent represents hydroxy$C_{1-6}$alkyl, for example —$CH_2OH$, and the $R^2$ at the 5-position may represent $C_{1-4}$alkoxy, for example $CH_3O$—.

In one embodiment n is equal to 2. One $R^2$ may be at the 3-position and the other may be at the 5-position:
(i) the $R^2$ at the 3-position may represent hydroxyl and the $R^2$ at the 5-position may represent $C_{1-4}$alkoxy, for example $CH_3O$—;
(ii) each $R^2$ may represent halogen, for example chlorine;
(iii) the $R^2$ at the 3-position may represent $C_{1-4}$alkoxy, for example $CH_3O$— and the $R^2$ at the 5-position may represent $C_{1-4}$alkyl substituted with —$NR^7R^8$ where $R^7$ and $R^8$ may each independently represent $C_{1-6}$alkyl, for example —$CH_2N(CH_2CH_3)_2$;
(iv) the $R^2$ at the 3-position may represent $C_{1-4}$alkoxy, for example $CH_3O$—, and the $R^2$ at the 5-position may represent halo$C_{1-4}$alkoxy, for example —$OCHF_2$;
(v) the $R^2$ at the 3-position may represent $C_{1-4}$alkoxy, for example $CH_3O$—, and the $R^2$ at the 5-position may represent halo$C_{1-4}$alkyl, for example —$CHF_2$; or
(vi) each $R^2$ may represent hydroxyl.

In one embodiment n is equal to 2. One $R^2$ may be at the 3-position and the other may be at the 5-position. Each $R^2$ may represent $C_{1-4}$alkoxy, for example each $R^2$ may be $CH_3O$—, $(CH_3)_2CHO$—, $CH_3CH_2O$—, $CD_3O$—. In one embodiment both $R^2$ are for example $CH_3O$—, or $CD_3O$—. In one embodiment both $R^2$ are $CH_3O$—.

In one embodiment n is equal to 2. One $R^2$ may be at the 4-position and the other may be at the 5-position. Each $R^2$ may represent $C_{1-4}$alkoxy, for example each $R^2$ may be $CH_3O$—.

In one embodiment n is equal to 2. One $R^2$ may be at the 5-position and the other may be at the 6-position. Each $R^2$ may represent $C_{1-4}$alkoxy, for example each $R^2$ may be $CH_3O$—.

In one embodiment n is equal to 2. One $R^2$ may be at the 2-position and the other may be at the 5-position:
(i) each $R^2$ may represent $C_{1-4}$alkoxy, for example each $R^2$ may be $CH_3O$—; or (ii) the $R^2$ at the 2-position may be halogen, for example chlorine, and the $R^2$ at the 5 position may represent $C_{1-4}$alkoxy, for example $CH_3O$—.

In one embodiment n is equal to 3. One $R^2$ may be at the 2-position, one may be at the 3-position and one may be at the 5-position:
(i) the $R^2$ at the 2-position may represent halogen, for example chlorine, the $R^2$ at the 3-position and the 5-position may each represent $C_{1-4}$alkoxy, for example each of these $R^2$ may be $CH_3O$—; or
(ii) the $R^2$ at the 2-position may represent $C_{1-4}$alkyl, for example —$CH_3$, the $R^2$ at the 3-position and the 5-position may each represent $C_{1-4}$alkoxy, for example each of these $R^2$ may be $CH_3O$—.

In one embodiment n is equal to 3. One $R^2$ may be at the 3-position, one may be at the 4-position and one may be at the 5-position:
(i) the $R^2$ at the 3-position may represent $C_{1-4}$alkoxy, for example $CH_3O$—, the $R^2$ at the 4-position and the 5-position may each represent halogen, for example fluorine; or;
(ii) the $R^2$ at the 3-position may represent $C_{1-4}$alkoxy, for example $CH_3O$—, the $R^2$ at the 4-position and the 5-position may be taken together to form a radical of formula —O—$(C(R^{17})_2)_p$—O— wherein $R^{17}$ represents hydrogen and p represents 1.

In one embodiment n is equal to 3. One $R^2$ may be at the 2-position, one may be at the 3-position and one may be at the 5-position: (i) the $R^2$ at the 2-position may represent halogen, for example fluorine, the $R^2$ at the 3-position and the 5-position may each represent $C_{1-4}$alkoxy, for example $CH_3O$—.

In one embodiment n is equal to 4. One $R^2$ may be at the 2-position, one may be at the 3-position, one may be at the 5-position and one may be at the 6-position, the $R^2$ at the 2-position and the 6-position may each represent halogen, for example chlorine or fluorine, the $R^2$ at the 3-position and the 5-position may each represent $C_{1-4}$alkoxy, for example $CH_3O$—.

$R^3$ may represent $C_{1-6}$alkyl, hydroxy$C_{1-6}$alkyl, hydroxy-halo$C_{1-6}$alkyl, hydroxy$C_{2-6}$alkynyl, halo$C_{1-6}$alkyl, halo$C_{1-6}$alkyl optionally substituted (e.g. substituted) with —O—C(=O)—$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —C(=O)—$NR^{10}R^{11}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with $R^9$ and optionally substituted with —O—C(=O)—$C_{1-6}$alkyl, $C_{1-6}$alkyl substituted with hydroxyl and $R^9$, —$C_{1-6}$alkyl-C($R^{12}$)=N—O—$R^{12}$, —S(=O)$_2$—$NR^{14}R^{15}$, $C_{1-6}$alkyl substituted with —S(=O)$_2$—$C_{1-6}$alkyl, $C_{1-6}$alkyl substituted with —C(=O)—$NR^{10}R^{11}$, $C_{1-6}$alkyl substituted with —C(=O)—$R^9$, $C_{2-6}$alkenyl substituted with $R^9$, $C_{2-6}$alkynyl substituted with $R^9$, hydroxy$C_{1-6}$alkoxy, $C_{2-6}$alkenyl, $C_{2-6}$alkynyl, $R^{13}$, $C_{1-6}$alkyl substituted with $C_{1-6}$alkoxy$C_{1-6}$alkyl-C(=O)— or $C_{1-6}$alkyl substituted with —P(=O)(O$C_{1-6}$alkyl)$_2$.

$R^3$ may represent $C_{1-6}$alkyl, hydroxy$C_{1-6}$alkyl, hydroxy-halo$C_{1-6}$alkyl, halo$C_{1-6}$alkyl, $C_{1-6}$alkyl substituted with —C(=O)—C$_{1-6}$alkyl, C$_{1-6}$alkoxyC$_{1-6}$alkyl wherein each C$_{1-6}$alkyl may optionally be substituted with one or two hydroxyl groups, C$_{1-6}$alkyl substituted with R$^9$, C$_{1-6}$alkyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, C$_{1-6}$alkyl substituted with —C(=O)—O—C$_{1-6}$alkyl, C$_{1-6}$alkyl substituted with —C(=O)—NR$^{10}$R$^{11}$, C$_{1-6}$alkyl substituted with carboxyl, C$_{1-6}$alkyl substituted with —O—C(=O)—NR$^{10}$R$^{11}$, C$_{1-6}$alkyl substituted with —NR$^{12}$—S(=O)$_2$—C$_{1-6}$alkyl, C$_{1-6}$alkyl substituted with —NR$^{12}$—S(=O)$_2$—NR$^{14}$R$^{15}$, C$_{1-6}$alkyl substituted with hydroxyl and R$^9$, —C$_{1-6}$alkyl-C(R$^{12}$)=N—O—R$^{12}$, C$_{1-6}$alkyl substituted with —C(=O)—NR$^{10}$R$^{11}$, C$_{1-6}$alkyl substituted with —C(=O)—R$^9$, C$_{2-6}$alkynyl substituted with R$^9$, hydroxyC$_{1-6}$alkoxy, C$_{2-6}$alkenyl, C$_{2-6}$alkynyl, R$^{13}$ or C$_{1-6}$alkyl substituted with C$_{1-6}$alkoxyC$_{1-6}$alkyl-C(=O)—.

In one embodiment R$^3$ represents C$_{1-6}$alkyl. R$^3$ may represent —CH$_3$, —CH$_2$CH$_3$, —CH$_2$CH$_2$CH$_3$ or —CH$_2$CH(CH$_3$)$_2$.

In one embodiment R$^3$ represents hydroxyC$_{1-6}$alkyl. R$^3$ may represent —CH$_2$CH$_2$OH, —CH$_2$CH$_2$CH$_2$OH, —CH$_2$CHOHCH$_3$, —CH$_2$CHOHCH$_2$CH$_3$, —CH$_2$CHOHCH(CH$_3$)$_2$, —CH$_2$CH$_2$C(OH)(CH$_3$)$_2$, —CH$_2$CHOHCH$_2$OH or —CH$_2$C(CH$_3$)$_2$OH. R$^3$ may represent —CD$_2$CD$_2$OH or —CD$_2$CD$_2$CD$_2$OH. R$^3$ may represent —CH(CH$_3$)CH$_2$OH.

In one embodiment R$^3$ represents haloC$_{1-6}$alkyl. R$^3$ may represent —CH$_2$CH$_2$CH$_2$Cl or —CH$_2$CH$_2$CH$_2$CH$_2$Cl. R$^3$ may represent —CH$_2$CH$_2$F or —CH$_2$CH$_2$I.

In one embodiment R$^3$ represents haloC$_{1-6}$alkyl optionally substituted with —O—C(=O)—C$_{1-6}$alkyl. R$^3$ may represent —CH$_2$CH(CF$_3$)—O—C(=O)CH$_3$.

In one embodiment R$^3$ represents hydroxyhaloC$_{1-6}$alkyl, for example R$^3$ may represent —CH$_2$CHOHCF$_3$.

In one embodiment R$^3$ represents hydroxyC$_{2-6}$alkynyl, for example R$^3$ may represent —CH$_2$—C≡C—CH$_2$OH or —CH$_2$—C≡C—C(CH$_3$)$_2$OH.

In one embodiment R$^3$ represents C$_{1-6}$alkyl substituted with —C(=O)—C$_{1-6}$alkyl, for example R$^3$ may represent CH$_3$—C(=O)—CH$_2$—, (CH$_3$)$_2$CH—C(=O)—CH$_2$I.

In one embodiment R$^3$ represents C$_{1-6}$alkoxyC$_{1-6}$alkyl wherein each C$_{1-6}$alkyl may optionally be substituted with one or two hydroxyl groups. R$^3$ may represent —CH$_2$CH$_2$OCH$_3$, —CH$_2$CH$_2$OCH$_2$CH$_3$ or —CH$_2$CHOHCH$_2$OCH$_3$.

In one embodiment R$^3$ represents C$_{1-6}$alkoxyC$_{1-6}$alkyl wherein each C$_{1-6}$alkyl may optionally be substituted with one or two hydroxyl groups or with —O—C(=O)—C$_{1-6}$alkyl. R$^3$ may represent —CH$_2$CH(—O—C(=O)CH$_3$)CH$_2$OCH$_3$.

In one embodiment R$^3$ represents C$_{1-6}$alkyl substituted with R$^9$.

In one embodiment when R$^3$ represents C$_{1-6}$alkyl substituted with R$^9$, R$^9$ represents optionally substituted C$_{3-8}$cycloalkyl, for example cyclopropyl or cyclopentyl. R$^3$ may represent —CH$_2$—C$_3$H$_5$ or —CH$_2$C$_5$H$_9$.

In one embodiment where the C$_{3-8}$cycloalkyl is cyclopropyl it is substituted by one hydroxyC$_{1-4}$alkyl, for example —CH$_2$OH.

In one embodiment where the C$_{3-8}$cycloalkyl is cyclopropyl it is substituted by one 6-membered aromatic monocyclic heterocyclyl containing one nitrogen heteroatom, for example 4-pyridinyl.

In another embodiment where the C$_{3-8}$cycloalkyl is cyclopropyl it is substituted by one Cl$_{1-6}$alkyl-O—C(=O)—, for example CH$_3$CH$_2$—O—C(=O)—.

In one embodiment when R$^3$ represents C$_{1-6}$alkyl substituted with R$^9$, R$^9$ represents an optionally substituted aromatic 5 membered monocyclic heterocyclyl containing a nitrogen and an oxygen heteroatom, for example isoxazolyl. In one embodiment the heterocyclyl is substituted with one or two C$_{1-4}$alkyl groups, for example —CH$_3$ groups. R$^3$ may represent methyl substituted with 5-isoxazoyl substituted in the 3 position with —CH$_3$ or methyl substituted with 3-isoxazoyl substituted in the 5 position with —CH$_3$.

In one embodiment when R$^3$ represents C$_{1-6}$alkyl substituted with R$^9$, R$^9$ represents an optionally substituted saturated 6 membered monocyclic heterocyclyl containing a nitrogen and an oxygen heteroatom, for example morpholinyl. R$^3$ may represent ethyl or propyl substituted by 4-morpholinyl. R$^3$ may represent methyl substituted by 3-morpholinyl. R$^3$ may represent methyl substituted by 6-morpholinyl.

In one embodiment the heterocyclyl is substituted with one or two C$_{1-4}$alkyl groups, for example —CH$_3$ groups. R$^3$ may represent ethyl or propyl substituted by 4-morpholinyl substituted in the 2 and 6 positions by —CH$_3$. R$^3$ may represent methyl substituted by 3-morpholinyl substituted in the 5 position by two —CH$_3$. R$^3$ may represent methyl substituted by 6-morpholinyl substituted in the 4 position by —CH(CH$_3$)$_2$. In one embodiment the heterocyclyl is substituted with one C$_{1-4}$alkyl group, for example —CH(CH$_3$)$_2$, and one =O. R$^3$ may represent methyl substituted by 6-morpholinyl substituted in the 3 position by =O and 4 position by —CH(CH$_3$)$_2$.

In another embodiment the heterocyclyl is substituted with phenylC$_{1-6}$alkyl, wherein the phenyl is optionally substituted with R$^{16}$, for example —CH$_2$—C$_6$H$_5$. R$^3$ may represent methyl substituted by 2-morpholinyl substituted in the 4 position by —CH$_2$—C$_6$H$_5$.

In one embodiment when R$^3$ represents C$_{1-6}$alkyl substituted with R$^9$, R$^9$ represents a saturated or an aromatic 3, 4, 5 or 6 membered monocyclic heterocyclyl containing one or two oxygen heteroatoms, for example ethylene oxide (oxiranyl), trimethylene oxide (oxetanyl), tetrahydrofuranyl, dioxolanyl, tetrahydropyranyl or furanyl. R$^3$ may be methyl substituted with 2-tetrahydrofuranyl, 2-dioxolane, ethylene oxide, 2-furanyl or 4-tetrahydropyranyl, In one embodiment when R$^3$ represents C$_{1-6}$alkyl substituted with R$^9$, R$^9$ represents an optionally substituted 4 membered heterocyclyl containing one oxygen heteroatom, for example oxetanyl, and the heterocyclyl is substituted with one C$_{1-4}$alkyl group, for example —CH$_3$. R$^3$ may be methyl substituted with 3-oxetanyl substituted in the 3 position by —CH$_3$.

In one embodiment when R$^3$ represents C$_{1-6}$alkyl substituted with R$^9$, R$^9$ represents an optionally substituted 4 membered heterocyclyl containing one oxygen heteroatom, for example oxetanyl, and the heterocyclyl is substituted with one C$_{1-4}$alkyl substituted with —NR$^{14}$R$^{15}$ group where one of R$^{14}$ and R$^{15}$ is hydrogen and the other is C$_{1-4}$alkyl, for example —CH(CH$_3$)$_2$. R$^3$ may be methyl substituted with 3-oxetanyl substituted in the 3 position by —CH$_2$NHCH(CH$_3$)$_2$.

In one embodiment when R$^3$ represents C$_{1-6}$alkyl substituted with R$^9$, R$^9$ represents an optionally substituted aromatic 6 membered monocyclic heterocycle containing one or two nitrogen heteroatoms, for example pyridinyl or pyrazinyl. R$^3$ may represent methyl substituted with 3-pyridinyl or 2-pyrazinyl. R$^3$ may represent propyl substituted with 4-pyridinyl.

In one embodiment when R$^3$ represents C$_{1-6}$alkyl substituted with R$^9$, R$^9$ represents an optionally substituted aromatic 6 membered monocyclic heterocycle containing two nitrogen heteroatoms, for example pyrimidinyl. $R^3$ may represent methyl or propyl substituted with 2-pyrimidinyl.

In one embodiment when $R^3$ represents $C_{1-6}$alkyl substituted with $R^9$, $R^9$ represents an optionally substituted aromatic 6 membered monocyclic heterocyclyl containing one nitrogen heteroatom, for example pyridinyl, substituted with one halogen, for example chlorine or bromine. $R^3$ may represent methyl substituted with 3-pyridinyl substituted in the 6 position by chlorine or 2-pyridinyl substituted in the 6 position by bromine.

In one embodiment when $R^3$ represents $C_{1-6}$alkyl substituted with $R^9$, $R^9$ represents an optionally substituted aromatic 6 membered monocyclic heterocyclyl containing one nitrogen heteroatom, for example pyridinyl, substituted with:
(i) one $C_{1-4}$alkyl, for example —$CH_3$. $R^3$ may represent propyl substituted with 6-pyridinyl substituted in the 4 position by —$CH_3$; or
(ii) one $C_{1-4}$alkoxy, for example —$OCH_3$. $R^3$ may represent propyl substituted with 2-pyridinyl substituted in the 3 position by —$OCH_3$. $R^3$ may represent methyl substituted with 2-pyridinyl substituted in the 6 position by —$OCH_3$;
(iii) one $C_{1-4}$alkyl substituted by —$NR^{14}R^{15}$. In one embodiment $R^{14}$ and $R^{15}$ each represent hydrogen. $R^3$ may represent methyl substituted with 6-pyridinyl substituted in the 2 position by —$CH_2NH_2$; or
(iv) one —$NR^{14}R^{15}$. In one embodiment one of $R^{14}$ and $R^{15}$ represents hydrogen and the other represents $C_{1-4}$alkyl, for example —$CH_3$. $R^3$ may represent methyl substituted with 6-pyridinyl substituted in the 2 position by —$NHCH_3$.

In one embodiment when $R^3$ represents $C_{1-6}$alkyl substituted with $R^9$, $R^9$ represents an optionally substituted aromatic 6 membered monocyclic heterocyclyl containing two nitrogen heteroatoms, for example pyrimidinyl, substituted with:
(i) one or two $C_{1-4}$alkoxy groups, for example —$OCH_3$. $R^3$ may represent propyl substituted with 2-pyrimidinyl substituted in the 4 position by —$OCH_3$. $R^3$ may represent methyl substituted with 2-pyrimidinyl substituted in the 4 and 6 positions by —$OCH_3$;
(ii) one hydroxyl group, for example —OH. $R^3$ may represent propyl substituted with 2-pyrimidinyl substituted in the 4 position by —OH.

In one embodiment when $R^3$ represents $C_{1-6}$alkyl substituted with $R^9$, $R^9$ represents an optionally substituted saturated 6 membered monocyclic heterocyclyl containing two nitrogen heteroatoms, for example piperazinyl. $R^3$ may represent methyl substituted with 3-piperazinyl.

In one embodiment when $R^3$ represents $C_{1-6}$alkyl substituted with $R^9$, $R^9$ represents an optionally substituted saturated 6 membered monocyclic heterocyclyl containing two nitrogen heteroatoms, for example piperazinyl substituted with $R^{13}$, for example said $R^{13}$ representing piperidinyl being substituted with one $C_{1-4}$alkyl-C(=O)—, for example —C(=O)—$CH_3$. $R^3$ may represent ethyl substituted with 1-piperazinyl substituted in the 4 position with 4-piperidinyl substituted in the 1 position with —C(=O)—$CH_3$.

In one embodiment when $R^3$ represents $C_{1-6}$alkyl substituted with $R^9$, $R^9$ represents an optionally substituted saturated 6 membered monocyclic heterocyclyl containing two nitrogen heteroatoms, for example piperazinyl substituted with $C_{1-4}$alkyl substituted with —C(=O)—$NR^{14}R^{15}$. $R^3$ may represent ethyl substituted with 1-piperazinyl substituted in the 4 position with —$CH_2$C(=O)NHCH($CH_3$)$_2$.

In one embodiment when $R^3$ represents $C_{1-6}$alkyl substituted with $R^9$, $R^9$ represents a partially saturated 6 membered monocyclic heterocyclyl containing one nitrogen heteroatom which may optionally be substituted. $R^3$ may represent ethyl or propyl substituted with 1,2,3,6-tetrahydropyridine.

In another embodiment when $R^3$ represents $C_{1-6}$alkyl substituted with $R^9$, $R^9$ represents an optionally substituted saturated 4 membered monocyclic heterocyclyl containing one nitrogen heteroatom, for example azetidinyl.

In another embodiment when $R^3$ represents $C_{1-6}$alkyl substituted with $R^9$, $R^9$ represents a saturated 4 membered monocyclic heterocyclyl containing one nitrogen heteroatom, for example azetidinyl, and the heterocyclyl is substituted with one or two halogens, for example fluorine. $R^3$ may represent propyl substituted by 1-azetidinyl substituted in the 3 position by two fluorines. In another embodiment when $R^3$ represents $C_{1-6}$alkyl substituted with $R^9$, $R^9$ represents a saturated 4 membered monocyclic heterocyclyl containing one nitrogen heteroatom, for example azetidinyl, and the heterocyclyl is substituted with one hydroxyl group. $R^3$ may represent propyl substituted by 1-azetidinyl substituted in the 3 position by one —OH.

In another embodiment when $R^3$ represents $C_{1-6}$alkyl substituted with $R^9$, $R^9$ represents a saturated 5 membered monocyclic heterocyclyl containing one nitrogen heteroatom, for example pyrrolidinyl. $R^3$ may represent ethyl or propyl substituted with 1-pyrrolidinyl or 2-pyrrolidinyl.

In another embodiment when $R^3$ represents $C_{1-6}$alkyl substituted with $R^9$, $R^9$ represents a saturated 5 membered monocyclic heterocyclyl containing one nitrogen heteroatom, for example pyrrolidinyl, and the heterocyclyl is substituted. For example the heterocyclyl is substituted with:
a) one or two halogens, for example fluorine. $R^3$ may represent propyl substituted with 1-pyrrolidinyl substituted in the 3 position by two fluorines or with 1-pyrrolidinyl substituted in the 3 position by one fluorine;
b) one halo$C_{1-4}$alkyl, for example —$CH_2$Cl. $R^3$ may represent propyl substituted with 1-pyrrolidinyl substituted in the 2 position by —$CH_2$Cl;
c) one hydroxyl group. $R^3$ may represent ethyl or propyl substituted with 1-pyrrolidinyl substituted in the 3 position by —OH;
d) one =O group. $R^3$ may represent ethyl or propyl substituted with 1-pyrrolidinyl substituted in the 2 position by =O;
e) one —S(=O)$_2$—$C_{1-4}$alkyl group and the $C_{1-4}$alkyl may be —$CH_3$. $R^3$ may represent propyl substituted with 1-pyrrolidinyl substituted in the 3 position by —S(=O)$_2$—$CH_3$;
f) one —$NR^{14}R^{15}$ group. In one embodiment $R^{14}$ and $R^{15}$ each represent hydrogen. $R^3$ may represent ethyl or propyl substituted with 1-pyrrolidinyl substituted in the 3 position with —$NH_2$. In another embodiment $R^{14}$ and $R^{15}$ each independently represent $C_{1-4}$alkyl optionally substituted with hydroxyl, for example —$CH_3$. $R^3$ may represent ethyl substituted with 1-pyrrolidinyl substituted in the 3 position with —N($CH_3$)$_2$. In another embodiment one of $R^{14}$ and $R^{15}$ is hydrogen and the other is $C_{1-4}$alkyl optionally substituted with hydroxyl, for example —$CH_3$. $R^3$ may represent propyl substituted with 1-pyrrolidinyl substituted in the 3 position with —$NHCH_3$;
g) one or two $C_{1-4}$alkyl groups, for example —$CH_3$ or —CH($CH_3$)$_2$. $R^3$ may represent ethyl or propyl substituted with 1-pyrrolidinyl substituted in the 2 position with —$CH_3$, 1-pyrrolidinyl substituted in the 2 and the 5 position with —$CH_3$ or 1-pyrrolidinyl substituted in the 2 position with two —$CH_3$;

h) one carboxyl group. $R^3$ may represent ethyl substituted with 1-pyrrolidinyl substituted in the 2 position with —C(=O)OH;
i) one hydroxy$C_{1-4}$alkyl, for example —CH$_2$OH, —C(CH$_3$)$_2$OH or —CH$_2$CH$_2$OH. $R^3$ may represent ethyl or propyl substituted with 1-pyrrolidinyl substituted in the 2 position with —CH$_2$OH;
j) $R^{13}$. In one embodiment $R^{13}$ represents a saturated 6-membered monocyclic heterocyclyl containing one nitrogen heteroatom. In another embodiment $R^{13}$ represents a saturated 6-membered monocyclic heterocyclyl containing one nitrogen and one oxygen heteroatom. In a further embodiment $R^{13}$ represents a saturated 6-membered monocyclic heterocyclyl containing one nitrogen and one oxygen heteroatom, and the heterocyclyl is substituted, for example substituted with two $C_{1-6}$alkyl groups, for example two —CH$_3$ groups. $R^3$ may represent propyl substituted with 1-pyrrolidinyl substituted in the 3 position by 1-piperidinyl, or propyl substituted with 1-pyrrolidinyl substituted in the 3 position by 4-morpholinyl substituted in positions 2 and 6 by —CH$_3$;
k) one cyano group. $R^3$ may represent ethyl or propyl substituted with 1-pyrrolidinyl substituted in the 3 position by —CN;
l) one cyano$C_{1-4}$alkyl, for example —CH$_2$CN. $R^3$ may represent propyl substituted with 1-pyrrolidinyl substituted in the 2 position by —CH$_2$CN. $R^3$ may represent ethyl substituted with 1-pyrrolidinyl substituted in the 2 position by —CH$_2$CN;
m) one $C_{1-4}$alkyl substituted with —NH—S(=O)$_2$-halo$C_{1-4}$alkyl, for example —CH$_2$NH—S(=O)$_2$—CF$_3$. $R^3$ may represent propyl substituted with 1-pyrrolidinyl substituted in the 2 position by —CH$_2$NH—S(=O)$_2$—CF$_3$; or
n) one $C_{1-6}$alkyl-O—C(=O)—, for example (CH$_3$)$_3$C—O—C(=O)— or CH$_3$—O—C(=O)—. $R^3$ may represent methyl or ethyl substituted by 2-pyrrolidinyl substituted in the 1 position by (CH$_3$)$_3$C—O—C(=O)— or substituted by 1-pyrrolidinyl substituted in the 2 position by CH$_3$—O—C(=O)—.

In another embodiment when $R^3$ represents $C_{1-6}$alkyl substituted with $R^9$, $R^9$ represents a saturated 5 membered monocyclic heterocyclyl containing one nitrogen heteroatom, for example pyrrolidinyl, and the heterocyclyl is substituted. For example the heterocyclyl is substituted with a 6-membered aromatic monocyclic heterocyclyl containing one or two nitrogen heteroatoms, for example pyridinyl or pyrimidinyl, and optionally substituted with $R^{16}$. In one embodiment $R^{16}$ represents $C_{1-4}$alkoxy, for example —OCH$_3$. $R^3$ may represent methyl substituted by 3-pyrrolidinyl substituted in the 1-position by 2-pyridinyl substituted in the 3-position by —OCH$_3$. $R^3$ may represent methyl substituted by 3-pyrrolidinyl substituted in the 1-position by 2-pyrimidinyl substituted in the 4-position by —OCH$_3$.

In another embodiment when $R^3$ represents $C_{1-6}$alkyl substituted with $R^9$, $R^9$ represents a saturated 6 membered monocyclic heterocyclyl containing one nitrogen heteroatom, for example piperidinyl. $R^3$ may represent methyl, ethyl or propyl substituted by 4-piperidinyl or 1-piperidinyl.

In another embodiment when $R^3$ represents $C_{1-6}$alkyl substituted with $R^9$, $R^9$ represents a saturated 6 membered monocyclic heterocyclyl containing one nitrogen heteroatom, for example piperidinyl, and the heterocyclyl is substituted. For example the heterocyclyl is substituted with:
a) one or two halogens, for example fluorine. $R^3$ may represent ethyl substituted by 1-piperidinyl substituted at the 4 position by two fluorines;
b) one hydroxyl group. $R^3$ may represent methyl or ethyl substituted by 1-piperidinyl substituted at the 4 position by one —OH or 4-piperidinyl substituted at the 4 position by one —OH;
c) one —NR$^{14}$R$^{15}$ group. In one embodiment $R^{14}$ and $R^{15}$ each represent hydrogen. $R^3$ may represent ethyl substituted by 1-piperidinyl substituted at the 3 position or the 4 position by —NH$_2$. In another embodiment $R^{14}$ and $R^{15}$ each independently represent $C_{1-4}$alkyl optionally substituted with hydroxyl, for example —CH$_3$. $R^3$ may represent ethyl substituted by 1-piperidinyl substituted at the 4 position by —N(CH$_3$)$_2$;
d) one or two $C_{1-4}$alkyl groups, for example —CH$_3$ or —CH(CH$_3$)$_2$. $R^3$ may represent methyl, ethyl or propyl substituted by 1-piperidinyl substituted at the 2 position by —CH$_3$, 1-piperidinyl substituted at the 2 and the 6 position by —CH$_3$, 4-piperidinyl substituted at the 1 position by —CH(CH$_3$)$_2$, 4-piperidinyl substituted at the 1 position by —CH$_3$, 1-piperidinyl substituted at the 3 and the 5 position by —CH$_3$;
e) one hydroxy$C_{1-4}$alkyl, for example —CH$_2$OH, —C(CH$_3$)$_2$OH or —CH$_2$CH$_2$OH. $R^3$ may represent ethyl substituted by 1-piperidinyl substituted in the 4 position by —C(CH$_3$)$_2$OH, 1-piperidinyl substituted in the 4 position by —CH$_2$CH$_2$OH; 1-piperidinyl substituted in the 4 position by —CH$_2$OH;
f) one cyano group. $R^3$ may represent ethyl or propyl substituted with 1-piperidinyl substituted at the 3 position with —CN;
g) one $C_{1-6}$alkyl-O—C(=O)—, for example CH$_3$CH$_2$—O—C(=O)—, (CH$_3$)$_3$C—O—C(=O)— or CH$_3$—O—C(=O)—. $R^3$ may represent methyl or ethyl substituted with 1-piperidinyl substituted in the 4 position by CH$_3$CH$_2$—O—C(=O)—, 4-piperidinyl substituted in the 1 position by (CH$_3$)$_3$C—O—C(=O)—;
h) one $C_{1-6}$alkyl-O—C(=O)—, for example (CH$_3$)$_3$C—O—C(=O)—, and one hydroxyl group. $R^3$ may represent methyl substituted with 4-piperidinyl substituted in the 4 position by —OH and in the 1 position by (CH$_3$)$_3$C—O—C(=O)—;
i) one $C_{1-6}$alkyl-O—C(=O)—, for example (CH$_3$)$_3$C—O—C(=O)—, and one $C_{1-4}$alkoxy group, for example —OCH$_3$. $R^3$ may represent methyl substituted with 4-piperidinyl substituted in the 4 position by —OCH$_3$ and in the 1 position by (CH$_3$)$_3$C—O—C(=O)—;
j) one $C_{1-4}$alkoxy group, for example —OCH$_3$. $R^3$ may represent methyl or ethyl substituted with 1-piperidinyl substituted in the 4 position by —OCH$_3$ or 4-piperidinyl substituted in the 4 position by —OCH$_3$;
k) one halo$C_{1-4}$alkyl group, for example —CF$_3$. $R^3$ may represent propyl substituted with 1-piperidinyl substituted in the 4 position by —CF$_3$; or
l) one —C(=O)—NR$^{14}$R$^{15}$ where $R^{14}$ and $R^{15}$ both represent hydrogen. $R^3$ may represent ethyl substituted with 1-piperidinyl substituted in the 3 position by —C(=O)—NH$_2$. $R^3$ may represent ethyl or propyl substituted with 1-piperidinyl substituted in the 2 position by —C(=O)—NH$_2$.

In another embodiment when $R^3$ represents $C_{1-6}$alkyl substituted with $R^9$, $R^9$ represents a saturated 6 membered monocyclic heterocyclyl containing one nitrogen heteroatom, for example piperidinyl, and the heterocyclyl is substituted. For example the heterocyclyl is substituted with:
a) one =O. $R^3$ may represent ethyl substituted by 1-piperidinyl substituted at the 4 position by =O, or propyl substituted by 1-piperidinyl substituted at the 2 position by =O;

b) one $C_{1-6}$alkyl substituted with —$NR^{14}R^{15}$ where $R^{14}$ and $R^{15}$ both represent hydrogen. $R^3$ may represent ethyl substituted with 1-piperidinyl substituted in the 4 position by —$CH_2NH_2$.

In another embodiment when $R^3$ represents $C_{1-6}$alkyl substituted with $R^9$, $R^9$ represents a saturated 6 membered monocyclic heterocyclyl containing one nitrogen heteroatom, for example piperidinyl, and the heterocyclyl is substituted. For example the heterocyclyl is substituted with a 6-membered aromatic monocyclic heterocyclyl containing two nitrogen heteroatoms, for example pyrimidinyl, and optionally substituted with $R^{16}$. In one embodiment $R^{16}$ represents $C_{1-4}$alkoxy, for example —$OCH_3$. $R^3$ may represent methyl substituted by 4-piperidinyl substituted in the 1-position by 2-pyrimidinyl substituted in the 4-position by —$OCH_3$.

In another embodiment when $R^3$ represents $C_{1-6}$alkyl substituted with $R^9$, $R^9$ represents a bicyclic heterocyclyl containing a benzene ring fused to a 5- or 6-membered ring containing 1, 2 or 3 ring heteroatoms. In one embodiment the bicyclic heterocyclyl contains a benzene ring fused to a 5-membered ring containing 1 ring heteroatom. In one embodiment the ring heteroatom is a nitrogen heteroatom. In one embodiment the bicyclic heterocyclyl is substituted with two =O groups on the 5-membered ring containing one ring heteroatom. $R^3$ may represent ethyl, propyl or butyl substituted with isoindolyl-1,3,-dione (e.g. isoindol-2-yl-1,3-dione, also known as phthalimidyl). $R^3$ may represent —CH($CH_3$)$CH_2$— substituted with isoindolyl-1,3,-dione.

In one embodiment when $R^3$ represents $C_{1-6}$alkyl (for example ethyl or propyl) substituted with $R^9$, $R^9$ represents an optionally substituted monocyclic heterocyclo containing at least one heteroatom selected from N, O or S. In one embodiment $R^9$ represents a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S; and $R^3$ represents $C_{1-6}$alkyl (for example ethyl or propyl) substituted with a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S. For example $R^3$ may represent ethyl substituted with 2-oxa-6-aza-spiro[3.3]heptane or $R^3$ may represent ethyl substituted with 1-piperidinyl substituted on the 4 position by 1,4-dioxolane e.g. to form 1,4-dioxa-8-aza-spiro[4.5]decane.

In another embodiment when $R^3$ represents $C_{1-6}$alkyl substituted with $R^9$, $R^9$ represents an optionally substituted aromatic 5 membered monocyclic heterocyclyl containing one sulphur heteroatom, for example thiophene. $R^3$ may represent methyl substituted with 2-thiophenyl. In one embodiment the aromatic 5 membered monocyclic heterocyclyl containing one sulphur heteroatom is substituted with one chlorine. $R^3$ may represent methyl substituted with 2-thiophenyl substituted at the 5 position by chlorine.

In another embodiment when $R^3$ represents $C_{1-6}$alkyl substituted with $R^9$, $R^9$ represents an optionally substituted aromatic 5 membered monocyclic heterocyclyl containing one sulphur and one nitrogen heteroatom, for example thiazole. The 5-membered heterocyclyl may be substituted with for example one $C_{1-4}$alkyl, for example —$CH_3$. $R^3$ may represent methyl substituted with 4-thiazolyl substituted in the 2 position by —$CH_3$.

In another embodiment when $R^3$ represents $C_{1-6}$alkyl substituted with $R^9$, $R^9$ represents a saturated 6 membered monocyclic heterocyclyl containing two nitrogen heteroatoms, for example piperazinyl. $R^3$ may represent ethyl or propyl substituted with 1-piperazinyl. In one embodiment when $R^3$ represents $C_{1-6}$alkyl substituted with $R^9$, $R^9$ represents a saturated 6 membered monocyclic heterocyclyl containing two nitrogen heteroatoms, for example piperazinyl, and the heterocyclyl is substituted. For example the heterocyclyl is substituted with:
a) one $C_{1-4}$alkyl-C(=O)—, for example $CH_3$—C(=O)—. $R^3$ may represent ethyl substituted with 1-piperazinyl substituted in the 4 position by $CH_3$—C(=O)—;
b) one hydroxy$C_{1-4}$alkyl, for example —$CH_2CH_2OH$. $R^3$ may represent ethyl substituted with 1-piperazinyl substituted in the 4 position by —$CH_2CH_2OH$;
c) one or two $C_{1-4}$alkyl, for example —$CH_3$. $R^3$ may represent ethyl or propyl substituted with 1-piperazinyl substituted at the 3 and 5 positions by —$CH_3$ or 1-piperazinyl substituted at the 4 position by —$CH_3$;
d) one =O. $R^3$ may represent ethyl substituted with 1-piperazinyl substituted in the 3 position by =O; or
e) one —C(=O)—$R^{13}$. $R^{13}$ may be $C_{3-8}$cycloalkyl, for example cyclopropyl. $R^3$ may represent ethyl substituted with 1-piperazinyl substituted in the 4 position by —C(=O)—$C_3H_5$.

In one embodiment when $R^3$ represents $C_{1-6}$alkyl substituted with $R^9$, $R^9$ represents a saturated 6 membered monocyclic heterocyclyl containing two nitrogen heteroatoms, for example piperazinyl, and the heterocyclyl is substituted. For example the heterocyclyl is substituted with two phenyl$C_{1-6}$alkyl groups wherein the phenyl is substituted with $R^{16}$. $R^{16}$ may represent $C_{1-4}$alkoxy, for example $CH_3O$—. $R^3$ may represent methyl substituted with 2-piperazinyl substituted in the 1 and 4 position by methylphenyl wherein the phenyl is substituted in the 4 position by $CH_3O$—.

In another embodiment when $R^3$ represents $C_{1-6}$alkyl substituted with $R^9$, $R^9$ represents an aromatic 5 membered monocyclic heterocyclyl containing four nitrogen heteroatoms, for example tetrazolyl. $R^3$ may represent ethyl substituted with 5-tetrazolyl.

In another embodiment when $R^3$ represents $C_{1-6}$alkyl substituted with $R^9$, $R^9$ represents an aromatic 5 membered monocyclic heterocyclyl containing one oxygen and two nitrogen heteroatoms, for example 1,3,4-oxadiazolyl. The heterocyclyl may be substituted. For example the heterocyclyl may be substituted with one —$NR^{14}R^{15}$ group, where each of $R^{14}$ and $R^{15}$ is hydrogen. Alternatively one of $R^{14}$ and $R^{15}$ may be hydrogen and the other may represent $C_{1-4}$alkyl optionally substituted with hydroxyl, for example —$CH_2CH_2OH$. $R^3$ may represent methyl substituted with 2-(1,3,4-oxadiazolyl) substituted at the 5 position by —$NH_2$ or 2-(1,3,4-oxadiazolyl) substituted at the 5 position by —NH—$CH_2CH_2OH$.

In another embodiment when $R^3$ represents $C_{1-6}$alkyl substituted with $R^9$, $R^9$ represents an optionally substituted aromatic 5 membered monocyclic heterocyclyl containing two nitrogen heteroatoms, for example pyrazolyl or imidazolyl. $R^3$ may represent methyl, ethyl or propyl substituted with 1-pyrazolyl or 2-imidazoyl. $R^3$ may represent methyl substituted with 3-pyrazolyl or 5-pyrazolyl. The heterocyclyl may be substituted. For example the heterocyclyl may be substituted with one or two $C_{1-4}$alkyl, for example —$CH_3$ or —$CH_2CH_3$. $R^3$ may represent methyl, ethyl or propyl substituted with 1-imidazolyl substituted at the 2 position by —$CH_3$, 3-pyrazolyl substituted at the 1 and 5 positions by —$CH_3$, 1-imidazolyl substituted at the 2 and 5 positions by —CH₃, 1-imidazolyl substituted at the 2 and 4 positions by —CH₃, 2-imidazolyl substituted at the 1 position by —CH₃ or 2-imidazolyl substituted at the 1 position by —CH₂CH₃. $R^3$ may represent methyl substituted with 2-imidazolyl substituted at the 5 position by —CH₃. $R^3$ may represent ethyl substituted with 1-pyrazolyl substituted at the 3 position by —CH₃. $R^3$ may represent methyl substituted with 4-pyrazolyl substituted at the 1 position by —CH₃. In one embodiment when $R^3$ represents $C_{1-6}$alkyl substituted with $R^9$, $R^9$ represents an optionally substituted aromatic 5 membered monocyclic heterocyclyl containing two nitrogen heteroatoms, for example imidazolyl. The heterocyclyl may be substituted. For example the heterocyclyl is substituted with one $C_{1-4}$alkyl, for example —CH₃, and with one —S(=O)₂—NR¹⁴R¹⁵. $R^{14}$ and $R^{15}$ may each represent $C_{1-4}$alkyl, for example —CH₃. $R^3$ may represent methyl substituted with 2-imidazolyl substituted in the 3 position by —S(=O)₂—N(CH₃)₂ and in the 5 position by —CH₃.

In one embodiment when $R^3$ represents $C_{1-6}$alkyl substituted with $R^9$, $R^9$ represents an optionally substituted aromatic 5 membered monocyclic heterocyclyl containing two nitrogen heteroatoms, for example pyrazolyl. The heterocyclyl may be substituted. For example the heterocyclyl is substituted with $R^{13}$. $R^{13}$ may represent a saturated 6 membered monocyclic heterocyclyl containing one oxygen heteroatom. $R^3$ may represent methyl substituted with 5-pyrazolyl substituted in the 2 position by 2-tetrahydropyran. $R^3$ may represent methyl substituted with 3-pyrazolyl substituted in the 1 position by 2-tetrahydropyran.

In one embodiment when $R^3$ represents $C_{1-6}$alkyl substituted with $R^9$, $R^9$ represents an optionally substituted aromatic 5 membered monocyclic heterocyclyl containing two nitrogen heteroatoms, for example imidazolyl. The heterocyclyl may be substituted. For example the heterocyclyl is substituted with —S(=O)₂—NR¹⁴R¹⁵. $R^{14}$ and $R^{15}$ may each represent $C_{1-4}$alkyl optionally substituted with a substituent selected from hydroxyl, $C_{1-4}$alkoxy, amino or mono- or di($C_{1-4}$alkyl)amino, for example —CH₃. $R^3$ may represent methyl substituted with 2-imidazoyl substituted in the 1 position by —S(=O)₂—N(CH₃)₂.

In another embodiment when $R^3$ represents $C_{1-6}$alkyl substituted with $R^9$, $R^9$ represents an optionally substituted aromatic 5 membered monocyclic heterocyclyl containing three nitrogen heteroatoms, for example triazolyl. $R^3$ may represent methyl substituted with 4-(1,2,3-triazolyl. The heterocyclyl may be substituted. For example the heterocyclyl is substituted with
a) one hydroxy$C_{1-4}$alkyl group, for example —CH₂CH₂OH. $R^3$ may represent methyl substituted with 4-(1,2,3-triazolyl) substituted in the 1 position by —CH₂CH₂OH or 4-(1,2,3-triazolyl) substituted in the 2 position by —CH₂OH; or
b) one $C_{1-4}$alkyl substituted with $C_{1-6}$alkyl-O—C(=O)— group, for example —CH₂—C(=O)—OCH₂CH₃. $R^3$ may represent methyl substituted with 4-(1,2,3-triazolyl) substituted in the 1 position by —CH₂—C(=O)—OCH₂CH₃.

In another embodiment when $R^3$ represents $C_{1-6}$alkyl substituted with $R^9$, $R^9$ represents an optionally substituted aromatic 5 membered monocyclic heterocyclyl containing three nitrogen heteroatoms, for example triazolyl. $R^3$ may represent ethyl substituted with 1-(1,2,4-triazolyl. The heterocyclyl may be substituted. For example the heterocyclyl is substituted with one $C_{1-4}$alkyl group, for example —CH₃. $R^3$ may represent ethyl or propyl substituted with 1-(1,2,4-triazolyl) substituted in the 3 position by —CH₃. $R^3$ may represent ethyl or propyl substituted with 2-(1,2,4-triazolyl) substituted in the 3 position by —CH₃.

In another embodiment when $R^3$ represents $C_{1-6}$alkyl substituted with $R^9$, $R^9$ represents a saturated 5 membered monocyclic heterocyclyl containing one nitrogen and one oxygen heteroatom, for example oxazolidinyl. The heterocyclyl may be substituted, for example substituted with one =O. $R^3$ may represent ethyl or propyl substituted with 3-oxazolidinyl substituted in the 2 position by =O. $R^3$ may represent methyl substituted with 5-oxazolidinyl substituted in the 2 position by =O. The heterocyclyl may be substituted, for example substituted with one =O and one $C_{1-6}$alkyl. $R^3$ may represent methyl substituted with 5-oxazolidinyl substituted in the 2 position by =O and in the 3 position by —CH(CH₃)₂.

In another embodiment when $R^3$ represents $C_{1-6}$alkyl substituted with $R^9$, $R^9$ represents a saturated 6 membered monocyclic heterocyclyl containing one nitrogen and one sulphur heteroatom, for example thiomorpholinyl. The heterocyclyl may be substituted, for example substituted with two =O groups on the sulphur heteroatom. $R^3$ may represent propyl substituted with 4-thiomorpholinyl substituted in the 1 position by two =O groups.

In another embodiment when $R^3$ represents $C_{1-6}$alkyl substituted with $R^9$, $R^9$ represents a saturated 7 membered monocyclic heterocyclyl containing two nitrogen heteroatoms, for example homopiperazinyl. $R^3$ may represent ethyl substituted with 1-homopiperazinyl.

In another embodiment when $R^3$ represents $C_{1-6}$alkyl substituted with $R^9$, $R^9$ represents a saturated 7 membered monocyclic heterocyclyl containing one nitrogen and one oxygen heteroatom, for example homomorpholinyl. $R^3$ may represent ethyl substituted with homomorpholinyl.

In another embodiment when $R^3$ represents $C_{1-6}$alkyl substituted with $R^9$, $R^9$ represents phenyl or naphthyl, in particular phenyl. $R^3$ may represent —CH₂—C₆H₅. When $R^9$ represents phenyl or naphthyl, in particular phenyl, the phenyl or naphthyl group may be substituted, for example by one chlorine. $R^3$ may represent methyl substituted with phenyl substituted in the 2, 3 or 4 position by chlorine.

In one embodiment $R^3$ represents cyano$C_{1-6}$alkyl, for example —CH₂CH₂CN or —CH₂CH₂CH₂CN.

In one embodiment $R^3$ represents $C_{1-6}$alkyl substituted with hydroxyl, halo or —NR¹⁰R¹¹. In a further embodiment $R^3$ represents $C_{1-6}$alkyl substituted with hydroxyl or —NR¹⁰R¹¹. In a yet further embodiment $R^3$ represents $C_{1-6}$alkyl substituted with —NR¹⁰R¹¹.

In one embodiment $R^3$ represents $C_{1-6}$alkyl substituted with hydroxyl, halo or —NR¹⁰R¹¹, wherein the $C_{1-6}$alkyl group is a straight chain alkyl group e.g. 2-ethyl, n-propyl, n-butyl. In one embodiment $R^3$ represents $C_{1-4}$alkyl substituted with —NR¹⁰R¹¹. In one embodiment $R^3$ represents $C_{1-4}$alkyl substituted —NR¹⁰R¹¹, wherein the $C_{1-4}$alkyl group is a straight chain alkyl group e.g. 2-ethyl, n-propyl, n-butyl. In one embodiment $R^3$ represents $C_{1-4}$alkyl substituted with —NR¹⁰R¹¹, wherein the $C_{1-4}$alkyl group is an ethyl group (—CH₂CH₂—).

In one embodiment when $R^3$ represents $C_{1-6}$alkyl substituted with —NR¹⁰R¹¹, $R^{10}$ and $R^{11}$ have the following meanings:
a) each of $R^{10}$ and $R^{11}$ represent hydrogen. $R^3$ may represent —CH₂CH₂NH₂, —CH₂CH₂CH₂NH₂ or —CH₂CH₂CH₂CH₂NH₂. $R^3$ may represent —CH₂CH(CH₃)NH₂, —CH(CH₃)CH₂NH₂;
b) one of $R^{10}$ and $R^{11}$ represents hydrogen and the other represents $C_{1-6}$alkyl, for example —CH₃, —CH₂CH₃ or —CH(CH₃)₂. $R^3$ may represent —CH₂CH₂NHCH₃, —CH₂CH₂CH₂NHCH₃, —CH₂CH₂NHCH₂CH₃, —CH$_2$CH$_2$NHCH(CH$_3$)$_2$, —CD$_2$-CD$_2$-NHCH(CH$_3$)$_2$ or —CH$_2$CH$_2$CH$_2$NHCH(CH$_3$)$_2$. R$^3$ may represent —CH(CH$_3$)CH$_2$NHCH(CH$_3$)$_2$;

c) each of R$^{10}$ and R$^{11}$ independently represent C$_{1-6}$alkyl, for example —CH$_2$CH$_3$ or —CH(CH$_3$)$_2$. R$^3$ may represent —CH$_2$CH$_2$N(CH$_2$CH$_3$)$_2$, —CH$_2$CH$_2$N(CH$_2$CH$_3$)(CH(CH$_3$)$_2$). Each of R$^{10}$ and R$^{11}$ may independently represent C$_{1-6}$alkyl, for example —CH$_3$. R$^3$ may represent —CH$_2$CH$_2$N(CH$_3$)$_2$ or —CH$_2$CH$_2$N(CH$_3$)CH(CH$_3$)$_2$;

d) one of R$^{10}$ and R$^{11}$ represents hydrogen and the other represents haloC$_{1-6}$alkyl, for example —CH$_2$CF$_3$, —CH$_2$CHF$_2$ or —CH$_2$CH$_2$F. R$^3$ may represent —CH$_2$CH$_2$CH$_2$NHCH$_2$CF$_3$, —CH$_2$CH$_2$NHCH$_2$CHF$_2$ or —CH$_2$CH$_2$NHCH$_2$CH$_2$F. HaloC$_{1-6}$alkyl may be —C(CH$_3$)$_2$CH$_2$F. R$^3$ may represent —CH(CH$_3$)CH$_2$NHCH$_2$CF$_3$, —CH$_2$CH(CH$_3$)NHCH$_2$CF$_3$, —CH$_2$CH$_2$NHCH$_2$CF$_3$, —CH$_2$CH$_2$CH$_2$NHCH$_2$CHF$_2$—CH$_2$CH$_2$NHCH$_2$CH$_2$CF$_3$, —CH$_2$CH$_2$CH$_2$NHCH$_2$CHF$_2$, —CH$_2$CH$_2$CH$_2$NHC(CH$_3$)$_2$CH$_2$F, —CD$_2$-CD$_2$-CD$_2$-NHCH$_2$CF$_3$;

e) one of R$^{10}$ and R$^{11}$ represents hydrogen and the other represents —C(=O)—C$_{1-6}$alkyl, for example —C(=O)-Me. R$^3$ may represent —CH$_2$CH$_2$NH—C(=O)—CH$_3$;

f) one of R$^{10}$ and R$^{11}$ represents hydrogen and the other represents —S(=O)$_2$—C$_{1-6}$alkyl, for example —S(=O)$_2$—CH$_3$, —S(=O)$_2$—CH$_2$CH$_3$ or —S(=O)$_2$—CH(CH$_3$)$_2$. R$^3$ may represent —CH$_2$CH$_2$NH—S(=O)$_2$—CH$_3$, —CH$_2$CH$_2$CH$_2$NH—S(=O)$_2$—CH$_3$, —CH$_2$CH$_2$NH—S(=O)$_2$—CH$_2$CH$_3$ or —CH$_2$CH$_2$NH—S(=O)$_2$—CH(CH$_3$)$_2$;

g) one of R$^{10}$ and R$^{11}$ represents hydrogen and the other represents —S(=O)$_2$—NR$^{14}$R$^{15}$, where R$^{14}$ and R$^{15}$ each represent C$_{1-4}$alkyl optionally substituted with hydroxyl, for example —CH$_3$. R$^3$ may represent —CH$_2$CH$_2$NH—S(=O)$_2$—N(CH$_3$)$_2$ or —CH$_2$CH$_2$CH$_2$NH—S(=O)$_2$—N(CH$_3$)$_2$;

h) one of R$^{10}$ and R$^{11}$ represents hydrogen and the other represents hydroxyC$_{1-6}$alkyl, for example —CH$_2$CH$_2$OH. R$^3$ may represent —CH$_2$CH$_2$NHCH$_2$CH$_2$OH;

i) one of R$^{10}$ and R$^{11}$ represents hydrogen and the other represents —C(=O)-hydroxyhaloC$_{1-6}$alkyl, for example —C(=O)—C(OH)(CH$_3$)CF$_3$. R$^3$ may represent —CH$_2$CH$_2$CH$_2$NH—C(=O)—C(OH)(CH$_3$)CF$_3$ or —CH$_2$CH$_2$NH—C(=O)—C(OH)(CH$_3$)CF$_3$;

j) one of R$^{10}$ and R$^{11}$ represents hydrogen and the other represents —C(=O)—R$^6$. R$^6$ may represent C$_{3-8}$cycloalkyl, for example cyclopropyl. R$^3$ may represent —CH$_2$CH$_2$NH—C(=O)—C$_3$H$_5$. Alternatively, R$^6$ may represent a saturated 6-membered monocyclic heterocyclyl containing one nitrogen heteroatom, for example piperidinyl. The heterocyclyl may be substituted, for example substituted by one C$_{1-6}$alkyl group, for example —CH$_3$ to form N-methyl piperidinyl. R$^3$ may represent —CH$_2$CH$_2$NH—C(=O)-(piperidin-3-yl) where the piperidinyl is substituted at the 1 position by —CH$_3$;

k) one of R$^{10}$ and R$^{11}$ represents hydrogen and the other represents cyanoC$_{1-6}$alkyl, for example —CH$_2$CH$_2$CN. R$^3$ may represent —CH$_2$CH$_2$NHCH$_2$CH$_2$CN R$^3$ may represent —CH$_2$CH$_2$CH$_2$NHCH$_2$CH$_2$CN;

l) one of R$^{10}$ and R$^{11}$ represents hydrogen and the other represents R$^6$. R$^6$ may represent C$_{3-8}$cycloalkyl, for example cyclopropyl or cyclopentyl, or R$^6$ may represent a saturated 6-membered monocyclic heterocyclyl containing one nitrogen heteroatom, for example piperidinyl. The heterocyclyl may be substituted, for example substituted with four C$_{1-6}$alkyl groups, for example —CH$_3$ to form for example 2,2,6,6-tetramethyl-piperidinyl. R$^3$ may represent —CH$_2$CH$_2$NHC$_3$H$_5$, —CH$_2$CH$_2$NHC$_5$H$_9$ or —CH$_2$CH$_2$NH-(2,2,6,6-tetramethyl-piperidin-4-yl). For example, the heterocyclyl may be substituted by one —S(=O)$_2$NR$^{14}$R$^{15}$, for example —S(=O)$_2$NH$_2$. R$^3$ may represent —CH$_2$CH$_2$NH-(piperidin-4-yl) where the piperidinyl is substituted in the 1 position by —S(=O)$_2$NH$_2$;

m) one of R$^{10}$ and R$^{11}$ represents hydrogen and the other represents C$_{1-6}$alkyl substituted with R$^6$. R$^6$ may represent C$_{3-8}$cycloalkyl, for example cyclopropyl. R$^3$ may represent —CH$_2$CH$_2$NHCH$_2$C$_3$H$_5$. Alternatively R$^6$ may represent a saturated, 5-membered monocyclic heterocyclyl containing one oxygen heteroatom. R$^3$ may represent —CH$_2$CH$_2$NHCH$_2$— (tetrahydrofuran-2-yl). Alternatively R$^6$ may represent an aromatic, 6-membered monocyclic heterocyclyl containing one nitrogen heteroatom. R$^3$ may represent —CH$_2$CH$_2$NHCH$_2$— (pyridin-6-yl);

n) one of R$^{10}$ and R$^{11}$ represents hydrogen and the other represents —C(=O)-haloC$_{1-6}$alkyl, for example —C(=O)—CF$_3$. R$^3$ may represent —CH$_2$CH$_2$NHC(=O)—CF$_3$ or —CH$_2$CH$_2$CH$_2$NHC(=O)—CF$_3$;

o) one of R$^{10}$ and R$^{11}$ represents hydrogen and the other represents C$_{1-6}$alkyl substituted with —Si(CH$_3$)$_3$. R$^3$ may represent —CH$_2$CH$_2$NHCH$_2$Si(CH$_3$)$_3$; or p) one of R$^{10}$ and R$^{11}$ represents hydrogen and the other represents C$_{1-6}$alkyl substituted with R$^6$. R$^6$ may represent phenyl. R$^6$ may represent phenyl substituted with —NR$^{14}$R$^{15}$ where R$^{14}$ and R$^{15}$ each represent hydrogen. In one embodiment one of R$^{10}$ and R$^{11}$ represents —CH$_3$ and the other represents —CH$_2$—C$_6$H$_5$. R$^3$ may represent —CH$_2$CH$_2$N(CH$_3$)CH$_2$—C$_6$H$_5$. In one embodiment one of R$^{10}$ and R$^{11}$ represents —CH(CH$_3$)$_2$ and the other represents —CH$_2$—C$_6$H$_5$ wherein the phenyl is substituted in the 4-position by —NH$_2$.

In one embodiment when R$^3$ represents C$_{1-6}$alkyl substituted with —NR$^{10}$R$^{11}$, R$^{10}$ and R$^{11}$ have the following meanings:

a) one of R$^{10}$ and R$^{11}$ represents C$_{1-6}$alkyl, for example —CH(CH$_3$)$_2$ and the other represents C$_{1-6}$alkyl substituted with —NR$^{14}$R$^{15}$ where R$^{14}$ and R$^{15}$ each represent hydrogen. R$^3$ may represent —CH$_2$CH$_2$N(CH(CH$_3$)$_2$)CH$_2$CH$_2$CH$_2$NH$_2$;

b) one of R$^{10}$ and R$^{11}$ represents hydrogen and the other represents C$_{1-6}$alkyl substituted with —C(=O)—NR$^{14}$R$^{15}$ where R$^{14}$ and R$^{15}$ each represent hydrogen. R$^3$ may represent —CH$_2$CH$_2$NHCH$_2$C(=O)NH$_2$ or —CH$_2$CH$_2$NHCH$_2$C(=O)NH$_2$;

c) one of R$^{10}$ and R$^{11}$ represents C$_{1-6}$alkyl, for example —CH$_3$ and the other represents C$_{1-6}$alkoxy, for example —OCH$_3$. R$^3$ may represent —CH$_2$CH$_2$CH$_2$N(CH$_3$)—OCH$_3$.

d) one of R$^{10}$ and R$^{11}$ represents hydrogen and the other represents C$_{1-6}$alkoxy, for example —OCH$_3$. R$^3$ may represent —CH$_2$CH$_2$NH—OCH$_3$; or e) one of R$^{10}$ and R$^{11}$ represents hydrogen and the other represents hydroxyhaloC$_{1-6}$alkyl, for example —CH$_2$CHOHCF$_3$. R$^3$ may represent —CH$_2$CH$_2$NHCH$_2$CHOHCF$_3$.

f) one of R$^{10}$ and R$^{11}$ represents hydrogen and the other represents carboxyl (i.e. —C(=O)—OH); R$^3$ may represent —CH$_2$CH$_2$CH$_2$NHCOOH.

In one embodiment R$^{10}$ represents hydrogen or C$_{1-6}$alkyl, for example hydrogen, —CH$_3$, —CH$_2$CH$_3$ or —CH(CH$_3$)$_2$. In one embodiment R$^{10}$ is hydrogen.

In one embodiment R$^{11}$ represents hydrogen, C$_{1-6}$alkyl, haloC$_{1-6}$alkyl, —C(=O)—C$_{1-6}$alkyl, —S(=O)$_2$—C$_{1-6}$alkyl, —S(=O)$_2$—NR$^{14}$R$^{15}$, hydroxyC$_{1-6}$alkyl, —C(=O)-hydroxyhaloC$_{1-6}$alkyl, —C(=O)—R$^6$, cyanoC$_{1-6}$alkyl, R$^6$, —C(=O)—$R^6$, $C_{1-6}$alkyl substituted with $R^6$, —C(=O)-halo$C_{1-6}$alkyl, $C_{1-6}$alkyl substituted with —Si(CH$_3$)$_3$.

In one embodiment $R^{11}$ represents hydrogen, —CH$_3$, —CH$_2$CH$_3$ or —CH(CH$_3$)$_2$, —CH$_2$CF$_3$, —CH$_2$CHF$_2$ or —CH$_2$CH$_2$F, —C(=O)—CH$_3$, —S(=O)$_2$—CH$_3$, —S(=O)$_2$—CH$_2$CH$_3$, —S(=O)$_2$—CH(CH$_3$)$_2$, —S(=O)$_2$—N(CH$_3$)$_2$, —CH$_2$CH$_2$OH, —C(=O)—C(OH)(CH$_3$)CF$_3$, —C(=O)— cyclopropyl, —CH$_2$CH$_2$CN, cyclopropyl, cyclopentyl, 2,2,6,6-tetramethyl-piperidinyl, —CH$_2$C$_3$H$_5$, —CH$_2$-tetrahydrofuranyl, —C(=O)-(1-methyl-piperidin-3-yl), —C(=O)—CF$_3$, —CH$_2$Si(CH$_3$)$_3$, —CH$_2$—C$_6$H$_5$.

In one embodiment $R^3$ represents —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$NHCH$_3$, —CH$_2$CH$_2$CH$_2$NHCH$_3$, —CH$_2$CH$_2$NHCH$_2$CH$_3$, —CH$_2$CH$_2$NHCH(CH$_3$)$_2$, —CH$_2$CH$_2$CH$_2$NHCH(CH$_3$)$_2$, —CH$_2$CH$_2$N(CH$_2$CH$_3$)$_2$, —CH$_2$CH$_2$N(CH$_2$CH$_3$)(CH(CH$_3$)$_2$), —CH$_2$CH$_2$CH$_2$NHCH$_2$CF$_3$, —CH$_2$CH$_2$NHCH$_2$CHF$_2$ or —CH$_2$CH$_2$NHCH$_2$CH$_2$F, —CH$_2$CH$_2$NH—C(=O)—CH$_3$, —CH$_2$CH$_2$NH—S(=O)$_2$—CH$_3$, —CH$_2$CH$_2$CH$_2$NH—S(=O)$_2$—CH$_3$, —CH$_2$CH$_2$NH—S(=O)$_2$—CH$_2$CH$_3$, —CH$_2$CH$_2$NH—S(=O)$_2$—CH(CH$_3$)$_2$, —CH$_2$CH$_2$NH—S(=O)$_2$—N(CH$_3$)$_2$, —CH$_2$CH$_2$CH$_2$NH—S(=O)$_2$—N(CH$_3$)$_2$, —CH$_2$CH$_2$NHCH$_2$CH$_2$OH, —CH$_2$CH$_2$NH—C(=O)—C(OH)(CH$_3$)CF$_3$, —CH$_2$CH$_2$NH—C(=O)—C(OH)(CH$_3$)CF$_3$, —CH$_2$CH$_2$NH—C(=O)—C$_3$H$_5$, —CH$_2$CH$_2$NHCH$_2$CN, CH$_2$CH$_2$NHC$_3$H$_5$, —CH$_2$CH$_2$NHC$_5$H$_9$, —CH$_2$CH$_2$—NHCO-(piperidin-3-yl) where the piperidin-3-yl) is substituted in the 1 position by —OCH$_3$, —CH$_2$CH$_2$NHCH$_2$C$_3$H$_5$, —CH$_2$CH$_2$NHCH$_2$(tetrahydrofuran-2-yl), —CH$_2$CH$_2$NHC(=O)—CF$_3$, —CH$_2$CH$_2$CH$_2$NHC(=O)—CF$_3$, —CH$_2$CH$_2$NH-(2,2,6,6-tetramethyl-piperidin-4-yl), —CH$_2$CH$_2$NHCH$_2$Si(CH$_3$)$_3$, —CH$_2$CH$_2$N(CH$_3$)CH$_2$—C$_6$H$_5$.

In one embodiment $R^3$ represents $C_{1-6}$alkyl substituted with hydroxyl and —NR$^{10}$R$^{11}$.

In one embodiment when $R^3$ represents $C_{1-6}$alkyl substituted with hydroxyl and —NR$^{10}$R$^{11}$ each of $R^{10}$ and $R^{11}$ represents hydrogen. $R^3$ may represent —CH$_2$CHOHCH$_2$NH$_2$.

In one embodiment when $R^3$ represents $C_{1-6}$alkyl substituted with hydroxyl and —NR$^{10}$R$^{11}$ one of $R^{10}$ and $R^{11}$ represents hydrogen and the other represents $C_{1-6}$alkyl, for example —CH$_3$, —CH(CH$_3$)$_2$. $R^3$ may represent —CH$_2$CHOHCH$_2$NHCH$_3$ or —CH$_2$CHOHCH$_2$NHCH(CH$_3$)$_2$.

In one embodiment when $R^3$ represents $C_{1-6}$alkyl substituted with hydroxyl and —NR$^{10}$R$^{11}$, one of $R^{10}$ and $R^{11}$ represents hydrogen and the other represents halo$C_{1-6}$alkyl, for example —CH$_2$CF$_3$. $R^3$ may represent —CH$_2$CHOHCH$_2$NHCH$_2$CF$_3$.

In one embodiment when $R^3$ represents $C_{1-6}$alkyl substituted with hydroxyl and —NR$^{10}$R$^{11}$ one of $R^{10}$ and $R^{11}$ represents $C_{1-6}$alkyl, for example —CH(CH$_3$)$_2$, and the other represents —C(=O)-halo$C_{1-6}$alkyl, for example —C(=O)—CH$_2$Cl. $R^3$ may represent —CH$_2$CHOHCH$_2$N(CH(CH$_3$)$_2$)—C(=O)CH$_2$Cl.

In one embodiment $R^3$ represents hydroxy$C_{1-6}$alkyl, wherein hydroxy$C_{1-6}$alkyl includes —CD$_2$CD$_2$OH, —CH$_2$CH$_2$CH$_2$OH, —CD$_2$CD$_2$CD$_2$OH, —CH$_2$CHOHCH$_3$, —CH$_2$CHOHCH$_2$CH$_3$, —CH$_2$CHOHCH(CH$_3$)$_2$, —CH$_2$CH$_2$C(OH)(CH$_3$)$_2$, —CH$_2$CHOHCH$_2$OH or —CH$_2$C(CH$_3$)$_2$OH.

In one embodiment $R^3$ represents $C_{1-6}$alkyl substituted with one or two halo atoms and —NR$^{10}$R$^{11}$. In one embodiment each of $R^{10}$ and $R^{11}$ represents hydrogen. $R^3$ may represent —CH$_2$CHFCH$_2$NH$_2$.

In one embodiment $R^3$ represents $C_{1-6}$alkyl substituted with —C(=O)—O—$C_{1-6}$alkyl. $R^3$ may represent —CH$_2$C(=O)—O—CH$_2$CH$_3$ or —CH$_2$CH$_2$—C(=O)—O—CH$_2$CH$_3$ $R^3$ may represent —CH(CH$_3$)C(=O)—O—CH$_2$CH$_3$.

In one embodiment $R^3$ represents $C_{1-6}$alkyl (for example methyl) substituted with $C_{1-6}$alkoxy$C_{1-6}$alkyl-C(=O)—. $R^3$ may represents-CH$_2$—C(=O)—CH$_2$OCH$_3$.

In one embodiment $R^3$ represents $C_{1-6}$alkyl substituted with —C(=O)—NR$^{10}$R$^{11}$.

In one embodiment when $R^3$ represents $C_{1-6}$alkyl substituted with —C(=O)—NR$^{14}$R$^{15}$, the $C_{1-6}$alkyl group is a straight chain alkyl group e.g. n-ethyl, n-propyl, n-butyl. In one embodiment $R^3$ represents $C_{1-4}$alkyl substituted with —C(=O)—NR$^{14}$R$^{15}$. In one embodiment when $R^3$ represents $C_{1-4}$alkyl substituted with —C(=O)—NR$^{14}$R$^{15}$, the $C_{1-4}$alkyl group is a straight chain alkyl group e.g. n-ethyl, n-propyl, n-butyl. In one embodiment when $R^3$ represents $C_{1-6}$alkyl substituted with —C(=O)—NR$^{14}$R$^{15}$, the $C_{1-6}$alkyl group is an ethyl group (—CH$_2$CH$_2$—).

In one embodiment when $R^3$ represents $C_{1-6}$alkyl substituted with —C(=O)—NR$^{10}$R$^{11}$, $R^{10}$ and $R^{11}$ have the following meanings:

a) $R^{10}$ and $R^{11}$ each represent hydrogen. $R^3$ may represent —CH$_2$C(=O)NH$_2$;

b) one of $R^{10}$ and $R^{11}$ represents hydrogen and the other represents $C_{1-6}$alkyl, e.g. —CH$_3$. $R^3$ may represent —CH$_2$C(=O)NHCH$_3$; $C_{1-6}$alkyl may be —CH(CH$_3$)$_2$. $R^3$ may represent —CH$_2$C(=O)NHCH(CH$_3$)$_2$ or —CH$_2$CH$_2$C(=O)NHCH(CH$_3$)$_2$;

c) one of $R^{10}$ and $R^{11}$ represents hydrogen and the other represents $C_{1-6}$alkoxy$C_{1-6}$alkyl wherein each $C_{1-6}$alkyl may optionally be substituted with one or two hydroxyl groups, for example —CH$_2$CH$_2$OCH$_3$. $R^3$ may represent —CH$_2$C(=O)—NHCH$_2$CH$_2$OCH$_3$;

d) one of $R^{10}$ and $R^{11}$ represents hydrogen and the other represents $C_{1-6}$alkyl substituted with $R^6$. $R^6$ may be a saturated 5-membered monocyclic heterocycle containing one nitrogen heteroatom, for example pyrrolidinyl. Alternatively $R^6$ may be an aromatic 5-membered monocyclic heterocycle containing two nitrogen heteroatoms, for example imidazolyl. $R^3$ may represent —CH$_2$C(=O)—NH—CH$_2$CH$_2$—(pyrrolidin-1-yl) or —CH$_2$C(=O)—NH—CH$_2$CH$_2$—(imidazol-2-yl);

e) one of $R^{10}$ and $R^{11}$ represents hydrogen and the other represents hydroxy$C_{1-6}$alkyl, for example —CH$_2$CH$_2$OH. $R^3$ may represent —CH$_2$C(=O)—NHCH$_2$CH$_2$OH; or f) one of $R^{10}$ and $R^{11}$ represents hydrogen and the other represents $C_{1-6}$alkyl substituted with —NR$^{14}$R$^{15}$ where $R^{14}$ and $R^{15}$ are both hydrogen. $R^3$ may represents —CH$_2$C(=O)—NHCH$_2$CH$_2$NH$_2$.

In one embodiment when $R^3$ represents $C_{1-6}$alkyl substituted with —C(=O)—NR$^{10}$R$^{11}$, $R^{10}$ and $R^{11}$ have the following meanings:

a) one of $R^{10}$ and $R^{11}$ represents hydrogen and the other represents halo$C_{1-6}$alkyl, for example —CH$_2$CF$_3$. $R^3$ may represent —CH$_2$CH$_2$C(=O)—NHCH$_2$CF$_3$;

b) one of $R^{10}$ and $R^{11}$ represents $C_{1-6}$alkyl, for example —CH$_3$ and the other represents $C_{1-6}$alkoxy, for example —OCH$_3$. $R^3$ may represent —CH$_2$CH$_2$C(=O)N(CH$_3$)—OCH$_3$.

c) one of $R^{10}$ and $R^{11}$ represents hydrogen and the other represents $R^6$. $R^6$ may be a six membered monocyclic heterocyclyl containing one or two nitrogen atoms and optionally substituted with one $C_{1-6}$alkyl or $C_{1-6}$alkoxy. $R^3$ may represent —CH$_2$C(=O)NH-(pyridin-2-yl) wherein the pyridin-2-Y1 is substituted in the 3-position by —OCH$_3$, —CH$_2$C(=O)NH— (pyridin-6-Y1) wherein the pyridin-6-Y1 is substituted in the 4-position by —CH$_3$ or —CH$_2$C(=O)NH-(pyrimidin-2-yl) wherein the pyrimidin-2-yl) is substituted in the 4-position by —OCH$_3$. R$^3$ may represent —CH$_2$C(=O)NH-(pyridin-3-yl), —CH$_2$C(=O)NH-(pyridin-6-yl) or —CH$_2$C(=O)NH-(pyridin-4-yl).

In one embodiment R$^3$ represents C$_{1-6}$alkyl substituted with carboxyl. R$^3$ may represent —CH$_2$C(=O)OH or —CH$_2$CH$_2$C(=O)OH.

In one embodiment R$^3$ represents C$_{1-6}$alkyl substituted with —O—C(=O)—NR$^{10}$R$^{11}$. In one embodiment one of R$^{10}$ and R$^{11}$ represents hydrogen and the other represents C$_{1-6}$alkyl, for example —CH$_3$. R$^3$ may represent —CH$_2$CH$_2$—O—C(=O)—NHCH$_3$.

In one embodiment R$^3$ represents C$_{1-6}$alkyl substituted with —NR$^{12}$—S(=O)$_2$—C$_{1-6}$alkyl. In one embodiment R$^{12}$ represents hydrogen. R$^3$ may represent —CH$_2$CH$_2$NH—S(=O)$_2$—CH$_3$, —CH$_2$CH$_2$CH$_2$NH—S(=O)$_2$—CH$_3$, —CH$_2$CH$_2$NH—S(=O)$_2$—CH(CH$_3$)$_2$ or —CH$_2$CH$_2$NH—S(=O)$_2$—CH$_2$CH$_3$.

In one embodiment R$^3$ represents C$_{1-6}$alkyl substituted with —NR$^{12}$—S(=O)$_2$—NR$^{14}$R$^{15}$. In one embodiment R$^{12}$ represents hydrogen and R$^{14}$ and R$^{15}$ each represent —CH$_3$. R$^3$ may represent —CH$_2$CH$_2$NH—S(=O)$_2$—N(CH$_3$)$_2$ or —CH$_2$CH$_2$CH$_2$NH—S(=O)$_2$—N(CH$_3$)$_2$.

In one embodiment R$^3$ represents C$_{1-6}$alkyl substituted with R$^9$ and optionally substituted with —O—C(=O)—C$_{1-6}$alkyl.

In one embodiment when R$^3$ represents C$_{1-6}$alkyl substituted with R$^9$ and optionally substituted with —O—C(=O)—C$_{1-6}$alkyl, R$^9$ represents 5-membered unsaturated ring fused to a 6-membered unsaturated ring, for example a furan ring fused to a pyridine ring, or a pyrrole ring fused to a pyridine ring, wherein the pyrrole ring is optionally substituted with one C$_{1-4}$alkyl, for example —CH$_3$. In one embodiment R$^9$ represents 1H-pyrrolo[3,2-b]pyridinyl, 1-methyl-1H-pyrrolo[3,2-b]pyridinyl or furo[3,2-b]pyridinyl.

In one embodiment R$^3$ represents C$_{1-6}$alkyl substituted with hydroxyl and R$^9$.

In one embodiment when R$^3$ represents C$_{1-6}$alkyl substituted with hydroxyl and R$^9$, R$^9$ represents a saturated 5 membered monocyclic heterocyclyl containing one nitrogen heteroatom, for example pyrrolidinyl. R$^3$ may represent propyl substituted with —OH and 1-pyrrolidinyl.

In one embodiment when R$^3$ represents C$_{1-6}$alkyl substituted with hydroxyl and R$^9$, R$^9$ represents a saturated 5 membered monocyclic heterocyclyl containing one nitrogen heteroatom, for example pyrrolidinyl, and the heterocyclyl is substituted. For example the heterocyclyl is substituted with a) two halo's, for example two fluorines. R$^3$ may represent propyl substituted with —OH and 1-pyrrolidinyl where the 1-pyrrolidinyl is substituted at the 3 position by two fluorines; or
b) a cyano group. R$^3$ may represent propyl substituted with —OH and 1-pyrrolidinyl where the 1-pyrrolidinyl is substituted at the 3 position by a cyano group.

In one embodiment when R$^3$ represents C$_{1-6}$alkyl substituted with hydroxyl and R$^9$, R$^9$ represents a saturated 6 membered monocyclic heterocycle containing one nitrogen and one oxygen heteroatom, for example morpholinyl. R$^3$ may represent propyl substituted with —OH and 4-morpholinyl.

In one embodiment when R$^3$ represents C$_{1-6}$alkyl substituted with hydroxyl and R$^9$, R$^9$ represents a saturated 6 membered monocyclic heterocycle containing one nitrogen heteroatom, for example piperidinyl. R$^3$ may represent propyl substituted with —OH and 1-piperidinyl.

In one embodiment when R$^3$ represents C$_{1-6}$alkyl substituted with hydroxyl and R$^9$, R$^9$ represents an aromatic 5 membered monocyclic heterocycle containing three nitrogen heteroatoms, for example 1,2,4-triazolyl. The heterocycle may be substituted by one C$_{1-4}$alkyl, for example —CH$_3$. R$^3$ may represent propyl substituted with —OH and 2-(1,2,4-triazolyl) substituted in the 3 position by —CH$_3$.

In one embodiment when R$^3$ represents C$_{1-6}$alkyl substituted with hydroxyl and R$^9$, R$^9$ represents an aromatic 5 membered monocyclic heterocycle containing two nitrogen heteroatoms, for example imidazolyl. The heterocycle may be substituted by one C$_{1-4}$alkyl, for example —CH$_3$. R$^3$ may represent propyl substituted with —OH and 1-imidazolyl substituted in the 2 position by —CH$_3$.

In one embodiment when R$^3$ represents C$_{1-6}$alkyl substituted with hydroxyl and R$^9$, R$^9$ represents an optionally substituted bicyclic heterocyclyl containing one nitrogen heteroatom, said bicyclic heterocyclyl may be substituted for example with two =O groups. R$^3$ may represent propyl substituted with hydroxyl and isoindole-1,3-dione.

In one embodiment R$^3$ represents —C$_{1-6}$alkyl-C(R$^{12}$)=N—O—R$^{12}$. R$^{12}$ may independently be chosen from hydrogen and C$_{1-4}$alkyl optionally substituted with C$_{1-4}$alkyloxy, for example —CH$_3$ or —CH(CH$_3$)$_2$. R$^3$ may represent —CH$_2$C(CH$_3$)=N—O—H, —CH$_2$C(CH$_2$OCH$_3$)=N—O—H or —CH$_2$C(CH(CH$_3$)$_2$)=N—O—H.

In one embodiment R$^3$ represents —S(=O)$_2$—NR$^{14}$R$^{15}$, where R$^{14}$ and R$^{15}$ may each be C$_{1-4}$alkyl. R$^3$ may be —S(=O)$_2$—N(CH$_3$)$_2$.

In one embodiment R$^3$ represents C$_{1-6}$alkyl substituted with —S(=O)$_2$—C$_{1-6}$alkyl. R$^3$ may be —CH$_2$CH$_2$—S(=O)$_2$—CH$_3$.

In one embodiment R$^3$ represents C$_{1-6}$alkyl substituted with —C(=O)—R$^9$. R$^9$ may represent a saturated 5-membered monocyclic heterocycle containing one nitrogen heteroatom, for example pyrrolidinyl. R$^3$ may represent —CH$_2$—C(=O)—R$^9$ and R$^9$ is 1-pyrrolidinyl.

In one embodiment R$^3$ represents C$_{2-6}$alkenyl substituted with R$^9$. R$^9$ may represent an optionally substituted aromatic 6-membered monocyclic heterocycle containing one or two nitrogen heteroatoms, for example pyridinyl or pyrimidinyl. The heterocyclyl may be substituted, for example with one C$_{1-4}$alkyl or one C$_{1-4}$alkoxy substituent, for example —CH$_3$ or —OCH$_3$. R$^3$ may represent —CH$_2$CH=CH-(2-pyrimidinyl), —CH$_2$CH=CH-(2-pyrimidinyl) wherein the 2-pyrimidinyl is substituted in the 4-position by —OCH$_3$, —CH$_2$CH=CH-(2-pyridinyl) wherein the 2-pyridinyl is substituted in the 4-position by —CH$_3$ or —CH$_2$CH=CH-(2-pyridinyl) wherein the 2-pyridinyl is substituted in the 3-position by —OCH$_3$.

In one embodiment R$^3$ represents C$_{2-6}$alkynyl substituted with R$^9$. R$^9$ may represent an optionally substituted aromatic 5-membered monocyclic heterocycle containing two nitrogen heteroatoms, for example imidazolyl. The heterocyclyl may be substituted, for example substituted with one C$_{1-4}$alkyl substituent, for example —CH$_3$. R$^3$ may represent —CH$_2$—C≡C-(2-imidazolyl) wherein the 2-imidazolyl is substituted in the 1 position by —CH$_3$ or —CH$_2$—C≡C-(5-imidazolyl) wherein the 5-imidazolyl is substituted in the 1 position by —CH$_3$.

In one embodiment R$^3$ represents C$_{2-6}$alkynyl substituted with R$^9$.

In one embodiment when R$^3$ represents C$_{2-6}$alkynyl substituted with R$^9$, R$^9$ represents an optionally substituted aromatic 6-membered monocyclic heterocycle containing one or two nitrogen heteroatoms, for example pyridinyl, pyrimidinyl or pyrazinyl. $R^3$ may represent —CH$_2$—C≡C— (4-pyridinyl), —CH$_2$—C≡C— (3-pyridinyl), —CH$_2$—C≡C— (2-pyridinyl), —CH$_2$—C≡C— (2-pyrimidinyl), —CH$_2$—C≡C— (6-pyrazinyl).

In one embodiment when $R^3$ represents $C_{2-6}$alkynyl substituted with $R^9$, $R^9$ represents an optionally substituted aromatic 6-membered monocyclic heterocycle containing one or two nitrogen heteroatoms, for example pyridinyl, pyrimidinyl or pyrazinyl and the heterocyclyl may be substituted, for example substituted with:

a) one hydroxyC$_{1-4}$alkyl. $R^3$ may represent —CH$_2$—C≡C— (6-pyridinyl) substituted in the 2 or 4-position with —CH$_2$OH;

b) one C$_{1-4}$alkoxy, for example —OCH$_3$, —OCH$_2$CH$_3$. $R^3$ may represent —CH$_2$—C≡C— (4-pyridinyl) substituted in the 6-position with —OCH$_3$, —CH$_2$—C≡C— (2-pyridinyl) substituted in the 3 or 5-position with —OCH$_3$, —CH$_2$—C≡C— (2-pyrimidinyl) substituted in the 4 or 6-position with —OCH$_3$, —CH$_2$—C≡C— (6-pyridinyl) substituted in the 2, 4 or 5-position with —OCH$_3$, —CH$_2$—C≡C— (6-pyrimidinyl) substituted in the 4-position with —OCH$_3$, —CH$_2$—C≡C— (5-pyrazinyl) substituted in the 6-position with —OCH$_3$, —CH$_2$—C≡C— (2-pyrimidinyl) substituted in the 6-position with —OCH$_2$CH$_3$, —C(CH$_3$)$_2$—C≡C— (2-pyrimidinyl) substituted in the 4-position with —OCH$_3$—CH$_2$—C≡C— (2-pyrimidinyl) substituted in the 4-position with —OCH(CH$_3$)$_2$;

c) one cyano. $R^3$ may represent —CH$_2$—C≡C— (6-pyridinyl) substituted in the 2 or the 4-position with cyano, —CH$_2$—C≡C— (4-pyridinyl) substituted in the 5 or 6-position with cyano;

d) one —NR$^{14}$R$^{15}$. $R^3$ may represent —CH$_2$—C≡C— (6-pyridinyl) substituted in the 2 or 4-position with —NH$_2$, —CH$_2$—C≡C— (6-pyridinyl) substituted in the 2-position with —NH$_2$, —CH$_2$—C≡C— (2-pyridinyl) substituted in the 3-position with —NH$_2$, —CH$_2$—C≡C— (3-pyrazinyl) substituted in the 6-position with —NH$_2$, —CH$_2$—C≡C— (6-pyridinyl) substituted in the 5-position with —NHCH$_3$, e) one C$_{1-4}$alkyl, for example —CH$_3$ or —CH$_2$CH$_3$. $R^3$ may represent —CH$_2$—C≡C— (6-pyridinyl) substituted in the 3 or 4-position with —CH$_3$, —CH$_2$—C≡C— (2-pyridinyl) substituted in the 3-position with —CH$_3$, —CH$_2$—C≡C— (2-pyrimidinyl) substituted in the 4-position with —CH$_3$, —CH$_2$—C≡C— (2-pyrimidinyl) substituted in the 6-position with —CH$_2$CH$_3$, f) one C$_{1-4}$alkyl, for example —CH$_3$ and one —NR$^{14}$R$^{15}$, for example —NH$_2$. $R^3$ may represent —CH$_2$—C≡C— (6-pyrimidinyl) substituted in the 2-position with —CH$_3$ and in the 4-position with —NH$_2$;

g) one halogen, for example —Cl and one —NR$^{14}$R$^{15}$, for example —NH$_2$. $R^3$ may represent —CH$_2$—C≡C— (6-pyrimidinyl) substituted in the 2-position with —NH$_2$ and in the 4-position with —Cl, h) one halogen, for example —Br, —Cl or —F. $R^3$ may represent —CH$_2$—C≡C— (2-pyrazinyl) substituted in the 3-position with —Cl, —CH$_2$—C≡C— (3-pyrazinyl) substituted in the 5-position with —Cl, —CH$_2$—C≡C— (2-pyridinyl) substituted in the 3-position with —F, —CH$_2$—C≡C— (5-pyridinyl) substituted in the 6-position with —Br;

i) one —C(=O)—NR$^{14}$R$^{15}$. $R^3$ may represent —CH$_2$—C≡C— (6-pyridinyl) substituted in the 4-position with —C(=O)—NH$_2$;

j) one C$_{1-4}$alkyl-O—C(=O)—. $R^3$ may represent —CH$_2$—C≡C— (6-pyridinyl) substituted in the 5-position with CH$_3$—O—C(=O)—, —CH$_2$—C≡C— (2-pyrimidinyl) substituted in the 6-position with CH$_3$—O—C(=O)—;

k) one haloC$_{1-4}$alkyl. $R^3$ may represent —CH$_2$—C≡C— (2-pyridinyl) substituted in the 3-position with —CF$_3$.

In one embodiment when $R^3$ represents $C_{2-6}$alkynyl substituted with $R^9$, $R^9$ represents an optionally substituted aromatic 5-membered monocyclic heterocyclyl containing one nitrogen and one sulphur heteroatom, for example thiazolyl. $R^3$ may represent —CH$_2$—C≡C— (5-thiazolyl).

In one embodiment when $R^3$ represents $C_{2-6}$alkynyl substituted with $R^9$, $R^9$ represents an optionally substituted phenyl. $R^3$ may be —CH$_2$—C≡C— (phenyl). The phenyl may be substituted, for example with one C$_{1-4}$alkoxy. $R^3$ may represent —CH$_2$—C≡C— (phenyl) where the phenyl is substituted in the 5-position by —OCH$_3$.

In one embodiment when $R^3$ represents $C_{2-6}$alkynyl substituted with $R^9$, $R^9$ represents an optionally substituted saturated 4-membered monocyclic heterocycle containing one nitrogen heteroatom, for example azetidinyl. The heterocyclyl may be substituted, for example with:

a) one hydroxyl and one C$_{1-4}$alkyl-O—C(=O)—. $R^3$ may represent —CH$_2$—C≡C— (3-azetidinyl) substituted in the 1-position by (CH$_3$)$_3$C—O—C(=O)— and in the 3-position by —OH;

b) one hydroxyl. $R^3$ may represent —CH$_2$—C≡C— (3-azetidinyl) substituted in the 3-position by —OH.

In one embodiment when $R^3$ represents $C_{2-6}$alkynyl substituted with $R^9$, $R^9$ represents an optionally substituted saturated 5-membered monocyclic heterocycle containing one nitrogen heteroatom, for example pyrrolidinyl. The heterocyclyl may be substituted, for example with:

a) one hydroxyl and one C$_{1-4}$alkyl-O—C(=O)—. $R^3$ may represent —CH$_2$—C≡C— (3-pyrrolidinyl) substituted in the 1-position by (CH$_3$)$_3$C—O—C(=O)— and in the 3-position by —OH;

b) one hydroxyl. $R^3$ may represent —CH$_2$—C≡C— (3-pyrrolidinyl) substituted in the 3-position by —OH.

In one embodiment when $R^3$ represents $C_{2-6}$alkynyl substituted with $R^9$, $R^9$ represents an optionally substituted saturated 6-membered monocyclic heterocycle containing one nitrogen heteroatom, for example piperidinyl. $R^3$ may represent —CH$_2$—C≡C— (4-piperidinyl). The heterocyclyl may be substituted, for example with:

a) one hydroxyl. $R^3$ may represent —CH$_2$—C≡C— (4-piperidinyl) substituted in the 4-position by —OH;

b) one C$_{1-4}$alkyl-O—C(=O)—. $R^3$ may represent —CH$_2$—C≡C— (4-piperidinyl) substituted in the 1-position by (CH$_3$)$_3$C—O—C(=O)—.

In one embodiment when $R^3$ represents $C_{2-6}$alkynyl substituted with $R^9$, $R^9$ represents an optionally substituted saturated 5-membered monocyclic heterocycle containing one oxygen heteroatom, for example tetrahydrofuranyl. The heterocyclyl may be substituted, for example with one hydroxyl. $R^3$ may represent —CH$_2$—C≡C— (4-tetrahydrofuranyl) substituted in the 3-position by —OH.

In one embodiment when $R^3$ represents $C_{2-6}$alkynyl substituted with $R^9$, $R^9$ represents an optionally substituted saturated 6-membered monocyclic heterocycle containing one oxygen heteroatom, for example tetrahydropyranyl. The heterocyclyl may be substituted, for example with one hydroxyl. $R^3$ may represent —CH$_2$—C≡C— (4-tetrahydropyranyl) substituted in the 4-position by —OH.

In one embodiment when $R^3$ represents $C_{2-6}$alkynyl substituted with $R^9$, $R^9$ represents a $C_{3-8}$cycloalkyl, for example cyclohexyl.

$R^3$ may represent —$CH_2$—C≡C— (cyclohexyl).

In one embodiment $R^3$ represents $C_{2-6}$alkynyl (e.g. —$CH_2$—C≡C—) substituted with $R^9$, wherein $R^9$ represents $C_{3-8}$cycloalkyl or 3 to 12 membered monocyclic or bicyclic heterocyclyl containing at least one heteroatom selected from N, O or S, said $C_{3-8}$cycloalkyl or 3 to 12 membered monocyclic or bicyclic heterocyclyl each optionally and each independently being substituted with 1, 2, 3, 4 or 5 substituents as defined herein.

In one embodiment $R^3$ represents $C_{2-6}$alkynyl (e.g. —$CH_2$—C≡C—) substituted with $R^9$, wherein $R^9$ represents an optionally substituted 4 to 8-membered monocyclic or bridged heterocyclyl, for example $R^9$ represents an optionally substituted azetidinyl, pyrrolidinyl, imidazolyl, thiazolyl, pyridinyl, pyrimidinyl, pyrazinyl, piperidinyl, tetrahydrofuranyl, tetrahydropyranyl, or 2,5-diaza-bicyclo[2.2.1]heptanyl.

In one embodiment $R^3$ represents $C_{2-6}$alkynyl (e.g. —$CH_2$—C≡C—) substituted with $R^9$, wherein $R^9$ represents an optionally substituted aromatic 5- or 6-membered monocyclic heterocyclyl, for example imidazolyl, thiazolyl, pyridinyl, pyrimidinyl or pyrazinyl.

an optionally substituted saturated 4-, 5-, or 6-membered monocyclic heterocyclyl, for example azetidinyl, pyrrolidinyl, piperidinyl, tetrahydrofuranyl, tetrahydropyranyl.

an optionally substituted 6 to 8 membered bridged heterocyclyl group, for example 2,5-diaza-bicyclo[2.2.1]heptanyl.

a $C_{3-8}$cycloalkyl, for example cyclohexyl.

In one embodiment $R^3$ represents $C_{2-6}$alkynyl (e.g. —$CH_2$—C≡C—) substituted with $R^9$, wherein $R^9$ represents an optionally substituted aromatic 5-membered monocyclic heterocycle containing two nitrogen heteroatoms, for example imidazolyl, an optionally substituted aromatic 6 membered monocyclic heterocycle containing one nitrogen heteroatom, for example pyridinyl, an optionally substituted aromatic 6 membered monocyclic heterocycle containing one or two nitrogen heteroatoms, for example pyridinyl, pyrimidinyl or pyrazinyl an optionally substituted aromatic 5-membered monocyclic heterocyclyl containing one nitrogen and one sulphur heteroatom, for example thiazolyl, an optionally substituted saturated 4-membered monocyclic heterocycle containing one nitrogen heteroatom, for example azetidinyl, an optionally substituted saturated 5-membered monocyclic heterocycle containing one nitrogen heteroatom, for example pyrrolidinyl, an optionally substituted saturated 5-membered monocyclic heterocycle containing one oxygen heteroatom, for example tetrahydrofuranyl, an optionally substituted saturated 6-membered monocyclic heterocycle containing one oxygen heteroatom, for example tetrahydropyranyl, a $C_{3-8}$cycloalkyl, for example cyclohexyl or a 6 to 8 membered bridged heterocyclyl group, for example 2,5-diaza-bicyclo[2.2.1]heptanyl.

In one embodiment when $R^3$ represents $C_{1-6}$alkyl substituted with $R^9$, $R^9$ represents an optionally substituted 6 to 8 membered bridged heterocyclyl group, for example 2,5-diaza-bicyclo[2.2.1]heptanyl optionally substituted by —C(═O)—O—$C_4$alkyl.

In one embodiment $R^3$ represents $C_{1-6}$alkyloxy$C_{1-6}$alkyl wherein each $C_{1-6}$alkyl may optionally be substituted with one or two hydroxyl groups. $R^3$ may represent —$CH_2CHOHCH_2OCH_3$.

In one embodiment $R^3$ represents $C_{2-6}$alkenyl. $R^3$ may represent —$CH_2$—CH═$CH_2$.

In one embodiment $R^3$ represents $C_{2-6}$alkynyl. $R^3$ may represent —$CH_2$—C≡C—H. $R^3$ may represent —$C(CH_3)_2$—C≡C—H.

In one embodiment $R^3$ represents $R^{13}$.

In one embodiment when $R^3$ represents $R^{13}$, $R^{13}$ represents a saturated 4-membered monocyclic heterocycle containing one oxygen heteroatom. $R^3$ may represent 3-oxetanyl.

In another embodiment when $R^3$ represents $R^{13}$, $R^{13}$ represents an optionally substituted $C_{3-8}$cycloalkyl. For example the $C_{3-8}$cycloalkyl may be substituted with one $NR^{14}R^{15}$ where one of $R^{14}$ and $R^{15}$ represents hydrogen and the other represents $C_{1-4}$alkyl optionally substituted with hydroxyl, for example —$CH(CH_3)_2$. $R^3$ may represent cyclohexanyl substituted in the 4 position by —NH—CH$(CH_3)_2$.

In one embodiment of the invention $R^3$ represents $C_{1-6}$alkyl substituted by $R^9$, wherein $R^9$ is a saturated heterocyclyl substituted by $R^{13}$, wherein $R^{13}$ is a saturated heterocyclyl which is optionally substituted, for example substituted by —C(═O)—$C_{1-6}$alkyl. In one embodiment $R^9$ is piperazinyl substituted by $R^{13}$, wherein $R^{13}$ is piperidinyl substituted by —C(═O)—$C_{1-6}$alkyl.

In one embodiment of the invention $R^3$ represents $C_{1-6}$alkyl substituted with —P(═O)(O$C_{1-6}$alkyl)$_2$. $R^3$ may represent —$CH_2CH_2$P(═O)(O$CH_2CH_3$)$_2$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{1-6}$alkyl substituted with —$NR^{10}R^{11}$, for example —$CH_2CH_2NHCH(CH_3)_2$.

In a further embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, $R^3$ represents $C_{1-6}$alkyl substituted with —$NR^{10}R^{11}$, for example —$CH_2CH_2$—$CH_2$—NH$CH_2CF_3$.

In a further embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, $R^3$ represents $C_{1-6}$alkyl substituted with —$NR^{10}R^{11}$, for example —$CH_2CH_2NH_2$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{2-6}$alkynyl substituted with —$R^9$, for example —$CH_2$—C≡C— (2-pyridinyl).

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{2-6}$alkynyl substituted with —$R^9$, for example —$CH_2$—C≡C— (2-pyridinyl) substituted in the 3-position by —$OCH_3$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CD_3O$—, and $R^3$ represents $C_{1-6}$alkyl substituted with —$NR^{10}R^{11}$, for example $R^3$ may represent —$CD_2$-$CD_2$-$NHCH(CH_3)_2$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{2-6}$alkynyl substituted with —$R^9$, for example —$CH_2$—C≡C— (6-pyridinyl) substituted in the 2-position by —$NH_2$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{2-6}$alkynyl substituted with —$R^9$, for example —$CH_2$—C≡C— (2-pyrimidinyl) substituted in the 4-position by —$OCH_3$.

In one embodiment of the invention $R^1$ represents $C_{1-6}$alkyl, for example —$CH(CH_3)_2$, each $R^{1a}$ represents hydrogen, n represents an integer equal to 2 and each $R^2$ represents $C_{1-4}$alkoxy, for example $CD_3O$—, and $R^3$ represents $C_{2-6}$alkynyl substituted with —$R^9$, for example —$CH_2$—C≡C— (4-pyridinyl).

In one embodiment of the invention $R^1$ represents $C_{1-6}$alkyl, for example —$CH(CH_3)_2$, each $R^{1a}$ represents hydrogen, n represents an integer equal to 2 and each $R^2$ represents $C_{1-4}$alkoxy, for example $CH_3O$—, and $R^3$ represents $C_{1-6}$alkoxy$C_{1-6}$alkyl wherein each $C_{1-6}$alkyl may optionally be substituted with one or two hydroxyl groups or with —O—C(=O)—$C_{1-6}$alkyl, for example —$CH_2CHOHCH_2OCH_3$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{2-6}$alkynyl substituted with —$R^9$, for example —$CH_2$—C≡C— (6-pyridinyl) substituted in the 4-position by —$CH_3$.

In one embodiment of the invention $R^1$ represents $C_{1-6}$alkyl substituted with —$NR^4R^5$, for example —$CH_2CH_2CH_2NH_2$, each $R^{1a}$ represents hydrogen, n represents an integer equal to 2 and each $R^2$ represents $C_{1-4}$alkoxy, for example $CH_3O$—, and $R^3$ represents hydroxyhalo$C_{1-6}$alkyl, for example —$CH_2CHOHCF_3$.

In one embodiment of the invention $R^1$ represents $C_{1-6}$alkyl, for example —$CH_3$, each $R^{1a}$ represents hydrogen, n represents an integer equal to 4 and two $R^2$ represent $C_{1-4}$alkoxy, for example $CH_3O$—, and two $R^2$ represent halogen, for example F, and $R^3$ represents $C_{1-6}$alkyl substituted with —$NR^{10}R^{11}$, for example —$CH_2CH_2NH(CH(CH_3)_2)$.

In one embodiment of the invention $R^1$ represents $C_{1-6}$alkyl, for example —$CH_3$, each $R^{1a}$ represents hydrogen, n represents an integer equal to 2 and each $R^2$ represents $C_{1-4}$alkoxy, for example $CH_3O$—, and $R^3$ represents $C_{1-6}$alkyl substituted with —$NR^{10}R^{11}$, for example —$CH_2CH_2CH_2NH_2$.

In a further embodiment the compound of formula (I) as defined herein is selected from the following compounds or is one of the following compounds:

N-(3,5-Dimethoxyphenyl)-N-[3-(1-methyl-1H-pyrazol-4-yl)quinoxalin-6-yl]ethane-1,2-diamine (compound 84)

3-{4-[3-(4-{7-[(Cyclopropylmethyl)(3,5-dimethoxyphenyl)amino]quinoxalin-2-yl}-1H-pyrazol-1-yl)propyl]piperazin-1-yl}propan-1-ol or HCl salt thereof (compound 130)

N-(3,5-Dimethoxyphenyl)-N'-(1-methylethyl)-N-[3-(1-methyl-1H-pyrazol-4-yl)quinoxalin-6-yl]ethane-1,2-diamine (compound 4)

2-[4-(7-{(Cyclopropylmethyl)[3-(2-hydroxyethoxy)-5-methoxyphenyl]amino}quinoxalin-2-yl)-1H-pyrazol-1-yl]ethanol or HCl salt thereof (compound 131)

N-(3,5-Dimethoxyphenyl)-N-[3-(1-methyl-1H-imidazol-2-yl)prop-2-yn-1-yl]-3-(1-methyl-1H-pyrazol-4-yl)quinoxalin-6-amine (compound 300)

1-(3-{(3,5-Dimethoxyphenyl)[3-(1-methyl-1H-pyrazol-4-yl)quinoxalin-6-yl]amino}propyl)pyrrolidin-2-one (compound 132)

(3S)-1-(2-{(3,5-Dimethoxyphenyl)[3-(1-methyl-1H-pyrazol-4-yl)quinoxalin-6-yl]amino}ethyl)pyrrolidine-3-carbonitrile (compound 133)

N-(3,5-Dimethoxyphenyl)-N-[3-(1-methyl-1H-pyrazol-4-yl)quinoxalin-6-yl]-N'-(2,2,2-trifluoroethyl)propane-1,3-diamine (compound 5)

2-(4-{7-[(3,5-Dimethoxyphenyl){2-[(1-methylethyl)amino]ethyl}amino]quinoxalin-2-yl}-1H-pyrazol-1-yl)-N-methylacetamide or HCl salt thereof (compound 134)

N-(3,5-Dimethoxyphenyl)-N-[3-(1-ethyl-1H-pyrazol-4-yl)quinoxalin-6-yl]-N'-(1-methylethyl)ethane-1,2-diamine or HCl salt thereof (compound 135)

N-(3,5-Dimethoxyphenyl)-N'-(1-methylethyl)-N-{3-[1-(tetrahydro-2H-pyran-4-ylmethyl)-1H-pyrazol-4-yl]quinoxalin-6-yl}ethane-1,2-diamine or HCl salt thereof (compound 136)

(2S)-3-{(3,5-Dimethoxyphenyl)[3-(1-methyl-1H-pyrazol-4-yl)quinoxalin-6-yl]amino}propane-1,2-diol (compound 98)

N-(3,5-Dimethoxyphenyl)-N'-(1-methylethyl)-N-[3-(1H-pyrazol-4-yl)quinoxalin-6-yl]ethane-1,2-diamine or HCl salt thereof (compound 137)

N-(3,5-Dimethoxyphenyl)-N-(1H-imidazol-2-ylmethyl)-3-(1-methyl-1H-pyrazol-4-yl)quinoxalin-6-amine (compound 99)

3-{(Cyclopropylmethyl)[3-(1-methyl-1H-pyrazol-4-yl)quinoxalin-6-yl]amino}-5-fluoro-N-methylbenzamide (compound 138)

1-{(3,5-Dimethoxyphenyl)[3-(1-methyl-1H-pyrazol-4-yl)quinoxalin-6-yl]amino}-3-[(2,2,2-trifluoroethyl)amino]propan-2-ol (compound 139)

3-[(2-{(3,5-Dimethoxyphenyl)[3-(1-methyl-1H-pyrazol-4-yl)quinoxalin-6-yl]amino}ethyl)amino]propanenitrile (compound 140)

4-{(3,5-Dimethoxyphenyl)[3-(1-methyl-1H-pyrazol-4-yl)quinoxalin-6-yl]amino}-2-methylbutan-2-ol (compound 141)

(2S)-1-{(3,5-Dimethoxyphenyl)[3-(1-methyl-1H-pyrazol-4-yl)quinoxalin-6-yl]amino}-3-[(2,2,2-trifluoroethyl)amino]propan-2-ol (compound 142)

N-[2-(4-Acetylpiperazin-1-yl)ethyl]-N-(3,5-dimethoxyphenyl)-3-(1-methyl-1H-pyrazol-4-yl)quinoxalin-6-amine (compound 143)

4-(2-{(3,5-Dimethoxyphenyl)[3-(1-methyl-1H-pyrazol-4-yl)quinoxalin-6-yl]amino}ethyl)piperazin-2-one (compound 144)

(2S)-1-{(3,5-Dimethoxyphenyl)[3-(1-methyl-1H-pyrazol-4-yl)quinoxalin-6-yl]amino}-3-[(1-methylethyl)amino]propan-2-ol or HCl salt thereof (compound 145)

N-(3,5-Dimethoxyphenyl)-3-(1-methyl-1H-pyrazol-4-yl)-N-(pyrazin-2-ylmethyl)quinoxalin-6-amine (compound 146)

N-(3,5-Dimethoxyphenyl)-N-{3-[1-(1-methylethyl)-1H-pyrazol-4-yl]quinoxalin-6-yl}-N'-(2,2,2-trifluoroethyl)propane-1,3-diamine or HCl salt thereof (compound 147)

(2R*)-3-{(3,5-Dimethoxyphenyl)[3-(1-methyl-1H-pyrazol-4-yl)quinoxalin-6-yl]amino}-1,1,1-trifluoropropan-2-ol (relative stereochemistry) (Compound 148)
(2S*)-3-{(3,5-Dimethoxyphenyl)[3-(1-methyl-1H-pyrazol-4-yl)quinoxalin-6-yl]amino}-1,1,1-trifluoropropan-2-ol (relative stereochemistry) (compound 149);
a N-oxide thereof, a pharmaceutically acceptable salt thereof or a solvate thereof.

In a further embodiment the compound of formula (I) as defined herein is selected from the following compounds or is one of the following compounds:
N-(3,5-Dimethoxyphenyl)-N-[3-(1-methyl-1H-pyrazol-4-yl)quinoxalin-6-yl]-N'-(2,2,2-trifluoroethyl)propane-1,3-diamine (compound 5)
N-(3,5-Dimethoxyphenyl)-N'-(1-methylethyl)-N-[3-(1-methyl-1H-pyrazol-4-yl)quinoxalin-6-yl]ethane-1,2-diamine (compound 4)
N-(3,5-Dimethoxyphenyl)-N-[3-(1-methyl-1H-pyrazol-4-yl)quinoxalin-6-yl]ethane-1,2-diamine (compound 84)
N-(3,5-Dimethoxyphenyl)-N-{3-[1-(1-methylethyl)-1H-pyrazol-4-yl]quinoxalin-6-yl}-N'-(2,2,2-trifluoroethyl)propane-1,3-diamine or HCl salt thereof (compound 147)
N-(3,5-Dimethoxyphenyl)-N'-(1-methylethyl)-N-[3-(1H-pyrazol-4-yl)quinoxalin-6-yl]ethane-1,2-diamine or HCl salt thereof (compound 137)
N-(3,5-Dimethoxyphenyl)-N'-(1-methylethyl)-N-{3-[1-(tetrahydro-2H-pyran-4-ylmethyl)-1H-pyrazol-4-yl]quinoxalin-6-yl}ethane-1,2-diamine or HCl salt thereof (compound 136)
N-(3,5-Dimethoxyphenyl)-N-[3-(1-ethyl-1H-pyrazol-4-yl)quinoxalin-6-yl]-N'-(1-methylethyl)ethane-1,2-diamine or HCl salt thereof (compound 135)
2-(4-{7-[(3,5-Dimethoxyphenyl){2-[(1-methylethyl)amino]ethyl}amino]quinoxalin-2-yl}-1H-pyrazol-1-yl)-N-methylacetamide or HCl salt thereof (compound 134)
N-(3,5-Dimethoxyphenyl)-N-[3-(1-methyl-1H-imidazol-2-yl)prop-2-yn-1-yl]-3-(1-methyl-1H-pyrazol-4-yl)quinoxalin-6-amine (compound 300);
a N-oxide thereof, a pharmaceutically acceptable salt thereof or a solvate thereof.

In a further embodiment the compound of formula (I) as defined herein is selected from the following compounds or is one of the following compounds:
N-(3,5-Dimethoxyphenyl)-N-[3-(1-methyl-1H-pyrazol-4-yl)quinoxalin-6-yl]-N'-(2,2,2-trifluoroethyl)propane-1,3-diamine (compound 5)
N-(3,5-Dimethoxyphenyl)-N'-(1-methylethyl)-N-[3-(1-methyl-1H-pyrazol-4-yl)quinoxalin-6-yl]ethane-1,2-diamine (compound 4)
N-(3,5-Dimethoxyphenyl)-N-[3-(1-methyl-1H-pyrazol-4-yl)quinoxalin-6-yl]ethane-1,2-diamine (compound 84);
a N-oxide thereof, a pharmaceutically acceptable salt thereof or a solvate thereof.

In a further embodiment the compound of formula (I) as defined herein is selected from the following compounds or is one of the following compounds:
N-(3,5-Dimethoxyphenyl)-N-[3-(1-methyl-1H-pyrazol-4-yl)quinoxalin-6-yl]propane-1,3-diamine; (compound 93)
2-(4-{7-[(3,5-Dimethoxyphenyl){2-[(1-methylethyl)amino]ethyl}amino]quinoxalin-2-yl}-1H-pyrazol-1-yl)ethanol; (compound 691)
N-(3,5-Dimethoxyphenyl)-N'-(1-methylethyl)-N-(3-{1-[2-(methylsulfonyl)ethyl]-1H-pyrazol-4-yl}quinoxalin-6-yl)ethane-1,2-diamine; (compound 678)
N-(3,5-Dimethoxyphenyl)-3-(1-methyl-1H-pyrazol-4-yl)-N-(3-pyridin-2-ylprop-2-yn-1-yl)quinoxalin-6-amine; (compound 691)
N-(3,5-Dimethoxyphenyl)-N-[3-(3-methoxypyridin-2-yl)prop-2-yn-1-yl]-3-(1-methyl-1H-pyrazol-4-yl)quinoxalin-6-amine; (compound 652)
N-{3,5-Bis[($^{2}$H$_3$)methyloxy]phenyl}-N'-(1-methylethyl)-N-[3-(1-methyl-1H-pyrazol-4-yl)quinoxalin-6-yl]($^{2}$H$_4$)ethane-1,2-diamine; (compound 618)
N-[3-(6-Aminopyridin-2-yl)prop-2-yn-1-yl]-N-(3,5-dimethoxyphenyl)-3-(1-methyl-1H-pyrazol-4-yl)quinoxalin-6-amine; (compound 689)
N-(3,5-Dimethoxyphenyl)-N-[3-(4-methoxypyrimidin-2-yl)prop-2-yn-1-yl]-3-(1-methyl-1H-pyrazol-4-yl)quinoxalin-6-amine; (compound 688)
N-{3,5-Bis[($^{2}$H$_3$)methyloxy]phenyl}-3-[1-(1-methylethyl)-1H-pyrazol-4-yl]-N-(3-pyridin-4-ylprop-2-yn-1-yl)quinoxalin-6-amine; (compound 653)
1-[(3,5-Dimethoxyphenyl){3-[1-(1-methylethyl)-1H-pyrazol-4-yl]quinoxalin-6-yl}amino]-3-methoxypropan-2-ol; or its hydrochloric acid salt; (compound 657)
N-(3,5-Dimethoxyphenyl)-3-(1-methyl-1H-pyrazol-4-yl)-N-[3-(4-methylpyridin-2-yl)prop-2-yn-1-yl]quinoxalin-6-amine; (compound 634)
3-[{3-[1-(3-Aminopropyl)-1H-pyrazol-4-yl]quinoxalin-6-yl}(3,5-dimethoxyphenyl)amino]-1,1,1-trifluoropropan-2-ol; or an enantiomer thereof; (compound 660 and 661)
N-(2,6-Difluoro-3,5-dimethoxyphenyl)-N'-(1-methylethyl)-N-[3-(1-methyl-1H-pyrazol-4-yl)quinoxalin-6-yl]ethane-1,2-diamine (compound 687);
a N-oxide thereof, a pharmaceutically acceptable salt thereof or a solvate thereof.

According to an aspect of the invention there is provided compounds of formula (I):

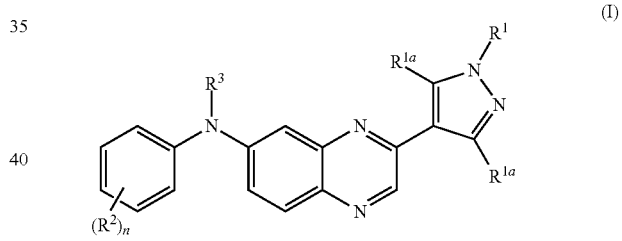

including any tautomeric or stereochemically isomeric form thereof, wherein
n represents an integer equal to 0, 1, 2, 3 or 4;
R$^1$ represents hydrogen, C$_{1-6}$alkyl, C$_{2-4}$alkenyl, hydroxyC$_{1-6}$alkyl, haloC$_{1-6}$alkyl, cyanoC$_{1-4}$alkyl, C$_{1-6}$alkoxyC$_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —NH—S(=O)$_2$—C$_{1-6}$alkyl, R$^6$, C$_{1-6}$alkyl substituted with R$^6$, C$_{1-6}$alkyl substituted with —C(=O)—R$^6$, hydroxyC$_{1-6}$alkyl substituted with R$^6$, or C$_{1-6}$alkyl substituted with —Si(CH$_3$)$_3$;
each R$^{1a}$ is independently selected from hydrogen, C$_{1-4}$alkyl, hydroxyC$_{1-4}$alkyl, C$_{1-4}$alkyl substituted with di(C$_{1-4}$alkyl)amino, and C$_{1-4}$alkyl substituted with one or more fluoro atoms;
each R$^2$ is independently selected from hydroxyl, halogen, cyano, C$_{1-4}$alkyl, C$_{2-4}$alkenyl, C$_{1-4}$alkoxy, hydroxyC$_{1-4}$alkyl, hydroxyC$_{1-4}$alkoxy, haloC$_{1-4}$alkyl, haloC$_{1-4}$alkoxy, C$_{1-4}$alkoxyC$_{1-4}$alkyl, R$^{13}$, C$_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ and —C(=O)—$NR^7R^8$; or when two $R^2$ groups are attached to adjacent carbon atoms they may be taken together to form a radical of formula —O—(C($R^{17}$)$_2$)$_p$—O— wherein $R^{17}$ represents hydrogen or fluorine and p represents 1 or 2;

$R^3$ represents $C_{1-6}$alkyl, hydroxy$C_{1-6}$alkyl, hydroxyhalo $C_{1-6}$alkyl, hydroxy$C_{2-6}$alkynyl, halo$C_{1-6}$alkyl, halo $C_{1-6}$alkyl optionally substituted with —O—C(=O)—$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —O—C(=O)—$NR^{10}R^{11}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with and $R^9$ and optionally substituted with —O—C(=O)—$C_{1-6}$alkyl, $C_{1-6}$alkyl substituted with hydroxyl and $R^9$, —$C_{1-6}$alkyl-C($R^{12}$)=N—O—$R^{12}$, —S(=O)$_2$—$NR^{14}R^{15}$, $C_{1-6}$alkyl substituted with —S(=O)$_2$—$C_{1-6}$alkyl, $C_{1-6}$alkyl substituted with —C(=O)—$NR^{10}R^{11}$, $C_{1-6}$alkyl substituted with —C(=O)—$R^9$, $C_{2-6}$alkenyl substituted with $R^9$, $C_{2-6}$alkynyl substituted with $R^9$, hydroxy$C_{1-6}$alkoxy, $C_{2-6}$alkenyl, $C_{2-6}$alkynyl, $R^{13}$ or $C_{1-6}$alkyl substituted with $C_{1-6}$alkoxy$C_{1-6}$alkyl-C(=O)— or $C_{1-6}$alkyl substituted with —P(=O)(O$C_{1-6}$alkyl)$_2$;

$R^4$ and $R^5$ each independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-14}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-14}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$; or when two of the substituents of $R^9$ are attached to the same atom, they may be taken together to form a 4 to 7-membered saturated monocyclic heterocyclyl containing at least one heteroatom selected from N, O or S;

$R^{10}$ and $R^{11}$ each independently represent hydrogen, $C_{1-6}$alkyl, cyano$C_{1-6}$alkyl, $C_{1-6}$alkyl substituted with —$NR^{14}R^{15}$, $C_{1-6}$alkyl substituted with —C(=O)—$NR^{14}R^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, —C(=O)—$C_{1-6}$alkyl, $C_{1-6}$alkoxy, or —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —$C(=O)NR^{14}R^{15}$;

the N-oxides thereof, the pharmaceutically acceptable salts thereof or the solvates thereof.

In one embodiment there is provided a compound of formula ($I^0$):

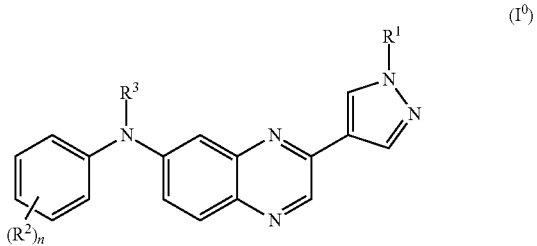

including any stereochemically isomeric form thereof, wherein n represents an integer equal to 0, 1, 2, 3 or 4;

$R^1$ represents hydrogen, $C_{1-6}$alkyl, $C_{2-4}$alkenyl, hydroxy $C_{1-6}$alkyl, halo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —NH—$S(=O)_2$—$C_{1-6}$alkyl, $R^6$, $C_{1-6}$alkyl substituted with $R^6$, $C_{1-6}$alkyl substituted with —$C(=O)$—$R^6$, hydroxy$C_{1-6}$alkyl substituted with $R^6$, or $C_{1-6}$alkyl substituted with —$Si(CH_3)_3$;

each $R^2$ is independently selected from halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo$C_{1-4}$alkoxy, $C_{1-4}$alkoxy $C_{1-4}$alkyl, $R^{13}$, $C_{1-4}$alkoxy substituted with $R^{13}$, —$C(=O)$—$R^{13}$, $C_{1-4}$alkyl substituted with $NR^7R^8$, $C_{1-4}$alkoxy substituted with $NR^7R^8$, —$NR^7R^8$ or —$C(=O)$—$NR^7R^8$;

$R^3$ represents $C_{1-6}$alkyl, hydroxy$C_{1-6}$alkyl, hydroxyhalo $C_{1-6}$alkyl, halo$C_{1-6}$alkyl, $C_{1-6}$alkyl substituted with —$C(=O)$—$C_{1-6}$alkyl, $C_{1-6}$alkoxy$C_{1-6}$alkyl wherein each $C_{1-6}$alkyl may optionally be substituted with one or two hydroxy groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —$C(=O)$—$O$—$C_{1-6}$alkyl, $C_{1-6}$alkyl substituted with —$O$—$C(=O)$—$NR^{10}R^{11}$, $C_{1-6}$alkyl substituted with carboxyl, $C_{1-6}$alkyl substituted with —$O$—$C(=O)$—$NR^{10}R^{11}$, $C_{1-6}$alkyl substituted with —$NR^{12}$—$S(=O)_2$—$C_{1-6}$alkyl, $C_{1-6}$alkyl substituted with —$NR^{12}$—$S(=O)_2$—$NR^{14}R^{15}$, $C_{1-6}$alkyl substituted with hydroxyl and $R^9$, —$C_{1-6}$alkyl-$C(R^{12})$=N—O—$R^{12}$, $C_{1-6}$alkyl substituted with —$C(=O)$—$NR^{10}R^{11}$, $C_{1-6}$alkyl substituted with —$C(=O)$—$R^9$, $C_{2-6}$alkynyl substituted with $R^9$, hydroxy$C_{1-6}$alkoxy, $C_{2-6}$alkenyl, $C_{2-6}$alkynyl, $R^{13}$ or $C_{1-6}$alkyl substituted with $C_{1-6}$alkoxy$C_{1-6}$alkyl-$C(=O)$—;

$R^4$ and $R^5$ independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl, $C_{1-6}$alkyl substituted with —NH—$S(=O)_2$—$NR^{14}R^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4, 5, 6 or 7-membered monocyclic heterocyclyl containing at least one heteroatom selected from N, O or S; said $C_{3-8}$cycloalkyl, $C_{3-8}$cycloalkenyl, phenyl, 4, 5, 6 or 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—$C(=O)$—, —$NR^{14}R^{15}$, —$C(=O)$—$NR^{14}R^{15}$, $C_{1-6}$alkyl substituted with —$NR^{14}R^{15}$, $C_{1-6}$alkyl substituted with —$C(=O)$—$NR^{14}R^{15}$, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl or $C_{1-6}$alkyl substituted with —NH—$S(=O)_2$—$NR^{14}R^{14}R^{15}$;

$R^7$ and $R^8$ independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl or a 3 to 12 membered monocyclic or bicyclic heterocyclyl containing at least one heteroatom selected from N, O or S, said $C_{3-8}$cycloalkyl, $C_{3-8}$cycloalkenyl, aryl or a 3 to 12 membered monocyclic or bicyclic heterocyclyl each optionally and each independently being substituted with 1 to 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—$C(=O)$—, $C_{1-4}$alkyl substituted with $C_{1-6}$alkyl-O—$C(=O)$—, $C_{1-4}$alkyl-$C(=O)$—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —$C(=O)$—$NR^{14}R^{15}$, $C_{1-4}$alkyl substituted with —$NR^{14}R^{15}$, $C_{1-4}$alkyl substituted with —$C(=O)$—$NR^{14}R^{15}$, $C_{1-4}$alkoxy, —$S(=O)_2$—$C_{1-4}$alkyl, —$S(=O)_2$-halo$C_{1-4}$alkyl, —$S(=O)_2$—$NR^{14}R^{15}$, $C_{1-4}$alkyl substituted with —$S(=O)_2$—$NR^{14}R^{15}$, $C_{1-4}$alkyl substituted with —NH—$S(=O)_2$—$C_{1-4}$alkyl, $C_{1-4}$alkyl substituted with —NH—$S(=O)_2$-halo$C_{1-4}$alkyl, $C_{1-4}$alkyl substituted with —NH—$S(=O)_2$—$NR^{14}R^{15}$, $R^{13}$, —$C(=O)$—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;

or when two of the substituents of $R^9$ are attached to the same atom, they may be taken together to form a 4, 5, 6 or 7-membered saturated monocyclic heterocyclyl containing at least one heteroatom selected from N, O or S;

$R^{10}$ and $R^{11}$ each independently represent hydrogen, $C_{1-6}$alkyl, cyano$C_{1-6}$alkyl, $C_{1-6}$alkyl substituted with —$NR^{14}R^{15}$, halo$C_{1-6}$alkyl, hydroxy$C_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl, —C(=O)-hydroxyC$_{1-6}$alkyl, —C(=O)-haloC$_{1-6}$alkyl, —C(=O)-hydroxyhaloC$_{1-6}$alkyl, C$_{1-6}$alkyl substituted with —Si(CH$_3$)$_3$, —S(=O)$_2$—C$_{1-6}$alkyl, —S(=O)$_2$-halo C$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O or S, wherein said C$_{3-8}$cycloalkyl or monocyclic heterocyclyl is optionally substituted with 1, 2 or 3 substituents each independently selected from halogen, hydroxyl, C$_{1-6}$alkyl, —(C=O)—C$_{1-6}$alkyl, C$_{1-6}$alkoxy, or —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino or mono- or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or —C(=O)NR$^{14}$R$^{15}$;

and a N-oxide thereof, a pharmaceutically acceptable salt thereof or a solvate thereof.

In one embodiment there is provided a compound of formula (I$^0$):

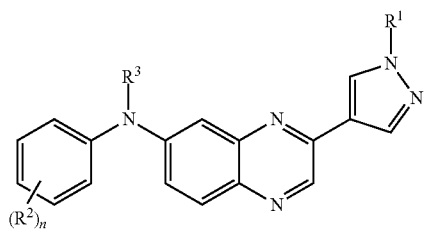

(I$^0$)

including any stereochemically isomeric form thereof, wherein n represents an integer equal to 0, 1, 2, 3 or 4;

R$^1$ represents hydrogen,

C$_{1-6}$alkyl, for example —CH$_3$, —CD$_3$, —CH$_2$CH$_3$, —CH$_2$CH$_2$CH$_3$, —CH$_2$CH(CH$_3$)$_2$, —CH(CH$_3$)$_2$, —CH$_2$CH(CH$_3$)$_2$, C$_{2-4}$alkenyl, for example —CH$_2$—CH=CH$_2$, hydroxyC$_{1-6}$alkyl, for example —CH$_2$CH$_2$OH, —CH$_2$C(CH$_3$)$_2$OH or CH$_2$CHOHCH$_2$OH, haloC$_{1-6}$alkyl, for example —CH$_2$CH$_2$F, CH$_2$CH$_2$CH$_2$Cl or CH$_2$CH$_2$Br, C$_{1-6}$alkoxyC$_{1-6}$alkyl wherein each C$_{1-6}$alkyl may optionally be substituted with one or two hydroxyl groups, for example —CH$_2$CH$_2$OCH$_3$, C$_{1-6}$alkyl substituted with —NR$^4$R$^5$, for example —CH$_2$CH$_2$NH$_2$ or —CH$_2$CH$_2$CH$_2$NH$_2$, —CH$_2$CH$_2$NHCH$_3$, —CH$_2$CH$_2$NHS(=O)$_2$N(CH$_3$)$_2$, —CH$_2$CH$_2$NHS(=O)$_2$CH$_3$, C$_{1-6}$alkyl substituted with —C(=O)—NR$^4$R$^5$, for example —CH$_2$C(=O)N(CH$_3$)$_2$, —CH$_2$C(=O)NHCH$_3$ or —C(CH$_3$)$_2$C(=O)NHCH$_3$, —C(CH$_3$)$_2$C(=O)NHCH$_2$CH$_2$OH or —CH$_2$C(=O)NHCH$_2$CH$_2$OH, —CH$_2$C(=O)NHCH$_2$CH$_2$OCH$_3$ or —C(CH$_3$)$_2$C(=O)NHCH$_2$CH$_2$OCH$_3$, —CH$_2$—C(=O)—NH—CH$_2$—CH$_2$— (pyrrolidin-1-yl), —CH$_2$CH$_2$CH$_2$NHCH$_2$CH$_2$—S(=O)$_2$—CH$_3$, —S(=O)$_2$—C$_{1-6}$alkyl, for example —S(=O)$_2$—CH$_3$, —S(=O)$_2$—NR$^{14}$R$^{15}$, for example —S(=O)$_2$—N(CH$_3$)$_2$, C$_{1-6}$alkyl substituted with —S(=O)$_2$—C$_{1-6}$alkyl, for example —CH$_2$CH$_2$S(=O)$_2$—CH$_3$, C$_{1-6}$alkyl substituted with —NH—S(=O)$_2$—C$_{1-6}$alkyl, for example —CH$_2$CH$_2$NHS(=O)$_2$—CH$_3$, R$^6$, for example 4-piperidinyl, 2-tetrahydropyranyl or 4-tetrahydropyranyl, 4-tetrahydrofuranyl, 3-azetidinyl substituted in the 1 position by —CH$_2$CH$_2$OH, 4-piperidinyl substituted on the nitrogen atom with (CH$_3$)$_3$C—O—C(=O)—, 4-piperidinyl substituted on the nitrogen atom with —S(=O)$_2$CH$_3$, 4-piperidinyl substituted on the nitrogen atom with —CH$_3$, C$_{1-6}$alkyl substituted with R$^6$, for example methyl or ethyl each substituted with 4-piperidinyl, 4-piperazinyl, 1-pyrrolidinyl or 4-tetrahydropyranyl; propyl substituted with morpholinyl where the morpholinyl is linked to the propyl through the N heteroatom; methyl, ethyl or propyl each substituted with 4-piperidinyl substituted on the nitrogen atom with (CH$_3$)$_3$C—O—C(=O)—, 4-piperidinyl substituted on the nitrogen atom with —CH$_3$, 4-piperazinyl substituted on the nitrogen atom with (CH$_3$)$_3$C—O—C(=O)—, 4-piperazinyl substituted on the nitrogen atom with —CH$_2$CH$_2$OH, 4-piperazinyl substituted on the nitrogen atom with —CH$_2$CH$_2$OH, 4-piperazinyl substituted on the nitrogen atom with —CH$_2$CH$_2$CH$_2$OH, 1-piperidinyl substituted in the 1 position by —OH, 1-piperidinyl substituted in the 1 position by —O—CH$_3$; methyl substituted with 2-thiophenyl substituted in the 5 position with chlorine; methyl substituted with 4-piperidinyl substituted on the nitrogen atom with (CH$_3$)$_3$C—O—C(=O)— and in the 4 position by —OH, C$_{1-6}$alkyl substituted with —C(=O)—R$^6$, for example —C(CH$_3$)$_2$—C(=O)-(piperazin-4-yl), —C(CH$_3$)$_2$—C(=O)-(piperazin-4-yl) substituted on the nitrogen atom in the 1 position by (CH$_3$)$_3$C—O—C(=O)—, —CH$_2$—C(=O)-(pyrrolidin-1-yl) substituted in the 3 position by —OH, hydroxyC$_{1-6}$alkyl substituted with R$^6$, for example —CH$_2$CHOHCH$_2$— substituted with 1-piperidinyl, C$_{1-6}$alkyl substituted with —Si(CH$_3$)$_3$, for example —CH$_2$Si(CH$_3$)$_3$, or cyanoC$_{1-4}$alkyl, for example —CH$_2$CH$_2$CN;

each R$^2$ is independently selected from hydroxyl, halogen, for example fluorine, chlorine or bromine, cyano, C$_{1-4}$alkyl, for example —CH$_3$, C$_{2-4}$alkenyl, for example —CH=CH$_2$, C$_{1-4}$alkoxy, for example CH$_3$O—, (CH$_3$)$_2$CHO—, CH$_3$CH$_2$O—, CD$_3$O—, hydroxyC$_{1-4}$alkyl, for example —CH$_2$OH, hydroxyC$_{1-4}$alkoxy, for example —OCH$_2$CH$_2$OH, haloC$_{1-4}$alkyl, for example —CF$_3$, haloC$_{1-4}$alkoxy, for example —OCH$_2$CH$_2$F, CHF$_2$O— or —OCF$_3$, C$_{1-4}$alkoxyC$_{1-4}$alkyl, for example —CH$_2$CH$_2$OCH$_3$, R$^{13}$, for example 2-dioxolanyl, C$_{1-4}$alkoxy substituted with R$^{13}$, for example —OCH$_2$C$_3$H$_5$, —C(=O)—R$^{13}$, for example —C(=O)-(1-pyrrolidinyl), C$_{1-4}$alkyl substituted with NR$^7$R$^8$, for example —CH$_2$N(CH$_2$CH$_3$)$_2$, —CH$_2$N(CH$_3$)$_2$ or —CH$_2$N(CH$_2$CH$_3$)(CH$_3$), $C_{1-4}$alkoxy substituted with $NR^7R^8$, for example —OCH$_2$CH$_2$NH$_2$, —NR$^7$R$^8$, for example —NHCH$_3$ or —N(CH$_3$)$_2$, —C(=O)—NR$^7$R$^8$; for example —C(=O)—NHCH$_3$, or two R$^2$ groups are attached to adjacent carbon atoms and together to form a radical of formula —O—(C(R$^{17}$)$_2$)$_p$—O— wherein R$^{17}$ represents hydrogen and p represents 1;

R$^3$ represents $C_{1-6}$alkyl, for example —CH$_3$, —CH$_2$CH$_3$, —CH$_2$CH$_2$CH$_3$ or —CH$_2$CH(CH$_3$)$_2$, hydroxy$C_{1-6}$alkyl, for example —CH$_2$CH$_2$OH, —CH$_2$CH$_2$CH$_2$OH, —CH$_2$CHOHCH$_3$, —CH$_2$CHOHCH$_2$CH$_3$, —CH$_2$CHOHCH(CH$_3$)$_2$, —CH$_2$CH$_2$C(OH)(CH$_3$)$_2$, —CH$_2$CHOHCH$_2$OH, —CH$_2$C(CH$_3$)$_2$OH, —CD$_2$CD$_2$OH, —CD$_2$CD$_2$CD$_2$OH, or —CH(CH$_3$)CH$_2$OH, hydroxyhalo$C_{1-6}$alkyl, for example —CH$_2$CHOHCF$_3$, halo$C_{1-6}$alkyl, for example —CH$_2$CH$_2$CH$_2$Cl, —CH$_2$CH$_2$CH$_2$CH$_2$Cl, —CH$_2$CH$_2$F or —CH$_2$CH$_2$I, halo$C_{1-6}$alkyl optionally substituted with —O—C(=O)—$C_{1-6}$alkyl, for example —CH$_2$CH(CF$_3$)—O—C(=O)CH$_3$, hydroxy$C_{2-6}$alkynyl, for example —CH$_2$—C≡C—CH$_2$OH or —CH$_2$—C≡C—C(CH$_3$)$_2$OH, $C_{1-6}$alkyl substituted with —C(=O)—$C_{1-6}$alkyl, for example CH$_3$—C(=O)—CH$_2$—, (CH$_3$)$_2$CH—C(=O)—CH$_2$—, $C_{1-6}$alkoxy$C_{1-6}$alkyl wherein each $C_{1-6}$alkyl may optionally be substituted with one or two hydroxy groups, for example —CH$_2$CH$_2$OCH$_3$, —CH$_2$CH$_2$OCH$_2$CH$_3$ or —CH$_2$CHOHCH$_2$OCH$_3$, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, for example —CH$_2$CH(—O—C(=O)CH$_3$)CH$_2$OCH$_3$, $C_{1-6}$alkyl substituted with R$^9$, for example —CH$_2$—C$_3$H$_5$ or —CH$_2$C$_5$H$_9$, $C_{1-6}$alkyl substituted with cyclopropyl substituted by —CH$_2$OH, CH$_3$CH$_2$—O—C(=O)-4-pyridinyl, methyl substituted with 5-isoxazolyl which is substituted in the 3 position with —CH$_3$. or substituted with 3-isoxazolyl which is substituted in the 5 position by —CH$_3$, ethyl or propyl substituted by 4-morpholinyl, methyl substituted by 3-morpholinyl, methyl substituted by 6-morpholinyl, ethyl or propyl substituted by 4-morpholinyl which is substituted in the 2 and 6 positions by —CH$_3$, methyl substituted by 2-morpholinyl which is substituted in the 4 position by —CH$_2$—C$_6$H$_5$ methyl substituted by 3-morpholinyl substituted in the 5 position by two —CH$_3$, methyl substituted by 6-morpholinyl substituted in the 4 position by —CH(CH$_3$)$_2$, methyl substituted by 6-morpholinyl substituted in the 3 position by =O and 4 position by —CH(CH$_3$)$_2$, methyl substituted by 2-morpholinyl substituted in the 4 position by —CH$_2$—C$_6$H$_5$, methyl substituted with 2-tetrahydrofuranyl, 2-dioxolane, ethylene oxide, 2-furanyl, or 4-tetrahydropyranyl, methyl substituted with 3-oxetanyl which is substituted in the 3 position by —CH$_3$, methyl substituted with 3-oxetanyl substituted in the 3 position by —CH$_2$NHCH(CH$_3$)$_2$, methyl substituted with 3-pyridinyl or 2-pyrazinyl or propyl substituted with 4-pyridinyl methyl or propyl substituted with 2-pyrimidinyl, methyl substituted with 3-pyridinyl which is substituted in the 6 position by chlorine or methyl substituted with 2-pyridinyl which is substituted in the 6 position by bromine, propyl substituted with 6-pyridinyl substituted in the 4 position by —CH$_3$, propyl substituted with 6-pyridinyl substituted in the 3 position by —OCH$_3$, methyl substituted with 2-pyridinyl substituted in the 6 position by —OCH$_3$, methyl substituted with 6-pyridinyl substituted in the 2 position by —CH$_2$NH$_2$, methyl substituted with 6-pyridinyl substituted in the 2 position by —NHCH$_3$, propyl substituted with 2-pyrimidinyl substituted in the 4 position by —OCH$_3$, methyl substituted with 2-pyrimidinyl substituted in the 4 and 6 positions by —OCH$_3$, propyl substituted with 2-pyrimidinyl substituted in the 4 position by —OH, methyl substituted with 3-piperazinyl, ethyl substituted with 1-piperazinyl which is substituted in the 4 position by 4-piperidinyl being substituted in the 1 position by —C(=O)—CH$_3$, ethyl substituted with 1-piperazinyl substituted in the 4 position with —CH$_2$C(=O)NHCH(CH$_3$)$_2$, ethyl or propyl substituted with 1,2,3,6-tetrahydropyridine, $C_{1-6}$alkyl substituted with azetidinyl, propyl substituted by 1-azetidinyl which is substituted in the 3 position by two fluorines, propyl substituted by 1-azetidinyl which is substituted in the 3 position by one —OH, ethyl or propyl substituted with 1-pyrrolidinyl or 2-pyrrolidinyl, propyl substituted with 1-pyrrolidinyl which is substituted in the 3 position by two fluorines or propyl substituted with 1-pyrrolidinyl which is substituted in the 3 position by one fluorine, propyl substituted with 1-pyrrolidinyl which is substituted in the 2 position by —CH$_2$Cl, ethyl or propyl substituted with 1-pyrrolidinyl which is substituted in the 3 position by —OH, ethyl or propyl substituted with 1-pyrrolidinyl which is substituted in the 2 position by =O, propyl substituted with 1-pyrrolidinyl which is substituted in the 3 position by —S(=O)$_2$—CH$_3$, ethyl or propyl substituted with 1-pyrrolidinyl which is substituted in the 3 position with —NH$_2$, ethyl substituted with 1-pyrrolidinyl which is substituted in the 3 position with —N(CH$_3$)$_2$, propyl substituted with 1-pyrrolidinyl which is substituted in the 3 position with —NHCH$_3$, ethyl or propyl substituted with a) 1-pyrrolidinyl which is substituted in the 2 position with —CH$_3$; b) 1-pyrrolidinyl which is substituted in the 2 and the 5 position with —CH$_3$; or c) 1-pyrrolidinyl which is substituted in the 2 position with two —CH$_3$, ethyl substituted with 1-pyrrolidinyl which is substituted in the 2 position with —C(=O)OH, ethyl or propyl substituted with 1-pyrrolidinyl which is substituted in the 2 position by —CH$_2$OH or with pyrrolidinyl which is substituted with —C(CH$_3$)$_2$OH or —CH$_2$CH$_2$OH, propyl substituted with a) 1-pyrrolidinyl which is substituted in the 3 position by 1-piperidinyl, or b) 1-pyrrolidinyl which is substituted in the 3 position by 4-morpholinyl being substituted in positions 2 and 6 by —CH$_3$, ethyl or propyl substituted with 1-pyrrolidinyl which is substituted in the 3 position by —CN, propyl substituted with 1-pyrrolidinyl which is substituted in the 2 position by —CH$_2$CN, or ethyl substituted with 1-pyrrolidinyl substituted in the 2 position by —CH$_2$CN, propyl substituted with 1-pyrrolidinyl which is substituted in the 2 position by —CH$_2$NH—S(=O)$_2$—CF$_3$, methyl or ethyl substituted by a) 2-pyrrolidinyl which is substituted in the 1 position by $(CH_3)_3C-O-C(=O)-$ or b) 1-pyrrolidinyl which is substituted in the 2 position by $CH_3-O-C(=O)-$, methyl substituted by 3-pyrrolidinyl substituted in the 1-position by 2-pyridinyl substituted in the 3-position by $-OCH_3$ or methyl substituted by 3-pyrrolidinyl substituted in the 1-position by 2-pyrimidinyl substituted in the 4-position by $-OCH_3$, methyl, ethyl or propyl substituted by 4-piperidinyl or 1-piperidinyl, ethyl substituted by 1-piperidinyl which is substituted at the 4 position by two fluorines, methyl or ethyl substituted by a) 1-piperidinyl which is substituted at the 4 position by one $-OH$ or b) 4-piperidinyl which is substituted at the 4 position by one $-OH$, ethyl substituted by 1-piperidinyl which is substituted at the 3 position or the 4 position by $-NH_2$, ethyl substituted by 1-piperidinyl which is substituted at the 4 position by $-N(CH_3)_2$, methyl, ethyl or propyl substituted by a) 1-piperidinyl which is substituted at the 2 position by $-CH_3$, b) 1-piperidinyl which is substituted at the 2 and the 6 position by $-CH_3$, c) 4-piperidinyl which is substituted at the 1 position by $-CH(CH_3)_2$, d) 4-piperidinyl which is substituted at the 1 position by $-CH_3$, e) 1-piperidinyl which is substituted at the 3 and the 5 position by $-CH_3$, ethyl substituted by a) 1-piperidinyl which is substituted in the 4 position by $-C(CH_3)_2OH$, b) 1-piperidinyl which is substituted in the 4 position by $-CH_2CH_2OH$, c) 1-piperidinyl which is substituted in the 4 position by $-CH_2OH$, ethyl or propyl substituted with 1-piperidinyl which is substituted at the 3 position with $-CN$, methyl or ethyl substituted with a) 1-piperidinyl which is substituted in the 4 position by $CH_3CH_2-O-C(=O)-$, or b) 4-piperidinyl which is substituted in the 1 position by $(CH_3)_3C-O-C(=O)-$, methyl substituted with 4-piperidinyl which is substituted in the 4 position by $-OH$ and in the 1 position by $(CH_3)_3C-O-C(=O)-$, methyl substituted with 4-piperidinyl which is substituted in the 4 position by $-OCH_3$ and in the 1 position by $(CH_3)_3C-O-C(=O)-$, methyl or ethyl substituted with a) 1-piperidinyl which is substituted in the 4 position by $-OCH_3$ or b) 4-piperidinyl which is substituted in the 4 position by $-OCH_3$, propyl substituted with 1-piperidinyl which is substituted in the 4 position by $-CF_3$, ethyl substituted with 1-piperidinyl which is substituted in the 3 position by $-C(=O)-NH_2$, ethyl or propyl substituted with 1-piperidinyl substituted in the 2 position by $-C(=O)-NH_2$, ethyl substituted by 1-piperidinyl substituted at the 4 position by $=O$, or propyl substituted by 1-piperidinyl substituted at the 2 position by $=O$, ethyl substituted with 1-piperidinyl substituted in the 4 position by $-CH_2NH_2$, methyl substituted by 4-piperidinyl substituted in the 1-position by 2-pyrimidinyl substituted in the 4-position by $-OCH_3$, ethyl, propyl or butyl substituted with isoindole-1,3-dione, $-CH(CH_3)CH_2$-substituted with isoindolyl-1,3,-dione, ethyl substituted with 2-oxa-6-aza-spiro[3.3.]heptane, ethyl substituted with 1,4-dioxa-8-aza-spiro[4.5]decane, methyl substituted with 2-thiophenyl, methyl substituted with 2-thiophenyl which is substituted at the 5 position by chlorine, methyl substituted with 4-thiazolyl which is substituted in the 2 position by $-CH_3$, ethyl or propyl substituted with 1-piperazinyl, ethyl substituted with 1-piperazinyl which is substituted in the 4 position by $CH_3-C(=O)-$, ethyl substituted with 1-piperazinyl which is substituted in the 4 position by $-CH_2CH_2OH$, ethyl or propyl substituted with a) 1-piperazinyl which is substituted at the 3 and 5 positions by $-CH_3$ or b) 1-piperazinyl which is substituted at the 4 position by $-CH_3$, ethyl substituted with 1-piperazinyl which is substituted in the 3 position by $=O$, ethyl substituted with 1-piperazinyl which is substituted in the 4 position by $-C(=O)-C_3H_5$, methyl substituted with 2-piperazinyl substituted in the 1 and 4 position by methylphenyl wherein the phenyl is substituted in the 4 position by $CH_3O-$, ethyl substituted with 5-tetrazolyl, methyl substituted with a) 2-(1,3,4-oxadiazoyl) which is substituted at the 5 position by $-NH_2$ or b) 2-(1,3,4-oxadiazolyl) which is substituted at the 5 position by $-NH-CH_2CH_2OH$, methyl, ethyl or propyl substituted with 1-pyrazolyl or 2-imidazolyl, methyl substituted with 3-pyrazolyl or 5-pyrazolyl, methyl, ethyl or propyl substituted with a) 1-imidazolyl which is substituted at the 2 position by $-CH_3$, b) 3-pyrazolyl which is substituted at the 1 and 5 positions by $-CH_3$, c) 1-imidazolyl which is substituted at the 2 and 5 positions by $-CH_3$, d) 1-imidazolyl which is substituted at the 2 and 4 positions by $-CH_3$, e) 2-imidazolyl which is substituted at the 1 position by $-CH_3$ or f) 2-imidazolyl which is substituted at the 1 position by $-CH_2CH_3$, methyl substituted with 2-imidazolyl substituted at the 5 position by $-CH_3$ ethyl substituted with 1-pyrazolyl substituted at the 3 position by $-CH_3$ methyl substituted with 4-pyrazolyl substituted at the 1 position by $-CH_3$-methyl substituted with 2-imidazolyl substituted in the 3 position by $-S(=O)_2-N(CH_3)_2$ and in the 5 position by $-CH_3$, methyl substituted with 5-pyrazolyl substituted in the 2 position by 2-tetrahydropyran, or methyl substituted with 3-pyrazolyl substituted in the 1 position by 2-tetrahydropyran methyl substituted with 2-imidazolyl which is substituted in the 1 position by $-S(=O)_2-N(CH_3)_2$, methyl substituted with 4-(1,2,3-triazolyl), methyl substituted with a) 4-(1,2,3-triazolyl) which is substituted in the 1 position by $-CH_2CH_2OH$ or b) 4-(1,2,3-triazolyl) which is substituted in the 2 position by $-CH_2OH$, methyl substituted with 4-(1,2,3-triazolyl) which is substituted in the 1 position by $-CH_2C(=O)-OCH_2CH_3$, ethyl substituted with 1-(1,2,4-triazolyl, ethyl or propyl substituted with 1-(1,2,4-triazolyl) substituted in the 3 position by $-CH_3$, ethyl or propyl substituted with 2-(1,2,4-triazolyl) substituted in the 3 position by $-CH_3$, ethyl or propyl substituted with 3-oxazolidinyl which is substituted in the 2 position by $=O$, methyl substituted with 5-oxazolidinyl substituted in the 2 position by $=O$, methyl substituted with 5-oxazolidinyl substituted in the 2 position by $=O$ and in the 3 position by $-CH(CH_3)_2$, propyl substituted with 4-thiomorpholinyl which is substituted in the 1 position by two $=O$ groups, ethyl substituted with 1-homopiperazinyl, ethyl substituted with homomorpholinyl, $-CH_2-C_6H_5$, methyl substituted with phenyl which is substituted in the 2, 3 or 4 position by chlorine, cyano$C_{1-6}$alkyl, for example —CH$_2$CH$_2$CN or —CH$_2$CH$_2$CH$_2$CN, $C_{1-6}$alkyl substituted with —NR$^{11}$R$^{11}$, for example —CH$_2$CH$_2$NH$_2$, —CH$_2$CH$_2$CH$_2$NH$_2$, —CH$_2$CH$_2$CH$_2$CH$_2$NH$_2$, —CH$_2$CH (CH$_3$)NH$_2$, —CH(CH$_3$)CH$_2$NH$_2$, —CH$_2$CH$_2$NHCH$_3$, —CH$_2$CH$_2$CH$_2$NHCH$_3$, —CH$_2$CH$_2$NHCH$_2$CH$_3$, —CH$_2$CH$_2$NHCH(CH$_3$)$_2$, —CD$_2$-CD$_2$-NHCH(CH$_3$)$_2$, —CH$_2$CH$_2$CH$_2$NHCH(CH$_3$)$_2$, —CH(CH$_3$)CH$_2$NHCH (CH$_3$)$_2$, —CH$_2$CH$_2$N(CH$_2$CH$_3$)$_2$, —CH$_2$CH$_2$N(CH$_2$CH$_3$)(CH(CH$_3$)$_2$), —CH$_2$CH$_2$N(CH$_3$)$_2$ or —CH$_2$CH$_2$N(CH$_3$)CH (CH$_3$)$_2$, —CH$_2$CH$_2$CH$_2$NHCH$_2$CF$_3$, —CH$_2$CH$_2$NHCH$_2$CHF$_2$ or —CH$_2$CH$_2$NHCH$_2$CH$_2$F, —CH(CH$_3$)CH$_2$NHCH$_2$CF$_3$, —CH$_2$CH(CH$_3$)NHCH$_2$CF$_3$, —CH$_2$CH$_2$NHCH$_2$CF$_3$, —CH$_2$CH$_2$CH$_2$NHCH$_2$CHF$_2$—CH$_2$CH$_2$NHCH$_2$CF$_3$, —CH$_2$CH$_2$CH$_2$NHCH$_2$CHF$_2$, —CH$_2$CH$_2$CH$_2$NHC(CH$_3$)$_2$CH$_2$F, —CD$_2$-CD$_2$-CD$_2$-NHCH$_2$CF$_3$, —CH$_2$CH$_2$NH—C(=O)—CH$_3$, —CH$_2$CH$_2$NH—S(=O)$_2$—CH$_3$, —CH$_2$CH$_2$CH$_2$NH—S(=O)$_2$—CH$_3$, —CH$_2$CH$_2$NH—S(=O)$_2$—CH$_2$CH$_3$ or —CH$_2$CH$_2$NH—S(=O)$_2$—CH(CH$_3$)$_2$, —CH$_2$CH$_2$NH—S(=O)$_2$—N(CH$_3$)$_2$ or —CH$_2$CH$_2$CH$_2$NH—S(=O)$_2$—N(CH$_3$)$_2$, —CH$_2$CH$_2$NHCH$_2$CH$_2$OH, —CH$_2$CH$_2$CH$_2$NH—C(=O)—C(OH)(CH$_3$)CF$_3$ or —CH$_2$CH$_2$NH—C(=O)—C(OH)(CH$_3$)CF$_3$, —CH$_2$CH$_2$NH—C(=O)—C$_3$H$_5$, —CH$_2$CH$_2$NH—C(=O)-(piperidin-3-yl) where the piperidinyl is substituted at the 1 position by —CH$_3$, —CH$_2$CH$_2$NHCH$_2$CH$_2$CN,
—CH$_2$CH$_2$CH$_2$NHCH$_2$CH$_2$CN, —CH$_2$CH$_2$NHC$_3$H$_5$, —CH$_2$CH$_2$NHC$_5$H$_9$ or —CH$_2$CH$_2$NH-(2,2,6,6-tetramethyl-piperidin-4-yl),
—CH$_2$CH$_2$NH-(piperidin-4-yl) where the piperidinyl is substituted in the 1 position by —S(=O)$_2$NH$_2$,
—CH$_2$CH$_2$NHCH$_2$C$_3$H$_5$, —CH$_2$CH$_2$NHCH$_2$— (tetrahydrofuran-2-yl), —CH$_2$CH$_2$NHCH$_2$-(pyridin-6-yl),
—CH$_2$CH$_2$NHC(=O)—CF$_3$ or —CH$_2$CH$_2$CH$_2$NHC(=O)—CF$_3$;
—CH$_2$CH$_2$NHCH$_2$Si(CH$_3$)$_3$,
—CH$_2$CH$_2$N(CH$_3$)CH$_2$—C$_6$H$_5$,
one of R$^{10}$ and R$^{11}$ represents —CH(CH$_3$)$_2$ and the other represents —CH$_2$—C$_6$H$_5$ wherein the phenyl is substituted in the 4-position by —NH$_2$,
—CH$_2$CH$_2$N(CH(CH$_3$)$_2$)CH$_2$CH$_2$CH$_2$NH$_2$,
—CH$_2$CH$_2$CH$_2$NHCH$_2$C(=O)NH$_2$ or —CH$_2$CH$_2$NHCH$_2$C(=O)NH$_2$,
—CH$_2$CH$_2$CH$_2$N(CH$_3$)—OCH$_3$,
—CH$_2$CH$_2$NH—OCH$_3$, or
—CH$_2$CH$_2$NHCH$_2$CHOHCF$_3$;
—CH$_2$CH$_2$CH$_2$NHCOOH.
$C_{1-6}$alkyl substituted with hydroxyl and —NR$^{10}$R$^{11}$, for example —CH$_2$CHOHCH$_2$NH$_2$, —CH$_2$CHOHCH$_2$NHCH$_3$ or —CH$_2$CHOHCH$_2$NHCH(CH$_3$)$_2$, —CH$_2$CHOHCH$_2$NHCH$_2$CF$_3$, —CH$_2$CHOHCH$_2$N(CH(CH$_3$)$_2$)—C(=O)CH$_2$Cl,
$C_{1-6}$alkyl substituted with one or two halogens and —NR$^{10}$R$^{11}$, for example —CH$_2$CHFCH$_2$NH$_2$,
$C_{1-6}$alkyl substituted with —C(=O)—O—$C_{1-6}$alkyl, for example —CH$_2$—C(=O)—O—CH$_2$CH$_3$ or —CH$_2$CH$_2$—C(=O)—O—CH$_2$CH$_3$, —CH(CH$_3$)C(=O)—O—CH$_2$CH$_3$,
$C_{1-6}$alkyl (for example methyl) substituted with $C_{1-6}$alkoxy$C_{1-6}$alkyl-C(=O)—, for example —CH$_2$—C(=O)—CH$_2$OCH$_3$,
$C_{1-6}$alkyl substituted with —O—C(=O)—NR$^{11}$R$^{11}$, for example —CH$_2$—C(=O)NH$_2$, —CH$_2$—C(=O)NHCH$_3$, —CH$_2$C(=O)NHCH(CH$_3$)$_2$ or —CH$_2$CH$_2$C(=O)NHCH(CH$_3$)$_2$, —CH$_2$—C(=O)—NHCH$_2$ OCH$_3$, —CH$_2$—C(=O)—NH—CH$_2$CH$_2$— (pyrrolidin-1-yl) or —CH$_2$—C(=O)—NH—CH$_2$CH$_2$— (imidazol-2-yl), —CH$_2$—C(=O)—NHCH$_2$CH$_2$OH, —CH$_2$—C(=O)—NHCH$_2$CH$_2$NH$_2$, —CH$_2$CH$_2$C(=O)—NHCH$_2$CF$_3$—CH$_2$CH$_2$C(=O)N(CH$_3$)—OCH$_3$,
—CH$_2$C(=O)NH-(pyridin-2-yl) wherein the pyridin-2-Y1 is substituted in the 3-position by —OCH$_3$, —CH$_2$C(=O)NH-(pyridin-6-yl) wherein the pyridin-6-Y1 is substituted in the 4-position by —CH$_3$ or —CH$_2$C(=O)NH-(pyrimidin-2-yl) wherein the pyrimidin-2-Y1 is substituted in the 4-position by —OCH$_3$, —CH$_2$C(=O)NH-(pyridin-3-yl), —CH$_2$C(=O)NH-(pyridin-6-yl) or —CH$_2$C(=O)NH-(pyridin-4-yl),
$C_{1-6}$alkyl substituted with carboxyl, for example —CH$_2$C(=O)OH or —CH$_2$CH$_2$C(=O)OH,
$C_{1-6}$alkyl substituted with —O—C(=O)—NR$^{11}$R$^{11}$, for example —CH$_2$CH$_2$—O—C(=O)—NHCH$_3$,
$C_{1-6}$alkyl substituted with —NR$^{12}$—S(=O)$_2$—$C_{1-6}$alkyl, for example —CH$_2$CH$_2$NH—S(=O)$_2$—CH$_3$, CH$_2$CH$_2$CH$_2$NH—S(=O)$_2$—CH$_3$, —CH$_2$CH$_2$NH—S(=O)$_2$—CH(CH$_3$)$_2$ or —CH$_2$CH$_2$NH—S(=O)$_2$—CH$_2$CH$_3$,
$C_{1-6}$alkyl substituted with —NR$^{12}$—S(=O)$_2$—NR$^{14}$R$^{15}$, for example —CH$_2$CH$_2$NH—S(=O)$_2$—N(CH$_3$)$_2$ or —CH$_2$CH$_2$CH$_2$NH—S(=O)$_2$—N(CH$_3$)$_2$,
$C_{1-6}$alkyl substituted with R$^9$ and optionally substituted with —O—C(=O)—$C_{1-6}$alkyl, R$^9$ represents 1H-pyrrolo[3,2-b]pyridinyl, 1-methyl-1H-pyrrolo[3,2-b]pyridinyl or furo[3,2-b]pyridinyl,
$C_{1-6}$alkyl substituted with hydroxyl and R$^9$, for example
propyl substituted with —OH and 1-pyrrolidinyl,
propyl substituted with —OH and 1-pyrrolidinyl where the 1-pyrrolidinyl is substituted at the 3 position by two fluorines,
propyl substituted with —OH and 1-pyrrolidinyl where the 1-pyrrolidinyl is substituted at the 3 position by a cyano group,
propyl substituted with —OH and 4-morpholinyl, propyl substituted with —OH and 1-piperidinyl,
propyl substituted with —OH and 2-(1,2,4-triazolyl) substituted in the 3 position by —CH$_3$,
propyl substituted with —OH and 1-imidazolyl substituted in the 2 position by —CH$_3$,
propyl substituted with —OH and isoindole-1,3-dione,
—$C_{1-6}$alkyl-C(R$^{12}$)=N—O—R$^{12}$, for example —CH$_2$C(CH$_3$)=N—O—H, —CH$_2$C(CH$_2$OCH$_3$)=N—O—H or —CH$_2$C(CH(CH$_3$)$_2$)=N—O—H—S(=O)$_2$—NR$^{14}$R$^{15}$, for example —S(=O)$_2$—N(CH$_3$)$_2$, $C_{1-6}$alkyl substituted with —S(=O)$_2$—$C_{1-6}$alkyl, for example —CH$_2$CH$_2$—S(=O)$_2$—CH$_3$,
$C_{1-6}$alkyl substituted with —C(=O)—NR$^{10}$R$^{11}$, for example
—CH$_2$C(=O)NH$_2$,
—CH$_2$C(=O)NHCH$_3$,
—CH$_2$C(=O)—NHCH$_2$CH$_2$OCH$_3$,
—CH$_2$C(=O)—NH—CH$_2$CH$_2$— (pyrrolidin-1-yl) or —CH$_2$C(=O)—NH—CH$_2$CH$_2$— (imidazol-2-yl),
—CH$_2$C(=O)—NHCH$_2$CH$_2$OH, —CH$_2$C(=O)—NHCH$_2$CH$_2$NH$_2$,
$C_{1-6}$alkyl substituted with —C(=O)—R$^9$, for example —CH$_2$C(=O)—R$^9$ and R$^9$ is 1-pyrrolidinyl,
$C_{2-6}$alkenyl substituted with R$^9$, for example —CH$_2$CH=CH-(2-pyrimidinyl), —CH$_2$CH=CH-(2-pyrimidinyl) wherein the 2-pyrimidinyl is substituted in the 4-position by —OCH$_3$, —CH$_2$CH=CH-(2-pyridinyl) wherein the 2-pyridinyl is substituted in the 4-position by —CH₃ or —CH₂CH=CH-(2-pyridinyl) wherein the 2-pyridinyl is substituted in the 3-position by —OCH₃, C$_{2-6}$alkynyl substituted with R⁹, for example —CH₂—C≡C— (2-imidazolyl) wherein the 2-imidazolyl is substituted in the 1 position by —CH₃ or —CH₂—C≡C— (5-imidazolyl) wherein the 5-imidazolyl is substituted in the 1 position by —CH₃, —CH₂—C≡C— (4-pyridinyl), —CH₂—C≡C— (3-pyridinyl), —CH₂—C≡C— (2-pyridinyl), —CH₂—C≡C— (2-pyrimidinyl), —CH₂—C≡C— (6-pyrazinyl), —CH₂—C≡C— (6-pyridinyl) substituted in the 2 or 4-position with —CH₂OH, —CH₂—C≡C— (4-pyridinyl) substituted in the 6-position with —OCH₃, —CH₂—C≡C— (2-pyridinyl) substituted in the 3 or 5-position with —OCH₃, —CH₂—C≡C— (2-pyrimidinyl) substituted in the 4 or 6-position with —OCH₃, —CH₂—C≡C— (6-pyridinyl) substituted in the 2, 4 or 5-position with —OCH₃, —CH₂—C≡C— (6-pyrimidinyl) substituted in the 4-position with —OCH₃, —CH₂—C≡C— (5-pyrazinyl) substituted in the 6-position with —OCH₃, —CH₂—C≡C— (2-pyrimidinyl) substituted in the 6-position with —OCH₂CH₃, —C(CH₃)₂—C≡C— (2-pyrimidinyl) substituted in the 4-position with —OCH₃, —CH₂—C≡C— (2-pyrimidinyl) substituted in the 4-position with —OCH(CH₃)₂; —CH₂—C≡C— (6-pyridinyl) substituted in the 2 or the 4-position with cyano, —CH₂—C≡C— (4-pyridinyl) substituted in the 5 or 6-position with cyano;

—CH₂—C≡C— (6-pyridinyl) substituted in the 2 or 4-position with —NH₂, —CH₂—C≡C— (6-pyrimidinyl) substituted in the 2-position with —NH₂, —CH₂—C≡C— (2-pyridinyl) substituted in the 3-position with —NH₂, —CH₂—C≡C— (3-pyrazinyl) substituted in the 6-position with —NH₂, —CH₂—C≡C— (6-pyridinyl) substituted in the 5-position with —NHCH₃, —CH₂—C≡C— (6-pyridinyl) substituted in the 3 or 4-position with —CH₃, —CH₂—C≡C— (2-pyridinyl) substituted in the 3-position with —CH₃, —CH₂—C≡C— (2-pyrimidinyl) substituted in the 4-position with —CH₃, —CH₂—C≡C— (2-pyrimidinyl) substituted in the 6-position with —CH₂CH₃, —CH₂—C≡C— (6-pyrimidinyl) substituted in the 2-position with —CH₃ and in the 4-position with —NH₂, —CH₂—C≡C— (6-pyrimidinyl) substituted in the 2-position with —NH₂ and in the 4-position with —Cl, —CH₂—C≡C— (2-pyrazinyl) substituted in the 3-position with —Cl, —CH₂—C≡C— (3-pyrazinyl) substituted in the 5-position with —Cl, —CH₂—C≡C— (2-pyridinyl) substituted in the 3-position with —F, —CH₂—C≡C— (5-pyridinyl) substituted in the 6-position with —Br;

—CH₂—C≡C— (6-pyridinyl) substituted in the 4-position with —C(=O)—NH₂;

—CH₂—C≡C— (6-pyridinyl) substituted in the 5-position with CH₃—O—C(=O)—, —CH₂—C≡C— (2-pyrimidinyl) substituted in the 6-position with CH₃—O—C(=O)—;

—CH₂—C≡C— (2-pyridinyl) substituted in the 3-position with —CF₃,

—CH₂—C≡C— (5-thiazolyl),

—CH₂—C≡C— (phenyl),

—CH₂—C≡C— (phenyl) where the phenyl is substituted in the 5-position by —OCH₃,

—CH₂—C≡C— (3-azetidinyl) substituted in the 1-position by C(CH₃)₃—O—C(=O)— and in the 3-position by —OH, —CH₂—C≡C— (3-azetidinyl) substituted in the 3-position by —OH, —CH₂—C≡C— (3-pyrrolidinyl) substituted in the 1-position by C(CH₃)₃—O—C(=O)— and in the 3-position by —OH, —CH₂—C≡C— (3-pyrrolidinyl) substituted in the 3-position by —OH, —CH₂—C≡C— (4-piperidinyl), —CH₂—C≡C— (4-piperidinyl) substituted in the 4-position by —OH, —CH₂—C≡C— (4-piperidinyl) substituted in the 1-position by C(CH₃)₃—O—C(=O)—, —CH₂—C≡C— (4-tetrahydrofuranyl) substituted in the 3-position by —OH, —CH₂—C≡C— (4-tetrahydropyranyl) substituted in the 4-position by —OH, —CH₂—C≡C— (cyclohexyl), C$_{1-6}$alkyl substituted with R⁹, R⁹ represents a 6 to 8 membered bridged heterocyclyl group, for example 2,5-diazabicyclo[2.2.1]heptanyl optionally substituted by —C(=O)—O—C₄alkyl, C$_{1-6}$alkyloxyC$_{1-6}$alkyl wherein each C$_{1-6}$alkyl may optionally be substituted with one or two hydroxyl groups, for example —CH₂CHOHCH₂OCH₃, C$_{2-6}$alkenyl, for example —CH₂—CH=CH₂, C$_{2-6}$alkynyl, for example —CH₂—C≡C—H or —C(CH₃)₂—C≡C—H, C$_{1-6}$alkyl substituted with C$_{1-6}$alkoxyC$_{1-6}$alkyl-C(=O)—, for example —CH₂—C(=O)—CH₂OCH₃, or R¹³, for example 3-oxetanyl, cyclohexanyl substituted in the 4 position by —NH—CH(CH₃)₂, C$_{1-6}$alkyl substituted by R⁹, wherein R⁹ is a saturated heterocyclyl substituted by R¹³, wherein R¹³ is a saturated heterocyclyl which is optionally substituted, for example substituted by —C(=O)—C$_{1-6}$alkyl. In one embodiment R⁹ is piperazinyl substituted by R¹³ wherein R¹³ is piperidinyl substituted by —C(=O)—C$_{1-6}$alkyl, C$_{1-6}$alkyl substituted by R⁹, wherein R⁹ is a saturated heterocyclyl substituted by R¹³, wherein R¹³ is a saturated heterocyclyl which is optionally substituted, for example substituted by —C(=O)—C$_{1-6}$alkyl. In one embodiment R⁹ is piperazinyl substituted by R¹³ wherein R¹³ is piperidinyl substituted by —C(=O)—C$_{1-6}$alkyl.

In one embodiment there is provided a compound of formula (I⁰):

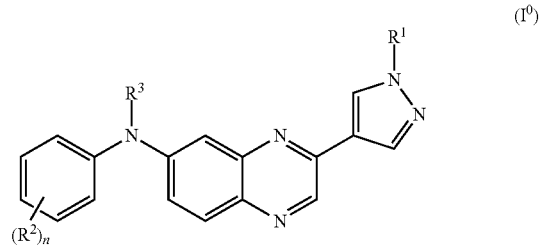

including any stereochemically isomeric form thereof, wherein n represents an integer equal to 0, 1, 2, or 3;

R¹ represents hydrogen, $C_{1-6}$alkyl, for example —CH$_3$, —CD$_3$, —CH$_2$CH$_3$, —CH$_2$CH$_2$CH$_3$, —CH$_2$CH(CH$_3$)$_2$, —CH(CH$_3$)$_2$, —CH$_2$CH(CH$_3$)$_2$, $C_{2-4}$alkenyl, for example —CH$_2$—CH=CH$_2$, hydroxyC$_{1-6}$alkyl, for example —CH$_2$CH$_2$OH, —CH$_2$C(CH$_3$)$_2$OH or CH$_2$CHOHCH$_2$OH, haloC$_{1-6}$alkyl, for example —CH$_2$CH$_2$F, CH$_2$CH$_2$CH$_2$Cl or CH$_2$CH$_2$Br, $C_{1-6}$alkoxyC$_{1-6}$alkyl wherein each C$_{1-6}$alkyl may optionally be substituted with one or two hydroxyl groups, for example —CH$_2$CH$_2$OCH$_3$, $C_{1-6}$alkyl substituted with —NR$^4$R$^5$, for example —CH$_2$CH$_2$NH$_2$ or —CH$_2$CH$_2$CH$_2$NH$_2$, —CH$_2$CH$_2$NHCH$_3$, —CH$_2$CH$_2$NHS(=O)$_2$N(CH$_3$)$_2$, —CH$_2$CH$_2$NHS(=O)$_2$N(CH$_3$)$_2$, $C_{1-6}$alkyl substituted with —C(=O)—NR$^4$R$^5$, for example —CH$_2$C(=O)N(CH$_3$)$_2$, —CH$_2$C(=O)NHCH$_3$ or —C(CH$_3$)$_2$C(=O)NHCH$_3$—C(CH$_3$)$_2$C(=O)NHCH$_2$CH$_2$OH or —CH$_2$C(=O)NHCH$_2$CH$_2$OH, —CH$_2$C(=O)NHCH$_2$CH$_2$OCH$_3$ or —C(CH$_3$)$_2$C(=O)NHCH$_2$CH$_2$OCH$_3$, —CH$_2$—C(=O)—NH—CH$_2$—CH$_2$—(pyrrolidin-1-yl), —CH$_2$CH$_2$CH$_2$NHCH$_2$CH$_2$—S(=O)$_2$—CH$_3$, —S(=O)$_2$—C$_{1-6}$alkyl, for example —S(=O)$_2$—CH$_3$, —S(=O)$_2$—NR$^{14}$R$^{15}$, for example —S(=O)$_2$—N(CH$_3$)$_2$, $C_{1-6}$alkyl substituted with —S(=O)$_2$—C$_{1-6}$alkyl, for example —CH$_2$CH$_2$S(=O)$_2$—CH$_3$, $C_{1-6}$alkyl substituted with —NH—S(=O)$_2$—C$_{1-6}$alkyl, for example —CH$_2$CH$_2$NHS(=O)$_2$—CH$_3$, R$^6$, for example 2-tetrahydropyranyl, 3-azetidinyl substituted in the 1 position by —CH$_2$CH$_2$OH, 4-piperidinyl substituted on the nitrogen atom with (CH$_3$)$_3$C—O—C(=O)—, 4-piperidinyl substituted on the nitrogen atom with —S(=O)$_2$CH$_3$, $C_{1-6}$alkyl substituted with R$^6$, for example methyl or ethyl each substituted with 4-piperidinyl, 4-piperazinyl, 1-pyrrolidinyl or 4-tetrahydropyranyl; propyl substituted with morpholinyl where the morpholinyl is linked to the propyl through the N heteroatom; methyl, ethyl or propyl each substituted with 4-piperidinyl substituted on the nitrogen atom with (CH$_3$)$_3$C—O—C(=O)—, 4-piperidinyl substituted on the nitrogen atom with —CH$_3$, 4-piperazinyl substituted on the nitrogen atom with (CH$_3$)$_3$C—O—C(=O)—, 4-piperazinyl substituted on the nitrogen atom with —CH$_2$CH$_2$OH, 4-piperazinyl substituted on the nitrogen atom with —CH$_2$CH$_2$CH$_2$OH, 1-piperidinyl substituted in the 1 position by —OH, 1-piperidinyl substituted in the 1 position by —O—CH$_3$; methyl substituted with 2-thiophenyl substituted in the 5 position with chlorine; methyl substituted with 4-piperidinyl substituted on the nitrogen atom with (CH$_3$)$_3$C—O—C(=O)— and in the 4 position by —OH, $C_{1-6}$alkyl substituted with —C(=O)—R$^6$, for example —C(CH$_3$)$_2$—C(=O)-(piperazin-4-yl), —C(CH$_3$)$_2$—C(=O)-(piperazin-4-yl) substituted on the nitrogen atom in the 1 position by C(CH$_3$)$_3$—O—C(=O)—, —CH$_2$—C(=O)-(pyrrolidin-1-yl) substituted in the 3 position by —OH, hydroxyC$_{1-6}$alkyl substituted with R$^6$, for example —CH$_2$CHOHCH$_2$— substituted with 1-piperidinyl; or $C_{1-6}$alkyl substituted with —Si(CH$_3$)$_3$, for example —CH$_2$Si(CH$_3$)$_3$;

each R$^2$ is independently selected from halogen, for example fluorine, chlorine or bromine, cyano, $C_{1-4}$alkyl, for example —CH$_3$, $C_{2-4}$alkenyl, for example —CH=CH$_2$, $C_{1-4}$alkoxy, for example CH$_3$O—, (CH$_3$)$_2$CHO—, CH$_3$CH$_2$O—, CD$_3$O—, hydroxyC$_{1-4}$alkyl, for example —CH$_2$OH, hydroxyC$_{1-4}$alkoxy, for example —OCH$_2$CH$_2$OH, haloC$_{1-4}$alkoxy, for example —OCH$_2$CH$_2$F or CHF$_2$O—, $C_{1-4}$alkoxyC$_{1-4}$alkyl, for example —CH$_2$CH$_2$OCH$_3$, R$^{13}$, for example 2-dioxolanyl, $C_{1-4}$alkoxy substituted with R$^{13}$, for example —OCH$_2$C$_3$H$_5$, —C(=O)—R$^{13}$, for example —C(=O)-(1-pyrrolidinyl), $C_{1-4}$alkyl substituted with NR$^7$R$^8$, for example —CH$_2$N(CH$_2$CH$_3$)$_2$, —CH$_2$N(CH$_3$)$_2$ or —CH$_2$N(CH$_2$CH$_3$)(CH$_3$), $C_{1-4}$alkoxy substituted with NR$^7$R$^8$, for example —OCH$_2$CH$_2$NH$_2$, —NR$^7$R$^8$, for example —NHCH$_3$, or —C(=O)—NR$^7$R$^8$; for example —C(=O)—NHCH$_3$;

R$^3$ represents $C_{1-6}$alkyl, for example —CH$_3$, —CH$_2$CH$_3$, —CH$_2$CH$_2$CH$_3$ or —CH$_2$CH(CH$_3$)$_2$, hydroxyC$_{1-6}$alkyl, for example —CH$_2$CH$_2$OH, —CH$_2$CH$_2$CH$_2$OH, —CH$_2$CHOHCH$_3$, —CH$_2$CHOHCH$_2$CH$_3$, —CH$_2$CHOHCH(CH$_3$)$_2$, —CH$_2$CH$_2$C(OH)(CH$_3$)$_2$, —CH$_2$CHOHCH$_2$OH or —CH$_2$C(CH$_3$)$_2$OH, hydroxyhaloC$_{1-6}$alkyl, for example —CH$_2$CHOHCF$_3$, haloC$_{1-6}$alkyl, for example —CH$_2$CH$_2$CH$_2$Cl or —CH$_2$CH$_2$CH$_2$CH$_2$Cl, $C_{1-6}$alkyl substituted with —C(=O)—C$_{1-6}$alkyl, for example CH$_3$—C(=O)—CH$_2$—, (CH$_3$)$_2$CH—C(=O)—CH$_2$—, $C_{1-6}$alkoxyC$_{1-6}$alkyl wherein each C$_{1-6}$alkyl may optionally be substituted with one or two hydroxy groups, for example —CH$_2$CH$_2$OCH$_3$, —CH$_2$CH$_2$OCH$_2$CH$_3$ or —CH$_2$CHOHCH$_2$OCH$_3$, $C_{1-6}$alkyl substituted with R$^9$, for example —CH$_2$—C$_3$H$_5$ or —CH$_2$C$_5$H$_9$, $C_{1-6}$alkyl substituted with cyclopropyl substituted by —CH$_2$OH or CH$_3$CH$_2$—O—C(=O)-methyl substituted with 5-isoxazoyl which is substituted in the 3 position with —CH$_3$.

or substituted with 3-isoxazoyl which is substituted in the 5 position by —CH$_3$, 3 ethyl or propyl substituted by 4-morpholinyl ethyl or propyl substituted by 4-morpholinyl which is substituted in the 2 and 6 positions by —CH$_3$ methyl substituted by 2-morpholinyl which is substituted in the 4 position by —CH$_2$—C$_6$H$_5$ methyl substituted with 2-tetrahydrofuranyl, 2-dioxolane, ethylene oxide, 2-furanyl, or 4-tetrahydropyranyl, methyl substituted with 3-oxetanyl which is substituted in the 3 position by —CH$_3$.

methyl substituted with 3-pyridinyl or 2-pyrazinyl.

methyl substituted with 3-pyridinyl which is substituted in the 6 position by chlorine or methyl substituted with 2-pyridinyl which is substituted in the 6 position by bromine, ethyl substituted with 1-piperazinyl which is substituted in the 4 position by 4-piperidinyl being substituted in the 1 position by —C(=O)—CH$_3$, ethyl or propyl substituted with 1,2,3,6-tetrahydropyridine, $C_{1-6}$alkyl substituted with azetidinyl, propyl substituted by 1-azetidinyl which is substituted in the 3 position by two fluorines, propyl substituted by 1-azetidinyl which is substituted in the 3 position by one —OH, ethyl or propyl substituted with 1-pyrrolidinyl or 2-pyrrolidinyl, propyl substituted with 1-pyrrolidinyl which is substituted in the 3 position by two fluorines or propyl substituted with 1-pyrrolidinyl which is substituted in the 3 position by one fluorine, propyl substituted with 1-pyrrolidinyl which is substituted in the 2 position by —CH$_2$Cl, ethyl or propyl substituted with 1-pyrrolidinyl which is substituted in the 3 position by —OH, ethyl or propyl substituted with 1-pyrrolidinyl which is substituted in the 2 position by =O, propyl substituted with 1-pyrrolidinyl which is substituted in the 3 position by —S(=O)$_2$—CH$_3$, ethyl or propyl substituted with 1-pyrrolidinyl which is substituted in the 3 position with —NH$_2$, ethyl substituted with 1-pyrrolidinyl which is substituted in the 3 position with —N(CH$_3$)$_2$, propyl substituted with 1-pyrrolidinyl which is substituted in the 3 position with —NHCH$_3$, ethyl or propyl substituted with a) 1-pyrrolidinyl which is substituted in the 2 position with —CH$_3$; b) 1-pyrrolidinyl which is substituted in the 2 and the 5 position with —CH$_3$; or c) 1-pyrrolidinyl which is substituted in the 2 position with two —CH$_3$, ethyl substituted with 1-pyrrolidinyl which is substituted in the 2 position with —C(=O)OH, ethyl or propyl substituted with 1-pyrrolidinyl which is substituted in the 2 position by —CH$_2$OH or with pyrrolidinyl which is substituted with —C(CH$_3$)$_2$OH or —CH$_2$CH$_2$OH, propyl substituted with a) 1-pyrrolidinyl which is substituted in the 3 position by 1-piperidinyl, or b) 1-pyrrolidinyl which is substituted in the 3 position by 4-morpholinyl being substituted in positions 2 and 6 by —CH$_3$, ethyl or propyl substituted with 1-pyrrolidinyl which is substituted in the 3 position by —CN, propyl substituted with 1-pyrrolidinyl which is substituted in the 2 position by —CH$_2$CN, propyl substituted with 1-pyrrolidinyl which is substituted in the 2 position by —CH$_2$NH—S(=O)$_2$—CF$_3$, methyl or ethyl substituted by a) 2-pyrrolidinyl which is substituted in the 1 position by (CH$_3$)$_3$C—O—C(=O)— or b) 1-pyrrolidinyl which is substituted in the 2 position by CH$_3$—O—C(=O)—, methyl, ethyl or propyl substituted by 4-piperidinyl or 1-piperidinyl, ethyl substituted by 1-piperidinyl which is substituted at the 4 position by two fluorines, methyl or ethyl substituted by a) 1-piperidinyl which is substituted at the 4 position by one —OH or b) 4-piperidinyl which is substituted at the 4 position by one —OH, ethyl substituted by 1-piperidinyl which is substituted at the 3 position or the 4 position by —NH$_2$, ethyl substituted by 1-piperidinyl which is substituted at the 4 position by —N(CH$_3$)$_2$, methyl, ethyl or propyl substituted by a) 1-piperidinyl which is substituted at the 2 position by —CH$_3$, b) 1-piperidinyl which is substituted at the 2 and the 6 position by —CH$_3$, c) 4-piperidinyl which is substituted at the 1 position by —CH(CH$_3$)$_2$, d) 4-piperidinyl which is substituted at the 1 position by —CH$_3$, e) 1-piperidinyl which is substituted at the 3 and the 5 position by —CH$_3$, ethyl substituted by a) 1-piperidinyl which is substituted in the 4 position by —C(CH$_3$)$_2$OH, b) 1-piperidinyl which is substituted in the 4 position by —CH$_2$CH$_2$OH, c) 1-piperidinyl which is substituted in the 4 position by —CH$_2$OH, ethyl or propyl substituted with 1-piperidinyl which is substituted at the 3 position with —CN, methyl or ethyl substituted with a) 1-piperidinyl which is substituted in the 4 position by CH$_3$CH$_2$—O—C(=O)—, or b) 4-piperidinyl which is substituted in the 1 position by (CH$_3$)$_3$C—O—C(=O)—, methyl substituted with 4-piperidinyl which is substituted in the 4 position by —OH and in the 1 position by (CH$_3$)$_3$C—O—C(=O)—, methyl substituted with 4-piperidinyl which is substituted in the 4 position by —OCH$_3$ and in the 1 position by (CH$_3$)$_3$C—O—C(=O)—, methyl or ethyl substituted with a) 1-piperidinyl which is substituted in the 4 position by —OCH$_3$ or b) 4-piperidinyl which is substituted in the 4 position by —OCH$_3$, propyl substituted with 1-piperidinyl which is substituted in the 4 position by —CF$_3$, ethyl substituted with 1-piperidinyl which is substituted in the 3 position by —C(=O)—NH$_2$, ethyl, propyl or butyl substituted with isoindole-1,3-dione, ethyl substituted with 2-oxa-6-aza-spiro[3.3.]heptane, ethyl substituted with 1,4-dioxa-8-aza-spiro[4.5]decane, methyl substituted with 2-thiophenyl, methyl substituted with 2-thiophenyl which is substituted at the 5 position by chlorine, methyl substituted with 4-thiazolyl which is substituted in the 2 position by —CH$_3$, ethyl or propyl substituted with 1-piperazinyl, ethyl substituted with 1-piperazinyl which is substituted in the 4 position by CH$_3$—C(=O)—, ethyl substituted with 1-piperazinyl which is substituted in the 4 position by —CH$_2$CH$_2$OH, ethyl or propyl substituted with a) 1-piperazinyl which is substituted at the 3 and 5 positions by —CH$_3$ or b) 1-piperazinyl which is substituted at the 4 position by —CH$_3$, ethyl substituted with 1-piperazinyl which is substituted in the 3 position by =O, ethyl substituted with 1-piperazinyl which is substituted in the 4 position by —C(=O)—C$_3$H$_5$, ethyl substituted with 5-tetrazolyl, methyl substituted with a) 2-(1,3,4-oxadiazoyl) which is substituted at the 5 position by —NH$_2$ or b) 2-(1,3,4-oxadiazoyl) which is substituted at the 5 position by —NH—CH$_2$CH$_2$OH, methyl, ethyl or propyl substituted with 1-pyrazoyl or 2-imidazolyl, methyl, ethyl or propyl substituted with a) 1-imidazoyl which is substituted at the 2 position by —CH$_3$, b) 3-pyrazolyl which is substituted at the 1 and 5 positions by —CH$_3$, c) 1-imidazolyl which is substituted at the 2 and 5 positions by —CH$_3$, d) 1-imidazolyl which is substituted at the 2 and 4 positions by —CH$_3$, e) 2-imidazolyl which is substituted at the 1 position by —CH$_3$ or f) 2-imidazolyl which is substituted at the 1 position by —CH$_2$CH$_3$, methyl substituted with 2-imidazolyl which is substituted in the 1 position by —S(=O)$_2$—N(CH$_3$)$_2$, methyl substituted with 4-(1,2,3-triazolyl), methyl substituted with a) 4-(1,2,3-triazolyl) which is substituted in the 1 position by —CH$_2$CH$_2$OH or b) 4-(1,2,3-triazolyl) which is substituted in the 2 position by —CH$_2$OH, methyl substituted with 4-(1,2,3-triazolyl) which is substituted in the 1 position by —CH$_2$C(=O)—OCH$_2$CH$_3$' ethyl or propyl substituted with 3-oxazolidinyl which is substituted in the 2 position by =O, propyl substituted with 4-thiomorpholinyl which is substituted in the 1 position by two =O groups, ethyl substituted with 1-homopiperazinyl,

—CH$_2$—C$_6$H$_5$, methyl substituted with phenyl which is substituted in the 2, 3 or 4 position by chlorine, $C_{1-6}$alkyl substituted with $-NR^{10}R^{11}$, for example $-CH_2CH_2NH_2$, $-CH_2CH_2CH_2NH_2$ or $-CH_2CH_2CH_2CH_2NH_2$, $-CH_2CH_2NHCH_3$, $-CH_2CH_2CH_2NHCH_3$, $-CH_2CH_2NHCH_2CH_3$, $-CH_2CH_2NHCH(CH_3)_2$ or $-CH_2CH_2CH_2NHCH(CH_3)_2$, $-CH_2CH_2N(CH_3CH_3)_2$, $-CH_2CH_2N(CH_2CH_3)(CH(CH_3)_2)$, $-CH_2CH_2CH_2NHCH_2CF_3$, $-CH_2CH_2NHCH_2CHF_2$ or $-CH_2CH_2NHCH_2CH_2F$, $-CH_2CH_2NH-C(=O)-CH_3$, $-CH_2CH_2NH-S(=O)_2-CH_3$, $-CH_2CH_2CH_2NH-S(=O)_2-CH_3$, $-CH_2CH_2NH-S(=O)_2-CH_2CH_3$ or $-CH_2CH_2NH-S(=O)_2-CH(CH_3)_2-CH_2CH_2NH-S(=O)_2-N(CH_3)_2$ or $-CH_2CH_2CH_2NH-S(=O)_2-N(CH_3)_2-CH_2CH_2NHCH_2CH_2OH$, $-CH_2CH_2CH_2NH-C(=O)-C(OH)(CH_3)CF_3$ or $-CH_2CH_2NH-C(=O)-C(OH)(CH_3)CF_3-CH_2CH_2NH-C(=O)-C_3H_5-CH_2CH_2NH-C(=O)$-(piperidin-3-yl) where the piperidinyl is substituted at the 1 position by $-CH_3$; $-CH_2CH_2NHCH_2CH_2CN-CH_2CH_2NHC_3H_5$, $-CH_2CH_2NHC_5H_9$ or $-CH_2CH_2NH$-(2,2,6,6-tetramethyl-piperidin-4-yl), $-CH_2CH_2NHCH_2C_3H_5$, $-CH_2CH_2NHCH_2$-(tetrahydrofuran-2-yl), $-CH_2CH_2NHC(=O)-CF_3$ or $-CH_2CH_2CH_2NHC(=O)-CF_3$, $-CH_2CH_2NHCH_2Si(CH_3)_3$, $-CH_2CH_2N(CH_3)CH_2-C_6H_5$, $-CH_2CH_2NH$-(piperidin-4-yl) where the piperidinyl is substituted in the 1 position by $-S(=O)_2NH_2$, $C_{1-6}$alkyl substituted with hydroxyl and $-NR^{10}R^{11}$, for example $-CH_2CHOHCH_2NH_2$, $-CH_2CHOHCH_2NHCH_3$ or $-CH_2CHOHCH_2NHCH(CH_3)_2$, $-CH_2CHOHCH_2NHCH_2CF_3$, $C_{1-6}$alkyl substituted with one or two halogens and $-NR^{10}R^{11}$, for example $-CH_2CHFCH_2NH_2$, $C_{1-6}$alkyl substituted with $-C(=O)-O-C_{1-6}$alkyl, for example $CH_2-C(=O)-O-CH_2CH_3$ or $-CH_2CH_2-C(=O)-O-CH_2CH_3$, $C_{1-6}$alkyl substituted with $-O-C(=O)-NR^{10}R^{11}$, for example $-CH_2-C(=O)NH_2$, $-CH_2-C(=O)NHCH_3$, $-CH_2-C(=O)-NHCH_2CH_2OCH_3$, $-CH_2-C(=O)-NH-CH_2CH_2$-(pyrrolidin-1-yl) or $-CH_2-C(=O)-NH-CH_2CH_2-$ (imidazol-2-yl), $-CH_2-C(=O)-NHCH_2CH_2OH$, $-CH_2-C(=O)-NHCH_2CH_2NH_2$, $C_{1-6}$alkyl substituted with carboxyl, for example $-CH_2C(=O)OH$ or $-CH_2CH_2C(=O)OH$, $C_{1-6}$alkyl substituted with $-O-C(=O)-NR^{10}R^{11}$, for example $-CH_2CH_2-O-C(=O)-NHCH_3$, $C_{1-6}$alkyl substituted with $-NR^{12}-S(=O)_2-C_{1-6}$alkyl, for example $-CH_2CH_2NH-S(=O)_2-CH_3$, $-CH_2CH_2CH_2NH-S(=O)_2-CH_3$, $-CH_2CH_2NH-S(=O)_2-CH(CH_3)_2$ or $-CH_2CH_2NH-S(=O)_2-CH_2CH_3$, $C_{1-6}$alkyl substituted with $-NR^{12}-S(=O)_2-NR^{14}R^{15}$, for example $-CH_2CH_2NH-S(=O)_2-N(CH_3)_2$ or $-CH_2CH_2CH_2NH-S(=O)_2-N(CH_3)_2$, $C_{1-6}$alkyl substituted with hydroxyl and $R^9$, for example propyl substituted with $-OH$ and 1-pyrrolidinyl,
propyl substituted with $-OH$ and 1-pyrrolidinyl where the 1-pyrrolidinyl is substituted at the 3 position by two fluorines,
propyl substituted with $-OH$ and 1-pyrrolidinyl where the 1-pyrrolidinyl is substituted at the 3 position by a cyano group,
propyl substituted with $-OH$ and 4-morpholinyl,
propyl substituted with $-OH$ and 1-piperidinyl,
propyl substituted with $-OH$ and isoindole-1,3-dione, $-C_{1-6}$alkyl-$C(R^{12})=N-O-R^{12}$, for example $-CH_2C(CH_3)=N-O-H$, $-CH_2C(CH_2OCH_3)=N-O-H$ or $-CH_2C(CH(CH_3)_2)=N-O-H$ $C_{1-6}$alkyl substituted with $-C(=O)-NR^{10}R^{11}$, for example
$-CH_2C(=O)NH_2$,
$-CH_2C(=O)NHCH_3$,
$-CH_2C(=O)-NHCH_2CH_2OCH_3$,
$-CH_2C(=O)-NH-CH_2CH_2-$ (pyrrolidin-1-yl) or $-CH_2C(=O)-NH-CH_2CH_2-$ (imidazol-2-yl),
$-CH_2C(=O)-NHCH_2CH_2OH$, $-CH_2C(=O)-NHCH_2CH_2NH_2$, $C_{1-6}$alkyl substituted with $-C(=O)-R^9$, for example $-CH_2C(=O)-R^9$ and $R^9$ is 1-pyrrolidinyl, $C_{2-6}$alkynyl substituted with $R^9$, for example $-CH_2-C\equiv C-$ (2-imidazolyl) wherein the 2-imidazolyl is substituted in the 1 position by $-CH_3$ or $-CH_2-C\equiv C-$ (5-imidazolyl) wherein the 5-imidazolyl is substituted in the 1 position by $-CH_3$, $C_{2-6}$alkenyl, for example $-CH_2-CH=CH_2$, $C_{2-6}$alkynyl, for example $-CH_2-C\equiv C-H$ $C_{1-6}$alkyl substituted with $C_{1-6}$alkoxy$C_{1-6}$alkyl-$C(=O)-$, for example $-CH_2-C(=O)-CH_2OCH_3$, or $R^{13}$.

In one embodiment the compound of formula (I) or formula ($I^0$) is a compound of formula ($I^{0'}$):

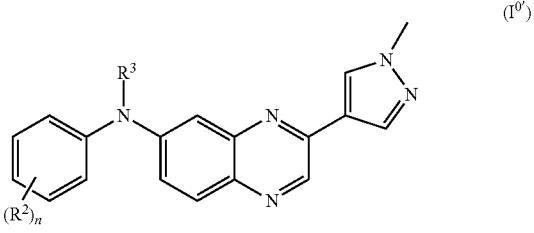

including any stereochemically isomeric form thereof;
and a N-oxide thereof, a pharmaceutically acceptable salt thereof or a solvate thereof, wherein n, $R^2$ and $R^3$ are as defined herein.

In one embodiment the compound of formula (I) or formula ($I^0$) is a compound of formula ($I^{0''}$),

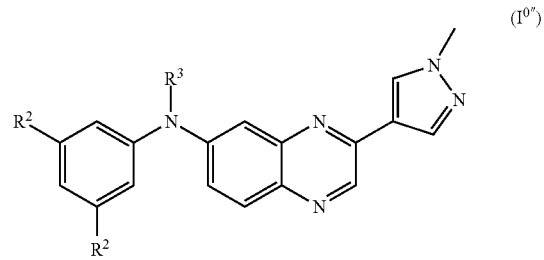

including any stereochemically isomeric form thereof;
and a N-oxide thereof, a pharmaceutically acceptable salt thereof or a solvate thereof, wherein $R^2$ and $R^3$ are as defined herein.

In one embodiment the compound of formula (I) or formula ($I^0$) is a compound of formula ($I^{0'''}$)

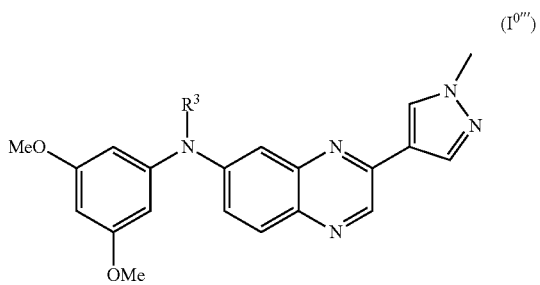

including any stereochemically isomeric form thereof;
and a N-oxide thereof, a pharmaceutically acceptable salt thereof or a solvate thereof, wherein $R^3$ is as defined herein.

In one embodiment there is provided a compound of formula ($I^{0'''}$) wherein $R^3$ is as defined in any of the embodiments above, in particular as defined at pages 86 line 20 to page 92 line 17.

In one embodiment the compound of formula (I) is a compound wherein one $R^{1a}$ is selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms; and the other $R^{1a}$ is selected from $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms; and wherein n, $R^1$, $R^2$ and $R^3$ are as defined herein.

In one embodiment the compound of formula (I) is a compound wherein each $R^{1a}$ is independently selected from $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms; and the other $R^{1a}$ is selected from $C_{1-4}$alkyl, hydroxy$C_{1-4}$alkyl, $C_{1-4}$alkyl substituted with amino or mono- or di($C_{1-4}$alkyl) amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms; and wherein n, $R^1$, $R^2$ and $R^3$ are as defined herein.

In one embodiment the compound of formula (I) is a compound wherein each $R^{1a}$ is hydrogen; and wherein n, $R^1$, $R^2$ and $R^3$ are as defined herein.

In one embodiment every alkyl group within the $R^3$ definition is a $C_{1-4}$alkyl group.

In one embodiment every alkyl group within the $R^3$ definition is a linear $C_{1-6}$alkyl group, in particular a linear $C_{1-4}$alkyl group.

In one embodiment the compound of formula (I) is a compound of formula (I'):

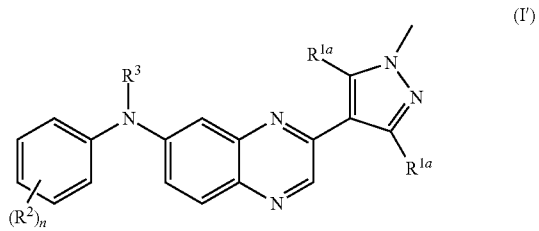

including any stereochemically isomeric form thereof;
and a N-oxide thereof, a pharmaceutically acceptable salt thereof or a solvate thereof, wherein n, $R^{1a}$, $R^2$ and $R^3$ are as defined herein.

In one embodiment the compound of formula (I) is a compound of formula (I'')

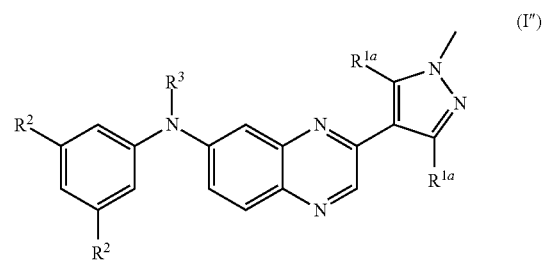

including any stereochemically isomeric form thereof;
and a N-oxide thereof, a pharmaceutically acceptable salt thereof or a solvate thereof, wherein $R^{1a}$, $R^2$ and $R^3$ are as defined herein.

In one embodiment the compound of formula (I) is a compound of formula (I''')

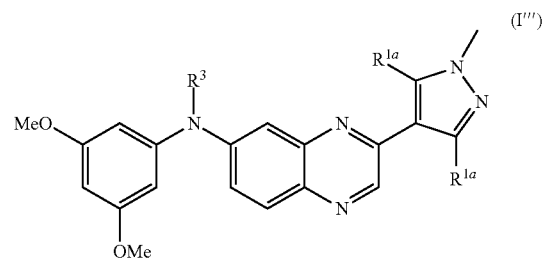

including any stereochemically isomeric form thereof;
and a N-oxide thereof, a pharmaceutically acceptable salt thereof or a solvate thereof, wherein $R^{1a}$ and $R^3$ is as defined herein.

In one embodiment there is provided a compound of formula (I), (I'), (I''), (I'''), ($I^0$), ($I^{0'}$), ($I^{0''}$) or ($I^{0'''}$) wherein every alkyl group within the $R^3$ definition is a linear $C_{1-6}$alkyl group. In one embodiment there is provided a compound of formula (I), (I'), (I''), (I'''), ($I^0$), ($I^{0'}$), ($I^{0''}$) or ($I^{0'''}$) wherein every alkyl group within the $R^3$ definition is a $C_{1-4}$alkyl group. In one embodiment there is provided a compound of formula (I), (I'), (I''), (I'''), ($I^0$), ($I^{0'}$), ($I^{0''}$) or ($I^{0'''}$) wherein every alkyl group within the $R^3$ definition is a linear $C_{1-4}$alkyl group.

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof as defined herein.

In general, compounds of formula (I) can be prepared according to the following reaction Scheme 1.

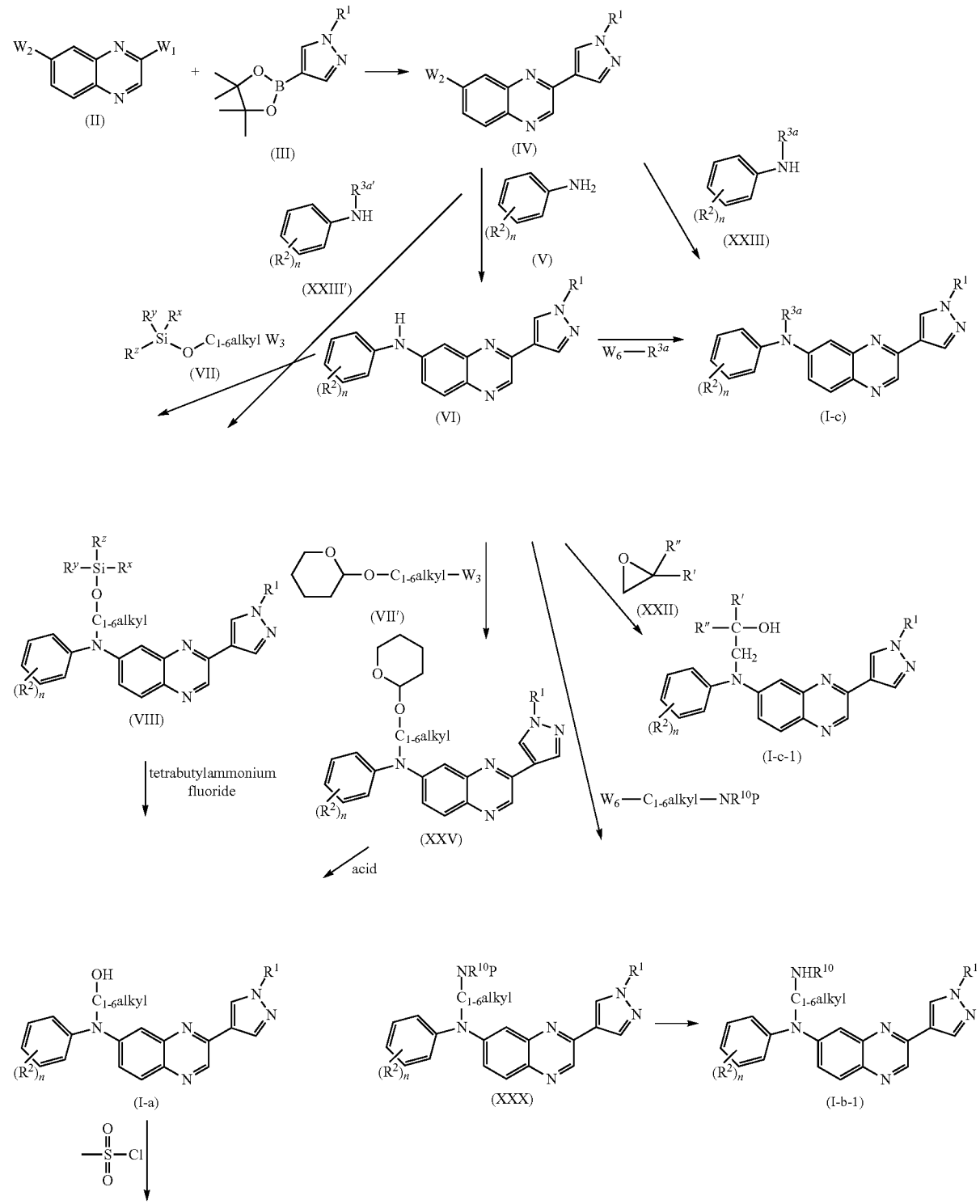

Scheme 1

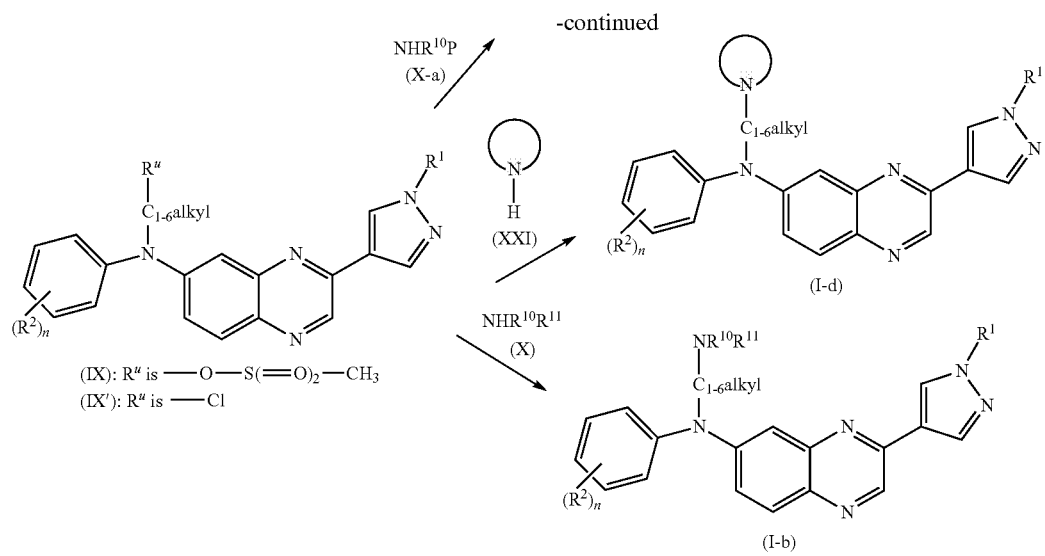

In scheme 1, an intermediate of formula (IV) is prepared by reacting an intermediate of formula (II) wherein $W_1$ and $W_2$, each independently represent a suitable leaving group, such as for example halo, e.g. chloro or bromo and the like, with an intermediate of formula (III) in the presence of a suitable catalyst, such as for example tetrakis(triphenylphosphine)palladium (0) or palladium (II) acetate, a suitable base, such as for example sodium carbonate, a suitable ligand, such as for example triphenylphosphine, and a suitable solvent or solvent mixture, such as for example ethylene glycol dimethylether and water. An intermediate of formula (II) wherein $W_1$ is chloro and $W_2$ is bromo can be prepared by reacting 7-bromo-2(1H)-quinoxalinone with phosphorus oxychloride, or alternatively with thionyl chloride and N,N-dimethylformamide in a suitable solvent, such as, for example toluene. An intermediate of formula (IV) can also be prepared by reacting 7-bromo-2-(1H-pyrazol-4-yl) quinoxaline with an intermediate $W_{10}$—$R^1$ wherein $W_{10}$ represents a suitable leaving group, such as for example halo, e.g. bromo and the like. An intermediate of formula (IV) wherein the $R^1$ substituent carries a suitable protective group can be prepared according to the same protocol but wherein 7-bromo-2-(1H-pyrazol-4-yl)quinoxaline is reacted with an intermediate $W_{10}$—$R^1$—P wherein P represents a suitable protective group, such as for example —C(=O)—O—C(CH$_3$)$_3$. The intermediate of formula (IV) is then further reacted in a next step with an intermediate of formula (V) in the presence of a suitable catalyst, such as for example palladium (II) acetate, a suitable base, such as sodium tert-butoxide or Cs$_2$CO$_3$, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water, resulting in an intermediate of formula (VI). Said intermediate of formula (VI) can then be reacted with an intermediate of formula (VII) wherein $W_3$ represents a suitable leaving group, such as for example halo, e.g. bromo and wherein $R^x$ and $R^y$ represent $C_{1-4}$alkyl, and $R^z$ represent $C_{1-4}$alkyl or phenyl, for instance $R^x$ and $R^y$ represent $CH_3$ and $R^z$ represents $C(CH_3)_3$ or phenyl, in the presence of a suitable base, such as for example sodium hydride, and a suitable solvent, such as for example N,N-dimethylformamide or N,N-dimethylacetamide, resulting in an intermediate of formula (VIII). Intermediates of formula (VIII) or intermediates of formula (VIII) wherein the $R^1$ substituent carries a suitable protective group can also be prepared by reacting an intermediate of formula (IV) or an intermediate of formula (IV) wherein the $R^1$ substituent carries a suitable protective group with an intermediate of formula (XXIII') wherein $R^{3a'}$ represent —$C_{1-6}$alkyl-O—Si($R^x$)($R^y$)($R^z$) in the presence of a suitable catalyst, such as for example palladium (II) acetate, a suitable ligand, such as for example racemic-2,2'-bis(diphenylphosphino)-1,1'-binaphtyl, a suitable base, such as for example Cs$_2$CO$_3$, and a suitable solvent, such as for example 1,2-dimethoxyethane. Intermediates of formula (VIII) can be converted into a compound of formula (I) wherein $R^3$ represents —$C_{1-6}$alkyl-OH, said compounds being represented by formula (I-a) or compounds of formula (I-a) wherein the $R^1$ substituent carries a suitable protective group, by reaction with tetrabutylammonium fluoride in the presence of a suitable solvent, such as for example tetrahydrofuran. This type of reaction can also be performed in the presence of a suitable acid, such as for example acetic acid or HCl, and a suitable solvent, such as for example tetrahydrofurane or dioxane. Alternatively, an intermediate of formula (VI) can react with an intermediate of formula (VII') wherein $W_3$ represents a suitable leaving group, such as for example halo, e.g. bromo and the like, in the presence of a suitable base, such as for example sodium hydride, and a suitable solvent, such as for example N,N-dimethylformamide or N,N-dimethylacetamide, resulting in an intermediate of formula (XXV) which can then be deprotected in the presence of a suitable acid, such as for example HCl, and a suitable solvent, such as for example an alcohol, e.g. methanol or isopropanol, to give a compound of formula (I-a). The compounds of formula (I-a) or compounds of formula (I-a) wherein the $R^1$ substituent carries a suitable protective group can be reacted with methanesulfonyl chloride in the presence of a suitable base, such as for example triethylamine, diisopropylethanamine or N,N-dimethyl-4-aminopyridine, and a suitable solvent, such as for example dichloromethane or tetrahydrofuran, to result in an intermediate of formula (IX) (mesylate derivative) or an intermediate of formula (IX') (chloride derivative) or intermediates of formula (IX) or (IX') wherein the $R^1$ substituent carries a suitable protective group. Intermediates of formula (IX) or (IX') can then be reacted with an intermediate of formula (X) to obtain a compound of formula (I) wherein $R^3$ represents $C_{1-6}$alkyl substituted with $NR^{10}R^{11}$, said compounds being represented by formula (I-b) or compounds of formula (I-b) wherein the $R^1$ substituent carries a suitable protective group. This reaction may optionally be performed in the presence of a suitable base, such as for example triethylamine, $K_2CO_3$, $Na_2CO_3$ or sodium hydride and optionally a suitable solvent, such as for example acetonitrile, tetrahydrofuran, dioxane, N,N-dimethylformamide, 1-methyl-pyrrolidinone, a suitable alcohol, e.g. 1-butanol and the like. This type of reaction can also be performed with a suitable salt of the intermediate of formula (X), e.g. HCl salt of intermediate of formula (X), or may be performed in the presence of potassium iodide. In this way compounds wherein $R^3$ represents iodo$C_{1-6}$alkyl can be obtained. Compounds of formula (I-b) wherein the $R^1$ substituent carries a suitable protective group can be converted in a compound of formula (I-b) by reaction with a suitable acid, such as for example trifluoroacetic acid, in the presence of a suitable solvent, such as for example dichloromethane.

Intermediates of formula (IX) can also react with a suitable nitrogen containing ring within the definition of $R^9$, said ring being represented by formula (XXI) or a suitable salt of an intermediate of formula (XXI), in the presence of a suitable solvent, such as for example acetonitrile, 1-methyl-2-pyrrolidinone, or an alcohol, e.g. 1-butanol, optionally in the presence of potassium iodide or a suitable base, such as for example $Na_2CO_3$, $K_2CO_3$ or triethylamine, resulting in a compound of formula (I-d). Intermediates of formula (IX) can also react with an intermediate of formula (X-a) wherein P represents a suitable protective group, such as for example —C(=O)—O—C(CH$_3$)$_3$, in the presence of a suitable base, such as for example sodium hydride, and a suitable solvent, such as for example dimethylacetamide, resulting in an intermediate of formula (XXX) which can be deprotected to a compound of formula (I-b-1) in the presence of a suitable acid, such as for example HCl or trifluoroacetic acid, and a suitable solvent, such as for example dichloromethane or an alcohol, e.g. methanol. Intermediates of formula (XXX) can also be prepared by reacting an intermediate of formula (VI) with an intermediate of formula $W_6$—$C_{1-6}$alkyl-$NR^{10}$P wherein $W_6$ represents a suitable leaving group, such as for example halo, e.g. bromo and the like, or —O—S(=O)$_2$—CH$_3$, and P is as defined above, in the presence of a suitable base, such as for example sodium hydride, and a suitable solvent, e.g. N,N-dimethylformamide or N,N-dimethylacetamide. Alternatively compounds of formula (I-d) or (1-b-1) can also be prepared by reacting respectively an intermediate of formula (VI) with an intermediate of formula $W_6$—$C_{1-6}$alkyl-Ncycle or $W_6$—$C_{1-6}$alkyl-$NHR^{10}$ wherein $W_6$ is as defined above.

Intermediates of formula (VI) can react with $W_6$—$R^{3a}$ wherein $W_6$ represents a suitable leaving group, such as for example halo, e.g. bromo and the like, or —O—S(=O)$_2$—CH$_3$, and $R^{3a}$ represents optionally substituted $C_{1-6}$alkyl, such as for example —CH$_2$—C$_3$H$_5$, in the presence of a suitable base, such as for example sodium hydride or $Cs_2CO_3$, and a suitable solvent, such as for example N,N-dimethylformamide, N,N-dimethylacetamide or acetonitrile, resulting in a compound of formula (I-c). In this way, compounds of formula (I-c) wherein $R^3$ represents —S(=O)$_2$—N(CH$_3$)$_2$ can also be prepared by reacting an intermediate of formula (VI) with dimethylsulfamoyl chloride, in the presence of a suitable base, such as for example NaH, and a suitable solvent, such as for example N,N-dimethylformamide.

Compounds of formula (I-c) wherein $R^{3a}$ represents —CH$_2$—C(OH)(R')(R") wherein R' represents optionally substituted $C_{1-4}$alkyl and R" represents hydrogen or optionally substituted $C_{1-4}$alkyl, said compounds being represented by formula (I-c-1), can be prepared by reacting the intermediate of formula (VI) with an intermediate of formula (XXII) in the presence of a suitable base, such as for example sodium hydride, $Cs_2CO_3$, or potassium hydroxide, and a suitable solvent, such as for example N,N-dimethylformamide, N,N-dimethylacetamide, acetonitrile or water.

Intermediates of formula (IV) can also react with an intermediate of formula (XXIII) in the presence of a suitable catalyst, such as for example palladium (II) acetate or tris(dibenzylideneacetone)dipalladium (0), a suitable base, such as for example sodium tert-butoxide, a suitable ligand, such as for example 1,1'-[1,1'-binaphthalene]-2,2'-diylbis[1, 1-diphenylphosphine] or 2-dicyclohexylphosphino-2'-(N,N-dimethylamino)biphenyl, and a suitable solvent, such as for example dioxane, resulting in a compound of formula (I-c).

Compounds of formula (I-b) wherein $R^{11}$ is $C_{1-6}$alkyl substituted with amino, said compounds being represented by formula (I-b-2), can also be prepared according to the following reaction Scheme 1A.

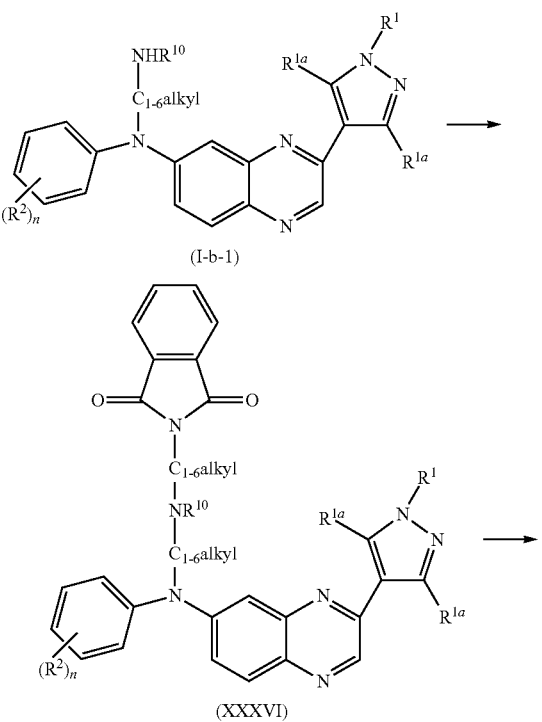

Scheme 1A

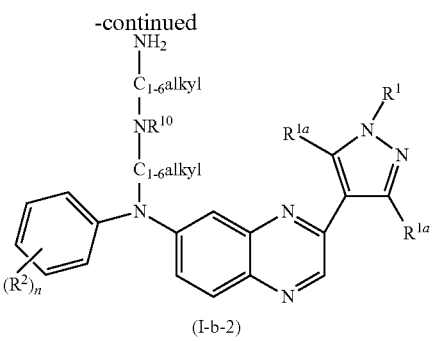

(I-b-2)

In Scheme 1A, a compound of formula (I-b-1) is reacted with N-(3-bromopropyl)phthalimide in the presence of a suitable base, such as for example potassium carbonate, and a suitable solvent, such as for example acetonitrile, resulting in an intermediate of formula (XXXVI) which can be converted into a compound of formula (I-b-2) by reaction with hydrazine in the presence of a suitable solvent, such as for example an alcohol, e.g. ethanol.

Compounds of formula (I-b) wherein $R^1$ is hydrogen, said compounds being represented by formula (I-b-3) can be prepared according to reaction Scheme 1A1.

Scheme 1A1

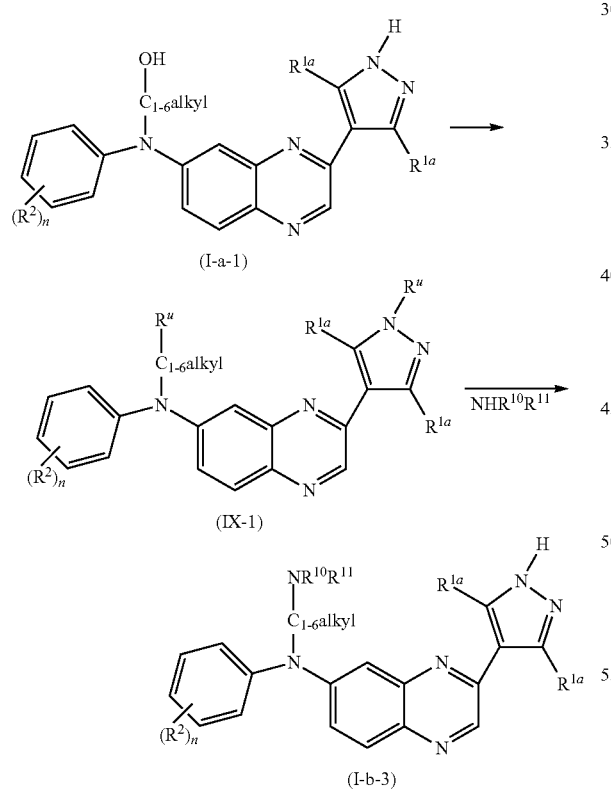

In Scheme 1A1, an intermediate of formula (I-a-1) is reacted with methanesulfonyl chloride in the presence of a suitable base, such as for example triethylamine, and a suitable solvent, such as for example dichloromethane resulting in an intermediate of formula (IX-1) wherein $R^u$ represents —O—S(=O)$_2$—CH$_3$, which is converted into a compound of formula (I-b-3) by reaction with an intermediate of formula (X) in the presence of a suitable solvent, such as for example acetonitrile.

It is considered to be within the knowledge of the person skilled in the art to recognize in which condition and for which definitions of $R^{1a}$ in the reactions of Scheme 1a and Scheme 1a1 a protective group may be appropriate for the reactions to be carried out. For instance, a hydroxyl group within the definition of $R^{1a}$ may be protected with a tert. butyldimethylsilyl moiety; a NH group within the definition of $R^{1a}$ may be protected with a —C(=O)—O—C(CH$_3$)$_3$ group.

It is also considered to be within the knowledge of the person skilled in the art to recognize appropriate deprotection reactions.

Compounds of formula (I) wherein $R^3$ represents optionally substituted $C_{2-6}$alkynyl, said compounds being represented by formula (I-k), can be prepared according to reaction Scheme 1B.

Scheme 1B

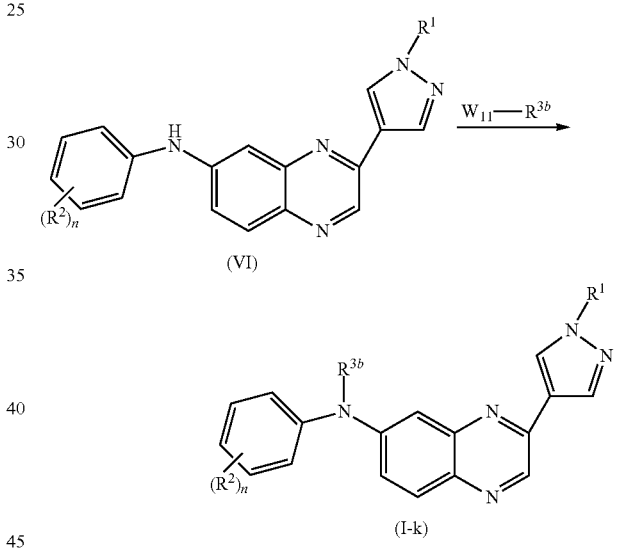

In Scheme 1B, an intermediate of formula (VI) is reacted with an intermediate of formula $W_{11}$—$R^{3b}$ wherein $R^{3b}$ represents optionally substituted $C_{2-6}$alkynyl and $W_{11}$ represents a suitable leaving group such as for example halo, e.g. chloro, or —O—S(=O)$_2$—CH$_3$, in the presence of a suitable base, such as for example NaH, and a suitable solvent, such as for example N,N-dimethylformamide. The intermediate $W_{11}$—$R^{3b}$ wherein $W_{11}$ represents —O—S(=O)$_2$—CH$_3$, can be prepared by reacting the corresponding alcohol derivative with methanesulfonyl chloride in the presence of a suitable base, such as for example triethylamine or 4-dimethylaminopyridine, and a suitable solvent, such as for example dichloromethane.

Compounds of formula (I-k), wherein $R^{3b}$ represents $C_{2-6}$alkynyl substituted with hydroxyl, said compounds being represented by formula (I-k-1), can be prepared according to the following reaction Scheme 1C.

Scheme 1C

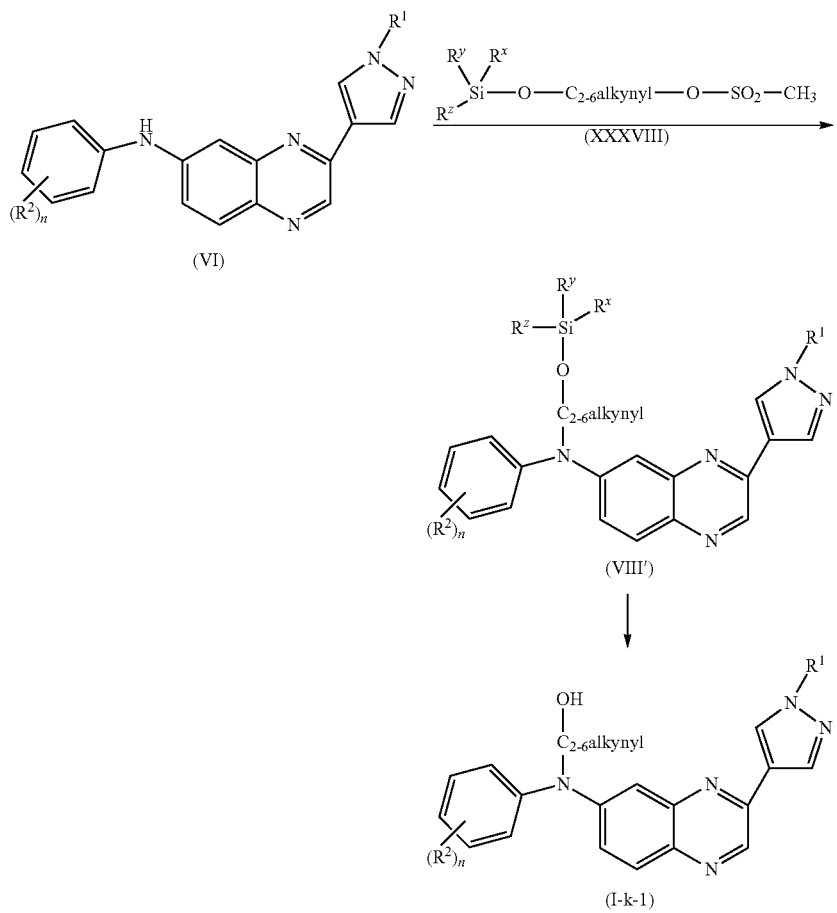

In Scheme 1C, an intermediate of formula (VI) is reacted with an intermediate of formula (XXXVIII) in the presence of a suitable base, such as for example NaH, and a suitable solvent, such as for example N,n-dimethylformamide, resulting in an intermediate of formula (VIII'), which is converted into a compound of formula (I-k-1) by reaction with a suitable acid, such as for example trifluoroacetic acid, in the presence of a suitable solvent, such as for example tetrahydrofuran.

Compounds of formula (I-k), wherein $R^{3b}$ represents $C_{2-6}$alkynyl, said compounds being represented by formula (I-k-2), can be prepared according to the following reaction Scheme 1D.

Scheme 1D

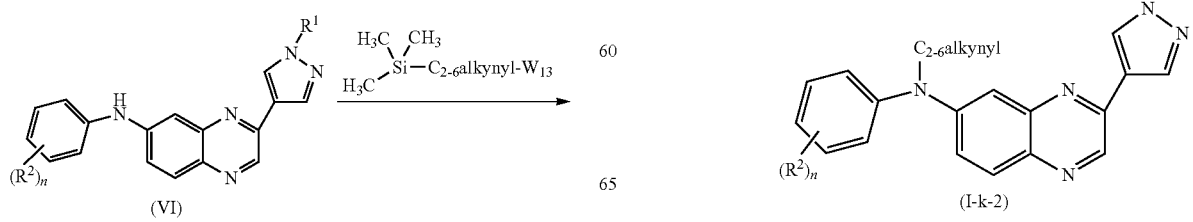

-continued

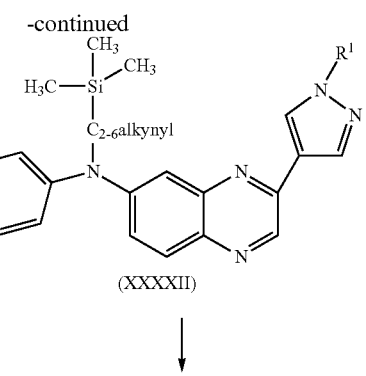

In Scheme 1D, a compound of formula (I-k-2) is prepared by deprotecting an intermediate of formula (XXXXII) in the presence of a suitable base, such as for example $K_2CO_3$, and a suitable solvent, such as for example an alcohol, e.g. methanol and the like. Said intermediate of formula (XXXXII) can be prepared by reacting an intermediate of formula (VI) with $W_{13}$—$C_{2-6}$alkynyl-Si(CH$_3$)$_3$ in the presence of a suitable base, such as for example NaH, and a suitable solvent, such as for example N,N-dimethylformamide.

Compounds of formula (I), wherein $R^3$ represents ethyl substituted with —P(=O)(OC$_{1-6}$alkyl)$_2$, said compounds being represented by formula (I-I), can be prepared according to the following reaction Scheme 1E.

Scheme 1E

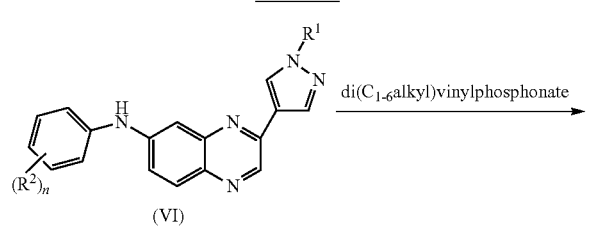

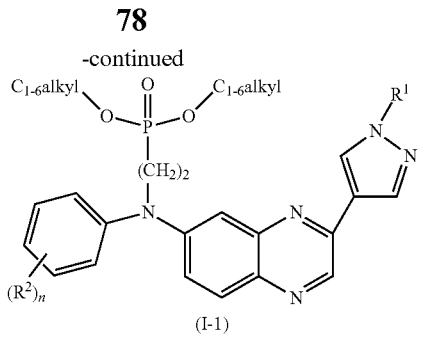

In scheme 1E, an intermediate of formula (VI) is reacted with di(C$_{1-6}$alkyl)vinylphosphonate in the presence of a suitable catalyst, such as for example tri-N-butylphosphine, and a suitable solvent, such as for example acetonitrile resulting in a compound of formula (I-I).

Intermediates of formula (VI) can also be prepared according to the following reaction Scheme 2.

Scheme 2

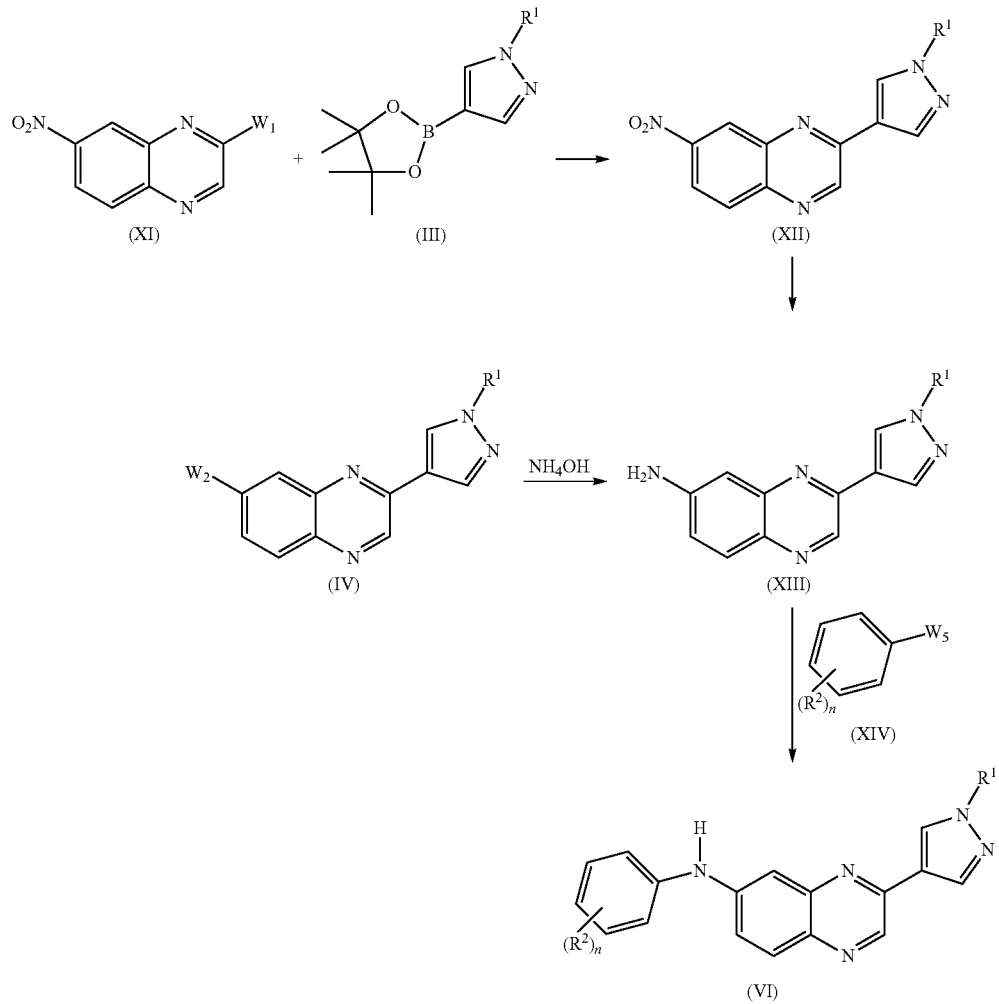

In Scheme 2, an intermediate of formula (XII) is prepared by reacting an intermediate of formula (XI) wherein $W_1$ represents a suitable leaving group, such as for example halo, e.g. chloro and the like, with an intermediate of formula (III) in the presence of a suitable catalyst, such as for example tetrakis(triphenylphosphine)palladium (0), a suitable base, such as for example $Na_2CO_3$, and a suitable solvent or solvent mixture, such as for example ethylene glycol dimethylether and water. The intermediate of formula (XII) is hydrogenated in a next step to an intermediate of formula (XIII) in the presence of a suitable catalyst, such as for example Nickel, and a suitable solvent, such as for example an alcohol, e.g. methanol, or tetrahydrofuran, or mixtures thereof. Intermediates of formula (XIII) can also be prepared by reacting an intermediate of formula (IV) with $NH_4OH$ in the presence of $Cu_2O$. In a next step, the intermediate of formula (XIII) is reacted with an intermediate of formula (XIV) wherein $W_5$ represents a suitable leaving group, such as for example halo, e.g. bromo and the like, in the presence of a suitable catalyst, such as for example palladium (II) acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example ethylene glycol dimethyl ether or dioxane, resulting in an intermediate of formula (VI). This reaction may also be performed in the presence of $Pd_2(dba)_3$ as catalyst, Xphos as ligand, a suitable base, such as for example $Cs_2CO_3$, and a suitable solvent, such as for example an alcohol, e.g. butanol.

Intermediates of formula (IV) wherein $R^1$ is hydrogen can be converted into an intermediate of formula (IV) wherein $R^1$ is other than hydrogen, said $R^1$ being represented by $R^{1'}$, by reaction with $W_{14}$—$R^{1'}$ wherein $W_{14}$ is a suitable leaving group, such as for example halo, e.g. bromo, in the presence of a suitable base, such as for example NaH, and a suitable solvent, such as for example N,N-dimethylformamide.

Intermediates of formula (VI) can alternatively also be prepared according to the following reaction Scheme 3.

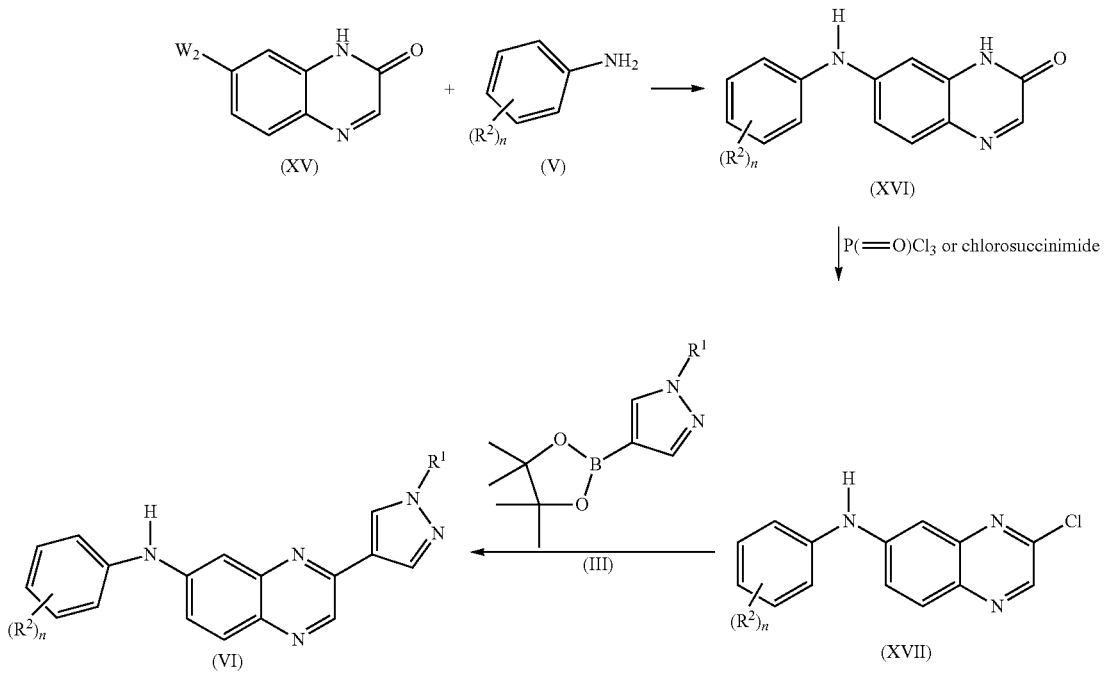

Scheme 3

In Scheme 3, an intermediate of formula (XV) is reacted with an intermediate of formula (V) in the presence of a suitable catalyst, such as for example palladium (II) acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example ethylene glycol dimethyl ether, resulting in an intermediate of formula (XVI). In a next step, the intermediate of formula (XVI) is reacted with $P(=O)Cl_3$ or chlorosuccinimide, optionally in the presence of a solvent, such as for example acetonitrile, resulting in an intermediate of formula (XVII) which is converted into an intermediate of formula (VI) by reaction with an intermediate of formula (III) in the presence of a suitable catalyst, such as for example tetrakis(triphenylphosphine)palladium (0) or tris(dibenzylideneacetone)dipalladium (0), a suitable base, such as for example $Na_2CO_3$ or $K_3PO_4$, optionally in the presence of a suitable ligand, such as for example 2-dicyclohexylphosphino-2',6'-dimethoxybiphenyl, and a- suitable solvent, such as for example ethylene glycol dimethylether.

In the above reaction, an intermediate of formula (III) can react in its protected form, such as for example

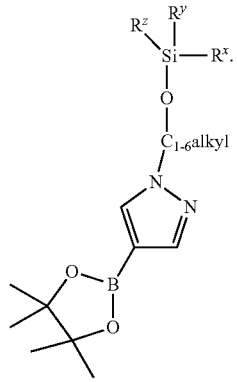

The resulting protected intermediate of formula (VI) can be converted into the deprotected —$C_{1-6}$alkyl-OH intermediate by reaction with tetrabutylammonium fluoride, in the presence of a suitable solvent, such as for example tetrahydrofuran. Said —$C_{1-6}$alkyl-OH can be converted into —$C_{1-6}$alkyl-NH$_2$ by first reacting the —$C_{1-6}$alkyl-OH with methanesulfonyl chloride in the presence of a suitable base, such as for example triethylamine, and a suitable solvent, such as for example dichloromethane, followed by reacting the obtained intermediate with di-tert-butyl-iminocarboxylate in the presence of a suitable base, such as for example NaH, and a suitable solvent, such as for example N,N-dimethylformamide, followed by reaction with a suitable acid, such as for example trifluoroacetic acid, in a suitable solvent, such as for example dichloromethane.

Intermediates of formula (VIII) can alternatively also be prepared according to the following reaction Scheme 4.

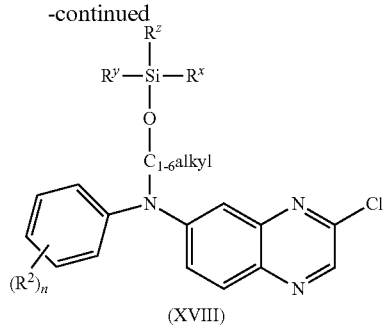

(XVIII)

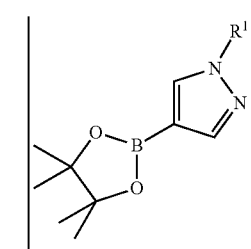

(III)

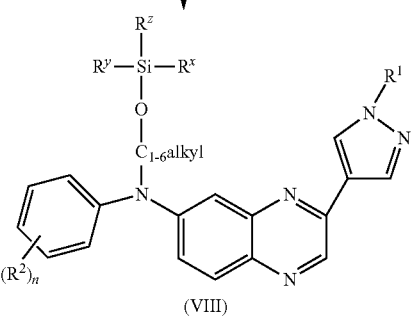

(VIII)

In Scheme 4, an intermediate of formula (XVII) is reacted with an intermediate of formula (VII) in the presence of a suitable base, such as for example sodium hydride, and a suitable solvent, such as for example N,N-dimethylformamide, resulting in an intermediate of formula (XVIII). The intermediate of formula (XVIII) can then be reacted with an intermediate of formula (III) in the presence of a suitable catalyst, such as for example Pd$_2$(dba)$_3$, a suitable base, such as for example K$_3$PO$_4$, a suitable ligand, such as for example 2-dicyclohexylphosphino-2',6'-dimethoxy-biphenyl or S-Phos, and a suitable solvent, such as for example dioxane or water or mixtures thereof.

Intermediates of formula (VIII') can be prepared according to the following reaction Scheme 4A.

Scheme 4

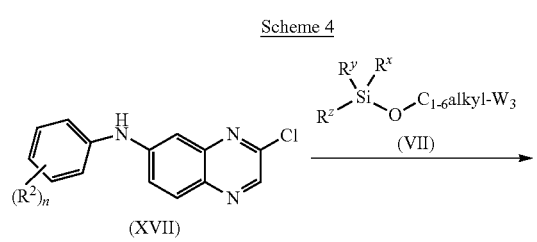

Scheme 4A

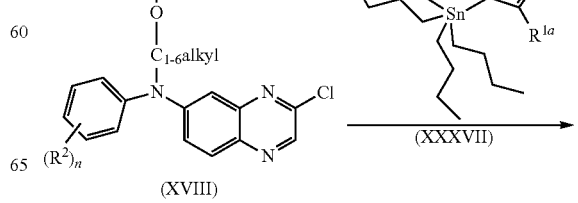

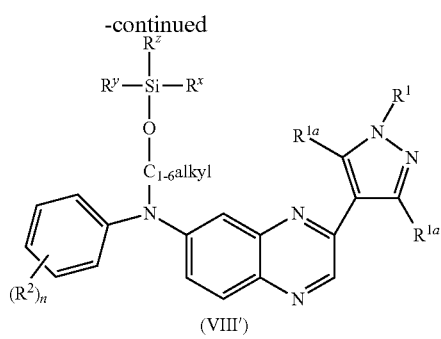

In Scheme 4A, an intermediate of formula (XVIII) is reacted with an intermediate of formula (XXXVII) in the presence of a suitable catalyst, such as for example tetrakis(triphenylphosphine)palladium (0), and a suitable solvent, such as for example toluene.

Intermediates of formula (VIII') can be further reacted according to the following reaction Scheme 4B.

example N,N-dimethylformamide. Said intermediates of formula (VIII'-b) can be converted into an intermediate of formula (VIII'-c) wherein $R^1$ represents an optionally substituted $R^6$, by reaction with optionally substituted $R^6$ in the presence of a suitable base, such as for example $K_2CO_3$, and a suitable solvent, such as for example acetonitrile. When in an intermediate of formula (VIII'-c) the $R^6$ carries a hydroxyl group as in an intermediate of formula (VIII'-c-1), then said hydroxyl group can be protected by a suitable protective group P, such as for example —O—C(=O)—$C_{1-6}$alkyl, by reaction with $C_{1-6}$alkyl-C(=O)—$W_{12}$, in the presence of a suitable base, such as for example triethylamine, 4-dimethylaminopyridine, and a suitable solvent, such as for example dichloromethane, resulting in an intermediate of formula (VIII'-c-2) which can be converted into an intermediate of formula (XXXIX) by reaction with tetrabutylammonium fluoride in the presence of a suitable solvent, such as for example tetrahydrofuran. Said intermediate of formula (XXXIX) can be converted into an intermediate of formula (XXXX) by reaction with methanesulfonyl chloride in the presence of a suitable base, such as for example Scheme 4B

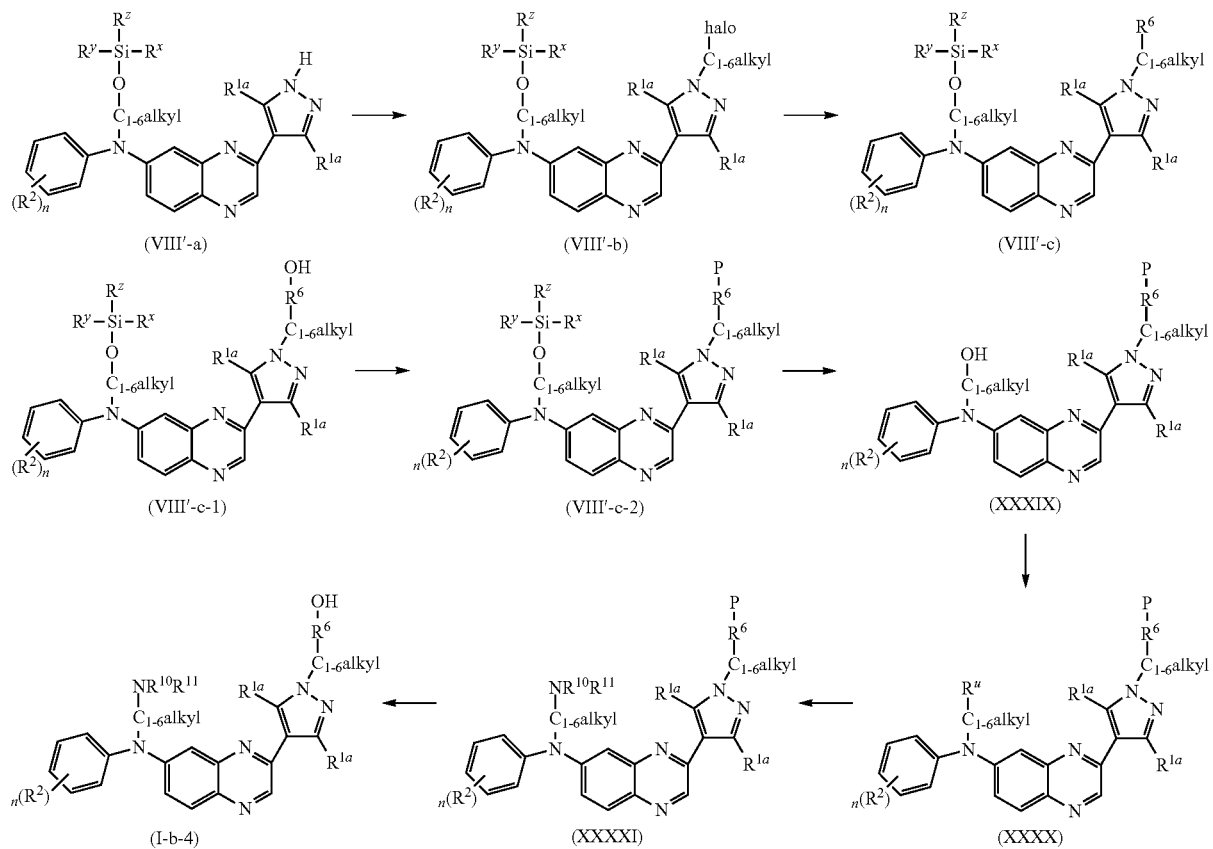

In Scheme 4B, intermediates of formula (VIII') wherein $R^1$ represents hydrogen, said intermediates being represented by formula (VIII'-a), can be converted into an intermediate of formula (VIII') wherein $R^1$ represents halo$C_{1-6}$alkyl, said intermediates being represented by formula (VIII'-b) by reaction with $W_{12}$—$C_{1-6}$alkyl-halo wherein $W_{12}$ represents a suitable leaving group, such as for example halo, e.g. chloro, in the presence of a suitable base, such as for example NaH, and a suitable solvent, such as for triethylamine, and a suitable solvent, such as for example dichloromethane, which can be converted into an intermediate of formula (XXXXI) by reaction with an intermediate of formula (X) in a suitable solvent, such as for example acetonitrile. Said intermediate of formula (XXXXI) can then be deprotected into a compound of formula (I-b-4) in the presence of a suitable base, such as for example $K_2CO_3$, and a suitable solvent, such as for example an alcohol, e.g. methanol and the like.

Intermediates of formula (VIII') can also be reacted to prepare compounds of the present invention according to the reaction schemes as presented in Scheme 1. It is considered to be within the knowledge of the person skilled in the art to recognize in which condition and for which definitions of $R^{1a}$ a protective group may be appropriate for the reactions to be carried out. For instance, a hydroxyl group within the definition of $R^{1a}$ may be protected with a tert. butyldimethylsilyl moiety; a NH group within the definition of $R^{1a}$ may be protected with a —C(=O)—O—C(CH$_3$)$_3$ group.

It is also considered to be within the knowledge of the person skilled in the art to recognize appropriate deprotection reactions.

Compounds of formula (I) wherein $R^3$ represents optionally substituted $C_{1-6}$alkyl, said compounds being represented by formula (I-c), can also be prepared according to the below reaction Scheme 5.

diate of formula (III) in the presence of a suitable catalyst, such as for example tetrakis(triphenyl)phosphine palladium or Pd$_2$(dba)$_3$ (tris(dibenzylideneacetone)dipalladium (0)), a suitable ligand, such as 2-dicyclohexylphosphino-2',6'-dimethoxybiphenyl, a suitable base, such as for example Na$_2$CO$_3$ or K$_3$PO$_4$, and a suitable solvent, such as for example ethylene glycol dimethylether or dioxane or water.

Compounds of formula (I-c) can alternatively also be prepared according to the below reaction Scheme 6.

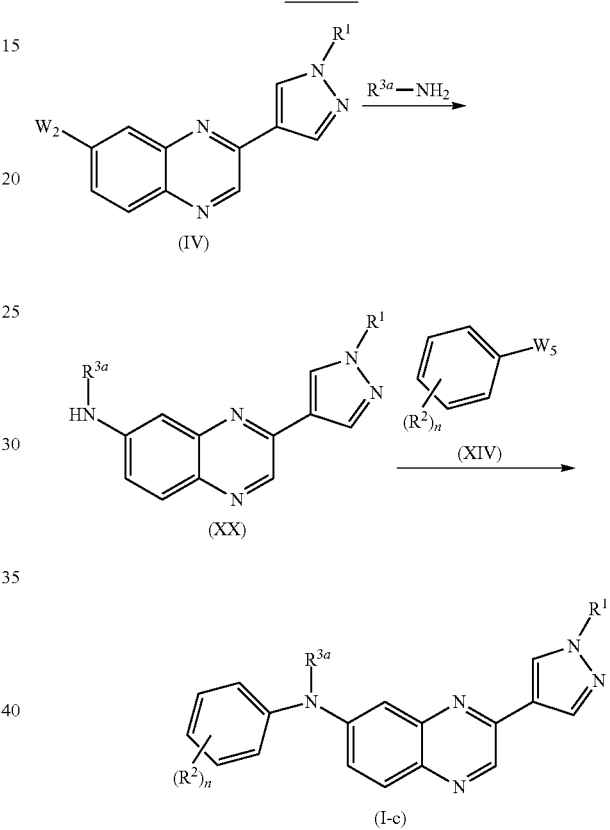

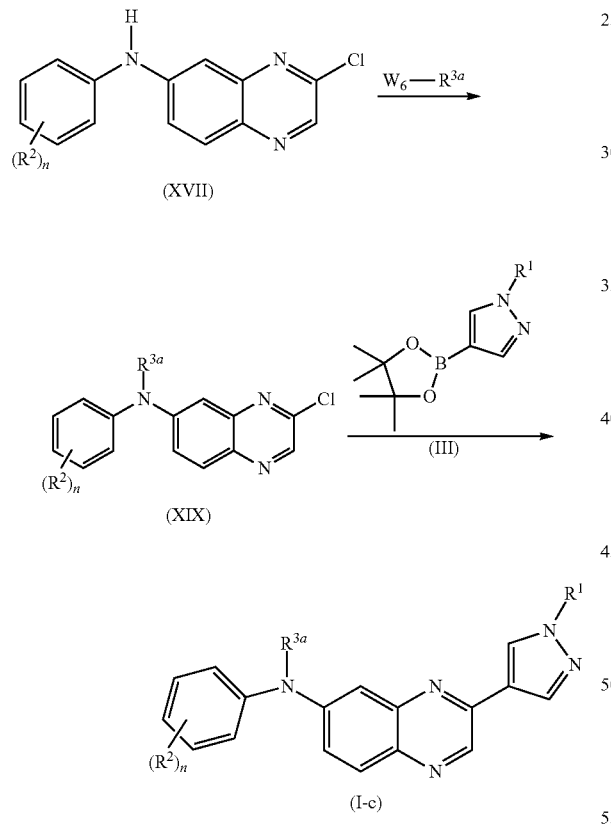

In Scheme 5, an intermediate of formula (XVII) is reacted with W$_6$—R$^{3a}$ wherein W$_6$ represents a suitable leaving group, such as for example halo, e.g. bromo and the like, and R$^{3a}$ represents optionally substituted $C_{1-6}$alkyl, such as for example —CH$_2$—C$_3$H$_5$, in the presence of a suitable base, such as for example sodium hydride, and a suitable solvent, such as for example N,N-dimethylformamide, resulting in an intermediate of formula (XIX). In a next step, the intermediate of formula (XIX) is reacted with an interme- In Scheme 6, an intermediate of formula (IV) is reacted with R$^{3a}$—NH$_2$ in the presence of a suitable catalyst, such as for example palladium (II) acetate, a suitable base, such as for example sodium tert-butoxide, and a suitable ligand, such as for example 1,1'-[1,1'-binaphthalene]-2,2'-diylbis[1,1-diphenylphosphine], resulting in an intermediate of formula (XX) which is reacted in a next step with an intermediate of formula (XIV) in the presence of a suitable catalyst, such as for example palladium (II) acetate or Pd$_2$(dba)$_3$ (tris(dibenzylidene acetone)dipalladium (0)), a suitable ligand such as for example 2-dicyclohexylphosphino-tris-isopropyl-biphenyl or 1,1'-[1,1'-binaphthalene]-2,2'-diylbis[1,1-diphenylphosphine], a suitable base, such as for example sodium tert-butoxide, and a suitable solvent, such as for example ethylene glycol dimethylether.

Compounds of formula (I) wherein $R^3$ is $C_{1-6}$alkyl substituted with 5-amino-1,3,4-oxadiazolyl can be prepared according to the below reaction Scheme 7.

Scheme 7

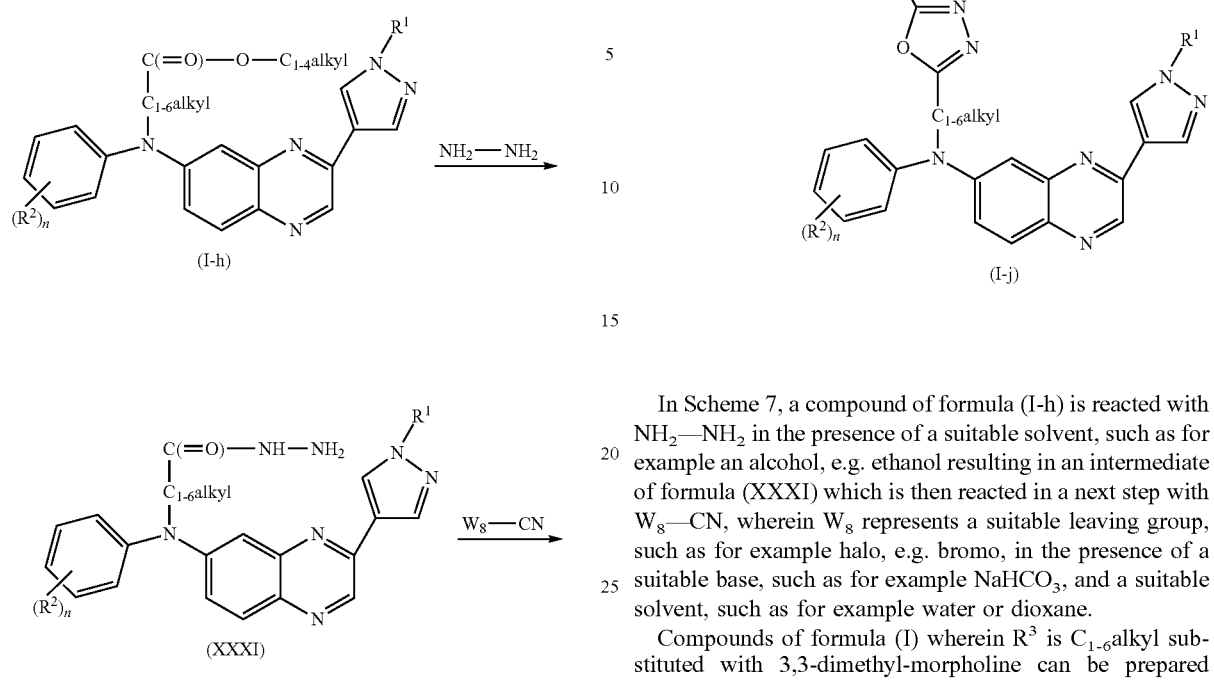

In Scheme 7, a compound of formula (I-h) is reacted with $NH_2-NH_2$ in the presence of a suitable solvent, such as for example an alcohol, e.g. ethanol resulting in an intermediate of formula (XXXI) which is then reacted in a next step with $W_8-CN$, wherein $W_8$ represents a suitable leaving group, such as for example halo, e.g. bromo, in the presence of a suitable base, such as for example $NaHCO_3$, and a suitable solvent, such as for example water or dioxane.

Compounds of formula (I) wherein $R^3$ is $C_{1-6}$alkyl substituted with 3,3-dimethyl-morpholine can be prepared according to the below reaction Scheme 7.A

Scheme 7A

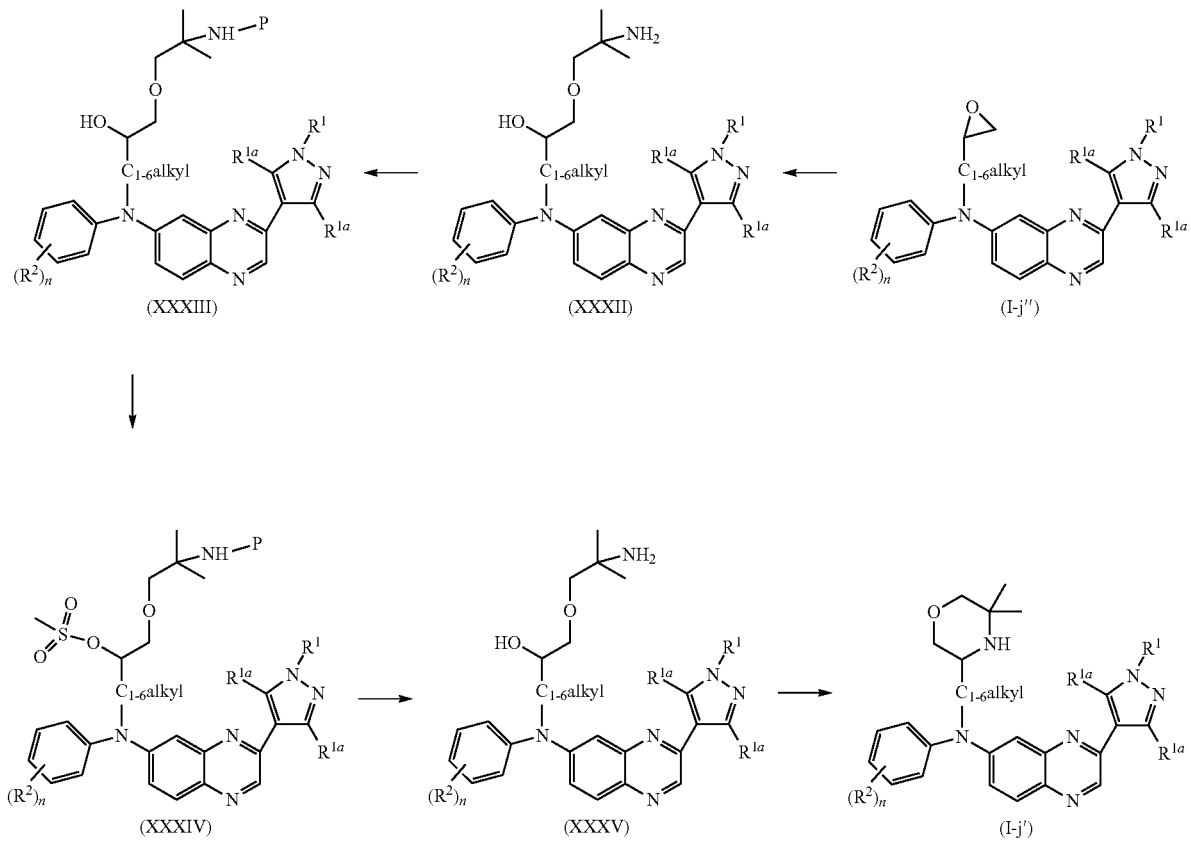

In Scheme 7A, a compound of formula (I-j") is reacted with 2-amino-2-methyl-1-propanol in the presence of a suitable base, such as for example NaH and in the presence of a suitable solvent, such as for example N,N-dimethylformamide resulting in an intermediate of formula (XXXII) of which the $NH_2$ moiety is protected by a suitable protecting group P, such as for example —C(=O)—O—C(CH$_3$)$_3$, by reaction with for instance di-tert-butyl dicarbonate in the presence of a suitable solvent, such as for example dioxane, and a suitable base, such as for example NaHCO$_3$, resulting in an intermediate of formula (XXXIII). In a next step, said intermediate is reacted with methanesulfonyl chloride in the presence of a suitable solvent, such as for example dichloromethane, and a suitable base, such as for example triethylamine resulting in an intermediate of formula (XXXIV) which is converted into an intermediate of formula (XXXV) by reaction with a suitable acid, such as for example trifluoroacetic acid, in the presence of a suitable solvent, such as for example dichloromethane. The intermediate of formula (XXXV) is converted into a compound of formula (I-j') by reaction with a suitable base, such as for example N,N-diisopropylethylamine and triethylamine in the presence of a suitable solvent, such as for example an alcohol, e.g. methanol.

As already shown above, compounds of formula (I) or some of the above-described intermediates can be prepared by deprotecting the corresponding protected compounds. Other protection-deprotection reactions are shown in the following reaction Scheme 8.

Scheme 8

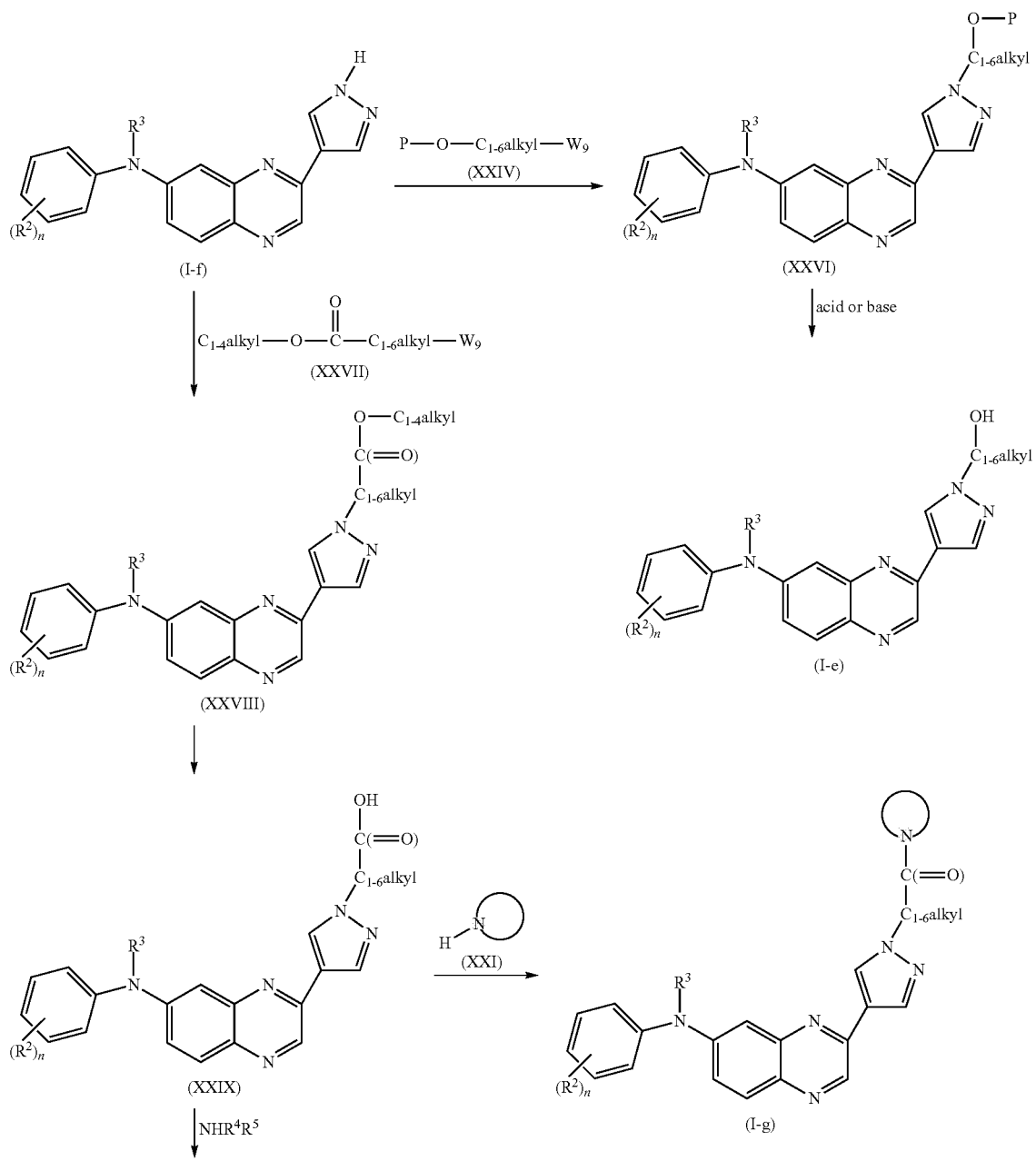

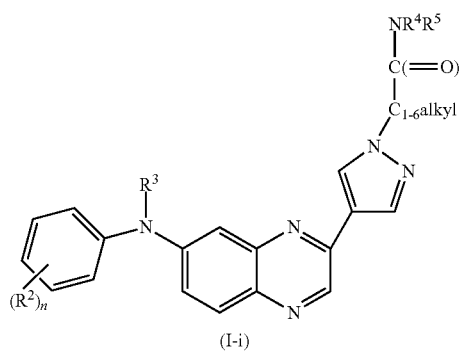

(I-i)

In Scheme 8, compounds of formula (I) wherein $R^1$ represents hydroxyC$_6$alkyl, said compounds being represented by formula (I-e), can be prepared by deprotecting an intermediate of formula (XXVI) in the presence of a suitable acid, such as for example HCl or trifluoroacetic acid, or a suitable de-silylating agent, such as for example tetrabutyl ammonium fluoride, and a suitable solvent, such as an alcohol, e.g. methanol, or tetrahydrofuran. Intermediates of formula (XXVI) can be prepared by reacting a compound of formula (I) wherein $R^1$ s hydrogen, said compounds being represented by formula (I-f), with an intermediate of formula (XXIV) wherein W9 represents a suitable leaving group, such as for example halo, e.g. bromo and the like, and P represents a suitable protective group, such as for example —O—Si(CH$_3$)$_2$(C(CH$_3$)$_3$) or

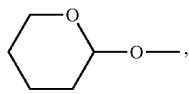

in the presence of a suitable base, such as for example sodium hydride or K$_2$CO$_3$, and a suitable solvent, such as for example N,N-dimethylformamide or acetonitrile. Compounds of formula (I) wherein $R^1$ represents C$_{1-6}$alkyl substituted with —C(=O)—R$^6$ wherein R$^6$ is an appropriate nitrogen containing ring linked to the C(=O) moiety via the nitrogen atom, said compounds being represented by formula (I-g), can be prepared by reacting an intermediate of formula (XXIX) with an intermediate of formula (XXI) in the presence of suitable peptide coupling reagents such as, 1-hydroxy-benzotriazole and 1-(3-dimethylaminopropyl)-3-ethyl carbodiimide HCl. Intermediates of formula (XXIX) can be prepared by reacting an intermediate of formula (XXVIII) with LiOH in the presence of a suitable solvent, such as for example tetrahydrofuran or water. Intermediates of formula (XXVIII) can be prepared by reacting a compound of formula (I-f) with an intermediate of formula (XXVII) wherein W$_9$ is as defined above, in the presence of a suitable base, such as for example sodium hydride, and a suitable solvent, such as for example N,N-dimethylformamide.

Compounds of formula (I-i) can be prepared starting from an intermediate of formula (XXIX) by reaction with NHR$^4$R$^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane.

Further protection-deprotection reactions can also be used as outlined in the following reaction Scheme 9.

Scheme 9

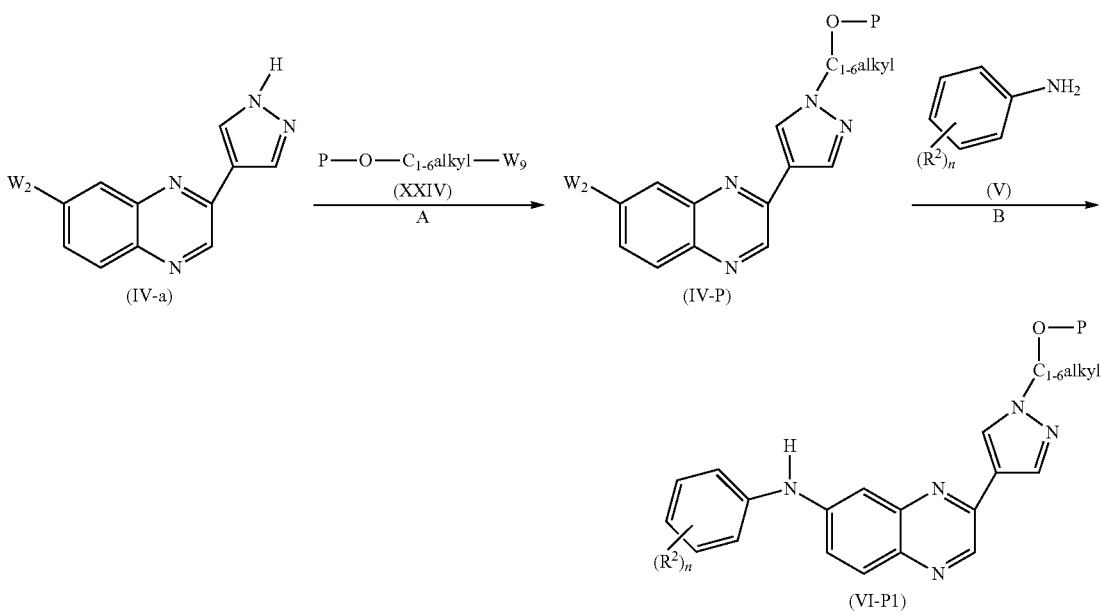

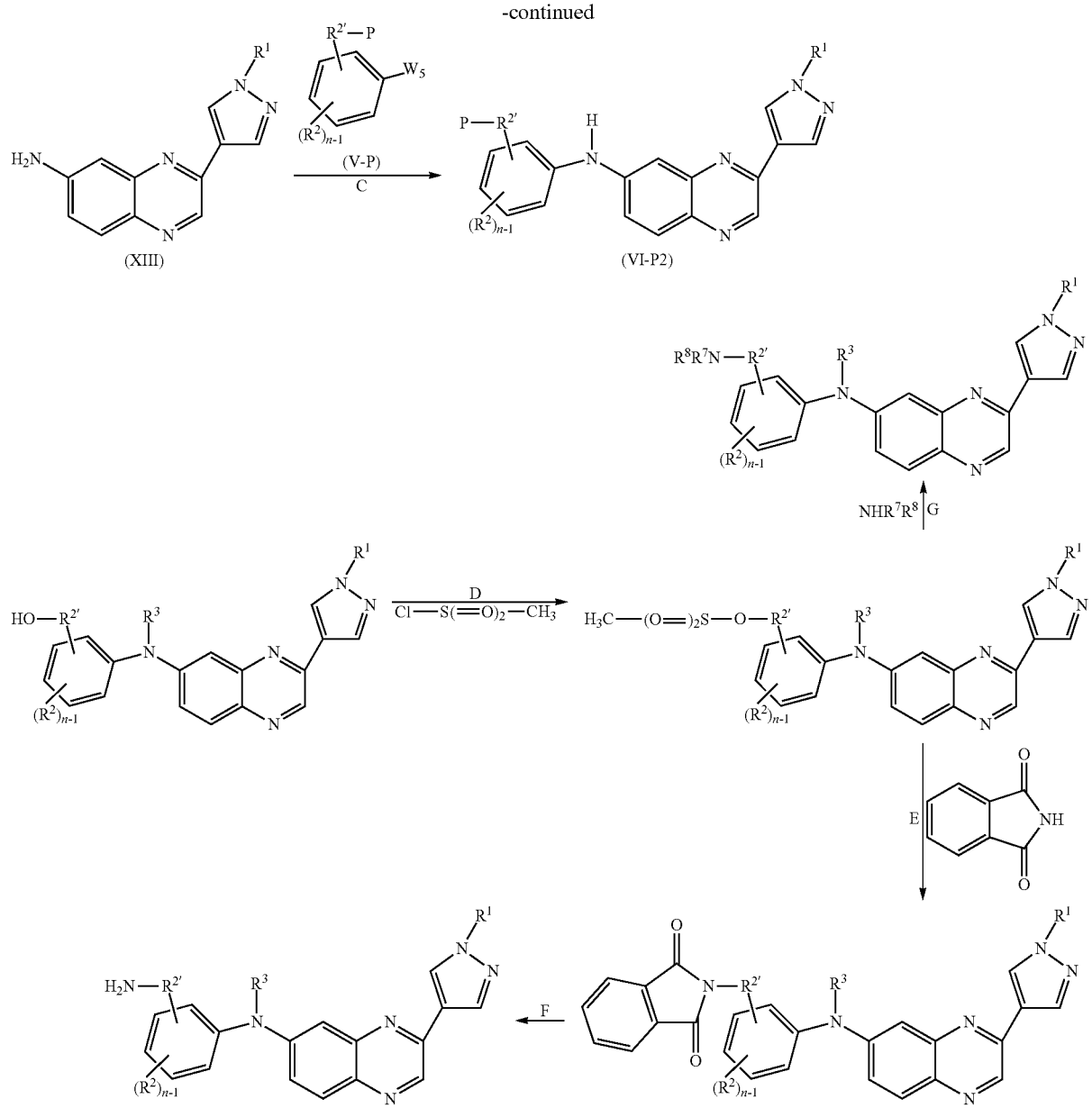

In Scheme 9, the following reaction conditions apply:
A; in the presence of a suitable base, such as for example sodium hydride, and a suitable solvent, such as for example N,N-dimethylformamide.
B: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.
C: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.
D: in the presence of a suitable base, such as for example triethylamine, and a suitable solvent, such as for example dichloromethane.
E: in the presence of a suitable base, such as for example $K_2CO_3$, and a suitable solvent, such as for example 1-methyl-2-pyrrolidinone.

F: in the presence of hydrazine monohydrate, and a suitable solvent, such as for example an alcohol, e.g. ethanol.

G: in the presence of a suitable base, such as for example $K_2CO_3$, and a suitable solvent, such as for example tetrahydrofuran.

It is considered to be within the knowledge of the person skilled in the art to recognize in which condition and on which part of the molecule a protective group may be appropriate. For instance, protective group on the $R^1$ substituent or on the pyrrazole moiety, or protective group on the $R^3$ substituent or on the $R^2$ substituent or combinations thereof. The skilled person is also considered to be able to recognize the most feasible protective group, such as for example —C(=O)—O—$C_{1-4}$alkyl or

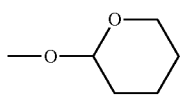

or O—Si(CH₃)₂(C(CH₃)₃) or —CH₂—O—CH₂CH₂—O—CH₃.

The present invention also comprises deuterated compounds. These deuterated compounds may be prepared by using the appropriate deuterated intermediates during the synthesis process. For instance an intermediate of formula (IV-a)

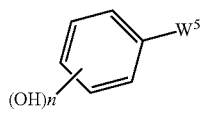

can be converted into an intermediate of formula (IV-b)

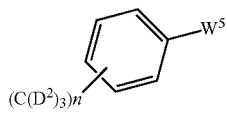

by reaction with iodomethane-D3 in the presence of a suitable base, such as for example cesium carbonate, and a suitable solvent, such as for example acetonitrile.

The compounds of formula (I) may also be converted into each other via art-known reactions or functional group transformations.

For instance, compounds of formula (I) wherein $R^1$ represents tetrahydropyranyl can be converted into a compound of formula (I) wherein $R^1$ represents hydrogen, by reaction with a suitable acid, such as for example HCl or trifluoroacetic acid, in the presence of a suitable solvent, such as for example dichloromethane, dioxane, or an alcohol, e.g. methanol, isopropanol and the like.

Compounds of formula (I) wherein $R^1$ or $R^3$ represent monohaloalkyl, can be converted into a compound of formula (I) wherein $R^1$ or $R^3$ represent $C_{1-6}$alkyl substituted with a ring moiety as defined hereinabove by the intermediate of formula (XXI) and linked to the $C_{1-6}$alkyl moiety by the nitrogen atom, by reaction with an intermediate of formula (XXI) optionally in the presence of a suitable base, such as for example triethylamine or $K_2CO_3$ or sodium hydride, and optionally in the presence of a suitable solvent, such as for example acetonitrile, N,N-dimethylformamide or 1-methyl-2-pyrrolidinone.

Compounds of formula (I) wherein $R^1$ or $R^3$ represents $C_{1-6}$alkyl-OH, can be converted into a compound of formula (I) wherein $R^1$ or $R^3$ represent $C_{1-6}$alkyl-F by reaction with diethylaminosulfur trifluoride in the presence of a suitable solvent, such as for example dichloromethane and in the presence of catalytic amounts of an alcohol, such as for example ethanol. Likewise, a compound of formula (I) wherein $R^1$ or $R^3$ represent $C_{1-6}$alkyl substituted with $R^6$ or $R^9$ wherein said $R^6$ or $R^9$ is substituted with OH, can be converted to a compound of formula (I) wherein $R^1$ or $R^3$ represent $C_{1-6}$alkyl substituted with $R^6$ or $R^9$ wherein said $R^6$ or $R^9$ is substituted with F, by reaction with diethylaminosulfur trifluoride in the presence of a suitable solvent, such as for example dichloromethane.

Compounds of formula (I) wherein $R^1$ or $R^3$ represent $C_{1-6}$alkyl substituted with $R^6$ or $R^9$ wherein said $R^6$ or $R^9$ is substituted with —C(=O)—O—$C_{1-6}$alkyl, can be converted into a compound of formula (I) wherein $R^1$ or $R^3$ represent $C_{1-6}$alkyl substituted with $R^6$ or $R^9$ wherein said $R^6$ or $R^9$ is substituted with —CH₂—OH, by reaction with LiAlH₄ in the presence of a suitable solvent, such as for example tetrahydrofuran.

Compounds of formula (I) wherein $R^3$ represents $C_{1-6}$alkyl substituted with 1,3-dioxo-2H-isoindol-2-yl, can be converted into a compound of formula (I) wherein $R^3$ represents $C_{1-6}$alkyl substituted with amino, by reaction with hydrazine monohydrate in the presence of a suitable solvent, such as for example an alcohol, e.g. ethanol.

Compounds of formula (I) wherein $R^1$ or $R^3$ represent $C_{1-6}$alkyl substituted with amino, can be converted into a compound of formula (I) wherein $R^1$ or $R^3$ represents $C_{1-6}$alkyl substituted with —NH—S(=O)₂—$C_{1-6}$alkyl, by reaction with Cl—S(=O)₂—$C_{1-6}$alkyl in the presence of a suitable base, such as for example triethylamine, and a suitable solvent, such as for example dichloromethane.

Compounds of formula (I) wherein $R^1$ or $R^3$ represents $C_{1-6}$alkyl substituted with halo, can be converted into a compound of formula (I) wherein $R^1$ or $R^3$ represent $C_{1-6}$alkyl substituted with $NR^4R^5$ or $NR^{10}R^{11}$, by reaction with $NHR^4R^5$ or $NHR^{10}R^{11}$, either using such amino in large excess or in the presence of a suitable base, such as for example $K_2CO_3$, and a suitable solvent, such as for example acetonitrile, N,N-dimethylacetamide or 1-methyl-pyrrolidinone.

Compounds of formula (I) wherein $R^1$ represents hydrogen, can be converted into a compound of formula (I) wherein $R^1$ represents polyhalo$C_{1-6}$alkyl or polyhydroxy$C_{1-6}$alkyl or $C_{1-6}$alkyl or —S(=O)₂—$NR^{14}R^{15}$ or —S(=O)₂—$C_{1-6}$alkyl, by reaction with polyhalo$C_{1-6}$alkyl-W or polyhydroxy$C_{1-6}$alkyl-W or $C_{1-6}$alkyl-W or W—S(=O)₂—$NR^{14}R^{15}$ or W—S(=O)₂—$C_{1-6}$alkyl, wherein W represents a suitable leaving group, such as for example halo, e.g. bromo and the like, in the presence of a suitable base, such as for example sodium hydride or $K_2CO_3$ or triethylamine or 4-dimethylamino-pyridine or diisopropylamine, and a suitable solvent, such as for example N,N-dimethylformamide or acetonitrile or dichloromethane. Compounds of formula (I) wherein $R^1$ represents hydrogen can also be converted into a compound of formula (I) wherein $R^1$ represents $C_{1-6}$alkyl-OH, by reaction with W—$C_{1-6}$alkyl-O—Si(CH₃)₂(C(CH₃)₃) in the presence of a suitable base, such as for example sodium hydride, and a suitable solvent, such as for example N,N-dimethylformamide. Compounds of formula (I) wherein $R^1$ represents hydrogen, can also be converted into compound of formula (I) wherein $R^1$ represents ethyl substituted with —S(=O)₂—$C_{1-6}$alkyl, by reaction with $C_{1-6}$alkyl-vinylsulfone, in the presence of a suitable base, such as for example triethylamine, and a suitable solvent, such as for example an alcohol, e.g. methanol or by reaction with $C_{1-6}$alkyl-2-bromoethylsulfone in the presence of a suitable deprotonating agent, such as for example NaH, and a suitable solvent, such as for example dimethylformamide.

Compounds of formula (I) wherein $R^1$ represents hydrogen can also be converted into a compound of formula (I) wherein $R^1$ represents —CH₂—CHOH—CH₂

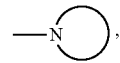

by reaction with

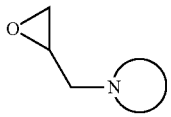

in the presence of a suitable base, such as for example sodium hydride, and a suitable solvent, such as for example N,N-dimethylformamide, wherein

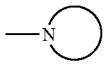

represents a suitable nitrogen containing ring within the definition of $R^6$. Compounds of formula (I) wherein $R^1$ represents $C_{1-6}$alkyl substituted with $R^6$ wherein said $R^6$ is substituted with —C(=O)—O—$C_{1-6}$alkyl or —S(=O)$_2$—$NR^{14}R^{15}$ or wherein $R^3$ represents $C_{1-6}$alkyl substituted with $R^9$ wherein said $R^9$ is substituted with —C(=O)—O—$C_{1-6}$alkyl or —S(=O)$_2$—$NR^{14}R^{15}$, can be converted into a compound of formula (I) wherein the $R^6$ or $R^9$ is unsubstituted, by reaction with a suitable acid, such as for example HCl and a suitable solvent, such as for example dioxane, acetonitrile or an alcohol, e.g. isopropylalcohol. Compounds of formula (I) wherein $R^1$ represents $C_{1-6}$alkyl substituted with $R^6$ wherein said $R^6$ is a ring moiety comprising a nitrogen atom which is substituted with —CH$_2$—OH or wherein $R^3$ represents $C_{1-6}$alkyl substituted with $R^9$ wherein said $R^9$ is a ring moiety comprising a nitrogen atom which is substituted with —CH$_2$—OH, can be converted into a compound of formula (I) wherein the $R^6$ or $R^9$ is unsubstituted, by reaction with sodium hydroxide, in the presence of a suitable solvent, such as for example tetrahydrofuran.

Compounds of formula (I) wherein $R^1$ represents $C_{1-6}$alkyl substituted with $R^6$ or $R^3$ represents $C_{1-6}$alkyl substituted with $R^9$, wherein said $R^6$ or said $R^9$ is unsubstituted, can be converted into a compound of formula (I) wherein said $R^6$ or said $R^9$ is substituted with $C_{1-6}$alkyl, by reaction with W—$C_{1-6}$alkyl wherein W is as defined above, in the presence of a suitable base. Such as for example sodium hydride, and a suitable solvent, such as for example N,N-dimethylformamide.

Compounds of formula (I) wherein $R^1$ or $R^3$ represent hydroxy$C_{1-6}$alkyl, can be converted into the corresponding carbonyl compound, by reaction with dess-Martin-periodinane, in the presence of a suitable solvent, such as for example dichloromethane.

Compounds of formula (I) wherein $R^1$ represents $C_{1-6}$alkyl substituted with $R^6$ or $R^3$ represents $C_{1-6}$alkyl substituted with $R^9$, wherein said $R^6$ or said $R^9$ is substituted with $C_{1-6}$alkyl-halo, can be converted into a compound of formula (I) wherein said $R^6$ or said $R^9$ is substituted with $C_{1-6}$alkyl-CN, by reaction with sodium cyanide, in the presence of a suitable solvent, such as for example water or an alcohol, e.g. ethanol.

Compounds of formula (I) wherein $R^1$ represents $C_{1-6}$alkyl substituted with $R^6$ wherein said $R^6$ is unsubstituted or wherein $R^3$ represents $C_{1-6}$alkyl substituted with $R^9$ wherein said $R^9$ is unsubstituted, can be converted into a compound of formula (I) wherein $R^6$ or $R^9$ is substituted with —CH$_3$ or —CH(CH$_3$)$_2$, by reaction with formaldehyde or acetone and NaBH$_3$CN, in the presence of a suitable solvent, such as for example tetrahydrofuran or an alcohol, e.g. methanol.

Compounds of formula (I) wherein $R^1$ contains a $R^6$ substituent substituted with OH or wherein $R^3$ contains a $R^9$ substituent substituted with OH, can be converted into a compound of formula (I) wherein the $R^6$ or $R^9$ substituent is substituted with $C_{1-6}$alkyloxy, by reaction with W—$C_{1-6}$alkyl, in the presence of a suitable base, such as for example sodium hydride, and a suitable solvent, such as for example N,N-dimethylformamide. Compounds of formula (I) wherein $R^1$ contains a $R^6$ substituent substituted with $C_{1-6}$alkyloxy or wherein $R^3$ contains a $R^9$ substituent substituted with $C_{1-6}$alkyloxy, can be converted into a compound of formula (I) wherein the $R^6$ or $R^9$ substituent is substituted with —OH by reaction with a suitable acid, such as for example hydrochloric acid. Compounds of formula (I) wherein $R^1$ contains a $R^6$ substituent substituted with halo or wherein $R^3$ contains a $R^9$ substituent substituted with halo can be converted into a compound of formula (I) wherein the $R^6$ or $R^9$ substituent is substituted with —$NR^{14}R^{15}$ by reaction with $NHR^{14}R^{15}$ in a suitable solvent, such as for example 1-methyl-pyrrolidinone. Compounds of formula (I) wherein $R^3$ represents $C_{1-6}$alkyl substituted with —C(=O)—O—$C_{1-6}$alkyl, can be converted into a compound of formula (I) wherein $R^3$ represents $C_{1-6}$alkyl substituted with COOH, by reaction with LiOH in the presence of a suitable solvent, such as for example tetrahydrofuran. Said compounds of formula (I) wherein $R^3$ represents $C_{1-6}$alkyl substituted with COOH, can be converted into a compound of formula (I) wherein $R^3$ represents $C_{1-6}$alkyl substituted with —C(=O)—NH$_2$ or —C(=O)—NHCH$_3$ or —C(=O)$NR^{11}R^{11}$, by reaction with NH(Si(CH$_3$)$_3$)$_2$ or MeNH$_3^+$Cl$^-$ or $NHR^{10}R^{11}$ in the presence of suitable peptide coupling reagents such as for example 1-(3-dimethylaminopropyl)-3-ethylcarbodiimide HCl and 1-hydroxybenzotriazole, a suitable base, such as for example triethylamine and a suitable solvent such as for example dichloromethane or N,N-dimethylformamide. Compounds of formula (I) wherein $R^3$ represents $C_{1-6}$alkyl substituted with —C(=O)—O—$C_{1-6}$alkyl, can also be converted into a compound of formula (I) wherein $R^3$ represents $C_{1-6}$alkyl substituted with 2-imidazolyl, by reaction under N$_2$ with ethylenediamine and trimethylaluminium in the presence of a suitable solvent, such as for example toluene and heptane. This compound of formula (I) wherein $R^3$ represents $C_{1-6}$alkyl substituted with 2-imidazolyl, can be converted into a compound of formula (I) wherein $R^3$ represents $C_{1-6}$alkyl substituted with —C(=O)—NH—(CH$_2$)$_2$—NH$_2$ by reaction with sodium hydroxide. Compounds of formula (I) wherein $R^3$ represents $C_{1-6}$alkyl substituted with COOH, can also be converted into a compound of formula (I) wherein $R^3$ represents $C_{1-6}$alkyl substituted with —C(=O)—N(CH$_3$)(OCH$_3$) by reaction with dimethylhydroxylamine, in the presence of carbonyldiimidazole and a suitable solvent, such as for example dichloromethane.

Compounds of formula (I) wherein $R^3$ represents $C_{1-6}$alkyl substituted with

can be converted into a compound of formula (I) wherein $R^3$ represents $C_{1-6}$alkyl substituted with 2OH's, by reaction with a suitable acid, such as for example trifluoroacetic acid, and a suitable solvent, such as for example dioxane or water. These compounds of formula (I) wherein $R^3$ represents $C_{1-6}$alkyl substituted with

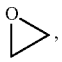

can also be converted into a compound of formula (I) wherein $R^3$ represents $C_{1-6}$alkyl substituted with OH and $NR^{10}R^{11}$, by reaction with $NH_2R^{10}R^{11}$ optionally in salt form, such as for example $NHR^{10}R^{11+}Cl^-$, optionally in the presence of a suitable base, such as for example sodium hydride or $Na_2CO_3$ or triethylamine or KI, and in the presence of a suitable solvent, such as for example N,N-dimethylformamide or an alcohol, e.g. 1-butanol or ethanol. Compounds of formula (I) wherein $R^3$ represents $C_{1-3}$alkyl substituted with —C(=O)—O—$C_{1-6}$alkyl, can be converted into a compound of formula (I) wherein $R^3$ represents $C_{1-3}$alkyl substituted with —C(CH$_3$)$_2$—OH, by reaction with iodomethane and Mg powder, in the presence of a suitable solvent, such as for example diethylether or tetrahydrofuran. Compounds of formula (I) wherein $R^3$ represents $C_{1-5}$alkyl substituted with —C(=O)—O—$C_{1-6}$alkyl, can be converted into a compound of formula (I) wherein $R^3$ represents $C_{1-6}$alkyl substituted with —OH, by reaction with $LiAlH_4$ in a suitable solvent, such as for example tetrahydrofuran.

Compounds of formula (I) wherein $R^3$ represents $C_{1-5}$alkyl substituted with —OH, can be converted into a compound of formula (I) wherein $R^3$ represents $C_{1-5}$alkyl substituted with —O—C(=O)—$C_{1-6}$alkyl by reaction with Cl—C(=O)—$C_{1-6}$alkyl in the presence of a suitable base, such as for example NaH, and a suitable solvent, such as for example tetrahydrofuran.

Compounds of formula (I) wherein $R^3$ represents —CH$_2$—CH=CH$_2$, can be converted into a compound of formula (I) wherein $R^3$ represents —CH$_2$—CHOH—CH$_2$—OH, by reaction with potassium permanganate, and a suitable solvent, such as for example acetone or water. Compounds of formula (I) wherein $R^3$ represents $C_{1-6}$alkyl substituted with —C(=O)—$C_{1-4}$alkyl, can be converted into a compound of formula (I) wherein $R^3$ represents $C_{1-6}$alkyl substituted with —C($C_{1-4}$alkyl)=N—OH, by reaction with hydroxylamine, in the presence of a suitable base, such as for example pyridine, and a suitable solvent, such as for example an alcohol, e.g. ethanol.

Compounds of formula (I) wherein $R^3$ represents $C_{1-6}$alkyl substituted with NH$_2$, can be converted into a compound of formula (I) wherein $R^3$ represents $C_{1-6}$alkyl substituted with —NH—C(=O)—$R^6$ or with —NH—C(=O)—$C_{1-6}$alkyl or with —NH—C(=O)-polyhydroxy$C_{1-6}$alkyl or with —NH—C(=O)-polyhalo$C_{1-6}$alkyl or with —NH—C(=O)-polyhydroxypolyhaloCvalkyl, by reaction with the corresponding COOH analogue, e.g. $R^6$—COOH or $CF_3$—C(CH$_3$)(OH)—COOH and the like, in the presence of suitable peptide coupling reagents such as 1-hydroxy-benzotriazole and 1-(3-dimethylamino)propyl)carbodiimide optionally in the presence of a suitable base, such as for example triethylamine. Said compounds of formula (I) wherein $R^3$ represents $C_{1-6}$alkyl substituted with NH$_2$, can also be converted into a compound of formula (I) wherein $R^3$ represents $C_{1-6}$alkyl substituted with NH—C(=O)—$CF_3$, by reaction with trifluoroacetic anhydride, in the presence of a suitable base, such as for example triethylamine, and a suitable solvent, such as for example tetrahydrofuran. Said compounds of formula (I) wherein $R^3$ represents $C_{1-6}$alkyl substituted with NH$_2$, can also be converted into a compound of formula (I) wherein $R^3$ represents $C_{1-6}$alkyl substituted with —NH-polyhalo$C_{1-6}$alkyl, e.g. —NH—CH$_2$—CH$_2$—F, by reaction with polyhalo$C_{1-6}$alkyl-W, with W as defined above, e.g. iodo-2-fluoroethane, in the presence of a suitable base, such as for example $K_2CO_3$, and a suitable solvent, such as for example N,N-dimethylformamide or dioxane.

Compounds of formula (I) wherein $R^3$ represents $C_{1-6}$alkyl substituted with cyano, can be converted into a compound of formula (I) wherein $R^3$ represents $C_{1-6}$alkyl substituted with tetrazolyl by reaction with sodium azide, and $NH_4^+Cl^-$ in the presence of a suitable solvent, such as for example N,N-dimethylformamide.

Compounds of formula (I) wherein $R^3$ represents —CH$_2$—C—CH, can be converted into a compound of formula (I) wherein $R^3$ represents

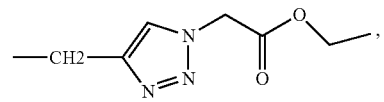

by reaction with ethyl azidoacetate in the presence of CuI and a suitable base, such as for example diisopropylamine, and a suitable solvent, such as for example tetrahydrofuran.

Compounds of formula (I) wherein $R^3$ represents —CH$_2$—C≡CH, can be converted into a compound of formula (I) wherein $R^3$ represents

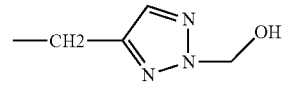

by reaction with sodium azide and formaldehyde, in the presence of a suitable catalyst, such as for example $CuSO_4$ and sodium L ascorbate, a suitable acid, such as for example acetic acid, and a suitable solvent, such as for example dioxane.

Compounds of formula (I) wherein $R^3$ represent $C_{2-6}$alkynyl, can be converted into a compound of formula (I) wherein $R^3$ represents $C_{2-6}$alkynyl substituted with $R^9$, by reaction with W—$R^9$ wherein W is as defined above, in the presence of a suitable catalyst, such as for example dichlorobis(triphenylphosphine)palladium, a suitable co-catalyst such as CuI, a suitable base, such as for example triethylamine, and a suitable solvent, such as for example dimethylsulfoxide.

Compounds of formula (I) wherein $R^3$ comprises $R^9$ substituted with halo, can be converted into a compound of formula (I) wherein $R^3$ comprises $R^9$ substituted with —$NR^{14}R^{15}$ by reaction with $NHR^{14}R^{15}$ in the presence of a suitable solvent, such as for example 1-methyl-2-pyrrolidinone.

Compounds of formula (I) wherein $R^3$ comprises $C_{2-6}$alkynyl, can be hydrogenated into a compound of formula (I) wherein $R^3$ comprises $C_{2-6}$alkyl in the presence of a suitable catalyst, such as for example palladium on charcoal, and a suitable solvent, such as for example ethylacetate.

Compounds of formula (I) wherein $R^3$ comprises $C_{2-6}$alkynyl, can be hydrogenated into a compound of formula (I) wherein $R^3$ comprises $C_{2-6}$alkenyl in the presence of a suitable catalyst, such as for example Lindlar catalyst, and a suitable solvent, such as for example ethylacetate.

Compounds of formula (I) wherein $R^3$ represents $C_{1-6}$alkyl substituted with —P(=O)(OC$_{1-6}$alkyl)$_2$ can be converted into a compound of formula (I) wherein $R^3$ represents $C_{1-6}$alkyl substituted with —P(=O)(OH)$_2$ by reaction with bromotrimethylsilane in the presence of a suitable solvent, such as for example dichloromethane.

Compounds of formula (I) wherein the $R^9$ substituent is substituted with =O, can be converted into the corresponding reduced $R^9$ substituent by reaction with a suitable reducing agent, such as for example LiAlH$_4$ in a suitable solvent, such as for example tetrahydrofuran.

Compounds of formula (I) wherein $R^3$ comprises —NHR$^{10}$ can be converted into a compound of formula (I) wherein $R^3$ comprises —NR$^{10}$—(C=O)— optionally substituted $C_{1-6}$alkyl, by reaction with the corresponding W—(C=O)— optionally substituted $C_{1-6}$alkyl wherein W represents a suitable leaving group, such as for example halo, e.g. chloro and the like, in the presence of a suitable base, such as for example triethylamine, and a suitable solvent, such as for example acetonitrile.

Compounds of formula (I) wherein $R^3$ represents $C_{1-6}$alkyl substituted with NR$^{10}$(benzyl) can be converted into a compound of formula (I) wherein $R^3$ represents $C_{1-6}$alkyl substituted with NHR$^{10}$, by reaction with 1-chloroethylchloroformate in the presence of a suitable solvent, such as for example dichloromethane Compounds of formula (I) wherein $R^1$ represents unsubstituted piperidine, can be converted into a compound of formula (I) wherein $R^1$ represents 1-methyl-piperidine, by reaction with iodomethane in the presence of a suitable base, such as for example potassium carbonate, and a suitable solvent, such as for example acetonitrile. Compounds of formula (I) wherein $R^1$ represents hydrogen can be converted into a compound of formula (I) wherein $R^1$ represents optionally substituted $C_{1-6}$alkyl, by reaction with optionally substituted $C_{1-6}$alkyl-W wherein W represents a suitable leaving group, such as for example halo, e.g. bromo and the like, in the presence of a suitable base, such as for example potassium carbonate, and a suitable solvent, such as for example acetonitrile.

Compounds of formula (I) wherein $R^2$ represents halo, e.g. bromo, can be converted into a compound of formula (I) wherein $R^2$ represents cyano, by reaction with zinc cyanide, in the presence of a suitable catalyst, such as for example Pd$_2$(dba)$_3$ and a suitable ligand, such as for example 1,1-bis(diphenylphosphino)ferrocene, in the presence of a suitable solvent, such as for example N,N-dimethylformamide.

Said $R^2$ substituent being cyano can be converted into —CH$_2$—NH$_2$ by hydrogenation in the presence of NH$_3$ and Nickel.

Compounds of formula (I) wherein $R^2$ represents —OCH$_3$ can be converted into a compounds of formula (I) wherein $R^2$ represents —OH by reaction with boron tribromide in the presence of a suitable solvent, such as for example dichloromethane.

Compounds of formula (I) wherein $R^2$ represents —OH can be converted into a compounds of formula (I) wherein $R^2$ represents —OCH$_3$ by reaction with methyl iodine in the presence of a suitable base, such as for example potassium carbonate, and a suitable solvent, such as for example N,N-dimethylformamide.

Compounds of formula (I) wherein $R^2$ represents hydrogen, can be converted into a compound of formula (I) wherein $R^2$ represents —CHOH—CF$_3$ by reaction with trifluoroacetaldehyde methyl hemiketal.

A further aspect of the invention is a process for the preparation of a compound of formula (I) as defined herein, which process comprises:

(i) deprotecting a compound of formula (XXX) wherein P represents a suitable protective group, such as for example a butyloxycarbonyl-group (—CO$_2$C(CH$_3$)$_3$) in the presence of a suitable acid, such as for example HCl or trifluoroacetic acid;

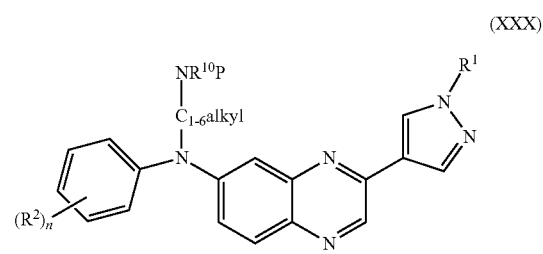

(XXX)

(ii) the reaction of a compound of the formula (IX) or (IX'):

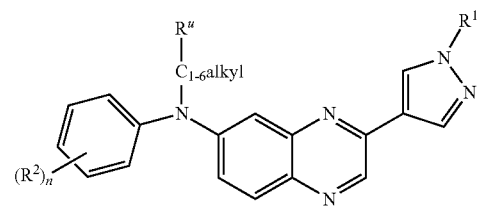

(IX): $R^u$ is —O—(S=O)$_2$—CH$_3$ (IX'): $R^u$ is Cl or a protected form thereof, with an appropriately substituted amine or a reactive derivative thereof, such as for example NHR$^{10}$R$^{11}$(X), NHR$^{10}$P (X-a) or

(XXI), for example in a sealed vessel, in the presence of a suitable base, such as for example sodium hydride and/or in the presence or absence of a solvent such as acetonitrile, N,N-dimethylformamide or N,N-dimethylacetamide; or (iii) the reaction of a compound of the formula (VI):

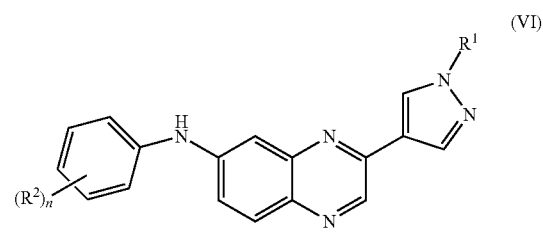

(VI)

or a protected form thereof, with a compound of formula W₆—C$_{1-6}$alkyl-NR$^{10}$P wherein P represents a suitable protective group and W₆ represents a suitable leaving group, such as for example halo, e.g. bromo and the like, or —O—S(=O)₂—CH₃, in the presence of a suitable base, such as for example sodium hydride, and a suitable solvent, e.g. N,N-dimethylformamide or N,N-dimethylacetamide, followed by removing P and optionally removing any further protecting group present; or (iv) the reaction of a compound of the formula (VI):

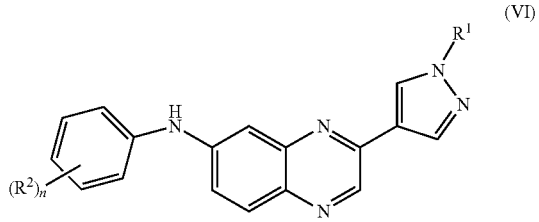

(VI)

or a protected thereof, with a compound of formula W₆—C$_{1-6}$alkyl-NHR$^{10}$ wherein W₆ represents a suitable leaving group, such as for example halo, e.g. bromo and the like, or —O—S(=O)₂—CH₃, in the presence of a suitable base, such as for example sodium hydride, and a suitable solvent, e.g. N,N-dimethylformamide or N,N-dimethylacetamide;

(v) the reaction of a compound of formula (XXXVI)

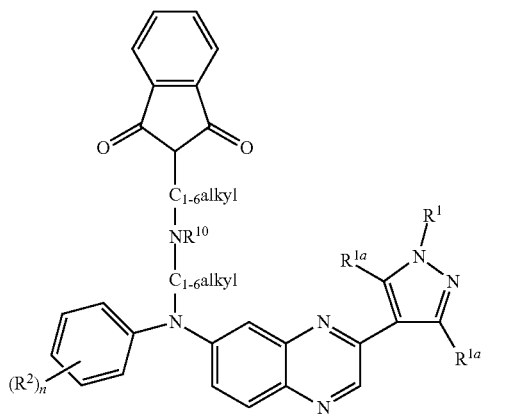

(XXXVI)

with hydrazine in the presence of a suitable solvent, such as for example an alcohol, e.g. ethanol;

(vi) the reaction of a compound of formula (IX-1) wherein R$^u$ represents —O—S(=O)₂—CH₃,

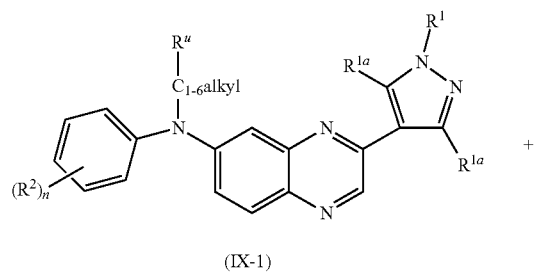

(IX-1)

NHR$^{10}$R$^{11}$ (X)

with an intermediate of formula (X) in the presence of a suitable solvent, such as for example acetonitrile;

(vii) the reaction of a compound of formula (VI)

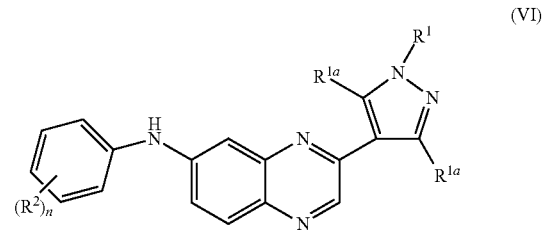

(VI)

with an intermediate of formula W$_{11}$—R$^{3b}$ wherein R$^{3b}$ represents optionally substituted C$_{2-6}$alkynyl and W$_{11}$ represents a suitable leaving group such as for example halo, e.g. chloro, or —O—S(=O)₂—CH₃, in the presence of a suitable base, such as for example NaH, and a suitable solvent, such as for example N,N-dimethylformamide;

(viii) the reaction of a compound of formula (VIII') wherein R$^x$ and R$^y$ represent Cl$_{1-4}$alkyl, and R$^z$ represent C$_{1-4}$alkyl or phenyl,

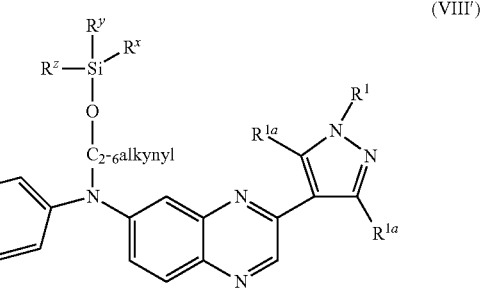

(VIII')

with a suitable acid, such as for example trifluoroacetic acid, in the presence of a suitable solvent, such as for example tetrahydrofuran;

(viii) deprotecting a compound of formula (XXXXII)

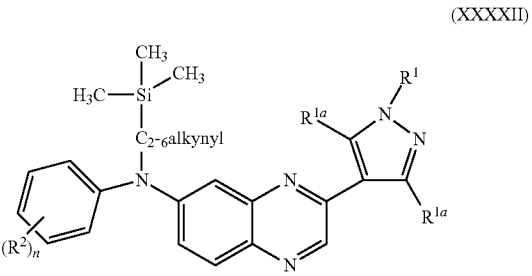

(XXXXII)

in the presence of a suitable base, such as for example K₂CO₃, and a suitable solvent, such as for example an alcohol, e.g. methanol and the like;

(ix) the reaction of a compound of formula (VI)

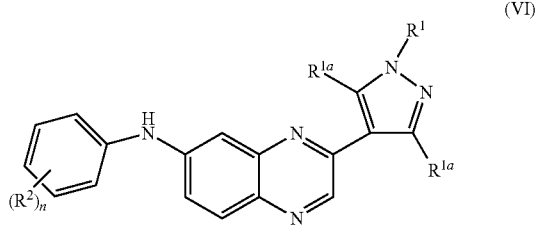
(VI)

with di($C_{1-6}$alkyl)vinylphosphonate in the presence of a suitable catalyst, such as for example tri-N-butylphosphine, and a suitable solvent, such as for example acetonitrile;

(x) deprotecting a compound of formula (XXXXI)

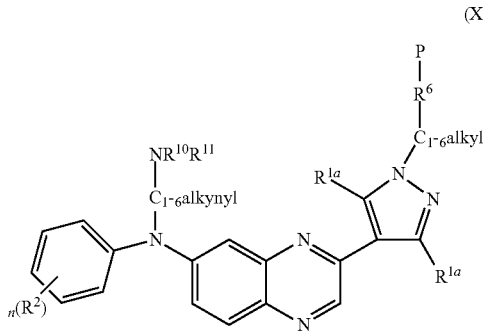
(XXXXI)

in the presence of a suitable base, such as for example $K_2CO_3$, and a suitable solvent, such as for example an alcohol, e.g. methanol and the like;

(xi) the reaction of a compound of formula (XIX) with a compound of formula (III)

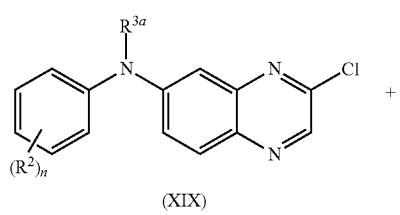
(XIX)

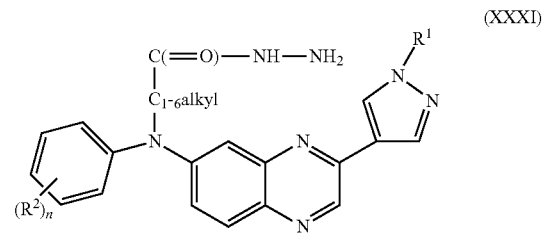
(III)

in the presence of a suitable catalyst, such as for example tetrakis(triphenyl)phosphine palladium or $Pd_2(dba)_3$ (tris(dibenzylideneacetone)dipalladium (0)), a suitable ligand, such as 2-dicyclohexylphosphino-2',6'-dimethoxybiphenyl, a suitable base, such as for example $Na_2CO_3$ or $K_3PO_4$, and a suitable solvent, such as for example ethylene glycol dimethylether or dioxane or water;

(xii) the reaction of a compound of formula (XX) wherein $R^{3a}$ represents optionally substituted $C_{1-6}$alkyl, with a compound of formula (XIV)

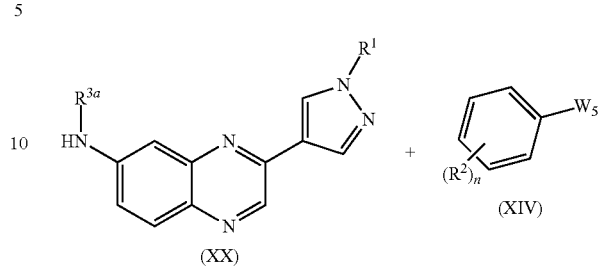
(XX) (XIV)

in the presence of a suitable catalyst, such as for example palladium (II) acetate or $Pd_2(dba)_3$ (tris(dibenzylidene acetone)dipalladium (0)), a suitable ligand such as for example 2-dicyclohexylphosphino-tris-isopropyl-biphenyl or 1,1'-[1,1'-binaphthalene]-2,2'-diylbis[1,1-diphenylphosphine], a suitable base, such as for example sodium tert-butoxide, and a suitable solvent, such as for example ethylene glycol dimethylether;

(xiii) the reaction of a compound of formula (XXXI)

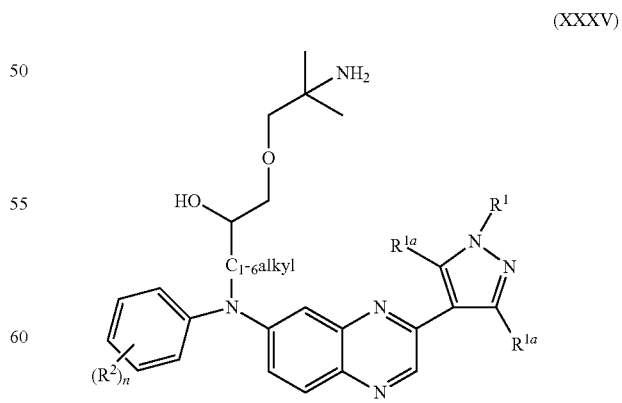
(XXXI)

with $W_8$—CN, wherein $W_8$ represents a suitable leaving group, such as for example halo, e.g. bromo, in the presence of a suitable base, such as for example $NaHCO_3$, and a suitable solvent, such as for example water or dioxane;

(xiv) the reaction of a compound of formula (XXXV)

(XXXV)

with a suitable base, such as for example N,N-diisopropylethylamine and triethylamine, in the presence of a suitable solvent, such as for example an alcohol, e.g. methanol;

(xv) deprotecting a compound of formula (XXVI) wherein P represents a suitable protective group such as for example —O—Si(CH$_3$)$_2$(C(CH$_3$)$_3$) or

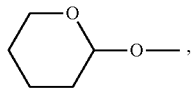

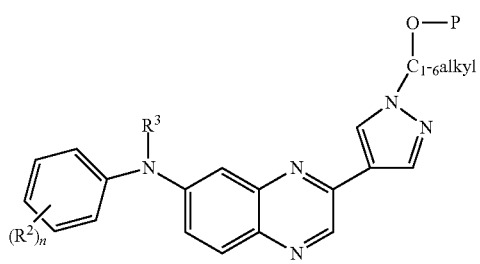

(XXVI)

in the presence of a suitable acid, such as for example HCl or trifluoroacetic acid, or a suitable de-silylating agent, such as for example tetrabutyl ammonium fluoride, and a suitable solvent, such as an alcohol, e.g. methanol, or tetrahydrofuran;

(xvi) the reaction of a compound of formula (XXIX) with a compound of formula (XXI)

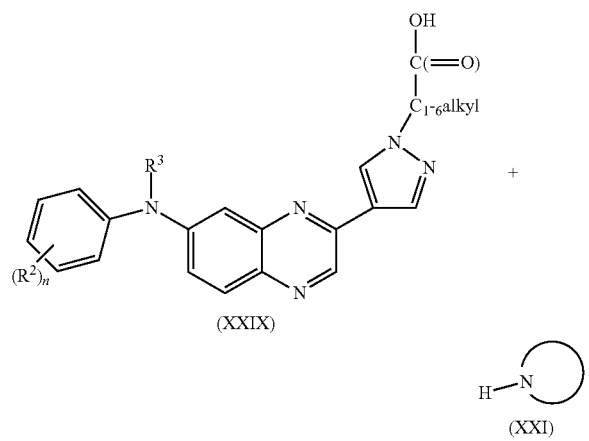

in the presence of suitable peptide coupling reagents such as, 1-hydroxy-benzotriazole and 1-(3-dimethylaminopropyl)-3-ethyl carbodiimide HCl;

(xvii) the reaction of a compound of formula (XXIX)

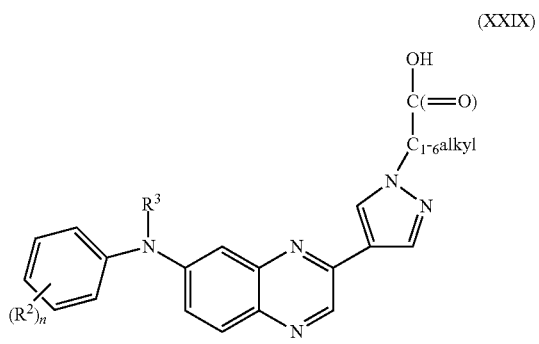

with NHR$^4$R$^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane;

(xviii) reacting the below compound

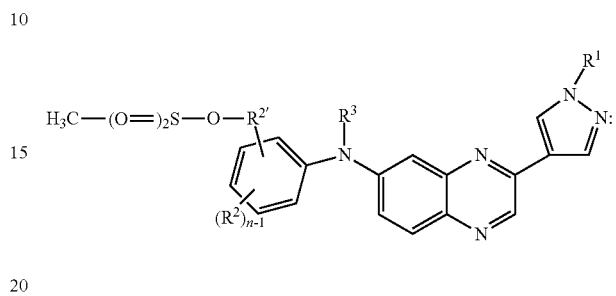

with NHR$^7$R$^8$ in the presence of a suitable base, such as for example K$_2$CO$_3$, and a suitable solvent, such as for example tetrahydrofuran;

(xviii) deprotecting the below compound

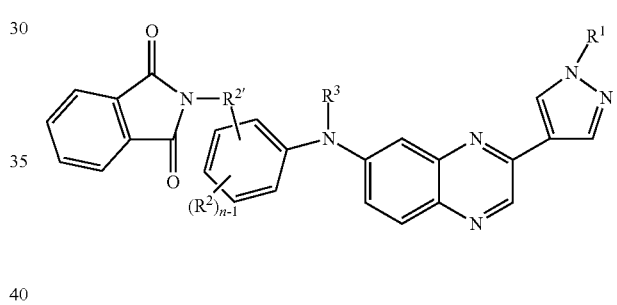

in the presence of hydrazine monohydrate, and a suitable solvent, such as for example an alcohol, e.g. ethanol;

wherein R$^1$, R$^{1a}$, R$^2$, R$^{10}$, and n are as defined herein; and optionally thereafter converting one compound of the formula (I) into another compound of the formula (I).

A further embodiment is a process for synthesis of a compound of formula (VI) wherein:

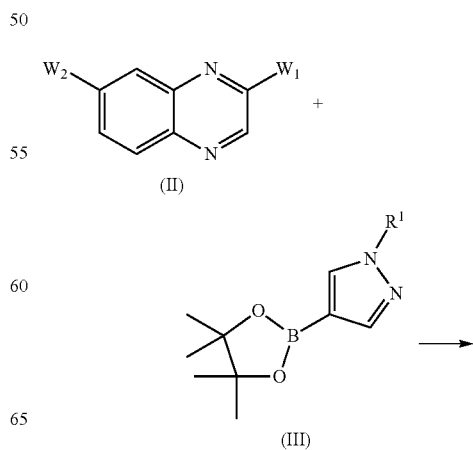

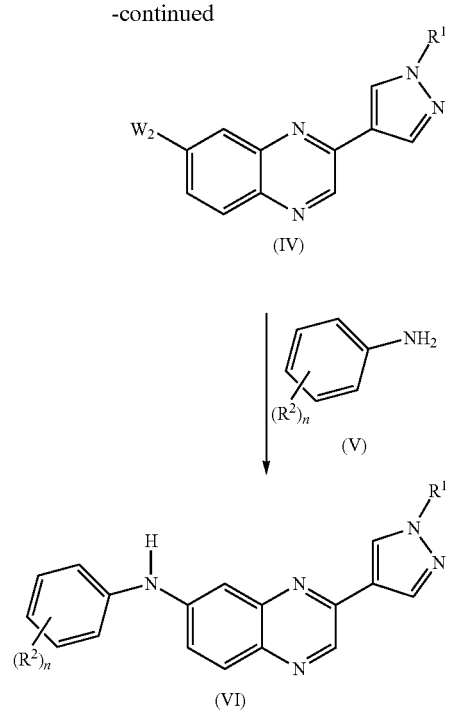

1) a compound of formula (II) is reacted with an intermediate of formula (III) in the presence of a suitable catalyst, such as for example tetrakis(triphenylphosphine)palladium (0) or palladium (II) acetate, a suitable base, such as for example sodium carbonate, a suitable ligand, such as for example triphenylphosphine, and a suitable solvent or solvent mixture, such as for example ethylene glycol dimethylether and water; wherein $W_1$ and $W_2$, each independently represent a suitable leaving group, such as for example halo, e.g. chloro or bromo;

and then 2) a compound of formula (IV) is reacted with an intermediate of formula (V) in the presence of a suitable catalyst, such as for example palladium (II) acetate, a suitable base, such as sodium tert-butoxide or $Cs_2CO_3$, a suitable ligand, such as for example 1,1'-[1,1'-binaphthalene]-2,2'-diylbis[1, 1-diphenylphosphine], and a suitable solvent or solvent mixture, such as for example dioxane or ethylene glycol dimethylether and water;

wherein optionally the intermediate of formula (II) wherein $W_1$ is chloro and $W_2$ is bromo is prepared by reacting 7-bromo-2(1H)-quinoxalinone with phosphorus oxychloride, or alternatively with thionyl chloride and N,N-dimethylformamide in a suitable solvent, such as, for example toluene;

or vice versa, wherein a compound of formula (II) is reacted with an intermediate of formula (V) first and then reacted with an intermediate of formula (III) using the methods described above.

In a further embodiment the invention provides a novel intermediate. In one embodiment the invention provides a novel intermediate of formula (II)-(XXXI). In another embodiment the invention provides a novel intermediate of formula (VI) or formula (IX). In another embodiment the invention provides a compound of formula (I-a)-(I-i).

Pharmaceutically Acceptable Salts, Solvates or Derivatives Thereof.

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof. According to a further aspect of the invention there is provided a compound as defined herein or a salt or solvate thereof. References to compounds of the formula (I) and sub-groups thereof as defined herein include within their scope the salts or solvates or tautomers or N-oxides of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I). Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

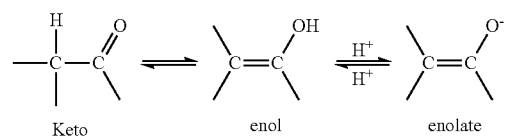

Keto      enol      enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.,* 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-6}$ alkyl group, a heterocyclyl group, or a $C_{5-20}$ aryl group, preferably a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-6}$alkyl (e.g., -Me, -Et, -nPr, -iPr, -nBu, -sBu, -iBu, -tBu); $C_{1-6}$-aminoalkyl [e.g., aminoethyl; 2-(N,N-diethylamino)ethyl; 2-(4-morpholino)ethyl); and acyloxy-$C_{1-7}$alkyl [e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl]. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembraneous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 µM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung (for example adenocarcinoma, small cell lung cancer and non-small cell lung carcinomas), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4;14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular the compounds are useful for the treatment of t(4;14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC, squamous cell carcinoma, liver cancer, kidney cancer, breast cancer, colon cancer, colorectal cancer, prostate cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T6741 of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105.

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevalence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intra-vaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetracarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example actinomycin D, bleomycin, mitomycin C, dactinomycin, caminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17 alpha-hydroxylase-17,20-lyase inhibitor (CYP17), e.g. abiraterone, abiraterone acetate.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art.

Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^3$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

EXPERIMENTAL PART

Hereinafter, the term 'CH$_3$CN' means acetonitrile, 'DCM' means dichloromethane, 'TBAF' means tetrabutylammonium fluoride, 'K$_2$CO$_3$' means potassium carbonate, 'MgSO$_4$' means magnesium sulphate, 'MeOH' means methanol, 'EtOH' means ethanol, 'EtOAc' means ethyl acetate, 'Et$_3$N' means triethylamine, 'HOBt' means 1-hydroxy-1H-benzotriazole, 'DPPP' means 1,3-propanediylbis [diphenylphosphine, 'DIPE' means diisopropyl ether, 'THF' means tetrahydrofuran, 'NH$_4$Cl' means ammonium chloride, 'Pd(PPh$_3$)$_4$' means tetrakis(triphenylphosphine)palladium, 'DIPEA' means N-ethyl-N-(1-methylethyl)-2-propylamine, 'DMF' means N,N-dimethylformamide, 'NaH' means sodium hydride, 'Pd$_2$(dba)$_3$' means tris(dibenzylideneacetone)dipalladium (0), 'HOAc' means acetic acid, 'PPh$_3$' means triphenylphosphine, 'NH$_4$OH' means ammonium hydroxide, 'TBDMSCl' means tert-butyldimethylsilyl chloride, 'S-Phos' means dicyclohexyl(2',6'-dimethoxy[1,1'-biphenyl]-2-yl)-phosphine, 'X-Phos' means dicyclohexyl[2',4',6'-tris(1-methylethyl)[1,1'-biphenyl]-2-yl]-phosphine, 'Na$_2$SO$_4$' means sodium sulfate, 'i-PrOH' means 2-propanol, 't-BuOH' means 2-methyl-2-propanol, 'K$_3$PO$_4$' means potassium phosphate, MP means melting point.

A. Preparation of the Intermediates

Example A1 a-1) Preparation of intermediate 1

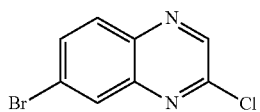 [SMILES: Clc1cnc2ccc(Br)cc2n1]

7-bromo-2(1H)-quinoxalinone (47.2 g; 210 mmol) was added to phosphorus oxychloride (470 mL). The reaction mixture was stirred at 100° C. for 2 hours, cooled down to room temperature and evaporated to dryness. The crude product was taken up into DCM and poured onto ice, water and K$_2$CO$_3$ powder. The mixture was filtered over celite. The celite was washed twice with DCM. The organic layer was decanted, dried over MgSO$_4$, filtered and evaporated to dryness to give 49 g (96%) of intermediate 1 (grey solid). MP=146° C.

Intermediate 1 was Alternatively Also Prepared Using the Following Procedure:

Thionyl chloride (407.5 mL; 5.59 mol), then N,N-dimethylformamide (34.6 mL; 0.45 mol) were added dropwise to a mixture of 7-bromo-2(1H)-quinoxalinone (500 g; 2.24 mol) in toluene (7.61 L). The reaction mixture was stirred at 80° C. for 17 hours then cooled to 35° C. and poured cautiously onto water. The bi-phasic mixture was stirred for 30 minutes and then decanted. The organic layer was evaporated to dryness and the residue crystallized in methyl-tert-butyl ether, filtered and the precipitate washed with methyl-tert-butyl ether and dried to give 407 g (74.7%) of intermediate 1. Filtrate was evaporated and re-crystallized in methyl-tert-butyl ether to provide a second fraction of 72 g (13.2%) of intermediate 1.

b-1) Preparation of intermediate 2

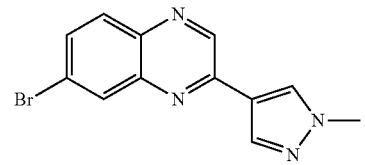 [SMILES: Cn1cc(-c2cnc3ccc(Br)cc3n2)cn1]

Under N$_2$, intermediate 1 (20 g; 82.1 mmol), 1-methyl-4-(4,4,5,5-tetramethyl-1,3,2-dioxaborolan-2-yl)-1H-pyrazole (17.1 g; 82.1 mmol), 2M sodium carbonate aqueous solution (410.1 mL; 82.1 mmol) in ethylene glycol dimethyl ether (200 mL) were degassed by bubbling nitrogen through for 15 minutes. Tetrakis(triphenylphosphine)palladium (0) (0.95 g; 0.82 mmol) was added and heated at reflux for 15 hours. The reaction mixture was poured into water and extracted with EtOAc. The organic layer was dried over MgSO$_4$, filtered and evaporated to dryness to give 29.9 g. The crude compound was purified by chromatography over silica gel (Irregular SiOH, 20-45 µm, 1000 g MATREX; mobile phase 0.1% NH$_4$OH, 98% DCM, 2% CH$_3$OH). The pure fractions were collected and concentrated till dryness to give 19.5 g (82%) of intermediate 2. MP=172° C.

Intermediate 2 was Alternatively Also Prepared Using the Following Procedure:

Intermediate 1 (502 g; 2.06 mol), 1-methyl-4-(4,4,5,5-tetramethyl-1,3,2-dioxaborolan-2-yl)-1H-pyrazole (450.42 g; 2.16 mol), triphenylphosphine (10.82 g; 0.041 mol) and palladium(II)acetate were added to a mixture of sodium carbonate (240.37 g; 2.267 mol), 1,2-dimethoxyethane (5.48 L) and water (1.13 L). The reaction mixture was stirred at reflux for 20 hours, then 1-methyl-4-(4,4,5,5-tetramethyl-1, 3,2-dioxaborolan-2-yl)-1H-pyrazole (42.9 g; 0.206 mol) was added and the reaction mixture refluxed until complete conversion (4 hours). The reaction mixture was poured out in water, stirred for 2 hours at room temperature, filtered and the precipitate was washed with water. The precipitate was then triturated in methanol and filtered. The precipitate was washed with methanol and dried to give 532.2 g (89%) of intermediate 2 (off-white powder).

| Intermediate prepared according to the above protocol | starting from |
|---|---|
| 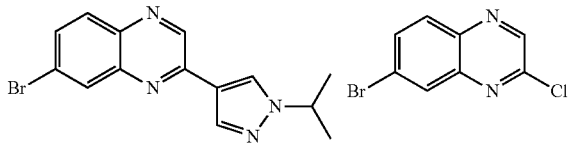 | | c-1) Preparation of intermediate 3

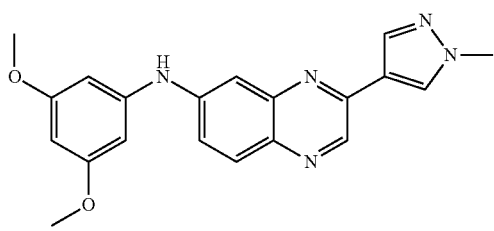 [SMILES: COc1cc(Nc2ccc3ncc(-c4cnn(C)c4)nc3c2)cc(OC)c1]

A mixture of intermediate 2 (20 g; 69.2 mmol), 3,5-dimethoxyaniline (10.6 g; 69.2 mmol), sodium tert-butoxide (20 g; 0.21 mol) and 1,1'-[1,1'-binaphthalene]-2,2'-diylbis[1,1-diphenylphosphine (2.2 g; 3.5 mmol) in dioxane (500 mL) was degassed at room temperature under $N_2$ flow. After 10 minutes, palladium(II) acetate (0.78 g; 3.5 mmol) was added portionwise at room temperature under $N_2$ flow. The reaction mixture was heated at 90° C. overnight. The reaction mixture was cooled to room temperature and partitioned between water and EtOAc. The organic layers were combined, dried over $MgSO_4$, filtered and concentrated to give 40 g of crude compound. This residue was taken up into $DCM/Et_2O$ (3/7) and the mixture was stirred for 30 minutes. The precipitate was filtered off and dried to give 20 g of intermediate 3 (brown solid). The filtrate was evaporated to dryness to give 40 g of a crude compound which was purified by chromatography over silica gel (Irregular SiOH, 20-45 µm, 450 g MATREX; Mobile phase 0.1% $NH_4OH$, 98% DCM, 2% $CH_3OH$). The pure fractions were concentrated to give 4.2 g of intermediate 3 (brown solid). MP=199° C. (DSC).

Overall yield=96.8%.

| Intermediate prepared according to the above protocol | starting from |
|---|---|
| 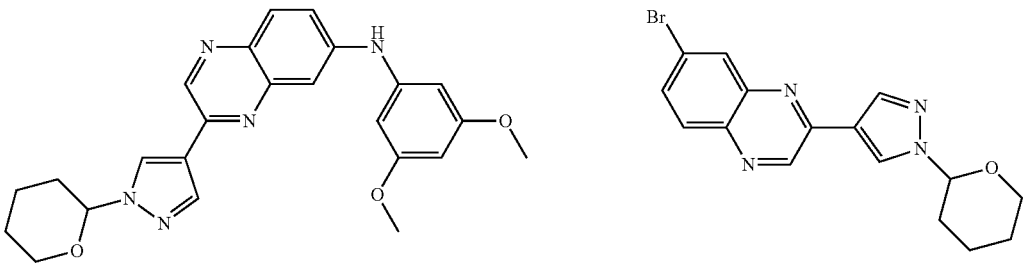 intermediate 49 | |
| 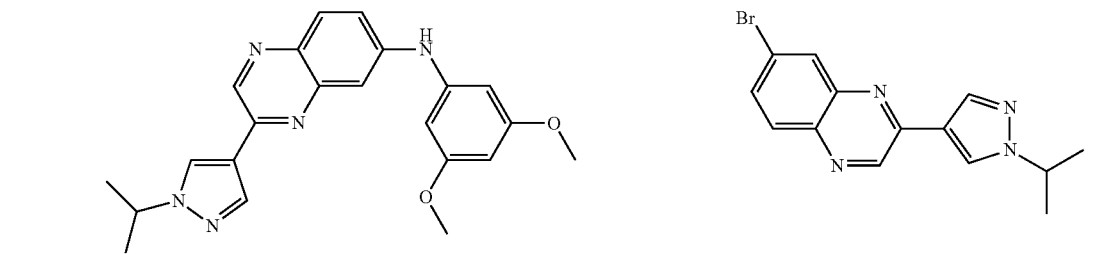 | |
| 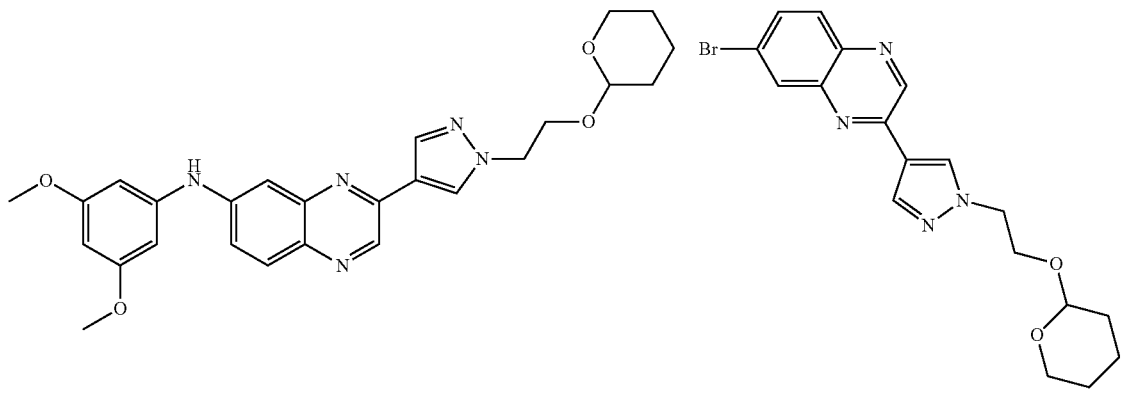 | |

| Intermediate prepared according to the above protocol | starting from |
|---|---|
| 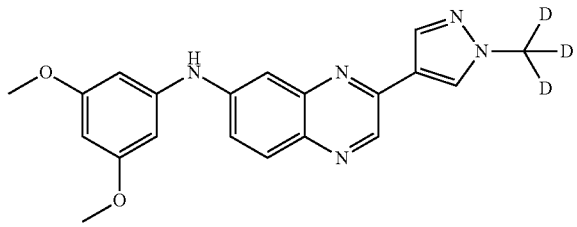 | 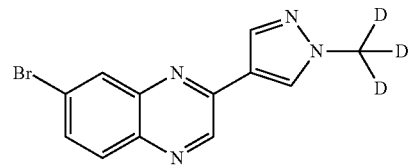 [SMILES: [2H]C([2H])([2H])n1cc(-c2cnc3ccc(Br)cc3n2)cn1] |

D = deuterium

Intermediate 3 was Alternatively Also Prepared Using the Following Procedure.

A mixture of intermediate 2 (80 g; 277 mmol), 3,5-dimethoxyaniline (47.6 g; 304 mmol) and cesium carbonate (108.2 g; 332 mmol) in 1,2-dimethoxyethane (1.1 L) was stirred at 80° C. under $N_2$ flow and then cooled to room temperature (solution A). In another flask under $N_2$, a mixture of palladium(II)acetate (0.62 g; 2.8 mmol) and racemic-2,2'-bis(diphenylphosphino)-1,1'-binaphtyl (1.76 g; 2.8 mmol) was stirred at 40° C. for 15 minutes and then added to solution A at 35° C. The new reaction mixture was stirred at 80° C. for 20 hours, cooled to 50° C. and water was added (1.11 L). The reaction mixture was seeded with crystals of intermediate 3 and extra water (0.55 L) was added before cooling to room temperature. The precipitate was filtered off and washed with water, then recrystallized in isopropylalcohol (with seeding). The precipitate was filtered off, washed with diisopropylether and dried to provide 79.2 g (79.2%) of intermediate 3.

Intermediate 3 was Alternatively Also Prepared Using the Following Procedure.

a-2) Preparation of intermediate 4

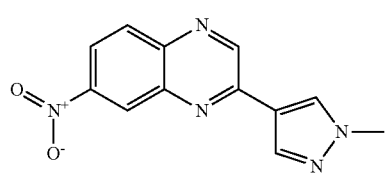 [SMILES: Cn1cc(-c2cnc3ccc([N+](=O)[O-])cc3n2)cn1]

2-Chloro-7-nitroquinoxaline (27.8 g, 133 mmol), 1-methyl-4-(4,4,5,5-tetramethyl-1,3,2-dioxaborolan-2-yl)-1H-pyrazole (30.4 g, 146 mmol), 2M $Na_2CO_3$ aqueous solution (66.3 mL, 133 mmol) in ethylene glycol dimethyl ether (330 mL) were degassed with $N_2$ for 15 minutes. Tetrakis(triphenylphosphine)palladium (0) (1.5 g, 1.33 mmol) was added and the reaction mixture was heated at 100° C. for 7 hours. The reaction was poured into water. The precipitate was filtered off, taken-up with EtOAc, then filtered and dried under vacuum to give 31.4 g (93%) of intermediate 4 (yellow solid). MP=231° C. (DSC).

| Intermediate prepared according to the above protocol | starting from |
|---|---|
| 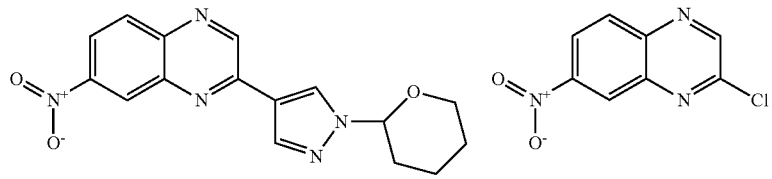 | | b-2) Preparation of intermediate 5

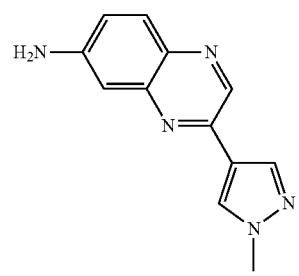 [SMILES: Cn1cc(-c2cnc3ccc(N)cc3n2)cn1]

A mixture of intermediate 4 (15.7 g, 61.5 mmol) and Raney nickel (16 g) in $CH_3OH$ (380 mL) and THF (60 mL) was hydrogenated under a 3 bars pressure overnight. The reaction mixture was filtered on a celite pad which was washed 3 times with $CH_3OH$/DCM (50/50), then several times with a mixture of MeOH/acetone. The combined filtrates were evaporated till dryness to give 13.1 g (95%) of intermediate 5 (brown solid). MP=240° C. (DSC).

| Intermediate prepared according to the above protocol | starting from |
|---|---|
| 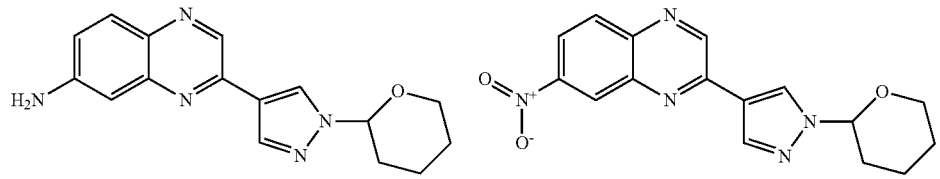 | |

Intermediate 5 was Alternatively Also Prepared Using the Following Procedure.

A 200 mL stainless steel autoclave was charged under $N_2$ atmosphere with intermediate 2 (5 g, 17.3 mmol), $NH_4OH$ (100 mL) and $Cu_2O$ (0.1 g) The autoclave was closed and the reaction was carried out for 16 hours at a temperature of 150° C. The reaction mixture was extracted with DCM, the organic layer was washed with water, dried ($MgSO_4$) and filtered. The filtrate was evaporated till dryness and the residue was purified by chromatography over silica gel (kromasil C18 100 A 5 µm, Eka nobel; mobile phase, from 90% of a 0.25% solution of ammonium bicarbonate in water, 10% MeOH to 100% MeOH). The pure fractions were collected to give 2.4 g (61.6%) of intermediate 5.

c-2) Preparation of intermediate 3

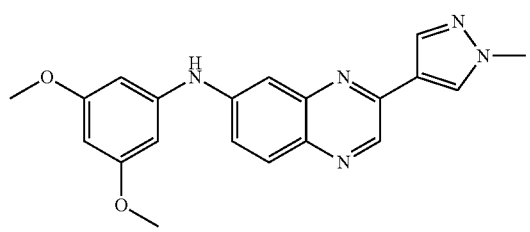

The experiment has been performed 3 times on the following amount.

A mixture of intermediate 5 (2.12 g, 9.4 mmol), 1-bromo-3,5-dimethoxybenzene (2.25 g, 10.4 mmol), sodium tert-butoxide (2.71 g, 28.3 mmol) and 1,1'-[1,1'-binaphthalene]-2,2'-diylbis[1,1-diphenylphosphine](0.29 g, 0.47 mmol) in ethylene glycol dimethyl ether (40 mL) was degassed with $N_2$ for 10 minutes. Palladium(II) acetate (0.21 g, 0.94 mmol) was added and the mixture was heated at 135° C. for 60 minutes under microwave irradiation The mixture was cooled to room temperature, poured into $H_2O$ and EtOAc. The 3 experiments were combined for the work up. The mixture was filtered over celite. The filtrate was extracted with EtOAc. The combined organic layers were dried over $MgSO_4$, filtered and evaporated to dryness to give 11.3 g of crude compound. The residue was purified by chromatography over silica gel (Irregular SiOH, 20-45 µm, (450 g) MATREX; mobile phase 0.1% $NH_4OH$, 95% DCM, 5% iPrOH). The pure fractions were collected and the solvent was evaporated, yielding 7.6 g (74%) of intermediate 3 (brown solid).

| Intermediate prepared according to the above protocol | starting from |
|---|---|
| 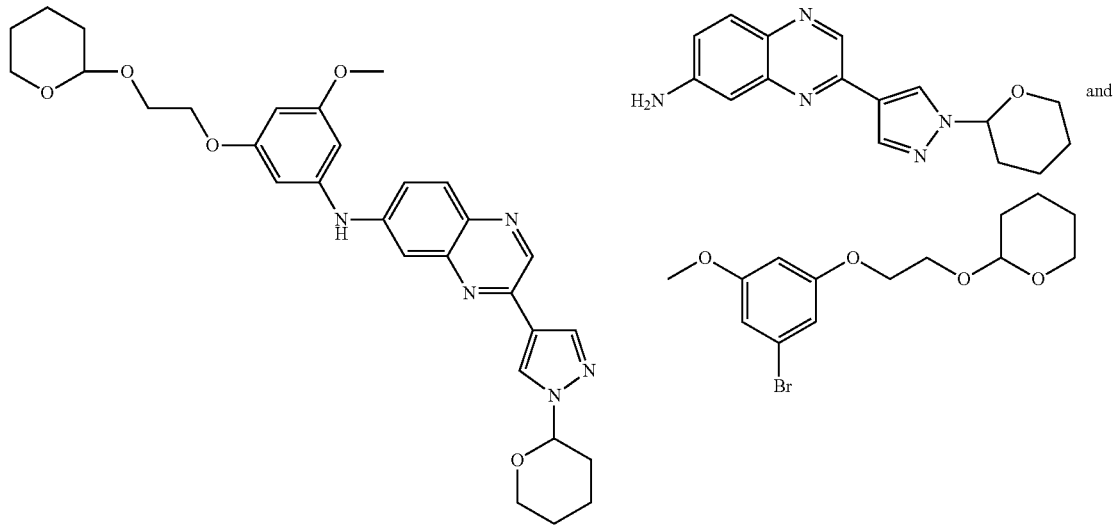 | |

| Intermediate prepared according to the above protocol | starting from |
|---|---|
| 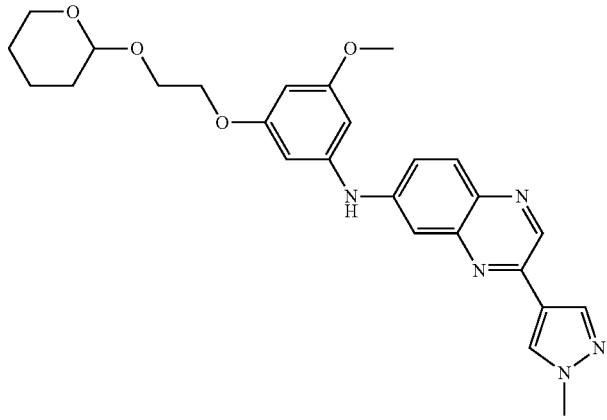 [SMILES: COc1cc(Nc2ccc3ncc(-c4cnn(C)c4)nc3c2)cc(OCCOC2CCCCO2)c1] | 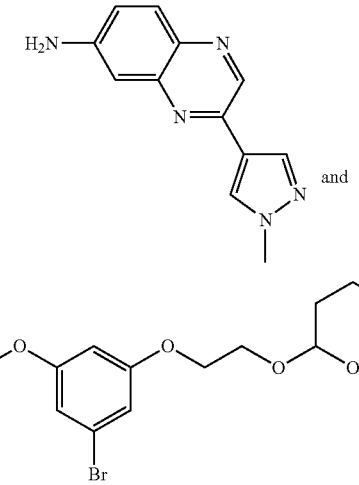 and |
| 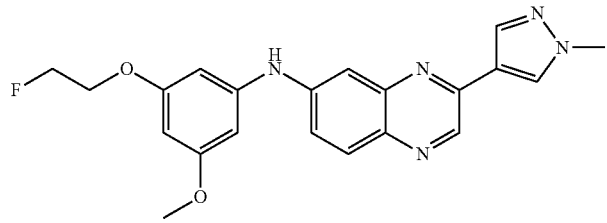 [SMILES: COc1cc(Nc2ccc3ncc(-c4cnn(C)c4)nc3c2)cc(OCCF)c1] | 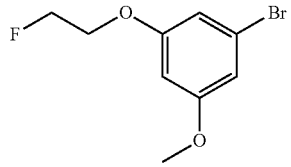 | a-4) Preparation of intermediate 6

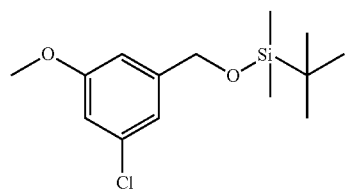 [SMILES: COc1cc(Cl)cc(CO[Si](C)(C)C(C)(C)C)c1]

Tert-butyldimethylsilyl chloride (2.096 g, 13.9 mmol) was added to 3-chloro-5-methoxybenzenemethanol (2 g, 11.6 mmol) in DCM (40 mL) at 0° C., followed by imidazole (2.5 g, 36.85 mmol). The reaction mixture was slowly allowed to warm to room temperature and stirred overnight. The reaction mixture was partitioned between EtOAc and water. The 2 phases were separated, the organic phase was dried (MgSO₄), filtered and concentrated to give an oil which solidified on standing. The residue was purified by chromatography over silica gel (Irregular SiOH, 15-40 μm, 90 g; mobile phase 30% EtOAc, 70% pentane). The fractions were collected and the solvent was evaporated, yielding 2.56 g (77%) of intermediate 6.

b-4) Preparation of intermediate 7

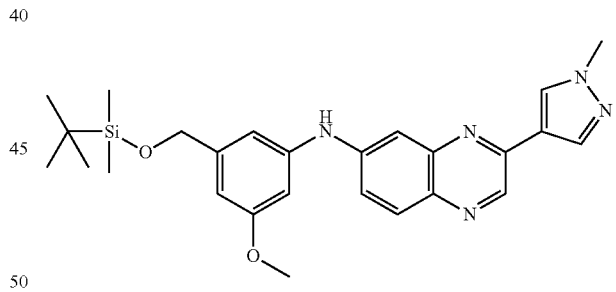

Intermediate 6 (1.39 g, 3.9 mmol), intermediate 5 (0.7 g, 3.1 mmol), Cs₂CO₃ (3 g, 0.3 mmol), tris(dibenzylideneacetone)dipalladium (0.28 g, 0.3 mmol) and X-Phos (0.33 g, 0.68 mmol) in t-BuOH (20 mL) were stirred at 100° C. under microwave irradiation for 3 hours. The reaction mixture was filtered through celite and the filtrate was concentrated to ⅓ of the initial volume. H₂O and EtOAc were added and the organic phase was separated, dried (MgSO₄), filtered and concentrated. The residue was purified by chromatography over silica gel (Hyperprep C18 HS BDS100 A 8 mu (Shandon); mobile phase gradient from 70% of a 0.25% solution of ammonium bicarbonate in water/30% CH₃CN to 10% of a 0.25% solution of ammoniumbicarbonate in water/90% CH₃CN). The pure fractions were collected and the solvent was evaporated, yielding 418 mg of intermediate 7.

a-5) Preparation of intermediate 8

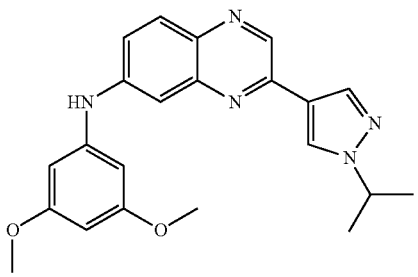 [SMILES: COc1cc(Nc2ccc3ncc(-c4cnn(C(C)C)c4)nc3c2)cc(OC)c1]

A mixture of intermediate 13 (see hereinafter) (9.45 g, 29.9 mmol), 1-(1-methylethyl)-4-(4,4,5,5-tetramethyl-1,3,2-dioxaborolan-2-yl)-1H-pyrazole (8.48 g, 35.9 mmol), potassium phosphate (15.88 g, 74.8 mmol) and dicyclohexyl(2',6'-dimethoxy[1,1'-biphenyl]-2-yl)phosphine (1.23 g, 3.0 mmol) in dioxane (125 mL) and H$_2$O (25 mL) was degassed at room temperature under N$_2$ flow. After 10 minutes, Pd(PPh$_3$)$_4$ (1.73 g, 1.5 mmol) was added portionwise. The reaction mixture was then heated at 80° C. overnight, then cooled to room temperature and poured out into ice water. EtOAc was added and the organic layer was washed with water, then with brine, dried (MgSO$_4$), filtered and the solvent was evaporated. The residue (20.2 g) was purified by chromatography over silica gel (Irregular SiOH, 20-45 µm, 1000 g MATREX; mobile phase 95% DCM, 5% MeOH, 0.1% NH$_4$OH). The product fractions were collected and the solvent was evaporated, yielding 10 g (85%). of intermediate 8.

Example A2

Preparation of intermediate 9

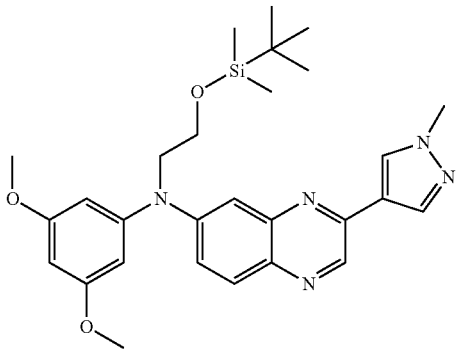 [SMILES: COc1cc(OC)cc(N(CCO[Si](C)(C)C(C)(C)C)c2ccc3ncc(-c4cnn(C)c4)nc3c2)c1]

NaH (1.77 g; 44.27 mmol) was added portionwise to a solution of intermediate 3 (8 g; 22.13 mmol) in N,N-dimethylformamide (160 mL) at 5° C. under N$_2$ flow. The reaction mixture was stirred at 5° C. for 1 hour. Then, (2-bromoethoxy)-tert-butyldimethylsilane (9.5 mL; 44.27 mmol) was added dropwise at 5° C. under N$_2$ flow. The reaction mixture was stirred for 1 hour at 5° C. then, allowed to warm to room temperature and stirred overnight. The reaction was poured out into ice water and EtOAc was added. The organic layer was separated, washed with brine, dried (MgSO$_4$), filtered and the solvent was evaporated to dryness to give 17 g of a residue which was purified by chromatography over silica gel (Irregular SiOH, 15-40 µm, 200 g; mobile phase gradient from 100% DCM to 96% DCM, 4% MeOH).

The pure fractions were collected and concentrated yielding 11 g (95%) of intermediate 9.

Intermediate 9 was Alternatively Also Prepared Using the Following Procedure.

a) Preparation of intermediate 40

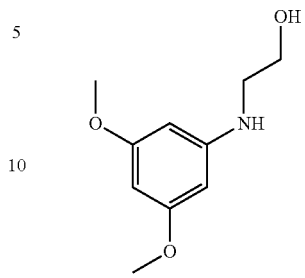

A mixture of 3,5-dimethoxyphenylamine (250 g; 1.63 mol), cesium carbonate (319 g; 0.98 mol) and water (0.33 L) in 1,2-dimethoxyethane (2 L) was heated to 60° C. Then carbonochloridic acid, 2-chloroethyl ester (250 g; 1.75 mol) was added dropwise at this temperature over 1 hour. A solution of potassium hydroxide (458 g; 8.2 mol) in water (1.3 L) was added in one portion. The reaction mixture was stirred at 60° C. for 30 minutes, then heated at 100° C. to distill off 1,2-dimethoxyethane using a Dean-Starck trap. The residue was cooled to 50° C. and extracted with methyl-tert-butyl ether (1.14 L). The organic layer was washed with water, dried (MgSO$_4$), filtered and the filtrate was evaporated till dryness. The residue was crystallized in a mixture of methyl-tert-butyl ether and heptane. The precipitate was filtered off and dried to provide 241.8 g (75%) of intermediate 40.

b) Preparation of intermediate 41

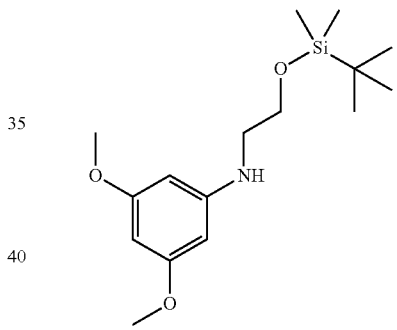

TBDMSCl (262.7 g; 1.74 mol) was added portionwise over 10 minutes, under a N$_2$ atmosphere, to a solution of intermediate 40 (327.4 g; 1.66 mol) and 1H-imidazole (124.3 g; 1.825 mol) in DCM (3.3 L) at room temperature. Upon completion of the reaction, water (3.3 L) was added and the organic layer was decanted, washed with water (3.3 L), dried (MgSO$_4$), filtered and the filtrate was filtered on silica gel and concentrated to give 496 g (95.9%) of intermediate 41, used crude for the next step.

c) Preparation of intermediate 9

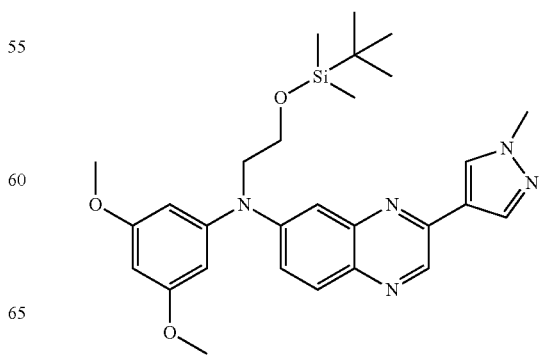

Under an inert atmosphere, a solution of palladium(II) acetate (1.16 g; 5.2 mmol), racemic 2,2'-bis(diphenylphosphino)-1,1'-binaphtyl (4.4 g; 6.9 mmol) in 1,2-dimethoxyethane (52 mL) was added at room temperature to a solution of intermediate 2 (100 g; 346 mmol), intermediate 41 (118.5 g; 380.5 mmol) and cesium carbonate (135 g; 415 mmol) in 1,2-dimethoxyethane (1.4 L). The reaction mixture was heated at 80° C. over 1 hour, stirred at this temperature for 2 hours and refluxed overnight. Water (0.5 L) and DCM (1.5 L) were then added at room temperature and the organic layer was separated, washed with water and evaporated till dryness to provide crude intermediate 9 (21 g) which can directly be used into the next step.

Example A3

Preparation of intermediate 10

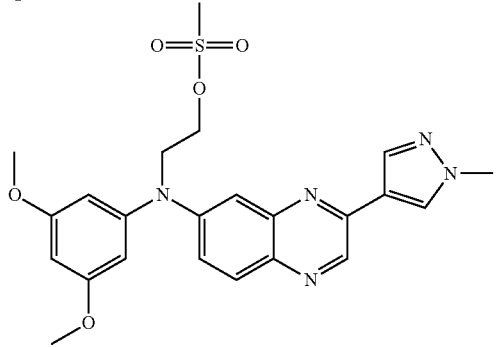 [SMILES: COc1cc(OC)cc(N(CCOS(C)(=O)=O)c2ccc3ncc(-c4cnn(C)c4)nc3c2)c1]

Methanesulfonyl chloride (3.8 mL; 49.33 mmol) was added dropwise to a solution of compound 1 (10 g; 24.66 mmol) and Et$_3$N (8.58 mL; 61.67 mmol) in DCM (250 mL) at 5° C. under N$_2$ flow. The reaction mixture was stirred at 5° C. for 1 hour, then 1 hour at room temperature. The reaction mixture was poured out into ice water and DCM was added. The organic layer was separated, dried (MgSO$_4$), filtered and the solvent was evaporated to dryness (30° C.). The residue was precipitated by addition of DIPE. The solid was filtered yielding, after drying, 10.09 g (94%) of intermediate 10 (red solid). MP=161° C. (kofler).

| Intermediate prepared according to the above protocol | starting from |
|---|---|
| Intermediate 17a | compound 3 |

Example A4 a-1) Preparation of intermediate 11

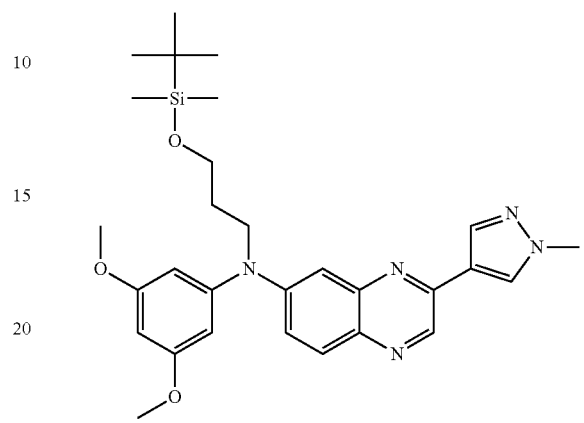

NaH (1.1 g; 27.67 mmol) was added portionwise to a solution of intermediate 3 (5 g; 13.83 mmol) in N,N-dimethylformamide (80 mL) at 5° C. under N$_2$ flow. The reaction mixture was stirred at 5° C. for 1 hour then (3-bromopropoxy) (1,1-dimethylethyl)dimethylsilane (6.41 mL, 27.67 mmol) was added dropwise at 5° C. under N$_2$ flow. The reaction mixture was stirred 1 hour at 5° C. then warmed to room temperature and stirred overnight. The reaction was poured out into ice water and EtOAc was added. The organic layer was separated, dried (MgSO$_4$), filtered and the solvent was evaporated to dryness to give a crude residue (9.1 g). Purification by chromatography over silica gel (Irregular SiOH, 15-40 μm; mobile phase gradient from 100% DCM to 98% DCM, 2% MeOH) afforded after concentration of the pure fractions 7 g (94%) of intermediate 11.

Intermediate 11 was Alternatively Also Prepared Using the Following Procedure.

NaH (31.65 g, 60% w/w in oil; 0.79 mol) was added portionwise over 15 minutes to a cooled (−2° C.) solution of intermediate 3 (130 g; 0.36 mol) in N,N-dimethylacetamide. The reaction mixture was stirred at −2° C. for 30 minutes before addition of (3-bromopropoxy) (1,1-dimethylethyl)dimethylsilane (100.2 g; 0.4 mol). The reaction mixture was further stirred at −2° C. for 1.5 hours and overnight at room temperature after removal of the cooling system. The reaction mixture was then poured out in water (2.5 L), DCM (1 L) was added and the pH was adjusted to 6 with acetic acid. The layers were separated, the organic layer was washed with water, dried (MgSO$_4$), filtered and concentrated till dryness to provide 167.2 g (87%) of intermediate 11.

| Intermediate prepared according to the above protocol | starting from |
|---|---|
| 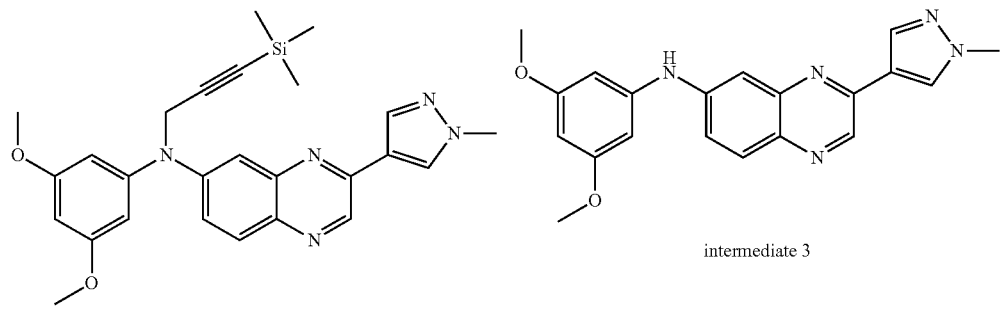 Intermediate 62 | intermediate 3 |

Intermediate 11 was Alternatively Also Prepared Using the Following Procedure.

a-2) Preparation of intermediate 12

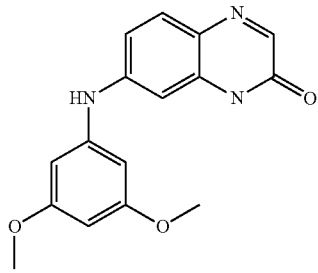 [SMILES: COc1cc(Nc2ccc3ncc(=O)[nH]c3c2)cc(OC)c1]

7-Bromo-2(1H)-quinoxalinone (25 g; 0.11 mol), 3,5-dimethoxyaniline (20.42 g; 0.133 mol), sodium tert-butoxide (32 g; 0.333 mol), 1,1'-[1,1'-binaphthalene]-2,2'-diylbis[1,1-diphenylphosphine](6.9 g; 0.011 mol) in ethylene glycol dimethyl ether (400 mL) were degassed with $N_2$ for 10 minutes. Palladium(II) acetate (2.5 g; 0.01 μmol) was added and the mixture refluxed for 5 hours. The reaction mixture was cooled to room temperature and the solvent was concentrated under vacuum to 150 mL. The residue was poured onto ice water (1.5 L) under stirring and EtOAc was added (100 mL). The suspension was stirred at room temperature overnight and the precipitate was filtered off, washed with water, then $CH_3CN$ and dried yielding 33 g of intermediate 12.

b-2-a) Preparation of intermediate 13

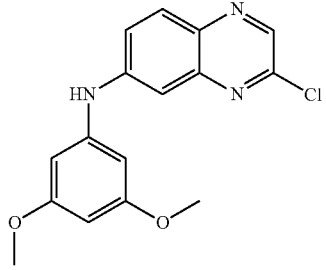 [SMILES: COc1cc(Nc2ccc3ncc(Cl)nc3c2)cc(OC)c1]

Intermediate 12 (30 g; 0.1 mol) was added portionwise at room temperature to phosphorus oxychloride (415 mL). Then the reaction mixture was heated at 80° C. and stirred at this temperature for 40 minutes. The mixture was cooled to room temperature and phosphorous oxychloride was removed under vacuum. The residue was carefully poured onto an aqueous solution of $K_2CO_3$. The aqueous layer was extracted with DCM. The organic layer was dried ($MgSO_4$), filtered and evaporated to dryness. The residue was purified by chromatography over silica gel (Irregular SiOH, 15-40 μm, 450 g; mobile phase, gradient from 100% DCM to 98% DCM, 2% MeOH). The product fractions were collected and the solvent was evaporated, to give 22.6 g (70%) of intermediate 13. MP=137° C. (Kofler).

Intermediate 13 was Alternatively Also Prepared Using the Following Procedure.

b-2-b) N-Chlorosuccinimide (11.23 g; 84.08 mmol) was added portionwise at room temperature to a suspension of $PPh_3$ (22.05 g, 84.08 mmol) in dioxane (500 mL). The reaction mixture was stirred for 30 minutes. Intermediate 12 (5 g; 16.8 mmol) was added and the reaction mixture was refluxed for 5 hours, then cooled to room temperature and basified with $Et_3N$ (10 mL) under stirring. The suspension was stirred overnight and the insoluble material was removed by filtration. The filtrate was concentrated and the residue (35 g) was purified by chromatography over silica gel (Irregular SiOH, 15-40 μm, 400 g; mobile phase 100% DCM). The pure fractions were collected and evaporated to dryness, yielding 2 g (37%) of intermediate 13.

c-2) Preparation of intermediate 14

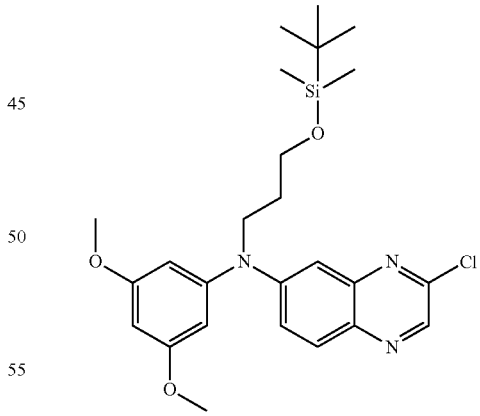

NaH (1.48 g; 37.1 mmol) was added portionwise to a solution of intermediate 13 (9 g; 28.50 mmol) in DMF (100 mL) at 5° C. under $N_2$ flow. The reaction mixture was stirred at 5° C. for 1 hour, then, (3-bromopropoxy)(1,1-dimethylethyl)dimethylsilane (8.58 mL; 37.1 mmol) was added dropwise at 5° C. under $N_2$ flow. The reaction mixture was stirred for 1 hour at 5° C. then allowed to warm to room temperature and stirred for 4 hours. The reaction was poured out into ice water and EtOAc was added. The organic layer was separated, washed with brine, dried ($MgSO_4$), filtered and the solvent was evaporated. The residue (17.5 g) was purified by chromatography over silica gel (Irregular SiOH, 20-45 μm, 1000 g, MATREX; mobile phase 98% DCM, 2% Cyclohexane). The pure fractions were collected and the solvent was evaporated, yielding 13.3 g (95%) of intermediate 14.

| Intermediate prepared according to the above protocol | starting from |
|---|---|
| 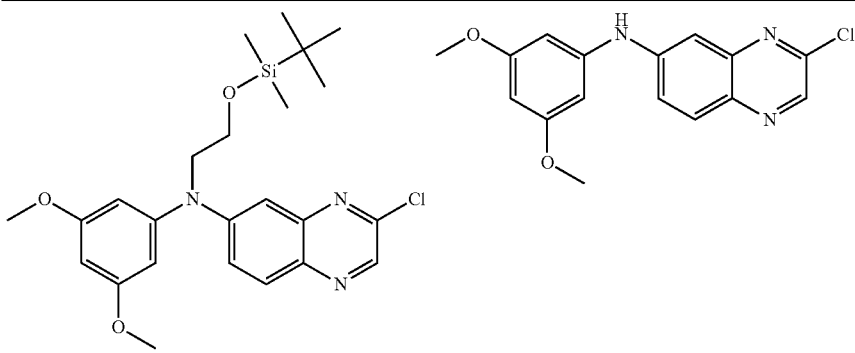 | | d-2) Preparation of intermediate 11

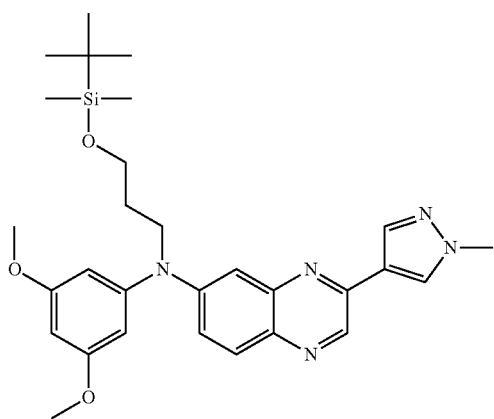 [SMILES: COc1cc(OC)cc(N(CCCO[Si](C)(C)C(C)(C)C)c2ccc3ncc(-c4cnn(C)c4)nc3c2)c1]

A mixture of intermediate 14 (15.5 g; 31.8 mmol), 1-methyl-4-(4,4,5,5-tetramethyl-1,3,2-dioxaborolan-2-yl)-1H-pyrazole (9.9 g; 47.6 mmol), potassium phosphate (13.5 g; 63.5 mmol) and dicyclohexyl(2',6'-dimethoxy[1,1'-biphenyl]-2-yl)phosphine (1.3 g; 3.2 mmol) in dioxane (380 mL) and H$_2$O (150 mL) was stirred at room temperature under N$_2$ flow. After 10 minutes, Pd$_2$(dba)$_3$ (1.45 g; 1.6 mmol) was added portionwise at room temperature under N$_2$ flow. The reaction mixture was heated at 80° C. overnight. The reaction mixture was cooled to room temperature and poured out into ice water. The mixture was filtered over celite. Celite was washed with DCM. The organic layer was washed with brine, dried (MgSO$_4$), filtered and the solvent was evaporated, yielding 21 g (99%) of intermediate 11.

| Intermediate prepared according to the above protocol | starting from |
|---|---|
| 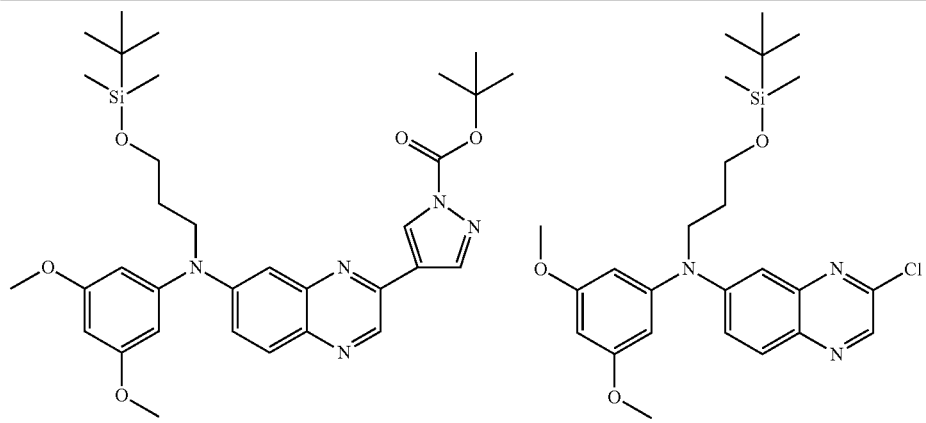 | |
| Intermediate 56 | (intermediate 14 = A4 c-2) |

Example A5 a) Preparation of intermediate 15

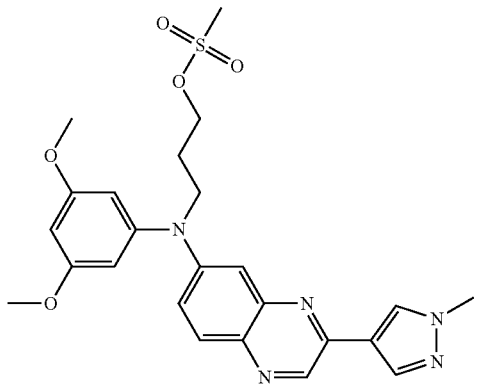

b) Preparation of intermediate 16

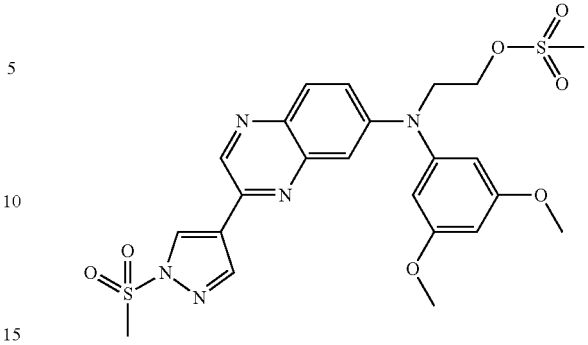

Methanesulfonyl chloride (0.97 mL, 12.52 mmol) was added dropwise to a suspension of compound 2 (0.98 g, 2.50 mmol) and Et$_3$N (2.09 mL, 15.02 mmol) in DCM (50 mL) at 5° C. under N$_2$. The mixture was stirred at room temperature for 3 hours. The solution was evaporated at room temperature yielding 1.38 g of intermediate 16. The residue was used without purification for the next step.

| Intermediate prepared according to the above protocol | starting from |
|---|---|
| 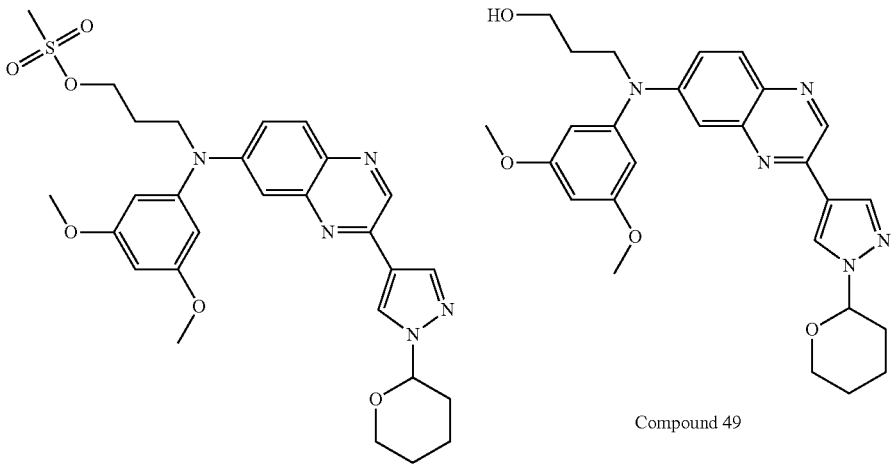 Intermediate 48 | Compound 49 |

Methanesulfonyl chloride (3.53 mL, 45.77 mmol) was added dropwise to a solution of compound 3 (9.6 g, 22.88 mmol) and triethylamine (7.96 mL, 57.21 mmol) in DCM (250 mL) at 5° C. under a N$_2$ flow. The reaction mixture was stirred for 1 hour allowing the temperature to rise to room temperature. The reaction mixture was poured out into ice water and DCM was added. The organic layer was separated, dried (MgSO$_4$), filtered and the solvent was evaporated to dryness. The crude residue was taken up into DIPE. The precipitated was filtered yielding, after drying, 10.5 g (92%) of intermediate 15.

c) Preparation of intermediate 143

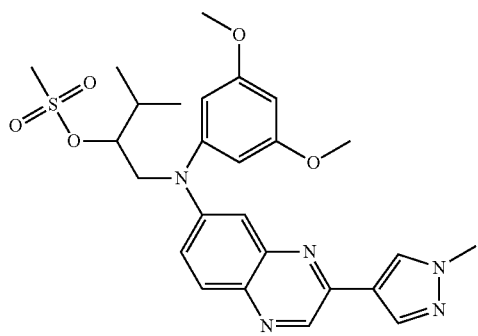 [SMILES: COc1cc(OC)cc(N(CC(OS(C)(=O)=O)C(C)C)c2ccc3ncc(-c4cnn(C)c4)nc3c2)c1]

Methanesulfonyl chloride (519 μL, 6.7 mmol) was added dropwise to a solution of compound 389 (1.5 g, 3.35 mmol), triethylamine (1.2 mL, 8.4 mmol), 4-dimethylaminopyridine (40.95 mg, 0.335 mmol) in DCM (50 mL) at 5° C. under $N_2$ flow. The reaction mixture was stirred at 5° C. for 1 hour, then at room temperature for 36 hours. Water and DCM were added and the organic layer was washed with water, dried ($MgSO_4$), filtered and the solvent was evaporated. The residue was crystallised from acetonitrile and $Et_2O$. The resulting solid was filtered and dried to give 622 mg (35%) of a yellow solid intermediate 143.

Example A6 a-1) Preparation of intermediate 17

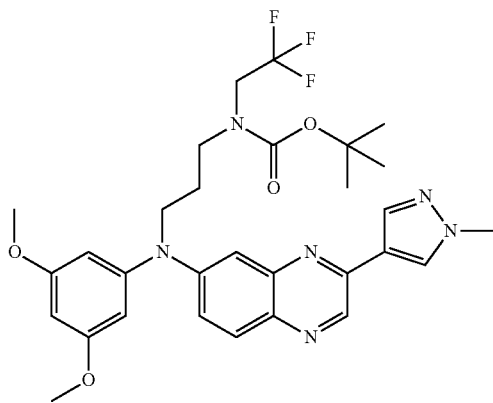 [SMILES: COc1cc(OC)cc(N(CCCN(CC(F)(F)F)C(=O)OC(C)(C)C)c2ccc3ncc(-c4cnn(C)c4)nc3c2)c1]

NaH (16.88 g; 0.42 mol) in suspension in heptane was slowly added to a solution of intermediate 17a (100 g; 0.201 mol) and 1,1-dimethylethyl ester N-(2,2,2-trifluoroethyl)-carbamic acid (48.03 g; 0.241 mol) in N,N-dimethylacetamide (1 L) at 0° C. The reaction mixture was stirred for 1 hour at 0° C., allowed to warm to room temperature in 1 hour and stirred at room temperature for 5 hours. The reaction mixture was carefully quenched with water (1 L) and the solution was extracted twice with DCM. The combined organic layers were washed with water, decanted and evaporated to dryness. The residue was dissolved in toluene, the organic layer was washed with water and evaporated to dryness to provide 147 g of intermediate 17 which was used without further purification in the next step.

Intermediate 17 was Alternatively Also Prepared Using the Following Procedure a-2) NaH (1 g; 24.94 mmol) was added portionwise to a solution of intermediate 3 (4.5 g; 12.47 mmol) and intermediate 69 (5.02 g; 14.96 mmol) in DMF (47 mL) at 5° C. The reaction mixture was heated at 60° C. for 1 hour, then cooled to room temperature, poured onto iced water and extracted with EtOAc. The organic layer was decanted, washed with water then brine, dried ($MgSO_4$), filtered and evaporated to dryness. The residue was combined with an analogously prepared product fraction (using 1.4 g of intermediate 3) and then purified by chromatography over silica gel (Irregular SiOH, 15/40 μm) mobile phase gradient from 99% DCM/1% $CH_3OH$ to 97% DCM/3% MeOH). The pure fractions were collected and evaporated to dryness yielding 5.8 g (77%) of intermediate 17. MP=113° C.

| Intermediate prepared according to the above protocol | starting from |
|---|---|

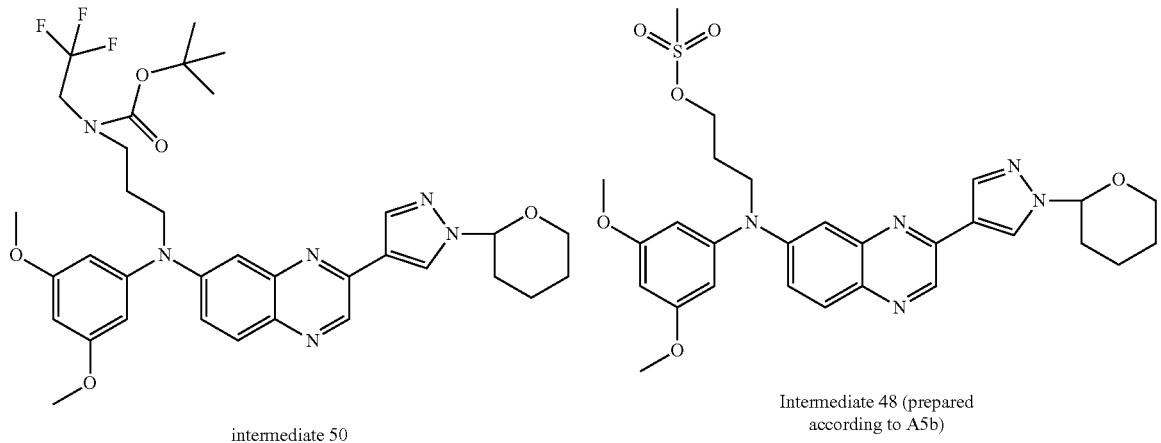

intermediate 50

Intermediate 48 (prepared according to A5b)

Example A7 a) Preparation of intermediate 18

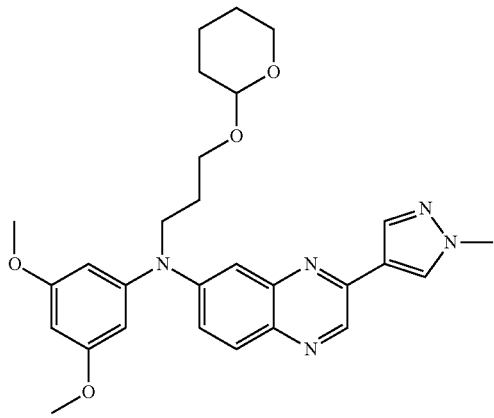 [SMILES: COc1cc(OC)cc(N(CCCOC2CCCCO2)c2ccc3ncc(-c4cnn(C)c4)nc3c2)c1]

NaH (830 mg; 20.75 mmol) was added portionwise to a solution of intermediate 3 (5 g; 13.84 mmol) in N,N-dimethylformamide (150 mL) at 5° C. under $N_2$ flow. The reaction mixture was stirred at 5° C. for 1 hour then a solution of 2-(3-bromopropoxy)tetrahydro-2H-pyran (3.5 mL; 20.75 mmol) was added dropwise at 5° C. under $N_2$ flow. The reaction mixture was stirred for 1 hour at 5° C., then allowed to warm to room temperature. The reaction was stirred at room temperature for 4 hours. The reaction was poured out into ice water and EtOAc was added. The organic layer was separated, washed with brine, dried (MgSO$_4$), filtered and the solvent was evaporated to give 8.46 g of intermediate 18.

| Intermediate prepared according to the above protocol | starting from |
|---|---|

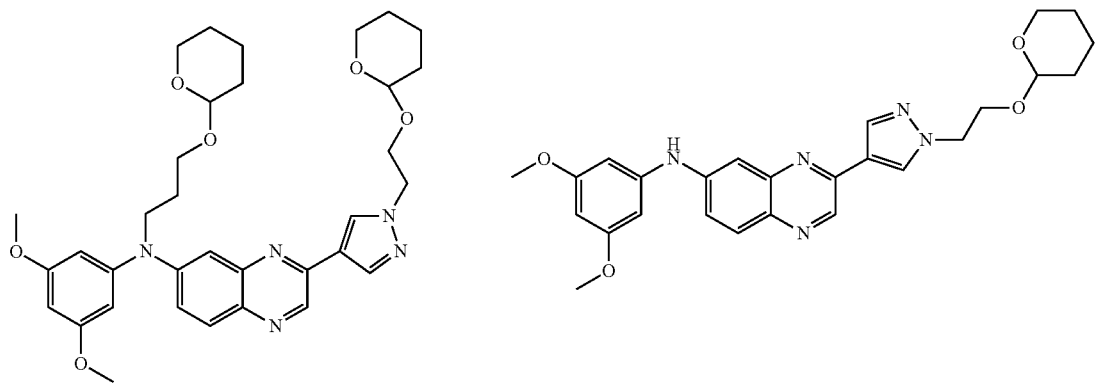

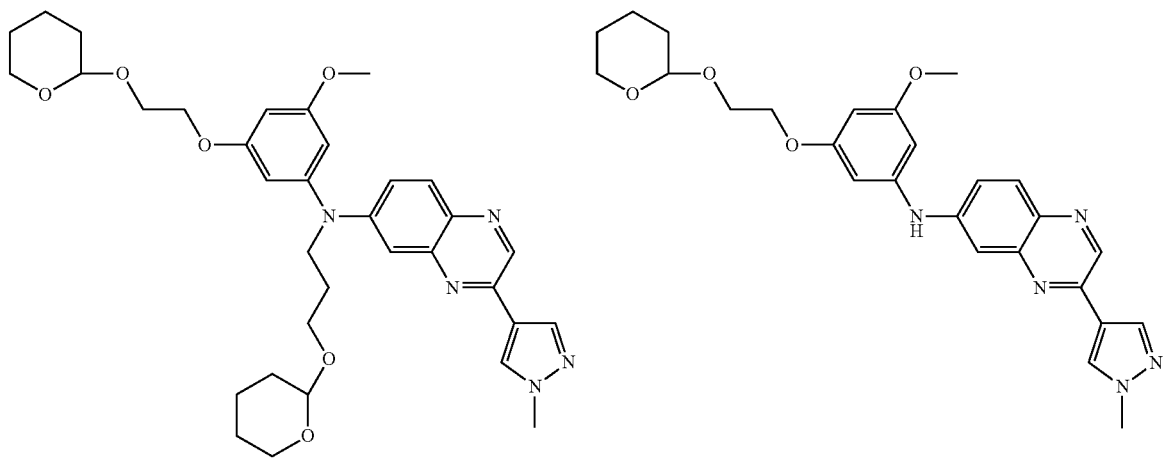

Intermediate 59

-continued
| Intermediate prepared according to the above protocol | starting from |
|---|---|
| a mixture of 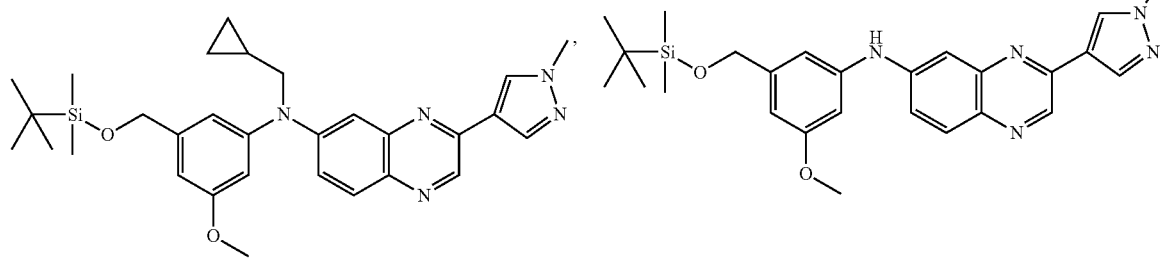 | |
| 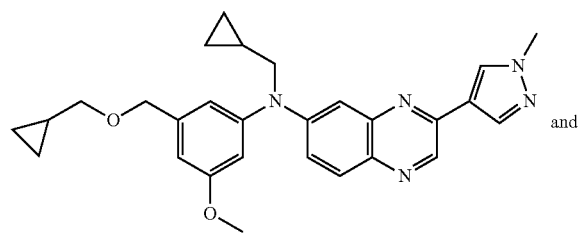 [SMILES: COc1cc(COCC2CC2)cc(N(CC2CC2)c2ccc3ncc(-c4cnn(C)c4)nc3c2)c1] and | |
| 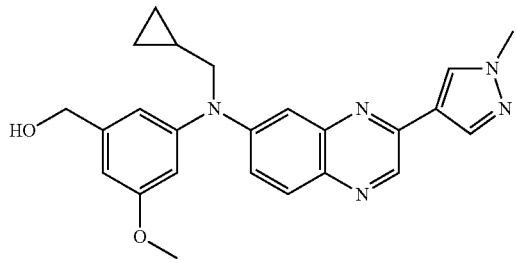 intermediate 60 | |
| 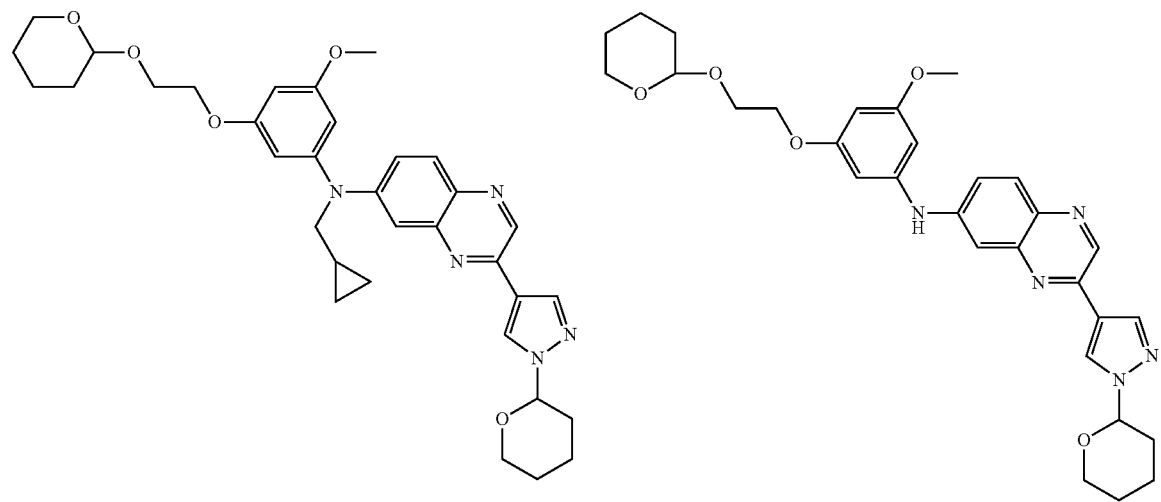 Intermediate 51 | |

-continued
| Intermediate prepared according to the above protocol | starting from |
|---|---|
| 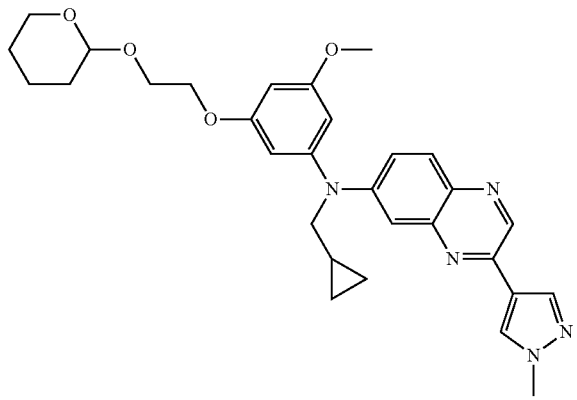<br>Intermediate 55 | 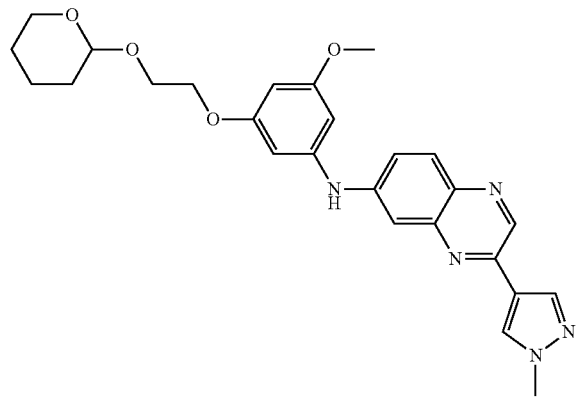 [SMILES: COc1cc(Nc2ccc3ncc(-c4cnn(C)c4)nc3c2)cc(OCCOC2CCCCO2)c1] |
| 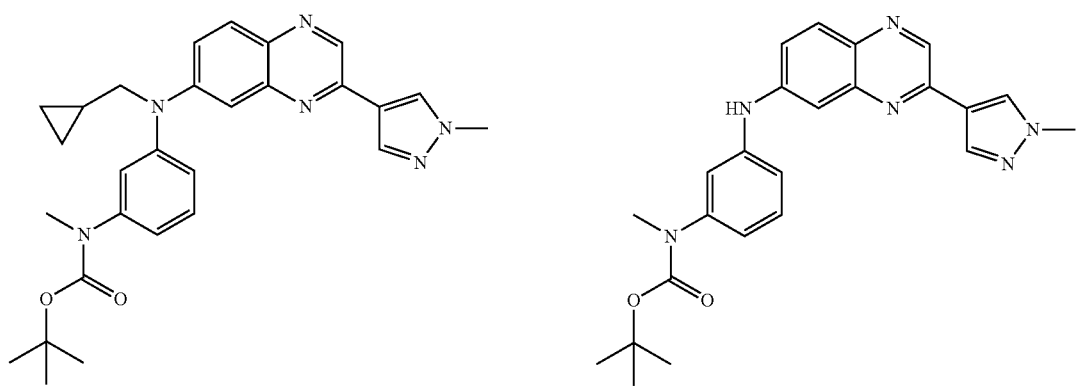<br>Intermediate 57 | |
| 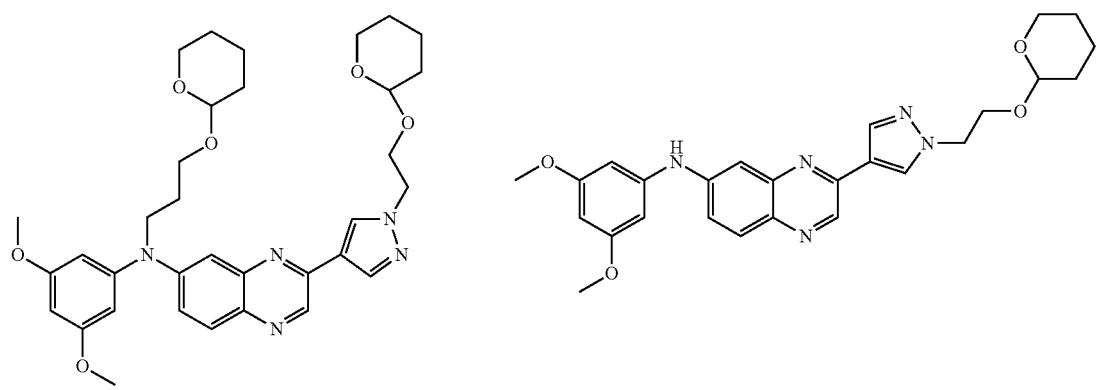<br>Intermediate 58 | |

Example A8 a) Preparation of intermediate 19

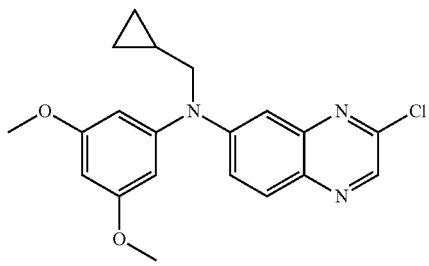 [SMILES: COc1cc(OC)cc(N(CC2CC2)c2ccc3ncc(Cl)nc3c2)c1]

NaH (882 mg; 22.04 mmol) was added portionwise to a solution of intermediate 13 (5.8 g; 18.4 mmol) in DMF (100 mL) under $N_2$ at 5° C. The reaction mixture was stirred for 20 minutes and (bromomethyl)cyclopropane (2.2 mL; 22.04 mmol) was added dropwise. The mixture was stirred for another 20 minutes at 5° C., then at room temperature for 1.5 hour. The reaction mixture was poured into $H_2O$ and extracted with EtOAc. The organic layer was dried ($MgSO_4$), filtered and evaporated to dryness, yielding 6.7 g (98%) of intermediate 19.

b) Preparation of intermediate 20

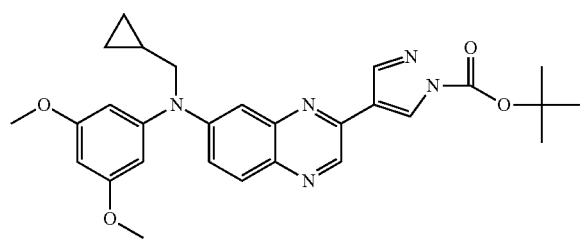 [SMILES: COc1cc(OC)cc(N(CC2CC2)c2ccc3ncc(/C(C=N)=C/NC(=O)OC(C)(C)C)nc3c2)c1]

A mixture of intermediate 19 (3 g; 8.1 mmol), 1-Boc-pyrazole-4-boronic acid pinacol ester (2.86 g; 9.7 mmol), potassium phosphate (3.44 g; 16.2 mmol), 2-dicyclohexylphosphino-2',6'-dimethoxybiphenyl (0.33 g; 0.811 mmol) in dioxane (60 mL) and $H_2O$ (6 mL) was stirred at room temperature under $N_2$ flow. After 10 minutes, tris(dibenzylideneacetone)dipalladium (0.3 g; 0.41 mmol) was added portionwise at room temperature and the mixture was heated at 80° C. overnight. The reaction mixture was cooled to room temperature and poured out into ice water. EtOAc was added and the mixture was filtered through a layer of celite. The celite was washed with EtOAc, then the filtrate was extracted with EtOAc, washed with brine, dried ($MgSO_4$), filtered and the solvent was evaporated. The residue was purified by chromatography over silica gel (Irregular SiOH, 15-40 µm, 300 g MERCK; mobile phase 0.05% $NH_4OH$, 99% DCM, 1% iPrOH). The pure fractions were collected and evaporated to dryness, yielding 1.48 g (36%) of intermediate 20.

| Intermediate prepared according to the above protocol | starting from |
|---|---|
| intermediate 47 | |

Example A9 a-1) Preparation of intermediate 21

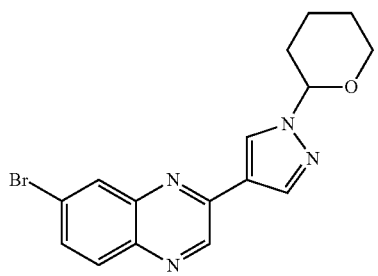 [SMILES: Brc1ccc2ncc(-c3cnn(C4CCCCO4)c3)nc2c1]

7-Bromo-2-chloroquinoxaline (10 g, 41.1 mmol), 1-(tetrahydro-2H-pyran-2-yl)-4-(4,4,5,5-tetramethyl-1,3,2-dioxaborolan-2-yl)-1H-pyrazole (11.42 g, 41.1 mmol), sodium carbonate 2M (20.5 mL, 41.1 mmol) in ethylene glycol dimethyl ether (100 mL) were degassed with $N_2$ for 15 minutes, $Pd(PPh_3)_4$ (1.4 g, 1.2 mmol) was added and heated at reflux for 20 hours. The reaction mixture was cooled to room temperature, poured into $H_2O$ and EtOAc. The precipitate was filtered and dried under vacuum to give 12 g (84%) of intermediate 21.

Intermediate 21 was Alternatively Also Prepared Using the Following Procedure.

a-2) Trifluoroacetic acid (5.55 µl; 0.075 mmol) was added dropwise to a solution of 7-bromo-2-(1H-pyrazol-4-yl)quinoxaline (410 mg; 1.5 mmol) and 3,4-dihydro-2H-pyran (0.16 mL; 1.8 mmol) in toluene (4 mL) and the reaction mixture was heated to 60° C. for 2 days, then cooled to room temperature and evaporated till dryness, yielding 550 mg of intermediate 21.

b) Preparation of intermediate 22

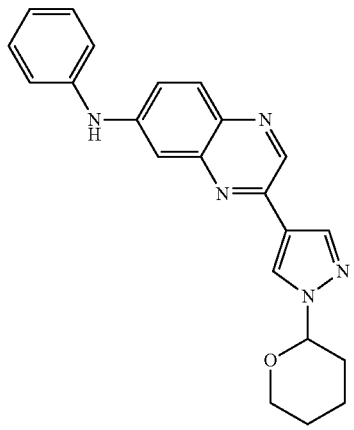 [SMILES: c1ccc(Nc2ccc3ncc(-c4cnn(C5CCCCO5)c4)nc3c2)cc1]

A mixture of intermediate 21 (1.5 g; 4.2 mmol), aniline (0.58 mL; 6.23 mmol), sodium tert-butoxide (1.2 g; 12.5 mmol) and 1,1'-[1,1'-binaphthalene]-2,2'-diylbis[1,1-diphenylphosphine](260 mg; 0.42 mmol) in ethylene glycol dimethyl ether (45 mL) was degassed with $N_2$ for 30 minutes, then palladium(II) acetate (93.7 mg; 0.42 mmol) was added. The reaction mixture was refluxed for 4 hours. $H_2O$/ice was added and the product was extracted with EtOAc. The organic layer was washed with $H_2O$, a saturated aqueous solution of NaCl, dried ($MgSO_4$), filtered and the solvent was evaporated till dryness. The crude product was purified by chromatography over silica gel (Irregular SiOH 15-40 µm, 90 g; mobile phase gradient from 99% DCM/1% MeOH to 97% DCM/3% MeOH/0.1% $NH_4OH$). The pure fractions were collected and the solvent was evaporated till dryness yielding 1.1 g (70%) of intermediate 22 A fraction (0.7 g) was re-purified by chromatography over silica gel (Sunfire Silica 5 µm 150×30.0 mm; mobile phase Gradient from 100% DCM to 0.4% $NH_4OH$, 96% DCM, 4% $CH_3OH$). The pure fractions were collected and the solvent was evaporated till dryness, yielding 0.071 g (4.5%) of intermediate 22.

c) Preparation of compound 123

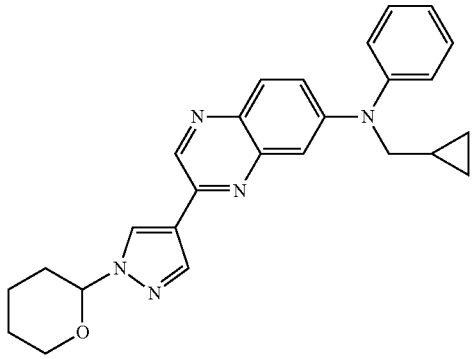 [SMILES: c1ccc(N(CC2CC2)c2ccc3ncc(-c4cnn(C5CCCCO5)c4)nc3c2)cc1]

NaH (116.3 mg; 2.9 mmol) was added portionwise to a solution of intermediate 22 (0.9 g; 2.4 mmol) in DMF (14 mL) at 5° C. The reaction mixture was stirred for 30 minutes. (Bromomethyl)cyclopropane (0.28 mL; 2.9 mmol) was added dropwise and the reaction mixture was stirred for 1 hour at 5° C., then at room temperature overnight. The reaction mixture was poured into $H_2O$ and extracted twice with EtOAc. The organic layer was washed with a saturated aqueous solution of NaCl, dried ($MgSO_4$), filtered and the solvent was evaporated till dryness. The crude product was purified by chromatography over silica gel (Irregular SiOH, 30 g, 15-40 µm; mobile phase 98% DCM/2% $CH_3OH$). The pure fractions were collected and the solvent was evaporated till dryness to give 0.5 g (48%) of compound. A fraction (0.4 g) was re-purified by chromatography over silica gel (Spherical SiOH, 10 µm, 60 g, PharmPrep MERCK; mobile phase 99% DCM, 1% MeOH). The pure fractions were collected and the solvent was evaporated, yielding 85 mg (8%) of compound 123.

d) Preparation of compound 54

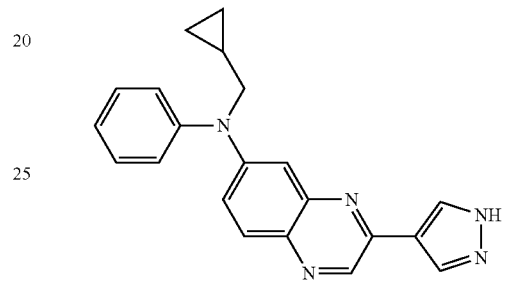

At 5° C., HCl/i-PrOH (80 µl 5/6N, 0.4 mmol) was added to a solution of compound 123 (85 mg; 0.2 mmol) in $CH_3OH$ (5 mL). The reaction mixture was stirred at 5° C. for 4 hours. Diethyl ether (8 mL) was added and the mixture was stirred for 30 minutes, then the precipitate was filtered and dried under vacuum, yielding 58 mg (71%) of compound 54 MP=138° C. (Kofler).

e) Preparation of intermediate 23

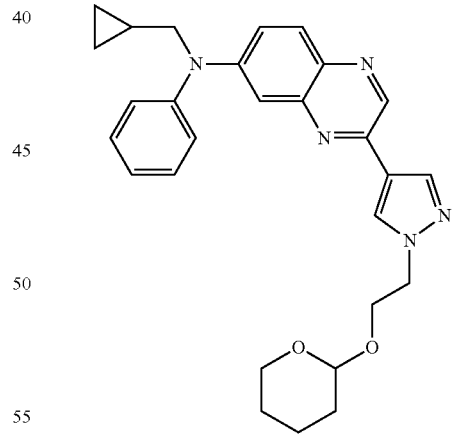

The reaction was done under a nitrogen atmosphere. NaH (0.058 g; 1.46 mmol) was added portionwise to a solution of compound 54 (0.25 g; 0.73 mmol) in DMF (5 mL) at 5° C. The reaction mixture was stirred for 30 minutes, then 2-(2-bromoethoxy)tetrahydro-2H-pyran (0.23 mL; 1.46 mmol) was added dropwise and the reaction mixture was further stirred overnight at room temperature. The reaction mixture was poured into an aqueous solution of potassium carbonate and extracted with EtOAc. The organic layer was dried ($MgSO_4$), filtered and evaporated to dryness. The crude product was purified by chromatography over silica gel (Irregular SiOH, 15-40 μm 30 g; mobile phase 0.1% NH₄OH, 99% DCM, 1% CH₃OH). The pure fractions were collected and the solvent was evaporated till dryness, yielding 250 mg (72%) of intermediate 23.
| Intermediate/compound prepared according to the above protocol | starting from |
|---|---|
| 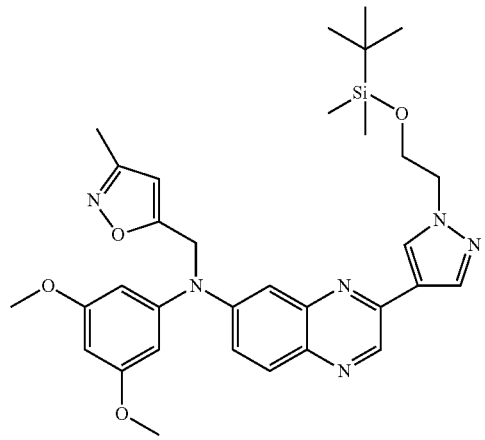<br>Intermediate 54 | 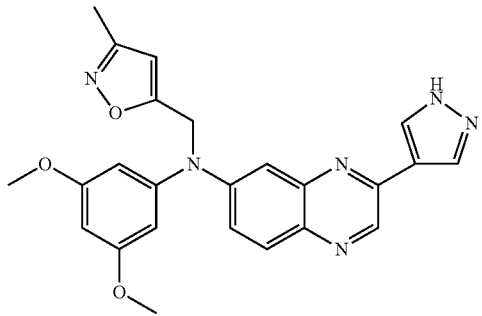 [SMILES: COc1cc(OC)cc(N(Cc2cc(C)no2)c2ccc3ncc(-c4cn[nH]c4)nc3c2)c1] |
| 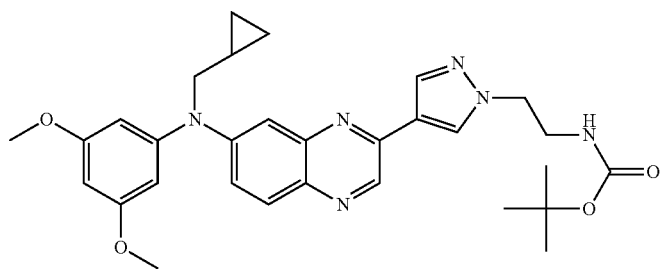<br>Intermediate 52 | 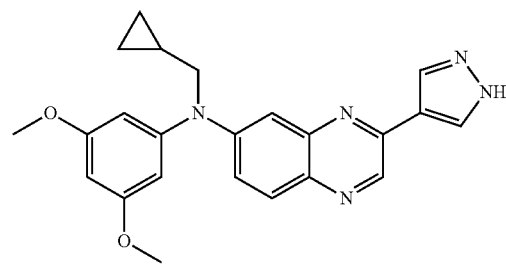<br>Compound 17 |
| 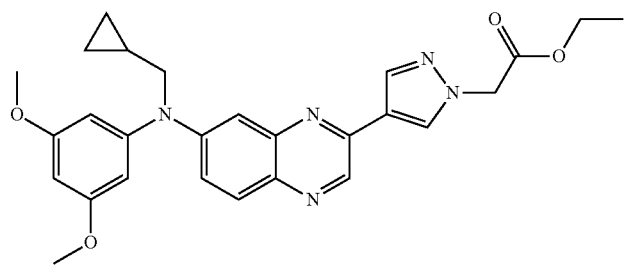<br>Intermediate 65 | 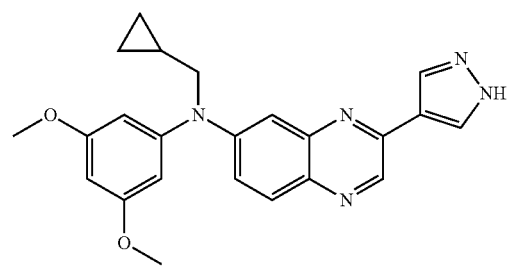<br>Compound 17 |
| 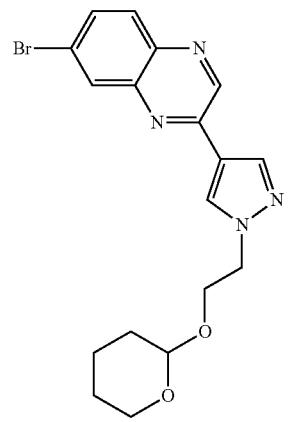 [SMILES: Brc1ccc2ncc(-c3cnn(CCOC4CCCCO4)c3)nc2c1] | 7-bromo-2-(1H-pyrazol-4-yl)quinoxaline |

Intermediate 691

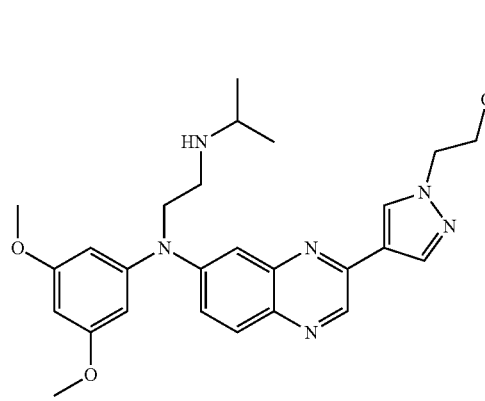

Example A10

Preparation of intermediate 24

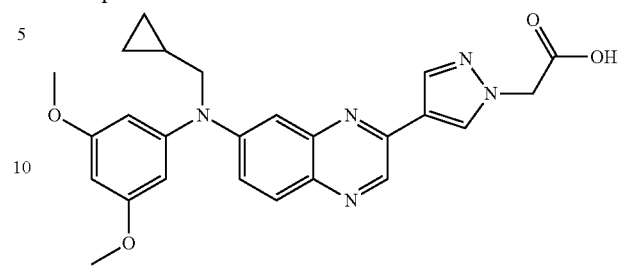

To a solution of intermediate 65 (1.1 g; 2.25 mmol) in THF (15 mL) and H₂O (15 mL) was added lithium hydroxide monohydrate (0.34 g; 4.5 mmol). The reaction mixture was stirred overnight at room temperature. THF was evaporated and H₂O and HCl were added. The precipitate was filtered and dried, yielding 976 mg (94%) of intermediate 24.

| Intermediate prepared according to the above protocol | starting from |
|---|---|
| 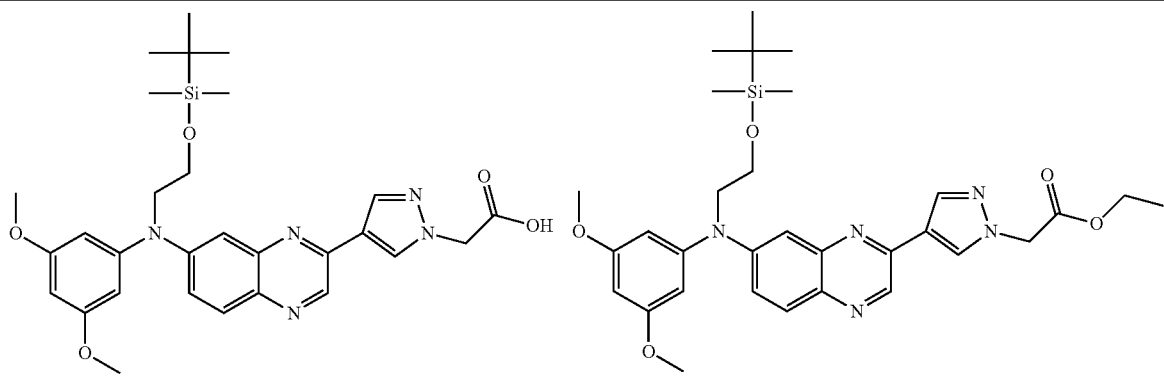 Intermediate 53 | | used to prepare compound 691 according to B14A, was prepared in an analogous way:

The experiment has been performed 4 times on the following amounts.

A mixture of compound 137 (HCl salt) (2 g; 4.6 mmol), 2-bromoethoxy-t-butyl dimethylsilane (1.3 mL; 7.4 mmol) and K₂CO₃ (1.3 g; 9.3 mmol) in CH₃CN (80 mL) was stirred at 80° C. for 24 hours. The reaction was poured out into ice water and EtOAc was added. The organic layers were combined, separated and washed with brine, dried (MgSO₄), filtered and the solvent was evaporated. The residue (12.3 g) was purified by chromatography over silica gel (SiOH 15-40 µm, 450; mobile phase gradient from 0.5% NH₄OH, 97% DCM, 3% MeOH to 0.5% NH₄OH, 90% DCM, 10% MeOH). The pure fractions were collected and concentrated to give 6 g of intermediate 691

Example A11

Preparation of intermediate 25

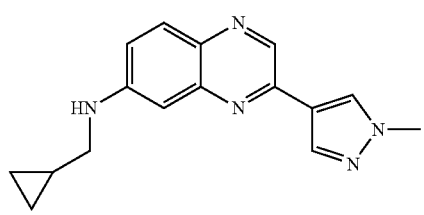 [SMILES: Cn1cc(-c2cnc3ccc(NCC4CC4)cc3n2)cn1]

A solution of intermediate 2 (1 g; 0.35 mmol), cyclopropanemethylamine (0.51 g, 6.9 mmol) 1,1'-[1,1'-Binaphthalene]-2,2'-diylbis[1,1-diphenylphosphine](0.215 g, 0.35 mmol) and sodium tert-butoxide (1.0 g, 10.4 mmol) in ethyleneglycol-dimethylether (15 mL) was degassed with N₂ for 10 minutes. Then palladium(II) acetate (47% Pd) (77.6 mg, 0.35 mmol) was added and the reaction was heated under microwave irradiation to 135° C. for 30 minutes. The reaction mixture was cooled to room temperature, then poured into an aqueous solution of K₂CO₃ and extracted with EtOAc. The organic layers were combined and dried (MgSO₄), filtered and evaporated to dryness. The residue was purified by chromatography over silica gel (Irregular SiOH, 15-40 μm; mobile phase, gradient from 10% DCM to 95% DCM/5% MeOH/0.1% NH₄OH). The pure fractions were collected and evaporated, yielding 710 mg (74%) of intermediate 25. MP=149° C. (kofler).

Example A12 a) Preparation of intermediate 26

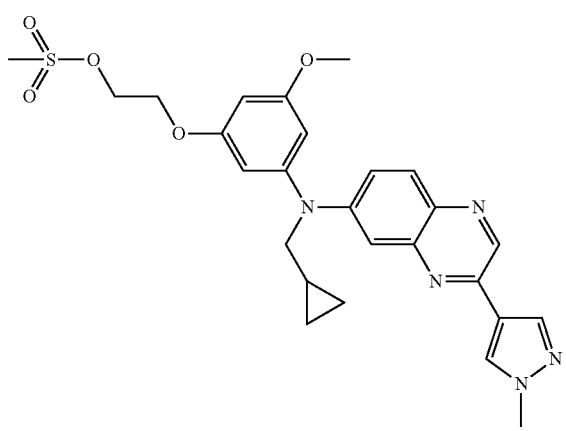 [SMILES: COc1cc(OCCOS(C)(=O)=O)cc(N(CC2CC2)c2ccc3ncc(-c4cnn(C)c4)nc3c2)c1]

Methanesulfonyl chloride (61 μL, 0.78 mmol) was added dropwise to a solution of compound 24 (0.13 g, 0.26 mmol), Et₃N (0.18 mL, 1.3 mmol) in DCM (10 mL) at 5° C. under N₂. The solution was stirred for 1.5 hours at 10° C. The solution was poured out into ice water, the organic layer was extracted, dried (MgSO₄) and evaporated to dryness at room temperature, yielding 137 mg of intermediate 26.

b) Preparation of intermediate 27

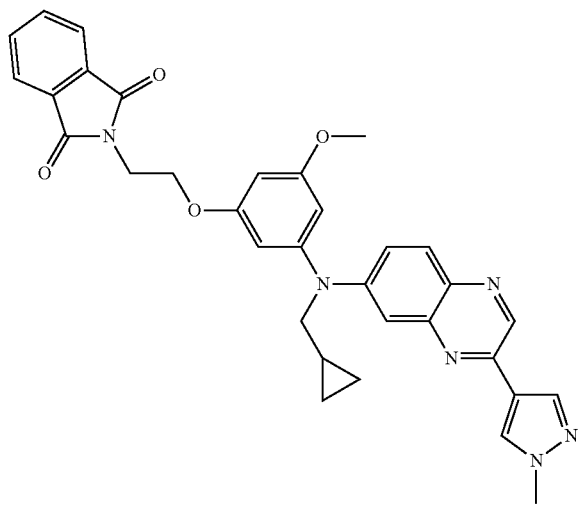 [SMILES: COc1cc(OCCN2C(=O)c3ccccc3C2=O)cc(N(CC2CC2)c2ccc3ncc(-c4cnn(C)c4)nc3c2)c1]

A solution of intermediate 26 (0.31 g; 0.0006 mol), phthalimide (0.17 g, 0.0012 mol) and K₂CO₃ (0.21 g; 0.0015 mol) in 1-methyl-2-pyrrolidinone (10 mL) were heated at 150° C. for 15 hours. The mixture was cooled to room temperature and evaporated to dryness. The residue was taken up with DCM, then an aqueous K₂CO₃ solution (10%) were added. The organic layer was separated, dried (MgSO₄), filtered and evaporated to dryness. The residue was purified by chromatography over silica gel (Spherical SiOH, 10 μm, 60 g PharmPrep MERCK; mobile phase 0.1% NH₄OH/99% DCM/1% MeOH). The product fractions were collected and the solvent was evaporated, yielding 212 mg (63%) of intermediate 27.

Example A13 a) Preparation of intermediate 28

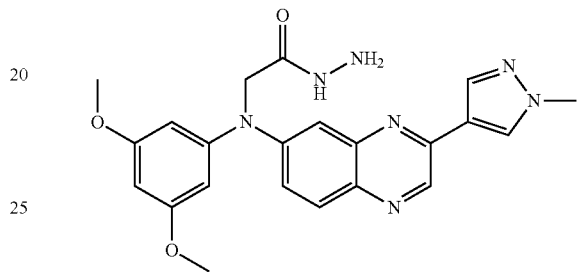

Hydrazine monohydrate (2.57 mL, 0.083 mol) was added to a solution of compound 65 (3.71 g, 8.29 mmol) in EtOH (35 mL). The mixture was stirred overnight at reflux. Hydrazine monohydrate (2.57 mL, 0.083 mol) was added again and the mixture was refluxed for 15 hours. After cooling down to room temperature, the precipitate was filtered off, washed with EtOH and dried to give 2.6 g (72%) of intermediate 28.

Example A14 a) Preparation of intermediate 29

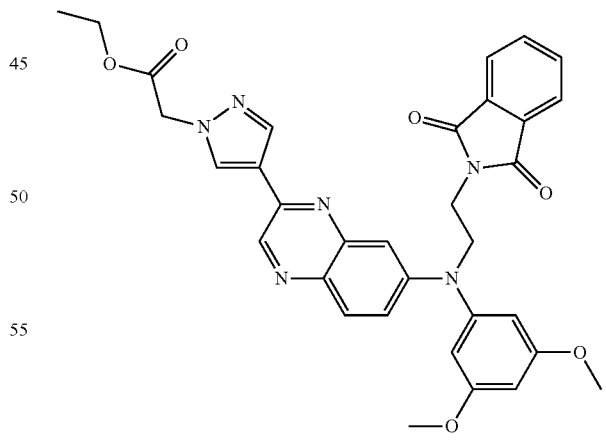

NaH (0.077 g; 2 mmol) was added portionwise to a solution of compound 107 (0.63 g; 1.2 mmol) in DMF (10 mL). The mixture was stirred at 10° C. for 60 minutes, then ethyl bromoacetate (0.16 mL, 1.45 mmol) was added. The resulting mixture was stirred at room temperature for 2 hours. The mixture was poured into water and the product was extracted with EtOAc. The organic layer was washed with water, brine, dried (MgSO$_4$), filtered and evaporated until dryness. The residue (1 g) was crystallized from diethyl ether. The precipitate was filtered and dried, yielding 0.55 g (75%) of intermediate 29.

Example A15 a) Preparation of intermediate 30

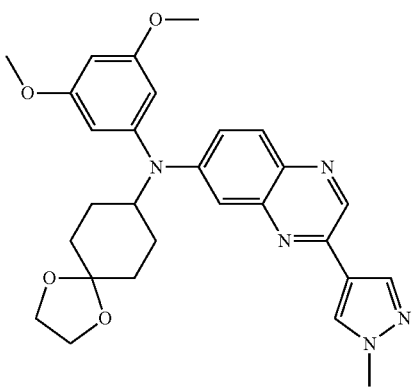 [SMILES: COc1cc(OC)cc(N(c2ccc3ncc(-c4cnn(C)c4)nc3c2)C2CCC3(CC2)OCCO3)c1]

To a mixture of intermediate 2 (700 mg; 2.4 mmol), intermediate 39 (781 mg; 2.66 mmol), sodium tert-butoxide (698 mg; 7.3 mmol), 1,1'-[1,1'-binaphthalene]-2,2'-diylbis[1,1-diphenylphosphine](151 mg; 0.24 mmol) in dioxane (12 mL) was degassed at room temperature under N$_2$ flow. After 10 minutes, palladium (II) acetate (109 mg; 0.48 mmol) was added at room temperature under N$_2$ flow. The reaction was performed under microwave irradiation at 130° C. for 1 hour. The reaction mixture was poured out onto ice water and filtered over celite. Celite was washed with DCM. The organic layer was decanted, dried (MgSO$_4$), filtered and evaporated. The residue was purified by chromatography over silica gel (Irregular SiOH, 15-40 μm, 300 g MERCK; mobile phase 0.1% NH$_4$OH, 97% DCM, 3% iPrOH). The product fractions were collected and the solvent was evaporated, yielding 320 mg (26%) of intermediate 30.

b) Preparation of intermediate 31

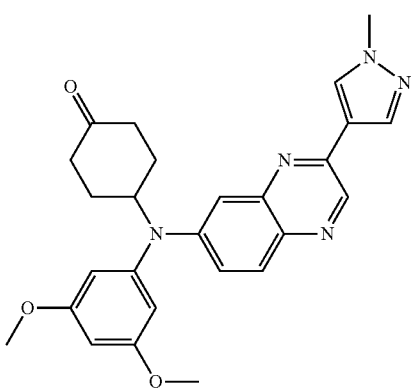 [SMILES: COc1cc(OC)cc(N(c2ccc3ncc(-c4cnn(C)c4)nc3c2)C2CCC(=O)CC2)c1]

Intermediate 30 (300 mg, 0.598 mmol) in HCl (3N) (10.96 mL, 33 mmol) and THF (10 mL) was stirred at 65° C. for 2 hours, then for 6 hours at 70° C., and poured out onto ice. The solution was made basic with K$_2$CO$_3$ powder and extracted with DCM. The organic layer was dried (MgSO$_4$), filtered and evaporated, yielding 270 mg (98%) of intermediate 31.

Example A16 a) Preparation of intermediate 32

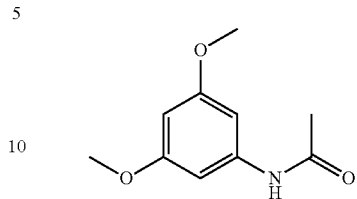

Acetic anhydride (3.24 mL) was added portionwise over ten minutes to a stirred suspension of 3,5-dimethoxyaniline (5 g, 32.64 mmol) in toluene (25 mL). After stirring at room temperature for 17 hours, petroleum ether was added and the precipitate collected by suction filtration and dried under vacuum. The crude product (6.1 g, 96%) was used in the next step without further purification.

b) Preparation of intermediate 33

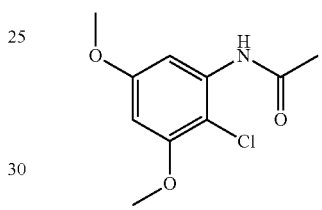

N-(3,5-dimethoxy-phenyl)-acetamide (intermediate 32) (15 g, 76.8 mmol) was dissolved in AcOH (50 mL). The solution was cooled to 0° C. and 32% aqueous hydrochloric acid solution (41 mL, 461 mmol) was added. A solution of sodium chlorate (3.5 g, 33 mmol) in water (4 mL) was added. The mixture was stirred for 30 minutes at 0° C. The reaction mixture was poured out onto ice and water and made basic with K$_2$CO$_3$ powder. The precipitate was filtered off and washed with water.

The residue was purified by chromatography over silica gel (Irregular SiOH, 15-40 μm, 300 g MERCK; mobile phase 80% DCM, 20% EtOAc) to give 8.8 g (50%) of intermediate 33.

c) Preparation of intermediate 34

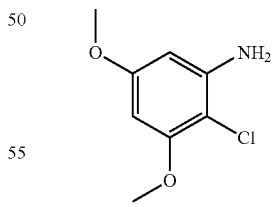

Potassium hydroxide (10.7 g, 192 mmol) was added to a solution of N-(2-Chloro-3,5-dimethoxy-phenyl)-acetamide (intermediate 33) (8.8 g, 38.3 mmol) in EtOH (500 mL) and water (50 mL) and the reaction mixture heated to reflux for 18 hours. Upon cooling, water was added (ca 30 mL) and the EtOH removed in vacuum. The residue was then partitioned between water and diethyl ether. The organic layer was separated, dried (MgSO$_4$), filtered and concentrated to afford 7 g (97%) of intermediate 34 (white solid).

Example A17

Preparation of intermediate 35

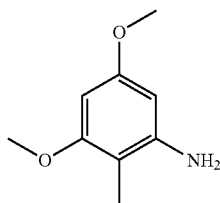

A mixture of 2,4-dimethoxy-6-nitrotoluene (2 g, 10.1 mmol) and nickel (2 g) in MeOH (30 mL) was hydrogenated under a 3 bars pressure for 6 hours. The product was filtered over a celite pad which was washed 3 times with a solution of MeOH/DCM (50/50). The combined filtrates were evaporated till dryness to give 1.68 g (99%) of intermediate 35.

Example A18 a) Preparation of intermediate 36

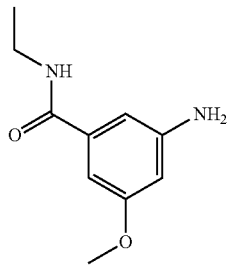

A mixture of 3-amino-5-methoxy-benzoic acid (300 mg, 1.8 mmol), 1-hydroxybenzotriazole (292 mg, 2.1 mmol), N-Ethyl-N'-β-dimethylaminocarbodiimide hydrochloride (413 mg, 2.1 mmol), and ethyl amine (2.7 mL, 5.4 mmol, 2M in MeOH) in dimethylformamide (6 mL) was stirred at room temperature overnight. The solvent was evaporated under vacuum and the residue partitioned between DCM and water. The organic layer was separated and the aqueous layer was extracted with further DCM. The combined organic layers were dried ($Na_2SO_4$) and concentrated. The residue was purified by column chromatography over silica gel eluting with 2% MeOH/DCM. The desired product fractions were collected and the solvent was evaporated, yielding 150 mg (43%) of intermediate 36 (colourless oil).

b) Preparation of intermediate 135

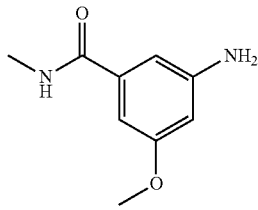

A mixture of 3-amino-5-fluorobenzoic acid (10 g; 64.5 mmol), methylamine in THF (96.7 mL; 193.4 mmol), 1-(3-dimethylaminopropyl)-3-ethylcarbodiimide hydrochloride (14.8 g; 77.4 mmol), 1-hydroxybenzotriazole (10.5 g; 77.4 mmol), in N,N-dimethylformamide (150 mL) was stirred at room temperature for 18 hours. The reaction mixture was poured out into a solution of sodium hydroxide 1 N and DCM was added. The organic layer was separated, washed with water, dried ($MgSO_4$), filtered and the solvent was evaporated.

The aqueous layer was neutralized with concentrated HCl and extracted with EtOAc. The organic layer was separated, dried ($MgSO_4$), filtered and evaporated till dryness to give 5 g of 3-amino-5-methoxy-N-methyl-benzamide (intermediate 135).

Example A19

Preparation of intermediate 37

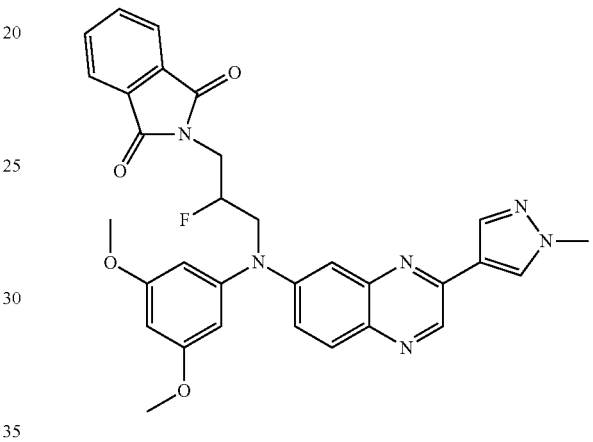

A solution of deoxofluor in toluene (0.478 mmol; 0.176 mL) was added dropwise to a solution of compound 124 (0.159 mmol; 90 mg) in DCM (8 mL) at 5° C. under $N_2$ flow. After 5 minutes, EtOH (a drop) was added. The mixture was stirred at 5° C. for 1 hour, then overnight at room temperature. The reaction mixture was poured out into ice water and DCM was added. The mixture was basified with $K_2CO_3$ 10% and the organic layer was separated, washed with brine, dried ($MgSO_4$), filtered and the solvent was evaporated. The obtained residue (0.090 g) was purified by column chromatography over silica gel (Irregular SiOH, 15/40 μm, 30 g; mobile phase gradient from 100% DCM to 97% DCM/3% MeOH). The product fractions were collected and the solvent was evaporated. The residue (0.070 g, 77%) was crystallized from diethyl ether/$CH_3CN$, filtered and dried under vacuum, yielding 0.055 g (60%) of intermediate 37.

Example A20

Preparation of intermediate 38

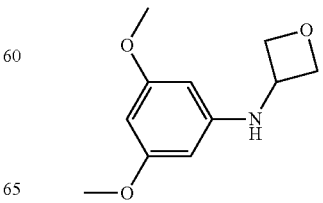

In a round bottom flask, 3,5-dimethoxybenzenamine (500 mg, 3.26 mmol), 3-oxetanone (588 mg, 8.16 mmol) and acetic acid (374 μL, 6.53 mmol) were diluted in MeOH (21 mL). The reaction mixture was stirred at room temperature for 1 hour. Then, sodium cyanoborohydride (410 mg, 6.53 mmol) in MeOH (5 mL) was added and the reaction mixture was stirred overnight at room temperature. Then, NaOH 3N (15 mL) was added and the mixture was stirred for 1 hour at room temperature. The reaction mixture was partitioned between water and DCM. The organic layer was dried (MgSO$_4$), filtered and concentrated. The residue (1 g) was purified by chromatography over silica gel (Irregular SiOH, 15-40 μm; mobile phase 100% DCM). The desired fractions were collected and the solvent was evaporated, yielding 377 mg (55%) of intermediate 38 (colorless oil).

Example A21

Preparation of intermediate 39

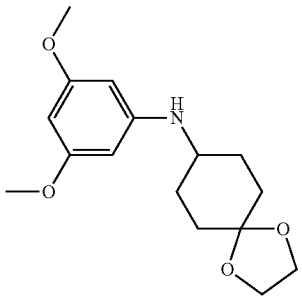 [SMILES: COc1cc(NC2CCC3(CC2)OCCO3)cc(OC)c1]

Sodium cyanoborohydride (4.55 g, 72.5 mmol) was added to a solution of 3,5-dimethoxyaniline (3.7 g, 24.15 mmol), 1,4-cyclohexanedione mono-ethylene ketal (15 g, 96.6 mmol) and acetic acid (5.5 mL, 96 mmol) in CH$_3$CN (50 mL) at room temperature (exothermicity observed). The reaction mixture was stirred overnight. Aqueous NaHCO$_3$ solution was added and the mixture was extracted twice with EtOAc. The combined organic layers were washed with brine, dried (MgSO$_4$), filtered and dried. The residue (21 g) was purified by column chromatography over silica gel (Irregular SiO$_2$, 15-40 μm, 90 g; mobile phase gradient from 100% DCM to 7% CH$_3$OH/93% DCM). The pure fractions were collected and evaporated to dryness to give 4.2 g (59%) of intermediate 39.

Example A22

Preparation of intermediate 42

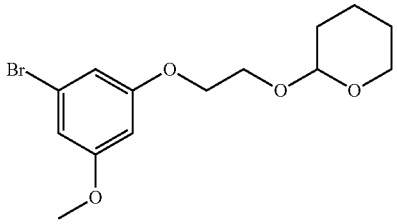 [SMILES: COc1cc(Br)cc(OCCOC2CCCCO2)c1]

A solution of 3-bromo-5-methoxy phenol (3.12 g; 15.4 mmol), 2-(2-bromoethoxy)tetrahydro-2H-pyran (2.66 mL; 16.9 mmol) and K$_2$CO$_3$ (1.63 g; 11.8 mmol) was heated at 80° C. in CH$_3$CN (40 mL) overnight. The solution was cooled and the mixture was poured into cooled water, the product was extracted with EtOAc, the organic layer was washed with H$_2$O and dried (MgSO$_4$), filtered and evaporated to dryness (5.5 g). The residue was purified by chromatography over silica gel (irregular SiOH, 15-40 μm, 200 g; mobile phase 80% cyclohexane, 20 EtOAc). The product fractions were collected and the solvent was evaporated, yielding 3.7 g (73%) of intermediate 42.

Example A23

Preparation of intermediate 43

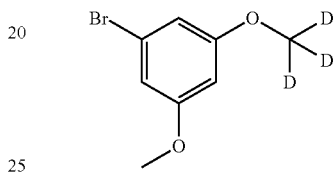

Sodium hydride (1.03 g, 25.86 mmol) was added portion wise to a solution of 3-bromo-5-methoxy phenol (3.5 g, 17.24 mmol) in DMF (20 mL) at 5° C. under N$_2$ flow. The reaction mixture was stirred at 5° C. for 0.5 hour, then a solution of deuterated-iodomethane (1.29 mL, 20.69 mmol) was added dropwise at 5° C. under N$_2$ flow. The reaction mixture was stirred for 1 hour at 5° C., then allowed to warm up to room temperature and stirred for 2 hours. The reaction was poured out into ice water, and EtOAc was added. The organic layer was separated, washed with brine, dried (MgSO$_4$), filtered and the solvent was evaporated to give 4 g of intermediate 43, used without further purification for the next step.

Example A24

Preparation of intermediate 44

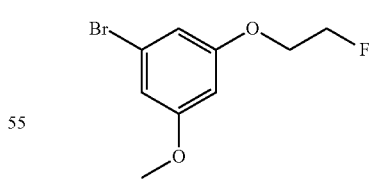

A solution of 3-bromo-5-methoxyphenol (2 g, 9.85 mmol), 1-bromo-2-fluoroethane (1.56 g, 0.012 mol) and K$_2$CO$_3$ (1.4 g, 10 mmol) was heated at 80° C. in CH$_3$CN (30 mL) overnight. The solution was cooled and the mixture was poured into cooled water, the product was extracted with Et$_2$O. The organic layer was dried (MgSO$_4$), filtered and evaporated to dryness to give 2.27 g of intermediate 44 used without further purification for the next step.

Example A25

Preparation of intermediate 45

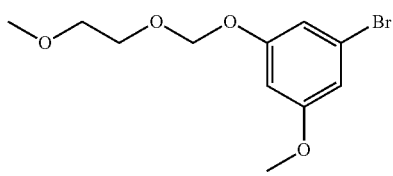 [SMILES: COCCOCOc1cc(Br)cc(OC)c1]

Under N$_2$ at 10° C., Hunig's base (9.64 mL; 55.16 mmol) was added to a solution of 3-bromo-5-methoxy phenol (5.6 g, 27.58 mmol) in THF (100 mL). 2-methoxyethoxymethylchloride (CAS 3970-21-6) (6.3 mL, 55.16 mmol) was added and the solution was stirred at room temperature overnight. The solution was poured into cooled water, and the product was extracted with EtOAc. The organic layer was dried (MgSO$_4$), filtered and evaporated to dryness to give 8 g (99.6%) of intermediate 45 used without further purification for the next step.

Example A26

Preparation of intermediate 46

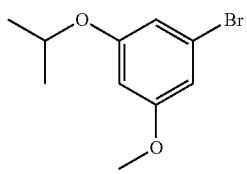

A solution of 3-bromo-5-methoxyphenol (0.3 g, 1.5 mmol), 2-iodopropane (0.21 mL, 1.6 mmol) and K$_2$CO$_3$ (1.63 g, 12 mmol) was heated at 80° C. in CH$_3$CN (20 mL) for 24 hours. The solution was cooled and the mixture was poured into cooled water, the product was extracted with EtOAc. The organic layer was washed with H$_2$O and dried (MgSO$_4$), filtered and evaporated to dryness to give 350 mg (97%) of intermediate 46 used without further purification for the next step.

Example A26A

Preparation of intermediate 136

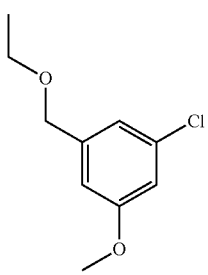

NaH (0.74 g; 18.4 mmol) was added portionwise to a solution of (3-chloro-5-methoxyphenyl)methanol (2.9 g; 16.7 mmol) in N,N-dimethylformamide (30 mL) at 5° C. under N$_2$ flow. The reaction mixture was stirred at 5° C. for 1 hour. Then ethyl iodide (0.96 mL; 12.0 mmol) was added dropwise at 5° C. under N$_2$ flow. The reaction mixture was allowed to warm to room temperature and stirred for 18 hours. The reaction was poured out into ice water and EtOAc was added. The organic layer was separated, washed with brine, dried (MgSO$_4$), filtered and the solvent was evaporated to dryness to give 0.8 g (25%) of intermediate 136.

Example A27 a) Synthesis of intermediate 66

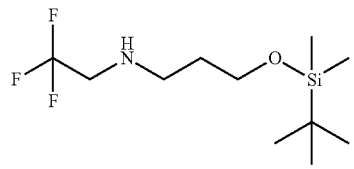 [SMILES: CC(C)(C)[Si](C)(C)OCCCNCC(F)(F)F]

A mixture of (3-bromopropoxy)-tert-butyldimethylsilane (20 g; 79 mmol) and 2,2,2-trifluoroethylamine (31 mL; 395 mmol) in DMSO (140 mL) was heated at 80° C. for 18 hours. The reaction mixture was cooled to room temperature, water was added and the mixture was extracted with Et$_2$O. The organic layer was dried (MgSO$_4$), filtered and evaporated till dryness to provide 19.5 g (91%) of intermediate 66.

b) Synthesis of intermediate 67

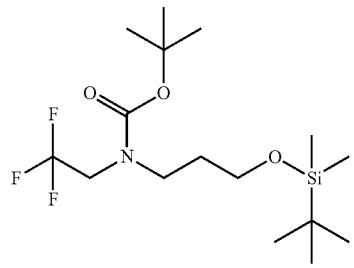 [SMILES: CC(C)(C)OC(=O)N(CCCO[Si](C)(C)C(C)(C)C)CC(F)(F)F]

Di-tert-butyl-dicarbonate (7.96; 36.5 mmol), triethylamine (6 mL; 43.11 mmol) and N,N-dimethyl-4-aminopyridine (202 mg; 1.7 mmol) were added to a solution of intermediate 66 (9 g; 33.16 mmol) in DCM (90 mL). The reaction mixture was stirred at room temperature for 2 hours, diluted with DCM and water. The organic layer was decanted, washed successively with water, a solution of HCl (0.5N) and an aqueous solution of K$_2$CO$_3$ (10%). The organic layer was dried (MgSO$_4$), filtered and evaporated till dryness to provide 11.3 g (92%) of intermediate 67.

c) Synthesis of intermediate 68

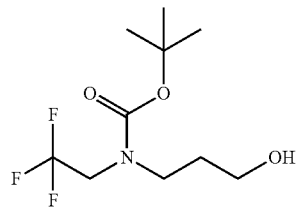 [SMILES: CC(C)(C)OC(=O)N(CCCO)CC(F)(F)F]

A mixture of intermediate 67 (10.8 g; 29.1 mmol) and tetrabutylammonium fluoride (34.9 mL of a 1M solution in THF; 34.9 mmol) in THF (80 mL) was stirred at room temperature overnight. Water was added and the reaction mixture extracted with DCM. The organic layer was dried (MgSO$_4$), filtered and evaporated till dryness. The residue was purified by chromatography over silica gel (Irregular SiOH, 15-40 μM, 80 g; mobile phase, gradient from 99% DCM, 1% MeOH to 96% DCM, 4% MeOH). The pure fractions were collected and evaporated till dryness to provide 3.65 g (49%) of intermediate 68.

d) Synthesis of intermediate 69

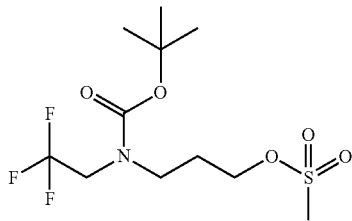 [SMILES: CC(C)(C)OC(=O)N(CCCOS(C)(=O)=O)CC(F)(F)F]

Methane sulfonyl chloride (431 μL; 5.8 mmol) was added dropwise to a solution of intermediate 68 (1 g; 3.9 mmol) and triethylamine (811 μL; 5.8 mmol) in DCM (15 mL) at 5° C. under N$_2$ flow. The reaction mixture was stirred for 30 minutes at room temperature. The reaction mixture was evaporated till dryness and the resulting intermediate 69 was used without further purification for the next step.

Example A28 a) Preparation of intermediate 70

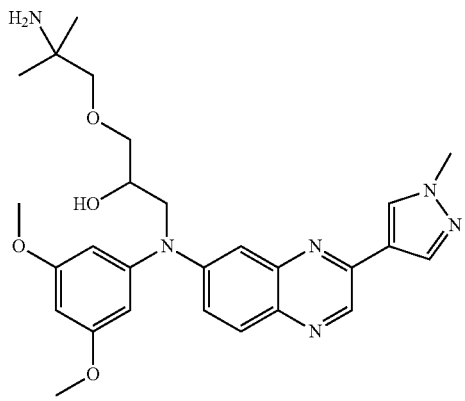 [SMILES: COc1cc(OC)cc(N(CC(O)COCC(C)(C)N)c2ccc3ncc(-c4cnn(C)c4)nc3c2)c1]

The experiment has been performed 5 times on the following amount.

NaH (0.25 g; 5.4 mmol) was added portionwise to a solution of 2-amino-2-methyl-1-propanol (1.54 mL; 16.1 mmol) in N,N-dimethylformamide (12 mL) at 5° C. under N$_2$ flow. The reaction mixture was stirred at 5° C. for 15 minutes. Then, compound 76 (1.4 g; 3.35 mmol) was added dropwise at 5° C. under N$_2$ flow. The reaction mixture was allowed to warm to room temperature and stirred overnight. The reaction was poured out into ice water and EtOAc was added. The organic layer was separated, washed with brine, dried (MgSO$_4$), filtered and the solvent was evaporated to dryness to give 10.5 g of a residue which was purified by chromatography over silica gel (Irregular SiOH, 15-40 μm, 300 g; mobile phase 1% NH$_4$OH, 90% DCM, 10% MeOH).

The pure fractions were collected and concentrated yielding 3.6 g (42%) of intermediate 70.

b) Preparation of intermediate 71

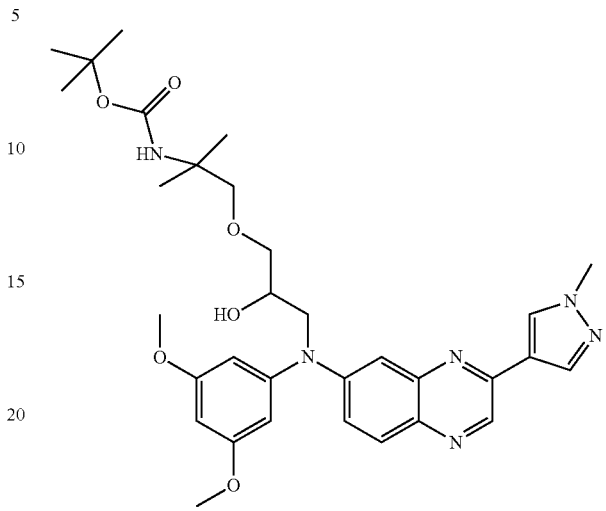

Di-tert-butyl dicarbonate (0.24 g; 1.1 mmol) was added to a solution of intermediate 70 (0.62 g; 1.1 mmol) and NaHCO$_3$(0.19 g; 2.3 mmol) in dioxane (15 mL) and water (15 mL). The mixture was stirred at room temperature for 18 hours. The reaction mixture was poured out into ice water and DCM was added. The organic layer was separated, dried (MgSO$_4$), filtered and the solvent was evaporated to dryness. The residue (0.8 g) was purified by chromatography over silica gel (SiOH, 5 μm 150*30 mm; mobile phase 0.2% NH$_4$OH, 98% DCM, 2% MeOH). The pure fractions were collected and the solvent was evaporated to give 0.59 g (85%) of intermediate 71.

c) Preparation of intermediate 72

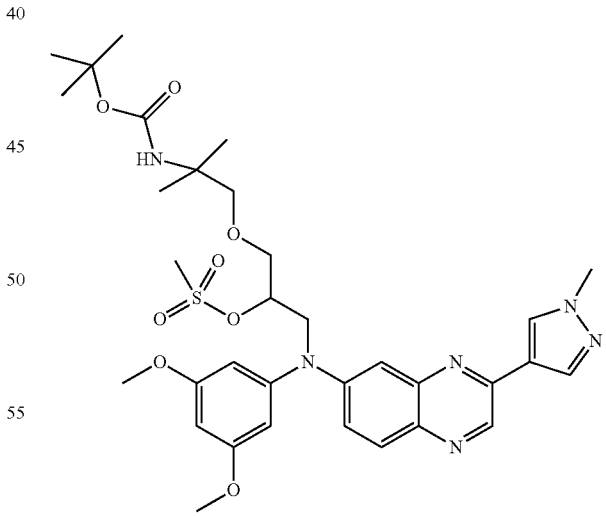

Methanesulfonyl chloride (0.96 mL; 12.4 mmol) was added dropwise to a solution of intermediate 71 (2.7 g, 4.45 mmol) and triethylamine (1.86 mL; 13.35 mmol) in DCM (25 mL) at 5° C. under a N$_2$ flow. The reaction mixture was stirred for 18 hours allowing the temperature to rise to room temperature. The reaction mixture was poured out into ice water and DCM was added. The organic layer was separated, dried (MgSO$_4$), filtered and the solvent was evaporated to dryness. The residue (4.1 g) was purified by chromatography over silica gel (Irregular SiOH, 20-45 μm, 450 g; mobile phase 0.2% NH$_4$OH, 97% DCM, 3% MeOH). The pure fractions were collected and the solvent was evaporated to give 3 g (100%) of intermediate 72.

d) Preparation of intermediate 73

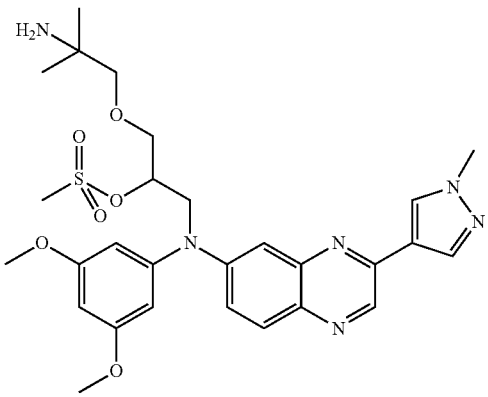 [SMILES: COc1cc(OC)cc(N(CC(COCC(C)(C)N)OS(C)(=O)=O)c2ccc3ncc(-c4cnn(C)c4)nc3c2)c1]

Trifluoroacetic acid (0.97 mL; 13.1 mmol) was added to a solution of intermediate 72 (0.6 g; 0.87 mmol) in DCM (12.5 mL) at 0° C. The reaction was stirred at room temperature for 1 hour. The mixture was poured out into ice water and DCM was added. The mixture was basified with a solution of NaHCO$_3$ and the organic layer was separated, dried over MgSO$_4$, filtered and the solvent was evaporated to give 597 mg of intermediate 73 used without further purification for the next step.

Example A29

Preparation of intermediate 74

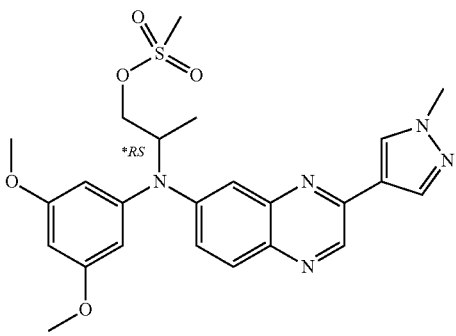 [SMILES: COc1cc(OC)cc(N(c2ccc3ncc(-c4cnn(C)c4)nc3c2)C(C)COS(C)(=O)=O)c1]

Methanesulfonyl chloride (3.32 mL; 42.9 mmol) was added dropwise to a solution of compound 606 (6 g; 14.3 mmol) and triethylamine (10 mL; 71.5 mmol) in DCM (240 mL) at 5° C. under a N$_2$ flow. The reaction mixture was stirred for 1 hour at 5° C. and allowed to rise to room temperature for 1 hour. The reaction mixture was poured out into ice water and DCM was added. The organic layer was separated, dried (MgSO$_4$), filtered and the solvent was evaporated to dryness to give 9.6 g of intermediate 74 used without further purification for the next step Example A30 a) Preparation of intermediate 75

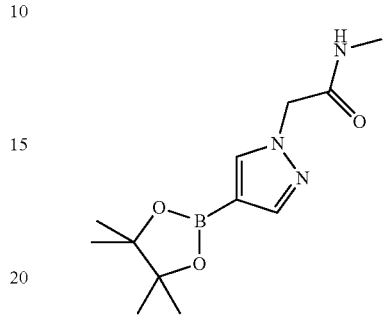

NaH (11.4 g; 82.5 mmol) was added portionwise to a solution of 4,4,5,5-tetramethyl-2-(1H-pyrazol-4-yl)-1,3,2-dioxaborolane (4 g; 20.6 mmol) in acetone (60 mL) at 5° C. under N$_2$ flow. The reaction mixture was stirred at 5° C. for 15 minutes. Then, acetamide, 2-bromo-N-methyl (6.3 g; 41.3 mmol) was added dropwise at 5° C. under N$_2$ flow. The reaction mixture was stirred at 65° C. for 24 hours. The reaction mixture was cooled to room temperature. The precipitate was filtered off and washed with DCM. The filtrate was evaporated till dryness, taken up into DIPE/diethyl ether and stirred at room temperature for 15 minutes. The precipitate was filtered off and washed with DCM. The filtrate was evaporated till dryness to afford 9 g of intermediate 75 used without further purification for the next step.

b) Preparation of intermediate 76

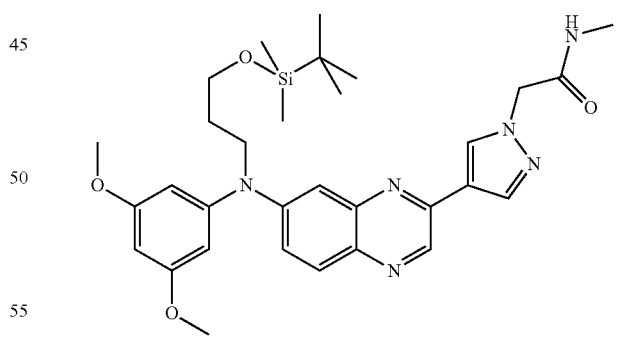

A mixture of intermediate 14 (5.7 g; 11.7 mmol), intermediate 75 (N-methyl-4-(4,4,5,5-tetramethyl-1,3,2-dioxaborolan-2-yl)-1H-acetamide) (6.2 g; 23.5 mmol), potassium phosphate (7.5 g; 35.2 mmol) and dicyclohexyl(2',6'-dimethoxy[1,1'-biphenyl]-2-yl)phosphine (0.482 g; 1.2 mmol) in dioxane (140 mL) and H$_2$O (60 mL) was stirred at room temperature under N$_2$ flow. After 10 minutes, Pd$_2$(dba)$_3$ (1 g; 1.2 mmol) was added portionwise at room temperature under N₂ flow. The reaction mixture was heated at 80° C. for 4 hours. The reaction mixture was cooled to room temperature and poured out into ice water. The mixture was filtered over a pad of Celite®, washed with DCM. The organic layer was washed with brine, dried (MgSO₄), filtered and the solvent was evaporated. The residue (8.3 g) was purified by chromatography over silica gel (Irregular SiOH, 20-40 µm, 450 g; mobile phase 0.1% NH₄OH, 98% DCM, 2% MeOH). The pure fractions were collected and concentrated to give 3.5 g (51%) of intermediate 76.

Example A31

Preparation of intermediate 77

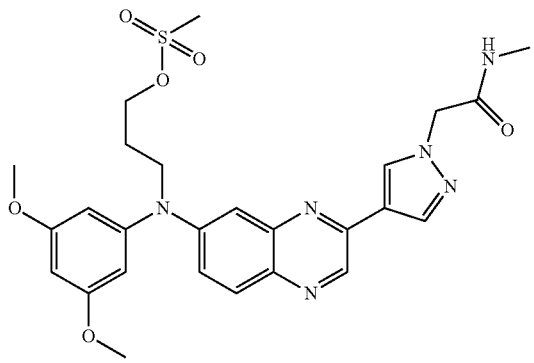 [SMILES: CNC(=O)Cn1cc(-c2cnc3ccc(N(CCCOS(C)(=O)=O)c4cc(OC)cc(OC)c4)cc3n2)cn1]

Methanesulfonyl chloride (0.73 mL; 9.4 mmol) was added dropwise to a solution of compound 614(1.5 g; 3.15 mmol) and triethylamine (2.2 mL; 15.7 mmol) in DCM (40 mL) at 5° C. under a N₂ flow. The reaction mixture was stirred for 1 hour at 5° C. and allowed the temperature to rise to room temperature for 1 hour. The reaction mixture was poured out into ice water and DCM was added. The organic layer was separated, dried (MgSO₄), filtered and the solvent was evaporated to dryness to give 2.5 g of intermediate 77 used without further purification for the next step.

Example A32 a) Preparation of intermediate 78

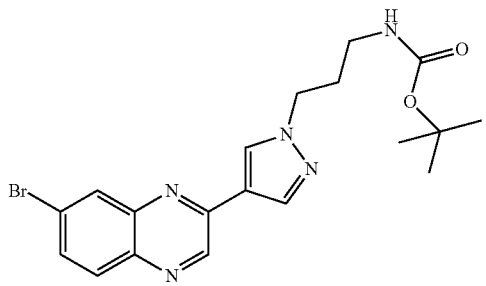 [SMILES: CC(C)(C)OC(=O)NCCCn1cc(-c2cnc3ccc(Br)cc3n2)cn1]

NaH (0.44 g; 10.9 mmol) was added portionwise to a solution of 7-bromo-2-(1H-pyrazol-4-yl)quinoxaline (1.5 g; 5.45 mmol) in N,N-dimethylformamide (40 mL) at 0° C. under N₂ flow. The reaction mixture was stirred at 5° C. for 15 minutes. Then, carbamic acid, N-(3-bromopropyl)-1,1-dimethylethyl ester (2.6 g; 10.9 mmol) was added dropwise at 5° C. under N₂ flow. The reaction mixture was stirred at room temperature for 18 hours. The reaction mixture was poured out into ice water, EtOAc was added. The organic layer was separated, washed with water, diethyl ether, dried (MgSO₄), filtered and evaporated to afford 1.3 g of intermediate 78 used without further purification for the next step.

b) Preparation of intermediate 79

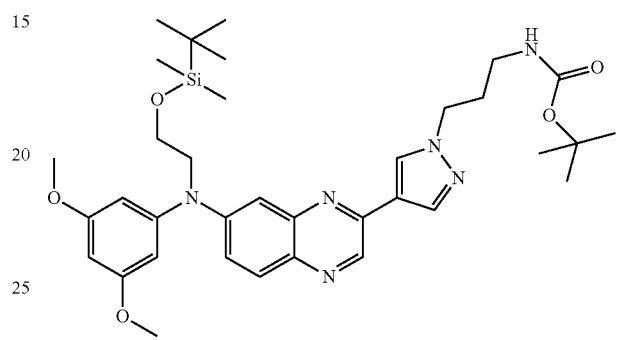

Under an inert atmosphere, a solution of palladium acetate (0.11 g; 0.48 mmol), racemic 2,2'-bis(diphenylphosphino)-1,1'-binaphtyl (0.3 g; 0.48 mmol)) was added to room temperature to a solution of intermediate 41 (3.3 g; 10.6 mmol), intermediate 78 (4.2 g; 9.63 mmol) and cesium carbonate (3.8 g; 11.6 mmol) in dimethoxyethane (50 mL). The reaction mixture was stirred at 85° C. for 3 days. The reaction mixture was cooled to room temperature and poured out into ice water, K₂CO₃ 10% and EtOAc was added. The mixture was filtered over a pad of Celite®. The organic layer was washed with brine, dried (MgSO₄), filtered and the solvent was evaporated. The residue (8.5 g) was purified by chromatography over silica gel (Irregular SiOH, 20-40 µm, 450 g; mobile phase 0.1% NH₄OH, 97% DCM, 3% MeOH). The pure fractions were collected and concentrated to give 3.3 g (52%) of intermediate 79.

c) Preparation of intermediate 80

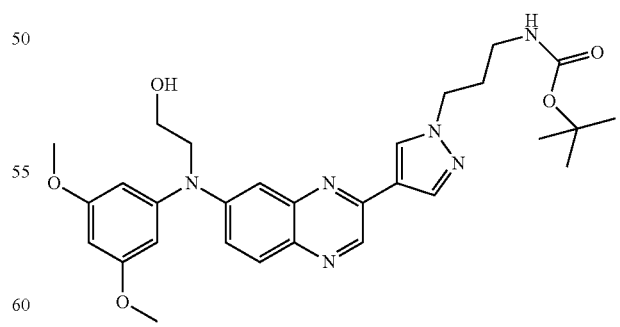

A 1M solution of tetrabutylammonium fluoride in THF (5.5 mL; 5.5 mmol) was added dropwise to a solution of intermediate 79 (3.3 g; 5 mmol) in THF (60 mL) at room temperature. The reaction mixture was stirred at room temperature for 3 hours. The mixture was poured out into ice water and EtOAc was added. The mixture was basified with K₂CO₃ 10% and the organic layer was separated, washed with brine, dried (MgSO₄), filtered and the solvent was evaporated to dryness. The residue was crystallized from diethyl ether/CH₃CN. The precipitate was filtered off, dried in vacuum to provide 2 g (73%) of intermediate 80.

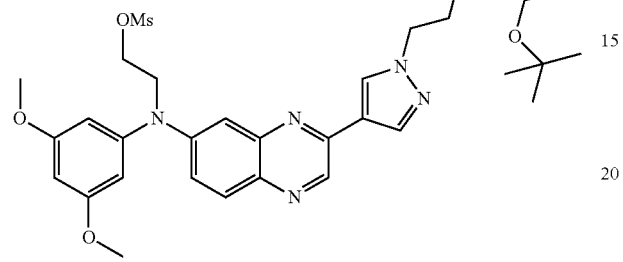

d) Preparation of intermediate 81

Methanesulfonyl chloride (0.85 mL; 10.9 mmol) was added dropwise to a solution of intermediate 80 (2 g; 3.65 mmol) and triethylamine (2.54 mL; 18.2 mmol) in DCM (50 mL) at 5° C. under a N₂ flow. The reaction mixture was stirred for 1 hour at 5° C. and allowed the temperature to rise to room temperature for 2 hours. The reaction mixture was poured out into ice water and DCM was added. The organic layer was separated, dried (MgSO₄), filtered and the solvent was evaporated to dryness to give 2.5 g of intermediate 81 used without further purification for the next step.

e) Preparation of intermediate 82

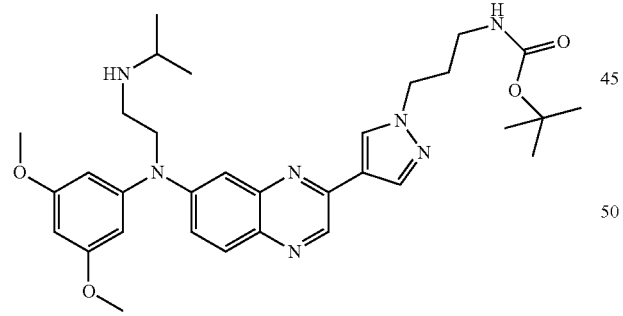

A mixture of intermediate 81 (2.5 g; 4 mmol) and isopropylamine (5.2 mL; 59.9 mmol) in acetonitrile (25 mL) was heated at 100° C. in a sealed vessel for 18 hours. The reaction mixture was cooled to room temperature. The reaction mixture was poured out into ice water, EtOAc was added. The organic layer was separated, washed with a solution of NaHCO₃, dried (MgSO₄), filtered and evaporated till dryness. The residue (3 g) was purified by chromatography over silica gel (Irregular SiOH, 20-40 μm, 450 g; mobile phase from 0.1% NH₄OH, 95% DCM, 5% MeOH). The pure fractions were collected and concentrated to give 1.1 g (47%) of intermediate 82.

Example A33 a) Preparation of intermediate 83

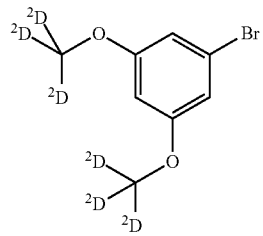 [SMILES: [2H]C([2H])([2H])Oc1cc(Br)cc(OC([2H])([2H])[2H])c1]

A mixture of 5-bromo-benzene-1,3-diol (7.3 g; 38.6 mmol), cesium carbonate (37.75 g; 115.9 mmol) and iodomethane-D3 (4.8 mL; 77.25 mmol) in CH₃CN (150 mL) was stirred at 80° C. for 18 hours. The reaction mixture was cooled to room temperature and poured out into ice water and EtOAc was added. The organic layer was washed with brine, dried (MgSO₄), filtered and the solvent was evaporated to afford 5.3 g of intermediate 83 used without further purification for the next step.

b) Preparation of intermediate 84

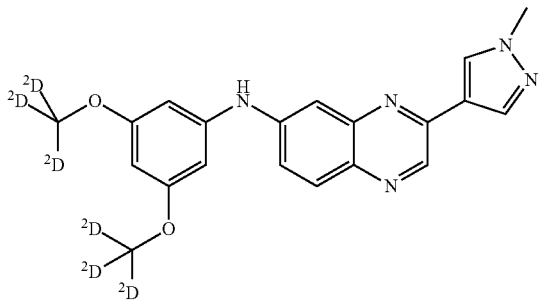 [SMILES: [2H]C([2H])([2H])Oc1cc(Nc2ccc3ncc(-c4cnn(C)c4)nc3c2)cc(OC([2H])([2H])[2H])c1]

Under an inert atmosphere, a solution of palladium acetate (0.21 g; 0.9 mmol), racemic 2,2'-bis(diphenylphosphino)-1,1'-binaphtyl (0.57 g; 0.9 mmol) was added to room temperature to a solution of intermediate 5 (2 g; 10.6 mmol), intermediate 83 (2.45 g; 11 mmol) and sodium tert butoxide (2.64 g; 27.4 mmol) in dioxane (150 mL). The reaction mixture was stirred at 100° C. for 4 days. The reaction mixture was cooled to room temperature and poured out into ice water and EtOAc was added. The mixture was filtered over a pad of Celite®. The organic layer was washed with brine, dried (MgSO₄), filtered and the solvent was evaporated. The residue (6 g) was purified by chromatography over silica gel (Irregular SiOH, 15-40 μm, 300 g; mobile phase 0.1% NH₄OH, 97% DCM, 3% MeOH). The pure fractions were collected and concentrated. The residue (4 g) was crystallized from diethyl ether. The precipitate was filtered off, dried in vacuum to provide 3.6 g (90%) of intermediate 84. MP: 198° C. (DSC)

c) Preparation of intermediate 85

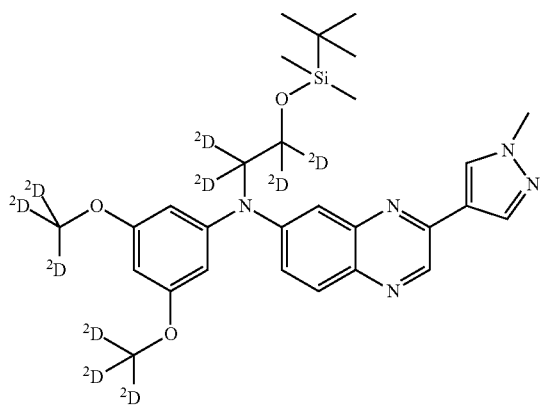 [SMILES: [2H]C([2H])([2H])Oc1cc(OC([2H])([2H])[2H])cc(N(c2ccc3ncc(-c4cnn(C)c4)nc3c2)C([2H])([2H])C([2H])([2H])O[Si](C)(C)C(C)(C)C)c1]

NaH (0.107 g; 2.69 mmol) was added portionwise to intermediate 84 (0.49 g; 1.35 mmol) in N,N-dimethylformamide (10 mL). The reaction mixture was stirred at 5° C. for 1 hour. Then, a solution of deuterated (2-bromoethoxy)(1,1-dimethylethyl)dimethyl-silane (deuterated version of CAS 86864-60-0; prepared by art-known deuteration method) (0.65 g; 2.7 mmol) was added dropwise at 5° C. under $N_2$ flow. The reaction mixture allowed to warm to room temperature and stirred for 4 hours. The reaction was poured out into ice water and EtOAc was added. The organic layer was separated and washed with brine, dried ($MgSO_4$), filtered and the solvent was evaporated to afford 0.88 g of intermediate 85 used without further purification for the next step.

Example A34

Preparation of intermediate 86

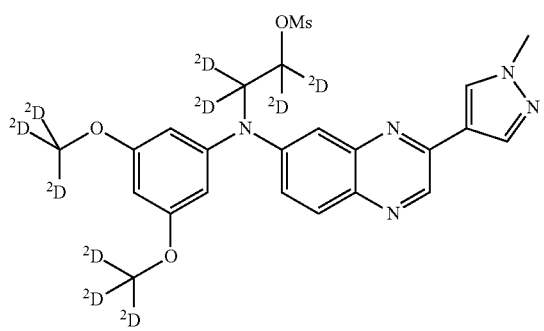 [SMILES: [2H]C([2H])([2H])Oc1cc(OC([2H])([2H])[2H])cc(N(c2ccc3ncc(-c4cnn(C)c4)nc3c2)C([2H])([2H])C([2H])([2H])OS(C)(=O)=O)c1]

Methanesulfonyl chloride (0.17 mL, 2.1 mmol) was added dropwise to a solution of compound 617 (0.294 g, 0.7 mmol) and triethylamine (0.49 mL, 3.5 mmol) in DCM (5 mL) at 5° C. under a $N_2$ flow. The reaction mixture was stirred for 1 hour at 5° C. and allowed the temperature to rise to room temperature for 1 hour. The reaction mixture was poured out into ice water and DCM was added. The organic layer was separated, dried ($MgSO_4$), filtered and the solvent was evaporated to dryness to give 0.45 g of intermediate 86 used without further purification for the next step.

Example A35

Preparation of intermediate 87

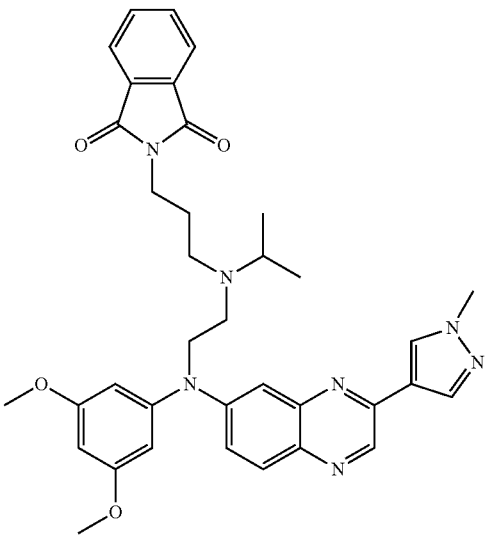 [SMILES: COc1cc(OC)cc(N(CCN(CCCN2C(=O)c3ccccc3C2=O)C(C)C)c2ccc3ncc(-c4cnn(C)c4)nc3c2)c1]

A mixture of compound 4 (1.3 g; 2.9 mmol), N-(3-bromopropyl)phthalimide (1.56 g; 5.8 mmol) and $K_2CO_3$ (0.805 g; 5.8 mmol) in $CH_3CN$ (100 mL) was stirred at 80° C. for 48 hours. The reaction mixture was cooled to room temperature, poured out into ice water and EtOAc was added. The organic layer was separated, washed with brine, dried ($MgSO_4$), filtered and the solvent was evaporated until dryness. The residue (0.566 g) was purified by chromatography over silica gel (SiOH, 15-40 μm, 50 g; mobile phase 0.1% $NH_4OH$, 96% DCM, 4% MeOH). The product fractions were collected and the solvent was evaporated to give 1.26 g (34%) of intermediate 87.

Example A36A

Preparation of intermediate 88

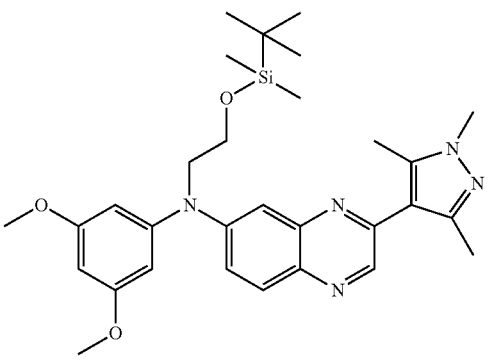 [SMILES: COc1cc(OC)cc(N(CCO[Si](C)(C)C(C)(C)C)c2ccc3ncc(-c4c(C)nn(C)c4C)nc3c2)c1]

A mixture of intermediate 88b

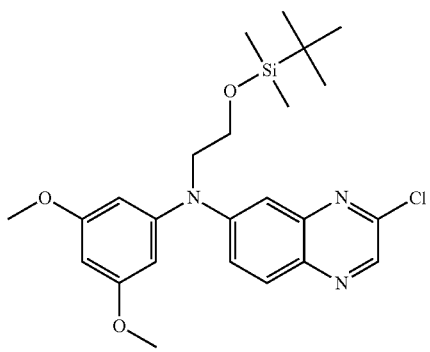 [SMILES: COc1cc(OC)cc(N(CCO[Si](C)(C)C(C)(C)C)c2ccc3ncc(Cl)nc3c2)c1]

(see A4c-2) (0.53 g; 1.1 mmol), 1,3,5-trimethyl-4-(tributylstannyl)-1H-Pyrazole (Synthesis, (13), 1949-1958; 2001) (1.33 g; 3.33 mmol) and tetrakis(triphenylphosphine)palladium(0) (0.064 g; 0.055 mmol) in toluene (3 mL) was stirred at 160° C. for 40 minutes using one single mode microwave (Biotage). The reaction mixture was cooled to room temperature and evaporated till dryness. The residue was purified by chromatography over silica gel (Irregular SiOH, 40 µm; mobile phase gradient from 90% DCM, 10% Heptane to 100% DCM, then 99% DCM 1% MeOH). The pure fractions were collected and concentrated to give 0.41 g (68%) of intermediate 88.

Intermediate 88b

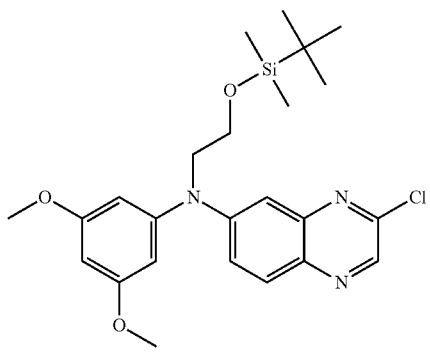 [SMILES: COc1cc(OC)cc(N(CCO[Si](C)(C)C(C)(C)C)c2ccc3ncc(Cl)nc3c2)c1]

solution of tetrabutylammonium fluoride (3.016 mmol; 3.016 ml) dropwise to a solution of intermediate 88b (2.742 mmol; 1.30 g) in THF (25 ml). The reaction mixture was stirred at room temperature overnight. The reaction mixture was poured out into ice water, EtOAc was added and the organic layer was separated, washed with brine, dried (MgSO$_4$), filtered and the solvent was evaporated. The residue was purified by column chromatography over silica gel (SiO$_2$=30 g-15/40 µm) Eluent: CH$_2$Cl$_2$ 100 to CH$_2$Cl$_2$ 98/MeOH 2, yielding intermediate 88a.

Alternative pyrazole derivatives which can be used in the above protocol can be prepared as follows:

A)
a) Preparation of intermediate 125

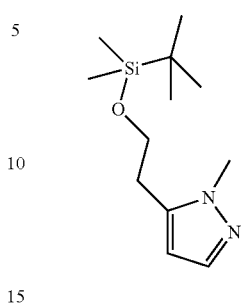

N-butyllithium 1.6M in hexane (33.5 mL; 53.6 mmol) was added dropwise to a solution of 1-methylpyrazole (4 g; 48.8 mmol) in THF (66 mL) at −78° C. under N$_2$ flow. The reaction mixture was stirred at 0° C., then (2-bromoethoxy)-tert-butyldimethylsilane (12.5 mL; 58.5 mmol) was added to the solution at −78° C. and was stirred for 1 hour. The temperature of the reaction mixture was allowed to rise to room temperature and stirred for 18 hours. The reaction mixture was poured out into ice water and EtOAc was added. The organic layer was separated, dried (MgSO$_4$), filtered and the solvent was evaporated. The residue (16 g) was purified by chromatography over silica gel (Irregular SiOH, 20-45 µm, 1000 g; mobile phase 65% Heptane, 35% EtOAc). The pure fractions were collected and concentrated to give 3 g (25%) of intermediate 125.

b) Preparation of intermediate 126

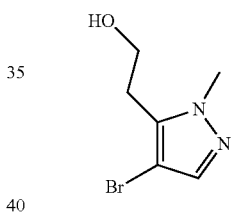

Pyridinium bromide perbromide 95% (3.5 g; 10.8 mmol) was added to a solution of intermediate 125 (2.6 g; 10.8 mmol) in MeOH (130 mL). The reaction mixture was stirred at 0° C. for 1 hour and room temperature for 18 hours. The solvent was evaporated and the residue was poured out into water and K$_2$CO$_3$ 10%. DCM was added and the organic layer was separated, dried (MgSO$_4$), filtered and the solvent was evaporated to dryness. The residue (2.5 g) was purified by chromatography over silica gel (Irregular SiOH, 20-40 µm, 300 g; mobile phase 0.1% NH$_4$OH, 97% DCM, 3% MeOH). The pure fractions were collected and concentrated to give 2 g (92%) of intermediate 126.

c) Preparation of intermediate 127

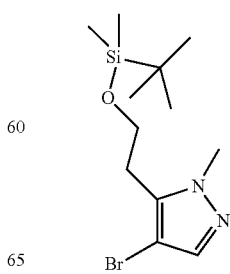

Tert-butyldimethylsilyl chloride (1.9 g; 12.7 mmol), imidazole (1.6 g; 23.4 mmol) were successively added to a solution of intermediate 126 (2 g; 9.75 mmol) in N,N-dimethylformamide (7 mL). The reaction mixture was stirred at room temperature for 18 hours. The reaction mixture was quenched with water and extracted with Et$_2$O. The organic layer was decanted, washed with water, then brine, dried (MgSO$_4$), filtered and evaporated to dryness. The residue was purified by chromatography over silica gel (SiOH, 10-40 μm, 90 g; mobile phase from 100% DCM to 97% DCM, 3% MeOH). The pure fractions were collected and concentrated to give 2.8 g (90%) of intermediate 127.

d) Preparation of intermediate 128

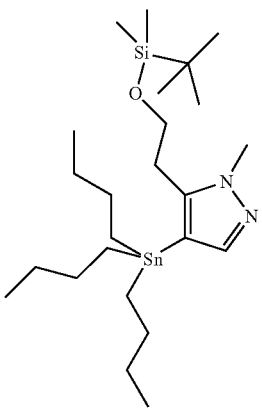 [SMILES: CCC[CH2][Sn]([CH2]CCC)([CH2]CCC)[c]1cnn(C)c1CCO[Si](C)(C)C(C)(C)C]

N-butyllithium 1.6M in hexane (0.22 mL; 0.35 mmol) was added dropwise to a solution of intermediate 127 (0.102 g; 0.32 mmol) in Et$_2$O (1.5 mL) at -78° C. under N$_2$ flow. The reaction mixture was stirred for 30 minutes, then tributyltin chloride (0.095 mL; 0.35 mmol) was added to the solution and was stirred at room temperature for 18 hours. The reaction mixture was poured out into ice water and Et$_2$O was added. The organic layer was separated, dried (MgSO$_4$), filtered and the solvent was evaporated to dryness. The residue (0.160 g) was purified by chromatography over silica gel (Spherical SiOH, 10 μm, 60 g; mobile phase 80% Heptane, 20% EtOAc). The pure fractions were collected and concentrated to give 0.055 g (32%) of intermediate 128.

B)
a) Preparation of intermediate 129

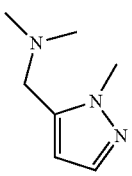

N-butyllithium 1.6M in hexane (25 mL; 40.2 mmol) was added dropwise to a solution of 1-methylpyrazole (3 mL; 35.5 mmol) in THF (50 mL) at -78° C. under N$_2$ flow. The reaction mixture was stirred at 0° C., then Eschenmoser's salt (8.1 g; 43.85 mmol) was added to the solution at -78° C. and was stirred for 1 hour. The temperature of the reaction mixture was allowed to rise to room temperature and stirred for 18 hours. The reaction mixture was poured out into ice water and EtOAc was added. The organic layer was separated, dried (MgSO$_4$), filtered and the solvent was evaporated to afford 3.1 g of intermediate 129.

b) Preparation of intermediate 130

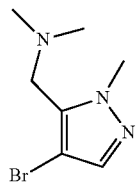

Pyridinium bromide perbromide 95% (6.9 g; 21.6 mmol) was added to a solution of intermediate 130 (3 g; 21.6 mmol) in MeOH (200 mL). The reaction mixture was stirred at 0° C. for 1 hour and room temperature for 18 hours. The solvent was evaporated and the residue was poured out into water and K$_2$CO$_3$ 10%. DCM was added and the organic layer was separated, dried (MgSO$_4$), filtered and the solvent was evaporated to dryness. The residue (3.1 g) was purified by chromatography over silica gel (Irregular SiOH, 20-40 μm, 450 g; mobile phase 0.1% NH$_4$OH, 97% DCM, 3% MeOH). The pure fractions were collected and concentrated to give 1.35 g (29%) of intermediate 130.

c) Preparation of intermediate 131

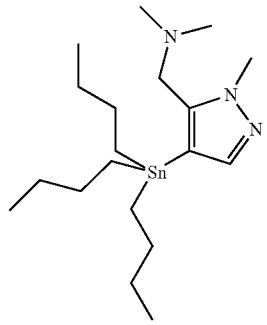 [SMILES: CCC[CH2][Sn]([CH2]CCC)([CH2]CCC)[c]1cnn(C)c1CN(C)C]

N-butyllithium 1.6M in hexane (0.8 mL; 1.26 mmol) was added dropwise to a solution of intermediate 130 (0.25 g; 1.15 mmol) in Et$_2$O/THF (1/2) (3 mL) at -78° C. under N$_2$ flow. The reaction mixture was stirred for 30 minutes. Then tributyltin chloride (1.58 mL; 5.8 mmol) was added to the solution and was stirred at room temperature for 18 hours. The reaction mixture was poured out into ice water and Et$_2$O was added. The organic layer was separated, dried (MgSO$_4$), filtered and the solvent was evaporated to dryness to give 0.52 g of intermediate 131 used without further purification for the next step.

Example A36B

Preparation of intermediate 89

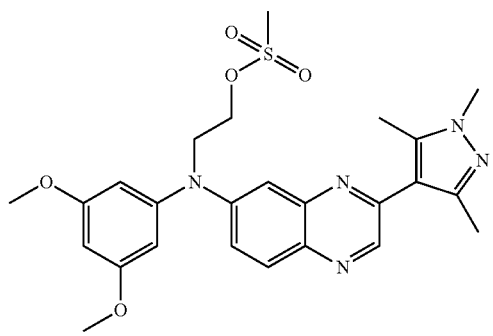 [SMILES: COc1cc(OC)cc(N(CCOS(C)(=O)=O)c2ccc3ncc(-c4c(C)nn(C)c4C)nc3c2)c1]

Methanesulfonyl chloride (0.066 mL; 0.85 mmol) was added dropwise to a solution of compound 622 (0.185 g; 0.43 mmol), triethylamine (0.14 mL; 0.98 mmol) and 4-dimethylaminopyridine (0.005 g; 0.043 mmol) in THF (5 mL) at 5° C. under a N₂ flow. The temperature of the reaction mixture was allowed to rise to room temperature for 2 hours. The reaction mixture was poured out into ice water and DCM was added. The organic layer was separated, dried (MgSO₄), filtered and the solvent was evaporated to dryness to give 0.26 g (yellow oil) of intermediate 89 used without further purification for the next step.

Example A37

Preparation of intermediate 91

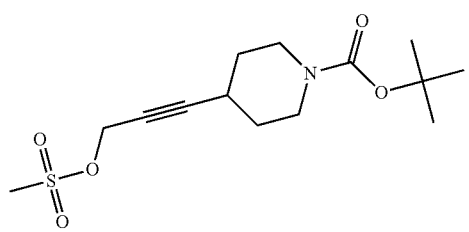 [SMILES: CC(C)(C)OC(=O)N1CCC(C#CCOS(C)(=O)=O)CC1]

Methanesulfonyl chloride (1 mL; 12.8 mmol) was added dropwise to a solution of 1-piperidinecarboxylic acid, 4-(3-hydroxy-1-propyn-1-yl)-, 1,1-dimethylethyl ester (2 g; 8.5 mmol), triethylamine (1.8 mL; 12.8 mmol) and 4-dimethylaminopyridine (10.4 g; 85 mmol) in DCM (20 mL) at 5° C. under a N₂ flow. The temperature of the reaction mixture was allowed to rise to room temperature for 18 hours. The reaction mixture was poured out into ice water and DCM was added. The organic layer was separated, dried (MgSO₄), filtered and the solvent was evaporated to dryness to give 1.41 g of intermediate 91 used without further purification for the next step.

Example A38

Preparation of intermediate 92

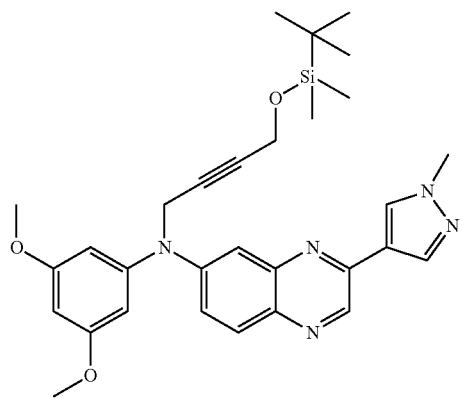 [SMILES: COc1cc(OC)cc(N(CC#CCO[Si](C)(C)C(C)(C)C)c2ccc3ncc(-c4cnn(C)c4)nc3c2)c1]

NaH (0.24 g; 6.0 mmol) was added portionwise to intermediate 3 (1 g; 3.0 mmol) in N,N-dimethylformamide (30 mL). The reaction mixture was stirred at 10° C. for 1 hour. Then 2-butyn-1-ol, 4-[[(1,1-dimethylethyl)dimethylsilyl]oxy]-, 1-methanesulfonate (4.2 g; 15.0 mmol) was added dropwise under N₂ flow. The reaction mixture was stirred at room temperature for 18 hours. The reaction was poured out into ice water and EtOAc was added. The organic layer was separated and washed with brine, dried (MgSO₄), filtered and the solvent was evaporated. The residue (4.2 g) was purified by chromatography over silica gel (Irregular SiOH 15-40 μm, 300 g; mobile phase 60% Heptane, 4% MeOH, 36% EtOAc). The pure fractions were collected and concentrated to give 0.185 g (11%) of intermediate 92.

Example A39

Preparation of intermediate 93

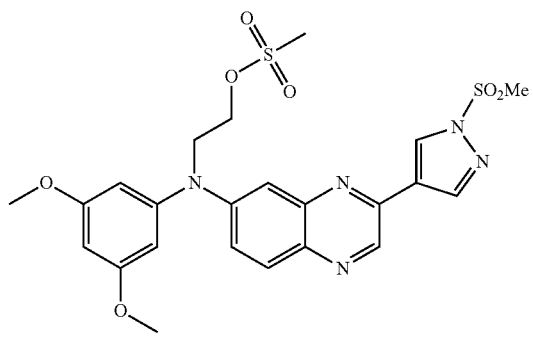 [SMILES: COc1cc(OC)cc(N(CCOS(C)(=O)=O)c2ccc3ncc(-c4cnn(S(C)(=O)=O)c4)nc3c2)c1]

Methanesulfonyl chloride (9.9 mL; 127.7 mmol) was added dropwise to a solution of compound 2 (10 g; 25.55 mmol), triethylamine (24.9 mL; 178.8 mmol) in DCM (400 mL) at 5° C. under a N₂ flow. The reaction mixture was stirred at room temperature for 2 hours. The reaction mixture was poured out into ice water and DCM was added. The organic layer was separated, dried (MgSO₄), filtered and the solvent was evaporated to dryness to give 17.6 g of intermediate 93 used without further purification for the next step.

Example A40

Preparation of intermediate 94

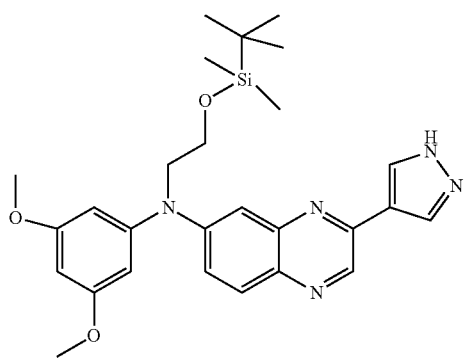

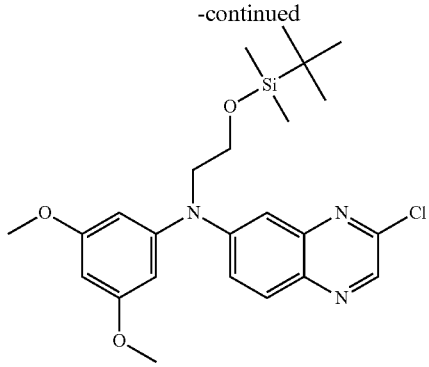

(see A4c-2)(9.5 g; 20 mmol), 4,4,5,5-tetramethyl-2-(1H-pyrazol-4-yl)-1,3,2-dioxaborolane (4.3 g; 22 mmol), potassium phosphate (8.5 g; 40 mmol) in dioxane (1 L) and water (120 mL) were degassed with $N_2$ for 15 minutes, then S-Phos (0.83 g; 2 mmol) and $Pd_2(dba)_3$ (7.6 g; 6.6 mmol) was added. The reaction mixture was heated at 80° C. for 15 hours. The reaction mixture was cooled to room temperature. The reaction mixture was poured out into ice water, EtOAc was added and was filtered off on a pad of Celite®. The organic layer was separated, washed with brine, dried ($MgSO_4$), filtered and evaporated till dryness. The residue (18.5 g) was purified by chromatography over silica gel (Irregular SiOH 20-45 µm, 1000 g; mobile phase 96% DCM, 4% MeOH). The pure fractions were collected and concentrated to give 5.1 g (51%) of intermediate 94.

Example A41 a) Preparation of intermediate 95

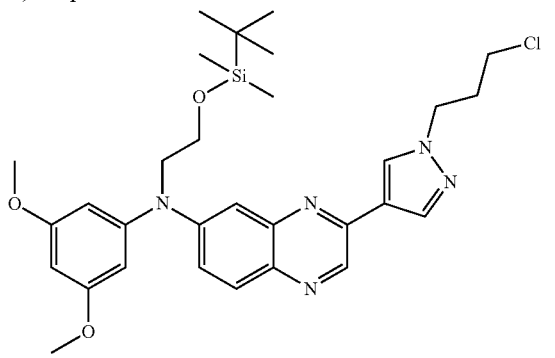

NaH (0.2 g; 4.75 mmol) was added portionwise to intermediate 94 (2 g; 4 mmol) in N,N-dimethylformamide (30 mL). The reaction mixture was stirred at 10° C. for 1 hour. Then 1-bromo-3-chloropropane (0.5 mL; 4.75 mmol) was added dropwise under $N_2$ flow. The reaction mixture was stirred at room temperature for 1 hour. The reaction was poured out into ice water and EtOAc was added. The organic layer was separated and washed with brine, dried ($MgSO_4$), filtered and the solvent was evaporated to afford 2.5 g of intermediate 95 used without further purification for the next step.

b) Preparation of intermediate 96

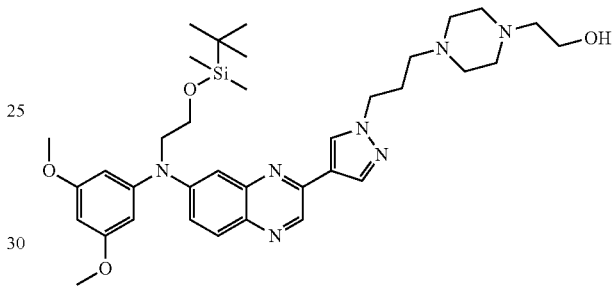

A mixture of intermediate 95 (1.1 g; 1.48 mmol), 1-(2-hydroxylethyl)piperazine (0.407 g; 2.95 mmol), $K_2CO_3$ (1.92 g; 14.74 mmol) in $CH_3CN$ (10 mL) was stirred at 90° C. for 12 hours. The reaction mixture was poured out into ice water and EtOAc was added. The organic layer was separated, dried ($MgSO_4$), filtered and the solvent was evaporated to dryness to give 0.9 g of intermediate 96 used without further purification for the next step.

c) Preparation of intermediate 97

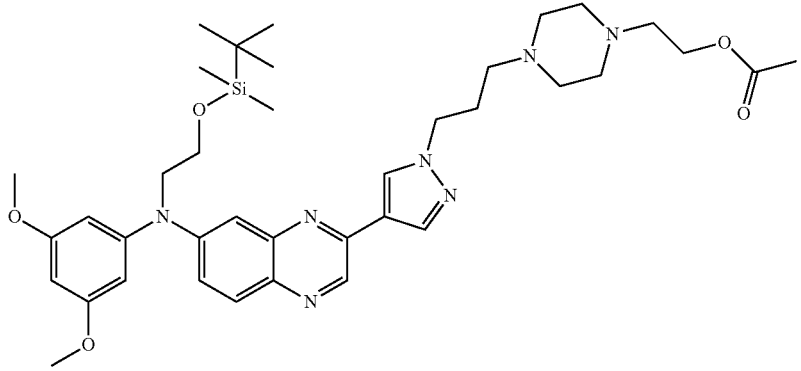 [SMILES: COc1cc(OC)cc(N(CCO[Si](C)(C)C(C)(C)C)c2ccc3ncc(-c4cnn(CCCN5CCN(CCOC(C)=O)CC5)c4)nc3c2)c1]

A mixture of intermediate 96 (0.56 g; 0.83 mmol), acetyl chloride (0.12 mL; 1.66 mmol), triethylamine (0.27 mL; 1.9 mmol) and 4-dimethylaminopyridine (0.01 g; 0.083 mmol) was stirred in DCM (10 mL) at 5° C. under a $N_2$ flow. The reaction mixture was stirred to room temperature for 18 hours. The reaction mixture was poured out into ice water and DCM was added. The organic layer was separated, dried ($MgSO_4$), filtered and the solvent was evaporated to dryness to give 0.85 g of intermediate 97 used without further purification for the next step.

d) Preparation of intermediate 98

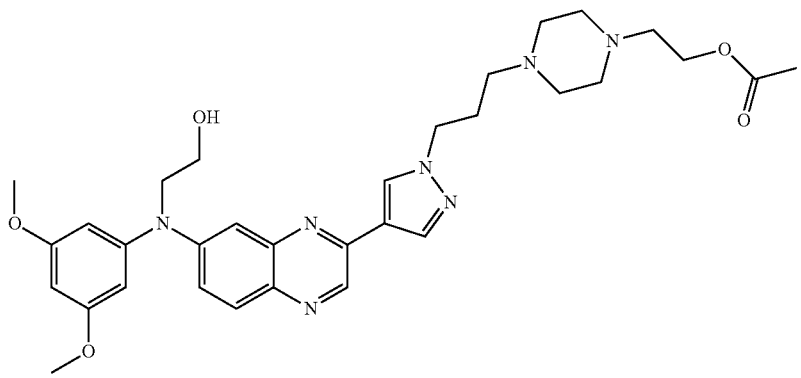 [SMILES: COc1cc(OC)cc(N(CCO)c2ccc3ncc(-c4cnn(CCCN5CCN(CCOC(C)=O)CC5)c4)nc3c2)c1]

A 1M solution of tetrabutylammonium fluoride in THF (2.5 mL, 2.5 mmol) was added dropwise to a solution of intermediate 97, (0.75 g, 0.84 mmol) in THF (5 mL) at room temperature. The reaction mixture was stirred at room temperature for 3 hours. The mixture was poured out into ice water, basified with $K_2CO_3$ 10% and EtOAc was added. The organic layer was separated, washed with brine, dried ($MgSO_4$), filtered and the solvent was evaporated to dryness. DCM and a few MeOH were added, then the insoluble fraction was filtered off and the filtrate was evaporated. The residue and the precipitate were combined and dissolved in DCM. The organic layer was washed with water, dried ($MgSO_4$), filtered and the solvent was evaporated to dryness. The residue (0.5 g) was purified by chromatography over silica gel (SiOH, 15-40 μm, 90 g; mobile phase from 0.3% $NH_4OH$, 97% DCM, 3% MeOH to 1% $NH_4OH$, 90% DCM, 10% MeOH). The pure fractions were collected and concentrated to give 0.238 g (47%) of intermediate 98.

e) Preparation of intermediate 99

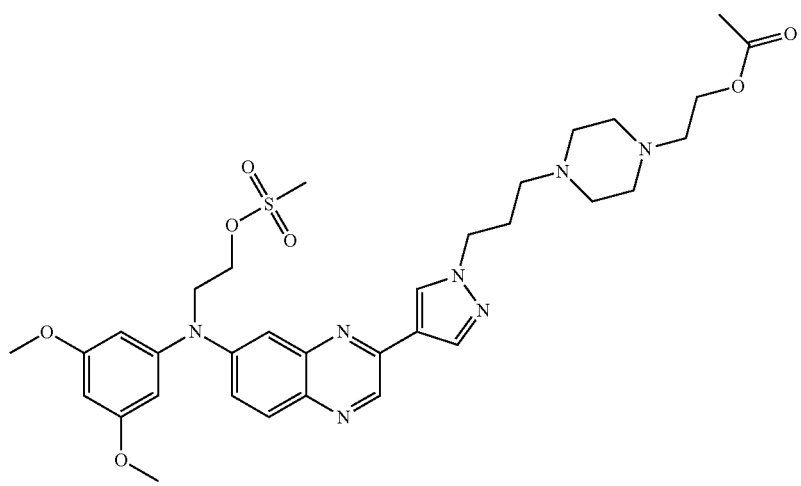 [SMILES: COc1cc(OC)cc(N(CCOS(C)(=O)=O)c2ccc3ncc(-c4cnn(CCCN5CCN(CCOC(C)=O)CC5)c4)nc3c2)c1]

Methanesulfonyl chloride (0.1 mL; 1.3 mmol) was added dropwise to a solution of intermediate 98 (0.19 g; 0.26 mmol) and triethylamine (0.11 mL; 0.78 mmol) in DCM (5 mL) at 5° C. under a N₂ flow. The reaction mixture was stirred at 10° C. for 2 hours. The reaction mixture was poured out into ice water and DCM was added. The organic layer was separated, dried (MgSO₄), filtered and the solvent was evaporated to dryness to give 0.51 g of intermediate 99-AAA used without further purification for the next step.

f) Preparation of intermediate 100

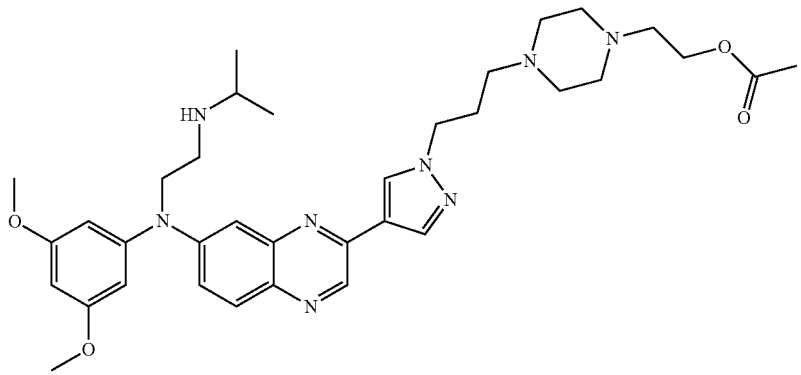 [SMILES: COc1cc(OC)cc(N(CCNC(C)C)c2ccc3ncc(-c4cnn(CCCN5CCN(CCOC(C)=O)CC5)c4)nc3c2)c1]

A mixture of intermediate 99 (0.51 g; 0.26 mmol) and isopropylamine (5.9 mL; 68.9 mmol) in acetonitrile (1 mL) was heated at 100° C. in a sealed vessel for 12 hours. The reaction mixture was cooled to room temperature. The reaction mixture was poured out into ice water, DCM was added. The organic layer was separated, washed, dried (MgSO₄), filtered and evaporated till dryness. The residue (0.59 g) was purified by chromatography over silica gel (Irregular SiOH, 15-40 µm, 30 g; mobile phase 0.7% NH₄OH, 93% DCM, 7% MeOH). The pure fractions were collected and concentrated to give 0.09 g (54%) of intermediate 100.

Example A42 a) Preparation of intermediate 101

A mixture of intermediate 5 (3 g; 13.3 mmol), intermediate 45 (3.9 g; 13.3 mmol), sodium tert-butoxide (3.9 g; 40 mmol) and 1,1'-[1,1'-binaphthalene]-2,2'-diylbis[1,1-diphenylphosphine (0.83 g; 1.33 mmol) in ethylene glycol dimethyl ether (100 mL) was degassed with N₂ for 10 minutes. Palladium(II) acetate (0.3 g; 1.33 mmol) was added and the mixture was stirred at 90° C. for 2 hours. The mixture was cooled down to room temperature, poured into H₂O and DCM. The mixture was filtered off on a pad of Celite®. The filtrate was extracted with DCM. The combined organic layers were dried (MgSO₄), filtered and evaporated to dryness to give 5 g of crude compound. The residue was purified by chromatography over silica gel (SiOH, 20-45 µm, 40 g; Mobile phase 0.1% NH₄OH, 97% DCM, 3% MeOH). The pure fractions were collected and the solvent was evaporated, yielding 3.6 g (62%) of intermediate 101.

b) Preparation of intermediate 102

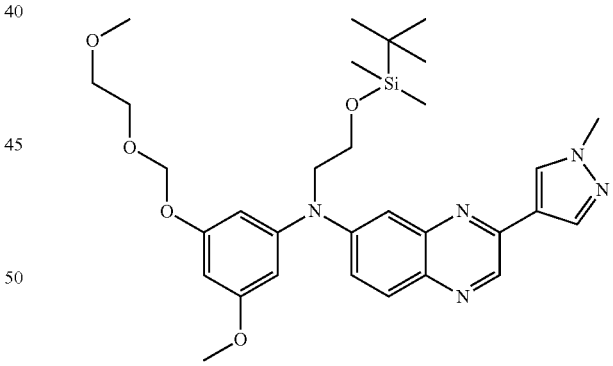

NaH (0.37 g; 9.2 mmol) was added portionwise to a solution of intermediate 101 (2 g; 4.6 mmol) in N,N-dimethylformamide (20 mL) at 5° C. under N₂ flow. The reaction mixture was stirred at 5° C. for 30 minutes. Then (2-bromoethoxy)-tert-butyldimethylsilane (1.3 mL; 6.0 mmol) was added dropwise at 5° C. under N₂ flow. The reaction mixture was stirred for 15 hours at room temperature. The reaction was poured out into ice water and EtOAc was added. The organic layer was separated, washed with brine, dried (MgSO₄), filtered and the solvent was evaporated to dryness to give 3 g of intermediate 102.

c) Preparation of intermediate 103

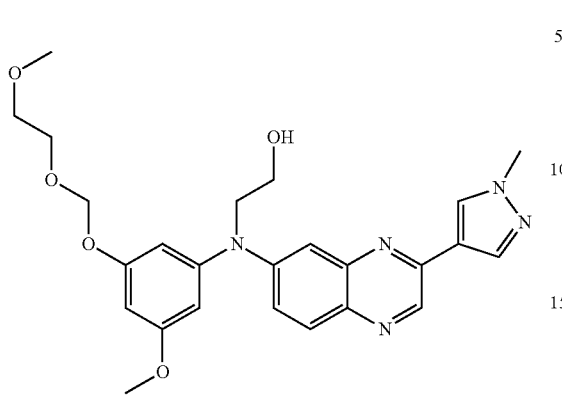

A 1M solution of tetrabutylammonium fluoride in THF (5 mL; 5 mmol) was added dropwise to a solution of intermediate 102 (3 g; 5 mmol) in THF (50 mL) at room temperature. The reaction mixture was stirred at room temperature for 15 hours. The mixture was poured out into ice water, basified with $K_2CO_3$ 10% and EtOAc was added. The organic layer was separated, washed with brine, dried ($MgSO_4$) and the solvent was evaporated to dryness. The residue (3 g) was purified by chromatography over silica gel (SiOH, 15-40 μm, 40 g; mobile phase 0.1% $NH_4OH$, 95% DCM, 5% MeOH). The pure fractions were collected and concentrated to give 2.2 g (61%) of intermediate 103.

d) Preparation of intermediate 104

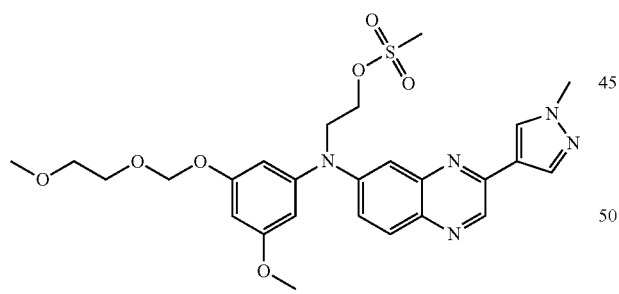

Methanesulfonyl chloride (0.7 mL; 9.2 mmol) was added dropwise to a solution of intermediate 103 (2.2 g; 4.6 mmol), triethylamine (1.6 mL; 11.5 mmol) in DCM (30 mL) at 5° C. under a $N_2$ flow. The reaction mixture was stirred at 10° C. for 2 hours. The reaction mixture was poured out into ice water and DCM was added. The organic layer was separated, dried ($MgSO_4$), filtered and the solvent was evaporated to dryness to give 2.8 g of intermediate 104 used without further purification for the next step.

e) Preparation of intermediate 105

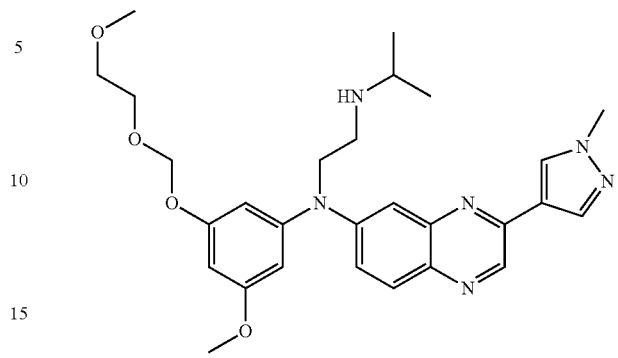

A mixture of intermediate 104 (2 g; 3.6 mmol) and 2-propanamine (1.6 mL; 17.9 mmol) in acetonitrile (15 mL) was heated at 100° C. in a sealed vessel for 18 hours. The reaction mixture was cooled to room temperature. The reaction mixture was poured out into ice water, EtOAc was added. The organic layer was separated, washed with brine, dried ($MgSO_4$), filtered and evaporated till dryness. The residue (2.2 g) was purified by chromatography over silica gel (SiOH, 15-40 μm, 40 g; mobile phase 0.1% $NH_4OH$, 95% DCM, 5% MeOH). The pure fractions were collected and concentrated to give 0.8 g (43%) of intermediate 105.

Example A43

Preparation of intermediate 107

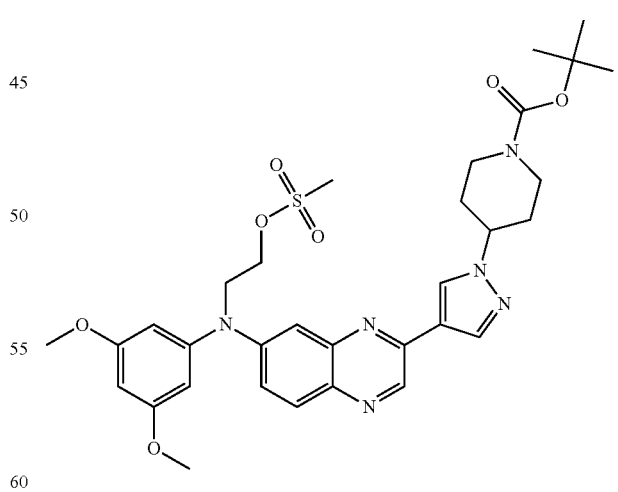

Methanesulfonyl chloride (0.19 mL; 2.4 mmol) was added dropwise to a solution of compound 625 (0.69 g; 1.2 mmol) (prepared according to the procedure described in B39 starting from

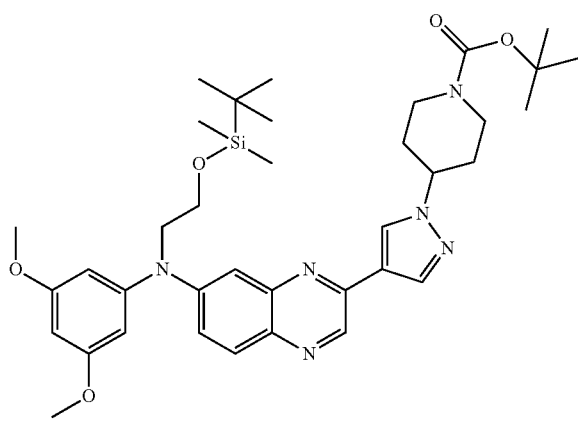 [SMILES: COc1cc(OC)cc(N(CCO[Si](C)(C)C(C)(C)C)c2ccc3ncc(-c4cnn(C5CCN(C(=O)OC(C)(C)C)CC5)c4)nc3c2)c1]

which is prepared according to the procedure described in A2c) starting from intermediate 41 and intermediate 106), triethylamine (0.4 mL; 3 mmol) in DCM (10 mL) at 5° C. under a $N_2$ flow. The reaction mixture was stirred at room temperature for 3 hours. The reaction mixture was poured out into ice water and DCM was added. The organic layer was separated, dried (MgSO$_4$), filtered and the solvent was evaporated to dryness to give 0.8 g of intermediate 107 as an orange oil used without further purification for the next step.

Intermediate 107 was converted into compound 650 according to the procedure described in B3 (first alternative protocol).

Example A43A

Preparation of intermediate 106

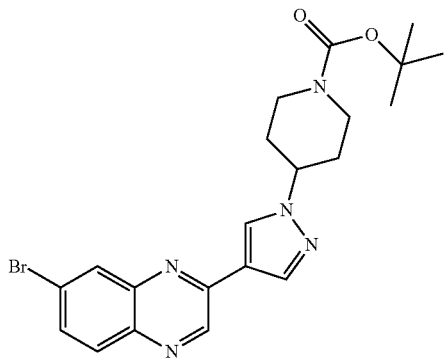 [SMILES: CC(C)(C)OC(=O)N1CCC(n2cc(-c3cnc4ccc(Br)cc4n3)cn2)CC1]

NaH (0.3 g; 7.2 mmol) was added portionwise to a solution of 7-bromo-2-(1H-pyrazol-4-yl)quinoxaline (1.6 g; 6 mmol) in N,N-dimethylformamide (100 mL) at 5° C. under $N_2$ flow. The reaction mixture was stirred at 5° C. for 1 hour. Then 4-methylsulfonyloxy-1-piperidinecarboxylate CAS [141699-59-4](3.5 g; 12.6 mmol) was added dropwise at 5° C. under $N_2$ flow. The reaction mixture was stirred for 18 hours at 100° C. The reaction was poured out into ice water and EtOAc was added. The organic layer was separated, washed with brine, dried (MgSO$_4$), filtered and the solvent was evaporated. The residue (8.4 g) was purified by chromatography over silica gel (Irregular, SiOH, 20-40 μm; 450 g; mobile phase 0.1% NH$_4$OH, 98% DCM, 2% MeOH). The pure fractions were collected and concentrated to give 3.7 g (67%) of intermediate 106 (yellow oil).

Example A44

Preparation of intermediate 109

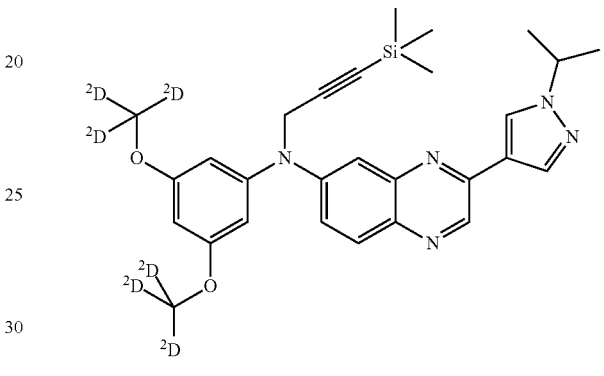

NaH (0.29 g; 7.4 mmol) was added portionwise to intermediate 108

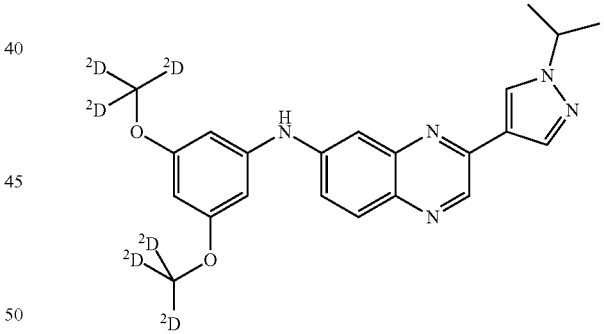

(1.5 g; 3.7 mmol) (prepared according to the procedure described in A33b) in N,N-dimethylformamide (25 mL). The reaction mixture was stirred at 0° C. for 30 minutes. Then 3-bromo-(1-trimethylsilyl)-1-propyne (1.6 mL; 10.2 mmol) was added dropwise at 5° C. under $N_2$ flow. The reaction mixture was stirred at 5° C. for 1 hour. The reaction was poured out into ice water and EtOAc was added. The organic layer was separated and washed with brine, dried (MgSO$_4$), filtered and the solvent was evaporated. The residue (2 g) was purified by chromatography over silica gel (SiOH 15-40 μm, 80 g mobile phase 98% DCM, 2% MeOH) to give 1.4 g of intermediate 109.

Example A45

Preparation of intermediate 110

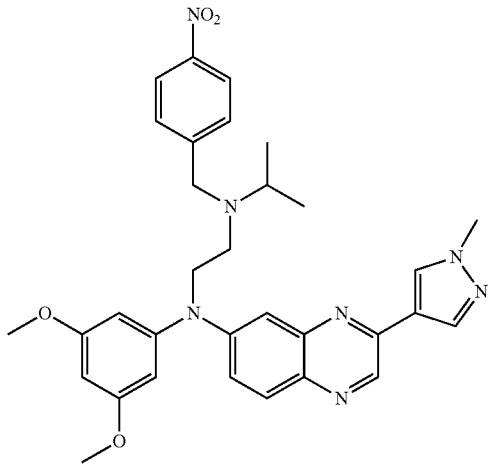 [SMILES: COc1cc(OC)cc(N(CCN(Cc2ccc([N+](=O)[O-])cc2)C(C)C)c2ccc3ncc(-c4cnn(C)c4)nc3c2)c1]

A mixture of compound 4 (0.5 g; 1.2 mmol), 4-nitrobenzyl bromide (0.29 g; 1.35 mmol) and $K_2CO_3$ (0.24 g; 51.8 mmol) in $CH_3CN$ (20 mL) was stirred at room temperature for 48 hours. The reaction mixture was cooled to room temperature, poured out into ice water and EtOAc was added. The organic layer was separated, washed with brine, dried ($MgSO_4$), filtered and the solvent was evaporated until dryness. The residue (0.8 g) was purified by chromatography over silica gel (Stability SiOH, 5 μm, 150*30 mm; mobile phase gradient from 71% Heptane, 1% MeOH, 28% EtOAc to 20% MeOH, 80% EtOAc). The product fractions were collected and the solvent was evaporated to give 0.34 g (52%) of intermediate 110.

Example A46 a) Preparation of intermediate 113

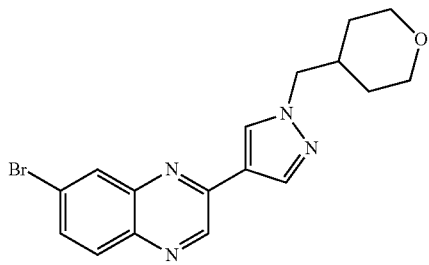 [SMILES: Brc1ccc2ncc(-c3cnn(CC4CCOCC4)c3)nc2c1]

NaH (0.52 g; 13 mmol) was added portionwise to 7-bromo-2-(1H-pyrazolyl-4-yl)quinoxaline (3 g; 11 mmol) in N,N-dimethylformamide (30 mL). The reaction mixture was stirred at 5° C. for 1 hour. Then 4-bromomethyltetrahydropyran (2.4 mL; 13 mmol) was added dropwise at 5° C. under $N_2$ flow. The reaction mixture was stirred at 5° C. for 1 hour, then was allowed to room temperature and stirred for 18 hours. The reaction was poured out into ice water and EtOAc was added. The organic layer was separated and washed with brine, dried ($MgSO_4$), filtered and the solvent was evaporated. The residue was crystallized from DIPE and $CH_3CN$. The precipitate was filtered and dried to give 2.6 g (64%) of intermediate 113.

b) Preparation of intermediate 112

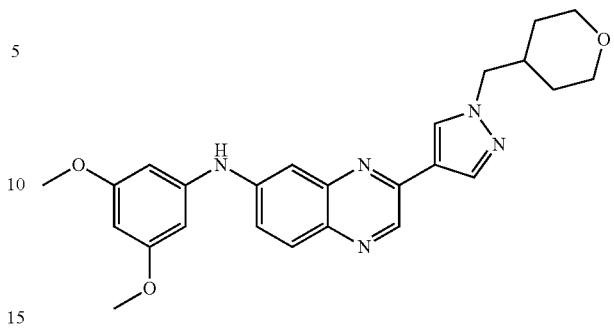

Under an inert atmosphere, a solution of palladium acetate (0.08 g; 0.35 mmol), racemic 2,2'-bis(diphenylphosphino)-1,1'-binaphtyl (0.22 g; 0.35 mmol) was added to room temperature to a solution of intermediate 113 (2.6 g; 7.0 mmol), 3,5-dimethoxyaniline (1 g; 7.0 mmol) and sodium tert butoxide (2 g; 21 mmol) in dioxane (40 mL). The reaction mixture was stirred at 90° C. for 18 hours. The reaction mixture was cooled to room temperature and poured out into ice water and DCM was added. The mixture was filtered over a pad of Celite®. The organic layer was washed with water, dried ($MgSO_4$), filtered and the solvent was evaporated. The residue (3.5 g) was purified by chromatography over silica gel (SiOH, 15-40 μm, mobile phase 98% DCM, 2% MeOH). The pure fractions were collected and concentrated to give 1.6 g (63%) of intermediate 112.

Example A47 a) Preparation of intermediate 114

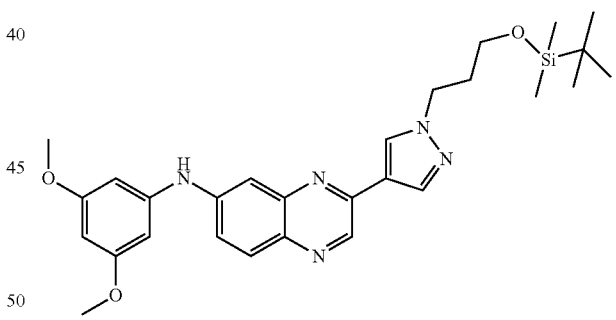

Intermediate 13 (9 g; 28.5 mmol), intermediate 132 (20.9 g; 57 mmol), potassium phosphate (12.1 g; 57 mmol) in dioxane (200 mL) and water (80 mL) were degassed with $N_2$ for 15 minutes, then S-Phos (1.2 g; 2.9 mmol) and $Pd_2(dba)_3$ (1.3 g, 1.4 mmol) were added. The reaction mixture was heated at 80° C. for 6 hours. The reaction mixture was cooled to room temperature. The reaction mixture was poured out into ice water, EtOAc was added and was filtered off on a pad of Celite®. The organic layer was separated, washed with brine, dried ($MgSO_4$), filtered and evaporated till dryness. The residue (28 g) was purified by chromatography over silica gel (Irregular SiOH 20-45 μm, 1000 g; mobile phase 99% DCM, 1% MeOH). The pure fractions were collected and concentrated to give 13.6 g (92%) of intermediate 114.

Intermediate 132

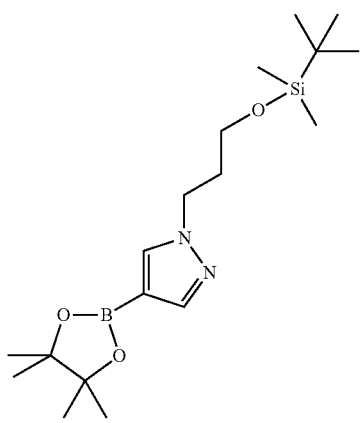 [SMILES: CC1(C)OB(c2cnn(CCCO[Si](C)(C)C(C)(C)C)c2)OC1(C)C]

was prepared as follows:

NaH (77.3 mmol; 3 g) was added to a solution of 4,4,5,5 tetramethyl-2-(1H-pyrazol-4-yl)-1,3,2-dioxaborolane (10 g; 51.5 mmol) in N,N-dimethylformamide (150 mL) at room temperature under N₂ flow. The reaction was stirred at room temperature for 1 hour. Then a solution of (3-bromopropoxy)-tert-butyldimethylsilane (18.5 mL; 77.3 mmol) was added dropwise at room temperature under N₂ flow. The reaction mixture was stirred at room temperature overnight. The reaction mixture was poured out into ice water and EtOAc was added. The organic layer was separated, washed with brine, dried (MgSO₄), filtered and the solvent was evaporated to give 23.8 g (70%) of intermediate 132 used without further purification.

Intermediate

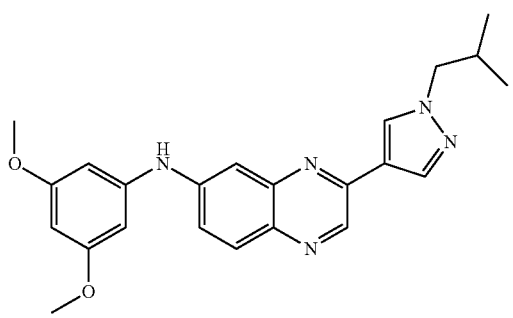 [SMILES: COc1cc(Nc2ccc3ncc(-c4cnn(CC(C)C)c4)nc3c2)cc(OC)c1]

was prepared according to the above protocol for intermediate 114.

b) Preparation of intermediate 115

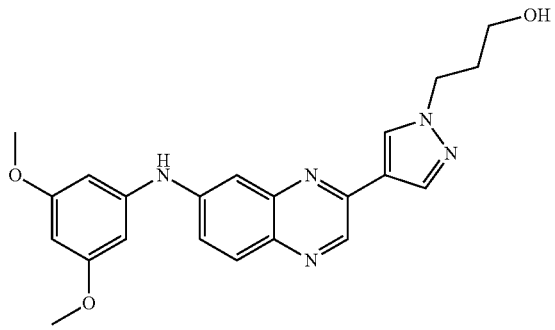 [SMILES: COc1cc(Nc2ccc3ncc(-c4cnn(CCCO)c4)nc3c2)cc(OC)c1]

A 1M solution of tetrabutylammonium fluoride in THF (24 mL; 24 mmol) was added dropwise to a solution of intermediate 114 (12.5 g; 24 mmol) in THF (250 mL) at room temperature. The reaction mixture was stirred at room temperature for 18 hours. The mixture was poured out into ice water, basified with K₂CO₃ 10% and EtOAc was added. The organic layer was separated, washed with brine, dried (MgSO₄), filtered and the solvent was evaporated to dryness. The residue was crystallized from diethyl ether. The precipitate was filtered off and dried to afford 8.8 g (90%) of intermediate 115. MP: 118° C. (Kofler).

c) Preparation of intermediate 116

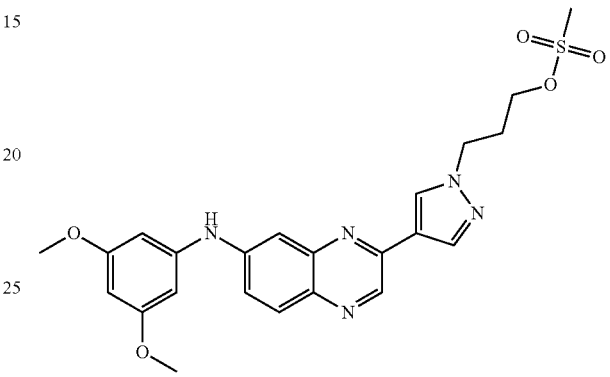

Methanesulfonyl chloride (1.9 mL; 24.7 mmol) was added dropwise to a solution of intermediate 115 (2 g; 5.0 mmol), triethylamine (4.9 mL; 34.5 mmol) in DCM (80 mL) at 5° C. under a N₂ flow. The reaction mixture was stirred at room temperature for 3 hours. The reaction mixture was poured out into ice water and DCM was added. The organic layer was separated, dried (MgSO₄), filtered and the solvent was evaporated to dryness to give 3.4 g of intermediate 116 used without further purification for the next step.

d) Preparation of intermediate 117

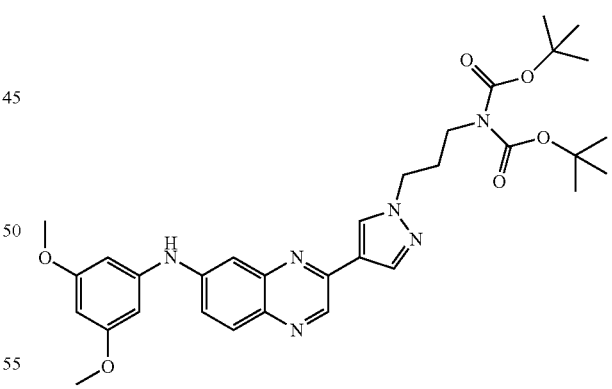

NaH (0.42 g; 10.4 mmol) was added portionwise to di-tert-butyl-iminocarboxylate (2.3 g; 10.4 mmol) in N,N-dimethylformamide (40 mL). The reaction mixture was stirred at 10° C. for 30 minutes. Then intermediate 116 (2.5 g; 5.2 mmol) was added dropwise under N₂ flow. The reaction mixture was stirred at room temperature for 18 hours, then stirred at 50° C. for 4 hours. The reaction was poured out into ice water and EtOAc was added. The organic layer was separated and washed with brine, dried (MgSO₄), filtered and the solvent was evaporated. The residue (4 g)

was purified by chromatography over silica gel (15-40 μm; 80 g; mobile phase 98% DCM, 20% MeOH). The pure fractions were collected and concentrated to give 1.7 g (54%) of intermediate 117.

e) Preparation of intermediate 118

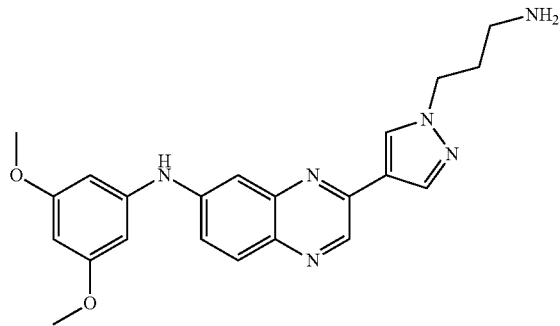 [SMILES: COc1cc(Nc2ccc3ncc(-c4cnn(CCCN)c4)nc3c2)cc(OC)c1]

Trifluoroacetic acid (3 mL; 39.7 mmol) was added to a solution of intermediate 117 (1.5 g; 2.5 mmol) in DCM (20 mL). The reaction was stirred at room temperature for 5 hours. The reaction mixture was poured out into ice water, basified with $K_2CO_3$ 10%, EtOAc was added. The layers were separated then the aqueous layer was evaporated till dryness. The residue was dissolved in MeOH. The precipitate was filtered off and the filtrate was evaporated till dryness. The residue was dissolved in DCM. The precipitate was filtered off and the filtrate was evaporated till dryness to afford 0.45 g (45%) of intermediate 118. MP: 96° C. (Kofler).

Example A48 a) Preparation of intermediate 119

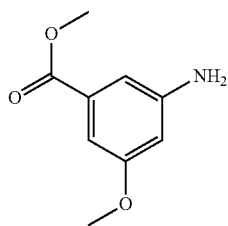

Thionyl chloride (26 mL; 359 mmol) was added dropwise to a solution of 3-amino-5-methoxybenzoic acid (10 g; 59.82 mmol) in MeOH (150 mL) at 0° C. The reaction mixture was stirred for 2 hours at room temperature. The precipitate was filtered off, washed with DIPE and dried under vacuo at 50° C. to give 8.6 g (79%) of intermediate 119 (a white solid).

b) Preparation of intermediate 120

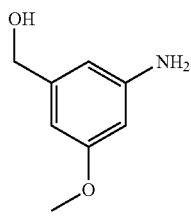

A solution of lithium 2.4M in THF (35.8 mL; 85.9 mmol) was added dropwise to a solution of intermediate 119 (8.62 g; 39.6 mmol) in dry THF (150 mL) at 0° C. under a $N_2$ flow. The reaction mixture was stirred for 2 hours at room temperature. The reaction mixture was treated with $NH_4Cl$ and stirred for 10 minutes at 0° C. The precipitate was filtered off and washed with EtOAc. The filtrate was separated and the organic layer was washed with brine, dried ($MgSO_4$), filtered and the solvent was evaporated to dryness. The residue (6 g) was purified by chromatography over silica gel (200 g; mobile phase gradient from 100% DCM to 7% MeOH in DCM). The pure fractions were collected and concentrated to give 3.26 g of intermediate 120.

c) Preparation of intermediate 121

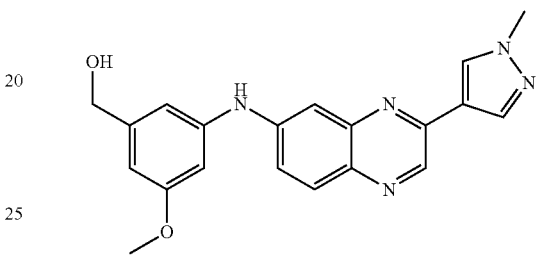

Under an inert atmosphere, a solution of tris(dibenzylacetone)palladium (0) (1.12 g; 1.2 mmol), 2-dicyclohexylphosphino-2',4',6'-tri-isopropyl-1,1'-biphenyl (1.28 g; 2.7 mmol) was added to room temperature to a solution of intermediate 2 (3.52 g; 12.2 mmol), intermediate 120 (3.3 g; 17.45 mmol) and cesium carbonate (11.9 g; 36.49 mmol) in t-BuOH (80 mL). The reaction mixture was stirred at 105° C. for 1 hour using one single mode microwave. The reaction mixture was cooled to room temperature, poured out into ice water (400 mL) and was stirred for 15 minutes. The precipitate was filtered off and washed with water. The precipitate was dissolved in DCM/MeOH (95/5) and the insoluble product was filtered off and dried to give 4.7 g of intermediate 121 used without further purification for the next step.

d) Preparation of intermediate 122

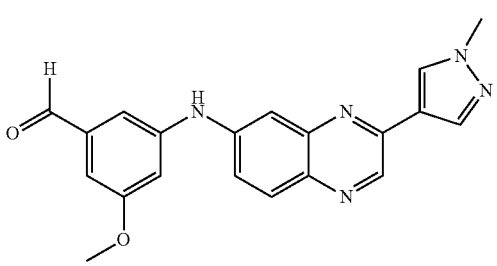 [SMILES: COc1cc(C=O)cc(Nc2ccc3ncc(-c4cnn(C)c4)nc3c2)c1]

$MnO_2$ (5.65 g; 65 mmol) was added to a solution of intermediate 121 (4.7 g; 13 mmol) in THF (270 mL). The reaction mixture was stirred at room temperature for 18 hours. The reaction mixture was filtered over a pad of Celite®. The filtrate was evaporated to give 1.5 g (32%) of intermediate 122 used without further purification for the next step.

e) Preparation of intermediate 123

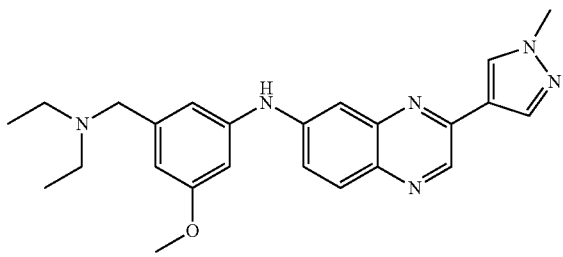 [SMILES: CCN(CC)Cc1cc(Nc2ccc3ncc(-c4cnn(C)c4)nc3c2)cc(OC)c1]

Intermediate 122 (0.3 g; 0.64 mmol) and diethylamine (0.14 g; 1.9 mmol) were added to Pd/C 10% (0.05 g) and 0.2 mL of a 4% solution of thiophene in DIPE in MeOH/THF (100 mL) under $N_2$ flow. The reaction mixture was stirred at 50° C. under 75 atm $H_2$ atmosphere until 1 eq hydrogen was absorbed. The reaction mixture was filtered over a pad of Celite®. The filtrate was evaporated to give 0.354 g of the intermediate 123.

Example A49

Preparation of intermediate 124

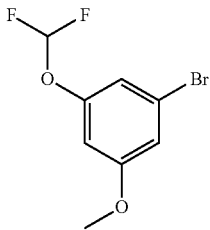

A mixture of 3-bromo-5-methoxyphenol (2 g; 9.8 mmol), cesium carbonate (6.4 g; 19.7 mmol) in N,N-dimethylformamide (20 mL) and water (4 mL) was degassed under $N_2$ flow for 1 hour, then acetic acid-2-chloro-2,2-difluoro-sodium salt (5.3 g; 34.5 mmol) was added. The reaction mixture was stirred at 120° C. for 2 days. The reaction was poured out into ice water and EtOAc was added. The organic layer was separated and washed with brine, dried ($MgSO_4$), filtered and the solvent was evaporated. The residue (2.5 g) was purified by chromatography over silica gel (Irregular SiOH, 15-40 μm, 300 g; mobile phase gradient from 95% Heptane, 5% EtOAc to 90% Heptane, 10% EtOAc). The pure fractions were collected and concentrated to give 0.56 g (23%) of intermediate 124.

Example A50 a) Preparation of intermediate 133

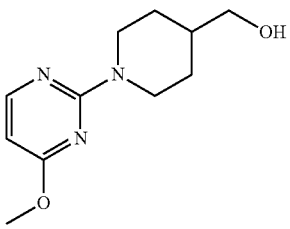 [SMILES: COc1ccnc(N2CCC(CO)CC2)n1]

A mixture of 2-chloro-4-methoxypyrimidine (1.24 g; 8.5 mmol), 4-piperidinemethanol (1.2 g; 10.25 mmol) and $K_2CO_3$ (2.4 g; 17.0 mmol) in $CH_3CN$ (15 mL) was stirred at 80° C. for 18 hours. The reaction mixture was poured out into ice water and DCM was added. The organic layer was separated, dried ($MgSO_4$), filtered and the solvent was evaporated to dryness. The residue (1.8 g) was purified by chromatography over silica gel (SiOH 15-40 μm, 40 g; mobile phase 0.1% $NH_4OH$, 99% DCM, 1% MeOH). The pure fractions were collected and concentrated to give 1.6 g (83%) of intermediate 133.

b) Preparation of intermediate 134

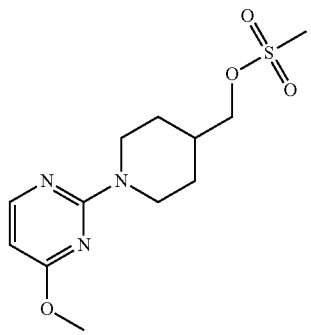 [SMILES: COc1ccnc(N2CCC(COS(C)(=O)=O)CC2)n1]

Methanesulfonyl chloride (0.94 mL; 12.1 mmol) was added dropwise to a solution of intermediate 133 (0.54 g; 2.42 mmol), triethylamine (2.4 mL; 16.9 mmol) in DCM (15 mL) at 5° C. under a $N_2$ flow. The reaction mixture was stirred at 10° C. for 1 hour. The reaction mixture was poured out into ice water and DCM was added. The organic layer was separated, dried ($MgSO_4$), filtered and the solvent was evaporated to dryness. The residue (1.1 g) was purified by chromatography over silica gel (SiOH 15-40 μm, 40 g; mobile phase from 99% DCM, 1% MeOH). The pure fractions were collected and concentrated to give 0.5 g (69%) of intermediate 134.

This intermediate was used in the preparation of compound 839.

Example A51 a) Preparation of intermediate 137

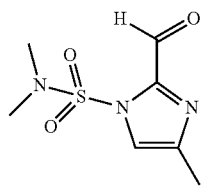

4-Methyl-1-dimethylsulfamoylimidazole (2.9 g, 15.6 mmol) was diluted in THF (105 mL). The resulting solution was cooled down to −78° C. and N butyl lithium 2M in cyclohexane (11.7 mL, 18.7 mmol) was added dropwise. The reaction mixture was stirred for 30 minutes at −78° C., N N-dimethylformamide (7.6 mL, 98.0 mmol) was added and the mixture was stirred for 1 hour at −78° C., then allowed to raise to room temperature in 1 hour. The reaction mixture was neutralized with an aqueous solution of $NH_4Cl$ and then poured out into water and EtOAc. The organic layer was dried ($MgSO_4$), filtered and concentrated to afford 3.7 g of intermediate 137.

b) Preparation of intermediate 138

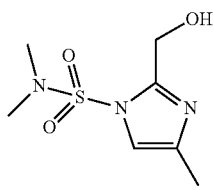

A mixture of intermediate 137 (3.7 g; 17 mmol) was dissolved in MeOH (32 mL). Then the reaction mixture was cooled down to 0° C. and sodium borohydride (0.6 g; 17 mmol) was added. The mixture was stirred for 1 hour at 0° C. The reaction mixture was then concentrated, poured out into water and EtOAc. The organic layer was dried (MgSO$_4$), filtered and concentrated to afford 2.9 g (78%) of intermediate 138. It was directly used in the next step without any further purification.

c) Preparation of intermediate 139

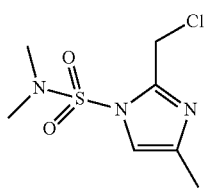

Intermediate 138 (3.2 g; 14.3 mmol) was dissolved in THF (26 mL) and N,N-dimethylformamide (13 mL). Then the solution was cooled down to 0° C. and triethylamine (4.1 mL; 28.6 mmol) followed by methanesulfonyl chloride (1.3 mL; 17.2 mmol) and lithium chloride (1.8 g; 43 mmol) were successively added. The mixture was stirred at room temperature over 2 hours. The reaction mixture was poured out into EtOAc and water. The organic layer was washed once with brine, dried (MgSO$_4$), filtered and concentrated. The residue (3.5 g) was purified by chromatography over silica gel (mobile phase gradient from 100% DCM to 0.1% NH$_4$OH, 99% DCM, 1% MeOH). The pure fractions were collected, the solvent was evaporated to afford 2.2 g (70%) of intermediate 139 used to prepare compound 695.

Example A52

Preparation of

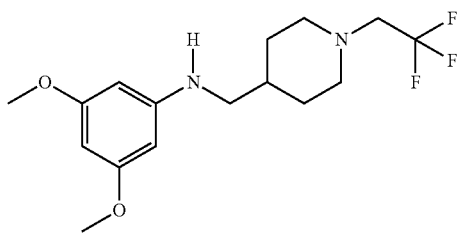 [SMILES: COc1cc(NCC2CCN(CC(F)(F)F)CC2)cc(OC)c1]

A mixture of 3,5-dimethoxyboronic acid (18.5 g; 101.5 mmol), 1-(2,2,2-trifluoroethyl)-4-piperidinemethanamine (16.6 g; 61.7 mmol), copper (II) acetate (18.5 g; 101.5 mmol) and triethylamine (59.8 mL; 425 mmol) in DCM (350 mL) was stirred at room temperature for 18 hours. The mixture was filtered and the filtrate was evaporated till dryness. The residue was purified by chromatography over silica gel (mobile phase gradient from 89% petroleum ether/11% ethyl acetate to 45% petroleum ether/55% ethyl acetate). The pure fractions were collected and the solvent was evaporated to give 3.8 g (19%) of compound.

Example A53

Preparation of intermediate 142

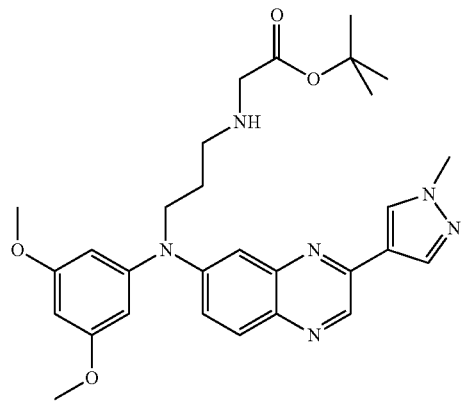 [SMILES: COc1cc(OC)cc(N(CCCNCC(=O)OC(C)(C)C)c2ccc3ncc(-c4cnn(C)c4)nc3c2)c1]

A mixture of intermediate 15 (1.8 g; 3.6 mmol) and glycine tert butyl ester (2.5 g; 18 mmol) in N,N-dimethylformamide (25 mL) was stirred at 80° C. for 6 hours in a sealed tube. The reaction was poured out into ice water and EtOAc was added. The organic layer was separated and washed with brine, dried (MgSO$_4$), filtered and the solvent was evaporated. The residue (2.52 g) was purified by chromatography over silica gel (SiOH 20-45 μm, 450 g; mobile phase 0.1% NH$_4$OH, 96% DCM, 4% MeOH). The pure fractions were collected and concentrated to afford 0.96 g (50%) of intermediate 142 used without further purification for the next step.

B. Preparation of the Compounds

Example B1

Preparation of compound 1

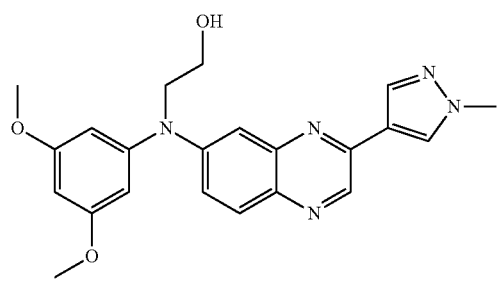 [SMILES: COc1cc(OC)cc(N(CCO)c2ccc3ncc(-c4cnn(C)c4)nc3c2)c1]

Tetrabutylammonium fluoride (38.5 mL, 38.5 mmol;) was added dropwise to a solution of intermediate 9 (20 g, 38.5 mmol) in THF (350 mL) at room temperature. The reaction mixture was stirred at room temperature for 5 hours. The mixture was poured out into ice water and EtOAc was added. The mixture was basified with K$_2$CO$_3$ 10% and the organic layer was separated, washed with brine, dried (MgSO$_4$), filtered and the solvent was evaporated. The residue was triturated from diethyl ether, filtered and dried under vacuum, yielding 11.7 g (75%) of compound 1. MP=153° C. (DSC).

Compound 1 was alternatively prepared using the following procedure.

525 g (1.01 mol) of intermediate 9 was dissolved in a mixture of THF (0.89 L), acetic acid (2.68 L) and water (0.89 L) and the reaction mixture was stirred at 50° C. upon complete conversion to the alcohol. The reaction mixture was evaporated till dryness. The residue was taken up in DCM (3.68 L) and water (3.68 L) and the pH of the mixture was adjusted to 7 using ammonia. The layers were separated. The aqueous layer was extracted with DCM (0.5 L) and the organic layers combined, dried (MgSO$_4$), filtered and evaporated till dryness. The residue was crystallized from toluene. The precipitate was filtered off, washed with toluene and dried to provide 204 g (49.8% yield) of compound 1.

a) Preparation of compound 2

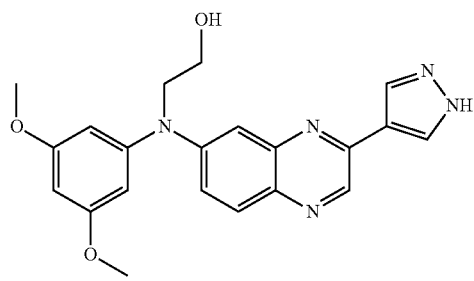 [SMILES: COc1cc(OC)cc(N(CCO)c2ccc3ncc(-c4cn[nH]c4)nc3c2)c1]

A mixture of intermediate 47 (1.50 g; 2.476 mmol), HCl 3N (2 mL) in dioxane (25 mL) was heated at 70° C. overnight. The reaction mixture was cooled to room temperature and poured out into ice water. EtOAc was added and the mixture was basified with an aqueous solution of K$_2$CO$_3$ (10%). The organic layer was separated, washed with brine, dried (MgSO$_4$), filtered and the solvent was evaporated. The compound was triturated from diethyl ether, filtered and dried under vacuum, yielding 0.790 g (81%) of compound 2. MP=169° C. (DSC).

Example B2 a) Preparation of compound 3

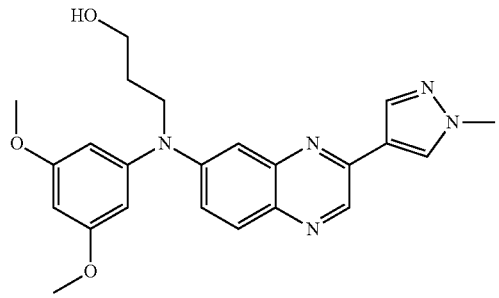 [SMILES: COc1cc(OC)cc(N(CCCO)c2ccc3ncc(-c4cnn(C)c4)nc3c2)c1]

Tetrabutylammonium fluoride (14.6 mL, 14.6 mmol) was added dropwise to a solution of intermediate 11 (6.5 g, 12.2 mmol) in THF (100 mL) at room temperature. The reaction mixture was stirred at room temperature overnight. The mixture was poured out into ice water and EtOAc was added. The mixture was basified with an aqueous solution of K$_2$CO$_3$ (10%) and the organic layer was separated, washed with brine, dried (MgSO$_4$), filtered and the solvent was evaporated to dryness to give 7.8 g of crude compound, which was purified by chromatography over silica gel (Irregular SiOH, 20-45 μm, 450 g MATREX; mobile phase 0.1% NH$_4$OH, 97% DCM, 3% MeOH). The pure fractions were collected and evaporated to yield 4.9 g (96%) of compound 3. The compound was crystallized from Et$_2$O/CH$_3$CN, the precipitate was filtered and dried to give 4.37 g (85%) of compound 3. MP=168° C. (Kofler).

Compound 3 was alternatively also prepared using the following procedure. Intermediate 11 (167.2 g; 313 mmol) was added to a mixture of acetic acid (846 mL), THF (282 mL) and water (282 mL) and the mixture was stirred at 50° C. for 18 hours and evaporated till dryness. The crude compound 3 was used without further purification to prepare intermediate 17a.

Compound 3 was alternatively also prepared using the following procedure B2b. b) HCl/i-PrOH (11.3 mL; 56.5 mmol) was added dropwise to a solution of intermediate 18 (8.5 g; 16.87 mmol) in CH$_3$OH (100 mL) at 10° C., and the mixture was stirred for 1 hour at room temperature. Ice water was added to the solution which was basified with NH$_4$OH. The product was extracted with DCM. The organic layer was dried (MgSO$_4$) and evaporated to dryness. The residue was purified by chromatography over silica gel (Irregular SiOH, 15-40 μm, 200 g; mobile phase, 97% DCM, 3% CH$_3$OH, 0.1% NH$_4$OH). The pure fractions were collected and evaporated to dryness to afford 3.7 g (52%) of compound 3 and 1.2 g of an impure fraction This impure fraction was purified by chromatography over silica gel (Irregular SiOH, 15-40 μm, 300 g MERCK; mobile phase 0.5% NH$_4$OH, 97% DCM, 3% CH$_3$OH). The pure fractions were collected and the solvent was evaporated, yielding 700 mg (10%) of compound 3.

Example B3

Preparation of compound 4

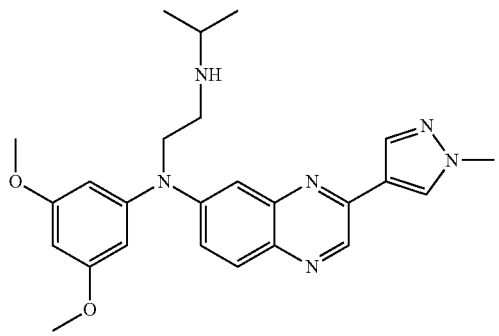 [SMILES: COc1cc(OC)cc(N(CCNC(C)C)c2ccc3ncc(-c4cnn(C)c4)nc3c2)c1]

A mixture of intermediate 10 (8.7 g; 17.99 mmol) and isopropylamine (61.3 mL, 719.68 mmol) was heated at 90° C. for 3 hours in a sealed vessel. The reaction mixture was cooled to room temperature and the mixture was evaporated till dryness. DCM and water were added and the organic layer was separated, washed with water, dried (MgSO$_4$), filtered and the solvent was evaporated. The residue (8 g) was crystallized from Et$_2$O/CH$_3$CN, filtered and dried under vacuum at 60° C., yielding 6.68 g (83%) of compound 4. MP=142° C. (DSC).

Compound 4 was alternatively prepared using the following procedure.

A mixture of intermediate 10 (322 g; 666 mmol) and 2-propanamine (196.8 g; 3.3 mol) in acetonitrile (2.66 L) was heated at 100° C. in a sealed vessel for 18 hours. The reaction mixture was cooled to room temperature and concentrated to ~30% of its initial volume. Water (1.5 L), 2-methyltetrahydrofuran (2.5 L) and NaHCO₃ (50 g) were added. The layers were separated, the organic layer was washed with a solution made of 50 g of NaHCO₃ in water (1 L), dried (MgSO₄), filtered over silica gel and evaporated till dryness. The residue was crystallized from 2-propanol. The precipitate was filtered off, dried in vacuum to provide 257.2 g (86.5%) of compound 4.

Compound 4 was alternatively prepared using the following procedure.

Intermediate 3 (20.0 g; 55.3 mmol), then tetra-N-butylammonium bromide (9.06 g; 27.7 mmol) were added at 2° C. under inert atmosphere to a solution of potassium hydroxide (46.6 g; 830 mmol) in THF (387 mL) and water (6 mL). The reaction was stirred at room temperature for 2 hours before portionwise addition of N-(2-chloroethyl)-2-propanamine HCl (CAS[6306-61-2]), and then at 50° C. upon complete conversion. Water was added, layers were separated and the organic layer concentrated, taken up in DCM/water, neutralized with HCl to neutral pH. Organic layer was washed with water, dried (MgSO₄), filtered and evaporated till dryness to give 26.6 g of compound 4.

Compound 4 as a HCl salt (0.1HCl) was prepared using the following procedure.

To a stirred mixture of 2-methyltetrahydrofuran (1.5 L) and KOH (140 g, 250 mmol) was added water (30 mL). Then intermediate 3 (60 g, 166 mmol)) and tetrabutylammoniumbromide (13.4 g, 41 mmol) were added and the mixture was heated at 50° C. for 1 hour while stirring. Then N-(2-chloroethyl)-2-propanamine HCl (CAS[6306-61-2]) (48 g, 299 mmol) was added in 1 portion. The mixture was stirred for 18 hours at 50° C. When the conversion was complete, water (600 mL) was added to the reaction mixture. The layers were separated and the organic layer was concentrated. The residue was dissolved in 2-propanol (120 mL) and HCl in 2-propanol was added at 60° C. After cooling, the HCl-salt was isolated via filtration. After drying at 50° C. in a vacuum drying oven the HCl-salt was obtained in 83% yield (compound 4a).

To 51.69 g (107 mmol) of the HCl salt from the previous step was added water (258 mL) and DCM (258 mL). The pH of the reaction mixture was adjusted using ammonium hydroxide (17.25 mL) until pH=9.5. The layers were separated and the organic layer was concentrated. The residue was crystallized from 2-propanol (258 mL). After drying at 50° C. under vacuum compound 4 was obtained in 91% yield (43.4 g).

Example B3A

Preparation of compound 6

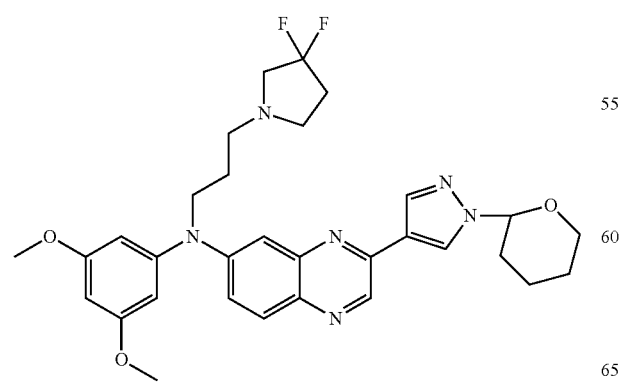

Intermediate 48 (7.2 g; 12.7 mmol), 3,3-difluoropyrrolidin hydrochloride (7.3 g; 50.7 mmol), sodium carbonate (6.72 g; 63.42 mmol), potassium iodide (2.1 g; 12.7 mmol) in 1-butanol (220 mL) were heated to 90° C. for 15 hours. The mixture was cooled to room temperature and poured into H₂O/K₂CO₃ and extracted with EtOAc. The organic layer was dried (MgSO₄), filtered and evaporated to dryness. The residue was purified by chromatography over silica gel (Irregular SiOH, 35-40 μm, Grace Resolv; mobile phase gradient from 100% DCM to 95% DCM, 5% MeOH, 0.1% NH₄OH). The desired product fraction was collected and the solvent was evaporated, yielding 3.2 g (44%) of compound 6.

Example B3B

Preparation of compound 580

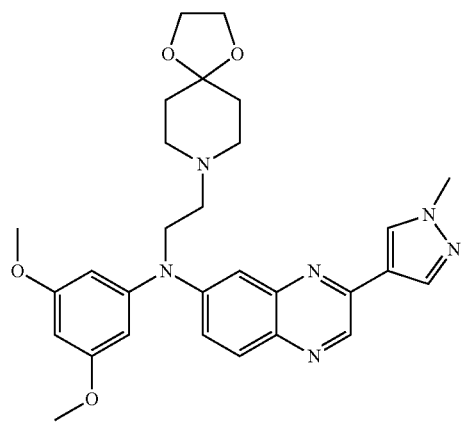 [SMILES: COc1cc(OC)cc(N(CCN2CCC3(CC2)OCCO3)c2ccc3ncc(-c4cnn(C)c4)nc3c2)c1]

A mixture of intermediate 10 (2.8 g; 5.8 mmol) and 1,4-dioxa-8-azaspiro[4-5]decane (1.5 g; 18 mmol) in 1-methyl-2-pyrrolidinone (10 mL) in a sealed tube was heated at 140° C. using one single mode microwave (Biotage Initiator EXP 60) for 1 hour. The reaction mixture was evaporated till dryness. The crude product (6 g) was purified by chromatography over silica gel (15-40 μm 300 g; mobile phase, 0.2% NH₄OH, 95% DCM, 5% MeOH). The pure fractions were collected and the solvent was evaporated till dryness to give 1.9 g (61%) of compound 580.

Example B3C

Preparation of compound 666 and 665

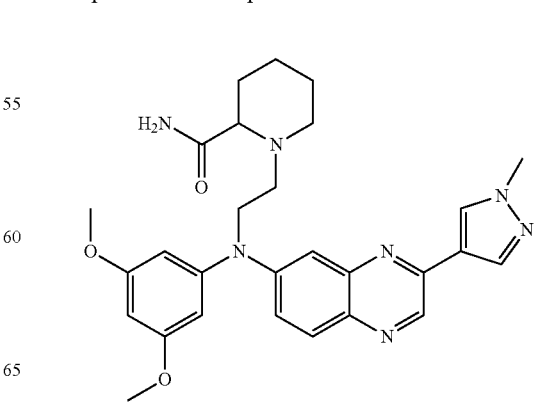

-continued

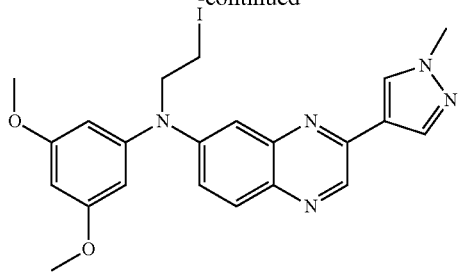

A mixture of intermediate 10 (0.3 g; 0.6 mmol), 2-piperidine-2-carboxamide (0.32 g; 2.5 mmol), potassium iodide (0.1 g; 0.6 mmol) and carbonate sodium (0.41 g; 4.4 mmol) in 1-butanol (12 mL) was stirred at 85° C. for 4 days. The reaction was poured into ice water and EtOAc was added. The organic layer was washed with brine, dried (MgSO$_4$), filtered and evaporated till dryness. The residue (0.33 g) was purified by preparative LC on (irregular, SiOH 15-40 μM, 30 g, mobile phase gradient from 0.1% NH$_4$OH, 98% DCM, 2% MeOH to 0.1% NH$_4$OH, 96% DCM, 4% MeOH). The pure fractions were collected and the solvent was evaporated. The first product (0.1 g) was crystallized from diethyl ether. The precipitate was filtered and dried to give 0.081 g (25%) of compound 665. MP: 206° C. (Kofler). The second product (0.1 g) was crystallized from diethyl ether. The precipitate was filtered and dried to give 0.082 g (25%) of compound 666. MP: 163° C. (Kofler).

Example B3D

Preparation of compound 677

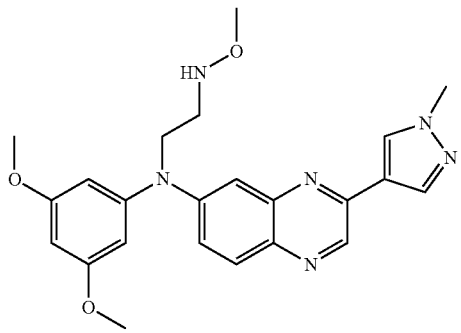 [SMILES: CONCCN(c1cc(OC)cc(OC)c1)c1ccc2ncc(-c3cnn(C)c3)nc2c1]

Intermediate 10 (1.3 g; 2.7 mmol), methoxylamine hydrochloride (2.3 g; 26.9 mmol) in triethylamine (15 mL; 107.5 mmol) were heated at 90° C. for 5 hours in a sealed tube. The reaction was poured out into ice water. The organic layer was separated and washed with water, dried (MgSO$_4$), filtered and the solvent was evaporated. The residue (2 g) was purified by chromatography over silica gel (SiOH, 15-40 μm, 300 g; mobile phase, 96% DCM, 4% i-PrOH). The pure fractions were collected and concentrated. The residue (0.38 g) was crystallized from diethyl ether. The precipitate was filtered and dried to afford 0.32 g (27%) of compound 677 MP: 177° C. (DSC).

Example B3E

Preparation of compound 923 (free base) and compound 886 (HCl salt)

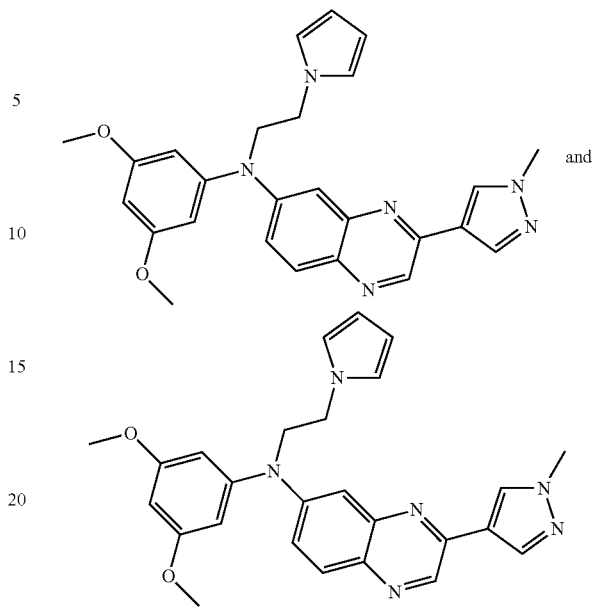

and as a HCl salt

A mixture of intermediate 10 (1.0 g; 2.07 mmol) and 3-pyrroline (628 μL, 8.3 mmol) in acetonitrile (4 mL) was heated at 90° C. for 90 minutes in a microwave biotage device. The reaction mixture was cooled to room temperature and the mixture was evaporated until dryness. DCM and water were added and the organic layer was separated, washed with water, dried (MgSO$_4$), filtered and the solvent was evaporated. The residue was chromatographed over silica gel (5 μm, mobile phase: gradient from NH$_4$OH 0.2%, DCM 98%, MeOH 2% to NH$_4$OH 0.8%, DCM 92%, MeOH 8%). The eluted fractions were evaporated and the residue was dissolved in DCM, and stirred at room temperature under air bubbling. for 24 hours. The solvent was evaporated to give a yellow foam which was chromatographed over silica gel (SiOH 10 μm 60 g, mobile phase 0.1% NH$_4$OH, 98% DCM, 2% MeOH). The desired product fractions were evaporated to provide 100 mg (11%) of compound 923. This compound was converted into the HCl salt in MeOH. The precipitate was filtered off, washed with MeOH and dried to give 41 mg (4%) of compound 886.

Example B3F

Preparation of compound 891 and 894

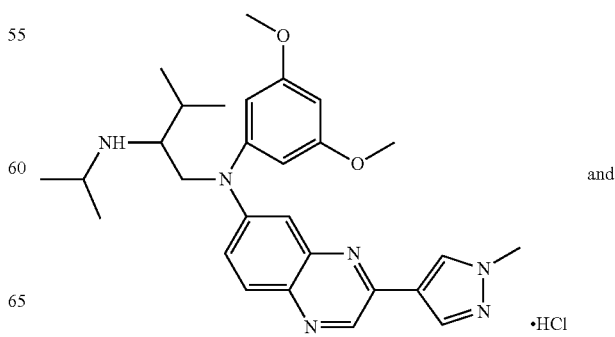

compound 894

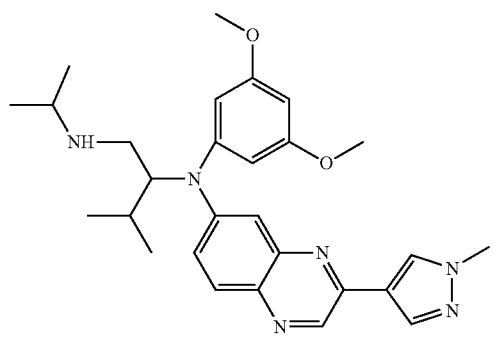

as a HCl salt and preparation of compound 924 and 925 compound 924

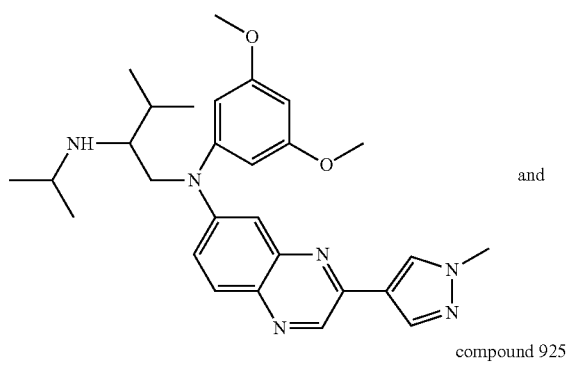

and compound 925

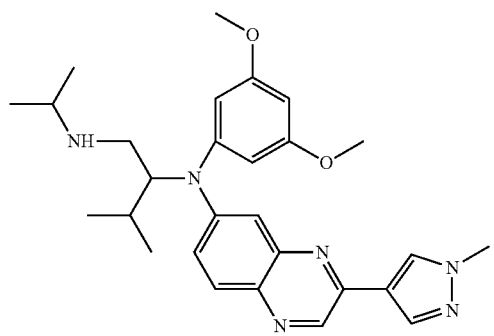

A mixture of intermediate 143 (622 mg, 1.2 mmol) in isopropylamine (8.06 mL, 94.6 mmol) was heated at 120° C. in a sealed vessel during 48 hours. The reaction mixture was cooled to room temperature and DCM was added. The organic layer was washed with water, dried (MgSO₄), filtered and the solvent was evaporated to give a yellow oil. This residue was purified by chromatography over silica gel (5 µm, mobile phase: gradient from 100% DCM to 0.7% NH₄OH, 93% DCM, 7% MeOH). The desired product fractions were collected and evaporated yielding 33 mg (6%) of compound 924 and 40 mg (7%) of compound 925. Compound 924 was converted into HCl salt in MeOH. The precipitate was filtered off, washed with Et₂O and dried to give 25 mg (4%) of compound 10891. Compound 925 was converted into HCl salt in MeOH. The solvent was evaporated, the residue was triturated into Et₂O, filtered off, washed with Et₂O and dried to give 51 mg (7%) of residue. This fraction was taken up from MeOH, and stirred 10 minutes at room temperature. The solvent was evaporated to dryness. The product was triturated, and dried, to give 24 mg (3%) of compound 894.

Example B4 a) Preparation of compound 5

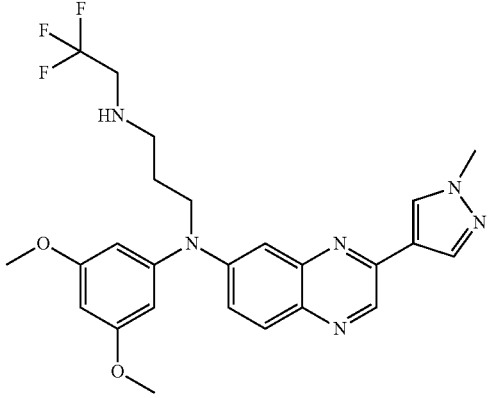 [SMILES: COc1cc(OC)cc(N(CCCNCC(F)(F)F)c2ccc3ncc(-c4cnn(C)c4)nc3c2)c1]

A solution of intermediate 17a (0.2 g; 0.402 mmol) in 2,2,2-trifluoroethylamine (2 mL; 25 mmol) was heated at 90° C. in a sealed tube for 12 hours. The reaction mixture was cooled to room temperature and poured out into ice water. EtOAc was added and the organic layer was separated, washed with brine, dried (MgSO₄), filtered and the solvent was evaporated. The residue was purified by chromatography over silica gel (Spherical SiOH, 10 µm, 60 g PharmPrep MERCK; mobile phase, 98% DCM, 2% CH₃OH). The pure fractions were collected and the solvent was evaporated. The residue (0.14 g, 69%) was crystallized from DIPE/diethyl ether/pentane (1/1/1). The precipitate was filtered and dried under vacuum, yielding 0.134 g (67%) of compound 5, MP=126° C. (DSC).

Compound 5 was alternatively also prepared using the following procedure B4b.

b) 3M HCl (60 mL) was added to a solution of intermediate 17 (9.49 mmol; 5.7 g) in CH₃OH (120 mL) at room temperature. The reaction mixture was heated at 60° C. overnight. The reaction mixture was cooled to room temperature, diluted with DCM and poured onto an iced solution of K₂CO₃ (10%). The mixture was stirred for 30 minutes and the organic layer was decanted, washed with water, dried (MgSO₄), filtered and evaporated to dryness. The residue was purified by HPLC. The residue (5.3 g) was purified by chromatography over silica gel (Irregular SiOH, 15-40 µm, 300 g MERCK; mobile phase 0.1% NH₄OH, 98% DCM, 2% CH₃OH). The pure fractions were collected and evaporated to dryness. The oily residue (3.93 g, 83%) was crystallized from DiPE/diethyl ether/CH₃CN. The precipitate was filtered off and dried, yielding 3.7 g (78%) of compound 5.

Compound 5 was alternatively also prepared using the following procedure.

A mixture of intermediate 17 (268.5 g; 447 mol) and trifluoroacetic acid (0.5 L) in DCM (2.24 L) was stirred at room temperature for 18 hours and then at 50° C. for 1 hour. The reaction mixture was evaporated till dryness, taken up in toluene (0.3 L) and evaporated again. The residue was dissolved in DCM (3 L) and water (2 L) and the pH adjusted to neutral with ammonia. The layers were separated, the aqueous layer was extracted with DCM (0.3 L) and the organic layers combined and evaporated till dryness. The residue was dissolved in EtOAc (1.5 L) and stirred for 1 hour with a mixture of silica gel (275 g). The silica gel was filtered off, washed with EtOAc and the filtrate evaporated till dryness to give 226 g of compound 5. It was crystallized from 2-propanol, filtered and dried to provide 180.8 g (80%) of compound 5.

Example B4A

Preparation of compound 7

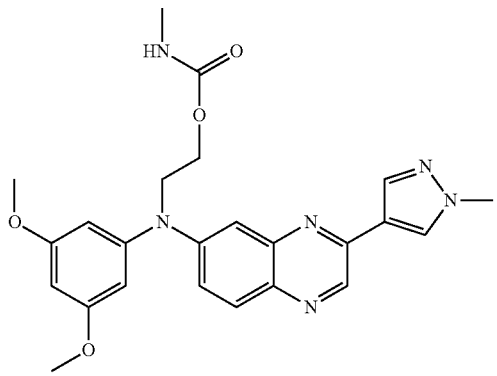 [SMILES: CNC(=O)OCCN(c1cc(OC)cc(OC)c1)c1ccc2ncc(-c3cnn(C)c3)nc2c1]

and compound 8

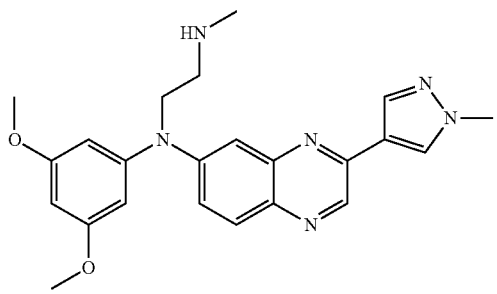 [SMILES: CNCCN(c1cc(OC)cc(OC)c1)c1ccc2ncc(-c3cnn(C)c3)nc2c1]

A methylamine solution in absolute ethyl alcohol (5.15 mL, 33% w/w, 41.4 mmol) was added dropwise to a suspension of intermediate 10 (2 g, 4.1 mmol), $K_2CO_3$ (2.86 g, 20.7 mmol) in dry $CH_3CN$ (40 mL) at room temperature. The mixture was heated at 80° C. overnight in a sealed vessel. The reaction mixture was cooled to room temperature and poured out into ice water. EtOAc was added and the organic layer was separated, washed with brine, dried ($MgSO_4$), filtered and the solvent was evaporated. The residue (1.85 g) was purified by chromatography over silica gel (Irregular SiOH, 15-40 µm, 300 g MERCK; mobile phase gradient from 0.1% $NH_4OH$, 95% DCM, 5% MeOH to 0.1% $NH_4OH$, 90% DCM, 10% MeOH). The desired fractions were collected and the solvents were evaporated, yielding 0.30 g of Fraction 1 (15%) and 1.25 g of Fraction 11 (72%). Fraction I was crystallized from diethyl ether, filtered and dried under vacuum, yielding 0.240 g (12%) of compound 7. MP=160-162° C. Fraction II was taken up with DCM and an aqueous solution of $K_2CO_3$ (10%). The mixture was stirred for 1 hour, then the organic layer was separated, dried ($MgSO_4$), filtered and the solvent was evaporated. The product was crystallized from diethyl ether/ $CH_3CN$, filtered and dried under vacuum at 60° C., yielding 1.05 g (59%) of compound 8. MP=180-182° C. (Kofler).

Example B4B

Preparation of compound 679

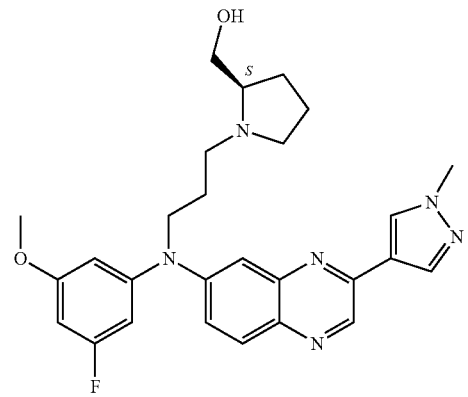

A mixture of intermediate 3-{(3-Fluoro-5-methoxyphenyl)[3-(1-methyl-1H-pyrazol-4-yl)quinoxalin-6-yl]amino}propyl methanesulfonate prepared according to A3 0.35 g; 0.72 mmol), (S)-(+)-2-pyrrolidine methanol (0.1 mL; 1 mmol) and triethylamine (0.4 mL; 2.9 mmol) in 1-methyl-2-pyrrolidinone (1 mL) was heated at 140° C. for days in a sealed tube. The reaction was poured out into ice water and EtOAc was added. The organic layer was separated and washed with brine, dried ($MgSO_4$), filtered and the solvent was evaporated. The residue (0.12 g) was purified by chromatography over silica gel (SiOH 5 µm; mobile phase gradient from 0.52% $NH_4OH$, 98% DCM, 2% MeOH to 0.8% $NH_4OH$, 92% DCM, 8% MeOH). The pure fractions were collected and concentrated to give 0.031 g (9%) of compound 679

Example B4C

Preparation of compound 694

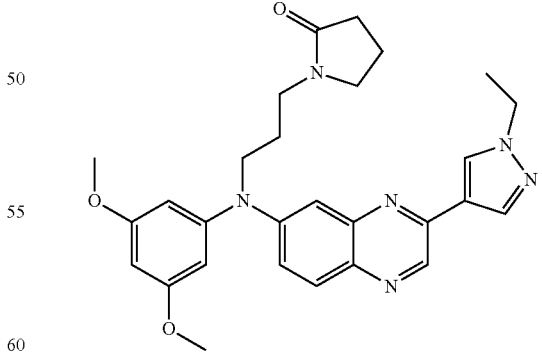

as a HCl salt

NaH (0.24 g; 5.9 mmol) was added portionwise to 2-pyrrolidinone (0.46 mL; 5.9 mmol) in N,N-dimethylformamide (30 mL) at 5° C. under $N_2$ flow. The reaction mixture was stirred at 5° C. for 1 hour, then intermediate

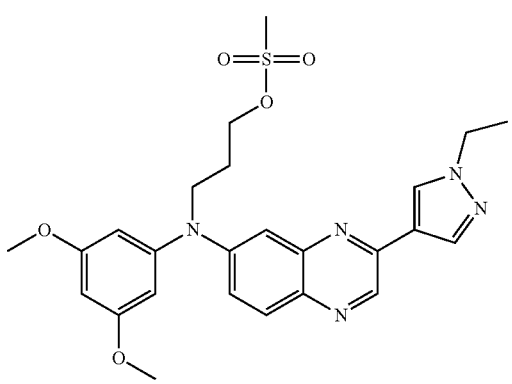 [SMILES: CCn1cc(-c2cnc3ccc(N(CCCOS(C)(=O)=O)c4cc(OC)cc(OC)c4)cc3n2)cn1]

prepared according to A5 (1 g; 2 mmol) was added at 5° C. under N₂ flow. The reaction mixture was allowed to warm to room temperature and stirred for 18 hours. The reaction was poured out into ice water. A precipitate was filtered, washed with water. The organic layer was separated and washed with water, dried (MgSO₄), filtered and the solvent was evaporated. The residue (0.8 g) was purified by chromatography over silica gel (Irregular SiOH, 15-40 µm, 300 g; mobile phase 0.1% NH₄OH, 97% DCM, 3% MeOH). The pure fractions were collected and concentrated. The residue was dissolved in isopropyl alcohol and stirred at 0° C., then 0.5 mL of HCl i-PrOH 5N was added dropwise. Diethyl ether was added and the solution was stirred at 0° C. for 1 hour and the precipitate was filtered and dried to afford 0.33 g (26%) of compound 694. MP: 197° C. (DSC).

Example B5

Preparation of compound 9

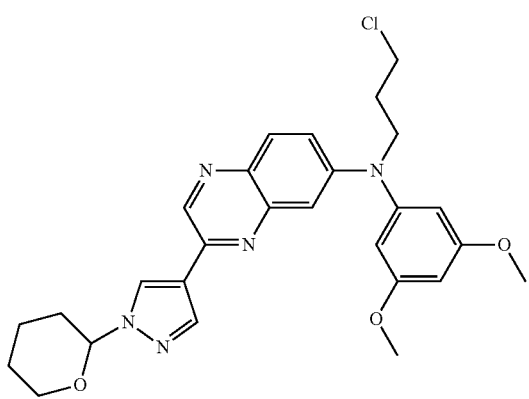 [SMILES: COc1cc(OC)cc(N(CCCCl)c2ccc3ncc(-c4cnn(C5CCCCO5)c4)nc3c2)c1]

NaH (0.556 g; 13.9 mmol) was added portionwise to a solution of intermediate 49 (3 g; 6.95 mmol) in DMF (85 mL) at 5° C. under N₂. The reaction mixture was stirred for 30 minutes. 1-bromo-3-chloropropane (2 mL; 20.9 mmol) was added dropwise and the mixture was stirred for 15 hours at room temperature, then poured into H₂O/K₂CO₃ and extracted with EtOAc. The organic layer was dried (MgSO₄), filtered and evaporated to dryness. The obtained residue was purified by Chromatography over silica gel (Irregular SiOH 15-40 µm, 90 g MERCK; mobile phase gradient from 100% DCM to 97% DCM, 3% MeOH, 0.1% NH₄OH). The desired product fractions were collected and the solvent was evaporated, yielding 2.94 g (86%) of compound 9.

a) Preparation of compound 10

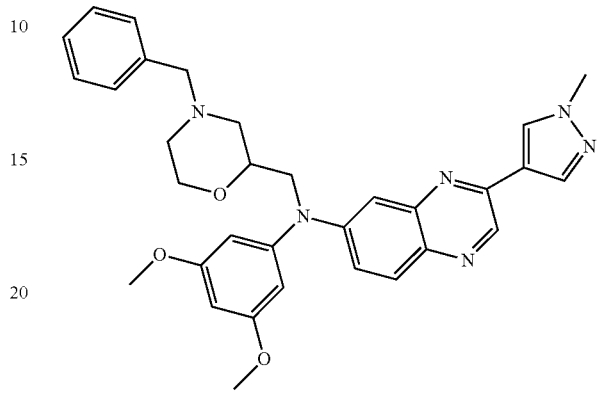

NaH (925 mg, 23.1 mmol) was added portionwise to a solution of intermediate 3 (4.18 g, 11.6 mmol) in DMF (52 mL) at 5° C. The mixture was stirred at 5° C. for 30 minutes, then a solution of 4-(phenylmethyl)-2-morpholinemethanol 2-methanesulfonate (4.95 g, 17.3 mmol) in DMF (13.5 mL) was added. The reaction mixture was heated at 60° C. for 18 hours. The mixture was poured into water and the product was extracted with EtOAc. The organic layer was washed with water and brine, dried (MgSO₄), filtered and evaporated. The obtained residue was purified by chromatography over silica gel (Irregular SiOH, 15-40 µm, 300 g MERCK; mobile phase 0.1% NH₄OH, 97% DCM, 3% MeOH). The desired product fraction was collected and the solvent was evaporated, yielding 2.74 g (43%, purity 90%) of a yellow foam. A sample (440 mg) was purified by achiral super critical fluid chromatography (AMINO 6 µm 150×21.2 mm; mobile phase, 0.3% 2-propylamine, 20% MeOH, 80% CO₂). The desired product fraction was collected and the solvent was evaporated, yielding 356 mg of a residue which was crystallized with DCM/Acetone/diethyl ether. The precipitate was filtered off and dried to give 188 mg of compound 10. MP=134° C. (Kofler).

b-1) Preparation of compound 11

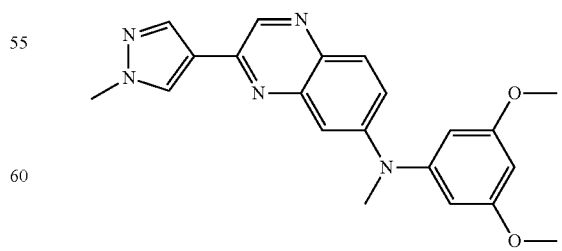

To a solution of intermediate 3 (67 mg, 0.18 mmol) in tetrahydrofuran (4 mL) was added NaH (12 mg, 0.28 mmol). The suspension was stirred at room temperature until no bubbles were observed, cooled to 0° C. and methyl iodide (0.08 mL, 1.3 mmol) was added drop wise. The reaction mixture was stirred at room temperature overnight, diluted with EtOAc and washed with brine. The organic layer was separated, dried (Na$_2$SO$_4$) and concentrated. The crude residue was purified by chromatography over silica gel to afford 38 mg (54%) of compound 11 (yellow powder).

b-2) Preparation of compound 12

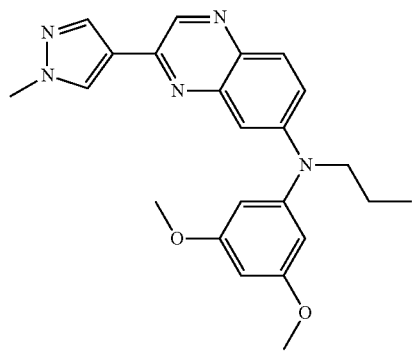 [SMILES: CCCN(c1cc(OC)cc(OC)c1)c1ccc2ncc(-c3cnn(C)c3)nc2c1]

To a solution of intermediate 3 (100 mg, 0.277 mmol) in tetrahydrofuran (3 mL) was added potassium hexamethyldisilazide (0.5M in toluene, 12 mg, 0.831 mmol). The reaction mixture was stirred at room temperature for 30 minutes and propyl bromide (0.30 mL) was added drop wise. The reaction mixture was stirred at room temperature for a further 3 hours and diluted with DCM and water. The solid residue was removed by filtration, dissolved in MeOH and combined with the other organic extracts, dried (MgSO$_4$) and then concentrated. The crude residue was purified by chromatography over silica gel to afford 10 mg (9%) of compound 12 (yellow powder).

b-3) Preparation of compound 13

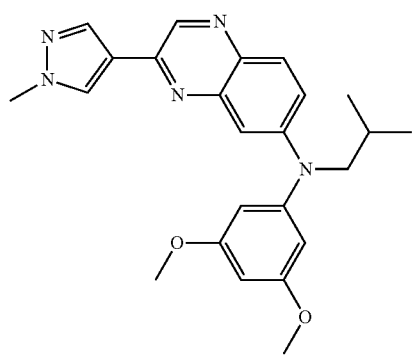 [SMILES: COc1cc(OC)cc(N(CC(C)C)c2ccc3ncc(-c4cnn(C)c4)nc3c2)c1]

A mixture of intermediate 3 (50 mg, 0.139 mmol), cesium carbonate (226 mg, 0.693 mmol) and 1-bromo-2-methyl propane (95 mg, 0.693 mmol) in CH$_3$CN (1 mL) was heated. The reaction mixture was heated in a CEM Discovery microwave at 100° C. for 1 hour. Upon cooling, the reaction mixture was partitioned between DCM and water. The organic layer was separated and the aqueous layer was extracted with further DCM. The combined organic layers were dried (MgSO$_4$) and concentrated. The crude residue was purified by chromatography over silica gel to afford 5 mg (9%) of compound 13 (yellow powder).

Example B6

Preparation of compound 14

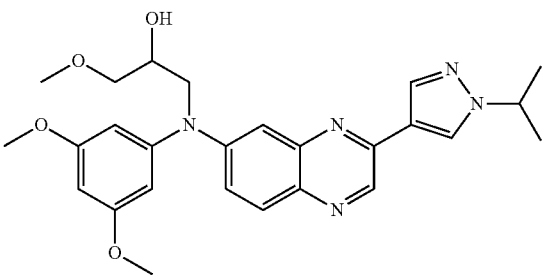 [SMILES: COCC(O)CN(c1cc(OC)cc(OC)c1)c1ccc2ncc(-c3cnn(C(C)C)c3)nc2c1]

and compound 14a

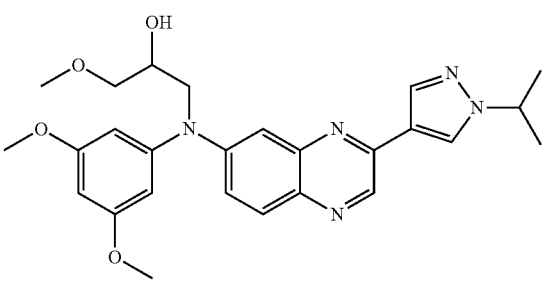 [SMILES: COCC(O)CN(c1cc(OC)cc(OC)c1)c1ccc2ncc(-c3cnn(C(C)C)c3)nc2c1]

as a HCl salt

NaH (513.5 mg, 12.8 mmol) was added portionwise to a solution of intermediate 8 (2.5 g, 6.4 mmol) in DMF (25 mL) at 5° C. under N$_2$ flow. The reaction mixture was stirred at 5° C. for 1 hour, then glycidyl methyl ether (1.1 mL, 12.8 mmol) was added dropwise at 5° C. under N$_2$ flow. The reaction mixture was stirred for 1 hour at 5° C., then allowed to warm up to room temperature. The reaction was stirred at 80° C. for 5 hours. The reaction was poured out into ice water and EtOAc was added. The organic layer was separated, washed with brine, dried (MgSO$_4$), filtered and the solvent was evaporated. The residue was purified by chromatography over silica gel (Irregular SiOH, 15-40 μm, 300 g MERCK; mobile phase 0.1% NH$_4$OH, 97.5% DCM, 2.5% MeOH). The desired product fractions were collected and the solvent was evaporated yielding 0.66 g (21.5%) of compound 14 which was converted into its HCl salt with HCl/2-propanol (5-6N) in MeOH. The mixture was evaporated, and the resulting solid was triturated into diethyl ether, filtered and dried to give 0.488 g (15%) of compound 14a (0.95 eq HCl) (mp=110° C., kofler).

Example B7

Preparation of compound 15

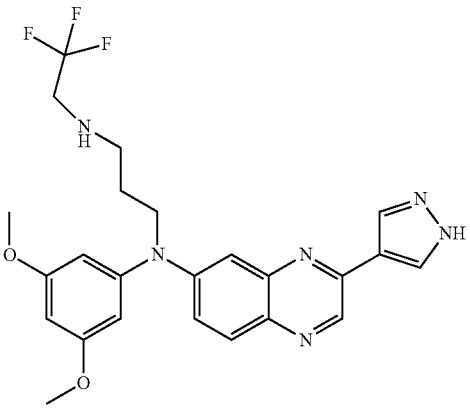 [SMILES: COc1cc(OC)cc(N(CCCNCC(F)(F)F)c2ccc3ncc(-c4cn[nH]c4)nc3c2)c1]

HCl 3N (13.5 mL) was added to a solution of intermediate 50 (2 g, 2.98 mmol) in CH$_3$OH (65 mL) at 5° C. The reaction mixture was stirred at room temperature for 2.5 hours then heated at 60° C. overnight. The solution was poured into ice water and basified with an aqueous solution of K$_2$CO$_3$ (10%). The product was extracted with DCM. The organic layer was washed with water, dried (MgSO$_4$), filtered and evaporated till dryness. The residue was purified by chromatography over silica gel (Irregular SiOH, 20-45 μm, 450 g MATREX; mobile phase 0.1% NH$_4$OH, 96% DCM, 4% MeOH). The desired fractions were collected and the solvent was evaporated. The residue was purified by achiral super critical fluid chromatography on (DIETHYLAMINOPROPYL 5 μm 150×21.2 mm; mobile phase 0.3% 2-propylamine, 80% CO$_2$, 20% MeOH). The desired fractions were collected and the solvent was evaporated. The residue was crystallized from CH$_3$CN/DIPE, the precipitate was filtered off and dried, yielding 760 mg (53%) of compound 15. MP=121° C. (DSC).

Example B8

Preparation of compound 16

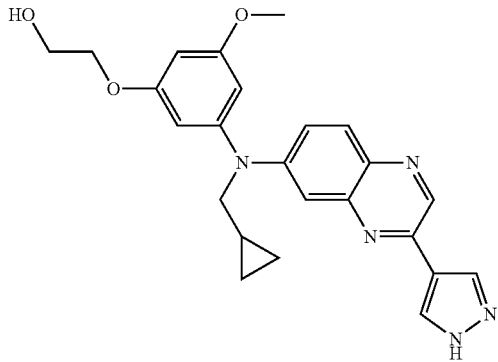 [SMILES: COc1cc(OCCO)cc(N(CC2CC2)c2ccc3ncc(-c4cn[nH]c4)nc3c2)c1]

HCl/i-PrOH (0.33 mL, 0.0017 mol) was added dropwise to a solution of intermediate 51 (0.25 g, 0.0004 mol) in CH$_{300}$H (6 mL) at 10° C. Then the mixture was stirred for 3 hours. The solution was concentrated, taken up with iced water, basified with NH$_4$OH and the product was extracted with DCM. The organic layer was dried (MgSO$_4$) and evaporated. The residue was purified by chromatography over silica gel (Irregular SiOH, 15-40 μm 30 g; mobile phase 1% NH$_4$OH, 92% DCM, 8% MeOH). The desired product fraction was collected and the solvent was evaporated, yielding 138 mg (78%) of compound 16, MP=80° C. (Kofler).

Example B9 a) Preparation of compound 17

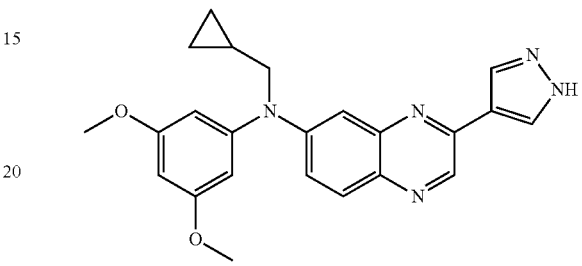

HCl 3N (4 mL) was added dropwise to a solution of intermediate 20 (1.5 g, 3.0 mmol) in dioxane (20 mL) at room temperature. The reaction mixture was heated at 70° C. overnight. The reaction was cooled to room temperature and poured out into ice water. EtOAc was added and the mixture was basified with an aqueous solution of K$_2$CO$_3$ (10%). The organic layer was separated, washed with brine, dried (MgSO$_4$), filtered and the solvent was evaporated. The compound was crystallized from diethyl ether, filtered and dried under vacuum at 60° C., yielding 1 g (83%) of compound 17. MP=158-160° C. (Kofler).

Compound 17 was alternatively also prepared using the following procedure B9b.

b) Under N$_2$, intermediate 19 (3.0 g; 8.1 mmol), 4-(4,4,5,5-tetramethyl-1,3,2-dioxaborolan-2-yl)-1H-pyrazole (1.9 g; 9.7 mmol), sodium carbonate 2M (6.1 mL; 12.2 mmol) in ethylene glycol dimethyl ether (30 mL) were degassed by bubbling nitrogen through for 10 minutes. Pd(PPh$_3$)$_4$ (0.75 g; 0.65 mmol) was added and the mixture was heated at reflux for 15 hours. The residue was poured into ice water and extracted with EtOAc. The organic layer was dried (MgSO$_4$), filtered and evaporated to dryness. The residue was purified by chromatography over silica gel (Irregular SiOH, 15-40 μm, 90 g; mobile phase gradient from 100% DCM to 95% DCM, 5% MeOH, 0.1% NH$_4$OH)$_{1-5}$-40 μm, 90 g). The pure fractions were collected and evaporated to dryness. The obtained residue was crystallized in DIPE, filtered and dried, yielding 1.66 g (51%) of compound 17.

Compound 17 was alternatively also prepared using the following procedure B9c. c) A mixture of intermediate 19 (3.3 g, 8.9 mmol), 1,1-dimethylethyl ester 4-(4,4,5,5-tetramethyl-1,3,2-dioxaborolan-2-yl)-1H-pyrazole-1-carboxylic acid (3.15 g, 10.7 mmol), potassium phosphate (3.79 g, 17.8 mmol), dicyclohexyl(2',6'-dimethoxy[1,1'-biphenyl]-2-yl) phosphine (0.37 g, 0.9 mmol) in dioxane (60 mL) and H$_2$O (6 mL) was stirred at room temperature under N$_2$ flow. After 10 minutes, Pd$_2$(dba)$_3$ (0.408 g, 0.446 mmol) was added portionwise at room temperature and the mixture was heated at 80° C. overnight. The reaction mixture was cooled to room temperature and poured out into ice water. EtOAc was added and the mixture was filtered through a layer of celite. The celite was washed with EtOAc, then the filtrate was extracted with EtOAc, washed with brine, dried (MgSO₄), filtered and the solvent was evaporated. The residue was purified by chromatography over silica gel (Irregular SiOH, 15/40 μm 30 g MERCK; mobile phase, gradient 100% DCM to 97% DCM, 3% MeOH). The desired product fraction was collected and the solvent was evaporated, yielding 3.30 g (73%) of compound 17.

Example B10

Preparation of compound 18

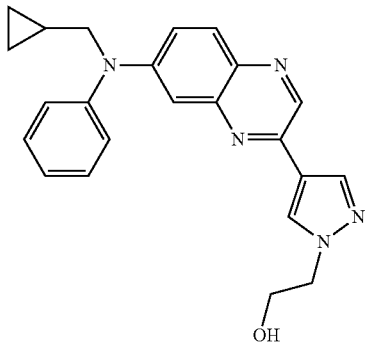 [SMILES: OCCn1cc(-c2cnc3ccc(N(CC4CC4)c4ccccc4)cc3n2)cn1]

At 5° C., HCl/i-PrOH 5/6N (213 μl; 1.06 mmol) was added to a solution of intermediate 23 (250 mg; 0.53 mmol) in CH₃OH (5 mL). The reaction mixture was stirred at 5° C. for 3 hours. H₂O and ice were added. An aqueous solution of K₂CO₃ (10%) was added until pH became basic and the product was extracted with DCM. The organic layer was washed with H₂O, brine dried (MgSO₄), filtered and the solvent was evaporated. The crude product was taken up in diethyl ether, filtered and dried under vacuum, yielding: 64 mg (31%) of compound 18. MP=132° C. (Kofler).

Example B11

Preparation of compound 19

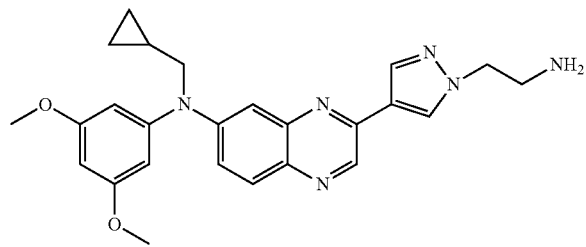 [SMILES: COc1cc(OC)cc(N(CC2CC2)c2ccc3ncc(-c4cnn(CCN)c4)nc3c2)c1]

A mixture of intermediate 52 (0.99 g, 1.8 mmol) in HCl 3N (3 mL) and dioxane (17 mL) was heated at 70° C. overnight. The reaction mixture was cooled to room temperature and poured out into ice water and EtOAc was added. The solution was basified with an aqueous solution of K₂CO₃ (10%) and the organic layer was separated, washed with brine, dried (MgSO₄), filtered and the solvent was evaporated. The residue was purified by chromatography over silica gel (Irregular SiOH, 15-40 μm 30 g MERCK; mobile phase, gradient 100% DCM to 98% DCM, 2% MeOH). The pure fractions were collected and evaporated to dryness, yielding 782 mg (97%) of compound 19. MP=130° C. (Kolfer).

Example B12

Preparation of compound 20

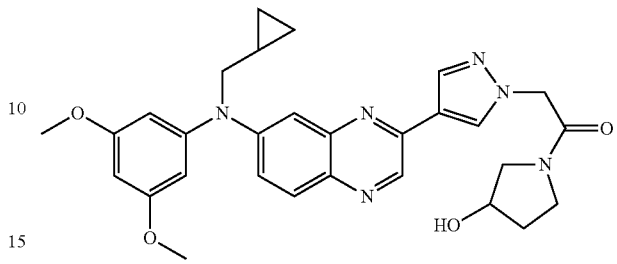

N3-(ethylcarbonimidoyl)-N1,N1-dimethyl-1,3-propanediamine hydrochloride (1:1) (0.12 g, 0.76 mmol) was added portionwise to a solution of intermediate 24 (0.23 g, 0.505 mmol), 3-pyrrolidinol (0.061 g, 0.76 mmol), 1-hydroxybenzotriazole (0.1 g, 0.76 mmol), Et₃N (0.105 mL, 0.76 mmol) in DCM (10 mL) at room temperature. The reaction mixture was stirred for 15 hours. The mixture was poured into H₂O and extracted with DCM. The organic layer was dried (MgSO₄), filtered and evaporated to dryness. The residue was crystallized in DIPE, filtered and dried. The product fraction was purified by chromatography over silica gel (Spherical SiOH, 10 μm 60 g, PharmPrep MERCK; mobile phase 0.5% NH₄OH, 94% DCM, 6% MeOH). The pure fractions were collected and evaporated to dryness. The residue was crystallized with DIPE, filtered and dried, yielding 186 mg (70%) of compound 20. MP=203.4° C. (DSC).

a) Preparation of compound 21

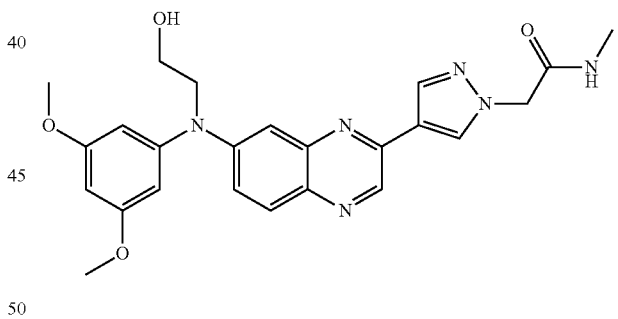

N3-(ethylcarbonimidoyl)-N1,N1-dimethyl-1,3-propanediamine hydrochloride (1:1) (227 mg; 1.46 mmol) was added to a mixture of intermediate 53 (550 mg; 0.98 mmol), methylamine hydrochloride (329 mg; 4.88 mmol), Et₃N (0.95 mL; 6.83 mmol), 1-hydroxybenzotriazole (198 mg; 1.46 mmol) in DCM (40 mL) at room temperature. The reaction mixture was stirred for 20 hours, then stirred for 2 days, poured into H₂O and extracted with DCM. The organic layer was dried (MgSO₄), filtered and evaporated to dryness. The residue was purified by chromatography over silica gel (Irregular SiOH, 15-40 μm, 30 g Merck; mobile phase, gradient from 100% DCM to 90% DCM, 10% MeOH, 0.1% NH₄OH). The desired product fraction was collected and the solvent was evaporated, yielding 76 mg (17%) of compound 21 which was crystallized in diethyl ether to give 59 mg (13%) of compound 21. MP=204.5° C. (DSC).

Compound 21 can also be prepared from the corresponding —O—Si(CH₃)₂—C(CH₃)₃ intermediate according to procedures described above, such as for example in Example B2.

Example B13

Preparation of compound 22

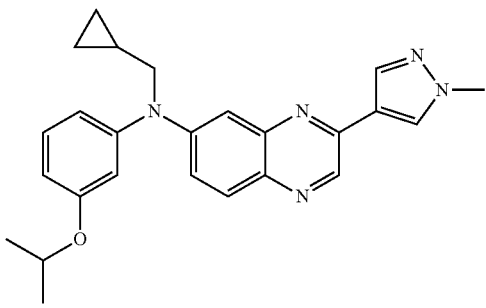 [SMILES: CC(C)Oc1cccc(N(CC2CC2)c2ccc3ncc(-c4cnn(C)c4)nc3c2)c1]

A mixture of intermediate 25 (0.4 g, 1.43 mmol), 1-bromo-3-isopropoxybenzene (0.46 mL, 2.86 mmol), sodium tert-butoxide (0.032 g, 0.14 mmol) and 1,1'-[1,1'-binaphthalene]-2,2'-diylbis[1,1-diphenylphosphine](0.413 g, 4.30 mmol) in ethylene glycol dimethyl ether (3 mL) was degassed with N₂ for 10 minutes. Palladium(II) acetate (47% Pd) (0.032 g, 0.14 mmol) was added and the mixture was heated at 135° C. under microwave irradiation for 60 minutes. The mixture was cooled to room temperature, poured into H₂O/K₂CO₃ and extracted with EtOAc. The organic layer was dried (MgSO₄), filtered and evaporated to dryness. The residue was purified by chromatography over silica gel (Irregular SiOH, 15-40 µm 30 g; mobile phase, 0.1% NH₄OH, 99% DCM, 1% MeOH). The pure fractions were collected and the solvent was evaporated. The residue was purified by chromatography over silica gel (X-Bridge-C18 5 µm 30*150 mm; mobile phase, gradient from 40% of a 0.5% solution of NH₄HCO₃ in water, 60% CH₃CN to 100% CH₃CN). The pure fractions were collected and the solvent was evaporated. The residue (0.187 g) was crystallized from DIPE/pentane (80/20), then the precipitate was filtered and dried under vacuum, yielding 0.128 g (22%) of compound 22. MP=109° C. (DSC).

Example B14

Preparation of compound 23

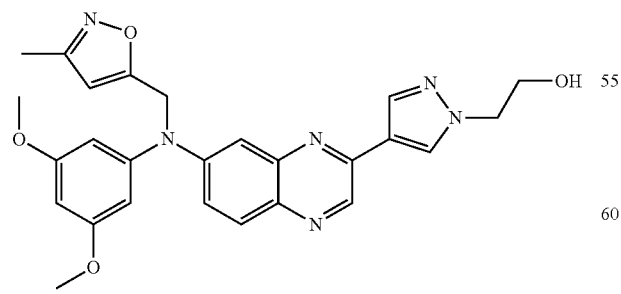

A solution of intermediate 54 (0.4 g, 0.666 mmol) and tetrabutylammonium fluoride (0.73 mL, 0.73 mmol) in THF (10 mL) was stirred at 0° C. for 2 hours. Water and EtOAc were added, the organic layer was separated, washed with water, then brine, dried (MgSO₄), filtered and the solvent was evaporated till dryness. The residue (0.4 g) was first purified by chromatography over silica gel (Irregular SiOH 15-40 µm 300 g MERCK; mobile phase, gradient from 98% DCM, 2% MeOH to 95% DCM, 5% MeOH). The pure fractions were collected and the solvent was evaporated. The residue was then purified by achiral super critical fluid chromatography on (AMINO 6 µm 150×21.2 mm; mobile phase, 0.3% 2-propylamine, 80% CO₂, 20% EtOH). The pure fractions were collected and the solvent was evaporated. The residue (0.165 g, 51%) was crystallized from DIPE, the precipitate was filtered and dried under vacuum, yielding 0.150 g (46%) of compound 23. MP=134° C. (Kofler).

Example B14A

Preparation of compound 691

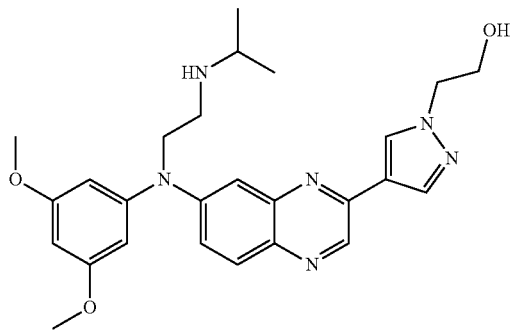 [SMILES: COc1cc(OC)cc(N(CCNC(C)C)c2ccc3ncc(-c4cnn(CCO)c4)nc3c2)c1]

A 1M solution of tetrabutylammonium fluoride in THF (12.7 mL; 12.7 mmol) was added dropwise to a solution of intermediate 691 (5 g; 8.5 mmol) in THF (50 mL) at room temperature. The reaction mixture was stirred at room temperature for 3 hours. The mixture was poured out into ice water and EtOAc was added. The mixture was basified with K₂CO₃ 10% and the organic layer was separated, washed with brine, dried (MgSO₄), filtered and the solvent was evaporated to dryness. The residue (3.5 g) was crystallized from diethyl ether. The precipitate was filtered off, dried in vacuum to provide 3.2 g (80%) of compound 691 MP: 99° C. (DSC).

Example B15

Preparation of compound 24

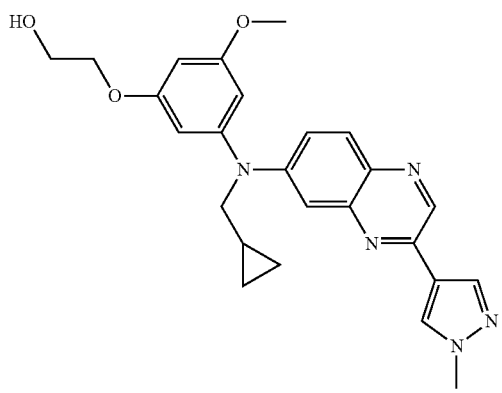 [SMILES: COc1cc(OCCO)cc(N(CC2CC2)c2ccc3ncc(-c4cnn(C)c4)nc3c2)c1]

HCl/i-PrOH (276 μL, 1.38 mmol) was added dropwise to a solution of intermediate 55 (183 mg, 0.35 mmol) in CH₃OH (2 mL) at 10° C. and then the mixture was stirred for 3 hours. Diethyl ether was added and the precipitate was filtered and dried, yielding 126 mg (76%) of compound 24. MP=80° C.

Example B16

Preparation of compound 25

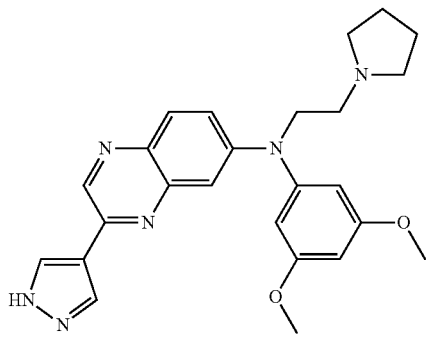 [SMILES: COc1cc(OC)cc(N(CCN2CCCC2)c2ccc3ncc(-c4cn[nH]c4)nc3c2)c1]

as a HCl salt

A mixture of intermediate 16 (1.37 g, 2.5 mmol) in pyrrolidine (30 mL) was heated at 80° C. for 3 hours. The mixture was cooled to room temperature and was evaporated until dryness. The residue was taken up in DCM and H₂O. The organic layer was extracted with DCM, dried (MgSO₄), filtered and evaporated to dryness. The residue (3 g) was purified by chromatography over silica gel (Irregular SiOH, 15-40 μm, 90 g MERCK; mobile phase, gradient from 98% DCM, 2% MeOH to 95% DCM, 5% MeOH). The pure fractions were collected and the solvent was evaporated, yielding the free base. The residue was dissolved in i-PrOH, then 1.04 mL of HCl 5N/i-PrOH (4 eq.) was added dropwise at 5° C. The salt was filtered, washed with DIPE and dried under vacuum at 60° C., yielding 0.53 g (40%) of compound 25. MP=259° C. (DSC).

Example B17

Preparation of compound 26

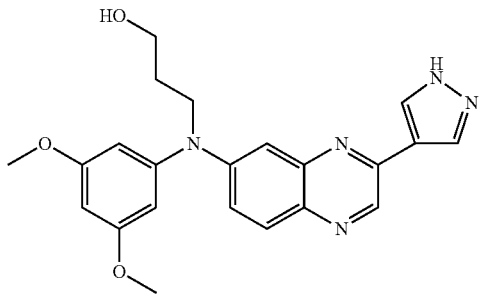 [SMILES: COc1cc(OC)cc(N(CCCO)c2ccc3ncc(-c4cn[nH]c4)nc3c2)c1]

HCl 3N (2 mL) was added dropwise to a solution of intermediate 56 (0.3 g, 0.484 mmol) in dioxane (8 mL). The solution was heated at 70° C. for 3 hours. The reaction was cooled to room temperature and poured out into ice water. EtOAc was added and the mixture was basified with an aqueous solution of K₂CO₃ (10%). The organic layer was separated, washed with brine, dried (MgSO₄), filtered and the solvent was evaporated. The residue (0.19 g) was crystallized from DIPE/CH₃CN. The precipitate was filtered and dried under vacuum, yielding 0.112 g (56%) of compound 26. MP=202° C. (DSC).

Example B18

Preparation of compound 27

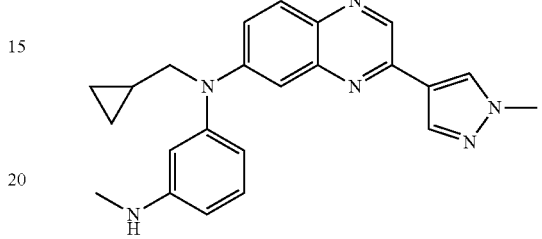

Intermediate 57 (0.425 g; 0.88 mmol), HCl 3N (3 mL) and dioxane (8 mL) were heated to 60° C. overnight. The mixture was cooled to room temperature, poured into H₂O and basified with K₂CO₃. The product was extracted with EtOAc, dried (MgSO₄), filtered and evaporated to dryness, yielding 322 mg (95%) of compound 27. MP=178° C. (DSC).

Example B19

Preparation of compound 28

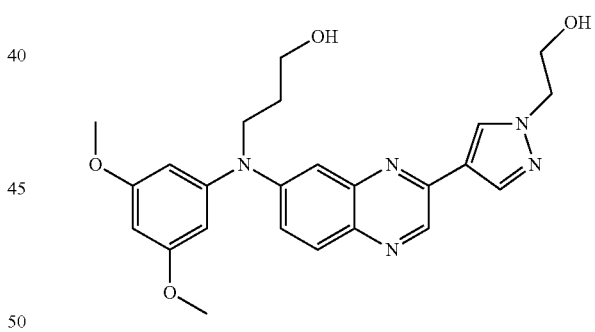

A mixture of intermediate 58 (0.3 g, 0.486 mmol) and amberlyst 15 ion exchange resin (0.03 g) in MeOH (8 mL) was stirred at 45° C. for 3 hours. The resin was filtered. The filtrate was poured out into water and was basified with an aqueous solution of K₂CO₃ (10%). EtOAc was added. The organic layer was separated, washed with brine, dried (MgSO₄), filtered and the solvent was evaporated. The residue (0.2 g) was purified by chromatography over silica gel (Irregular SiOH, 15-40 μm, 30 g MERCK; mobile phase, gradient from 98% DCM, 2% MeOH to 95% DCM, 5% MeOH). The pure fractions were collected and the solvent was evaporated. The residue (0.18 g) was crystallized from DIPE/CH₃CN (80/20). The precipitate was filtered off and dried under vacuum, yielding 0.114 g (52%) of compound 28. MP=142° C. (DSC).

Example B20

Preparation of compound 29

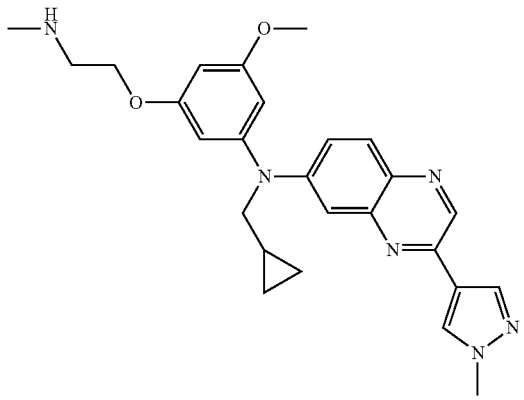 [SMILES: CNCCOc1cc(OC)cc(N(CC2CC2)c2ccc3ncc(-c4cnn(C)c4)nc3c2)c1]

A 2M solution of methylamine in THF (4.8 mL, 0.0097 mol) was added to a solution of intermediate 26 (0.14 g, 0.0003 mol) and K$_2$CO$_3$ (0.1 g, 0.0007 mol) in THF (5 mL). The solution was heated to 100° C. in a sealed tube for 24 hours, then cooled to room temperature and poured into H$_2$O/NaCl. The mixture was extracted with DCM. The organic layer was dried (MgSO$_4$), filtered and evaporated to dryness. The residue was purified by chromatography (Irregular SiOH, 15-40 µm, 30 g; mobile phase, 95% DCM, -5% MeOH, 0.1% NH$_4$OH). The product fractions were collected and the solvent was evaporated, yielding 103 mg (86%) of compound 29. MP=80° C. (Kofler).

Example B21

Preparation of compound 301

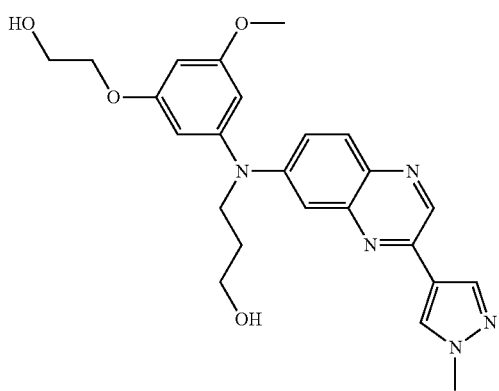 [SMILES: COc1cc(OCCO)cc(N(CCCO)c2ccc3ncc(-c4cnn(C)c4)nc3c2)c1]

HCl/i-PrOH (0.4 mL, 0.002 mol) was added dropwise to a solution of intermediate 59 (0.31 g, 0.0005 mol) in CH$_3$OH (5 mL) at 10° C. and the mixture was stirred for 2 hours. The solution was evaporated to dryness, then the residue was taken up with ice water, basified with NH$_4$OH and the product was extracted with DCM. The organic layer was dried (MgSO$_4$) and evaporated to dryness. The residue was purified by chromatography over silica gel (Sunfire Silica 5 µm 150×30.0 mm); mobile phase, gradient from 0.2% NH$_4$OH, 98% DCM, 2% MeOH to 1.1% NH$_4$OH, 89% DCM, 11% MeOH). The product fractions were collected and the solvent was evaporated, yielding 106 mg (47%) of compound 30. MP=80° C. (Kofler).

Example B22

Preparation of compound 31

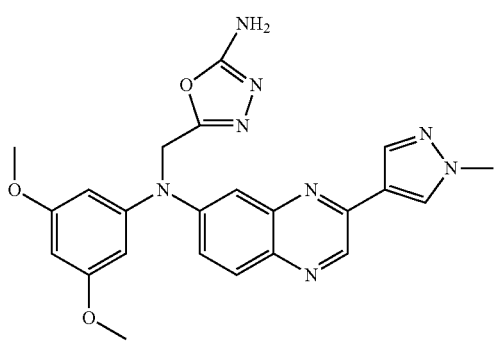 [SMILES: COc1cc(OC)cc(N(Cc2nnc(N)o2)c2ccc3ncc(-c4cnn(C)c4)nc3c2)c1]

To intermediate 28 (0.4 g, 0.92 mmol) in dioxane (8 mL) was added cyanogenbromide (0.099 g, 0.93 mmol) at room temperature. Then sodium hydrogencarbonate (0.0775 g, 0.92 mmol) in H$_2$O (distilled, 4.8 mL) was added. The mixture was stirred at room temperature for 5 hours. The mixture was extracted with EtOAc and dried (MgSO$_4$), filtered and evaporated till dryness. The residue was taken up by diethyl ether, filtered and dried to give 0.42 g (99%) of compound 31. MP=254° C. (Kofler).

Example B23

Preparation of compound 32

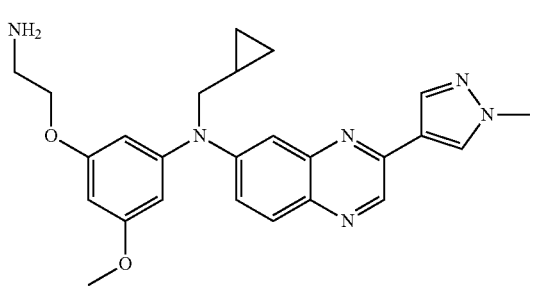 [SMILES: COc1cc(OCCN)cc(N(CC2CC2)c2ccc3ncc(-c4cnn(C)c4)nc3c2)c1]

Hydrazine monohydrate (81 µL, 2.58 mmol) was added to a solution of intermediate 27 (0.21 g, 0.37 mmol) in EtOH (10 mL). The mixture was heated at 80° C. for 5 hours. The mixture was cooled to room temperature, evaporated and the residue was poured into water. The aqueous layer was extracted with DCM, washed with brine, dried (MgSO$_4$), filtered and evaporated to dryness. The residue was purified by chromatography (Irregular SiOH, 15-40 µm, 10 g; mobile phase, 95% DCM-5% MeOH-0.5% NH$_4$OH). The pure fractions were collected and the solvent was evaporated, yielding 97 mg (59%) of compound 32, MP=80° C. (Kofler).

Example B24

Preparation of compound 33

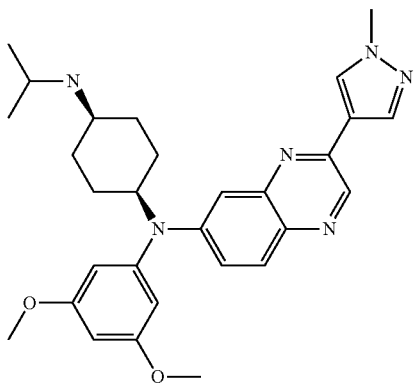 [SMILES: COc1cc(OC)cc(N(c2ccc3ncc(-c4cnn(C)c4)nc3c2)[C@H]2CC[C@@H](NC(C)C)CC2)c1]

Intermediate 31 (270 mg, 0.59 mmol), sodium triacetatohydroborate (312 mg, 1.475 mmol) and isopropylamine (100 µl, 1.2 mmol) in CH$_3$CN (6 mL) were stirred at room temperature for 24 hours. Isopropylamine (500 µl, 5.8 mmol) was added and the reaction mixture was stirred at room temperature for 12 hours, then sodium triacetatohydroborate (312 mg, 1.5 mmol) was added and the reaction mixture was stirred for 24 hours. 10% K$_2$CO$_3$ aqueous solution was added. The reaction mixture was extracted twice with DCM, dried (MgSO$_4$), filtered and evaporated. The residue (437 mg) was purified by chromatography over silica gel (Sunfire Silica 5 µm 150×30.0 mm mobile phase, gradient from 0.2% NH$_4$OH, 98% DCM, 2% MeOH to 0.8% NH$_4$OH, 92% DCM, 8% MeOH). The desired product fraction was collected and the solvent was evaporated, to give 113 mg of compound 33 (cis).

Example B25

Preparation of compound 34

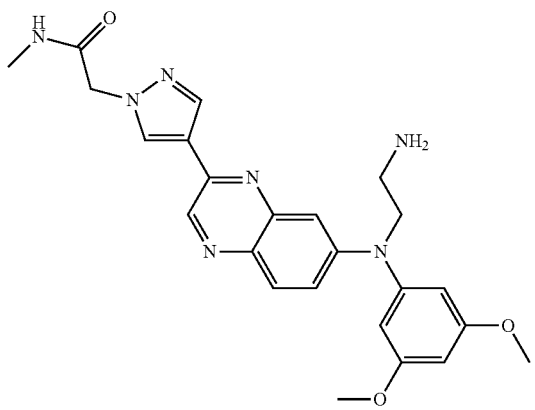

Intermediate 29 (0.5 g, 0.8 mmol) and methylamine 40% in H$_2$O (28 mL, 0.33 mol) were heated in dioxane (20 mL) at 120° C. in a sealed tube for 5 hours. The solution was cooled and evaporated to dryness. The residue was purified by chromatography over silica gel (Sunfire Silica 5 µm 150×30.0 mm; mobile phase, gradient from 0.2% NH$_4$OH, 98% DCM, 2% MeOH to 1.4% NH$_4$OH, 86% DCM, 14% MeOH). The pure fractions were collected and the solvent was evaporated. The product was crystallized with diethyl ether. The precipitate was filtered and dried, yielding 118 mg (31%) of compound 34, MP=174° C. (DSC).

Example B26

Preparation of compound 35

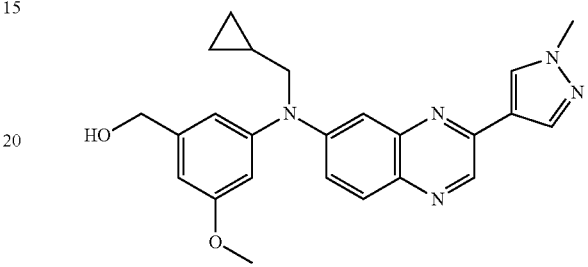

To a mixture of intermediate 60 (268 mg, 0.51 mmol) was added THF (20 mL), followed by tetrabutylammonium fluoride (2.53 mL, solution 1M in THF; 2.53 mmol). The reaction mixture was stirred at room temperature overnight. The reaction mixture was concentrated. EtOAc and H$_2$O were added and the two phases were separated. The organic phase was dried (MgSO$_4$), filtered and concentrated. The residue was purified by chromatography over silica gel (Hyperprep C18 HS BDS100 A 8 mu (Shandon); mobile phase, gradient from 90% of a 0.25% solution of ammoniumbicarbonate in water, 10% CH$_3$CN to 100% CH$_3$CN). The product fractions were collected and the solvent was evaporated. The residue was dissolved in CH$_3$CN/H$_2$O and lyophilized, yielding 55 mg of compound 35.

Example B27

Preparation of compound 36

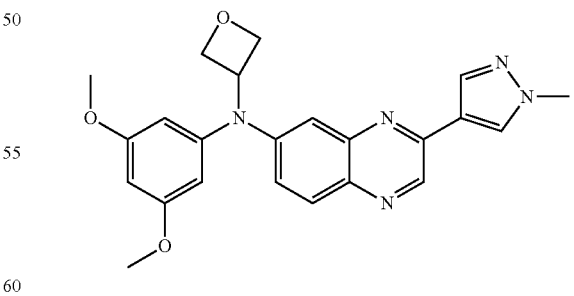

A mixture of 7-bromo-2-(1-methyl-1H-pyrazol-4-yl)quinoxaline (521 mg, 1.8 mmol), intermediate 38 (377 mg, 1.8 mmol), sodium tert-butoxide (520 mg, 5.4 mol) in dioxane (10 mL) was degassed at room temperature under N$_2$ flow. After 10 minutes, palladium(II) acetate (47% Pd) (20 mg, 0.09 mmol) and 1,1'-[1,1'-binaphthalene]-2,2'-diylbis[1,1- diphenylphosphine](56 mg, 0.09 mmol) were added portion-wise at room temperature under N₂ flow. The reaction mixture was heated at 90° C. overnight, then cooled to room temperature and partitioned between water and DCM. The organic layer was dried (MgSO₄), filtered and concentrated. The residue was purified by chromatography over silica gel (Irregular SiOH, 15-40 μm, 30 g mobile phase, 98% DCM, 2% MeOH). The product fractions were collected and the solvent was evaporated. The residue was again purified by achiral super critical fluid chromatography on (2 ETHYL-PYRIDINE 6 μm 150×21.2 mm; mobile phase, 0.3% 2-propylamine, 15% MeOH, 85% CO₂). The product fractions were collected and the solvent was evaporated. The residue was taken up in diethyl ether, filtered and dried, yielding 0.209 g (27%) of compound 36. MP=164° C. (kofler).

Example B27A

Preparation of compound 920

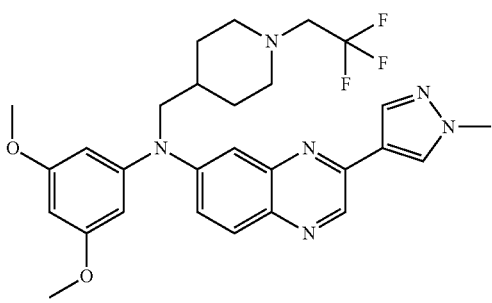 [SMILES: COc1cc(OC)cc(N(CC2CCN(CC(F)(F)F)CC2)c2ccc3ncc(-c4cnn(C)c4)nc3c2)c1]

A mixture of intermediate

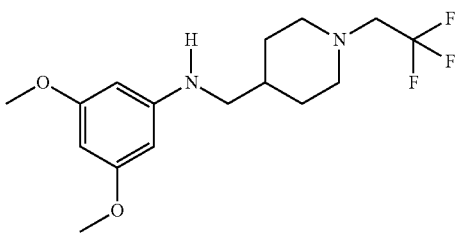 [SMILES: COc1cc(NCC2CCN(CC(F)(F)F)CC2)cc(OC)c1]

(see A52) (0.5 g; 1.5 mmol), intermediate 2 (0.36 g; 1.3 mmol) and sodium tert-butoxide (0.36 g; 1.3 mmol) in dry dioxane (40 mL) was degassed at room temperature under N₂ flow. After 10 minutes, 2-dicyclohexylphosphino-2'-(N, N-dimethylamino)biphenyl (50 mg; 0.13 mmol) and tris(dibenzylideneacetone)dipalladium(0) (115 mg; 0.13 mmol) were added and the reaction mixture was heated at 100° C. for 4 hours. The reaction mixture was cooled to room temperature, poured into a mixture of water and brine, filtered through a pad of Celite®, extracted with EtOAc, washed with water, dried (MgSO₄), filtered and evaporated to dryness to give 1.1 g of residue. The residue was purified by chromatography over silica gel (5 μm, mobile phase:

gradient from 71% Heptane, 1% MeOH, 28% AcOEt to 20% MeOH, 80% AcOEt). The desired fractions were collected and evaporated to give 240 mg of residue. The residue was taken-up in Et₂O, filtered and dried to give 144 mg of compound 920, mp=123° C. (DSC).

Example B28

Preparation of compound 37

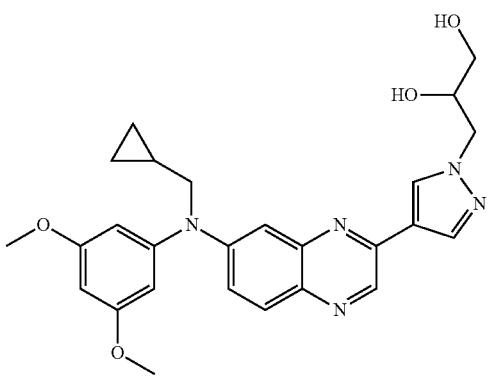 [SMILES: COc1cc(OC)cc(N(CC2CC2)c2ccc3ncc(-c4cnn(CC(O)CO)c4)nc3c2)c1]

At 0° C., potassium permanganate (0.117 g, 0.738 mmol) was added to a solution of compound 51 (0.326 g, 0.738 mmol) in acetone (10 mL) and H₂O (2.5 mL). The solution was stirred at room temperature overnight and was then poured on ice water. DCM was added and the mixture was filtered through a celite layer. The organic layer was extracted, dried (MgSO₄) and evaporated to dryness. The residue (0.23 g) was purified by chromatography over silica gel (Spherical SiOH, 10 μm, 60 g PharmPrep MERCK; mobile phase, 95% DCM, 5% MeOH, 0.1% NH₄OH). The desired product fraction was collected and the solvent was evaporated, yielding 0.150 g of compound 37, which was crystallized in DIPE, filtered and dried, yielding 0.139 g (40%) of compound 37. MP=154° C. (DSC).

Example B29

Preparation of compound 38

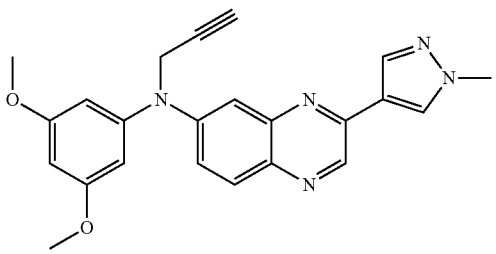 [SMILES: C#CCN(c1cc(OC)cc(OC)c1)c1ccc2ncc(-c3cnn(C)c3)nc2c1]

A mixture of intermediate 62 (3.9 g, 8.3 mmol) and K₂CO₃ (1.15 g, 8.3 mmol) in MeOH (150 mL) was stirred at room temperature for 18 hours. The reaction mixture was quenched with water and extracted with DCM. The organic layer was decanted, washed with brine, dried (MgSO$_4$), filtered and evaporated to dryness. The solid residue was taken up with diethyl ether and the precipitate was filtered off and dried, yielding 2.84 g (85%) of compound 38. MP=168° C., (Kofler).

Example B30

Preparation of compound 39

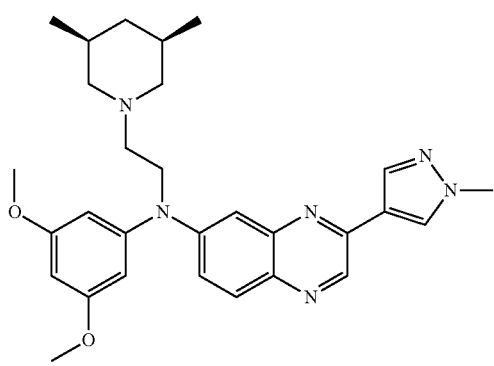 [SMILES: COc1cc(OC)cc(N(CCN2C[C@H](C)C[C@H](C)C2)c2ccc3ncc(-c4cnn(C)c4)nc3c2)c1]

and compound 40 as a HCl salt

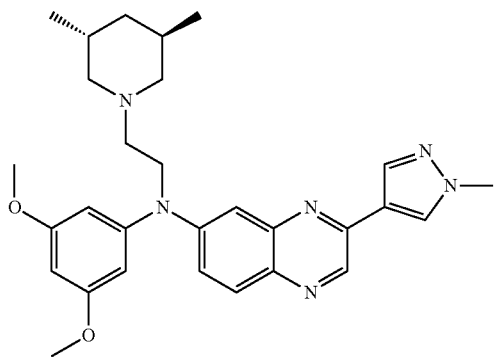 [SMILES: COc1cc(OC)cc(N(CCN2C[C@H](C)C[C@@H](C)C2)c2ccc3ncc(-c4cnn(C)c4)nc3c2)c1]

Intermediate 10 (365 mg, 0.75 mmol) in 3,5-dimethylpiperidine (5 mL) was heated to 80° C. overnight. Then 5 mL of 3,5-dimethylpiperidine was added to the solution and heated at 80° C. for 5 hours. The solution was evaporated to dryness, then the residue was poured into H$_2$O and extracted with EtOAc. The organic layer was dried (MgSO$_4$), filtered and evaporated. The residue (853 mg) was purified by chromatography over silica gel (Sunfire Silica 5 µm 150× 30.0 mm; mobile phase, gradient from 0.1% NH$_4$OH, 99% DCM, 1% MeOH to 0.8% NH$_4$OH, 92% DCM, 8% MeOH). The desired product fractions were collected and the solvents were evaporated to give 41.8 mg (11%) of Fraction 1 and 115.7 mg (31%) of compound 39. MP=80° C. (Kofler) (gummed). Fraction I was dissolved in isopropyl alcohol. The mixture was stirred at 0° C., then 67 µL (4 eq) of HCl in isopropyl alcohol 5N was added dropwise to the mixture. Diethyl ether was added to the solution and was stirred at 0° C. for 1 hour. The precipitate was filtered and dried to give 38.3 mg (10%) of compound 40 MP=80° C. (Kofler) (gummed).

Example B31

Preparation of compound 41

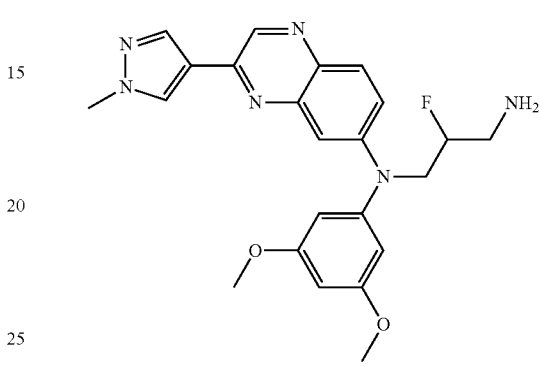

A mixture of intermediate 37 (0.22 g, 0.39 mmol), hydrazine monohydrate (0.085 mL, 2.72 mmol) in EtOH (5 mL) was heated at 80° C. overnight. The reaction mixture was cooled to room temperature and poured out into ice water. EtOAc was added and the organic layer was separated, washed with brine, dried (MgSO$_4$), filtered and the solvent was evaporated till dryness. The residue (0.250 g) was purified by chromatography over silica gel (Spherical SiOH, 10 µm, 60 g PharmPrep MERCK; mobile phase 0.1% NH$_4$OH, 96% DCM, 4% MeOH). The product fractions were collected and the solvent was evaporated. The residue (0.120 g, 70%) was crystallized from diethyl ether/CH$_3$CN, filtered and dried under vacuum at 60° C., yielding 0.110 g (65%) of compound 41. MP 168° C. (Kofler); 169° C. (DSC).

Example B32

Preparation of compound 33

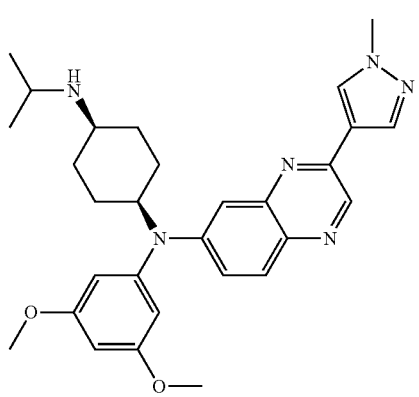 [SMILES: COc1cc(OC)cc(N(c2ccc3ncc(-c4cnn(C)c4)nc3c2)[C@H]2CC[C@@H](NC(C)C)CC2)c1]

and compound 43

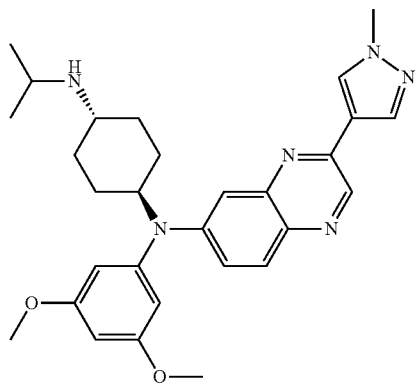 [SMILES: COc1cc(OC)cc(N(c2ccc3ncc(-c4cnn(C)c4)nc3c2)[C@H]2CC[C@H](NC(C)C)CC2)c1]

Intermediate 31 (270 mg, 0.59 mmol), sodium triacetoxyborohydride (312 mg, 1.48 mmol) and isopropylamine (100 μl, 1.2 mmol) in CH₃CN (6 mL) were stirred at room temperature for 24 hours. Isopropylamine (500 μl, 5.8 mmol) was added and the reaction mixture was stirred at room temperature for 12 hours, then sodium triacetoxyborohydride (312 mg, 1.5 mmol) was added and the mixture was stirred for 24 hours. 10% K₂CO₃ aqueous solution was added. The reaction mixture was extracted twice with DCM, dried (MgSO₄), filtered and evaporated. The residue (437 mg) was purified by chromatography over silica gel (Sunfire Silica 5 μm 150×30.0 mm; mobile phase, gradient from 0.2% NH₄OH, 98% DCM, 2% MeOH to 0.8% NH₄OH, 92% DCM, 8% MeOH). The product fractions were collected and the solvent was evaporated to give 113 mg (38%) of compound 33 and 42 mg (14%) of compound 43

Example B33

Preparation of compound 604

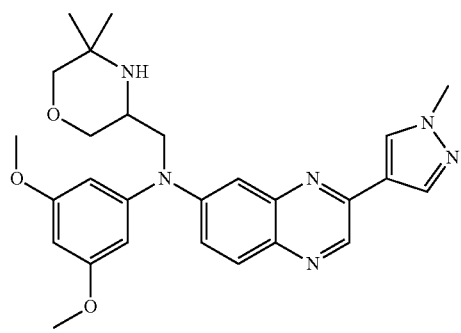 [SMILES: COc1cc(OC)cc(N(CC2COCC(C)(C)N2)c2ccc3ncc(-c4cnn(C)c4)nc3c2)c1]

N,N-diisopropylethylamine (0.86 mL; 5.2 mmol) and triethylamine (0.73 mL; 5.2 mmol) were added to a solution of intermediate 73 (0.6 g; 0.87 mmol) in methanol (7.5 mL). The reaction was stirred at 80° C. for 15 hours, cooled down to room temperature and diluted with DCM and water. The organic layer was separated, washed with water, dried (MgSO₄), filtered and evaporated till dryness. The residue was purified by chromatography over silica gel (Spherical SiOH, 10 μm, 60 g; mobile phase 0.1% NH₄OH, 97% DCM, 3% MeOH). The pure fractions were collected, the solvent was evaporated. The residue (0.25 g, 59%) was crystallized from diethyl ether/CH₃CN. The precipitate was filtered off and dried under vacuum, yielding 215 mg (51%) of compound 604. MP: 157° C. (DSC)

Example B34

Preparation of compound 605

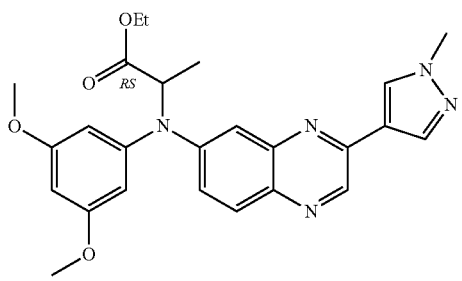 [SMILES: CCOC(=O)C(C)N(c1cc(OC)cc(OC)c1)c1ccc2ncc(-c3cnn(C)c3)nc2c1]

NaH (1.1 g; 27.7 mmol) was added portionwise to N,N-dimethylformamide (100 mL), after few minutes intermediate 3 (5 g; 13.8 mmol) was added portionwise at 5° C. under N₂ flow. The reaction mixture was stirred at 5° C. for 30 minutes. Then, a solution of ethyl-2-bromopropionate (3.6 mL; 27.7 mmol) in N,N-dimethylformamide (7 mL) was added dropwise at 5° C. under N₂ flow. The reaction mixture was allowed to warm to room temperature and stirred for 3 hours. The reaction was poured out into ice water. The precipitate was filtered, washed with water. The organic layer was separated and washed with water, dried (MgSO₄), filtered and the solvent was evaporated. The residue (7.51 g) was purified by chromatography over silica gel (Irregular SiOH, 20-40 μm, 450 g; mobile phase 0.1% NH₄OH, 98% DCM, 2% MeOH). The pure fractions were collected and concentrated yielding 5.3 g (84%) of compound 605.

Example B35

Preparation of a compound 607 (mixture of enantiomers)

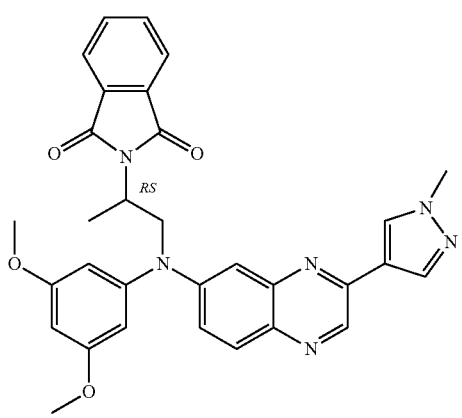

-continued

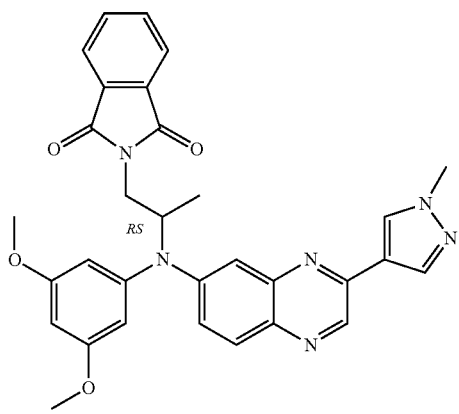

A solution of intermediate 74 (8 g; 16.08 mmol) and potassium phthalimide (6 g; 32.16 mmol) in CH$_3$CN (110 mL) was heated at 120° C. for 2 hours using one single mode microwave. The reaction mixture was cooled to room temperature and poured out into ice water. The precipitate was filtered, washed with water and DCM. The organic layer was separated and washed with water, dried (MgSO$_4$), filtered and the solvent was evaporated to give 7.4 g of compound 607 used without further purification for the next step.

Example B36

Preparation of compound 313

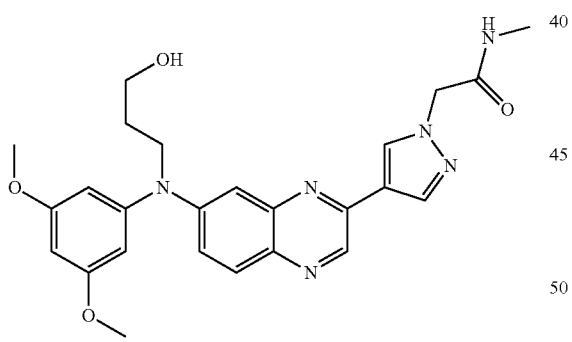

A 1M solution of tetrabutylammonium fluoride in THF (7.7 mL; 7.7 mmol) was added dropwise to a solution of intermediate 76 (3.5 g; 5.9 mmol) in THF (75 mL) at room temperature. The reaction mixture was stirred at room temperature for 3 hours. The mixture was poured out into ice water and EtOAc was added. The mixture was basified with K$_2$CO$_3$ 10% and the organic layer was separated, washed with brine, dried (MgSO$_4$), filtered and the solvent was evaporated to dryness. The residue (4.4 g) was crystallized from diethyl ether. The precipitate was filtered off, dried in vacuum to provide 2.62 g (93%) of compound 313 MP: 176° C. (DSC).

Example B37

Preparation of compound 615

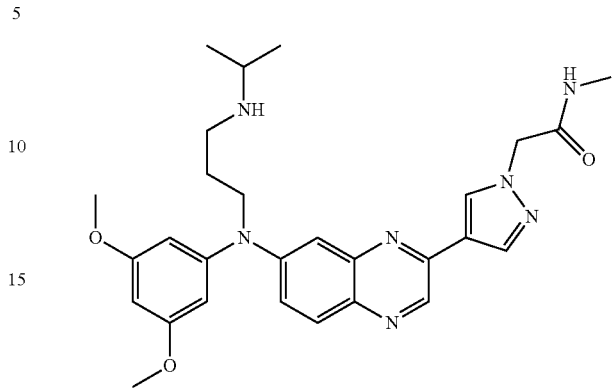

A mixture of intermediate 77 (2 g; 3.6 mmol) and isopropylamine (1.55 g; 18 mmol) in acetonitrile (30 mL) was heated at 100° C. in a sealed vessel for 18 hours. The reaction mixture was cooled to room temperature. The reaction mixture was poured out into ice water, EtOAc was added. The organic layer was separated, washed with a solution of NaHCO$_3$, dried (MgSO$_4$), filtered and evaporated till dryness. The residue (2.5 g) was purified by chromatography over silica gel (Irregular SiOH, 20-40 µm, 450 g; mobile phase 0.5% NH$_4$OH, 90% DCM, 10% MeOH). The pure fractions were collected and concentrated. The residue (0.85 g) was crystallized from diethyl ether, the precipitate was filtered off, dried in vacuum to provide 0.76 g (41%) of compound 615. MP: 134° C. (DSC)

Example B38

Preparation of compound 616

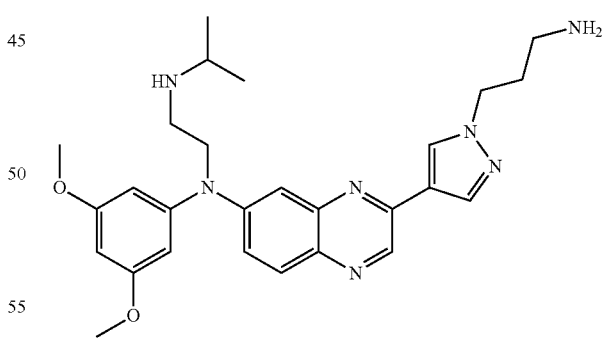

Trifluoroacetic acid (6.5 mL; 84.8 mmol) was added to a solution of intermediate 82 in DCM (50 mL) at 10° C. The reaction mixture was stirred at room temperature for 18 hours. The reaction mixture was concentrated, the residue was taken-up with DCM, washed with K$_2$CO$_3$ 10%. The organic layer was dried (MgSO$_4$), filtered and evaporated to dryness. The residue was crystallized from diethyl ether. The precipitate was filtered off, dried in vacuum to provide 0.65 g (65%) of compound 616. MP: 170° C. (Kofler)

Example B39

Preparation of compound 617

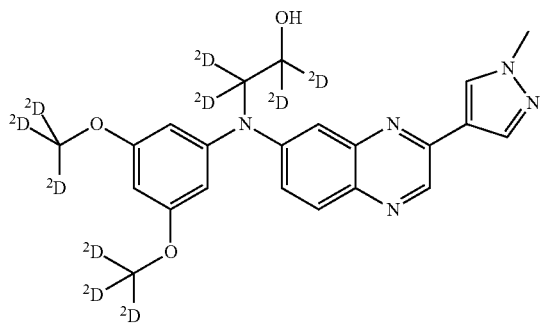 [SMILES: [2H]C([2H])([2H])Oc1cc(OC([2H])([2H])[2H])cc(N(c2ccc3ncc(-c4cnn(C)c4)nc3c2)C([2H])([2H])C([2H])([2H])O)c1]

A 1M solution of tetrabutylammonium fluoride in THF (1.82 mL, 1.8 mmol) was added dropwise to a solution of intermediate 85 (0.88 g, 1.65 mmol) in THF (20 mL) at room temperature. The reaction mixture was stirred at room temperature for 18 hours. The mixture was poured out into ice water and EtOAc was added. The mixture was basified with $K_2CO_3$ 10%, the organic layer was separated, washed with brine, dried ($MgSO_4$), filtered and the solvent was evaporated to dryness.

The residue (0.68 g) was purified by chromatography over silica gel (Spherical SiOH, 10 µm, 60 g; mobile phase 0.1% $NH_4OH$, 97% DCM, 3% MeOH). The pure fractions were collected and concentrated. The residue (0.54 g) was crystallized from diethyl ether. The precipitate was filtered off, dried in vacuum to provide 0.444 g (65%) of compound 617. MP: 149° C. (DSC)

Example B40

Preparation of compound 618

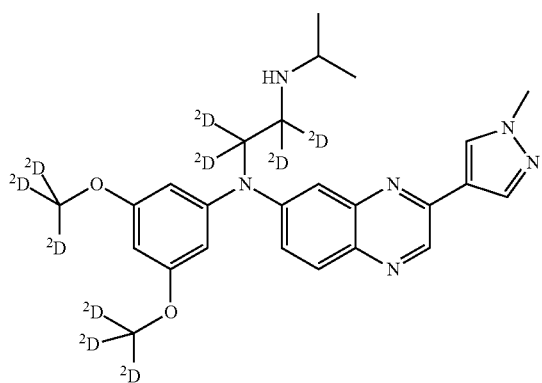 [SMILES: [2H]C([2H])([2H])Oc1cc(OC([2H])([2H])[2H])cc(N(c2ccc3ncc(-c4cnn(C)c4)nc3c2)C([2H])([2H])C([2H])([2H])NC(C)C)c1]

A mixture of intermediate 86 (0.446 g; 0.91 mmol) and isopropylamine (6.2 mL; 72.3 mmol) in acetonitrile (14 mL) was heated at 140° C. in a sealed vessel for 1 hour using one single mode microwave. The reaction mixture was cooled to room temperature. The reaction mixture was poured out into ice water, EtOAc was added. The organic layer was separated, washed with a solution of $NaHCO_3$, dried ($MgSO_4$), filtered and evaporated till dryness. The residue (0.423 g) was purified by chromatography over silica gel (Spherical SiOH, 10 µm, 60 g; mobile phase 0.5% $NH_4OH$, 95% DCM, 5% MeOH). The pure fractions were collected and concentrated. The residue (0.3 g) was crystallized from diethyl ether, the precipitate was filtered off, dried in vacuum to provide 0.21 g (52%) of compound 618. MP: 139° C. (DSC).

Example B41

Preparation of compound 619

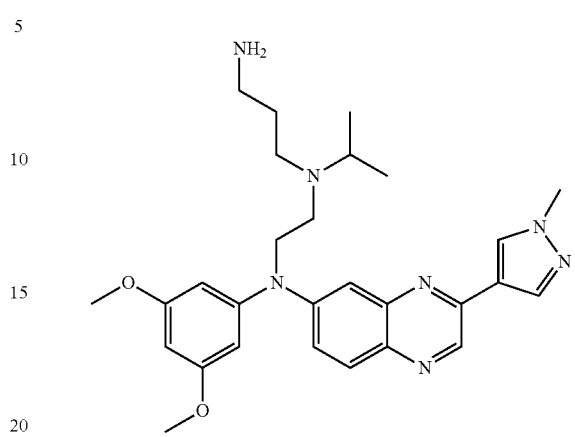

as a HCl salt

A mixture of intermediate 87 (1.26 g; 0.99 mmol), hydrazine monohydrate (0.22 mL; 7.0 mmol) in EtOH (20 mL) was stirred at 80° C. for 3 hours. The reaction mixture was cooled to room temperature and poured out into ice water. The organic layer was separated, washed with brine, dried ($MgSO_4$), filtered and the solvent was evaporated until dryness. The residue (0.566 g) was purified by chromatography over silica gel (SiOH, 5 µm, 150*30 mm; mobile phase gradient 0.2% $NH_4OH$, 98% DCM, 2% MeOH to 1.2% $NH_4OH$, 88% DCM, 12% MeOH). The product fractions were collected and the solvent was evaporated. The residue (0.385 g, 77%) was dissolved in isopropyl alcohol. The reaction mixture was stirred at 0° C. then 0.6 mL of HCl in isopropyl alcohol 5N was added dropwise to the solution. Diethyl ether was added to the solution and was stirred at 0° C. for 1 hour.

The precipitate was filtered off, dried in vacuum to provide 0.42 g (69%) of compound 619. MP: 210° C. (Kofler)

Example B42 a) Preparation of compound 620

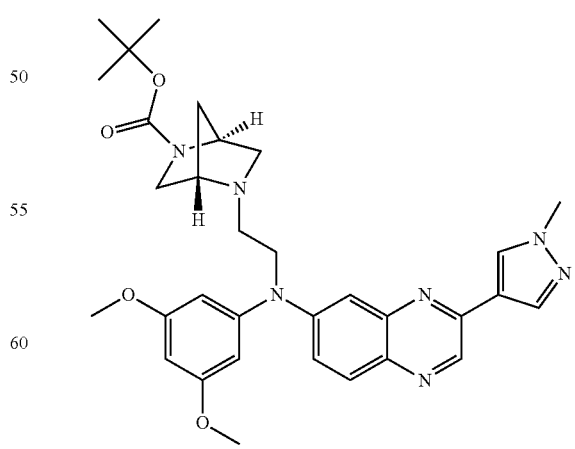

A mixture of intermediate 10 (1.4 g; 2.9 mmol), tert butyl (1S,4S)-(−)-2,5-diazabicyclo[2.2.1]heptane-2-carboxylate (0.69 g; 3.5 mmol) and K₂CO₃ (0.8 g; 5.8 mmol) in CH₃CN (20 mL) was stirred at 80° C. for 48 hours.

The reaction mixture was cooled to room temperature, poured out into ice water EtOAc was added. The organic layer was separated, washed with brine, dried (MgSO₄), filtered and the solvent was evaporated until dryness. The residue (1.6 g) was purified by chromatography over silica gel (Irregular SiOH, 20-45 μm, 450 g; mobile phase 0.1% NH₄OH, 94% DCM, 6% MeOH). The product fractions were collected and the solvent was evaporated. The residue (0.74 g) was purified with super critical fluid chromatography (Amino 6 μm, 150*21.1 mm; mobile phase 90% CO₂, 10% MeOH). The product fractions were collected and the solvent was evaporated. The residue (0.6 g, 36%) was crystallized from diethyl ether. The precipitate was filtered off, dried in vacuum to provide 0.444 g (26%) of compound 620. MP: 114° C. (Kofler)

b) Preparation of compound 621

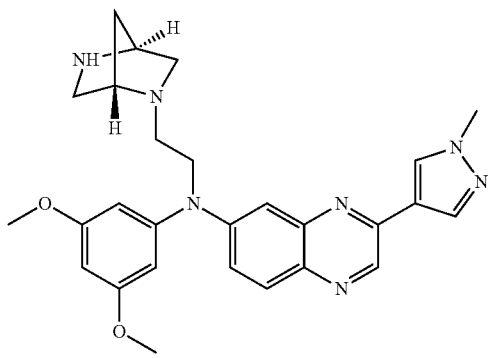 [SMILES: COc1cc(OC)cc(N(CCN2C[C@@H]3C[C@H]2CN3)c2ccc3ncc(-c4cnn(C)c4)nc3c2)c1]

as a HCl salt

A 5N solution of HCl in i-PrOH (0.48 mL, 2.4 mmol) was added dropwise to a solution of compound 620 (0.35 g, 0.6 mmol) in CH₃OH (10 mL) at 5° C. and the mixture was then stirred 3 days at room temperature. Diethyl ether was added and the precipitate was filtered off, was dried under vacuum to afford 0.33 g (94%) of the compound 621. MP: >260° C. (Kofler)

Example B43

Preparation of compound 622

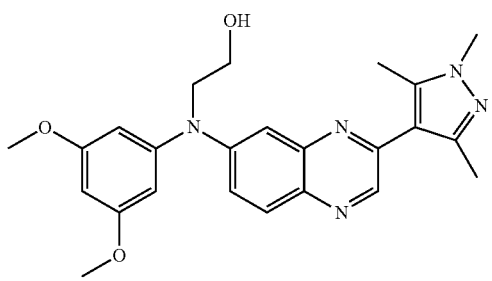 [SMILES: COc1cc(OC)cc(N(CCO)c2ccc3ncc(-c4c(C)nn(C)c4C)nc3c2)c1]

A 1M solution of tetrabutylammonium fluoride in THF (1.1 mL; 1.1 mmol) was added dropwise to a solution of intermediate 88 (0.43 g; 0.79 mmol) in THF (6 mL) at room temperature. The reaction mixture was stirred at room temperature for 18 hours. The mixture was poured out into ice water. The precipitate was filtered off, washed with water and CH₃CN and dried to afford 0.13 g (40%) of compound 622. MP: 190° C. (Kofler)

Example B44

Preparation of compound 623

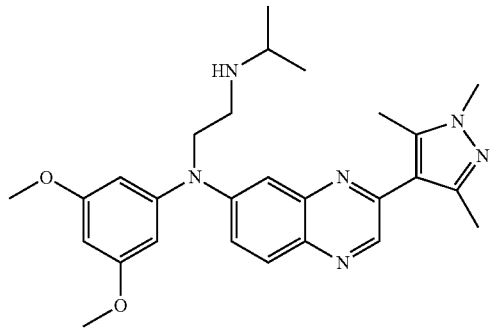 [SMILES: COc1cc(OC)cc(N(CCNC(C)C)c2ccc3ncc(-c4c(C)nn(C)c4C)nc3c2)c1]

as a HCl salt

A mixture of intermediate 89 (0.26 g; 0.43 mmol) and isopropylamine (5 mL) in acetonitrile (2 mL) was heated at 90° C. in a sealed vessel for 18 hours. The reaction mixture was cooled to room temperature. The reaction mixture was poured out into ice water, DCM was added. The organic layer was separated, washed, dried (MgSO₄), filtered and evaporated till dryness. The residue (0.28 g) was purified by chromatography over silica gel (Irregular SiOH, 15-40 μm, 30 g; mobile phase 0.4% NH₄OH, 96% DCM, 4% MeOH). The pure fractions were collected and concentrated. The residue (0.156 g, 77%) was dissolved in CH₃CN. HCl in isopropyl alcohol 5N was added dropwise to the solution. The solvent was evaporated, dried in vacuum to give 0.162 g (70%) of compound 623. MP: 133° C. (Kofler)

Example B45

Preparation of compound 630

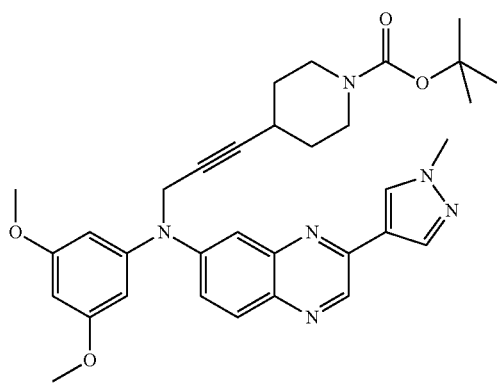 [SMILES: COc1cc(OC)cc(N(CC#CC2CCN(C(=O)OC(C)(C)C)CC2)c2ccc3ncc(-c4cnn(C)c4)nc3c2)c1]

NaH (0.54 g; 13.3 mmol) was added portionwise to intermediate 3 (2.4 g; 6.66 mmol) in N N-dimethylformamide (36 mL). The reaction mixture was stirred at 0° C. for 30 minutes. Then intermediate 91 (2.2 mL; 10 mmol) was added dropwise at 5° C. under N₂ flow. The reaction mixture was stirred at room temperature for 18 hours. The reaction was poured out into ice water and EtOAc was added. The organic layer was separated and washed with brine, dried (MgSO$_4$), filtered and the solvent was evaporated. The residue (4.2 g) was purified by chromatography over silica gel (Irregular SiOH 15-40 μm, 300 g; mobile phase 0.1% NH$_4$OH, 98.5% DCM, 1.5% MeOH). The pure fractions were collected and concentrated to give 0.793 g (21%) of compound 630. MP: 67° C. (Kofler).

Example B46

Preparation of compound 632

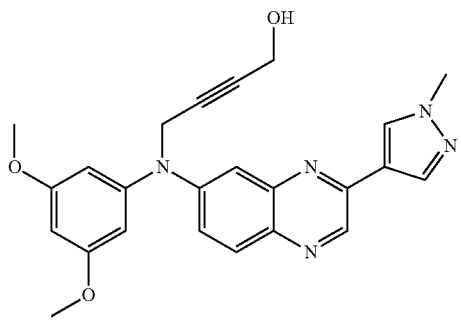 [SMILES: COc1cc(OC)cc(N(CC#CCO)c2ccc3ncc(-c4cnn(C)c4)nc3c2)c1]

Trifluoroacetic acid (0.073 mL; 0.25 mmol) was added to a solution of intermediate 92 (0.135 g; 0.25 mmol) in THF (5 mL). The reaction was stirred at room temperature for 24 hours. The reaction mixture was poured out into ice water; EtOAc was added. The organic layer was separated, washed with brine, dried (MgSO$_4$), filtered and the solvent was evaporated. The residue (0.151 g) was purified by chromatography over silica gel (SiOHSiOH, 5 μm, 150*30 mm; mobile phase gradient from 70% Heptane, 2% MeOH, 28% EtOAc to 20% MeOH, 80% EtOAc). The pure fractions were collected and concentrated. The residue (0.04 g) was crystallized from diethyl ether. The precipitate was filtered and dried to afford 0.033 g (31%) of compound 632. MP: 156° C. (DSC)

Example B47

Preparation of compound 638

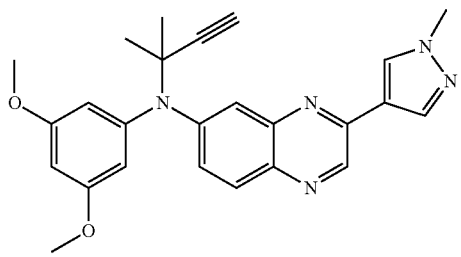 [SMILES: C#CC(C)(C)N(c1cc(OC)cc(OC)c1)c1ccc2ncc(-c3cnn(C)c3)nc2c1]

NaH (0.65 g; 16.6 mmol) was added portionwise to intermediate 3 (3 g; 8.3 mmol) in N,N-dimethylformamide (25 mL). The reaction mixture was stirred at 10° C. for 30 minutes. Then 3-chloro-3-methyl-1-butyne (1.2 g; 10.8 mmol) was added dropwise under N$_2$ flow. The reaction mixture was stirred at room temperature for 48 hours. The reaction was poured out into ice water and EtOAc was added. The organic layer was separated and washed with brine, dried (MgSO$_4$), filtered and the solvent was evaporated. The residue (4 g) was purified by chromatography over silica gel (mobile phase gradient from 71% Heptane, 1% MeOH, 28% EtOAc to 20% MeOH, 80% EtOAc). The pure fractions were collected and concentrated to give 0.152 g (4%) of compound 638 used without further purification for the next step.

Example B47A

Preparation of compound 919

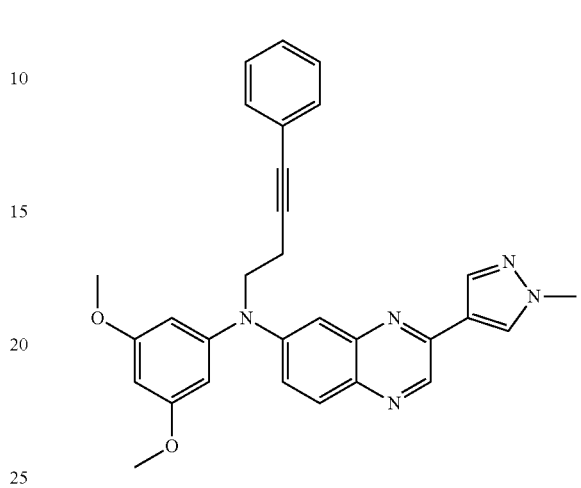

Sodium hydride (0.24 g; 6.1 mmol) was added portionwise to a solution of intermediate 3 (1.1 g; 3 mmol) in DMF (10 mL) at 5° C. under N$_2$ flow. The reaction mixture was stirred at 5° C. for 30 minutes. Then a solution of (4-chloro-2-butyn-1-yl)-benzene (1 g; 6.1 mmol) was added dropwise at 5° C. under N$_2$ flow. The reaction mixture was stirred for 1 hour at 5° C., then stirred at room temperature overnight. The reaction was poured out into ice water and EtOAc was added. The organic layer was separated, washed with brine, dried (MgSO$_4$), filtered and the solvent was evaporated to dryness. The residue was purified by chromatography over silica gel (SiOH 15-40 μm 300 g, mobile phase: 0.1% NH$_4$OH, 98% DCM, 2% MeOH). The desired fractions were collected and evaporated to give 0.66 g of residue which was then purified by achiral Supercritical Fluid Chromatography on (5 μm, mobile phase, 60% CO$_2$, 40% mixture of MeOH/iPrOH 50/50 v/v). The desired fractions were collected and evaporated to give 282 mg (19%) of compound 919. This fraction was crystallized from Et$_2$O to give 143 mg of compound 919 (mp=130° C.).

Example B48

Preparation of compound 641

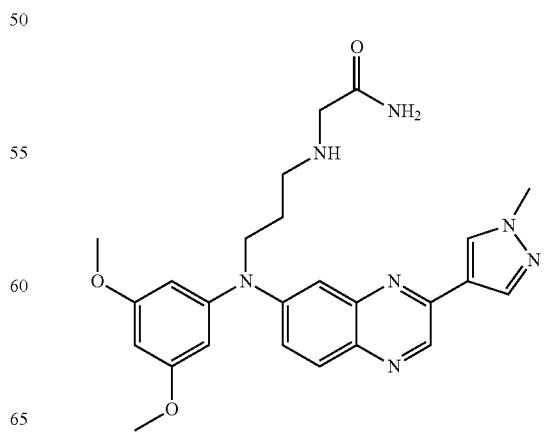

A mixture of intermediate 17a (0.3 g; 0.6 mmol), glycinamide hydrochloride (0.2 g; 1.8 mmol), potassium iodide (0.1 g; 0.6 mmol), sodium carbonate (0.32 g; 3.0 mmol) in 1-BuOH (12 mL) was stirred at 85° C. for 18 hours. The reaction was poured out into ice water and EtOAc was added. The organic layer was separated and washed with brine, dried (MgSO$_4$), filtered and the solvent was evaporated. The residue (0.28 g) was purified by chromatography over silica gel (SiOH 5 μm, 150*30 mm; mobile phase gradient from 0.2% NH$_4$OH, 98% DCM, 2% MeOH to 0.9% NH$_4$OH, 91% DCM, 9% MeOH). The pure fractions were collected and concentrated. The residue (0.100 g) was crystallized from diethyl ether. The precipitate was filtered and dried to afford 0.081 g (28%) of compound 641. MP: 155° C. (DSC).

Example B49

Preparation of compound 137

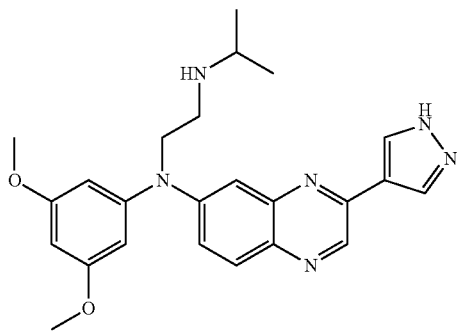 [SMILES: COc1cc(OC)cc(N(CCNC(C)C)c2ccc3ncc(-c4cn[nH]c4)nc3c2)c1]

A mixture of intermediate 93 (12.8 g; 23.4 mmol) and isopropylamine (61 mL; 500 mmol) in acetonitrile (500 mL) was heated at 100° C. in a sealed vessel for 18 hours. The reaction mixture was cooled down to room temperature. The reaction was poured out into ice water and EtOAc was added. The organic layer was washed with brine, dried (MgSO$_4$), filtered over silica gel and evaporated till dryness. The residue (13 g) was purified by chromatography over silica gel (Irregular SiOH 20-40 μm, 1000 g; mobile phase 0.5% NH$_4$OH, 95% DCM, 10% MeOH). The pure fractions were collected and concentrated to give 8 g (55%) of the free base which was converted into its HCl salt as compound 137.

Example B50

Preparation of compound 2

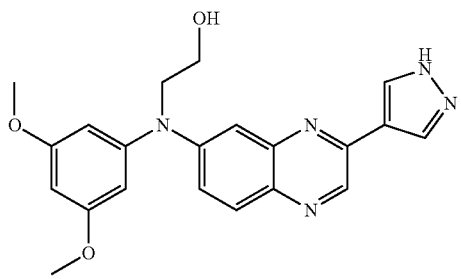 [SMILES: COc1cc(OC)cc(N(CCO)c2ccc3ncc(-c4cn[nH]c4)nc3c2)c1]

A 1M solution of tetrabutylammonium fluoride in THF (30.3 mL; 30.3 mmol) was added dropwise to a solution of intermediate 94 (10.2 g; 20.2 mmol) in THF (70 mL) at room temperature. The reaction mixture was stirred at room temperature for 3 hours. The mixture was poured out into ice water, basified with K$_2$CO$_3$ 10% and EtOAc was added. The organic layer was separated, washed with brine, dried (MgSO$_4$), filtered and the solvent was evaporated to dryness. The residue was crystallized from diethyl ether. The precipitate was filtered off and dried to afford 5.9 g (75%) of compound 2. MP: 169° C. (DSC).

Example B51

Preparation of compound 644

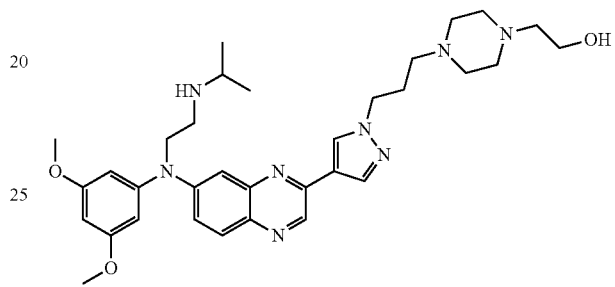

as a HCl salt

A mixture of intermediate 100 (0.09 g; 0.14 mmol) and K$_2$CO$_3$ (0.058 g; 0.42 mmol) in MeOH (1.1 mL) was stirred at room temperature for 1 hour. The reaction mixture was poured out into ice water and DCM was added. The organic layer was separated, dried (MgSO$_4$), filtered and the solvent was evaporated to dryness. The residue (0.2 g) was purified by chromatography over silica gel (Irregular SiOH 15-40 μm, 30 g; mobile phase 0.5% NH$_4$OH, 93% DCM, 7% MeOH). The pure fractions were collected and concentrated. The residue was dissolved in EtOH/CH$_3$CN and acidified with HCl/i-PrOH 5N. The precipitate was filtered off and dried to give 0.053 g (46%) of compound 644 as a chlorhydrate.

Example B52

Alternative preparation of compound 93

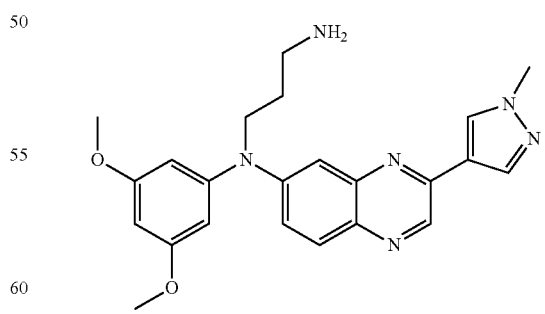

Intermediate 3 (10 g; 27.7 mmol) was added to a solution of potassium hydroxide (27.4 g; 415 mmol), tetrabutylammonium bromide (1.34 g; 4.0 mmol) in (280 mL) and water (3 mL). The reaction mixture was stirred at 50° C. for 30 minutes, then 3-bromopropylamine hydrochloride (9.7 g;

44.3 mmol) was added portionwise and stirred at 50° C. for 2 hours. The reaction mixture was cooled to room temperature. The reaction was poured out into ice water and EtOAc was added. The organic layer was separated and washed with brine, dried (MgSO$_4$), filtered and the solvent was evaporated. The residue (20 g) was purified by chromatography (Irregular SiOH 20-45 µm, 1000 g; mobile phase 1% NH$_4$OH, 90% DCM, 10% MeOH). The pure fractions were collected and concentrated. The residue was crystallized from diethyl ether. The precipitate was filtered and dried to give 10.5 g (90%) of compound 93. MP: 178° C. (DSC)

Example B53

Preparation of compound 645

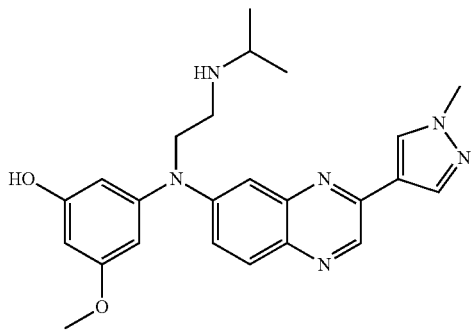 [SMILES: COc1cc(O)cc(N(CCNC(C)C)c2ccc3ncc(-c4cnn(C)c4)nc3c2)c1]

A 5N solution of HCl in i-PrOH (2.5 mL; 12.5 mmol) was added dropwise to a solution of intermediate 105 (0.8 g, 1.54 mmol) in CH$_3$OH (25 mL) at 10° C. and then the mixture was stirred for 18 hours at room temperature. The red precipitate was filtered, rinsed with diethyl ether and dried. The precipitate was taken up with DCM and washed with a solution of NaOH 1M. The organic layer was washed with water, dried (MgSO$_4$), filtered and evaporated till dryness. The residue was crystallized from diethyl ether. The precipitate was filtered and dried under vacuum to give 0.22 g (34%) of compound 645. MP: 188° C. (DSC)

Example B54

Preparation of compound 646

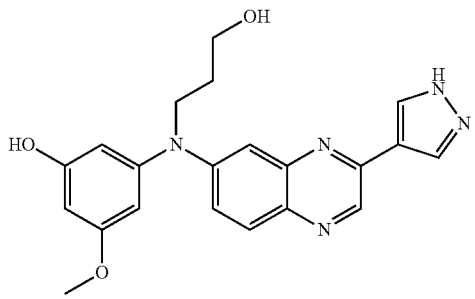 [SMILES: COc1cc(O)cc(N(CCCO)c2ccc3ncc(-c4cn[nH]c4)nc3c2)c1]

A 5N solution of HCl in i-PrOH (1.1 mL; 5.7 mmol) was added dropwise to a solution of intermediate

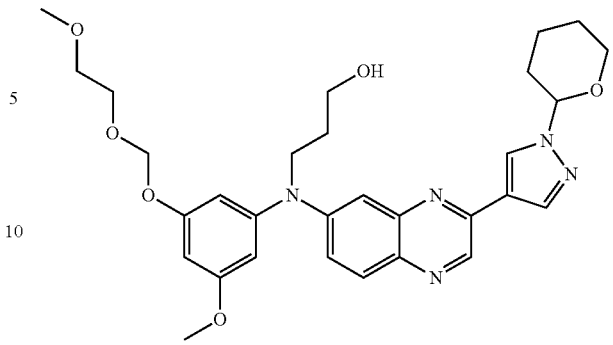

(0.8 g; 1.4 mmol) (prepared according to the procedure described for intermediate 103 in A42a-c) in CH$_3$OH (20 mL) at 10° C. and then the mixture was stirred for 18 hours. The reaction mixture was taken up with DCM and washed with a solution of hydroxide de sodium 1M, the organic layer was washed with water, dried over MgSO$_4$, filtered and evaporated till dryness. The residue (1.3 g) was purified by chromatography over silica gel (Irregular, SiOH, 15-40 µm, 300 g; mobile phase from 0.5% NH$_4$OH, 93% DCM, 7% MeOH to 1% NH$_4$OH, 90% DCM, 10% MeOH). The pure fractions were collected and concentrated. The residue was crystallized from diethyl ether, the precipitate was filtered and dried under vacuum to give 0.11 g (19%) of compound 646. MP: 125° C. (Kofler)

Example B55

Preparation of compound 647

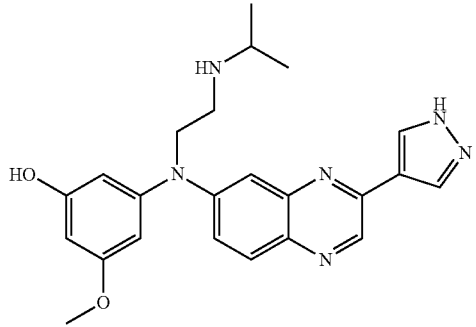 [SMILES: COc1cc(O)cc(N(CCNC(C)C)c2ccc3ncc(-c4cn[nH]c4)nc3c2)c1]

as a HCl salt

A 5N solution of HCl in i-PrOH (0.7 mL; 3.4 mmol) was added dropwise to a solution of intermediate

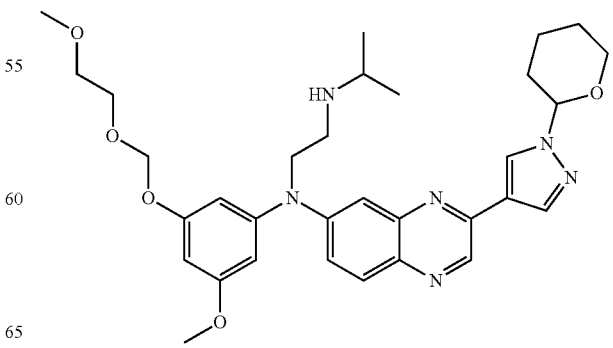

(0.5 g; 0.8 mmol) (prepared according to the procedure described for intermediate 105 in A42e) in CH₃OH (20 mL) at 10° C. and then the mixture was stirred 18 hours. The reaction mixture was evaporated till dryness and the residue was taken up with DCM and basified with a solution of sodium hydroxide 1N. The organic layer was washed with water, dried (MgSO₄), filtered and evaporated till dryness. The residue was crystallized from diethyl ether and 1 mL of HCl 3N. The precipitate was filtered and dried to afford 0.2 g (49%) of compound 647. MP: 133° C. (Kofler)

Example B56

Preparation of compound 655

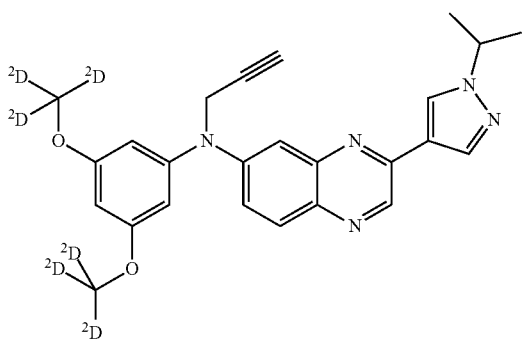 [SMILES: [2H]C([2H])([2H])Oc1cc(OC([2H])([2H])[2H])cc(N(CC#C)c2ccc3ncc(-c4cnn(C(C)C)c4)nc3c2)c1]

K₂CO₃ (0.38 g; 2.7 mmol) was added to intermediate 109 (1.4 g; 2.7 mmol) in MeOH (40 mL). The solution was stirred at room temperature for 3 hours. The reaction mixture was poured out into water and EtOAc was added. The organic layer was dried (MgSO₄), filtered and evaporated till dryness to give 1.2 g of compound 655.

Example B57

Preparation of compound 658

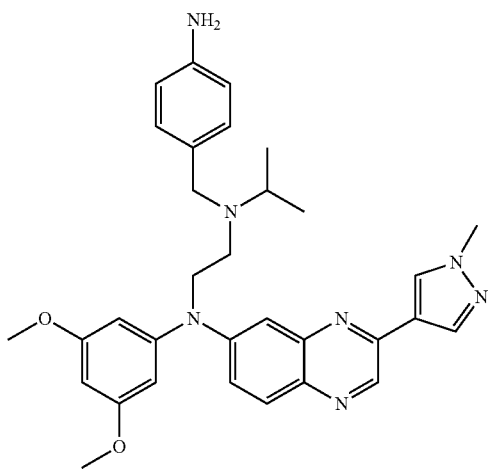

Intermediate 110 (0.4 g; 0.67 mmol) was hydrogenated at room temperature in MeOH (20 mL) with Nickel de Raney (0.4 g; 6.88 mmol) as a catalyst in pressure vessel (3 bars). After 5 hours the catalyst was filtered off on a pad of Celite® and the filtrate was concentrated in vacuo until dryness. The residue (0.32 g) was purified by chromatography over silica gel (Spherical SiOH, 10 μm, 60 g; mobile phase, 0.1% NH₄OH, 98% DCM, 2% MeOH). The pure fractions were collected and evaporated to dryness. The residue (0.19 g) was crystallized from diethyl ether. The precipitate was filtered and dried to give 0.16 g (42%) of compound 658. MP: 152° C. (DSC).

Example B58

Preparation of compound 659

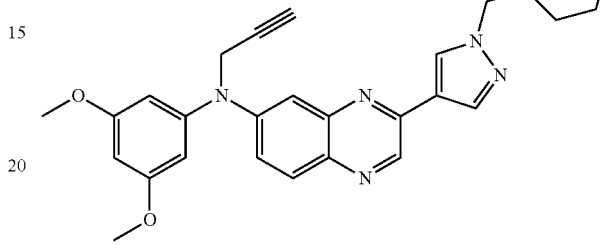

K₂CO₃ (0.17 g, 1.19 mmol) was added to intermediate 111

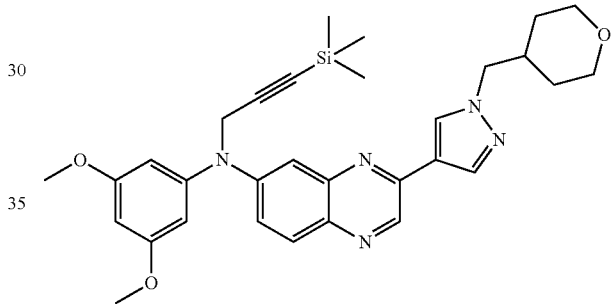

(0.66 g, 1.19 mmol) (prepared according to the procedure described in A44 starting from intermediate 112) in MeOH (20 mL). The solution was stirred at room temperature for 3 hours. The reaction mixture was poured out into water and EtOAc was added. The organic layer was dried over MgSO₄, filtered and evaporated till dryness. The residue was crystallized from CH₃CN and diethyl ether, the precipitate was filtered and dried to give 0.25 g (44%) of compound 659. MP: 106° C. (DSC).

Example B59

Preparation of compounds 660 and 661

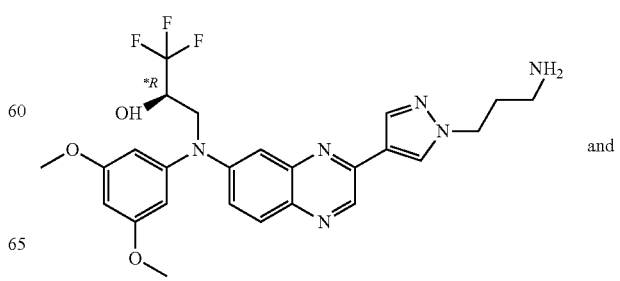

compound 660 and compound 661

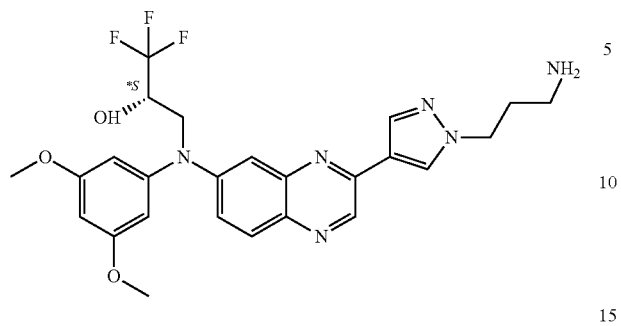

compound 892

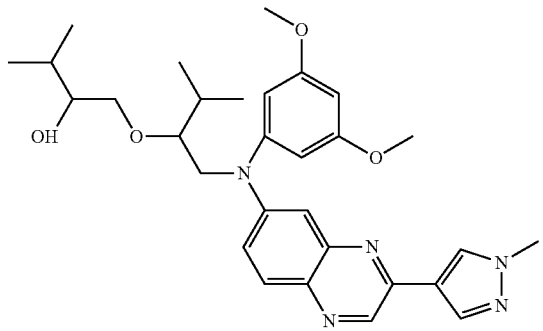

NaH (0.19 g; 4.7 mmol) was added portionwise to intermediate 118 (0.95 g; 2.4 mmol) in N,N-dimethylformamide (10 mL). The reaction mixture was stirred at 5° C. for 1 hour. Then 1,2-epoxy-3,3,3-trifluoropropane (0.4 mL; 4.7 mmol) was added dropwise at 5° C. under $N_2$ flow. The reaction mixture was stirred at 5° C. for 1 hour, then was allowed to rise to room temperature, stirred for 18 hours and 3 hours at 60° C. The reaction was poured out into ice water and EtOAc was added. The organic layer was separated, washed with brine, dried (MgSO$_4$), filtered and the solvent was evaporated. The residue (1.44 g) was purified by chromatography over silica gel (Irregular, SiOH 20-45 μm, 450 g, mobile phase gradient from 0.5% NH$_4$OH, 98% DCM, 2% MeOH to 1% NH$_4$OH, 88% DCM, 12% MeOH). The pure fractions were collected and evaporated to provide 1.44 g of residue. The enantiomers were separated by chiral super critical fluid chromatography (CHIRALPAK AD-H 5 μm 250×20 mm; mobile phase, 0.3% 2-propylamine, 55% CO$_2$, 45% MeOH). The desired product fractions were collected and the solvent was evaporated. The first eluted enantiomer (0.15 g) was crystallized from diethyl ether. The precipitate was filtered and dried to afford 0.11 g (9%) of compound 660 (R*, MP=154° C. (DSC)). The second eluted enantiomer (0.15 g) was crystallized from diethyl ether. The precipitate was filtered and dried to afford 0.116 g (10%) of compound 661 (S*, MP=151° C. (DSC)).

Example B59A

Preparation of compounds 926 (free base) and 892 (HCl salt)

Compound 926

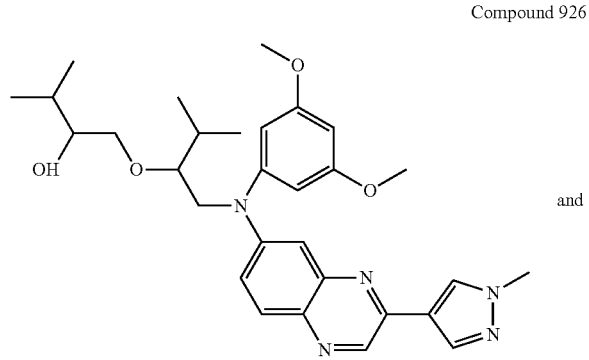

and as a HCl salt

The following reaction was performed two times:

Sodium hydride (2.0 g, 49.8 mmol) was added portionwise to a solution of intermediate 3 (9 g, 24.9 mmol) in DMF (140 mL) at 5° C. under N$_2$ flow. The reaction mixture was stirred at 5° C. for 1 hour, then 1.2-epoxy-3-methylbutane (5.3 mL, 49.8 mmol) was added dropwise at 5° C. under N$_2$ flow. The reaction mixture was stirred 1 hour at 5° C., then stirred at 80° C. for 3 hours. The reaction was poured out into ice water and EtOAc was added. The organic layer was separated, washed with brine, dried (MgSO$_4$), filtered and the solvent was evaporated to give a brown oil. The residue was purified by chromatography over silica gel (SiOH 20-45 μm, mobile phase (0.1% NH$_4$OH, 97.5% DCM, 2.5% MeOH). The desired product fraction were collected and evaporated to provide 1.2 g (11%) of compound 389 and 3.36 g (25%) of compound 926. This later fraction was repurified by chromatography over silica gel (SiOH 20-45 μm 450 g, mobile phase 0.1% NH$_4$OH, 98% DCM, 2% MeOH). The product fraction was collected and evaporated to provide 1.1 g (8%) of compound 926. A fraction (300 mg) was converted into the HCl salt in MeOH. The solid was filtered, washed with Et$_2$O and dried to give 159 mg of a red powder compound 892.

Example B60

Preparation of compound 664

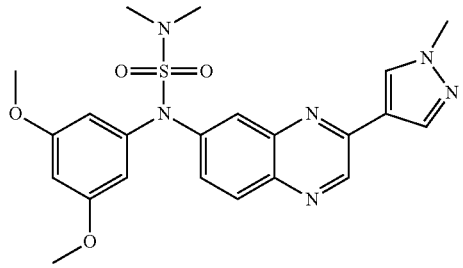 [SMILES: COc1cc(OC)cc(N(c2ccc3ncc(-c4cnn(C)c4)nc3c2)S(=O)(=O)N(C)C)c1]

NaH (0.11 g; 2.8 mmol) was added portionwise to intermediate 3 (0.5 g; 1.4 mmol) in N, N-dimethylformamide (3 mL). The reaction mixture was stirred at 5° C. for 1 hour. Then dimethylsulfamoyl chloride (0.3 mL; 2.8 mmol) was added dropwise at 5° C. under $N_2$ flow. The reaction mixture was stirred at 5° C. for 1 hour, then was allowed to rise to room temperature and stirred for 6 hours. The reaction was poured out into ice water and EtOAc was added. The organic layer was separated, washed with brine, dried ($MgSO_4$), filtered and the solvent was evaporated. The residue (0.8 g) was purified by chromatography over silica gel (SiOH 5 μm, 150*30 mm, mobile phase gradient from 100% DCM to 0.4% $NH_4OH$, 96% DCM, 4% MeOH). The pure fractions were collected and evaporated. The residue (0.05 g) was crystallized from diethyl ether. The precipitate was filtered and dried to afford 0.046 g (7%) of compound 664. MP: 80° C. (Kofler).

Example B61

Preparation of compound 667 and 668 compound 667

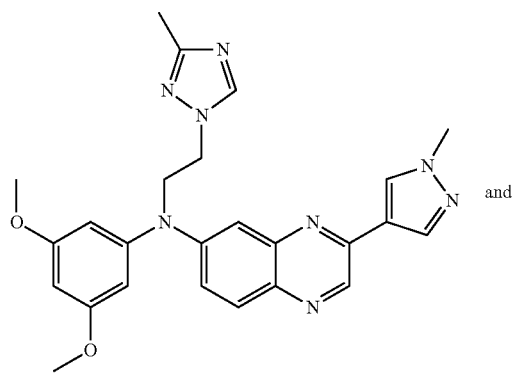

and compound 668

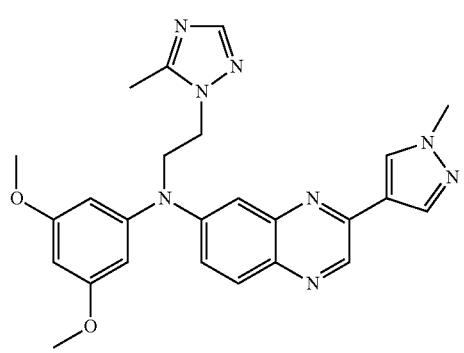

A solution of intermediate 10 (1 g; 2 mmol), 3-methyl-11H-1,2,4-triazole (0.35 g, 4.2 mmol) and $K_2CO_3$ (0.72 g; 5.2 mmol) in 1-methyl-2-pyrrolidinone (35 mL) was stirred at 15135° C. for 18 hours. The reaction mixture was cooled down to room temperature and diluted with EtOAc and water. The organic layer was separated, washed with water, dried ($MgSO_4$), filtered and evaporated till dryness. The residue (1.8 g) was purified by chromatography over silica gel (SiOH 20-45 μm, 450 g; mobile phase 0.1% $NH_4OH$, 97% DCM, 3% MeOH). The pure fractions were collected and the solvent was evaporated. The residue (0.72 g) was separated by chiral super critical fluid chromatography (CHIRALPAK AD-H 5 μm 250×20 mm; mobile phase, 0.3% 2-propylamine, 50% $CO_2$, 50% isopropanol). The desired product fractions were collected and the solvent was evaporated. The first product was crystallized from diethyl ether. The precipitate was filtered and dried to give 0.25 g (26%) of compound 667. MP: 181° C. (DSC). The second-product was crystallized from diethyl ether. The precipitate was filtered and dried to give 0.27 g (28%) of compound 668. MP: 137° C. (DSC).

Example B62

Preparation of compound 669

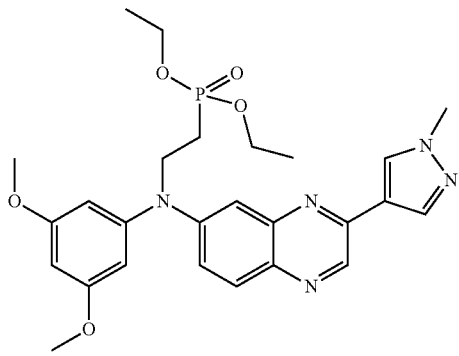 [SMILES: CCOP(=O)(CCN(c1cc(OC)cc(OC)c1)c1ccc2ncc(-c3cnn(C)c3)nc2c1)OCC]

The experiment has been performed 6 times on the following amounts.

A mixture of intermediate 3 (0.5 g; 1.4 mmol), diethyl (vinyl)phosphonate (0.5 mL; 3 mmol) and tri-N-butylphosphine (0.035 mL; 0.1 mmol) in $CH_3CN$ (2 mL) was stirred at 140° C. for 15 hours in a sealed tube. The reaction mixture was cooled down to room temperature and diluted with DCM and water. The organic layers were separated, combined, dried ($MgSO_4$), filtered and evaporated till dryness. The residue (7 g) was purified by chromatography over silica gel (SiOH 20-45 μm, 450 g; mobile phase 0.1% $NH_4OH$, 95% DCM, 5% iPrOH). The pure fractions were collected, the solvent was evaporated. The residue (3.1 g) was crystallized from $CH_3CN$ and diethyl ether, the precipitate was filtered off and dried to give 0.88 g (21%) of compound 669. MP: 122° C. (DSC).

Example B63

Preparation of compound 693

as a HCl salt

Trifluoroacetic acid (7 mL; 94.7 mmol) was added to a solution of

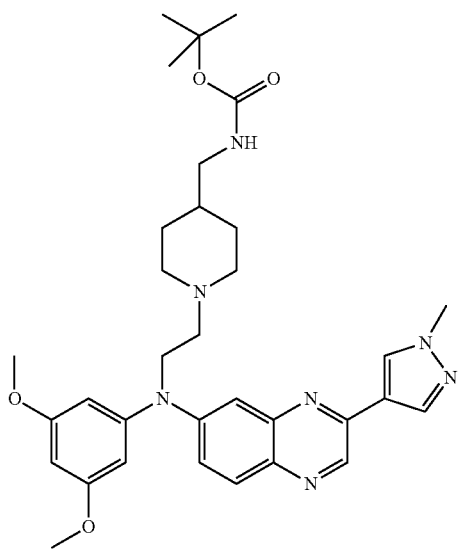 [SMILES: COc1cc(OC)cc(N(CCN2CCC(CNC(=O)OC(C)(C)C)CC2)c2ccc3ncc(-c4cnn(C)c4)nc3c2)c1]

prepared according to a protocol as described in B3B (1.2 g; 2 mmol) in DCM (60 mL). Then the solution was stirred at room temperature for 2 hours. The reaction mixture was poured out into ice water and basified with NH₄OH. The product was extracted with DCM. The organic layer was dried (MgSO₄), filtered and the solvent was evaporated. The residue was crystallized from diethyl ether and the precipitate was filtered off.

The precipitate was dissolved in isopropyl alcohol and stirred at 0° C., then 0.8 mL of HCl i-PrOH 5N was added dropwise. Diethyl ether was added and the solution was stirred at 0° C. for 1 hour. The precipitate was filtered and dried to afford 0.48 g (35%) of compound 693 MP: 151° C. (DSC).

Example B64

Preparation of compound 846

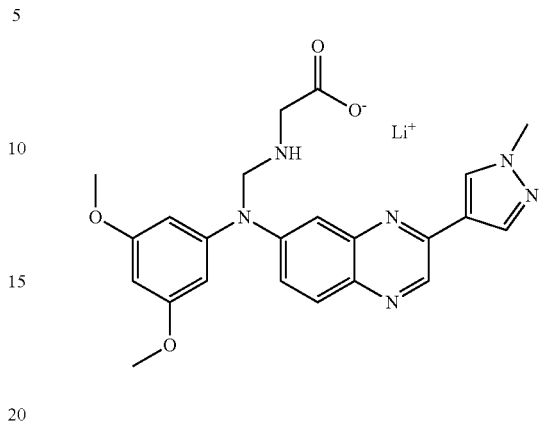

Lithium hydroxide monohydrate (0.085 g; 2.0 mmol) was added portionwise to a solution of intermediate 142 (0.72 g; 1.4 mmol) in THF (20 mL) and H₂O (6 mL) at room temperature. The reaction mixture was stirred at 70° C. for 24 hours. The reaction mixture was evaporated until dryness. The residue was taken up with diethyl ether. The precipitate was filtered off and dried under vacuum, yielding 0.577 g (88%) of compound 846. MP: 170° C. (Kofler)

Example B65

Preparation of compound 763

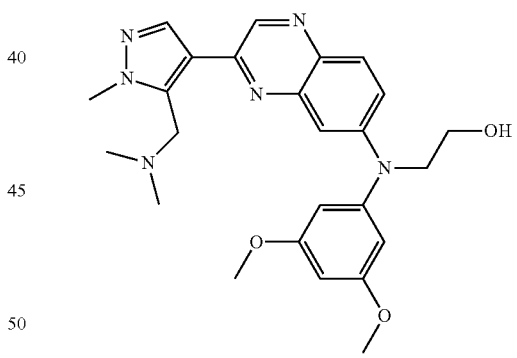

Reaction performed in a microwave device (biotage) in a sealed tube.

Intermediate 88a (198.6 mg, 0.552 mmol), intermediate 131 (520 mg, 1.21 mmol) and tetrakis(triphenylphosphine) palladium (0) (31.89 mg, 0.028 mmol) in toluene (2.6 ml) were stirred at 160° C. for 40 minutes. Toluene (2.6 ml) was added and the reaction mixture was stirred at 160° C. for 40 minutes. Water was added and the reaction mixture was extracted with AcOEt. The organic layer was dried (MgSO₄), filtered and dried to give a yellow oil. This oil was crystallized from CH₃CN. The crystals were dried (room temperature) to give compound 763 as a yellow powder. MP: 176° C.

C. Conversion Reactions

Conversion 1

Preparation of compound 44a

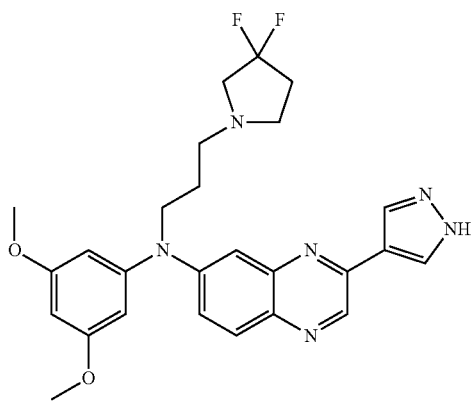 [SMILES: COc1cc(OC)cc(N(CCCN2CCC(F)(F)C2)c2ccc3ncc(-c4cn[nH]c4)nc3c2)c1]

and compound 44.

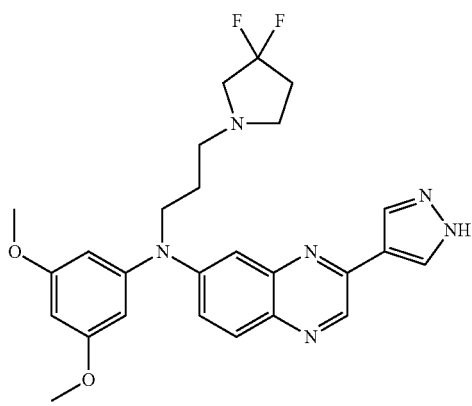 [SMILES: COc1cc(OC)cc(N(CCCN2CCC(F)(F)C2)c2ccc3ncc(-c4cn[nH]c4)nc3c2)c1]

HCl

HCl (5.53 mL; 27.65 mmol) was added to a solution of compound 6 (3.2 g; 5.53 mmol) in CH₃OH (70 mL) and heated to 60° C. for 8 hours. The reaction mixture was cooled to room temperature, poured into H₂O, basified with K₂CO₃ and extracted with EtOAc. The organic layer was dried (MgSO₄), filtered and evaporated to dryness. The residue was purified by chromatography over silica gel (Irregular SiOH, 15-40 μm 30 g MERCK; mobile phase, gradient 100% DCM to 90% DCM, 10% MeOH, 0.1% NH₄OH). The desired fraction was collected and the solvent was evaporated. The compound 44a 1.95 g (71%) was dissolved in diisopropyl alcohol and HCl (5 to 6N in alcohol) (3 mL), stirred for 30 minutes and evaporated to dryness. The residue was crystallized in diethyl ether, yielding 1.537 g (47%) of compound 44. MP=215.29° C. (DSC).

Conversion 2

Preparation of compound 45

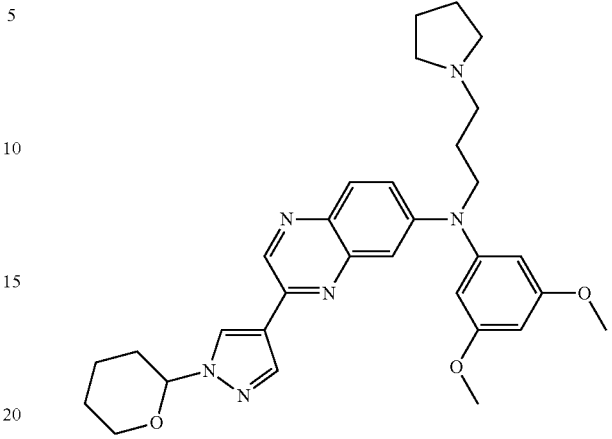

Compound 9 (3.02 g; 5.95 mmol) in pyrrolidine (50 mL) was heated at 70° C. for 2 hours. The reaction mixture was cooled to room temperature and evaporated to dryness. The residue was poured into H₂O and extracted with EtOAc. The organic layer was dried (MgSO₄), filtered and evaporated to dryness. The residue (4.04 g) was purified by chromatography over silica gel (Irregular SiOH, 15-40 μm, 90 g; mobile phase, gradient from 100% DCM to 90% DCM/10% MeOH/0.1% NH₄OH). The desired fractions were collected and the solvent was evaporated, yielding 1.83 g (57%) of compound 45.

Conversion 2A

Preparation of compound 344

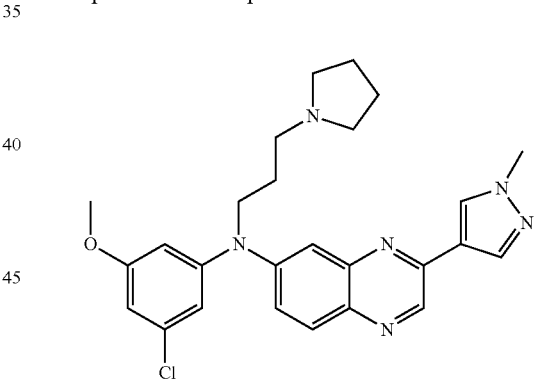

as a HCl salt

A solution of compound 310 (0.93 g; 2.1 mmol), pyrrolidine (0.52 mL; 6.4 mL), K₂CO₃ (0.3 g; 2.2 mmol) in CH₃CN (50 mL) was stirred at 80° C. for 24 hours. The reaction mixture was cooled down to room temperature, poured out into ice water and extracted with EtOAc. The organic layer was separated and washed with water, dried (MgSO₄), filtered and the solvent was evaporated. The residue (0.9 g) was purified by chromatography over silica gel (SiOH, 5 μm; mobile phase gradient from 0.2% NH₄OH, 98% DCM, 2% MeOH to 1.3% NH₄OH, 87% DCM, 13% MeOH). The pure fractions were collected and concentrated. The residue (0.52 g) was dissolved in MeOH and converted into the hydrochloric acid salt with HCl/2-propanol. Et₂O was added and the precipitate was stirred for 30 minutes, filtered off and dried to afford 0.55 g (47%) of compound 344. MP: 162° C. (DSC)

Conversion 2B

Preparation of compound 692 and 563

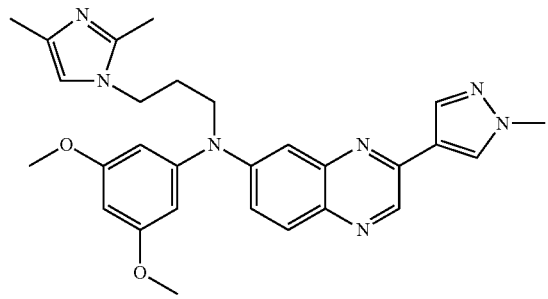

as a HCl salt

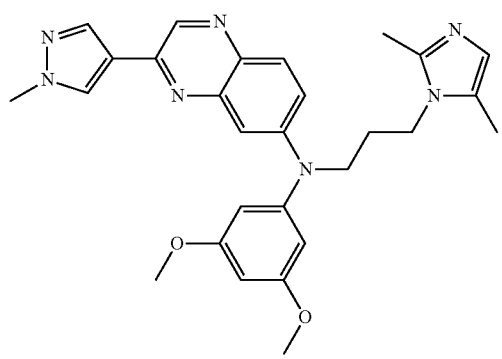

as a HCl salt

NaH (0.13 g; 3.3 mmol) was added portionwise to 2,4-dimethylimidazole (0.3 g; 3 mmol) in N,N-dimethylformamide (25 mL) at 5° C. under N₂ flow. The reaction mixture was stirred at 5° C. for 30 minutes, then compound 236 (1 g; 2.4 mmol) was added at 5° C. under N₂ flow. The reaction mixture was allowed to warm to room temperature and stirred for 18 hours. The reaction was poured out into ice water. The organic layer was separated and washed with water, dried (MgSO₄), filtered and the solvent was evaporated. The residue (1.8 g) was purified by chromatography over silica gel (SiOH, 15-40 μm, 300 g; mobile phase 0.5% NH₄OH, 95% DCM, 5% MeOH). The pure fractions were collected and concentrated. The residue (1 g) was purified by achiral super critical fluid chromatography (Amino 6 μm; mobile phase 0.3% isopropylamine, 15% MeOH, 85% CO₂). The pure fractions were collected and the solvent was evaporated till dryness. The first fraction (0.44 g) was further purified by chromatography over silica gel (SiOH, 5 μm; mobile phase gradient from 0.4% NH₄OH, 96% DCM, 4% MeOH to 1.5% NH₄OH, 85% DCM, 15% MeOH). The pure fractions were collected and concentrated. The residue (0.38 g) was dissolved in acetone, then HCl 4N in dioxane was added dropwise. Diethyl ether was added and the precipitate was filtered and dried to afford 0.39 g (27%) of compound 692. MP: 157° C. (DSC).

The second fraction was dissolved in CH₃CN, then HCl 4N in dioxane was added dropwise. The precipitate was filtered and dried to afford 0.11 g (8%) of compound 563. MP: 201° C. (DSC).

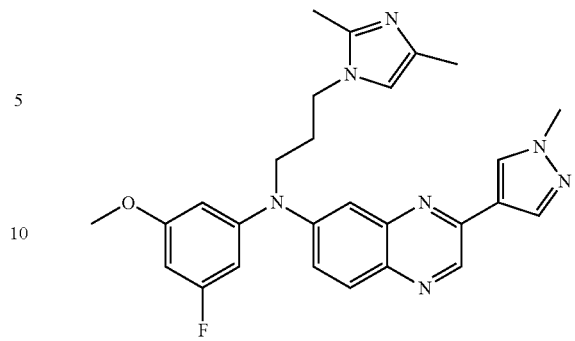

can be prepared according to the above protocol.

Conversion 3

Preparation of compound 46

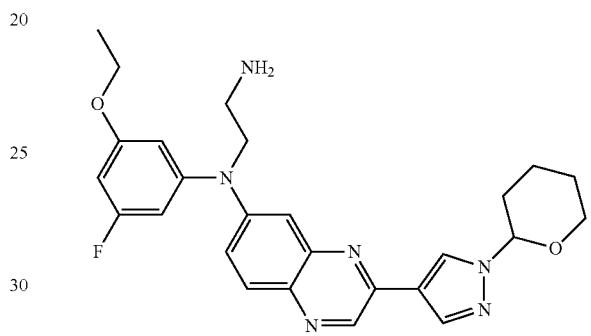

Hydrazine monohydrate (0.15 mL; 4.8 mmol) was added to a solution of compound 47 (0.420 g; 0.7 mmol) in EtOH (20 mL). The mixture was heated at 80° C. for 24 hours. The mixture was cooled to room temperature, evaporated and the residue was poured into water. The organic layer was extracted with DCM, washed with brine, dried (MgSO₄), filtered and evaporated to dryness. The crude product was purified by chromatography over silica gel (Sunfire Silica 5 μm 150×30.0 mm; mobile phase, gradient from 0% NH₄OH, 100% DCM, 0% MeOH to 0.8% NH₄OH, 92% DCM, 8% MeOH). The pure fractions were collected and the solvent was evaporated till dryness, yielding 56 mg (71%) of compound 46.

Conversion 4

Preparation of compound 48

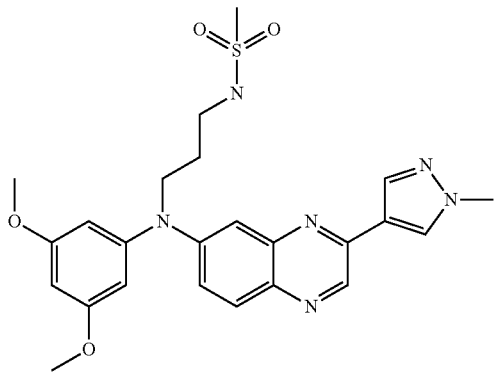 [SMILES: COc1cc(OC)cc(N(CCCNS(C)(=O)=O)c2ccc3ncc(-c4cnn(C)c4)nc3c2)c1]

Methanesulfonyl chloride (0.093 mL, 1.2 mmol) was added to a solution of compound 93 (250 mg, 0.6 mmol) and Et₃N (0.25 mL, 1.8 mmol) in DCM (10 mL) at 5° C. The mixture was stirred at room temperature for 24 hours. The reaction was poured out into ice water and DCM was added. The organic layer was separated, washed with brine, dried (MgSO₄), filtered and the solvent was evaporated. The crude product was crystallized from diethyl ether. The precipitate was filtered and dried under vacuum to give 118 mg (40%) of compound 48. MP=189° C. (DSC).

Conversion 5 a) Preparation of Compound 50

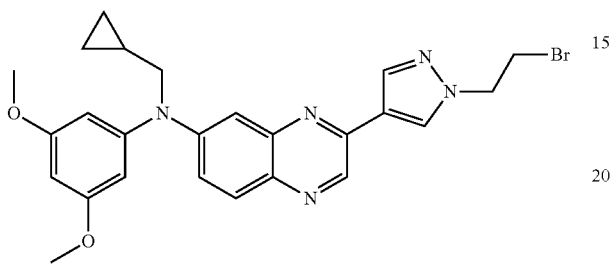

NaH (44.8 mg, 1.12 mmol) was added portionwise to a solution of compound 17 (0.3 g, 0.75 mmol) in DMF (5 mL) at 5° C. under N₂. The reaction mixture was stirred for 30 minutes, then 1,2-dibromoethane (0.194 mL, 2.24 mmol) was added dropwise. The reaction mixture was stirred at room temperature for 5 hours, then poured into H₂O/K₂CO₃ and extracted with EtOAc. The organic layer was dried (MgSO₄), filtered and evaporated to dryness. The residue was purified by chromatography over silica gel (Irregular SiOH, 15-40 μm MERCK; mobile phase, gradient 100% DCM to 97% DCM, 3% MeOH, 0.1% NH₄OH). The pure fractions were collected and evaporated to dryness, yielding 0.236 g (63%) of compound 50.

b) Preparation of Compound 52

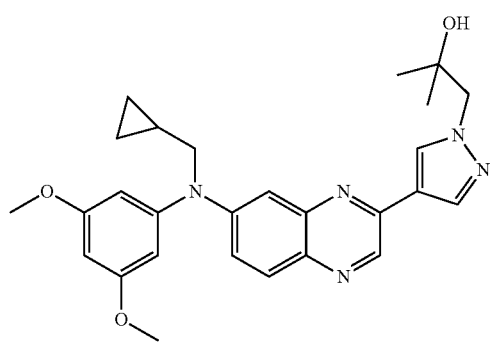 [SMILES: COc1cc(OC)cc(N(CC2CC2)c2ccc3ncc(-c4cnn(CC(C)(C)O)c4)nc3c2)c1]

Compound 17 (214 mg; 0.53 mmol), 1-chloro-2-methyl-2-propanol (0.13 mL; 1.28 mmol), K₂CO₃ (147 mg; 1.1 mmol) in DMF (9 mL) were heated to 120° C. for 72 hours. The reaction mixture was cooled to room temperature, poured into H₂O/K₂CO₃ and extracted with EtOAc. The organic layer was dried (MgSO₄), filtered and evaporated to dryness. The residue (277 mg) was purified by chromatography over silica gel (Irregular SiOH, 15-40 μm, 30 g; mobile phase, gradient from 100% DCM to 90% DCM, 10% MeOH, 0.1% NH₄OH) The pure fractions were collected and evaporated to dryness. The residue (226 mg) was crystallized in diethyl ether, yielding 178 mg (90%) of compound 52. MP=159° C. (DSC).

c) Preparation of Compound 53

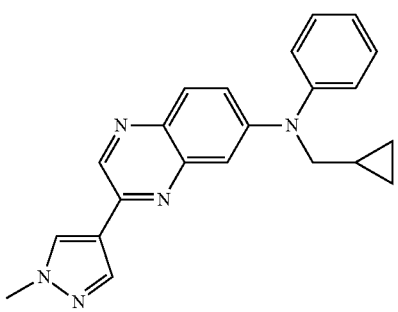 [SMILES: Cn1cc(-c2cnc3ccc(N(CC4CC4)c4ccccc4)cc3n2)cn1]

A mixture of compound 54 (130 mg; 0.38 mmol), iodomethane (23.7 μl; 0.38 mmol) and K₂CO₃ (105.3 mg; 0.76 mmol) in CH₃CN (10 mL) was refluxed overnight. More iodomethane (23.7 μl; 0.38 mmol) and K₂CO₃ (105.3 mg; 0.76 mmol) were added and the reaction mixture was refluxed 8 more hours. The reaction mixture was poured onto water and the product was extracted with EtOAc. The organic layer was washed with brine, dried (MgSO₄), filtered off and the solvent was evaporated. The residue was purified by chromatography over silica gel (Irregular SiOH, 15-40 μm, 30 g; mobile phase, 0.1% NH₄OH, 98% DCM, 2% MeOH). The pure fractions were collected and the solvent was evaporated till dryness. The residue was crystallized in diethyl ether, filtered and dried, yielding 29 mg (21%) of compound 53.

d) Preparation of Compound 55

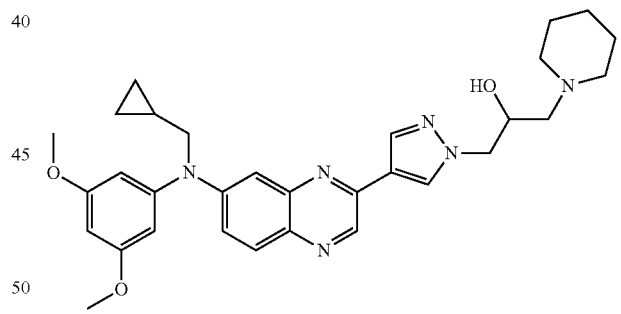

NaH (0.59 g, 1.495 mmol) was added portionwise to a solution of compound 17 (0.3 g, 0.75 mmol) in DMF (6 mL). The mixture was stirred at 0° C. for 1 hour, then 1-(2-oxiranylmethyl)-piperidine (0.316 mg, 2.24 mmol) was added. The resulting mixture was stirred at 5° C. for 1 hour and at 90° C. overnight. The mixture was poured out into water and extracted with DCM. The organic layer was dried, filtered and concentrated till dryness. The residue was purified by chromatography over silica gel (Spherical SiOH, 10 μm, 60 g PharmPrep MERCK; mobile phase, 0.7% NH₄OH, 93% DCM, 7% MeOH). The pure fractions were collected and the solvent was evaporated). The pure fractions were collected and the solvent was evaporated, yielding 0.045 g (11%) of compound 55.

e) Preparation of Compound 56

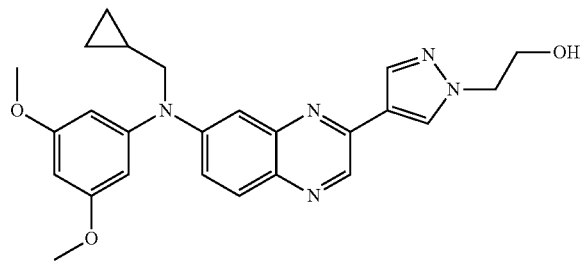 [SMILES: COc1cc(OC)cc(N(CC2CC2)c2ccc3ncc(-c4cnn(CCO)c4)nc3c2)c1]

NaH (179.3 mg, 4.5 mmol) was added portionwise to a solution of compound 17 (1.5 g, 3.7 mmol) in DMF (20 mL). The mixture was stirred at 0° C. for 1 hour, then (2-bromoethoxy)-tert-butyldimethylsilane (0.96 mL, 04.5 mmol) was added. The resulting mixture was stirred at room temperature for 4 hours. The mixture was poured out into water and extracted with DCM. The organic layer was dried, filtered and concentrated till dryness to give 2.1 g of a crude residue. Tetrabutylammonium fluoride (3.75 mL, 1M solution in THF, 3.75 mmol) was added dropwise to a solution of the above residue in THF (25 mL) at room temperature and stirred at room temperature for 5 hours. The reaction mixture was poured out into ice water, basified with $K_2CO_3$ and extracted by EtOAc. The organic layer was separated, washed with brine, dried ($MgSO_4$), filtered and concentrated till dryness. The residue was purified by chromatography over silica gel (Irregular SiOH, 15-40 μm 50 g; mobile phase, gradient 100% DCM to 97% DCM, 3% MeOH, 0.1% $NH_4OH$). The desired product fractions were collected and the solvent was evaporated, yielding 1.3 g (77%) of compound 56 which was triturated in $Et_2O$, filtered and dried under vacuum at 60° C. to give 1.22 g (73%) of compound 56. MP=147.5° C. (DSC).

f) Preparation of Compound 57

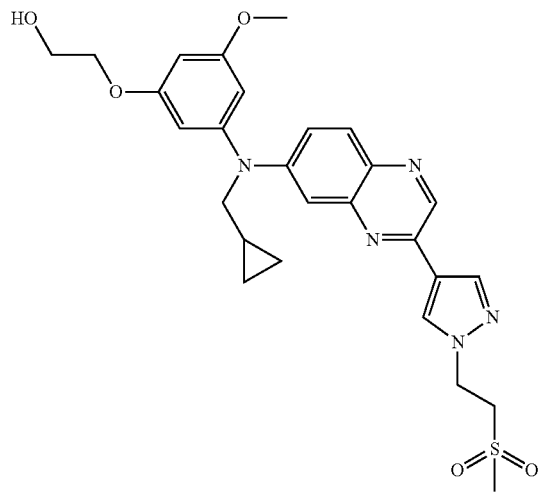 [SMILES: COc1cc(OCCO)cc(N(CC2CC2)c2ccc3ncc(-c4cnn(CCS(C)(=O)=O)c4)nc3c2)c1]

Compound 16 (0.02 g, 0.046 mmol), methyl vinyl sulfone (33 μL, 0.4 mmol), $Et_3N$ (15.5 mL, 0.11 mmol) in $CH_3OH$ (2 mL) were heated to 120° C. under microwave irradiation for 30 minutes. The mixture was evaporated to dryness and purified by chromatography over silica gel (Irregular SiOH, 15-40 μm, 30 g; mobile phase 95% DCM, 5% MeOH, 0.5% $NH_4OH$). The desired fractions were collected and the solvent was evaporated, yielding 22.3 mg (90%) of compound 57. MP=80° C. (Kofler).

g) Preparation of Compound 58

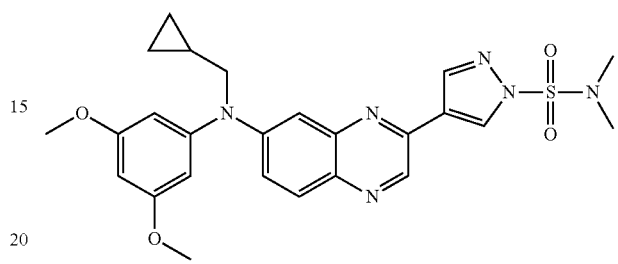

Dimethylsulfamoylchloride (0.06 mL, 0.56 mmol) was added dropwise to a solution of compound 17 (0.15 g, 0.37 mmol), 4-methylaminopyridine (0.0045 g, 0.037 mmol), $Et_3N$ (0.104 mL, 0.75 mmol) in DCM (5 mL) at 5° C. under $N_2$ flow. The reaction mixture was stirred at 5° C. for 1 hour, then overnight at room temperature. The reaction mixture was poured out into ice water and DCM was added. The organic layer was separated, dried ($MgSO_4$), filtered and the solvent was evaporated. The residue was purified by chromatography over silica gel (Irregular SiOH, 15/40 μm, 30 g MERCK; mobile phase, gradient 100% DCM to 97% DCM, 3% MeOH). The desired fractions were collected and the solvent was evaporated. The compound was crystallized from diethyl ether, filtered and dried under vacuum at 60° C., yielding 0.065 g (34%) of compound 58. MP=163° C. (DSC).

h) Preparation of Compound 59

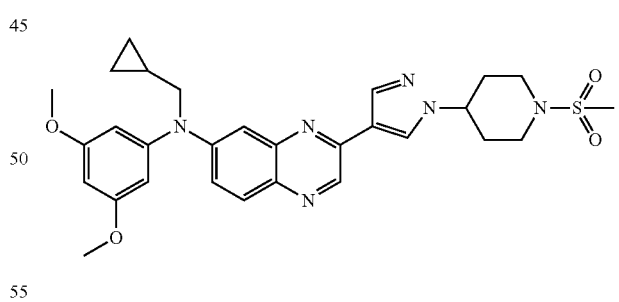

Compound 60 (prepared according to conversion 7 reaction from compound 127) (0.073 g, 0.15 mmol) was dissolved in DCM (5 mL), N,N-diisopropylethylamine (0.037 mL, 0.23 mmol) was added. To this solution, methanesulfonylchloride (0.035 mL, 0.23 mmol) was added dropwise at 0° C. and the mixture was stirred overnight. Water and DCM were added. The organic layer was extracted with DCM. The organic layer was dried, filtered and concentrated. The residue (0.1 g) was purified by chromatography over silica gel (Irregular SiOH, 15-40 μm, 30 g MERCK; mobile phase, 98% DCM, 2% MeOH). The pure fractions were collected and the solvent was evaporated. The residue (0.089 g) was crystallized from DIPE. The precipitate was filtered, dried under vacuum, yielding 0.04 g (47%) of compound 59. MP=200° C. (Kofler).

i) Preparation of Compound 51

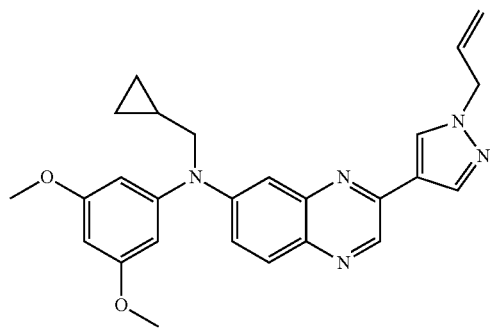 [SMILES: C=CCn1cc(-c2cnc3ccc(N(CC4CC4)c4cc(OC)cc(OC)c4)cc3n2)cn1]

NaH (0.25 mmol) was added portionwise to a solution of compound 17 (0.125 mmol) in DMF (4 mL). The mixture was stirred at 5° C. for 30 minutes, then allyl bromide (0.19 mmol) was added. The resulting mixture was stirred at room temperature for 2 hours. The mixture was poured into water and the product was extracted with EtOAc. The organic layer was washed with water, brine, dried (MgSO$_4$), filtered and evaporated till dryness, yielding 60 mg (100%) of compound 51.

Conversion 6

Preparation of compound 61

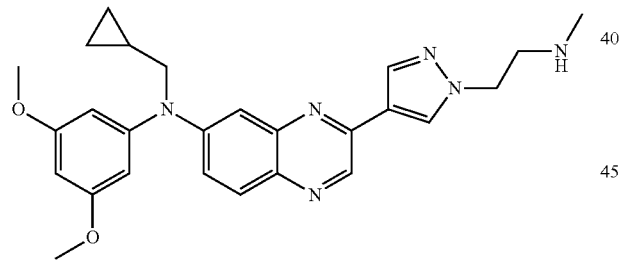

Compound 50 (0.319 g, 0.63 mmol), K$_2$CO$_3$ (0.347 g, 2.51 mmol), methylamine in 2M THF (0.94 mL, 1.88 mmol) in CH$_3$CN (25 mL) were heated at 80° C. for 15 hours. The mixture was cooled to room temperature, poured into H$_2$O/K$_2$CO$_3$ and extracted with EtOAc. The organic layer was dried (MgSO$_4$), filtered and evaporated to dryness. The residue was purified by chromatography over silica gel (Spherical SiOH, 10 µm, 60 g PharmPrep MERCK; mobile phase, gradient from 0.2% NH$_4$OH, 95% DCM, 5% MeOH to 0.2% NH$_4$OH, 90% DCM, 10% MeOH). The pure fractions were collected and evaporated to dryness. The product was crystallized with DIPE and pentane, filtered and dried, yielding 157 mg (55%) of compound 61. MP=103° C. (DSC).

Conversion 7

Preparation of compound 62

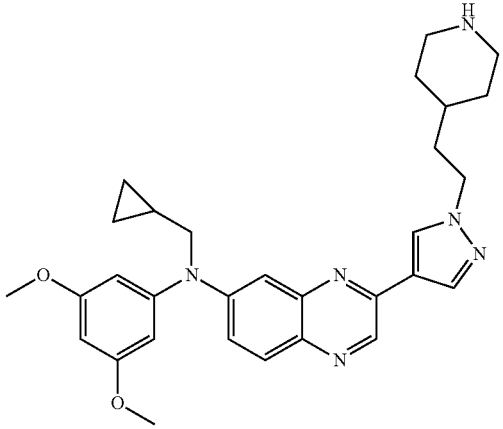 [SMILES: COc1cc(OC)cc(N(CC2CC2)c2ccc3ncc(-c4cnn(CCC5CCNCC5)c4)nc3c2)c1]

Compound 63 (0.280 g, 0.46 mmol), 3N HCl (4 mL) and dioxane (4 mL) were heated to 60° C. for 5 hours. The mixture was cooled to room temperature, poured into H$_2$O and basified with K$_2$CO$_3$. The product was extracted with EtOAc, dried (MgSO$_4$), filtered and evaporated to dryness. The residue was crystallized with DIPE and diethyl ether, filtered and dried, yielding 100 mg (43%) of compound 62. MP=221° C. (DSC).

Conversion 8

Preparation of compound 64

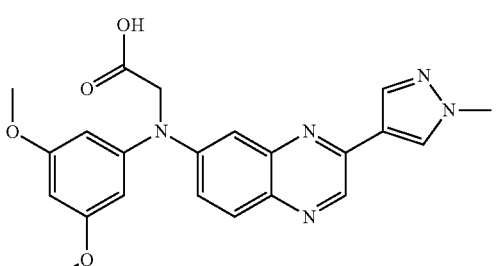

Lithium hydroxide monohydrate (43 mg; 1.0 mmol) was added portionwise to a solution of compound 65 (230 mg; 0.5 mmol) in THF (5 mL) and H$_2$O (2 mL) at room temperature. The reaction mixture was stirred at room temperature overnight. The reaction mixture was evaporated till dryness. The residue was taken up with water and the mixture was acidified with HCl 3N. After stirring, the precipitate was filtered, washed with water and dried under vacuum, yielding 0.206 g (88%) of compound 64.

Conversion 9

Preparation of compound 66

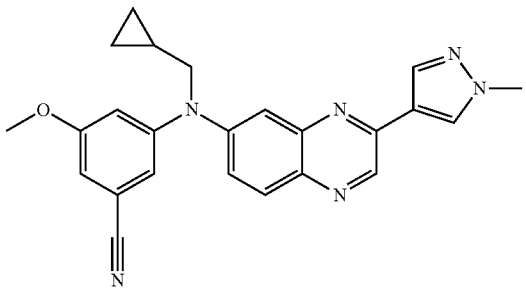

A mixture of compound 67 (0.245 g, 0.53 mmol), zinc cyanide (0.093 g, 0.79 mmol), Pd₂(dba)₃ (0.024 g, 0.026 mmol), Zinc (0.017 g, 0.26 mmol) and 1,1'-bis(diphenylphosphino)ferrocene (0.036 g, 0.066 mmol) in N,N-dimethylacetamide (2 mL) was heated at 140° C. for 1 hour under microwave irradiation. The reaction was poured out into ice water and DCM was added. The organic layer was separated, washed with brine, dried (MgSO₄), filtered and the solvent was evaporated. The residue (0.27 g) was purified by chromatography over silica gel (Irregular SiOH, 15-40 μm, 30 g MERCK; mobile phase, gradient from 98% DCM, 2% MeOH to 94% DCM, 6% MeOH). The pure fractions were collected and the solvent was evaporated. The residue (0.2 g, 92%) was crystallized from DIPE. The precipitate was filtered, dried under vacuum, yielding 0.046 g (21%) of compound 66. MP=143° C.

Conversion 10

Preparation of compound 68

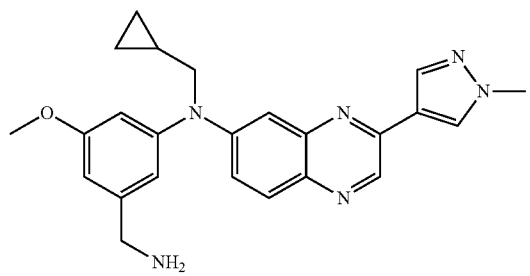

as a HCl salt

A solution of compound 66 (0.1 g, 0.24 mmol) and Nickel (0.1 g, 1.70 mmol) in ammonia and MeOH (4 mL of a 7N solution) was hydrogenated under 2 atmospheres of H₂ for 3 hours at room temperature, using Nickel as the catalyst. The catalyst was removed by filtration through celite, washed with DCM and the filtrate was concentrated. The residue (0.1 g) was purified by chromatography over silica gel (Irregular SiOH, 15-40 μm, 30 g MERCK; mobile phase gradient from 98% DCM, 2% MeOH to 94% DCM, 6% MeOH). The pure fractions were collected and the solvent was evaporated. The residue (0.075 g, 74%) was dissolved in iPrOH, 0.11 mL of HCl 5N/iPrOH was added dropwise at 5° C. The salt was filtered, washed with DIPE and dried under vacuum at 60° C., yielding 0.032 g (29%) of compound 68.

Conversion 11

Preparation of compound 69

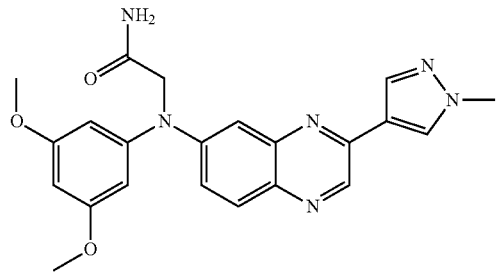

A mixture of compound 64 (Li-salt) (500 mg, 1.18 mmol), 1,1,1-trimethyl-N-(trimethylsilyl)silanamine (0.5 mL, 2.35 mmol), N3-(ethylcarbonimidoyl)-N1,N1-dimethyl-1,3-propanediamine hydrochloride (1:1) (365 mg, 2.35 mmol), HOBt (318 mg, 2.35 mmol), Et₃N (0.33 mL, 2.35 mmol) in DMF (80 mL) was stirred at room temperature overnight. The mixture was poured out into ice water and EtOAc was added. The organic layer was separated, washed with brine, dried (MgSO₄), filtered and the solvent was evaporated to dryness. The residue (167 mg) was triturated from diethyl ether, filtered and dried under vacuum to give 141 mg (29%) of compound 69. MP=264° C. (DSC).

Conversion 12

Preparation of compound 70

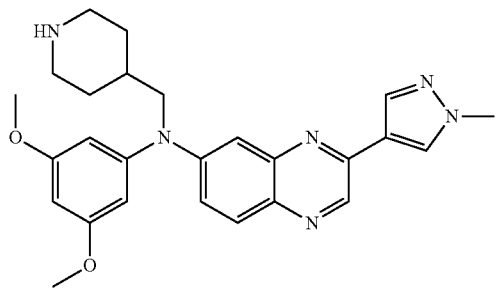 [SMILES: COc1cc(OC)cc(N(CC2CCNCC2)c2ccc3ncc(-c4cnn(C)c4)nc3c2)c1]

as a HCl salt

HCl (0.496 mL; 2.5 mmol) was added dropwise to a solution of compound 71 (277 mg; 0.50 mmol) in isopropyl alcohol (20 mL). The reaction mixture was heated at 50° C. for 4 hours, then 70° C. for 4 hours. The mixture was poured into H₂O and basified with K₂CO₃, then extracted with EtOAc. The organic layer was dried (MgSO₄), filtered and evaporated to dryness. The residue was purified by chromatography over silica gel (Irregular SiOH, 15-40 μm, MERCK; mobile phase, gradient 100% DCM to 80% DCM, 20% MeOH, 0.1% NH₄OH). The product fractions were collected and the solvent was evaporated. The residue (110 mg) was dissolved in diisopropyl alcohol and HCl (0.2 mL of a 5 to 6N in isopropyl alcohol) was added. The mixture was stirred for 30 minutes and evaporated to dryness. Then the residue was crystallized in diethyl ether, yielding 110 mg (39%) of compound 70. M.P=163° C. (DSC).

Conversion 13

Preparation of compound 72

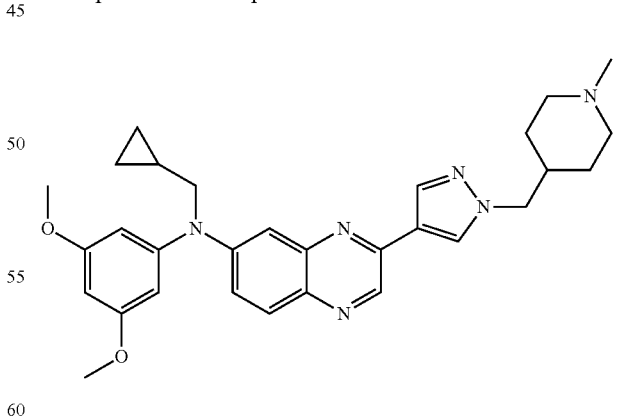

Formaldehyde (0.045 mL, 0.60 mmol) was added to a solution of compound 73 (prepared according to conversion 7 reaction from compound 128) (0.15 g, 0.30 mmol) in MeOH (2 mL) and THF (2 mL) at room temperature. Then sodium cyanoborohydride (0.028 g, 0.45 mmol) was added and the mixture was stirred at room temperature for 1 hour. The mixture was poured out into ice. The organic layer was extracted with DCM, dried (MgSO$_4$), filtered off and evaporated till dryness. The residue (0.1 g) was purified by chromatography over silica gel (Irregular SiOH, 15-40 μm, 30 g MERCK; mobile phase, gradient from 95% DCM, 5% MeOH to 80% DCM, 20% MeOH). The pure fractions were collected and the solvent was evaporated. The residue (60 mg, 39%) was crystallized from DIPE/diethyl ether. The precipitate was filtered, dried under vacuum, yielding 0.046 g (30%) of compound 72. MP=120° C. (Kofler).

Conversion 14

Preparation of compound 74

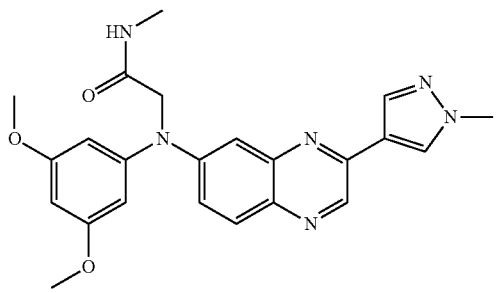 [SMILES: CNC(=O)CN(c1cc(OC)cc(OC)c1)c1ccc2ncc(-c3cnn(C)c3)nc2c1]

A mixture of compound 64 (0.14 g, 0.33 mmol), methylamine hydrochloride (0.052 g, 1.67 mmol), N3-(ethylcarbonimidoyl)-N1,N1-dimethyl-1,3-propanediamine hydrochloride (1:1) (0.077 g, 0.50 mmol), 1-hydroxybenzotriazole (0.068 g, 0.50 mmol), triethylamine (0.325 mL, 2.34 mmol) in DCM (14 mL) was stirred at room temperature overnight. The reaction mixture was poured out into ice water and DCM was added. The organic layer was separated, washed with brine, dried (MgSO$_4$), filtered and the solvent was evaporated. The residue was purified by chromatography over silica gel (Stability Silica 5 μm 150×30.0 mm; mobile phase, gradient from 0% NH$_4$OH, 100% DCM, 0% MeOH to 0.7% NH$_4$OH, 93% DCM, 7% MeOH). The product fraction was collected and the solvent was evaporated. The residue was triturated from diethyl ether, filtered and dried under vacuum at 60° C., yielding 0.078 g (54%) of compound 74. MP=252-254° C. (Kofler).

Conversion 15

Preparation of compound 75

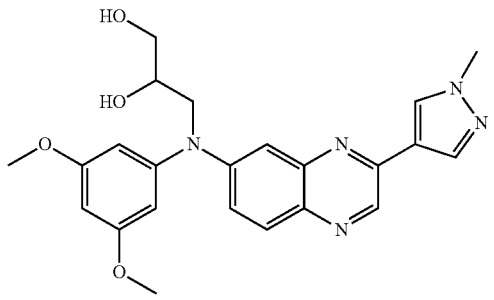 [SMILES: COc1cc(OC)cc(N(CC(O)CO)c2ccc3ncc(-c4cnn(C)c4)nc3c2)c1]

Trifluoroacetic acid (1.07 mL; 14.37 mmol) was added to a solution of compound 76 (2 g; 4.79 mmol) in H$_2$O (19.5 mL) and dioxane (80 mL). The reaction mixture was heated to reflux for 5 hours, poured into H$_2$O and basified with K$_2$CO$_3$, extracted with EtOAc. The organic layer was dried (MgSO$_4$), filtered and evaporated to dryness. The residue was purified by chromatography over silica gel (Irregular SiOH, 35-40 μm, 80 g Grace Resolv; mobile phase, gradient 100% DCM to 90% DCM, 10% MeOH, 0.1% NH$_4$OH). The product fraction was collected and the solvent was evaporated. The residue (2.1 g) was crystallized in Et$_2$O and CH$_3$CN, yielding 1.61 g (77%) of compound 75. MP=187° C. (DSC).

Conversion 16

Preparation of compound 75

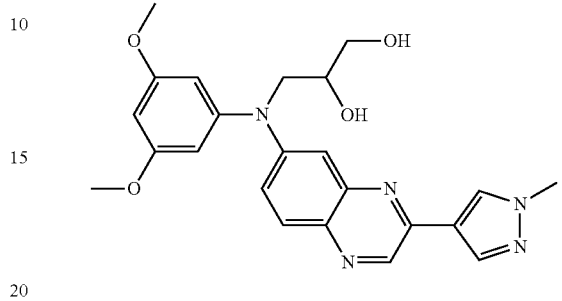

At 0° C., potassium permanganate (0.11 g, 0.7 mol) was added to a solution of compound 121 (0.28 g, 0.0007 mol) in acetone (8 mL)/H$_2$O (2.5 mL). The solution was stirred at room temperature for 4 hours and then poured into ice water. DCM was added and the mixture was filtered through a celite layer. The organic layer was extracted, dried (MgSO$_4$) and evaporated to dryness. The residue (200 mg) was purified by chromatography over silica gel (Stability Silica 5 μm 150×30.0 mm; mobile phase gradient from 0.2% NH$_4$OH, 98% DCM, 2% MeOH to 1.1% NH$_4$OH, 89% DCM, 11% MeOH). The pure fractions were collected and the solvent was evaporated. The residue (100 mg, 33%) was crystallized from CH$_3$CN/diethyl ether, yielding 77 mg (25%) of compound 75. MP=186° C. (DSC).

Conversion 17

Preparation of compound 78

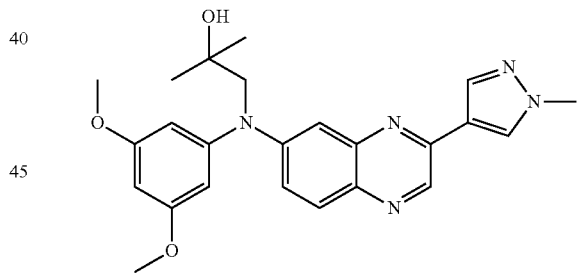

Iodomethane (0.5 mL, 8.0 mmol) was added very slowly to a suspension of Mg (0.196 g, 8.0 mmol) in diethyl ether (2 mL) at room temperature under N$_2$. When the Grignard reagent was started, diethyl ether (10 mL) was added and the reaction was stirred for 30 minutes. This mixture was added dropwise to a solution of compound 65 (0.240 g, 0.54 mmol) in THF (12 mL) at room temperature under N$_2$. The reaction mixture was refluxed for 2 hours, then cooled to room temperature. The mixture was poured into H$_2$O/NH$_4$Cl and extracted with EtOAc. The organic layer was dried (MgSO$_4$), filtered and evaporated to dryness to afford a crude residue (0.248 g) which was purified by super critical fluid chromatography (CYANO 6 μm 150×21.1 mm; mobile phase, 0.3% isopropylamine, 7% MeOH, 93% CO$_2$). The pure fractions were evaporated yielding 90 mg of compound 78 which was crystallized in Et$_2$O to afford 57 mg (24%) of compound 78. MP=162° C. (DSC).

Conversion 18
Preparation of compound 79a

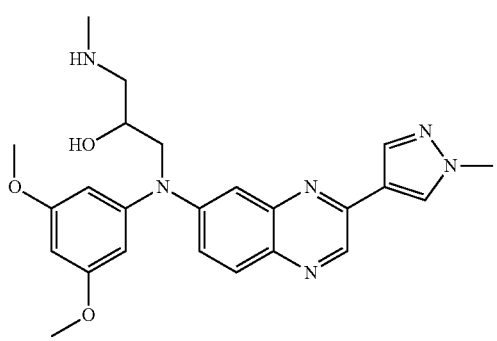 [SMILES: CNCC(O)CN(c1cc(OC)cc(OC)c1)c1ccc2ncc(-c3cnn(C)c3)nc2c1]

and compound 79

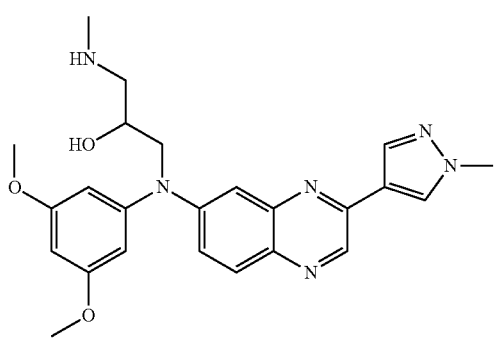 [SMILES: CNCC(O)CN(c1cc(OC)cc(OC)c1)c1ccc2ncc(-c3cnn(C)c3)nc2c1]

as a HCl salt

A mixture of compound 76 (0.505 g; 1.21 mmol) and methylamine in 2M THF (6.05 mL, 12.1 mmol) in DMF (8 mL) was heated at 100° C. for 15 hours in a sealed vessel, cooled to room temperature and poured into H₂O and K₂CO₃, extracted with EtOAc. The organic layer was dried (MgSO₄), filtered and evaporated to dryness. The residue was purified by chromatography over silica gel (Irregular SiOH, 15-40 µm 30 g MERCK; mobile phase, gradient from 100% DCM to 90% DCM, 10% MeOH, 0.1% NH₄OH). The pure fractions were evaporated yielding 0.406 g (75%) of compound 79a which was dissolved in diisopropyl alcohol. HCl (5 to 6N) was added. The mixture was stirred for 30 minutes, evaporated to dryness. Then the residue was crystallized in Et₂O, yielding 0.4 g (62%) of compound 79. MP=224° C. (DSC).

Conversion 19
Preparation of compound 80

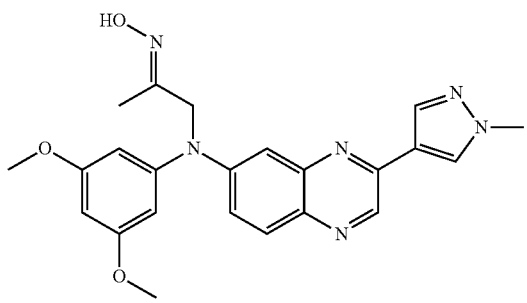

(E-isomer) and compound 81

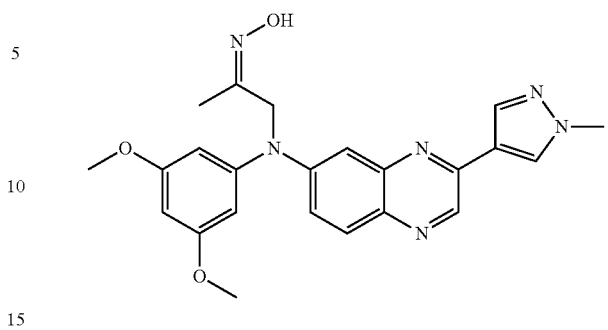

(Z-isomer)

Hydroxylamine hydrochloride (0.043 g, 0.62 mmol) was added to a solution of compound 82 (0.13 g, 0.31 mmol) and pyridine (0.13 mL) in EtOH (4 mL) at room temperature. The mixture was stirred at room temperature overnight. The reaction was poured out into ice water and EtOAc was added. The organic layer was separated, washed with brine, dried (MgSO₄), filtered and the solvent was evaporated. The residue was purified by chromatography over silica gel (Spherical SiOH, 10 µm, 60 g PharmPrep MERCK; mobile phase, 0.1% NH₄OH, 98% DCM, 2% MeOH). Two different residues were collected and the solvent was evaporated for each of them. The first residue was crystallized from DIPE/CH₃CN (90/10). The precipitate was filtered and dried under vacuum, yielding 0.087 g (64%) of compound 80 (E-isomer). MP=144° C. (Kofler).

The second residue (0.068 g) was crystallized from DIPE/CH₃CN (90/10). The precipitate was filtered and dried under vacuum, yielding 0.051 g (38%) of compound 81 (Z-isomer). MP=199° C. (Kofler).

Conversion 20
Preparation of compound 83

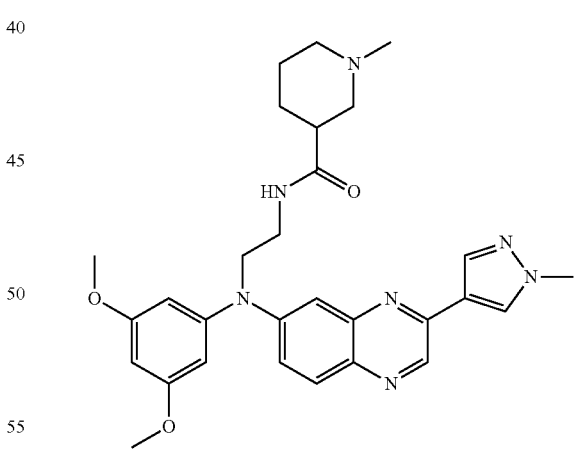

N3-(ethylcarbonimidoyl)-N1,N1-dimethyl-1,3-propanediamine hydrochloride (1:1) (129 mg; 0.83 mmol) was added to a solution of compound 84 (223 mg; 0.55 mmol), 1-methyl-3-piperidinecarboxylic acid hydrochloride (1:1) (148.8 mg; 0.82 mmol), 1-hydroxybenzotriazole (112 mg; 0.615 mmol), 4-methylmorpholine (182 µl; 1.66 mmol) in DMF (8 mL) at room temperature. The reaction mixture was stirred for 24 hours, then poured into H₂O/K₂CO₃ and extracted with EtOAc. The organic layer was dried (MgSO₄), filtered and evaporated to dryness. The residue was purified by chromatography over silica gel (Spherical SiOH, 10 µm, 60 g PharmPrep MERCK; mobile phase, 0.5% NH4OH, 97% DCM, 3% MeOH). The product fractions were collected and the solvent was evaporated. The residue was crystallized in diethyl ether, yielding 122 mg (42%) of compound 83. MP 142° C. (DSC).

Conversion 21

Preparation of compound 8

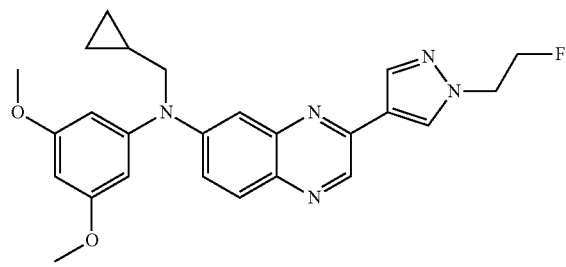 [SMILES: COc1cc(OC)cc(N(CC2CC2)c2ccc3ncc(-c4cnn(CCF)c4)nc3c2)c1]

At 0° C., under N2, diethylaminosulfur trifluoride (0.224 mL, 1.68 mmol) in DCM (2 mL) was added dropwise to a solution of compound 56 (0.250 g, 0.56 mmol) in DCM (4 mL). The mixture was stirred overnight at room temperature. An aqueous solution of K2CO3 (10%) was added. The mixture was extracted with DCM. The organic layer was separated, dried (MgSO4), filtered and the solvent was evaporated. The residue (246 mg) was purified by chromatography over silica gel (Sunfire Silica 5 µm 150×30.0 mm; mobile phase, gradient from 0% NH4OH, 100% DCM, 0% MeOH to 0.3% NH4OH, 97% DCM, 3% MeOH). The pure fractions were collected and evaporated to dryness. The residue (58 mg) was crystallized with DIPE, filtered and dried, yielding 36 mg (14%) of compound 85.

Conversion 22

Preparation of compound 86

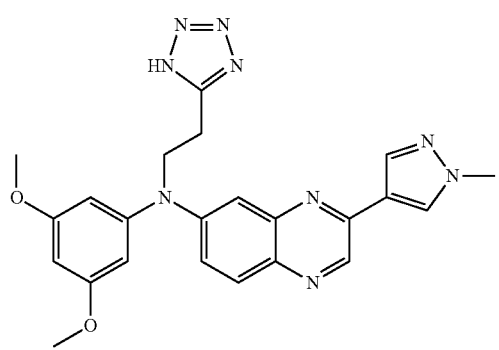 [SMILES: COc1cc(OC)cc(N(CCc2nnn[nH]2)c2ccc3ncc(-c4cnn(C)c4)nc3c2)c1]

A mixture of compound 122 (0.5 g, 1.21 mmol), sodium azide (0.235 g, 3.62 mmol), ammonium chloride (194 mg; 3.62 mmol) in N,N-dimethylformamide (10 mL) was heated at 140° C. for 72 hours. The reaction mixture was cooled to room temperature and poured out into ice water. EtOAc was added and the organic layer was separated. The aqueous layer was acidified with HCl 3N. EtOAc was added and the mixture was stirred. The organic layer was separated, dried (MgSO4), filtered and the solvent was evaporated. The residue (0.42 g) was purified by chromatography over silica gel (Spherical SiOH, 10 µm, 60 g PharmPrep MERCK; mobile phase, 93% DCM, 7% MeOH). The product fractions were collected and the solvent was evaporated. The residue (0.110 g, 20%) was crystallized from diethyl ether/CH3CN, filtered and dried under vacuum at 60° C., yielding 0.070 g (12%) of compound 86. MP=196° C. (DSC).

Conversion 23

Preparation of compound 87

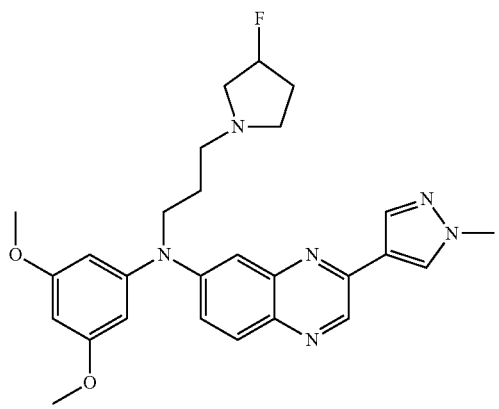 [SMILES: COc1cc(OC)cc(N(CCCN2CCC(F)C2)c2ccc3ncc(-c4cnn(C)c4)nc3c2)c1]

Diethylaminosulfur trifluoride (276 µl; 2.25 mmol) was added dropwise to a solution of compound 88 (550 mg; 1.12 mmol) in DCM (14 mL) at 0° C. The reaction mixture was stirred at room temperature for 2 hours and was then poured into H2O/K2CO3. The organic layer was extracted, dried (MgSO4), filtered and evaporated to dryness. The residue (629 mg) was purified by chromatography over silica gel (Spherical SiOH, 10 µm, 60 g PharmPrep MERCK; mobile phase, 0.5% NH4OH, 97% DCM, 3% MeOH). The product fractions were collected and the solvent was evaporated. The residue (100 mg) was purified by achiral super critical fluid chromatography on (2 ETHYLPYRIDINE 6 µm 150×21.2 mm; mobile phase, 0.3% 2-propylamine, 87% CO2, 13% MeOH). The product fractions were collected and the solvent was evaporated. The residue (0.08 g) was crystallized in Et2O yielding 72 mg (15%) of compound 87.

Conversion 24

Preparation of compound 89

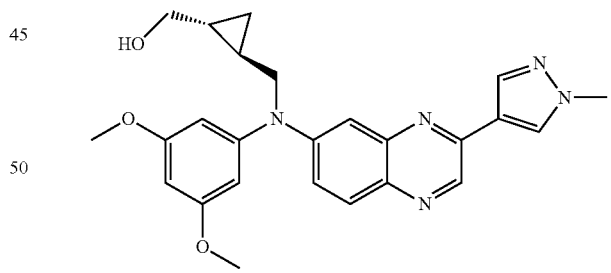

LiAlH4 (0.031 g, 0.82 mmol) was added portionwise to a mixture of compound 90 (0.2 g, 0.41 mmol) in THF (10 mL) at 5° C. under N2. The mixture was stirred at 5° C. for 3 hours. EtOAc followed by H2O was added dropwise to the mixture at −5° C. The suspension was passed through a short pad of celite. The organic layer was separated, dried (MgSO4), filtered and the solvent was evaporated. The residue was purified by chromatography over silica gel (Sunfire Silica 5 µm 150×30.0 mm; mobile phase, gradient from 0% NH4OH, 100% DCM, 0% MeOH to 0.8% NH4OH, 92% DCM, 8% MeOH). The pure fractions were collected and the solvent was evaporated. The residue was crystallized from DIPE. The precipitate was filtered and dried under vacuum, yielding 73 mg (40%) of compound 89. MP=126° C. (DSC).

Conversion 25

Preparation of compound 91

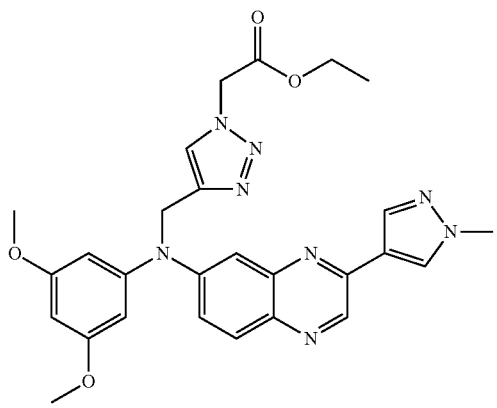 [SMILES: CCOC(=O)Cn1cc(CN(c2cc(OC)cc(OC)c2)c2ccc3ncc(-c4cnn(C)c4)nc3c2)nn1]

Copper(I) iodide (52.697 mg, 0.28 mmol), then N,N-diisopropylethylamine (0.829 mL, 4.75 mmol) were added at 5° C. to a solution of compound 38 (1.105 g, 2.78 mmol) and ethyl azidoacetate (1.38 mL, 5.53 mmol) in THF (35 mL). The reaction mixture was stirred at room temperature for 18 hours. The mixture was quenched with water and extracted with EtOAc. The organic layer was decanted, dried ($MgSO_4$), filtered and evaporated to dryness. The residue was purified by chromatography over silica gel (Irregular SiOH, 15-40 μm, 300 g MERCK; mobile phase, 0.1% $NH_4OH$, 97% DCM, 3% MeOH). The fractions were collected yielding 430 mg of residue which was further purified by achiral super critical fluid chromatography on (AMINO 6 μm 150×21.2 mm; mobile phase, 0.3% 2-propylamine, 90% $CO_2$, 10% MeOH). The pure fractions were collected and evaporated to dryness yielding two fractions.

The first fraction (90 mg) was crystallized from $CH_3CN$/DiPE. The precipitate was filtered off and dried yielding 74 mg (5%) of compound 91, MP=88° C. (DSC). The second fraction yielded 360 mg (25%) of compound 91.

Conversion 26

Preparation of compound 92

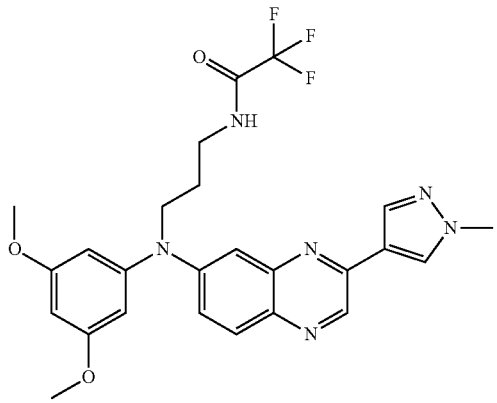 [SMILES: COc1cc(OC)cc(N(CCCNC(=O)C(F)(F)F)c2ccc3ncc(-c4cnn(C)c4)nc3c2)c1]

Compound 93 (740 mg, 1.77 mmol), $Et_3N$ (0.54 mL, 3.89 mmol) and trifluoroacetic anhydride (0.37 mL, 2.65 mmol) in THF (25 mL) were stirred at room temperature overnight. The reaction mixture was poured into water and extracted with DCM. The organic layer was washed with an aqueous solution of $K_2CO_3$(10%), then with water, then dried ($MgSO_4$), filtered and evaporated to dryness. The residue (800 mg) was purified by chromatography over silica gel (Irregular SiOH, 15-40 μm, 30 g; mobile phase, 0.2% $NH_4OH$, 98% DCM, 2% MeOH). The product fractions were collected and the solvent was evaporated. The residue (730 mg) was crystallized from diethyl ether/DIPE to give 465 mg (51%) of compound 92. MP=139° C. (DSC).

Conversion 27

Preparation of compound 300

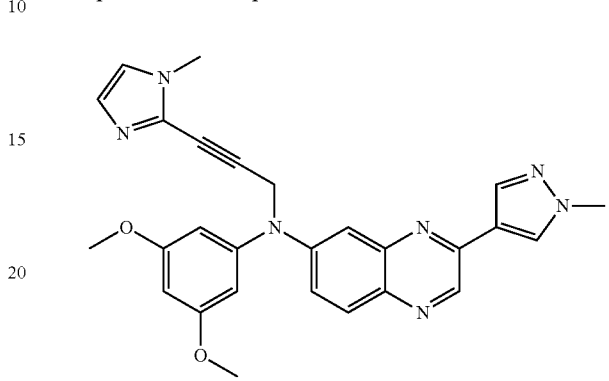

A suspension of compound 38 (1.38 g; 3.46 mmol), 2-iodo-1-methyl-1H-imidazole (0.45 g; 2.16 mmol) and $Et_3N$ (3.0 mL; 21.6 mmol) in DMSO (25 mL) was degassed under $N_2$. Dichlorobis(triphenylphosphine)-palladium (304 mg; 0.43 mmol) and copper(I) iodide (41 mg; 0.22 mmol) were added and the reaction mixture was stirred at 90° C. for 1.5 hours. The reaction mixture was cooled to room temperature, poured onto water and extracted with EtOAc. The organic layer was decanted, washed with brine, dried ($MgSO_4$), filtered and evaporated to dryness. The residue was purified by chromatography over silica gel (Irregular SiOH, 15-40 μm, 300 g MERCK; mobile phase, 0.4% $NH_4OH$, 96% DCM, 4% MeOH). The pure fractions were collected and evaporated to dryness. The residue (780 mg) was then purified by achiral super critical fluid chromatography on (2 AMINO 6 μm 150×21.2 mm; mobile phase, 0.3% 2-propylamine, 80% $CO_2$, 20% MeOH). The pure fractions were collected and evaporated to dryness, yielding 430 mg (41%) of compound 300. This fraction was taken up with $CH_3CN$. The precipitate was filtered off and dried yielding 377 mg (36%) of compound 300. MP=192° C. (DSC).

Conversion 28

Preparation of compound 94

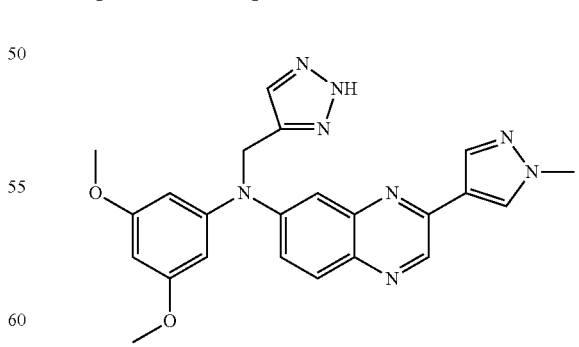

A mixture of compound 109 (2.5 g, 5.29 mmol) in NaOH 3M (7 mL) and THF (40 mL) was stirred at room temperature for 18 hours. The reaction mixture was quenched with a 10% solution of $NH_4Cl$ and EtOAc was added. The pH was adjusted to 4.5 by adding HCl 3N. The organic layer Conversion 29

Preparation of compound 95a

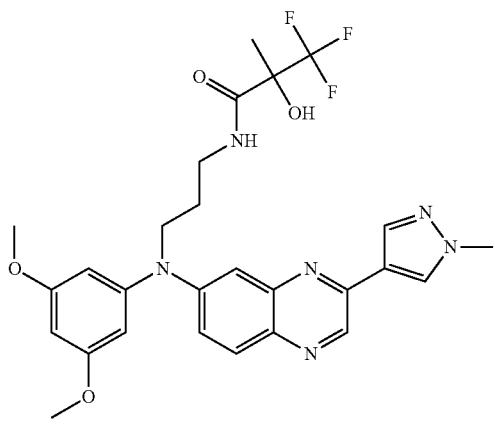 [SMILES: COc1cc(OC)cc(N(CCCNC(=O)C(C)(O)C(F)(F)F)c2ccc3ncc(-c4cnn(C)c4)nc3c2)c1]

and compound 95

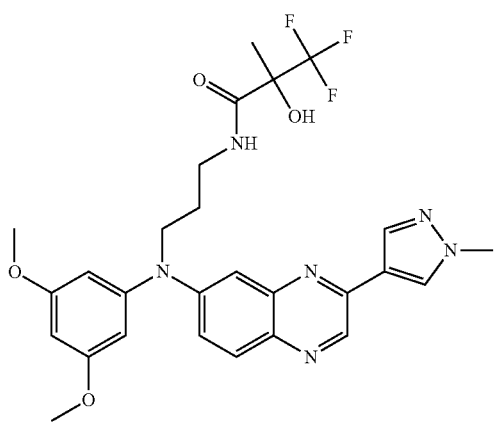 [SMILES: COc1cc(OC)cc(N(CCCNC(=O)C(C)(O)C(F)(F)F)c2ccc3ncc(-c4cnn(C)c4)nc3c2)c1]

as a HCl salt

A mixture of compound 93 (0.15 g, 0.36 mmol), 3,3,3-trifluoro-2-hydroxy-2-methylpropanoic acid (0.085 g, 0.54 mmol), N3-(ethylcarbonimidoyl)-N1,N1-dimethyl-1,3-propanediamine hydrochloride (1:1) (0.083 g, 0.54 mmol), 1-hydroxybenzotriazole (0.073 g, 0.54 mmol), Et$_3$N (0.075 mL, 0.54 mmol) in DCM (4 mL) was stirred at room temperature overnight. The reaction mixture was poured out into ice water and DCM was added. The organic layer was separated, washed with brine, dried (MgSO$_4$), filtered and the solvent was evaporated. The residue (0.250 g) was purified by chromatography over silica gel (Spherical SiOH, 10 μm, 60 g PharmPrep MERCK; mobile phase, 0.1% NH$_4$OH, 98% DCM, 2% MeOH). The product fractions were collected and the solvent was evaporated. The compound 95a was dissolved in CH$_3$CN, cooled to 5° C. and a solution of HCl 5N/iPrOH (0.3 mL) was added dropwise. The mixture was evaporated till dryness at room temperature. The mixture was taken up with diethyl ether, then the precipitate was filtered off and dried under vacuum at 60° C., yielding 0.172 g (80%) of compound 95.

Conversion 30

Preparation of compound 96

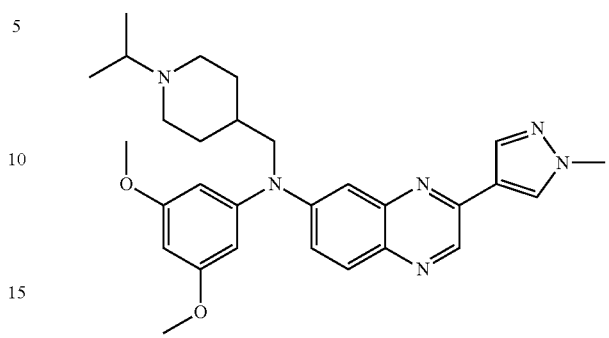

Acetone (0.322 mL, 4.361 mmol) was added to a solution of compound 70 (0.2 g, 0.436 mmol) in MeOH (5 mL) and THF (5 mL) at room temperature. Then sodium cyanoborohydride (0.055 g, 0.872 mmol) was added and the mixture was stirred at room temperature overnight. Acetone (0.129 mL, 1.745 mmol) and sodium cyanoborohydride (0.055 g, 0.872 mmol) were added and the mixture was stirred at room temperature for the weekend. The mixture was poured out into ice, then the organic layer was extracted with DCM, dried (MgSO$_4$), filtered off and evaporated till dryness. The residue (254 mg) was purified by chromatography over silica gel (Irregular SiOH, 15-40 μm, 300 g Merck; mobile phase, gradient from 100% DCM to 90% DCM, 10% CH$_3$OH, 0.1% NH$_4$OH). The pure fractions were collected and evaporated to dryness. The product (236 mg) was crystallized with DIPE, filtered and dried, yielding 186 mg (85%) of compound 96. MP=168° C. (DSC).

Conversion 31

Preparation of compound 97

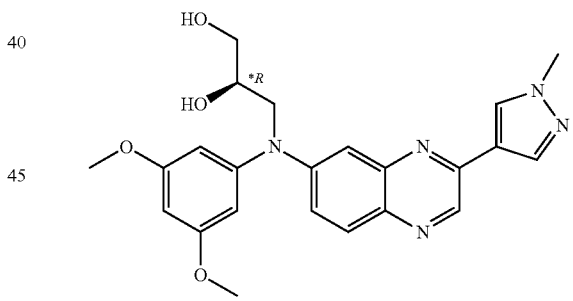

and compound 98

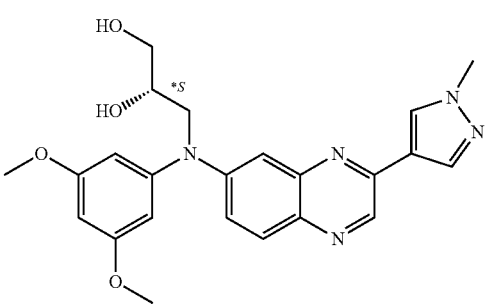 [SMILES: COc1cc(OC)cc(N(C[C@H](O)CO)c2ccc3ncc(-c4cnn(C)c4)nc3c2)c1]

*means relative stereochemistry

The enantiomers of compound 75 (5.4 g) were separated by chiral super critical fluid chromatography (CHIRALPAK AD-H 5 μm 250×20 mm; mobile phase, 0.3% 2-propylamine, 40% $CO_2$, 60% MeOH). The desired product fractions were collected and the solvent was evaporated. The first eluted enantiomer (2.1 g) was crystallized in diethyl ether, yielding 1.965 g (36%) of compound 97 (R*, MP=188° C. (DSC)). The second enantiomer (2.1 g) was crystallized in diethyl ether, yielding 2 g (37%) of compound 98 (S*, MP=186° C. (DSC).

Conversion 32

Preparation of compound 99

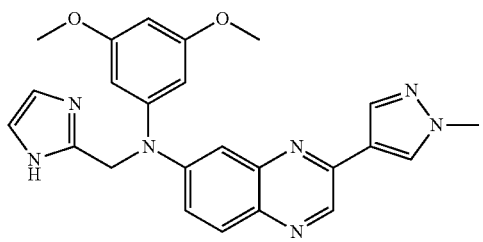

A mixture of compound 100 (0.5 g, 0.91 mmol) in HCl 4M in dioxane (2 mL) and $CH_3CN$ (10 mL) was heated at 50° C. overnight. The mixture was poured out into ice, basified with (10 mL) was heated at 50° C. overnight. The mixture was poured out into ice, basified with $K_2CO_3$ and extracted with DCM. The organic layer was dried ($MgSO_4$), filtered and evaporated till dryness to give 0.4 g (99%) of compound 99.

Conversion 33

Preparation of compound 101

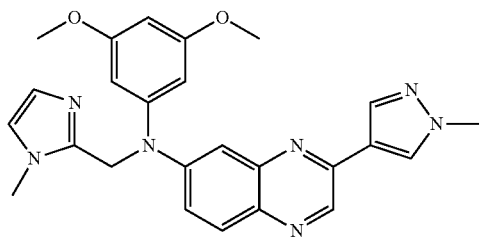 [SMILES: COc1cc(OC)cc(N(Cc2nccn2C)c2ccc3ncc(-c4cnn(C)c4)nc3c2)c1]

Sodium hydride (0.054 g, 1.36 mmol) was added portionwise to a solution of compound 99 (0.4 g, 0.9 mmol) in DMF (4 mL) at 5° C. under $N_2$ flow. The reaction mixture was stirred at 5° C. for 1 hour, then iodomethane (68 μL, 1.09 mmol) was added dropwise at 5° C. under $N_2$ flow. The reaction mixture was stirred for 1 hour at 5° C., then at room temperature overnight. The reaction was poured out into ice and extracted with EtOAc. The organic layer was washed with brine, dried ($MgSO_4$), filtered and evaporated till dryness. The residue (0.71 g) was purified by chromatography over silica gel (Sunfire Silica 5 μm 150×30.0 mm; mobile phase, gradient from 0.2% $NH_4OH$, 98% DCM, 2% MeOH to 0.8% $NH_4OH$, 92% DCM, 8% MeOH). The pure fractions were evaporated till dryness. The residue was crystallized from diethyl ether and dried, yielding 0.172 g (42%) of compound 101. MP=186° C., (Kofler).

Conversion 34

Preparation of compound 102

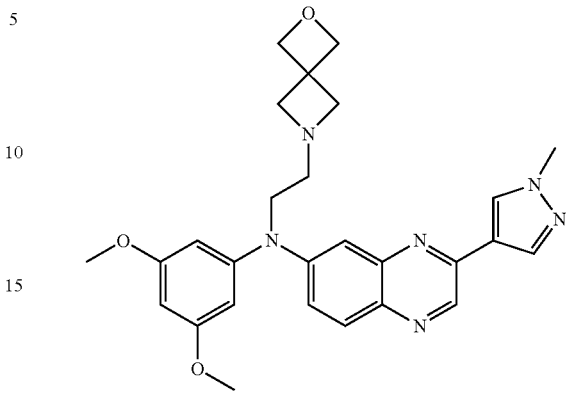

3,3-Bis(bromomethyl)oxetane (1.592 g, 6.52 mmol) was added to compound 84 (2.2 g, 5.44 mmol) and sodium carbonate (0.961 g, 9.1 mmol) in 1,4-dioxane (80 mL) at room temperature. The reaction mixture was stirred at reflux for 7 days, then cooled to room temperature. The mixture was filtered. The filtrate was concentrated under reduced pressure. The residue was purified by chromatography over silica gel (mobile phase, gradient from 99% DCM, 1% of a solution of $NH_3$ in MeOH to 97.5% DCM, 2.5% of a solution of $NH_3$ in MeOH). The pure fractions were collected and concentrated under reduced pressure, yielding 880 mg (33%) of compound 102.

Conversion 35

Preparation of compound 103

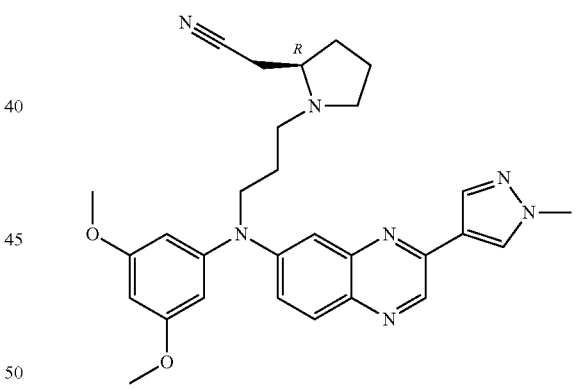

as a HCl salt

Sodium cyanide (0.094 g, 1.92 mmol) was added portionwise to a solution of compound 104 (0.5 g, 0.96 mmol) in EtOH (10 mL) and $H_2O$ (3 mL) at room temperature. The reaction mixture was heated at 60° C. overnight. The reaction mixture was cooled to room temperature and poured out into ice water. EtOAc was added and the solution was basified with an aqueous solution of $K_2CO_3$ (10%). The organic layer was separated, washed with brine, dried ($MgSO_4$), filtered and the solvent was evaporated. The residue (0.63 g) was purified by chromatography over silica gel (Spherical SiOH, 10 μm 60 g PharmPrep MERCK; mobile phase 0.1% $NH_4OH$, 98% DCM, 2% MeOH). The pure fractions were collected and the solvent was evaporated, yielding 0.37 g of compound (75%). This compound was further purified by chiral super critical fluid chromatography on (CHIRALPAK AD-H 5 μm 250×20 mm; mobile phase, 0.3% 2-propylamine, 60% EtOH, 40% CO$_2$). The desired product fractions were collected and the solvent was evaporated. The residue (0.240 g, 49%) was dissolved in CH$_3$CN and cooled at 5° C. A solution of HCl 5N/i-PrOH (0.28 mL) was added dropwise at 5° C. The solution was evaporated till dryness. The residue was triturated with diethyl ether, filtered and dried under vacuum at 60° C., yielding 0.250 g (42%) of compound 103.

Preparation of compound 105

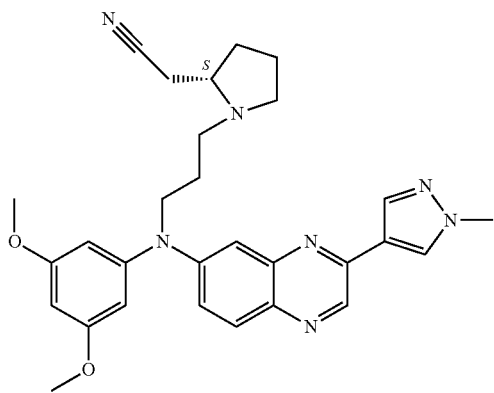

as a HCl salt a-1) Preparation of intermediate 63

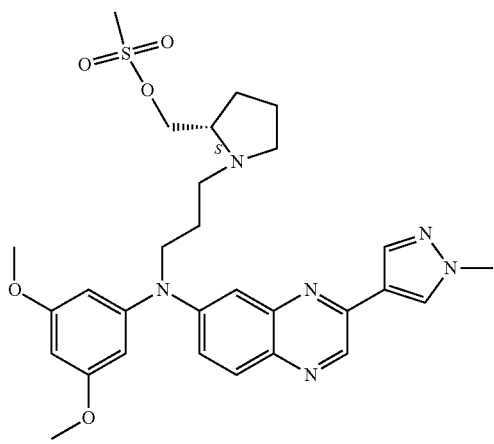

and compound 126

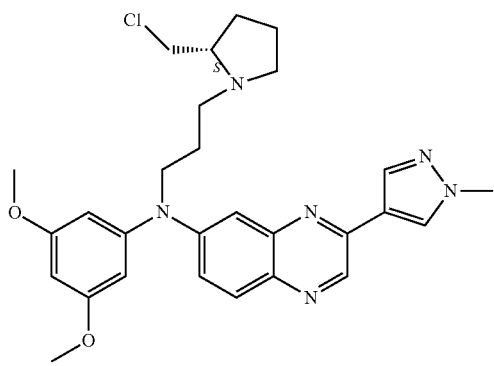

Methanesulfonyl chloride (0.18 mL; 2.31 mmol) was added dropwise to a solution of compound 108 (580 mg; 1.15 mmol), Et$_3$N (0.4 mL; 2.88 mmol) in DCM (10 mL) at 5° C. under N$_2$ flow. The reaction mixture was stirred at 5° C. for 2 hours. The reaction mixture was poured out into ice water and DCM was added. The organic layer was separated, dried (MgSO$_4$), filtered and the solvent was evaporated, yielding 0.65 g (97%) of intermediate 63 and compound 126.

a-2) Sodium cyanide (0.110 g, 2.24 mmol) was added portionwise to a solution of intermediate 63 (0.65 g, 1.12 mmol) in EtOH (10 mL) and H$_2$O (3 mL) at room temperature. The reaction mixture was heated at 60° C. overnight. The reaction mixture was cooled to room temperature and poured out into ice water. EtOAc was added and the solution was basified with an aqueous solution of K$_2$CO$_3$ (10%). The organic layer was separated, washed with brine, dried (MgSO$_4$), filtered and the solvent was evaporated. The residue (was purified by chromatography over silica gel (Sunfire Silica 5 μm 150×30.0 mm; mobile phase, gradient from 0% NH$_4$OH, 100% DCM to 0.5% NH$_4$OH, 95% DCM, 5% MeOH). The fractions were collected and the solvent was evaporated. The residue was further purified by chiral super critical fluid chromatography (CHIRALPAK AD-H 5 μm 250×20 mm; mobile phase, 0.3% 2-propylamine, 40% EtOH, 60% CO$_2$). The product fractions were collected and the solvent was evaporated. The residue (0.220 g, 38%) was dissolved from CH$_3$CN and cooled at 5° C. A solution of HCl 5N/iPrOH (0.258 mL) was added dropwise at 5° C. and the mixture was evaporated till dryness. The residue was triturated from diethyl ether, filtered and dried under vacuum at 60° C., yielding 0.215 g (32%) of compound 105.

Conversion 36

Preparation of compound 109

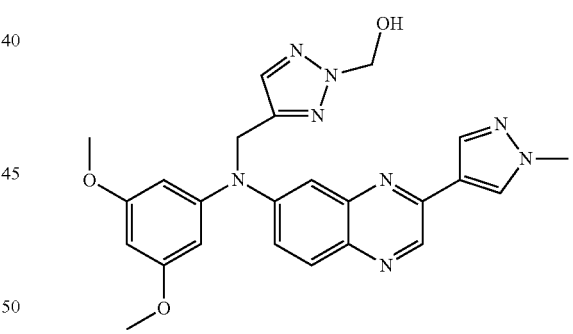

Sodium azide (84.1 mg, 1.29 mmol) was added at 5° C. to a solution of formaldehyde (0.65 mL, 8.62 mmol) and HOAc (74 μl, 1.29 mmol) in dioxane (1.5 mL). The reaction mixture was stirred for 15 minutes and a solution of compound 38 (310 mg, 0.78 mmol) in dioxane (1.5 mL) was added. The reaction mixture was stirred at 5° C. for 10 minutes, then sodium L-ascorbate (34 mg, 0.17 mmol) was added, followed by a solution of copper sulfate in water (0.53 mL, 0.043 mmol). The reaction mixture was allowed to warm to room temperature and stirred for 3 hours. Water was added and the reaction mixture was extracted with EtOAc. The organic layer was decanted, washed with brine, dried (MgSO$_4$), filtered and evaporated to dryness, yielding 367 mg (100%) of compound 109.

Conversion 37

Preparation of compound 110

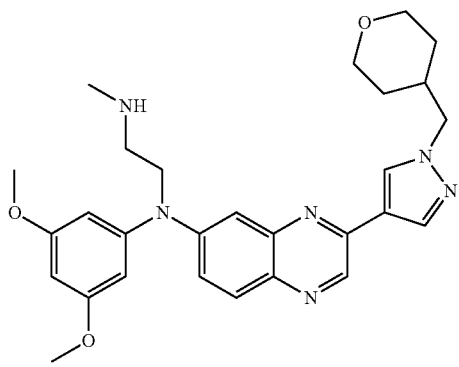 [SMILES: CNCCN(c1cc(OC)cc(OC)c1)c1ccc2ncc(-c3cnn(CC4CCOCC4)c3)nc2c1]

To a solution of compound III (prepared according to conversion 5a reaction from compound 129) (170 mg, 0.29 mmol) in DCM (20 mL) was added 1-chloroethyl chloroformate (37 µl, 0.34 mmol) and the reaction was stirred at room temperature for 90 minutes. The solvent was removed under reduced pressure. To the residue was added MeOH (20 mL) and the solution was heated to 40° C. for 1 hour. The reaction mixture was cooled to room temperature and evaporated under reduced pressure to yield a red solid. The residue (170 mg) was purified by chromatography over silica gel (Hyperprep C18 HS BDS100 A 8 mu (Shandon); mobile phase, gradient from 80% of a 0.5% solution of ammonium carbonate in water, 20% MeOH to 20% of a 0.5% solution of ammonium carbonate in water, 80% MeOH). The product fractions were collected and the solvent was evaporated, yielding 64 mg (44%) of compound 110.

Conversion 38

Preparation of compound 82

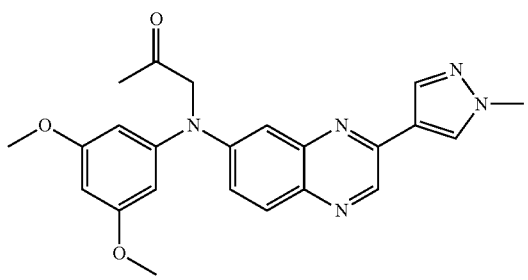

Dess-martin periodinane (5.16 mL, 1.55 mmol) was added dropwise at 0° C. to compound 113 (0.59 g, 1.41 mmol) in DCM (10 mL) under $N_2$ flow. The mixture was stirred at room temperature for 2 hours, poured out into ice and basified with an aqueous solution of $K_2CO_3$ (10%). The organic layer was extracted with DCM, dried ($MgSO_4$), filtered off and evaporated till dryness. The residue was purified by chromatography over silica gel (Irregular SiOH, 15-40 µm; mobile phase, gradient from 98% DCM/2% MeOH to 95% DCM/5% MeOH). The pure fractions were collected and the solvent was evaporated yielding 0.47 g (65%) of compound 82.

Conversion 39

Preparation of compound 114

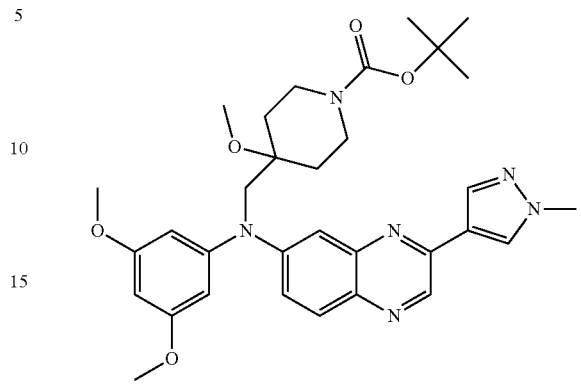

Sodium hydride (104 mg; 2.61 mmol) was added portionwise to a solution of compound 115 (500 mg; 0.87 mmol) in N,N-dimethylformamide (8 mL) at 5° C. under $N_2$ flow. The reaction mixture was stirred at 5° C. for 1 hour, then a solution of iodomethane (0.16 mL; 2.61 mmol) was added dropwise at 5° C. The reaction mixture was stirred overnight at room temperature. The reaction was poured out into ice water and EtOAc was added. The organic layer was separated, washed with brine, dried ($MgSO_4$), filtered and the solvent was evaporated. The obtained residue (0.55 g) was purified by chromatography over silica gel (Irregular SiOH, 15/40 µm, 30 g; mobile phase, gradient from 100% DCM to 96% DCM, 4% MeOH. The product fractions were collected and the solvent was evaporated, yielding 0.39 g (76%) of compound 114.

Conversion 40

Preparation of compound 116

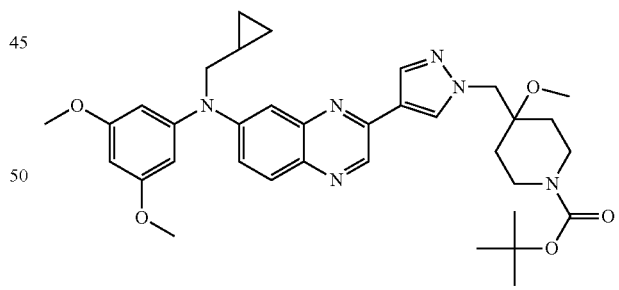

Sodium hydride (0.066 g, 1.66 mmol) was added portionwise to a solution of compound 117 (0.51 g, 0.83 mmol) in N,N-dimethylformamide (10 mL) at 5° C. under $N_2$ flow. The mixture was stirred for 1 hour at 5° C., then iodomethane (0.103 mL, 1.66 mmol) was added portionwise at 5° C. The reaction mixture was stirred for 1 hour at 5° C., then warmed to room temperature. The mixture was stirred at room temperature overnight. The mixture was poured out into ice water and EtOAc was added. The organic layer was separated, dried ($MgSO_4$), filtered and the solvent was evaporated. The residue was purified by chromatography over silica gel (Irregular SiOH, 15/40 μm, 30 g MERCK; mobile phase, gradient from 100% DCM to 98% DCM, 2% MeOH). The product fractions were collected and the solvent was evaporated, yielding 0.400 g (76%) of compound 116.

Conversion 41 a) Preparation of Compound 118

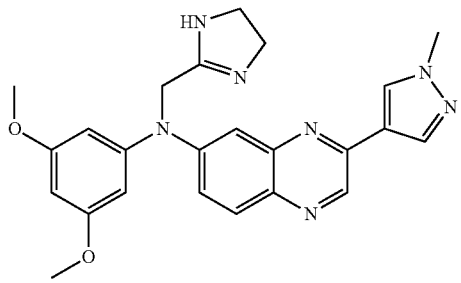 [SMILES: COc1cc(OC)cc(N(CC2=NCCN2)c2ccc3ncc(-c4cnn(C)c4)nc3c2)c1]

To a stirred mixture of ethylenediamine (0.226 mL, 3.38 mmol) and dry toluene (15 mL) cooled on an ice bath and under nitrogen was added dropwise trimethylaluminium in heptane (1M, 4 mL, 4 mmol). The mixture was stirred at room temperature for 60 minutes and then compound 65 (300 mg, 0.670 mmol) in dry toluene (7 mL) was added. The mixture was heated to reflux for 3 hours and was then allowed to cool to room temperature. MeOH (50 mL) was added cautiously. The mixture was stirred at room temperature for 5 minutes and then filtered through Celite. The organic layers were concentrated and purified over chromatography over silica gel. The desired fractions were collected and the solvent evaporated, yielding compound 118 ((4,5-dihydro-1H-imidazol-2-ylmethyl)-(3,5-dimethoxy-phenyl)-[3-(1-methyl-1H-pyrazol-4-yl)-quinoxalin-6-yl]-amine) (100 mg).

b) Preparation of Compound 119

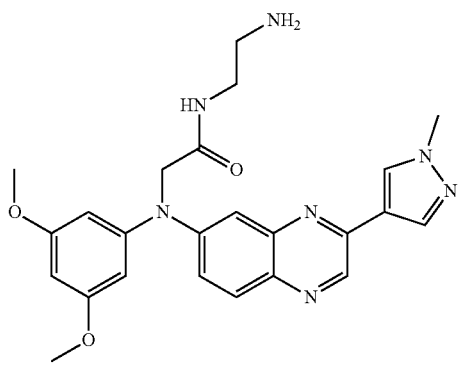 [SMILES: COc1cc(OC)cc(N(CC(=O)NCCN)c2ccc3ncc(-c4cnn(C)c4)nc3c2)c1]

Compound 118 was heated to 100° C. in aqueous sodium hydroxide (2N, 5 mL) overnight to promote the ring opening reaction. 1,4-dioxane was added (5 mL) and the reaction was continued for a further 10 hours at 100° C. The reaction was allowed to cool and was extracted with EtOAc (2×). The organic layers were dried (MgSO$_4$) and concentrated. Hydrochloric acid in MeOH was added and the product was precipitated with diethyl ether. The bright red solid was isolated by filtration and was dried in a vacuum oven to give compound 119 (N-(2-Amino-ethyl)-2-{(3,5-dimethoxy-phenyl)-[3-(1-methyl-1H-pyrazol-4-yl)-quinoxalin-6-yl]-amino}-acetamide) (80 mg).

Conversion 42

Preparation of compound 120

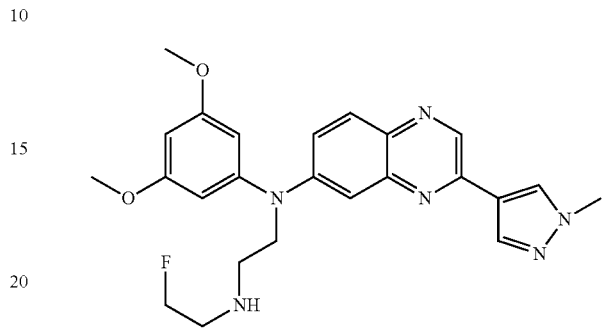

To a solution of compound 84 (36 mg, 0.89 mol, 1 equiv.) in dioxane (3 mL) and DMF (1.5 mL) was added 1-iodo-2-fluoroethane (16 mg, 0.89 mmol) and K$_2$CO$_3$ (25 mg, 1.78 mmol). The reaction mixture was heated to 90° C. for 5.5 hours and a further amount of DMF was added (1.5 mL) and the reaction mixture was heated to 100° C. for 1.5 hour. The solvents were removed under reduced pressure and the reaction mixture was partitioned between EtOAc and water. The layers were separated, dried (MgSO$_4$) and concentrated under reduced pressure. The crude mixture was purified by HPLC to give compound 120 (17 mg).

Conversion 43

Preparation of compound 124

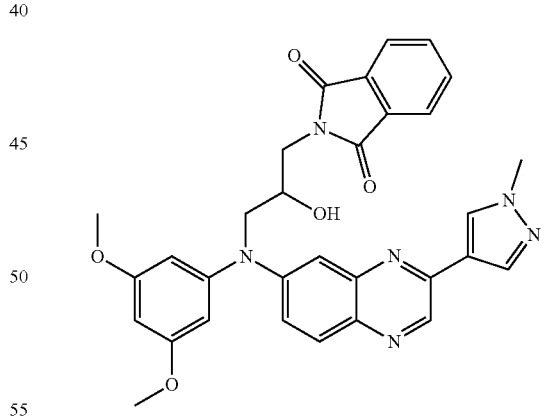

A solution of compound 76 (0.254 g; 0.608 mmol), potassium phthalimide (0.68 g, 3.65 mmol) in N-methyl-pyrrolidone (5 mL) was heated under microwave irradiation for 1.5 hour at 150° C. The solution was cooled and the mixture was poured into cooled water. The product was extracted with EtOAc. The organic layer was washed with H$_2$O, dried (MgSO$_4$), filtered and evaporated to dryness to give compound 124 used without further purification for the next step.

Conversion 44

Preparation of compound 125

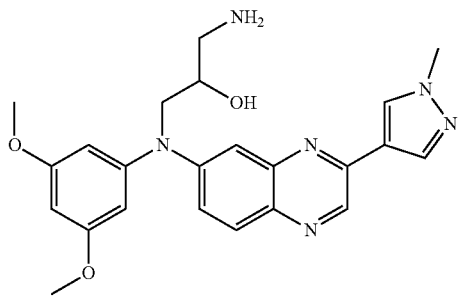 [SMILES: COc1cc(OC)cc(N(CC(O)CN)c2ccc3ncc(-c4cnn(C)c4)nc3c2)c1]

Compound 124 was heated in EtOH (20 mL) with hydrazine monohydrate (0.57 mL; 18.25 mmol) at 80° C. for 5 hours. The mixture was cooled to room temperature, evaporated and the residue was poured into water. The organic layer was extracted with DCM, washed with brine, dried (MgSO$_4$), filtered and evaporated to dryness to give 400 mg of crude product. The residue was purified by chromatography over silica gel (Spherical SiOH, 10 μm, 60 g, Pharm-Prep MERCK; mobile phase 0.5% NH$_4$OH, 95% DCM, 5% MeOH). The pure fractions were collected and evaporated to give 140 mg (53%) of compound 125. MP=99° C. (DSC).

Conversion 45

Preparation of compound 606

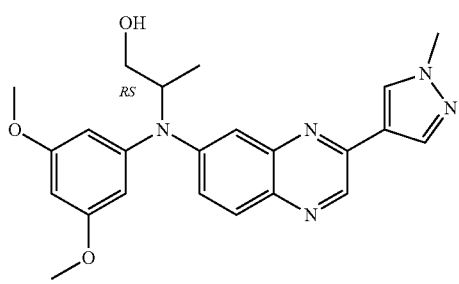 [SMILES: COc1cc(OC)cc(N(c2ccc3ncc(-c4cnn(C)c4)nc3c2)C(C)CO)c1]

A solution of compound 605 (5.3 g; 11.55 mmol) in THF dry (105 mL) was added dropwise to a solution of lithium aluminium hydride (0.789 g; 20.79 mmol) in THF dry (105 mL) at 0° C. under a N$_2$ flow. The reaction mixture was stirred for 2 hours at 0° C. EtOAc was added dropwise to the reaction mixture, then water was added dropwise. The organic layer was separated, washed with brine, dried (MgSO$_4$), filtered and the solvent was evaporated to dryness. The residue (5 g) was purified by chromatography over silica gel (Irregular SiOH, 20-45 μm, 1000 g; mobile phase gradient from 0.1% NH$_4$OH, 97% DCM, 3% MeOH to 0.1% NH$_4$OH, 94% DCM, 6% MeOH). The pure fractions were collected and concentrated. The residue (4 g, 75%) was crystallized from DIPE. The precipitate was filtered off and dried under vacuum, yielding 3.5 g (65%) of the compound 606. MP: 97° C. (DSC)

Conversion 46

Preparation of compounds 608, 609, 610, 611

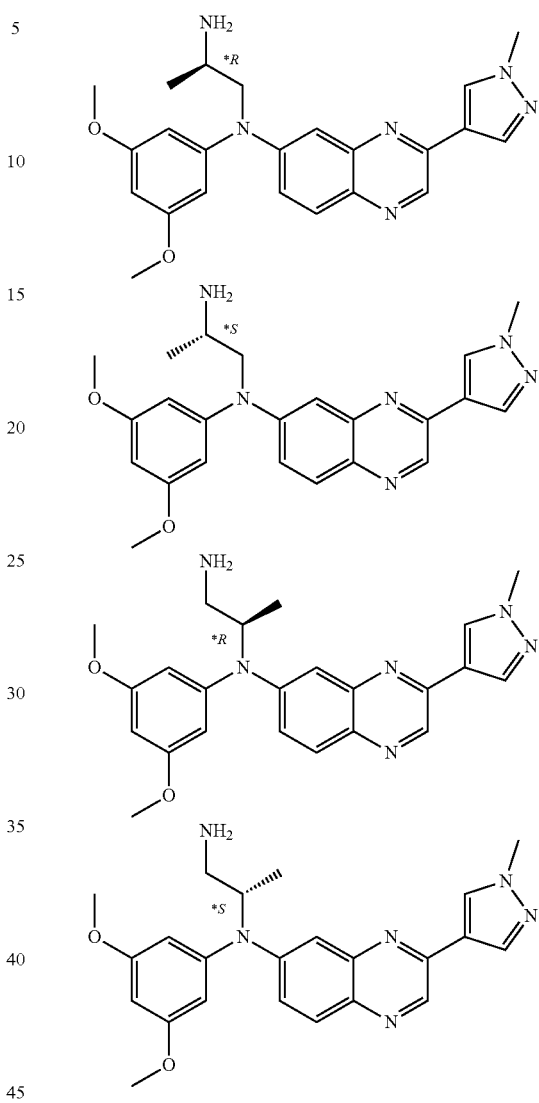

*means relative stereochemistry

Compound 607 (7.4 g; 6.74 mmol), hydrazine monohydrate (2.52 mL; 80.94 mmol) in EtOH (240 mL) was heated at 80° C. for 2 hours. The reaction mixture was cooled to room temperature and poured out into ice water. DCM was added and the organic layer was separated, washed with water, dried (MgSO$_4$), filtered and the solvent was evaporated until dryness. The residue (5.1 g) was purified by chromatography over silica gel (Irregular; SiOH 20-45 μm; 450 g; mobile phase 0.5% NH$_4$OH, 93% DCM, 7% MeOH). The product fractions were collected and the solvent was evaporated to give 1.1 g of fraction I=compound 896 (enantiomeric mixture) and 1.1 g of fraction II=compound 897 (enantiomeric mixture).

The enantiomers of fraction I and II were separated by chiral super critical fluid chromatography (CHIRALPAK AD-H 5 μm 250×20 mm; mobile phase, 0.3% 2-propylamine, 60% CO$_2$, 40% isopropanol). The desired product fractions were collected and the solvent was evaporated. The first eluted enantiomer of fraction I (0.52 g) was crystallized in CH$_3$CN, yielding 0.325 g (12%) of compound 608 (R*, MP=159° C. (DSC)). The second enantiomer of fraction I (0.53 g) was crystallized in CH₃CN, yielding 0.284 g (10%) of compound 609 (S*, MP=155° C. (DSC)).

The first eluted enantiomer of fraction II (0.47 g) was crystallized in CH₃CN/diethyl ether, yielding 0.327 g (12%) of compound 610 (R*, MP=150° C. (DSC)). The second enantiomer of fraction II (0.475 g) was crystallized in CH₃CN, yielding 0.258 g (9%) of compound 611 (S*, MP=148° C. (DSC)).

Conversion 47 a) Preparation of Compound 612

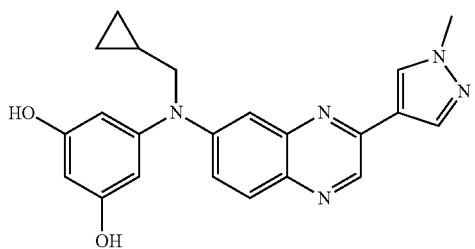 [SMILES: Cn1cc(-c2cnc3ccc(N(CC4CC4)c4cc(O)cc(O)c4)cc3n2)cn1]

Boron tribromide (11.55 mL; 11.55 mmol) was added dropwise to a solution of compound 202 in DCM (10 mL) at 0° C. The solution was allowed to rise slowly to room temperature and stirred for 3 days. The reaction was quenched with MeOH at 0° C. Then, a solution of saturated NH₃ was added to neutralize the reaction mixture. The reaction was poured out into ice water and EtOAc was added. The organic layer was separated, washed with brine, dried (MgSO₄), filtered and the solvent was evaporated. The residue (1 g) was purified by chromatography over silica gel (C18, 10 µm, 250 g, 5 cm; mobile phase 0.25% (NH₄)₂CO₃ solution in water, CH₃CN). The pure fractions were collected and concentrated to afford 0.160 g (22%) of compound 612.

b) Preparation of Compound 613

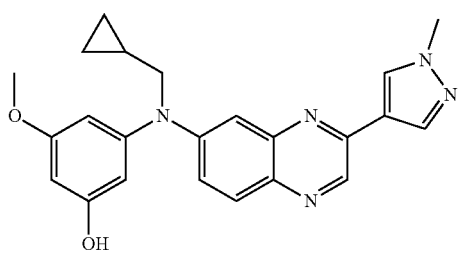 [SMILES: COc1cc(O)cc(N(CC2CC2)c2ccc3ncc(-c4cnn(C)c4)nc3c2)c1]

Potassium carbonate (0.057 g; 0.41 mmol) was added to a solution of compound 612 (0.080 g; 0.21 mmol) in N,N-dimethylformamide (15 mL). The reaction mixture was stirred at room temperature for 1 hour. Then methyl iodine (0.013 mL; 0.21 mmol) was added to the reaction mixture and stirred at room temperature for 4 days. The reaction mixture was concentrated under reduced pressure to approximately ⅓ of its initial volume. The residue was poured out into ice water and EtOAc was added. The organic layer was separated, washed with brine, dried (MgSO₄), filtered and the solvent was evaporated. The residue (0.05 g) was purified by chromatography over silica gel (RP Vydac Denali C18, 10 µm, 250 g, 5 cm; mobile phase 0.25% (NH₄)₂CO₃ solution in water, CH₃CN). The pure fractions were collected and concentrated. The residue (0.025 g) was separated by chiral super critical fluid chromatography (CHIRALPAK Diacel OJ-H 20×25 0 mm; mobile phase, CO₂, MeOH with 0.2% 2-propylamine). The desired product fractions were collected and the solvent was evaporated to give 0.007 g (9%) of compound 613.

Conversion 48

Preparation of compound 625

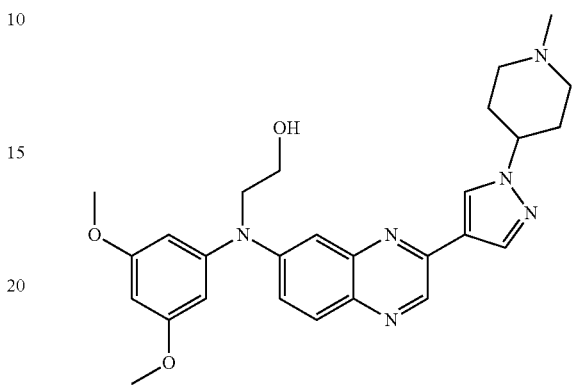

Iodomethane (0.096 mL; 1.54 mmol) was added to a solution of compound 624 (0.73 g; 1.54 mmol) and K₂CO₃ (0.213 g; 1.54 mmol) in CH₃CN (20 mL). The reaction mixture was stirred at 60° C. for 5 hours. The reaction mixture was poured out into ice water and EtOAc was added. The organic layer was separated, dried (MgSO₄), filtered and the solvent was evaporated. The residue (0.666 g) was purified by chromatography over silica gel (Spherical SiOH, 10 µm, 60 g; mobile phase gradient from 0.5% NH₄OH, 95% DCM, 5% MeOH to 1% NH₄OH, 90% DCM, 10% MeOH). The pure fractions were collected and concentrated to give 0.3 g (38%) of compound 625. MP: 156° C. (DSC).

Conversion 49 a) Preparation of Compound 626

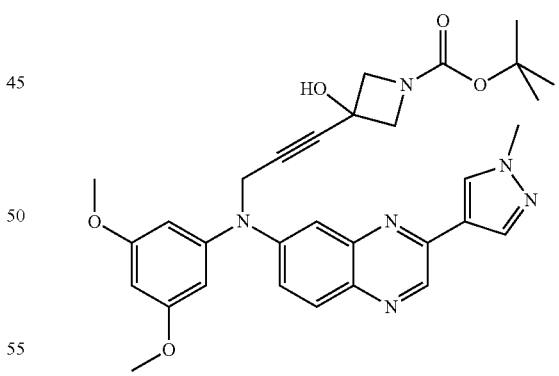

Compound 38 (2 g; 5.0 mmol) was dissolved in THF (80 mL), then the solution was cooled at −78° C. and n-butyl-lithium 1.6M in hexane (3.1 mL; 5.0 mmol) was added. The reaction mixture was allowed to slowly rise to −30° C. and stirred for 45 minutes. 1-Boc-azetidinone (0.715 g; 4.17 mmol) in THF (8 mL) was added to the reaction mixture at −78° C. and stirred for 1 hour, then the reaction mixture was allowed to rise to room temperature for 1 hour. The solution was poured out into ice water and NH₄Cl, EtOAc were added. The organic layer was separated, dried (MgSO₄), filtered and the solvent was evaporated. The residue (2.86 g) was purified by chromatography over silica gel (Irregular SiOH, 20-45 µm, 450 g; mobile phase 0.1% NH₄OH, 96% DCM, 4% MeOH). The pure fractions were collected and concentrated to give 0.343 g (15%) of compound 626.

b) Preparation of Compound 627

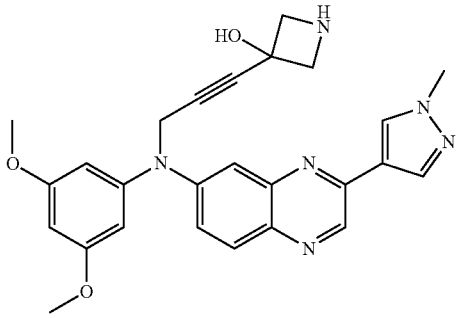 [SMILES: COc1cc(OC)cc(N(CC#CC2(O)CNC2)c2ccc3ncc(-c4cnn(C)c4)nc3c2)c1]

Trifluoroacetic acid (1.4 mL; 17.9 mmol) was added to a solution of compound 626 (0.17 g; 0.3 mmol). The reaction was stirred at 70° C. for 2 hours. The reaction mixture was cooled to room temperature and evaporated. The reaction mixture was poured out into ice water, DCM was added and basified with NH₄OH. The organic layer was separated, dried (MgSO₄), filtered and the solvent was evaporated. The residue (0.35 g) was purified by chromatography over silica gel (Irregular SiOH, 15-40 µm, 30 g; mobile phase 0.5% NH₄OH, 95% DCM, 5% MeOH). The pure fractions were collected and concentrated to give 0.048 g (34%) of compound 627.

Conversion 50

Preparation of compounds 628 and 629

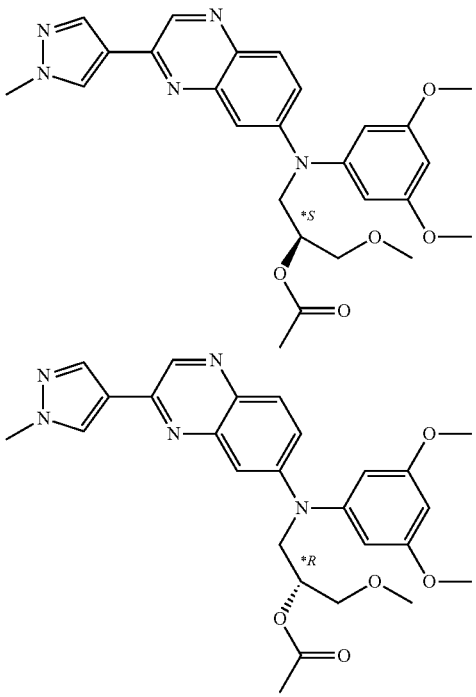

NaH (0.22 g; 5.56 mmol) was added portionwise to compound 14 (0.5 g; 1.1 mmol) in THF (30 mL). The reaction mixture was stirred at 0° C. for 1 hour. Then, acetyl chloride (0.8 mL; 11.1 mmol) was added dropwise at 5° C. under N₂ flow. The reaction mixture was stirred at 50° C. for 18 hours. The reaction was poured out into ice water and EtOAc was added. The organic layer was separated and washed with brine, dried (MgSO₄), filtered and the solvent was evaporated. The residue (0.51 g) was purified by chromatography over silica gel (SiOH 5 µm, 250*30 mm; mobile phase gradient from 100% DCM to 0.5% NH₄OH, 95% DCM, 5% MeOH). The pure fractions were collected and concentrated to give 220 mg of product. The enantiomers were separated by chiral super critical fluid chromatography (CHIRALPAK AD-H 5 µm 250×20 mm; mobile phase, 60% CO₂, 40% isopropanol). The desired product fractions were collected and the solvent was evaporated. The first eluted enantiomer (0.105 g) was crystallized in diethyl ether, yielding 0.050 g (9%) of compound 628 (S*, MP=122° C.). The second enantiomer (0.096 g) was crystallized in diethyl ether, yielding 0.051 g (9%) of compound 629 (R*, MP=124° C.).

Conversion 51

Preparation of compound 631

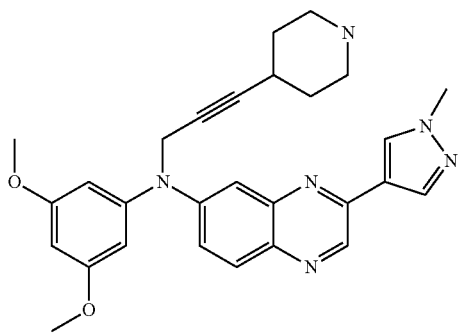 [SMILES: COc1cc(OC)cc(N(CC#CC2CCNCC2)c2ccc3ncc(-c4cnn(C)c4)nc3c2)c1]

as a HCl salt

Trifluoroacetic acid (0.52 mL; 6.9 mmol) was added to a solution of compound 630 (0.4 g; 0.7 mmol) in DCM (7 mL). The reaction was stirred at room temperature for 24 hours. The reaction mixture was poured out into ice water, DCM was added and basified with K₂CO₃. The organic layer was separated, dried (MgSO₄), filtered and the solvent was evaporated. The residue (0.5 g) was purified by chromatography over silica gel (Irregular SiOH, 15-40 µm, 30 g; mobile phase 0.5% NH₄OH, 97% DCM, 3% MeOH). The pure fractions were collected and concentrated. HCl in isopropyl alcohol 5N was added dropwise to the residue (0.41 g). Acetone and diethyl ether were added. The precipitate was filtered off and dried in vacuum to give 0.383 g (98%) of compound 631. MP: 189° C. (Kofler)

Conversion 52

Preparation of compound 633

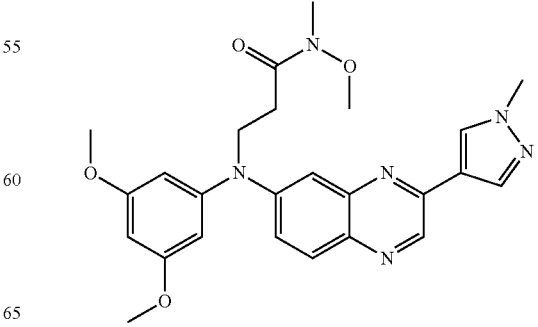

1,1' carbonyldiimidazole (1.1 g, 6.6 mmol) was added portion wise to a solution of compound 297 (2.4 g; 5.6 mmol) in DCM (60 mL). Then the reaction mixture was stirred at room temperature for 1 hour. N,O-dimethylhydroxylamine hydrochloride (0.65 g; 6.6 mmol) was added and the reaction mixture was stirred at room temperature for 72 hours. The reaction mixture was quenched with water and extracted with DCM. The organic layer was decanted, dried (MgSO$_4$), filtered and evaporated to dryness. The residue (2.6 g) was purified by chromatography over silica gel (Irregular SiOH 15-40 µm, 300 g; mobile phase 0.3% NH$_4$OH, 98% DCM, 2% MeOH). The pure fractions were collected and concentrated to give 0.185 g (11%). The residue (0.5 g) was crystallized from diethyl ether. The precipitate was filtered and dried to afford 0.28 g (11%) of compound 633. MP: 130° C. (DSC)

Conversion 53

Preparation of compound 635

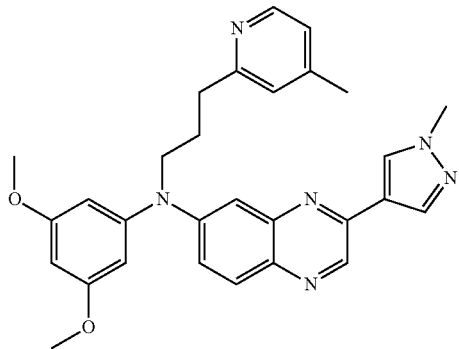 [SMILES: COc1cc(OC)cc(N(CCCc2cc(C)ccn2)c2ccc3ncc(-c4cnn(C)c4)nc3c2)c1]

Compound 634 (0.26 g; 0.53 mmol) was hydrogenated at room temperature in EtOAc (10 mL) with Pd/C (0.05 g) as a catalyst under atmospheric pressure. After 18 hours the catalyst was filtered off on a pad of Celite® and the filtrate was concentrated in vacuo until dryness. The residue (0.256 g) was purified by chromatography over silica gel (SiOHSiOH, 5 µm, 150*30 mm; mobile phase gradient from 100% DCM to 0.8% NH$_4$OH, 92% DCM, 8% MeOH). The pure fractions were collected and concentrated. The residue (0.085 g) was crystallized from CH$_3$CN/DIPE. The precipitate was filtered and dried to afford 0.075 g (29%) of compound 635. MP: 110° C. (DSC)

Conversion 54

Preparation of compounds 637 and 636

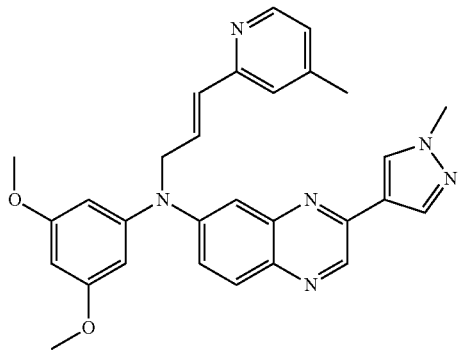

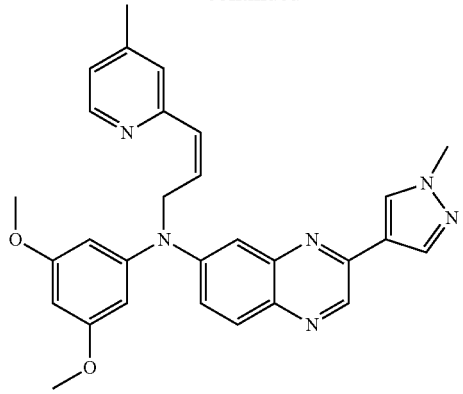

Compound 634 (0.38 g; 0.78 mmol) was hydrogenated at room temperature in EtOAc (40 mL) with Lindlar catalyst (0.075 g) as a catalyst under atmospheric pressure. After 9 hours the catalyst was filtered off on a pad of Celite®, washed with DCM/MeOH and the filtrate was concentrated in vacuo until dryness. The residue (0.474 g) was purified by chromatography over silica gel (SiOHSiOH, 5 µm, 150*30 mm; mobile phase gradient from 100% DCM to 0.8% NH$_4$OH, 92% DCM, 8% MeOH). The pure fractions were collected and concentrated to give two fractions. The first fraction (0.135 g) was crystallized from diethyl ether. The precipitate was filtered and dried to afford 0.099 g (26%) of compound 636 (Z). MP: >260° C. (Kofler). The second fraction was crystallized from diethyl ether. The precipitate was filtered and dried to afford 0.048 g (13%) of compound 637 (E). MP: 80° C. (Kofler).

Conversion 55

Preparation of compound 640

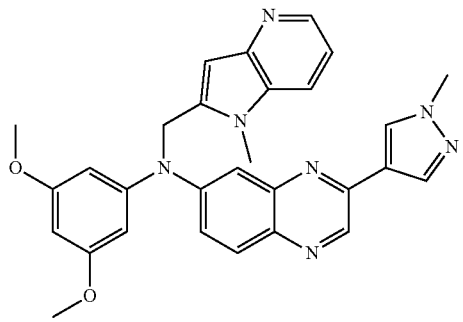 [SMILES: COc1cc(OC)cc(N(Cc2cc3ncccc3n2C)c2ccc3ncc(-c4cnn(C)c4)nc3c2)c1]

Potassium tert-butoxide (0.054 g; 0.48 mmol) was added to a solution of compound 809 (0.24 g; 0.48 mmol) in THF (15 mL) and the reaction mixture was stirred at 10° C. for 2 hours. The reaction was poured out into ice water and EtOAc was added. The organic layer was separated and washed with brine, dried (MgSO$_4$), filtered and the solvent was evaporated. The residue (0.44 g) was purified by chromatography over silica gel (SiOH 5 µm, 150*30 mm; mobile phase gradient from 70% Heptane, 2% MeOH, 28% EtOAc to 20% MeOH, 80% EtOAc). The pure fractions were collected and concentrated. The residue (0.132 g) was crystallized from diethyl ether. The precipitate was filtered and dried to afford 0.087 g (37%) of compound 640. MP: 241° C. (DSC).

Conversion 56
Preparation of compound 642

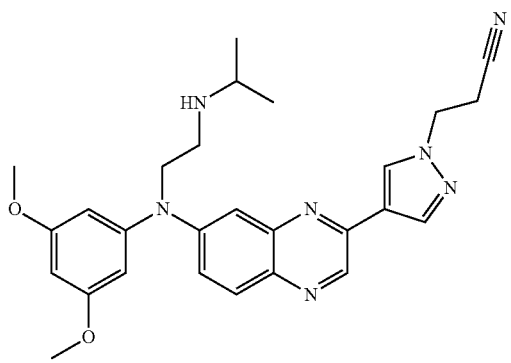 [SMILES: COc1cc(OC)cc(N(CCNC(C)C)c2ccc3ncc(-c4cnn(CCC#N)c4)nc3c2)c1]

A mixture of compound 137 (0.51 g; 1.1 mmol), 3-bromopropionitrile (0.11 mL; 1.4 mmol) and $K_2CO_3$ (0.8 g; 5.6 mmol) in $CH_3CN$ (15 mL) was stirred at 80° C. for 6 hours. The reaction was poured out into ice water and EtOAc was added. The organic layer was separated and washed with brine, dried ($MgSO_4$), filtered and the solvent was evaporated. The residue (0.5 g) was purified by chromatography over silica gel (SiOH 5 μm, 150*30 mm; mobile phase gradient from 0.2% $NH_4OH$, 98% DCM, 2% MeOH to 0.9% $NH_4OH$, 91% DCM, 9% MeOH). The pure fractions were collected and concentrated. The residue (0.35 g) was crystallized from diethyl ether. The precipitate was filtered and dried to afford 0.257 g (47%) of compound 642. MP: 127° C. (DSC).

Conversion 57
Preparation of compound 643

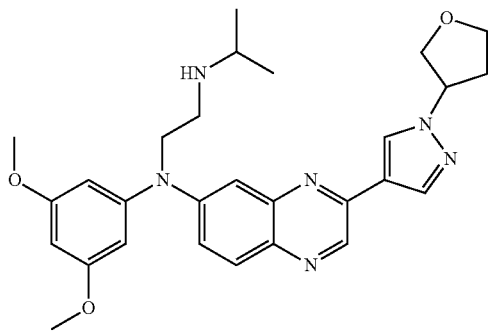 [SMILES: COc1cc(OC)cc(N(CCNC(C)C)c2ccc3ncc(-c4cnn(C5CCOC5)c4)nc3c2)c1]

as a HCl salt 3-hydroxytetrahydrofuran (0.19 mL; 2.3 mmol) and triphenylphosphine (0.61; 2.3 mmol) was added to a solution of compound 137 (0.5 g; 1.16 mmol) in THF (14 mL) under $N_2$ flow. The reaction mixture was stirred at room temperature for 10 minutes, then diisopropyl azodicarboxylate (0.46 mL; 2.3 mmol) was added and the reaction mixture was stirred for 24 hours. The reaction was poured out into ice water and EtOAc was added. The organic layer was separated and washed with brine, dried ($MgSO_4$), filtered and the solvent was evaporated. The residue (2 g) was purified by chromatography over silica gel (SiOH 5 μm, 150*30 mm; mobile phase 0.5% $NH_4OH$, 95% DCM, 5% MeOH). The pure fractions were collected and concentrated. The residue (0.19 g) was dissolved in MeOH, 2.3 mL of HCl i-PrOH was added, then the chlorhydrate was crystallized from diethyl ether. The precipitate was filtered off and dried to afford 0.178 g (25%) of compound 643. MP: 160° C. (Kofler)

Conversion 58
Preparation of compound 648

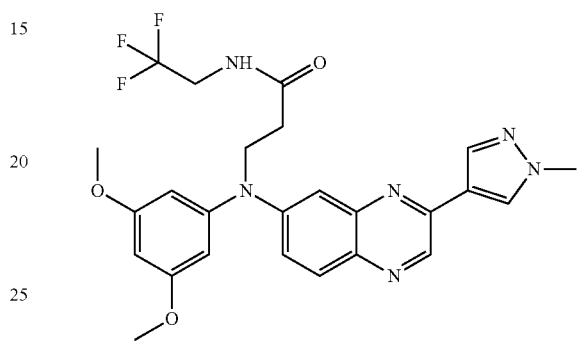

A mixture of compound 297 (1.65 g, 3.8 mmol), 2,2,2-trifluoroethylamine (1.4 mL, 9.4 mmol), 1-hydroxybenzotriazole (3.6 g, 9.4 mmol), triethylamine (1 mL, 7.5 mmol) in N,N-dimethylformamide (50 mL) was stirred at room temperature for 18 hours. The reaction mixture was poured out into ice water and EtOAc was added. The organic layer was separated, washed with brine, dried ($MgSO_4$), filtered and the solvent was evaporated. The residue (3.2 g) was purified by chromatography over silica gel (Irregular Silica 20×40; mobile phase 0.1% $NH_4OH$, 97% DCM, 3% MeOH). The product fraction was collected and the solvent was evaporated. The residue was triturated from diethyl ether, filtered and dried under vacuum at 60° C., yielding 1.15 g (65%) of compound 648, MP=196° C. (DSC).

Conversion 59
Preparation of compound 651

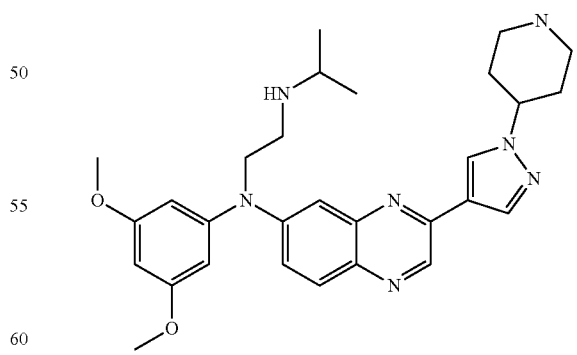

Trifluoroacetic acid (1 mL; 14.3 mmol) was added to a solution of compound 650 (0.44 g; 0.7 mmol) in DCM (5.2 mL) at 0-5° C. The reaction mixture was stirred at room temperature for 2 hours, then was quenched with $K_2CO_3$ 10%. The organic layer was washed with water, dried (MgSO$_4$), filtered and evaporated till dryness. The residue (0.45 g) was purified by chromatography over silica gel (Irregular Silica 15×40; 30 g, mobile phase 1% NH$_4$OH, 90% DCM, 10% MeOH). The product fraction was collected and the solvent was evaporated. The residue was crystallized from diethyl ether/CH$_3$CN, filtered and dried under vacuum at 60° C., yielding 0.26 g (72%) of compound 651, MP=122° C. (Kofler).

Conversion 60

Preparation of compound 652

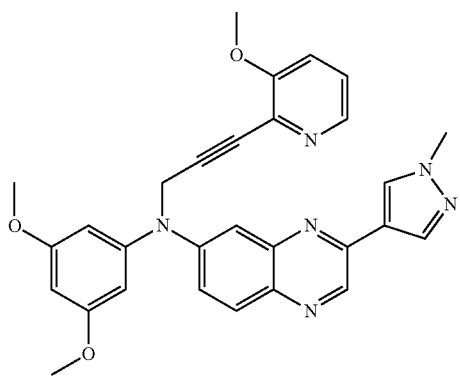 [SMILES: COc1cc(OC)cc(N(CC#Cc2ncccc2OC)c2ccc3ncc(-c4cnn(C)c4)nc3c2)c1]

A suspension of compound 38 (1 g; 3.5 mmol), 2-bromo-3-methoxypyridine (0.25 g; 0.35 mmol) and Et$_3$N (3.0 mL; 21.5 mmol) in DMSO (20 mL) was degassed under N$_2$ flow. Dichlorobis(triphenylphosphine)-palladium (0.25 g; 0.36 mmol) and copper(I) iodide (0.034 g; 0.18 mmol) were added and the reaction mixture was stirred at 90° C. for 40 minutes. The reaction mixture was cooled to room temperature, poured out into water and EtOAc was added. The mixture was filtered off on a pad of Celite®. The organic layer was decanted, washed with brine, dried (MgSO$_4$), filtered and evaporated to dryness. The residue (1.4 g) was purified by chromatography over silica gel (Irregular SiOH, 20-40 μm, 450 g; mobile phase, 0.1% NH$_4$OH, 97% DCM, 3% MeOH). The pure fractions were collected and evaporated to dryness. The residue was crystallized from diethyl ether. The precipitate was filtered and dried to give 0.6 g (65%) of compound 652. MP: 144° C. (DSC)

Conversion 61

Preparation of compounds 656 and 657

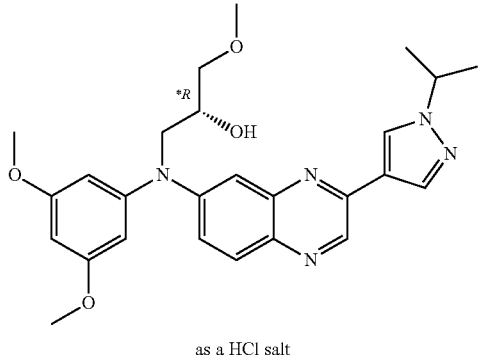

as a HCl salt

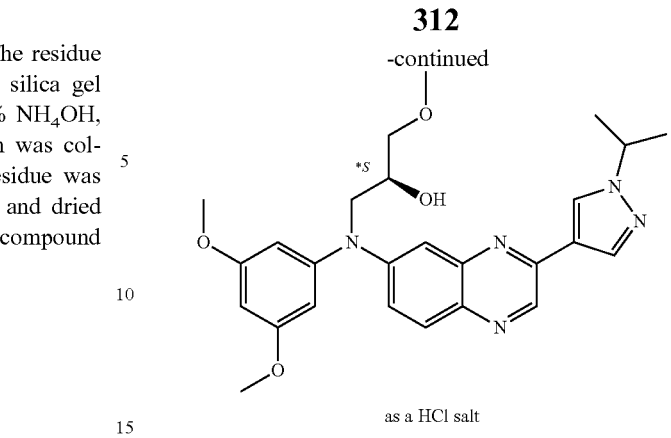

as a HCl salt

Compound 14a (3.4 g) was purified by chromatography over silica gel (Irregular SiOH, 15-40 μm, 300 g; mobile phase, 0.1% NH$_4$OH, 98% DCM, 2% MeOH). The pure fractions were collected and evaporated to dryness. The residue (1 g) was separated by chiral super critical fluid chromatography (CHIRALPAK AD-H 5 μm 250×20 mm; mobile phase, 40% 2-propylamine, 60% CO$_2$). The desired product fractions were collected and the solvent was evaporated. The first eluted enantiomer (0.5 g) was dissolved in diethyl ether, 5 equivalents of HCl in i-PrOH were added and stirred at room temperature for 18 hours. The precipitate was filtered and dried to afford 0.29 g (8%) of compound 656(R*, MP=95° C. (Kofler)). The second enantiomer (0.55 g) was purified by achiral SFC on (Amino 6 μm 150*21.2 mm, mobile phase, 90% CO$_2$, 10% MeOH). The desired product fractions were collected and the solvent was evaporated. The residue (0.47 g) was dissolved in diethyl ether, 5 equivalents of HCl in i-PrOH were added and stirred at room temperature for 18 hours. The precipitate was filtered and dried to afford 0.36 g (11%) of compound 657 (S*, MP=110° C. (Kofler)).

Conversion 62

Preparation of compound 663

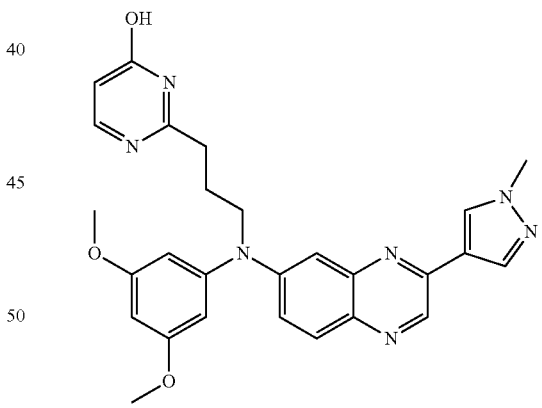

Compound 662 (0.25 g; 0.49 mmol) in HCl (1M in H$_2$O) (12.2 mL; 12.2 mmol) was stirred at 60° C. for 24 hours. The reaction mixture was cooled down to room temperature, evaporated till dryness. Then the residue was taken up DCM and washed with K$_2$CO$_3$ 10%. The organic layer was separated and dried (MgSO$_4$), filtered and the solvent was evaporated. The residue (0.2 g) was purified by chromatography over silica gel (SiOH 5 μm, 150*30 mm, mobile phase, gradient from 0.2% NH$_4$OH, 98% DCM, 2% MeOH to 1.1% NH$_4$OH, 89% DCM, 11% MeOH). The pure fractions were collected and evaporated. The residue was crystallized from diethyl ether. The precipitate was filtered and dried to afford 0.1 g (41%) of compound 663. MP: 200° C. (DSC).

Conversion 63
Preparation of compound 670

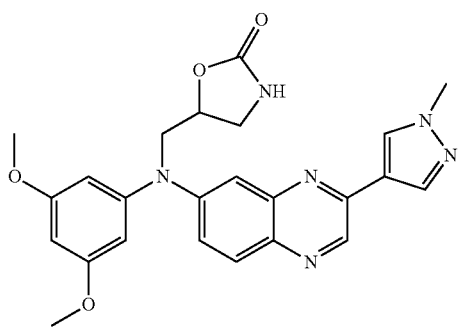 [SMILES: COc1cc(OC)cc(N(CC2CNC(=O)O2)c2ccc3ncc(-c4cnn(C)c4)nc3c2)c1]

1,1'carbonyldiimidazole (0.5 g, 3 mmol) was added to a solution of compound 125 (1.2 g, 2.8 mmol) in THF (20.5 mL) at 0° C. under $N_2$ flow. The reaction mixture was stirred at room temperature for 2 hours. The reaction was poured out into ice water and EtOAc was added. The organic layer was washed with brine, dried (MgSO$_4$), filtered and evaporated. The residue (1.3 g) was purified by chromatography over silica gel (Irregular SiOH, 20-45 μm, 300 g; mobile phase 0.2% NH$_4$OH, 96% DCM, 4% iPrOH). The pure fractions were collected, the solvent was evaporated. The residue (0.98 g) was crystallized from CH$_3$CN and diethyl ether. The precipitate was filtered off and dried to give 0.8 g (64%) of compound 670. MP: 157° C. (DSC).

Conversion 64
Preparation of compound 671 and 672

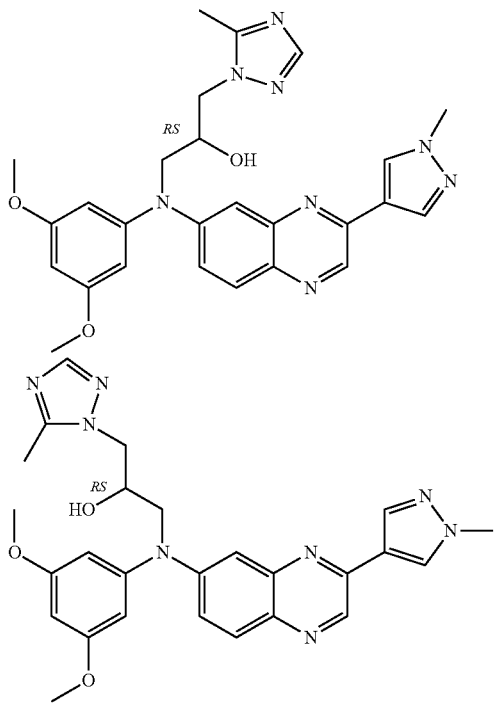

A mixture of compound 76 (1.5 g; 3.6 mmol) and 3-methyl-1H-1,2,4-triazole (3.7 mL; 28.9 mmol) in 1-methyl-2-pyrrolidinone (4 mL) in a sealed tube was heated at 140° C. using one single mode microwave (Biotage Initiator EXP 60) for 40 minutes. The reaction mixture was poured out into ice water and EtOAc was added. The organic layer was separated, washed with brine, dried (MgSO$_4$), filtered and the solvent was evaporated to dryness. The crude product (2.1 g) was purified by chromatography over silica gel (15-40 μm 300 g; mobile phase, 0.5% NH$_4$OH, 93% DCM, 7% MeOH). The pure fractions were collected and the solvent was evaporated till dryness. The residue (1 g) was purified by chromatography over silica gel (Cyano 6 μm 150*21 mm; mobile phase, 90% CO$_2$, 10% EtOH). The desired product fractions were collected and the solvent was evaporated. The first isomer (0.3 g) was crystallized in CH$_3$CN/diethyl ether, yielding 0.26 g (15%) of compound 671 MP=144° C. (DSC). The second isomer (0.34 g) was crystallized in CH$_3$CN/diethyl ether, yielding 0.26 g (15%) of compound 672 MP=194° C. (DSC).

Conversion 65
Preparation of compound 673

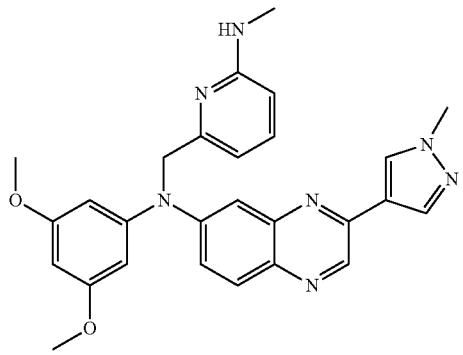 [SMILES: CNc1cccc(CN(c2cc(OC)cc(OC)c2)c2ccc3ncc(-c4cnn(C)c4)nc3c2)n1]

A mixture of compound 584 (0.64 g; 1.2 mmol) and methylamine in 2M THF (3 mL; 6 mmol) in 1-methyl-2-pyrrolidinone (5 mL) was heated at 140° C. for 24 hours in a sealed tube. The reaction mixture was poured out into ice water and EtOAc was added. The organic layer was separated, washed with brine, dried (MgSO$_4$), filtered and the solvent was evaporated to dryness. The crude product (1 g) was purified by chromatography over silica gel (5 μm; mobile phase gradient from 100% DCM to 0.6% NH$_4$OH, 94% DCM, 6% MeOH). The pure fractions were collected and the solvent was evaporated till dryness. The residue was crystallized from acetone and diethyl ether. The precipitate was filtered and dried to give 0.34 g (58%) of compound 673. MP: 180° C. (Kofler)

Conversion 66
a) Preparation of Compound 674

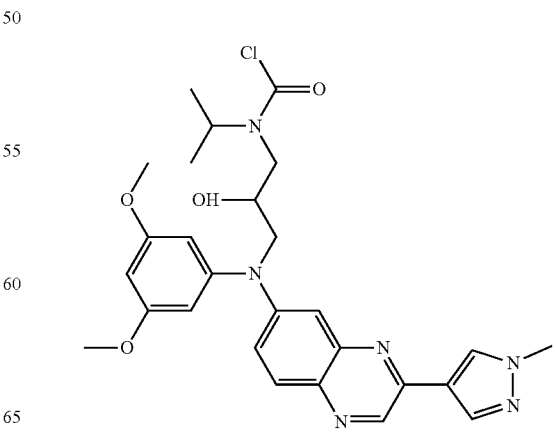

Chloroacetyl chloride (0.23 mL; 2.9 mmol) was added dropwise to a solution of compound 409 (1.3 g, 2.7 mmol) and triethylamine (1.14 ml, 8.2 mmol) in acetonitrile (40 ml) at 0° C. under nitrogen. The reaction mixture was stirred for 2 hours at room temperature, then at 110° C. overnight. Water was added and the reaction mixture was extracted with DCM, dried (MgSO$_4$), filtered and dried to provide 1.5 g of compound 674 used without further purification in the next step.

b) Preparation of Compound 675

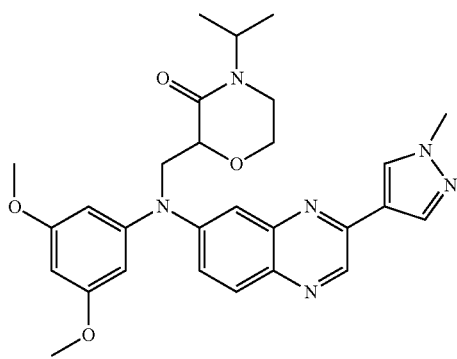 [SMILES: COc1cc(OC)cc(N(CC2OCCN(C(C)C)C2=O)c2ccc3ncc(-c4cnn(C)c4)nc3c2)c1]

Potassium tert butoxide was added portionwise to a solution of compound 674 (2.6 g; 4.7 mmol) in isopropanol (58 mL) and THF (58 mL). The reaction mixture was stirred at room temperature for 2 hours, then was poured out into ice water and DCM was added. The organic layer was separated, dried (MgSO$_4$), filtered and the solvent was evaporated to dryness. The crude product (2.1 g) was purified by chromatography over silica gel (20-45 µm 450 g; mobile phase gradient from 0.2% NH$_4$OH, 96.5% DCM, 3.5% MeOH to 1% NH$_4$OH, 89% DCM, 10% MeOH). The pure fractions were collected and the solvent was evaporated till dryness. The residue (0.61 g) was crystallized from diethyl ether and CH$_3$CN. The precipitate was filtered and dried to give 0.49 g (21%) of compound 675. MP: 187° C. (Kofler)

c) Preparation of Compound 676

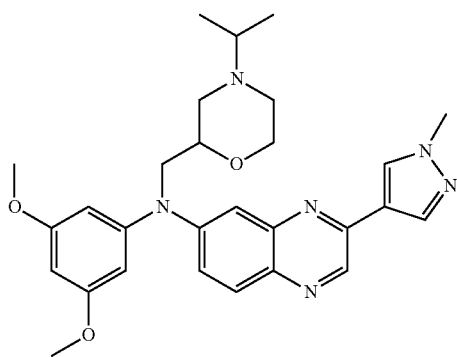 [SMILES: COc1cc(OC)cc(N(CC2CN(C(C)C)CCO2)c2ccc3ncc(-c4cnn(C)c4)nc3c2)c1]

Lithium aluminium hydride (0.028 g; 0.73 mmol) was added to a solution of compound 674 (0.25 g; 0.48 mmol) in THF (20 mL) under N$_2$ flow between 0-5° C. The reaction mixture was stirred between 0-5° C. for 1 hour. EtOAc was added dropwise to the reaction mixture, then water was added dropwise. The organic layer was separated, washed with brine, dried (MgSO$_4$), filtered and the solvent was evaporated to dryness. The crude product (1 g) was purified by chromatography over silica gel (5 µm; mobile phase, gradient from 100% DCM to 0.6% NH$_4$OH, 94% DCM, 6% MeOH). The pure fractions were collected and the solvent was evaporated till dryness. The residue (0.155 g) was purified by achiral Super critical fluid chromatography (2-ethylpyridine 6 µm; mobile phase 0.3% isopropylamine, 20% MeOH, 80% CO$_2$). The pure fractions were collected and the solvent was evaporated till dryness.

The residue (0.053 g) was purified by chromatography over silica gel (15-40 µm 10 g; mobile phase gradient from 100% DCM to 0.6% NH$_4$OH, 94% DCM, 6% MeOH). The pure fractions were collected and the solvent was evaporated till dryness to afford 0.043 g (18%) of compound 677 MP: 88° C. (Kofler)

Conversion 67 a) Preparation of Compound 678

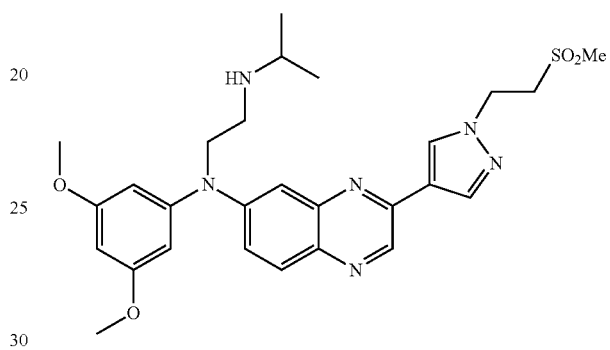

The experiment has been performed 3 times on the following amount.

A mixture of compound 137 (HCl salt) (1 g; 2.3 mmol), 2-bromoethyl-methylsulfone (0.5 mL; 2.8 mmol) and K$_2$CO$_3$ (0.6 g; 4.6 mmol) in CH$_3$CN (33 mL) was stirred at 80° C. for 2 hours. The reaction was poured out into ice water and EtOAc was added. The organic layers were separated and washed with brine, combined, dried (MgSO$_4$), filtered and the solvent was evaporated. The residue (5.2 g) was purified by chromatography over silica gel (SiOH 15-40 µm, 450; mobile phase gradient from 0.5% NH$_4$OH, 96% DCM, 4% MeOH to 0.5% NH$_4$OH, 90% DCM, 10% MeOH). The pure fractions were collected and concentrated. The residue (3.2 g) was crystallized from diethyl ether. The precipitate was filtered and dried to afford 2.2 g (78%) of compound 678. MP: 148° C. (DSC).

Conversion 68 a) Preparation of Compound 680

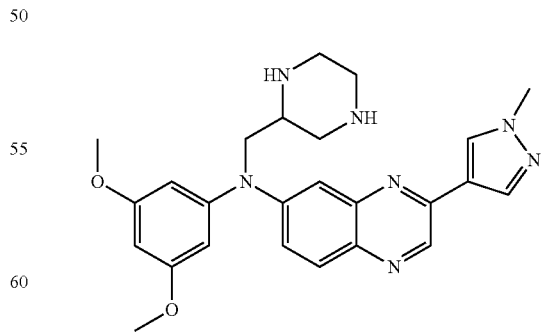

Compound 681 (0.97 g; 1.4 mmol) in trifluoroacetic acid (28.5 mL) was heated at 100° C. for 24 hours in a sealed tube. The reaction mixture was evaporated till dryness. The crude product was diluted in DCM and basified with NaHCO₃. The organic layer was separated and dried (MgSO₄), filtered and the solvent was evaporated. The residue (1.2 g) was purified by chromatography over silica gel (SiOH 15-40 μm, 300 g; mobile phase gradient from 0.5% NH₄OH, 92% DCM, 8% MeOH to 0.5% NH₄OH, 90% DCM, 10% MeOH). The pure fractions were collected and concentrated. The residue (0.4 g) was purified by chromatography over silica gel (SiOH 10 μm, 60 g; mobile phase 0.5% NH₄OH, 93% DCM, 7% MeOH). The pure fractions were collected and concentrated. The residue was crystallized from DIPE/CH₃CN. The precipitate was filtered and dried to give 0.29 g (45%) of compound 680. MP: 167° C. (DSC).

Conversion 69
a) Preparation of Compound 682

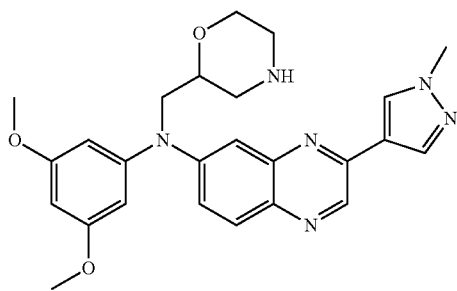 [SMILES: COc1cc(OC)cc(N(CC2CNCCO2)c2ccc3ncc(-c4cnn(C)c4)nc3c2)c1]

Palladium 10% on carbon (0.65 g; 6 mmol) was added to a solution of compound 10 (1.5 g; 2.7 mmol) in MeOH (30 mL). The reaction mixture was stirred at room temperature under 3 bars. After 24 hours the catalyst was filtered off on a pad of Celite® and the filtrate was concentrated. The residue (1.2 g) was purified by chromatography over silica gel (SiOH 20-40 μm, 450 g; mobile phase gradient from 0.2% NH₄OH, 96% DCM, 4% MeOH to 0.2% NH₄OH, 95% DCM, 5% MeOH). The pure fractions were collected and concentrated. The residue (0.25 g) was purified by achiral super critical fluid chromatography (2-ethylpyridine 6 μm; mobile phase 0.3% isopropylamine, 20% MeOH, 80% CO₂). The pure fractions were collected and the solvent was evaporated till dryness. The residue was crystallized from diethyl ether and CH₃CN. The precipitate was filtered off and dried to afford 0.15 g (12%) of compound 682. MP: 149° C. (Kofler).

Conversion 70
a) Preparation of Compound 683

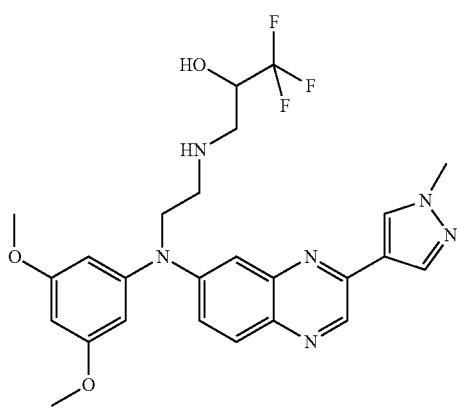 [SMILES: COc1cc(OC)cc(N(CCNCC(O)C(F)(F)F)c2ccc3ncc(-c4cnn(C)c4)nc3c2)c1]

A mixture of compound 84 (1 g; 2.5 mmol) and 1.2-epoxy-3.3.3-trifluoropropane (0.4 mL; 4.9 mmol) in MeOH (15 mL) was heated at 60° C. for 2 hours. The reaction mixture was cooled down to room temperature and evaporated till dryness. The residue (1.6 g) was purified by chromatography over silica gel (SiOH, 15-40 μm, 300 g; mobile phase gradient from, 0.1% NH₄OH, 98% DCM, 2% MeOH to 0.1% NH₄OH, 97% DCM, 3% MeOH). The pure fractions were collected and concentrated. The residue (0.56 g) was crystallized from diethyl ether. The precipitate was filtered and dried to afford 0.2 g (16%) of compound 683. MP: 123° C. (DSC).

Conversion 71
Preparation of compound 685

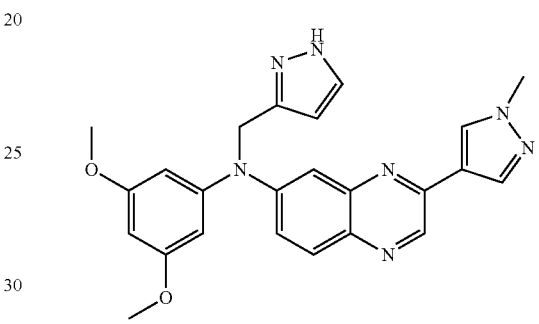

as a HCl salt

At 5° C., A 5N solution of HCl in i-PrOH 5/6N (2.4 mL; 12 mmol) was added to a solution of compound 686 (0.9 g; 1.7 mmol) in CH₃OH (3 mL). The reaction mixture was stirred at 5° C. for 2 hours, then for 15 hours at room temperature. The precipitate was filtered off and dried under vacuum to afford 0.425 g (52%) of compound 685. MP=203° C. (Kofler).

Conversion 72
Preparation of compound 696

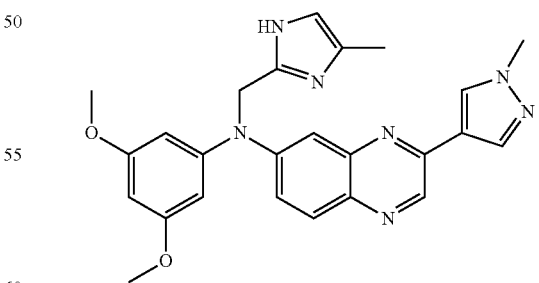

as a HCl salt

Hydrogen chloride (4M in dioxane) (6.8 mL; 27.2 mmol) was added to a solution of compound 695 (1.9 g; 3.4 mmol) in CH₃CN (37 mL) and was stirred at 50° C. for 18 hours.

The reaction mixture was poured out into ice water. The precipitate was filtered and dried to give 0.3 g (15%) of compound 696. MP: 188° C. (Kofler)

Conversion 73

Preparation of compound 902

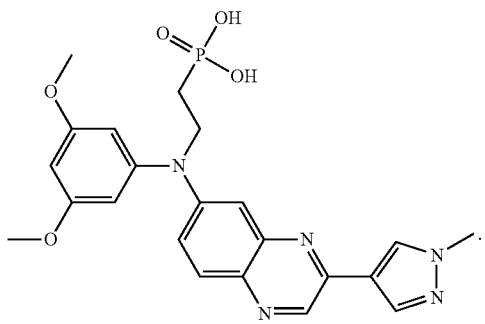

HBr

A mixture of compound 669 (200 mg, 0.38 mmol) and bromotrimethylsilane (3.16 ml, 23.975 mmol) in anhydrous DCM (4 ml) was stirred at room temperature for 3 hours. The solvent was evaporated, the resulting residue was diluted with MeOH-Water (1:1, 10 ml) and stirred for 20 minutes. The precipitate was filtered, washed with AcOEt and dried to give 149 mg (82%) of compound 902.

Conversion 74

Preparation of compound 906

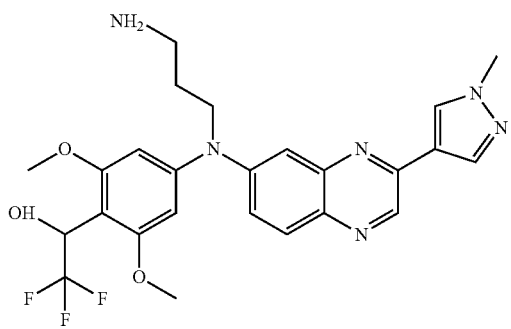 [SMILES: COc1cc(N(CCCN)c2ccc3ncc(-c4cnn(C)c4)nc3c2)cc(OC)c1C(O)C(F)(F)F]

Compound 93 (340 mg, 0.81 mmol) was added at 0° C. to trifluoroacetaldehyde methyl hemiketal (311 μL, 3.25 mmol) and the mixture was stirred at 0° C. for 4 h 30. The mixture was evaporated and the residue purified by chromatography over silica gel (5 μm. mobile phase: gradient from 0.2% NH$_4$OH, 98% DCM, 2% MeOH to 1.3% NH$_4$OH, 87% DCM, 13% MeOH). The desired product fractions were collected and the solvent was evaporated. yielding 41 mg. The residue was taken up in Et$_2$O filtered and dried. to give 29 mg of compound 906.

Conversion 75

Preparation of compound 918

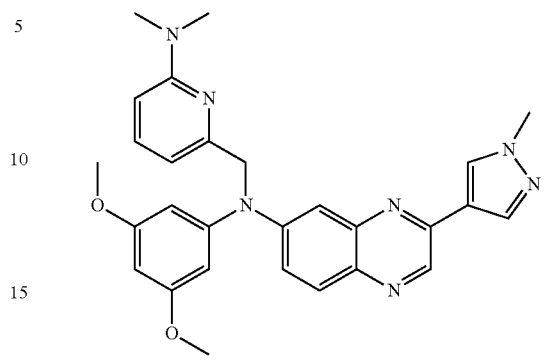

A mixture of compound 584 (397 mg; 0.75 mmol), dimethylamine (3 mL of a 2.0 M solution in tetrahydrofuran; 6 mmol) in 1-methyl-2-pyrrolidinone (11 mL) was stirred at 140° C. for 24 hours in a sealed tube. The mixture was poured into ice-water and EtOAc was added. The organic layer was separated, dried (MgSO$_4$), filtered and the filtrate was evaporated until dryness to afford 607 mg of residue, which was purified by chromatography over silica gel (15-40 μm, 90 g, mobile phase DCM/CH$_3$OH/NH$_4$OH: 98/2/0.1) The desired fractions were collected and evaporated to dryness to give 461 mg of residue which was repurified by chromatography over silica gel (5 μm, mobile phase: gradient from 100% DCM to 0.6% NH$_4$OH, 94% DCM, 6% MeOH) The desired fractions were collected and evaporated to dryness to give 390 mg. This residue was purified by achiral Supercritical Fluid Chromatography on (Diethylaminopropyl 5 μm, mobile phase 0.3% isopropylamine, 92% CO$_2$, 8% MeOH). The desired fractions were collected and evaporated to dryness to give 233 mg of residue which were. crystallized from Et$_2$O. The precipitate was filtered and dried to give 211 mg (57%) of compound 918.

Conversion 76

Preparation of compound 757

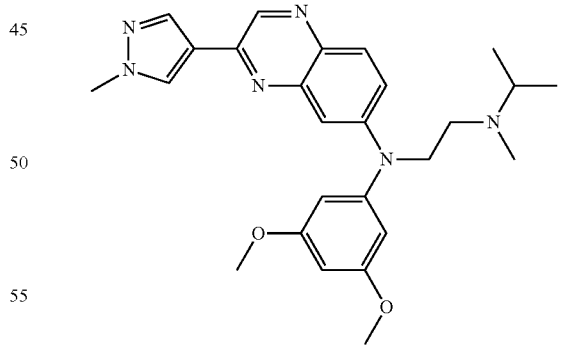

At 5° C., under N$_2$ atmosphere, NaH (447.83 mg, 11.2 mmol) was added to a mixture of compound 4 (2 g, 4.48 mmol) in DMF (40 mL). The reaction mixture was stirred at 10° C. for 30 minutes, then iodomethane (0.335 ml, 5.375 mmol) was added dropwise. The reaction mixture was cooled to room temperature and stirred at room temperature for 2 hours. Poured into H$_2$O+NaCl and extracted with AcOEt. The organic layer was washed with H$_2$O, dried (MgSO$_4$), filtered and evaporated to dryness to give 2 g of residue. The residue was purified by flash chromatography over silica gel (15-40 μm, 40 g, CH$_2$Cl$_2$/CH$_3$OH/NH$_4$OH: 96/4/0.1). The pure fractions were collected and evaporated to dryness to give 2 fractions: 1.05 g of compound 757 and 0.3 g of compound 757.

The following compounds were prepared according to reaction protocols of one of the above Examples using alternative starting materials as appropriate. Those indicated with NMR* have NMR data hereinafter.

In the table =CoX (or =BX) indicates that the preparation of this compound is described in Conversion X (or Method BX).

In the table ~CoX (or ~BX) indicates that this compound is prepared according to Conversion X (or Method BX).

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

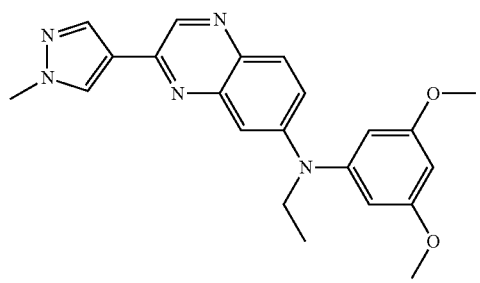

200; ~B5b-1; NMR*

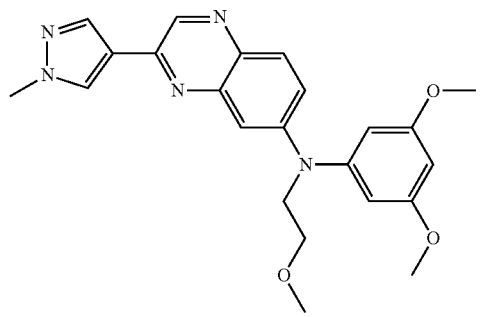

204; ~B5b-2; NMR*

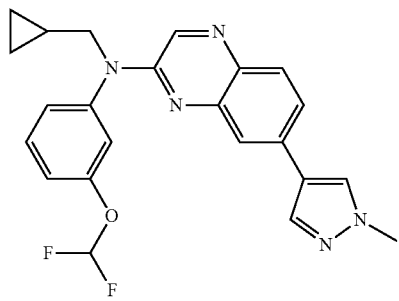

as a HCl salt
209; ~B5

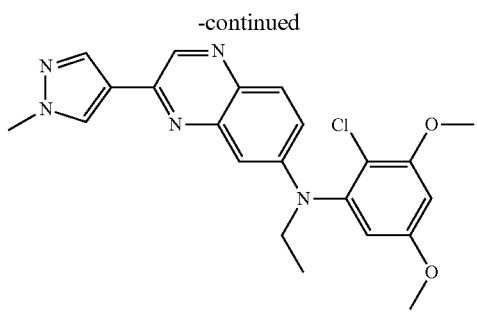

201; ~B5b-1; NMR*

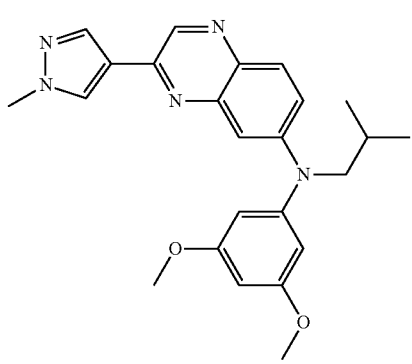

13; =B5 b-3; NMR*

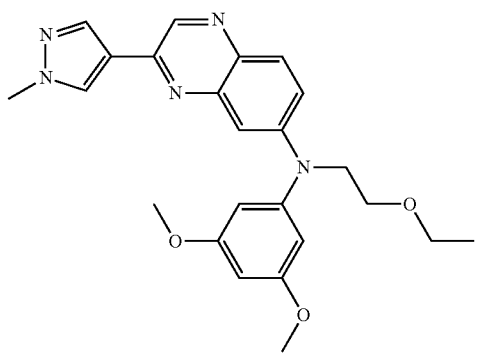

210; ~B5

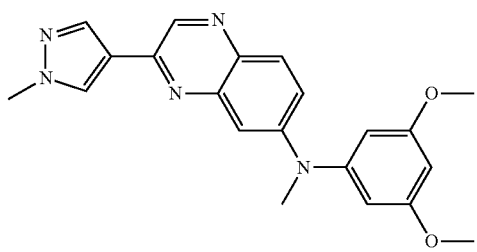

11; =B5 b-1; NMR*

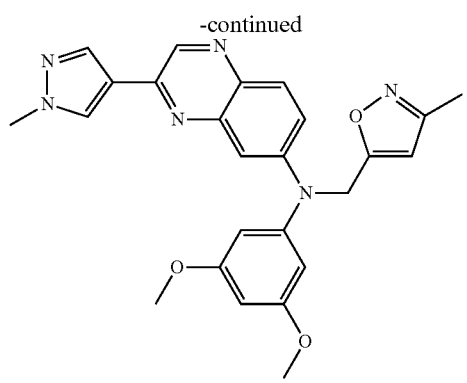
205; ~B5b-2; NMR*
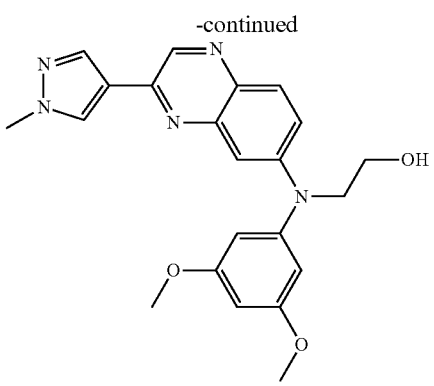
1; =B1
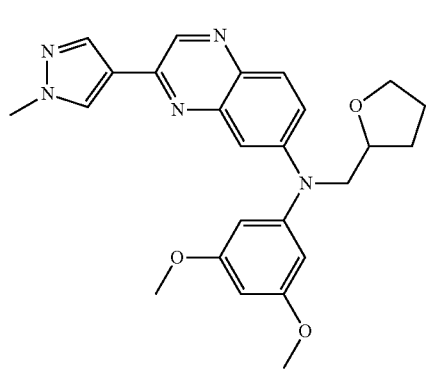
211; ~B5
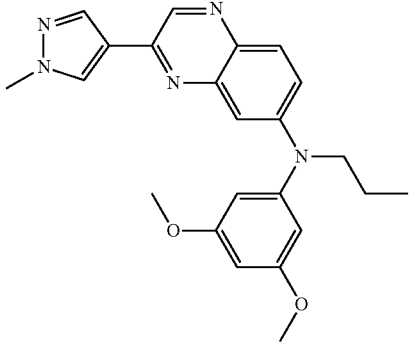
12; =B5 b-2; NMR*
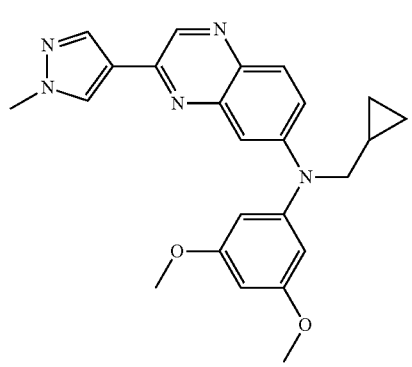
202; ~B5/~B5b-1; NMR*
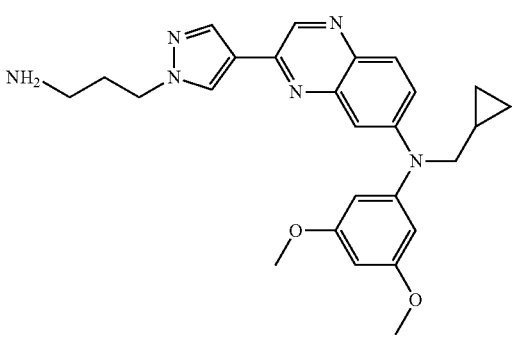
as a HCl salt
207; ~B11
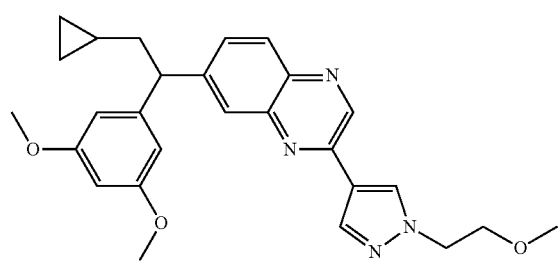
206; ~Co 5a
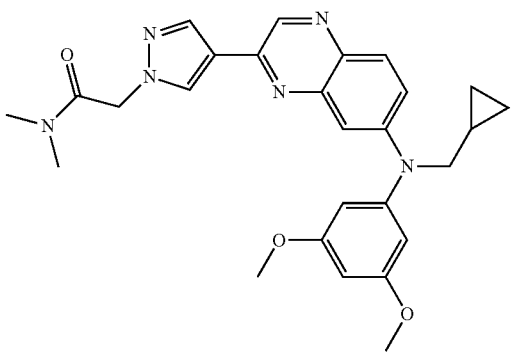
212; ~B12

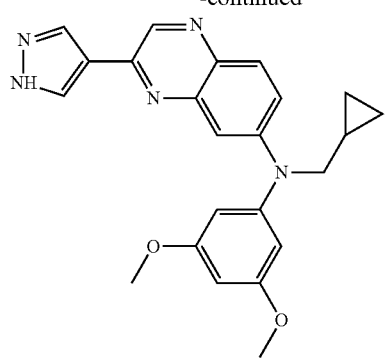
17; =B9 a/b/c
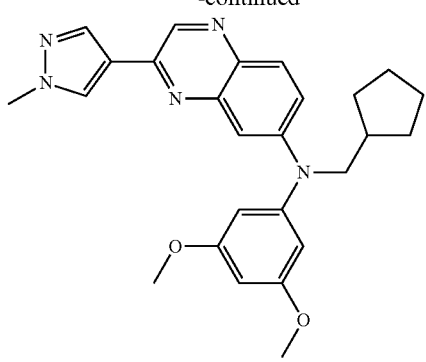
208; ~B5
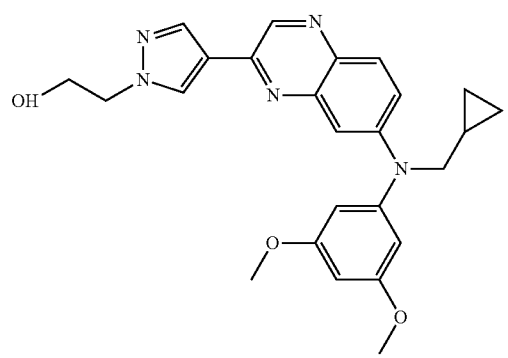
56; =Co5e/~B14
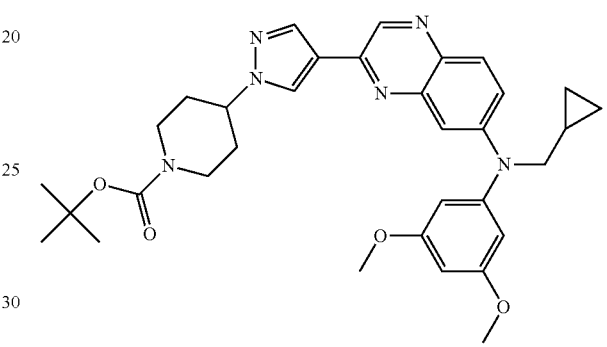
127; ~B9c
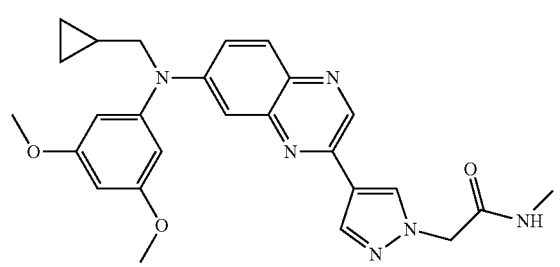
213; ~B12
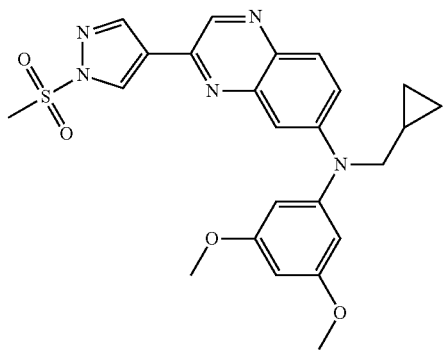
214; ~Co5g
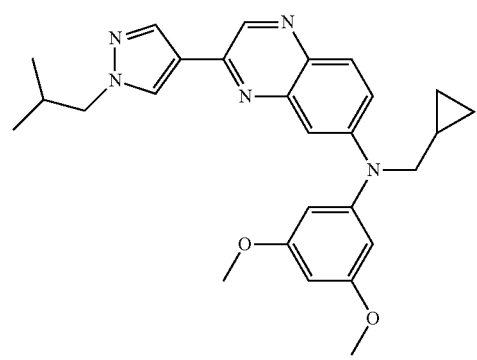
203; ~B9c
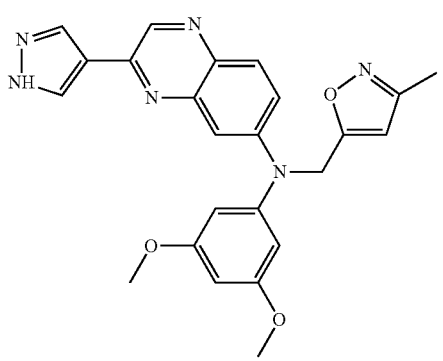
217; ~B9a

327
-continued
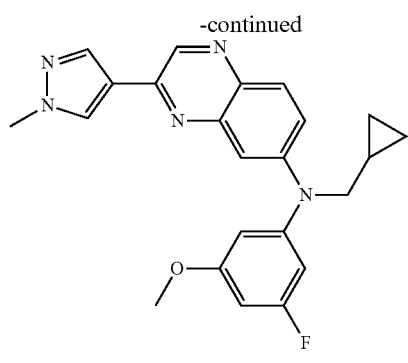
222; ~B5
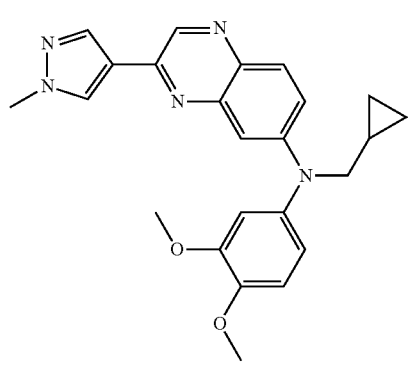
215; ~B5
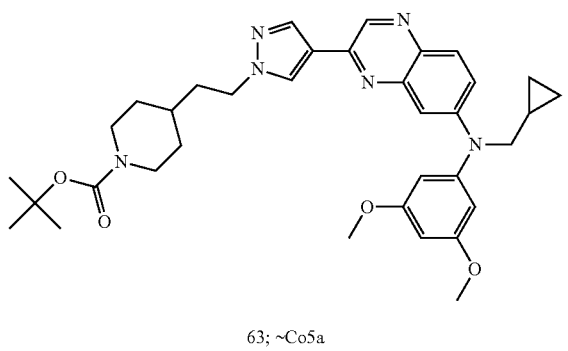
63; ~Co5a
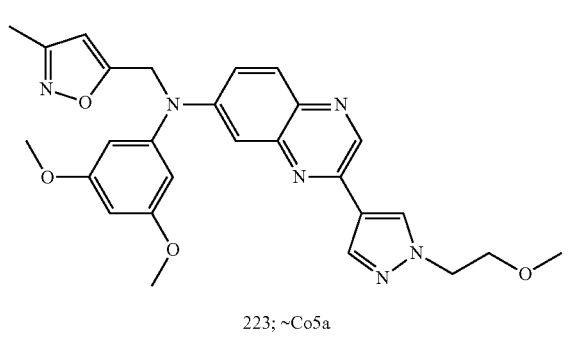
223; ~Co5a
328
-continued
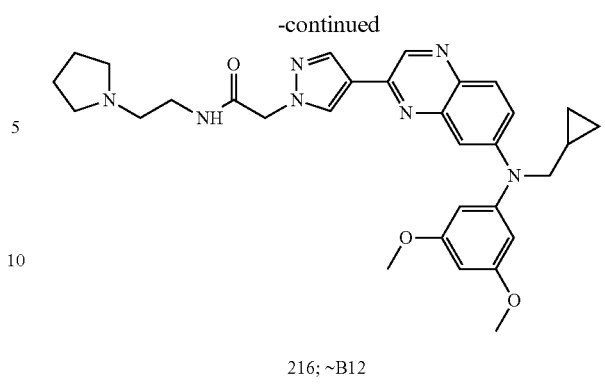
216; ~B12
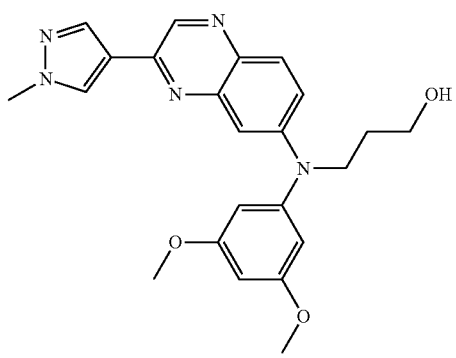
3; =B2 a/b
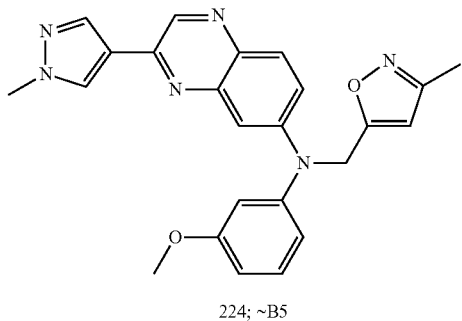
224; ~B5
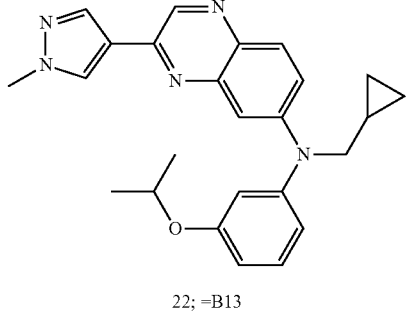
22; =B13

329
-continued
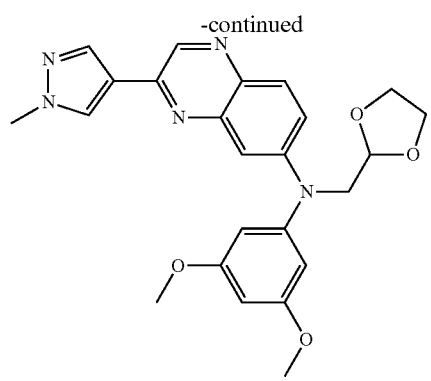
218; ~B5
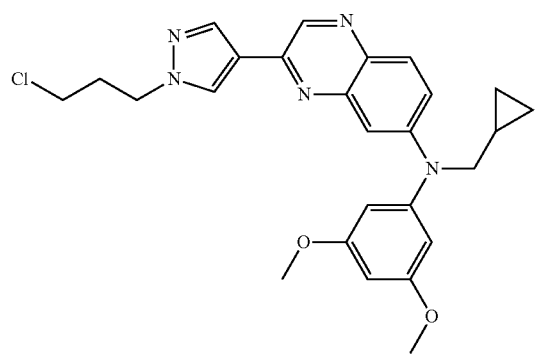
225; ~Co5a
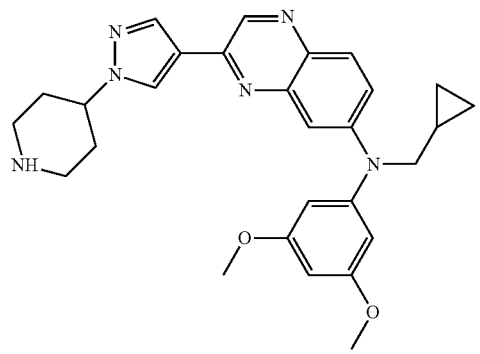
60; ~Co7
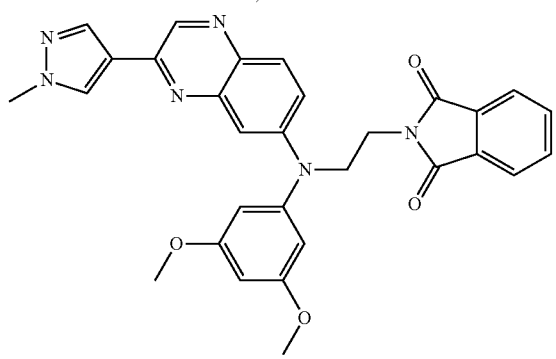
219; ~B3/B4a
330
-continued
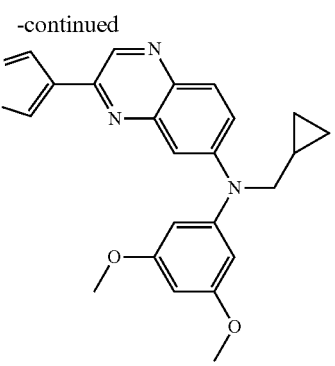
as a HCl salt
62; =Co7
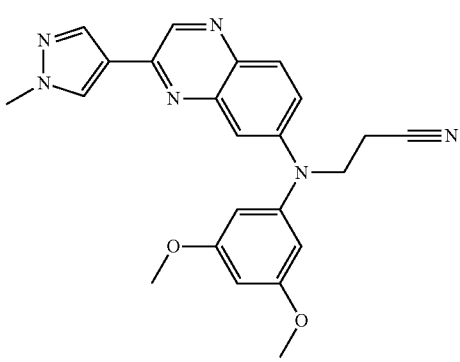
122; ~B5
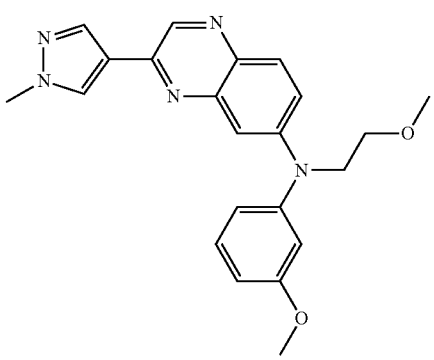
220; ~B5
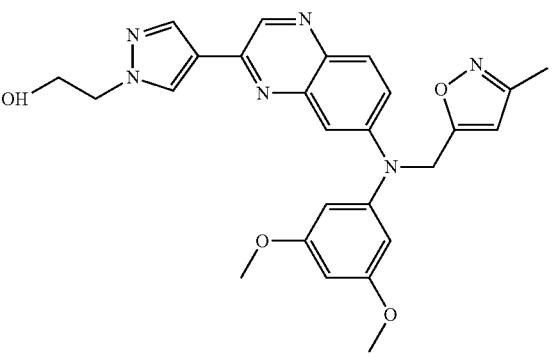
23; =B14

331
-continued
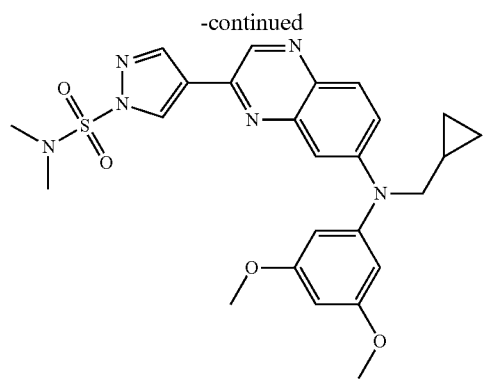
58; =Co5g
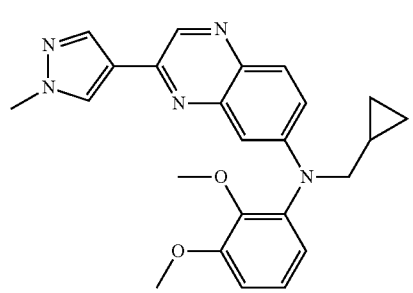
221; ~B5
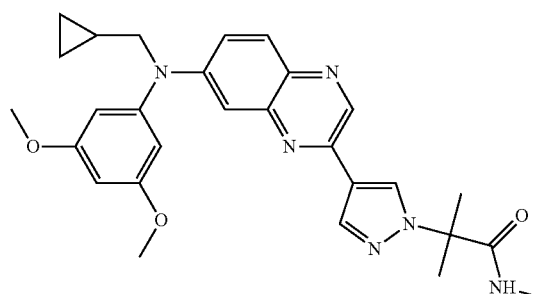
226; ~B12
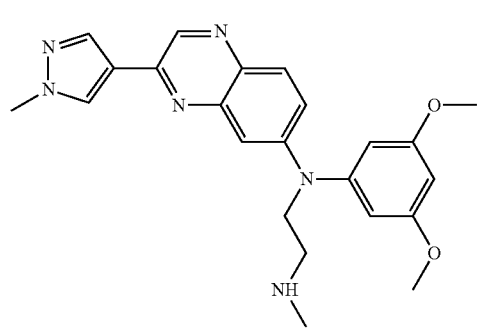
8; =B4A ~B3a/B3/B4a
332
-continued
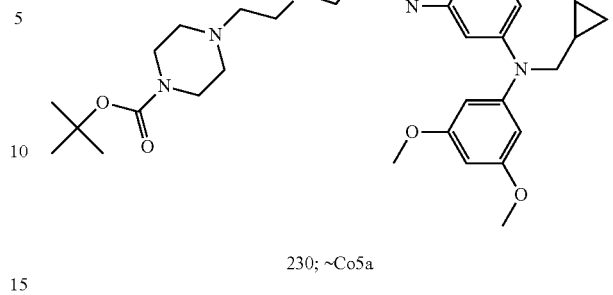
230; ~Co5a
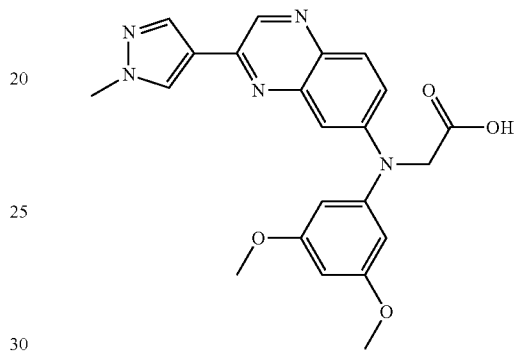
as aHCl salt
64; =Co8
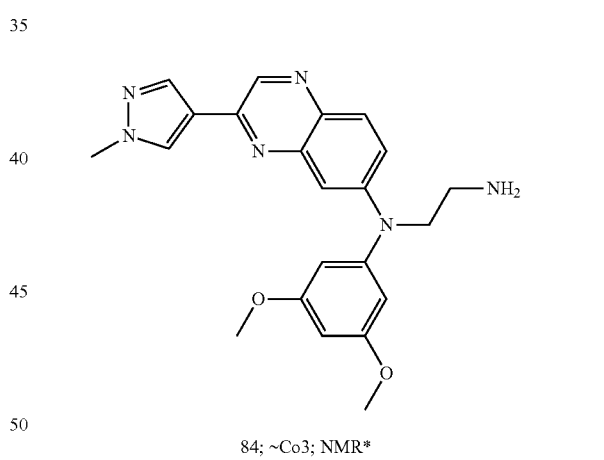
84; ~Co3; NMR*
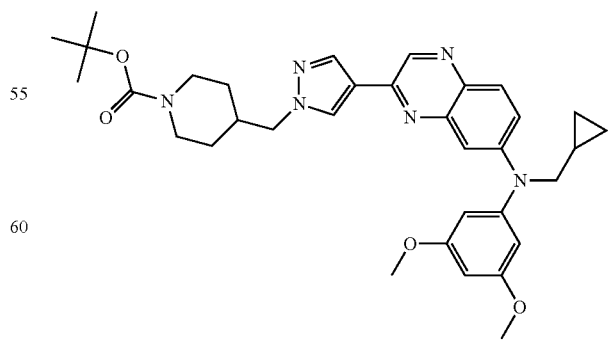
128; ~Co5a 333
-continued
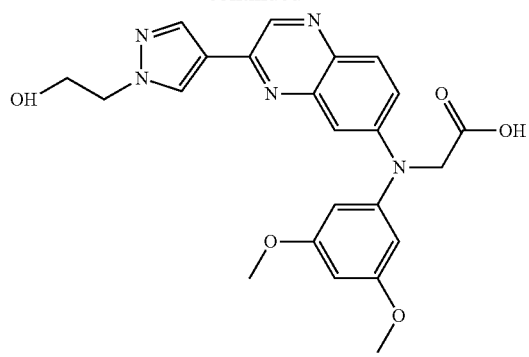
233; ~B1/B2a
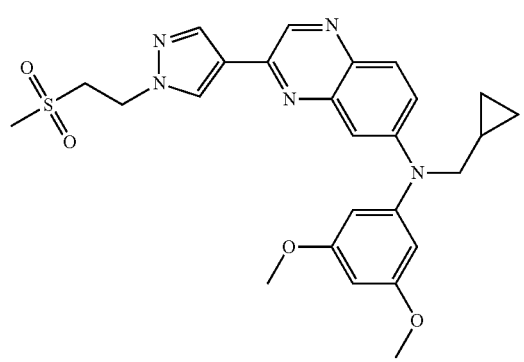
227; ~Co5a
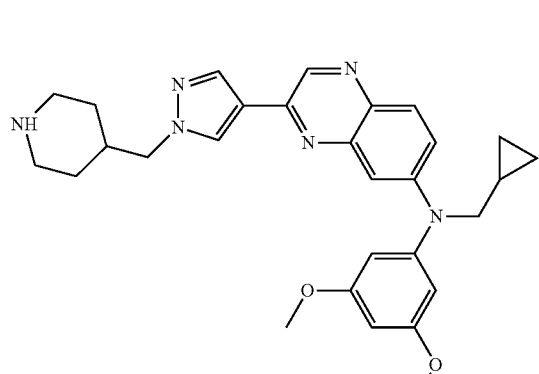
73; ~Co7
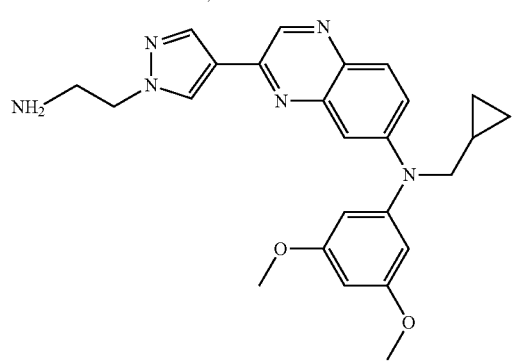
19; =B11
334
-continued
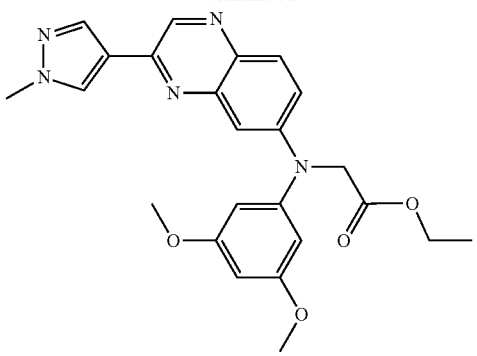
65; ~B5 b-1
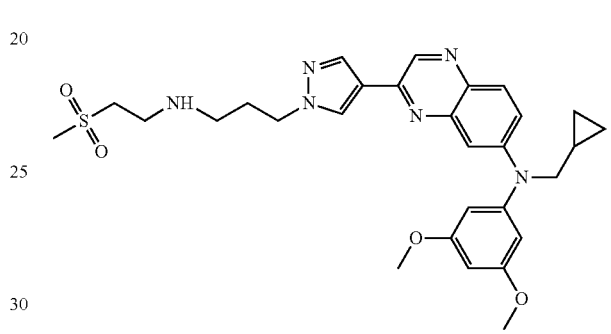
231; ~Co5f
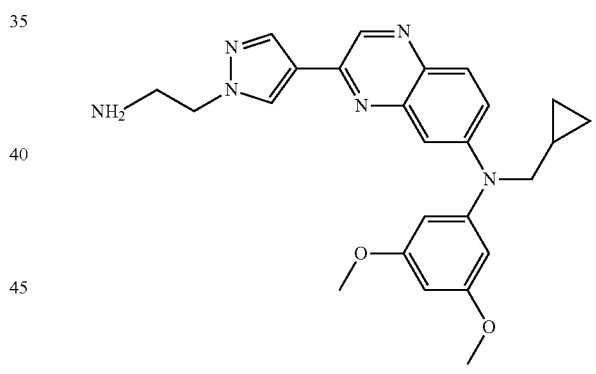
as a HCl salt
234; =B11
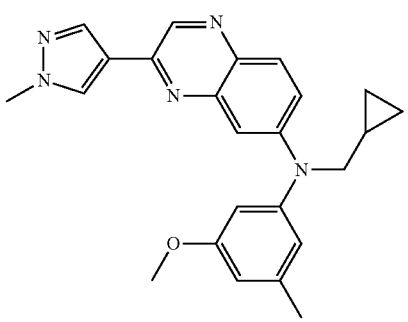
228; ~B5

335
-continued
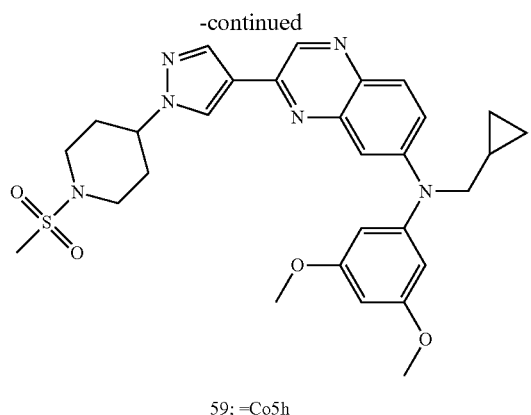
59; =Co5h
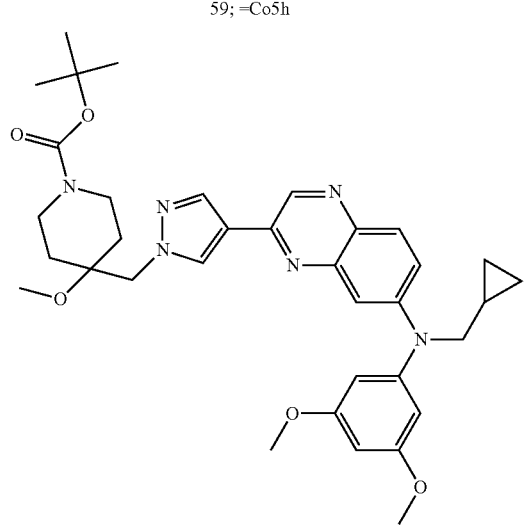
116; =Co40
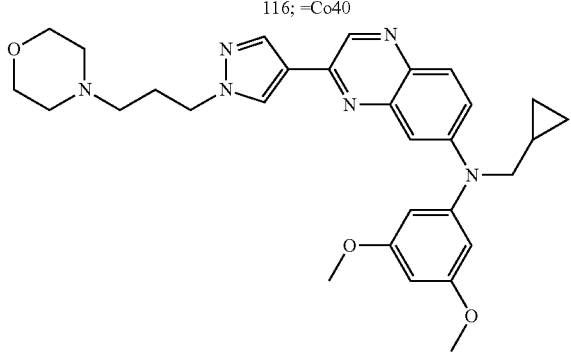
as a HCl salt
229; ~Co6
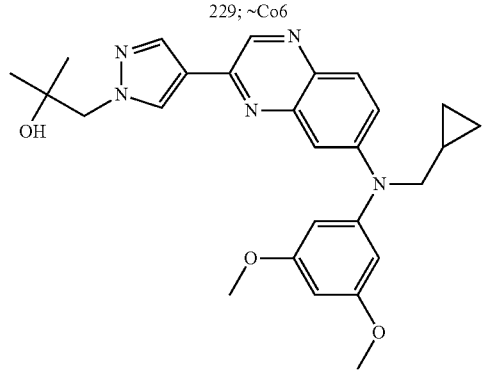
52; = Co5b
336
-continued
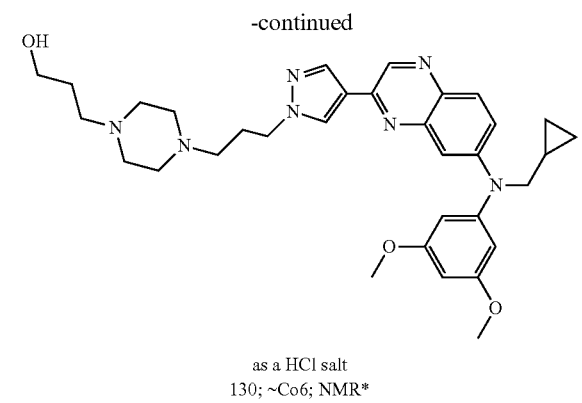
as a HCl salt
130; ~Co6; NMR*
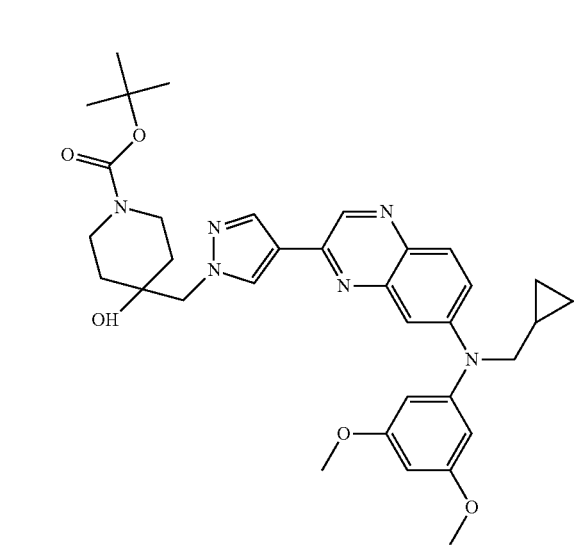
117; ~B9c
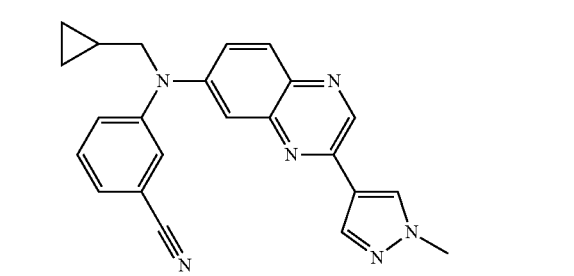
232; ~B5
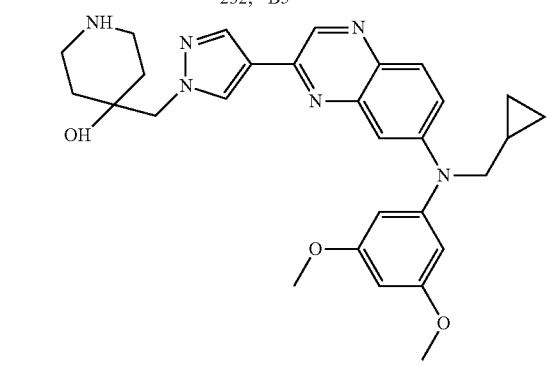
235; ~Co7

-continued
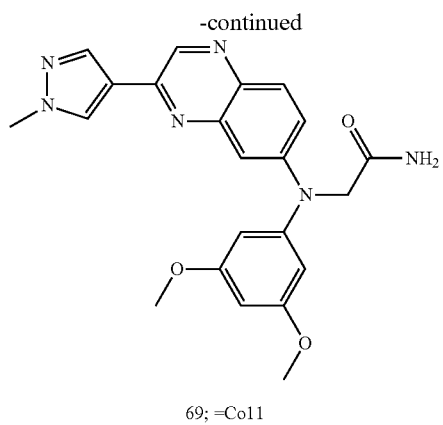
69; =Co11
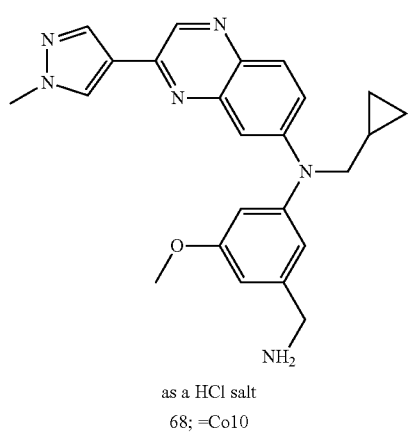
as a HCl salt
68; =Co10
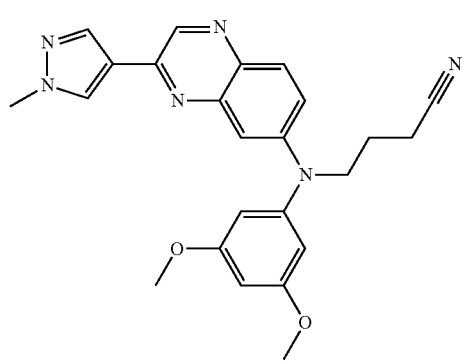
242; ~B5
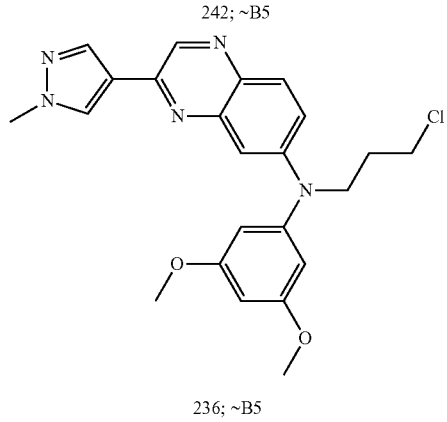
236; ~B5
-continued
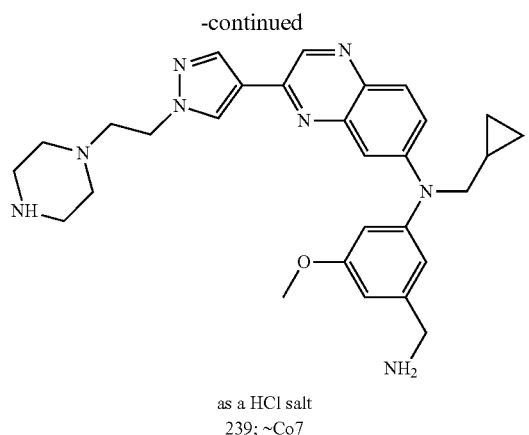
as a HCl salt
239; ~Co7
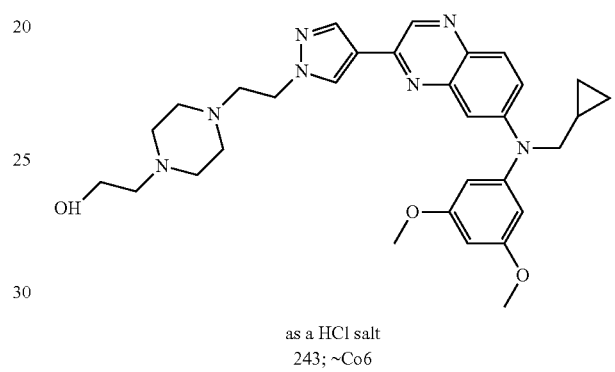
as a HCl salt
243; ~Co6
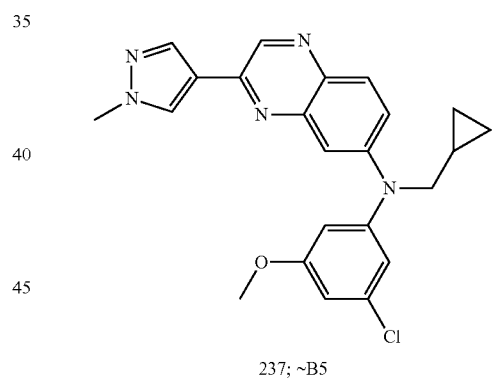
237; ~B5
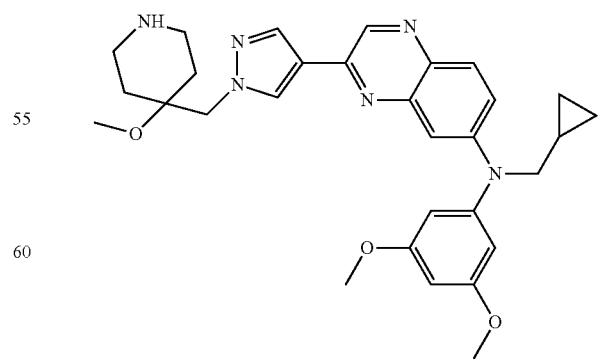
240; ~Co7

339
-continued
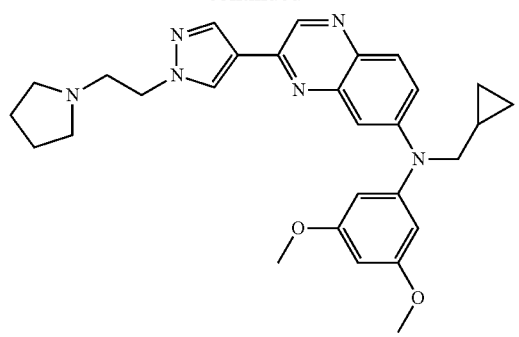
as a HCl salt
244; ~Co5a
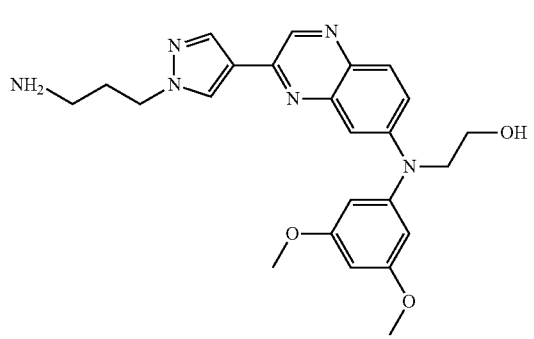
as a HCl salt
238; ~B1/B2a
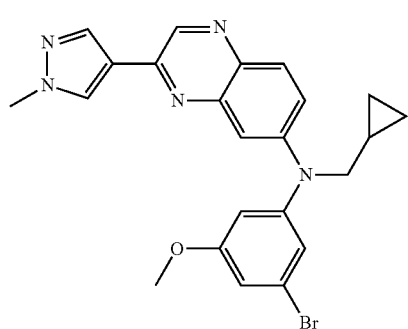
67; ~B5
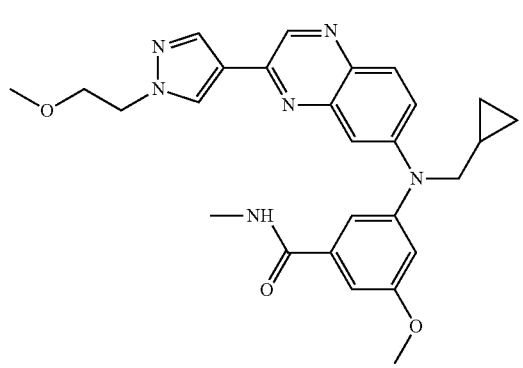
245; ~B5
340
-continued
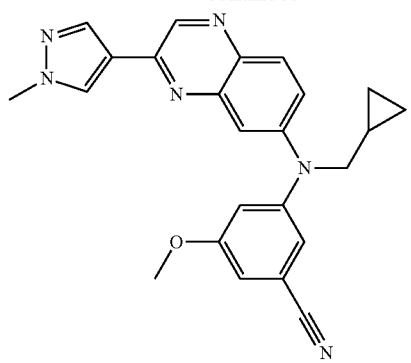
66; =Co9
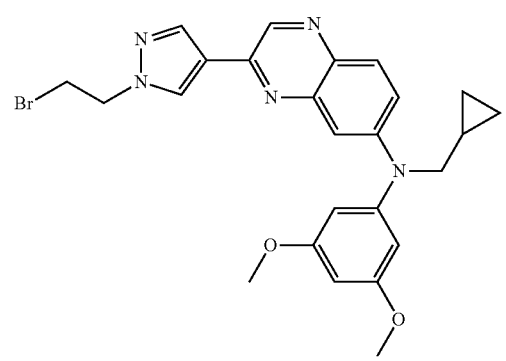
50; ~Co5a
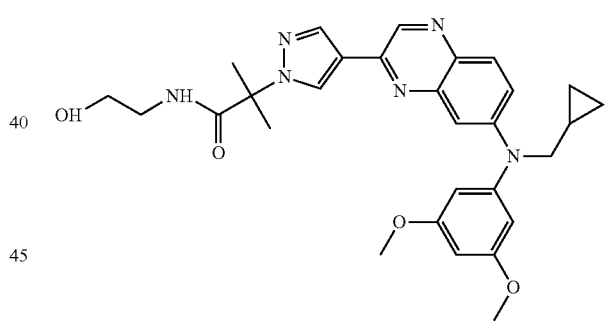
246; ~B12
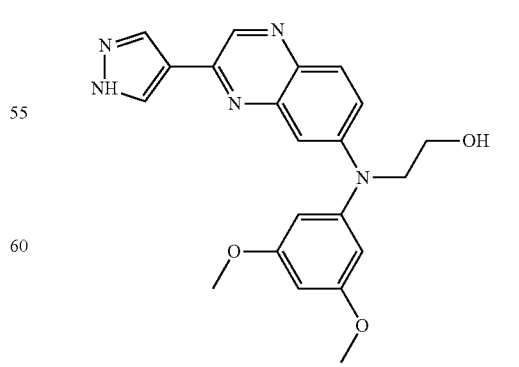
2; ~B1a/B17; =B50

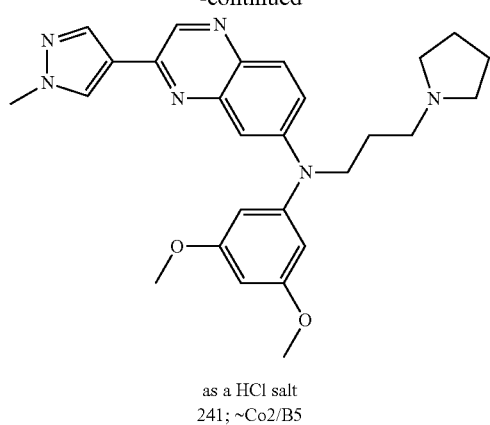
as a HCl salt
241; ~Co2/B5
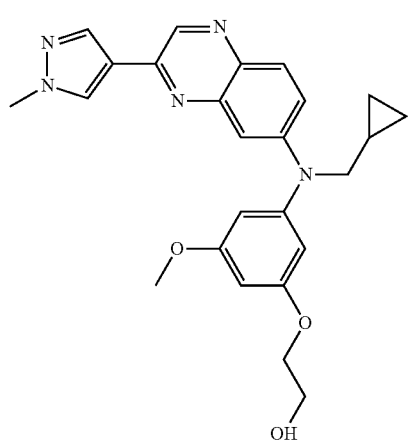
24; =B15
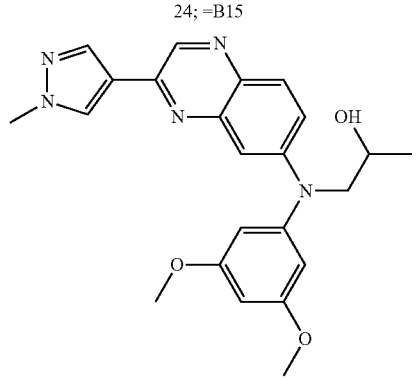
113; ~B6
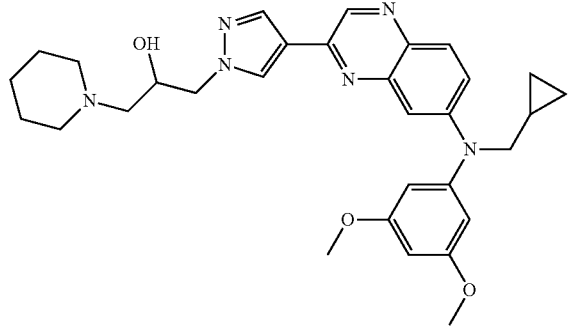
55; =Co5d
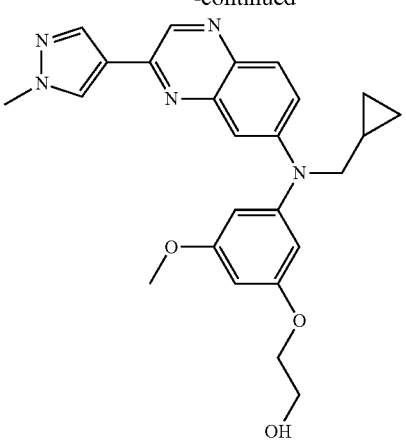
as a HCl salt
247; =B15
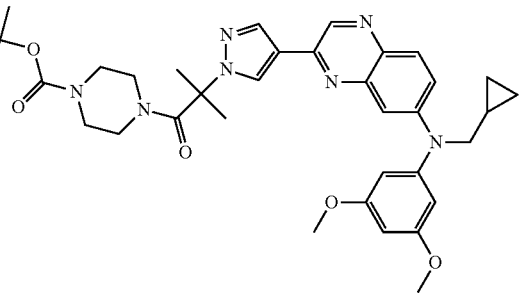
248; ~B12
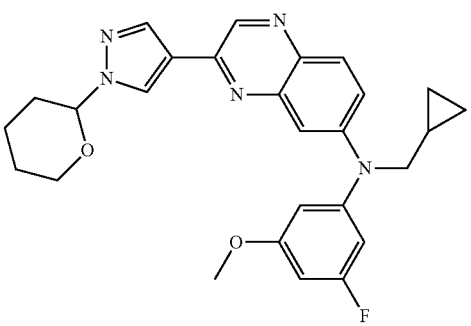
252; ~B5
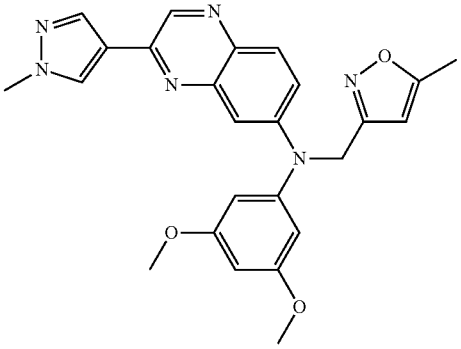
256; =B5

-continued
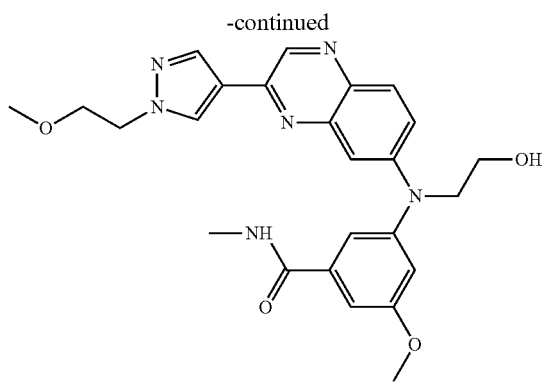
249; ~B1/B2a
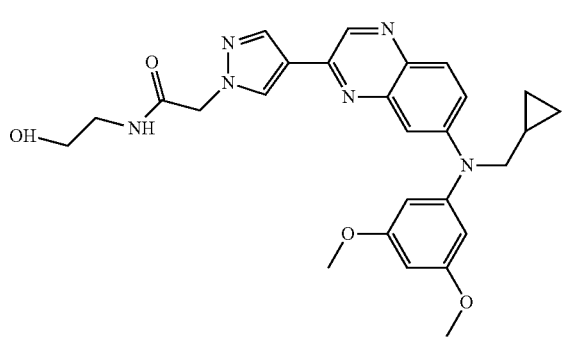
253; ~B12
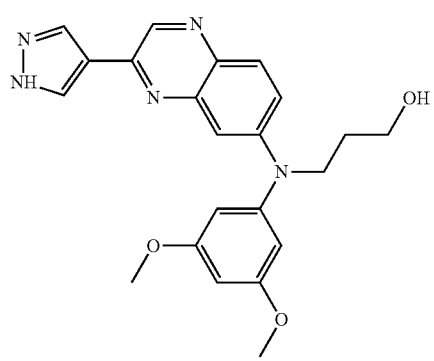
26; =B17
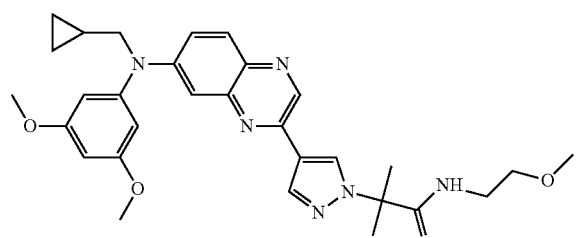
250; ~B12
-continued
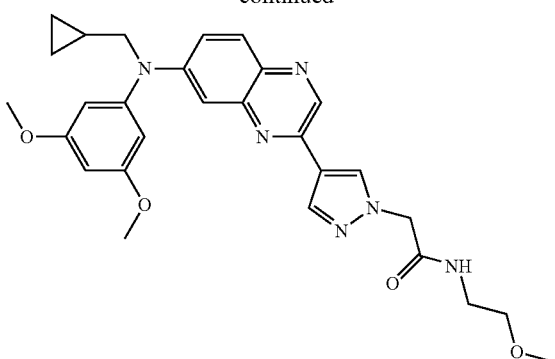
254; ~B12
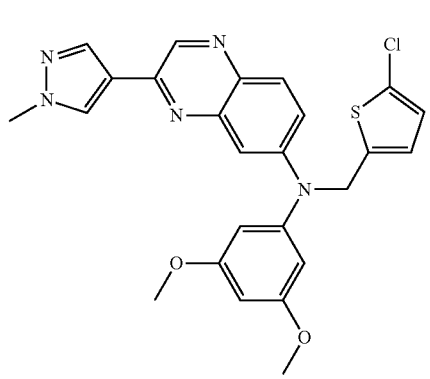
257; ~B5
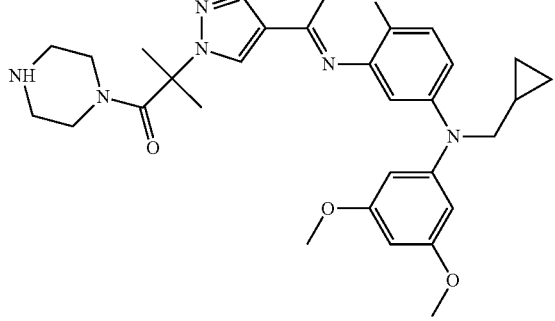
251; ~Co7
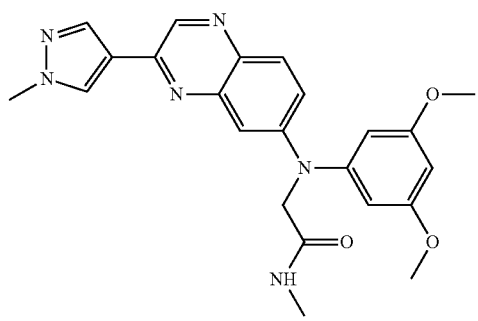
74; =Co14

-continued
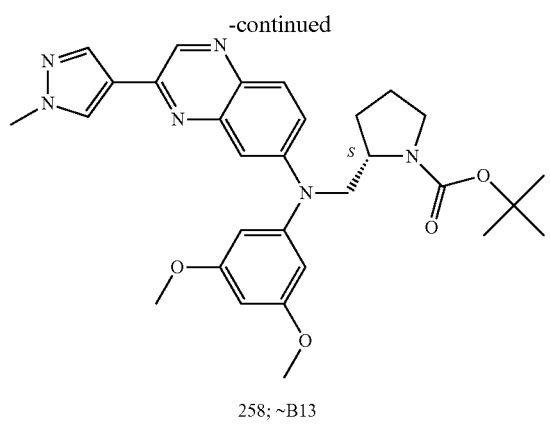
258; ~B13
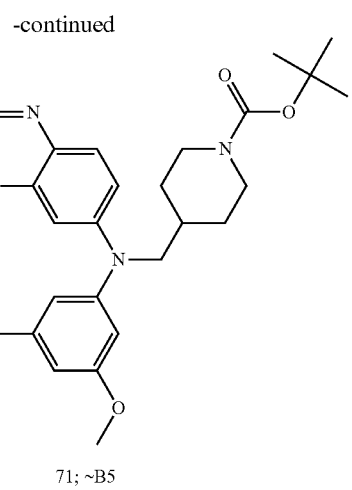
71; ~B5
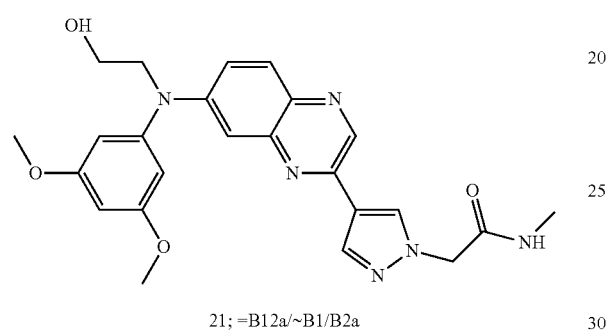
21; =B12a/~B1/B2a
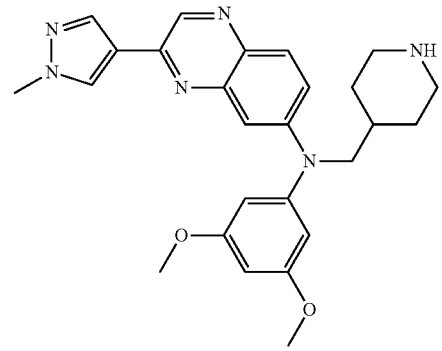
70; =Co12
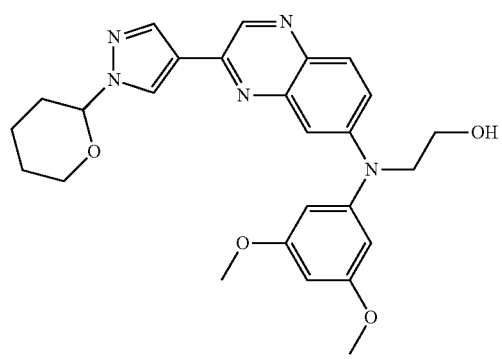
255; ~B1/B2a/B3/B4a
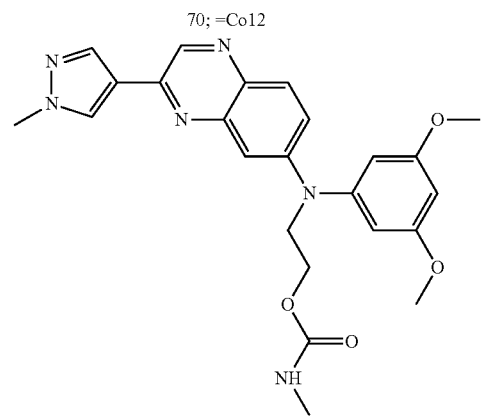
7; ~B3/B3A
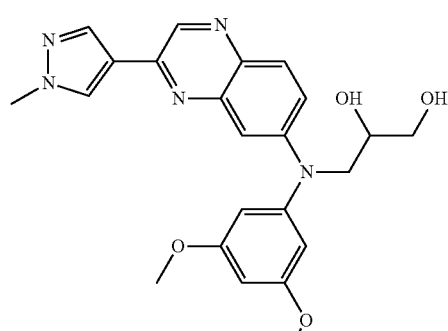
75; =Co15/Co16
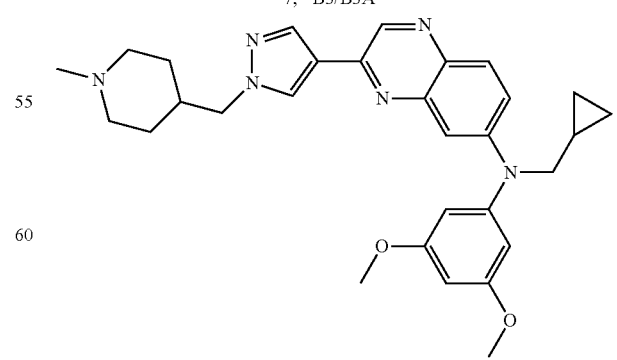
72; =Co13

347
-continued
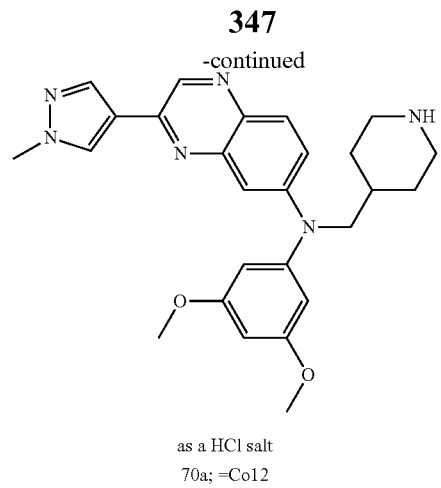
as a HCl salt
70a; =Co12
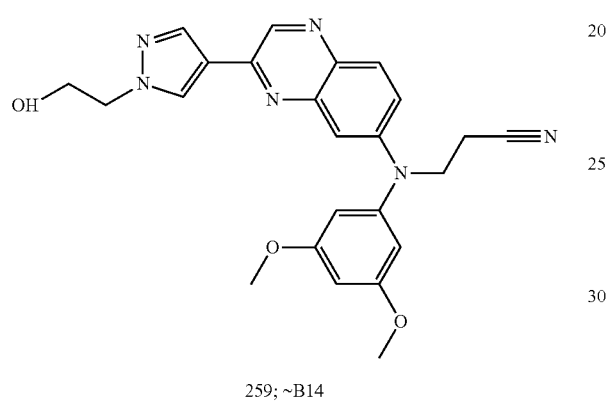
259; ~B14
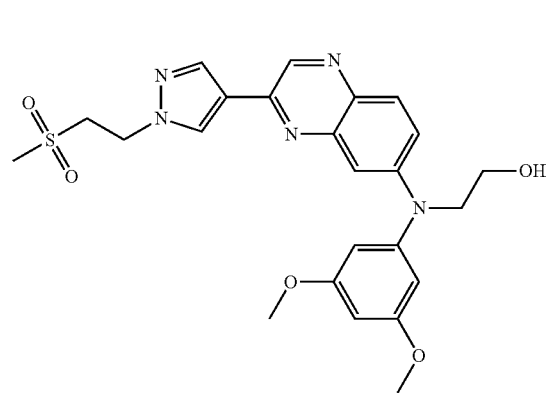
260; ~B1/B2a
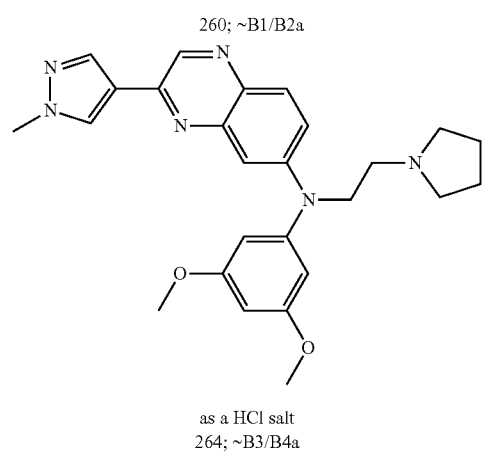
as a HCl salt
264; ~B3/B4a
348
-continued
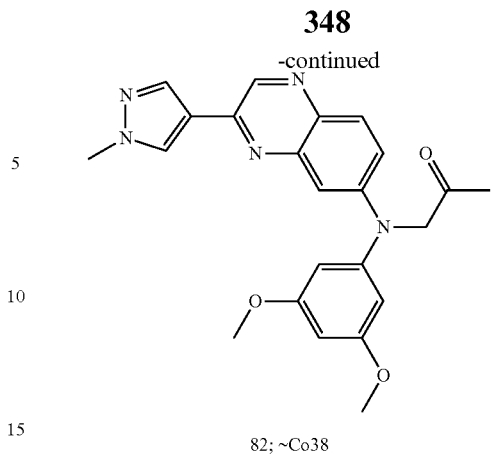
82; ~Co38
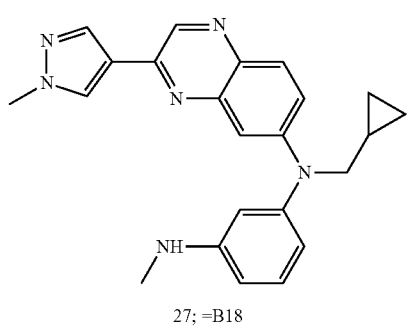
27; =B18
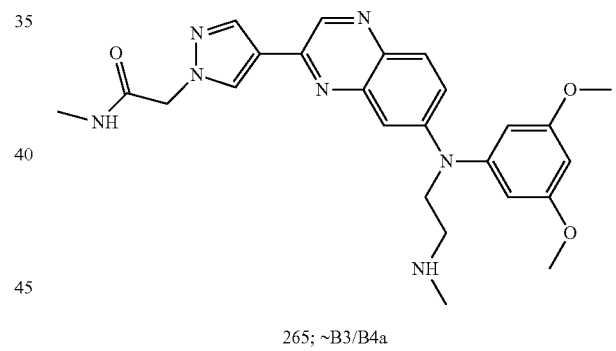
265; ~B3/B4a
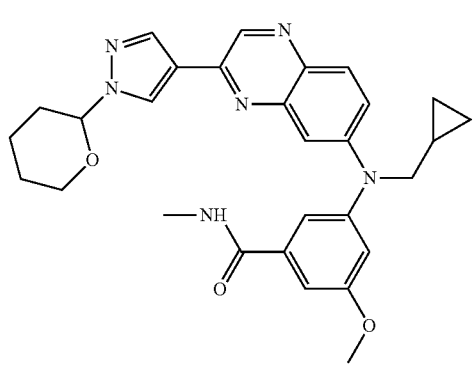
270; ~B5

-continued
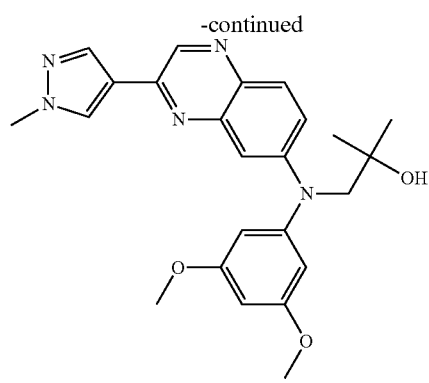
78; =Co16/~B6
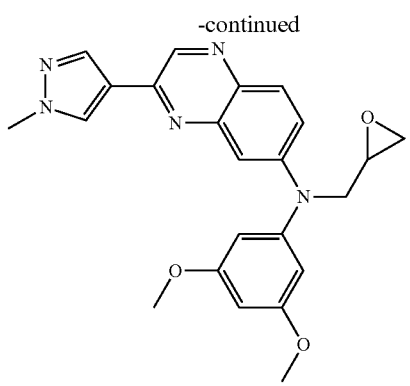
76; ~B5
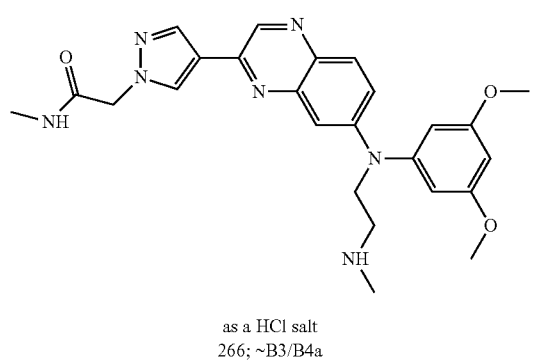
as a HCl salt
266; ~B3/B4a
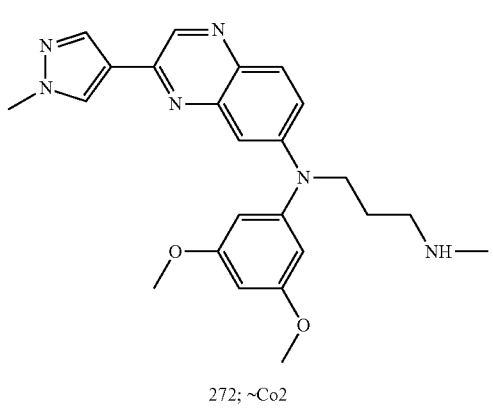
272; ~Co2
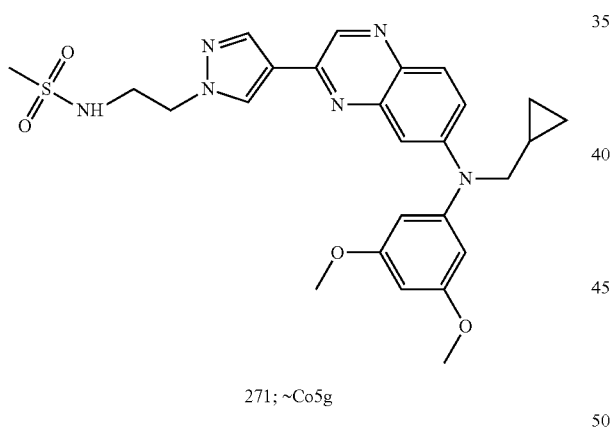
271; ~Co5g
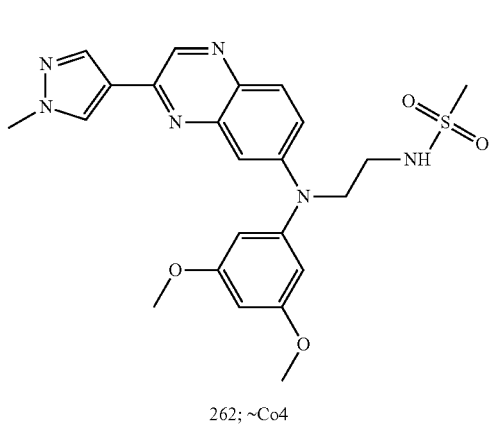
262; ~Co4
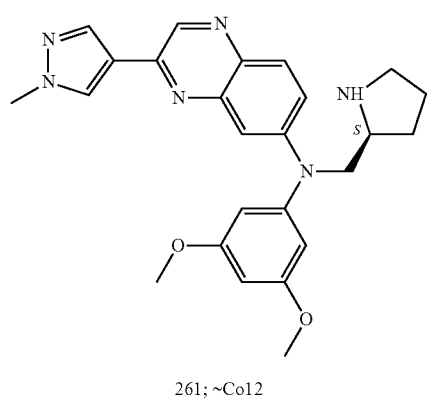
261; ~Co12
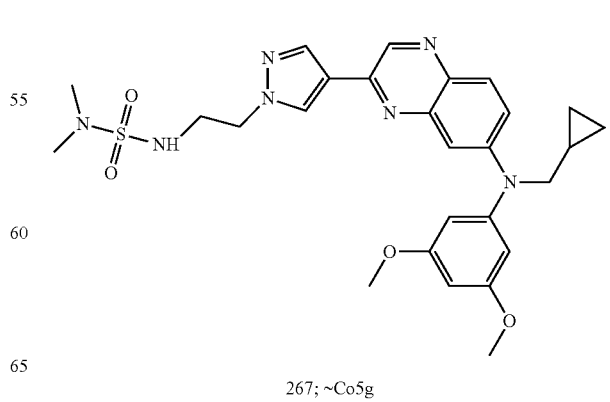
267; ~Co5g 351
-continued
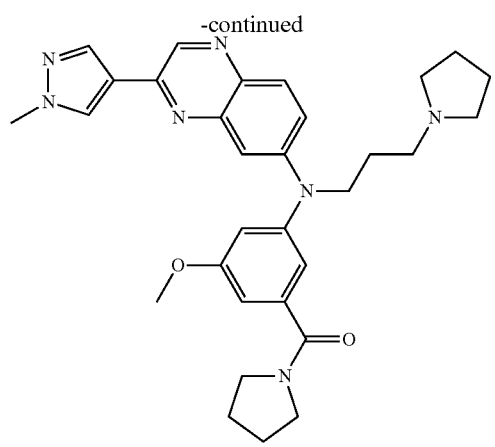
273; ~B5
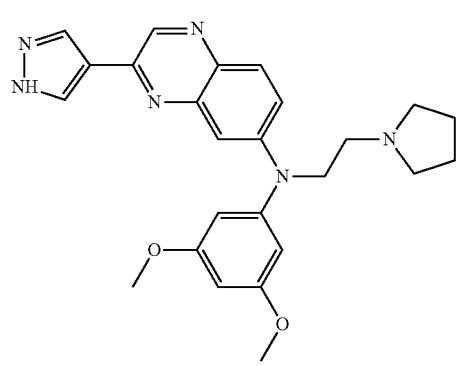
as a HCl salt
25; =B16
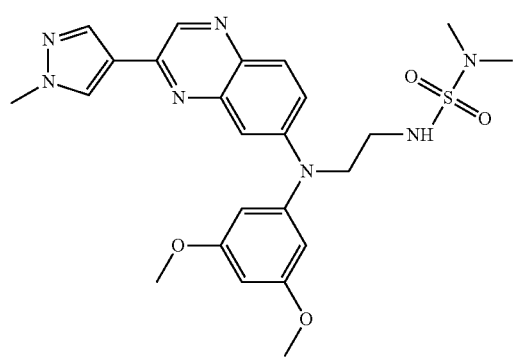
268; ~Co4
352
-continued
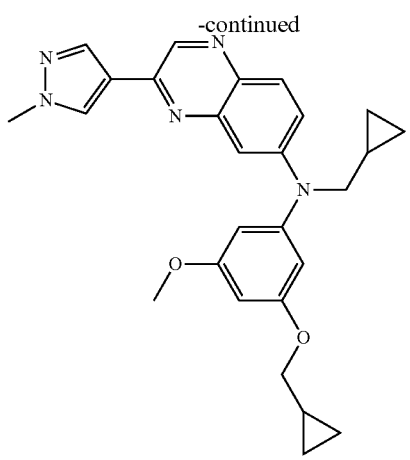
as a HCl salt
274; ~B5
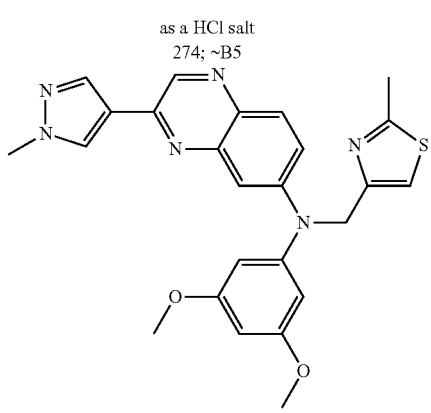
263; ~B5
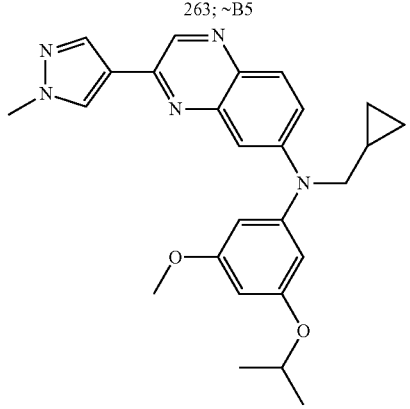
as a HCl salt
269; ~B5
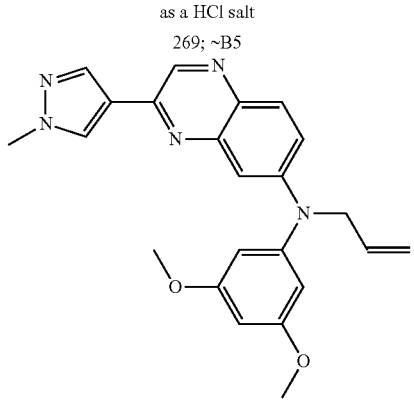
121; ~B5

353
-continued
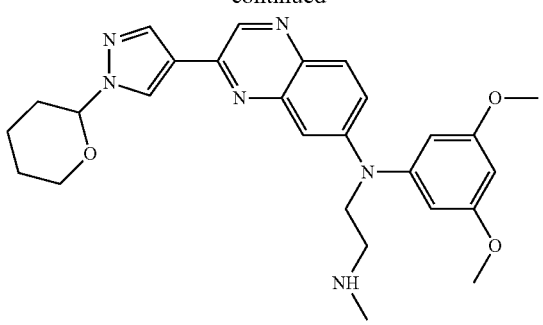
275; ~B3/B4a
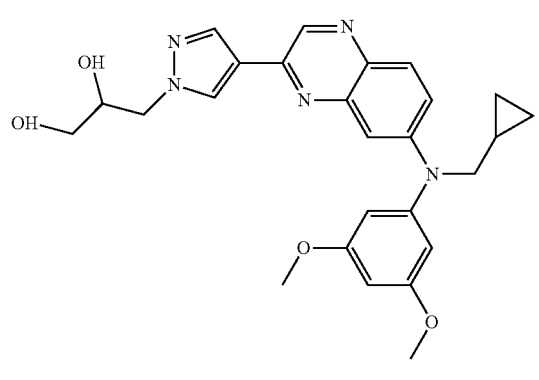
37; =B28
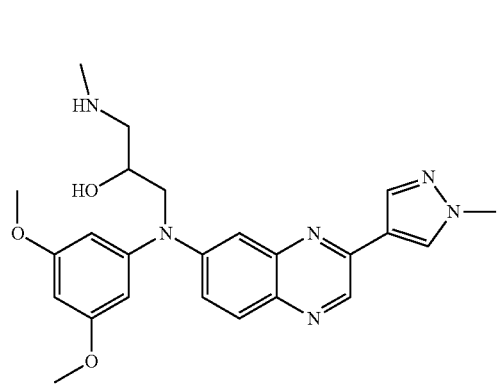
as a HCl salt
79a and 79; =Co18
354
-continued
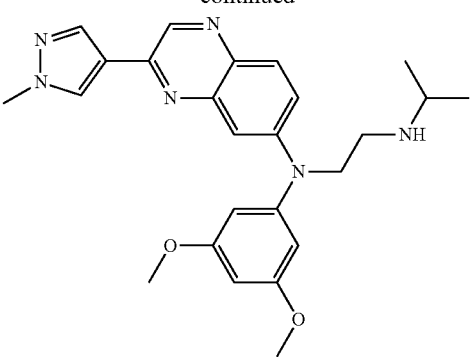
4 =B3; NMR*
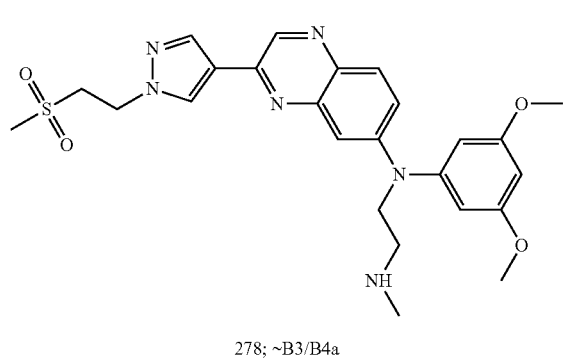
278; ~B3/B4a
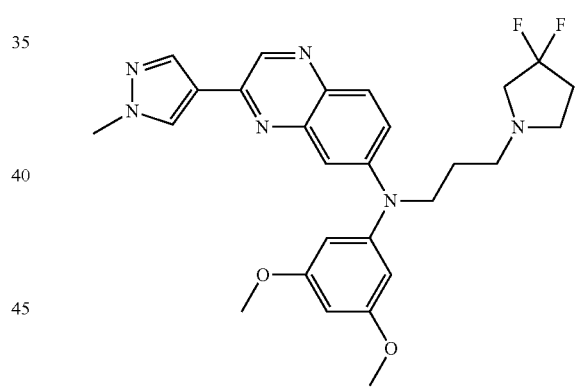
as a HCl salt
602; ~B3/B4a
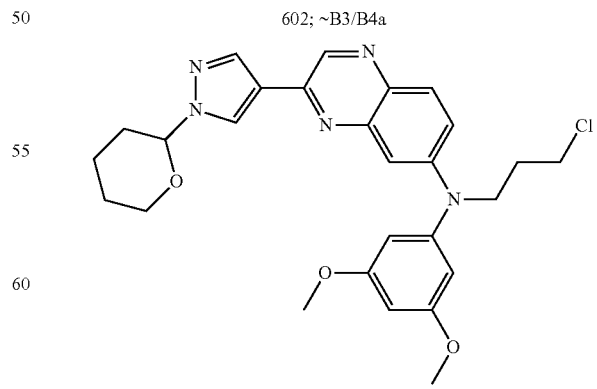
9; ~B5

355
-continued
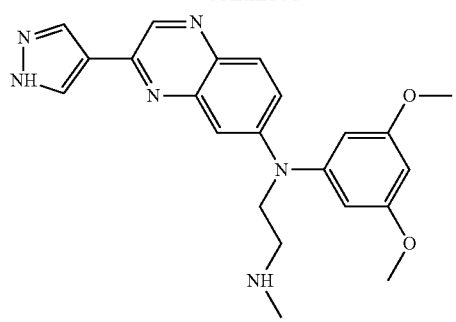
279; ~Co1
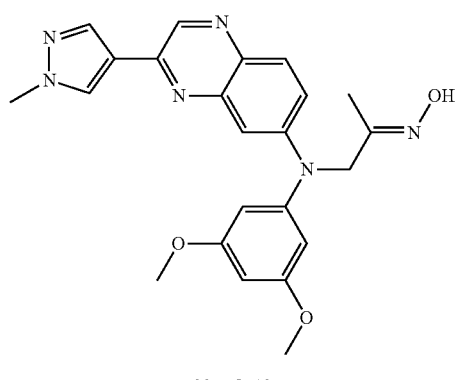
80; ~Co19
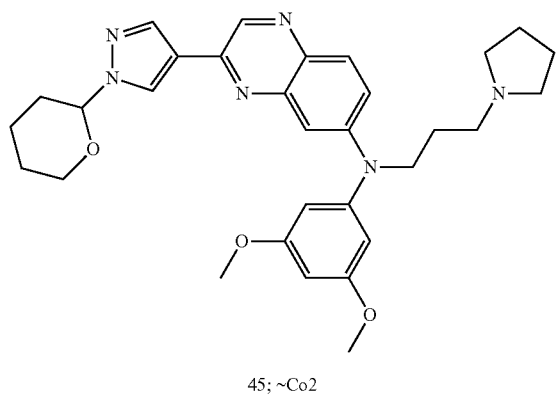
45; ~Co2
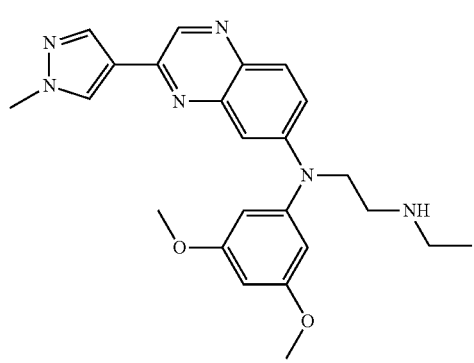
280; ~B3a/B3/B4a
356
-continued
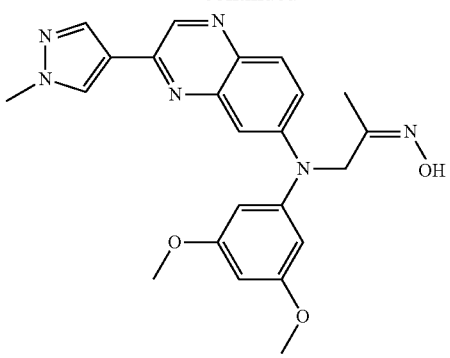
81; =Co19
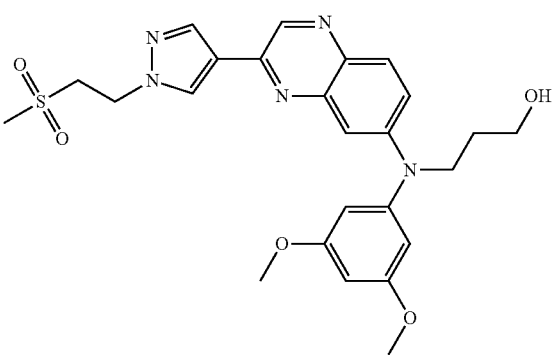
276; ~B1/B2a
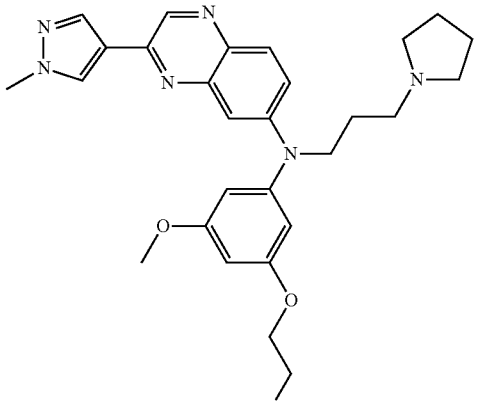
281; ~B15
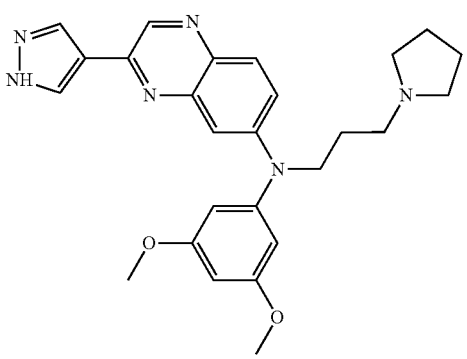
284; ~Co1

357
-continued
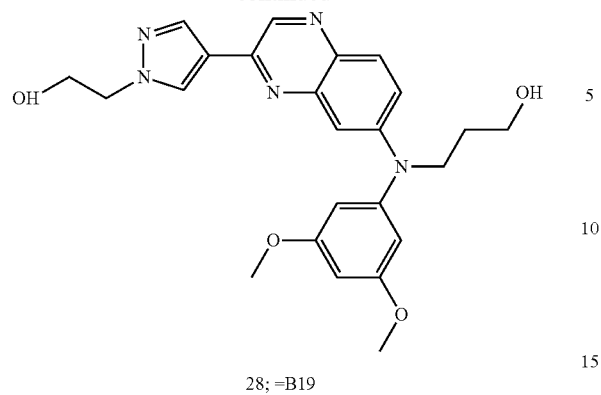
28; =B19
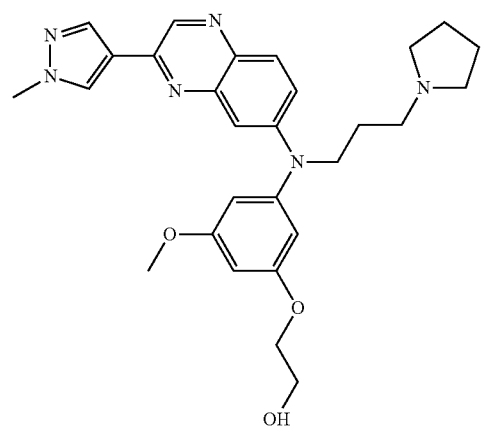
as a HCl salt
282; ~B15
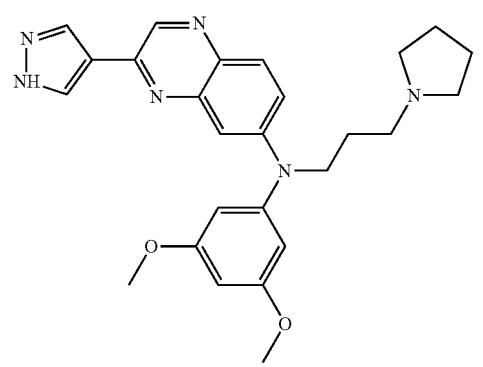
as a HCl salt
285; ~Co1
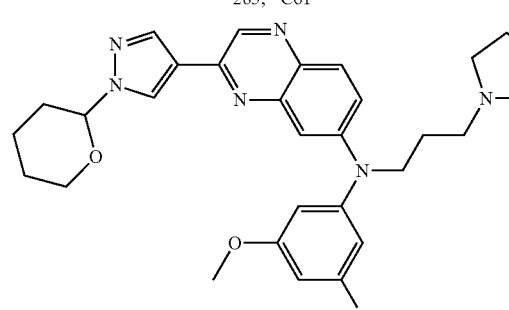
277; ~B5
358
-continued
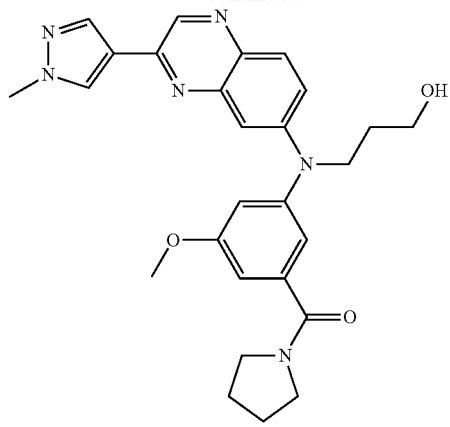
as a HCl salt
283; ~B2b
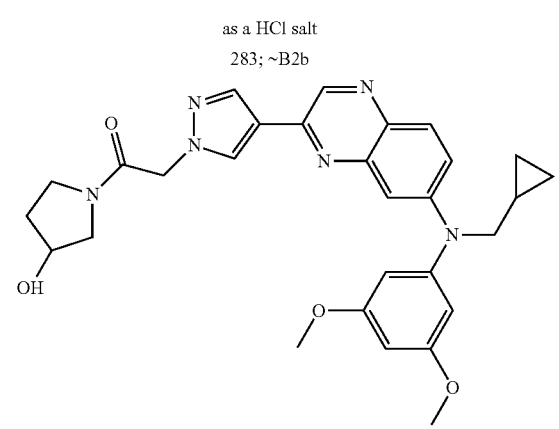
20; =B12
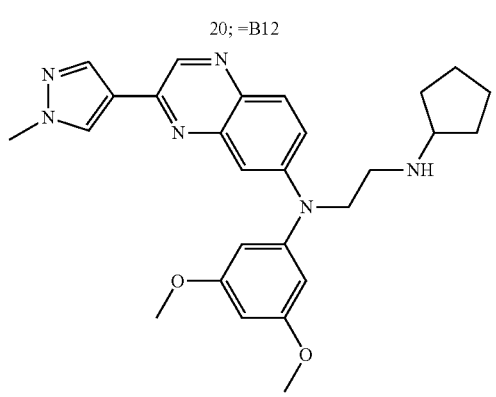
286; ~B3/B4a
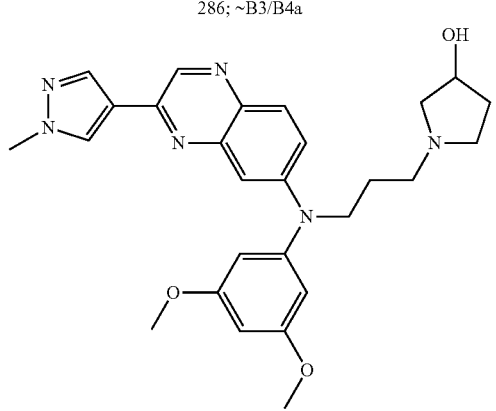
88; ~Co2/B3/B4a 359
-continued
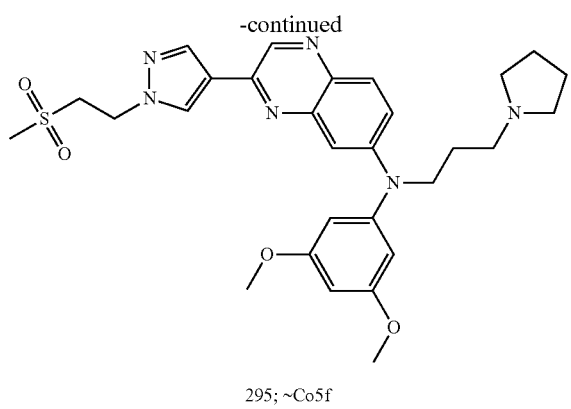
295; ~Co5f
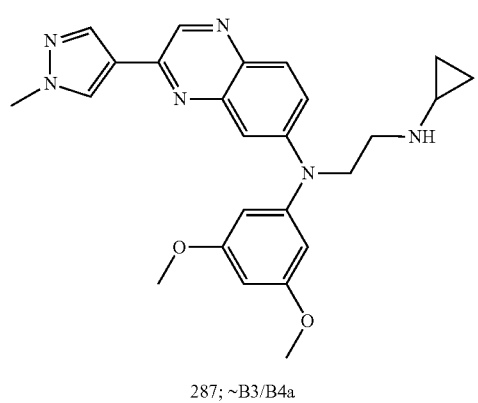
287; ~B3/B4a
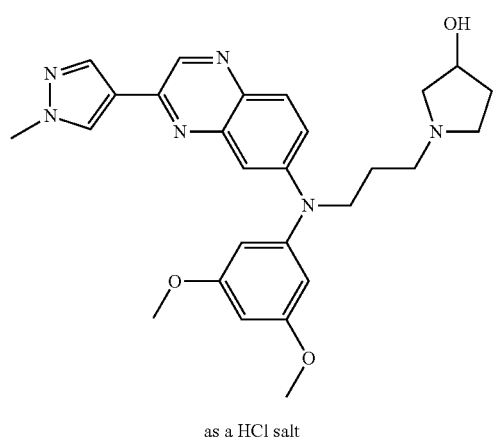
as a HCl salt
291; ~Co2/B3/B4a
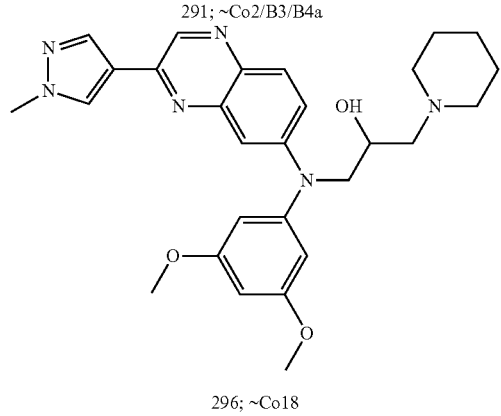
296; ~Co18
360
-continued
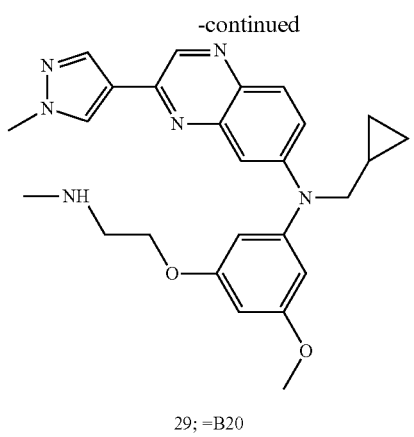
29; =B20
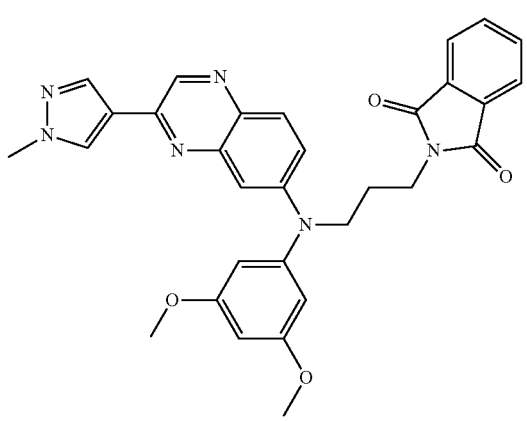
292; ~B3/B4a
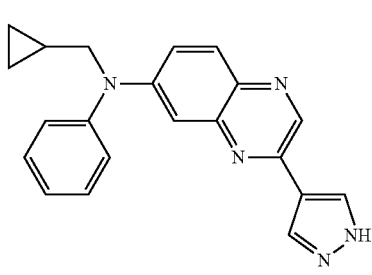
as a HCl salt
54;; ~Co1
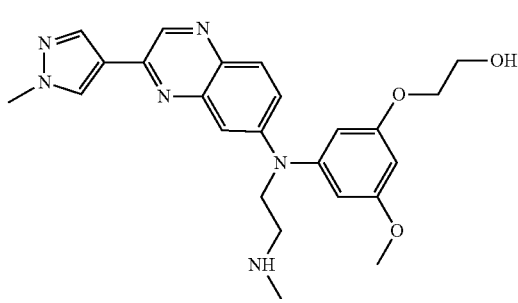
as a HCl salt
288; ~B15

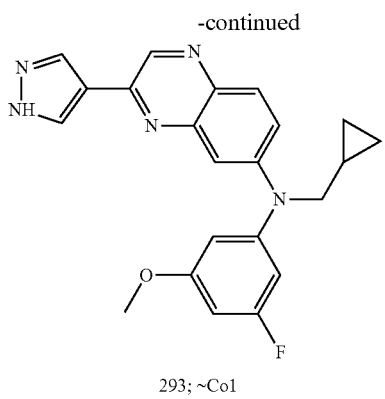
293; ~Co1
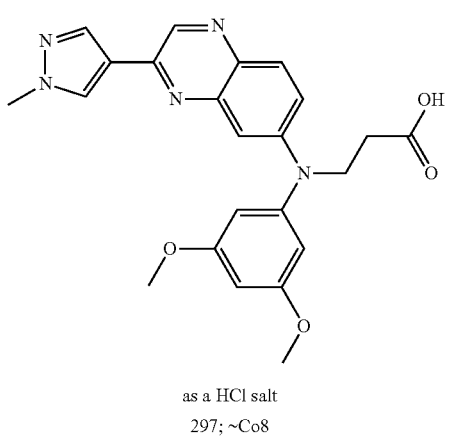
as a HCl salt
297; ~Co8
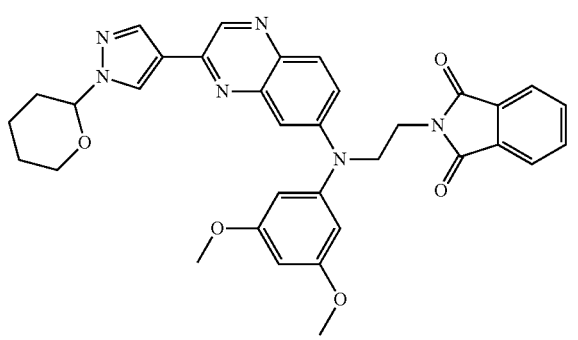
289; ~B3/B4a
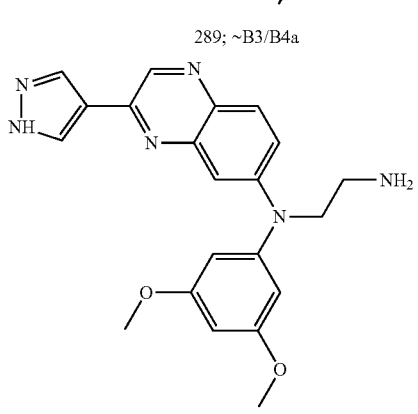
as a HCl salt
294; ~Co1
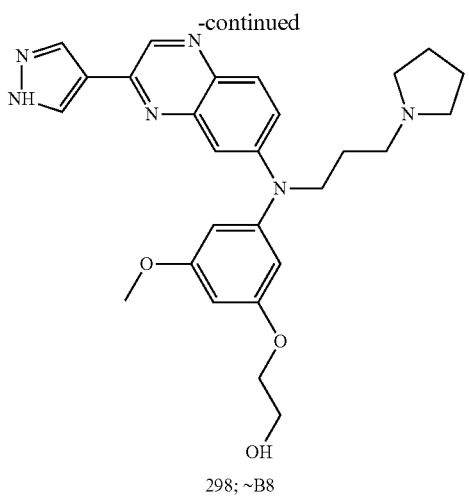
298; ~B8
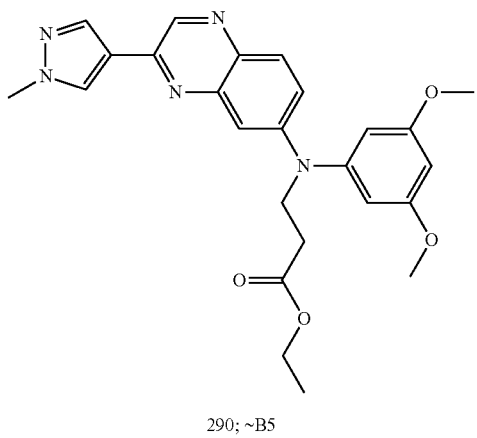
290; ~B5
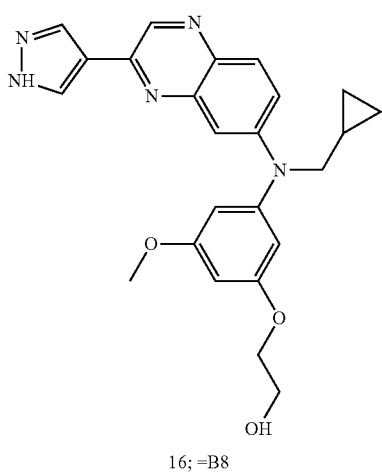
16; =B8

363
-continued
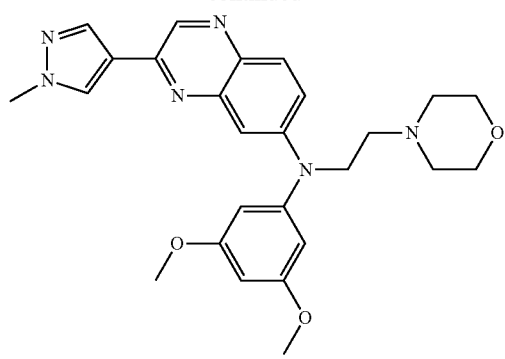
as a HCl salt
299; ~B3/B4a
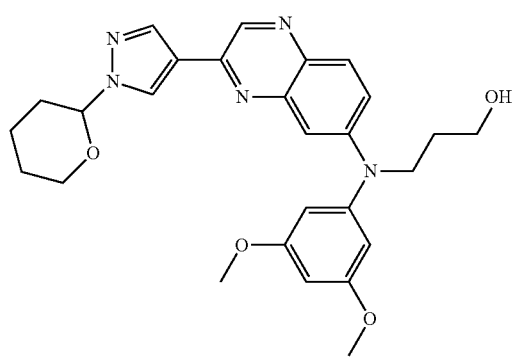
49; ~B1
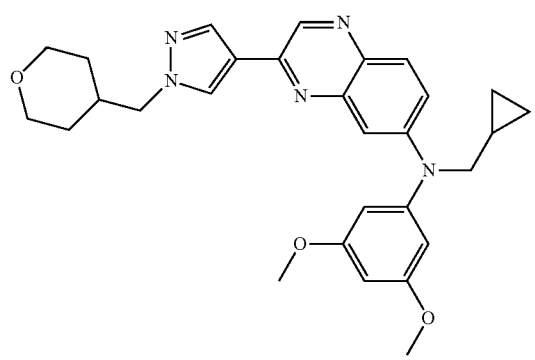
305; ~Co5a
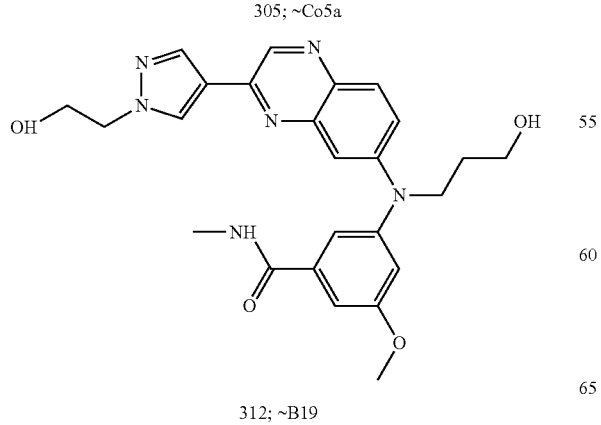
312; ~B19
364
-continued
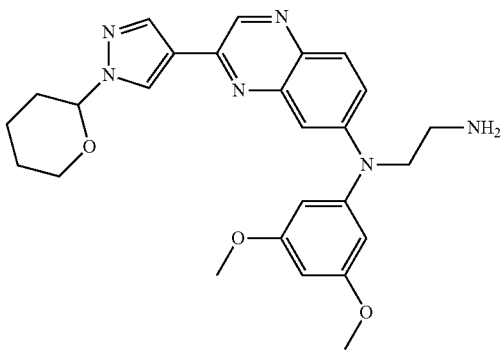
301; ~Co3
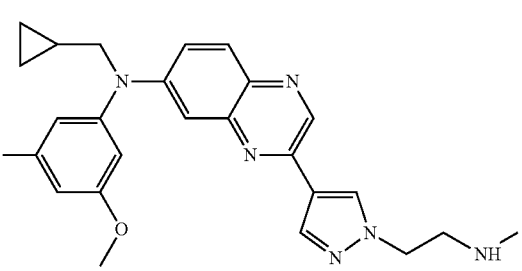
61; =Co6
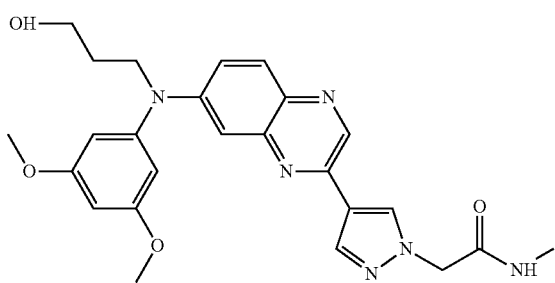
313; =B36
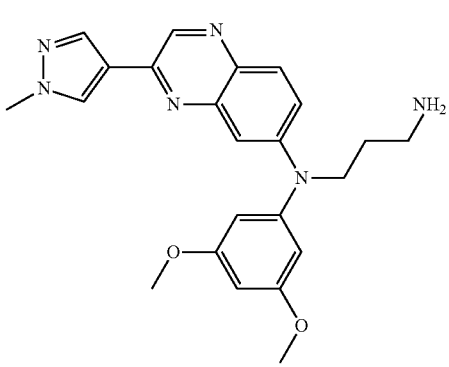
93; ~Co3;; NMR; =B52*

365
-continued
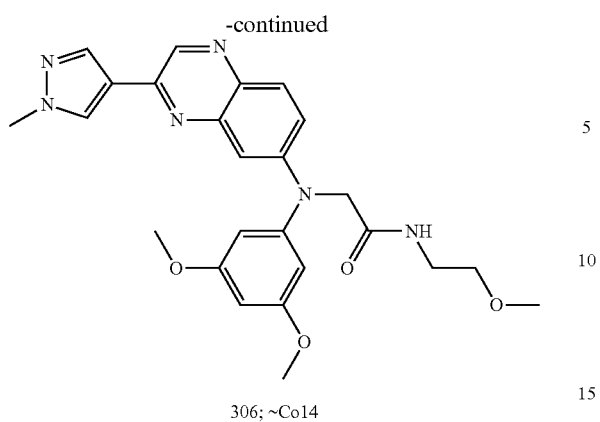
306; ~Co14
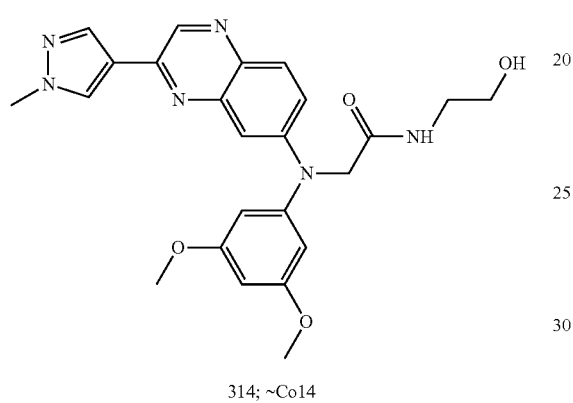
314; ~Co14
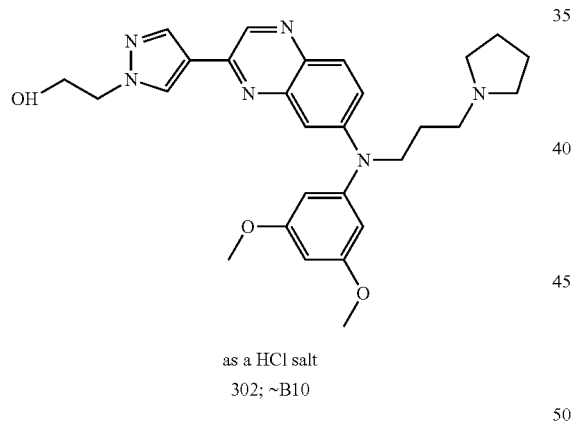
as a HCl salt
302; ~B10
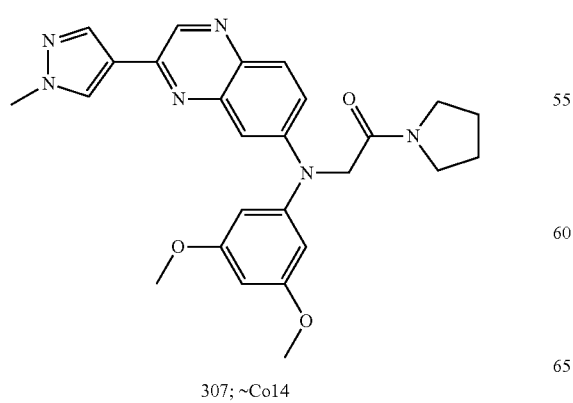
307; ~Co14
366
-continued
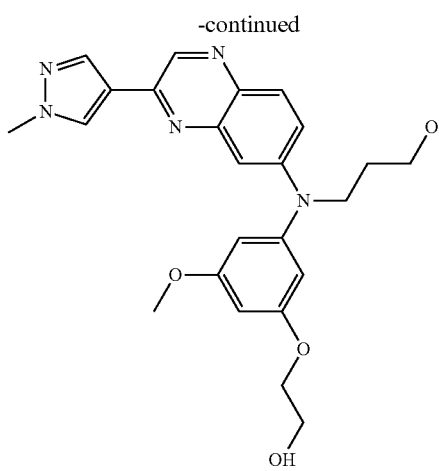
30; =B21
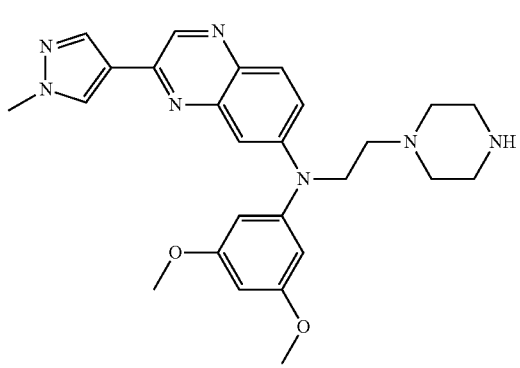
as a HCl salt
303; ~B3/B4a
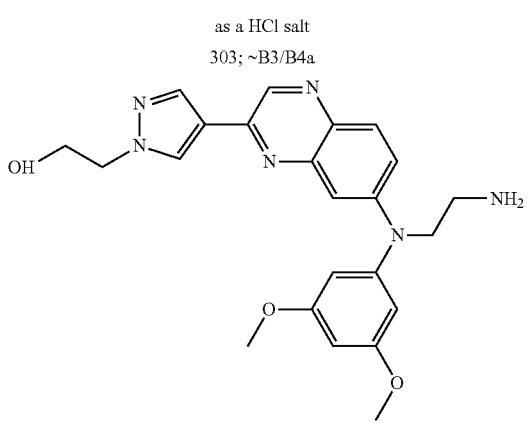
as a HCl salt
308; ~B10
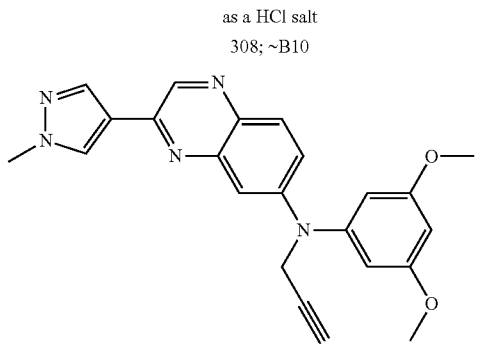
38; ~B29

-continued
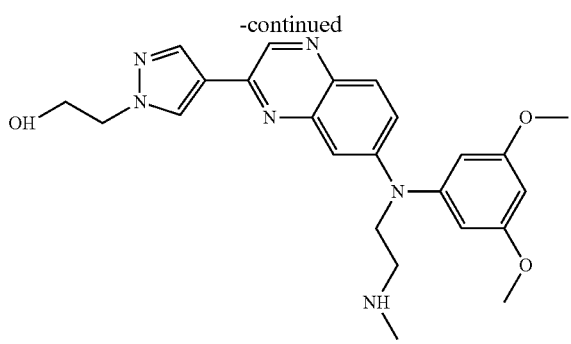
304; ~B10
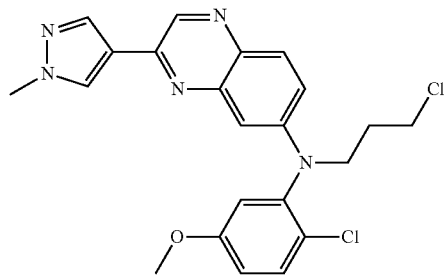
310; ~B5
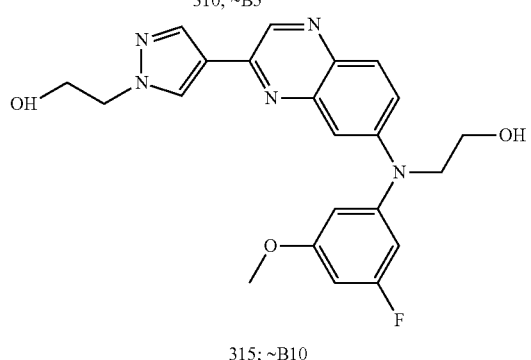
315; ~B10
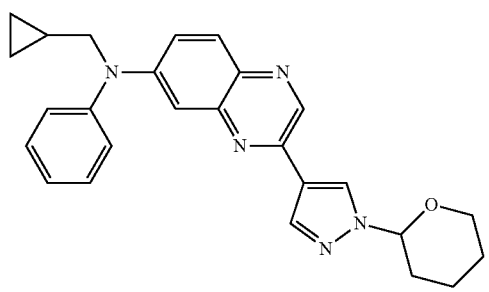
123; =A9c/~B5
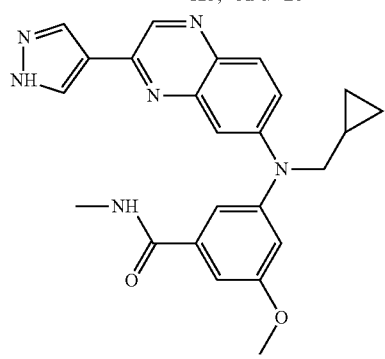
311; ~Co1
-continued
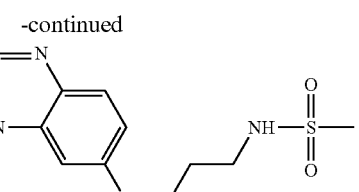
48; =Co4
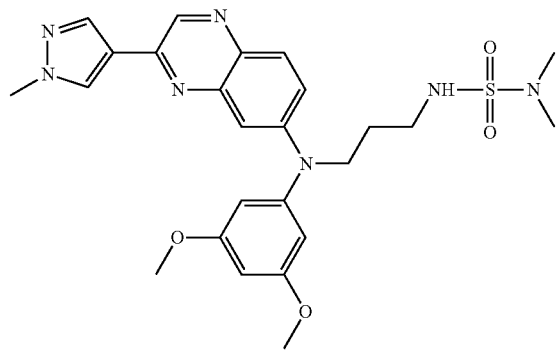
316; ~Co4
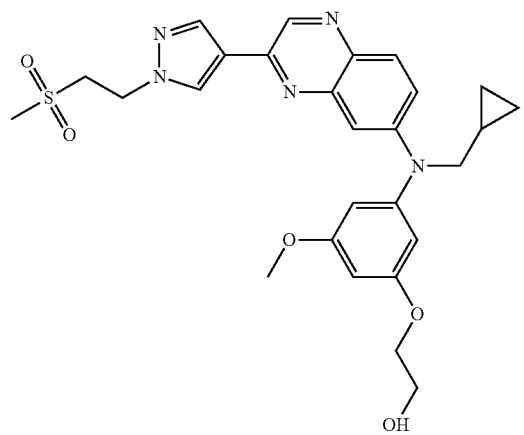
57; =Co5f
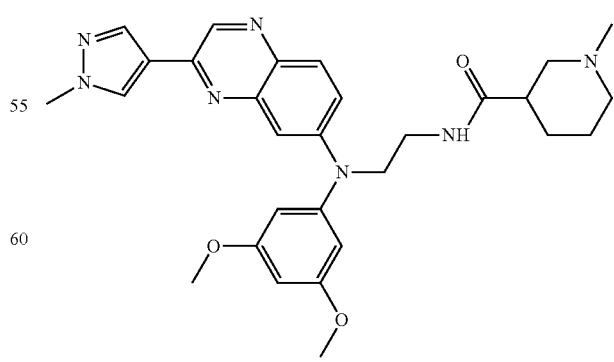
83; =Co20

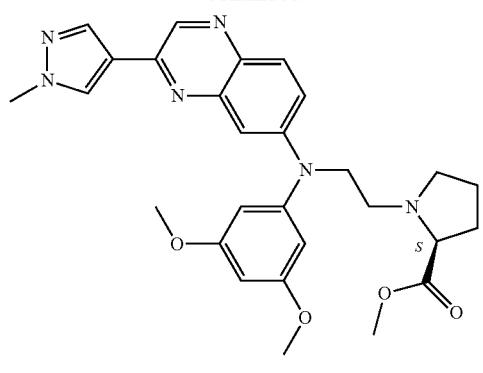
317; ~B3/B4a
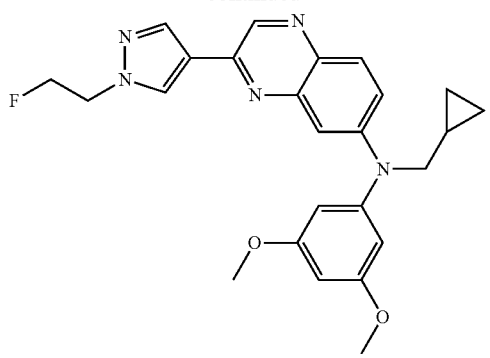
85; =Co21
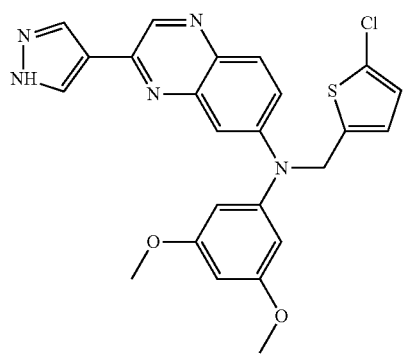
323; ~B9a
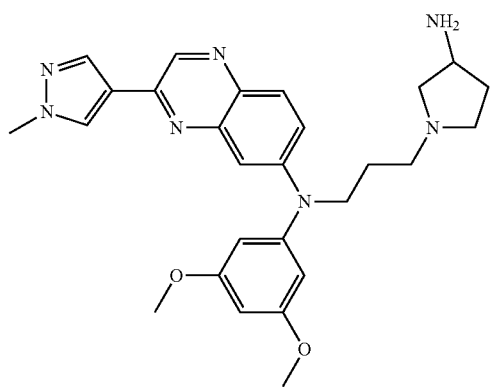
328; ~B7
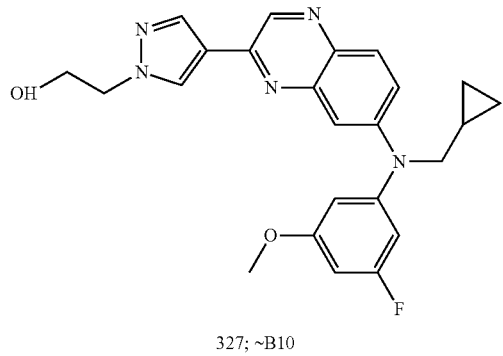
327; ~B10
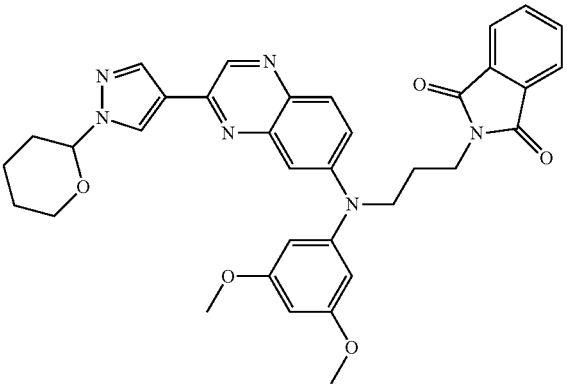
319; ~B3/B4a
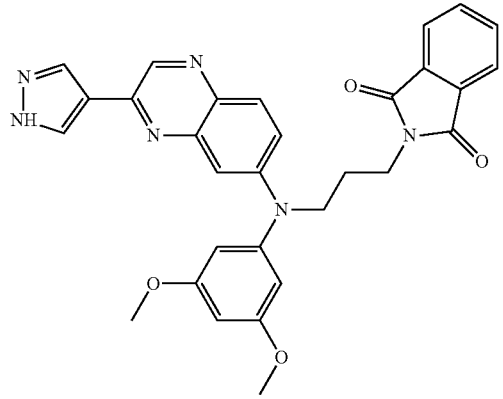
318; ~Co1
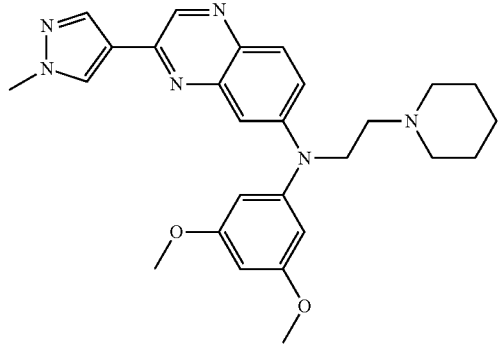
324; ~B3/B4

| 371 | 372 |
|---|---|
| -continued | -continued |
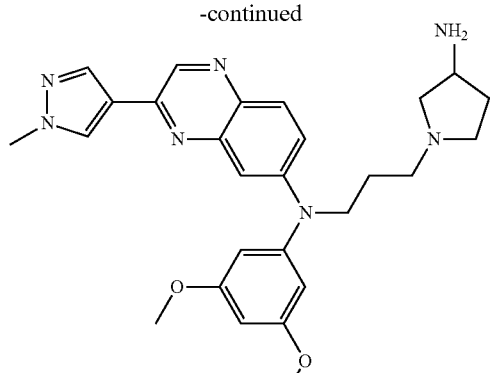
as a HCl salt
329; ~B7
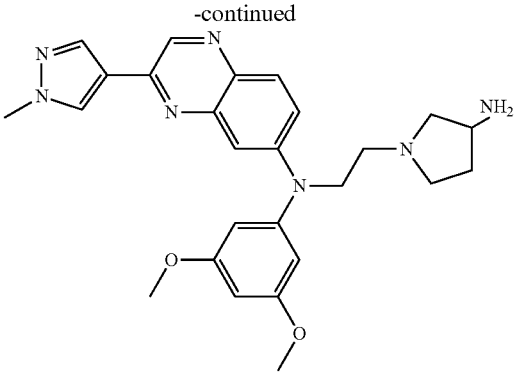
as a HCl salt
321; ~B7
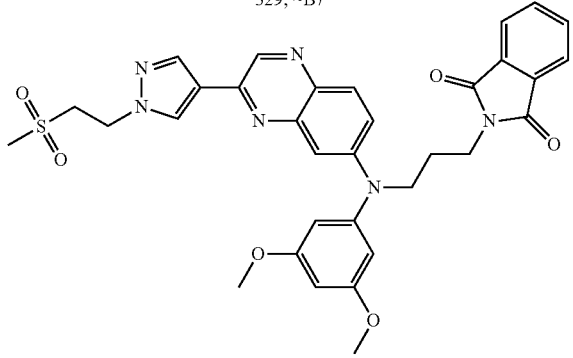
320; ~Co5f
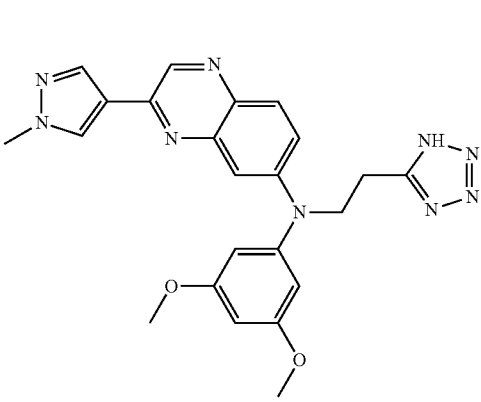
86; =Co22
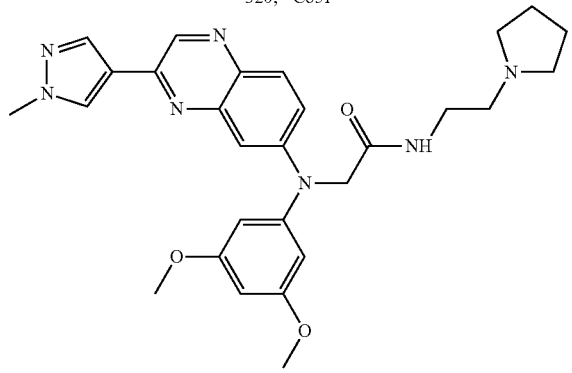
325; ~Co14
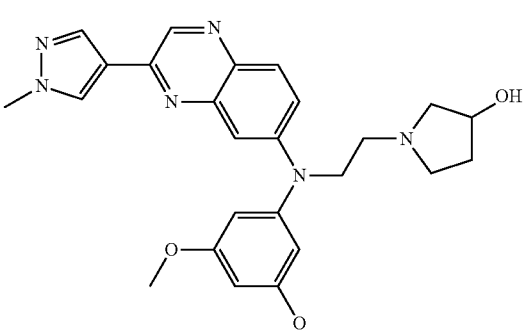
331; ~B3/B4a
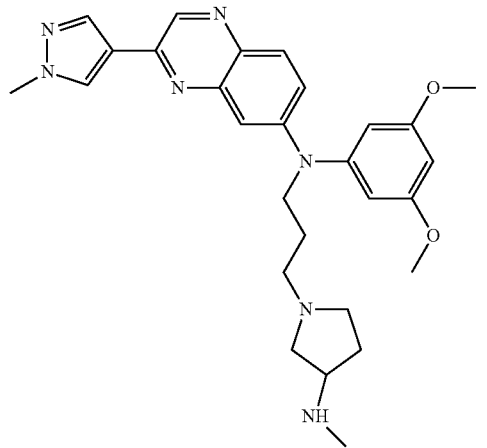
as a HCl salt
330; ~B3/B4a
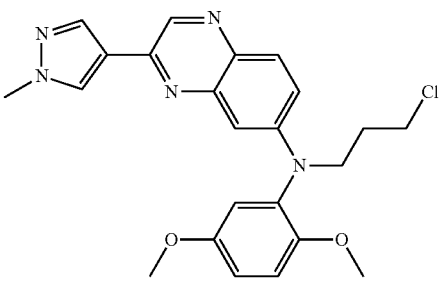
322; ~B5

-continued
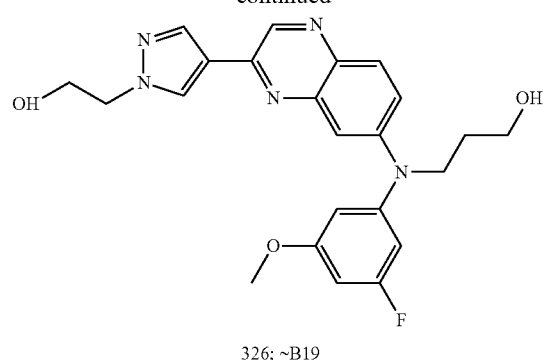
326; ~B19
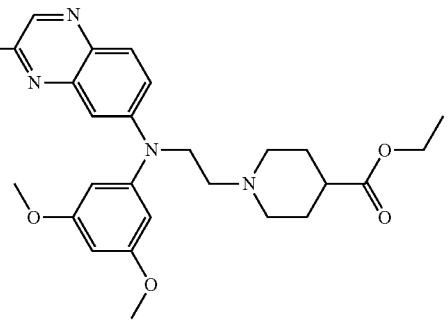
343; ~B3/B4a
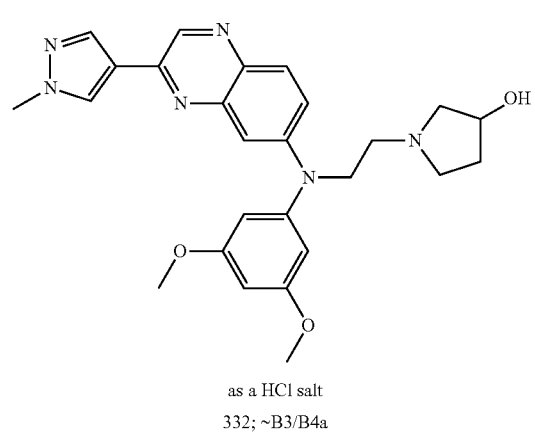
as a HCl salt
332; ~B3/B4a
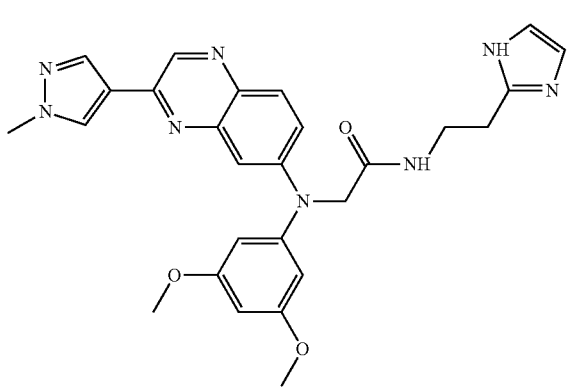
334; ~Co14
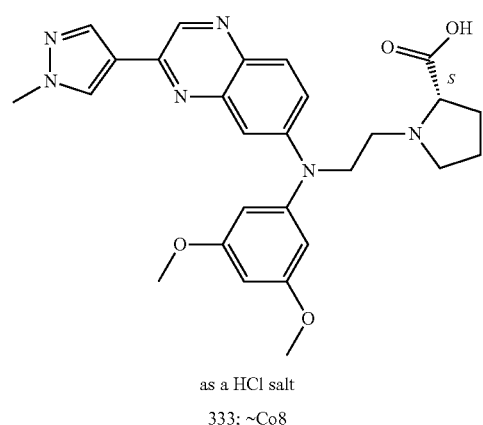
as a HCl salt
333; ~Co8
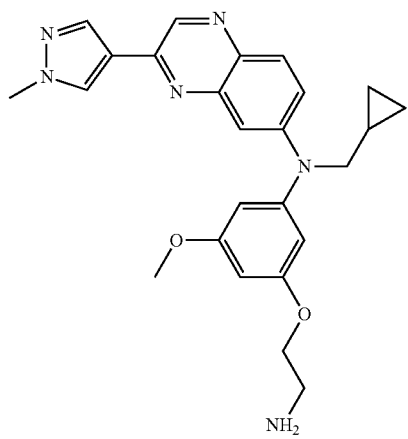
32; =B23
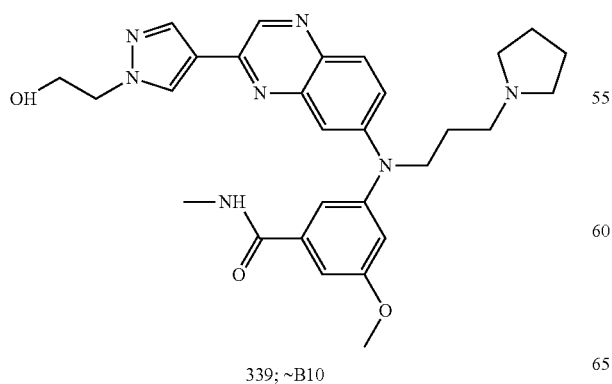
339; ~B10
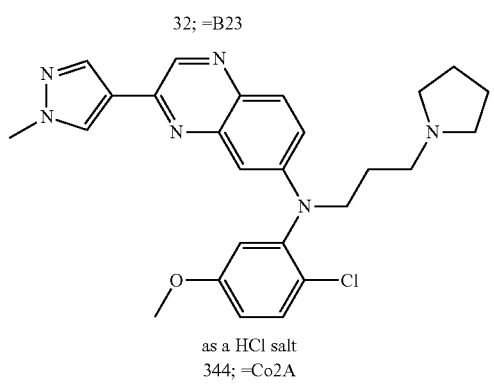
as a HCl salt
344; =Co2A -continued
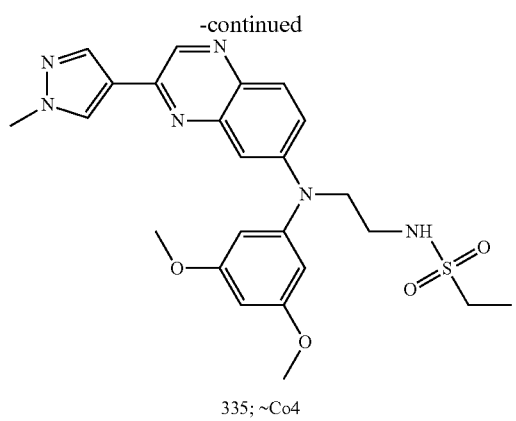
335; ~Co4
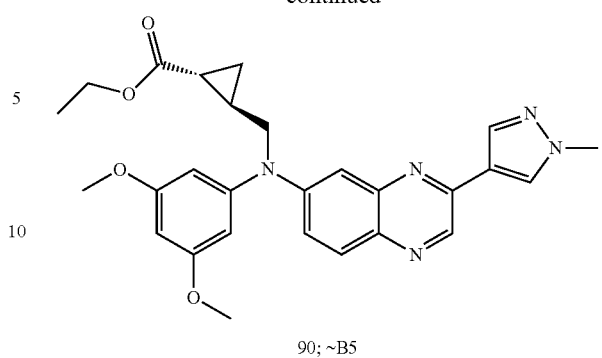
90; ~B5
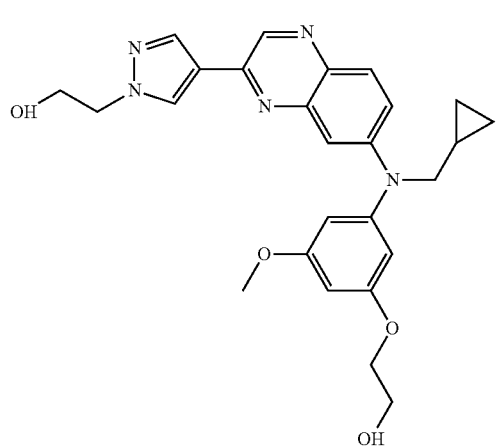
as a HCl salt
131; ~B8; NMR*
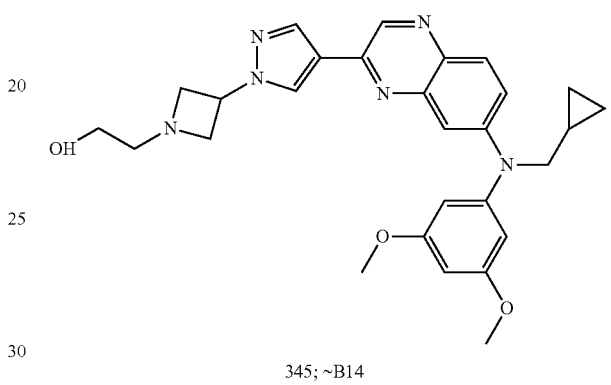
345; ~B14
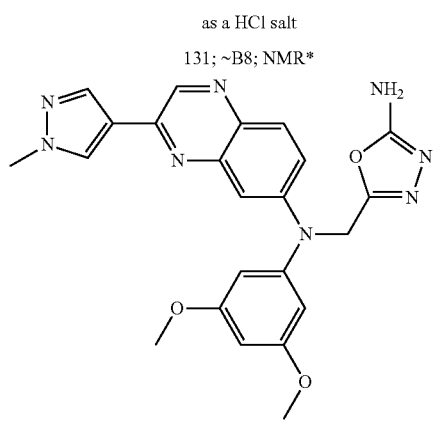
31; =B22
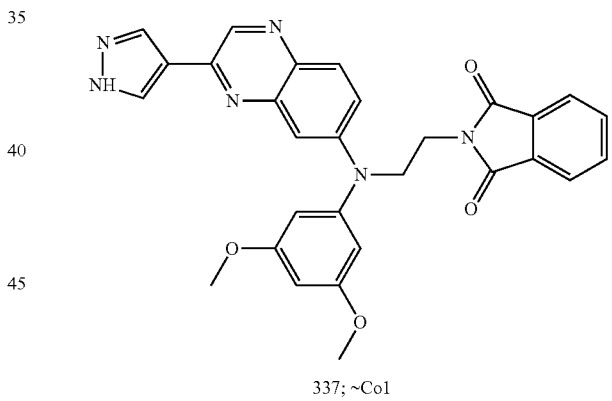
337; ~Co1
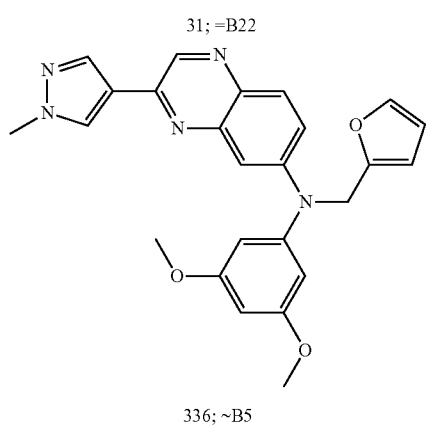
336; ~B5
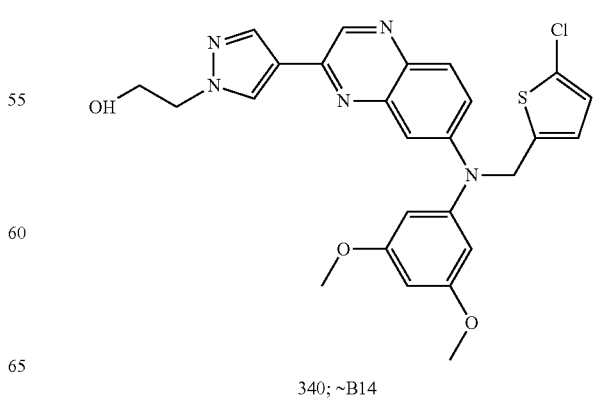
340; ~B14

377
-continued
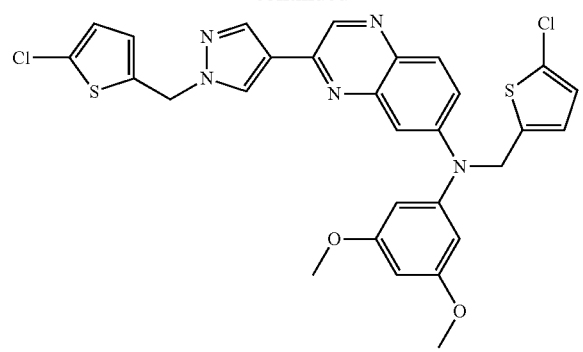
346; ~B9
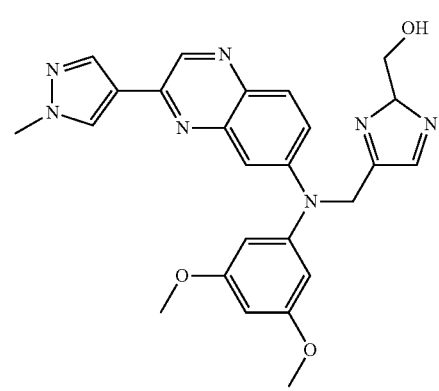
109; =Co36
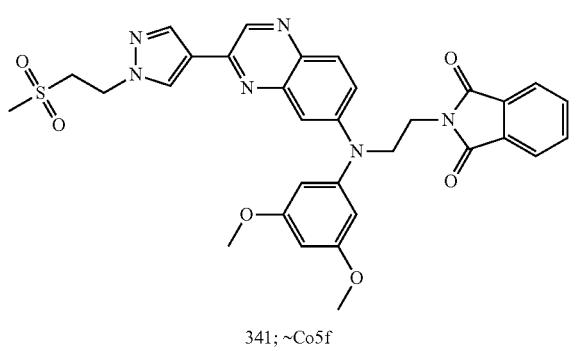
341; ~Co5f
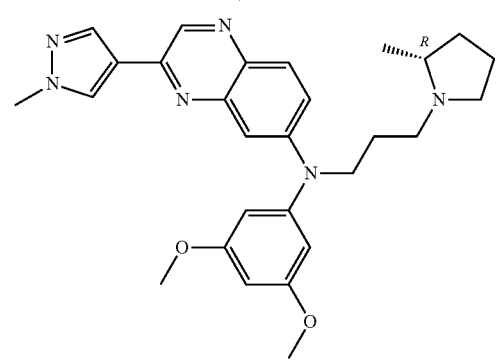
as a HCl salt
347; ~B3/B4a
378
-continued
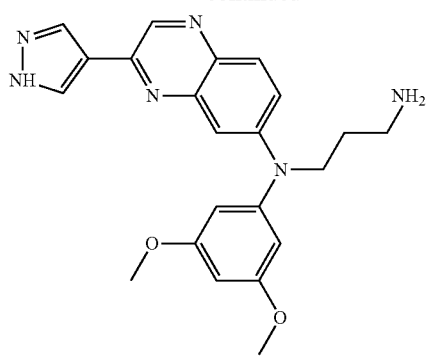
338; ~Co1/Co3
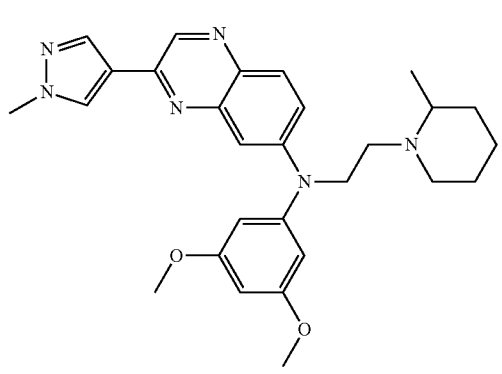
as a HCl salt
342; ~B3/B4a
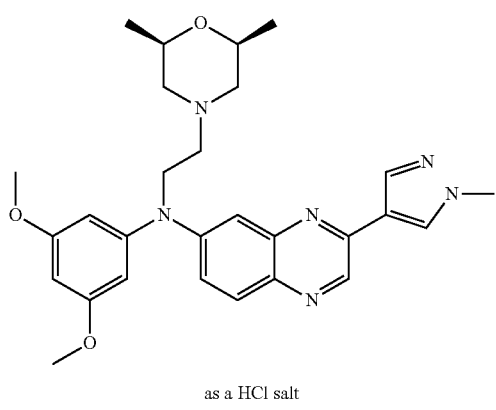
as a HCl salt
348; ~B3/B4a
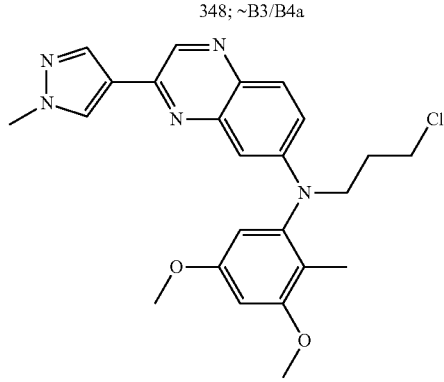
349; ~B5

379
-continued
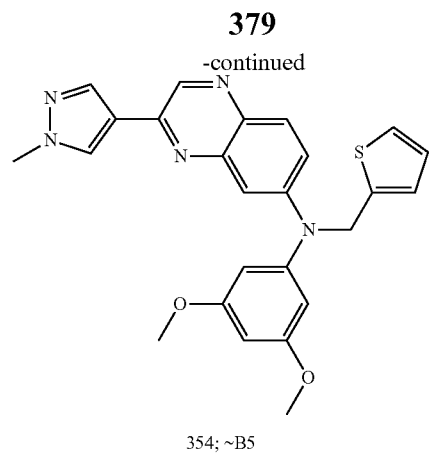
354; ~B5
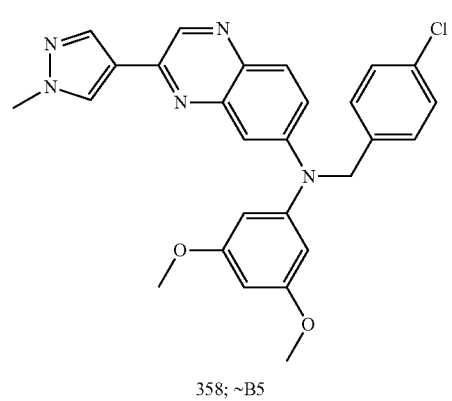
358; ~B5
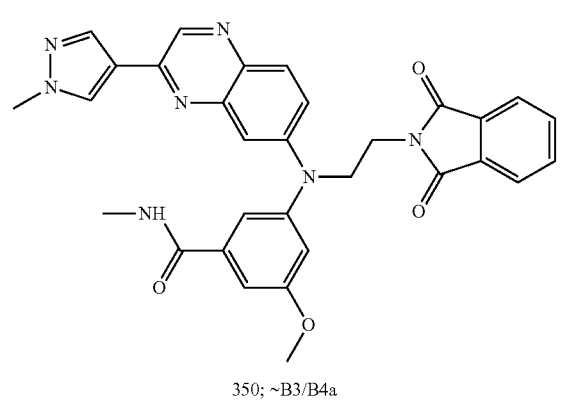
350; ~B3/B4a
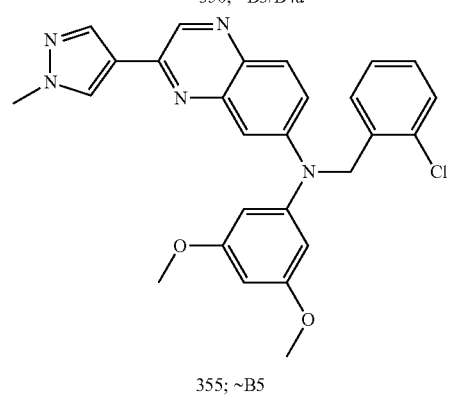
355; ~B5
380
-continued
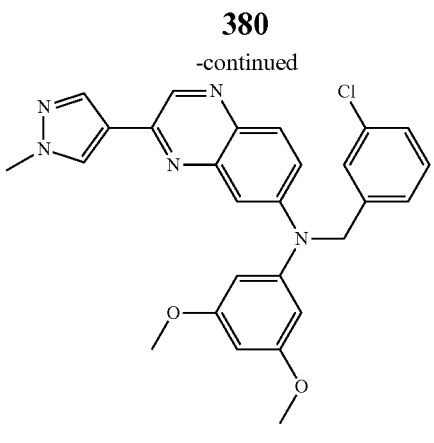
359; ~B5
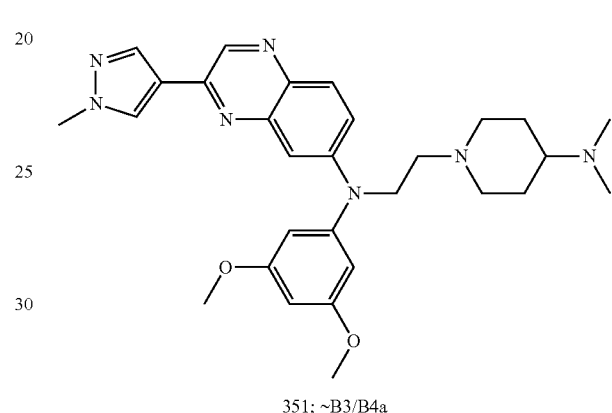
351; ~B3/B4a
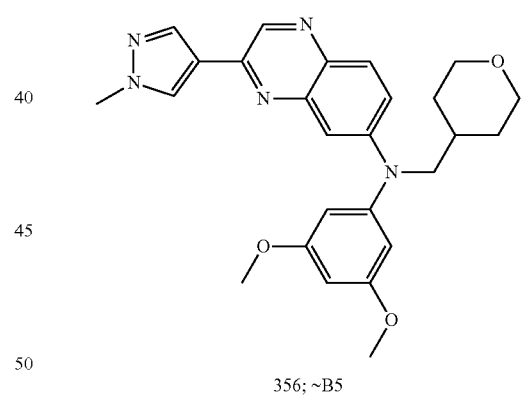
356; ~B5
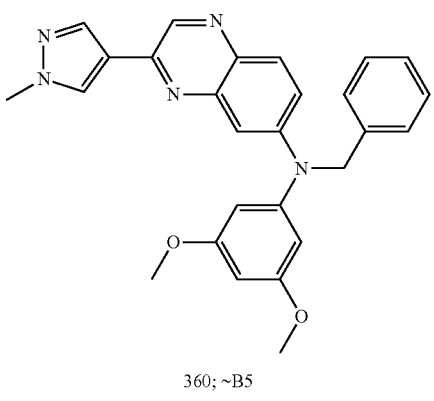
360; ~B5

-continued
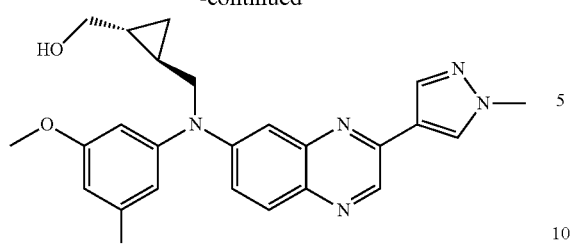
89; =Co24
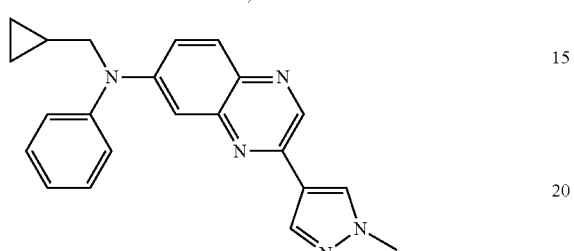
53; =Co5c
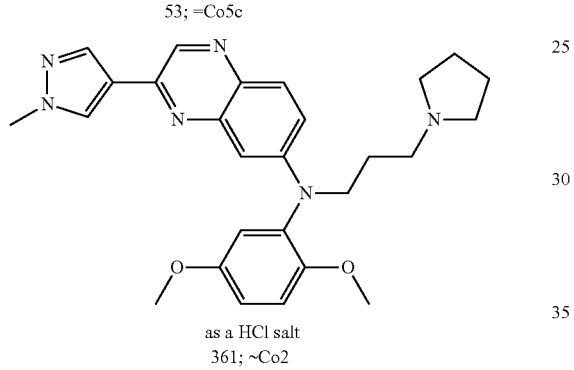
as a HCl salt
361; ~Co2
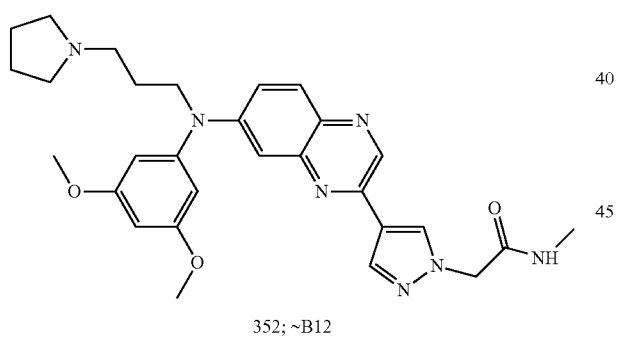
352; ~B12
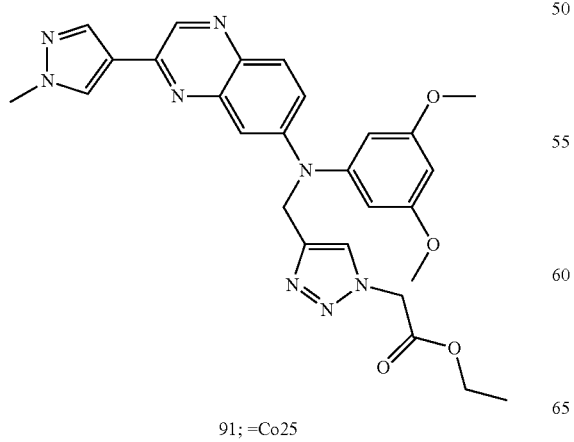
91; =Co25
-continued
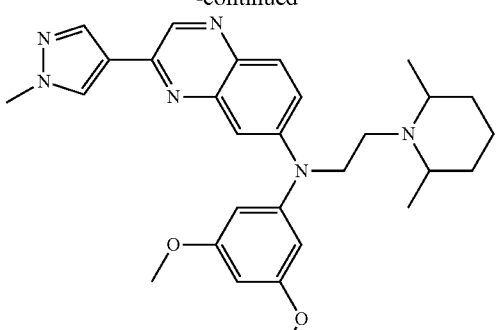
362; ~B3/B4a
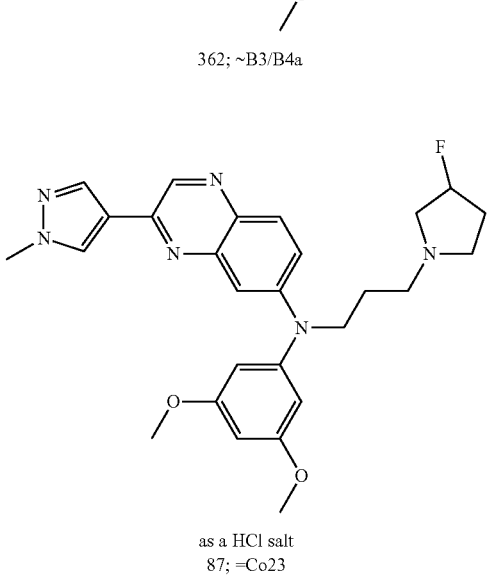
as a HCl salt
87; =Co23
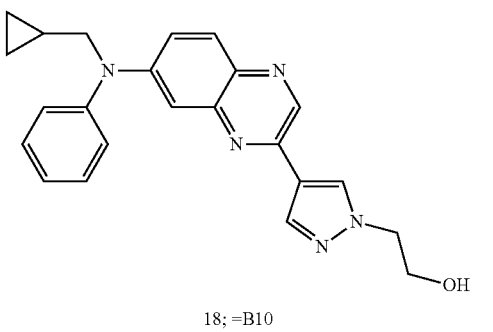
18; =B10
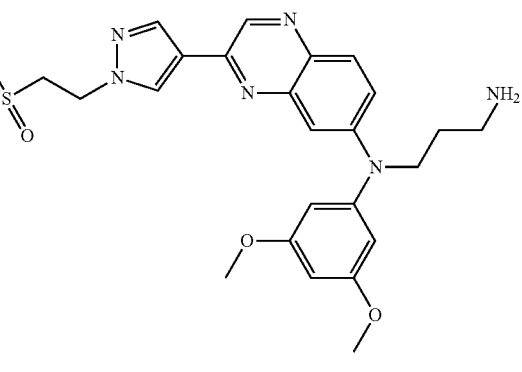
363; ~Co3

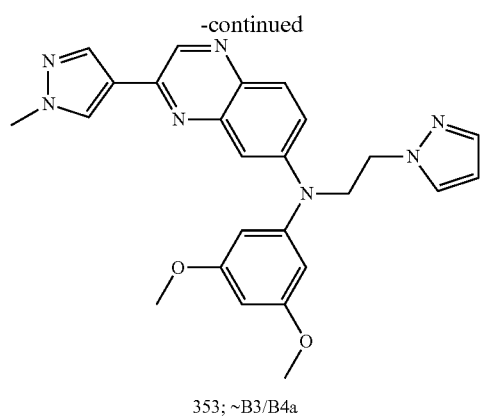
353; ~B3/B4a
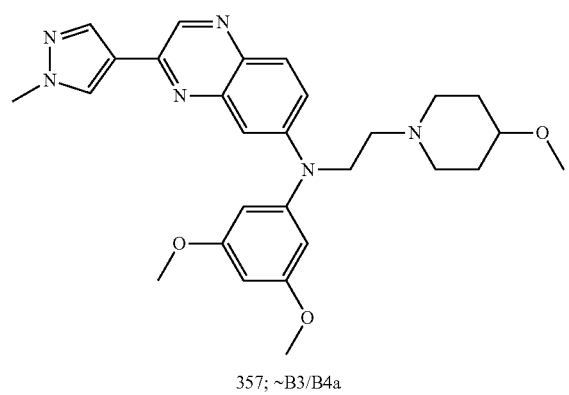
357; ~B3/B4a
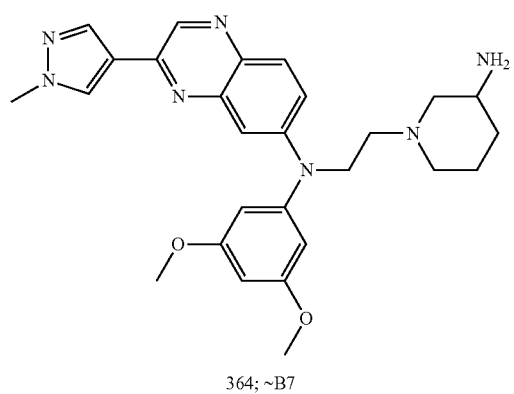
364; ~B7
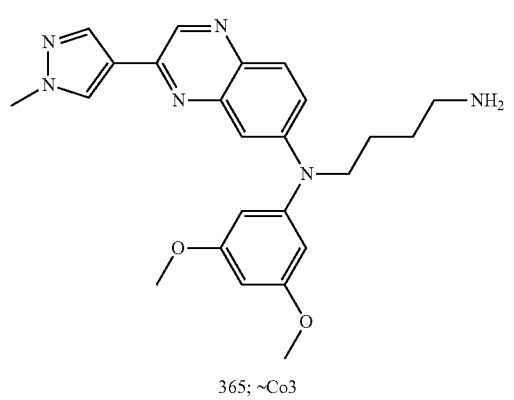
365; ~Co3
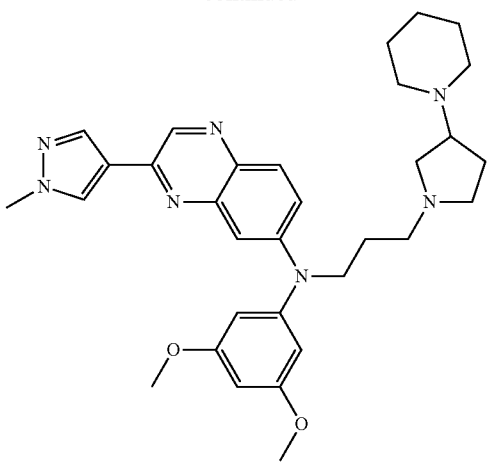
371; ~B3/B4a
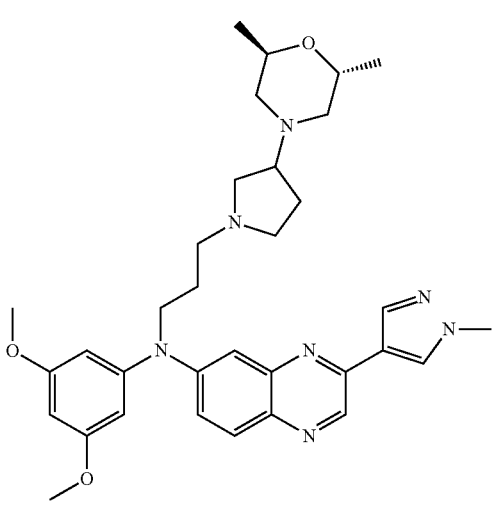
as a HCl salt
376; ~B3/B4a
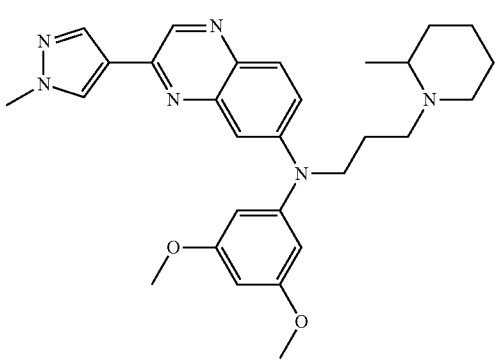
as a HCl salt
366; ~B3/B4a 385
-continued
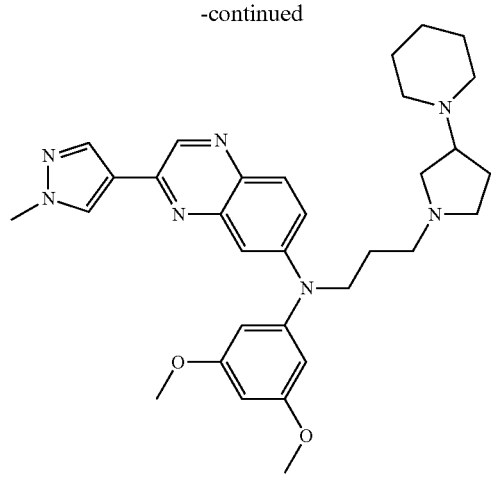
as a HCl salt
372; ~B3/B4a
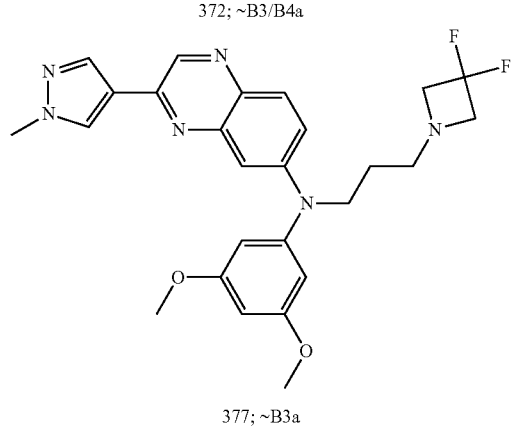
377; ~B3a
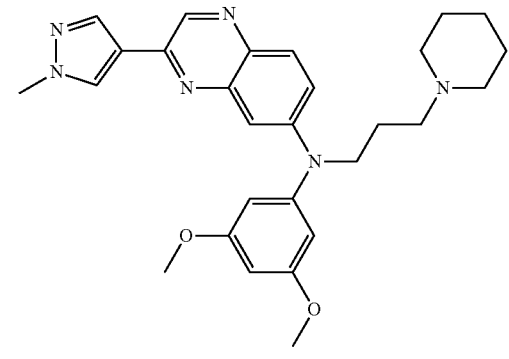
as a HCl salt
367; ~B3/B4a
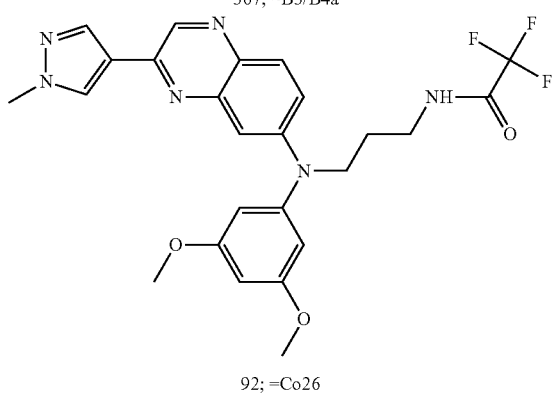
92; =Co26
386
-continued
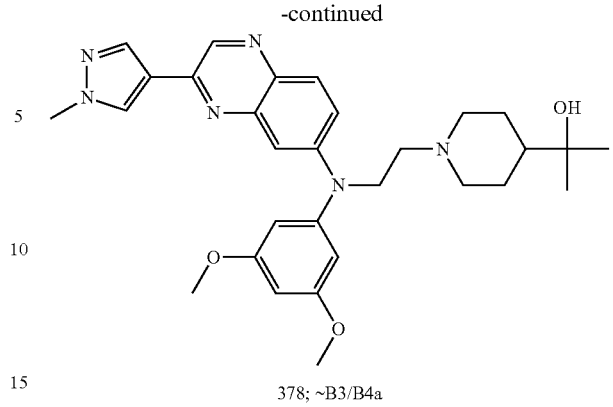
378; ~B3/B4a
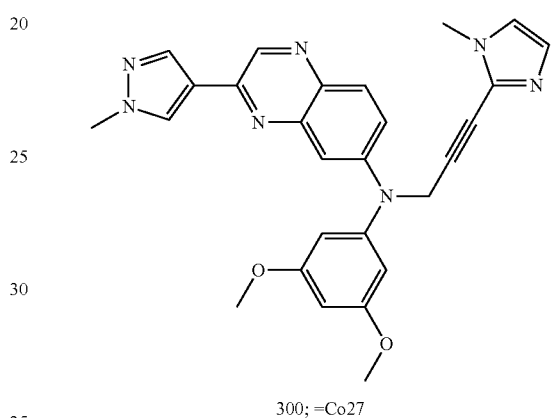
300; =Co27
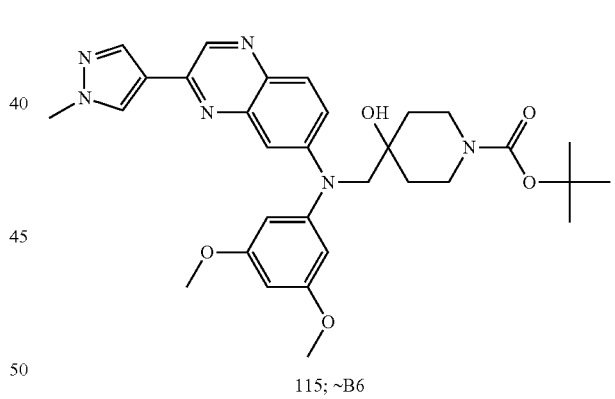
115; ~B6
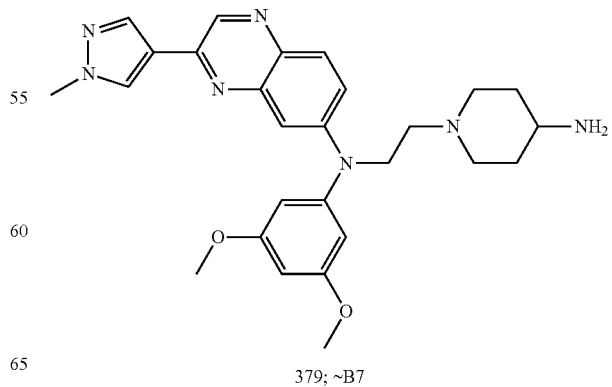
379; ~B7

387
-continued
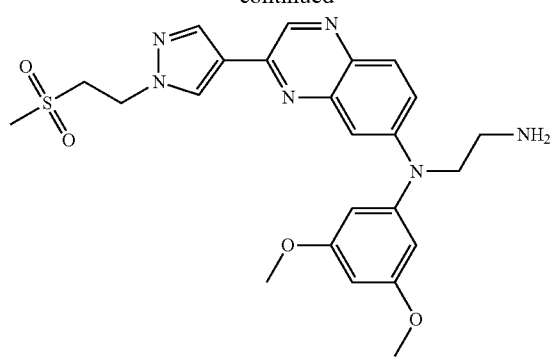
368; ~Co3
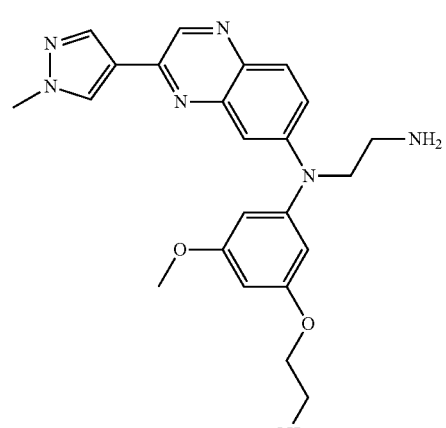
as a HCl salt
373; ~B15
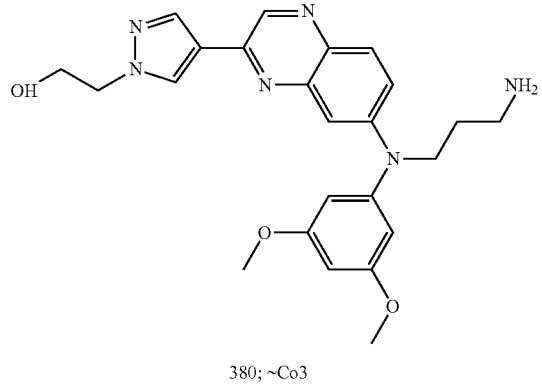
380; ~Co3
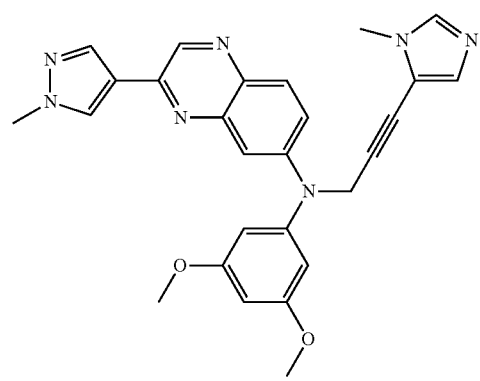
369; ~Co27
388
-continued
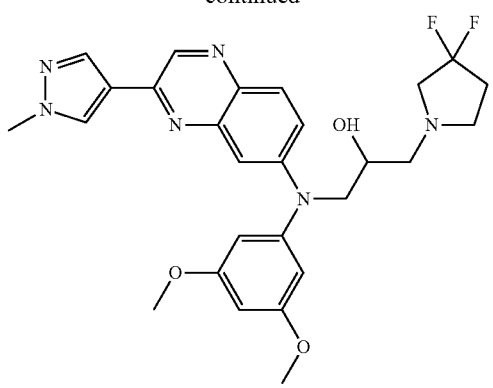
as a HCl salt
374; ~Co18
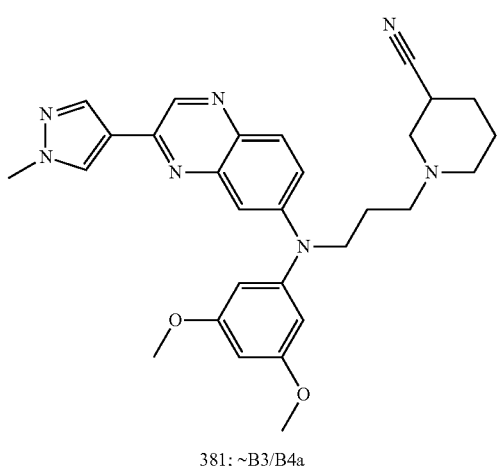
381; ~B3/B4a
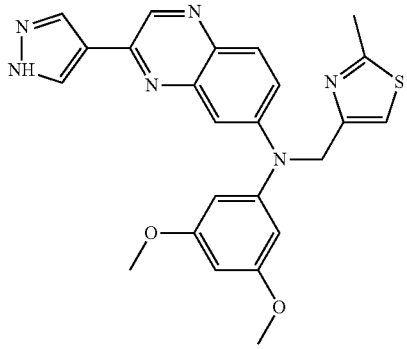
370; ~B9b
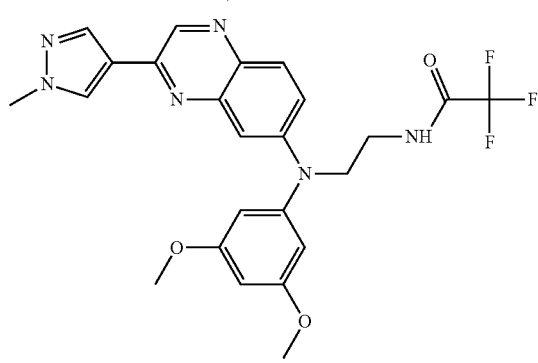
375; ~Co26

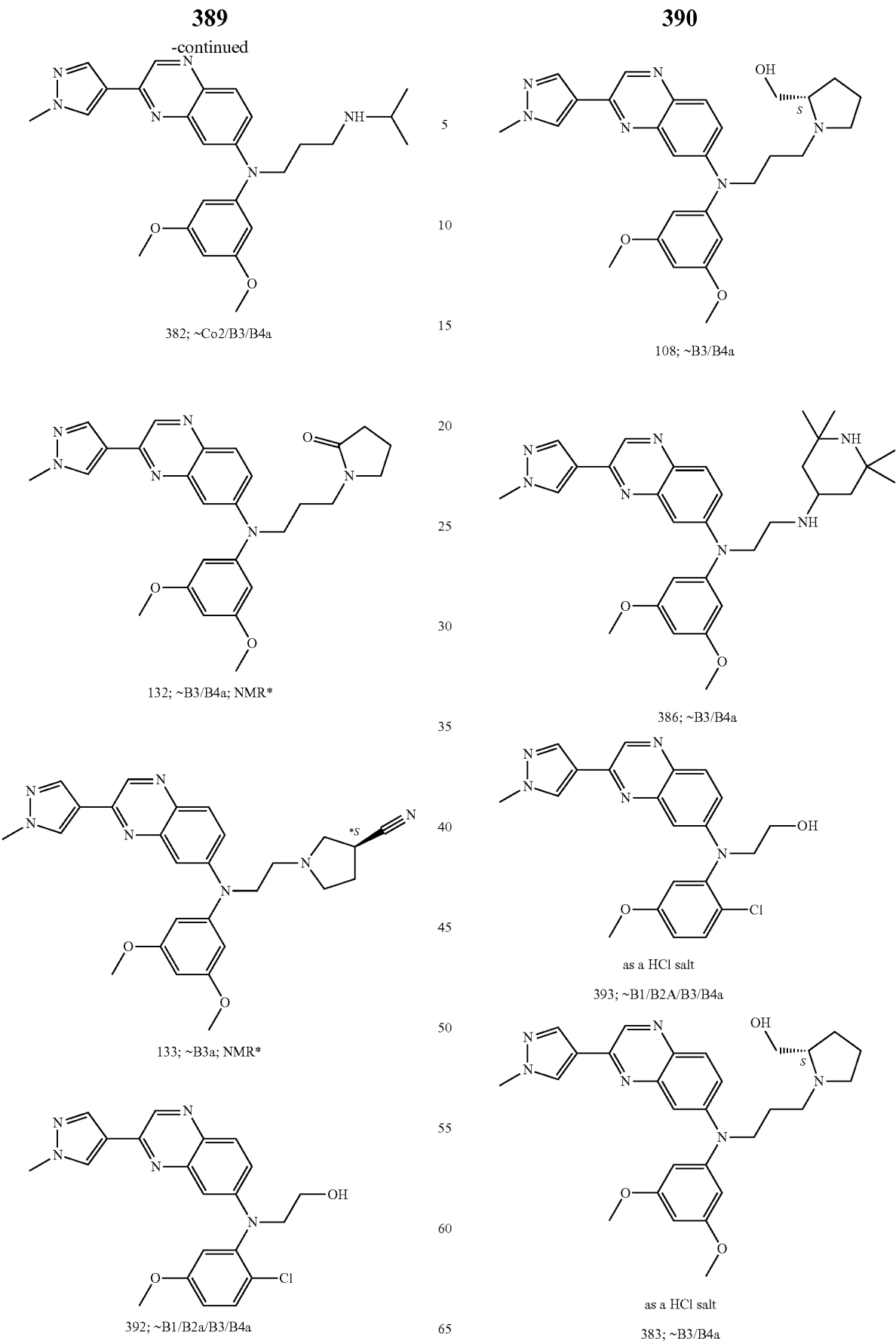

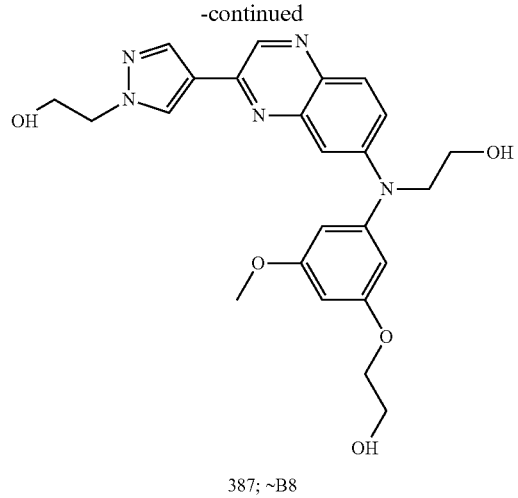
387; ~B8
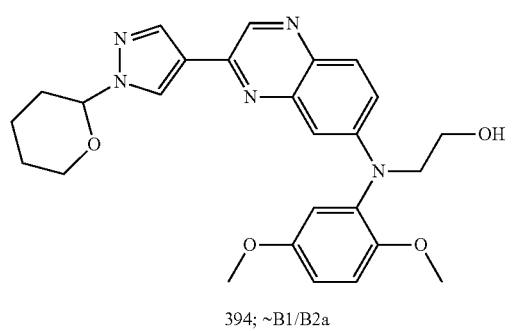
394; ~B1/B2a
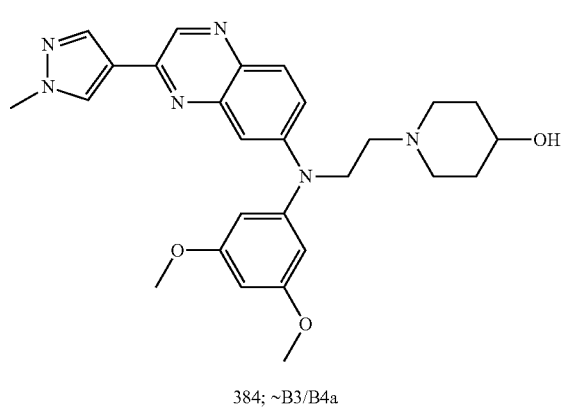
384; ~B3/B4a
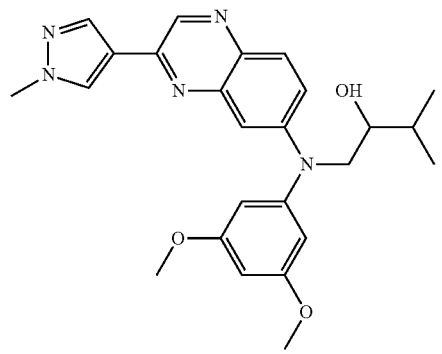
389; ~B6
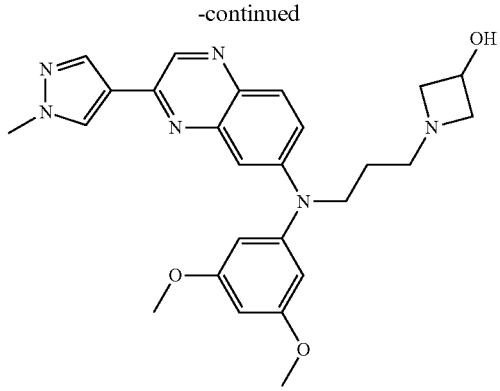
395; ~B3a
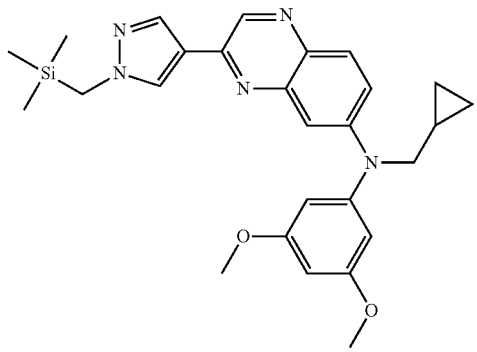
385; ~Co5c
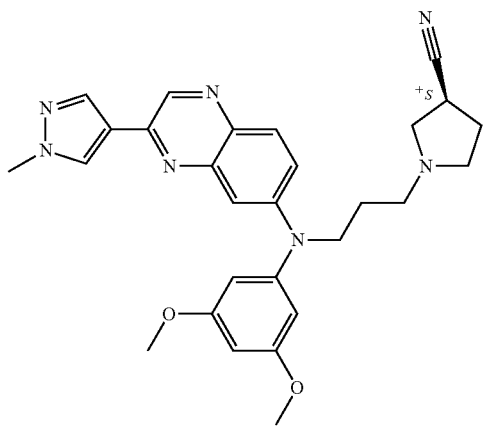
as a HCl salt
390; ~B3a
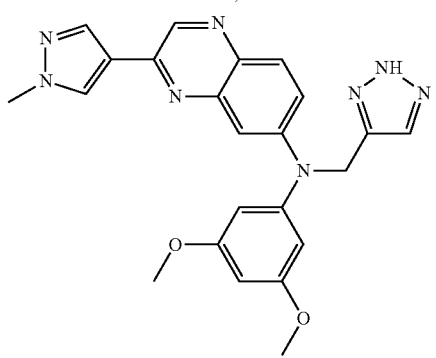
94; =Co28

393
-continued
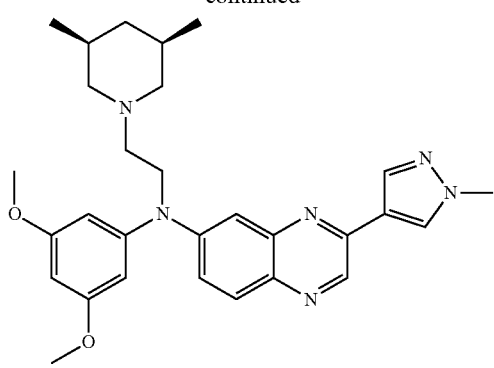
39; =B30
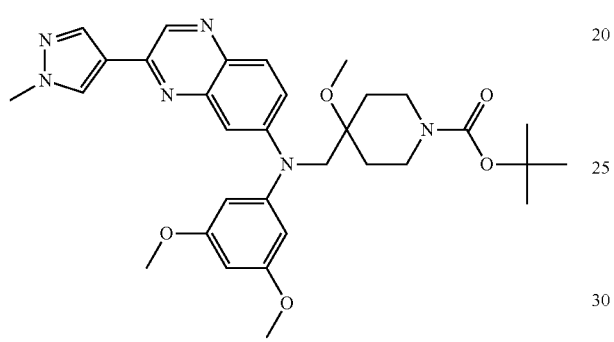
114; =Co39
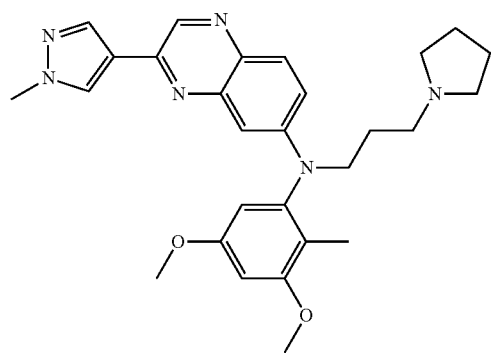
as a HCl salt
396; ~Co2
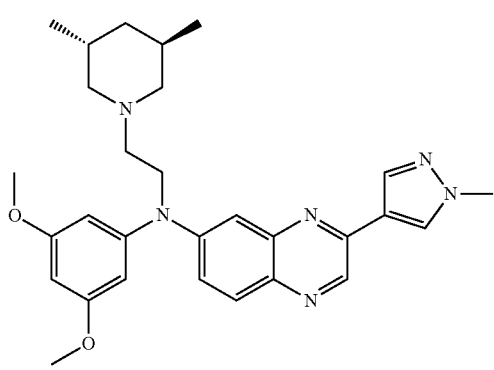
as a HCl salt
40; =B30
394
-continued
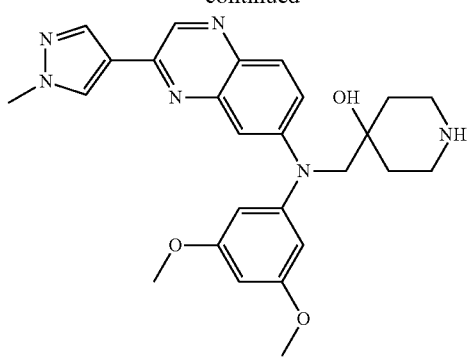
391; ~Co12
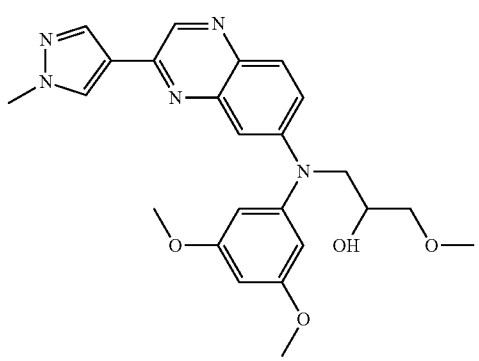
397; ~B6
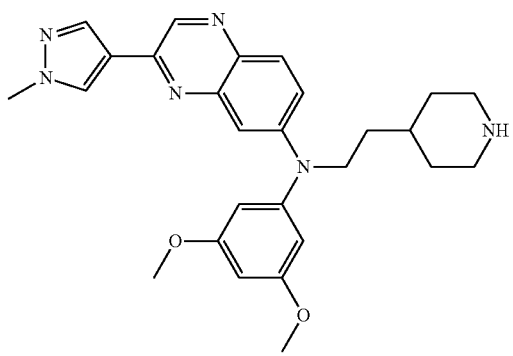
398; ~Co12
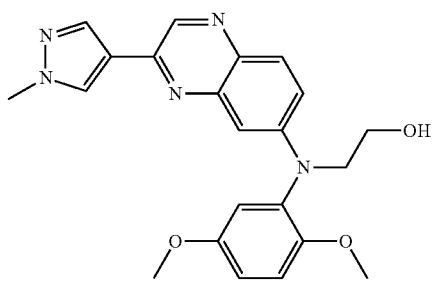
as a HCl salt
405; ~B1/B2a/B3/B4a -continued
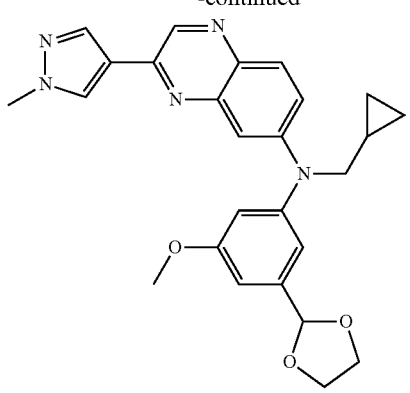
411; ~B13
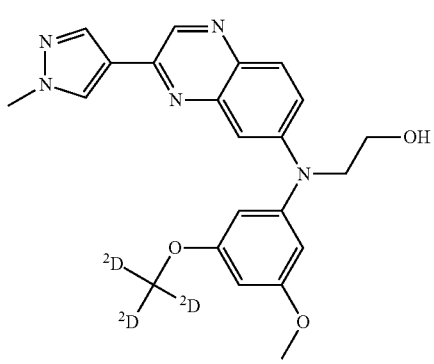
399; ~B1/B2a
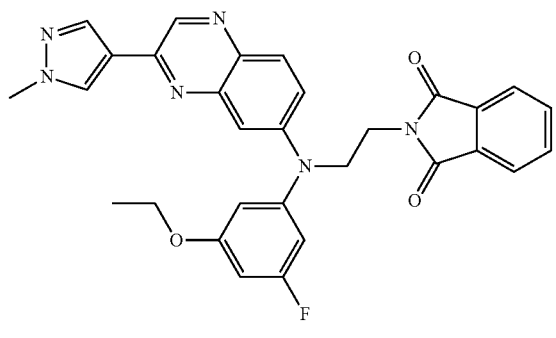
406; ~B3/B4a
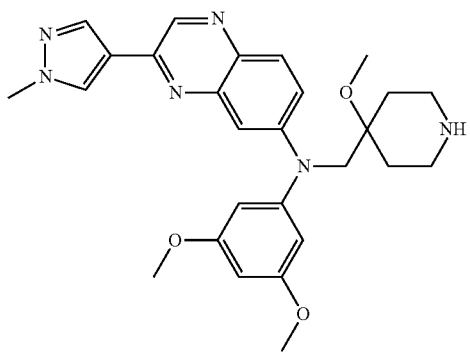
as a HCl salt
412; ~Co12
-continued
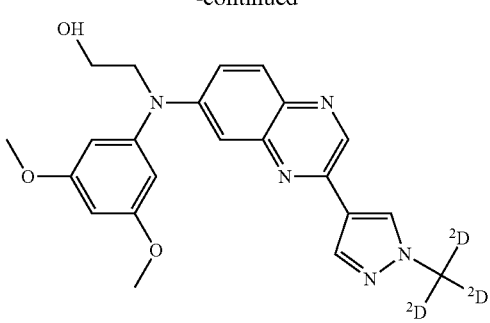
400; ~B1/B2a
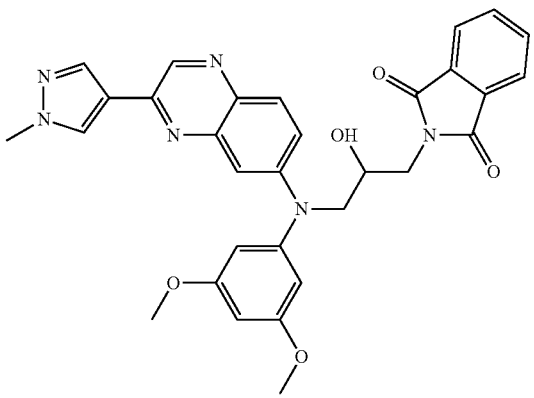
124; ~B6/Co18
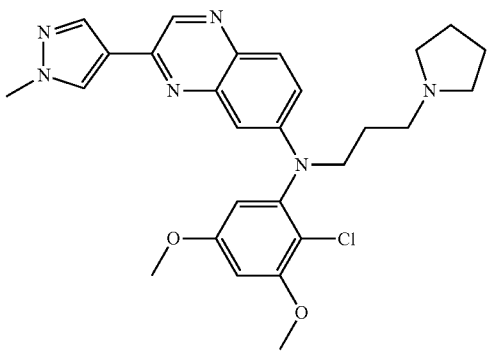
as a HCl salt
413; ~Co2
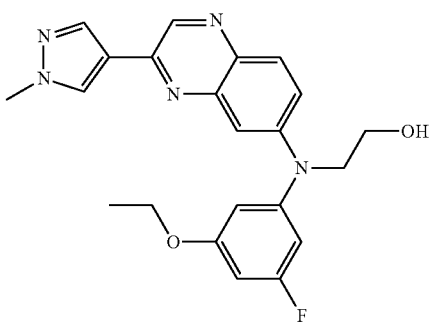
401; ~B1/B2a

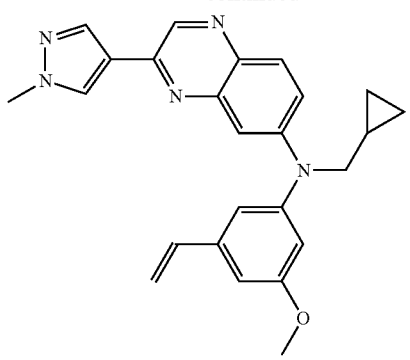
as a HCl salt
407; ~B5
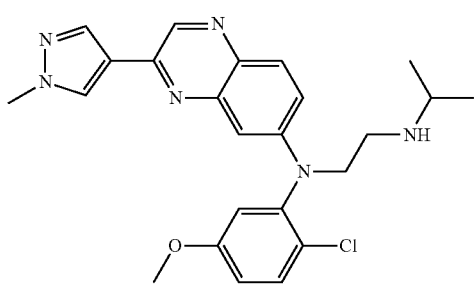
as a HCl salt
414; ~B3/B4a
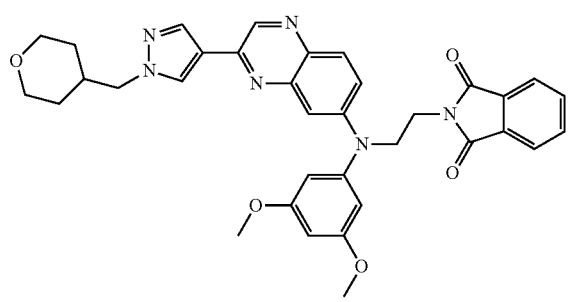
402; ~Co5a
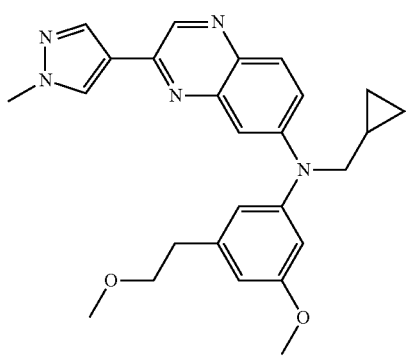
as a HCl salt
408; ~B5
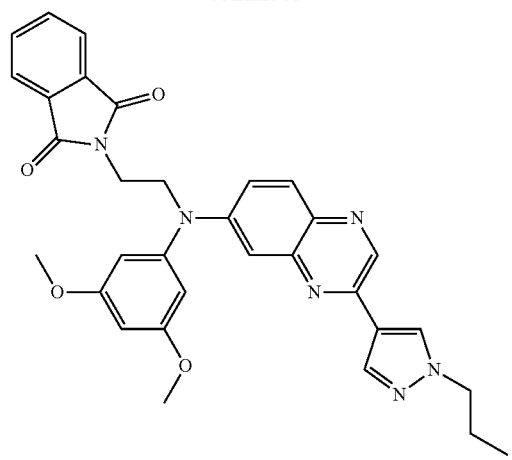
415; ~Co5a
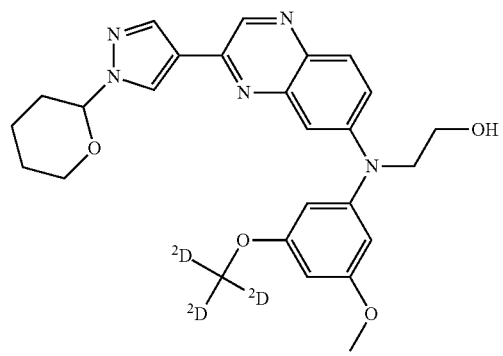
403; ~B1/B2a
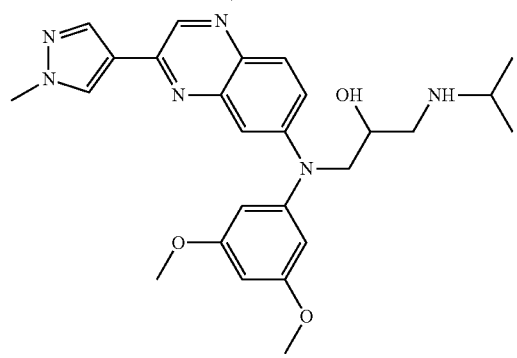
409; ~Co18
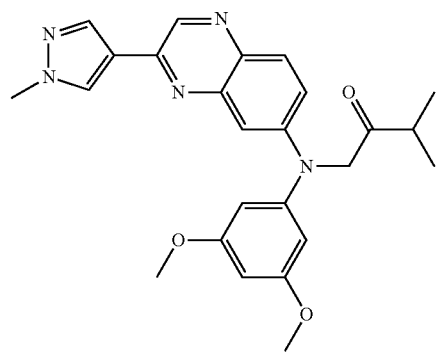
416; ~Co38

-continued
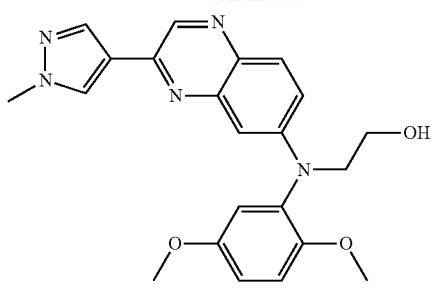
404; ~B1/B2a/B3/B4a
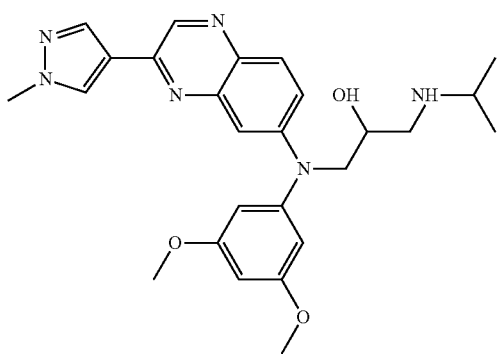
as a HCl salt
410; ~Co18
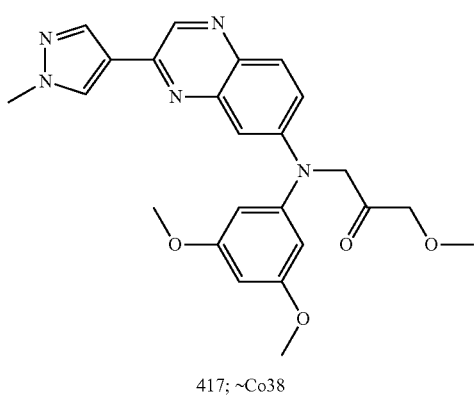
417; ~Co38
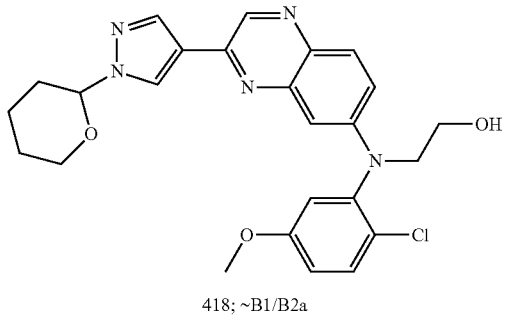
418; ~B1/B2a
-continued
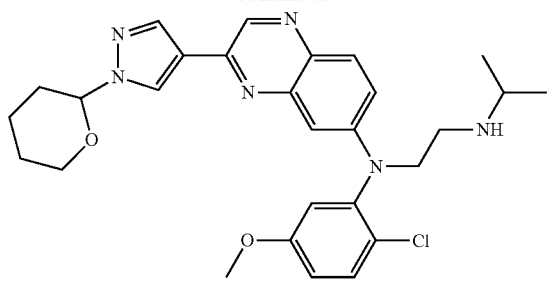
425; ~B3/B4a
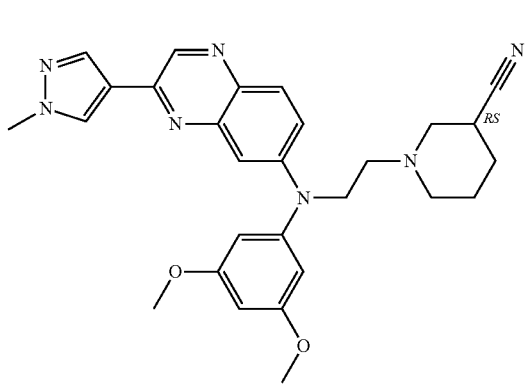
430; ~B3/B4a
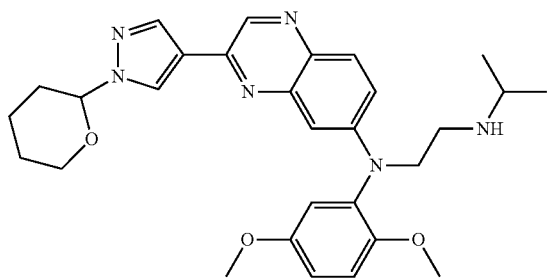
419; ~B3/B4a
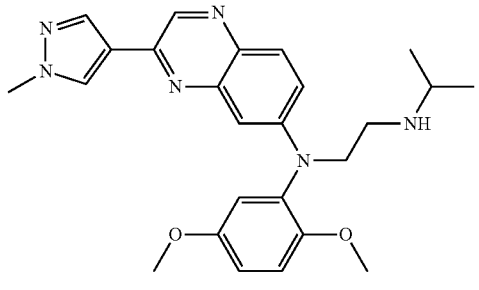
426; ~B3/B4a 401
-continued
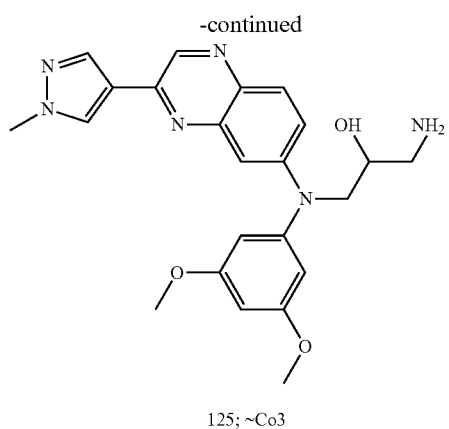
125; ~Co3
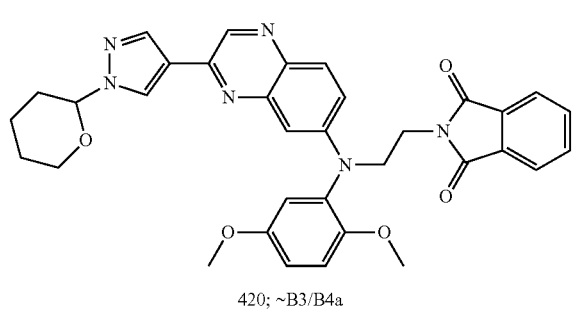
420; ~B3/B4a
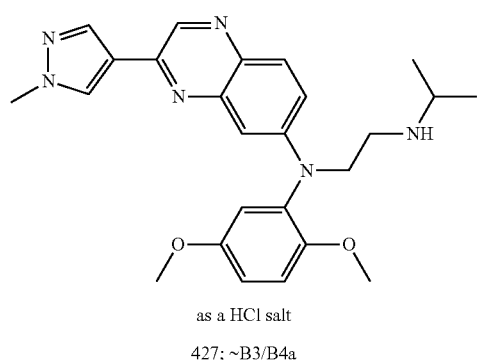
as a HCl salt
427; ~B3/B4a
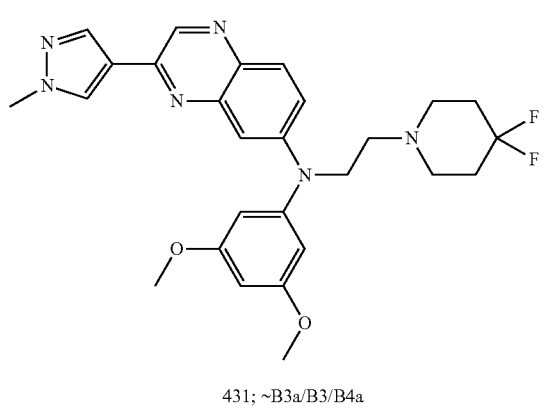
431; ~B3a/B3/B4a
402
-continued
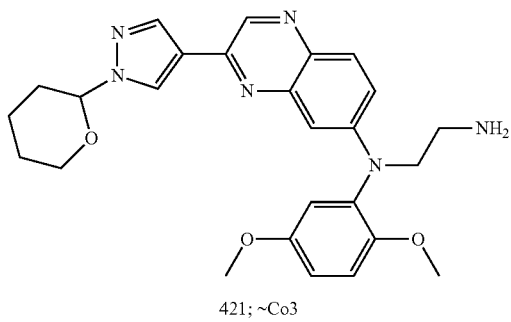
421; ~Co3
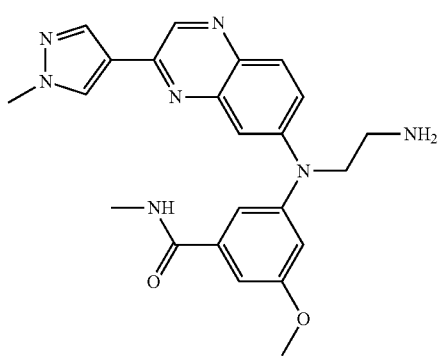
428; ~Co3
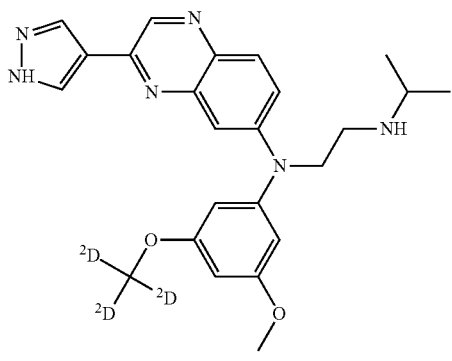
as a HCl salt
432; ~Co1
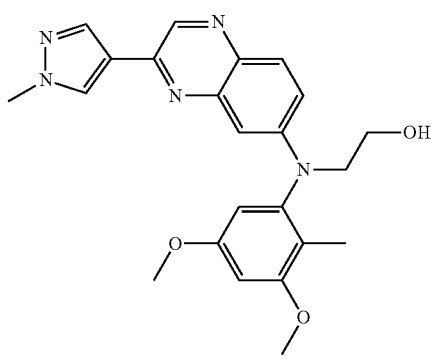
422; ~B1/B2a/B3/B4a 403
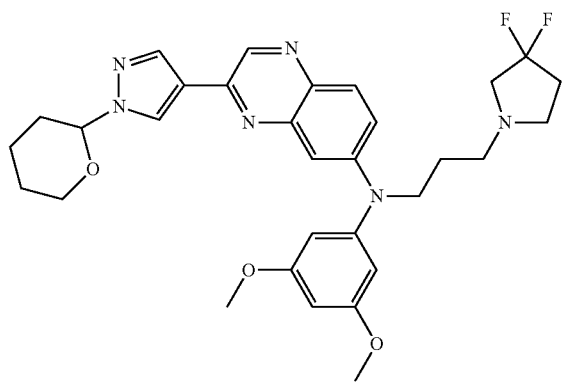
6; ~B3a
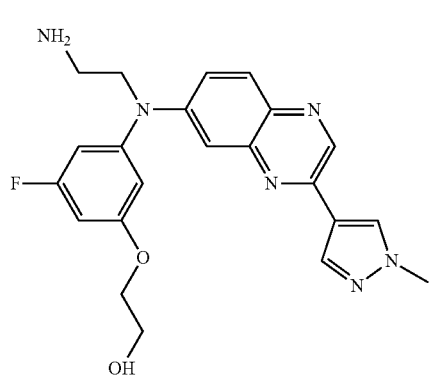
433; ~B15
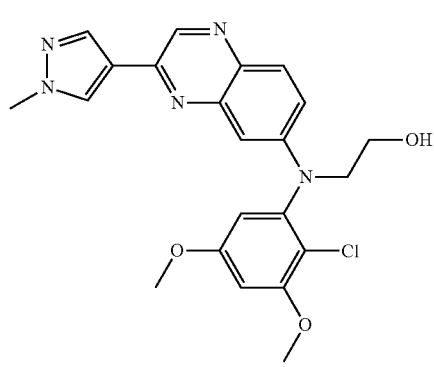
423; ~B1/B2a/B3/B4a
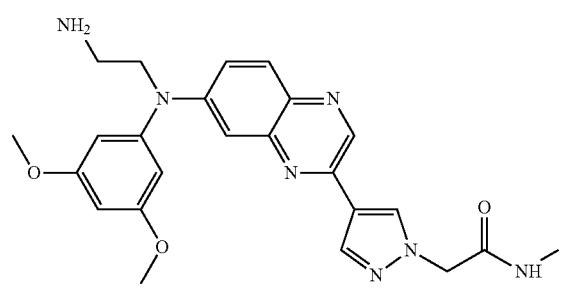
34; =B25
404
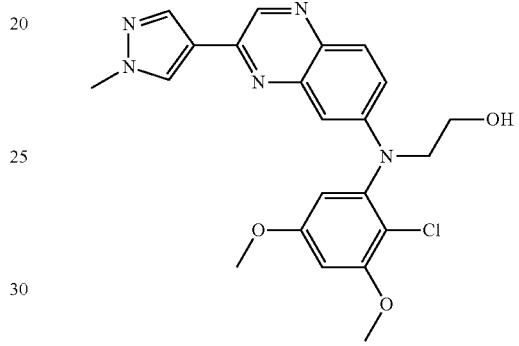
434; ~Co24
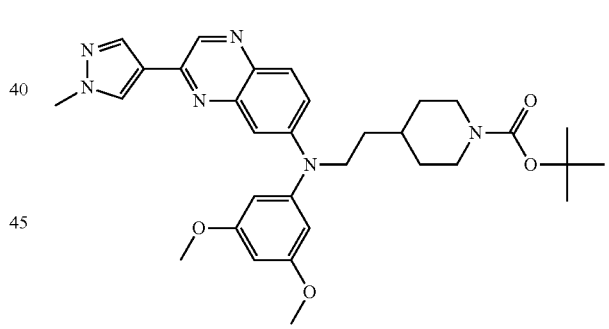
as a HCl salt
424; ~B1/B2a/B3/B4a
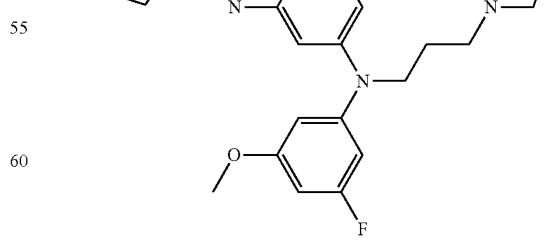
429; ~B5
as a HCl salt
435; ~Co1

405
-continued
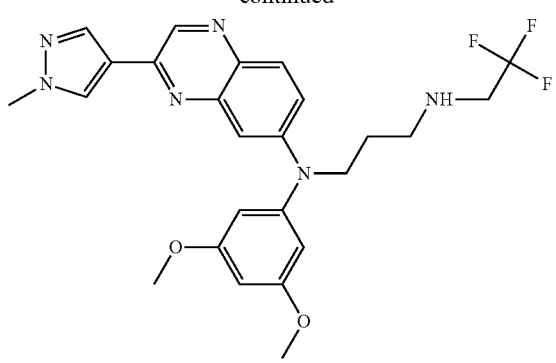
5; =B1a/B4a/b; NMR*
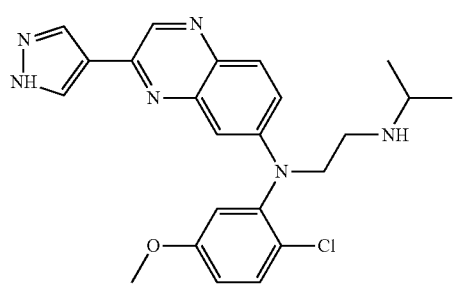
440; ~Co1
as a HCl salt
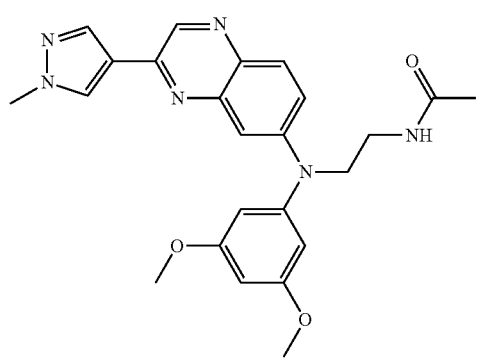 [SMILES: COc1cc(OC)cc(N(CCN(C)C(C)C)c2ccc3ncc(-c4cnn(C)c4)nc3c2)c1]
447; ~Co4
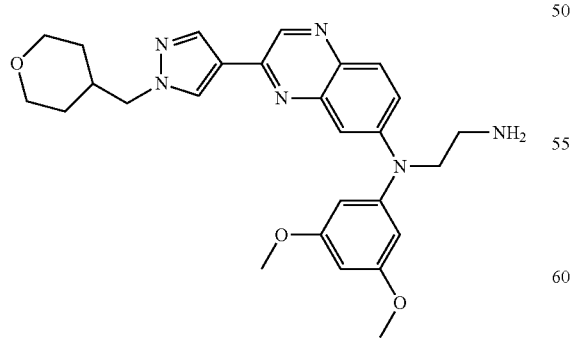
as a HCl salt
436; ~Co3
406
-continued
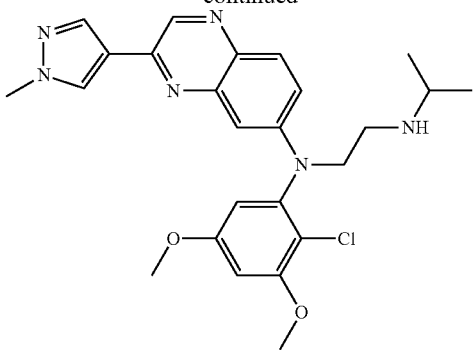
as a HCl salt
441; ~B3/B4a
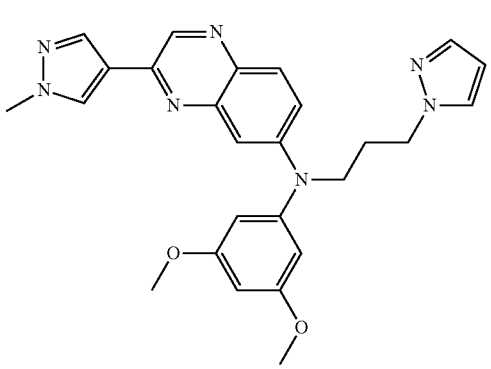
as a HCl salt
448; ~B3/B4a
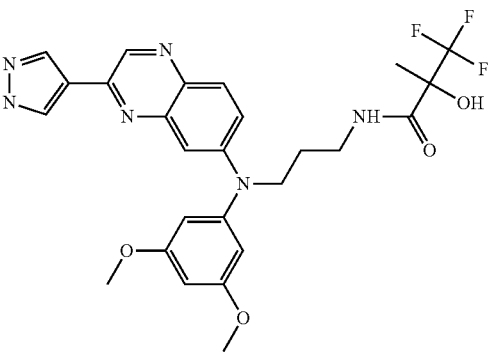
and
as a HCl salt
95a and 95; =Co29

-continued
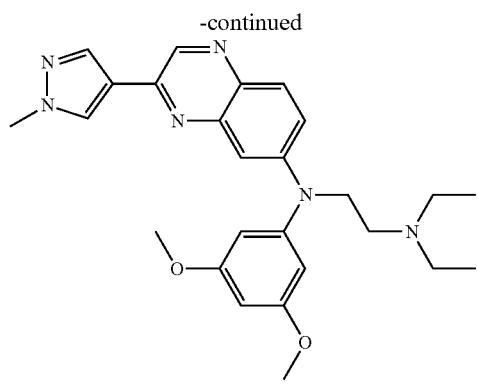
442; ~B3/B4a
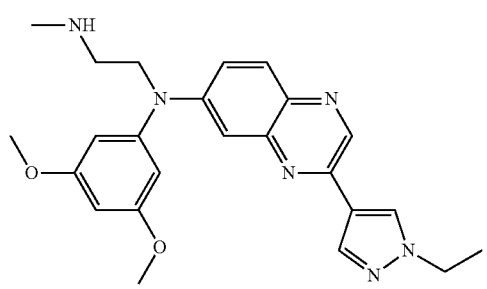
449; ~B3/B4a
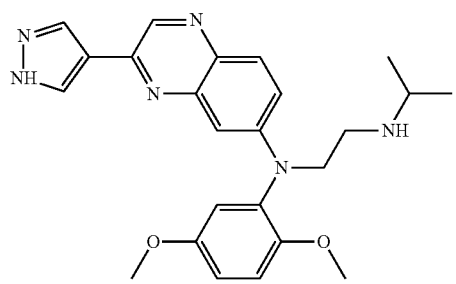
437; ~B10/Co1
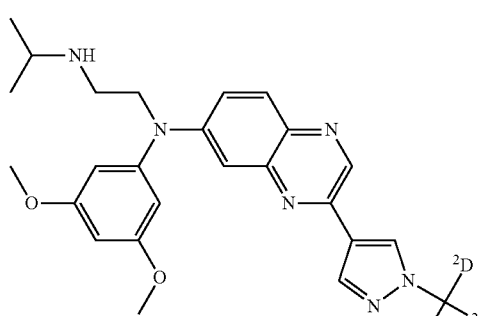
443; ~B3/B4a
-continued
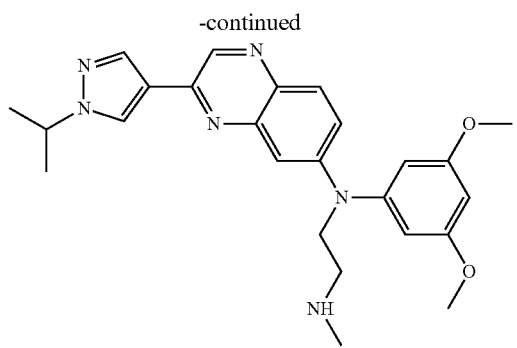
as a HCl salt
450; ~B3a
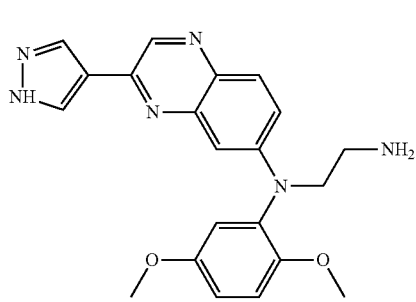
as a HCl salt
438; ~Co1
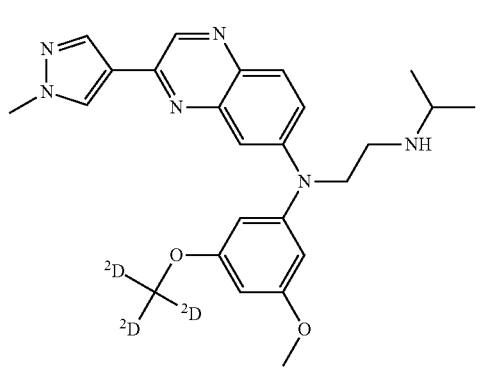
444; ~B3/B4a
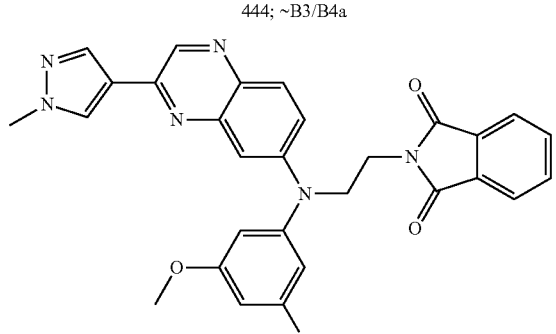
451; ~B3/B4a -continued
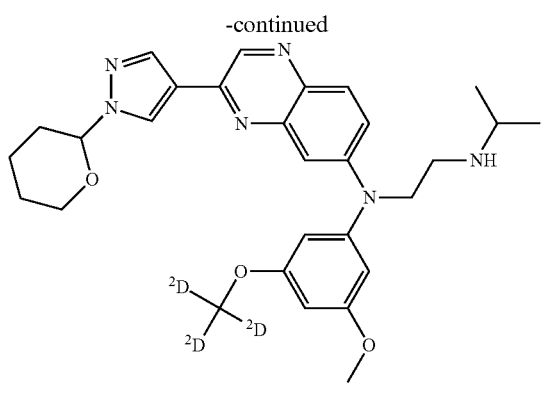
439; ~B3/B4a
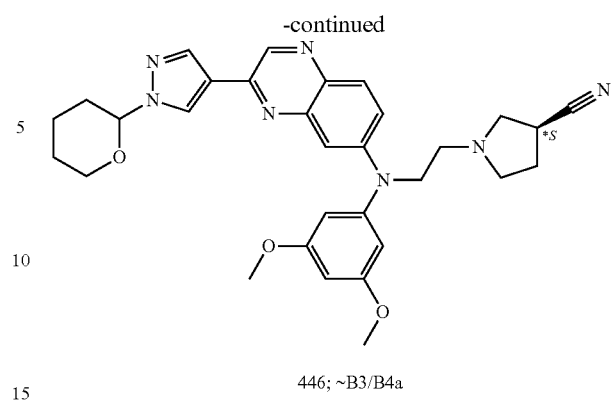
446; ~B3/B4a
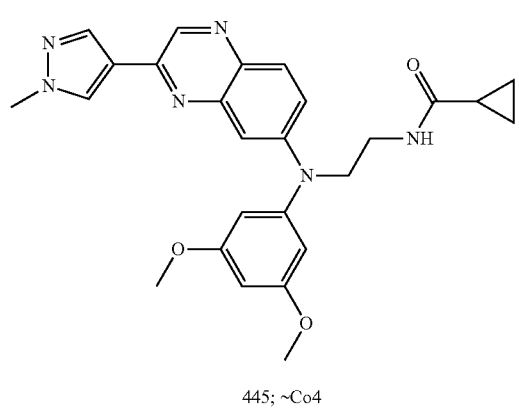
445; ~Co4
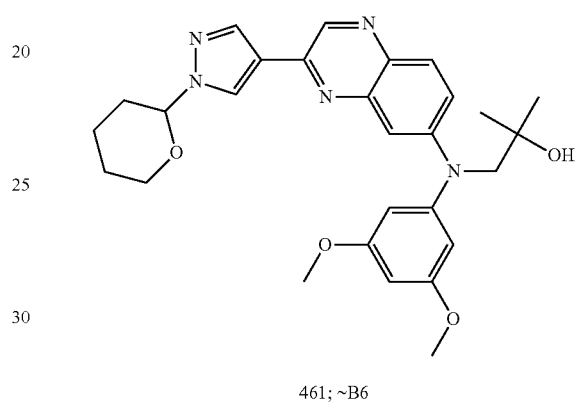
461; ~B6
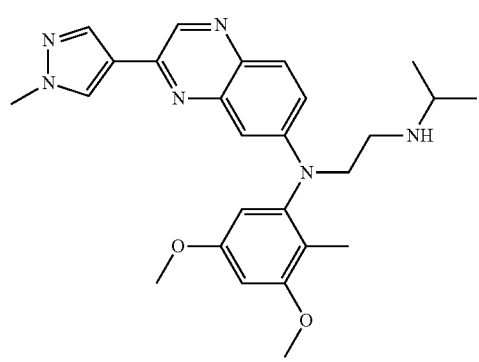
as a HCl salt
452; ~B3/B4a
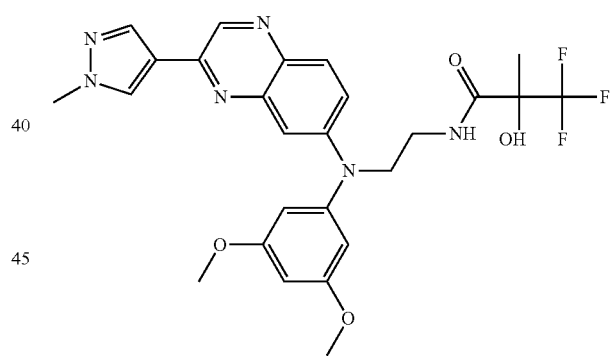
454; ~Co29
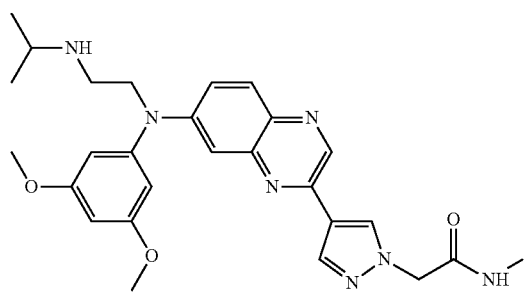
as a HCl salt
134; ~B3/B4a; NMR*
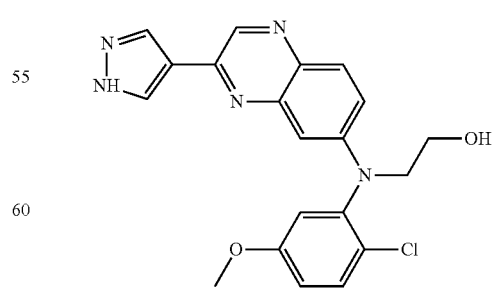
as a HCl salt
453; ~Co1

411
-continued
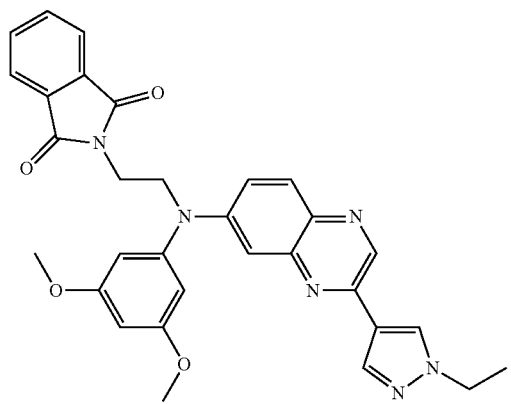
462; ~Co5c
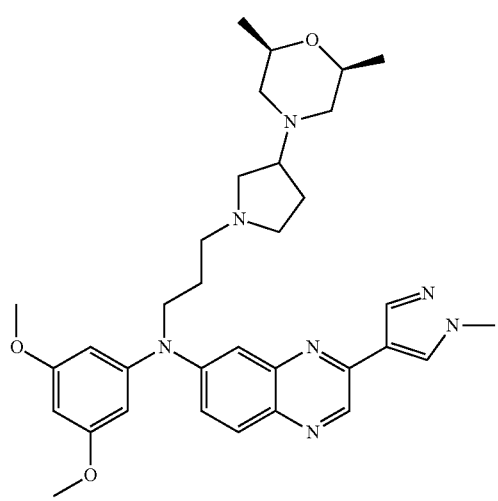
as a HCl salt
455; ~B3/B4a
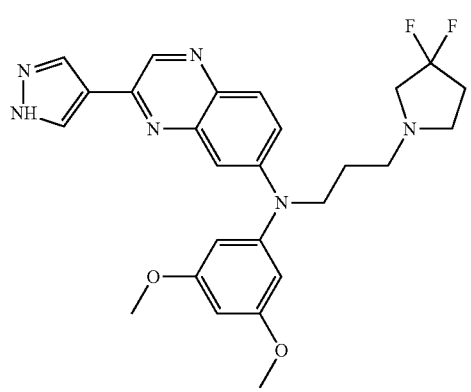
and
412
-continued
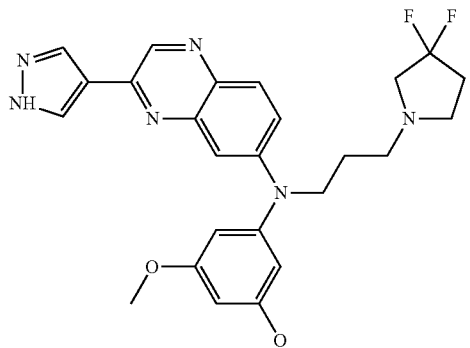
as a HCl salt
44a and 44; =Co1
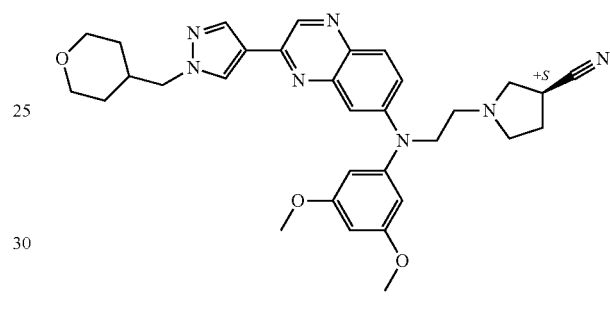
463; ~Co5a
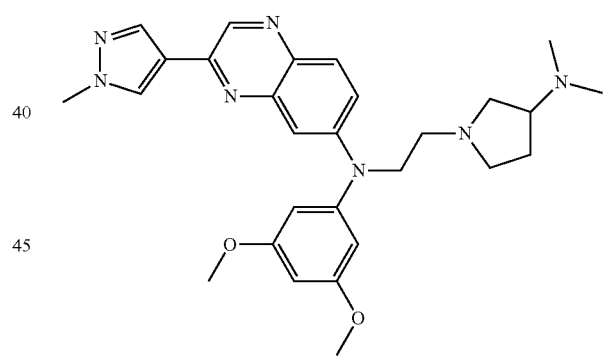
456; ~B3/B4a
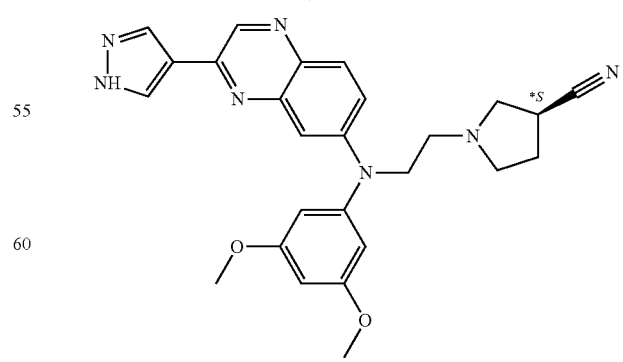
458; ~Co1

-continued
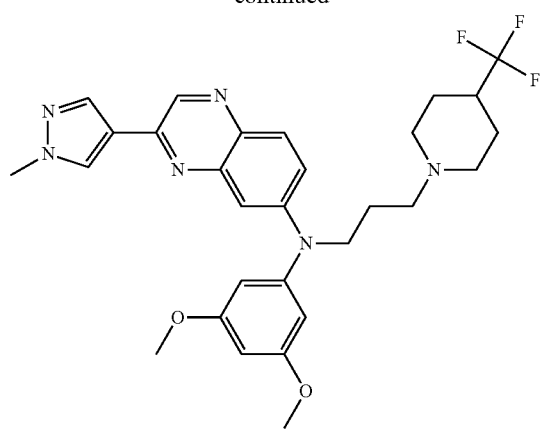
464; ~B3a
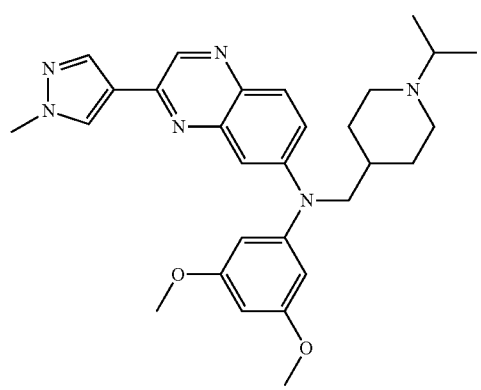
96; =Co30
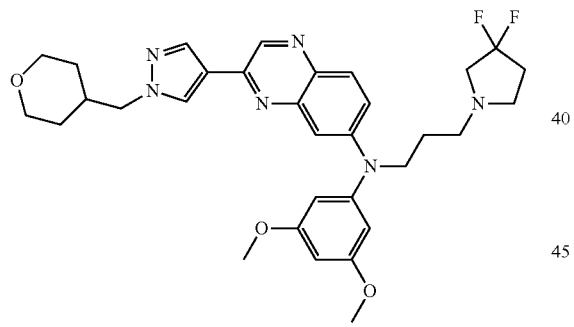
as a HCl salt
459; ~B3a
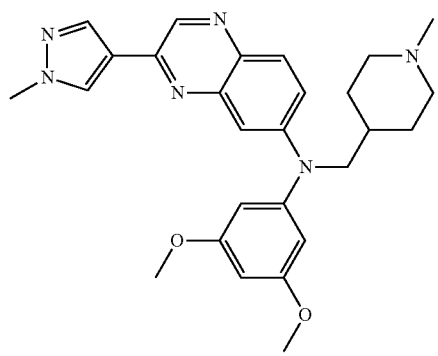
465; ~Co30
-continued
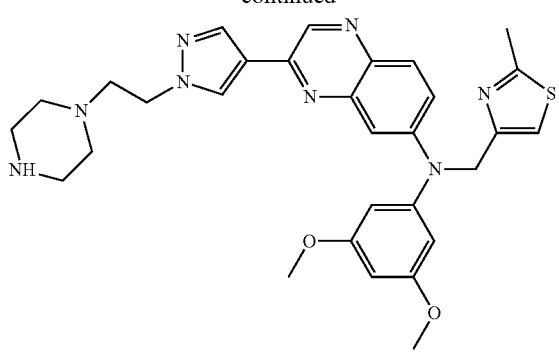
457; ~B9a
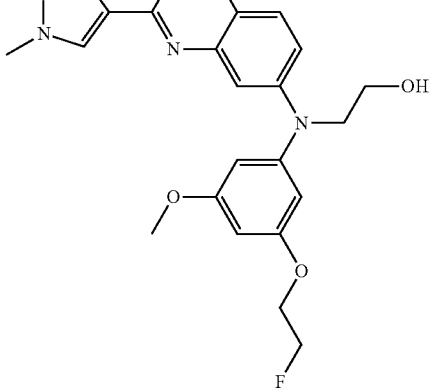
460; ~B1/B2a/B3/B4a
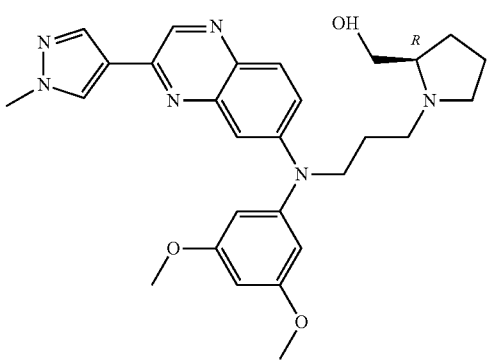
466; ~B3/B4a
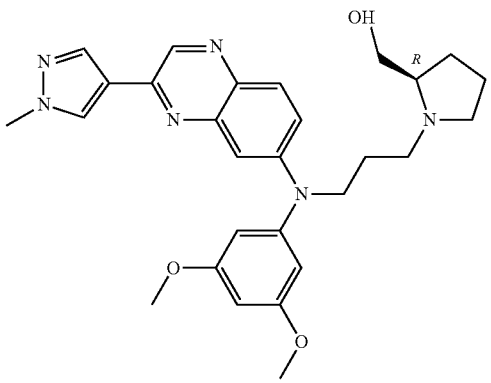
467; ~B3/B4a 415
-continued
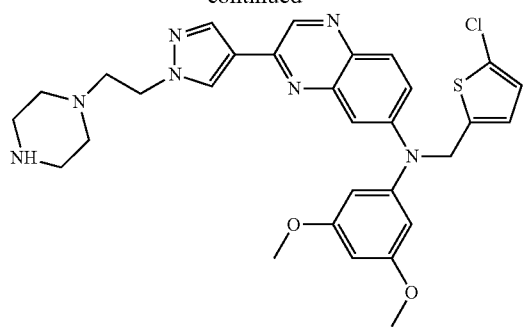
as a HCl salt
474; ~B9a
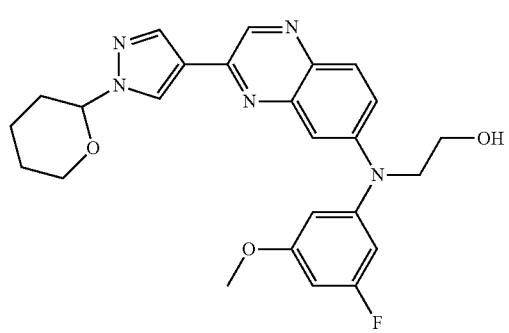
479; ~B1
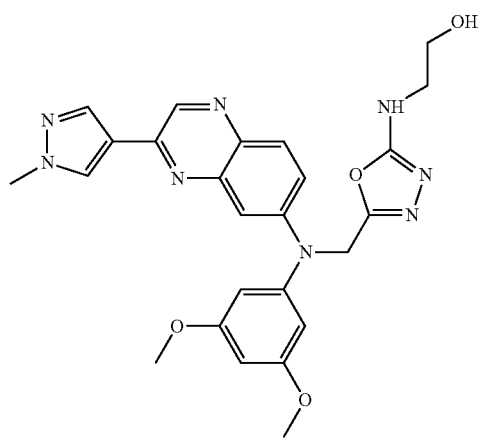
468; ~B1/B2a
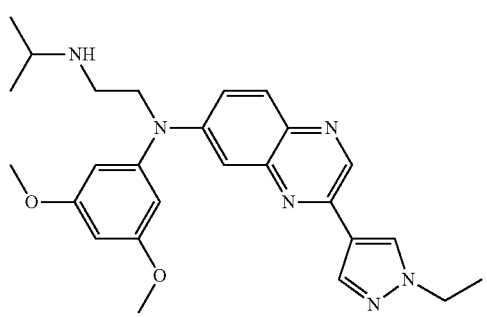
as a HCl salt
135; ~B3/B4a; NMR*
416
-continued
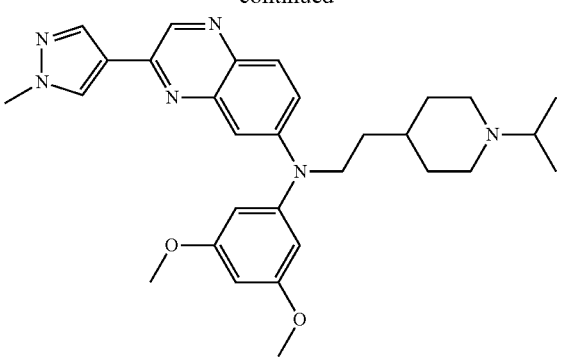
480; ~Co30
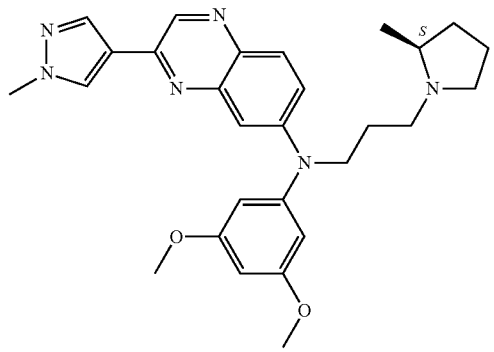
as a HCl salt
469; ~B3/B4a
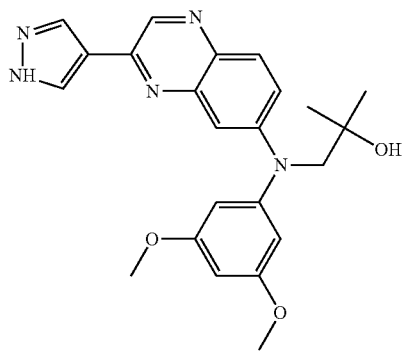
475; ~Co1
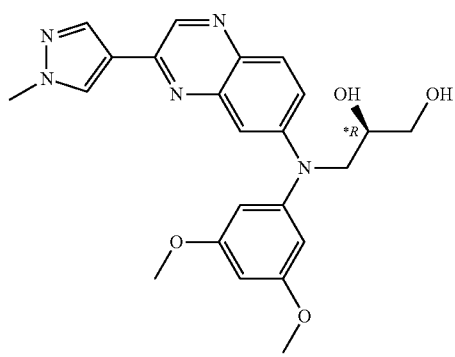
97; =Co31/~Co15

417
-continued
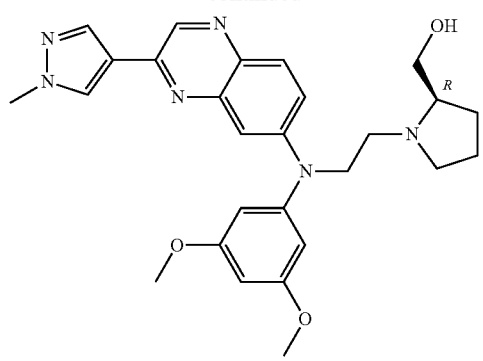
470; ~B3/B4a
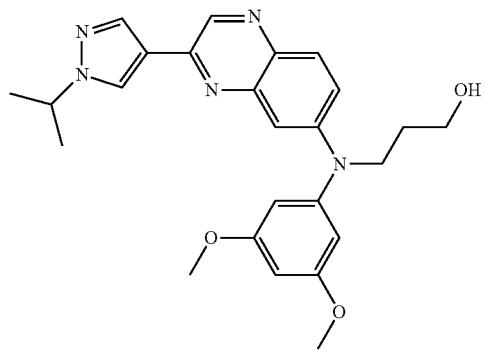
476; ~B1/B2a
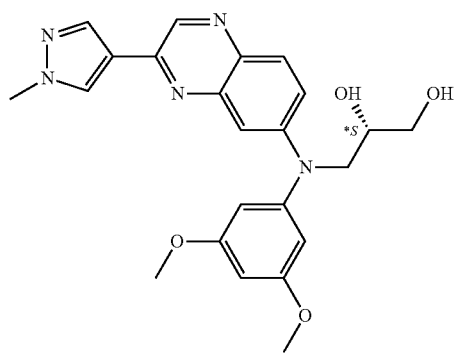
98; =Co31/~Co15; NMR*
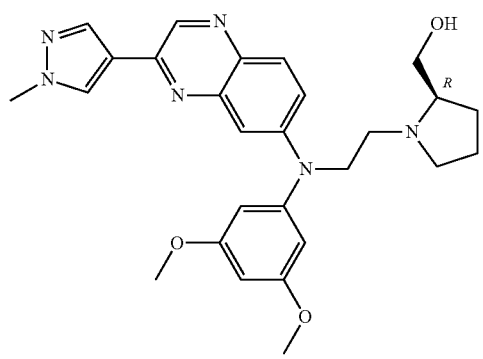
as a HCl salt
471; ~B3/B4a
418
-continued
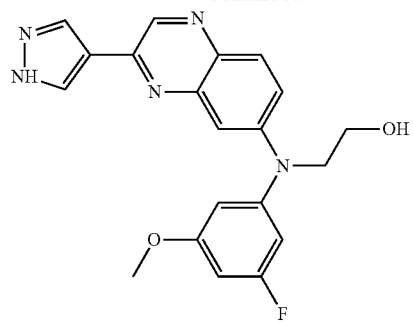
477; ~Co1
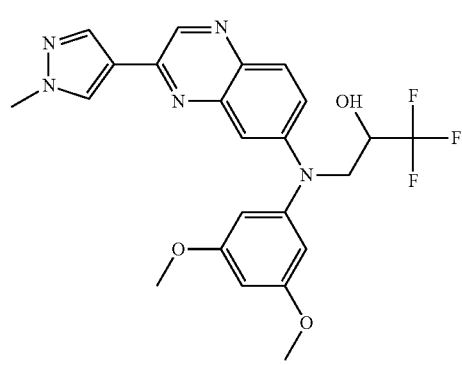
481; ~B6
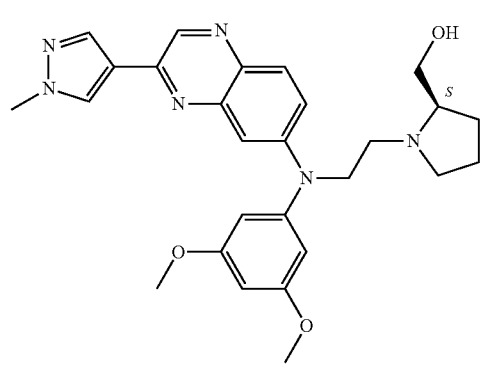
472; ~B3/B4a
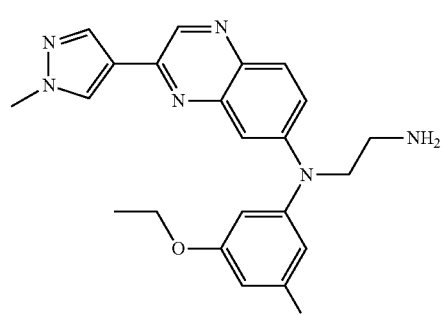
478; ~Co3

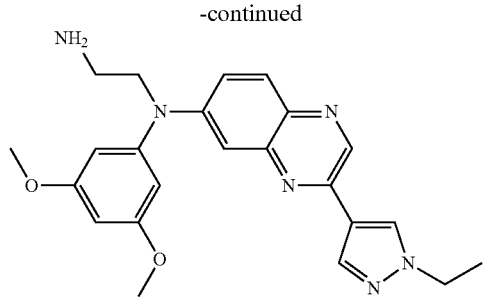
482; ~Co3
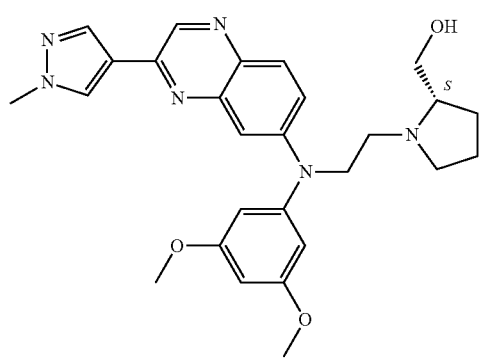
as a HCl salt
473; ~B3/B4a
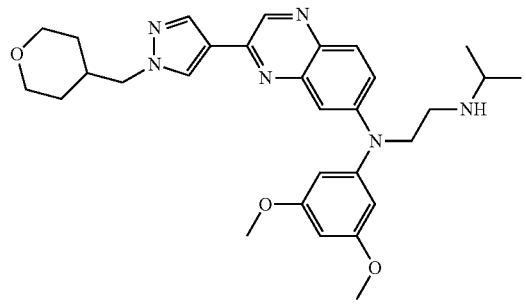
as a HCl salt
136; ~B3/B4a; NMR*
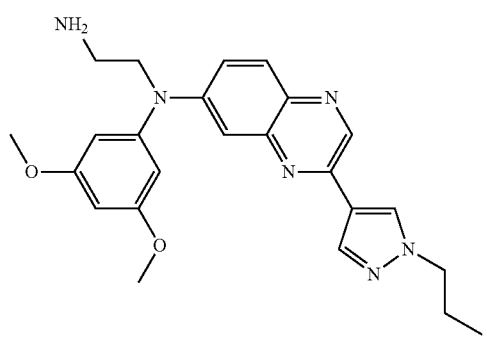
as a HCl salt
483; ~Co3
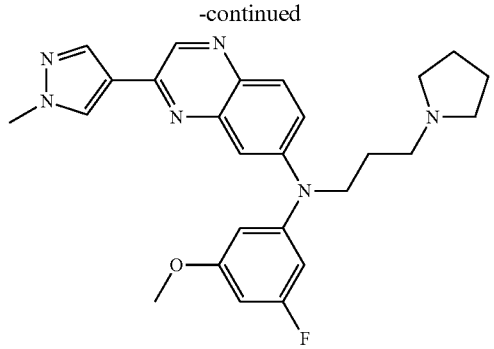
484; ~B5
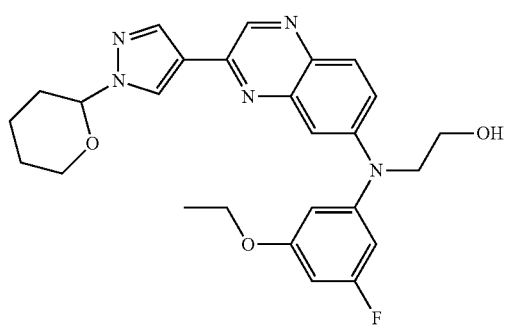
491; ~B1/B2a
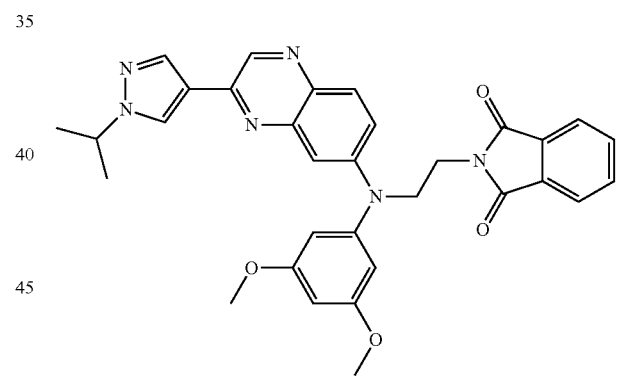
497; ~B3/B4a
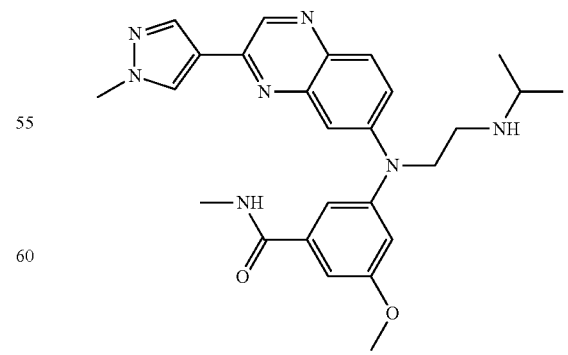
485; ~B3/B4a 421
-continued
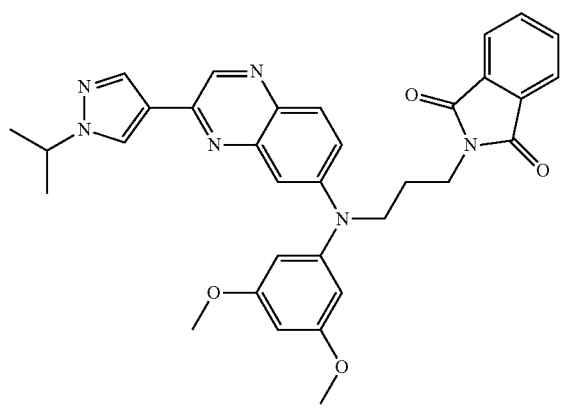
492; ~B3/B4a
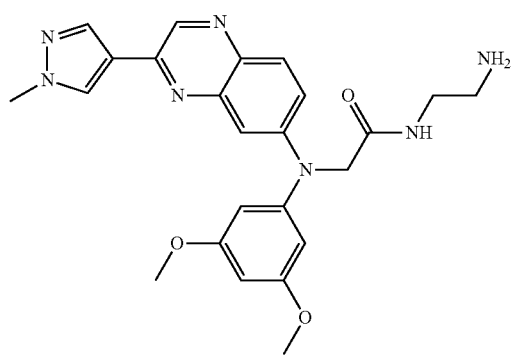
as a HCl salt
119; =Co41b
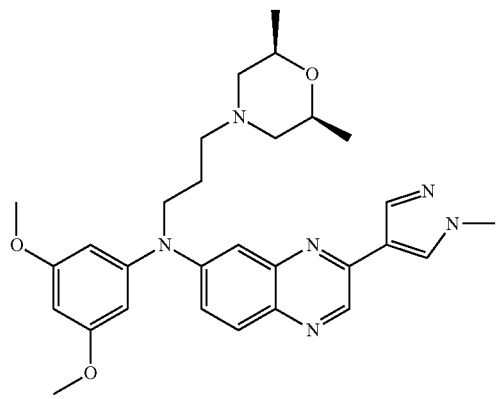
486; ~B5
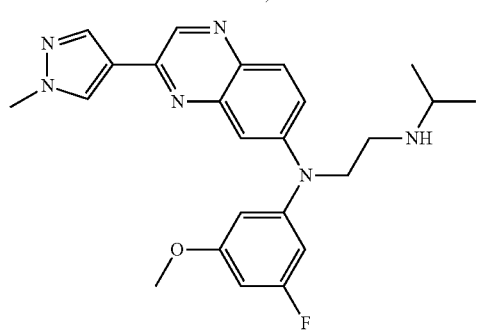
493; ~B3/B4a
422
-continued
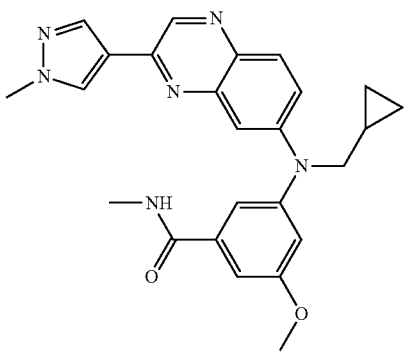
498; ~B5b-1
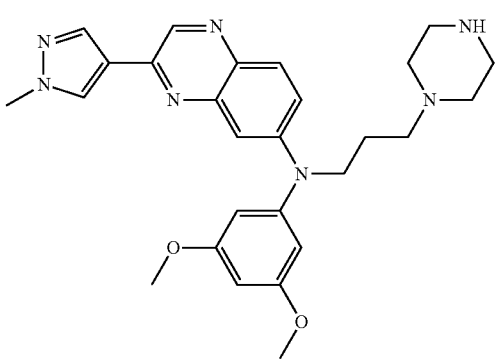
487; ~B3/B4a
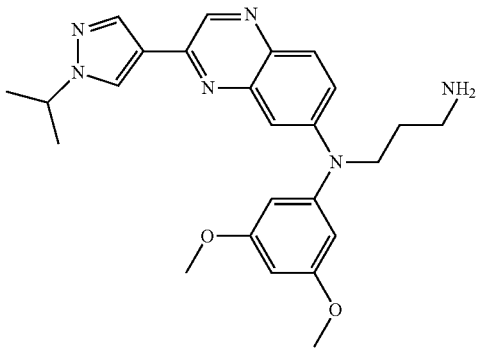
494; ~Co3
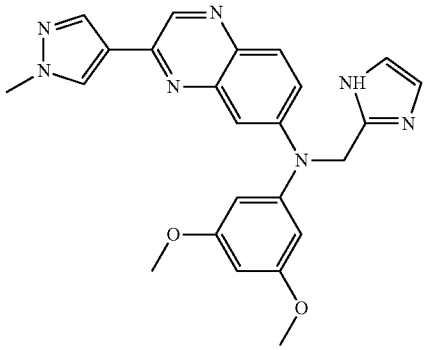
99; =Co32; NMR*

-continued
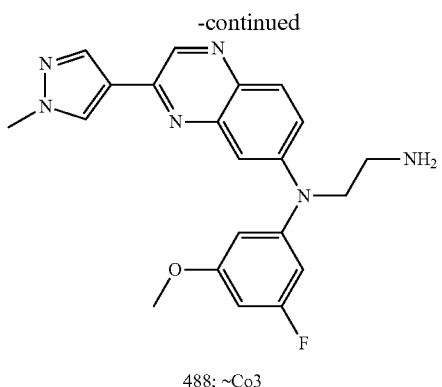
488; ~Co3
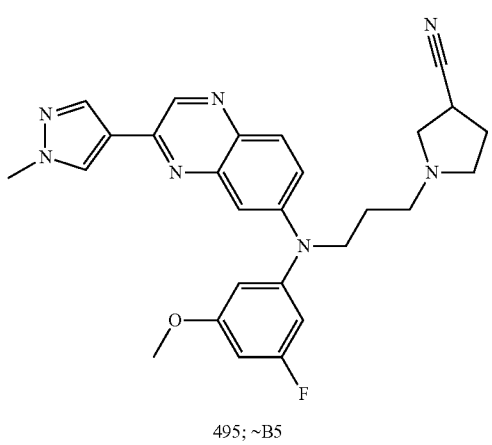
495; ~B5
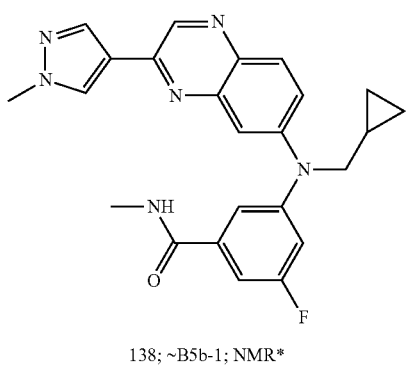
138; ~B5b-1; NMR*
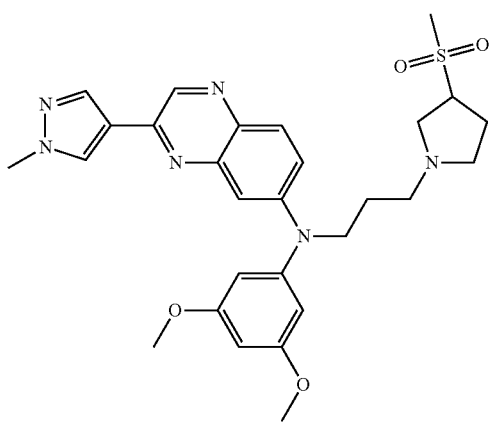
489; ~B3a
-continued
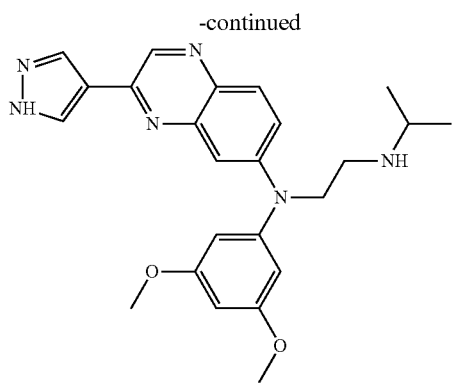
as a HCl salt
137; ~Co1; NMR*; = B49
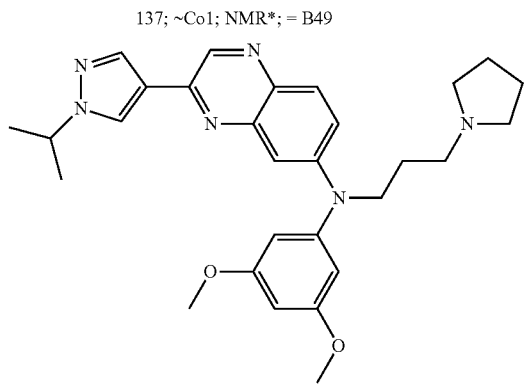
as a HCl salt
499; ~Co5
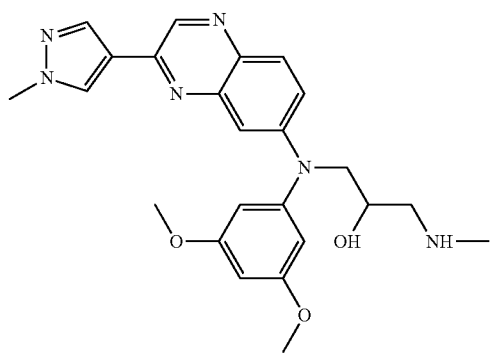
as a HCl salt
490; ~Co18
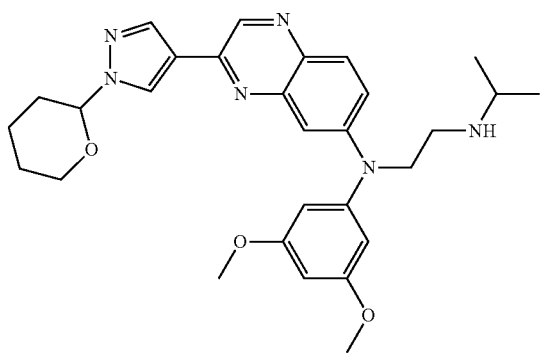
496; ~B3/B4a -continued
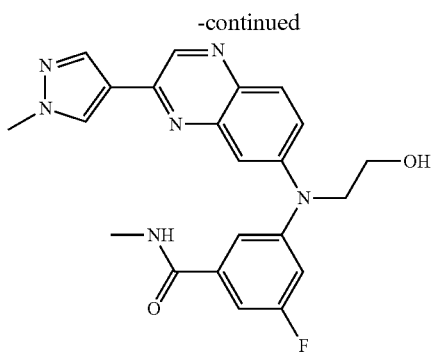
500; ~B1/B2a
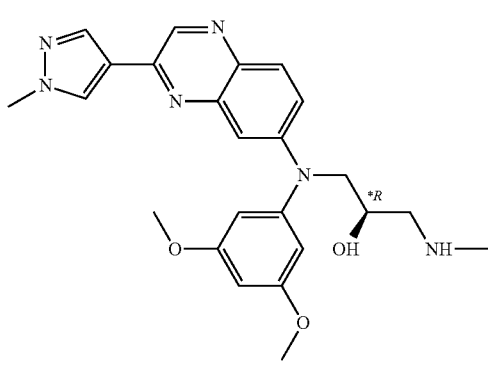
501; ~Co18
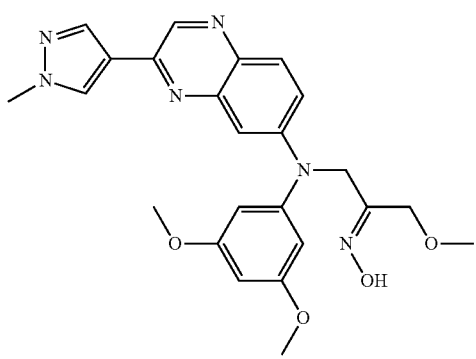
506; ~Co19
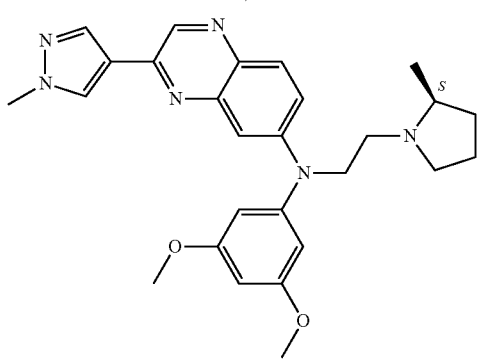
as a HCl salt
512; ~B3/B4a
-continued
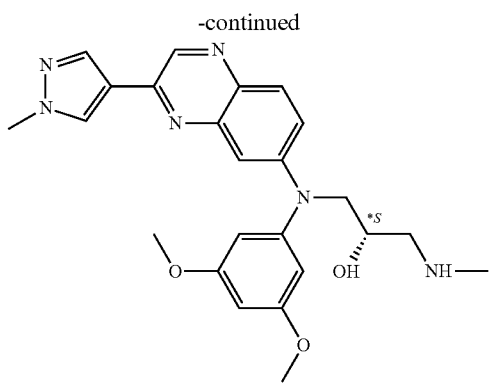
502; ~Co18
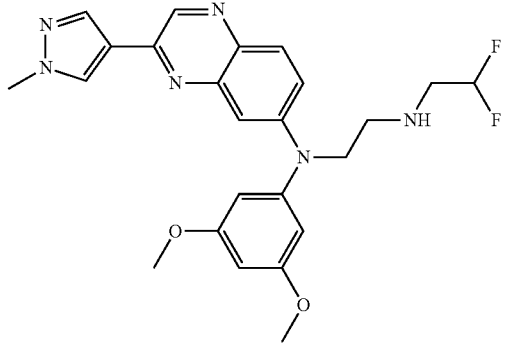
507; ~Co19
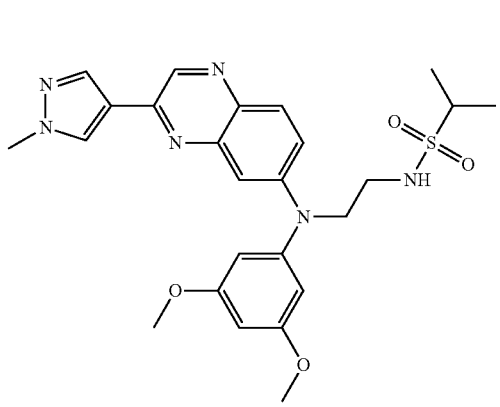
513; ~B3/B4a
503; ~Co4

427
-continued
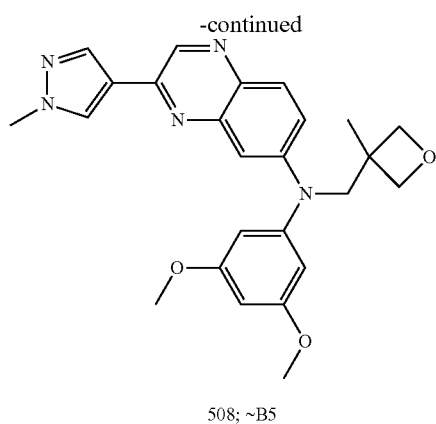
508; ~B5
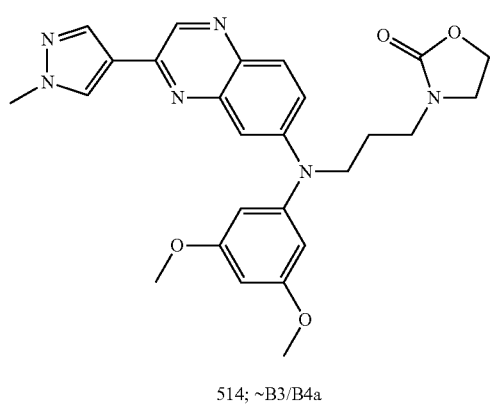
514; ~B3/B4a
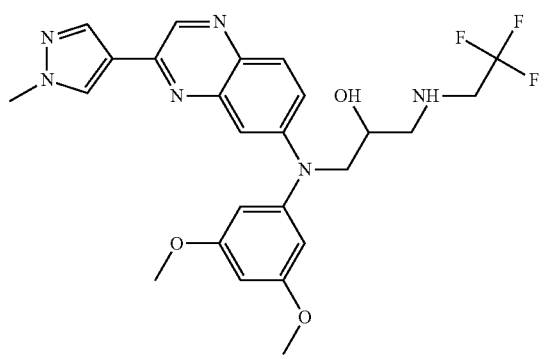
139; ~Co18;; NMR*
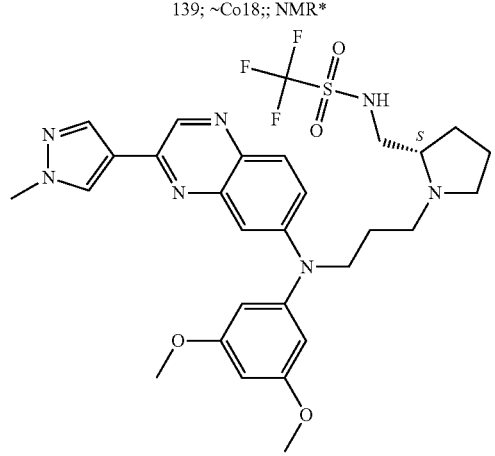
509; ~B3a
428
-continued
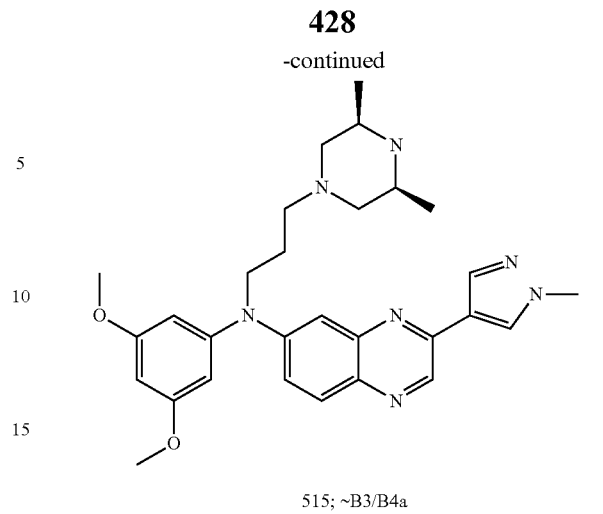
515; ~B3/B4a
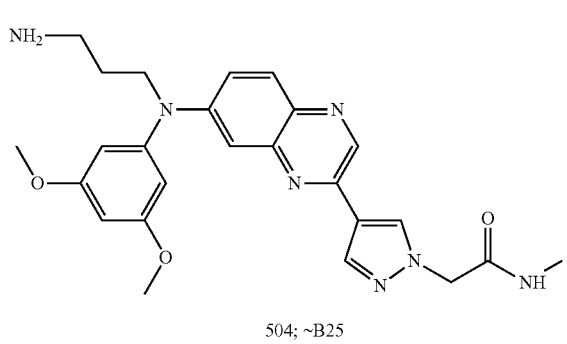
504; ~B25
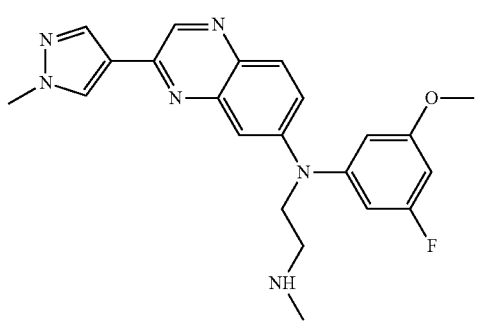
510; ~B3/B4a
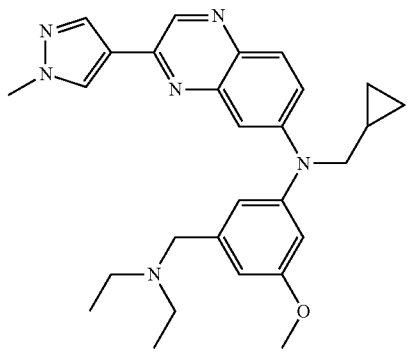
516; ~B5

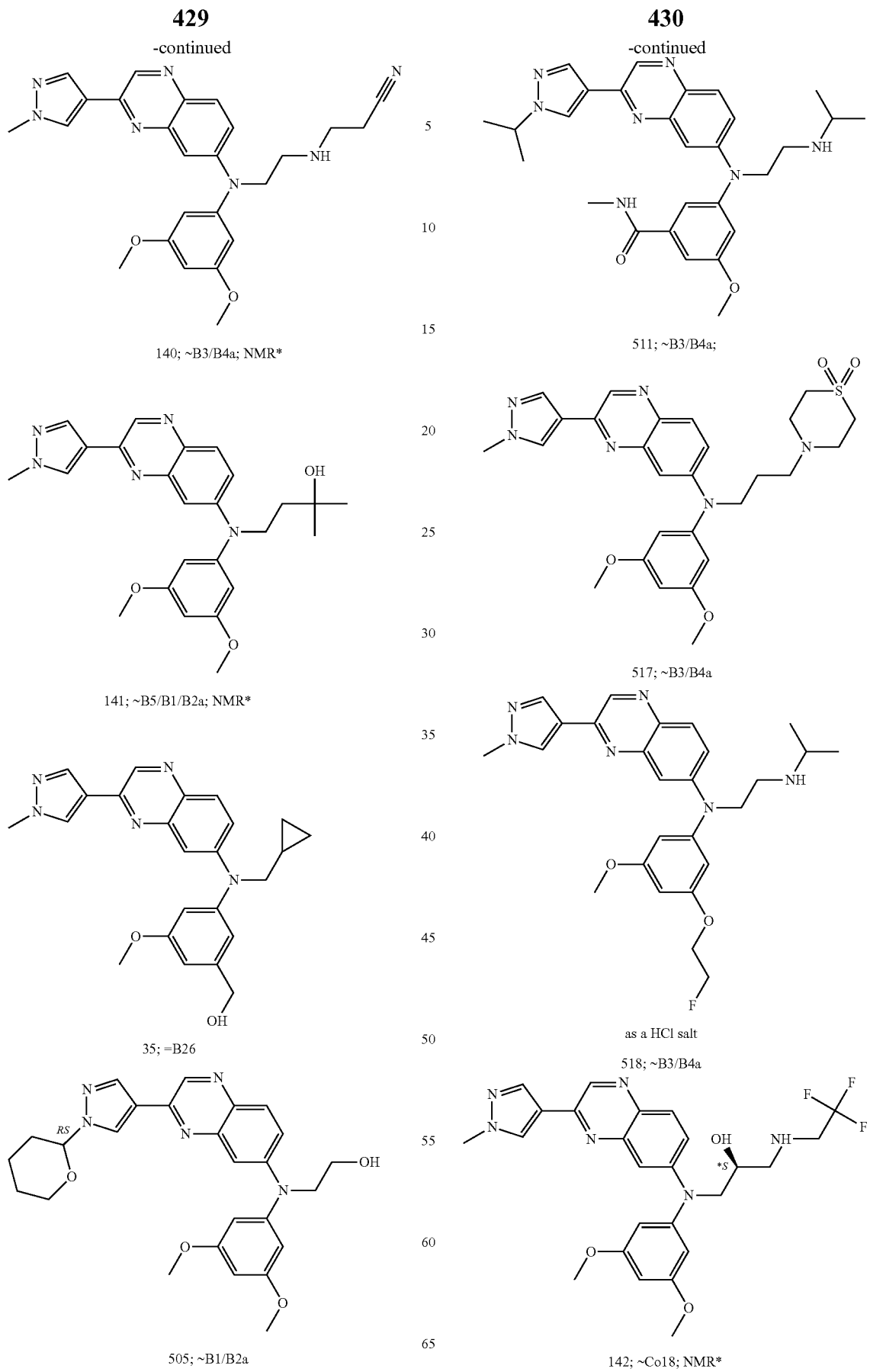

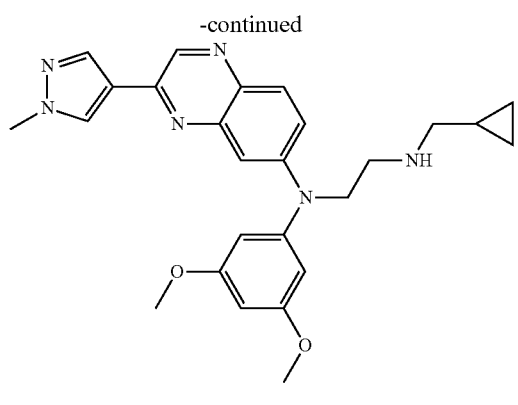
529; ~B3a
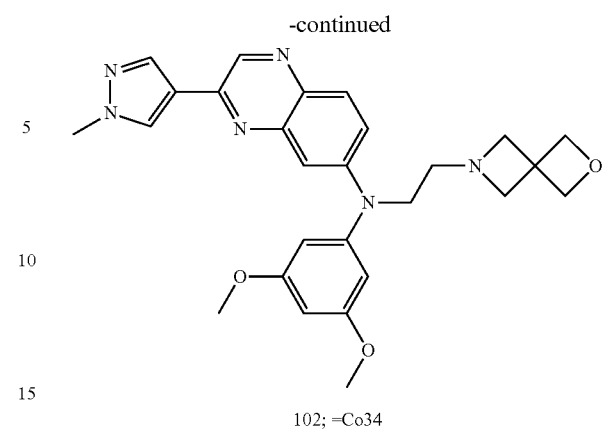
102; =Co34
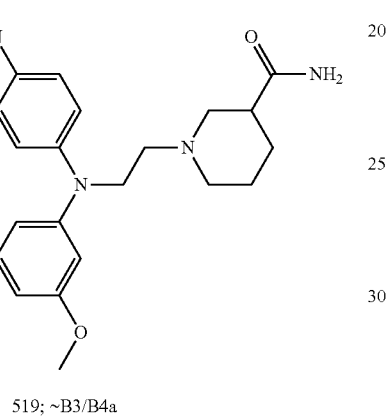
519; ~B3/B4a
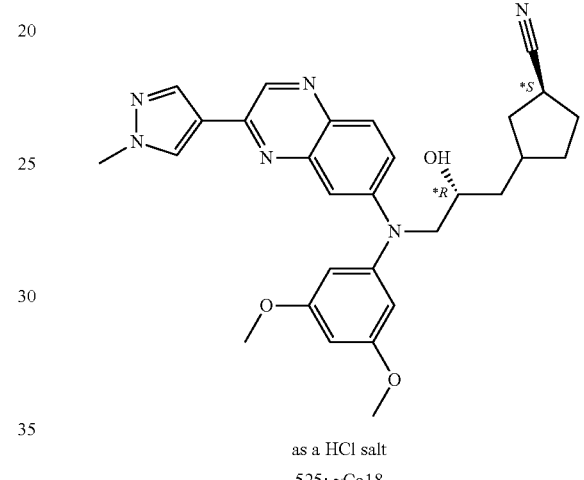
as a HCl salt
525; ~Co18
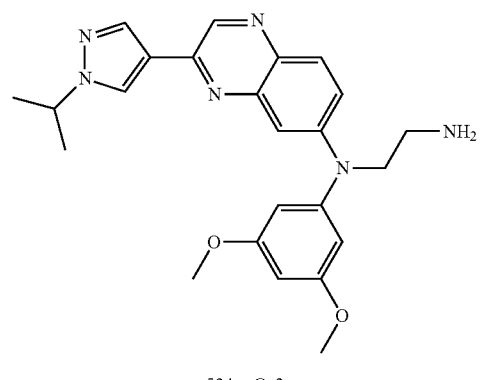
524; ~Co3
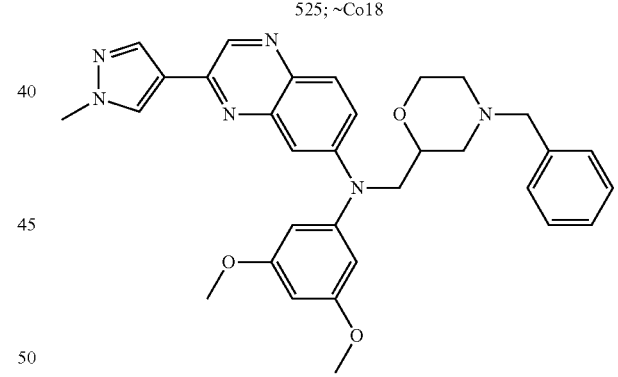
10; =B5a
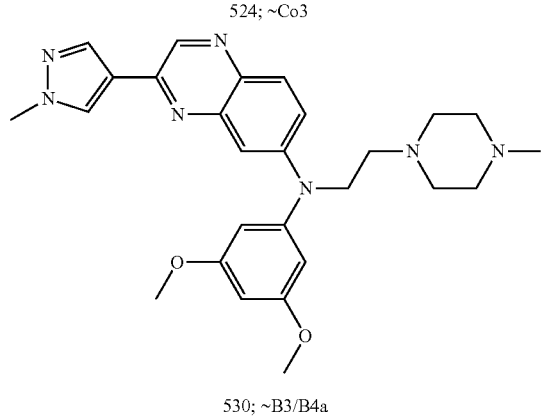
530; ~B3/B4a
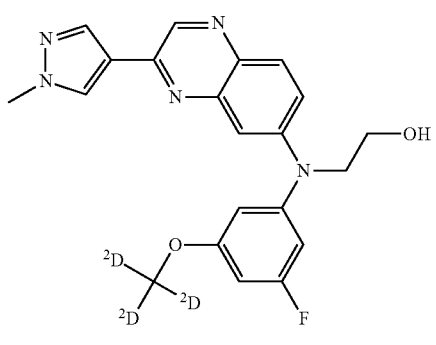
520; ~B1/B2a

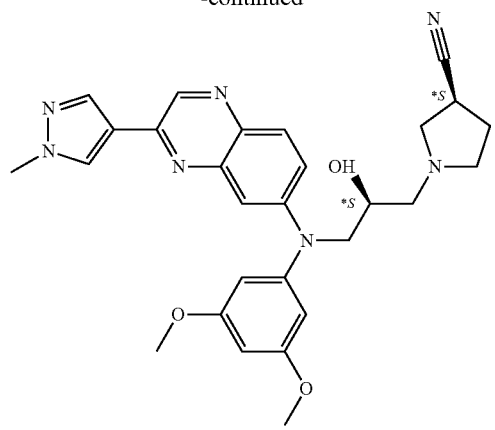
as a HCl salt
526; ~Co18
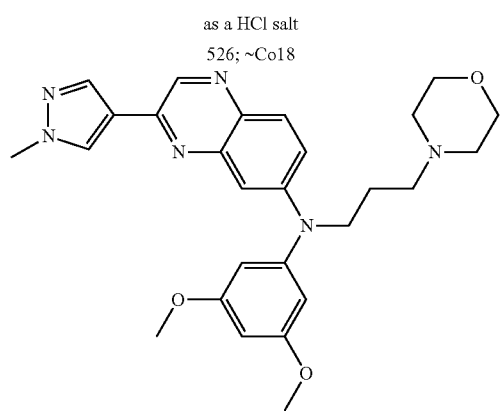
as a HCl salt
531; ~B3/B4a
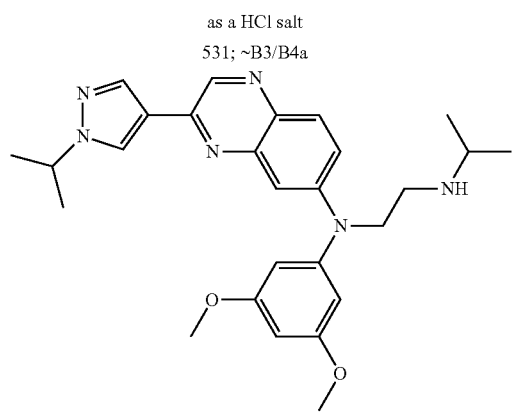
as a HCl salt
521; ~B3/B4a
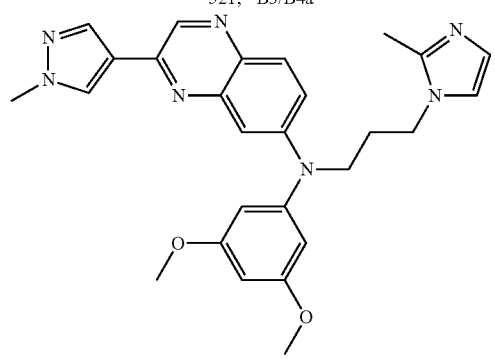
527; ~Co2
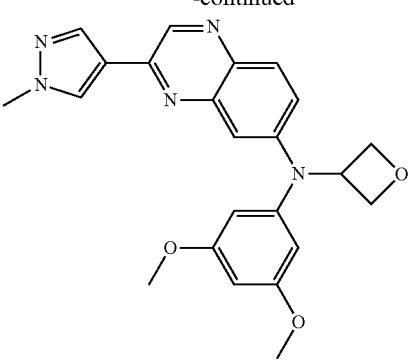
36; =B27
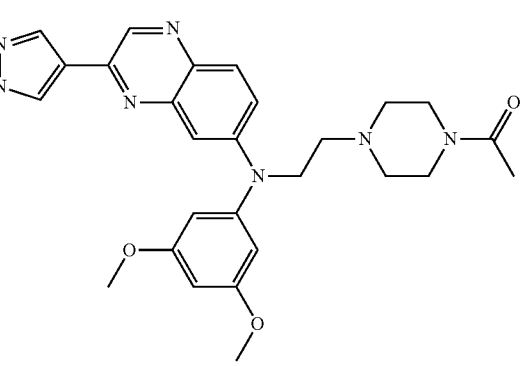
522; ~B3/B4a
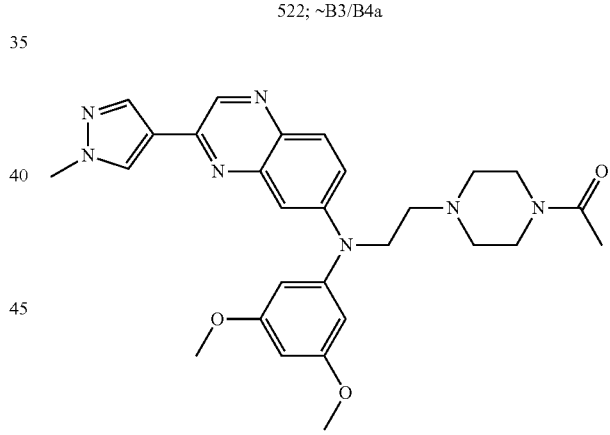
143; ~B3/B4a; NMR*
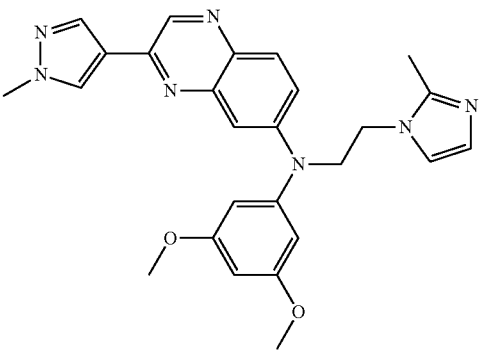
532; ~B3/B4a 435
-continued
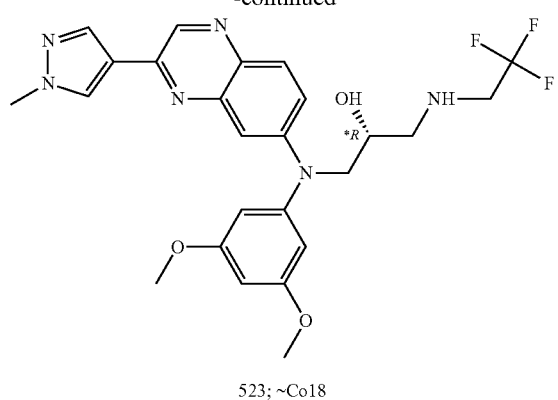
523; ~Co18
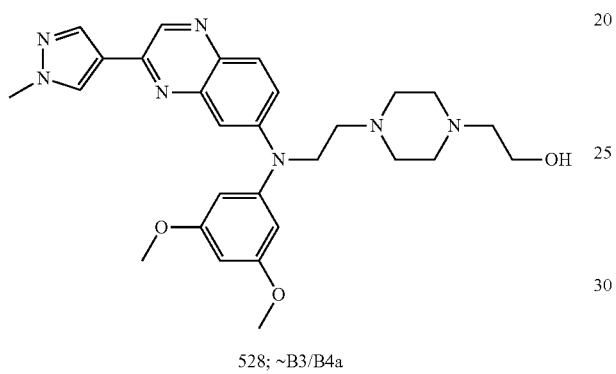
528; ~B3/B4a
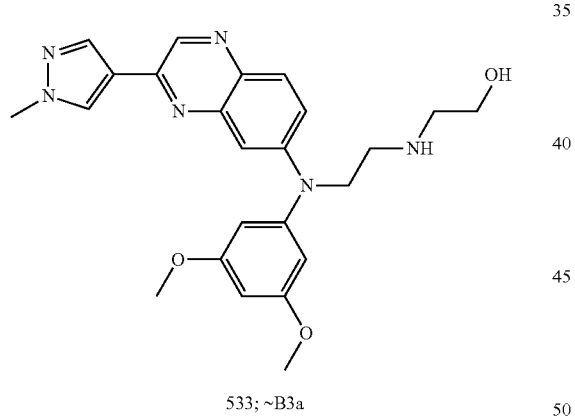
533; ~B3a
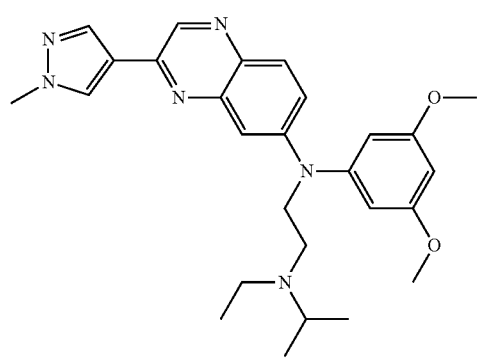
as a HCl salt
534; ~B3a
436
-continued
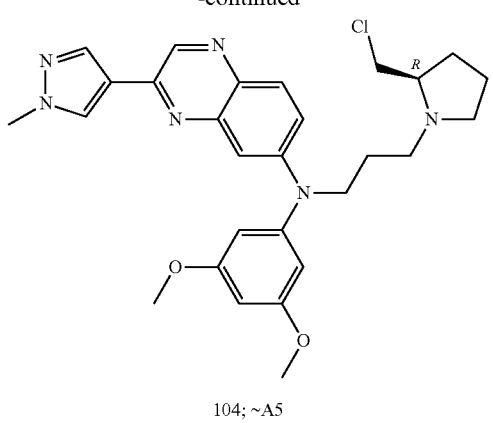
104; ~A5
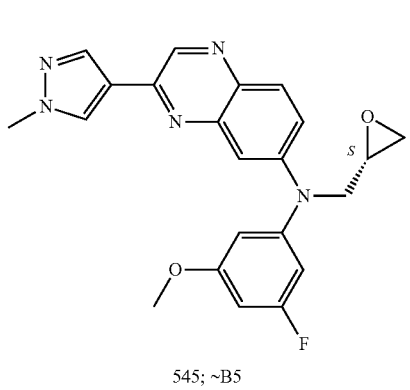
545; ~B5
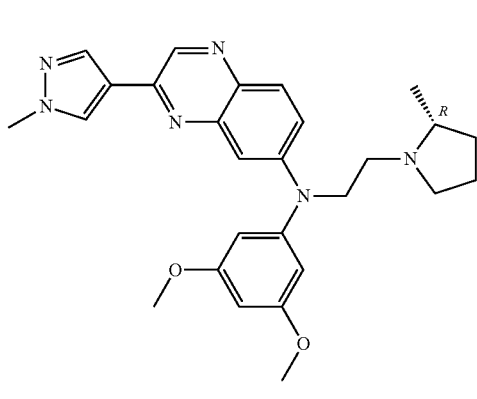
as a HCl salt
535; ~B3/B4a
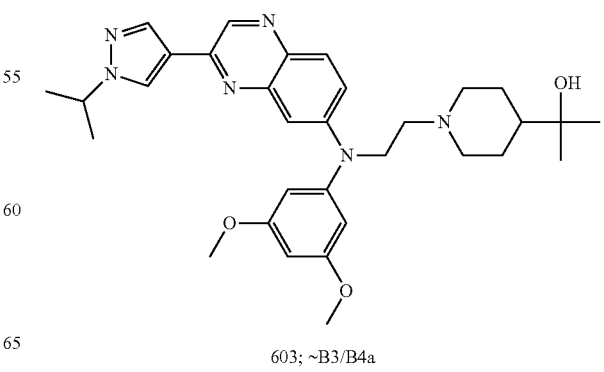
603; ~B3/B4a -continued
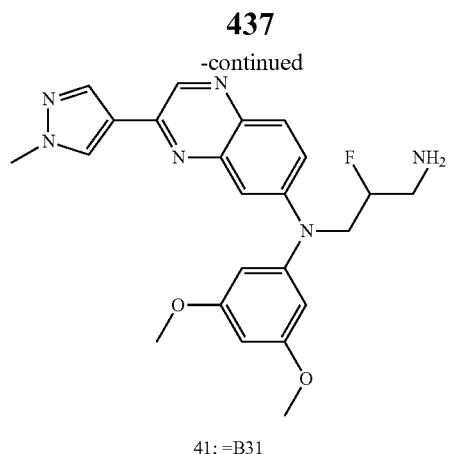
41; =B31
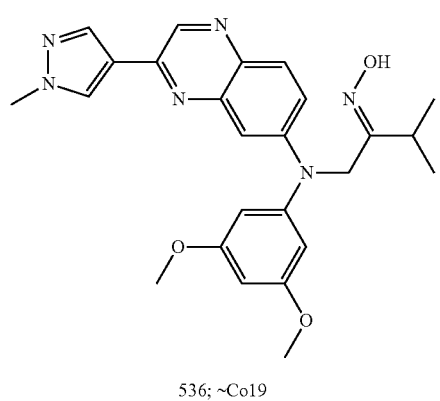
536; ~Co19
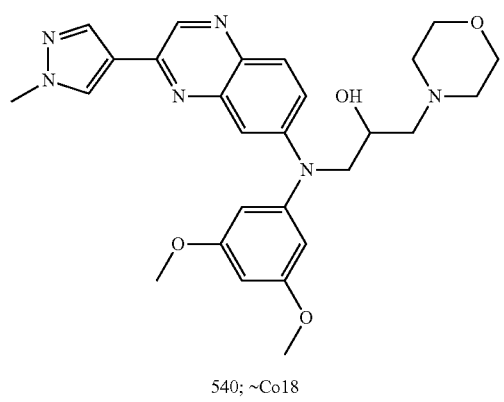
540; ~Co18
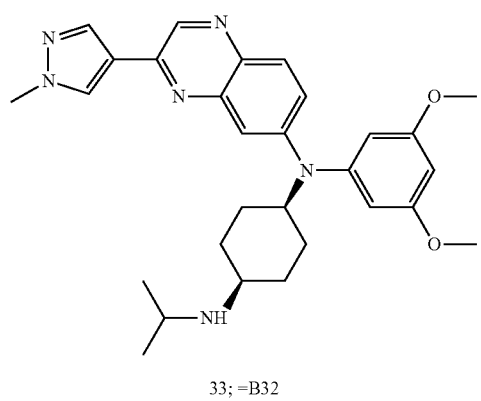
33; =B32
-continued
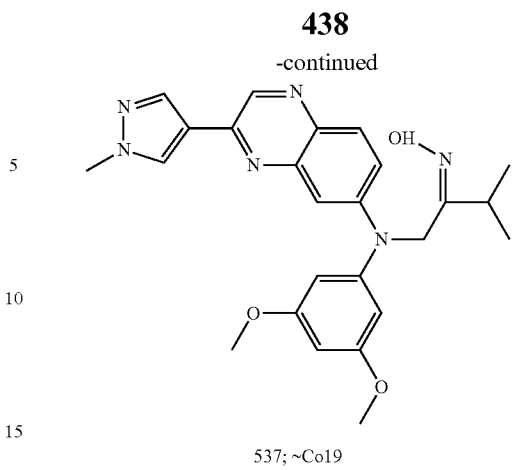
537; ~Co19
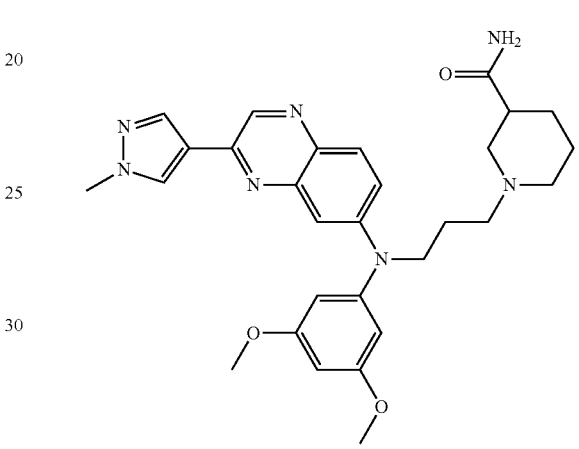
541; ~B3/B4a
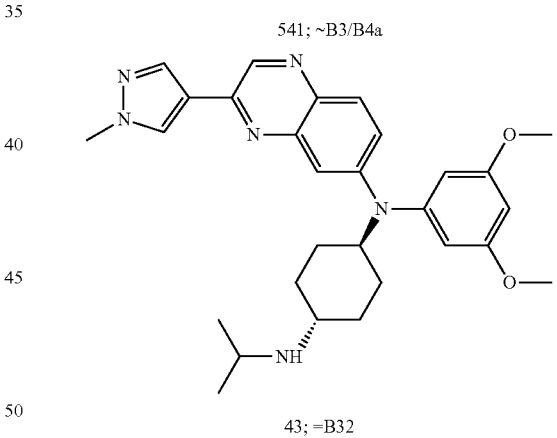
43; =B32
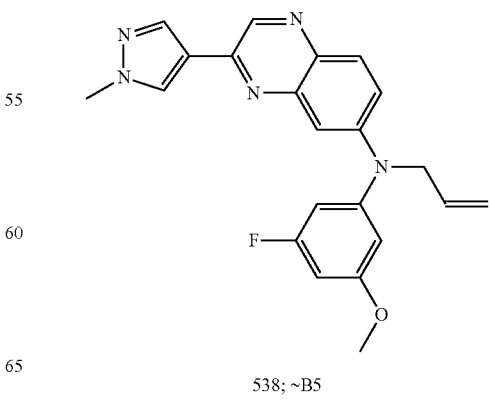
538; ~B5

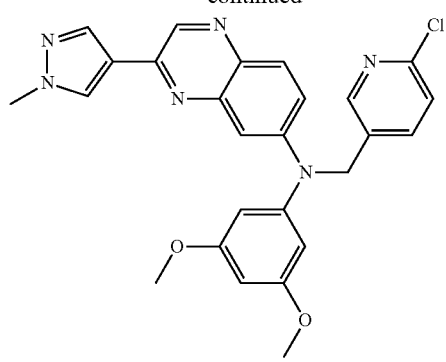
542; ~B5
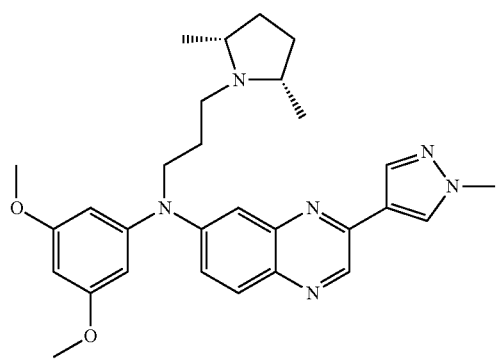
as a HCl salt
546; ~B3/B4a
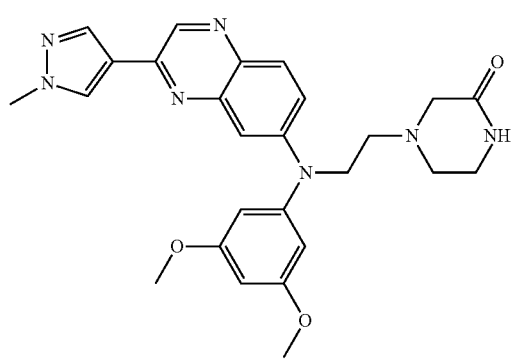
144; ~B3/B4a; NMR*
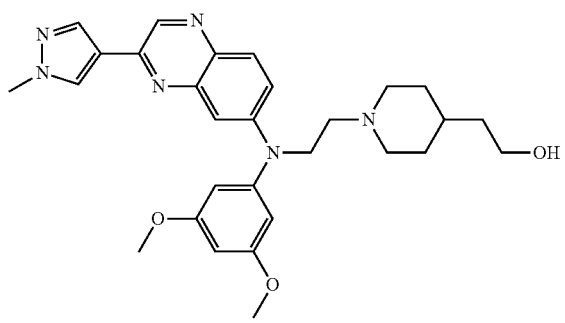
543; ~B3/B4a
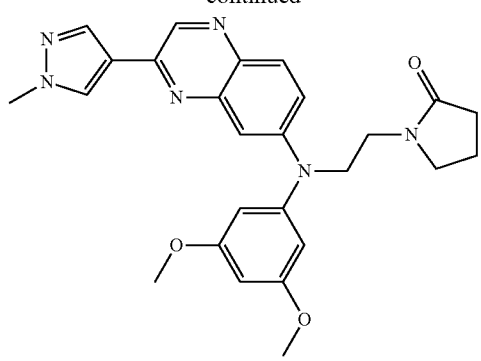
547; ~B3/B4a
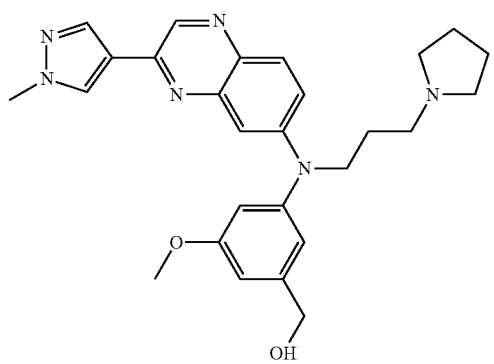
539; ~B5
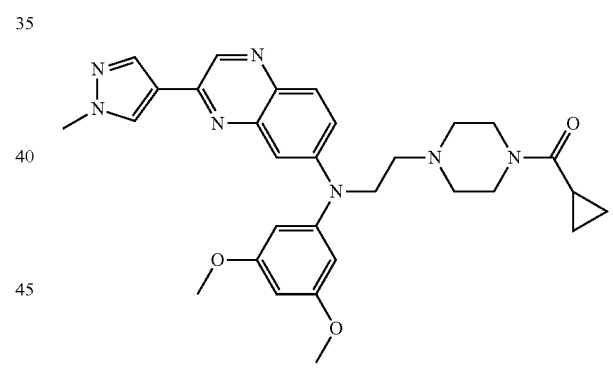
544; ~Co4
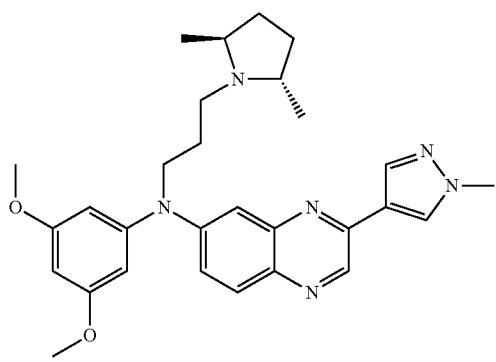
as a HCl salt
548; ~B3/B4a -continued
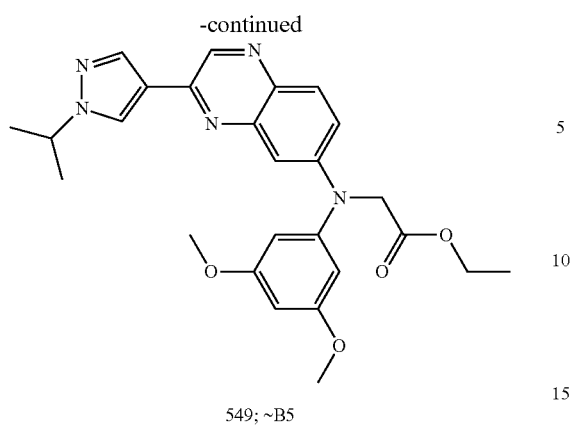
549; ~B5
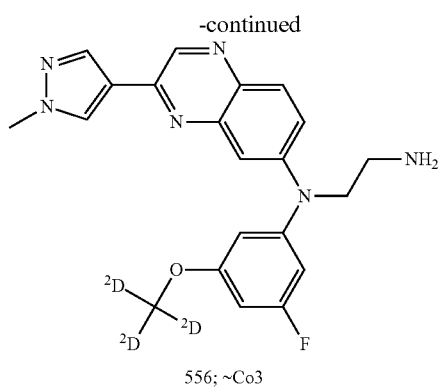
556; ~Co3
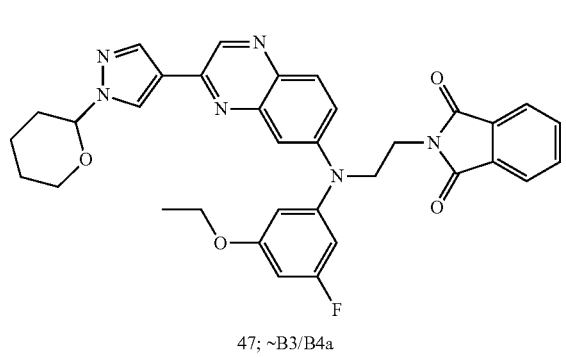
47; ~B3/B4a
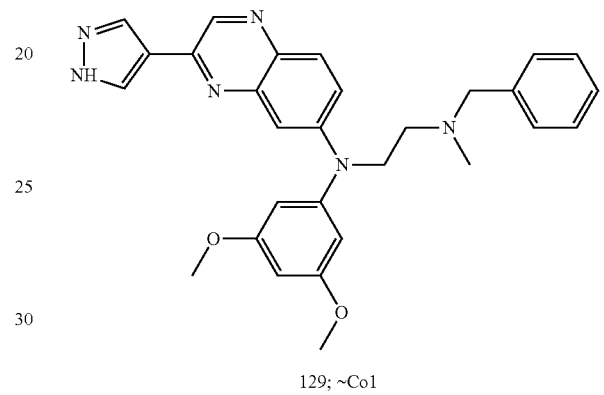
129; ~Co1
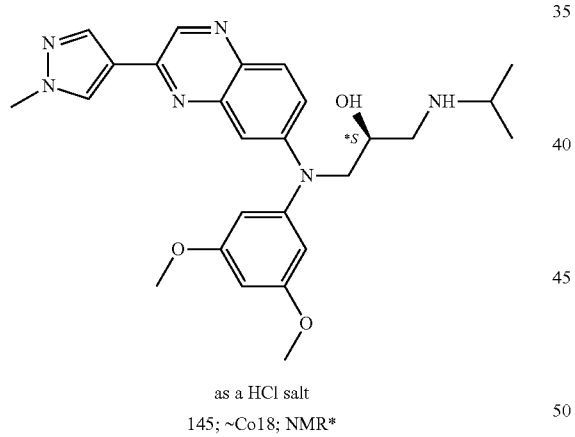
as a HCl salt
145; ~Co18; NMR*
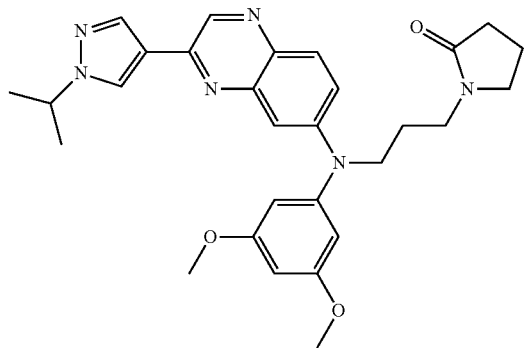
551; ~B3/B4a
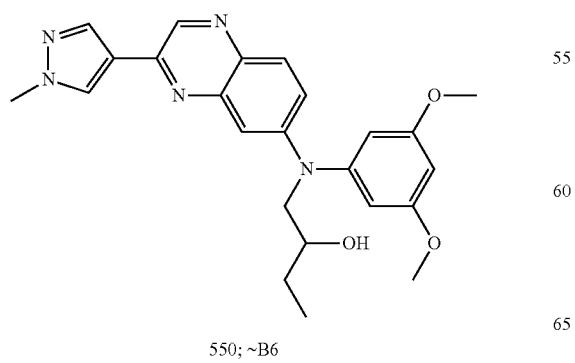
550; ~B6
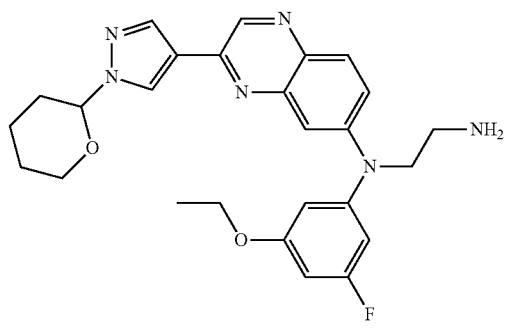
46; ~Co3

443
-continued
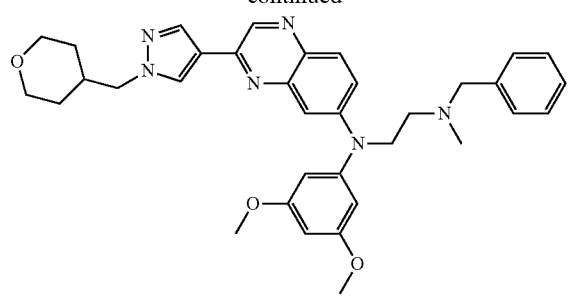
111; ~Co5a
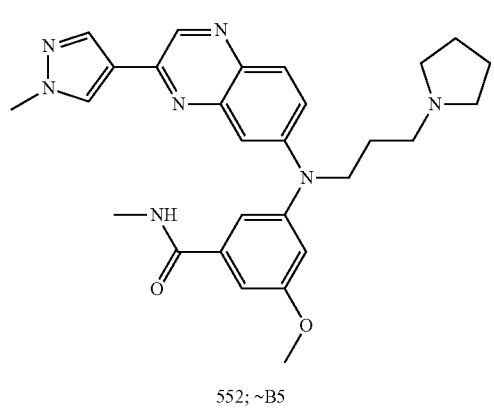
552; ~B5
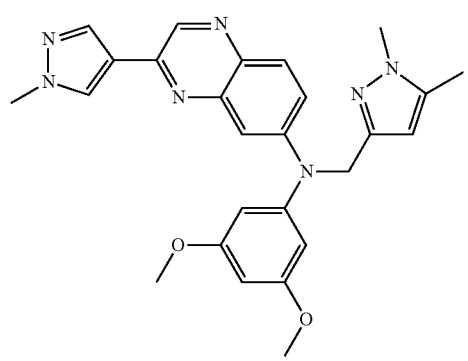
557; ~B5a
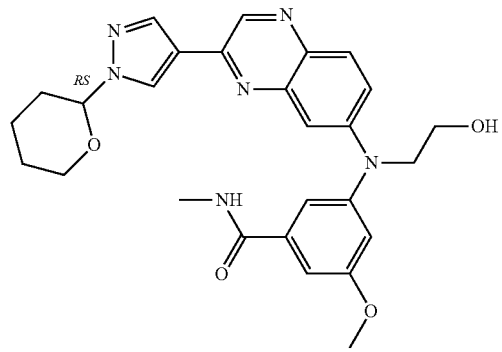
560; ~B1/B2a
444
-continued
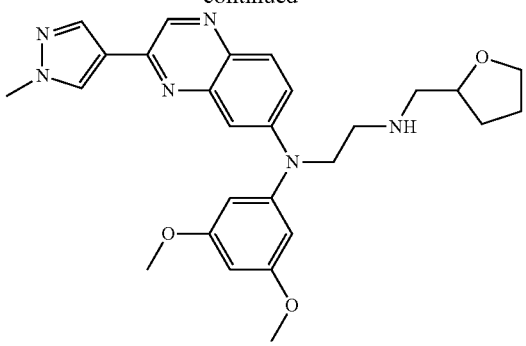
as a HCl salt
553; ~B3a
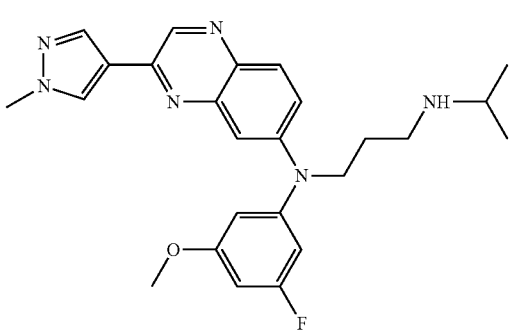
558; ~Co3
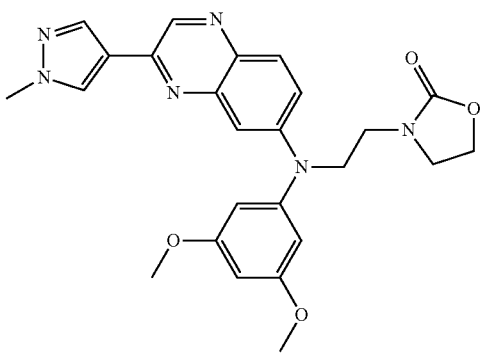
561; ~B3/B4a
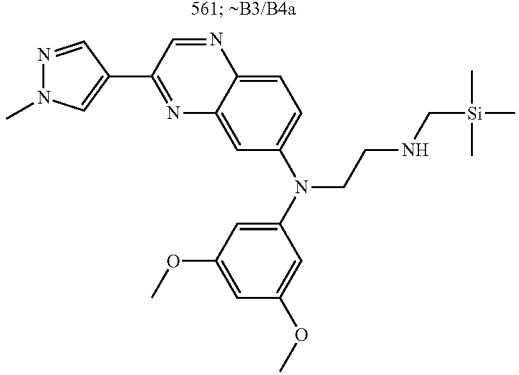
as a HCl salt
554; ~B3/B4a

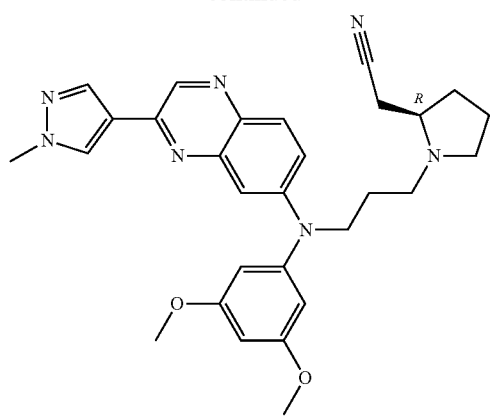
as a HCl salt
103; =Co35
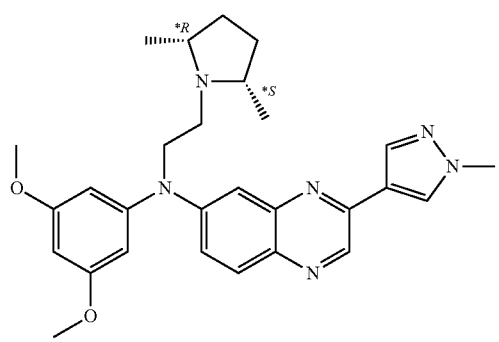
562; ~B3/B4a
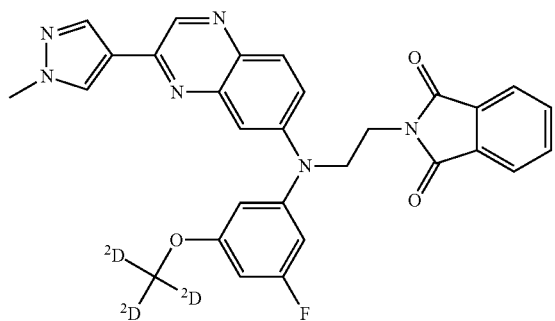
555; ~B3/B4a
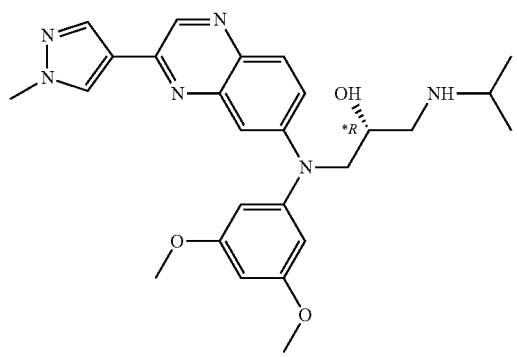
as a HCl salt
559; ~Co18
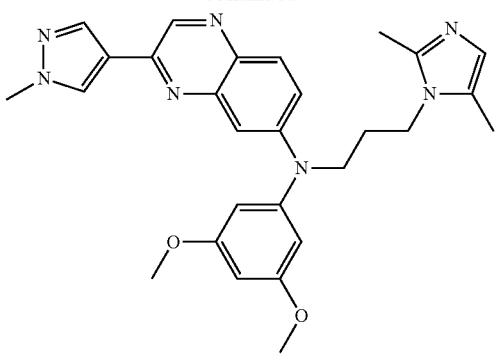
as a HCl salt
563; =Co2B
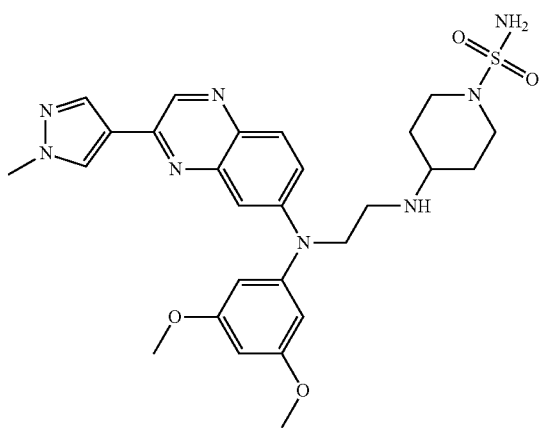
564; ~B3/B4a
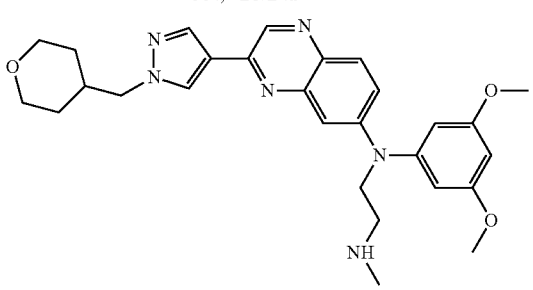
as a HCl salt
110; =Co37
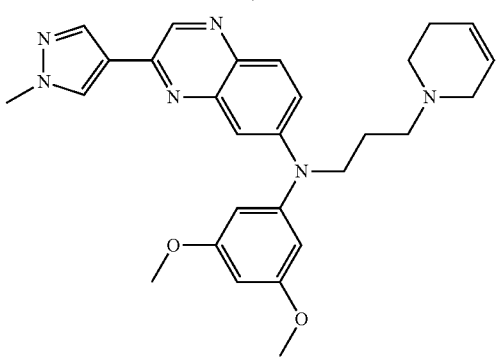
as a HCl salt
578; ~B3/B4a

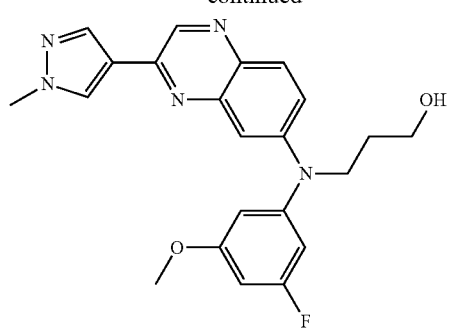
565; ~B1/B2a
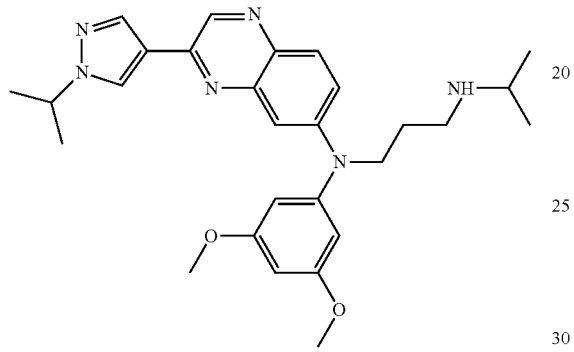
as a HCl salt
570; ~B3/B4a
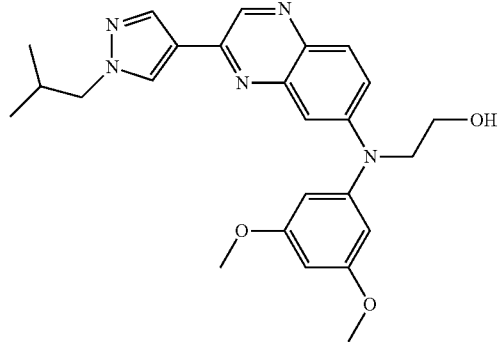
579; ~B1/B2a
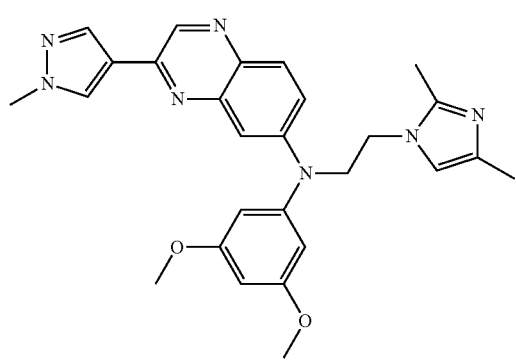
as a HCl salt
566; ~B3/B4a
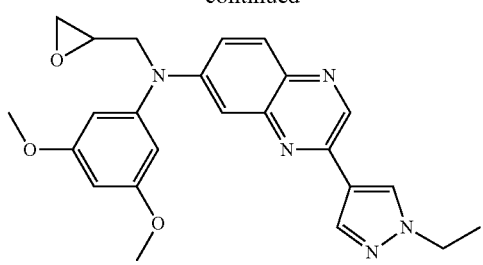
571; ~B5
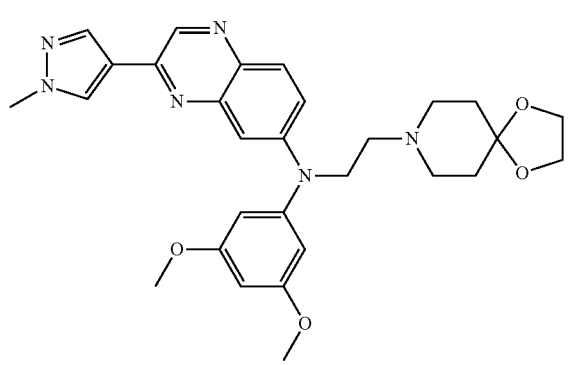
580; =B3B
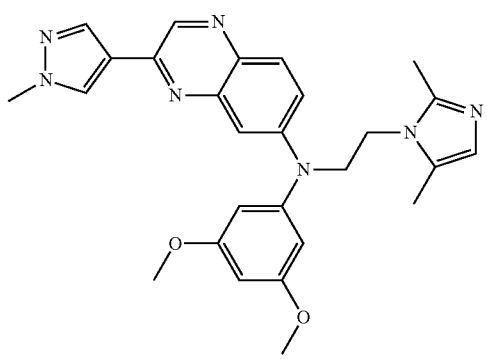
567; ~B3/B4a
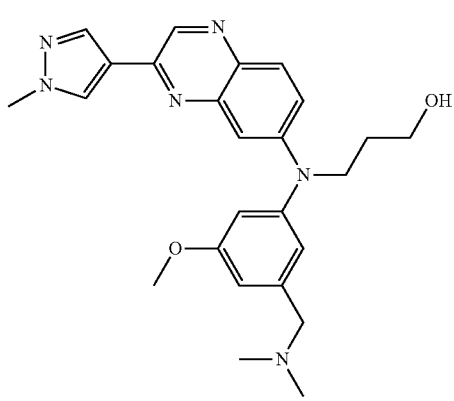
574; ~B1/B2a 449
-continued
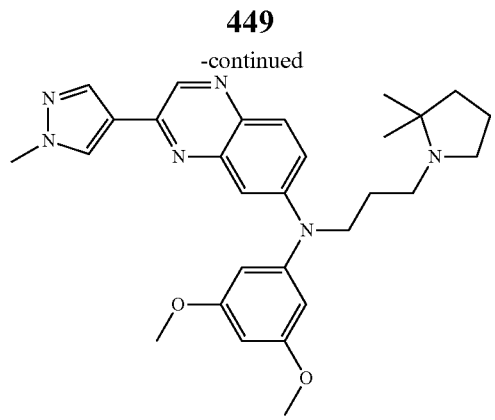
as a HCl salt
581; ~B3a
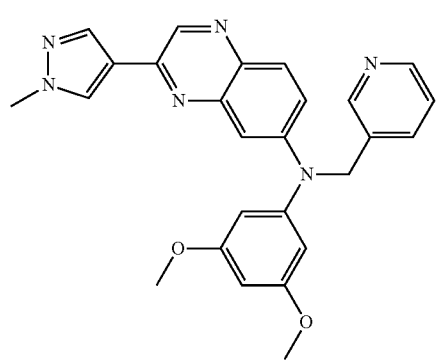
568; ~B5
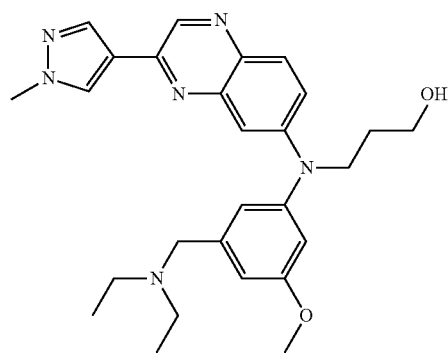
575; ~B1/B2a
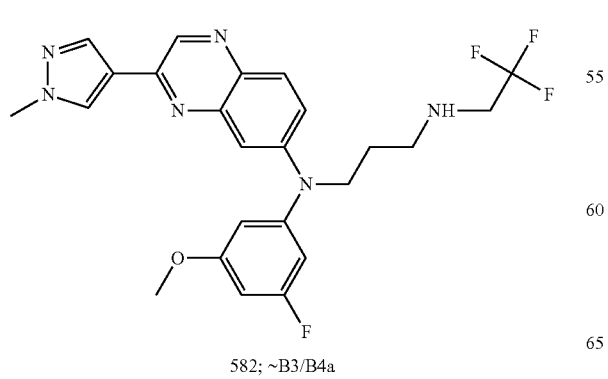
582; ~B3/B4a
450
-continued
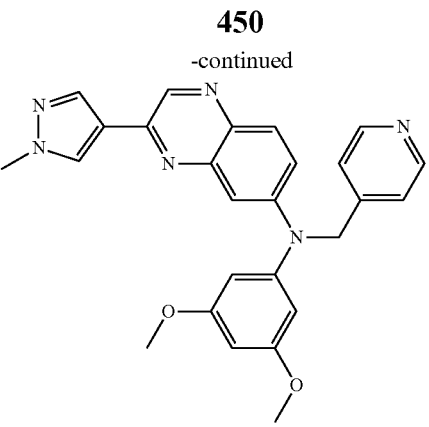
569; ~B5
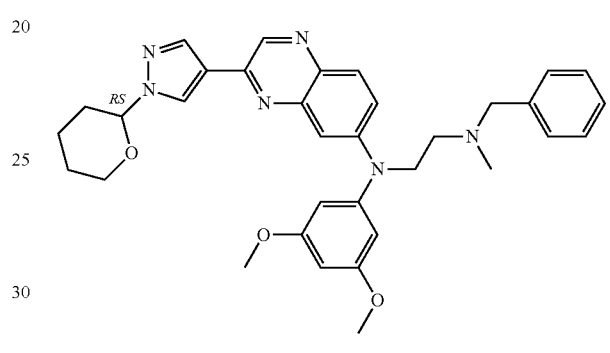
576; ~B5
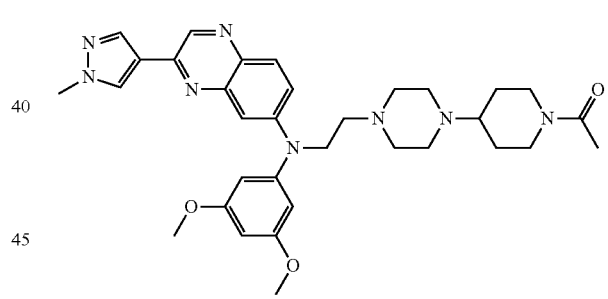
583; ~B3/B4a
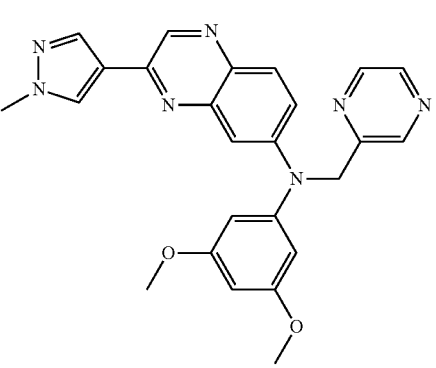
146; ~B5; NMR*

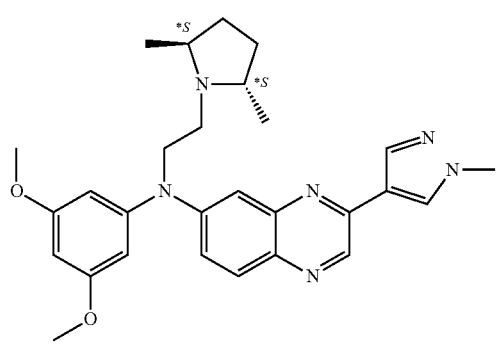
577; ~B3/B4a
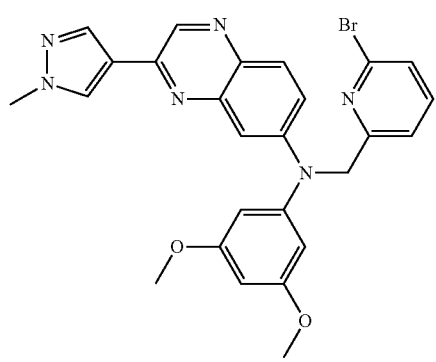
584; ~B5a
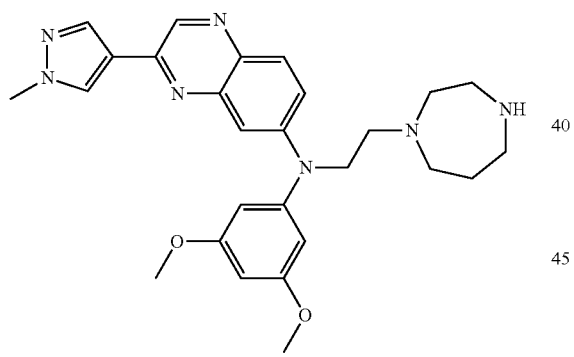
•oxalate
585; ~B3/B4a
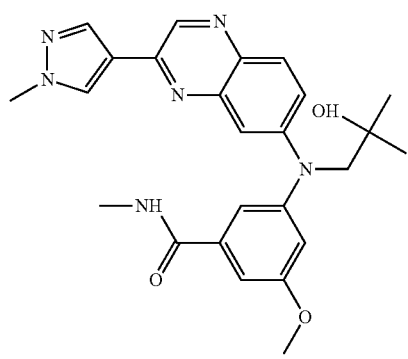
589; ~Co16
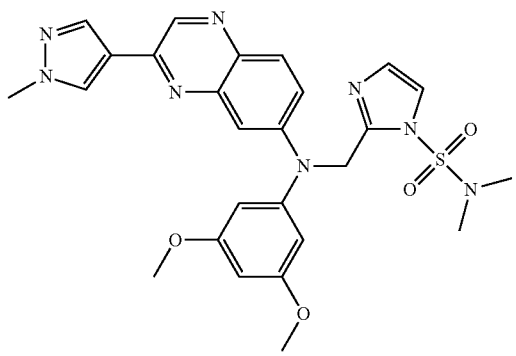
100; ~B5 b-3
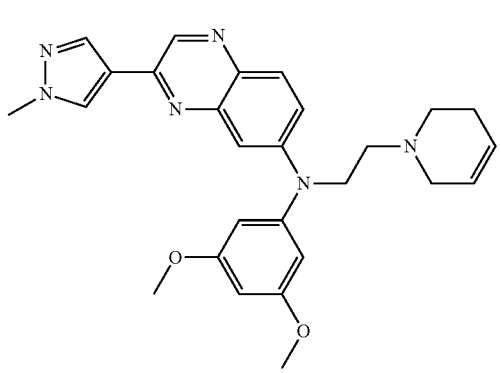
as a HCl salt
586; ~B3/B4a
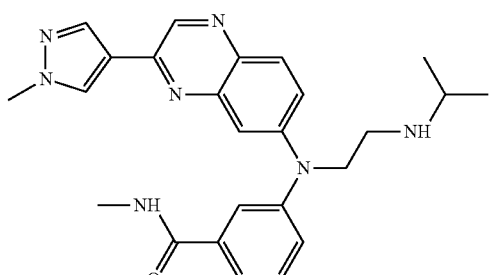
590; ~B3
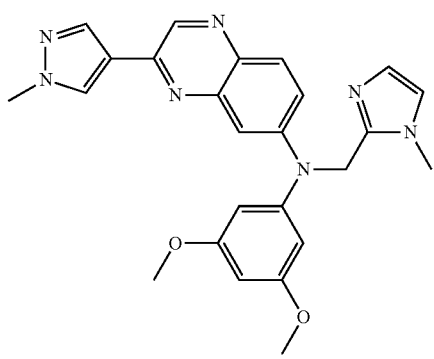
101; =Co33

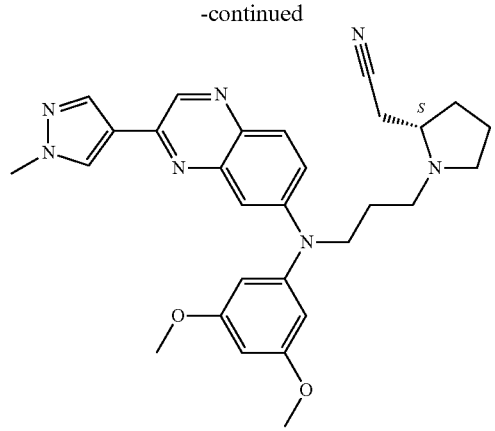
as a HCl salt
105; =Co35a
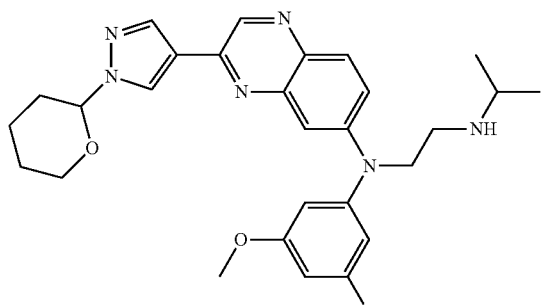
591; ~B3/B4a
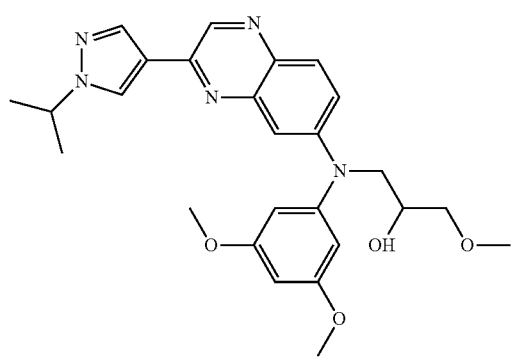
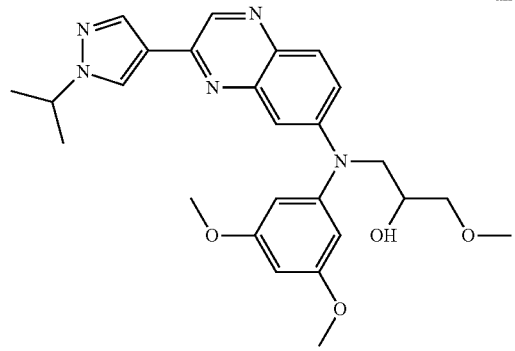
as a HCl salt
14 and 14a; ~B6
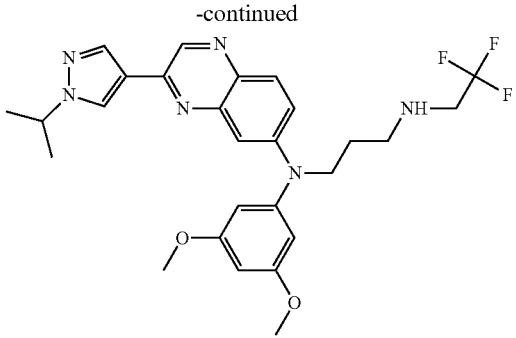
as a HCl salt
147; ~B3/B4a; NMR*
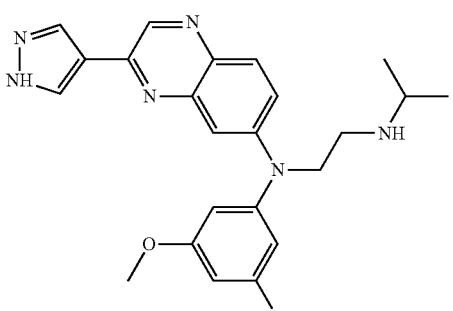
as a HCl salt
592; ~Co1
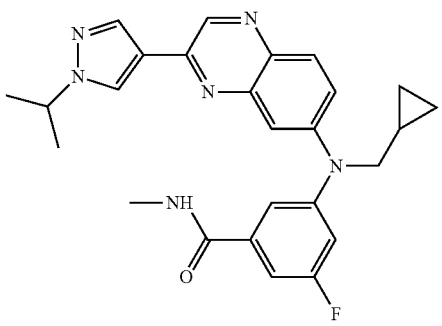
594; ~B5
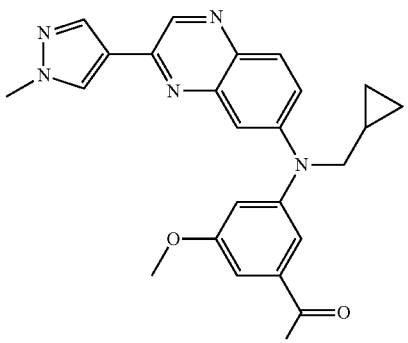
587; ~B5b-1
and -continued
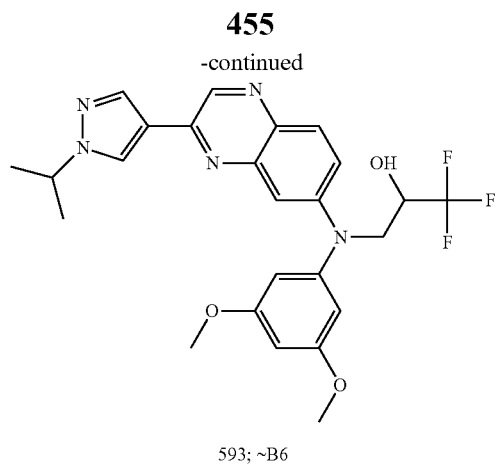
593; ~B6
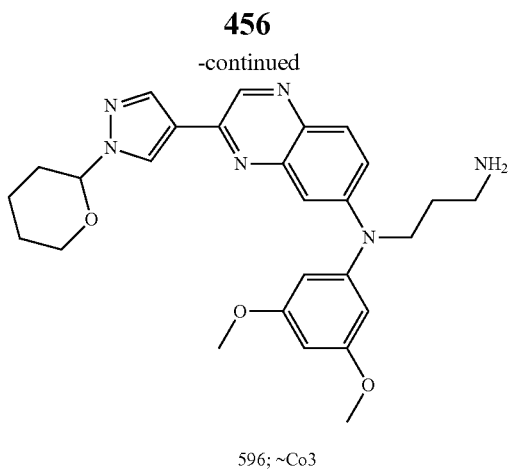
596; ~Co3
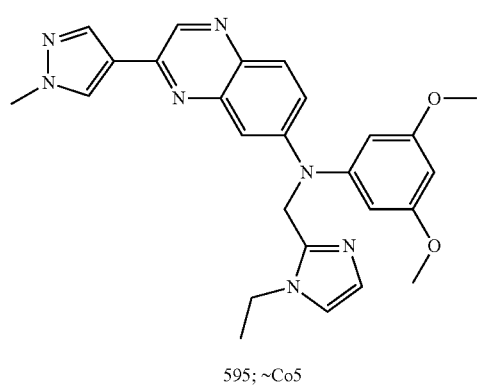
595; ~Co5
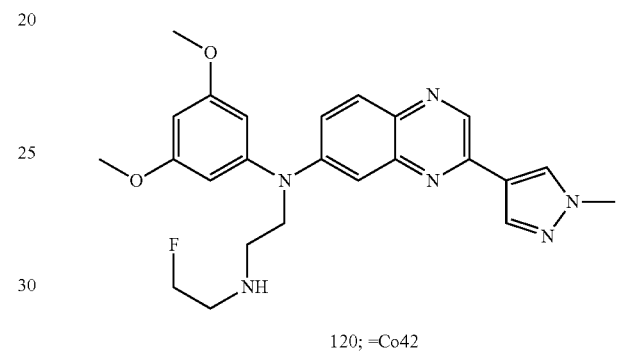
120; =Co42
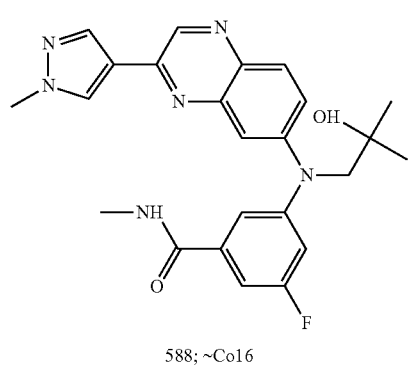
588; ~Co16
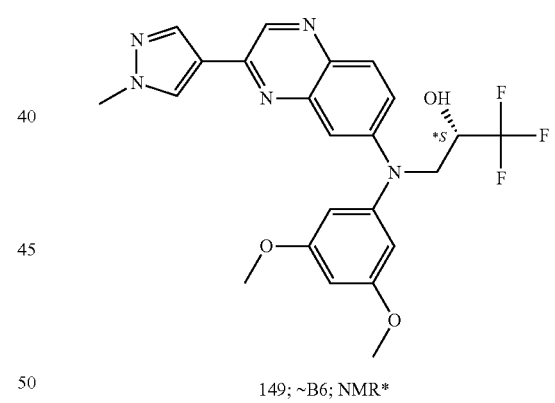
149; ~B6; NMR*
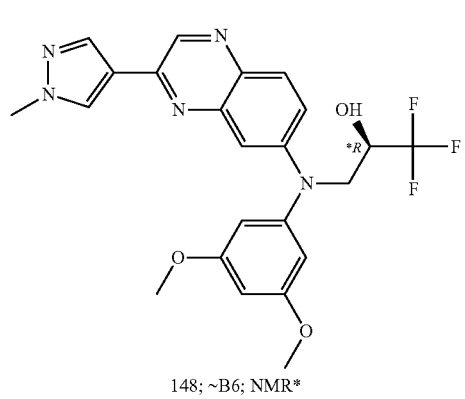
148; ~B6; NMR*
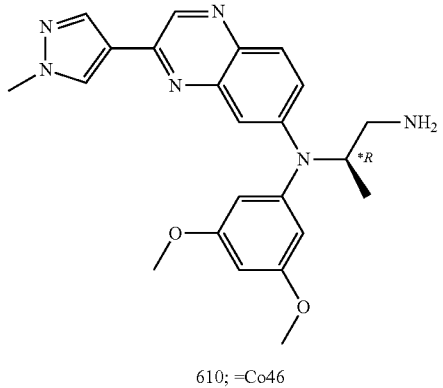
610; =Co46

457
-continued
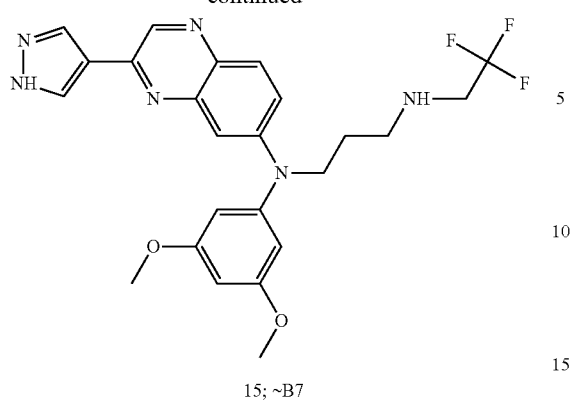
15; ~B7
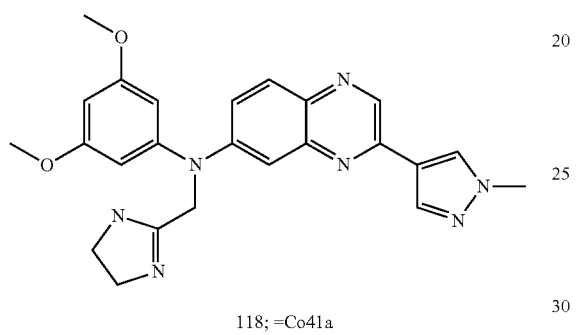
118; =Co41a
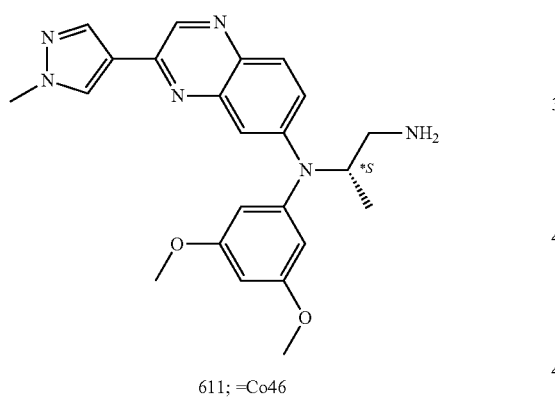
611; =Co46
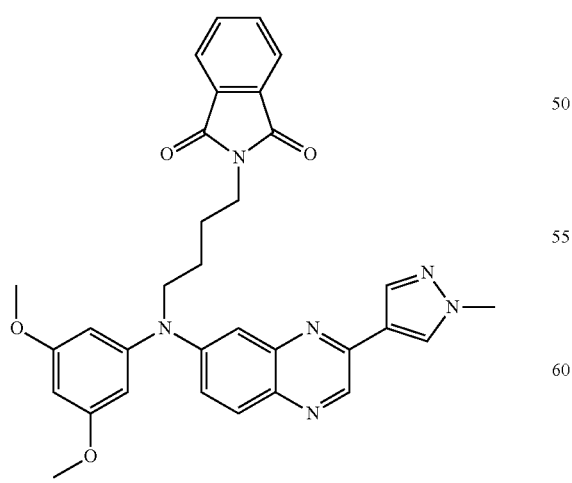
597; ~Co2
458
-continued
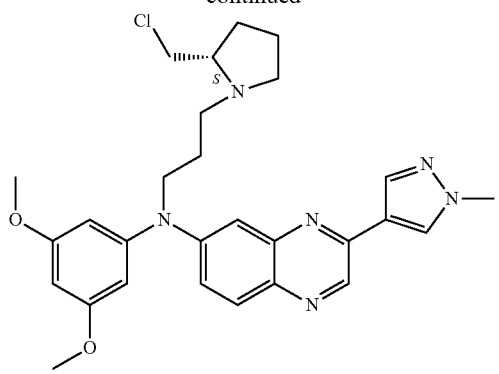
126; ~A5
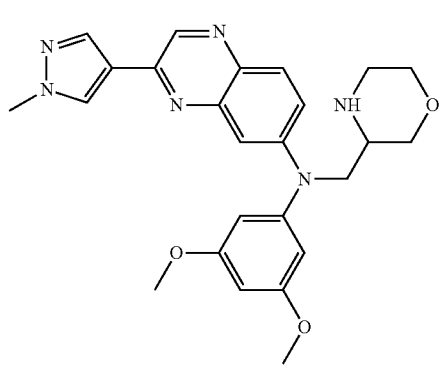
697; ~B33
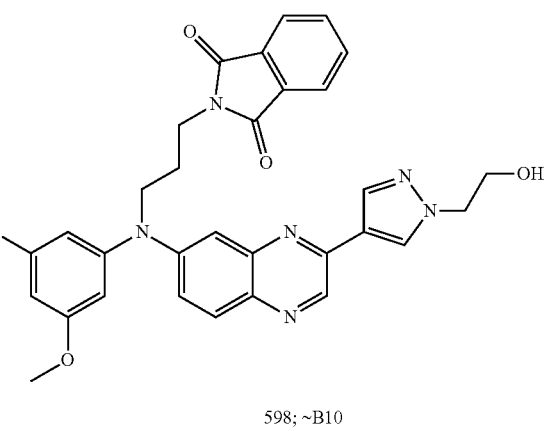
598; ~B10
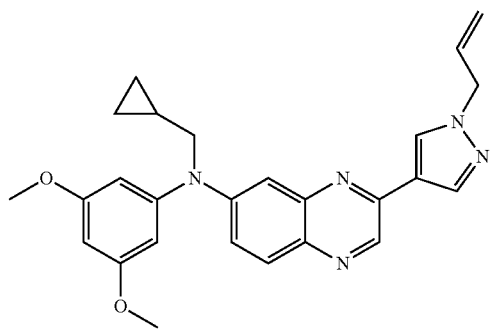
51; ~Co5a -continued
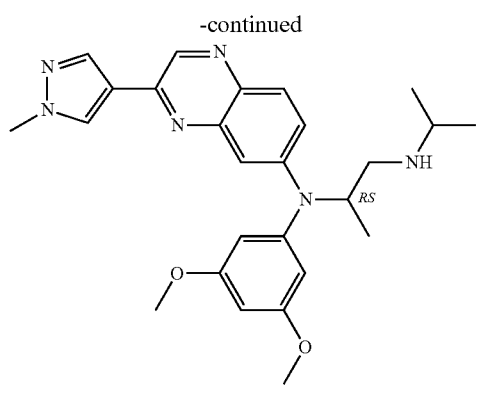
698; ~Co46
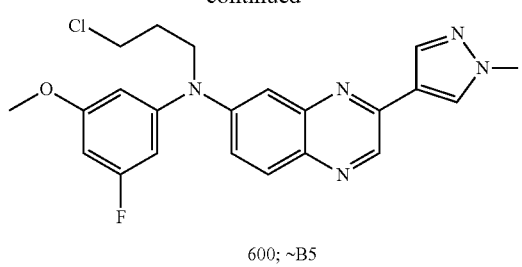
600; ~B5
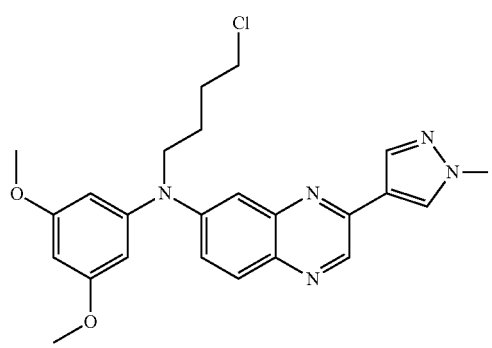
599; ~B5
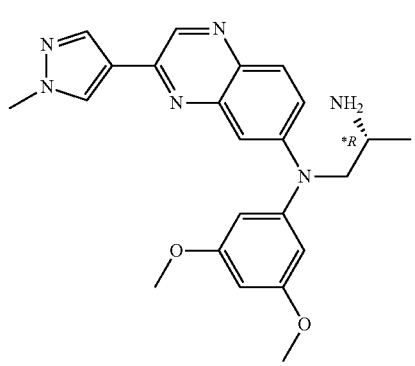
608; =Co46
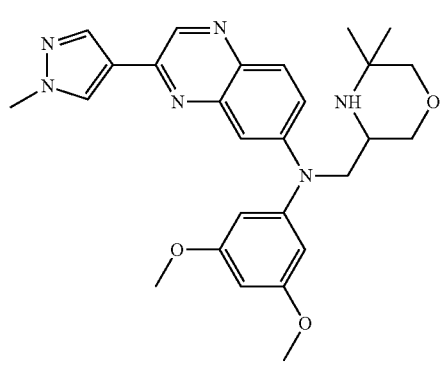
604; =B33
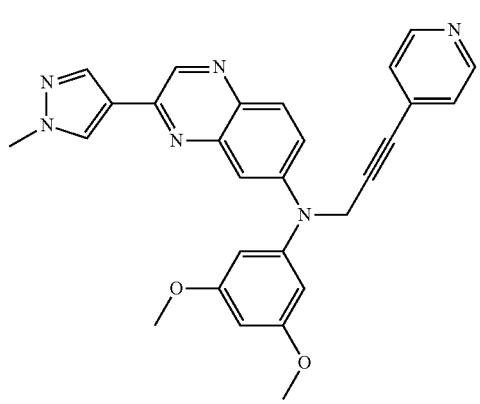
700; ~Co27
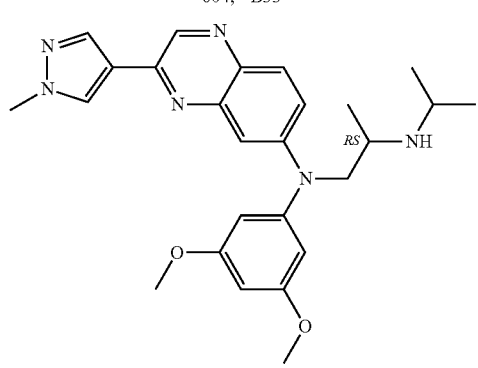
as a HCl salt
699; ~Co46
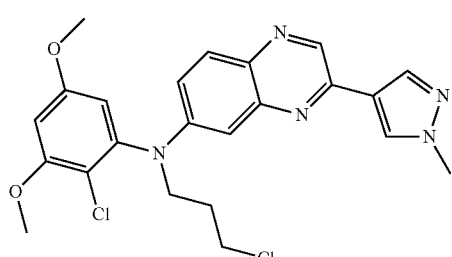
601; ~B5

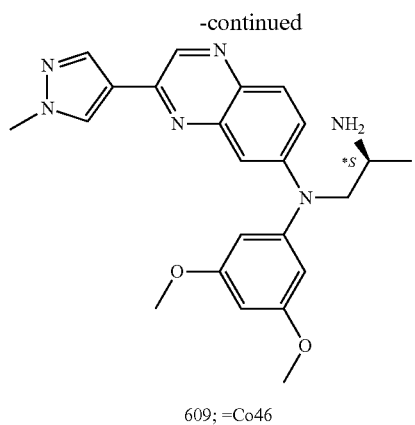
609; =Co46
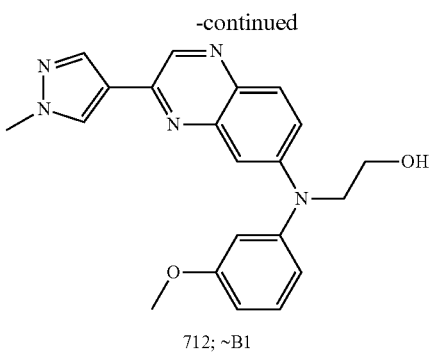
712; ~B1
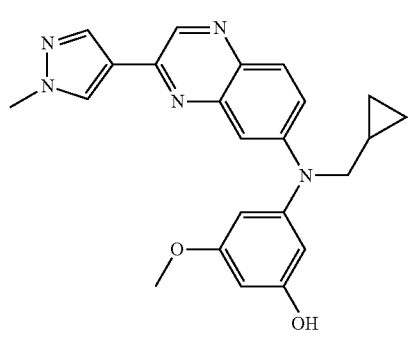
613; =Co47b
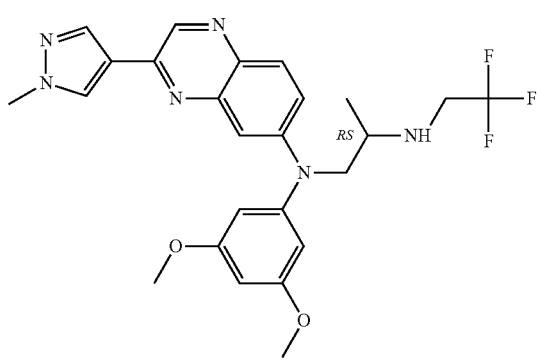
702; ~Co46
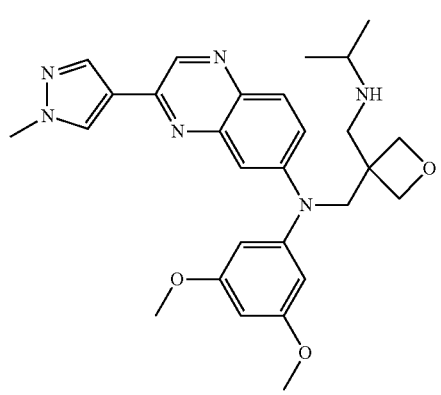
701; ~B3
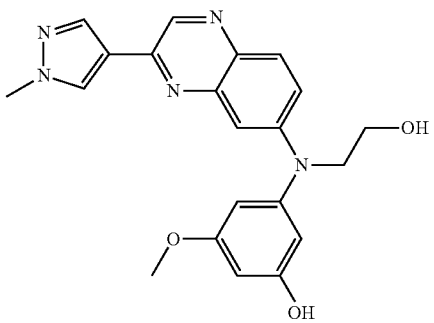
706; ~B53
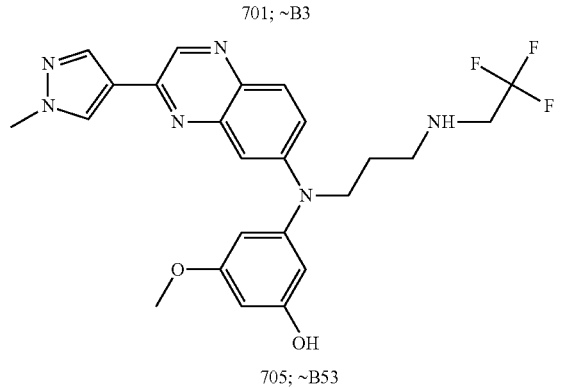
705; ~B53
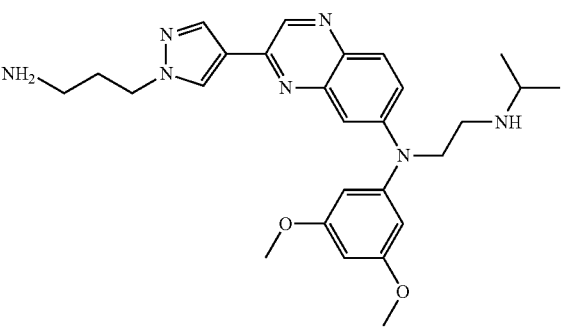
•trifluoroacetate
616; = B38

-continued
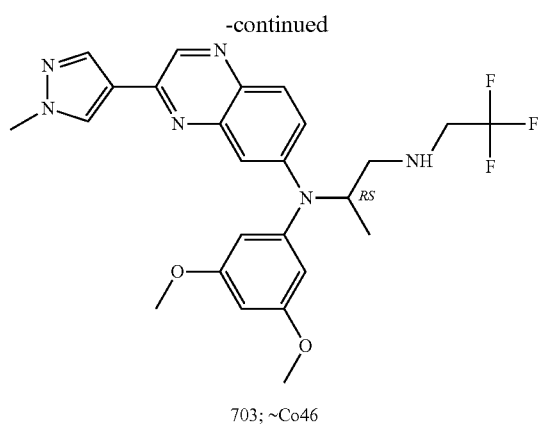
703; ~Co46
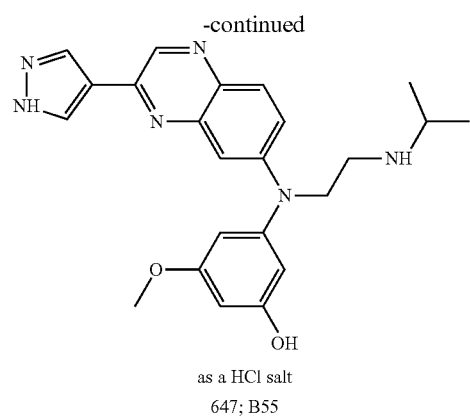
as a HCl salt
647; B55
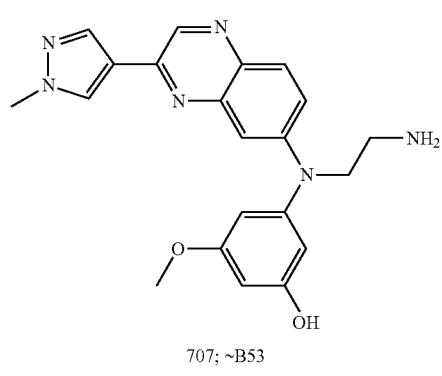
707; ~B53
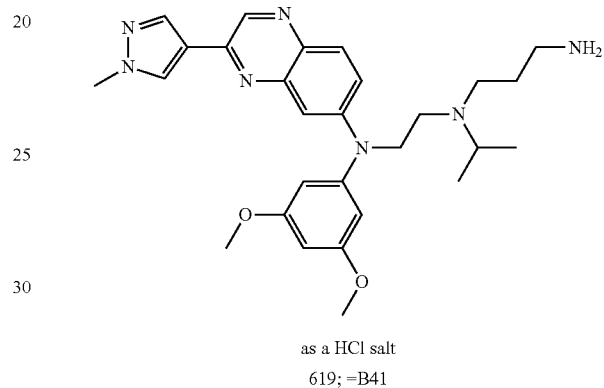
as a HCl salt
619; =B41
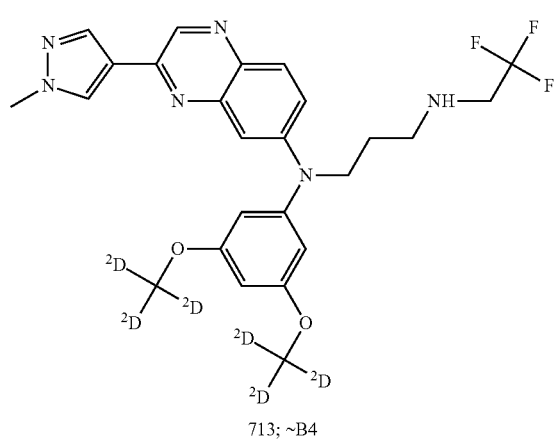
713; ~B4
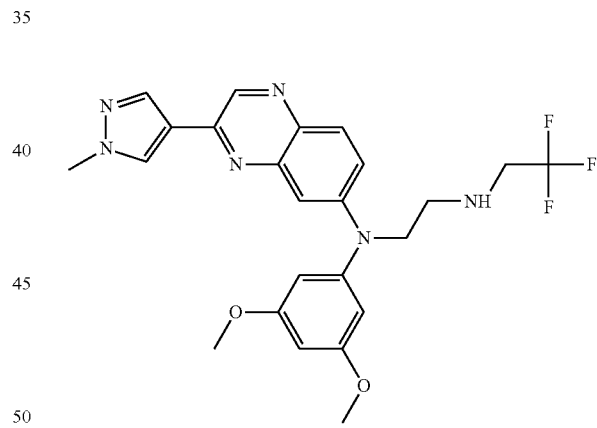
704; ~B4b
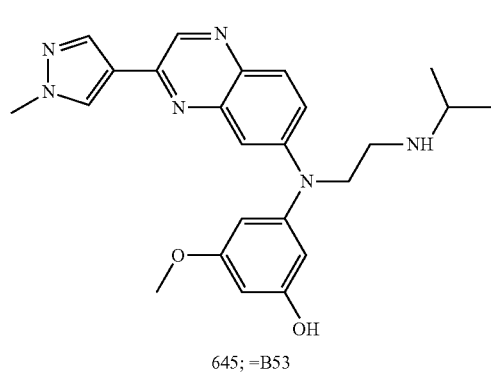
645; =B53
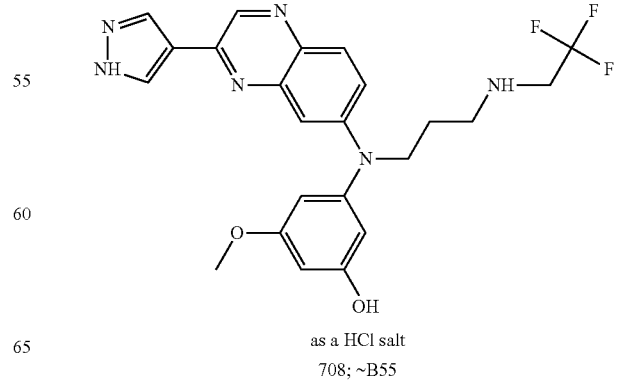
as a HCl salt
708; ~B55

-continued
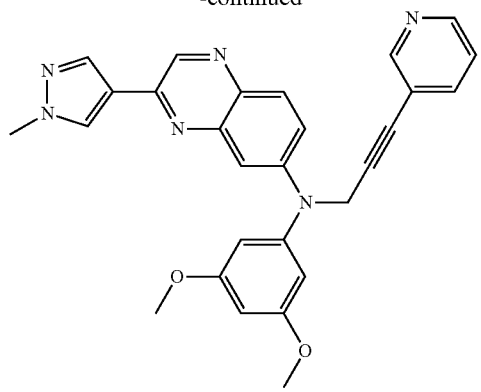
714; ~Co27
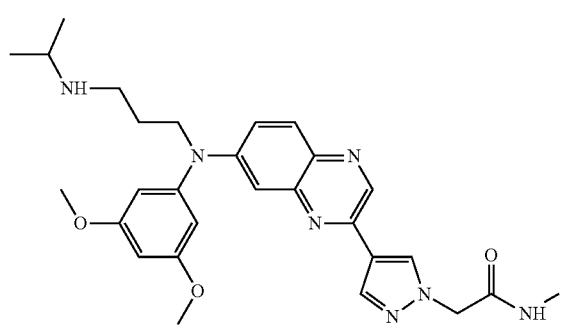
615; =B37
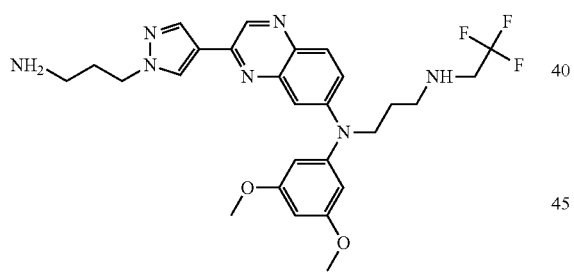
as a HCl salt
709; ~B38
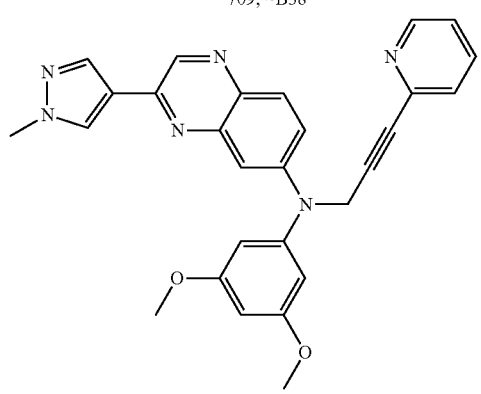
690; ~Co27
-continued
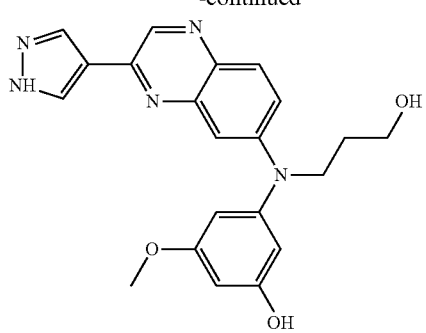
646; B54
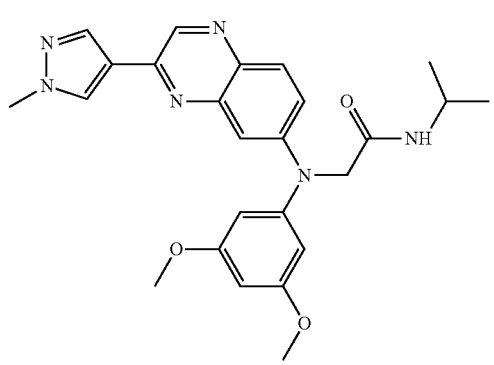
710; ~Co14
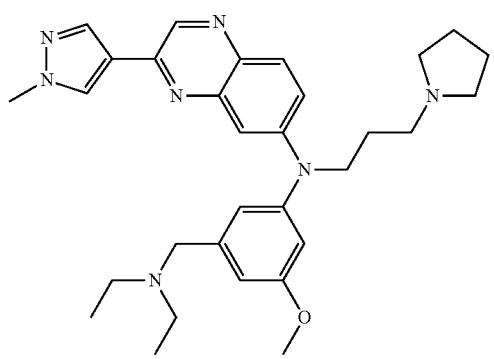
721; ~B4
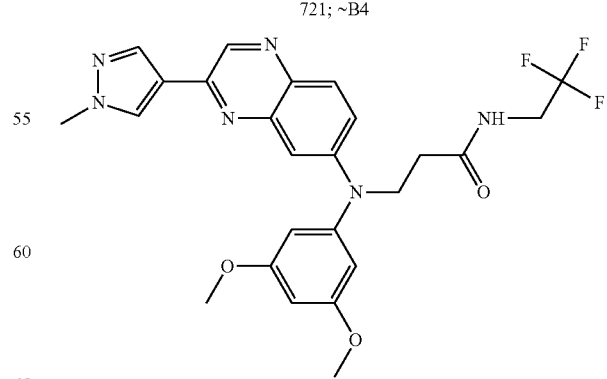
648; =Co58

-continued
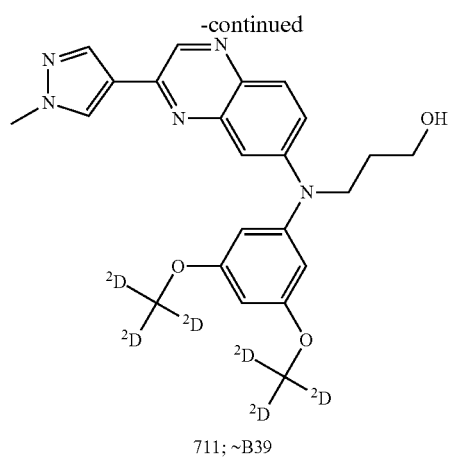
711; ~B39
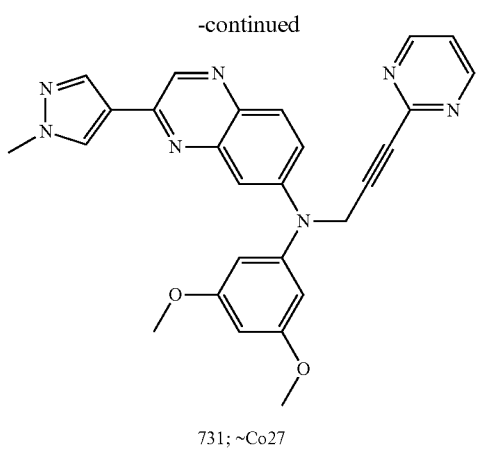
731; ~Co27
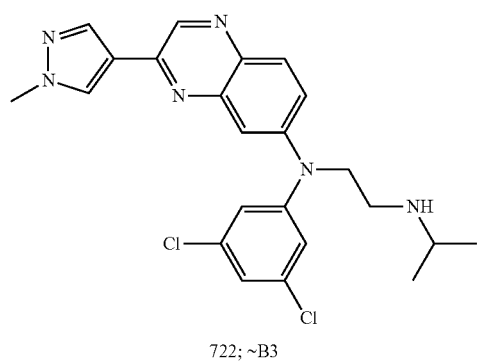
722; ~B3
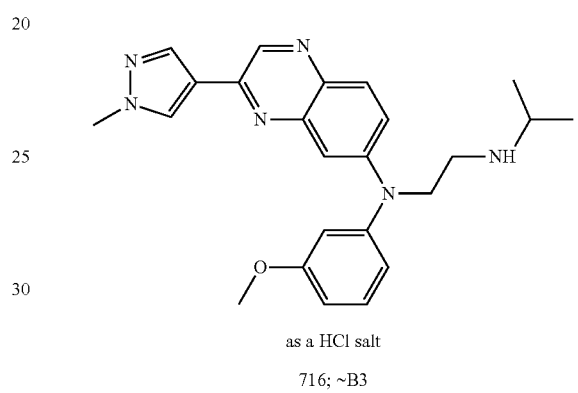
as a HCl salt
716; ~B3
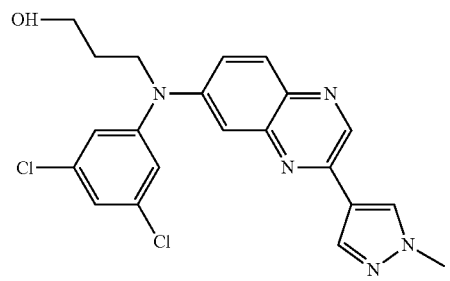
715; ~B2
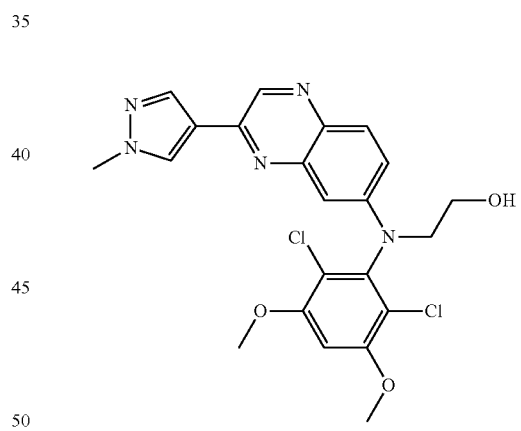
725; ~B1
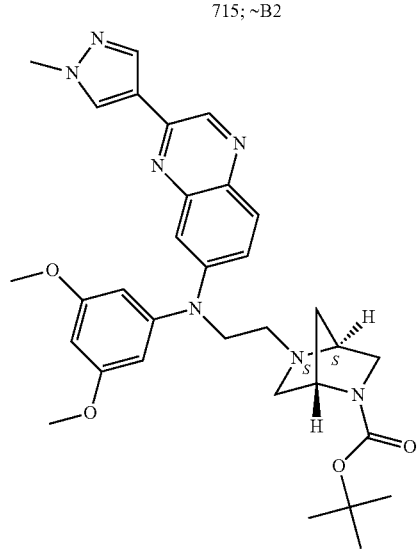
620; =B42a
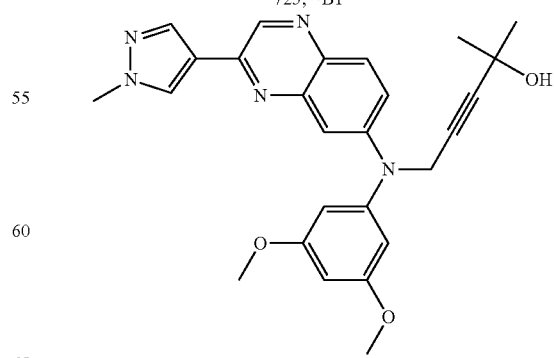
732; ~Co49

-continued
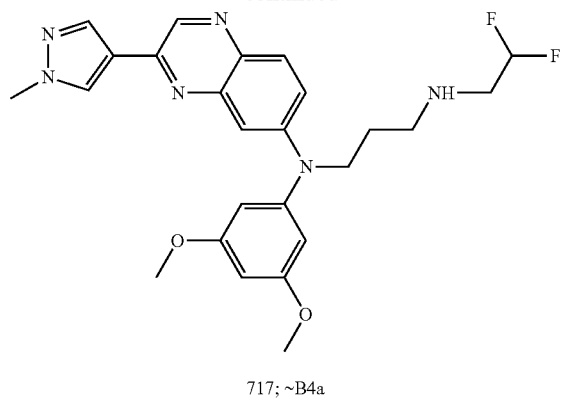
717; ~B4a
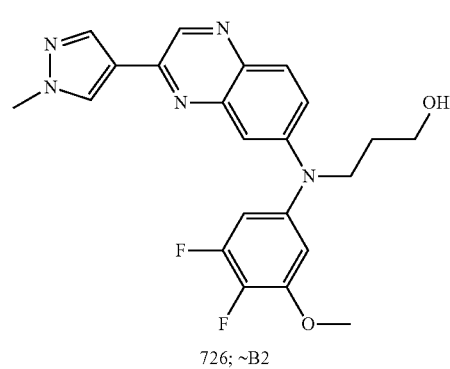
726; ~B2
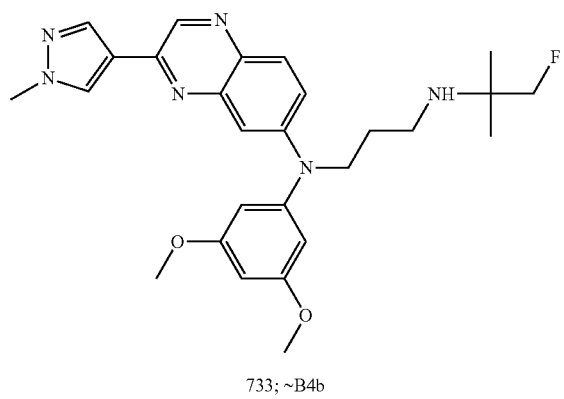
733; ~B4b
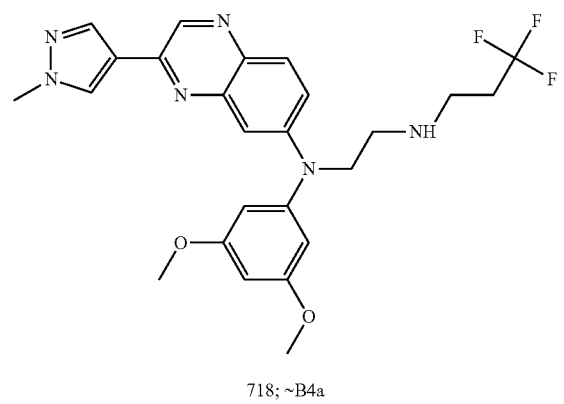
718; ~B4a
-continued
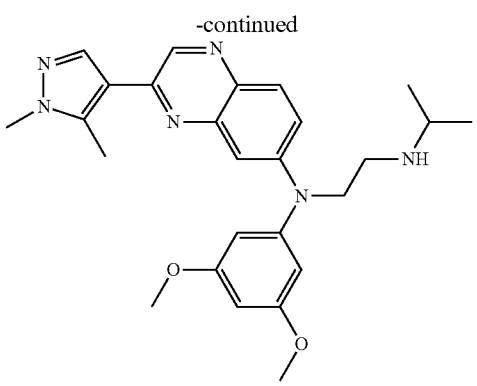
727; ~B44
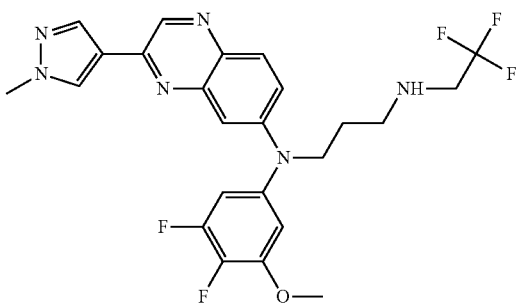
as a HCl salt
734; ~B4b
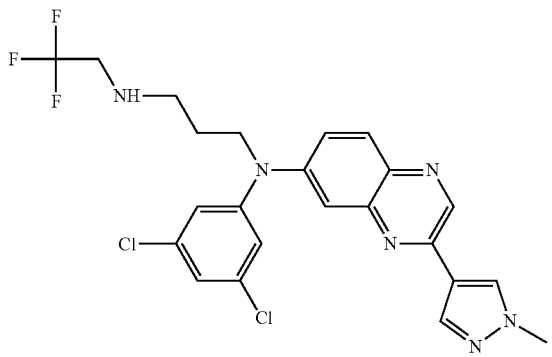
719; ~B4a
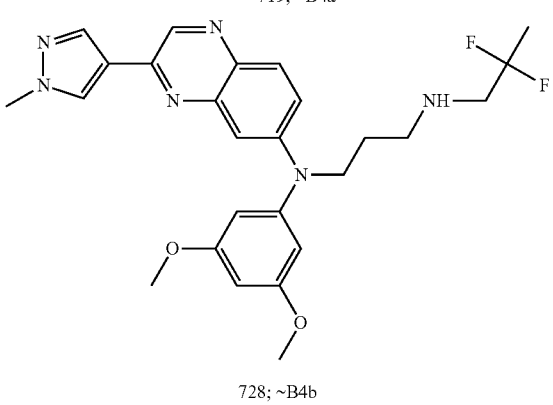
728; ~B4b -continued
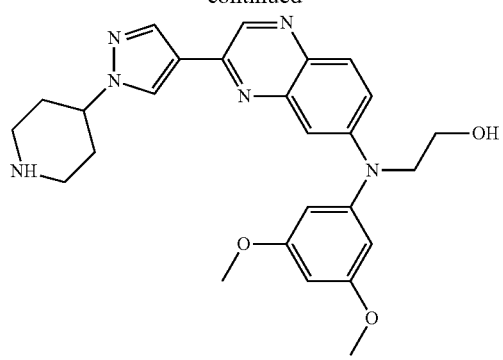
624; ~B11
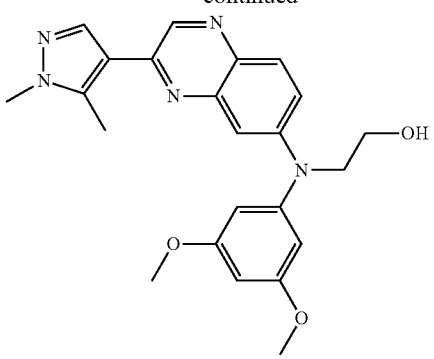
723; ~B43
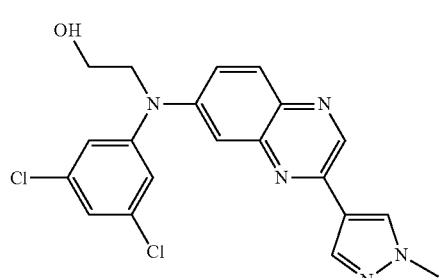
720; ~B1
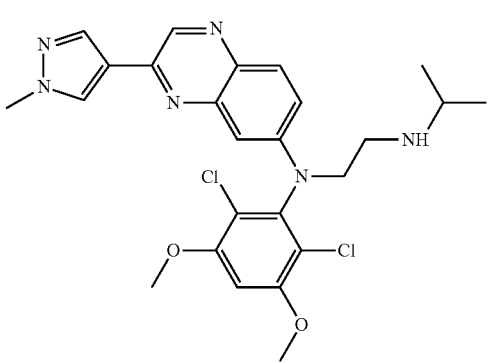
729; ~B3
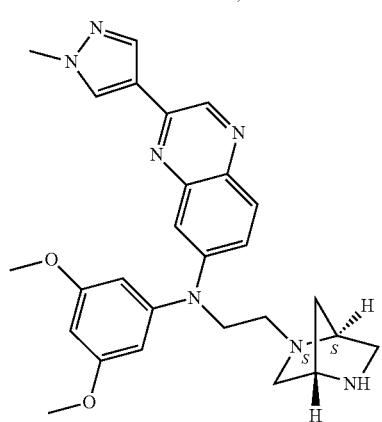
as a HCl salt
621; =B42b
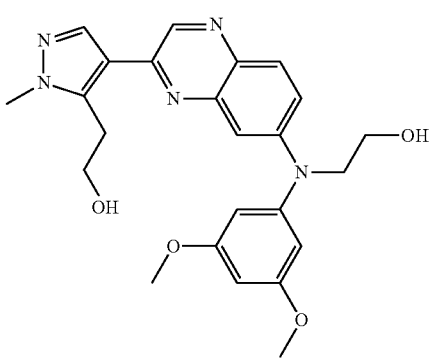
736; ~B43
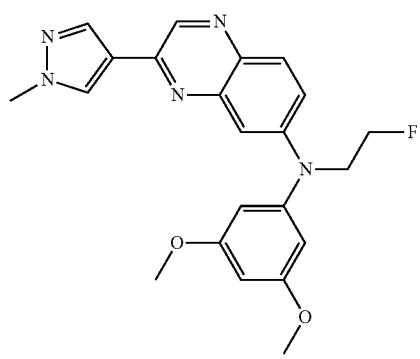
735; ~B5
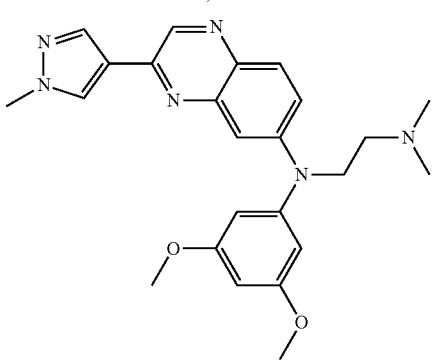
724; ~B3

473
-continued
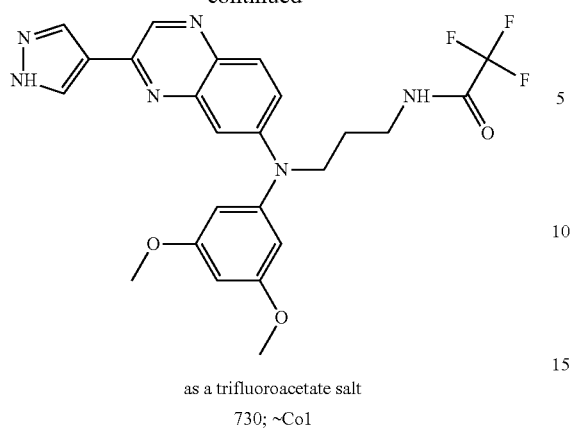
as a trifluoroacetate salt
730; ~Co1
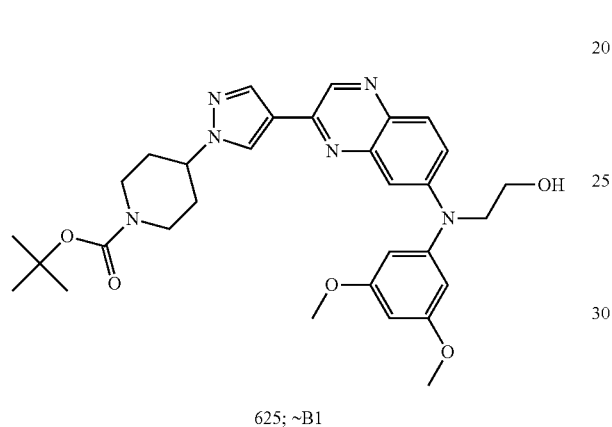
625; ~B1
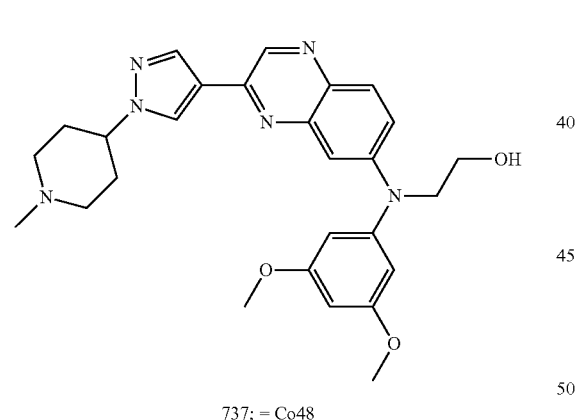
737; = Co48
651; =Co59
474
-continued
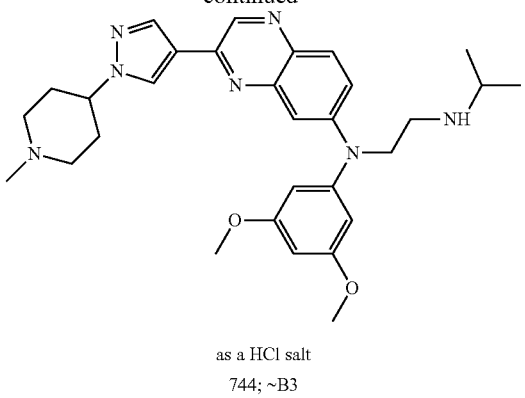
as a HCl salt
744; ~B3
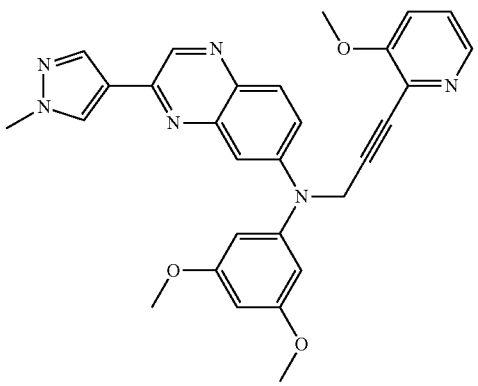
652; =Co60
617; =B39
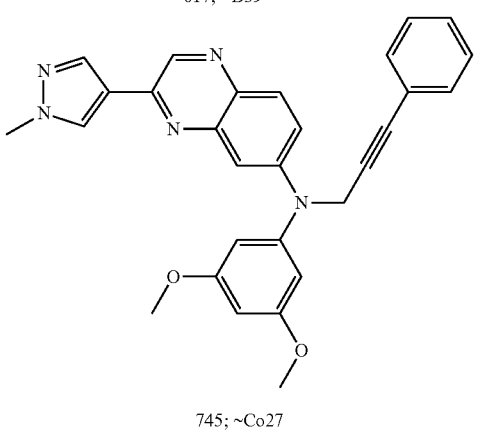
745; ~Co27

475
-continued
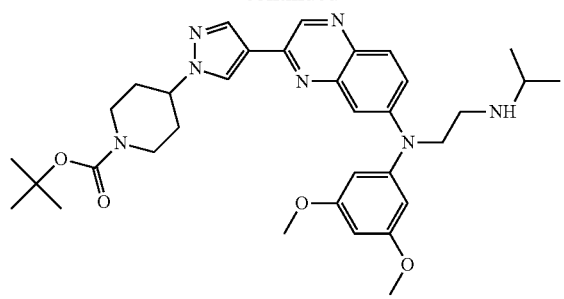
650; ~B3(1st altern. protocol)
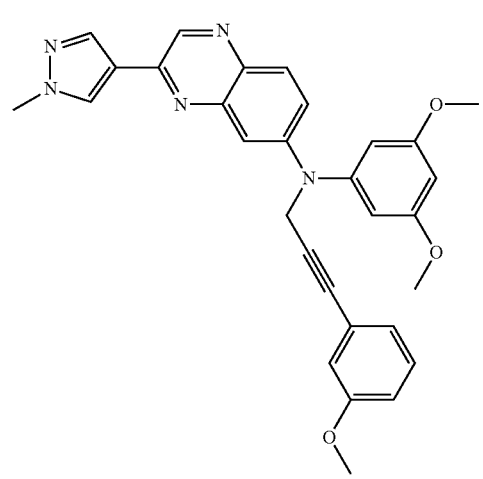
741; ~Co27
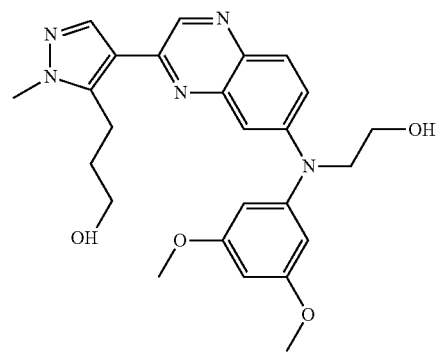
746; ~B1
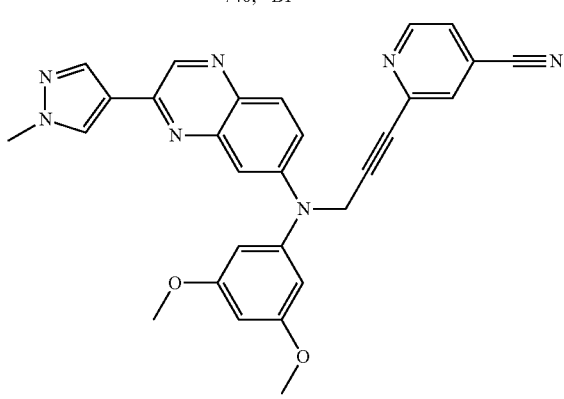
738; ~Co27
476
-continued
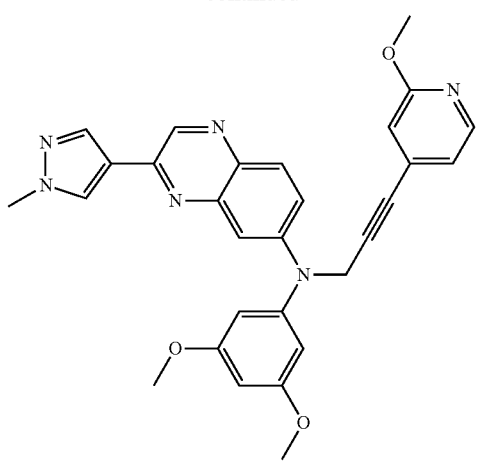
742; ~Co27
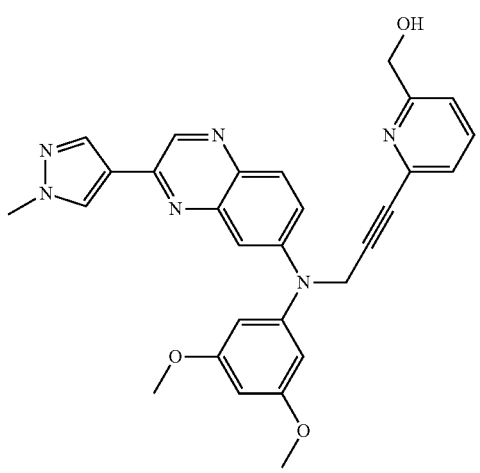
747; ~Co27
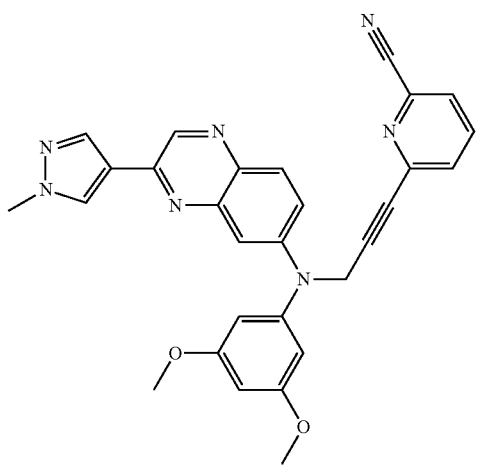
739; ~Co27

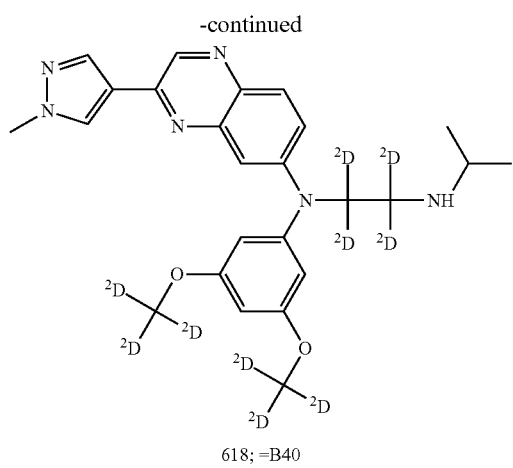
618; =B40
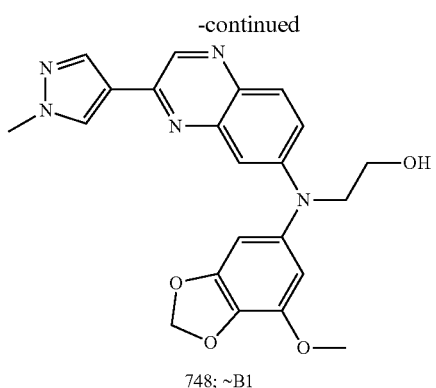
748; ~B1
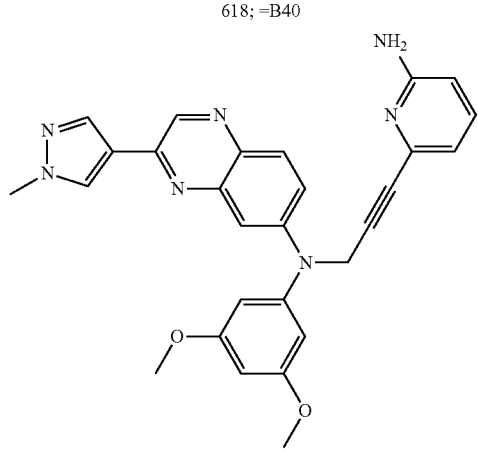
689; ~Co27
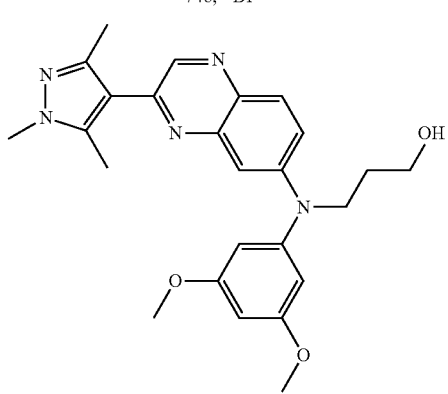
749; ~B43
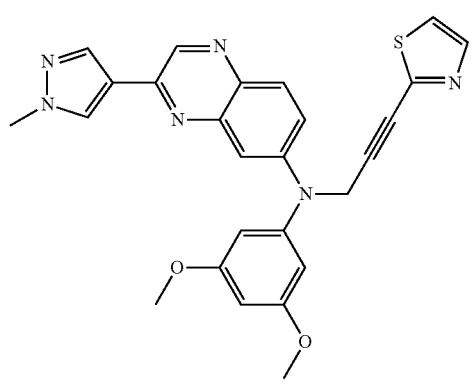
740; ~Co27
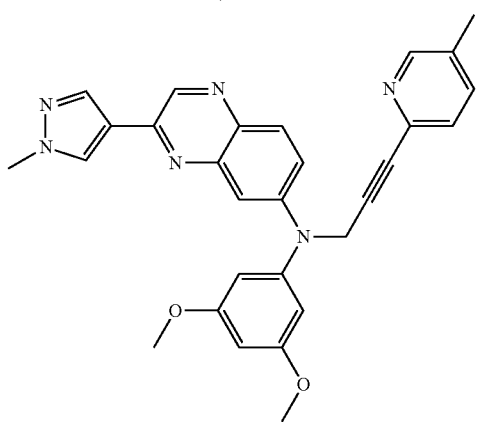
753; ~Co27
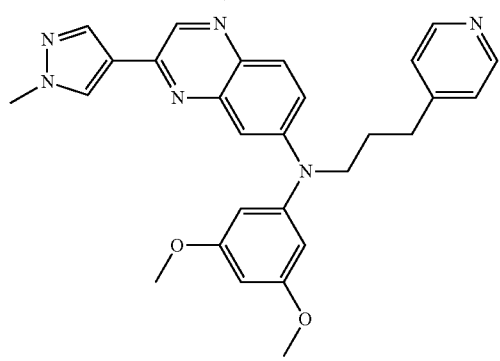
743; ~B5
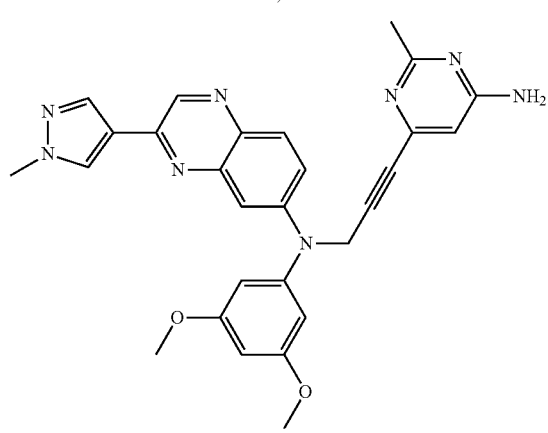
760; ~Co27

-continued
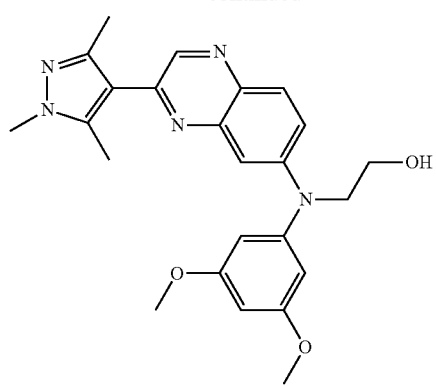
622; =B43
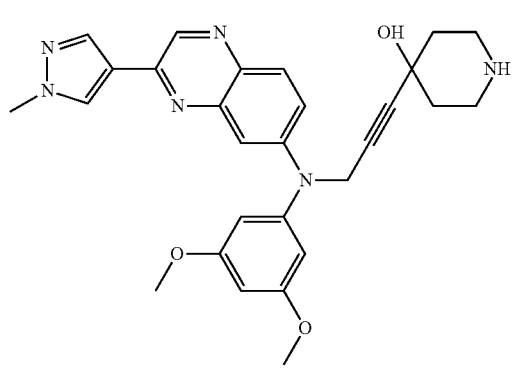
754; ~Co49b
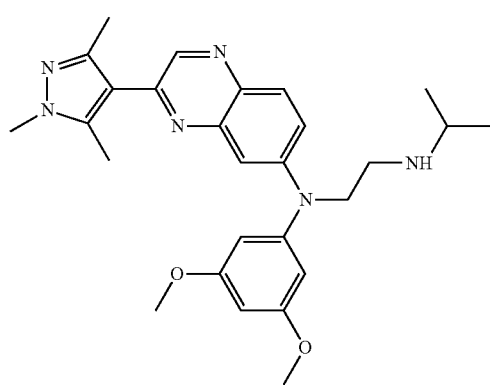
as a HCl salt
623; =B44
-continued
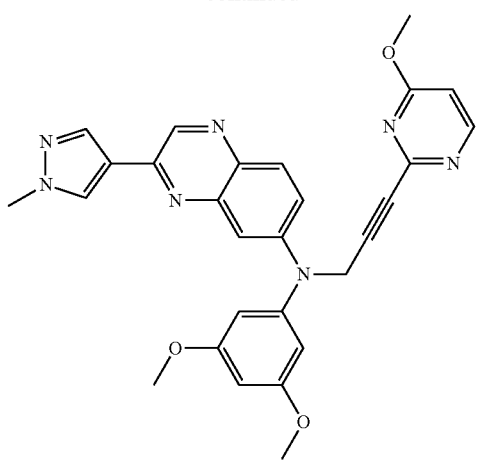
688; ~Co60
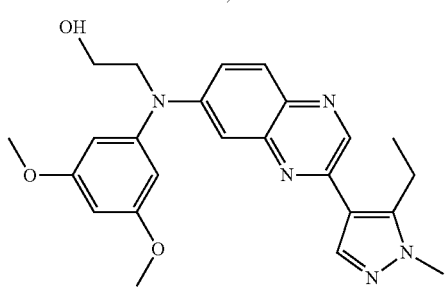
755; ~B1
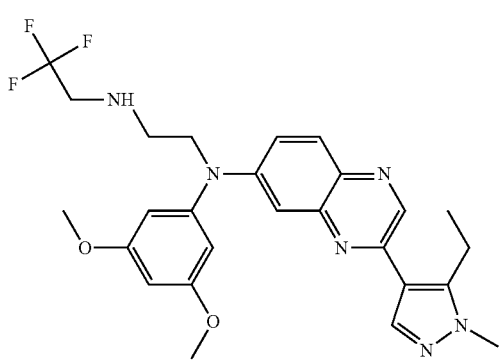
761; ~B4
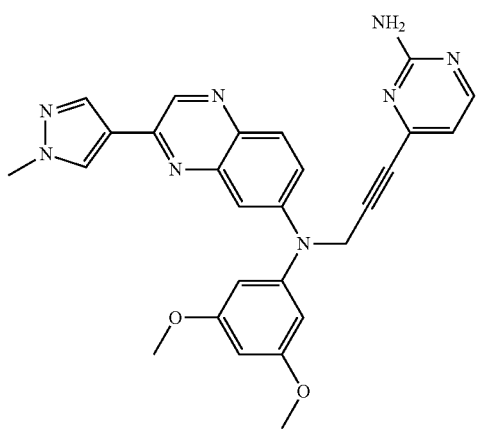
750; ~Co27

-continued
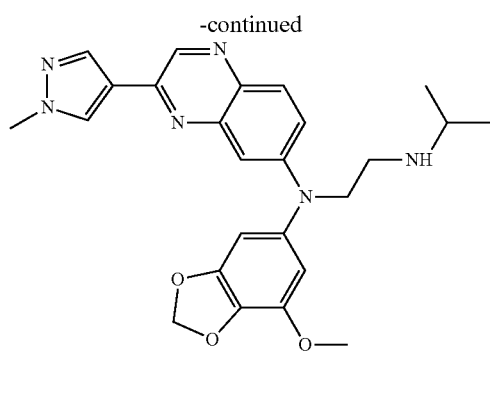
756; ~B3
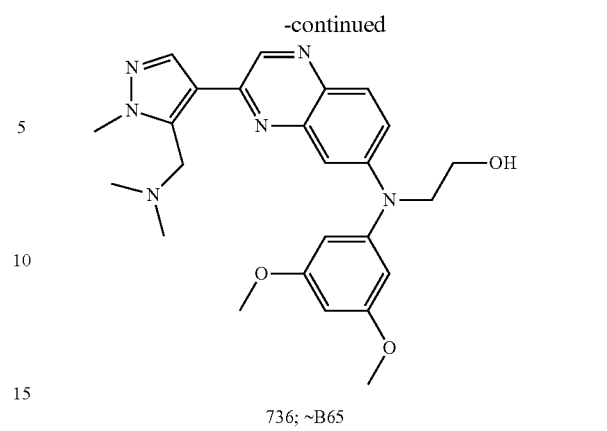
736; ~B65
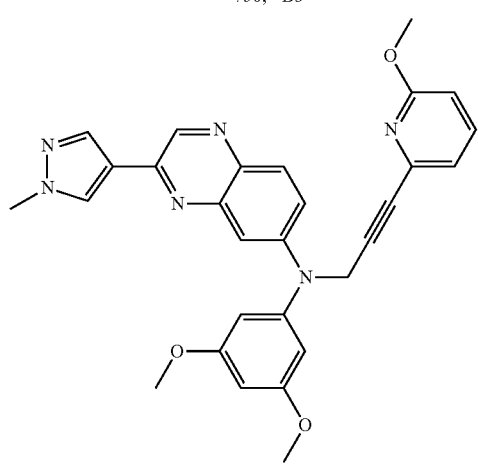
762; ~Co27
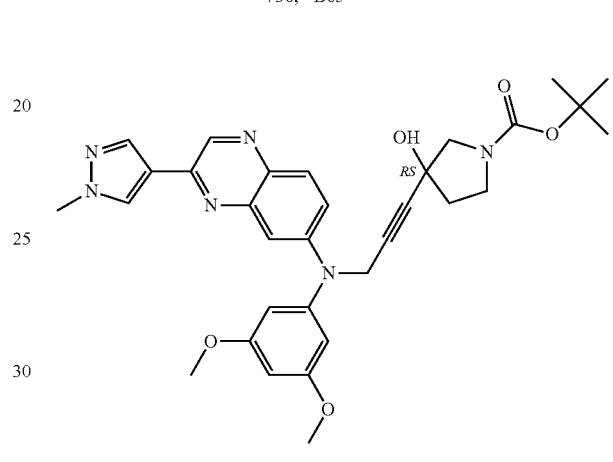
751; ~Co49a
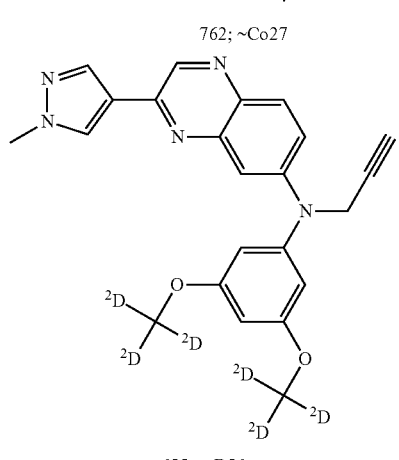
655;; =B56
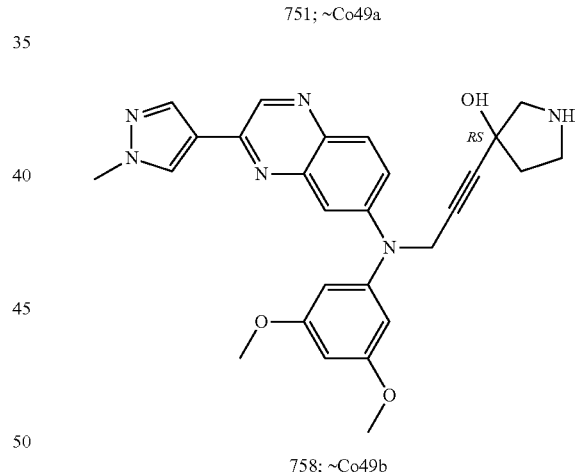
758; ~Co49b
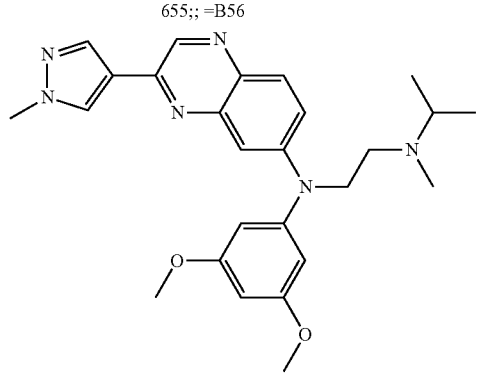
757; =co76
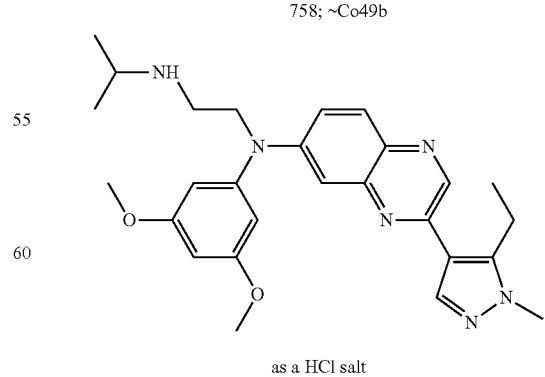
as a HCl salt
764; ~B44

483                                           484
-continued
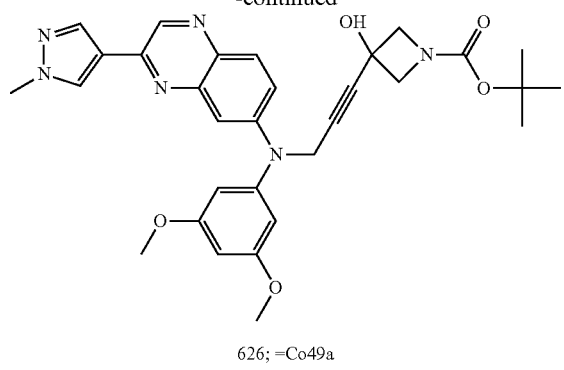
626; =Co49a
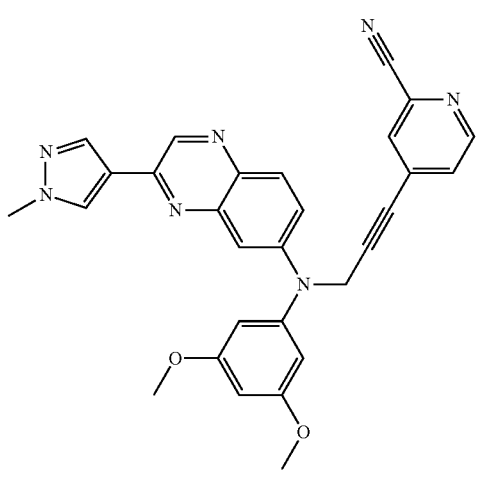
752; ~Co27
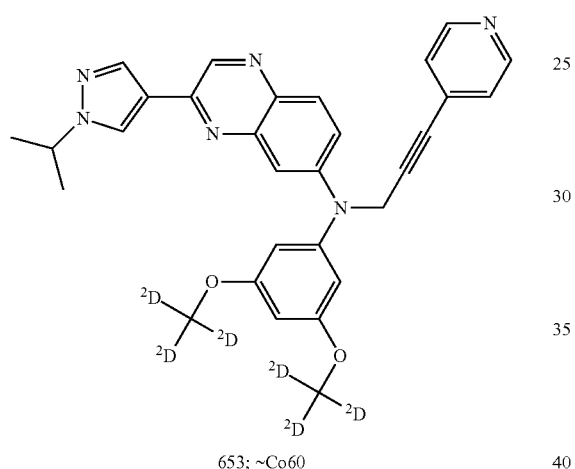
653; ~Co60
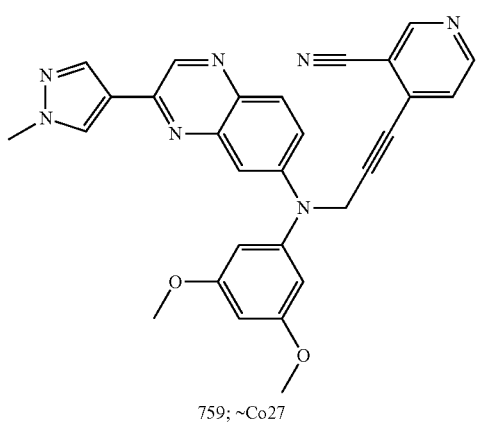
759; ~Co27
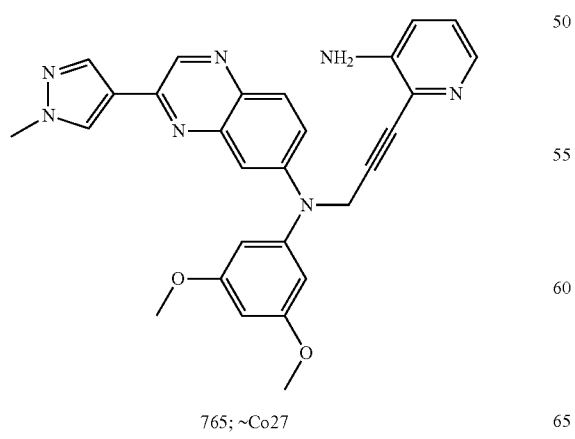
765; ~Co27
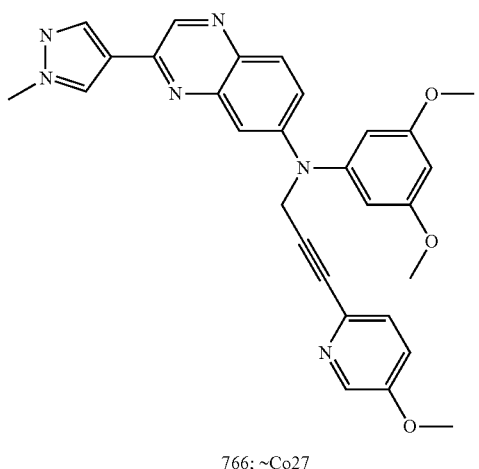
766; ~Co27

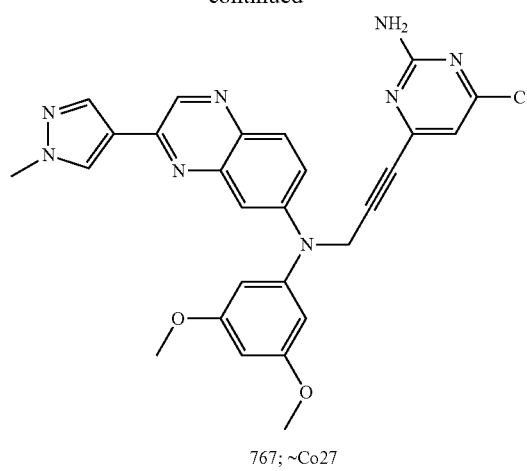
767; ~Co27
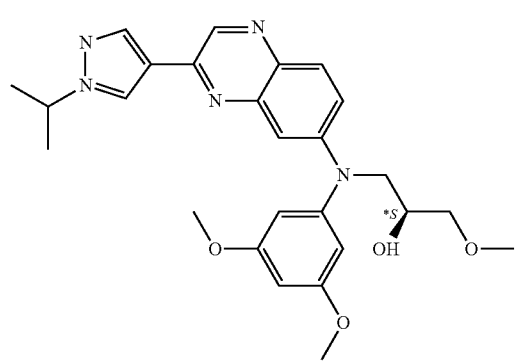
as a HCl salt
657; =Co61
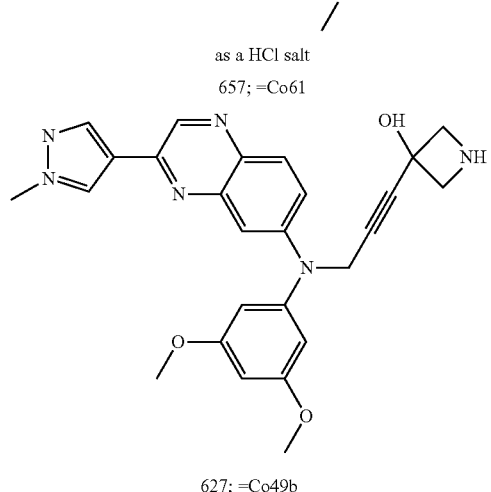
627; =Co49b
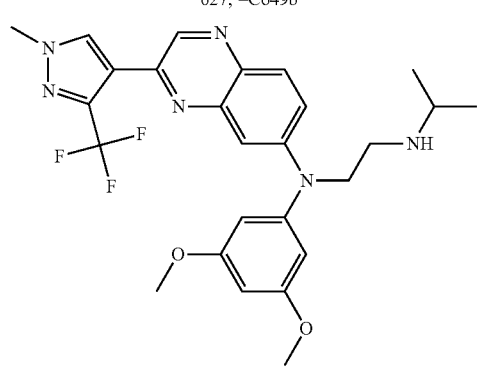
as a HCl salt
768; ~B3
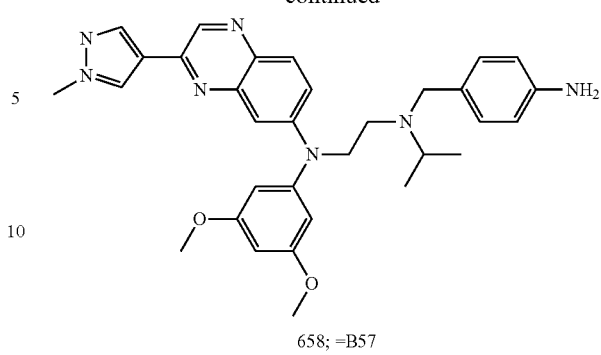
658; =B57
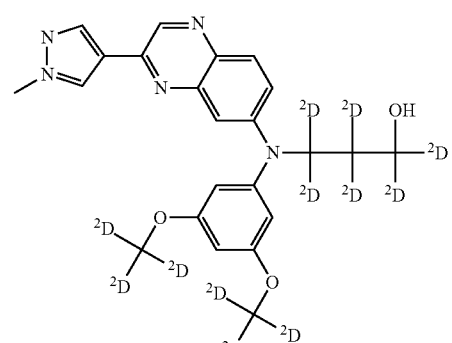
775; ~B2
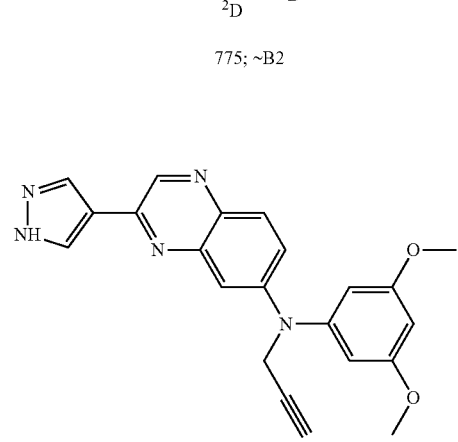
769; ~B9/B29
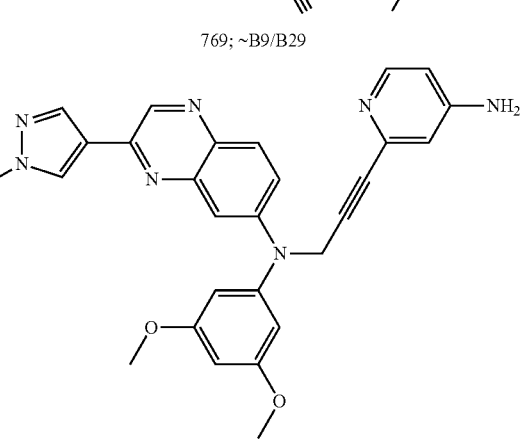
771; ~Co27

-continued
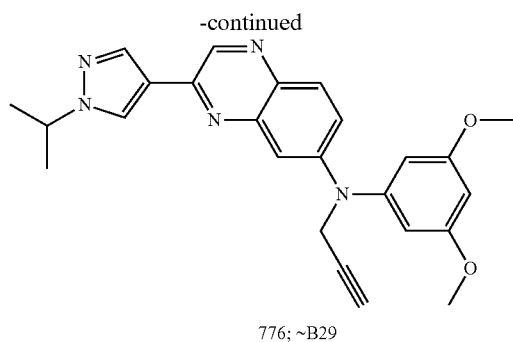
776; ~B29
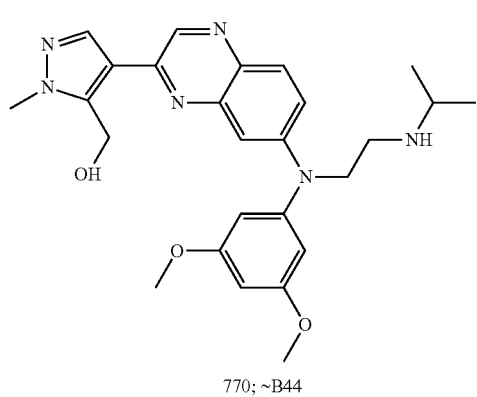
770; ~B44
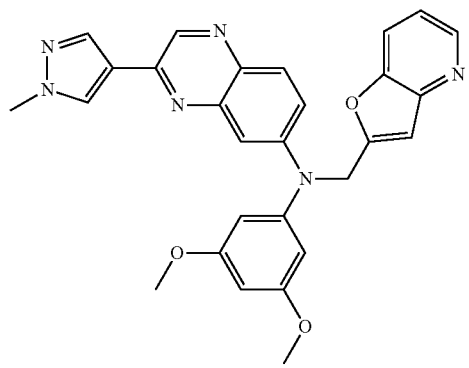
772; ~Co27
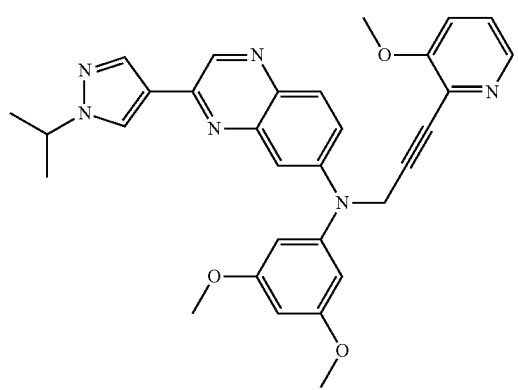
777; ~Co27
-continued
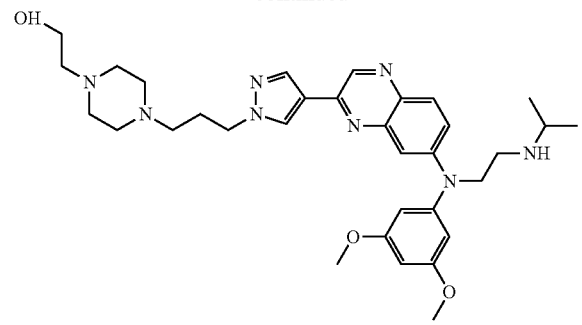
as a HCl salt
644; =B51
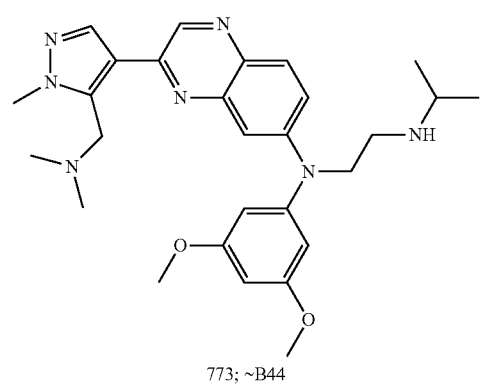
773; ~B44
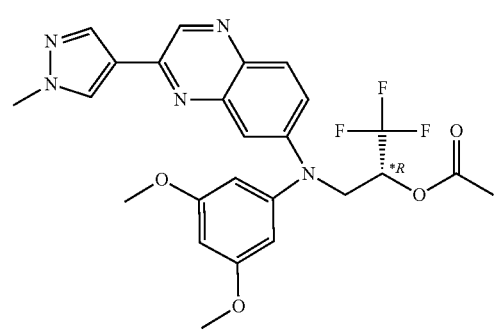
778; ~Co50
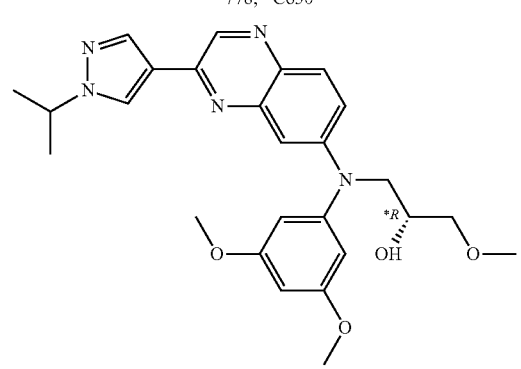
as a HCl salt
656; =Co61

-continued
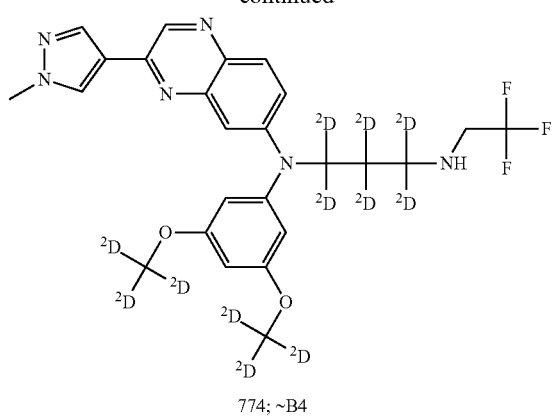
774; ~B4
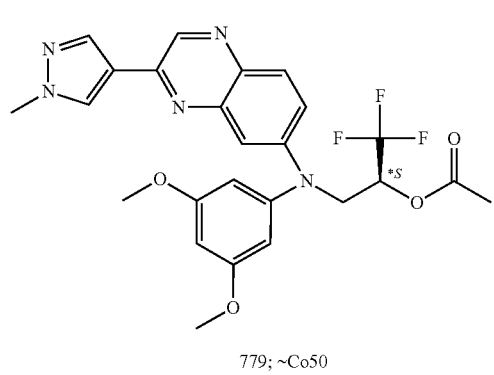
779; ~Co50
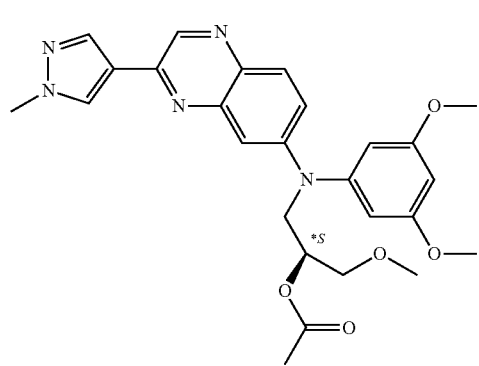
628; =Co50
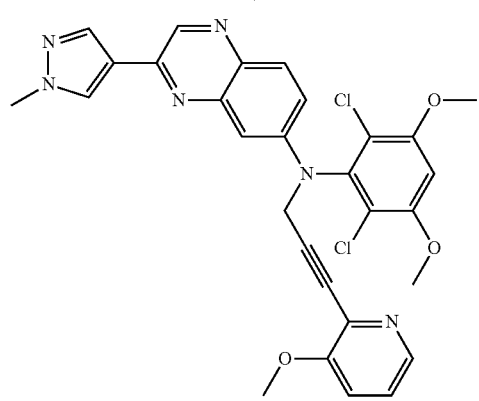
785; ~Co27
-continued
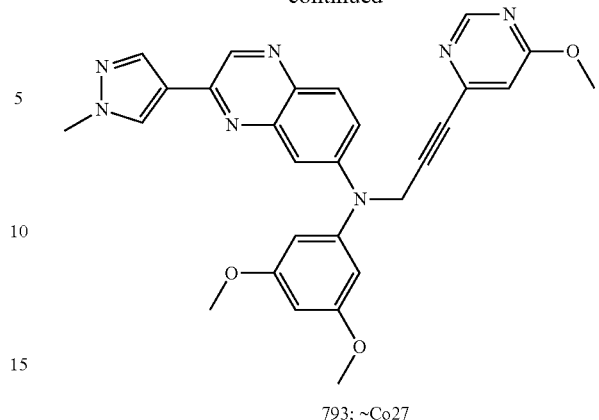
793; ~Co27
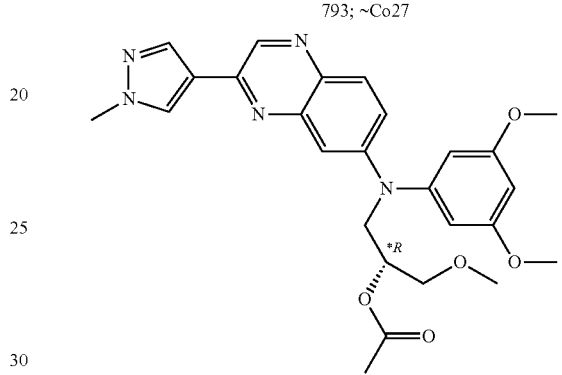
629; =Co50
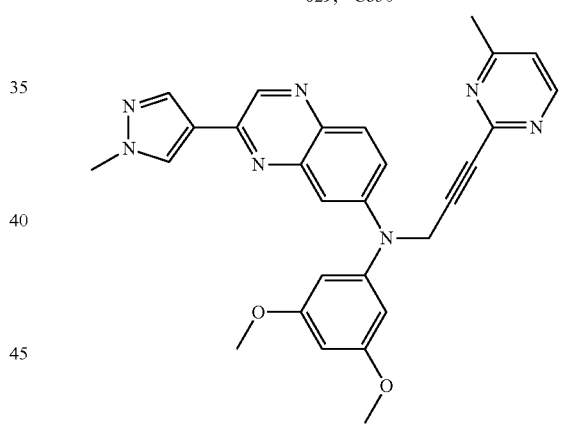
786; ~Co27
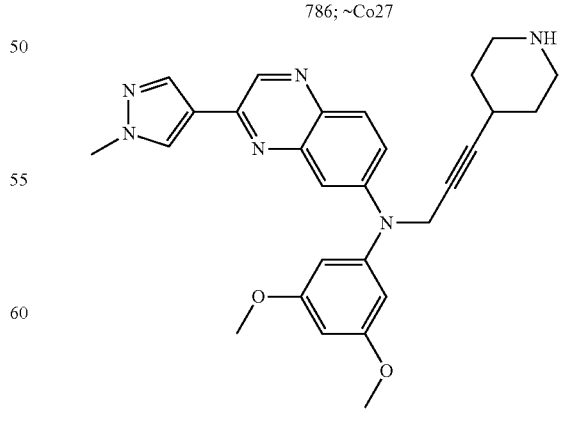
as a HCl salt
631; =Co51

-continued
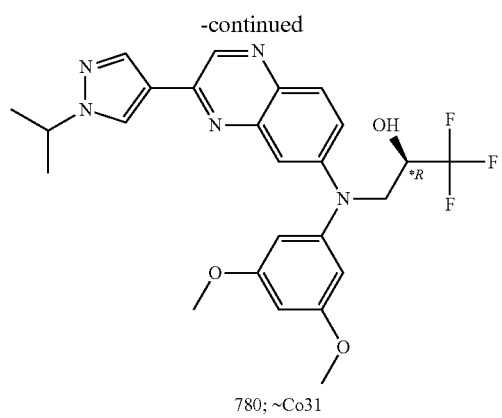
780; ~Co31
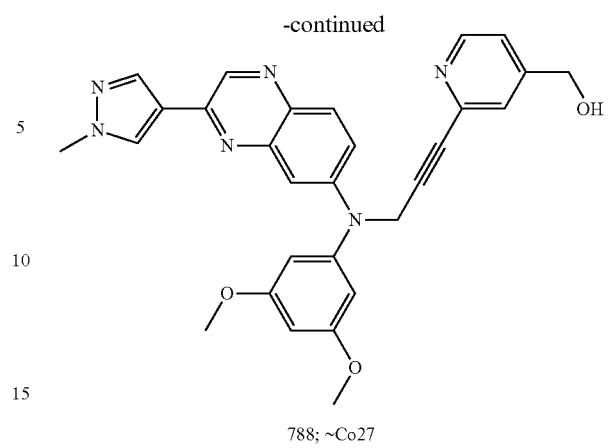
788; ~Co27
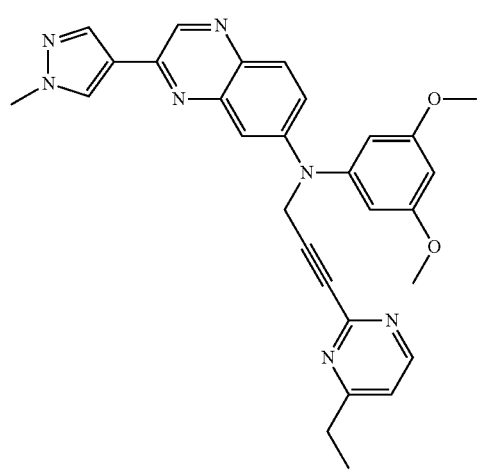
787; ~Co27
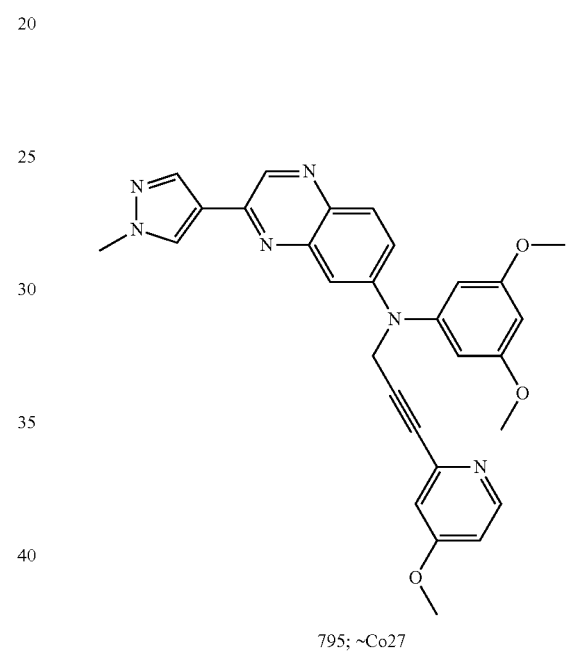
795; ~Co27
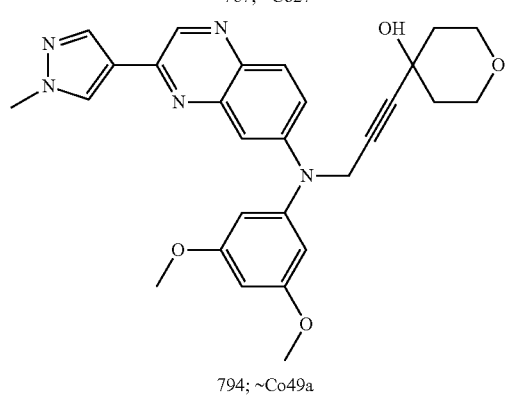
794; ~Co49a
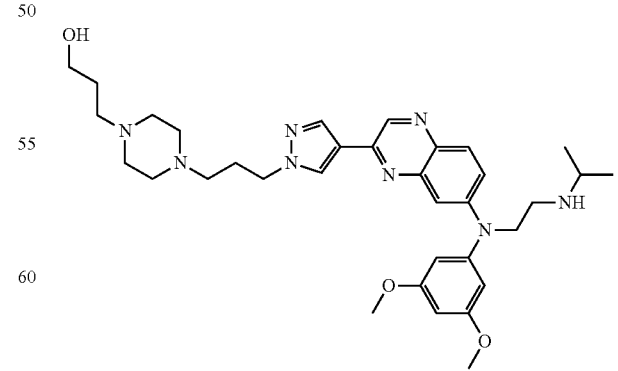
781; ~Co31
as a HCl salt
782: ~B51

493
-continued
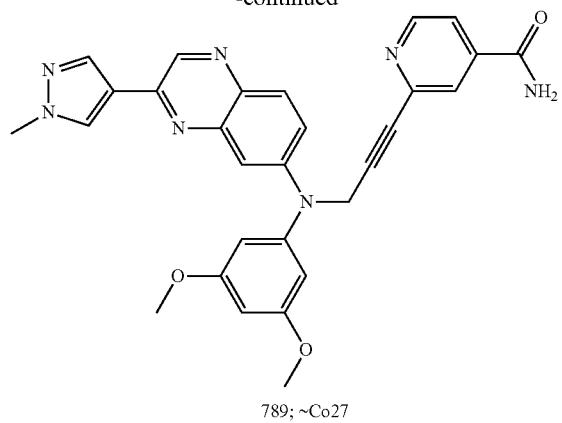
789; ~Co27
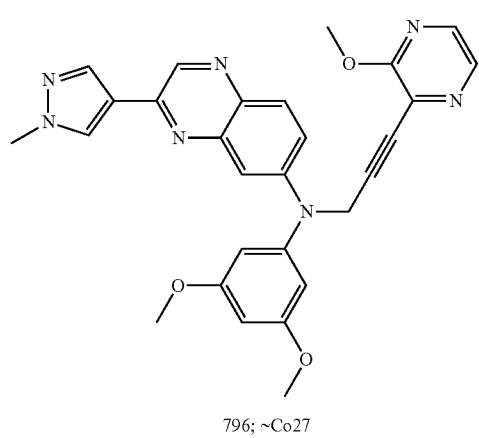
796; ~Co27
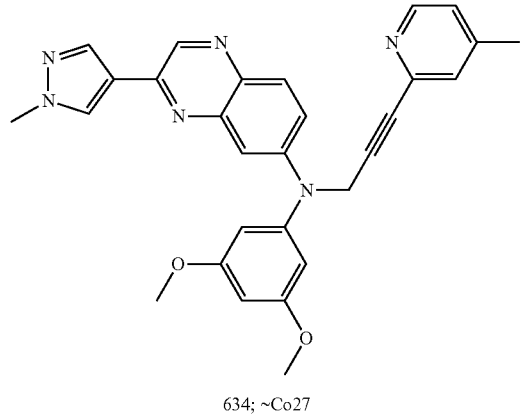
634; ~Co27
494
-continued
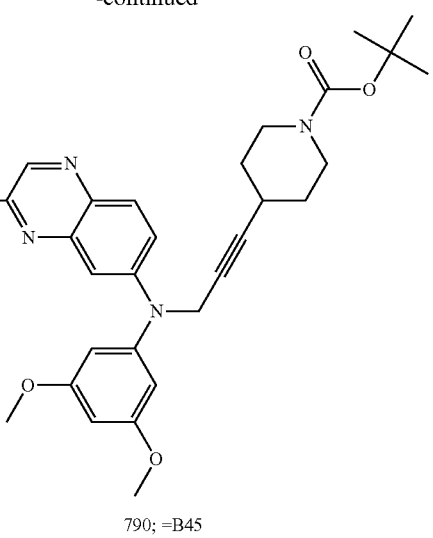
790; =B45
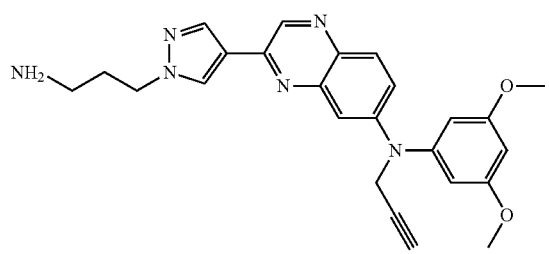
797; ~A4
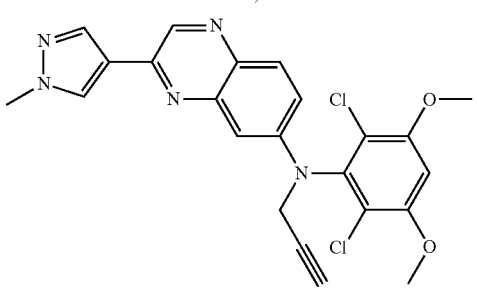
783; ~B29
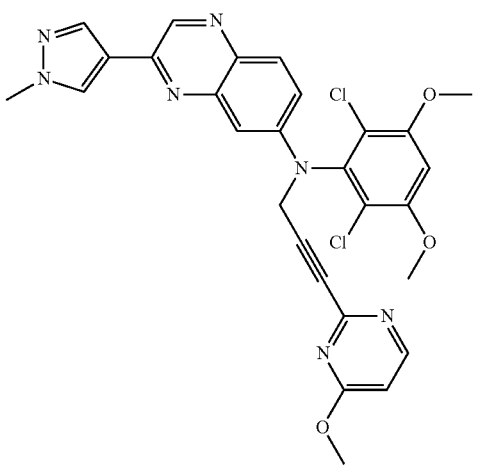
791; ~Co27

-continued
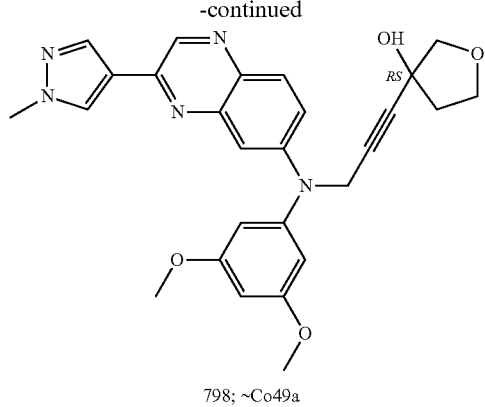
798; ~Co49a
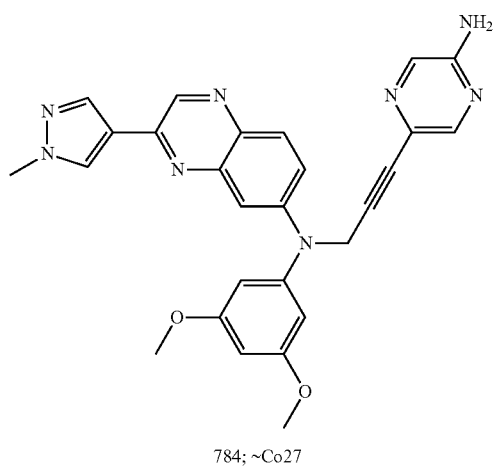
784; ~Co27
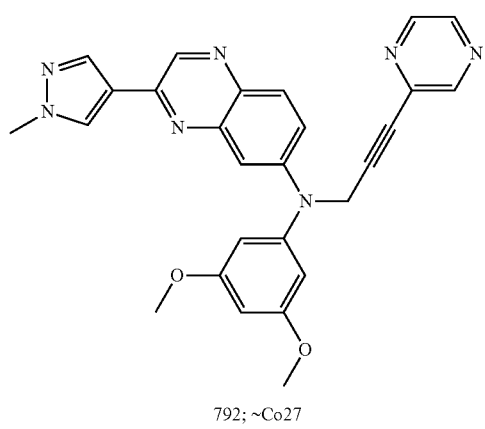
792; ~Co27
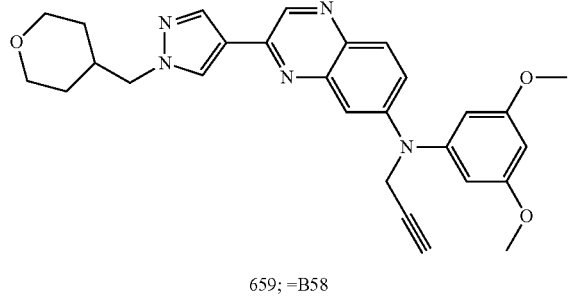
659; =B58
-continued
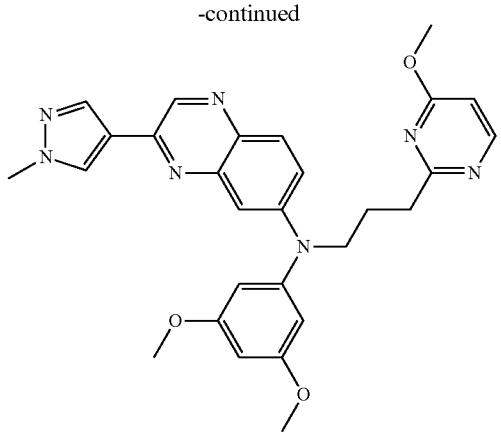
662; ~Co53
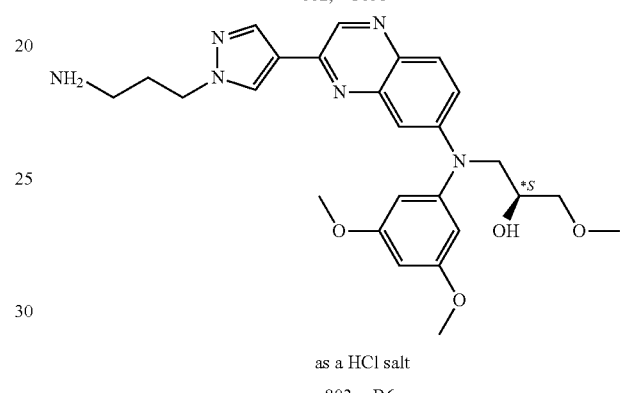
as a HCl salt
803; ~B6
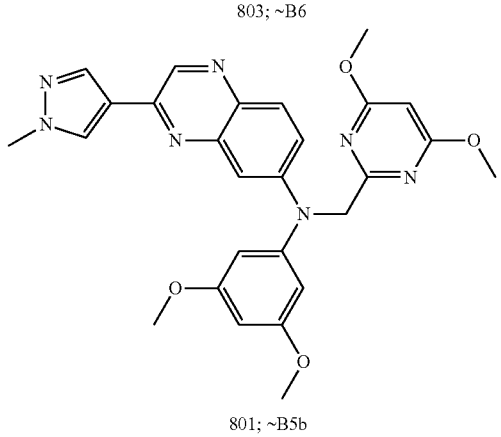
801; ~B5b
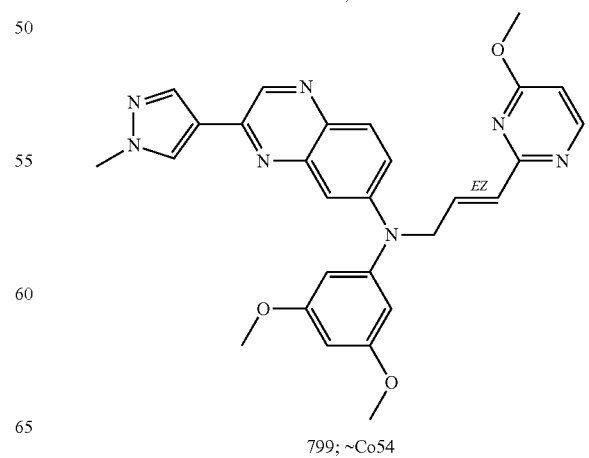
799; ~Co54

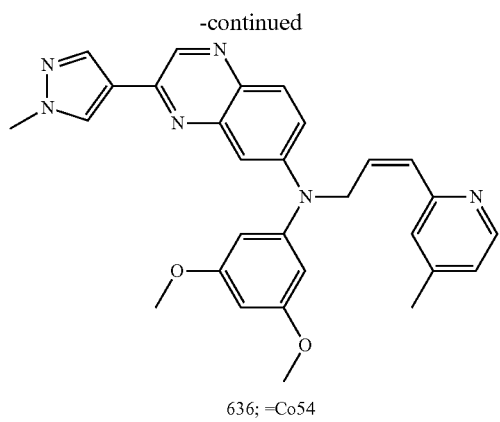
636; =Co54
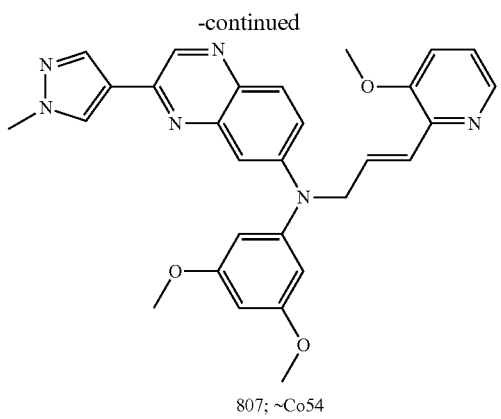
807; ~Co54
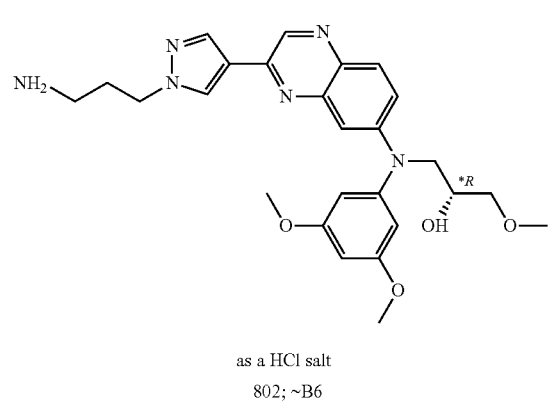
as a HCl salt
802; ~B6
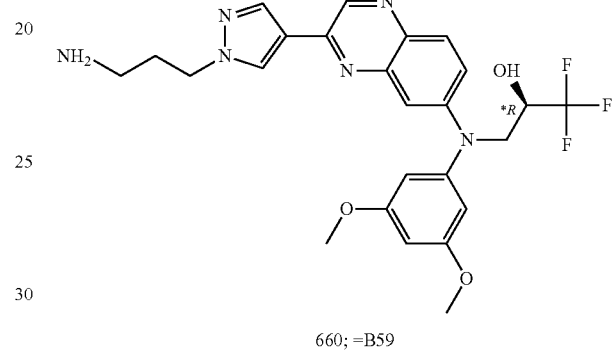
660; =B59
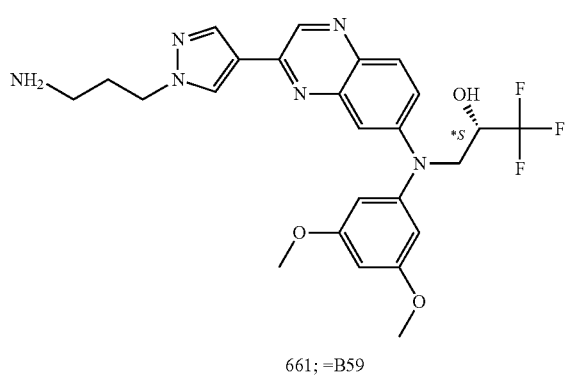
661; =B59
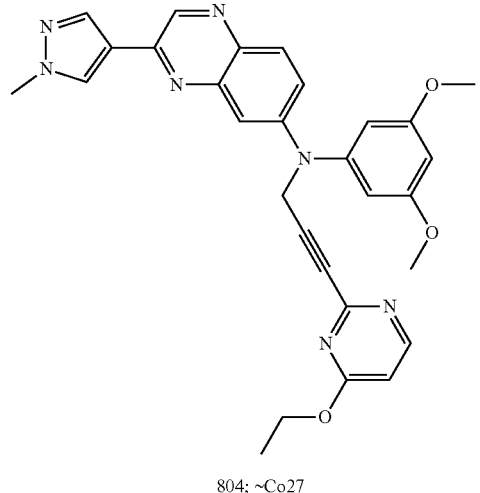
804; ~Co27
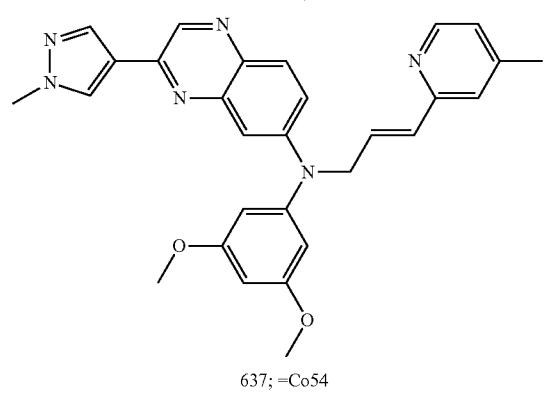
637; =Co54
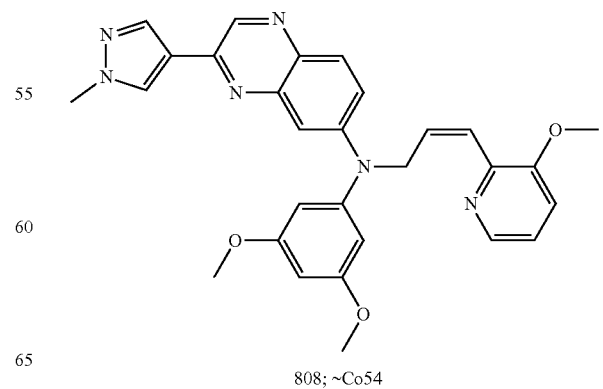
808; ~Co54

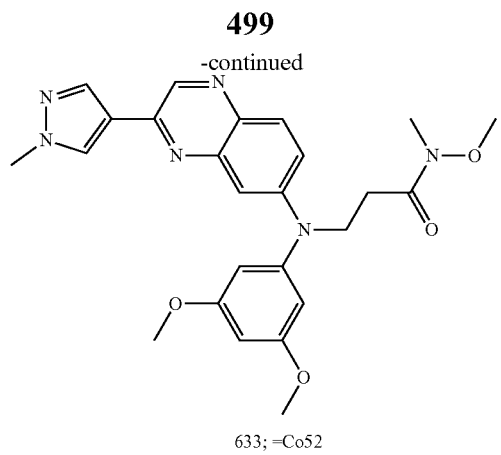
633; =Co52
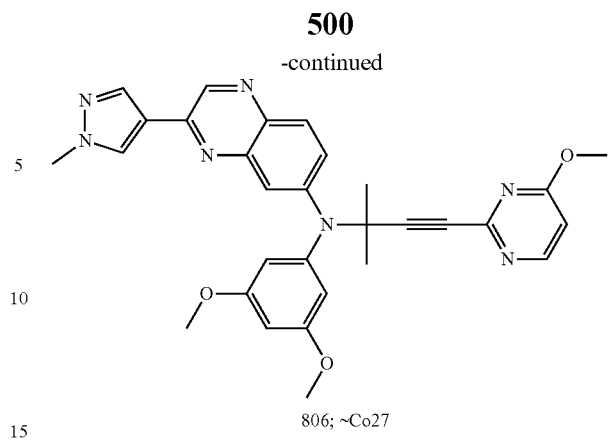
806; ~Co27
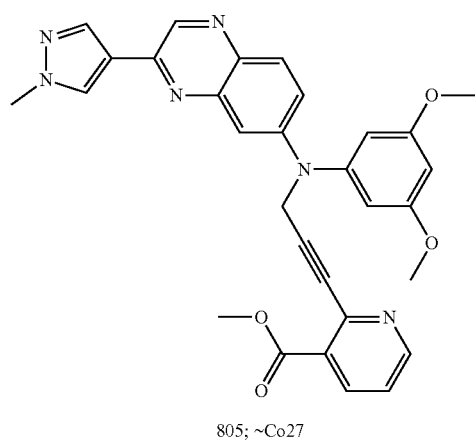
805; ~Co27
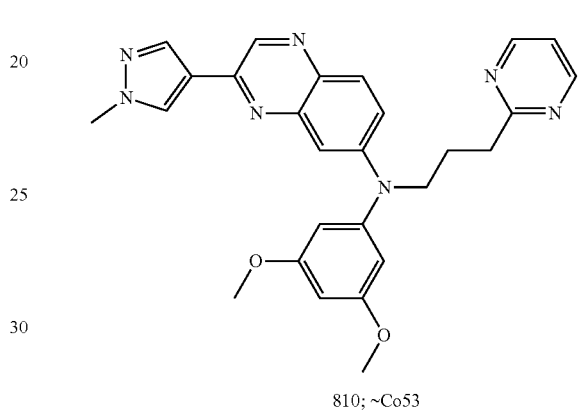
810; ~Co53
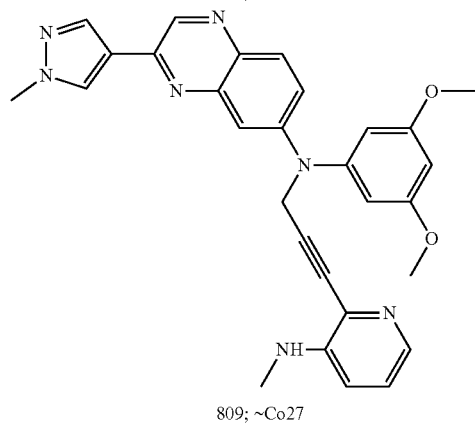
809; ~Co27
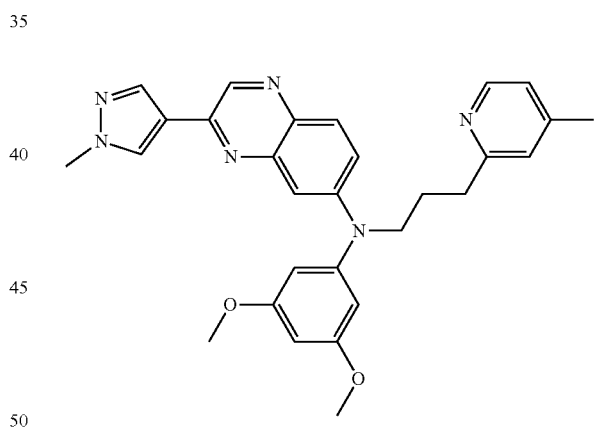
635; =Co53
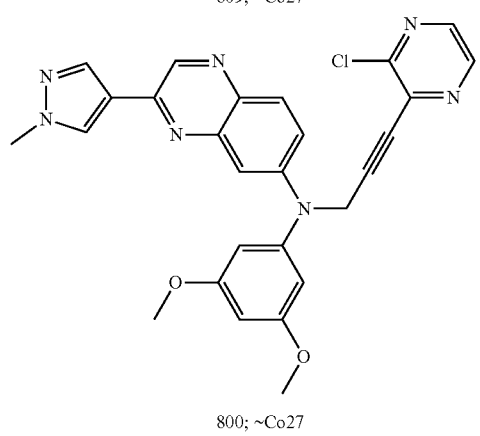
800; ~Co27
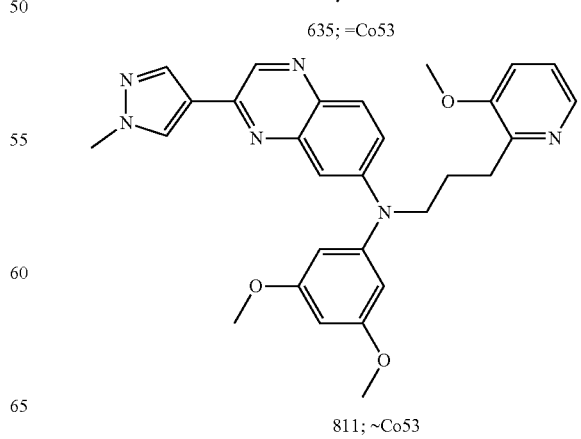
811; ~Co53

| 501 | 502 |
|---|---|
| -continued | -continued |
| 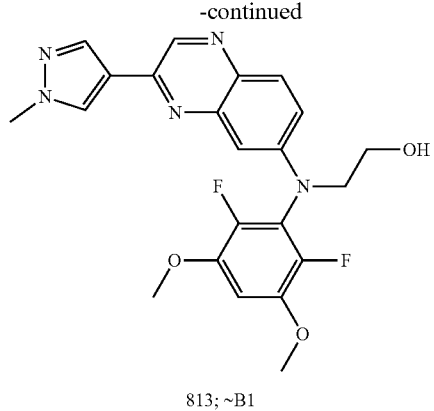 813; ~B1 | 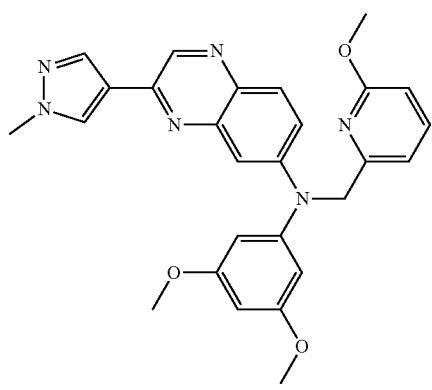 815; ~B5 |
| 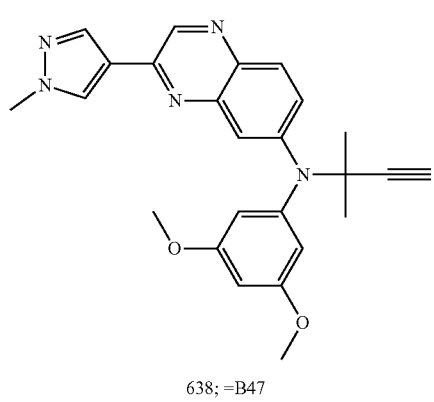 638; =B47 | 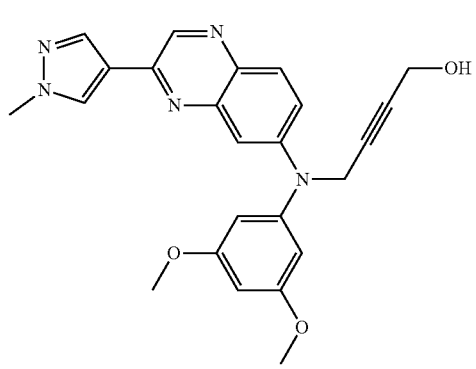 632; =B46 |
| 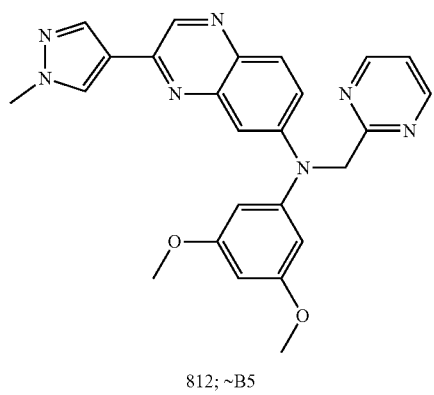 812; ~B5 | 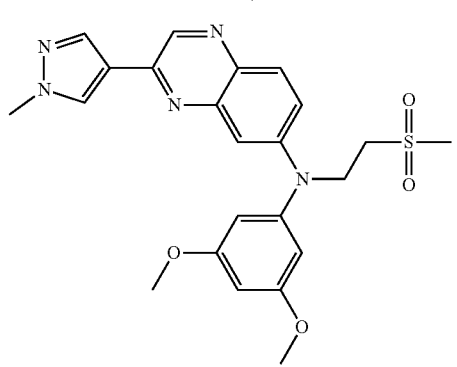 828; ~B5b |
| 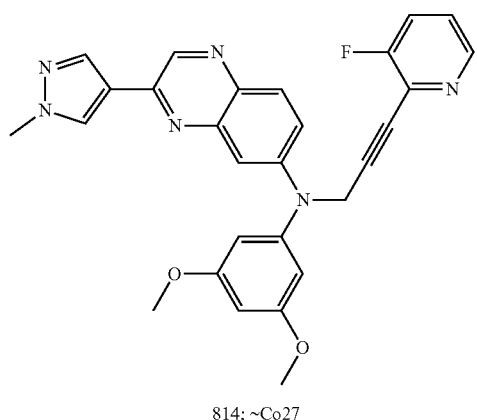 814; ~Co27 | 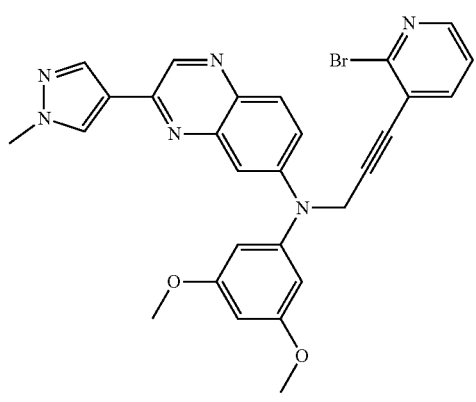 816; ~Co27 |

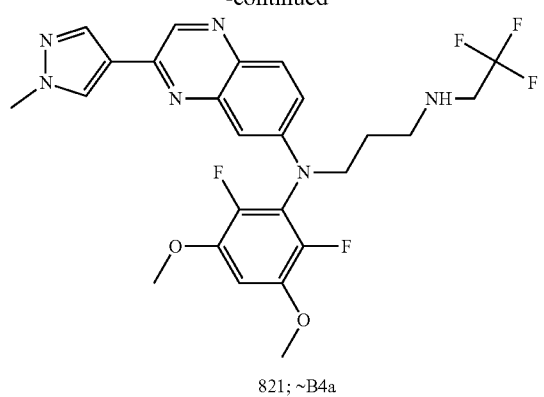
821; ~B4a
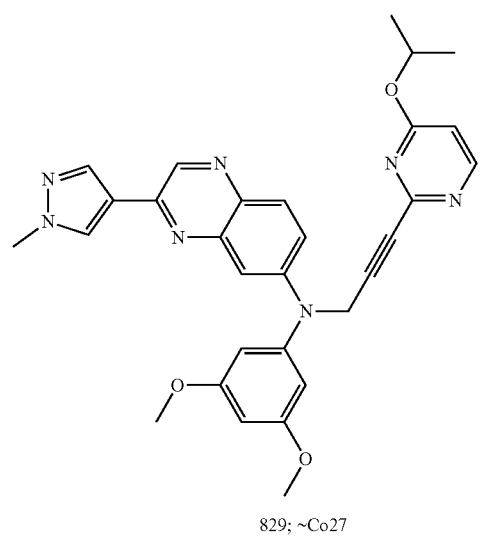
829; ~Co27
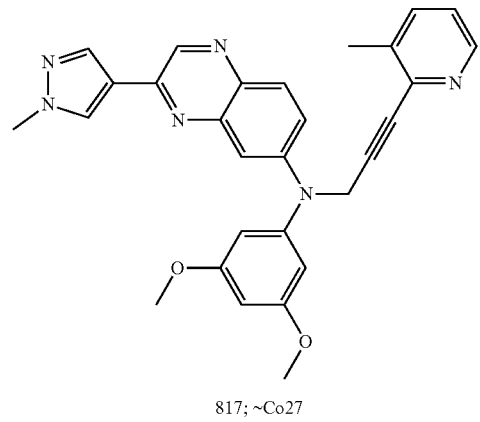
817; ~Co27
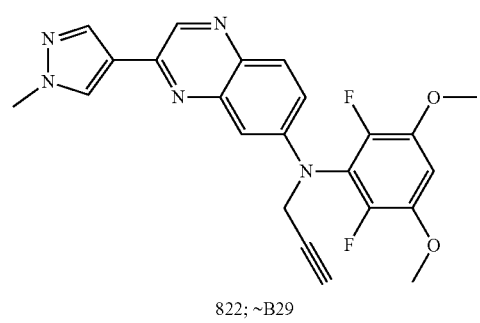
822; ~B29
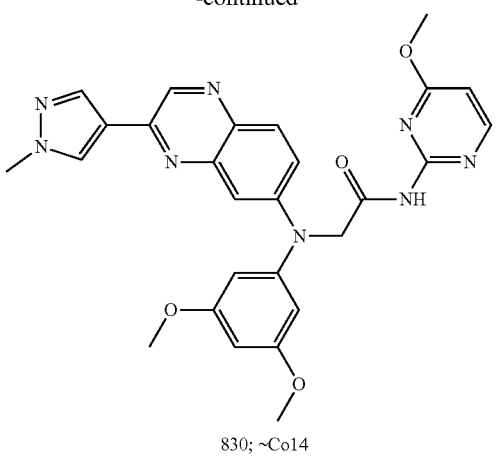
830; ~Co14
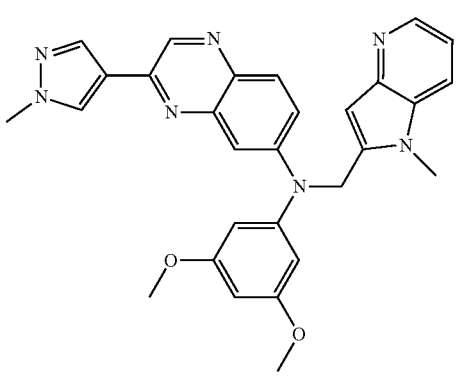
640; =Co55
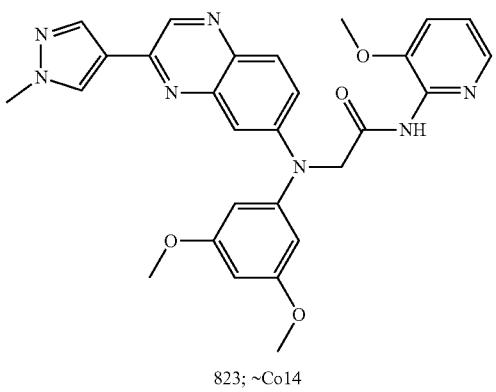
823; ~Co14
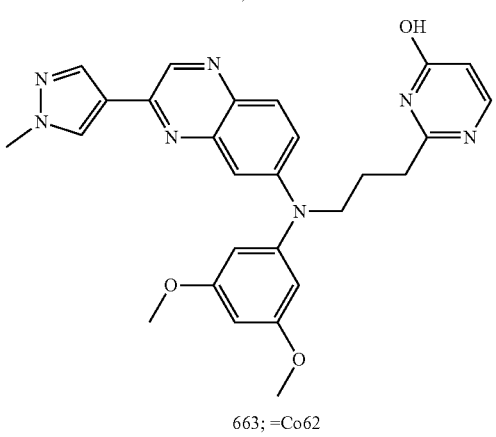
663; =Co62

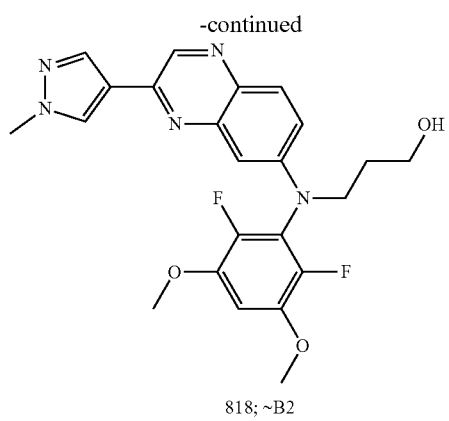
818; ~B2
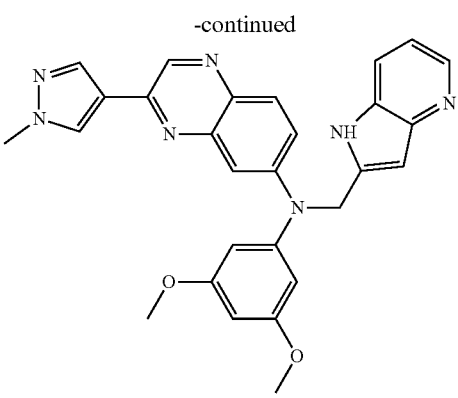
825; ~Co55
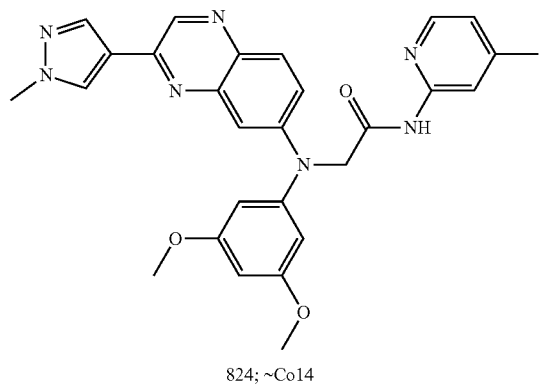
824; ~Co14
831; ~Co27
664; =B60
687; ~B3
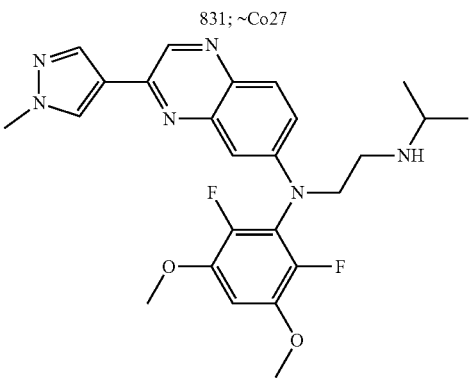
819; ~Co54
826; ~Co27

-continued
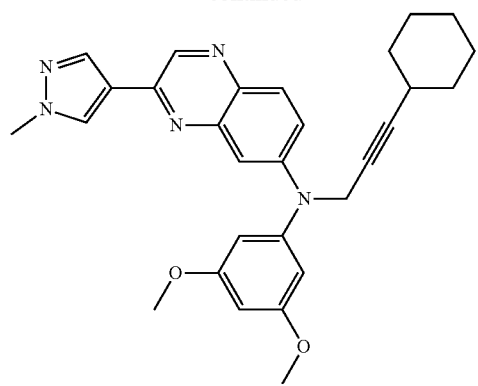
832; ~Co27
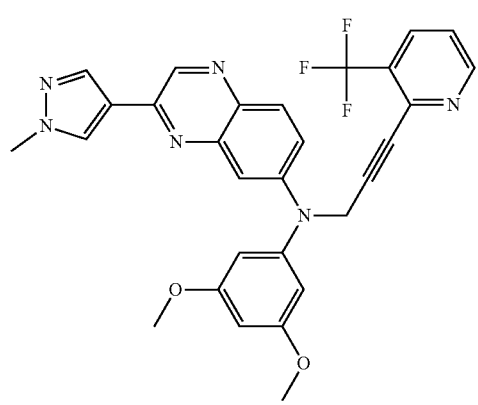
820; ~Co27
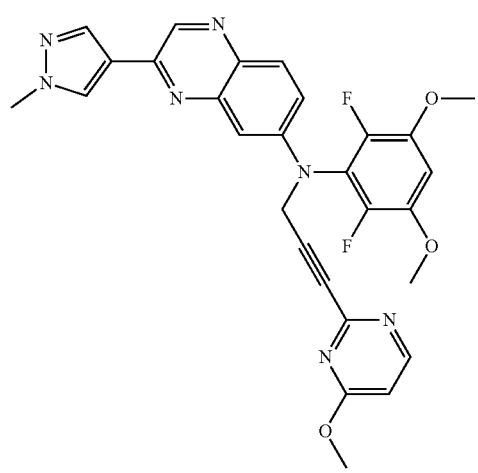
827; ~Co27
-continued
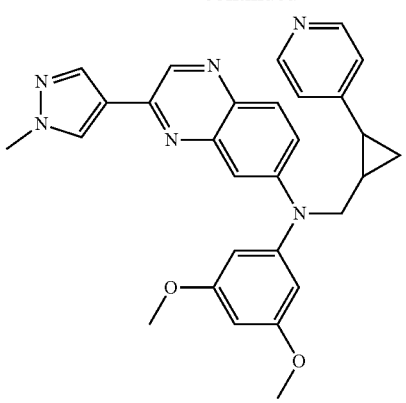
833; ~B5a
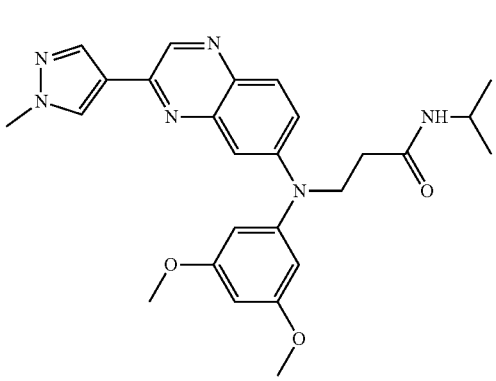
834; ~Co14
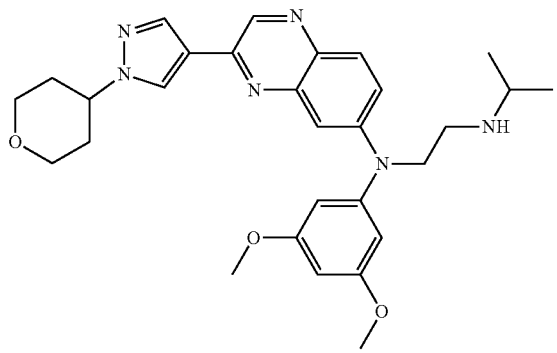
840; ~Co57
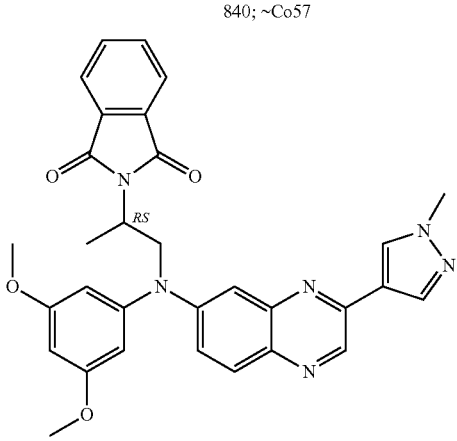

509
-continued
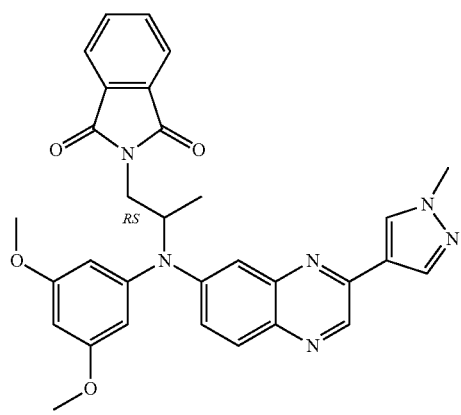
607; =B35
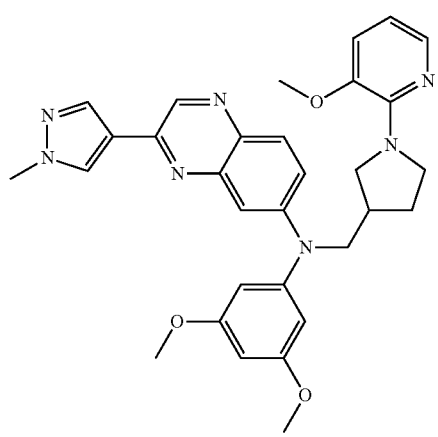
835; ~B5a
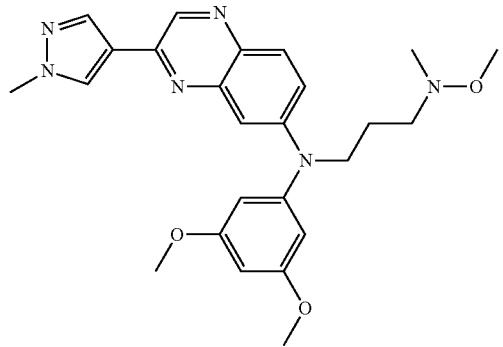
841; ~B48
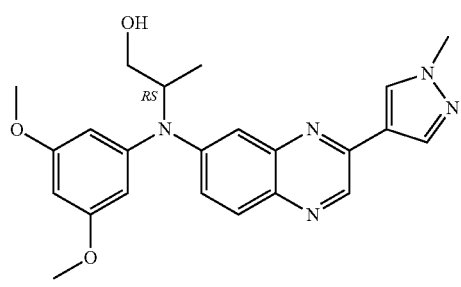
606; =Co45
510
-continued
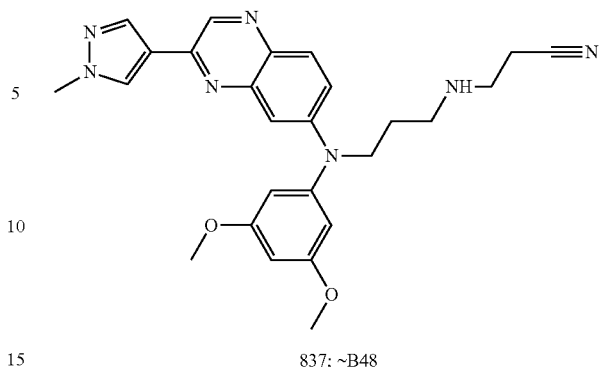
837; ~B48
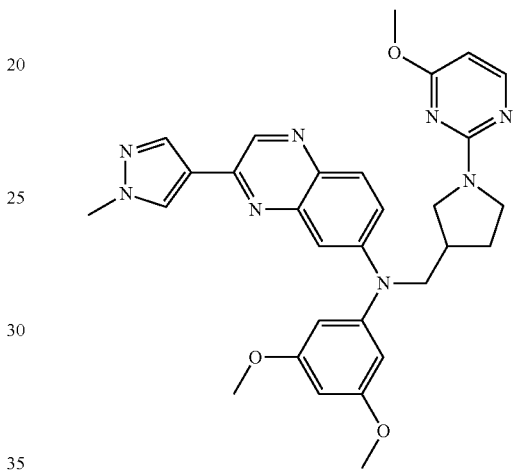
842~B5a
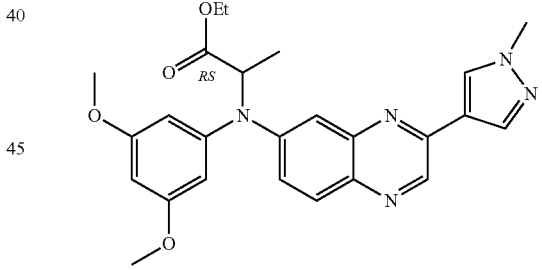
605; =B34
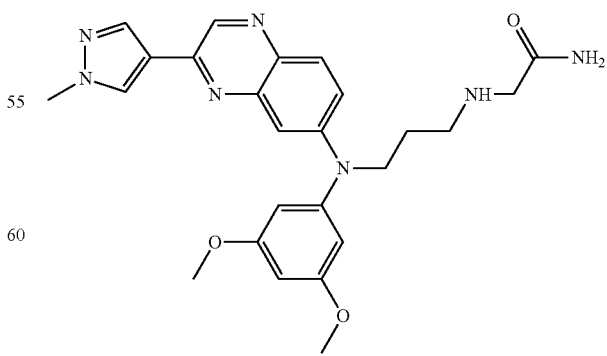
641; =B48

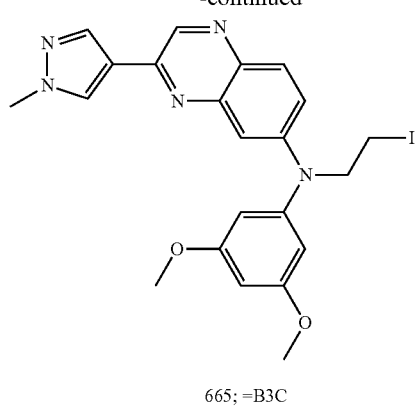
665; =B3C
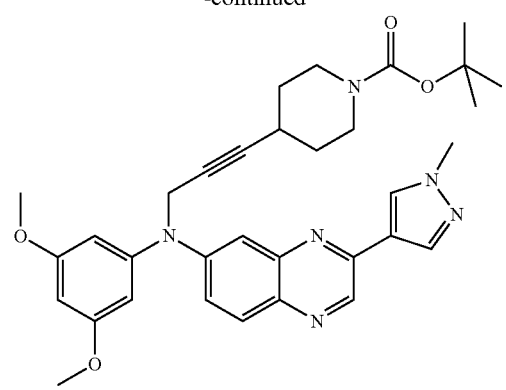
630; =B45
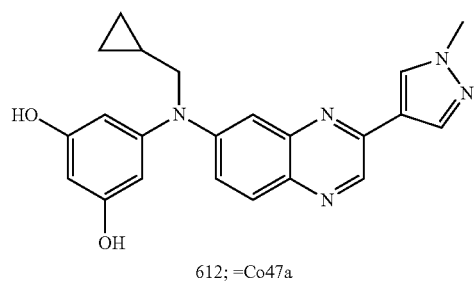
612; =Co47a
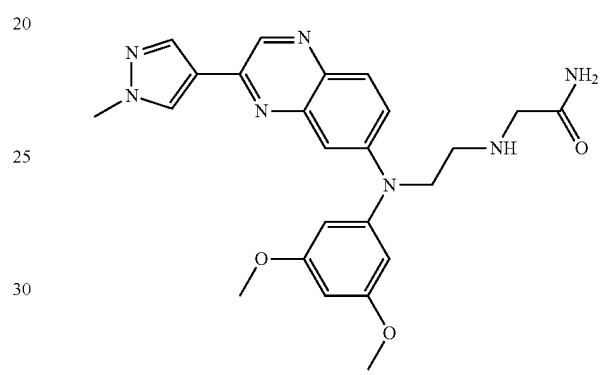
838; ~B48
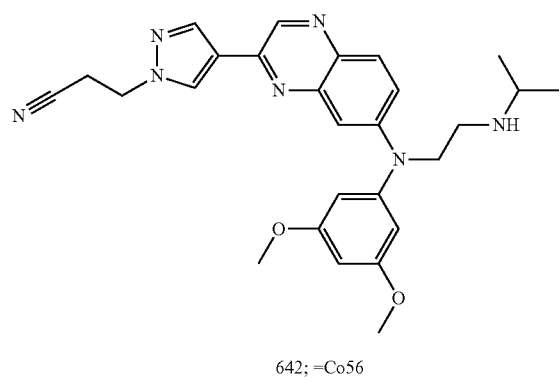
642; =Co56
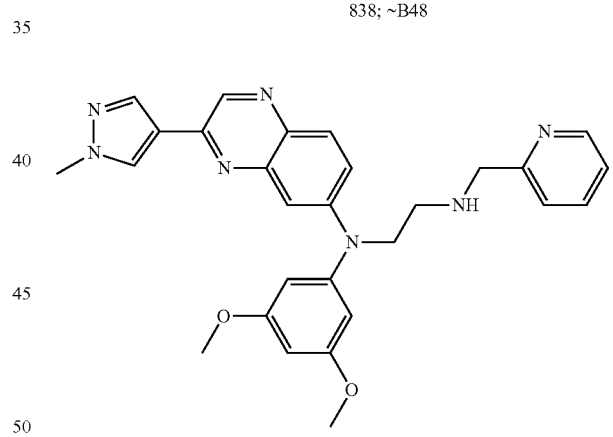
836; ~B48
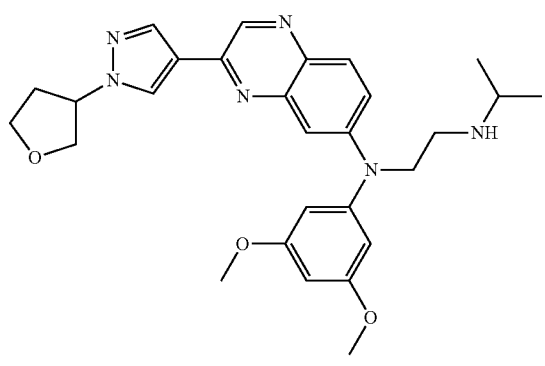
as a HCl salt
643; =Co57
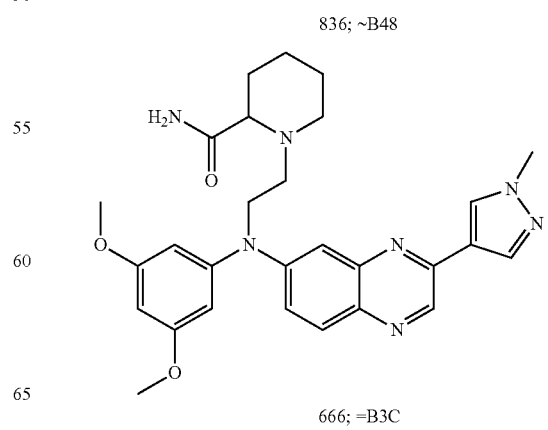
666; =B3C

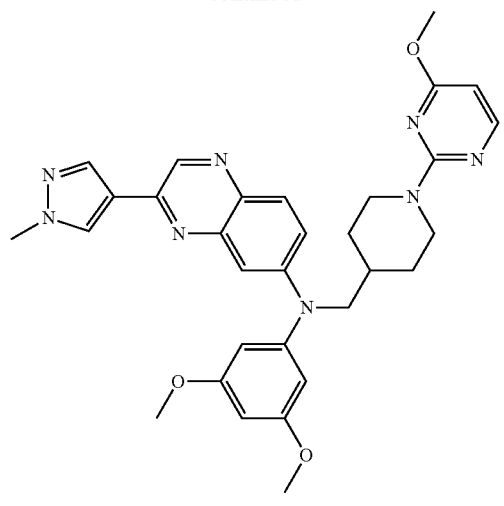
839; ~B5a
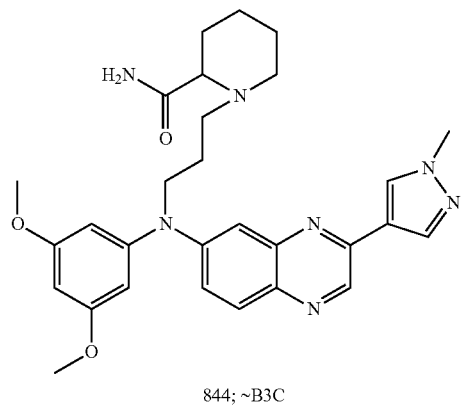
844; ~B3C
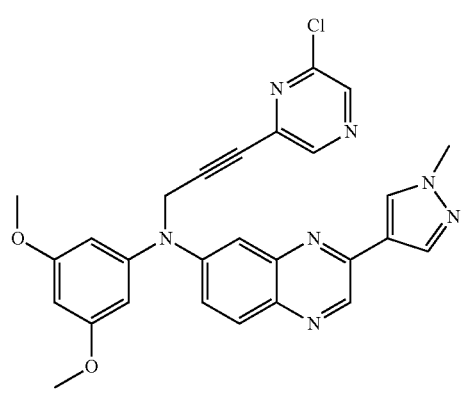
845; ~Co27
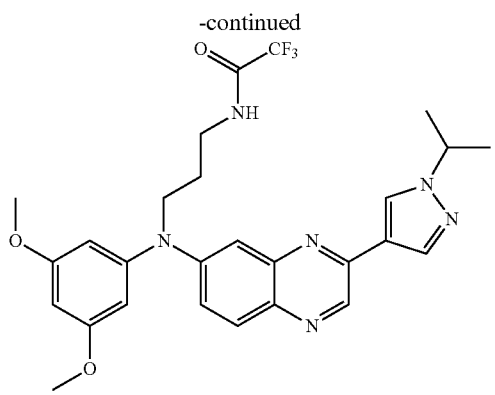
851; ~Co26
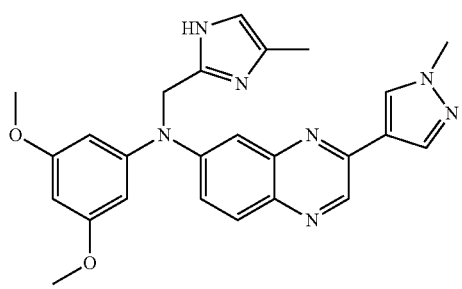
as a HCl salt
696; =Co 72
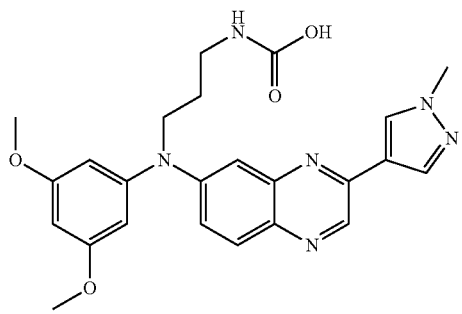
Lithium (+1)
846; =B64
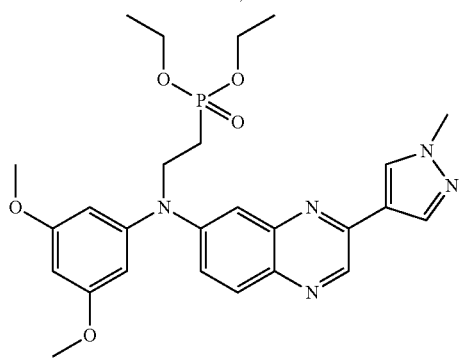
669; =B62

515
-continued
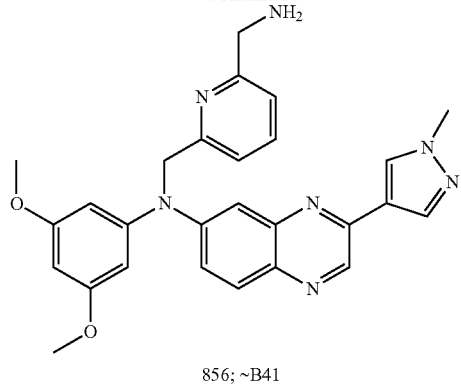
856; ~B41
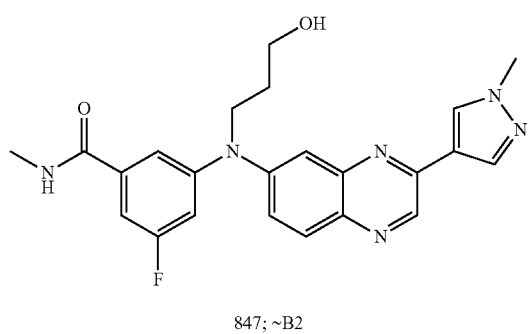
847; ~B2
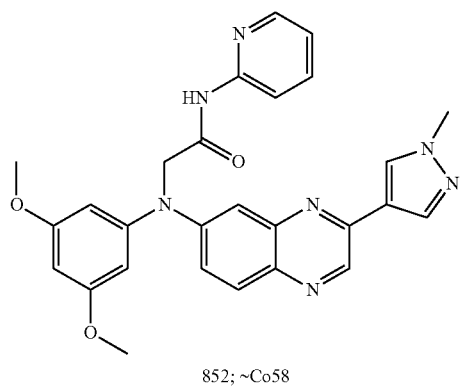
852; ~Co58
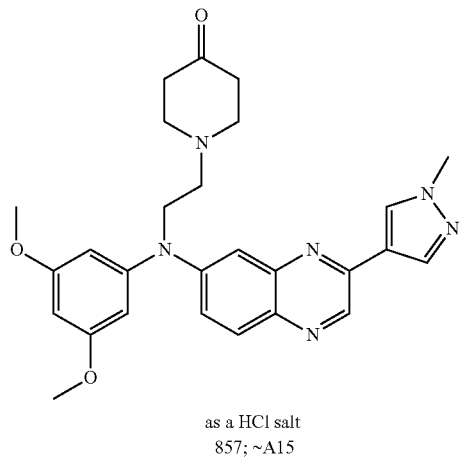
as a HCl salt
857; ~A15
516
-continued
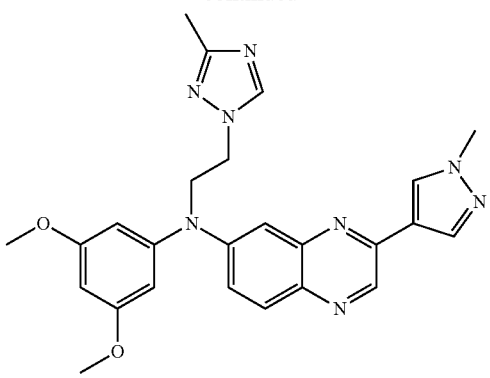
667; =B61
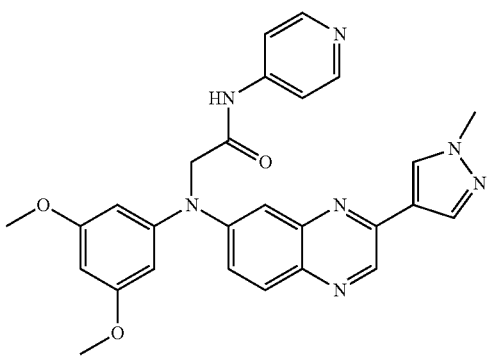
853; ~Co58
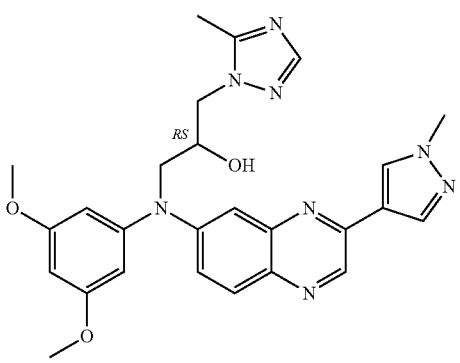
671; =Co 64
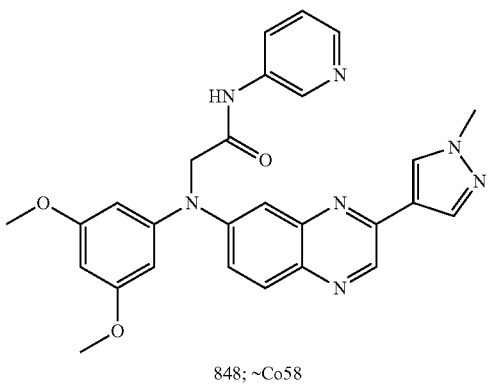
848; ~Co58

517
-continued
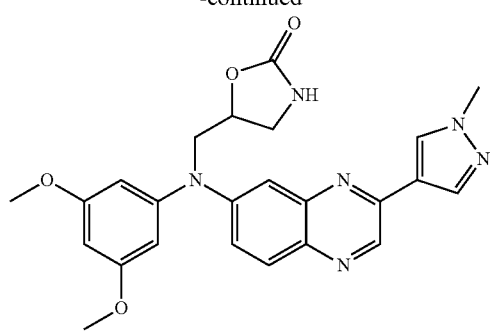
670; =Co 63
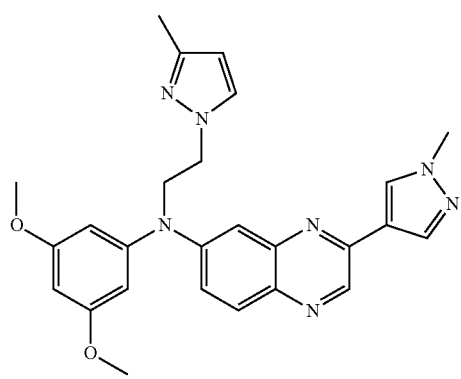
858; ~B3
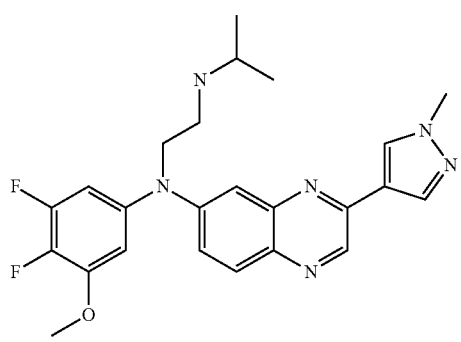
849; ~B3
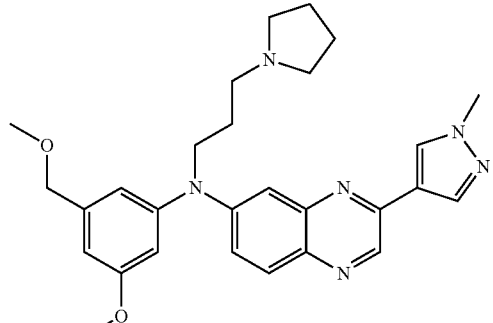
854; ~B5
518
-continued
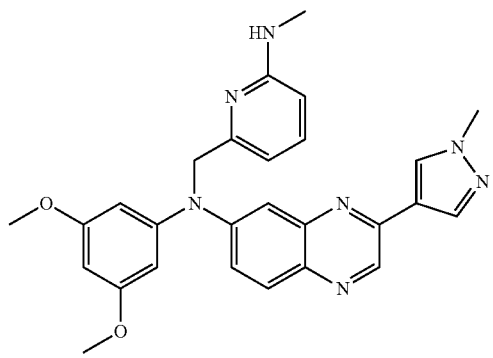
673; =Co 65
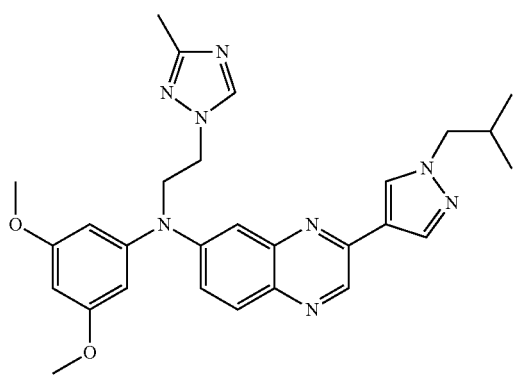
850; ~B61
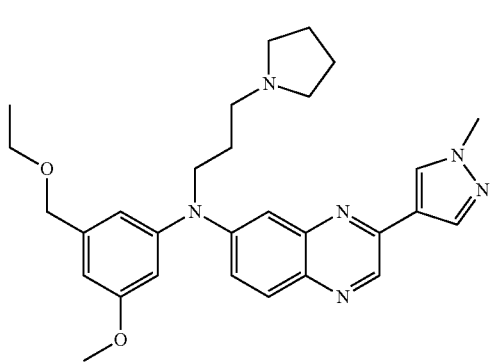
855; ~B5
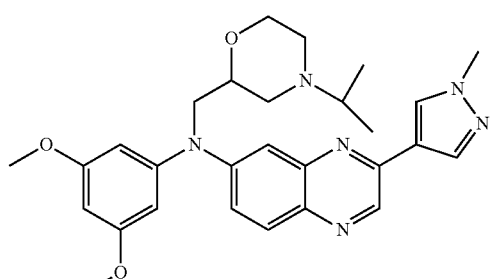
676; =Co 66c)

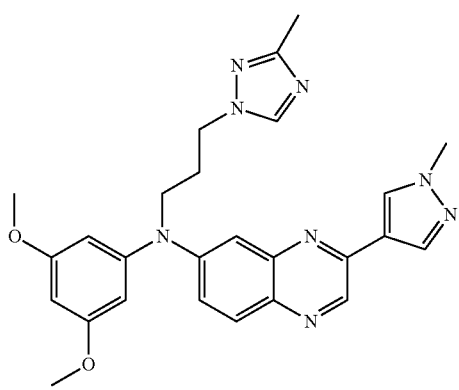
859; ~B61
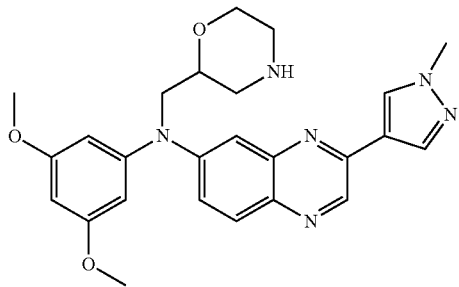
682; =Co 69
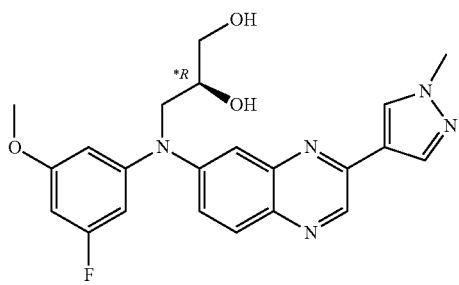
867; ~Co61
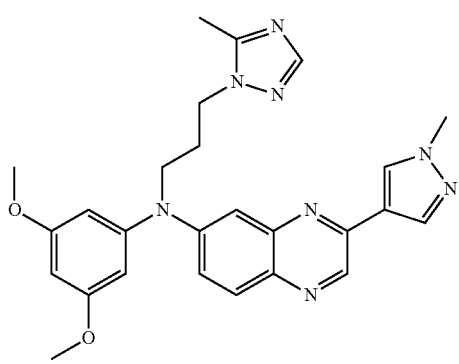
860; ~B61
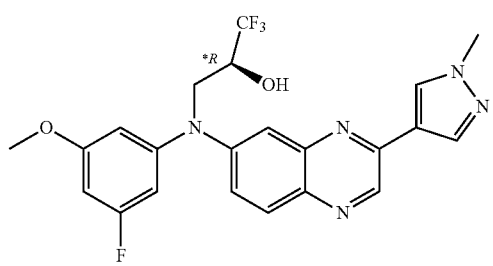
863; ~B59
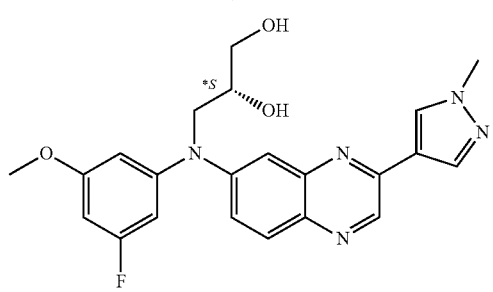
868; ~Co61
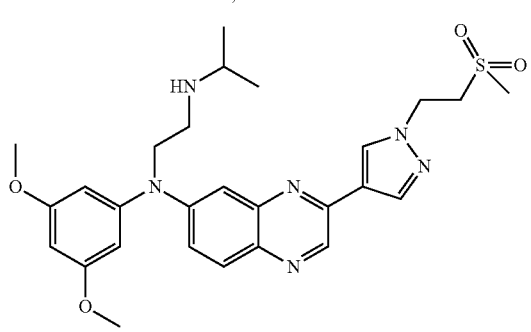
678; =Co 67
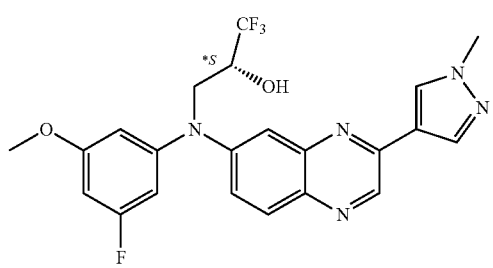
864; ~B59
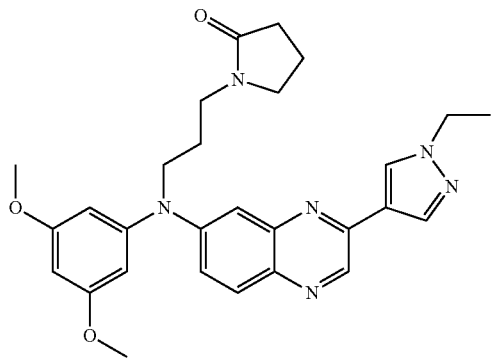
as a HCl salt
694 =B4C 521
-continued
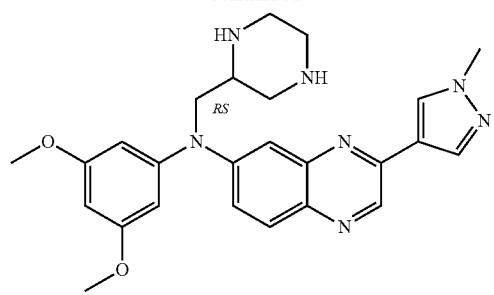
680; =Co 68
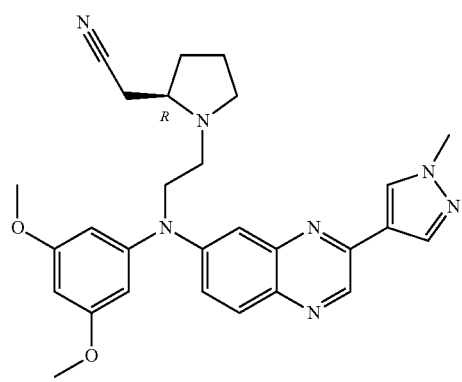
865; =Co35
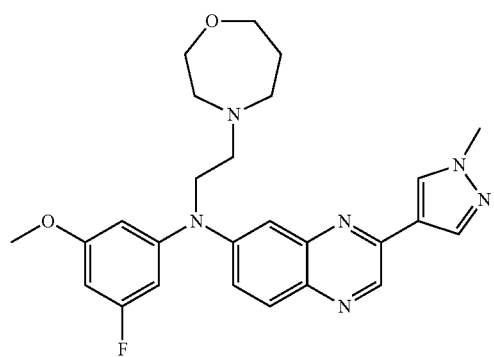
.oxalate
869; ~B3
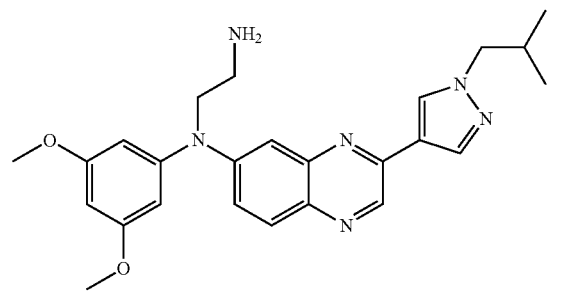
as a HCl salt
861; ~Co3
522
-continued
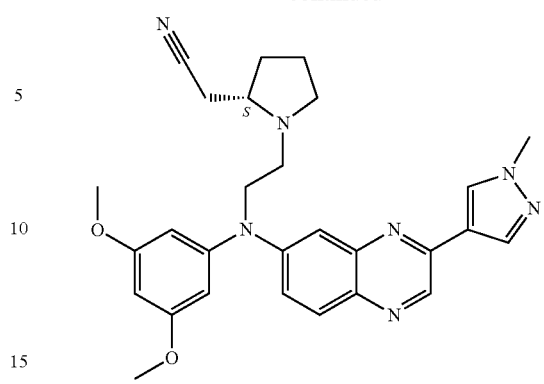
866; ~Co35
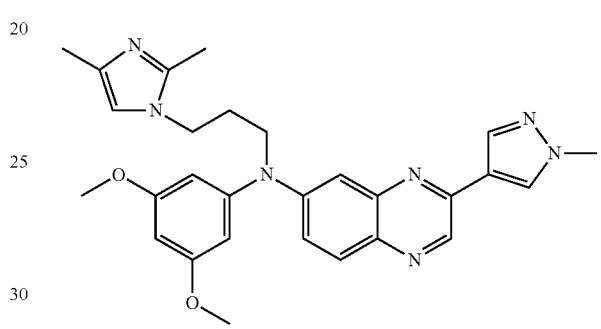
as a HCl salt
692; =Co2B
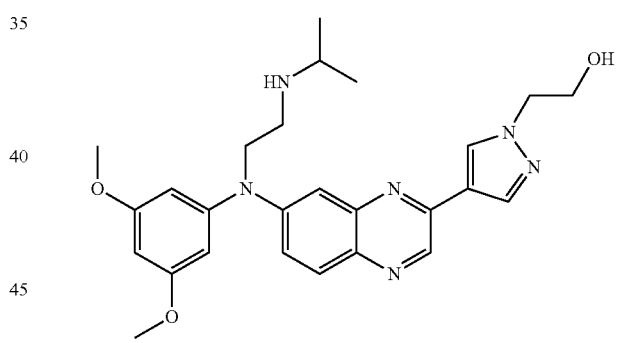
691; =B14A
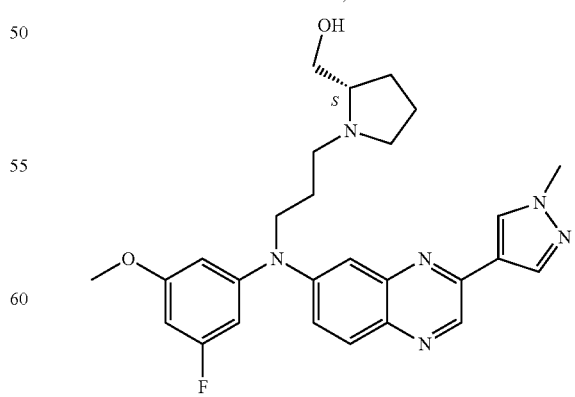
679; =B4B

523
-continued
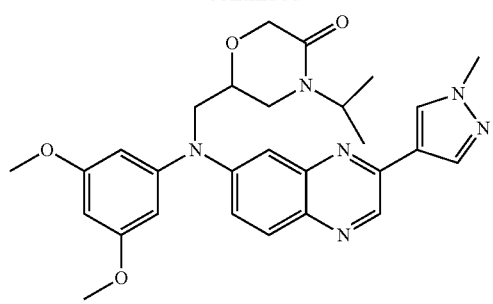
675; =Co 66b)
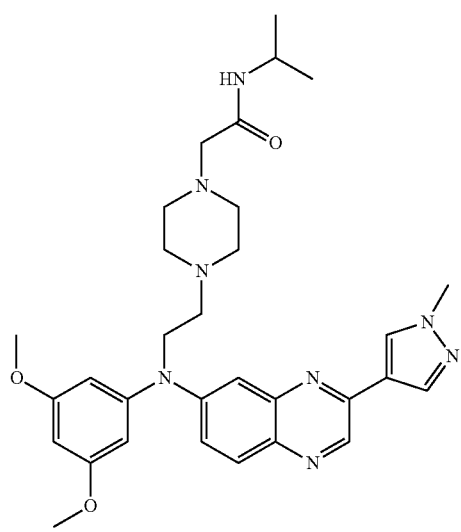
as a HCl salt
862; ~B3
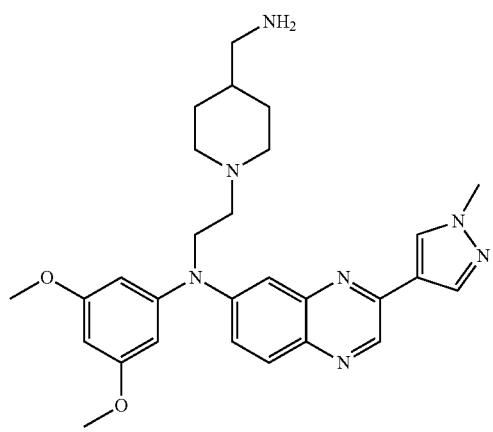
as a HCl salt
693; =B63
524
-continued
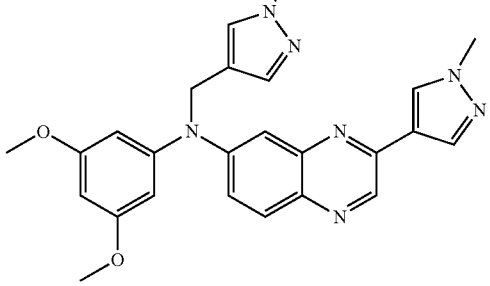
870; ~B5
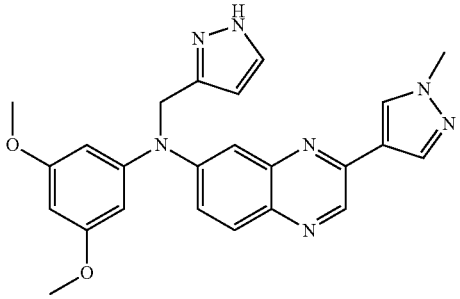
as a HCl salt
685; =Co 71
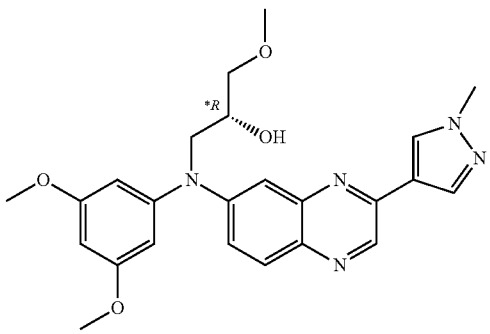
as a HCl salt
875; ~Co61
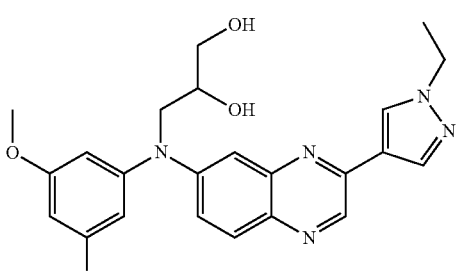
871; ~B6

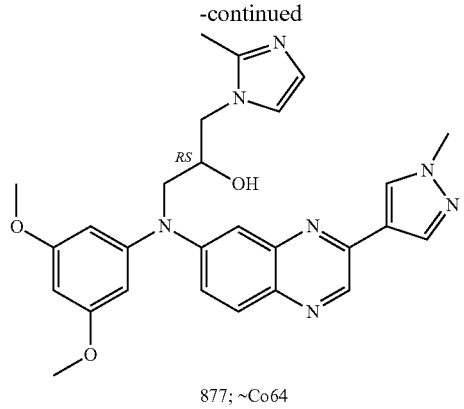
877; ~Co64
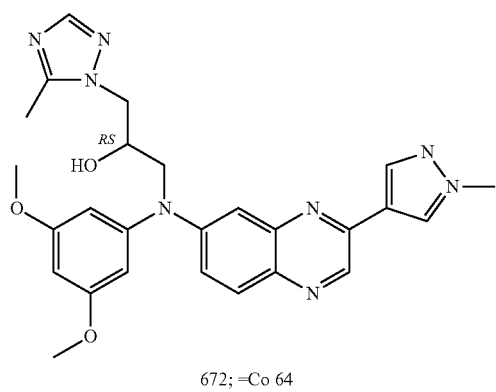
672; =Co 64
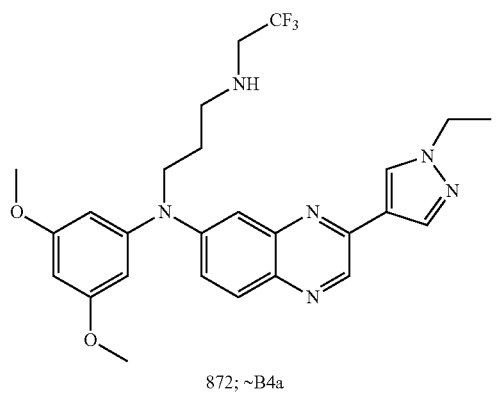
872; ~B4a
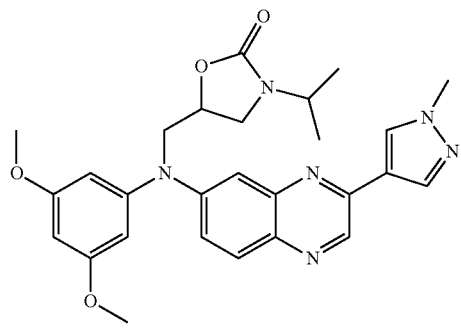
878; ~Co63
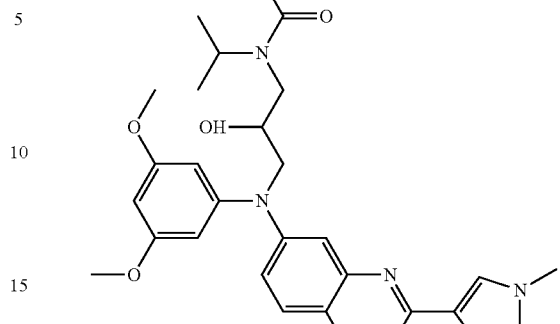
674; =Co 66a)
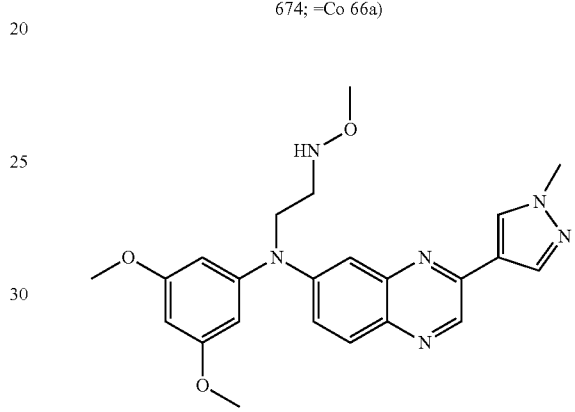
677; =B3D
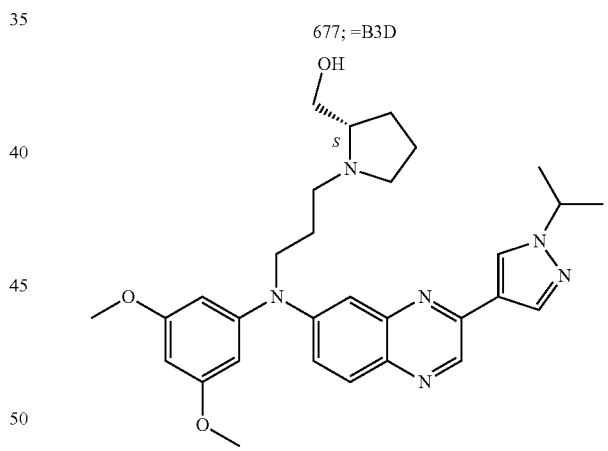
as a HCl salt
879; ~B4B
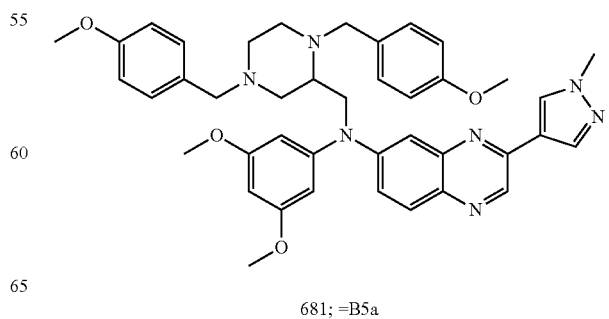
681; =B5a -continued
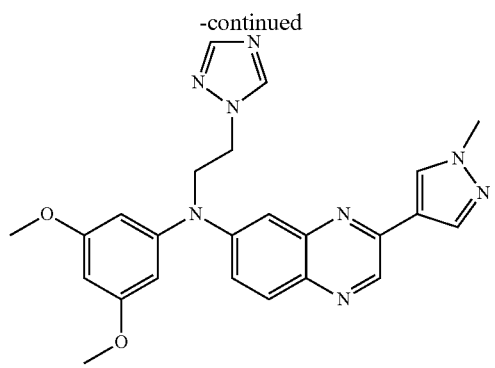
873; ~B3
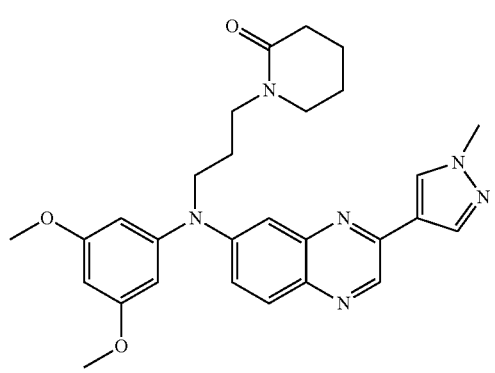
880; ~A2
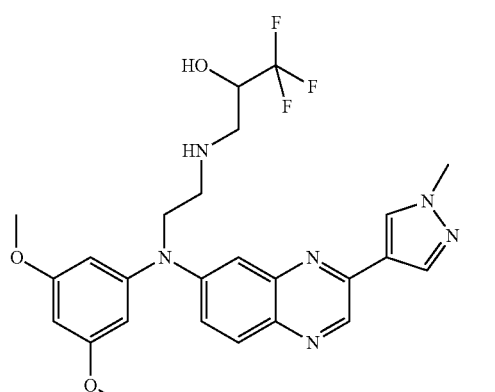
683; =Co 70
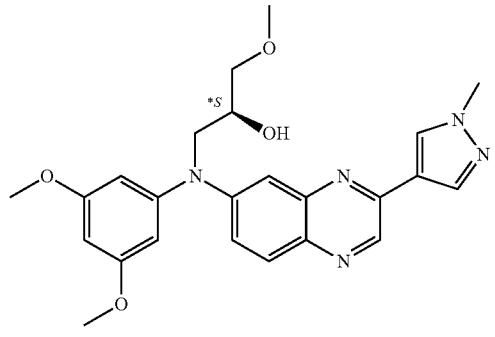
as a HCl salt
874; ~Co61
-continued
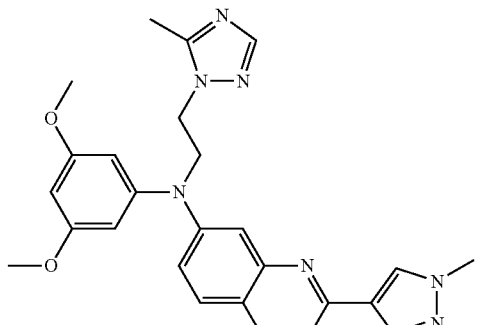
668; =B61
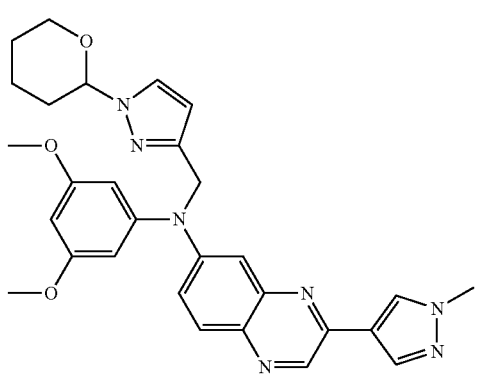
686; =B5a
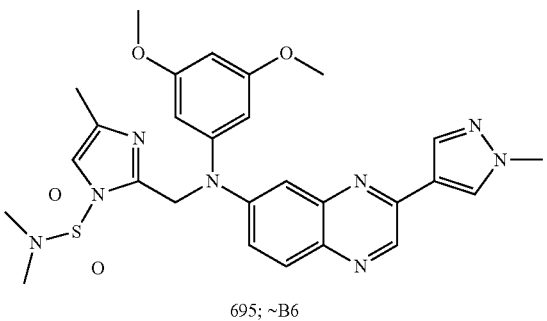
695; ~B6
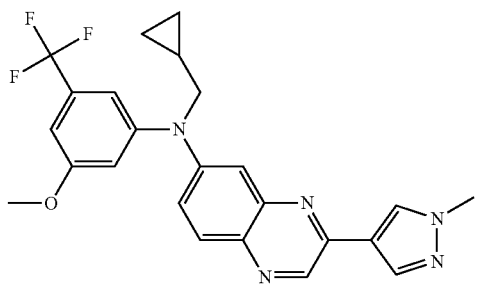
882; ~B5

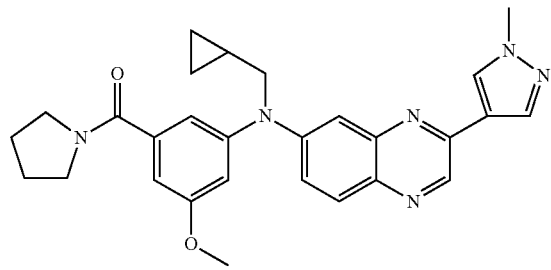
884; ~B5
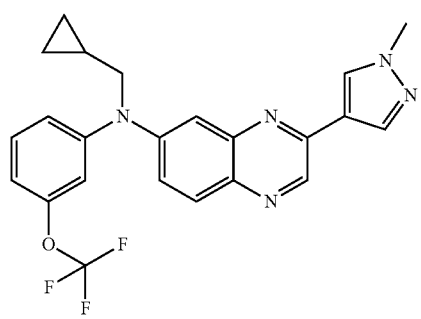
as a HCl salt
881; ~B5
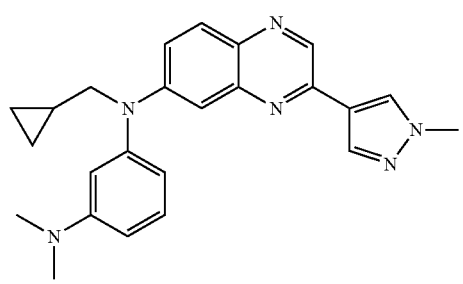
as a HCl salt
883; ~B5
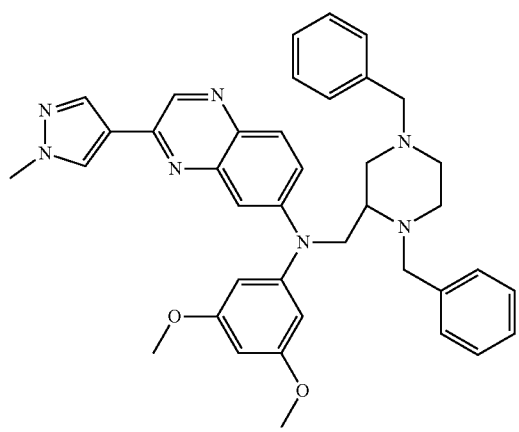
885; ~B5a
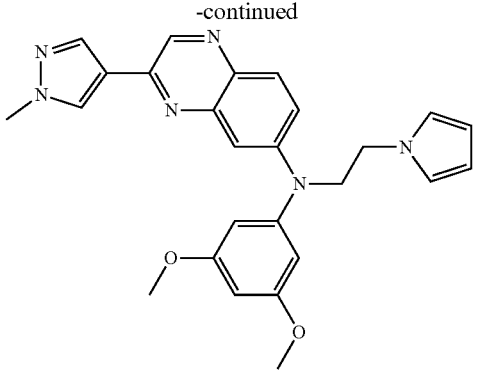
as a HCl salt
886; ~B3E
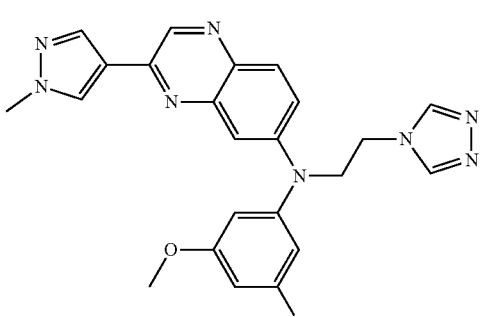
887; ~B3
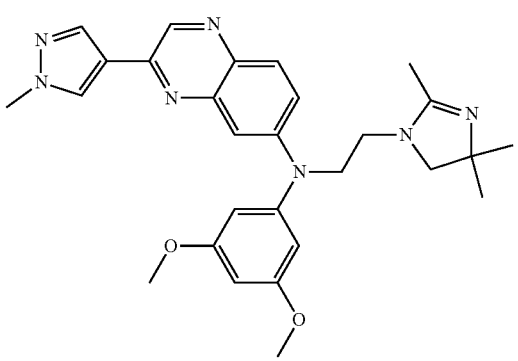
888; ~B3C
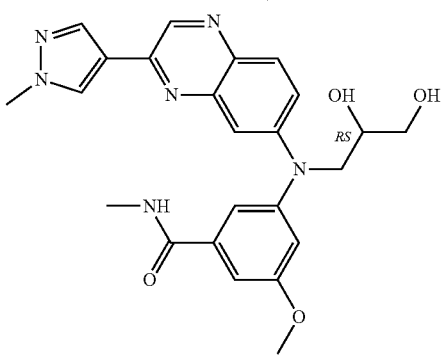
889; ~Co15

-continued
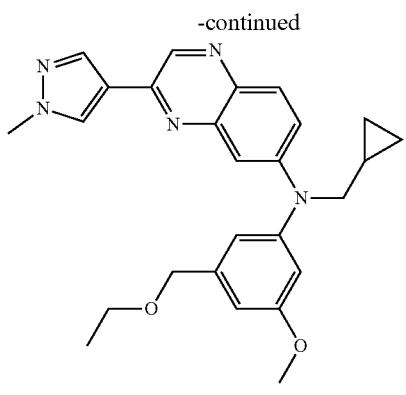
890; ~B5b1
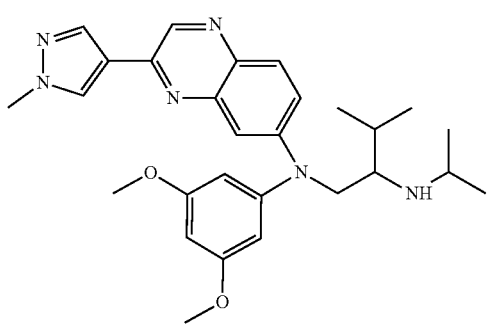
as a HCl salt
891; ~B3F
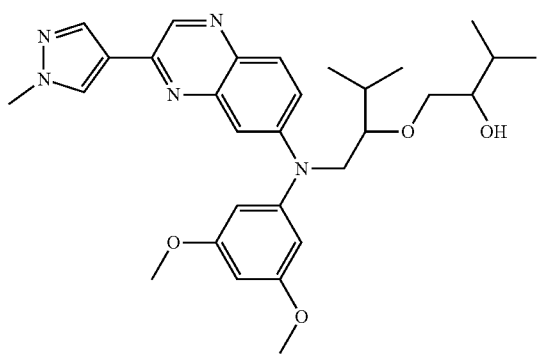
as a HCl salt
892; ~B59A
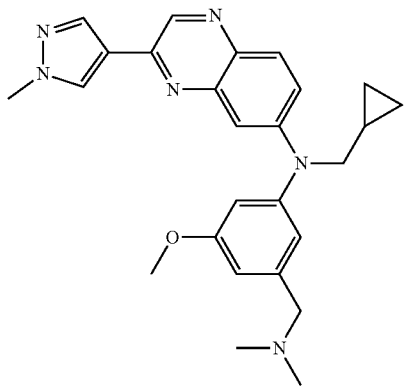
893; ~B5b1
-continued
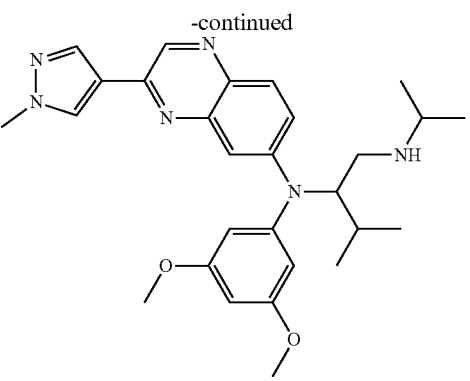
as a HCl salt
894; ~B3F
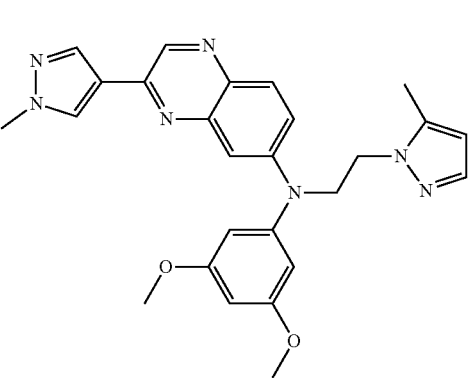
895; ~B3
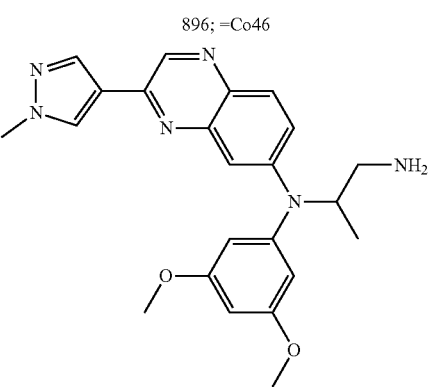
896; =Co46
897; =Co46

-continued
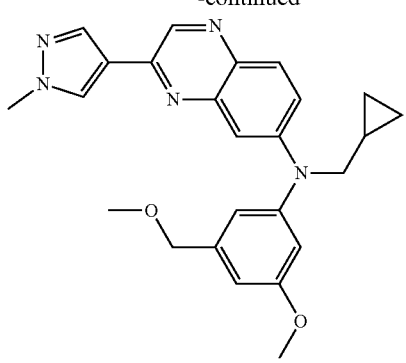
898; ~B5b1
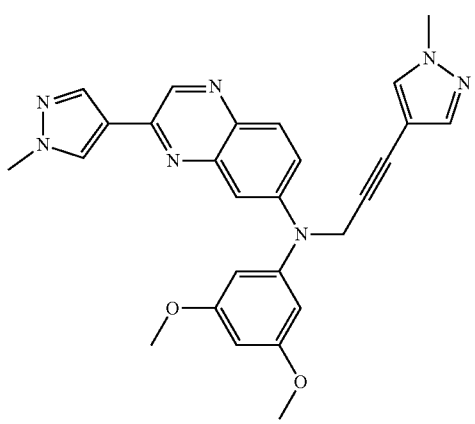
899; ~Co47
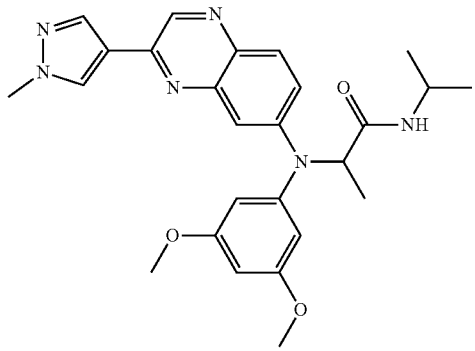
900; ~Co11
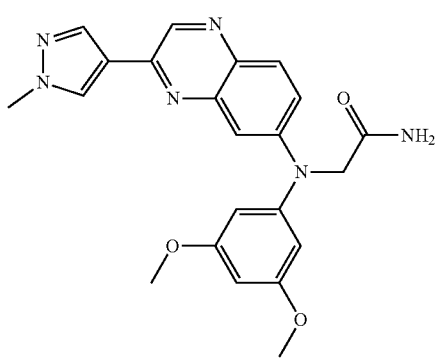
901; ~Co11
-continued
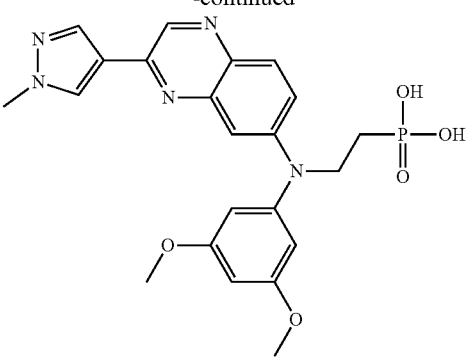
•HBr
902; ~Co73
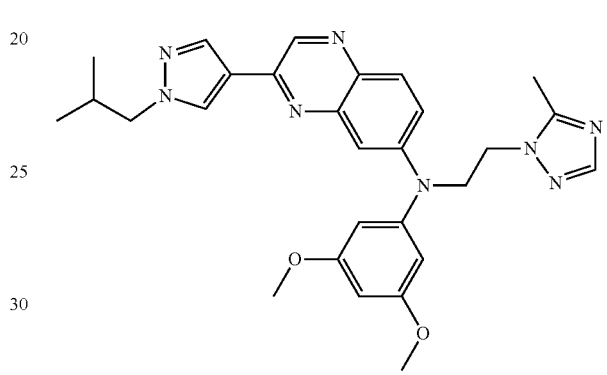
903; ~B4A
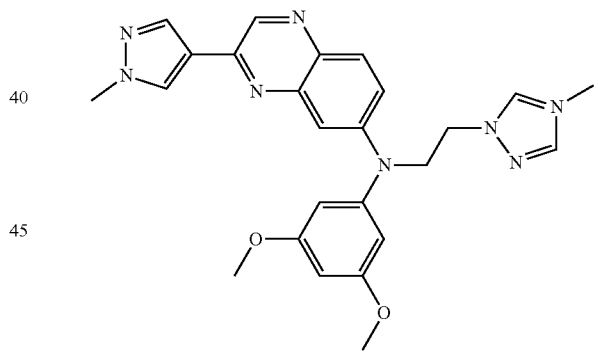
904; ~B4A
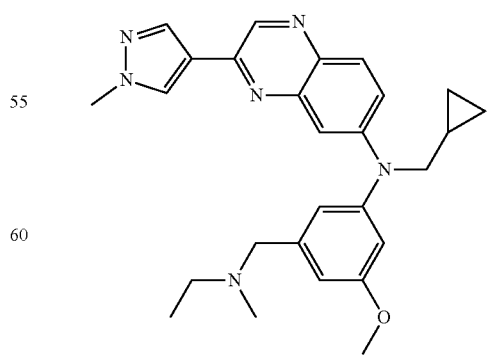
905; ~B5b1

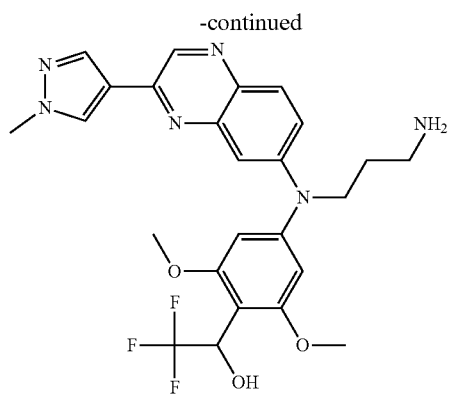
906; ~Co74
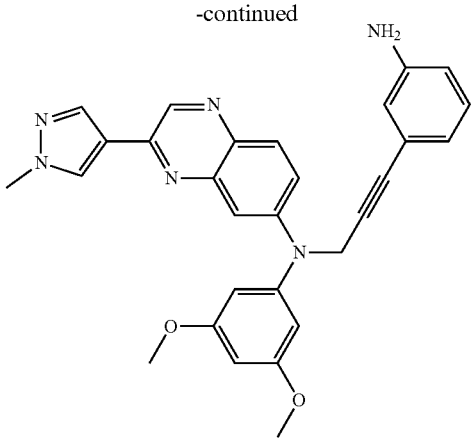
909; ~Co47
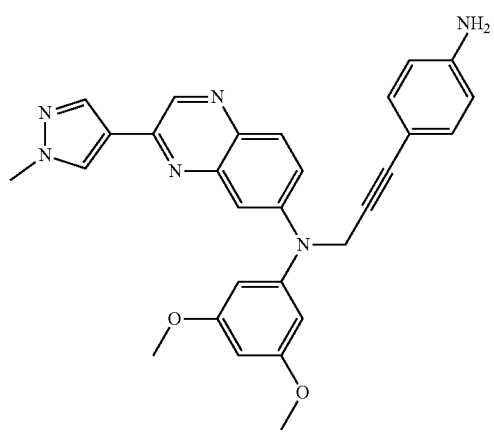
907; ~Co47
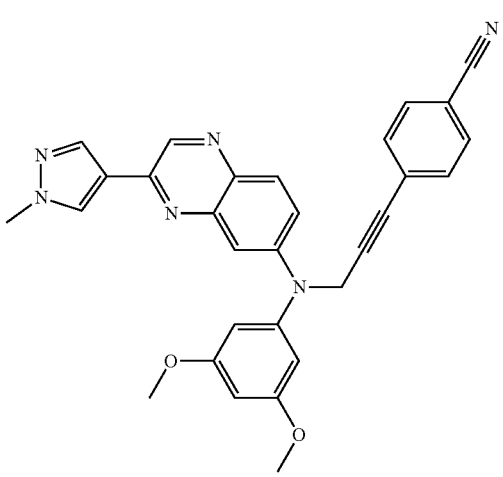
910; ~Co47
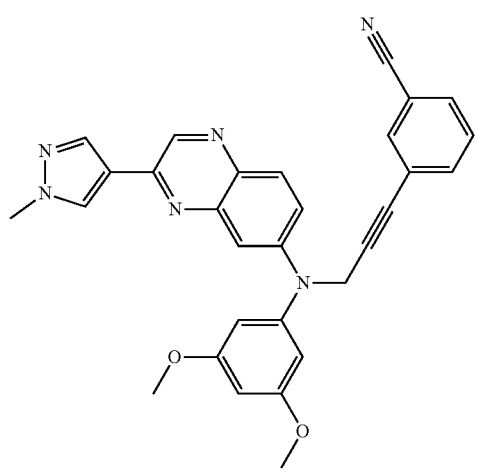
908; ~Co47
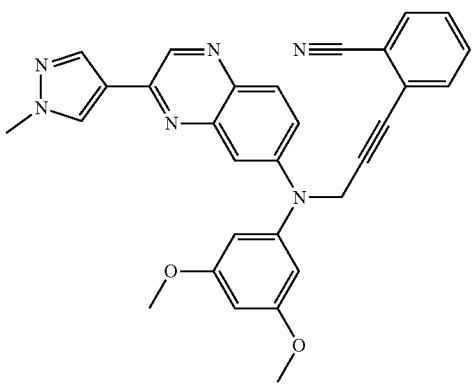
911; ~Co47

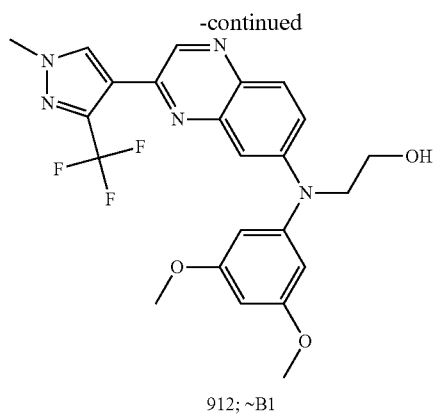
912; ~B1
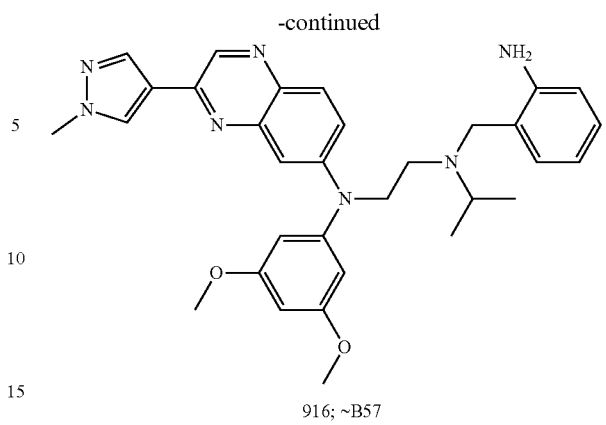
916; ~B57
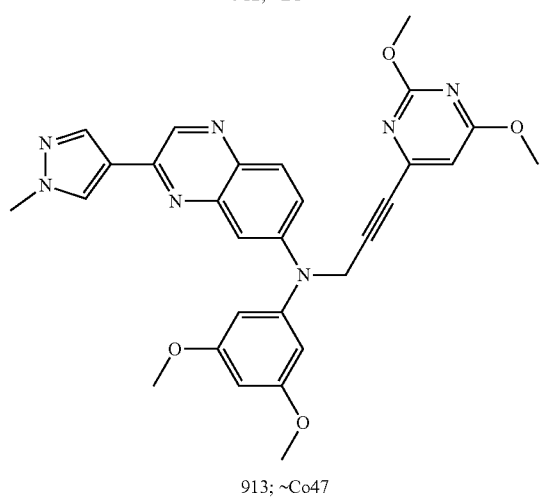
913; ~Co47
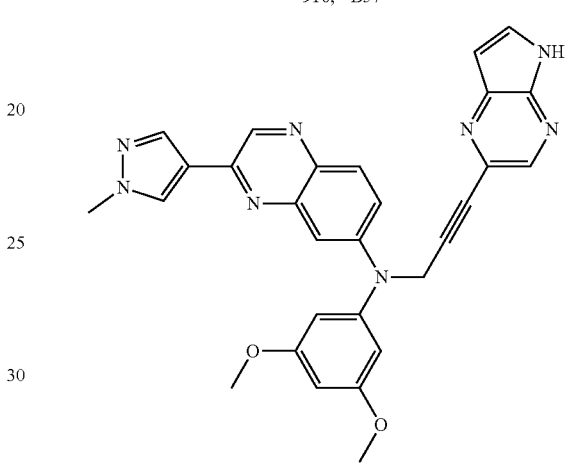
917; =Co47
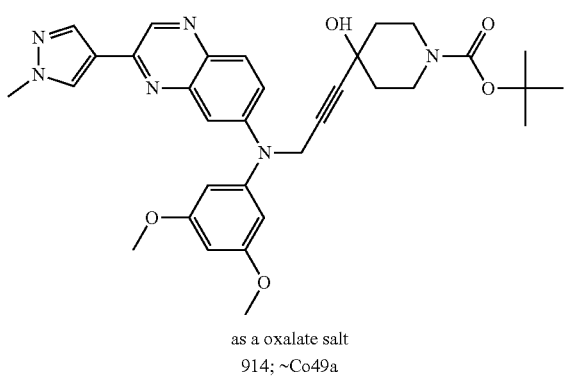
as a oxalate salt
914; ~Co49a
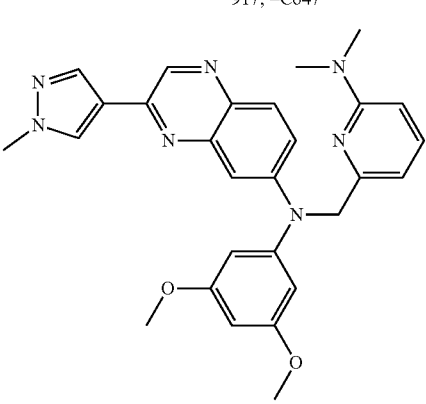
918; ~Co75
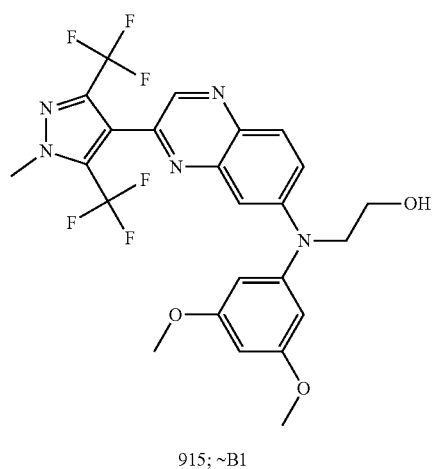
915; ~B1
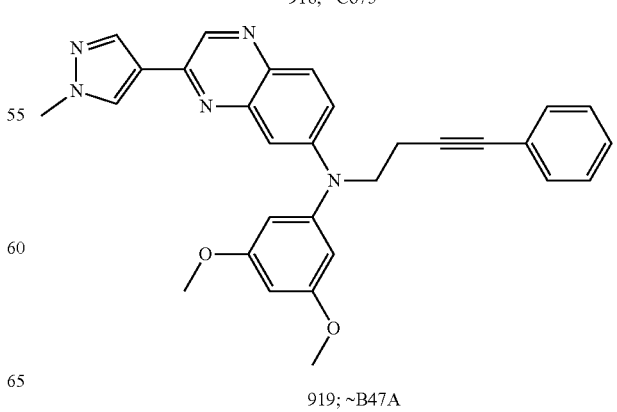
919; ~B47A

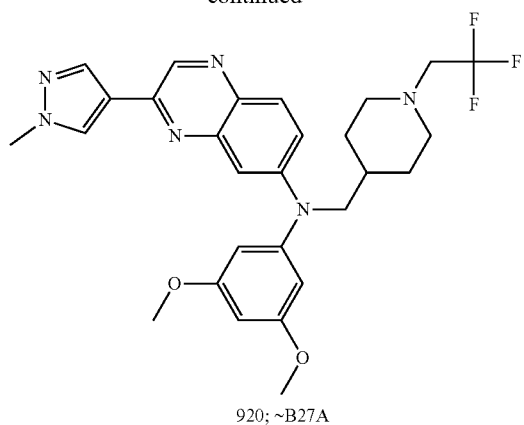
920; ~B27A
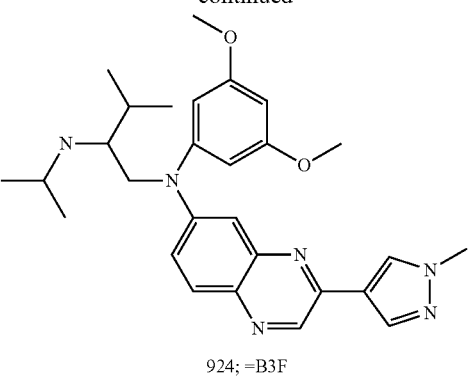
924; =B3F
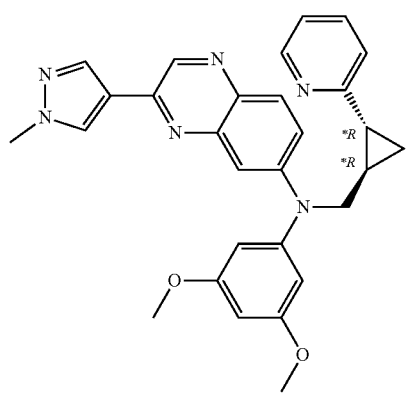
921; ~B5a
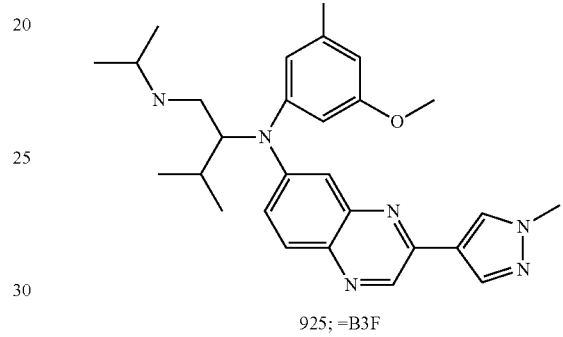
925; =B3F
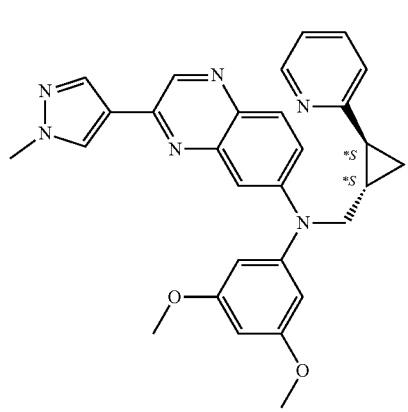
922; ~B5a
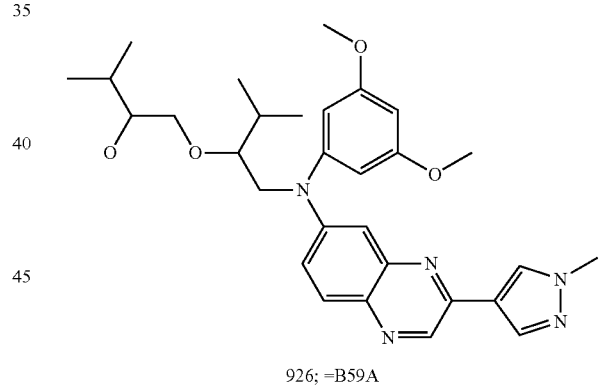
926; =B59A
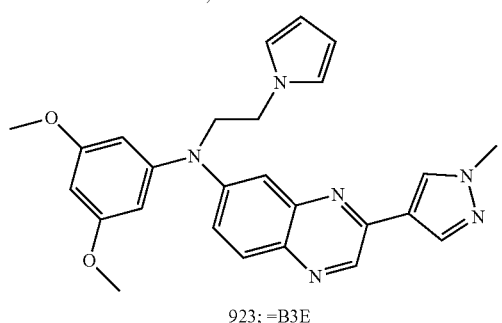
923; =B3E
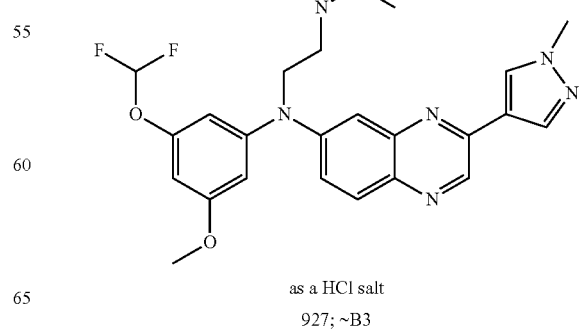
as a HCl salt
927; ~B3

-continued

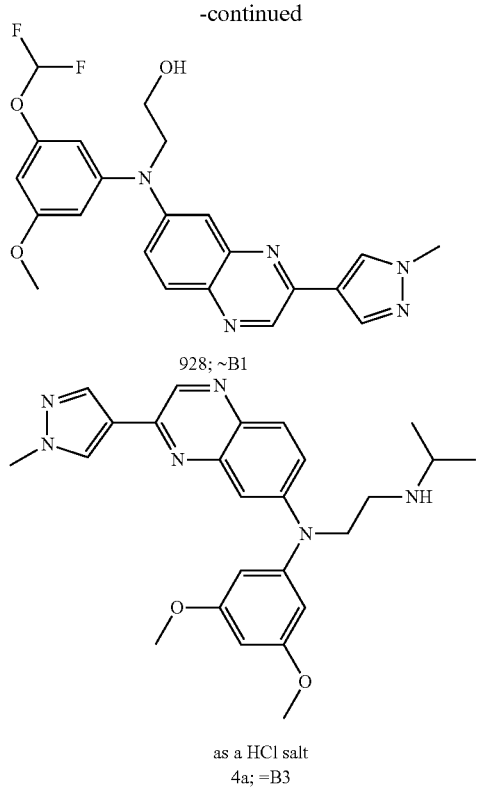

928; ~B1 as a HCl salt
4a; =B3

Analytical Part
LC/GC/NMR
General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

Method 1

In addition to the general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Method 2

In addition to the general procedure A: Column heater was set at 45° C. Reversed phase HPLC was carried out on an Atlantis C18 column (3.5 µm, 4.6×100 mm) with a flow rate of 1.6 ml/min. Two mobile phases (mobile phase A: 70% methanol+30% H$_2$O; mobile phase B: 0.1% formic acid in H$_2$O/methanol 95/5) were employed to run a gradient condition from 100% B to 5% B+95% A in 9 minutes and hold these conditions for 3 minutes. An injection volume of 10 µl was used.

Cone voltage was 10 V for positive ionization mode and 20 V for negative ionization mode.

Method 3

In addition to the general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 µl was used.

Cone voltage was 10 V for positive ionization mode and 20 V for negative ionization mode.

Method 9

In addition to the general procedure A: Reversed phase HPLC was carried out on a Waters Xterra-RP C18 column (3.5 µm, 4.6×100 mm) with a flow rate of 0.8 ml/min. Two mobile phases (mobile phase A: 100% 7 mM ammonium acetate; mobile phase B: 100% acetonitrile) were employed to run a gradient condition from 80% A and 20% B (hold for 0.5 minute) to 90% B in 4.5 minutes, 90% B for 4 minutes and reequilibrated with initial conditions for 3 minutes. An injection volume of 5 ml was used. Cone voltage was 20 V for positive and negative ionization mode. Mass spectra were acquired by scanning from 100 to 1000 in 0.4 seconds using an interscan delay of 0.3 seconds.

Method 10

In addition to the general procedure A: Reversed phase HPLC was carried out on a Xterra-MS C18 column (3.5 µm, 4.6×100 mm) with a flow rate of 0.8 ml/min. Two mobile phases (mobile phase A: 100% 7 mM ammonium acetate; mobile phase B: 100% acetonitrile; were employed to run a gradient condition from 80% A, 20% B (hold for 0.5 minute) to 10% A, 90% B in 4.5 minutes, hold at 10% A and 90% B for 4 minutes and reequilibrated with initial conditions for 3 minutes. An injection volume of 10 ml was used. Cone voltage was 20 V for positive and negative ionization mode. Mass spectra were acquired by scanning from 100 to 1000 in 0.4 seconds using an interscan delay of 0.3 seconds General Procedure B The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Method 4

In addition to the general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in H$_2$O/methanol 95/5; mobile phase B: methanol) were used to run a gradient condition from 95%

A and 5% B to 5% A and 95% B in 1.3 minutes and hold for 0.2 minutes. An injection volume of 0.5 µl was used. Cone voltage was 10 V for positive ionization mode and 20 V for negative ionization mode.

Method 5

In addition to the general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 30 V for positive ionization mode and 30 V for negative ionization mode.

General Procedure C

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 6

In addition to the general procedure C: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

Method 7

In addition to the general procedure C: Reversed phase UPLC was carried out on a Waters Acquity BEH (bridged ethylsiloxane/silica hybrid) C18 column (1.7 µm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 ml was used. Cone voltage was 20V for positive and negative ionization mode. Mass spectra were acquired by scanning from 100 to 1000 in 0.2 seconds using an interscan delay of 0.1 seconds.

General Procedure D

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray mass spectrometer from Waters). Nitrogen was used as the nebulizer gas. Data acquisition was performed with a Waters-Micromass MassLynx-Openlynx data system.

Method 8

In addition to the general procedure D: Reversed phase HPLC was carried out on a Supelco Ascentis Express C18 column (2.7 µm, 3.0×50 mm) with a flow rate of 0.7 ml/min. Two mobile phases (mobile phase A: 100% 7 mM ammonium acetate; mobile phase B: 100% acetonitrile) were employed to run a gradient condition from 80% A and 20% B (hold for 0.5 minute) to 5% A and 95% B in 2.5 minutes, hold for 4.5 minutes and back to the initial conditions in 1.5 minutes and hold for 1 min. An injection volume of 5 □l was used. Cone voltage was 20 V for positive and negative ionization mode. Mass spectra were acquired by scanning from 100 to 1000 in 0.4 seconds using an interscan delay of 0.3 seconds.

TABLE A1 physico-chemical data
If physio-chemical data were generated multiple times for a compound then all data is listed

| Comp No. | Melting Point (° C.) | Kofler (K) or DSC | HPLC Rt (min) | MS M+ (H+) | LC/GC/MS method |
|---|---|---|---|---|---|
| 202 | | | 1.39 | 416 | 4 |
| | | | 1.25 | 416 | 5 |
| 17 | 159 | K | 3.83 | 402 | 6 |
| 203 | 110 | K | 4.66 | 458 | 6 |
| 206 | 101.91 | DSC | 4.15 | 460 | 6 |
| 207 | 126 | K | 3.41 | 459 | 6 |
| | 126 | K | | | |
| | 126 | K | | | |
| 56 | 147.56 | DSC | 3.73 | 446 | 6 |
| | 141.67 | DSC | 3.73 | 446 | 6 |
| | 144 | K | | | |
| 208 | 158 | K | 4.57 | 444 | 6 |
| 209 | 166.2 | DSC | 4.14 | 422 | 6 |
| 210 | 176.79 | DSC | 3.89 | 434 | 6 |
| | 176 | K | | | |
| 211 | 187.05 | DSC | 3.79 | 446 | 6 |
| 1 | 152.97 | DSC | 3.12 | 406 | 6 |
| | 152.4 | DSC | 3.12 | 406 | 6 |
| | 154 | K | | | |
| 212 | 145.81 | DSC | 3.8 | 487 | 6 |
| 213 | 170.82 | DSC | 3.7 | 473 | 6 |
| 214 | 207.88 | DSC | 4.29 | 480 | 6 |
| | 209 | K | | | |
| 215 | 190 | K | 3.8 | 416 | 6 |
| 216 | 162.91 | DSC | 3.54 | 556 | 6 |
| 22 | 108.61 | DSC | 4.52 | 414 | 6 |
| 60 | 90 | K | 3.55 | 485 | 6 |
| 122 | 202.94 | DSC | 3.42 | 415 | 6 |
| 58 | 165 | K | 4.53 | 509 | 6 |
| | 163.09 | DSC | | | |
| 3 | 168 | K | 3.22 | 420 | 6 |
| | 145 | K | 3.23 | 420 | 6 |
| 218 | 204.29 | DSC | 3.59 | 448 | 6 |
| 219 | 215.88 | DSC | 3.77 | 535 | 6 |
| 220 | 94.96 | DSC | 3.67 | 390 | 6 |
| 221 | 123.95 | DSC | 4.02 | 416 | 6 |
| 222 | 142 | K | 4.23 | 404 | 6 |
| 223 | | | 3.69 | 501 | 6 |
| 224 | 128.96 | DSC | 3.6 | 427 | 6 |
| 62 | 220.78 | DSC | 3.64 | 513 | 6 |
| 23 | 134 | K | 3.33 | 487 | 6 |
| 226 | 164.73 | DSC | 4.04 | 501 | 6 |
| 8 | 181 | K | 2.7 | 419 | 6 |
| | 185 | K | 2.75 | 419 | 6 |
| | 179.61 | DSC | | | |

TABLE A1-continued physico-chemical data
If physio-chemical data were generated multiple times for a compound then all data is listed

| Comp No. | Melting Point (° C.) | Kofler (K) or DSC | HPLC Rt (min) | MS M+ (H+) | LC/GC/MS method |
|---|---|---|---|---|---|
| 84 | from: 133.17 to 139.07 | DSC | from 2.65 to 2.67 | 405 | 6 |
| 227 | 165.51 | DSC | 3.87 | 508 | 6 |
| 65 | | | 3.7 | 448 | 6 |
| 228 | 132 | K | 4.31 | 400 | 6 |
| 229 | 123.16 | DSC | 4.01 | 529 | 6 |
| 73 | | | 3.5 | 499 | 6 |
| 231 | 106.81 | DSC | 3.72 | 565 | 6 |
| 59 | 200 | K | 4.08 | 563 | 6 |
| 52 | 159.08 | DSC | 3.99 | 474 | 6 |
| 232 | | | 3.84 | 381 | 6 |
| 64 | | | 2.31 | 420 | 6 |
| 233 | 183.6 | DSC | 2.87 | 436 | 6 |
| 234 | 130 | K | 3.44 | 445 | 6 |
| 130 | 218 | K | 3.54 | 586 | 6 |
| | | DSC | 2.76 | 586 | 7 |
| 235 | 154.8 | DSC | 3.37 | 515 | 6 |
| | 154 | K | | | |
| 69 | 260.14 | DSC | 2.8 | 419 | 6 |
| | >260 | K | 2.84 | 419 | 6 |
| | 263.87 | DSC | | | |
| 236 | | | 1.28 | 438 | 5 |
| | | | 1.28 | 438 | 5 |
| 237 | 80 | K | 4.44 | 420 | 6 |
| 238 | 133.66 | DSC | 2.68 | 449 | 6 |
| 66 | | | 3.95 | 411 | 6 |
| 2 | 169.26 | DSC | 2.94 | 392 | 6 |
| | 169.13 | DSC | 2.94 | 392 | 6 |
| 113 | 177 | K | 3.27 | 420 | 6 |
| 68 | 165 | K | 2.86 | 415 | 6 |
| 239 | 160 | K | 3.48 | 514 | 6 |
| 240 | 132 | K | 3.55 | 529 | 6 |
| | 132.96 | DSC | | | |
| 241 | 167.79 | DSC | 2.97 | 473 | 6 |
| | 149.64 | DSC | 2.96 | 473 | 6 |
| 55 | | | 3.9 | 543 | 6 |
| 242 | 196.25 | DSC | 3.53 | 429 | 6 |
| 243 | 146.13 | DSC | 3.52 | 558 | 6 |
| 244 | 155 | K | 4 | 499 | 6 |
| 245 | 70 | K | 3.37 | 487 | 6 |
| 246 | 149.27 | DSC | 3.78 | 531 | 6 |
| 24 | 80 | K | 3.44 | 446 | 6 |
| 249 | | | 2.63 | 477 | 6 |
| 250 | 104.64 | DSC | 4.13 | 545 | 6 |
| 251 | 127.97 | DSC | 3.7 | 556 | 6 |
| 21 | 204.45 | DSC | 2.86 | 463 | 6 |
| | 205.05 | DSC | 2.86 | 463 | 6 |
| 72 | 120 | K | 3.67 | 513 | 6 |
| 253 | 167.45 | DSC | 3.5 | 503 | 6 |
| 254 | 173.43 | DSC | 3.77 | 517 | 6 |
| 74 | 253 | K | 2.97 | 433 | 6 |
| 70a | 163.31 | DSC | 2.86 | 459 | 6 |
| 256 | 171 | K | 3.69 | 457 | 6 |
| | 173.42 | DSC | | | |
| 26 | 202.6 | DSC | 3.04 | 406 | 6 |
| 257 | 140.28 | DSC | 4.37 | 492 | 6 |
| 75 | 186.76 | DSC | 2.87 | 436 | 6 |
| | 186.1 | DSC | 2.87 | 436 | 6 |
| | | | 2.87 | 436 | 6 |
| 7 | | | 3.31 | 463 | 6 |
| 259 | 163.47 | DSC | 3.14 | 445 | 6 |
| | 156 | K | | | |
| 260 | 188.74 | DSC | 3.03 | 498 | 6 |
| 27 | 176.76 | DSC | 3.94 | 385 | 6 |
| 78 | 162.1 | | 3.38 | 434 | 6 |
| | 161.7 | | 3.38 | 434 | 6 |
| | 165.99 | | 3.17 | 434 | 8 |
| 261 | 180.29 | DSC | 2.79 | 445 | 6 |
| | 183 | K | | | |
| 262 | 130.64 | DSC | 3.21 | 483 | 6 |
| 25 | 245.28 | DSC | 2.96 | 445 | 6 |
| | 259.39 | DSC | 2.96 | 445 | 6 |
| 263 | 168.45 | DSC | 3.74 | 473 | 6 |
| 264 | | | 3.14 | 459 | 6 |
| 265 | 190 | K | 2.51 | 476 | 6 |
| | 186.88 | DSC | | | |
| | 186.88 | DSC | | | |
| 266 | 157.15 | DSC | 2.52 | 476 | 6 |
| 76 | 158.57 | DSC | 3.5 | 418 | 6 |
| 267 | 160.27 | DSC | 4.02 | 552 | 6 |
| 268 | 158.2 | DSC | 3.45 | 512 | 6 |
| | 177.91 | DSC | 3.46 | 512 | 6 |
| 269 | 155.79 | DSC | 4.46 | 444 | 6 |
| 271 | 181.91 | DSC | 3.82 | 523 | 6 |
| 272 | 178.46 | DSC | 2.77 | 433 | 6 |
| | 176.95 | DSC | 2.78 | 433 | 6 |
| | 180 | K | | | |
| 273 | | | 2.73 | 540 | 6 |
| 274 | 176.3 | DSC | 4.45 | 456 | 6 |
| 4 | from 134 to 142 | DSC or K | From 2.95 to 2.99 | 447 | 6 |
| 276 | 188.62 | DSC | 3.12 | 512 | 6 |
| 28 | 142.35 | DSC | 2.98 | 450 | 6 |
| 37 | 154.05 | DSC | 3.55 | 476 | 6 |
| 278 | | | 2.66 | 511 | 6 |
| 279 | 193.59 | DSC | 2.58 | 405 | 6 |
| | 199 | K | | | |
| 281 | | | 2.55 | 503 | 6 |
| 283 | 128.64 | DSC | 2.87 | 487 | 6 |
| 79a + 79 | | | 2.81 | 489 | 6 |
| 602 | 158.84 | DSC | 4.07 | 509 | 6 |
| 80 | 144 | K | 3.33 | 433 | 6 |
| 81 | 199 | K | 3.32 | 433 | 6 |
| 285 | 183.33 | DSC | 2.8 | 459 | 6 |
| | | | 2.83 | 459 | 6 |
| 286 | 114.64 | DSC | 3.24 | 473 | 6 |
| | 114 | K | | | |
| 287 | 156 | K | 3.49 | 445 | 6 |
| | 156.77 | DSC | | | |
| 29 | 80 | K | 3.03 | 459 | 6 |
| 288 | 142 | K | 2.37 | 449 | 6 |
| 291 | | | 2.85 | 489 | 6 |
| 293 | | | 3.96 | 390 | 6 |
| 294 | 184 | K | 2.52 | 391 | 6 |
| | | | 2.54 | 391 | 6 |
| 16 | 80 | K | 3.21 | 432 | 6 |
| 20 | 203.41 | DSC | 3.53 | 529 | 6 |
| 295 | 155.31 | DSC | 2.91 | 565 | 6 |
| 296 | 126.47 | DSC | 3.03 | 503 | 6 |
| 54 | 138 | K | 3.93 | 342 | 6 |
| 297 | 140 | K | 2.45 | 434 | 6 |
| 298 | | | 2.41 | 489 | 6 |
| 299 | 201 | DSC | 3.41 | 475 | 6 |
| 49 | 168.25 | DSC | 2.85 | 490 | 7 |
| 93 | 175.51 | DSC | 2.72 | 419 | 6 |
| | 176.71 | DSC | 2.62 | 419 | 6 |
| 302 | 222.79 | DSC | 2.77 | 503 | 6 |
| 303 | 194.82 | DSC | 2.8 | 474 | 6 |
| 304 | 131.93 | DSC | 2.54 | 449 | 6 |
| | 130 | K | | | |
| 305 | 117.44 | DSC | 4.26 | 500 | 6 |
| 61 | 103.14 | DSC | 3.57 | 459 | 6 |
| 306 | 185 | K | 3.07 | 477 | 6 |
| | 182.27 | DSC | | | |
| 307 | 132 | K | 3.33 | 473 | 6 |
| | 168.8 | DSC | | | |
| 308 | 192 | K | 2.5 | 435 | 6 |
| 311 | 262.42 | DSC | 3.07 | 429 | 6 |
| 312 | 184.29 | DSC | 2.42 | 477 | 6 |

TABLE A1-continued physico-chemical data
If physio-chemical data were generated multiple times for a compound then all data is listed

| Comp No. | Melting Point (° C.) | Kofler (K) or DSC | HPLC Rt (min) | MS M+ (H+) | LC/GC/MS method |
|---|---|---|---|---|---|
| 313 | 176.49 | DSC | 2.95 | 477 | 6 |
|  | 176.31 | DSC | 2.96 | 477 | 6 |
| 314 | 201.43 | DSC | 2.78 | 463 | 6 |
|  | 201 | K |  |  |  |
| 30 | 80 | K | 2.72 | 450 | 6 |
| 38 | 168 | K | 3.63 | 400 | 6 |
| 315 | 139 | K | 2.98 | 424 | 6 |
| 48 | 189.27 | DSC | 3.27 | 497 | 6 |
| 316 | 158.73 | DSC | 3.51 | 526 | 6 |
| 320 | 193.76 | DSC |  |  |  |
| 321 | 265.41 | DSC | 2.8 | 474 | 6 |
| 57 |  |  | 3.29 | 538 | 6 |
| 323 | 166.37 | DSC | 4.19 | 478 | 6 |
| 85 |  | DSC | 4.16 | 448 | 6 |
| 324 | 144.1 | DSC | 3.6 | 473 | 6 |
|  |  |  | 3.6 | 473 | 6 |
| 325 |  |  | 2.76 | 516 | 6 |
| 86 | 195.95 | DSC | 2.52 | 458 | 6 |
| 326 |  |  | 3.07 | 438 | 6 |
| 83 | 141.79 | DSC | 2.89 | 530 | 6 |
| 327 |  |  | 3.86 | 434 | 6 |
| 329 |  |  | 2.87 | 488 | 6 |
| 330 | 139.15 | DSC | 2.96 | 502 | 6 |
| 332 | 141.98 | DSC | 2.92 | 475 | 6 |
| 333 | 150 | K | 2.56 | 503 | 6 |
| 334 | 125 | K | 2.75 | 513 | 6 |
| 335 | 122.79 | DSC | 3.34 | 497 | 6 |
| 336 | 60 | K | 3.9 | 442 | 6 |
|  |  |  | 3.9 | 442 | 6 |
| 338 | 198.91 | DSC | 2.6 | 405 | 6 |
| 339 | 187.62 | DSC | 2.3 | 530 | 6 |
|  | 80 | K |  |  |  |
| 32 |  |  | 2.98 | 445 | 6 |
| 131 | 183.2 | DSC | 3.14 | 476 | 6 |
| 340 | 184.2 | DSC | 3.99 | 522 | 6 |
| 342 | 228.85 | DSC | 3.7 | 487 | 6 |
| 343 | 80 (199) | K | 3.96 | 545 | 6 |
|  |  |  |  |  | (6) |
| 344 | 161.91 | DSC | 3.06 | 477 | 6 |
|  |  |  |  |  | (6) |
| 31 | 244 | K | 2.93 | 459 | 6 |
|  | 250.38 | DSC | 2.93 | 459 | 6 |
|  | 254 | K |  |  |  |
| 345 | 115.62 | DSC | 3.65 | 501 | 6 |
| 346 | 131.39 | DSC | 4.99 | 608 | 6 |
| 347 | 135 | K | 3.1 | 487 | 6 |
| 348 | 169.44 | DSC | 3.8 | 503 | 6 |
| 350 |  |  | 0.83 | 562 | 5 |
| 351 | 110 | K | 2.89 | 516 | 6 |
| 89 | 126.66 | DSC | 3.33 | 446 | 6 |
| 352 |  |  | 2.75 | 530 | 6 |
| 87 | 125 | K | 3.63 | 491 | 6 |
| 353 | 168 | K | 3.46 | 456 | 6 |
| 354 | 70 | K | 4.05 | 458 | 6 |
| 355 | 184 | K | 4.44 | 486 | 6 |
|  | 184.23 | DSC |  |  |  |
| 356 | 154.94 | DSC | 3.71 | 460 | 6 |
| 53 |  |  | 4.19 | 356 | 6 |
| 91 |  |  | 3.44 | 529 | 6 |
| 18 | 132 | K | 3.8 | 386 | 6 |
| 357 | 129.47 | DSC | 3.53 | 503 | 6 |
| 358 | 114.12 | DSC | 4.37 | 486 | 6 |
|  | 110 | K |  |  |  |
| 359 | 114.97 | DSC | 4.34 | 486 | 6 |
|  | 126 | K |  |  |  |
| 360 | 133.89 | DSC | 4.15 | 452 | 6 |
|  | 130 | K |  |  |  |
| 361 | 188 | K | 2.87 | 473 | 6 |
| 362 | 80 | K | 3.77 | 501 | 6 |
| 363 | 172.65 | DSC | 2.69 | 511 | 6 |
|  | 175.38 | DSC | 2.68 | 511 | 6 |
| 364 |  |  | 2.94 | 488 | 6 |
|  |  |  | 2.91 | 488 | 6 |
| 365 | 164.92 | DSC | 2.83 | 433 | 6 |
| 366 |  |  | 3.21 | 501 | 6 |
| 367 |  |  | 3.17 | 487 | 6 |
| 300 | 193.25 | DSC | 3.4 | 480 | 6 |
|  | 191.77 | DSC | 3.4 | 480 | 6 |
|  | 191.77 | DSC | 3.4 | 480 | 6 |
| 368 |  |  | 2.63 | 497 | 6 |
| 369 |  |  | 3.4 | 480 | 6 |
| 370 | 94 | K | 3.51 | 459 | 6 |
| 372 | 176.98 | DSC | 3.3 | 556 | 6 |
| 92 | 148.61 | DSC | 3.67 | 515 | 6 |
|  | 138.58 | DSC | 3.6 | 515 | 6 |
|  | 148.29 | DSC | 3.6 | 515 | 6 |
| 373 | 165 | K | 2.34 | 435 | 6 |
| 374 | 206.48 | DSC | 3.65 | 525 | 6 |
| 375 | 188.66 | DSC | 3.61 | 501 | 6 |
|  | 229.66 | DSC | 3.61 | 501 | 6 |
| 376 | 214.67 | DSC | 3.5 | 586 | 6 |
| 377 | 112.31 | DSC | 3.89 | 495 | 6 |
|  |  |  | 3.25 | 531 | 6 |
| 378 |  |  | 3.26 | 531 | 6 |
| 379 | 80 | K | 2.8 | 488 | 6 |
|  | 146.1 | DSC | 2.83 | 488 | 6 |
| 380 | 70 | K | 2.54 | 449 | 6 |
| 381 | 132.63 | DSC | 3.98 | 512 | 6 |
| 382 | 118 | K | 2.91 | 461 | 6 |
|  | 113 | K | 2.94 | 461 | 6 |
|  | 109.12 | DSC | 2.95 | 461 | 6 |
|  | 112.07 | DSC |  |  |  |
|  | 104.44 | DSC |  |  |  |
| 132 | 132.47 | DSC | 3.31 | 487 | 6 |
|  | 130.95 | DSC | 3.31 | 487 | 6 |
|  | 138 | K |  |  |  |
| 383 | 120 | DSC | 2.92 | 503 | 6 |
|  |  |  | 2.91 | 503 | 6 |
| 384 | 80 | K | 2.99 | 489 | 6 |
| 385 | 119.77 | DSC | 4.93 | 488 | 6 |
| 39 |  |  | 4.33 | 501 | 6 |
| 40 |  |  | 4.66 | 501 | 6 |
| 133 | 126.47 | DSC | 3.55 | 484 | 6 |
|  | 125.21 | DSC | 3.55 | 484 | 6 |
| 386 | 80 | K | 2.98 | 544 | 6 |
| 387 | 162.58 | DSC | 2.45 | 466 | 6 |
| 389 | 156.45 | DSC | 3.75 | 448 | 6 |
|  | 160 | K |  |  |  |
| 390 |  |  | 3.7 | 498 | 6 |
| 391 | 190 | K | 2.63 | 475 | 6 |
| 393 | 193.78 | DSC | 3.22 | 410 | 6 |
| 395 | 118.99 | DSC | 2.83 | 475 | 6 |
| 94 | 115.24 | DSC | 3.1 | 443 | 6 |
|  |  |  | 3.11 | 443 | 6 |
| 396 | 156 | K | 3.14 | 487 | 6 |
| 397 | 132.82 | DSC | 3.24 | 450 | 6 |
| 398 |  |  | 2.96 | 473 | 6 |
| 399 |  |  | 3.12 | 409 | 6 |
| 400 |  |  | 3.12 | 409 | 6 |
| 401 | 138 | K | 3.47 | 408 | 6 |
| 405 | 191.73 | DSC | 3.01 | 406 | 6 |
| 407 | 146 | K | 4.37 | 412 | 6 |
| 408 | 130 | K | 4.1 | 444 | 6 |
| 410 |  |  | 2.83 | 477 | 6 |
| 411 |  |  | 8.92 | 458 | 2 |
|  |  |  | 5.93 | 458 | 1 |
| 412 | 180 | K | 2.85 | 489 | 6 |
| 413 | 146 | K | 3.03 | 507 | 6 |
| 414 |  |  | 3.1 | 451 | 6 |
| 422 | 234.9 | DSC | 3.28 | 420 | 6 |
| 424 |  |  | 3.16 | 440 | 6 |
| 426 |  |  | 2.82 | 447 | 6 |

TABLE A1-continued physico-chemical data
If physio-chemical data were generated multiple times for a compound then all data is listed

| Comp No. | Melting Point (° C.) | Kofler (K) or DSC | HPLC Rt (min) | MS M+ (H+) | LC/GC/MS method |
|---|---|---|---|---|---|
| 428 | | | 0.56 | 432 | 5 |
| 34 | 173.67 | DSC | 2.46 | 462 | 6 |
| 430 | | | 3.78 | 498 | 6 |
| 125 | 99.31 | DSC | 2.58 | 435 | 6 |
| 431 | 147.77 | DSC | 3.99 | 509 | 6 |
| 432 | 251.77 | DSC | 2.79 | 436 | 6 |
| 433 | | | 2.39 | 423 | 6 |
| 434 | | | 2.96 | 487 | 6 |
| 435 | | | 2.89 | 447 | 6 |
| 5 | from 123.12 to 128 | DSC or K | 3.63 to 3.91 | 501 | 8 or 6 |
| 436 | | | 2.86 | 489 | 6 |
| 95a + 95 | | | 3.49 | 559 | 6 |
| 437 | | | 2.66 | 433 | 6 |
| 438 | 140.67 | DSC | 2.44 | 391 | 6 |
| 440 | | | 2.9 | 437 | 6 |
| 441 | | | 3.04 | 481 | 6 |
| 442 | 120.06 | DSC | 3.39 | 461 | 6 |
| 443 | 138.47 | DSC | 2.94 | 450 | 6 |
| 444 | 137.16 | DSC | 2.95 | 450 | 6 |
| 445 | 182.81 | DSC | 3.31 | 473 | 6 |
| | 227.95 | DSC | | | |
| | 227.75 | DSC | | | |
| 447 | | | 3.05 | 447 | 6 |
| 448 | 80 | K | 3.6 | 470 | 6 |
| 449 | 118.96 | DSC | 3.05 | 447 | 6 |
| 450 | 224.87 | DSC | 3.6 | 470 | 6 |
| 452 | | | 3.13 | 461 | 6 |
| 453 | | | 3.04 | 396 | 6 |
| 134 | 184 | DSC | 2.71 | 504 | 6 |
| | 194 | K | 2.72 | 504 | 6 |
| 454 | 244.06 | DSC | 3.25 | 545 | 8 |
| 455 | 155 | K | 3.13 | 586 | 8 |
| 456 | 143.58 | DSC | 2.9 | 502 | 8 |
| 96 | 168.08 | DSC | 2.94 | 501 | 8 |
| 457 | | | 3.2 | 571 | 6 |
| 458 | 171.31 | DSC | 3.34 | 470 | 6 |
| 44a + 44 | 215.29 | DSC | 3.84 | 495 | 6 |
| 459 | 99.32 | DSC | 4.23 | 593 | 6 |
| 460 | | | 3.14 | 438 | 6 |
| 463 | | | 3.72 | 568 | 6 |
| 464 | | | 4.39 | 555 | 6 |
| 465 | 141.31 | DSC | 2.91 | 473 | 6 |
| 467 | 135 | K | 2.89 | 503 | 6 |
| 468 | 130 | K | 2.84 | 503 | 6 |
| 469 | 135 | K | 3.05 | 487 | 6 |
| 471 | 140 | K | 3.14 | 489 | 6 |
| 473 | 140 | K | 3.14 | 489 | 6 |
| 474 | | | 3.56 | 590 | 6 |
| 135 | 194 | DSC K | 3.13 | 461 | 6 |
| 475 | 152.98 | DSC | 3.18 | 420 | 6 |
| 476 | 170.9 | DSC | 3.6 | 448 | 6 |
| 477 | 80 | K | 3.05 | 380 | 6 |
| 478 | 70 | K | 2.93 | 407 | 6 |
| 136 | 166 | DSC | 3.14 | 531 | 6 |
| 480 | | DSC | 3.13 | 515 | 6 |
| 97 | 187.39 | DSC | 2.87 | 436 | 6 |
| | 187.8 | DSC | 2.87 | 436 | 6 |
| 98 | 186.98 | DSC | 2.87 | 436 | 6 |
| | 186.27 | DSC | 2.87 | 436 | 6 |
| 481 | 172.5 | DSC | 3.67 | 474 | 6 |
| 482 | 106 | K | 2.82 | 419 | 6 |
| 483 | 134 | K | 3.01 | 433 | 6 |
| 484 | | | 3.03 | 461 | 6 |
| 485 | | | 0.62 | 474 | 5 |
| 487 | 143.13 | DSC | 4.82 | 488 | 1 |
| 488 | 96.65 | DSC | 2.73 | 393 | 6 |
| | | | 2.73 | 393 | 6 |
| 489 | 128.03 | DSC | 3.4 | 551 | 6 |
| 490 | 223.8 | DSC | 2.63 | 449 | 6 |
| 493 | 87.6 | DSC | 3.05 | 435 | 6 |
| 494 | 135.12 | DSC | 3.02 | 447 | 6 |
| 495 | | | 3.83 | 486 | 6 |
| 137 | | | 2.8 | 433 | 6 |
| 499 | 130 | K | 3.34 | 501 | 6 |
| 500 | | | 0.69 | 421 | 5 |
| 501 | 154.26 | DSC | 2.63 | 449 | 6 |
| 502 | 153.17 | DSC | 2.65 | 449 | 6 |
| 503 | | | 3.48 | 511 | 6 |
| 139 | | | 3.53 | 517 | 6 |
| 504 | 101.17 | DSC | 2.53 | 476 | 6 |
| | 104.18 | DSC | 2.53 | 476 | 6 |
| 140 | 123.19 | DSC | 3.25 | 458 | 6 |
| | 128.99 | DSC | 3.26 | 458 | 6 |
| 506 | | | 3.42 | 463 | 6 |
| 507 | | | 3.36 | 463 | 6 |
| 508 | 165.94 | DSC | 3.49 | 446 | 6 |
| 509 | | | 3.42 | 634 | 6 |
| 510 | 70 | K | 2.77 | 407 | 6 |
| 141 | 150 | K | 3.29 | 448 | 8 |
| | 171.28 | DSC | 3.54 | 448 | 6 |
| | 156.7 | DSC | | | |
| 511 | | | 0.74 | 502 | 5 |
| 512 | 180 | K | 3.41 | 473 | 6 |
| 513 | 160.65 | DSC | 3.55 | 469 | 6 |
| 514 | 139 | K | 3.3 | 489 | 6 |
| | 135.37 | DSC | | | |
| 515 | | | 4.78 | 516 | 3 |
| 516 | | | 0.98 | 471 | 5 |
| | | | 1.08 | 471 | 4 |
| 35 | | | 0.92 | 416 | 5 |
| 517 | 187.18 | DSC | | | |
| 518 | 187.66 | DSC | 3.01 | 479 | 6 |
| 519 | 163.93 | DSC | 3.08 | 516 | 6 |
| 102 | | | 0.89 | 487 | 4 |
| 521 | | | 0.91 | 475 | 5 |
| 522 | 134.16 | DSC | 2.99 | 503 | 6 |
| 523 | 125.77 | DSC | 3.53 | 517 | 6 |
| 142 | 126.8 | DSC | 3.53 | 517 | 6 |
| 524 | 122.12 | DSC | 3 | 433 | 6 |
| 525 | 223.34 | DSC | 3.32 | 514 | 6 |
| 526 | 234.8 | DSC | 3.32 | 514 | 6 |
| 527 | 144 | K | 3.19 | 484 | 6 |
| | 145.21 | | | | |
| 143 | 184.72 | DSC | 3.15 | 516 | 6 |
| 528 | 110.16 | DSC | 2.86 | 518 | 6 |
| 529 | 141.1 | DSC | 3.06 | 459 | 6 |
| 530 | 132.62 | DSC | 2.96 | 488 | 6 |
| | 132.62 | DSC | | | |
| 10 | | | 4.28 | 551 | 6 |
| 531 | | | 3.53 | 489 | 6 |
| 36 | 160.14 | DSC | 3.38 | 418 | 6 |
| 532 | 164 | K | 3.06 | 470 | 6 |
| | 165 | DSC | | | |
| 533 | 180.45 | DSC | 2.71 | 449 | 6 |
| | 181.17 | DSC | | | |
| 534 | 205.99 | DSC | 3.6 | 475 | 6 |
| 535 | 180 | K | 3.4 | 473 | 6 |
| | 179.19 | DSC | | | |
| 536 | 209.5 | DSC | 3.72 | 461 | 6 |
| 537 | 201.67 | DSC | 3.7 | 461 | 6 |
| 538 | | | 4.04 | 390 | 6 |
| 144 | 225.35 | DSC | 2.96 | 488 | 6 |
| | 222 | K | | | |
| 539 | | | 0.64 | 473 | 5 |
| 603 | | | 1.01 | | 5 |
| 540 | 130.63 | DSC | 3.19 | 505 | 6 |
| 541 | 162.74 | DSC | 2.99 | 530 | 6 |
| 542 | 147.16 | DSC | 3.85 | 487 | 6 |
| | 155 | K | | | |

TABLE A1-continued physico-chemical data
If physio-chemical data were generated multiple times for a compound then all data is listed

| Comp No. | Melting Point (° C.) | Kofler (K) or DSC | HPLC Rt (min) | MS M+ (H+) | LC/GC/MS method |
|---|---|---|---|---|---|
| 543 | 149.47 | DSC | 3.04 | 517 | 6 |
| 544 | | | 3.43 | 542 | 6 |
| 41 | 168 | K | 2.86 | 437 | 6 |
| | 169.24 | DSC | | | |
| 33 | 83 | K | 3.02 | 501 | 6 |
| 43 | 107 | K | 3.08 | 501 | 6 |
| 546 | 135 | K | 3.13 | 501 | 6 |
| 547 | 217 | K | 3.22 | 473 | 6 |
| 548 | 135 | K | 3.13 | 501 | 6 |
| 551 | | | 1.02 | 515 | 5 |
| 552 | | | 0.87 | 500 | 4 |
| | | | 0.63 | 500 | 5 |
| 553 | | | 3.22 | 489 | 6 |
| 554 | | | 3.48 | 491 | 6 |
| 556 | | | 2.72 | 396 | 6 |
| 557 | 189 | K | 3.42 | 470 | 6 |
| 558 | 94 | K | 3 | 449 | 6 |
| 103 | 140 | K | 3.94 | 512 | 6 |
| 559 | 98.59 | DSC | 2.79 | 477 | 6 |
| 145 | 94.44 | DSC | 2.8 | 477 | 6 |
| 129 | | | 1.1 | 495 | 4 |
| | | | 1.13 | 495 | 5 |
| 111 | | | 1.27 | 593 | 5 |
| | | | 1.33 | 593 | 4 |
| | | | 1.27 | 593 | 5 |
| | | | 1.27 | 593 | 5 |
| | | | 1.28 | 593 | 5 |
| 560 | | | 0.74 | 547 | 5 |
| 561 | 219 | K | 3.19 | 475 | 6 |
| 562 | | | 3.8 | 487 | 6 |
| 563 | 193 | K | 3.2 | 498 | 6 |
| | 200.75 | DSC | | | |
| 564 | | | 2.99 | 567 | 6 |
| 565 | 152 | K | 3.34 | 408 | 6 |
| 566 | 183 | K | 3.09 | 484 | 6 |
| 567 | | | 3.1 | 484 | 6 |
| 568 | 164.5 | DSC | 3.4 | 453 | 6 |
| | 167 | K | | | |
| 569 | 139 | K | 3.38 | 453 | 6 |
| | 139.45 | DSC | | | |
| 146 | 163 | K | 3.36 | 454 | 6 |
| | 158.48 | DSC | | | |
| 110 | | | 0.78 | 503 | 5 |
| 570 | | | 0.88 | 489 | 5 |
| 575 | | | 0.71 | 475 | 5 |
| 576 | | | 1.36 | 579 | 5 |
| 577 | | | 3.57 | 487 | 6 |
| 578 | | | 3.5 | 485 | 6 |
| 581 | | | 3.17 | 501 | 6 |
| 582 | 127 | K | 4.03 | 489 | 6 |
| 583 | 136.49 | DSC | 3 | 599 | 6 |
| 584 | 140 | K | 4.07 | 531 | 6 |
| 585 | | | 2.87 | 488 | 6 |
| 586 | | | 3.82 | 471 | 6 |
| 105 | 135 | K | 3.94 | 512 | 6 |
| 147 | | | 4.25 | 529 | 6 |
| 592 | 194 | K | 2.89 | 421 | 6 |
| 593 | 168 | K | 4.01 | 502 | 6 |
| 148 | 149.13 | DSC | 3.67 | 474 | 6 |
| 149 | 146.61 | DSC | 3.67 | 474 | 6 |
| 100 | 73 | K | 3.63 | 549 | 6 |
| | | | 3.63 | 549 | 6 |
| 101 | 186 | K | 3.16 | 456 | 6 |
| 14 + 14a | 110 | K | 3.62 | 478 | 6 |
| 594 | 214.83 | DSC | | | |
| 595 | 105 | K | 3.13 | 470 | 8 |
| 15 | 114.76 | DSC | 3.62 | 487 | 6 |
| 604 | 157 | DSC | 3.16 | 489 | 8 |
| 608 | 159 | DSC | 2.66 | 419 | 8 |
| 609 | 155 | DSC | 2.65 | 419 | 8 |
| 610 | 150 | DSC | 2.66 | 419 | 8 |
| 611 | 148 | DSC | 2.68 | 419 | 8 |
| 697 | 171 | DSC | 2.97 | 461 | 6 |
| 698 | 111 | DSC | 3.03 | 461 | 6 |
| 699 | 150 | DSC | 2.99 | 461 | 6 |
| 700 | 133 | DSC | 2.85 | 477 | 7 |
| 613 | | | 1.26 | 402 | 4 |
| 701 | 68 | DSC | 3.18 | 503 | 6 |
| 702 | 129 | DSC | 3.89 | 501 | 6 |
| 703 | 80 | K | 3.92 | 501 | 6 |
| 645 | 188 | DSC | 2.44 | 433 | 6 |
| 704 | 151 | DSC | 3.74 | 487 | 6 |
| 615 | 134 | DSC | 2.62 | 519 | 6 |
| 646 | 125 | K | 2.51 | 392 | 6 |
| 648 | 196 | DSC | 3.42 | 515 | 6 |
| 705 | 135 | DSC | 3.3 | 487 | 6 |
| 706 | 182 | K | 2.58 | 392 | 6 |
| 707 | 186 | K | 2.23 | 391 | 6 |
| 647 | 133 | K | 2.3 | 419 | 6 |
| 708 | 152 | K | 3.1 | 473 | 6 |
| 709 | 175 | K | 3.25 | 544 | 6 |
| 710 | 206 | DSC | 3.24 | 461 | 6 |
| 711 | 166 | DSC | 3.15 | 426 | 6 |
| 712 | 124 | DSC | 3.02 | 376 | 6 |
| 616 | 170 | K | 2.42 | 246 | 6 |
| 713 | 127 | K | 3.83 | 507 | 6 |
| 619 | 210 | K | 3.07 | 505 | 6 |
| 714 | 128 | K | 3.62 | 477 | 6 |
| 690 | 138 | K | 3.63 | 477 | 6 |
| 716 | 247 | DSC | 2.81 | 417 | 6 |
| 717 | 125 | DSC | 3.59 | 483 | 6 |
| 718 | 103 | DSC | 3.66 | 501 | 6 |
| 719 | 119 | DSC | 4.59 | 509 | 6 |
| 720 | 175 | DSC | | | |
| 721 | | | 0.67 | 528 | 4 |
| 722 | 138 | K | 3.57 | 455 | 6 |
| 724 | 176 | DSC | 3.07 | 433 | 6 |
| 620 | 114 | K | 3.89 | 587 | 6 |
| 725 | 227 | DSC | 3.11 | 474 | 6 |
| 727 | 109 | DSC | 3.01 | 461 | 6 |
| 728 | 109 | DSC | 3.77 | 497 | 6 |
| 621 | >260 | K | 2.7 | 486 | 6 |
| 729 | 183 | DSC | 2.99 | 515 | 6 |
| 730 | 139 | K | 3.4 | 501 | 6 |
| 731 | 237 | DSC | 339 | 478 | 6 |
| 732 | 160 | K | 3.46 | 458 | 6 |
| 733 | 70 | K | | | |
| 734 | 178 | K | 3.97 | 507 | 6 |
| 624 | 147 | K | 2.65 | 475 | 6 |
| 735 | 143 | DSC | 3.56 | 408 | 6 |
| 736 | 68 | K | 2.39 | 450 | 7 |
| 625 | 104 | K | 3.06 | 575 | 7 |
| 737 | 156 | DSC | 2.28 | 489 | 7 |
| 652 | 142 | DSC | 2.84 | 507 | 7 |
| 650 | 66 | K | 2.98 | 616 | 7 |
| 738 | 197 | DSC | 2.99 | 502 | 7 |
| 739 | 179 | DSC | 2.99 | 502 | 7 |
| 740 | 167 | DSC | 2.97 | 483 | 7 |
| 651 | 122 | K | 2.05 | 516 | 7 |
| 617 | 149 | DSC | 2.44 | 416 | 7 |
| 741 | 85 | K | 3.34 | 506 | 7 |
| 742 | 115 | K | 3.2 | 507 | 7 |
| 618 | 139 | DSC | 2.3 | 457 | 7 |
| 743 | 135 | DSC | 2.83 | 481 | 7 |
| 744 | 200 | K | 2.23 | 530 | 7 |
| 745 | 110 | K | 3.36 | 476 | 7 |
| 746 | 62 | K | 2.44 | 464 | 7 |
| 747 | 68 | K | 2.67 | 507 | 7 |
| 689 | 203 | DSC | 2.77 | 492 | 7 |
| 749 | 86 | K | 2.64 | 448 | 7 |
| 622 | 190 | K | 2.57 | 434 | 7 |
| 688 | 175 | DSC | 6.04 | 508 | 7 |
| 750 | 148 | DSC | 2.61 | 493 | 7 |
| 655 | | | 8.11 | 506 | 10 |

TABLE A1-continued physico-chemical data
If physio-chemical data were generated multiple times for a compound then all data is listed

| Comp No. | Melting Point (° C.) | Kofler (K) or DSC | HPLC Rt (min) | MS M+ (H$^+$) | LC/GC/MS method |
|---|---|---|---|---|---|
| 751 | | | 2.99 | 585 | 7 |
| 752 | 169 | K | 3.01 | 502 | 7 |
| 753 | 155 | DSC | 3.01 | 491 | 7 |
| 754 | 167 | K | 2.19 | 499 | 7 |
| 755 | 152 | K | 2.72 | 434 | 7 |
| 756 | 118 | K | 2.23 | 461 | 7 |
| 757 | 126 | K | 2.64 | 461 | 7 |
| 758 | | | 2.22 | 485 | 7 |
| 653 | 146 | DSC | 311 | 511 | 7 |
| 759 | 180 | K | 2.85 | 502 | 7 |
| 760 | 221 | K | 2.51 | 507 | 7 |
| 623 | 133 | K | 2.43 | 475 | 7 |
| 761 | 119 | K | 3.2 | 515 | 7 |
| 762 | 137 | K | 3.18 | 507 | 7 |
| 763 | 176 | K | 2.27 | 463 | 7 |
| 764 | 126 | K | 2.56 | 475 | 7 |
| 765 | 199 | DSC | 2.65 | 492 | 7 |
| 766 | 125 | DSC | 2.93 | 507 | 7 |
| 767 | 220 | K | 2.9 | 527 | 7 |
| 768 | 158 | DSC | 2.79 | 515 | 7 |
| 770 | 130 | K | 2.27 | 477 | 7 |
| 644 | 96 | K | 2.06 | 603 | 7 |
| 656 | 95 | K | 2.83 | 478 | 7 |
| 657 | 110 | K | 2.83 | 478 | 7 |
| 658 | 152 | DSC | 3.19 | 552 | 7 |
| 771 | 93 | K | 2.56 | 492 | 7 |
| 772 | 154 | DSC | 2.84 | 493 | 7 |
| 773 | | | 2.3 | 504 | 7 |
| 774 | 80 | K | 3 | 513 | 7 |
| 627 | | | 2.2 | 471 | 7 |
| 775 | 133 | K | 2.51 | 432 | 7 |
| 776 | | | 6.62 | 428 | 9 |
| 777 | 119 | DSC | 3.11 | 535 | 7 |
| 778 | 148 | K | 3.13 | 516 | 7 |
| 779 | 148 | K | 3.13 | 516 | 7 |
| 628 | 122 | K | 2.84 | 492 | 7 |
| 629 | 124 | K | 2.84 | 492 | 7 |
| 780 | 188 | K | 3.12 | 502 | 7 |
| 781 | 186 | K | 3.12 | 502 | 7 |
| 782 | 170 | K | 4.31 | 617 | 7 |
| 634 | 80 | K | 621 | 491 | 7 |
| 783 | 220 | K | 6.05 | 468 | 7 |
| 784 | 163 | DSC | 2.61 | 493 | 7 |
| 785 | 190 | K | 2.83 | 575 | 7 |
| 786 | 125 | DSC | 2.79 | 492 | 7 |
| 787 | 181 | DSC | 2.95 | 503 | 7 |
| 788 | 146 | K | 2.57 | 507 | 7 |
| 789 | 204 | K | 2.49 | 520 | 7 |
| 790 | 67 | K | 3.47 | 583 | 7 |
| 791 | 130 | K | 2.94 | 576 | 7 |
| 792 | 153 | DSC | 2.82 | 478 | 7 |
| 793 | 161 | DSC | 3 | 508 | 7 |
| 631 | 194 | DSC | 2.39 | 483 | 7 |
| 794 | | | 2.6 | 500 | 7 |
| 795 | 182 | K | 2.95 | 507 | 7 |
| 796 | 189 | DSC | 3.04 | 508 | 7 |
| 797 | | | 3.18 | 443 | 8 |
| 798 | | | 2.62 | 486 | 7 |
| 659 | 106 | DSC | 3.05 | 484 | 7 |
| 662 | 122 | K | 3.07 | 512 | 7 |
| 799 | 114 | DSC | 3.05 | 510 | 7 |
| 661 | 154 | DSC | 2.47 | 518 | 7 |
| 660 | 151 | DSC | 2.47 | 518 | 7 |
| 633 | 130 | DSC | 2.69 | 477 | 7 |
| 800 | 134 | DSC | 3.05 | 512 | 7 |
| 801 | 127 | DSC | 3.21 | 514 | 7 |
| 802 | 80 | K | 2.19 | 493 | 7 |
| 803 | 80 | K | 2.19 | 493 | 7 |
| 636 | 80 | K | 3.35 | 493 | 7 |
| 637 | >260 | K | 3.07 | 493 | 7 |
| 804 | 195 | DSC | 3.1 | 522 | 7 |
| 805 | 156 | DSC | 2.91 | 535 | 7 |
| 806 | 182 | K | 3.19 | 536 | 7 |
| 807 | 96 | K | 3.01 | 509 | 7 |
| 808 | 162 | DSC | 3.25 | 509 | 7 |
| 809 | 150 | DSC | 2.93 | 506 | 7 |
| 810 | 131 | DSC | 2.76 | 482 | 7 |
| 635 | 111 | DSC | 3.11 | 495 | 7 |
| 811 | 127 | DSC | 3.08 | 511 | 7 |
| 812 | 170 | DSC | 2.65 | 454 | 7 |
| 813 | 166 | K | 2.4 | 442 | 7 |
| 814 | 160 | DSC | 2.98 | 495 | 7 |
| 815 | 123 | DSC | 3.24 | 483 | 7 |
| 816 | 176 | DSC | 3.12 | 555 | 7 |
| 817 | 155 | DSC | 3.01 | 491 | 7 |
| 640 | 241 | DSC | 2.71 | 506 | 7 |
| 819 | 80 | K | 2.96 | 480 | 7 |
| 687 | 162 | DSC | 2.23 | 483 | 7 |
| 820 | 161 | DSC | 3.11 | 545 | 7 |
| 632 | 157 | DSC | 2.59 | 430 | 7 |
| 821 | 127 | K | 296 | 537 | 7 |
| 822 | 135 | K | 2.78 | 436 | 7 |
| 823 | 218 | DSC | 2.53 | 526 | 7 |
| 824 | 212 | DSC | 2.82 | 510 | 7 |
| 825 | 237 | DSC | 2.55 | 492 | 7 |
| 826 | 202 | DSC | 2.74 | 543 | 7 |
| 827 | 187 | DSC | 2.82 | 544 | 7 |
| 828 | 209 | DSC | 2.56 | 468 | 7 |
| 829 | 154 | DSC | 3.24 | 536 | 7 |
| 830 | 241 | DSC | 2.65 | 527 | 7 |
| 663 | 200 | DSC | 2.38 | 498 | 7 |
| 664 | 80 | K | 2.77 | 469 | 7 |
| 831 | 178 | DSC | 2.84 | 536 | 7 |
| 832 | 111 | DSC | 3.67 | 482 | 7 |
| 833 | 153 | DSC | 2.79 | 493 | 7 |
| 834 | 198 | DSC | 2.63 | 475 | 7 |
| 835 | 144 | DSC | 3.24 | 552 | 7 |
| 837 | | | 2.63 | 472 | 7 |
| 641 | 155 | K | 2.27 | 476 | 7 |
| 642 | 127 | DSC | 2.36 | 486 | 7 |
| 838 | 171 | DSC | 2.28 | 462 | 7 |
| 839 | 126 | DSC | 3.49 | 567 | 7 |
| 840 | 158 | DSC | 2.44 | 517 | 7 |
| 841 | | | 3.08 | 463 | 7 |
| 842 | 154 | DSC | 3.24 | 553 | 7 |
| 665 | 206 | K | 3.3 | 516 | 7 |
| 643 | 160 | K | 2.4 | 503 | 7 |
| 836 | | | 2.57 | 496 | 7 |
| 606 | 142 | K | 3.25 | 420 | 6 |
| 666 | 163 | K | 2.68 | 516 | 7 |
| 844 | 125 | K | 2.68 | 530 | 7 |
| 845 | 167 | DSC | 3.18 | 512 | 7 |
| 846 | 170 | K | 2.49 | 477 | 6 |
| 847 | | | 0.79 | 435 | 5 |
| 667 | 181 | DSC | 3.07 | 471 | 7 |
| 848 | 223 | K | 3.13 | 496 | 7 |
| 849 | 80 | K | 3.11 | 453 | 7 |
| 850 | 142 | DSC | 3.67 | 513 | 7 |
| 851 | 137 | DSC | 4 | 543 | 7 |
| 669 | 122 | DSC | 3.55 | 526 | 7 |
| 852 | 233 | K | 3.43 | 496 | 7 |
| 853 | 254 | K | 3.12 | 496 | 7 |
| 670 | 157 | K | 3.03 | 461 | 6 |
| 855 | | | 1.01 | 501 | 4 |
| | | | 0.86 | 501 | 5 |
| 696 | 188 | K | 3.07 | 456 | 6 |
| 856 | 97 | K | 2.96 | 482 | 6 |
| 857 | 180 | K | 3.43 | 487 | 6 |
| 671 | 144 | DSC | 2.97 | 501 | 6 |
| 858 | 154 | K | 3.58 | 470 | 6 |
| 673 | 181 | DSC | 3.76 | 482 | 6 |
| | 180 | K | | | |
| 676 | 88 | K | 3.71 | 503 | 6 |
| 859 | 80 | K | 3.22 | 485 | 6 |

TABLE A1-continued physico-chemical data
If physio-chemical data were generated multiple times for a compound then all data is listed

| Comp No. | Melting Point (° C.) | Kofler (K) or DSC | HPLC Rt (min) | MS M+ (H+) | LC/GC/MS method |
|---|---|---|---|---|---|
| 860 | 151 | DSC | 3.21 | 485 | 6 |
| 678 | 148 | DSC | 2.27 | 539 | 7 |
|  |  |  | 2.87 | 539 | 6 |
| 680 | 167 | DSC | 2.58 | 460 | 6 |
| 861 | 156 | K | 3.22 | 447 | 6 |
| 691 | 99 | DSC | 2.17 | 477 | 7 |
|  |  |  | 2.73 | 477 | 6 |
| 862 | 178 | K | 3.44 | 573 | 6 |
| 682 | 149 | K | 2.86 | 461 | 6 |
| 863 | 170 | K | 3.77 | 462 | 6 |
| 864 | 154 | K | 3.77 | 462 | 6 |
| 865 | 146 | DSC | 3.81 | 498 | 6 |
| 866 | 144 | DSC | 3.81 | 498 | 6 |
| 679 |  |  | 2.99 | 491 | 6 |
| 693 | 151 | DSC | 2.79 | 502 | 6 |
| 867 | 178 | K | 2.98 | 424 | 6 |
| 868 | 178 | K | 2.98 | 424 | 6 |
| 694 | 197 | DSC | 3.49 | 501 | 6 |
| 869 | 138 | K | 3.46 | 489 | 6 |
| 692 | 157 | K | 3.19 | 498 | 6 |
| 675 | 187 | K | 3.44 | 517 | 6 |
| 870 | 173 | K | 3.34 | 456 | 6 |
| 685 | 203 | K | 3.17 | 442 | 6 |
| 871 | 154 | DSC | 3.05 | 450 | 6 |
| 872 | 89 | DSC | 4.08 | 515 | 6 |
| 677 | 177 | DSC | 3.44 | 435 | 6 |
| 873 | 183 | DSC | 3.07 | 457 | 6 |
| 874 | 107 | K | 3.24 | 450 | 6 |
| 875 | 98 | K | 3.24 | 450 | 6 |
| 877 | 213 | DSC | 2.94 | 500 | 6 |
| 878 | 143 | DSC | 3.52 | 503 | 6 |
| 879 |  |  | 0.89 | 531 | 5 |
| 880 | 135 | DSC | 3.45 | 501 | 6 |
| 668 | 137 | DSC |  |  |  |
| 672 | 194 | DSC |  |  |  |
| 683 | 123 | DSC |  |  |  |
| 881 | 156.5 | DSC | 4.53 | 440 | 6 |
| 882 | 164 | K | 4.46 | 454 | 6 |
| 883 | 194 | DSC | 4.35 | 399 | 6 |
| 884 | 80 | K | 3.58 | 483 | 6 |
| 885 | 148 | DSC | 5.13 | 640 | 6 |
| 886 | 130 | K | 3.97 | 455 | 6 |
| 887 | 245 | DSC | 2.81 | 457 | 6 |
| 888 |  |  | 2.96 | 500 | 6 |
| 889 |  |  | 0.6 |  | 5 |
| 890 |  |  | 6.18 | 444 | 1 |
| 891 | 186 | K | 3.89 | 489 | 6 |
| 892 | 157 | K | 4.32 | 534 | 6 |
| 893 |  |  | 1.05 | 443 | 4 |
| 894 |  |  | 3.58 | 489 | 6 |
| 895 | 182 | DSC | 3.56 | 470 | 6 |
| 896 | 166 | DSC | 2.74 | 419 | 6 |
| 897 | 153 | DSC | 2.75 | 419 | 6 |
| 898 |  |  | 6.24 | 430 | 1 |
| 899 |  |  | 3.6 | 480 | 6 |
| 900 | 214 | DSC | 3.47 | 475 | 6 |
| 901 | 208 | DSC | 3.02 | 433 | 6 |
| 902 | >260 | K | 2.34 | 470 | 6 |
| 903 | 153 | DSC | 3.65 | 513 | 6 |
| 904 | 181 | DSC | 3.07 | 471 | 6 |
| 905 |  |  | 0.98 | 457 | 5 |
| 906 |  |  | 2.83 | 517 | 6 |
| 907 |  |  | 2.97 | 491 | 7 |
| 908 |  |  | 3.19 | 501 | 7 |
| 909 |  |  | 2.99 | 491 | 7 |
| 910 |  |  | 3.18 | 501 | 7 |
| 911 |  |  | 3.13 | 501 | 7 |
| 912 | 102 | K | 2.89 | 474 | 7 |
| 913 | 170 | K | 3.1 | 538 | 7 |
| 914 | 166 | K | 3.01 | 599 | 7 |
| 915 |  |  | 3.22 | 542 | 7 |
| 916 | 70 | K | 3.53 | 552 | 7 |
| 917 | 222 | DSC | 2.73 | 517 | 7 |
| 918 |  |  | 3.36 | 496 | 7 |
| 919 | 130 | DSC | 3.5 | 490 | 7 |
| 920 | 123.5 | DSC | 3.39 | 541 | 7 |
| 921 | 123 | DSC | 3.07 | 493 | 7 |
| 922 | 123 | DSC | 3.07 | 493 | 7 |
| 927 | 152 | K | 2.52 | 483 | 7 |
| 928 | 130 | K | 5.42 | 442 | 9 |

NMR Data

The below NMR experiments were carried out using a Bruker Avance 500 and a Bruker Avance DRX 400 spectrometers at ambient temperature, using internal deuterium lock and equipped with reverse triple-resonance ($^1$H, $^{13}$C, $^{15}$N TXI) probe head for the 500 MHz and with reverse double-resonance ($^1$H, $^{13}$C, SEI) probe head for the 400 MHz. Chemical shifts (δ) are reported in parts per million (ppm).

Compound 131

$^1$H NMR (500 MHz, DMSO-d$_6$) δ 9.01 (s, 1H), 8.60 (s, 1H), 8.28 (s, 1H), 7.79 (d, J=9.1 Hz, 1H), 7.27 (dd, J=2.5, 9.1 Hz, 1H), 7.16 (d, J=2.5 Hz, 1H), 6.38-6.49 (m, 3H), 4.82 (br. s., 2H), 4.23 (t, J=5.7 Hz, 2H), 3.96 (t, J=4.9 Hz, 2H), 3.80 (t, J=5.7 Hz, 2H), 3.71-3.75 (m, 5H), 3.69 (t, J=4.9 Hz, 2H), 1.05-1.26 (m, 1H), 0.42-0.51 (m, 2H), 0.16-0.25 (m, 2H)

Compound 149

$^1$H NMR (500 MHz, DMSO-d$_6$) δ 9.00 (s, 1H), 8.58 (s, 1H), 8.22 (s, 1H), 7.80 (d, J=9.1 Hz, 1H), 7.31 (dd, J=2.5, 9.1 Hz, 1H), 7.25 (d, J=2.5 Hz, 1H), 6.80 (br. s., 1H), 6.49 (d, J=1.9 Hz, 2H), 6.42 (br. s., 1H), 4.15-4.31 (m, 2H), 3.89-4.00 (m, 4H), 3.74 (s, 6H)

Compound 148

$^1$H NMR (500 MHz, DMSO-d$_6$) δ 9.00 (s, 1H), 8.58 (s, 1H), 8.22 (s, 1H), 7.80 (d, J=9.1 Hz, 1H), 7.31 (dd, J=2.5, 9.1 Hz, 1H), 7.25 (d, J=2.5 Hz, 1H), 6.80 (br. s., 1H), 6.49 (d, J=1.9 Hz, 2H), 6.42 (br. s., 1H), 4.15-4.31 (m, 2H), 3.89-4.00 (m, 4H), 3.74 (s, 6H)

Compound 147

$^1$H NMR (400 MHz, DMSO-d$_6$) δ 9.76 (br. s., 1H), 9.01 (s, 1H), 8.64 (s, 1H), 8.22 (s, 1H), 7.79 (d, J=9.3 Hz, 1H), 7.26 (dd, J=2.8, 9.3 Hz, 1H), 7.18 (d, J=2.8 Hz, 1H), 6.36-6.51 (m, 3H), 4.58 (spt, J=6.6 Hz, 1H), 4.03-4.19 (m, 2H), 3.93 (t, J=7.3 Hz, 2H), 3.75 (s, 6H), 3.09-3.20 (m, 2H), 2.08 (td, J=7.3, 14.5 Hz, 2H), 1.49 (d, J=6.6 Hz, 6H)

Compound 146

$^1$H NMR (400 MHz, DMSO-d$_6$) δ 8.99 (s, 1H), 8.71 (s, 1H), 8.65 (t, J=1.5 Hz, 1H), 8.51-8.56 (m, 2H), 8.19 (s, 1H), 7.79 (d, J=9.1 Hz, 1H), 7.39 (dd, J=2.8, 9.1 Hz, 1H), 7.22 (d, J=2.8 Hz, 1H), 6.55 (d, J=2.1 Hz, 2H), 6.37 (t, J=2.1 Hz, 1H), 5.31 (s, 2H), 3.91 (s, 3H), 3.72 (s, 6H)

Compound 145

$^1$H NMR (500 MHz, DMSO-d$_6$) δ 8.98 (br. s., 2H), 8.55 (s, 1H), 8.20 (s, 1H), 7.79 (d, J=9.1 Hz, 1H), 7.34 (dd, J=2.6, 9.1 Hz, 1H), 7.26 (d, J=2.6 Hz, 1H), 6.55 (d, J=1.9 Hz, 2H), 6.43 (s, 1H), 4.17 (br. s., 1H), 3.88-3.99 (m, 6H), 3.75 (s, 6H), 3.30 (td, J=6.3, 11.9 Hz, 1H), 3.02-3.16 (m, 1H), 2.96 (q, J=9.6 Hz, 1H), 1.22 (d, J=6.3 Hz, 6H)

Compound 144

¹H NMR (500 MHz, DMSO-d₆) δ 8.96 (s, 1H), 8.55 (s, 1H), 8.21 (s, 1H), 7.77 (d, J=9.5 Hz, 1H), 7.73 (br. s., 1H), 7.27 (dd, J=2.7, 9.5 Hz, 1H), 7.14 (d, J=2.7 Hz, 1H), 6.45 (d, J=2.2 Hz, 2H), 6.38-6.41 (m, 1H), 3.99 (t, J=6.6 Hz, 2H), 3.93 (s, 3H), 3.73 (s, 6H), 3.14 (br. s., 2H), 3.01 (s, 2H), 2.68 (t, J=6.6 Hz, 2H), 2.63 (t, J=5.2 Hz, 2H)

Compound 143

¹H NMR (500 MHz, DMSO-d₆) δ 8.96 (s, 1H), 8.55 (s, 1H), 8.21 (s, 1H), 7.77 (d, J=9.1 Hz, 1H), 7.28 (dd, J=2.5, 9.1 Hz, 1H), 7.14 (d, J=2.5 Hz, 1H), 6.44 (d, J=2.2 Hz, 2H), 6.32-6.42 (m, 1H), 3.98 (t, J=6.9 Hz, 2H), 3.93 (s, 3H), 3.73 (s, 6H), 3.35-3.43 (m, 4H), 2.63 (t, J=6.9 Hz, 2H), 2.44 (t, J=4.9 Hz, 2H), 2.38 (t, J=4.9 Hz, 2H), 1.97 (s, 3H)

Compound 142

¹H NMR (500 MHz, DMSO-d₆) δ 8.95 (s, 1H), 8.55 (s, 1H), 8.20 (s, 1H), 7.75 (d, J=9.5 Hz, 1H), 7.34 (dd, J=2.7, 9.5 Hz, 1H), 7.22 (d, J=2.7 Hz, 1H), 6.49 (d, J=1.9 Hz, 2H), 6.38 (t, J=1.9 Hz, 1H), 5.16 (d, J=5.1 Hz, 1H), 3.83-4.00 (m, 5H), 3.69-3.78 (m, 7H), 3.19-3.31 (m, 2H), 2.68-2.78 (m, 1H), 2.66 (td, J=6.1, 12.1 Hz, 1H), 2.30-2.40 (m, 1H)

Compound 141

¹H NMR (500 MHz, DMSO-d₆) δ 8.95 (s, 1H), 8.55 (s, 1H), 8.21 (s, 1H), 7.76 (d, J=9.1 Hz, 1H), 7.26 (dd, J=2.5, 9.1 Hz, 1H), 7.14 (d, J=2.5 Hz, 1H), 6.34-6.44 (m, 3H), 4.49 (s, 1H), 3.84-3.99 (m, 5H), 3.74 (s, 6H), 1.66-1.86 (m, 2H), 1.16 (s, 6H)

Compound 140

¹H NMR (500 MHz, DMSO-d₆) δ 8.95 (s, 1H), 8.55 (s, 1H), 8.20 (s, 1H), 7.76 (d, J=9.1 Hz, 1H), 7.28 (dd, J=2.5, 9.1 Hz, 1H), 7.14 (d, J=2.5 Hz, 1H), 6.46 (d, J=1.9 Hz, 2H), 6.41 (t, J=1.9 Hz, 1H), 3.83-3.96 (m, 5H), 3.74 (s, 6H), 2.82 (t, J=6.7 Hz, 2H), 2.78 (t, J=6.7 Hz, 2H), 2.57 (t, J=6.7 Hz, 2H), 2.22 (br. s., 1H)

Compound 139

¹H NMR (500 MHz, DMSO-d₆) δ 8.95 (s, 1H), 8.55 (s, 1H), 8.20 (s, 1H), 7.75 (d, J=9.5 Hz, 1H), 7.34 (dd, J=2.7, 9.5 Hz, 1H), 7.22 (d, J=2.7 Hz, 1H), 6.49 (d, J=1.9 Hz, 2H), 6.38 (t, J=1.9 Hz, 1H), 5.16 (d, J=5.1 Hz, 1H), 3.83-4.00 (m, 5H), 3.69-3.78 (m, 7H), 3.19-3.31 (m, 2H), 2.68-2.78 (m, 1H), 2.66 (td, J=6.1, 12.1 Hz, 1H), 2.30-2.40 (m, 1H)

Compound 137

¹H NMR (400 MHz, DMSO-d₆) δ 9.10 (br.s., 3H), 8.49 (s, 2H), 7.84 (d, J=9.6 Hz, 1H), 7.39 (dd, J=2.7, 9.6 Hz, 1H), 7.29 (d, J=2.7 Hz, 1H), 6.52 (d, J=2.1 Hz, 2H), 6.46 (t, J=2.1 Hz, 1H), 4.21 (t, J=7.3 Hz, 2H), 3.76 (s, 6H), 3.35 (m, 1H), 3.15 (br. s., 2H), 1.25 (d, J=6.1 Hz, 6H)

Compound Number 98

¹H NMR (500 MHz, DMSO-d₆) δ 8.95 (s, 1H), 8.56 (s, 1H), 8.21 (s, 1H), 7.75 (d, J=9.1 Hz, 1H), 7.34 (dd, J=2.5, 9.1 Hz, 1H), 7.25 (d, J=2.5 Hz, 1H), 6.50 (d, J=2.2 Hz, 2H), 6.37 (t, J=2.2 Hz, 1H), 5.01 (d, J=2.8 Hz, 1H), 4.70-4.79 (m, 1H), 4.03 (dd, J=3.6, 14.9 Hz, 1H), 3.92 (s, 3H), 3.81 (br. s., 1H), 3.73 (s, 6H), 3.68 (dd, J=8.1, 14.9 Hz, 1H), 3.36-3.48 (m, 2H)

Compound 136

¹H NMR (500 MHz, DMSO-d₆) δ 9.03 (br.s., 2H), 8.58 (s, 1H), 8.25 (s, 1H), 7.83 (d, J=9.5 Hz, 1H), 7.36 (dd, J=2.5, 9.5 Hz, 1H), 7.23 (d, J=2.5 Hz, 1H), 6.52 (d, J=1.9 Hz, 2H), 6.46 (t, J=1.9 Hz, 1H), 4.19-4.21 (m, 2H), 4.10 (d, J=6.9 Hz, 2H), 3.84 (dd, J=2.8, 11.7 Hz, 2H), 3.76 (s, 6H), 3.31-3.38 (td, J=6.1, 11.7 Hz, 1H), 3.27 (t, J=11.7 Hz, 2H), 3.14-3.18 (m, 2H), 2.16-2.08 (m, 1H), 1.43 (d, J=11.7 Hz, 2H), 1.18-1.37 (m, 8H)

Compound 135

¹H NMR (500 MHz, DMSO-d₆) δ 9.03 (br.s., 2H), 8.62 (s, 1H), 8.23 (s, 1H), 7.83 (d, J=9.5 Hz, 1H), 7.36 (dd, J=2.5, 9.5 Hz, 1H), 7.25 (d, J=2.5 Hz, 1H), 6.51 (d, J=2.2 Hz, 2H), 6.46 (t, J=2.2 Hz, 1H), 3.76 (s, 6H), 4.12-4.27 (m, 4H), 3.30-3.43 (m, 1H), 3.07-3.19 (m, 2H), 1.44 (t, J=7.2 Hz, 3H), 1.25 (d, J=6.3 Hz, 6H)

Compound 134

¹H NMR (500 MHz, DMSO-d₆) δ 9.05 (s, 1H), 8.93 (m, 1H), 8.57 (s, 1H), 8.25 (s, 1H), 8.18 (q, J=4.6 Hz, 1H), 7.83 (d, J=9.1 Hz, 1H), 7.33 (dd, J=2.5, 9.1 Hz, 1H), 7.28 (d, J=2.5 Hz, 1H), 6.52 (d, J=2.2 Hz, 2H), 6.46 (t, J=2.2 Hz, 1H), 4.88 (s, 2H), 4.19 (t, J=7.6 Hz, 2H), 3.75 (s, 6H), 3.29-3.42 (m, 1H), 3.16 (br. s., 2H), 2.64 (d, J=4.6 Hz, 3H), 1.25 (d, J=6.6 Hz, 6H)

Compound Number 5

¹H NMR (500 MHz, DMSO-d₆) δ 8.95 (s, 1H), 8.55 (s, 1H), 8.20 (s, 1H), 7.75 (d, J=9.1 Hz, 1H), 7.28 (dd, J=2.5, 9.1 Hz, 1H), 7.12 (d, J=2.5 Hz, 1H), 6.40 (s, 3H), 3.93 (s, 3H), 3.88 (t, J=7.1 Hz, 2H), 3.74 (s, 6H), 3.11-3.28 (m, 2H), 2.68-2.72 (m, 2H), 2.39-2.48 (m, 1H), 1.78 (quin, J=7.1 Hz, 2H)

Compound 133

¹H NMR (500 MHz, DMSO-d₆) δ 8.97 (s, 1H), 8.56 (s, 1H), 8.21 (s, 1H), 7.77 (d, J=9.5 Hz, 1H), 7.27 (dd, J=2.5, 9.5 Hz, 1H), 7.12 (d, J=2.5 Hz, 1H), 6.29-6.49 (m, 3H), 3.96 (t, J=6.8 Hz, 2H), 3.93 (s, 3H), 3.74 (s, 6H), 3.19-3.29 (m, 1H), 2.70-2.85 (m, 5H), 2.42-2.46 (m, 1H), 2.10-2.24 (m, 1H), 1.88-1.98 (m, 1H)

Compound 132

¹H NMR (500 MHz, DMSO-d₆) δ 8.96 (s, 1H), 8.55 (s, 1H), 8.20 (s, 1H), 7.76 (d, J=9.3 Hz, 1H), 7.23 (dd, J=2.8, 9.3 Hz, 1H), 7.07 (d, J=2.8 Hz, 1H), 6.41 (s, 3H), 3.93 (s, 3H), 3.81 (t, J=7.4 Hz, 2H), 3.74 (s, 6H), 3.23-3.32 (m, 4H), 2.23 (t, J=8.1 Hz, 2H), 1.93 (m, 2H), 1.84 (m, 2H)

Compound Number 300

¹H NMR (400 MHz, DMSO-d₆) δ 9.05 (s, 1H), 8.54-8.63 (m, 1H), 8.24 (s, 1H), 7.84 (d, J=9.1 Hz, 1H), 7.41 (d, J=2.5 Hz, 1H), 7.34 (dd, J=2.5, 9.1 Hz, 1H), 7.20 (s, 1H), 6.88 (s, 1H), 6.50 (s, 2H), 6.42-6.47 (m, 1H), 4.99 (s, 2H), 3.93 (s, 3H), 3.74 (s, 6H), 3.53 (s, 3H)

Compound Number 4

¹H NMR (500 MHz, DMSO-d₆) δ 8.95 (s, 1H), 8.55 (s, 1H), 8.20 (s, 1H), 7.76 (d, J=9.1 Hz, 1H), 7.27 (dd, J=2.8, 9.1 Hz, 1H), 7.13 (d, J=2.8 Hz, 1H), 6.46 (d, J=2.2 Hz, 2H), 6.40 (t, J=2.2 Hz, 1H), 3.93 (s, 3H), 3.88 (t, J=6.9 Hz, 2H), 3.74 (s, 6H), 2.79 (t, J=6.9 Hz, 2H), 2.70 (m, 1H), 1.69 (br. s., 1H), 0.95 (d, J=6.3 Hz, 6H)

Compound Number 84

¹H NMR (500 MHz, DMSO-d₆) δ 8.94 (s, 1H), 8.55 (s, 1H), 8.20 (s, 1H), 7.75 (d, J=9.3 Hz, 1H), 7.28 (dd, J=2.5, 9.30 Hz, 1H), 7.15 (d, J=2.5 Hz, 1H), 6.45 (d, J=2.2 Hz, 2H), 6.38-6.42 (m, 1H), 3.93 (s, 3H), 3.82 (t, J=7.1 Hz, 2H), 3.74 (s, 6H), 2.80 (t, J=7.1 Hz, 2H), 1.55 (br. s., 2H)

Compound 130

¹H NMR (500 MHz, DMSO-d₆) δ 9.00 (s, 1H), 8.69 (s, 1H), 8.33 (s, 1H), 7.79 (d, J=9.5 Hz, 1H), 7.28 (dd, J=2.7, 9.5 Hz, 1H), 7.14 (d, J=2.7 Hz, 1H), 6.38-6.47 (m, 3H), 5.55 (br.s., 1H), 4.34 (t, J=6.6 Hz, 2H), 3.62-3.91 (m, 12H), 3.36-3.55 (m, 6H), 3.09-3.31 (m, 4H), 2.28-2.38 (m, 2H), 1.75-1.97 (m, 2H), 1.10-1.23 (m, 1H), 0.43-0.52 (m, 2H), 0.15-0.24 (m, 2H)

The below NMR experiments were carried out using a Bruker Avance AV400 spectrometer, using an internal deuterium lock and equipped with a 4-nucleus (¹H, ¹³C, ¹⁹F, ³¹P) probe head. Chemical shifts (δ) are reported in parts per million (ppm) at 27° C.

Compound 138

¹H NMR (400 MHz, DMSO-d6): 9.07 (1H, s), 8.59 (1H, s), 8.56-8.47 (1H, m), 8.27-8.21 (1H, m), 7.87 (1H, d), 7.54-7.47 (1H, m), 7.43-7.32 (3H, m), 7.27-7.18 (1H, m), 3.98-3.89 (3H, m), 3.83 (2H, d), 2.76 (3H, d), 1.23-1.13 (1H, m), 0.50-0.41 (2H, m), 0.22-0.14 (2H, m).

Compound Number 99

$^1$H NMR (400 MHz, Me-d3-OD): 8.89 (1H, s), 8.40 (1H, s), 8.23 (1H, s), 7.79 (1H, d), 7.41 (1H, dd), 7.30 (1H, d), 7.01 (2H, s), 6.53 (2H, s), 6.47-6.40 (1H, m), 4.57 (2H, s), 4.01 (3H, s), 3.77 (7H, s).

Compound 200

$^1$H NMR (400 MHz, DMSO-d6): 8.96 (1H, s), 8.56 (1H, s), 8.21 (1H, s), 7.76 (1H, d), 7.25 (1H, dd), 7.11 (1H, d), 6.46-6.36 (3H, m), 3.99-3.82 (5H, m), 3.75 (6H, s), 1.23 (3H, t).

Compound 201

$^1$H NMR (400 MHz, DMSO-d6): 8.92 (1H, s), 8.54 (1H, s), 8.20 (1H, s), 7.76 (1H, d), 6.99 (1H, dd), 6.81 (2H, dd), 6.64 (1H, d), 3.92 (6H, d), 3.88-3.73 (5H, m), 1.24 (3H, t).

Compound 11

$^1$H NMR (400 MHz, DMSO-d6): 8.98 (1H, s), 8.56 (1H, s), 8.22 (1H, s), 7.78 (1H, d), 7.30 (1H, dd), 7.16 (1H, d), 6.43 (2H, d), 6.40 (1H, t), 3.94 (3H, s), 3.74 (6H, s), 3.41 (3H, s).

Compound 202

$^1$H NMR (400 MHz, DMSO-d6): 8.96 (1H, s), 8.56 (1H, s), 8.21 (1H, s), 7.77 (1H, d), 7.26 (1H, dd), 7.13 (1H, d), 6.42 (3H, s), 3.93 (3H, s), 3.82-3.70 (8H, m), 1.24-1.12 (1H, m), 0.53-0.43 (2H, m), 0.26-0.16 (2H, m).

Compound 12

$^1$H NMR (400 MHz, DMSO-d6): 8.96 (1H, s), 8.56 (1H, s), 8.21 (1H, s), 7.76 (1H, d), 7.26 (1H, dd), 7.08 (1H, d), 6.41 (3H, dd), 3.93 (3H, s), 3.79 (2H, t), 3.75 (6H, s), 1.73-1.63 (2H, m), 0.96 (3H, t)

Compound 204

$^1$H NMR (400 MHz, DMSO-d6): 9.00-8.94 (1H, m), 8.59-8.53 (1H, m), 8.25-8.18 (1H, m), 7.77 (1H, d), 7.30 (1H, dd), 7.17 (1H, d), 6.44 (2H, d), 6.40 (1H, t), 4.03 (2H, t), 3.94 (3H, s), 3.74 (6H, s), 3.60 (2H, t), 3.29 (3H, s).

Compound 13

$^1$H NMR (400 MHz, DMSO-d6): 8.97 (1H, s), 8.56 (1H, s), 8.21 (1H, s), 7.77 (1H, d), 7.30 (1H, dd), 7.10 (1H, d), 6.41 (3H, s), 3.93 (3H, s), 3.74 (6H, s), 3.69 (2H, d), 2.09-1.97 (1H, m), 0.98 (6H, d).

Compound 205

$^1$H NMR (400 MHz, DMSO-d6): 9.02 (1H, s), 8.60-8.54 (1H, m), 8.22 (1H, s), 7.82 (1H, d), 7.36 (1H, dd), 7.24 (1H, d), 6.48 (2H, d), 6.40 (1H, t), 6.32 (1H, s), 5.25 (2H, s), 3.97-3.89 (3H, m), 3.78-3.69 (7H, m), 3.29 (3H, s), 2.18 (3H, s).

Pharmacological Part

Biological Assays A

FGFR1 (Enzymatic Assay)

In a final reaction volume of 30 µL, FGFR1 (h) (25 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an IC$_{50}$ (M) and pIC$_{50}$ (−log IC$_{50}$) value.

FGFR2 (Enzymatic Assay)

In a final reaction volume of 30 µL, FGFR2 (h) (150 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 0.4 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in (Relative Fluorescence Units). In this assay, the inhibitory effect of different compound concentrations (range 10 µM to 0.1 nM) was determined and used to calculate an IC$_{50}$ (M) and pIC$_{50}$ (−log IC$_{50}$) value.

FGFR3 (Enzymatic Assay)

In a final reaction volume of 30 µL, FGFR3 (h) (40 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 25 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an IC$_{50}$ (M) and pIC$_{50}$ (−log IC$_{50}$) value.

FGFR4 (Enzymatic Assay)

In a final reaction volume of 30 µL, FGFR4 (h) (60 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an IC$_{50}$ (M) and pIC$_{50}$ (−log IC$_{50}$) value.

KDR (VEGFR2) (Enzymatic Assay)

In a final reaction volume of 30 µL, KDR (h) (150 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 3 µM ATP in the presence of compound (1% DMSO final). After incubation for 120 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an IC$_{50}$ (M) and pIC$_{50}$ (−log IC$_{50}$) value.

Ba/F3-FGFR1 (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-FGFR1-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 µM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-FGFR3 (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-FGFR3-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 µM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-KDR (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-KDR-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 µM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-Flt3 (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-Flt3-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 µM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Data for the compounds of the invention in the above assays are provided in Table A2.

TABLE A2

| Co. No. | FGFR1 $pIC_{50}$ | FGFR2 $pIC_{50}$ | FGFR3 $pIC_{50}$ | FGFR4 $pIC_{50}$ | VEGFR2 (KDR) $pIC_{50}$ | BAF3-FGFR1 (MIN IL3) $pIC_{50}$ | BAF3-FGFR1 (PLUS IL3) $pIC_{50}$ | BAF3-FGFR3 (MIN IL3) $pIC_{50}$ | BAF3-FGFR3 (PLUS IL3) $pIC_{50}$ | BAF3-KDR (MIN IL3) $pIC_{50}$ | BAF3-KDR (PLUS IL3) $pIC_{50}$ | BAF3-FLT3 (MIN IL3) $pIC_{50}$ | BAF3_FLT3 (PLUS IL3) $pIC_{50}$ |
|---|---|---|---|---|---|---|---|---|---|---|---|---|---|
| 200 | 8.53 | 8.11 | 8.73 | 7.92 | 7.05 | 6.41 | <5 | 6.61 | <5 | 5.79 | <5 | 5.2 | <5 |
| 11 | 8.36 | 7.91 | 8.66 | 7.76 | 7.43 | 6.3 | <5 | 6.43 | <5 | 6.06 | <5 | 5.71 | <5 |
| 202 | 8.11 | 7.71 | ~8.33 | 7.61 | 6.58 | 5.95 | <5 | 6.1 | <5 | 5.14 | <5 | <5 | <5 |
|  | 8.18 | 7.9 | 8.45 | 7.6 | 6.72 | 6.15 | <5 | 5.93 | <5 | 5.18 | <5 | <5 | <5 |
| 17 | 7.93 | 7.48 | 8.15 | 7.13 | 6.39 | 5.95 | <5 | 5.67 | <5 | <5 | <5 | <5 | <5 |
| 203 | 7.26 | 7.19 | 7.75 | 6.73 | 6.17 | 5.49 | <5 | 5.54 | <5 | <5 | <5 | <5 | <5 |
| 204 | 8.27 | 7.93 | 8.47 | 7.55 | 6.79 | 6.53 | <5 | 6.64 | <5 | 5.35 | <5 | <5 | <5 |
| 205 | 8.85 | 8.46 | 9 | 8.55 | 7.07 | 6.42 | <5 | 7.09 | <5 | 5.52 | <5 | 5.24 | <5 |
| 206 | 8.15 | 7.91 | 8.52 | 7.46 | 6.67 | 5.79 | <5 | 6.15 | <5 | <5 | <5 | <5 | <5 |
| 207 | 8.86 | 8.32 | 8.64 | 7.45 | 7.18 | 5.59 | <5 | ~5.56 | ~5.24 | <5 | <5 | <5 | <5 |
| 56 | 8.35 | 8.19 | 8.68 | 7.55 | 6.92 | 6.12 | <5 | 5.72 | <5 | <5 | <5 | <5 | <5 |
|  | 8.37 | 8.09 | 8.55 | 7.57 | 6.97 | 6.28 | <5 | 5.9 | <5 | 5.06 | <5 | <5 | <5 |
| 208 | 7.35 | 7.21 | 7.26 | 6.8 | 5.82 | 5.73 | <5 | 5.66 | <5 | <5 | <5 | <5 | <5 |
| 209 | 5.92 | ~6.07 | 6.22 | 5.29 | 6.18 | <5 | <5 | <5 | <5 | <5 | <5 | <5 | <5 |
| 210 | 8.37 | 8.03 | 8.45 | 7.75 | 6.75 | 6.7 | <5 | 6.53 | <5 | 5.26 | <5 | <5 | <5 |
| 211 | 8.29 | 7.88 | 8.13 | 7.39 | 6.7 | 6.44 | <5 | 6.01 | <5 | 5.26 | <5 | <5 | <5 |
| 1 | 8.59 | 8.5 | 9.05 | 8.25 | 7.07 | 7.04 | <5 | 6.89 | <5 | 6.03 | <5 | <5 | <5 |
|  | 8.64 | 8.41 | 8.95 | 8.27 | 7.1 | 6.56 | <5 | 6.86 | <5 | 5.6 | <5 | 5.09 | <5 |
| 212 | 8.43 | 8.15 | 8.86 | 7.83 | 6.92 | 6.36 | <5 | 5.98 | <5 | ~5.02 | <5 | <5 | <5 |
| 213 | 8.33 | 8.09 | 8.55 | 7.74 | 6.65 | 6.45 | <5 | 6.06 | <5 | <5 | <5 | <5 | <5 |
| 214 | 7.16 | 7 | 7.39 | 6.33 | 5.74 | <5 | <5 | <5 | <5 | <5 | <5 | <5 | <5 |
| 216 | 8.86 | 8.28 | 8.58 | 7.66 | 6.79 | 5.69 | <5 | 6.05 | ~5.02 | ~5.06 | ~5.09 | ~5.26 | ~5.2 |
| 22 | 5.99 | 6.07 | 6.12 | <5 | 5.92 | <5 | <5 | <5 | <5 | <5 | <5 | <5 | <5 |
| 60 | 8.99 | 8.42 | 9.01 | 7.84 | 7.37 | 5.8 | ~5.19 | 6.15 | ~5.27 | ~5.27 | ~5.26 | ~5.27 | ~5.08 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 122 | 8.77 | 8.49 | 9.1 | 8.21 | 7.12 | 6.36 | <5 | 6.87 | <5 | 5.47 | <5 | <5 | <5 |
| 58 | 6.17 | 6.39 | 6.78 | <6 | <6 | <5 | <5 | ~5.09 | <5 | <5 | <5 | <5 | <5 |
| 3 | 8.71 | 8.63 | 9.03 | 8.29 | 7.75 | 7.24 | <5 | 7.1 | <5 | 5.91 | <5 | 5.22 | <5 |
|  | 8.77 | 8.49 | 8.97 | 8.25 | 7.39 |  |  |  |  |  |  |  |  |
| 218 | 8.42 | ~8.05 | 8.29 | 7.63 | 6.62 | 6.71 | <5 | 6.61 | <5 | <5 | <5 | <5 | <5 |
| 219 | 6.95 | 6.92 | 7.23 | 6.12 | <6 | 5.05 | <5 | 5.23 | <5 | <5 | <5 | <5 | <5 |
| 220 | 7.27 | 7.01 | 7.53 | 6.59 | 6.48 | 5.44 | <5 | 5.34 | <5 | <5 | <5 | <5 | <5 |
| 221 | 6.63 | 6.62 | 7.08 | <6 | 6.97 | <5 | <5 | ~5 | <5 | <5 | <5 | <5 | <5 |
| 223 | 8.74 | 8.44 | 9.04 | 8.37 | 6.95 | 6.73 | <5 | 7 | <5 | 5.3 | <5 | <5 | <5 |
| 224 | 7.84 | 7.83 | 8.2 | 7.51 | 7.19 | 5.64 | <5 | 5.6 | <5 | 5.37 | <5 | 5.23 | <5 |
| 62 | 8.9 | 8.45 | 9.06 | 7.92 | 7.55 | 5.88 | ~5.25 | 6.06 | ~5.25 | ~5.27 | ~5.27 | ~5.27 | ~5.26 |
| 23 | 8.73 | 8.54 | 9.15 | 8.35 | 6.91 | 7.02 | <5 | 6.74 | <5 | 5.28 | <5 | <5 | <5 |
| 226 | 8.16 | 8.07 | 8.69 | 7.52 | 6.46 | 6 | <5 | 6.11 | <5 | <5 | <5 | <5 | <5 |
| 8 | 8.84 | 8.48 | 8.61 | 7.98 | 7.15 | 5.96 | <5 | 7.12 | <5 | <5 | <5 | <5 | <5 |
|  | 8.84 | 8.82 | 8.49 | 7.95 | 7.55 | 6.07 | <5 | 7.07 | <5 | <5 | <5 | <5 | <5 |
| 84 | 8.76 | 8.55 | 8.75 | 8.1 | 7.43 | 6.57 | <5 | 6.92 | <5 | 5.63 | <5 | <5 | <5 |
|  | 8.67 | 8.8 | 8.73 | 8.03 | 7.56 | 7.29 | <5 | 7.16 | <5 | 5.96 | <5 | <5 | <5 |
|  | 8.76 | 8.61 | 8.71 | 8.12 | 7.44 | 6.75 | <5 | 6.82 | <5 | 5.73 | <5 | <5 | <5 |
|  | 8.66 | 8.71 | 8.73 | 7.95 | 7.43 | 6.47 | <5 | 7.06 | <5 | 5.75 | <5 | <5 | <5 |
|  | 8.74 | 8.48 | 8.62 | 7.8 | 7.3 | 6.58 | <5 | 7.15 | <5 | 5.57 | <5 | <5 | <5 |
|  | 8.92 | 8.47 | 8.69 | 7.88 | 7.08 | 6.1 | <5 | 7.03 | <5 | 5 | <5 | <5 | <5 |
|  | 8.96 | 8.56 | 8.74 | 8.06 | 7.46 | 6.08 | <5 | 7.07 | <5 | <5 | <5 | <5 | <5 |
|  | 8.78 | 8.4 | 8.66 | 7.97 | 7.52 | 5.94 | <5 | 7.11 | <5 | <5 | <5 | <5 | <5 |
|  | 8.81 | 8.64 | 8.64 | 7.98 | 7.27 | 6.87 | <5 | 7.29 | <5 | 5.73 | <5 | <5 | <5 |
| 227 | 8.27 | 8.03 | 8.6 | 7.8 | 6.78 | 5.76 | <5 | 6.57 | <5 | <5 | <5 | <5 | <5 |
| 65 | 8.51 | 8.19 | 8.35 | 7.49 | 6.46 | 6 | <5 | 6.56 | <5 | <5 | <5 | <5 | <5 |
| 229 | 8.53 | 8.14 | 8.95 | 7.64 | 6.68 | 5.75 | <5 | 6.39 | <5 | <5 | <5 | <5 | <5 |
| 73 | 8.73 | 8.53 | 8.64 | 7.46 | 7.31 | 6.09 | ~5.07 | 6 | ~5.25 | ~5.23 | ~5.24 | ~5.25 | <5 |
| 231 | 8.16 | 8.29 | 8.45 | 7.38 | 7 | 5.71 | <5 | 6.23 | <5 | ~5.08 | <5 | <5 | <5 |
| 59 | 7.76 | 7.95 | 8.07 | 6.99 | 6.59 | 6.34 | <5 | 6.55 | <5 | <5 | <5 | <5 | <5 |
| 52 | 8.04 | 7.82 | 8.21 | 7.28 | 6.91 | 5.7 | <5 | 6.17 | <5 | <5 | <5 | <5 | <5 |
| 232 | <6 | <6 | 6.17 | <6 | <5 | <5 | <5 | <5 | <5 | <5 | <5 | <5 | <5 |
| 64 | 7.67 | 7.39 | 7.29 | 7.09 | <6 | 6.17 | <5 | 5.75 | <5 | <5 | <5 | <6 | <5 |
| 233 | 8.76 | 8.57 | 8.93 | 8.13 | 7.27 | 6.66 | <5 | 6.97 | <5 | 5.59 | <5 | <5 | <5 |
| 19 | 8.09 | 8.01 | 8.17 | 6.93 | 6.86 | 5.2 | <5 | ~5.68 | ~5.23 | <5 | <5 | ~5.18 | <5 |
| 130 | 8.32 | 8.19 | 8.54 | 7.37 | 7.69 | 6.16 | ~5.25 | 6.06 | ~5.33 | ~5.62 | ~5.3 | ~5.28 | ~5.26 |
| 235 | 8.78 | 8.53 | 8.68 | 7.42 | 7.26 | 5.72 | <5 | 6.15 | <5 | <5 | <5 | <5 | <5 |
| 69 | 7.72 | 7.33 | 7.93 | 6.95 | 6.16 | 5.99 | <5 | 6.29 | <5 | <5 | <5 | <5 | <5 |
|  | 7.72 | 7.43 | 7.77 | 7.02 | 6.05 | 5.55 | <5 | 6.1 | <5 | <5 | <5 | <5 | <5 |
| 237 | 6.84 | 6.99 | 7.35 | 6.5 | 6.14 | ~5.16 | <5 | ~5.17 | <5 | <5 | <5 | <5 | <5 |
| 238 | 9.01 | 8.57 | 8.88 | 7.76 | 7.54 | 6.2 | <5 | 6.89 | <5 | 5.32 | <5 | <5 | <5 |
| 66 | 6.54 | 6.96 | 7.22 | 6.18 | <6 | <5 | <5 | ~5.04 | <5 | <5 | <5 | <5 | <5 |
| 2 | ~8.64 | 8.48 | 9.02 | 8.03 | 6.86 | 6.51 | <5 | 7.04 | <5 | 5.41 | <5 | <5 | <5 |
|  | 8.56 | 8.33 | 8.79 | 7.97 | 7.34 | 7.1 | <5 | 7.05 | <5 | 5.49 | <5 | <5 | <5 |
| 113 | 8.35 | 8.18 | 8.71 | 7.8 | 6.69 | 6.71 | <5 | 6.95 | <5 | 5.45 | <5 | <5 | <5 |
| 68 | 5.86 | 5.99 | ~6.06 | <5 | 5.91 | <5 | <5 | ~5.11 | ~5.15 | <5 | <5 | 5.21 | <5 |
| 239 | ~8.66 | 8.5 | 8.76 | 7.33 | 7.14 | 5.94 | <5 | 5.91 | ~5.28 | 5.25 | ~5.21 | ~5.26 | ~5.25 |
| 240 | 8.7 | 8.26 | 8.75 | 7.17 | 7.01 | 6.08 | <5 | 5.71 | ~5.26 | ~5.14 | ~5.26 | ~5.26 | <5 |
| 241 | 9.12 | 8.86 | 9.05 | 8.51 | 7.74 | 8.02 | <5 | 8.03 | ~5.06 | 6.69 | <5 | ~5.09 | <5 |
|  | 9.43 | 8.78 | 8.73 | 8.59 | 7.61 | 7.97 | <5 | 8.01 | ~5.08 | 6.65 | <5 | ~5.14 | <5 |
| 55 | 8.72 | 8.52 | 8.75 | 7.24 | 7.12 | 6.1 | ~5.16 | 5.95 | ~5.27 | ~5.24 | ~5.25 | ~5.26 | ~5.2 |
| 242 | 8.62 | 8.61 | 8.9 | 8.01 | 7.44 | 6.96 | <5 | 7 | <5 | 5.77 | <5 | <5 | <5 |
| 243 | 8.66 | 8.36 | 8.89 | 7.61 | 7.04 | 6.01 | <5 | 6.01 | ~5.25 | ~5.02 | ~5.2 | ~5.21 | ~5.19 |
| 244 | 8.27 | 8.29 | 8.49 | 7 | 6.76 | 5.84 | <5 | 5.77 | ~5.25 | ~5.05 | ~5.08 | ~5.24 | <5 |
| 245 | 8.2 | 8.02 | 8.37 | 6.71 | 6.87 | 6.91 | <5 | 6.82 | <5 | 5.94 | <5 | <5 | <5 |
| 246 | 8.22 | 8.09 | 8.65 | 7.28 | 6.47 | 5.69 | <5 | 6.11 | <5 | <5 | <5 | <5 | <5 |
| 24 | 7.88 | 7.94 | 8.52 | 7.32 | 6.82 | 5.97 | <5 | 5.86 | <5 | ~5.01 | <5 | <5 | <5 |
| 249 | 8.45 | 8.31 | 8.65 | 7.09 | 7.36 | 6.55 | <5 | 6.56 | <5 | 5.64 | <5 | <5 | <5 |
| 250 | 8.35 | 8.08 | 8.59 | 7.37 | 6.49 | 5.73 | <5 | 6.09 | <5 | <5 | <5 | <5 | <5 |
| 251 | 7.73 | 7.73 | 7.93 | 6.12 | 6.34 | 5.31 | <5 | ~5.29 | ~5.26 | ~5.12 | ~5.23 | ~5.26 | ~5.37 |
| 21 | 8.75 | 8.48 | 9.07 | 8.07 | 6.79 | 6.75 | <5 | 6.8 | <5 | 5.56 | <5 | <5 | <5 |
| 72 | 8.8 | ~8.5 | 8.91 | 7.33 | 7.22 | 6.1 | ~5.05 | 6.03 | ~5.29 | ~5.28 | ~5.26 | ~5.27 | ~5.19 |
| 253 | 8.54 | 8.33 | 8.74 | 7.6 | 6.78 | 5.92 | <5 | 6.07 | <5 | <5 | <5 | <5 | <5 |
| 254 | 8.41 | 8.19 | 8.52 | 7.52 | 6.35 | 6.13 | <5 | 6.11 | <5 | <5 | <5 | <5 | <5 |
| 74 | 7.78 | 7.9 | 8 | 7.07 | <6 | 6.14 | <5 | 6.42 | <5 | <5 | <5 | <5 | <5 |
| 70a | 8.57 | 8.52 | 8.23 | 7.58 | 7.23 | 6.91 | <5 | 7.13 | <5 | 5.77 | <5 | <5 | <5 |
| 256 | 9.21 | 8.54 | 8.88 | 8.31 | 7.28 | 7 | <5 | 6.89 | <5 | <5 | <5 | <5 | <5 |
| 26 | 8.76 | 8.47 | 8.9 | 8.11 | 7.14 | 6.85 | <5 | 6.76 | <5 | 5.64 | <5 | 5.22 | <5 |
| 257 | 7.96 | 7.58 | 7.9 | 7.59 | 6.49 | 6.46 | <5 | 6.57 | <5 | <5 | <5 | <5 | <5 |
| 75 | 8.73 | 8.42 | 8.87 | 8.12 | 7.15 | 7.05 | <5 | 6.9 | <5 | 5.7 | <5 | <5 | <5 |
|  | 8.5 | 8.42 | 8.79 | 8.1 | 6.77 | 6.69 | <5 | 7.11 | <5 | 5.5 | <5 | <5 | <5 |
| 7 | 8.3 | 8.17 | 8.57 | 7.92 | 6.66 | 6.36 | <5 | 6.58 | <5 | 5.26 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 259 | 8.81 | 8.63 | 9.1 | 8.4 | 7.28 | 7.24 | <5 | 7.17 | <5 | 5.45 | <5 | <5 | <5 |
| 260 | 8.79 | 8.51 | 8.9 | 8.18 | 7.47 | 7.2 | <5 | 6.88 | <5 | 5.58 | <5 | <5 | <5 |
| 27 | 6.13 | 6.56 | 6.3 | <6 | 6.4 | 5.67 | <5 | <5 | <5 | 6.17 | <5 | 5.32 | <5 |
| 78 | 8.13 | 7.93 | 8.4 | 7.42 | 6.77 | 6.19 | <5 | 6.12 | <5 | 5.24 | <5 | <5 | <5 |
|  | 8.22 | 8.11 | 8.36 | 7.45 | 6.96 | 6.63 | <5 | 6.46 | <5 | ~5.68 | <5 | <5 | <5 |
|  | 8.1 | 8.03 | 8.43 | 7.52 | 6.68 | 6.26 | <5 | 6.26 | <5 | 5.38 | <5 | <5 | <5 |
| 261 | 8.71 | 8.5 | 8.39 | 8.14 | 7.38 | 5.96 | <5 | 7.07 | <5 | <5 | <5 | <5 | <5 |
| 262 | 9.29 |  | 9.35 | 8.91 | 7.86 | 7.74 | <5 | 7.87 | <5 | 6.75 | <5 | <5 | <5 |
| 25 | 9.11 | 8.64 | 8.43 | 7.92 | 7.04 | 7.36 | <5 | 7.22 | <5 | 5.73 | <5 | <5 | <5 |
|  | 8.78 | 8.61 | 8.52 | 7.78 | 7.11 | 7.35 | <5 | 7.36 | <5 | 5.86 | <5 | <5 | <5 |
| 263 | 8.75 | 8.52 | 8.75 | 8.14 | 7.39 | 6.72 | <5 | 6.75 | <5 | 5.54 | <5 | <5 | <5 |
| 264 | 8.97 | 8.75 | 8.45 | 8.09 | 7.78 | 7.47 | <5 | 7.58 | <5 | 6.12 | <5 | <5 | <5 |
| 265 | 8.79 | 8.59 | 8.44 | 8.04 | 7.05 | 6.51 | <5 | 6.65 | <5 | 5.24 | <5 | <5 | <5 |
| 266 | 8.76 | 8.62 | 8.33 | 7.97 | 7.37 | 5.79 | <5 | 6.9 | <5 | <5 | <5 | <5 | <5 |
| 76 | 8.46 | 8.19 | 8.43 | 7.65 | 7.05 | 7.18 | 5 | 6.92 | <5 | 6.08 | 5.02 | 5.09 | <5 |
| 267 | 7.83 | 7.7 | 8 | 7.43 | 6.2 | 5.69 | <5 | 5.76 | <5 | <5 | <5 | <5 | <5 |
| 268 | 9.43 | 8.74 | 9.14 | 9.05¶ | 7.96 | 7.74 | <5 | 8.09 | <5 | 6.69 | <5 | <5 | <5 |
|  | 9.25 | 8.75 | 9.41 | 8.78 | 7.96 | 7.86 | <5 | 7.89 | <5 | 6.69 | <5 | <5 | <5 |
| 269 | 6.28 | 6.44 | 6.51 | <6 | <6 | <5 | <5 | <5 | <5 | <5 | <5 | <5 | <5 |
| 271 | 8.14 | 7.87 | 8.58 | 7.61 | 6.75 | 6.14 | <5 | 6.19 | <5 | ~5.06 | <5 | <5 | <5 |
| 272 | 9.02 | 8.75 | 8.82 | 8.37 | 7.6 | 7.36 | <5 | 7.77 | <5 | 6.24 | <5 | ~5.18 | <5 |
| 273 | 7.11 | 7.09 | 6.71 | <6 | 6.29 | 5.73 | <5 | 5.68 | <5 | 5.29 | <5 | <5 | <5 |
| 274 | 6.1 | 6.27 | 6.65 | <6 | ~6 | <5 | <5 | <5 | <5 | <5 | <5 | <5 | <5 |
| 121 | 8.12 | 7.86 | 8.2 | 7.02 | 6.63 | 6.14 | <5 | ~6.06 | <5 | 5.55 | <5 | 5.35 | <5 |
| 4 | 9.01 | 8.35 | 8.42 | 8.21 | 7.32 | 7.23 | <5 | 7.31 | <5 | 5.48 | <5 | ~5.05 | <5 |
|  | 8.77 | 8.81 | 8.49 | 8.18 | 7.43 | 7.08 | <5 | 7.82 | <5 | 6.05 | <5 | <5 | <5 |
|  | 8.73 | 8.76 | 8.5 | 8.23 | 7.46 | 7.72 | <5 | 7.86 | <5 | 6.11 | <5 | 5 | <5 |
|  | 8.96 | 8.73 | 8.57 | 8.31 | 7.46 | 7.6 | <5 | 8.05 | <5 | 5.96 | <5 | <5 | <5 |
|  | 8.92 | 8.67 | 8.44 | 8.25 | 7.33 | 8.07 | <5 | 8.07 | <5 | 6.48 | <5 | <5 | <5 |
|  | 9.09 | 8.58 | 8.6 | 8.29 | 7.45 | 7.61 | <5 | 8.13 | <5 | 6.04 | <5 | <5 | <5 |
|  | 9.01 | 8.64 | 8.56 | 8.33 | 7.5 | 7.61 | <5 | 7.98 | ~5.12 | 6 | <5 | <5 | <5 |
|  | 8.99 | 8.56 | 8.6 | 8.18 | 7.58 | 7.89 | <5 | 7.8 | <5 | 6.24 | <5 | <5 | <5 |
| 276 | 8.6 | 8.46 | 8.93 | 8.17 | 7.23 | 6.99 | <5 | ~7.17 | <5 | 5.65 | <5 | <5 | <5 |
| 28 | 8.62 | 8.47 | 8.83 | 8.09 | 7.35 | 7.15 | <5 | 7.14 | <5 | 5.58 | <5 | <5 | <5 |
| 37 | 8.04 | 7.99 | 8.62 | 7.59 | 7.14 | 5.88 | ~5.07 | 5.82 | <5 | ~5.1 | <5 | <5 | <5 |
| 278 | 8.46 | 8.34 | 8.44 | 7.66 | 7.18 | 5.92 | <5 | 7.09 | <5 | <5 | <5 | <5 | <5 |
| 279 | 8.43 | 8.3 | 8.4 | 7.5 | 7.16 | 5.76 | <5 | 7.04 | <5 | <5 | <5 | <5 | <5 |
| 280 | 8.66 | 8.39 | 8.44 | 7.87 | 7.31 | 6.94 | <5 | 7.49 | <5 | 5.34 | <5 | <5 | <5 |
| 281 | 8.41 | 8.36 | 8.18 | 7.59 | 7.14 | 7.33 | <5 | 7.1 | <5 | 5.94 | <5 | ~5.15 | <5 |
| 283 | 6.39 | 6.65 | 6.68 | <6 | 6.31 | 5.23 | <5 | ~5.21 | <5 | ~5.18 | <5 | <5 | <5 |
| 79/79a | 8.62 | 8.55 | 8.58 | 7.82 | 6.91 | 7.29 | <5 | 7.58 | <5 | 5.8 | <5 | <5 | <5 |
| 602 | 8.06 | 8.14 | 8.13 | 7.51 | 7 | 6.57 | <5 | 6.6 | <5 | 5.28 | <5 | <5 | <5 |
| 81 | 8.21 | 8.16 | 8.84 | 7.48 | 7.02 | 6.61 | <5 | 6.43 | <5 | 5.24 | <5 | <5 | <5 |
| 80 | 8.33 | 8.13 | 8.72 | 7.59 | 6.86 | 6.69 | <5 | 6.59 | <5 | 5.31 | <5 | <5 | <5 |
| 284 | 9.07 | 8.8 | 8.68 | 8.4 | 7.39 | 7.69 | <5 | 7.82 | ~5.08 | 5.72 | <5 | <5 | <5 |
|  | 9.26 | 8.8 | 8.8 | 8.33 | 7.73 | 7.56 | <5 | 7.77 | ~5.01 | 6.17 | <5 | ~5.1 | <5 |
| 286 | 8.75 | 8.49 | 8.56 | 8.14 | 7.68 | 7.24 | <5 | 7.32 | 5.03 | 5.86 | <5 | <5 | <5 |
| 287 | 8.33 | 8.3 | 8.63 | 7.8 | 7.69 | 6.38 | <5 | 6.75 | <5 | <5 | <5 | <5 | <5 |
| 29 | ~6.1 | 6.1 | 6.32 | <6 | ~5.96 | <5 | <5 | 5.24 | 5.28 | <5 | <5 | 5.22 | <5 |
| 288 | 7.65 | ~7.77 | 7.73 | 7.04 | 6.76 | 5.15 | <5 | 6.58 | <5 | <5 | <5 | <5 | <5 |
| 291 | 8.87 | 8.71 | 8.77 | 8.39 | 7.97 | 7.72 | <5 | 7.79 | <5 | 6.65 | <5 | <5 | <5 |
| 293 | 7.01 | 6.99 | 7.49 | 6.49 | 6.23 | <5 | <5 | <5 | <5 | <5 | <5 | <5 | <5 |
| 294 | 8.67 | 8.4 | 8.64 | 7.69 | 7.28 | 5.78 | <5 | 6.9 | <5 | <5 | <5 | <5 | <5 |
|  | 8.62 | 8.6 | 8.52 | 7.75 | 7.07 | 6.24 | <5 | 6.94 | <5 | 5.4 | <5 | <5 | <5 |
| 16 | 7.81 | 7.78 | 8.34 | 7.39 | 6.53 | 6.17 | <5 | 5.78 | <5 | <5 | <5 | <5 | <5 |
| 20 | 8.25 | 8.31 | 8.84 | 7.85 | 7.16 | 6.07 | <5 | 6.06 | <5 | ~5 | <5 | <5 | <5 |
| 295 | 8.86 | 8.61 | 8.75 | 8.14 | 7.6 | 7.97 | <5 | 7.79 | <5 | 6.32 | <5 | <5 | <5 |
| 296 | 8.61 | 8.53 | 8.46 | 8 | 6.87 | 7.47 | <5 | 7.65 | <5 | 5.96 | <5 | <5 | <5 |
| 54 | 6.16 | 6.07 | 6.11 | <6 | ~6.04 | <5 | <5 | <5 | <5 | <5 | <5 | <5 | <5 |
| 297 | 8.19 | 8.35 | 8.5 | 7.66 | 7.24 | 5.35 | <5 | 5.56 | <5 | <5 | <5 | <5 | <5 |
| 298 | 8.42 | 8.45 | 8.18 | 7.65 | 6.72 | 6.71 | <5 | 6.37 | <5 | 5.21 | <5 | <5 | <5 |
| 299 | 8.06 | 8.23 | 8.48 | 7.72 | 7.31 | 6.81 | <5 | 6.88 | <5 | 5.74 | <5 | <5 | <5 |
| 49 | 8.93 | 8.34 | 9.19 | 8.33 | 7.53 | 7.13 | <5 | 7.06 | <5 | 5.58 | <5 | 5.43 | <5 |
| 93 | 8.95 | 8.66 | 8.86 | 8.23 | 7.65 | 6.98 | <5 | 6.97 | <5 | 5.81 | <5 | <5 | <5 |
|  | 8.85 | 8.46 | 8.64 | 8.04 | 7.58 | 6.8 | <5 | 6.42 | <5 | 5.47 | <5 | ~5.01 | <5 |
| 302 | 8.97 | 8.72 | 8.68 | 8.28 | 7.59 | 7.93 | <5 | 7.91 | <5 | 6.64 | <5 | <5 | <5 |
| 303 | 8.43 | 8.48 | 8.33 | 7.66 | 7.92 | 6.73 | <5 | 6.7 | ~5.01 | 6.43 | <5 | <5 | <5 |
| 304 | 8.15 | 7.82 | 8.13 | 7.33 | 7.13 | 5.74 | <5 | 7.08 | <5 | <5 | <5 | <5 | <5 |
| 305 |  |  |  |  |  | 6.38 | <5 | 6.67 | <5 | 5.07 | <5 | <5 | <5 |
| 61 |  |  |  |  |  | 5.83 | ~5.19 | ~5.67 | ~5.28 | ~5.15 | ~5.25 | 5.12 | ~5.12 |
| 306 |  |  |  |  |  | 5.74 | <5 | 5.64 | <5 | <5 | <5 | <5 | <5 |
| 307 |  |  |  |  |  | 5.74 | <5 | 5.63 | <5 | <5 | <5 | <5 | <5 |
| 308 |  |  |  |  |  | 6.1 | <5 | 6.87 | <5 | <5 | <5 | 6.84 | <5 |
| 311 |  |  |  |  |  | 6.38 | <5 | 6.45 | <5 | 5.38 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 312 | | | | | | 5.76 | <5 | 5.86 | <5 | <5 | <5 | <5 | <5 |
| 313 | 8.67 | 8.53 | 9.01 | 8.27 | 7.08 | 6.98 | <5 | 7.1 | <5 | 5.65 | <5 | <5 | <5 |
| | | | | | | 6.56 | <5 | 7.09 | <5 | 5.56 | <5 | 5.09 | <5 |
| 314 | | | | | | 5.92 | <5 | 6.05 | <5 | <5 | <5 | <5 | <5 |
| 30 | | | | | | 6.71 | <5 | 6.32 | <5 | 5.42 | <5 | 5.21 | <5 |
| 38 | 8.69 | 8.21 | 8.55 | 7.78 | 7.06 | 5.93 | <5 | 6.5 | <5 | 5.14 | <5 | <5 | <5 |
| 315 | | | | | | 6.6 | <5 | 6.07 | <5 | 5.34 | <5 | <5 | <5 |
| 48 | | | | | | 7.43 | <5 | 7.53 | <5 | 6.45 | <5 | <5 | <5 |
| 316 | | | | | | 7.44 | <5 | 7.48 | <5 | 6.35 | <5 | <5 | <5 |
| 321 | 8.85 | 8.7 | 8.68 | 7.99 | 7.72 | 6.6 | <5 | 6.92 | <5 | 5.81 | <5 | <5 | <5 |
| 57 | 7.97 | 7.84 | 8.42 | 7.35 | 6.54 | 5.92 | <5 | 6.31 | <5 | <5 | <5 | <5 | <5 |
| 323 | 6.58 | 6.78 | 6.84 | <6 | <6 | <5 | <5 | <5 | <5 | <5 | <5 | <5 | <5 |
| 85 | 7.78 | 7.84 | 8.18 | 7.04 | 6.59 | 5.56 | <5 | 6.14 | <5 | <5 | <5 | <5 | <5 |
| 324 | 8.81 | 8.65 | 8.5 | 7.9 | 7 | 7.12 | <5 | 7.46 | <5 | 5.63 | <5 | <5 | <5 |
| 325 | 7.57 | 7.7 | 7.3 | 6.51 | 6.12 | 5.79 | <5 | 6.26 | <5 | <5 | <5 | <5 | <5 |
| 86 | 8.39 | 8.13 | 8.58 | 7.85 | 7.1 | <5 | <5 | <5 | <5 | <5 | <5 | <5 | <5 |
| 326 | 8.04 | 8.05 | 8.48 | 7.46 | 6.79 | 6.18 | <5 | 6.39 | <5 | 5.12 | <5 | <5 | <5 |
| 83 | 8.47 | 8.45 | 7.97 | 7.35 | 6.98 | 6.68 | <5 | 6.86 | <5 | 5.63 | <5 | <5 | <5 |
| 327 | 6.88 | 7.11 | 7.52 | 6.51 | 6.16 | <5 | <5 | 5 | <5 | <5 | <5 | <5 | <5 |
| 328 | 9.14 | 8.71 | 8.78 | 8.29 | 7.7 | 6.94 | <5 | 7.13 | 5.11 | 5.76 | <5 | ~5.12 | <5 |
| 330 | 8.85 | 8.65 | 8.51 | 7.75 | 7.47 | 6.49 | <5 | 6.7 | ~5.08 | ~5.56 | ~5.08 | ~5.19 | <5 |
| 332 | 8.82 | 8.67 | 8.52 | 7.85 | 7.33 | 7.27 | <5 | 7.57 | <5 | 6.04 | <5 | <5 | <5 |
| 333 | 8.47 | 8.39 | 8.42 | 7.86 | 7.15 | 5.68 | <5 | 6.13 | <5 | <5 | <5 | <5 | <5 |
| 334 | 7.37 | 7.2 | 7.29 | 6.61 | <6 | <5 | <5 | <5 | <5 | <5 | <5 | <5 | <5 |
| 335 | 9.06 | 8.84 | 9.23 | 8.68 | 7.67 | 7.13 | <5 | 7.6 | <5 | 6.09 | <5 | <5 | <5 |
| 336 | 8.51 | 8.5 | 8.7 | 7.88 | 6.86 | 6.36 | <5 | 6.85 | <5 | 5.37 | <5 | <5 | <5 |
| 338 | 9.21 | ~8.93 | 8.89 | 8.16 | 7.43 | 6.52 | <5 | 7.12 | <5 | 5.53 | <5 | <5 | <5 |
| 339 | 8.24 | 8.19 | 8.04 | 7.16 | 7.17 | 5.92 | <5 | 6.11 | <5 | <5 | <5 | <5 | <5 |
| 32 | 6.56 | 6.4 | 6.61 | <6 | <6 | <5 | <5 | 5.37 | <5 | <5 | <5 | <5 | <5 |
| 131 | 7.94 | 8.01 | 8.47 | 7.35 | 6.71 | 6.1 | <5 | 6.31 | <5 | 5.07 | <5 | <5 | <5 |
| 340 | 8.05 | 8.05 | 8.39 | 7.3 | 6.6 | 6.54 | <5 | 7.26 | <5 | 5.22 | <5 | <5 | <5 |
| 342 | 8.91 | 8.6 | 8.43 | 7.93 | 7.26 | 7.31 | <5 | 7.59 | <5 | 5.83 | <5 | <5 | <5 |
| 343 | 8.55 | 8.47 | 8.42 | 7.6 | 7.02 | 6.52 | <5 | 6.56 | <5 | 5.28 | <5 | <5 | <5 |
| 344 | 8.68 | 8.47 | 8.18 | 7.35 | 7.24 | 6.9 | <5 | 7.22 | <5 | 5.95 | <5 | 6.12 | <5 |
| 31 | 9.01 | 8.51 | 9.21 | 8.42 | 7.24 | 6.85 | <5 | 7.41 | <5 | 5.71 | <5 | 5.32 | <5 |
| | 8.86 | 8.61 | 9.06 | 8.51 | 7.34 | 6.96 | <5 | 7.29 | <5 | 5.87 | <5 | 5.53 | <5 |
| 345 | 8.38 | 8.41 | 8.73 | 7.63 | 7.06 | 5.82 | <5 | 6.32 | ~5.02 | ~5.01 | <5 | ~5.01 | <5 |
| 346 | ~6.64 | 6.55 | 6.45 | 6.59 | <6 | 5.17 | <5 | 5.68 | <5 | <5 | <5 | <5 | <5 |
| 347 | 8.85 | 8.67 | 8.64 | 8.24 | 7.2 | 7.46 | <5 | 7.99 | <5 | 6.09 | <5 | ~5.12 | <5 |
| 348 | 8.07 | 7.91 | 8.04 | 7.37 | 6.61 | 6.21 | <5 | 6.61 | <5 | 5.21 | <5 | <5 | <5 |
| 351 | 8.34 | 8.29 | 7.8 | 6.98 | 7.04 | 5.93 | <5 | 6.59 | <5 | ~5.38 | <5 | <5 | <5 |
| 89 | 8.43 | 8.35 | 8.52 | 7.6 | 7.01 | 6.33 | <5 | 6.82 | <5 | 5.31 | <5 | <5 | <5 |
| 352 | 8.98 | 8.54 | 8.64 | 8.29 | 7.37 | 7.5 | <5 | 7.89 | <5 | 5.89 | <5 | <5 | <5 |
| 87 | 9.01 | 8.73 | 8.88 | 8.46 | 7.62 | 7.51 | <5 | 7.89 | <5 | 6.39 | <5 | 5.07 | <5 |
| 353 | 7.68 | 7.73 | 8.07 | 7.06 | 6.33 | 5.64 | <5 | 6.2 | <5 | <5 | <5 | <5 | <5 |
| 354 | 8.51 | 8.08 | 8.43 | 7.7 | 6.57 | 6.2 | <5.52 | 6.68 | <5.52 | <5.52 | <5.52 | <5.52 | <5.52 |
| 355 | 7.49 | 7.21 | 7.19 | 6.21 | 6.23 | 5.19 | <5 | 5.55 | <5 | <5 | <5 | <5 | <5 |
| 356 | ~8.07 | 8.06 | 8.23 | 7.49 | 6.83 | 6.2 | <5 | 6.56 | <5 | 5.22 | <5 | <5 | <5 |
| 53 | 6.45 | 6.47 | 6.38 | ~6.15 | 6.34 | <5 | <5 | <5 | <5 | <5 | <5 | <5 | <5 |
| 91 | 7.91 | 7.71 | 8.25 | 7.47 | 6.59 | <5 | <5 | ~5.27 | <5 | <5 | <5 | <5 | <5 |
| 18 | 7.3 | 6.9 | 6.98 | 6.58 | 6.64 | 5.44 | <5 | 6.07 | <5 | <5 | <5 | <5 | <5 |
| 357 | 8.74 | 8.37 | 8.38 | 7.7 | 7.11 | 6.91 | <5 | 7.38 | <5 | 5.69 | <5 | <5 | <5 |
| 358 | 6.83 | 7.01 | 6.97 | 6.64 | <6 | <5 | <5 | 5.12 | <5 | <5 | <5 | <5 | <5 |
| 359 | 7.65 | 7.57 | 7.66 | 7.12 | 6.14 | 5.69 | <5 | 6.15 | <5 | <5 | <5 | <5 | <5 |
| 360 | 7.87 | 7.67 | 7.89 | 6.9 | 6.16 | 5.5 | <5 | 5.98 | <5 | <5 | <5 | <5 | <5 |
| 361 | 7.47 | 7.42 | 7.27 | 6.15 | 6.1 | 5.67 | <5 | 6.05 | <5 | 5.17 | <5 | 5.25 | <5 |
| 362 | 8.62 | 8.26 | 8.32 | 7.78 | 7.09 | 6.6 | <5 | 7.17 | <5 | 5.54 | <5 | <5 | <5 |
| 363 | 8.92 | 8.71 | 8.95 | 8.36 | 7.51 | 6.52 | <5 | 6.7 | <5 | 5.28 | <5 | <5 | <5 |
| | 9 | 8.75 | 8.84 | 8.35 | 7.33 | 5.8 | <5 | 6.57 | <5 | 5.07 | <5 | <5 | <5 |
| 364 | 8.41 | 8.19 | 8.23 | 7.59 | 7.69 | 5.94 | <5 | 6.45 | <5 | 5.8 | <5 | <5 | <5 |
| 365 | 8.64 | 8.41 | 8.57 | 7.97 | 7.52 | 6.29 | <5 | 6.94 | <5 | 5.74 | <5 | <5 | <5 |
| 366 | 8.94 | 8.6 | 8.62 | 8.18 | 7.31 | 7.23 | <5 | 7.92 | <5 | 5.95 | <5 | <5 | <5 |
| 367 | 9.26 | 8.86 | 8.94 | 8.54 | 7.47 | 7.17 | <5 | 7.63 | <5 | 6.02 | <5 | <5 | <5 |
| 300 | 8.15 | 7.99 | 8.38 | 7.9 | 7.01 | >8 | <5 | >8 | <5 | 5.29 | <5 | 5.09 | <5 |
| | 8.14 | 8.46 | 8.41 | 7.87 | 7.2 | 7.9 | 5.28 | 8.18 | ~5.12 | 5.56 | 5.1 | 5.33 | 5.17 |
| | 8.35 | 8.41 | 8.59 | 7.84 | 7.02 | 6.92 | <5 | 7.81 | <5 | 5.21 | <5 | 5.11 | <5 |
| 368 | ~8.96 | 8.7 | 8.81 | 8.09 | 7.23 | 5.93 | <5 | 6.41 | <5 | 5.14 | <5 | <5 | <5 |
| 369 | 7.76 | 7.93 | 7.5 | 6.73 | 7.63 | 5.2 | <5 | 5.57 | <5 | <5 | <5 | <5 | <5 |
| 370 | 8.68 | 8.57 | 8.61 | 8 | 6.86 | 5.95 | <5 | 6.51 | <5 | <5 | <5 | <5 | <5 |
| 371 | 8.8 | 8.68 | 8.42 | 8.17 | 7.24 | 6.04 | ~5.03 | 6.64 | ~5.17 | 5.58 | 5.13 | ~5.22 | ~5.13 |
| 92 | 9.09 | 8.57 | 8.99 | 8.74 | 7.64 | 6.65 | <5 | 7.72 | <5 | 5.79 | <5 | <5 | <5 |
| | 8.96 | 8.6 | 8.97 | 8.73 | 7.81 | 7.39 | <5 | 7.55 | <5 | 6.16 | <5 | <5 | <5 |
| | 9.04 | 8.45 | 8.99 | 8.58 | 7.65 | 7.74 | <5 | 7.83 | <5 | 6.23 | <5 | <5 | <5 |
| 373 | 7.96 | 7.97 | 7.97 | 7.26 | 6.62 | 5.63 | <5 | 6.1 | <5 | <5 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 374 | | | | | | 6.55 | <5 | 6.96 | <5 | 5.15 | <5 | <5 | <5 |
| 375 | 8.63 | 8.59 | 9.06 | 8.19 | 6.99 | 6.88 | <5 | 7.36 | <5 | 5.3 | <5 | <5 | <5 |
| | | | | | | 7.13 | <5 | 7.17 | <5 | 5.84 | <5 | <5 | <5 |
| 376 | | | | | | 6.92 | <5 | 7.32 | <5 | 5.91 | <5 | 5.04 | <5 |
| 377 | | | | | | 6.26 | <5 | 6.75 | <5 | 5.41 | <5 | <5 | <5 |
| 378 | 8.46 | 8.41 | 8.19 | 7.66 | 6.86 | 7.18 | <5 | 7.37 | <5 | 5.43 | <5 | <5 | <5 |
| | | | | | | 7.43 | <5 | 7.57 | <5 | 5.83 | <5 | <5 | <5 |
| 379 | 8.23 | 8.52 | 8.25 | 7.51 | 7.22 | 6.13 | <5 | 6.49 | ~5.19 | 5.14 | <5 | <5 | <5 |
| | | | | | | 6.48 | <5 | 6.59 | 5.1 | ~5.49 | ~5.08 | ~5.16 | <5 |
| 380 | | | | | | 6.69 | <5 | 6.85 | <5 | 5.32 | <5 | <5 | <5 |
| 381 | | | | | | 6.81 | <5 | 7.14 | <5 | 5.59 | <5 | <5 | <5 |
| 382 | 8.96 | 8.69 | 8.67 | 8.05 | 6.93 | 7.29 | <5 | 7.63 | ~5.05 | 5.56 | <5 | <5 | <5 |
| | | | | | | 7.5 | <5 | 7.69 | <5 | 5.79 | <5 | <5 | <5 |
| 132 | 8.12 | 8.54 | 8.43 | 7.73 | 7.46 | 6.26 | <5 | 6.75 | <5 | 5.4 | <5 | <5 | <5 |
| | | | | | | 6.84 | <5 | 6.65 | <5 | 5.68 | <5 | <5 | <5 |
| 108 | 9 | 8.86 | 8.74 | 8.19 | 7.5 | 7.67 | <5 | 7.68 | <5 | 6.15 | <5 | 5.12 | <5 |
| | | | | | | 7.45 | <5 | 7.59 | <5 | 5.98 | <5 | <5 | <5 |
| 384 | | | | | | 7.21 | <5 | 7.51 | <5 | 5.51 | <5 | <5 | <5 |
| 385 | | | | | | 5.49 | <5 | 5.81 | <5 | <5 | <5 | <5 | <5 |
| 39 | | | | | | 6.56 | <5 | 6.8 | <5 | 5.23 | <5 | <5 | <5 |
| 40 | | | | | | 6.25 | <5 | 6.47 | <5 | 5.19 | <5 | <5 | <5 |
| 133 | 8.52 | 8.28 | 8.73 | 7.94 | 7.08 | 6.82 | <5 | 7.06 | <5 | 5.62 | <5 | <5 | <5 |
| | | | | | | 6.74 | <5 | 7.12 | <5 | 5.64 | <5 | <5 | <5 |
| 386 | | | | | | ~5.56 | <5 | 5.79 | ~5.11 | <5 | 5.05 | <5 | <5 |
| 387 | | | | | | 5.25 | <5 | 5.57 | <5 | <5 | <5 | <5 | <5 |
| 389 | | | | | | 6.67 | <5 | 6.98 | <5 | 5.23 | <5 | <5 | <5 |
| 390 | | | | | | 7.17 | <5 | 7.25 | <5 | 5.62 | <5 | <5 | <5 |
| 391 | | | | | | 5.8 | <5 | 6.13 | <5 | <5 | <5 | <5 | <5 |
| 392 | 7.91 | 7.77 | 8.19 | 7.14 | 6.9 | 5.95 | <5 | 6.05 | <5 | 5.34 | <5 | 5.37 | <5 |
| 395 | 9.35 | 8.81 | 8.87 | 8.72 | 8.08 | 7.78 | <5 | 7.88 | <5 | 6.75 | <5 | <5 | <5 |
| 94 | 8.76 | 8.29 | 9.05 | 8.2 | 7.1 | 6.41 | <5 | 6.74 | <5 | 5.31 | <5 | <5 | <5 |
| | 8.47 | 8.47 | 8.85 | 8.19 | 7.07 | 6.9 | <5 | 7.1 | <5 | 5.62 | <5 | <5 | <5 |
| 396 | 8.66 | 8.45 | 8.23 | 8.05 | 7.59 | 7.78 | <5 | 8.02 | ~5.16 | 6.62 | <5 | 5.08 | <5 |
| 397 | 8.43 | 8.36 | 8.96 | 7.98 | 6.87 | 6.75 | <5 | ~7.07 | <5 | 5.26 | <5 | <5 | <5 |
| 398 | 8.85 | 8.59 | 8.67 | 8 | 7.75 | 6.44 | <5 | 6.54 | ~5.25 | 5.95 | <5 | ~5.16 | <5 |
| 399 | 8.58 | 8.37 | 9.05 | 8.24 | 7.08 | 6.59 | <5.52 | 6.87 | <5 | 5.65 | <5 | 5.1 | <5 |
| 400 | 8.55 | 8.46 | 9.01 | 8.15 | 7.14 | 6.55 | <5 | 6.5 | <5 | 5.67 | <5 | 5.1 | <5 |
| 401 | 7.75 | 7.78 | 8.31 | 7.14 | 6.76 | 5.75 | <5 | 5.93 | <5 | 5.33 | <5 | <5 | <5 |
| 405 | 7.2 | 6.89 | 7.08 | 6.59 | <6 | 5.62 | <5 | 5.79 | <5 | <5 | <5 | <5 | <5 |
| 407 | 7.21 | 6.84 | 7.25 | 6.35 | 6.11 | <5 | <5 | ~5.08 | <5 | <5 | <5 | <5 | <5 |
| 408 | 6.41 | 6.74 | 6.49 | <6 | ~6 | <6 | <5 | 6.38 | <5 | <5 | <5 | <5 | <5 |
| 409 | 8.84 | 8.55 | 8.58 | 8.11 | 6.57 | 6.82 | <5 | 6.78 | <5 | 5.47 | <5 | <5 | <5 |
| 411 | 6.62 | 6.75 | 6.75 | 6 | 6.13 | <5 | <5 | <5 | <5 | <5 | <5 | <5 | <5 |
| 412 | 8.14 | 8.36 | 8.1 | 7.42 | 6.93 | 6.35 | <5 | 6.03 | <5 | 5.31 | <5 | <5 | <5 |
| 413 | 8.74 | 8.5 | 8.37 | 8.17 | 7.76 | 7.79 | <5 | 7.94 | 5.09 | 6.4 | <5 | 5.11 | <5 |
| 414 | 8.54 | 8.43 | 8.27 | 7.64 | 7.17 | 6.65 | <5 | 6.57 | ~5.15 | 5.89 | <5 | ~5.98 | <5 |
| 422 | 8.72 | 8.42 | 8.74 | 8.12 | 7.49 | 6.67 | <5 | 7.29 | <5 | 5.84 | <5 | <5 | <5 |
| 423 | 8.73 | 8.46 | 8.81 | 8.18 | 7.42 | 7.4 | <5 | 7.65 | <5 | 6.07 | <5 | ~5.07 | <5 |
| 426 | 6.94 | 6.8 | 6.69 | <6 | <6 | 5.43 | <5 | 5.59 | <5 | <5 | <5 | ~5.05 | <5 |
| 428 | 8.52 | 8.46 | 8.38 | 7.17 | 7.73 | 5.99 | <5 | 5.8 | <5 | 5.25 | <5 | <5 | <5 |
| 34 | 8.7 | 8.4 | 8.54 | 7.93 | 7.04 | 5.88 | <5 | 5.81 | <5 | <5 | <5 | <5 | <5 |
| 430 | 8.15 | 8 | 8.32 | 7.7 | 7.26 | 6.13 | <5 | 6.26 | <5 | 5.25 | <5 | <5 | <5 |
| 125 | 8.49 | 8.31 | 8.5 | 7.84 | 6.87 | 6.38 | <5 | 6.38 | <5 | 5.49 | <5 | <5 | <5 |
| 431 | 7.9 | 7.83 | 8.01 | 7.49 | 6.78 | 5.8 | <5 | 6.17 | <5 | ~5.13 | <5 | <5 | <5 |
| 432 | 8.91 | 8.55 | 8.52 | 8.22 | 7.26 | 7.04 | <5 | 7.32 | <5 | 5.81 | <5 | <5 | <5 |
| 433 | 7.94 | 7.78 | 7.99 | 7.51 | 7.18 | 5.67 | <5 | 5.63 | <5 | 5.24 | <5 | 5.1 | <5 |
| 434 | 8.66 | 8.4 | 8.94 | 8.33 | 7.07 | 6.49 | <5 | 7.03 | <5 | 5.49 | <5 | 5.09 | <5 |
| 435 | 8.9 | 8.73 | 8.71 | 8.15 | 6.9 | 6.66 | <5 | 6.63 | ~5.19 | 5.51 | <5 | 5.28 | <5 |
| 5 | 8.14 | 7.89 | 8.12 | 7.6 | 6.87 | ~6.13 | <5 | 5.49 | <5 | <5 | <5 | <5 | <5 |
| | 8.12 | 7.96 | 8.2 | 7.82 | 7.01 | 6.32 | <5 | ~6.61 | <5 | 5.06 | <5 | <5 | <5 |
| | 8.14 | 7.89 | 8.31 | 7.74 | 7.1 | 6.33 | <5 | 6.51 | <5 | 5.11 | <5 | <5 | <5 |
| | 8.04 | 8.3 | 8.54 | 7.81 | 6.92 | 6.45 | <5 | 6.58 | <5 | 5.43 | <5 | <5 | <5 |
| | 8.02 | 8.2 | 8.66 | 7.67 | 6.96 | 6.08 | <5 | 6.4 | <5 | 5.32 | <5 | <5 | <5 |
| | 8.1 | 8.26 | 8.59 | 7.6 | 7 | 6.22 | <5 | 6.45 | <5 | 5.37 | <5 | <5 | <5 |
| | 7.91 | 7.94 | 8.08 | 7.58 | 6.66 | 5.87 | <5 | 6.62 | <5 | 5.23 | <5 | <5 | <5 |
| | 8.22 | 8.26 | 8.45 | 7.81 | 6.86 | 6.24 | <5 | 6.62 | <5 | 5.29 | <5 | <5 | <5 |
| 436 | 8.93 | 8.68 | 8.88 | 8.19 | 7.56 | 6.7 | <5 | 6.72 | <5 | 5.9 | <5 | <5 | <5 |
| 95/95a | 8.77 | 8.55 | 8.77 | 8.52 | 7.68 | 6.83 | <5 | 6.75 | <5 | 5.97 | <5 | <5 | <5 |
| 437 | 6.81 | 6.87 | 6.8 | <6 | <6 | 5.31 | <5 | 5.35 | <5 | <5 | ~5.66 | <5 | <5 |
| 438 | 6.91 | 6.71 | 6.4 | <6 | <6 | 5.26 | <5 | 5.41 | <5 | <5 | <5 | <5 | <5 |
| 440 | 8.56 | 8.32 | 8.07 | 7.36 | 7.09 | 6.62 | <5 | 6.57 | ~5.02 | 5.67 | <5 | 5.93 | <5 |
| 441 | 8.65 | 8.46 | 8.31 | 8.27 | 7.75 | 8.19 | <5 | 8.39 | ~5.11 | 6.96 | <5 | 5.1 | <5 |
| 442 | 8.79 | 8.52 | 8.41 | 7.98 | 7.06 | 7.37 | <5 | 7.37 | <5 | 5.76 | ~5.61 | <5 | <5 |
| 443 | 9.06 | 8.64 | 8.54 | 8.32 | 7.33 | 7.53 | <5 | 7.86 | ~5.13 | 5.89 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 444 | 9.04 | 8.5 | 8.56 | 8.36 | 7.33 | 7.62 | <5 | 7.85 | ~5.1 | 5.96 | <5 | <5 | <5 |
| 445 | 8.58 | 8.32 | 8.8 | 8.22 | 6.76 | 6.53 | <5 | 6.85 | <5 | 5.46 | <5 | <5 | <5 |
| 447 | 8.74 | 8.33 | 8.92 | 8.49 | 6.88 | 7.08 | <5 | 7.57 | <5 | 5.65 | <5 | <5 | <5 |
| 448 | 8.8 | 8.41 | 8.64 | 7.96 | 7.31 | 6.38 | <5 | 6.37 | <5 | 5.57 | <5 | ~5.11 | <5 |
| 449 | 8.61 | 8.45 | 8.37 | 7.84 | 7.2 | 6.77 | <5 | 6.86 | <5 | 5.63 | <5 | <5 | <5 |
| 450 | 8.69 | 8.54 | 8.53 | 7.97 | 7.26 | 7.07 | <5 | 7.21 | <5 | 5.6 | <5 | <5 | <5 |
| 452 | 8.54 | 8.19 | 7.9 | 7.81 | 7.44 | 7.81 | <5 | 7.94 | ~5.16 | 6.4 | <5 | 5.06 | <5 |
| 453 | 7.98 | 7.74 | 8 | 6.88 | 6.64 | 5.68 | <5 | 5.76 | <5 | <5 | <5 | <5 | <5 |
| 134 | 8.72 | 8.47 | 8.31 | 8.08 | 6.98 | 7.66 | <5 | 7.69 | <5 | 5.39 | <5 | <5 | <5 |
|  | 8.63 | 8.55 | 8.45 | 8.21 | 6.98 | 7.79 | <5 | 7.95 | <5 | 5.76 | <5 | <5 | <5 |
| 454 | 8.77 | 8.43 | 8.67 | 8.17 | 7.35 | 6.74 | <5 | 7.19 | <5 | 5.83 | <5 | <5 | <5 |
| 455 | 8.54 | 8.34 | 8.28 | 8.1 | 7.21 | 7.1 | <5 | 7.22 | <5 | 5.74 | <5 | <5 | <5 |
| 456 | 8.74 | 8.47 | 8.5 | 8.05 | 7.13 | 6.44 | <5 | 6.6 | ~5.22 | 5.69 | <5 | <5 | <5 |
| 96 | 7.6 | 7.7 | 7.51 | 6.74 | 6.32 | 5.77 | <5 | 5.9 | ~5.21 | ~5.06 | <5 | ~5 | <5 |
| 457 | 9.08 | 8.58 | 8.85 | 8.07 | 7.3 | 6.19 | <5 | 6.31 | ~5.25 | 5.46 | <5 | ~5.11 | ~5.05 |
| 458 | 8.44 | 8.31 | 8.55 | 7.89 | 6.97 | 6.79 | <5 | 6.81 | <5 | 5.28 | <5 | <5 | <5 |
| 44/44a | 8.1 | 7.98 | 7.84 | 7.51 | 6.51 | 6.06 | <5 | 6.09 | <5 | 5.04 | <5 | <5 | <5 |
| 459 | 8.24 | 8.06 | 8.18 | 7.54 | 6.76 | 6.27 | <5 | 6.84 | <5 | 5.15 | <5 | <5 | <5 |
| 460 | 7.76 | 8.04 | 8.17 | 6.94 | 7.05 | 6.7 | <5 | ~6.69 | <5 | 5.53 | <5 | <5 | <5 |
| 463 |  |  | 8.54 | 7.65 |  | 7.42 | <5 |  |  | 6.04 | <5 | <5 | <5 |
| 464 | 8.58 | 8.65 | 8.57 | 8.4 | 7.88 | 6.86 | <5 | 7.34 | <5 | 5.71 | <5 | <5 | <5 |
| 465 | 8.31 | 8.36 | 8.38 | 7.4 | 7.06 | 6.34 | <5 | 6.73 | ~5.15 | 5.35 | <5 | <5 | <5 |
| 467 | 9.05 | 8.69 | 8.77 | 8.33 | 7.43 | 7.76 | <5 | 7.95 | <5 | 5.77 | <5 | <5 | <5 |
| 468 | 8.02 | 7.71 | 7.72 | 7.16 | 6.61 | 5.52 | <5 | 5.61 | <5 | ~5.04 | <5 | <5 | <5 |
| 469 | 9.23 | 8.76 | 8.77 | 8.52 | 7.4 | 8.12 | <5 | 8.08 | <5 | 5.8 | <5 | <5 | <5 |
| 470 | 8.75 | 8.56 | 8.55 | 7.83 | 7.1 | 6.6 | <5 | 7.03 | <5 | 5.38 | <5 | <5 | <5 |
| 472 | 8.69 | 8.61 | 8.63 | 8.08 | 7.58 | 7.32 | <5 | 7.62 | <5 | 5.57 | <5 | <5 | <5 |
| 474 | 8.39 | 8.48 | 8.37 | 7.75 | 7.9 | 5.8 | ~5.56 | 6.04 | ~5.5 | ~5.62 | ~5.29 | ~5.37 | ~5.38 |
| 135 | 9.11 | 8.75 | 8.86 | 8.47 | 7.74 | 7.79 | <5 | 7.83 | ~5.11 | 5.82 | <5 | <5 | <5 |
| 475 | ~7.88 | 7.83 | 8.35 | 7.24 | 6.85 | 6.08 | <5 | 6.06 | <5 | 5.09 | <5 | <5 | <5 |
| 476 | 8.32 | 8.6 | 9.15 | 8.37 | 7.57 | 6.85 | <5 | 7.02 | <5 | 5.46 | <5 | 5.53 | <5 |
| 477 | 8.06 | 7.96 | 8.39 | 7.46 | 6.74 | 5.92 | <5 | 5.98 | <5 | <5 | <5 | <5 | <5 |
| 478 | 7.91 | 7.97 | 8.06 | 7.01 | 7.02 | 5.44 | <5 | 5.7 | <5 | 5.04 | <5 | <5 | <5 |
| 136 | 8.82 | 8.66 | 8.64 | 8.36 | 7.63 | 8.02 | <5 | 8.06 | ~5.11 | 5.88 | <5 | ~5.06 | <5 |
| 480 | 8.9 | 8.64 | 8.68 | 8 | 7.57 | 6.7 | ~5.24 | 6.78 | ~5.36 | 5.89 | ~5.1 | ~5.3 | ~5.25 |
| 97 | 8.38 | 8.51 | 8.94 | 7.86 | 6.95 | 6.96 | <5 | 7 | <5 | 5.62 | <5 | 5.06 | <5 |
|  | 8.13 | 8.19 | 8.75 | 7.9 | 6.94 | 6.38 | <5 | 6.8 | <5 | 5.12 | <5 | <5 | <5 |
| 98 | 8.88 | 8.56 | 9.03 | 8.32 | 7.21 | 7.01 | <5 | 7.25 | <5 | 5.28 | <5 | <5 | <5 |
|  | 8.64 | 8.62 | 8.96 | 8.24 | 6.79 | 7.13 | <5 | 7.59 | <5 | 5.82 | <5 | <5 | <5 |
| 481 | 8.64 | 8.49 | 9.07 | 8.42 | 6.92 | 6.89 | <5 | 7.3 | <5 | 5.27 | <5 | <5 | <5 |
| 482 | 8.95 | 8.6 | 8.79 | 8 | 7.59 | 6.49 | <5 | 6.45 | <5 | 5.59 | <5 | <5 | <5 |
| 483 | 8.82 | 8.74 | 8.88 | 8.32 | 7.69 | 6.41 | <5 | 6.82 | <5 | 5.68 | <5 | <5 | <5 |
| 485 | 8.25 | 8.16 | 7.97 | 7.3 | 7.75 | 7.33 | <5 | 7.39 | <5 | 5.91 | <5 | 5.13 | <5 |
| 486 | 8.57 | 8.45 | 8.38 | 7.7 | 7.01 | 6.34 | <5 | 6.71 | <5 | 5.17 | <5 | <5 | <5 |
| 487 | 8.35 | 8.36 | 8.29 | 7.62 | 7.48 | 6.35 | <5 | 6.4 | ~5.25 | ~5.56 | <5 | ~5.14 | ~5 |
| 488 | 7.99 | 8.12 | 8.02 | 7.26 | 6.73 | 6.11 | <5 | 6.5 | <5 | 5.32 | <5 | <5 | <5 |
|  | 7.92 | 7.88 | 8.01 | 7.41 | 6.65 | 5.7 | <5 | 6.58 | <5 | 5.13 | <5 | <5 | <5 |
| 489 | 8.9 | 8.55 | 8.79 | 8.11 | 7.54 | 7.42 | <5 | 7.9 | <5 | 6.34 | <5 | ~5.1 | <5 |
| 490 | 8.62 | 8.65 | 8.5 | 7.88 | 6.9 | 7.02 | <5 | 7.26 | <5 | 5.78 | <5 | <5 | <5 |
| 493 | 8.67 | 8.53 | 8.57 | 7.95 | 6.99 | 7.27 | <5 | 7.35 | <5 | 5.79 | <5 | 5.25 | <5 |
| 494 | 9.21 | 8.64 | 8.99 | 8.26 | 7.69 | 7.11 | <5 | 7.22 | <5 | 6 | <5 | ~5.11 | <5 |
| 495 | 8.17 | 8.35 | 8.24 | 7.58 | 6.93 | 6.7 | <5 | 6.9 | <5 | 5.47 | <5 | <5 | <5 |
| 137 | 8.79 | 8.47 | 8.37 | 8.12 | 6.98 | 7.57 | <5 | 7.74 | <5 | 5.88 | <5 | <5 | <5 |
| 119 | 7.8 | 7.89 | 7.64 | 6.92 | 6.13 | 5.71 | <5 | 5.94 | <5 | <5 | <5 | <5 | <5 |
| 498 | 8.33 | 8.3 | 8.42 | 6.85 | 7.05 | 6.73 | <5 | 7.06 | <5 | 5.65 | <5 | 5.01 | <5 |
| 99 | 9.07 | 8.72 | 9.09 | 8.95 | 7.02 | 7.54 | <5 | 8.12 | <5 | 5.63 | <5 | <5 | <5 |
|  | 8.99 | 8.79 | 9.19 | 8.79 | 7.29 | 7.73 | <5 | 8.11 | <5 | 5.59 | <5 | <5 | <5 |
| 138 | 8.5 | 8.32 | 8.56 | 7.06 | 7.34 | 6.92 | <5 | 6.98 | <5 | 6.16 | <5 | 5.39 | <5 |
|  | 8.34 | 8.3 | 8.52 | 7.07 | 7.16 | 6.64 | <5 | 7.11 | <5 | 5.81 | <5 | 5.11 | <5 |
|  | 8.53 | 8.5 | 8.6 | 7.13 | 7.49 | 6.95 | ~5.18 | 6.83 | 5.25 | 6.21 | 5.29 | 5.61 | 5.17 |
| 499 | 8.74 | 8.4 | 8.56 | 8.13 | 7.5 | 7.39 | <5 | 7.7 | <5 | 6.09 | <5 | ~5.16 | <5 |
| 500 | 8.73 | 8.55 | 8.58 | 7.36 | 7.66 | 7.06 | <5 | 7.24 | <5 | 6.29 | <5 | <5 | <5 |
|  | 8.71 | 8.15 | 8.62 | 7.53 | 7.71 |  |  |  |  |  |  |  |  |
| 501 | 8.7 | 8.75 | 8.56 | 7.95 | 7.12 | 7.19 | <5 | 7.08 | <5 | 5.88 | <5 | <5 | <5 |
| 502 | 8.76 | 8.75 | 8.62 | 8.06 | 7.2 | 7.44 | <5 | 7.49 | <5 | 5.96 | <5 | <5 | <5 |
| 503 | 8.91 | 8.74 | 8.96 | 8.65 | 7.83 | 7.83 | <5 | 7.9 | <5 | 6.32 | <5 | <5 | <5 |
| 139 | 8.18 | 8.28 | 8.39 | 7.87 | 6.86 | 7.02 | <5 | 6.97 | <5 | 5.29 | <5 | <5 | <5 |
| 504 | 9.06 | 8.9 | 8.93 | 8.27 | 7.39 | 7.01 | <5 | 6.62 | <5 | 5.15 | <5 | <5 | <5 |
|  | 8.99 | 8.82 | 8.83 | 8.1 | 7.39 | 6.95 | <5 | 6.71 | <5 | 5.16 | <5 | <5 | <5 |
| 140 | 8.22 | 8.33 | 8.5 | 8.07 | 7.12 | 6.42 | <5 | 7.04 | <5 | 5.5 | <5 | <5 | <5 |
|  | 8.59 | 8.68 | 8.71 | 8.16 | 7.48 | 6.82 | <5 | 7.16 | <5 | 5.53 | <5 | <5 | <5 |
| 506 | 7.55 | 7.91 | 7.87 | 6.92 | 6.7 | 6.13 | <5 | 6.27 | <5 | 5.37 | <5 | <5 | <5 |
| 507 | 8.1 | 8.22 | 8.22 | 7.32 | 6.66 | 6.51 | <5 | 6.41 | <5 | 5.22 | <5 | <5 | <5 |
| 508 | 7.56 | 7.89 | 7.96 | 6.97 | 7.07 | 6.44 | <5 | 6.19 | <5 | 5.31 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 509 | | | 8.57 | 8.43 | >8 | <5 | | 6.76 | | 7.05 | <5 | 5.31 | <5 |
| 510 | 8.25 | 8.34 | 8.1 | 7.34 | 6.89 | 6.95 | <5 | 7.58 | <5 | 5.53 | <5 | <5 | <5 |
| 141 | 9.01 | 8.82 | 9.22 | 8.42 | 7.63 | 7.49 | <5 | 7.58 | <5 | 6.16 | <5 | <5 | <5 |
| | 8.9 | 8.45 | 8.92 | 8.37 | 7.49 | 6.86 | <5 | 6.99 | <5 | 5.68 | <5 | <5 | <5 |
| 511 | 8.08 | 8.13 | 8 | 7.55 | 7.46 | 7.71 | <5 | 8.1 | <5 | 6.94 | <5 | 5.68 | <5 |
| 512 | 8.6 | 8.62 | 8.52 | 7.88 | 7.13 | 7.72 | <5 | 7.75 | <5 | 5.73 | <5 | <5 | <5 |
| 513 | 8.86 | 8.7 | 9.08 | 8.17 | 7.27 | 7.12 | <5 | 7.15 | <5 | 5.68 | <5 | <5 | <5 |
| 514 | 8.31 | 8.56 | 8.45 | 7.81 | 7.51 | 6.91 | <5 | 7 | <5 | 5.94 | <5 | <5 | <5 |
| 515 | 7.77 | 7.94 | 7.47 | 6.73 | 6.63 | 6.13 | ~5.24 | 6.34 | 5.29 | ~5.45 | 5.19 | ~5.33 | ~5.09 |
| 35 | 7.3 | 7.45 | 7.32 | 6.39 | 6.21 | 5.72 | <5 | 5.64 | <5 | 5.08 | <5 | 5.41 | <5 |
| 517 | 7.95 | 8.22 | 8.32 | 7.54 | 7.34 | 6.77 | <5 | 7.01 | <5 | 5.89 | <5 | <5 | <5 |
| 518 | 8.37 | 8.55 | 8.2 | 7.43 | 7.2 | 7.02 | <5 | 7.58 | 5.2 | 6.08 | <5 | 5.25 | <5 |
| 519 | 8.74 | 8.62 | 8.62 | 8.1 | 7.07 | 7.5 | <5 | 7.3 | <5 | 5.74 | <5 | <5 | <5 |
| 102 | 8.53 | 8.47 | 8.52 | 7.78 | 7.24 | 7.07 | <5 | 7.37 | <5 | 5.93 | <5 | <5 | <5 |
| 521 | 8.76 | 8.77 | 8.56 | 8.42 | 7.74 | 8.17 | <5 | 8.19 | <5 | 6.3 | <5 | 5.01 | <5 |
| 522 | 8.71 | 8.51 | 8.51 | 7.93 | 6.98 | 7.52 | <5 | 7.58 | <5 | ~6.02 | <5 | <5 | <5 |
| 523 | 8.14 | 8.42 | 8.44 | 8.08 | 6.68 | 6.6 | <5 | 6.84 | <5 | 5.22 | <5 | <5 | <5 |
| 142 | 8.36 | 8.39 | 8.53 | 7.97 | 6.75 | 6.7 | <5 | 6.94 | <5 | 5.48 | <5 | <5 | <5 |
| 524 | 8.75 | 8.55 | 8.71 | 8.11 | 7.61 | 6.85 | <5 | 7.2 | <5 | 5.75 | <5 | <5 | <5 |
| 525 | 8.03 | 8.43 | 8.49 | 7.72 | 6.64 | 6.73 | <5 | 7.05 | <5 | 5.54 | <5 | <5 | <5 |
| 526 | 8.29 | 8.47 | 8.32 | 7.76 | 7.07 | 7.42 | <5 | 7.48 | <5 | 5.86 | <5 | <5 | <5 |
| 527 | 8.18 | 8.26 | 8.42 | 7.77 | 7.69 | 6.32 | <5 | 6.67 | ~5.01 | 5.94 | ~5.02 | 5.11 | <5 |
| 143 | 8.01 | 8.21 | 7.95 | 7.3 | 7.03 | 6.66 | <5 | 7.02 | <5 | 5.75 | <5 | <5 | <5 |
| 528 | 8.44 | 8.58 | 8.24 | 7.54 | 7.44 | 6.89 | <5 | 7.18 | <5 | 6.19 | <5 | <5 | <5 |
| 529 | 8.64 | 8.52 | 8.47 | 8.06 | 7.35 | 7.27 | <5 | 7.51 | 5.13 | 6.07 | ~5 | 5.12 | <5 |
| 530 | 8.44 | 8.59 | 8.43 | 7.62 | 7.46 | 6.92 | <5 | 7.34 | 5.21 | 6.34 | <5 | 5.1 | <5 |
| 10 | 8.21 | 8.12 | 8.21 | 7.96 | 6.43 | 6.97 | <5 | 7.13 | <5 | <5 | <5 | <5 | <5 |
| 531 | 8.57 | 8.67 | 8.65 | 7.97 | 7.34 | 7.36 | <5 | 7.68 | <5 | 6.24 | <5 | <5 | <5 |
| 36 | 7.97 | 8.29 | 8.66 | 7.6 | 6.84 | 6.35 | <5 | 6.59 | <5 | 5.52 | <5 | 5.13 | <5 |
| 532 | 7.28 | 7.36 | 7.22 | 6.47 | 6.24 | 5.82 | <5 | 6.09 | <5 | <5 | <5 | <5 | <5 |
| 533 | 8.76 | 8.65 | 8.49 | 8.01 | 7.34 | 7.37 | <5 | 7.63 | <5 | 6.31 | <5 | <5 | <5 |
| 534 | 8.63 | 8.66 | 8.46 | 7.92 | 7.1 | 7.41 | <5 | 7.74 | <5 | 6.16 | <5 | <5 | <5 |
| 535 | 8.81 | 8.7 | 8.4 | 8.18 | 7.43 | 7.48 | <5 | 7.99 | 5.15 | 6.35 | <5 | <5 | <5 |
| 536 | 7.03 | 7.33 | 7.7 | 6.76 | <6 | 5.66 | <5 | 5.85 | <5 | <5 | <5 | <5 | <5 |
| 537 | 8.16 | 8.14 | 7.93 | 7.23 | 6.95 | 6.2 | <5 | 6.18 | <5 | 5.33 | <5 | 5.12 | <5 |
| 538 | 7.25 | 7.52 | 7.8 | 6.99 | 6.38 | 5.39 | <5 | 5.44 | <5 | 5.18 | <5 | <5 | <5 |
| | 7.25 | 7.52 | 7.8 | 6.99 | 6.38 | 5.39 | <5 | 5.44 | <5 | 5.18 | <5 | <5 | <5 |
| 144 | 7.92 | 8.31 | 8.41 | 7.52 | 7 | 6.45 | <5 | 6.58 | <5 | 5.34 | <5 | <5 | <5 |
| 539 | 7.76 | 8.1 | 7.79 | 7.15 | 6.35 | 6.5 | <5 | 6.65 | <5 | 5.35 | <5 | <5 | <5 |
| 603 | 8.53 | 8.56 | 8.22 | 7.6 | 7.14 | 7.52 | <5 | 7.51 | <5 | 5.74 | <5 | <5 | <5 |
| 540 | 8.32 | 8.28 | 8.35 | 7.57 | 6.68 | 7.24 | <5 | 7.37 | <5 | 5.5 | <5 | <5 | <5 |
| 541 | 8.62 | 8.81 | 8.66 | 8.13 | 7.56 | 7.67 | <5 | 7.83 | <5 | 6.38 | <5 | <5 | <5 |
| 542 | 8.52 | 8.5 | 8.59 | 8.24 | 7.14 | 6.67 | <5 | 6.77 | <5 | 5.11 | <5 | <5 | <5 |
| 543 | 8.7 | 8.54 | 8.39 | 7.73 | 7.18 | 7.52 | <5 | 7.62 | <5 | 5.68 | <5 | <5 | <5 |
| 544 | 8.14 | 8.11 | 7.71 | 7.08 | 6.71 | 6.66 | <5 | 6.79 | <5 | 5.37 | <5 | <5 | <5 |
| 41 | 8.73 | 8.78 | 8.83 | 8.3 | 7.57 | 7.35 | <5 | 7.36 | <5 | 5.93 | <5 | <5 | <5 |
| 33 | 8.73 | 8.75 | 8.51 | 8.17 | 7.47 | 7.88 | <5 | 7.87 | <5 | 6.02 | <5 | 5.07 | <5 |
| 43 | 8.55 | 8.62 | 8.24 | 7.6 | 7.16 | 6.94 | ~5.26 | 7.04 | ~5.34 | 5.65 | ~5.3 | ~5.42 | ~5.27 |
| 546 | 8.69 | 8.6 | 8.45 | 8.15 | 6.9 | 8.31 | <5 | 8.09 | <5 | 5.56 | <5 | <5 | <5 |
| 547 | 7.48 | 7.62 | 7.86 | 6.89 | 6.58 | 6.13 | <5 | 6.3 | <5 | <5 | <5 | <5 | <5 |
| 548 | 8.53 | 8.71 | 8.39 | 8.13 | 7.18 | 7.86 | <5 | 7.96 | ~5.14 | 5.89 | ~5.02 | 5.14 | <5 |
| 551 | 8.33 | 8.51 | 8.6 | 7.72 | 7.63 | 6.88 | <5 | 7.1 | <5 | 5.95 | <5 | <5 | <5 |
| 552 | 8.14 | 8.4 | 8.01 | 7.11 | 7.43 | 7.35 | <5 | 7.07 | <5 | 6.08 | <5 | 5.09 | <5 |
| 553 | 8.31 | 8.36 | 8.27 | 7.85 | 7.17 | 7.26 | <5 | 7.2 | <5 | 5.88 | <5 | <5 | <5 |
| 554 | 8.14 | 8.32 | 8.22 | 7.89 | 7.2 | 7.14 | <5 | 7.07 | <5 | 6 | ~5.04 | 5.15 | <5 |
| 556 | 7.88 | 8.15 | 8.01 | 7.38 | 6.93 | 6.23 | <5 | 6.21 | <5 | 5.16 | <5 | <5 | <5 |
| 557 | 7.82 | 8.12 | 8.01 | 6.97 | 6.61 | 6.09 | <5 | 6.22 | <5 | <5 | <5 | <5 | <5 |
| 558 | 8.39 | 8.56 | 8.32 | 7.66 | 6.78 | 7.01 | <5 | 6.99 | ~5.17 | 5.55 | 5.09 | 5.44 | <5 |
| 103 | 8.7 | 8.73 | 8.75 | 8.06 | 7.47 | 7.37 | <5 | 7.3 | <5 | 5.95 | <5 | 5.07 | <5 |
| 559 | 8.6 | 8.61 | 8.39 | 7.71 | 6.44 | 7.3 | <5 | 7.19 | <5 | 5.58 | <5 | <5 | <5 |
| 145 | 8.72 | 8.72 | 8.48 | 7.92 | 6.7 | 7.68 | <5 | 7.67 | <5 | 5.52 | <5 | <5 | <5 |
| 561 | 7.5 | 7.9 | 8.05 | 7.03 | 6.52 | 6.2 | <5 | 6.31 | <5 | 5.18 | <5 | <5 | <5 |
| 562 | 8.57 | 8.49 | 8.3 | 7.86 | 7.39 | 7.49 | <5 | ~7.7 | <5 | 5.9 | <5 | <5 | <5 |
| 563 | 8 | 8.35 | 8.11 | 7.32 | 7.97 | 6.23 | <5 | 6.28 | <5 | 5.72 | <5 | 5.09 | <5 |
| 564 | 8.37 | 8.51 | 8.26 | 7.71 | 7.23 | 7.11 | <5 | 6.91 | <5 | 5.77 | <5 | <5 | <5 |
| 565 | 8.1 | 8.28 | 8.47 | 7.58 | 6.95 | 6.44 | <5 | 6.64 | <5 | 5.24 | <5 | <5 | <5 |
| 566 | 7 | 7.22 | 7.27 | 6.51 | <6 | 5.83 | <5 | 5.88 | <5 | <5 | <5 | <5 | <5 |
| 567 | 7.18 | 7.23 | 7.32 | 6.82 | 6.17 | 6.1 | <5 | 6.24 | <5 | <5 | <5 | <5 | <5 |
| 568 | 8.57 | 8.65 | 8.9 | 7.91 | 7.11 | 6.85 | <5 | 7.06 | <5 | 5.52 | <5 | <5 | <5 |
| 569 | 7.77 | 7.81 | 7.78 | 6.93 | 6.7 | 5.85 | <5 | 6.05 | <5 | ~5.09 | <5 | <5 | <5 |
| 146 | 8.62 | 8.67 | 8.78 | 7.79 | 6.96 | 6.98 | <5 | 7.01 | <5 | 5.23 | <5 | <5 | <5 |
| 110 | 8.25 | 8.19 | 8.2 | 7.66 | 7.39 | 7.46 | <5 | 7.81 | <5 | 6.09 | <5 | <5 | <5 |
| 570 | 8.88 | 8.95 | 8.71 | 8.26 | 7.47 | 7.46 | <5 | 7.81 | ~5.03 | 5.89 | <5 | 5.18 | <5 |
| 577 | 8.43 | 8.42 | 8.18 | 7.75 | 7.28 | 7.74 | <5 | 7.74 | <5 | 6.26 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 578 | 8.76 | 8.9 | 8.6 | 8.22 | 7.53 | 8.03 | <5 | 8.11 | ~5.04 | 6.51 | <5 | 5.2 | <5 |
| 581 | ~8.76 | 8.72 | 8.28 | 7.94 | 6.95 | 7.82 | <5 | 7.94 | <5 | 5.82 | <5 | ~5.04 | <5 |
| 582 | 7.49 | 7.68 | 7.72 | 7.08 | 6.57 | 5.5 | <5 | 5.97 | <5 | <5 | <5 | <5 | <5 |
| 583 |  |  | 7.97 | 7.22 |  | 7.2 | <5 |  |  | 5.82 | <5 | <5 | <5 |
| 584 | 7.85 | 8.08 | 8.05 | 7.4 | 6.57 | 6.68 | <5 | 6.72 | <5 | <5 | <5 | <5 | <5 |
| 585 | 8.32 | 8.36 | 8.15 | 7.21 | 7.4 | 6.74 | <5 | 6.6 | ~5.1 | 6.05 | <5 | 5.25 | <5 |
| 586 | 8.54 | 8.67 | 8.65 | 7.94 | 7.2 | 7.75 | <5 | 7.62 | <5 | 5.69 | <5 | <5 | <5 |
| 105 | 8.69 | 8.51 | 8.74 | 8.03 | 7.52 | 7.99 | <5 | 7.78 | <5 | 5.97 | <5 | <5 | <5 |
| 147 | 7.99 | 8.2 | 8.28 | 7.45 | 6.9 | 6.68 | <5 | 6.78 | <5 | ~5.07 | <5 | <5 | <5 |
| 588 | 8.01 | 7.95 | 8.04 | 6.63 | 7.02 |  |  |  |  |  |  |  |  |
| 120 | 8.71 | 8.34 | 8.42 | 8.13 | 7.37 | 6.77 | <5 | 6.93 | <5 | 5.6 | <5 | <5 | <5 |
| 589 | 7.76 | 7.91 | 7.99 | 6.61 | 6.72 |  |  |  |  |  |  |  |  |
| 590 | 8.64 | 8.5 | 8.4 | 7.95 | 7.96 |  |  |  |  |  |  |  |  |
| 592 | 8.78 | 8.68 | 8.49 | 8.01 | 6.87 | 7.1 | <5 | 7.17 | <5 | 5.71 | <5 | 5.21 | <5 |
| 593 | 8.56 | 8.55 | 9 | 8.49 | 6.87 | 6.99 | <5 | 7.35 | <5 | 5.49 | <5 | <5 | <5 |
| 148 | 8.93 | 8.74 | 9.21 | 8.6 | 6.86 | 7.3 | <5 | >8 | <5 | 5.49 | <5 | <5 | <5 |
| 149 | 8.36 | 8.4 | 8.63 | 7.93 | 6.56 | 6.88 | <5 | 7.26 | <5 | 5.12 | <5 | <5 | <5 |
| 100 | 8.74 | 8.21 | 8.43 | 7.67 | 6.6 | 6.28 | <5 | 6.43 | <5 | <5 | <5 | <5 | <5 |
| 101 | 8.12 | 7.69 | 8.05 | 7.34 | 6.44 | 6.59 | <5 | 6.44 | <5 | ~5.01 | <5 | <5 | <5 |
| 14/14a | 8.76 | 8.3 | 8.75 | 8.25 | 7.16 | 6.93 | <5 | 7.28 | <5 | 5.37 | <5 | <5 | <5 |
| 594 | 8.71 | 8.29 | 8.8 | 7.23 | 7.48 | 6.75 | <5 | ~7.11 | <5 | 5.53 | <5 | 5.15 | <5 |
| 595 | 8.15 | 7.55 | 7.66 | 7.03 | 6.52 | 5.28 | <5 | 5.27 | <5 | <5 | <5 | <5 | <5 |
| 604 | 9.12 | 8.47 | 8.51 | 8.34 | 7.65 | ~7.59 | <5 | ~7.54 | <5 | 6.06 | <5 | 5.07 | <5 |
| 608 | 8.33 | 8.12 | 8 | 7.35 | 6.99 | 6.7 | <5 | 6.88 | <5 | 5.07 | <5 | <5 | <5 |
| 609 | 8.42 | 8.13 | 8.09 | 7.42 | 6.91 | 6.63 | <5 | 6.6 | <5 | 5.22 | <5 | 5.06 | 5 |
| 610 | 8.68 | 8.21 | 8.29 | 7.68 | 7.25 | 6.92 | <5 | ~7.13 | <5 | 5.14 | <5 | <5 | <5 |
| 611 | 8.47 | 8.12 | 8.29 | 7.83 | 6.57 | 6.63 | <5 | 6.93 | <5 | <5 | <5 | <5 | <5 |
| 697 | 8.66 | 8.37 | 8.4 | 7.89 | 7.26 | 7.26 | <5 | 6.7 | <5 | 5.82 | <5 | <5 | <5 |
| 698 | 8.85 | 8.31 | 8.28 | 7.94 | 7.1 | 7.3 | <5 | ~8.18 | <5 | 5.95 | <5 | <5 | <5 |
| 699 | 8.82 | 8.36 | 8.42 | 7.78 | 7.19 | ~7.43 | <5 | ~7.54 | <5 | 5.57 | <5 | ~5 | <5 |
| 700 | 9.01 | 8.47 | 8.52 | 8.15 | ~6 | 7.98 | 5.26 | 8.27 | <5 | <5 | <5 | 5.25 | <5 |
|  | 8.57 | 8.09 | 8.32 | 7.99 | 6.5 | 7.79 | 5.25 | ~8.49 | <5 | <5 | <5 | 5.4 | <5 |
| 613 | 8.39 | 7.91 | 8.42 | 7.5 | 7.08 | 6.35 | <5 | ~6.61 | <5 | 5.13 | <5 | <5 | <5 |
| 701 | 8.26 | 8 | 7.84 | 6.94 | ~6.23 | 6.81 | <5 | 6.89 | <5 | <5 | <5 | <5 | <5 |
| 702 | 8.1 | 7.94 | 8.28 | 7.49 | 6.96 | 6.01 | <5 | 6.57 | <5 | <5 | <5 | <5 | <5 |
| 703 | 8.32 | 8.03 | 8.61 | 8.25 | 7.07 | 6.98 | <5 | 7.22 | <5 | 5.12 | <5 | <5 | <5 |
| 645 | 8.6 | 8.28 | 8.66 | 7.66 | 7.41 | 7.27 | <5 | ~6.95 | <5 | 5.83 | <5 | 5.85 | <5 |
| 704 | 8.38 | 8.07 | 8.59 | 7.88 | 7.24 | 6.26 | <5 | 6.94 | <5 | 5.28 | <5 | 5.07 | <5 |
| 15 | 8.15 | 7.92 | 8.28 | 7.41 | 6.87 | 6.36 | <5 | 6.53 | <5 | <5 | <5 | <5 | <5 |
| 615 | 8.83 | 8.56 | 8.66 | 7.98 | 7 | 7.56 | <5 | 6.89 | <5 | 5.25 | <5 | <5 | <5 |
| 646 | 8.53 | 8.37 | 8.91 | 7.86 | 7.31 | 6.07 | <5 | ~6.18 | <5 | 5.18 | <5 | 4.99 | <5 |
| 648 | 9.01 | 8.69 | 9.31 | 8.43 | 7.27 | 7.34 | <5 | 7.52 | <5 | 5.64 | <5 | <5 | <5 |
| 705 | 8.1 | 7.99 | 8.34 | 7.42 | 7.21 | 6 | <5 | 6.58 | <5 | 5.42 | <5 | 5.24 | <5 |
|  | 8.24 | 7.92 | 8.05 | 7.71 | 6.86 | 6.4 | <5 | 6.81 | <5 | 5.27 | <5 | 5.17 | <5 |
|  | 8.28 | 8.06 | 8.19 | 7.6 | 7.15 | 6.24 | <5 | 6.76 | <5 | 5.35 | <5 | 5.25 | <5 |
| 706 | 8.6 | 8.41 | 9.08 | 7.77 | 7.32 | 6.49 | <5 | 6.79 | <5 | 5.59 | <5 | 5.11 | <5 |
| 707 | 8.17 | 7.63 | 8.23 | 6.8 | 7.11 | 6.09 | <5 | 6.13 | <5 | <5 | <5 | <5 | <5 |
| 647 | 9.04 | 8.61 | 8.92 | 7.74 | 7.34 | 6.88 | <5 | 7.04 | <5 | <5 | <5 | 5.19 | <5 |
| 708 | 8.11 | 7.85 | 7.94 | 7.47 | 6.65 | 5.92 | <5 | 6.2 | <5 | 4.99 | <5 | ~5 | <5 |
| 709 | 8.45 | 8.24 | 8.42 | 7.7 | 7.42 | 6.22 | 5.04 | 6.31 | ~5.02 | 5.28 | <5 | 5.32 | 5.14 |
| 710 | 7.55 | 7.48 | 7.65 | 6.81 | 6.39 | 5.75 | <5 | 6.08 | <5 | <5 | <5 | <5 | <5 |
| 7011 | 8.79 | 8.43 | 9.02 | 8.27 | 7.41 | 7.24 | <5 | ~7.38 | <5 | 5.79 | <5 | 5.13 | <5 |
| 712 | 7.42 | 7.41 | 7.69 | 6.82 | 6.96 | 5.65 | <5 | 5.95 | <5 | 5.24 | <5 | <5 | <5 |
| 616 | 9.11 | 8.24 | 8.14 | 7.68 | 7.39 | 7.22 | <5 | ~6.99 | <5 | 5.59 | <5 | 5.04 | <5 |
| 713 | 7.88 | 8.01 | 8.12 | 7.59 | 7.01 | 7.07 | <5 | 6.69 | <5 | 5.33 | <5 | <5 | <5 |
| 619 | 8.49 | 8.3 | 7.91 | 7.5 | 7.03 | 7.23 | ~5.18 | 6.81 | ~5.28 | 5.41 | ~5.2 | ~5.35 | ~5.33 |
| 714 | 7.24 | 7.38 | 7.18 | 7.04 | 6.06 | 5.58 | <5 | ~5.6 | <5 | <5 | <5 | <5 | <5 |
| 690 | 7.98 | 8.01 | 7.97 | 7.53 | 6.34 | 7.9 | 5.02 | ~7.97 | ~5.02 | <5 | <5 | 5.15 | <5 |
|  | 8.37 | 7.89 | 8.24 | 7.73 | 6.2 | 7.49 | 5.26 | ~7.62 | <5 | 5.13 | 5 | 5.24 | 5.01 |
| 716 | 8.22 | 8.14 | 7.82 | 7.27 | 7.01 | 6.97 | <5 | ~6.57 | <5 | 5.59 | <5 | 5.36 | <5 |
| 717 | 8.8 | 8.36 | 8.76 | 8.06 | 7.32 | 7.19 | <5 | ~6.69 | <5 | 5.56 | <5 | <5 | <5 |
| 718 | 8.38 | 8.09 | 8.19 | 7.9 | 6.98 | 5.61 | <5 | 5.46 | <5 | <5 | <5 | 5.04 | <5 |
| 719 | 6.36 | 6.36 | 6.6 | 6.27 | 6.08 | <5 | <5 | <5 | <5 | <5 | <5 | <5 | <5 |
| 721 | 6.88 | 6.99 | 6.65 | <6 | <6 | <5 | <5 | <5 | <5 | <5 | <5 | <5 | <5 |
| 722 | 7.96 | 7.92 | 7.54 | 7.35 | 6.72 | 5.62 | ~5.24 | 5.53 | ~5.24 | 5.19 | 5.21 | 5.31 | ~5.23 |
| 724 | 8.81 | 8.2 | 8.49 | 7.77 | 7.05 | 7.3 | <5 | ~6.99 | <5 | 5.92 | <5 | <5 | <5 |
| 620 | 7.73 | 7.5 | 7.7 | 6.91 | 7.02 | 6.17 | <5 | 6.46 | <5 | 5.11 | <5 | <5 | <5 |
| 725 | 8.72 | 8.18 | 8.73 | 7.75 | 7.13 | 7.29 | <5 | 6.96 | <5 | 5.73 | <5 | 5.07 | <5 |
| 727 | 8.8 | 8.33 | 8.29 | 8.12 | 7.04 | 7.44 | 5.21 | 6.91 | ~5.14 | 5.8 | <5 | ~5.16 | <5 |
| 728 | 8.58 | 8.42 | 8.49 | 7.81 | 7.22 | 6.87 | <5 | 6.81 | <5 | 5.53 | <5 | <5 | <5 |
| 621 | 8.57 | 8.22 | 8.25 | 7.66 | 7.49 | 6.87 | <5 | 7.02 | <5 | 5.64 | <5 | <5 | <5 |
| 729 | 8.8 | 8.04 | 8.01 | 7.8 | 7.5 | 7.68 | 5.17 | 7.13 | ~5.21 | 6.33 | <5 | 5.33 | 5.14 |
| 730 | 9.12 | 8.53 | 9.11 | 8.79 | 7.47 | 7.52 | 5.03 | 6.99 | <5 | 6.13 | <5 | <5 | <5 |
| 731 | 8.08 | 7.8 | 8.03 | 7.64 | 6.85 | 7.28 | 5.15 | 7.26 | 5.14 | 5.21 | 5.04 | 5.24 | 5.12 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 732 | 8.84 | 8.38 | 8.92 | 8.16 | 6.77 | 6.9 | <5 | 7.09 | <5 | 5.14 | <5 | <5 | <5 |
| 733 | 8.93 | 8.47 | 8.7 | 8.25 | 7.18 | 7.8 | 5.12 | 6.98 | ~5.15 | 5.92 | <5 | ~5.11 | <5 |
| 734 | 6.59 | 6.36 | 6.46 | 6.15 | 6.21 | <5 | <5 | <5 | <5 | <5 | <5 | <5 | <5 |
| 624 | 8.73 | 8.2 | 8.78 | 7.64 | 7.4 | | | | | | | | |
| 735 | 8.56 | 8.18 | 8.92 | 7.77 | 7.23 | 6.6 | 5.52 | 6.59 | <5 | <5 | <5 | 5.81 | 5.2 |
| 736 | 8.19 | 7.75 | 8.48 | 7.72 | 6.78 | 6.65 | <5 | 6.4 | <5 | 5.4 | <5 | 5.31 | <5 |
| 625 | 8.51 | 8.12 | 8.85 | 8.11 | 7.33 | 6.54 | <5 | 6.45 | <5 | <5 | <5 | 5.22 | <5 |
| 737 | 8.7 | ~8.19 | 8.85 | 7.89 | 7.42 | 7.21 | ~5.01 | 6.72 | ~5.05 | 5.71 | ~5.02 | 5.45 | <5 |
| 652 | 7.31 | 7.31 | 7.65 | 6.96 | <6 | 7.1 | <5 | 7.37 | <5 | <5 | <5 | <5 | <5 |
|  | 7.65 | 7.44 | 7.46 | 7.23 | 6.43 | 7 | <5 | ~7.4 | <5 | <5 | <5 | <5 | <5 |
|  | 7.71 | 7.41 | 7.62 | 7.18 | 6.45 | 7.05 | <5 | 7.39 | <5 | <5 | <5 | 5.15 | <5 |
| 650 | 9.17 | 8.43 | 8.5 | 8.19 | 7.95 | 7.05 | 5.35 | 7 | ~5.23 | 6.01 | 5.42 | 5.37 | 5.32 |
| 738 | 8.19 | 7.91 | 7.96 | 7.94 | 5.78 | 8.17 | 5.11 | 8.59 | <5 | <5 | <5 | 5.08 | <5 |
|  | 8.67 | 8.1 | 8.38 | 8.29 | 6.31 | 8.59 | 5.53 | 8.04 | <5 | 5.06 | 5.03 | 5.16 | <5 |
| 739 | 7.77 | 7.47 | 7.6 | 7.36 | 6.52 | 6.51 | <5 | 6.29 | <5 | <5 | <5 | <5 | <5 |
| 740 | 8.18 | 8.19 | 8.1 | 7.54 | 6.43 | 7.68 | 5.47 | 7.71 | <5 | 5.46 | 5.13 | 5.32 | <5 |
|  | 8.38 | 7.99 | 8.21 | 7.84 | 6.63 | 7.77 | 5.25 | 7.67 | <5 | 5.34 | 5.23 | 5.35 | <5 |
| 651 | 9.44 | 8.54 | 8.47 | 8.07 | 7.7 | 8.15 | <5 | 7.65 | ~5.12 | 5.61 | 5.75 | 5.24 | <5 |
| 617 | 8.62 | 8.25 | 8.82 | 7.91 | 7.11 | 7.21 | 5.21 | 7.06 | <5 | 5.86 | <5 | 5.47 | <5 |
| 741 | 6.87 | 6.39 | 6.77 | 6.23 | <6 | 5.55 | 5.08 | 5.35 | <5 | 5.04 | <5 | 5.08 | <5 |
| 742 | 6.92 | 6.51 | 6.7 | <6 | <6 | 5.98 | <5 | 6.14 | <5 | <5 | <5 | <5 | <5 |
| 618 | 9.34 | 8.76 | 8.55 | 8.21 | 7.63 | 7.81 | <5 | ~7.19 | <5 | 6.04 | <5 | 5.1 | <5 |
| 743 | 8.57 | 8.28 | 8.64 | 7.85 | 7.58 | 6.58 | <5 | 5.88 | <5 | 5.51 | <5 | 5.01 | <5 |
|  | 8.42 | 8.14 | 8.56 | 7.71 | 7.57 | 6.41 | ~5.02 | 6.41 | <5 | 5.55 | ~5 | 5.11 | <5 |
| 744 | 8.85 | 8.53 | 8.34 | 7.71 | 7.19 | 7.28 | 5.37 | 7.32 | ~5.25 | 6.1 | 5.4 | 5.41 | 5.21 |
| 745 | 6.58 | 6.4 | 6.54 | 6.42 | <6 | 5.23 | <5 | 5.15 | <5 | <5 | <5 | <5 | <5 |
| 746 | 8.26 | 7.98 | 8.35 | 7.84 | 6.74 | 6.72 | <5 | 6.95 | <5 | 5.22 | <5 | 5.65 | <5 |
| 747 | 7.55 | 7.33 | 7.32 | 7.16 | 6.4 | 6.56 | ~5.06 | 6.28 | <5 | 5.04 | <5 | 5.06 | <5 |
| 689 | 7.48 | 7.37 | 7.24 | 7.04 | 6.22 | 6.62 | 5.12 | 6.34 | <5 | 5.01 | <5 | 5.21 | <5 |
| 749 | 7.31 | 7.35 | 7.46 | 7.11 | 6.17 | 5.57 | <5 | 5.92 | <5 | <5 | <5 | <5 | <5 |
| 622 | 7.26 | 7.11 | 7.42 | 6.92 | 6.2 | 5.64 | <5 | 5.91 | <5 | 5.1 | <5 | <5 | <5 |
| 688 | 8.58 | 8.13 | 7.9 | 7.98 | 6.33 | 8.7 | 5.27 | 8.69 | <5 | 5.1 | 5.06 | 5.13 | 5.04 |
|  | 8.77 | 8.37 | 8.64 | 8.13 | ~6.33 | 8.56 | 5.32 | 8.5 | ~5.03 | 5.11 | 5.09 | 5.2 | 5.08 |
|  | 8.96 | 8.28 | 8.46 | 8.18 | 6.22 | 8.54 | 5.2 | ~7.02 | <5 | <5 | 5.04 | 5.27 | 5.05 |
| 750 | 8.72 | 8.26 | 8.3 | 7.95 | 6.51 | 7.72 | 5.87 | 7.51 | ~5.59 | 5.65 | 5.61 | 5.66 | ~5.53 |
| 752 | 7.12 | 6.64 | 6.79 | 6.43 | 6.08 | 5.85 | 5.17 | 5.99 | ~5.14 | 5.29 | 5.21 | 5.33 | 5.17 |
| 753 | 6.65 | 6.49 | 6.6 | 6.16 | <6 | 5.38 | <5 | 5.59 | <5 | <5 | <5 | 5.09 | <5 |
| 754 | 8.23 | 8.15 | 7.99 | 6.68 | 7.01 | 5.73 | <5 | 5.58 | <5 | <5 | <5 | <5 | <5 |
| 755 | 8.04 | 7.77 | 8.07 | 7.49 | 6.75 | 6.2 | 5.01 | 6.29 | <5 | 5.37 | <5 | 5.6 | 5.02 |
| 756 | 8.87 | 8.54 | 8.37 | 7.89 | 7.47 | 7.67 | <5 | ~7.75 | <5 | 6.08 | <5 | <5 | <5 |
| 757 | 8.85 | 8.41 | 8.3 | 7.71 | 7.37 | 7.5 | <5 | ~7.44 | <5 | 6.04 | <5 | <5 | <5 |
| 758 | 8.06 | 8.14 | 7.75 | 6.83 | 6.68 | 6.11 | <5 | 6.05 | <5 | 5.13 | <5 | <5 | <5 |
| 653 | 8.21 | 8.02 | 7.96 | 7.55 | 6.46 | 7.8 | 5.22 | ~8.21 | ~5.08 | 5.23 | 5.14 | 5.31 | ~5.09 |
| 759 | 8.11 | 8.07 | 7.86 | 7.2 | 7.52 | 6.32 | 5.96 | 6.45 | 5.69 | 5.84 | 5.81 | 6.12 | 5.91 |
| 760 | 8.22 | 8.35 | 8.25 | 7.75 | ~6.55 | 7.61 | 5.85 | 7.94 | 5.61 | 5.76 | 5.69 | 5.98 | 5.74 |
| 623 | 8.09 | 7.97 | 7.5 | 7.42 | 6.61 | 6.76 | <5 | 7.03 | <5 | 5.54 | <5 | <5 | <5 |
| 761 | 8 | 7.75 | 7.9 | 7.19 | 6.99 | 5.72 | <5 | 5.75 | <5 | 5.09 | <5 | <5 | <5 |
| 762 | 7.04 | 6.54 | 6.66 | 6.18 | <6 | 5.15 | <5 | 5.09 | <5 | <5 | <5 | <5 | <5 |
| 763 | 7.39 | 7.14 | 7.62 | 6.41 | <6 | 5.75 | <5 | 5.77 | <5 | <5 | <5 | <5 | <5 |
| 764 | 8.75 | 8.47 | 8.15 | 7.69 | <6 | 7.16 | 5.17 | 6.99 | ~5.08 | 5.75 | ~5 | 5.19 | 5.02 |
| 765 | 7.98 | 8.01 | 8.19 | 7.54 | 7.41 | 7.18 | <5 | 7.63 | <5 | 5.08 | <5 | 5.12 | <5 |
| 766 | 6.87 | 6.64 | 6.71 | 6.27 | <6 | <5 | <5 | <5 | <5 | <5 | <5 | <5 | <5 |
| 767 | 8.19 | 7.79 | 7.89 | 7.45 | 6.7 | 7.07 | 5.69 | 7.28 | ~5.56 | <5 | 5.6 | 5.67 | 5.53 |
| 768 | 8.6 | 8.16 | 8 | 7.16 | <6 | 6.46 | <5 | 6.38 | <5 | 5.31 | <5 | <5 | <5 |
| 770 | 8.74 | 8.48 | 7.98 | 7.69 | 7.78 | 7.5 | <5 | ~7.62 | <5 | 5.65 | ~5 | <5 | <5 |
| 644 | 8.81 | 8.29 | 8.62 | 7.69 | <6 | 7.22 | <5 | 7.1 | <5 | 5.62 | <5 | <5 | <5 |
| 656 | 8.59 | 8.46 | 8.96 | 8.14 | 6.81 | 7.16 | <5 | ~7.63 | <5 | 5.49 | <5 | 5.11 | <5 |
|  | 8.73 | 8.5 | 9.29 | 8.38 | 7.28 | 7.21 | <5 | 7.46 | <5 | 5.64 | <5 | 5.21 | <5 |
| 657 | 8.32 | 8.27 | 8.6 | 7.61 | <6 | 7 | <5 | 7.14 | <5 | 5.56 | <5 | <5 | <5 |
|  | 8.58 | 8.38 | 8.87 | 7.87 | 7.32 | 7.15 | <5 | 7.28 | <5 | 5.49 | <5 | <5 | <5 |
| 658 | 8.41 | 8.23 | 7.95 | 7.48 | 6.85 | 7.33 | <5 | 7.31 | <5 | 5.56 | <5 | <5 | <5 |
| 771 | 8.78 | 8.53 | 8.48 | 8.33 | 6.63 | 7.98 | 6.06 | 8.23 | 5.63 | 5.68 | 5.64 | 5.77 | 5.6 |
| 772 | 7.84 | 7.89 | 8.11 | 7.76 | <6 | 6.34 | 5.73 | 6.41 | <5 | 5.88 | 5.36 | 6.07 | 5.74 |
|  | 7.91 | 7.99 | 8.33 | 7.58 | 6.99 | 6.32 | 6.09 | 6.36 | <5 | 5.91 | 5.66 | 6.16 | 5.71 |
| 773 | 7.9 | 7.82 | 7.18 | 7.02 | 6.9 | 6.41 | <5 | 6.51 | <5 | 5.11 | <5 | <5 | <5 |
| 774 | 8 | 8.12 | 8.04 | 7.65 | 7.08 | 6.71 | <5 | 6.75 | <5 | 5.37 | <5 | 5.02 | <5 |
| 627 | 8.4 | 8.43 | 8.21 | 7.65 | 6.86 | 6.75 | <5 | 6.53 | <5 | 5.17 | <5 | <5 | <5 |
| 775 | 8.4 | 8.47 | 8.69 | 7.9 | 7.44 | 7.17 | <5 | 7.21 | <5 | 5.74 | <5 | 5.16 | <5 |
| 777 | 7.28 | 7.36 | 7.55 | 6.85 | ~6.54 | 6.98 | <5 | 7.51 | <5 | <5 | <5 | <5 | <5 |
| 778 | 7.52 | 7.44 | 7.26 | 6.5 | 6.17 | 7.58 | <5 | 7.73 | <5 | 5.25 | <5 | <5 | <5 |
| 779 | 7.41 | 7.23 | 7.02 | 6.32 | ~6 | 6.6 | <5 | 6.74 | <5 | <5 | <5 | <5 | <5 |
| 628 | 7.43 | 7.32 | 7.46 | 6.75 | 6.69 | 6.57 | <5 | 6.69 | <5 | 5.16 | <5 | <5 | <5 |
| 629 | 7.59 | 7.59 | 7.66 | 6.7 | 6.64 | 6.83 | <5 | 7.04 | <5 | 5.08 | <5 | <5 | <5 |
| 780 | 8.66 | 8.23 | 8.46 | 8.32 | 7.05 | 7.7 | <5 | ~7.96 | <5 | 5.37 | <5 | <5 | <5 |

TABLE A2-continued

| Co. No. | FGFR1 pIC50 | FGFR2 pIC50 | FGFR3 pIC50 | FGFR4 pIC50 | VEGFR2 (KDR) pIC50 | BAF3-FGFR1 (MIN IL3) pIC50 | BAF3-FGFR1 (PLUS IL3) pIC50 | BAF3-FGFR3 (MIN IL3) pIC50 | BAF3-FGFR3 (PLUS IL3) pIC50 | BAF3-KDR (MIN IL3) pIC50 | BAF3-KDR (PLUS IL3) pIC50 | BAF3-FLT3 (MIN IL3) pIC50 | BAF3_FLT3 (PLUS IL3) pIC50 |
|---|---|---|---|---|---|---|---|---|---|---|---|---|---|
| 781 | 8.23 | 8.11 | 8.34 | 7.78 | 6.86 | 7.08 | <5 | 7.15 | <5 | 5.14 | <5 | <5 | <5 |
| 782 | 8.66 | 8.38 | 8.13 | 7.78 | 7.74 | 7.59 | <5 | 7.44 | <5 | 5.86 | <5 | <5 | <5 |
| 634 | 8.05 | 7.82 | 7.75 | 7.56 | <6 | 7.96 | 5.23 | 8.03 | <5 | <5 | <5 | 5.05 | <5 |
| 783 | 7.69 | 7.67 | 7.81 | 6.73 | 6.7 | 6.3 | <5 | 6.24 | <5 | 5.31 | <5 | <5 | <5 |
| 784 | 7.08 | 7.15 | 7.21 | 6.82 | 6.42 | 5.4 | <5 | 5.88 | <5 | <5 | <5 | <5 | <5 |
| 785 | 8.18 | 7.91 | 7.84 | 7.45 | 7.11 | 8.58 | <5 | 8.23 | <5 | 5.06 | <5 | <5 | <5 |
| 786 | 7.9 | 7.79 | 7.89 | 7.46 | 6.32 | 7.72 | 5.16 | 7.97 | <5 | 5.07 | 5.05 | 5.13 | 5.02 |
| 787 | 7.56 | 7.36 | 7.48 | 7.17 | 6.26 | 7.31 | 5.13 | 7.72 | <5 | 5.11 | 5.07 | 5.12 | ~5 |
| 788 | 8.62 | 8.34 | 8.28 | 7.83 | 6.27 | 8.35 | 5.11 | 8.47 | <5 | 5.05 | <5 | 5.13 | <5 |
| 789 | 8.75 | 8.23 | 8.33 | 8.01 | 6.1 | 8.55 | <5 | 8.61 | <5 | <5 | <5 | <5 | <5 |
| 790 | 6.56 | 6.53 | 6.59 | 6.53 | <6 | <6 | 5.21 | <5 | 5.23 | <5 | <5 | <5 | <5 |
| 791 | 7.9 | 7.77 | 7.68 | 7.83 | 6.86 | 8.11 | 5.17 | 8.38 | <5 | 5.66 | 5.04 | 5.2 | <5 |
| 792 | 7.81 | 7.69 | 7.73 | 7.4 | 6.45 | 7.33 | 5.43 | 7.75 | <5 | 5.51 | ~5 | 5.34 | 5.12 |
| 793 | 7.15 | 7.05 | 6.92 | 6.64 | <6 | 6.94 | 5.72 | 7.32 | 5.38 | 5.41 | 5.38 | 5.5 | 5.4 |
| 631 | 8.15 | 8.24 | 7.53 | 6.89 | 6.47 | 6.51 | 5.2 | 6.49 | ~5.14 | 5.33 | ~5.1 | 5.29 | ~5.09 |
| 794 | 7.78 | 7.85 | 7.48 | 6.84 | 6.06 | 6.16 | <5 | 6.11 | <5 | <5 | <5 | <5 | <5 |
| 795 | 8.5 | 8.15 | 8.18 | 8.3 | 5.71 | 8.32 | 5.36 | 8.63 | ~5.18 | 5.3 | 5.27 | 5.43 | ~5.25 |
| 796 | 7.21 | 7.05 | 7.12 | 6.76 | 6.1 | 6.83 | <5 | 7.23 | <5 | <5 | <5 | <5 | <5 |
| 798 | 7.53 | 7.66 | 7.72 | 7.06 | 6.02 | 6.08 | <5 | 6.33 | <5 | <5 | <5 | <5 | <5 |
| 659 | 8.26 | 8.11 | 8.59 | 7.56 | 6.75 | 6.69 | <5 | 7.12 | <5 | 5.15 | <5 | 5.01 | <5 |
| 662 | 7.55 | 7.69 | 7.63 | 7.26 | 7.11 | 6 | <5 | 6.21 | <5 | 5.27 | <5 | <5 | <5 |
| 799 | 7.42 | 7.6 | 7.57 | 7.13 | 6.95 | 6.76 | <5 | 6.87 | <5 | 5.52 | <5 | <5 | <5 |
| 661 | 8.71 | 8.53 | 8.63 | 7.72 | 7.05 | 6.72 | <5 | 6.66 | <5 | <5 | <5 | <5 | <5 |
| 660 | 8.98 | 8.6 | 8.9 | 8.09 | 7.23 | 7.16 | <5 | 7.14 | <5 | 5.18 | <5 | <5 | <5 |
| 633 | 8.29 | 8.37 | 8.53 | 7.81 | 6.81 | 6.76 | <5 | 6.85 | <5 | 5.38 | <5 | <5 | <5 |
| 800 | 7.9 | 7.8 | 7.74 | 7.28 | 6.44 | 6.66 | 5.47 | 6.85 | ~5.33 | 5.48 | 5.5 | 5.42 | 5.41 |
| 801 | 7.58 | 7.55 | 7.65 | 7.19 | 6.49 | 5.74 | <5 | 5.77 | <5 | <5 | <5 | <5 | <5 |
| 802 | 8.68 | 8.44 | 8.85 | 7.77 | 7.25 | 6.71 | <5 | 6.99 | <5 | 5.17 | <5 | <5 | <5 |
| 803 | 8.4 | 8.14 | 8.42 | 7.16 | 7.02 | 6.59 | <5 | 6.67 | <5 | 5.16 | <5 | <5 | <5 |
| 636 | 7.35 | 7.4 | 7.12 | 6.5 | 6.01 | 5.66 | <5 | 5.95 | <5 | 5.11 | <5 | <5 | <5 |
| 637 | 7.11 | 7.33 | 6.94 | 6.68 | <6 | 5.65 | <5 | 6.05 | <5 | <5 | <5 | <5 | <5 |
| 804 | 8.16 | 8.02 | 7.72 | 7.5 | <6 | 8.44 | 5.12 | 8.61 | <5 | 5.15 | 5.09 | 5.1 | 5.06 |
| 805 | 7.71 | 7.63 | 7.59 | 7.33 | <6 | 7.13 | <5 | 7.63 | <5 | <5 | <5 | <5 | <5 |
| 806 | 7.04 | 6.75 | 6.75 | <6 | <6 | 5.14 | <5 | 5.06 | <5 | <5 | <5 | <5 | <5 |
| 807 | 7.05 | 6.86 | 7 | 6.71 | <6 | 5.58 | <5 | 5.79 | <5 | <5 | <5 | <5 | <5 |
| 808 | 7.32 | 7.03 | 7.14 | 6.6 | 6.19 | 5.96 | <5 | 6 | <5 | 5.22 | <5 | 5.04 | <5 |
| 809 | 7.89 | 7.49 | 7.73 | 7.32 | 6.02 | 7.47 | 5.23 | ~7.53 | <5 | 5.09 | 5.11 | 5.13 | 5.01 |
| 810 | 7.73 | 7.67 | 7.88 | 7.2 | 6.91 | 6.26 | 5.59 | 6.24 | <5 | 5.71 | <5 | 5.28 | <5 |
| 635 | 8.05 | 7.97 | 7.94 | 7.48 | 6.75 | 6.59 | <5 | ~6.53 | <5 | 5.25 | <5 | <5 | <5 |
| 811 | 7.58 | 7.47 | 7.6 | 7.09 | 6.78 | 6.14 | <5 | ~6.03 | <5 | 5.15 | <5 | <5 | <5 |
| 812 | 8.25 | 8.09 | 8.03 | 7.19 | 6.72 | 7.07 | <5 | 6.8 | <5 | 5.21 | <5 | <5 | <5 |
| 813 | 8.86 | 8.59 | 8.8 | 8.67 | 7.93 | 8.63 | <5 | 8.27 | <5 | 6.87 | <5 | 5.5 | <5 |
| 814 | 7.35 | 7.47 | 7.56 | 7.18 | <6 | 7.03 | 5.1 | 7.14 | <5 | 5.03 | <5 | <5 | <5 |
| 815 | 7.48 | 7.62 | 7.82 | 7.03 | 6.37 | 6.42 | <5 | 6.3 | <5 | <5 | <5 | <5 | <5 |
| 816 | 6.96 | 7.09 | 7.29 | 6.63 | ~6.03 | 6.81 | <5 | 6.93 | <5 | <5 | <5 | <5 | <5 |
| 817 | 7.65 | 7.59 | 7.77 | 7.27 | 6.25 | 7.35 | 5.12 | ~7.49 | <5 | <5 | <5 | <5 | <5 |
| 640 | 7.25 | 7.64 | 7.72 | 7.41 | 6.61 | 5.82 | <5 | 5.62 | <5 | <5 | <5 | <5 | <5 |
| 819 | 7.74 | 7.78 | 7.93 | 6.95 | 7.12 | 6.28 | <5 | 6.17 | <5 | 5.47 | <5 | <5 | <5 |
| 687 | 8.75 | 8.45 | 8.31 | 7.95 | 7.76 | >8 | 5.22 | >8 | <5 | 7.61 | <5 | 5.85 | <5 |
| 820 | 6.79 | 7.08 | 7.04 | 6.27 | <6 | 5.74 | <5 | 5.81 | <5 | <5 | <5 | <5 | <5 |
| 632 | 8.81 | 8.63 | 8.92 | 7.86 | 6.98 | 7.23 | 5.16 | 7.03 | <5 | 5.69 | <5 | 5.1 | <5 |
| 821 | 8.86 | 8.53 | 8.68 | 8.56 | 7.85 | >8 | <5 | >8 | <5 | 6.61 | <5 | 4.99 | <5 |
| 822 | 9.03 | 8.79 | 9.1 | 8.45 | 7.65 | 7.82 | <5 | 7.66 | <5 | 6.2 | <5 | 5.19 | <5 |
| 823 | 7.13 | 6.92 | 7.08 | 6.31 | <6 | 5.71 | <5 | 5.7 | <5 | <5 | <5 | <5 | <5 |
| 824 | 7.36 | 7.49 | 7.57 | 7.12 | <6 | 6.04 | <5 | 6.1 | <5 | <5 | <5 | <5 | <5 |
| 825 | 8.08 | 8.24 | 8.47 | 7.86 | 7.04 | 6.64 | <5 | 6.81 | <5 | 5.3 | <5 | <5 | <5 |
| 826 | 8.76 | 8.51 | 8.62 | 8.36 | 7.64 | 9.22 | 5.14 | 9.41 | <5 | 5.97 | 5.09 | 5.32 | <5 |
| 827 | 8.73 | 8.47 | 8.64 | 8.5 | 7.58 | 9.2 | 5.33 | 9.42 | 5.01 | 6.33 | 5.3 | 5.48 | 5.15 |
| 828 | 8.28 | 8.28 | 8.8 | 7.69 | 7.07 | 7.12 | <5 | 7.22 | <5 | 5.62 | <5 | <5 | <5 |
| 829 | 7.82 | 7.52 | 7.54 | 7 | <6 | 8.22 | 5.34 | 8.43 | <5 | 5.11 | ~5 | 5.07 | <5 |
| 830 | 7.54 | 7.6 | 7.62 | 6.87 | 6.15 | | | | | | | | |
| 663 | 8.81 | 8.71 | ~8.95 | 8.32 | 7.39 | 7.55 | <5 | ~7.61 | <5 | 6.66 | <5 | <5 | <5 |
| 664 | 7.79 | ~7.69 | 7.98 | 7 | ~6.61 | 5.64 | <5 | 5.34 | 5.03 | <5 | <5 | <5 | <5 |
| 831 | 7.69 | ~8 | 7.75 | 7.21 | 6.42 | 6.13 | 5.38 | 6.76 | 5.44 | 5.19 | 5.23 | 5.5 | 5.3 |
| 832 | 6.45 | 6.61 | 6.43 | <6 | <6 | 5.02 | <5 | <5 | <5 | <5 | <5 | <5 | <5 |
| 833 | 7.29 | 7.43 | 7.4 | ~6.5 | 6.98 | 5.54 | <5 | 5.78 | <5 | 5.11 | <5 | <5 | <5 |
| 834 | 7.98 | 8.25 | 8.48 | 7.79 | 6.71 | 7.07 | <5 | 7.25 | <5 | 5.11 | <5 | <5 | <5 |
| 837 | 8.73 | ~8.85 | 8.6 | 7.88 | 7.68 | | | | | | | | |
| 641 | 9 | ~9.05 | 8.92 | 8.25 | 7.43 | 7.5 | <5 | | | 6.22 | <5 | <5 | <5 |
| 642 | 8.86 | 8.98 | 8.77 | 8.42 | 7.74 | >8 | <5 | | | 6.42 | <5 | <5 | <5 |
| 838 | | | 8.6 | 7.85 | | 7.05 | <5 | | | 5.98 | <5 | <5 | <5 |
| 839 | | | <6 | <6 | | <5 | <5 | | | <5 | <5 | <5 | <5 |
| 840 | | | 8.51 | 8.13 | | >8 | <5 | | | 6.57 | <5 | 5.16 | <5 |
| 881 | 5.1 | 5.2 | <5 | <5 | 5.8 | <5 | <5 | <5 | <5 | <5 | <5 | <5 | <5 |

TABLE A2-continued

| Co. No. | FGFR1 pIC$_{50}$ | FGFR2 pIC$_{50}$ | FGFR3 pIC$_{50}$ | FGFR4 pIC$_{50}$ | VEGFR2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3_FLT3 (PLUS IL3) pIC$_{50}$ |
|---|---|---|---|---|---|---|---|---|---|---|---|---|---|
| 882 | 5.3 | 5.4 | 5.4 | 5.1 | 5.3 | <5 | <5 | <5 | <5 | <5 | <5 | <5 | <5 |
| 883 | 5.7 | 5.8 | 5.7 | <5 | 6.2 | <5 | <5 | <5 | <5 | <5 | <5 | <5 | <5 |
| 884 | 6.0 | 6.3 | 6.1 | 5.5 | 6.2 | <5 | <5 | <5 | <5 | <5 | <5 | <5 | <5 |
| 885 | 7.17 | 6.92 | 7.33 | 6.5 | <6 | 5.33 | <5 |  |  | <5 | <5 | <5 | <5 |
| 886 | 7.44 | 7.67 | 7.76 | 7.06 | 6.31 | ~5.49 | <5 | 5.91 | <5 | <5 | <5 | <5 | <5 |
| 887 | 7.41 | 7.6 | 7.75 | 6.91 | 6.29 | 5.51 | <5 | 5.71 | <5 | <5 | <5 | <5 | <5 |
| 888 | 6.8 | 7.07 | 6.74 | <6 | <6 | 5.4 | <5 | ~5.14 | <5 | <5 | <5 | <5 | <5 |
| 889 | 8.38 | 8.38 | 8.39 | 7.14 | 7.26 | 5.27 | <5 | 5.71 | <5 | <5 | <5 | <5 | <5 |
| 890 | 6.46 | 6.62 | 6.42 | <6 | 6.21 | <5 | <5 | <5 | <5 | <5 | <5 | <5 | <5 |
| 891 | 7.44 | 7.43 | 7.36 | 6.87 | <6 | 5.96 | <5 | 6.15 | <5 | <5 | <5 | 5.02 | <5 |
| 892 | 6.69 | 6.89 | 6.65 | <6 | <6 | <5 | <5 | <5 | <5 | <5 | <5 | <5 | <5 |
| 893 | 6.36 | 6.38 | 6.34 | <6 | 6.09 | 5.04 | <5 | 5.01 | <5 | <5 | <5 | 5.07 | <5 |
| 894 | 6.98 | 6.73 | 6.55 | <6 | <6 |  |  |  |  |  |  |  |  |
| 895 | 7.26 | 7.16 | 7.49 | 6.64 | <6 | 5.44 | <5 | 5.55 | <5 | <5 | <5 | <5 | <5 |
| 896 | 8.47 | 7.96 | 7.98 | 7.4 | 6.7 | 6.87 | <5 | 6.87 | <5 | 5.46 | <5 | <5 | <5 |
| 897 | 8.87 | 8 | 8.34 | 7.9 | 6.83 | 7.14 | <5 | 7.23 | <5 | 5.59 | <5 | <5 | <5 |
| 898 | 6.77 | 6.63 | 6.45 | <6 | 6.16 | 5.15 | <5 | ~5.12 | <5 | <5 | <5 | <5 | <5 |
| 899 | 7.09 | 6.78 | 6.76 | 6.42 | <6 | 5.39 | <5 | 5.22 | <5 | <5 | <5 | <5 | <5 |
| 900 | 7.62 | 7.53 | 7.54 | 6.66 | <6 | 5.32 | <5 | 5.33 | <5 | <5 | <5 | <5 | <5 |
| 901 | 7.78 | 7.7 | 8.27 | 7.32 | <6 | 6.37 | <5 | 6.56 | <5 | <5 | <5 | <5 | <5 |
| 902 | 8.48 | 8.33 | 8.81 | 8.33 | 7.32 | <5 | <5 | <5 | <5 | <5 | <5 | <5 | <5 |
| 903 | 6.87 | 6.84 | 7.19 | 6.07 | <6 | <5 | <5 | <5 | <5 | <5 | <5 | <5 | <5 |
| 904 | 7.1 | 7.26 | 7.59 | 6.89 | 6.09 | 5.73 | <5 | 6.01 | <5 | <5 | <5 | <5 | <5 |
| 905 | <6 | <6 | <6 | <6 | 6.14 | <5 | <5 | <5 | <5 | <5 | <5 | 5.26 | 5.05 |
| 906 | 7.7 | 7.21 | 7.35 | 6.63 | 6.25 | 5.21 | <5 | 5.23 | <5 | <5 | <5 | <5 | <5 |
| 907 | 6.92 | 6.35 | 6.91 | 6.35 | <6 | 5.12 | <5 | ~5.09 | <5 | <5 | <5 | <5 | <5 |
| 908 | 7.21 | 6.55 | 6.83 | 6.49 | <6 | 7.01 | <5 | 5.41 | <5 | <5 | <5 | <5 | <5 |
| 909 | 6.83 | 6.83 | 6.84 | 6.52 | <6 | 5.2 | <5 | ~5.03 | <5 | <5 | <5 | <5 | <5 |
| 910 | 6.66 | 6.18 | 6.33 | 6.04 | <6 | 5.12 | <5 | <5 | <5 | <5 | <5 | <5 | <5 |
| 911 | 6.76 | 6.57 | 6.56 | 6.47 | <6 | 5.04 | <5 | 5.06 | <5 | <5 | <5 | <5 | <5 |
| 912 | 7.19 | 7.11 | 7.29 | 6.64 | 6.26 | 5.59 | <5 | 5.65 | <5 | <5 | <5 | <5 | <5 |
| 913 | <6 | ~6 | <6 | <6 | <6 | 5.1 | <5 | 5.05 | <5 | <5 | <5 | <5 | <5 |
| 914 | 6.8 | 6.72 | 6.21 | <6 | <6 | 5.08 | <5 | 5.09 | <5 | <5 | <5 | <5 | <5 |
| 915 | <6 | <6 | <6 | <6 | <6 | <5 | <5 | <5 | <5 | <5 | <5 | <5 | <5 |
| 916 | 8 | 7.69 | 7.86 | 7.23 | 6.63 | 6.91 | <5 | 6.81 | <5 | 5.26 | <5 | <5 | <5 |
| 917 | <6 | <6 | <6 | <6 | <6 | <6 | <5 | 6.09 | <5 | <5 | <5 | <5 | <5 |
| 918 | 7.04 | 6.99 | 7.21 | 6.42 | 6.08 | 5.7 | <5 | ~5.63 | <5 | <5 | <5 | <5 | <5 |
| 919 | 6.59 | 6.53 | 6.91 | <6 | <6 | <5 | <5 | ~5.05 | <5 | <5 | <5 | <5 | <5 |
| 920 | 7.39 | 7.15 |  | 6.87 | ~6.31 | 5.6 | <5 |  |  | <5 | <5 | <5 | <5 |
| 921 | ~6.63 |  |  |  | 6.47 | <5 | <5 |  |  | <5 | <5 | <5 | <5 |
| 922 | 6.92 | 7.21 |  |  | 6.75 | <5 | <5 |  |  | <5 | <5 | <5 | <5 |
| 923 | 7.44 | 7.67 | 7.76 | 7.06 | 6.31 | ~5.49 | <5 | 5.91 | <5 | <5 | <5 | <5 | <5 |
| 924 | 7.44 | 7.43 | 7.36 | 6.87 | <6 | 5.96 | <5 | 6.15 | <5 | <5 | <5 | 5.02 | <5 |
| 926 | 6.69 | 6.89 | 6.65 | <6 | <6 | <5 | <5 | <5 | <5 | <5 | <5 | <5 | <5 |
| 925 | 6.98 | 6.73 | 6.55 | <6 | <6 |  |  |  |  |  |  |  |  |

Biological Assays B
FGFR3, VEGFR2 and PDGFR In Vitro Kinase Inhibitory Activity Assays Enzymes (from Upstate), prepared at 2× final concentration, were incubated with test compounds, biotinylated Flt3 substrate (biotin-VASSDNEYFYVDF) (Cell Signalling Technology Inc.) and ATP in the appropriate assay buffer (Table 1). The reaction was allowed to proceed for 3 hours (FGFR3), 1 hour (VEGFR2, PDGFR-beta) at room temperature on a plate shaker at 700 rpm before being stopped with 35 mM EDTA, pH 8 (FGFR3, VEGFR2) or 55 mM EDTA, pH 8 (PDGFR-beta). 5× detection mix (50 mM HEPES pH 7.5, 0.1% BSA, 11.34 nM Eu-anti-pY (PY20) (PerkinElmer) 74 nM SA-XL665 (Cisbio) for FGFR3, 50 mM HEPES, pH 7.5, 0.1% BSA, 11.34 nM Eu-anti-pY (PY20), 187.5 nM SA-XL665 for VEGFR2 and 50 mM HEPES pH 7.5, 0.1% BSA, 11.34 nM Eu-anti-pY (PT66) (PerkinElmer), 375 nM SA-XL665 (Cisbio) for PDGFR-beta) was then added to each well and the plate sealed and incubated at room temperature for one hour on a plate shaker at 700 rpm. The plate was then read on a Packard Fusion plate reader or a BMG Pherastar both in TRF mode.

TABLE 1

Final assay conditions for FGFR3, VEGFR2 and PDGFR-beta assays

| Enzyme | 1 × Assay Buffer | Flt3 substrate concentration | ATP concentration |
|---|---|---|---|
| FGFR3 | A | 0.125 μM | 8 μM |
| VEGFR2 | B | 0.5 μM | 0.5 μM |
| PDGFR-beta | C | 1 μM | 70 μM |

Kinase Assay buffers were:
A: 50 mM HEPES pH 7.5, 6 mM MnCl$_2$, 1 mM DTT, 0.01% TritonX-100
B: 50 mM HEPES pH 7.5, 6 mM MnCl$_2$, 1 mM DTT, 0.01% TritonX-100, 0.1 mM Sodium orthovanadate
C: 20 mM HEPES pH 7.5, 10 mM MnCl$_2$, 0.01% Triton X-100, 1 mM DTT, 0.1 mM Sodium orthovanadate FGFR3 and VEGFR2 Data for the compounds of the invention in the above assays are provided in Table A3.

Ba/F3-TEL-FGFR3 & Ba/F3 (WT) Cell Proliferation Assays

Stably transfected Ba/F3-TEL-FGFR3 cells were plated out into black 96-well tissue culture plates with clear bottoms in RPMI medium containing 10% FBS and 0.25 mg/ml G418 at a density of $5 \times 10^3$ cells/well (200 µl per well). The parental wild-type Ba/F3 cells (DSMZ no.: ACC 300) were plated out into black 96-well tissue culture plates with clear bottoms in RPMI medium containing 10% FBS and 2 ng/ml mouse IL-3 (R&D Systems) at a density of $2.5 \times 10^3$ cells/well (200 µl per well). Plates were placed in an incubator overnight before adding the compounds the following day. Dilutions of compounds were made in DMSO starting at 10 mM and were diluted into the wells to give a final DMSO concentration of 0.1% in assay. Compounds were left on the cells for 72 hours before the plates were removed from the incubator and 20 µl of Alamar Blue™ (Biosource) was added to each well. Plates were placed in the incubator for 4-6 hours before reading plates at 535 nm (excitation)/590 nm (emission) on a Fusion plate reader (Packard). Where inhibition is high an $IC_{50}$ can be determined.

Data for the compounds of the invention in the above assays are provided in Table A3.

TABLE A3

| Compound number | FGFR3 pIC$_{50}$ (µM) | VEGFR2 pIC$_{50}$ (µM) | BAF3_TEL_FGFR3 pIC$_{50}$ (µM) | BAF3_WT pIC$_{50}$ (µM) |
|---|---|---|---|---|
| 201 | 8.96 | 7.31 | 7.89 | 5.55 |
| 12 | 8.09 | 6.66 | 7.27 | 5.44 |
| 13 | 7.77 | 5.96 | 6.85 | |
| 215 | 6.21 | | | |
| 222 | 7.89 | 5.85 | 6.74 | 5.24 |
| 228 | 7.22 | 5.96 | | |
| 19 | 8.30 | 6.72 | 6.74 | 5.77 |
| 24 | | 6.77 | 7.43 | |
| 247 | | 6.77 | 7.43 | |
| 70 & 70a | 8.54 | 7.25 | 8.43 | 6.31 |
| 281 | | 7.31 | 8.66 | |
| 282 | | 7.31 | 8.66 | |
| 284 | 9.29 | 7.70 | 8.96 | 5.64 |
| 285 | 9.29 | 7.70 | 8.96 | 5.64 |
| 88 & 291 | 9.19 | 8.05 | 9.24 | 5.72 |
| 305 | 8.72 | 6.30 | 7.58 | |
| 61 | 8.29 | 6.80 | 6.46 | 5.72 |
| 306 | 7.51 | 5.82 | 6.89 | |
| 307 | | 5.72 | 6.46 | |
| 308 | 8.82 | 7.57 | 8.57 | |
| 311 | 8.54 | 6.92 | 7.96 | |
| 312 | 8.77 | 7.44 | 6.64 | |
| 314 | 7.89 | 6.31 | 6.80 | |
| 30 | 8.52 | 6.89 | 7.58 | |
| 315 | 8.42 | 6.82 | 7.70 | |
| 48 | | 7.92 | 8.92 | |
| 316 | | 7.80 | 9.05 | |
| 328 | 8.85 | 7.80 | 8.06 | 5.96 |
| 329 | 8.85 | 7.80 | 8.06 | 5.96 |
| 331 | 8.74 | 7.48 | 8.60 | 5.13 |
| 332 | 8.74 | 7.48 | 8.60 | 5.13 |
| 371 | 8.87 | 7.44 | 8.20 | 6.21 |
| 372 | 8.87 | 7.44 | 8.20 | 6.21 |
| 374 | 8.62 | 6.68 | 8.21 | |
| 377 | 8.49 | 6.92 | 8.38 | |
| 380 | 9.09 | 7.64 | 8.77 | 5.04 |
| 381 | 8.82 | 7.17 | 8.42 | |
| 108 | 9.21 | 7.52 | | |
| 383 | 9.21 | 7.52 | | |
| 384 | 8.80 | 7.23 | 9.05 | 5.28 |
| 39 | 8.58 | 6.82 | 7.96 | |
| 40 | 8.21 | 6.37 | 7.66 | |
| 386 | 7.57 | 6.17 | 6.92 | 6.08 |
| 389 | 9.15 | 6.72 | 8.43 | |
| 390 | | 7.57 | 9.23 | |
| 391 | 8.15 | 7 | 7.31 | |

TABLE A3-continued

| Compound number | FGFR3 pIC$_{50}$ (µM) | VEGFR2 pIC$_{50}$ (µM) | BAF3_TEL_FGFR3 pIC$_{50}$ (µM) | BAF3_WT pIC$_{50}$ (µM) |
|---|---|---|---|---|
| 392 | 8.44 | 7.04 | 7.92 | 5.72 |
| 393 | 8.44 | 7.04 | 7.92 | 5.72 |
| 404 | 7 | 5.82 | | |
| 405 | 7 | 5.82 | | |
| 409 | 9.05 | 6.70 | 8.89 | 5.60 |
| 410 | 9.05 | 6.70 | 8.89 | 5.60 |
| 423 | | 7.68 | 9.17 | 5.72 |
| 424 | | 7.68 | 9.17 | 5.72 |
| 426 | 6.82 | 5.77 | | |
| 427 | 6.82 | 5.77 | | |
| 463 | | 7.47 | 9.34 | 6.35 |
| 466 | | 7.47 | 9.41 | 5.46 |
| 467 | | 7.47 | 9.41 | 5.46 |
| 470 & 471 | 8.74 | 7.09 | 8.96 | 5.80 |
| 472 | 9 | 7.60 | 9.04 | |
| 473 | 9 | 7.60 | 9.04 | |
| 484 | 8.70 | | 9.10 | 6.23 |
| 509 | | 8.28 | | |
| 516 | 5.72 | 5.21 | | |
| 516 | 7 | 6.70 | | |

The invention claimed is:

1. A method for treating a subject suffering from a disease state or condition mediated by a FGFR kinase, said method comprising administering to the subject a compound selected from the group consisting of a compound of formula (I)

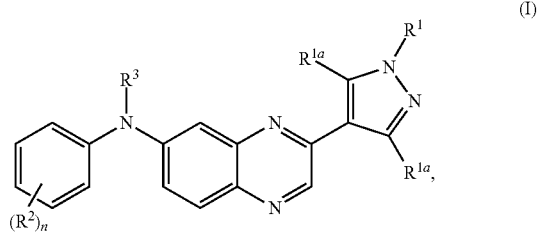

a tautomeric form, stereochemically isomeric form and isotopic form thereof, wherein n is an integer equal to 0, 1, 2, 3 or 4;

$R^1$ is
hydrogen,
$C_{1-6}$alkyl,
$C_{2-4}$alkenyl,
hydroxy$C_{1-6}$alkyl,
halo$C_{1-6}$alkyl,
hydroxyhalo$C_{1-6}$alkyl,
cyano$C_{1-4}$alkyl,
$C_{1-6}$alkoxy$C_{1-6}$alkyl wherein each $C_{1-6}$alkyl is optionally substituted with one or two hydroxyl groups,
$C_{1-6}$alkyl substituted with —NR$^4$R$^5$,
$C_{1-6}$alkyl substituted with —C(=O)—NR$^4$R$^5$,
—S(=O)$_2$—C$_{1-6}$alkyl,
—S(=O)$_2$-halo$C_{1-6}$alkyl,
—S(=O)$_2$—NR$^{14}$R$^{15}$,
$C_{1-6}$alkyl substituted with —S(=O)$_2$—C$_{1-6}$alkyl,
$C_{1-6}$alkyl substituted with —S(=O)$_2$-halo$C_{1-6}$alkyl,
$C_{1-6}$alkyl substituted with —S(=O)$_2$—NR$^{14}$R$^{15}$,
$C_{1-6}$alkyl substituted with —NH—S(=O)$_2$—C$_{1-6}$alkyl,
$C_{1-6}$alkyl substituted with —NH—S(=O)$_2$-halo$C_{1-6}$alkyl, $C_{1-6}$alkyl substituted with —$NR^{12}$—$S(=O)_2$—$NR^{14}R^{15}$,
$R^6$,
$C_{1-6}$alkyl substituted with $R^6$,
$C_{1-6}$alkyl substituted with —$C(=O)$—$R^6$,
hydroxy$C_{1-6}$alkyl substituted with $R^6$,
$C_{1-6}$alkyl substituted with —$Si(CH_3)_3$,
$C_{1-6}$alkyl substituted with —$P(=O)(OH)_2$ or
$C_{1-6}$alkyl substituted with —$P(=O)(OC_{1-6}alkyl)_2$;
each $R^{1a}$ is independently selected from
hydrogen,
$C_{1-4}$alkyl,
hydroxy$C_{1-4}$alkyl,
$C_{1-4}$alkyl substituted with amino or mono- or di($C_{1-4}$alkyl)amino or —$NH(C_{3-8}cycloalkyl)$,
cyano$C_{1-4}$alkyl,
$C_{1-4}$alkoxy$C_{1-4}$alkyl, and
$C_{1-4}$alkyl substituted with one or more fluoro atoms;
each $R^2$ is independently selected from
hydroxyl,
halogen,
cyano,
$C_{1-4}$alkyl,
$C_{2-4}$alkenyl,
$C_{2-4}$alkynyl,
$C_{1-4}$alkoxy,
hydroxy$C_{1-4}$alkyl,
hydroxy$C_{1-4}$alkoxy,
halo$C_{1-4}$alkyl,
halo$C_{1-4}$alkoxy,
hydroxyhalo$C_{1-4}$alkyl,
hydroxyhalo$C_{1-4}$alkoxy,
$C_{1-4}$alkoxy$C_{1-4}$alkyl,
halo$C_{1-4}$alkoxy$C_{1-4}$alkyl,
$C_{1-4}$alkoxy$C_{1-4}$alkyl wherein each $C_{1-4}$alkyl is optionally substituted with one or two hydroxyl groups,
hydroxyhalo$C_{1-4}$alkoxy$C_{1-4}$alkyl,
$R^{13}$,
$C_{1-4}$alkyl substituted with $R^{13}$,
$C_{1-4}$alkyl substituted with —$C(=O)$—$R^{13}$,
$C_{1-4}$alkoxy substituted with $R^{13}$,
$C_{1-4}$alkoxy substituted with —$C(=O)$—$R^{13}$,
—$C(=O)$—$R^{13}$,
$C_{1-4}$alkyl substituted with —$NR^7R^8$,
$C_{1-4}$alkyl substituted with —$C(=O)$—$NR^7R^8$,
$C_{1-4}$alkoxy substituted with —$NR^7R^8$,
$C_{1-4}$alkoxy substituted with —$C(=O)$—$NR^7R^8$,
—$NR^7R^8$ and
—$C(=O)$—$NR^7R^8$; or
when two $R^2$ groups are attached to adjacent carbon atoms they are optionally taken together to form a radical of formula:
—O—$(C(R^{17})_2)_p$—O—;
—X—CH=CH—; or
—X—CH=N—; wherein $R^{17}$ is hydrogen or fluorine, p is 1 or 2 and X is O or S;
$R^3$ is
hydroxyl,
$C_{1-6}$alkoxy,
hydroxy$C_{1-6}$alkoxy,
$C_{1-6}$alkoxy substituted with —$NR^{10}R^{11}$,
$C_{1-6}$alkyl,
$C_{2-6}$alkenyl,
$C_{2-6}$alkynyl,
halo$C_{1-6}$alkyl optionally substituted with —O—C(=O)—$C_{1-6}$alkyl,
hydroxy$C_{1-6}$alkyl optionally substituted with —O—C(=O)—$C_{1-6}$alkyl,
hydroxy$C_{2-6}$alkenyl,
hydroxy$C_{2-6}$alkynyl,
hydroxyhalo$C_{1-6}$alkyl,
cyano$C_{1-6}$alkyl,
$C_{1-6}$alkyl substituted with carboxyl,
$C_{1-6}$alkyl substituted with —C(=O)—$C_{1-6}$alkyl,
$C_{1-6}$alkyl substituted with —C(=O)—O—$C_{1-6}$alkyl,
$C_{1-6}$alkyl substituted with $C_{1-6}$alkoxy$C_{1-6}$alkyl-O—C(=O)—,
$C_{1-6}$alkyl substituted with $C_{1-6}$alkoxy$C_{1-6}$alkyl-C(=O)—,
$C_{1-6}$alkyl substituted with —O—C(=O)—$C_{1-6}$alkyl,
$C_{1-6}$alkoxy$C_{1-6}$alkyl wherein each $C_{1-6}$alkyl is optionally substituted with one or two hydroxyl groups or with —O—C(=O)—$C_{1-6}$alkyl,
$C_{2-6}$alkenyl substituted with $C_{1-6}$alkoxy,
$C_{2-6}$alkynyl substituted with $C_{1-6}$alkoxy,
$C_{1-6}$alkyl substituted with $R^9$ and optionally substituted with —O—C(=O)—$C_{1-6}$alkyl,
$C_{1-6}$alkyl substituted with —C(=O)—$R^9$,
$C_{1-6}$alkyl substituted with hydroxyl and $R^9$,
$C_{2-6}$alkenyl substituted with $R^9$,
$C_{2-6}$alkynyl substituted with $R^9$,
$C_{1-6}$alkyl substituted with —$NR^{10}R^{11}$,
$C_{2-6}$alkenyl substituted with —$NR^{10}R^{11}$,
$C_{2-6}$alkynyl substituted with —$NR^{10}R^{11}$,
$C_{1-6}$alkyl substituted with hydroxyl and —$NR^{10}R^{11}$,
$C_{1-6}$alkyl substituted with one or two halogens and —$NR^{10}R^{11}$,
—$C_{1-6}$alkyl-$C(R^{12})=N$—O—$R^{12}$,
$C_{1-6}$alkyl substituted with —C(=O)—$NR^{10}R^{11}$,
$C_{1-6}$alkyl substituted with —O—C(=O)—$NR^{10}R^{11}$,
—$S(=O)_2$—$C_{1-6}$alkyl,
—$S(=O)_2$-halo$C_{1-6}$alkyl,
—$S(=O)_2$—$NR^{14}R^{15}$,
$C_{1-6}$alkyl substituted with —$S(=O)_2$—$C_{1-6}$alkyl,
$C_{1-6}$alkyl substituted with —$S(=O)_2$-halo$C_{1-6}$alkyl,
$C_{1-6}$alkyl substituted with —$S(=O)_2$—$NR^{14}R^{15}$,
$C_{1-6}$alkyl substituted with —$NR^{12}$—$S(=O)_2$—$C_{1-6}$alkyl,
$C_{1-6}$alkyl substituted with —NH—$S(=O)_2$-halo$C_{1-6}$alkyl,
$C_{1-6}$alkyl substituted with —$NR^{12}$—$S(=O)_2$—$NR^{14}R^{15}$,
$R^{13}$,
$C_{1-6}$alkyl substituted with —$P(=O)(OH)_2$ or
$C_{1-6}$alkyl substituted with —$P(=O)(OC_{1-6}alkyl)_2$;
$R^4$ and $R^5$ are each independently
hydrogen,
$C_{1-6}$alkyl,
hydroxy$C_{1-6}$alkyl,
halo$C_{1-6}$alkyl,
hydroxyhalo$C_{1-6}$alkyl,
$C_{1-6}$alkoxy$C_{1-6}$alkyl wherein each $C_{1-6}$alkyl is optionally substituted with one or two hydroxyl groups,
—$S(=O)_2$—$C_{1-6}$alkyl,
—$S(=O)_2$-halo$C_{1-6}$alkyl,
—$S(=O)_2$—$NR^{14}R^{15}$,
$C_{1-6}$alkyl substituted with —$S(=O)_2$—$C_{1-6}$alkyl,
$C_{1-6}$alkyl substituted with —$S(=O)_2$-halo$C_{1-6}$alkyl,
$C_{1-6}$alkyl substituted with —$S(=O)_2$—$NR^{14}R^{15}$,
$C_{1-6}$alkyl substituted with —NH—$S(=O)_2$—$C_{1-6}$alkyl,
$C_{1-6}$alkyl substituted with —NH—$S(=O)_2$-halo$C_{1-6}$alkyl, $C_{1-6}$alkyl substituted with $-NH-S(=O)_2-NR^{14}R^{15}$,
$R^{13}$ or
$C_{1-6}$alkyl substituted with $R^{13}$;

$R^6$ is $C_{3-8}$cycloalkyl, $C_{3-8}$cycloalkenyl, phenyl, 4 to 7-membered monocyclic heterocyclyl containing at least one heteroatom selected from N, O and S; said $C_{3-8}$cycloalkyl, $C_{3-8}$cycloalkenyl, phenyl, 4 to 7-membered monocyclic heterocyclyl, each optionally and each independently substituted by 1, 2, 3, 4 or 5 substituents, each substituent independently selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O-C(=O)-, $-NR^{14}R^{15}$, $-C(=O)-NR^{14}R^{15}$, $C_{1-6}$alkyl substituted with $-NR^{14}R^{15}$, $C_{1-6}$alkyl substituted with $-C(=O)-NR^{14}R^{15}$, $-S(=O)_2-C_{1-6}$alkyl, $-S(=O)_2$-halo$C_{1-6}$alkyl, $-S(=O)_2-NR^{14}R^{15}$, $C_{1-6}$alkyl substituted with $-S(=O)_2-C_{1-6}$alkyl, $C_{1-6}$alkyl substituted with $-S(=O)_2$-halo$C_{1-6}$alkyl, $C_{1-6}$alkyl substituted with $-S(=O)_2-NR^{14}R^{15}$, $C_{1-6}$alkyl substituted with $-NH-S(=O)_2-C_{1-6}$alkyl, $C_{1-6}$alkyl substituted with $-NH-S(=O)_2$-halo$C_{1-6}$alkyl and $C_{1-6}$alkyl substituted with $-NH-S(=O)_2-NR^{14}R^{15}$;

$R^7$ and $R^8$ are each independently hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ is $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O and S, said $C_{3-8}$cycloalkyl, $C_{3-8}$cycloalkenyl, phenyl, naphthyl, or 3 to 12 membered monocyclic or bicyclic heterocyclyl each optionally and each independently substituted with 1, 2, 3, 4 or 5 substituents, each substituent independently selected from
=O,
$C_{1-4}$alkyl,
hydroxyl,
carboxyl,
hydroxy$C_{1-4}$alkyl,
cyano,
cyano$C_{1-4}$alkyl,
$C_{1-4}$alkyl-O-C(=O)-,
$C_{1-4}$alkyl substituted with $C_{1-4}$alkyl-O-C(=O)-,
$C_{1-4}$alkyl-C(=O)-,
$C_{1-4}$alkoxy$C_{1-4}$alkyl wherein each $C_{1-4}$alkyl is optionally substituted with one or two hydroxyl groups,
halogen,
halo$C_{1-4}$alkyl,
hydroxyhalo$C_{1-4}$alkyl,
$-NR^{14}R^{15}$,
$-C(=O)-NR^{14}R^{15}$,
$C_{1-4}$alkyl substituted with $-NR^{14}R^{15}$,
$C_{1-4}$alkyl substituted with $-C(=O)-NR^{14}R^{15}$,
$C_{1-4}$alkoxy,
$-S(=O)_2-C_{1-4}$alkyl,
$-S(=O)_2$-halo$C_{1-4}$alkyl,
$-S(=O)_2-NR^{14}R^{15}$,
$C_{1-4}$alkyl substituted with $-S(=O)_2-NR^{14}R^{15}$,
$C_{1-4}$alkyl substituted with $-NH-S(=O)_2-C_{1-4}$alkyl,
$C_{1-4}$alkyl substituted with $-NH-S(=O)_2$-halo$C_{1-4}$alkyl,
$C_{1-4}$alkyl substituted with $-NH-S(=O)_2-NR^{14}R^{15}$,
$R^{13}$,
$-C(=O)-R^{13}$,
$C_{1-4}$alkyl substituted with $R^{13}$,
phenyl optionally substituted with $R^{16}$,
phenyl$C_{1-6}$alkyl wherein the phenyl is optionally substituted with $R^{16}$, and
a 5 or 6-membered aromatic monocyclic heterocyclyl containing at least one heteroatom selected from N, O and S wherein said heterocyclyl is optionally substituted with $R^{16}$;
or when two of the substituents of $R^9$ are attached to the same atom, they are optionally taken together to form a 4 to 7-membered saturated monocyclic heterocyclyl containing at least one heteroatom selected from N, O and S;

$R^{10}$ and $R^{11}$ are each independently
hydrogen,
carboxyl,
$C_{1-6}$alkyl,
cyano$C_{1-6}$alkyl,
$C_{1-6}$alkyl substituted with $-NR^{14}R^{15}$,
$C_{1-6}$alkyl substituted with $-C(=O)-NR^{14}R^{15}$,
halo$C_{1-6}$alkyl,
hydroxy$C_{1-6}$alkyl,
hydroxyhalo$C_{1-6}$alkyl,
$C_{1-6}$alkoxy,
$C_{1-6}$alkoxy$C_{1-6}$alkyl wherein each $C_{1-6}$alkyl is optionally substituted with one or two hydroxyl groups,
$R^6$,
$C_{1-6}$alkyl substituted with $R^6$,
$-C(=O)-R^6$,
$-C(=O)-C_{1-6}$alkyl,
$-C(=O)$-hydroxy$C_{1-6}$alkyl,
$-C(=O)$-halo$C_{1-6}$alkyl,
$-C(=O)$-hydroxyhalo$C_{1-6}$alkyl,
$C_{1-6}$alkyl substituted with $-Si(CH_3)_3$,
$-S(=O)_2-C_{1-6}$alkyl,
$-S(=O)_2$-halo$C_{1-6}$alkyl,
$-S(=O)_2-NR^{14}R^{15}$,
$C_{1-6}$alkyl substituted with $-S(=O)_2-C_{1-6}$alkyl,
$C_{1-6}$alkyl substituted with $-S(=O)_2$-halo$C_{1-6}$alkyl,
$C_{1-6}$alkyl substituted with $-S(=O)_2-NR^{14}R^{15}$,
$C_{1-6}$alkyl substituted with $-NH-S(=O)_2-C_{1-6}$alkyl,
$C_{1-6}$alkyl substituted with $-NH-S(=O)_2$-halo$C_{1-6}$alkyl or
$C_{1-6}$alkyl substituted with $-NH-S(=O)_2-NR^{14}R^{15}$;

$R^{12}$ is hydrogen or $C_{1-4}$alkyl optionally substituted with $C_{1-4}$alkoxy;

$R^{13}$ is $C_{3-8}$cycloalkyl or a saturated 4 to 6-membered monocyclic heterocyclyl containing at least one heteroatom selected from N, O and S, wherein said $C_{3-8}$cycloalkyl or monocyclic heterocyclyl is optionally substituted with 1, 2 or 3 substituents each independently selected from halogen, hydroxyl, $C_{1-6}$alkyl, $-C(=O)-C_{1-6}$alkyl, $C_{1-6}$alkoxy, and $-NR^{14}R^{15}$;

$R^{14}$ and $R^{15}$ are each independently
hydrogen, or
halo$C_{1-4}$alkyl, or
$C_{1-4}$alkyl optionally substituted with a substituent selected from hydroxyl, $C_{1-4}$alkoxy, amino and mono- or di($C_{1-4}$alkyl)amino; and $R^{16}$ is hydroxyl, halogen, cyano, $C_{1-4}$alkyl, $C_{1-4}$alkoxy, $-NR^{14}R^{15}$ or $-C(=O)NR^{14}R^{15}$;

or an N-oxide thereof, a pharmaceutically acceptable salt thereof or a solvate thereof.

2. A method according to claim 1, wherein the compound is selected from the group consisting of a compound of formula (I), a tautomeric form, stereochemically isomeric form and isotopic form thereof, wherein $R^1$ is
hydrogen,
$C_{1-6}$alkyl,
hydroxy$C_{1-6}$alkyl,
halo$C_{1-6}$alkyl,
$C_{1-6}$alkoxy$C_{1-6}$alkyl wherein each $C_{1-6}$alkyl is optionally substituted with one or two hydroxyl groups,
$C_{1-6}$alkyl substituted with —$NR^4R^5$,
$C_{1-6}$alkyl substituted with —C(=O)—$NR^4R^5$,
—S(=O)$_2$—$C_{1-6}$alkyl,
—S(=O)$_2$—$NR^{14}R^{15}$,
$C_{1-6}$alkyl substituted with —S(=O)$_2$—$C_{1-6}$alkyl,
$C_{1-6}$alkyl substituted with —NH—S(=O)$_2$—$C_{1-6}$alkyl,
$R^6$,
$C_{1-6}$alkyl substituted with $R^6$,
$C_{1-6}$alkyl substituted with —C(=O)—$R^6$,
hydroxy$C_{1-6}$alkyl substituted with $R^6$, or
$C_{1-6}$alkyl substituted with —Si(CH$_3$)$_3$;
each $R^{1a}$ is hydrogen;
$R^{10}$ and $R^{11}$ are each independently
hydrogen,
$C_{1-6}$alkyl,
cyano$C_{1-6}$alkyl,
$C_{1-6}$alkyl substituted with —$NR^{14}R^{15}$,
$C_{1-6}$alkyl substituted with —C(=O)—$NR^{14}R^{15}$,
halo$C_{1-6}$alkyl,
hydroxy$C_{1-6}$alkyl,
hydroxyhalo$C_{1-6}$alkyl,
$C_{1-6}$alkoxy,
$C_{1-6}$alkoxy$C_{1-6}$alkyl wherein each $C_{1-6}$alkyl is optionally substituted with one or two hydroxyl groups,
$R^6$,
$C_{1-6}$alkyl substituted with $R^6$,
—C(=O)—$R^6$,
—C(=O)—$C_{1-6}$alkyl,
—C(=O)-hydroxy$C_{1-6}$alkyl,
—C(=O)-halo$C_{1-6}$alkyl,
—C(=O)-hydroxyhalo$C_{1-6}$alkyl,
$C_{1-6}$alkyl substituted with —Si(CH$_3$)$_3$,
—S(=O)$_2$—$C_{1-6}$alkyl,
—S(=O)$_2$-halo$C_{1-6}$alkyl,
—S(=O)$_2$—$NR^{14}R^{15}$,
$C_{1-6}$alkyl substituted with —S(=O)$_2$—$C_{1-6}$alkyl,
$C_{1-6}$alkyl substituted with —S(=O)$_2$-halo$C_{1-6}$alkyl,
$C_{1-6}$alkyl substituted with —S(=O)$_2$—$NR^{14}R^{15}$,
$C_{1-6}$alkyl substituted with —NH—S(=O)$_2$—$C_{1-6}$alkyl,
$C_{1-6}$alkyl substituted with —NH—S(=O)$_2$-halo$C_{1-6}$alkyl or
$C_{1-6}$alkyl substituted with —NH—S(=O)$_2$—$NR^{14}R^{15}$;
or an N-oxide thereof, a pharmaceutically acceptable salt thereof or a solvate thereof.

3. A method according to claim 1, wherein the compound is selected from the group consisting of a compound of formula (I), a tautomeric form, stereochemically isomeric form and isotopic form thereof, wherein each $R^{1a}$ is hydrogen; or an N-oxide thereof, a pharmaceutically acceptable salt thereof or a solvate thereof.

4. A method according to claim 1, wherein the compound is selected from the group consisting of a compound of formula (I), a tautomeric form, stereochemically isomeric form and isotopic form thereof, wherein $R^1$ is $C_{1-6}$alkyl; or an N-oxide thereof, a pharmaceutically acceptable salt thereof or a solvate thereof.

5. A method according to claim 1, wherein the compound is selected from the group consisting of a compound of formula (I), a tautomeric form, stereochemically isomeric form and isotopic form thereof, wherein $R^1$ is CH$_3$— or CD$_3$-; or an N-oxide thereof, a pharmaceutically acceptable salt thereof or a solvate thereof.

6. A method according to claim 1, wherein the compound is selected from the group consisting of a compound of formula (I), a tautomeric form, stereochemically isomeric form and isotopic form thereof, wherein $R^2$ is independently selected from halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo $C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ and —C(=O)—$NR^7R^8$; or an N-oxide thereof, a pharmaceutically acceptable salt thereof or a solvate thereof.

7. A method according to claim 6, wherein the compound is selected from the group consisting of a compound of formula (I), a tautomeric form, stereochemically isomeric form and isotopic form thereof, wherein $R^2$ is $C_{1-4}$alkoxy; or an N-oxide thereof, a pharmaceutically acceptable salt thereof or a solvate thereof.

8. A method according to claim 6, wherein the compound is selected from the group consisting of a compound of formula (I), a tautomeric form, stereochemically isomeric form and isotopic form thereof, wherein $R^2$ is CH$_3$O— or CD$_3$O—; or an N-oxide thereof, a pharmaceutically acceptable salt thereof or a solvate thereof.

9. A method according to claim 1, wherein the compound is selected from the group consisting of a compound of formula (I), a tautomeric form, stereochemically isomeric form and isotopic form thereof, wherein $R^3$ is
$C_{1-6}$alkyl,
hydroxy$C_{1-6}$alkyl,
hydroxyhalo$C_{1-6}$alkyl,
halo$C_{1-6}$alkyl,
$C_{1-6}$alkyl substituted with —C(=O)—$C_{1-6}$alkyl,
$C_{1-6}$alkoxy$C_{1-6}$alkyl wherein each $C_{1-6}$alkyl is optionally substituted with one or two hydroxyl groups,
$C_{1-6}$alkyl substituted with $R^9$,
$C_{1-6}$alkyl substituted with —$NR^{10}R^{11}$,
$C_{1-6}$alkyl substituted with hydroxyl and —$NR^{10}R^{11}$,
$C_{1-6}$alkyl substituted with one or two halogens and —$NR^{10}R^{11}$,
$C_{1-6}$alkyl substituted with —C(=O)—O—$C_{1-6}$alkyl,
$C_{1-6}$alkyl substituted with —O—C(=O)—$NR^{10}R^{11}$,
$C_{1-6}$alkyl substituted with carboxyl,
$C_{1-6}$alkyl substituted with —$NR^{12}$—S(=O)$_2$—$C_{1-6}$alkyl,
$C_{1-6}$alkyl substituted with —$NR^{12}$—S(=O)$_2$—$NR^{14}R^{15}$,
$C_{1-6}$alkyl substituted with hydroxyl and $R^9$,
—$C_{1-6}$alkyl-C($R^{12}$)=N—O—$R^{12}$,
$C_{1-6}$alkyl substituted with —C(=O)—$NR^{10}R^{11}$,
$C_{1-6}$alkyl substituted with —C(=O)—$R^9$,
$C_{2-6}$alkynyl substituted with $R^9$,
hydroxy$C_{1-6}$alkoxy,
$C_{2-6}$alkenyl,
$C_{2-6}$alkynyl or
$R^{13}$;
or an N-oxide thereof, a pharmaceutically acceptable salt thereof or a solvate thereof.

10. A method according to claim 1, wherein the compound is selected from the group consisting of a compound of formula (I), a tautomeric form, stereochemically isomeric form and isotopic form thereof, wherein $R^1$ is $C_{1-6}$alkyl, each $R^{1a}$ is hydrogen, n is an integer equal to 2, each $R^2$ is $C_{1-4}$alkoxy, and $R^3$ is $C_{1-6}$alkyl substituted with $-NR^{10}R^{11}$; or an N-oxide thereof, a pharmaceutically acceptable salt thereof or a solvate thereof.

11. A method according to claim 10, wherein the compound is selected from the group consisting of a compound of formula (I), a tautomeric form, stereochemically isomeric form and isotopic form thereof, wherein $R^{10}$ is hydrogen, $-CH_3$, $-CH_2CH_3$ or $-CH(CH_3)_2$ and $R^{11}$ is hydrogen, $-CH_3$, $-CH_2CH_3$, $-CH(CH_3)_2$, $-CH_2CF_3$, $-CH_2CHF_2$, $-CH_2CH_2F$, $-C(=O)-CH_3$, $-S(=O)_2-CH_3$, $-S(=O)_2-CH_2CH_3$, $-S(=O)_2-CH(CH_3)_2$, $-S(=O)_2-N(CH_3)_2$, $-CH_2CH_2OH$, $-C(=O)-C(OH)(CH_3)CF_3$, $-C(=O)$-cyclopropyl, $-CH_2CH_2CN$, cyclopropane, cyclopentane, 2,2,6,6-tetramethyl-piperidine, $-CH_2C_3H_5$, $-CH_2-$ tetrahydrofuran, $-C(=O)$-(1-methyl-piperidin-3-yl), $-C(=O)-CF_3$, $-CH_2Si(CH_3)_3$, or $-CH_2-C_6H_5$; or an N-oxide thereof, a pharmaceutically acceptable salt thereof or a solvate thereof.

12. A method according to claim 10, wherein the compound is selected from the group consisting of a compound of formula (I), a tautomeric form, stereochemically isomeric form and isotopic form thereof, wherein $R^1$ is $-CH_3$, each $R^{1a}$ is hydrogen, n is an integer equal to 2, each $R^2$ is $CH_3O-$, and $R^3$ is $-CH_2CH_2NHCH(CH_3)_2$; or an N-oxide thereof, a pharmaceutically acceptable salt thereof or a solvate thereof.

13. A method according to claim 10, wherein the compound is selected from the group consisting of a compound of formula (I), a tautomeric form, stereochemically isomeric form and isotopic form thereof, wherein $R^1$ is $-CH_3$, each $R^{1a}$ is hydrogen, n is an integer equal to 2, each $R^2$ is $CH_3O-$, and $R^3$ is $-CH_2CH_2-CH_2-NHCH_2CF_3$ or $-CH_2-CH_2NH_2$; or an N-oxide thereof, a pharmaceutically acceptable salt thereof or a solvate thereof.

14. A method according to claim 1, wherein the compound is N-(3,5-dimethoxyphenyl)-N'-(1-methylethyl)-N-[3-(1-methyl-1H-pyrazol-4-yl)quinoxalin-6-yl]ethane-1,2-diamine; or an N-oxide thereof, a pharmaceutically acceptable salt thereof or a solvate thereof.

15. A method according to claim 14, wherein the compound is N-(3,5-dimethoxyphenyl)-N'-(1-methylethyl)-N-[3-(1-methyl-1H-pyrazol-4-yl)quinoxalin-6-yl]ethane-1,2-diamine.

16. A method according to claim 1, wherein the compound is selected from:
N-(3,5-dimethoxyphenyl)-N-[3-(1-methyl-1H-pyrazol-4-yl)quinoxalin-6-yl]-N'-(2,2,2-trifluoroethyl)propane-1,3-diamine; and
N-(3,5-dimethoxyphenyl)-N-[3-(1-methyl-1H-pyrazol-4-yl)quinoxalin-6-yl]ethane-1,2-diamine;
or an N-oxide thereof, a pharmaceutically acceptable salt thereof or a solvate thereof.

17. A method according to claim 16, wherein the compound is selected from:
N-(3,5-dimethoxyphenyl)-N-[3-(1-methyl-1H-pyrazol-4-yl)quinoxalin-6-yl]-N'-(2,2,2-trifluoroethyl)propane-1,3-diamine; and
N-(3,5-dimethoxyphenyl)-N-[3-(1-methyl-1H-pyrazol-4-yl)quinoxalin-6-yl]ethane-1,2-diamine.

18. A method for treating a subject suffering from cancer, said method comprising administering to the subject a compound selected from the group consisting of a compound of formula (I)

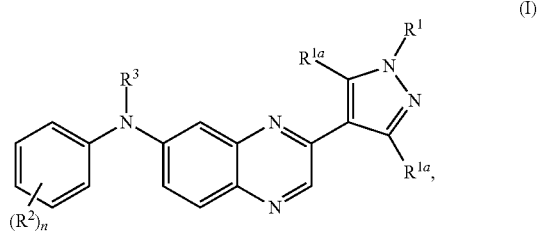

a tautomeric form, stereochemically isomeric form and isotopic form thereof, wherein
n is an integer equal to 0, 1, 2, 3 or 4;
$R^1$ is
  hydrogen,
  $C_{1-6}$alkyl,
  $C_{2-4}$alkenyl,
  hydroxy$C_{1-6}$alkyl,
  halo$C_{1-6}$alkyl,
  hydroxyhalo$C_{1-6}$alkyl,
  cyano$C_{1-4}$alkyl,
  $C_{1-6}$alkoxy$C_{1-6}$alkyl wherein each $C_{1-6}$alkyl is optionally substituted with one or two hydroxyl groups,
  $C_{1-6}$alkyl substituted with $-NR^4R^5$,
  $C_{1-6}$alkyl substituted with $-C(=O)-NR^4R^5$,
  $-S(=O)_2-C_{1-6}$alkyl,
  $-S(=O)_2$-halo$C_{1-6}$alkyl,
  $-S(=O)_2-NR^{14}R^{15}$,
  $C_{1-6}$alkyl substituted with $-S(=O)_2-C_{1-6}$alkyl,
  $C_{1-6}$alkyl substituted with $-S(=O)_2$-halo$C_{1-6}$alkyl,
  $C_{1-6}$alkyl substituted with $-S(=O)_2-NR^{14}R^{15}$,
  $C_{1-6}$alkyl substituted with $-NH-S(=O)_2-C_{1-6}$alkyl,
  $C_{1-6}$alkyl substituted with $-NH-S(=O)_2$-halo$C_{1-6}$alkyl,
  $C_{1-6}$alkyl substituted with $-NR^{12}-S(=O)_2-NR^{14}R^{15}$,
  $R^6$,
  $C_{1-6}$alkyl substituted with $R^6$,
  $C_{1-6}$alkyl substituted with $-C(=O)-R^6$,
  hydroxy$C_{1-6}$alkyl substituted with $R^6$,
  $C_{1-6}$alkyl substituted with $-Si(CH_3)_3$,
  $C_{1-6}$alkyl substituted with $-P(=O)(OH)_2$ or
  $C_{1-6}$alkyl substituted with $-P(=O)(OC_{1-6}$alkyl$)_2$;
each $R^{1a}$ is independently selected from
  hydrogen,
  $C_{1-4}$alkyl,
  hydroxy$C_{1-4}$alkyl,
  $C_{1-4}$alkyl substituted with amino or mono- or di($C_{1-4}$alkyl)amino or $-NH(C_{3-8}$cycloalkyl),
  cyano$C_{1-4}$alkyl,
  $C_{1-4}$alkoxy$C_{1-4}$alkyl, and
  $C_{1-4}$alkyl substituted with one or more fluoro atoms;
each $R^2$ is independently selected from
  hydroxyl,
  halogen,
  cyano,
  $C_{1-4}$alkyl,
  $C_{2-4}$alkenyl,
  $C_{2-4}$alkynyl,
  $C_{1-4}$alkoxy,
  hydroxy$C_{1-4}$alkyl,
  hydroxy$C_{1-4}$alkoxy,
  halo$C_{1-4}$alkyl,
  halo$C_{1-4}$alkoxy, hydroxyhalo$C_{1-4}$alkyl,
hydroxyhalo$C_{1-4}$alkoxy,
$C_{1-4}$alkoxy$C_{1-4}$alkyl,
halo$C_{1-4}$alkoxy$C_{1-4}$alkyl,
$C_{1-4}$alkoxy$C_{1-4}$alkyl wherein each $C_{1-4}$alkyl is optionally substituted with one or two hydroxyl groups,
hydroxyhalo$C_{1-4}$alkoxy$C_{1-4}$alkyl,
$R^{13}$,
$C_{1-4}$alkyl substituted with $R^{13}$,
$C_{1-4}$alkyl substituted with —C(=O)—$R^{13}$,
$C_{1-4}$alkoxy substituted with $R^{13}$,
$C_{1-4}$alkoxy substituted with —C(=O)—$R^{13}$,
—C(=O)—$R^{13}$,
$C_{1-4}$alkyl substituted with —$NR^7R^8$,
$C_{1-4}$alkyl substituted with —C(=O)—$NR^7R^8$,
$C_{1-4}$alkoxy substituted with —$NR^7R^8$,
$C_{1-4}$alkoxy substituted with —C(=O)—$NR^7R^8$,
—$NR^7R^8$ and —C(=O)—$NR^7R^8$; or
when two $R^2$ groups are attached to adjacent carbon atoms they are optionally taken together to form a radical of formula:
—O—(C($R^{17}$)$_2$)$_p$—O—;
—X—CH=CH—; or
—X—CH=N—; wherein $R^{17}$ is hydrogen or fluorine, p is 1 or 2 and X is O or S;

$R^3$ is
hydroxyl,
$C_{1-6}$alkoxy,
hydroxy$C_{1-6}$alkoxy,
$C_{1-6}$alkoxy substituted with —$NR^{11}R^{11}$,
$C_{1-6}$alkyl,
$C_{2-6}$alkenyl,
$C_{2-6}$alkynyl,
halo$C_{1-6}$alkyl optionally substituted with —O—C(=O)—$C_{1-6}$alkyl,
hydroxy$C_{1-6}$alkyl optionally substituted with —O—C(=O)—$C_{1-6}$alkyl,
hydroxy$C_{2-6}$alkenyl,
hydroxy$C_{2-6}$alkynyl,
hydroxyhalo$C_{1-6}$alkyl,
cyano$C_{1-6}$alkyl,
$C_{1-6}$alkyl substituted with carboxyl,
$C_{1-6}$alkyl substituted with —C(=O)—$C_{1-6}$alkyl,
$C_{1-6}$alkyl substituted with —C(=O)—O—$C_{1-6}$alkyl,
$C_{1-6}$alkyl substituted with $C_{1-6}$alkoxy$C_{1-6}$alkyl-O—C(=O)—,
$C_{1-6}$alkyl substituted with $C_{1-6}$alkoxy$C_{1-6}$alkyl-C(=O)—,
$C_{1-6}$alkyl substituted with —O—C(=O)—$C_{1-6}$alkyl,
$C_{1-6}$alkoxy$C_{1-6}$alkyl wherein each $C_{1-6}$alkyl is optionally substituted with one or two hydroxyl groups or with —O—C(=O)—$C_{1-6}$alkyl,
$C_{2-6}$alkenyl substituted with $C_{1-6}$alkoxy,
$C_{2-6}$alkynyl substituted with $C_{1-6}$alkoxy,
$C_{1-6}$alkyl substituted with $R^9$ and optionally substituted with —O—C(=O)—$C_{1-6}$alkyl,
$C_{1-6}$alkyl substituted with —C(=O)—$R^9$,
$C_{1-6}$alkyl substituted with hydroxyl and $R^9$,
$C_{2-6}$alkenyl substituted with $R^9$,
$C_{2-6}$alkynyl substituted with $R^9$,
$C_{1-6}$alkyl substituted with —$NR^{10}R^{11}$,
$C_{2-6}$alkenyl substituted with —$NR^{10}R^{11}$,
$C_{2-6}$alkynyl substituted with —$NR^{10}R^{11}$,
$C_{1-6}$alkyl substituted with hydroxyl and —$NR^{10}R^{11}$,
$C_{1-6}$alkyl substituted with one or two halogens and —$NR^{10}R^{11}$,
—$C_{1-6}$alkyl-C($R^{12}$)=N—O—$R^{12}$,
$C_{1-6}$alkyl substituted with —C(=O)—$NR^{10}R^{11}$,
$C_{1-6}$alkyl substituted with —O—C(=O)—$NR^{10}R^{11}$,
—S(=O)$_2$—$C_{1-6}$alkyl,
—S(=O)$_2$-halo$C_{1-6}$alkyl,
—S(=O)$_2$—$NR^{14}R^{15}$,
$C_{1-6}$alkyl substituted with —S(=O)$_2$—$C_{1-6}$alkyl,
$C_{1-6}$alkyl substituted with —S(=O)$_2$-halo$C_{1-6}$alkyl,
$C_{1-6}$alkyl substituted with —S(=O)$_2$—$NR^{14}R^{15}$,
$C_{1-6}$alkyl substituted with —$NR^{12}$—S(=O)$_2$—$C_{1-6}$alkyl,
$C_{1-6}$alkyl substituted with —NH—S(=O)$_2$-halo$C_{1-6}$alkyl,
$C_{1-6}$alkyl substituted with —$NR^{12}$—S(=O)$_2$—$NR^{14}R^{15}$,
$R^{13}$,
$C_{1-6}$alkyl substituted with —P(=O)(OH)$_2$ or
$C_{1-6}$alkyl substituted with —P(=O)(O$C_{1-6}$alkyl)$_2$;

$R^4$ and $R^5$ are each independently
hydrogen,
$C_{1-6}$alkyl,
hydroxy$C_{1-6}$alkyl,
halo$C_{1-6}$alkyl,
hydroxyhalo$C_{1-6}$alkyl,
$C_{1-6}$alkoxy$C_{1-6}$alkyl wherein each $C_{1-6}$alkyl is optionally substituted with one or two hydroxyl groups,
—S(=O)$_2$—$C_{1-6}$alkyl,
—S(=O)$_2$-halo$C_{1-6}$alkyl,
—S(=O)$_2$—$NR^{14}R^{15}$,
$C_{1-6}$alkyl substituted with —S(=O)$_2$—$C_{1-6}$alkyl,
$C_{1-6}$alkyl substituted with —S(=O)$_2$-halo$C_{1-6}$alkyl,
$C_{1-6}$alkyl substituted with —S(=O)$_2$—$NR^{14}R^{15}$,
$C_{1-6}$alkyl substituted with —NH—S(=O)$_2$—$C_{1-6}$alkyl,
$C_{1-6}$alkyl substituted with —NH—S(=O)$_2$-halo$C_{1-6}$alkyl,
$C_{1-6}$alkyl substituted with —NH—S(=O)$_2$—$NR^{14}R^{15}$,
$R^{13}$ or
$C_{1-6}$alkyl substituted with $R^{13}$;

$R^6$ is $C_{3-8}$cycloalkyl, $C_{3-8}$cycloalkenyl, phenyl, 4 to 7-membered monocyclic heterocyclyl containing at least one heteroatom selected from N, O and S; said $C_{3-8}$cycloalkyl, $C_{3-8}$cycloalkenyl, phenyl, 4 to 7-membered monocyclic heterocyclyl, each optionally and each independently substituted by 1, 2, 3, 4 or 5 substituents, each substituent independently selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl and $C_{1-6}$alkyl substituted with —NH—S(=O)$_2$—$NR^{14}R^{15}$;

$R^7$ and $R^8$ are each independently hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ is $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O and S, said $C_{3-8}$cycloalkyl, $C_{3-8}$cycloalkenyl, phenyl, naphthyl, or 3 to 12 membered monocyclic or bicyclic heterocyclyl each optionally and each independently substituted with 1, 2, 3, 4 or 5 substituents, each substituent independently selected from
=O,
$C_{1-4}$alkyl,
hydroxyl,
carboxyl,
hydroxy$C_{1-4}$alkyl,
cyano,
cyano$C_{1-4}$alkyl,
$C_{1-4}$alkyl-O—C(=O)—,
$C_{1-4}$alkyl substituted with $C_{1-4}$alkyl-O—C(=O)—,
$C_{1-4}$alkyl-C(=O)—,
$C_{1-4}$alkoxy$C_{1-4}$alkyl wherein each $C_{1-4}$alkyl is optionally substituted with one or two hydroxyl groups,
halogen,
halo$C_{1-4}$alkyl,
hydroxyhalo$C_{1-4}$alkyl,
—$NR^{14}R^{15}$,
—C(=O)—$NR^{14}R^{15}$,
$C_{1-4}$alkyl substituted with —$NR^{14}R^{15}$,
$C_{1-4}$alkyl substituted with —C(=O)—$NR^{14}R^{15}$,
$C_{1-4}$alkoxy,
—S(=O)$_2$—$C_{1-4}$alkyl,
—S(=O)$_2$-halo$C_{1-4}$alkyl,
—S(=O)$_2$—$NR^{14}R^{15}$,
$C_{1-4}$alkyl substituted with —S(=O)$_2$—$NR^{14}R^{15}$,
$C_{1-4}$alkyl substituted with —NH—S(=O)$_2$—$C_{1-4}$alkyl,
$C_{1-4}$alkyl substituted with —NH—S(=O)$_2$-halo $C_{1-4}$alkyl,
$C_{1-4}$alkyl substituted with —NH—S(=O)$_2$—$NR^{14}R^{15}$,
$R^{13}$,
—C(=O)—$R^{13}$,
$C_{1-4}$alkyl substituted with $R^{13}$,
phenyl optionally substituted with $R^{16}$,
phenyl$C_{1-6}$alkyl wherein the phenyl is optionally substituted with $R^{16}$, and
a 5 or 6-membered aromatic monocyclic heterocyclyl containing at least one heteroatom selected from N, O and S wherein said heterocyclyl is optionally substituted with $R^{16}$;
or when two of the substituents of $R^9$ are attached to the same atom, they are optionally taken together to form a 4 to 7-membered saturated monocyclic heterocyclyl containing at least one heteroatom selected from N, O and S;
$R^{10}$ and $R^{11}$ are each independently
hydrogen,
carboxyl,
$C_{1-6}$alkyl,
cyano$C_{1-6}$alkyl,
$C_{1-6}$alkyl substituted with —$NR^{14}R^{15}$,
$C_{1-6}$alkyl substituted with —C(=O)—$NR^{14}R^{15}$,
halo$C_{1-6}$alkyl,
hydroxy$C_{1-6}$alkyl,
hydroxyhalo$C_{1-6}$alkyl,
$C_{1-6}$alkoxy,
$C_{1-6}$alkoxy$C_{1-6}$alkyl wherein each $C_{1-6}$alkyl is optionally substituted with one or two hydroxyl groups,
$R^6$,
$C_{1-6}$alkyl substituted with $R^6$,
—C(=O)—$R^6$,
—C(=O)—$C_{1-6}$alkyl,
—C(=O)-hydroxy$C_{1-6}$alkyl,
—C(=O)-halo$C_{1-6}$alkyl,
—C(=O)-hydroxyhalo$C_{1-6}$alkyl,
$C_{1-6}$alkyl substituted with —Si(CH$_3$)$_3$,
—S(=O)$_2$—$C_{1-6}$alkyl,
—S(=O)$_2$-halo$C_{1-6}$alkyl,
—S(=O)$_2$—$NR^{14}R^{15}$,
$C_{1-6}$alkyl substituted with —S(=O)$_2$—$C_{1-6}$alkyl,
$C_{1-6}$alkyl substituted with —S(=O)$_2$-halo$C_{1-6}$alkyl,
$C_{1-6}$alkyl substituted with —S(=O)$_2$—$NR^{14}R^{15}$,
$C_{1-6}$alkyl substituted with —NH—S(=O)$_2$—$C_{1-6}$alkyl,
$C_{1-6}$alkyl substituted with —NH—S(=O)$_2$-halo $C_{1-6}$alkyl or
$C_{1-6}$alkyl substituted with —NH—S(=O)$_2$—$NR^{14}R^{15}$;
$R^{12}$ is hydrogen or $C_{1-4}$alkyl optionally substituted with $C_{1-4}$alkoxy;
$R^{13}$ is $C_{3-8}$cycloalkyl or a saturated 4 to 6-membered monocyclic heterocyclyl containing at least one heteroatom selected from N, O and S, wherein said $C_{3-8}$cycloalkyl or monocyclic heterocyclyl is optionally substituted with 1, 2 or 3 substituents each independently selected from halogen, hydroxyl, $C_{1-6}$alkyl, —C(=O)—$C_{1-6}$alkyl, $C_{1-6}$alkoxy, and —$NR^{14}R^{15}$;
$R^{14}$ and $R^{15}$ are each independently
hydrogen, or
halo$C_{1-4}$alkyl, or
$C_{1-4}$alkyl optionally substituted with a substituent selected from hydroxyl, $C_{1-4}$alkoxy, amino and mono- or di($C_{1-4}$alkyl)amino; and
$R^{16}$ is hydroxyl, halogen, cyano, $C_{1-4}$alkyl, $C_{1-4}$alkoxy, —$NR^{14}R^{15}$ or —C(=O)$NR^{14}R^{15}$;
or an N-oxide thereof, a pharmaceutically acceptable salt thereof or a solvate thereof.

19. A method according to claim 18, wherein the cancer is selected from multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

20. A method according to claim 18, wherein the cancer is selected from lung cancer, squamous cell carcinoma, liver cancer, kidney cancer, breast cancer, colon cancer, colorectal cancer, and prostate cancer.

21. A method according to claim 19, wherein the cancer is multiple myeloma.

22. A method according to claim 21, wherein the cancer is t(4;14) translocation positive multiple myeloma.

23. A method according to claim 19, wherein the cancer is bladder cancer.

24. A method according to claim 23, wherein the cancer is bladder cancer with a FGFR3 chromosomal translocation.

25. A method according to claim 23, wherein the cancer is bladder cancer with a FGFR3 point mutation.

26. A method according to claim 18, wherein the cancer is a tumor with a mutant of FGFR1, FGFR2, FGFR3 or FGFR4.

27. A method according to claim 18, wherein the cancer is a tumor with a gain-of-function mutant of FGFR2 or FGFR3.

28. A method according to claim 18, wherein the cancer is a tumor with over-expression of FGFR1.

29. A method according to claim 18, wherein the cancer is urothelial carcinoma.

30. A method according to claim 18, wherein the compound is N-(3,5-dimethoxyphenyl)-N'-(1-methylethyl)-N-[3-(1-methyl-1H-pyrazol-4-yl)quinoxalin-6-yl]ethane-1,2- diamine; or an N-oxide thereof, a pharmaceutically acceptable salt thereof or a solvate thereof.

31. A method according to claim 30, wherein the compound is N-(3,5-dimethoxyphenyl)-N'-(1-methylethyl)-N-[3-(1-methyl-1H-pyrazol-4-yl)quinoxalin-6-yl]ethane-1,2-diamine.

32. A method according to claim 18, wherein the compound is selected from:
N-(3,5-dimethoxyphenyl)-N-[3-(1-methyl-1H-pyrazol-4-yl)quinoxalin-6-yl]-N'-(2,2,2-trifluoroethyl)propane-1,3-diamine; and
N-(3,5-dimethoxyphenyl)-N-[3-(1-methyl-1H-pyrazol-4-yl)quinoxalin-6-yl]ethane-1,2-diamine;
or an N-oxide thereof, a pharmaceutically acceptable salt thereof or a solvate thereof.

33. A method for treating a subject suffering from a carcinoma, wherein the carcinoma is selected from a carcinoma of the bladder, breast, colon, kidney, epidermis, liver, lung, oesophagus, head and neck, gall bladder, ovary, pancreas, stomach, gastrointestinal (also known as gastric) cancer, cervix, endometrium, thyroid, prostate, or skin, a hematopoietic tumour of lymphoid lineage; a hematopoietic tumour of myeloid lineage; multiple myeloma; thyroid follicular cancer; a tumour of mesenchymal origin; a tumour of the central or peripheral nervous system; melanoma; seminoma; teratocarcinoma; osteosarcoma; xeroderma pigmentosum; keratoctanthoma; or Kaposi's sarcoma, said method comprising administering to the subject a compound selected from the group consisting of a compound of formula (I)

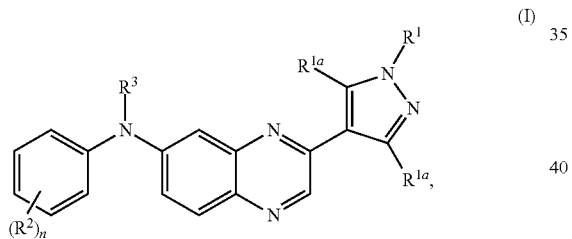

a tautomeric form, stereochemically isomeric form and isotopic form thereof, wherein
n is an integer equal to 0, 1, 2, 3 or 4;
$R^1$ is
  hydrogen,
  $C_{1-6}$alkyl,
  $C_{2-4}$alkenyl,
  hydroxy$C_{1-6}$alkyl,
  halo$C_{1-6}$alkyl,
  hydroxyhalo$C_{1-6}$alkyl,
  cyano$C_{1-4}$alkyl,
  $C_{1-6}$alkoxy$C_{1-6}$alkyl wherein each $C_{1-6}$alkyl is optionally substituted with one or two hydroxyl groups,
  $C_{1-6}$alkyl substituted with —$NR^4R^5$,
  $C_{1-6}$alkyl substituted with —C(=O)—$NR^4R^5$,
  —S(=O)$_2$—$C_{1-6}$alkyl,
  —S(=O)$_2$-halo$C_{1-6}$alkyl,
  —S(=O)$_2$—$NR^{14}R^{15}$,
  $C_{1-6}$alkyl substituted with —S(=O)$_2$—$C_{1-6}$alkyl,
  $C_{1-6}$alkyl substituted with —S(=O)$_2$-halo$C_{1-6}$alkyl,
  $C_{1-6}$alkyl substituted with —S(=O)$_2$—$NR^{14}R^{15}$,
  $C_{1-6}$alkyl substituted with —NH—S(=O)$_2$—$C_{1-6}$alkyl,
  $C_{1-6}$alkyl substituted with —NH—S(=O)$_2$-halo$C_{1-6}$alkyl,
  $C_{1-6}$alkyl substituted with —$NR^{12}$—S(=O)$_2$—$NR^{14}R^{15}$,
  $R^6$,
  $C_{1-6}$alkyl substituted with $R^6$,
  $C_{1-6}$alkyl substituted with —C(=O)—$R^6$,
  hydroxy$C_{1-6}$alkyl substituted with $R^6$,
  $C_{1-6}$alkyl substituted with —Si(CH$_3$)$_3$,
  $C_{1-6}$alkyl substituted with —P(=O)(OH)$_2$ or
  $C_{1-6}$alkyl substituted with —P(=O)(O$C_{1-6}$alkyl)$_2$;
each $R^{1a}$ is independently selected from
  hydrogen,
  $C_{1-4}$alkyl,
  hydroxy$C_{1-4}$alkyl,
  $C_{1-4}$alkyl substituted with amino or mono- or di($C_{1-4}$alkyl)amino or —NH($C_{3-8}$cycloalkyl),
  cyano$C_{1-4}$alkyl,
  $C_{1-4}$alkoxy$C_{1-4}$alkyl, and
  $C_{1-4}$alkyl substituted with one or more fluoro atoms;
each $R^2$ is independently selected from
  hydroxyl,
  halogen,
  cyano,
  $C_{1-4}$alkyl,
  $C_{2-4}$alkenyl,
  $C_{2-4}$alkynyl,
  $C_{1-4}$alkoxy,
  hydroxy$C_{1-4}$alkyl,
  hydroxy$C_{1-4}$alkoxy,
  halo$C_{1-4}$alkyl,
  halo$C_{1-4}$alkoxy,
  hydroxyhalo$C_{1-4}$alkyl,
  hydroxyhalo$C_{1-4}$alkoxy,
  $C_{1-4}$alkoxy$C_{1-4}$alkyl,
  halo$C_{1-4}$alkoxy$C_{1-4}$alkyl,
  $C_{1-4}$alkoxy$C_{1-4}$alkyl wherein each $C_{1-4}$alkyl is optionally substituted with one or two hydroxyl groups,
  hydroxyhalo$C_{1-4}$alkoxy$C_{1-4}$alkyl,
  $R^{13}$,
  $C_{1-4}$alkyl substituted with $R^{13}$,
  $C_{1-4}$alkyl substituted with —C(=O)—$R^{13}$,
  $C_{1-4}$alkoxy substituted with $R^{13}$,
  $C_{1-4}$alkoxy substituted with —C(=O)—$R^{13}$, —C(=O)—$R^{13}$,
  $C_{1-4}$alkyl substituted with —$NR^7R^8$,
  $C_{1-4}$alkyl substituted with —C(=O)—$NR^7R^8$,
  $C_{1-4}$alkoxy substituted with —$NR^7R^8$,
  $C_{1-4}$alkoxy substituted with —C(=O)—$NR^7R^8$,
  —$NR^7R^8$ and
  —C(=O)—$NR^7R^8$; or
when two $R^2$ groups are attached to adjacent carbon atoms they are optionally taken together to form a radical of formula:
  —O—(C($R^{17}$)$_2$)$_p$—O—;
  —X—CH=CH—; or
  —X—CH=N—; wherein $R^{17}$ is hydrogen or fluorine, p is 1 or 2 and X is O or S;
$R^3$ is
  hydroxyl,
  $C_{1-6}$alkoxy,
  hydroxy$C_{1-6}$alkoxy,
  $C_{1-6}$alkoxy substituted with —$NR^{11}R^{11}$,
  $C_{1-6}$alkyl,
  $C_{2-6}$alkenyl,
  $C_{2-6}$alkynyl, haloC$_{1-6}$alkyl optionally substituted with —O—C(=O)—C$_{1-6}$alkyl,
hydroxyC$_{1-6}$alkyl optionally substituted with —O—C(=O)—C$_{1-6}$alkyl,
hydroxyC$_{2-6}$alkenyl,
hydroxyC$_{2-6}$alkynyl,
hydroxyhaloC$_{1-6}$alkyl,
cyanoC$_{1-6}$alkyl,
C$_{1-6}$alkyl substituted with carboxyl,
C$_{1-6}$alkyl substituted with —C(=O)—C$_{1-6}$alkyl,
C$_{1-6}$alkyl substituted with —C(=O)—O—C$_{1-6}$alkyl,
C$_{1-6}$alkyl substituted with C$_{1-6}$alkoxyC$_{1-6}$alkyl-O—C(=O)—,
C$_{1-6}$alkyl substituted with C$_{1-6}$alkoxyC$_{1-6}$alkyl-C(=O)—,
C$_{1-6}$alkyl substituted with —O—C(=O)—C$_{1-6}$alkyl,
C$_{1-6}$alkoxyC$_{1-6}$alkyl wherein each C$_{1-6}$alkyl is optionally substituted with one or two hydroxyl groups or with —O—C(=O)—C$_{1-6}$alkyl,
C$_{2-6}$alkenyl substituted with C$_{1-6}$alkoxy,
C$_{2-6}$alkynyl substituted with C$_{1-6}$alkoxy,
C$_{1-6}$alkyl substituted with R$^9$ and optionally substituted with —O—C(=O)—C$_{1-6}$alkyl,
C$_{1-6}$alkyl substituted with —C(=O)—R$^9$,
C$_{1-6}$alkyl substituted with hydroxyl and R$^9$,
C$_{2-6}$alkenyl substituted with R$^9$,
C$_{2-6}$alkynyl substituted with R$^9$,
C$_{1-6}$alkyl substituted with —NR$^{10}$R$^{11}$,
C$_{2-6}$alkenyl substituted with —NR$^{10}$R$^{11}$,
C$_{2-6}$alkynyl substituted with —NR$^{10}$R$^{11}$,
C$_{1-6}$alkyl substituted with hydroxyl and —NR$^{10}$R$^{11}$,
C$_{1-6}$alkyl substituted with one or two halogens and —NR$^{10}$R$^{11}$,
—C$_{1-6}$alkyl-C(R$^{12}$)=N—O—R$^{12}$,
C$_{1-6}$alkyl substituted with —C(=O)—NR$^{10}$R$^{11}$,
C$_{1-6}$alkyl substituted with —O—C(=O)—NR$^{10}$R$^{11}$,
—S(=O)$_2$—C$_{1-6}$alkyl,
—S(=O)$_2$-haloC$_{1-6}$alkyl,
—S(=O)$_2$—NR$^{14}$R$^{15}$,
C$_{1-6}$alkyl substituted with —S(=O)$_2$—C$_{1-6}$alkyl,
C$_{1-6}$alkyl substituted with —S(=O)$_2$-haloC$_{1-6}$alkyl,
C$_{1-6}$alkyl substituted with —S(=O)$_2$—NR$^{14}$R$^{15}$,
C$_{1-6}$alkyl substituted with —NR$^{12}$—S(=O)$_2$—C$_{1-6}$alkyl,
C$_{1-6}$alkyl substituted with —NH—S(=O)$_2$-halo C$_{1-6}$alkyl,
C$_{1-6}$alkyl substituted with —NR$^{12}$—S(=O)$_2$—NR$^{14}$R$^{15}$,
R$^{13}$,
C$_{1-6}$alkyl substituted with —P(=O)(OH)$_2$ or
C$_{1-6}$alkyl substituted with —P(=O)(OC$_{1-6}$alkyl)$_2$;
R$^4$ and R$^5$ are each independently
hydrogen,
C$_{1-6}$alkyl,
hydroxyC$_{1-6}$alkyl,
haloC$_{1-6}$alkyl,
hydroxyhaloC$_{1-6}$alkyl,
C$_{1-6}$alkoxyC$_{1-6}$alkyl wherein each C$_{1-6}$alkyl is optionally substituted with one or two hydroxyl groups,
—S(=O)$_2$—C$_{1-6}$alkyl,
—S(=O)$_2$-haloC$_{1-6}$alkyl,
—S(=O)$_2$—NR$^{14}$R$^{15}$,
C$_{1-6}$alkyl substituted with —S(=O)$_2$—C$_{1-6}$alkyl,
C$_{1-6}$alkyl substituted with —S(=O)$_2$-haloC$_{1-6}$alkyl,
C$_{1-6}$alkyl substituted with —S(=O)$_2$—NR$^{14}$R$^{15}$,
C$_{1-6}$alkyl substituted with —NH—S(=O)$_2$—C$_{1-6}$alkyl,
C$_{1-6}$alkyl substituted with —NH—S(=O)$_2$-halo C$_{1-6}$alkyl,
C$_{1-6}$alkyl substituted with —NH—S(=O)$_2$—NR$^{14}$R$^{15}$,
R$^{13}$ or
C$_{1-6}$alkyl substituted with R$^{13}$;
R$^6$ is C$_{3-8}$cycloalkyl, C$_{3-8}$cycloalkenyl, phenyl, 4 to 7-membered monocyclic heterocyclyl containing at least one heteroatom selected from N, O and S; said C$_{3-8}$cycloalkyl, C$_{3-8}$cycloalkenyl, phenyl, 4 to 7-membered monocyclic heterocyclyl, each optionally and each independently substituted by 1, 2, 3, 4 or 5 substituents, each substituent independently selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl and C$_{1-6}$alkyl substituted with —NH—S(=O)$_2$—NR$^{14}$R$^{15}$;
R$^7$ and R$^8$ are each independently hydrogen, C$_{1-6}$alkyl, hydroxyC$_{1-6}$alkyl, haloC$_{1-6}$alkyl, hydroxyhalo C$_{1-6}$alkyl or C$_{1-6}$alkoxyC$_{1-6}$alkyl;
R$^9$ is C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O and S, said C$_{3-8}$cycloalkyl, C$_{3-8}$cycloalkenyl, phenyl, naphthyl, or 3 to 12 membered monocyclic or bicyclic heterocyclyl each optionally and each independently substituted with 1, 2, 3, 4 or 5 substituents, each substituent independently selected from
=O,
C$_{1-4}$alkyl,
hydroxyl,
carboxyl,
hydroxyC$_{1-4}$alkyl,
cyano,
cyanoC$_{1-4}$alkyl,
C$_{1-4}$alkyl-O—C(=O)—,
C$_{1-4}$alkyl substituted with C$_{1-4}$alkyl-O—C(=O)—,
C$_{1-4}$alkyl-C(=O)—,
C$_{1-4}$alkoxyC$_{1-4}$alkyl wherein each C$_{1-4}$alkyl is optionally substituted with one or two hydroxyl groups,
halogen,
haloC$_{1-4}$alkyl,
hydroxyhaloC$_{1-4}$alkyl,
—NR$^{14}$R$^{15}$,
—C(=O)—NR$^{14}$R$^{15}$,
C$_{1-4}$alkyl substituted with —NR$^{14}$R$^{15}$,
C$_{1-4}$alkyl substituted with —C(=O)—NR$^{14}$R$^{15}$,
C$_{1-4}$alkoxy,
—S(=O)$_2$—C$_{1-4}$alkyl,
—S(=O)$_2$-haloC$_{1-4}$alkyl,
—S(=O)$_2$—NR$^{14}$R$^{15}$,
C$_{1-4}$alkyl substituted with —S(=O)$_2$—NR$^{14}$R$^{15}$,
C$_{1-4}$alkyl substituted with —NH—S(=O)$_2$—C$_{1-4}$alkyl,
C$_{1-4}$alkyl substituted with —NH—S(=O)$_2$-halo C$_{1-4}$alkyl,

601

$C_{1-4}$alkyl substituted with —NH—S($=$O)$_2$—NR$^{14}$R$^{15}$,
R$^{13}$,
—C($=$O)—R$^{13}$,
$C_{1-4}$alkyl substituted with R$^{13}$,
phenyl optionally substituted with R$^{16}$,
phenyl$C_{1-6}$alkyl wherein the phenyl is optionally substituted with R$^{16}$, and
a 5 or 6-membered aromatic monocyclic heterocyclyl containing at least one heteroatom selected from N, O and S wherein said heterocyclyl is optionally substituted with R$^{16}$;
or when two of the substituents of R$^9$ are attached to the same atom, they are optionally taken together to form a 4 to 7-membered saturated monocyclic heterocyclyl containing at least one heteroatom selected from N, O and S;
R$^{10}$ and R$^{11}$ are each independently
hydrogen,
carboxyl,
$C_{1-6}$alkyl,
cyano$C_{1-6}$alkyl,
$C_{1-6}$alkyl substituted with —NR$^{14}$R$^{15}$,
$C_{1-6}$alkyl substituted with —C($=$O)—NR$^{14}$R$^{15}$,
halo$C_{1-6}$alkyl,
hydroxy$C_{1-6}$alkyl,
hydroxyhalo$C_{1-6}$alkyl,
$C_{1-6}$alkoxy,
$C_{1-6}$alkoxy$C_{1-6}$alkyl wherein each $C_{1-6}$alkyl is optionally substituted with one or two hydroxyl groups,
R$^6$,
$C_{1-6}$alkyl substituted with R$^6$,
—C($=$O)—R$^6$,
—C($=$O)—$C_{1-6}$alkyl,
—C($=$O)-hydroxy$C_{1-6}$alkyl,
—C($=$O)-halo$C_{1-6}$alkyl,
—C($=$O)-hydroxyhalo$C_{1-6}$alkyl,
$C_{1-6}$alkyl substituted with —Si(CH$_3$)$_3$,
—S($=$O)$_2$—$C_{1-6}$alkyl,
—S($=$O)$_2$-halo$C_{1-6}$alkyl,
—S($=$O)$_2$—NR$^{14}$R$^{15}$,
$C_{1-6}$alkyl substituted with —S($=$O)$_2$—$C_{1-6}$alkyl,
$C_{1-6}$alkyl substituted with —S($=$O)$_2$-halo$C_{1-6}$alkyl,
$C_{1-6}$alkyl substituted with —S($=$O)$_2$—NR$^{14}$R$^{15}$,
$C_{1-6}$alkyl substituted with —NH—S($=$O)$_2$—$C_{1-6}$alkyl,
$C_{1-6}$alkyl substituted with —NH—S($=$O)$_2$-halo$C_{1-6}$alkyl or
$C_{1-6}$alkyl substituted with —NH—S($=$O)$_2$—NR$^{14}$R$^{14}$R$^{15}$;
R$^{12}$ is hydrogen or $C_{1-4}$alkyl optionally substituted with $C_{1-4}$alkoxy;
R$^{13}$ is $C_{3-8}$cycloalkyl or a saturated 4 to 6-membered monocyclic heterocyclyl containing at least one heteroatom selected from N, O and S, wherein said $C_{3-8}$cycloalkyl or monocyclic heterocyclyl is optionally substituted with 1, 2 or 3 substituents each independently selected from halogen, hydroxyl, $C_{1-6}$alkyl, —C($=$O)—$C_{1-6}$alkyl, $C_{1-6}$alkoxy, and —NR$^{14}$R$^{15}$;
R$^{14}$ and R$^{15}$ are each independently
hydrogen, or
halo$C_{1-4}$alkyl, or
$C_{1-4}$alkyl optionally substituted with a substituent selected from hydroxyl, $C_{1-4}$alkoxy, amino and mono- or di($C_{1-4}$alkyl)amino; and
R$^{16}$ is hydroxyl, halogen, cyano, $C_{1-4}$alkyl, $C_{1-4}$alkoxy, —NR$^{14}$R$^{15}$ or —C($=$O)NR$^{14}$R$^{15}$;

602 or an N-oxide thereof, a pharmaceutically acceptable salt thereof or a solvate thereof.

34. A method according to claim 33, wherein the carcinoma is glioblastoma multiforme.

35. A method according to claim 33, wherein the compound is N-(3,5-dimethoxyphenyl)-N'-(1-methylethyl)-N-[3-(1-methyl-1H-pyrazol-4-yl)quinoxalin-6-yl]ethane-1,2-diamine; or an N-oxide thereof, a pharmaceutically acceptable salt thereof or a solvate thereof.

36. A method according to claim 35, wherein the compound is N-(3,5-dimethoxyphenyl)-N'-(1-methylethyl)-N-[3-(1-methyl-1H-pyrazol-4-yl)quinoxalin-6-yl]ethane-1,2-diamine.

37. A method of inhibiting a FGFR kinase, which method comprises contacting the kinase with a kinase-inhibiting compound selected from the group consisting of a compound of formula (I)

(I)

a tautomeric form, stereochemically isomeric form and isotopic form thereof, wherein
n is an integer equal to 0, 1, 2, 3 or 4;
R$^1$ is
hydrogen,
$C_{1-6}$alkyl,
$C_{2-4}$alkenyl,
hydroxy$C_{1-6}$alkyl,
halo$C_{1-6}$alkyl,
hydroxyhalo$C_{1-6}$alkyl,
cyano$C_{1-4}$alkyl,
$C_{1-6}$alkoxy$C_{1-6}$alkyl wherein each $C_{1-6}$alkyl is optionally substituted with one or two hydroxyl groups,
$C_{1-6}$alkyl substituted with —NR$^4$R$^5$,
$C_{1-6}$alkyl substituted with —C($=$O)—NR$^4$R$^5$,
—S($=$O)$_2$—$C_{1-6}$alkyl,
—S($=$O)$_2$-halo$C_{1-6}$alkyl,
—S($=$O)$_2$—NR$^{14}$R$^{15}$,
$C_{1-6}$alkyl substituted with —S($=$O)$_2$—$C_{1-6}$alkyl,
$C_{1-6}$alkyl substituted with —S($=$O)$_2$-halo$C_{1-6}$alkyl,
$C_{1-6}$alkyl substituted with —S($=$O)$_2$—NR$^{14}$R$^{15}$,
$C_{1-6}$alkyl substituted with —NH—S($=$O)$_2$—$C_{1-6}$alkyl,
$C_{1-6}$alkyl substituted with —NH—S($=$O)$_2$-halo$C_{1-6}$alkyl,
$C_{1-6}$alkyl substituted with —NR$^{12}$—S($=$O)$_2$—NR$^{14}$R$^{15}$,
R$^6$,
$C_{1-6}$alkyl substituted with R$^6$,
$C_{1-6}$alkyl substituted with —C($=$O)—R$^6$,
hydroxy$C_{1-6}$alkyl substituted with R$^6$,
$C_{1-6}$alkyl substituted with —Si(CH$_3$)$_3$,
$C_{1-6}$alkyl substituted with —P($=$O)(OH)$_2$ or
$C_{1-6}$alkyl substituted with —P($=$O)(OC$_{1-6}$alkyl)$_2$;
each R$^{1a}$ is independently selected from
hydrogen,
$C_{1-4}$alkyl, hydroxyC$_{1-4}$alkyl,
C$_{1-4}$alkyl substituted with amino or mono- or di(C$_{1-4}$alkyl)amino or —NH(C$_{3-8}$cycloalkyl),
cyanoC$_{1-4}$alkyl,
C$_{1-4}$alkoxyC$_{1-4}$alkyl, and
C$_{1-4}$alkyl substituted with one or more fluoro atoms;
each R$^2$ is independently selected from
hydroxyl,
halogen,
cyano,
C$_{1-4}$alkyl,
C$_{2-4}$alkenyl,
C$_{2-4}$alkynyl,
C$_{1-4}$alkoxy,
hydroxyC$_{1-4}$alkyl,
hydroxyC$_{1-4}$alkoxy,
haloC$_{1-4}$alkyl,
haloC$_{1-4}$alkoxy,
hydroxyhaloC$_{1-4}$alkyl,
hydroxyhaloC$_{1-4}$alkoxy,
C$_{1-4}$alkoxyC$_{1-4}$alkyl,
haloC$_{1-4}$alkoxyC$_{1-4}$alkyl,
C$_{1-4}$alkoxyC$_{1-4}$alkyl wherein each C$_{1-4}$alkyl is optionally substituted with one or two hydroxyl groups,
hydroxyhaloC$_{1-4}$alkoxyC$_{1-4}$alkyl,
R$^{13}$,
C$_{1-4}$alkyl substituted with R$^{13}$,
C$_{1-4}$alkyl substituted with —C(=O)—R$^{13}$,
C$_{1-4}$alkoxy substituted with R$^{13}$,
C$_{1-4}$alkoxy substituted with —C(=O)—R$^{13}$,
—C(=O)—R$^{13}$,
C$_{1-4}$alkyl substituted with —NR$^7$R$^8$,
C$_{1-4}$alkyl substituted with —C(=O)—NR$^7$R$^8$,
C$_{1-4}$alkoxy substituted with —NR$^7$R$^8$,
C$_{1-4}$alkoxy substituted with —C(=O)—NR$^7$R$^8$,
—NR$^7$R$^8$ and
—C(=O)—NR$^7$R$^8$; or
when two R$^2$ groups are attached to adjacent carbon atoms they are optionally taken together to form a radical of formula:
—O—(C(R$^{17}$)$_2$)$_p$—O—;
—X—CH=CH—; or
—X—CH=N—; wherein R$^{17}$ is hydrogen or fluorine, p is 1 or 2 and X is O or S;
R$^3$ is
hydroxyl,
C$_{1-6}$alkoxy,
hydroxyC$_{1-6}$alkoxy,
C$_{1-6}$alkoxy substituted with —NR$^{10}$R$^{11}$,
C$_{1-6}$alkyl,
C$_{2-6}$alkenyl,
C$_{2-6}$alkynyl,
haloC$_{1-6}$alkyl optionally substituted with —O—C(=O)—C$_{1-6}$alkyl,
hydroxyC$_{1-6}$alkyl optionally substituted with —O—C(=O)—C$_{1-6}$alkyl,
hydroxyC$_{2-6}$alkenyl,
hydroxyC$_{2-6}$alkynyl,
hydroxyhaloC$_{1-6}$alkyl,
cyanoC$_{1-6}$alkyl,
C$_{1-6}$alkyl substituted with carboxyl,
C$_{1-6}$alkyl substituted with —C(=O)—C$_{1-6}$alkyl,
C$_{1-6}$alkyl substituted with —C(=O)—O—C$_{1-6}$alkyl,
C$_{1-6}$alkyl substituted with C$_{1-6}$alkoxyC$_{1-6}$alkyl-O—C(=O)—,
C$_{1-6}$alkyl substituted with C$_{1-6}$alkoxyC$_{1-6}$alkyl-C(=O)—,
C$_{1-6}$alkyl substituted with —O—C(=O)—C$_{1-6}$alkyl,
C$_{1-6}$alkoxyC$_{1-6}$alkyl wherein each C$_{1-6}$alkyl is optionally substituted with one or two hydroxyl groups or with —O—C(=O)—C$_{1-6}$alkyl,
C$_{2-6}$alkenyl substituted with C$_{1-6}$alkoxy,
C$_{2-6}$alkynyl substituted with C$_{1-6}$alkoxy,
C$_{1-6}$alkyl substituted with R$^9$ and optionally substituted with —O—C(=O)—C$_{1-6}$alkyl,
C$_{1-6}$alkyl substituted with —C(=O)—R$^9$,
C$_{1-6}$alkyl substituted with hydroxyl and R$^9$,
C$_{2-6}$alkenyl substituted with R$^9$,
C$_{2-6}$alkynyl substituted with R$^9$,
C$_{1-6}$alkyl substituted with —NR$^{10}$R$^{11}$,
C$_{2-6}$alkenyl substituted with —NR$^{10}$R$^{11}$,
C$_{2-6}$alkynyl substituted with —NR$^{10}$R$^{11}$,
C$_{1-6}$alkyl substituted with hydroxyl and —NR$^{10}$R$^{11}$,
C$_{1-6}$alkyl substituted with one or two halogens and —NR$^{10}$R$^{11}$,
C$_{1-6}$alkyl-C(R$^{12}$)=N—O—R$^{12}$,
C$_{1-6}$alkyl substituted with —C(=O)—NR$^{10}$R$^{11}$,
C$_{1-6}$alkyl substituted with —O—C(=O)—NR$^{10}$R$^{11}$,
—S(=O)$_2$—C$_{1-6}$alkyl,
—S(=O)$_2$-haloC$_{1-6}$alkyl,
—S(=O)$_2$—NR$^{14}$R$^{15}$,
C$_{1-6}$alkyl substituted with —S(=O)$_2$—C$_{1-6}$alkyl,
C$_{1-6}$alkyl substituted with —S(=O)$_2$-haloC$_{1-6}$alkyl,
C$_{1-6}$alkyl substituted with —S(=O)$_2$—NR$^{14}$R$^{15}$,
C$_{1-6}$alkyl substituted with —NR$^{12}$—S(=O)$_2$—C$_{1-6}$alkyl,
C$_{1-6}$alkyl substituted with —NH—S(=O)$_2$-halo C$_{1-6}$alkyl,
C$_{1-6}$alkyl substituted with —NR$^{12}$—S(=O)$_2$—NR$^{14}$R$^{15}$,
R$^{13}$,
C$_{1-6}$alkyl substituted with —P(=O)(OH)$_2$ or
C$_{1-6}$alkyl substituted with —P(=O)(OC$_{1-6}$alkyl)$_2$;
R$^4$ and R$^5$ are each independently
hydrogen,
C$_{1-6}$alkyl,
hydroxyC$_{1-6}$alkyl,
haloC$_{1-6}$alkyl,
hydroxyhaloC$_{1-6}$alkyl,
C$_{1-6}$alkoxyC$_{1-6}$alkyl wherein each C$_{1-6}$alkyl is optionally substituted with one or two hydroxyl groups,
—S(=O)$_2$—C$_{1-6}$alkyl,
—S(=O)$_2$-haloC$_{1-6}$alkyl,
—S(=O)$_2$—NR$^{14}$R$^{15}$,
C$_{1-6}$alkyl substituted with —S(=O)$_2$—C$_{1-6}$alkyl,
C$_{1-6}$alkyl substituted with —S(=O)$_2$-haloC$_{1-6}$alkyl,
C$_{1-6}$alkyl substituted with —S(=O)$_2$—NR$^{14}$R$^{15}$,
C$_{1-6}$alkyl substituted with —NH—S(=O)$_2$—C$_{1-6}$alkyl,
C$_{1-6}$alkyl substituted with —NH—S(=O)$_2$-halo C$_{1-6}$alkyl,
C$_{1-6}$alkyl substituted with —NH—S(=O)$_2$—NR$^{14}$R$^{15}$,
R$^{13}$ or
C$_{1-6}$alkyl substituted with R$^{13}$;
R$^6$ is C$_{3-8}$cycloalkyl, C$_{3-8}$cycloalkenyl, phenyl, 4 to 7-membered monocyclic heterocyclyl containing at least one heteroatom selected from N, O and S; said C$_{3-8}$cycloalkyl, C$_{3-8}$cycloalkenyl, phenyl, 4 to 7-membered monocyclic heterocyclyl, each optionally and each independently substituted by 1, 2, 3, 4 or 5 substituents, each substituent independently selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl and C$_{1-6}$alkyl substituted with —NH—S(=O)$_2$—NR$^{14}$R$^{15}$;

R$^7$ and R$^8$ are each independently hydrogen, C$_{1-6}$alkyl, hydroxyC$_{1-6}$alkyl, haloC$_{1-6}$alkyl, hydroxyhaloC$_{1-6}$alkyl or C$_{1-6}$alkoxyC$_{1-6}$alkyl;

R$^9$ is C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O and S, said C$_{3-8}$cycloalkyl, C$_{3-8}$cycloalkenyl, phenyl, naphthyl, or 3 to 12 membered monocyclic or bicyclic heterocyclyl each optionally and each independently substituted with 1, 2, 3, 4 or 5 substituents, each substituent independently selected from
=O,
C$_{1-4}$alkyl,
hydroxyl,
carboxyl,
hydroxyC$_{1-4}$alkyl,
cyano,
cyanoC$_{1-4}$alkyl,
C$_{1-4}$alkyl-O—C(=O)—,
C$_{1-4}$alkyl substituted with C$_{1-4}$alkyl-O—C(=O)—,
C$_{1-4}$alkyl-C(=O)—,
C$_{1-4}$alkoxyC$_{1-4}$alkyl wherein each C$_{1-4}$alkyl is optionally substituted with one or two hydroxyl groups,
halogen,
haloC$_{1-4}$alkyl,
hydroxyhaloC$_{1-4}$alkyl,
—NR$^{14}$R$^{15}$,
—C(=O)—NR$^{14}$R$^{15}$,
C$_{1-4}$alkyl substituted with —NR$^{14}$R$^{15}$,
C$_{1-4}$alkyl substituted with —C(=O)—NR$^{14}$R$^{15}$,
C$_{1-4}$alkoxy,
—S(=O)$_2$—C$_{1-4}$alkyl,
—S(=O)$_2$-haloC$_{1-4}$alkyl,
—S(=O)$_2$—NR$^{14}$R$^{15}$,
C$_{1-4}$alkyl substituted with —S(=O)$_2$—NR$^{14}$R$^{15}$,
C$_{1-4}$alkyl substituted with —NH—S(=O)$_2$—C$_{1-4}$alkyl,
C$_{1-4}$alkyl substituted with —NH—S(=O)$_2$-haloC$_{1-4}$alkyl,
C$_{1-4}$alkyl substituted with —NH—S(=O)$_2$—NR$^{14}$R$^{15}$,
R$^{13}$,
—C(=O)—R$^{13}$,
C$_{1-4}$alkyl substituted with R$^{13}$,
phenyl optionally substituted with R$^{16}$,
phenylC$_{1-6}$alkyl wherein the phenyl is optionally substituted with R$^{16}$, and
a 5 or 6-membered aromatic monocyclic heterocyclyl containing at least one heteroatom selected from N, O and S wherein said heterocyclyl is optionally substituted with R$^{16}$;
or when two of the substituents of R$^9$ are attached to the same atom, they are optionally taken together to form a 4 to 7-membered saturated monocyclic heterocyclyl containing at least one heteroatom selected from N, O and S;

R$^{10}$ and R$^{11}$ are each independently
hydrogen,
carboxyl,
C$_{1-6}$alkyl,
cyanoC$_{1-6}$alkyl,
C$_{1-6}$alkyl substituted with —NR$^{14}$R$^{15}$,
C$_{1-6}$alkyl substituted with —C(=O)—NR$^{14}$R$^{15}$,
haloC$_{1-6}$alkyl,
hydroxyC$_{1-6}$alkyl,
hydroxyhaloC$_{1-6}$alkyl,
C$_{1-6}$alkoxy,
C$_{1-6}$alkoxyC$_{1-6}$alkyl wherein each C$_{1-6}$alkyl is optionally substituted with one or two hydroxyl groups,
R$^6$,
C$_{1-6}$alkyl substituted with R$^6$,
—C(=O)—R$^6$,
—C(=O)—C$_{1-6}$alkyl,
—C(=O)-hydroxyC$_{1-6}$alkyl,
—C(=O)-haloC$_{1-6}$alkyl,
—C(=O)-hydroxyhaloC$_{1-6}$alkyl,
C$_{1-6}$alkyl substituted with —Si(CH$_3$)$_3$,
—S(=O)$_2$—C$_{1-6}$alkyl,
—S(=O)$_2$-haloC$_{1-6}$alkyl,
—S(=O)$_2$—NR$^{14}$R$^{15}$,
C$_{1-6}$alkyl substituted with —S(=O)$_2$—C$_{1-6}$alkyl,
C$_{1-6}$alkyl substituted with —S(=O)$_2$-haloC$_{1-6}$alkyl,
C$_{1-6}$alkyl substituted with —S(=O)$_2$—NR$^{14}$R$^{15}$,
C$_{1-6}$alkyl substituted with —NH—S(=O)$_2$—C$_{1-6}$alkyl,
C$_{1-6}$alkyl substituted with —NH—S(=O)$_2$-haloC$_{1-6}$alkyl or
C$_{1-6}$alkyl substituted with —NH—S(=O)$_2$—NR$^{14}$R$^{14}$R$^{15}$;

R$^{12}$ is hydrogen or C$_{1-4}$alkyl optionally substituted with C$_{1-4}$alkoxy;

R$^{13}$ is C$_{3-8}$cycloalkyl or a saturated 4 to 6-membered monocyclic heterocyclyl containing at least one heteroatom selected from N, O and S, wherein said C$_{3-8}$cycloalkyl or monocyclic heterocyclyl is optionally substituted with 1, 2 or 3 substituents each independently selected from halogen, hydroxyl, C$_{1-6}$alkyl, —C(=O)—C$_{1-6}$alkyl, C$_{1-6}$alkoxy, and —NR$^{14}$R$^{15}$;

R$^{14}$ and R$^{15}$ are each independently
hydrogen, or
haloC$_{1-4}$alkyl, or
C$_{1-4}$alkyl optionally substituted with a substituent selected from hydroxyl, C$_{1-4}$alkoxy, amino and mono- or di(C$_{1-4}$alkyl)amino; and R$^{16}$ is hydroxyl, halogen, cyano, C$_{1-4}$alkyl, C$_{1-4}$alkoxy, —NR$^{14}$R$^{15}$ or —C(=O)NR$^{14}$R$^{15}$;

or an N-oxide thereof, a pharmaceutically acceptable salt thereof or a solvate thereof.

38. A method according to claim 37, wherein the compound is N-(3,5-dimethoxyphenyl)-N'-(1-methylethyl)-N-[3-(1-methyl-1H-pyrazol-4-yl)quinoxalin-6-yl]ethane-1,2-diamine; or an N-oxide thereof, a pharmaceutically acceptable salt thereof or a solvate thereof.

39. A method according to claim 38, wherein the compound is N-(3,5-dimethoxyphenyl)-N'-(1-methylethyl)-N-[3-(1-methyl-1H-pyrazol-4-yl)quinoxalin-6-yl]ethane-1,2-diamine.

40. A method according to claim 1, further comprising administering to the subject one or more other anticancer agents.

41. A method according to claim 40, wherein the one or more other anticancer agents comprises a kinase inhibitor.

42. A method according to claim 40, wherein the compound is N-(3,5-dimethoxyphenyl)-N'-(1-methylethyl)-N-[3-(1-methyl-1H-pyrazol-4-yl)quinoxalin-6-yl]ethane-1,2-diamine; or an N-oxide thereof, a pharmaceutically acceptable salt thereof or a solvate thereof.

43. A method according to claim 42, wherein the compound is N-(3,5-dimethoxyphenyl)-N'-(1-methylethyl)-N-[3-(1-methyl-1H-pyrazol-4-yl)quinoxalin-6-yl]ethane-1,2-diamine.

44. A method according to claim 20 wherein the lung cancer is NSCLC.

45. A method according to claim 33 wherein the carcinoma is adenocarcinoma of the lung, small cell lung cancer or non-small cell lung carcinoma.

\* \* \* \* \*

UNITED STATES PATENT AND TRADEMARK OFFICE
CERTIFICATE OF CORRECTION

PATENT NO.         : 9,464,071 B2                                        Page 1 of 1
APPLICATION NO.    : 14/505020
DATED              : October 11, 2016
INVENTOR(S)        : Saxty et al.

It is certified that error appears in the above-identified patent and that said Letters Patent is hereby corrected as shown below:

In the Claims

Column 596, Line 15: Claim 18, Delete "$NR^{14}R^{14}R^{15}$;" and insert -- $NR^{14}R^{15}$ --

Column 598, Line 64: Claim 33, Delete "-$NR^{11}R^{11}$," and insert -- -$NR^{10}R^{11}$, --

Column 601, Line 50: Claim 33, Delete "$NR^{14}R^{14}R^{15}$;" and insert -- $NR^{14}R^{15}$ --

Column 606, Line 36: Claim 37, Delete "$NR^{14}R^{14}R^{15}$;" and insert -- $NR^{14}R^{15}$ --

Signed and Sealed this
Twenty-seventh Day of December, 2016

Michelle K. Lee
*Director of the United States Patent and Trademark Office*